(12) United States Patent
Krupnick et al.

(10) Patent No.: US 11,897,929 B2
(45) Date of Patent: Feb. 13, 2024

(54) COMPOSITIONS AND METHODS FOR TARGETED CYTOKINE DELIVERY

(71) Applicant: Washington University, St. Louis, MO (US)

(72) Inventors: Alexander Sasha Krupnick, St. Louis, MO (US); Daved Henry Fremont, St. Louis, MO (US); Eric Reed Lazear, St. Louis, MO (US); John Westwick, Houston, TX (US)

(73) Assignee: Washington University, St. Louis, MO (US)

( * ) Notice: Subject to any disclaimer, the term of this patent is extended or adjusted under 35 U.S.C. 154(b) by 271 days.

(21) Appl. No.: 17/238,995

(22) Filed: Apr. 23, 2021

(65) Prior Publication Data

US 2021/0284706 A1    Sep. 16, 2021

Related U.S. Application Data

(63) Continuation of application No. 16/075,069, filed as application No. PCT/US2017/016688 on Feb. 6, 2017, now Pat. No. 11,053,293.

(60) Provisional application No. 62/419,146, filed on Nov. 8, 2016, provisional application No. 62/350,056, filed on Jun. 14, 2016, provisional application No. 62/342,630, filed on May 27, 2016, provisional application No. 62/292,046, filed on Feb. 5, 2016.

(51) Int. Cl.
| | |
|---|---|
| C07K 14/55 | (2006.01) |
| A61K 47/68 | (2017.01) |
| A61P 35/00 | (2006.01) |
| C07K 16/28 | (2006.01) |
| A61K 38/00 | (2006.01) |
| C07K 14/54 | (2006.01) |
| C07K 14/545 | (2006.01) |
| C07K 14/705 | (2006.01) |
| C07K 14/52 | (2006.01) |

(52) U.S. Cl.
CPC .......... *C07K 14/55* (2013.01); *A61K 47/6849* (2017.08); *A61P 35/00* (2018.01); *C07K 14/52* (2013.01); *C07K 14/545* (2013.01); *C07K 14/5418* (2013.01); *C07K 14/5443* (2013.01); *C07K 14/70596* (2013.01); *C07K 16/2851* (2013.01); *A61K 38/00* (2013.01)

(58) Field of Classification Search
None
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 7,371,371 B2 | 5/2008 | Epstein et al. |
| 9,273,136 B2 | 3/2016 | Rader et al. |
| 10,184,009 B2 | 1/2019 | Ast et al. |
| 10,793,613 B2 | 10/2020 | Krupnick et al. |
| 11,053,293 B2 | 7/2021 | Krupnick et al. |
| 2003/0124678 A1 | 7/2003 | Epstein et al. |
| 2005/0249706 A1 | 11/2005 | Bermudes et al. |
| 2008/0274047 A1 | 11/2008 | Romagne et al. |
| 2009/0098609 A1 | 4/2009 | Gillies et al. |
| 2011/0150870 A1 | 6/2011 | Rader et al. |
| 2011/0311517 A1 | 12/2011 | Li et al. |
| 2012/0244112 A1 | 9/2012 | Ast et al. |
| 2014/0286898 A1 | 9/2014 | Gavin et al. |
| 2015/0216937 A1 | 8/2015 | Wen et al. |
| 2018/0201689 A1 | 7/2018 | Fang et al. |
| 2019/0092831 A1 | 3/2019 | Krupnick et al. |

(Continued)

FOREIGN PATENT DOCUMENTS

| | | |
|---|---|---|
| CN | 107226866 | 10/2017 |
| JP | 2009511550 A | 3/2009 |

(Continued)

OTHER PUBLICATIONS

Banerjee et al., Retargeting IL-2 Signaling to NKG2D-Expressing Tumor-Infiltrating Leukocytes Improves Adoptive Transfer Immunotherapy. J Immunol (2021) 207 (1): 333-343.*

(Continued)

*Primary Examiner* — Ruixiang Li
(74) *Attorney, Agent, or Firm* — Polsinelli PC

(57) ABSTRACT

The present disclosure encompasses compositions and methods for targeted cytokine delivery. The compositions disclosed herein comprise a cytokine linked to an NKG2D ligand or PD1 ligand and may improve immunotherapy by limiting side effects associated with immunotherapy. The present disclosure also encompasses compositions and methods for recruiting cytotoxic lymphocytes to target cells using NKG2D receptor ligands or PD1 ligands. The compositions disclosed herein comprise a NKG2D receptor ligand and a targeting molecule and may improve immunotherapy by limiting side effects associated with immunotherapy.

5 Claims, 93 Drawing Sheets
(92 of 93 Drawing Sheet(s) Filed in Color)
Specification includes a Sequence Listing.

(56) References Cited

U.S. PATENT DOCUMENTS

| | | |
|---|---|---|
| 2019/0119345 A1 | 4/2019 | Krupnick et al. |
| 2021/0032306 A1 | 2/2021 | Krupnick et al. |

FOREIGN PATENT DOCUMENTS

| | | |
|---|---|---|
| JP | 2011506406 A | 3/2011 |
| WO | 2001071005 | 9/2001 |
| WO | 2003015697 A2 | 2/2003 |
| WO | 2003048334 | 6/2003 |
| WO | 2003048334 A2 | 6/2003 |
| WO | 2016100375 | 6/2003 |
| WO | 2007002905 | 1/2007 |
| WO | 2010017103 A2 | 2/2010 |
| WO | 2012107417 A1 | 8/2012 |
| WO | 2012178137 A1 | 12/2012 |
| WO | 2016100375 A2 | 6/2016 |
| WO | 2016164937 A2 | 10/2016 |
| WO | 2017136818 | 8/2017 |
| WO | 2017136818 A2 | 8/2017 |

OTHER PUBLICATIONS

Lundholm, M. et al., "Prostate Tumor-Derived Exosomes Down-Regulate NKG2D Expression on Natural Killer Cells and CD8+ T Cells: Mechanism of Immune Evasion," PLoS One, Sep. 2014, pp. 1-9, vol. 9, No. 9, e108925.

Luteijn, R. et al., "Cowpox Virus Protein CPXV012 Eludes CTLs by Blocking ATP Binding to TAP," J. Immunol., 2014, pp. 1578-1589, vol. 193.

Mancia, F. et al., "Optimization of Protein Production in Mammalian Cells with a Coexpressed Fluorescent Marker," Structure, Aug. 2004, pp. 1355-1360, vol. 12, Elsevier Ltd.

Marcus, A. et al., "Evidence for Natural Killer Cell Memory," Curr. Biol., Sep. 9, 2013, pp. R817-R820, vol. 23.

Mccoy, W. et al., "Cowpox virus employs a two-pronged strategy to outflank MHCI antigen presentation," NIH Public Access Author Manuscript, available in PMC Sep. 1, 2014, pp. 1-7, published in final edited form as: Mol. Immunol., Sep. 2013, pp. 156-158, vol. 55, No. 2.

Mccoy, W. et al., "Structural Mechanism of ER Retrieval of MHC Class I by Cowpox," PLoS Biol., Nov. 2012, pp. 1-13, vol. 10, No. 11, e1001432.

Mcfarland, B. et al., "Symmetry Recognizing Asymmetry: Analysis of the Interactions between the C-Type Lectin-like Immunoreceptor NKG2D and MHC Class I-like Ligands," Structure, Apr. 2003, pp. 411-422, vol. 11, Elsevier Science Ltd.

Meiraz, A. et al., "Switch from perforin-expressing to perforin-deficient CD8(+) T cells accounts for two distinct types of effector cytotoxic T lymphocytes in vivo," Immunol., 2009, pp. 69-82, vol. 128, Blackwell Publishing Ltd.

Meresse, B. et al., "Coordinated Induction by IL 15 of a TCR-Independent NKG2D Signaling Pathway Converts CTL into Lymphokine-Activated Killer Cells in Celiac Disease," Immunity, Sep. 2004, pp. 357-366, vol. 21, Cell Press.

Mistry, A. et al., "Regulation of ligands for the activating receptor NKG2D," Immunol., 2007, pp. 439-447, vol. 121, Blackwell Publishing Ltd.

Mitra, S. et al., "Interleukin-2 Activity Can Be Fine Tuned with Engineered Receptor Signaling Clamps," Immunity, May 19, 2015, pp. 826-838, vol. 42, Elsevier Inc.

Morin, A. et al., "Collaboration gets the most out of software," eLIFE, 2013, pp. 1-6, vol. 2, No. e01456.

Nachmani, D. et al., "Diverse Herpesvirus MicroRNAs Target the Stress-Induced Immune Ligand MICB to Escape Recognition by Natural Killer Cells," Cell Host Microbe, Apr. 23, 2009, pp. 376-385, vol. 5, Elsevier Inc.

Nash, W. et al., "Know thyself: NK-cell inhibitory receptors prompt self-tolerance, education, and viral control," Front. Immunol., Apr. 2014, pp. 1-12, vol. 5, No. 175.

NCBI accession No. NM_001267706, Dec. 23, 2018; 5 pgs.
NCBI accession No. NM_001314029, Dec. 23, 2018; 4 pgs.
NCBI accession No. NM_014143, Dec. 23, 2018; 4 pgs.
NCBI accession No. NM_025239, Jan. 27, 2019; 5 pgs.
NCBI accession No. NP_001254635, Dec. 23, 2018; 3 pgs.
NCBI accession No. NP_001300958, Dec. 23, 2018; 3 pgs.
NCBI accession No. NP_054862, Dec. 24, 2018; 3 pgs.
NCBI accession No. NP_079515, Jan. 27, 2019; 3 pgs.
NCBI accession No. NR_052005, Feb. 6, 2019; 5 pgs.
NCBI accession No. XM_005251600, Mar. 26, 2018; 2 pgs.
NCBI accession No. XP_005251657, Mar. 26, 2018; 2 pgs.

Notice of Allowance dated May 19, 2020 from related U.S. Appl. No. 15/536,580; 5 pgs.

Notice of Allowance dated Jun. 12, 2020 from related European Patent Application No. 15870897.4; 7 pgs.

Notice of Allowance dated Feb. 22, 2021 from related U.S. Appl. No. 16/075,069 ; 7 pgs.

Obeidy, P. et al., "NKG2D and its ligands," Int. J. Biochem. Cell Biol., 2009, pp. 2364-2367, vol. 41, Elsevier Ltd.

O'Callaghan, C. et al., "Molecular Competition for NKG2D: H60 and RAE1 Compete Unequally for NKG2D with Dominance of H60," Immunity, Aug. 2001, pp. 201-211, vol. 15, Cell Press.

Office Action dated Dec. 20, 2018 from related European Patent Application No. 15870897.4; 4 pgs.

Office Action dated Oct. 2, 2019 from related European Patent Application No. 15870897.4; 4 pgs.

Office Action dated Sep. 19, 2019 from related U.S. Appl. No. 15/536,580; 9 pgs.

Office Action dated Jan. 16, 2020 from related U.S. Appl. No. 15/536,580; 8 pgs.

Office Action dated Aug. 7, 2020 from related U.S. Appl. No. 16/075,069; 15 pgs.

Office Action dated Oct. 21, 2020 from related European Patent Application No. 17748340.1; 8 pgs.

Ogasawara, K. et al., "Impairment of NK cell function by NKG2D modulation in NOD mice," Immunity, Jan. 2003, pp. 41-51, vol. 18, Cell Press.

Orange, J. et al., "Viral evasion of natural killer cells." Nat. Immunol., Nov. 2002, pp. 1006-1012, vol. 3, No. 11.

Otwinowski, Z. et al., "Processing of X-Ray Diffraction Data Collected in Oscillation Mode," Methods Enzymol., Part of Special Issue Macromolecular Crystallography Part A, 1997, pp. 307-326, vol. 276, Academic Press, Inc.

Pappworth, I. et al., "The Switch from Latent to Productive Infection in Epstein-Barr Virus-Infected B Cells Is Associated with Sensitization to NK Cell Killing," J. Virol., Jan. 2007, pp. 474-482, vol. 81, No. 2.

Park, J. et al., "Modulation of CD4+ T Lymphocyte Lineage Outcomes with Targeted, Nanoparticle-Mediated Cytokine Delivery," NIH Public Access, Author Manuscript, available in PMC Feb. 7, 2012, pp. 1-16, published in final edited form as: Mol. Pharm., Feb. 7, 2011, pp. 143-152, vol. 8, No. 1.

Plonquet, A. et al., "Peripheral blood natural killer cell count is associated with clinical outcome in patients with aaIPI 2-3 diffuse large B-cell lymphoma," Annals of Oncology, 2007, pp. 1209-1215, vol. 18.

Poschke, I., et al., "A phase I clinical trial combining dendritic cell vaccination with adoptive T cell transfer in patients with stage IV melanoma," Cancer Immunol. Immunother., 2014, pp. 1061-1071, vol. 63.

Radaev, S. et al., "Conformational Plasticity Revealed by the Cocrystal Structure of NKG2D and Its Class I MHC-like Ligand ULBP3," Immunity, Dec. 2001, pp. 1039-1049, vol. 15, Cell Press.

Radaev, S. et al., "Structure and Function of Natural Killer Cell Surface Receptors," Annu. Rev. Biophys. Biomol. Struct., Jun. 2003, pp. 93-114, vol. 32.

Rathanaswami, P. et al., "High-affinity binding measurements of antibodies to cell-surface-expressed antigens," Anal. Biochem., Feb. 1, 2008, pp. 52-60, vol. 373, No. 1, Elsevier.

Raulet, D. et al., "Regulation of ligands for the NKG2D activating receptor," NIH Public Access Author Manuscript, available in PMC Nov. 25, 2014, pp. 1-34, published in final edited form as: Annu. Rev. Immunol., 2013, pp. 413-441, vol. 31.

(56) References Cited

OTHER PUBLICATIONS

Raulet, D., "Roles of the NKG2D Immunoreceptor and its Ligands," Nat. Rev. Immunol., Oct. 2003, pp. 781-790, vol. 3.
Rosenberg, S. et al., "Experience with the Use of High-Dose Interleukin-2 in the Treatment of 652 Cancer Patients," Ann. Surg., Oct. 1989, pp. 474-484, vol. 210, No. 4.
Rosenberg, S., "IL-2: The First Effective Immunotherapy for Human Cancer," J. Immunol., 2014, pp. 5451-5458, vol. 192.
Champsaur, M. et al., "Effect of NKG2D ligand expression on host immune responses," Immunol. Rev., 2010, pp. 267-285, vol. 235.
Extended European Search Report dated Jul. 9, 2021 from related European Patent Application No. 21155548.7; 7 pgs.
Office Action dated Mar. 23, 2021 from related Japanese Patent Application No. 2018-540749; 16 pgs., with English translation.
Office Action dated Aug. 24, 2021 from related Japanese Patent Application No. 2018-540749; 5 pgs., with English translation.
Office Action dated Dec. 7, 2021 from related Japanese Patent Application No. 2018-540749; 12 pgs., with English translation.
Office Action dated Dec. 17, 2021 from related Chinese Patent Application No. 201780022070.9; 17 pgs., with English translation.
Chinese Application No. 201780022070.9, filed Feb. 6, 2017, Fourth Office Action dated Sep. 2, 2022; 12 pages.
Griffin, B. et al., "Herpesviruses and immunity: The art of evasion," Vet Microbiol., Jun. 16, 2010, pp. 89-100, vol. 143, No. 1.
Groh, V. et al., "Stimulation of T cell autoreactivity by anomalous expression of NKG2D and its MIC ligands in rheumatoid arthritis," PNAS, Aug. 5, 2003, pp. 9452-9457, vol. 100, No. 16.
Gutbrodt, K. et al., "Antibody-Based Delivery of IL2 and Cytotoxics Eradicates Tumors in Immunocompetent Mice," Mol. Cancer Ther., 2014, pp. 1772-1776, vol. 13, No. 7, American Association for Cancer Research.
Hahn, M. et al., "Unconventional topology of self peptide-major histocompatibility complex binding by a human autoimmune T cell receptor," Nat. Immunol., May 2005, pp. 490-496, vol. 6, No. 5, Nature Publishing Group.
Hank, J. et al., "Distinct Clinical and Laboratory Activity of Two Recombinant Interleukin-2 Preparations," Clin. Cancer Res., Feb. 1999, pp. 281-289, vol. 5.
Hansen, T. et al., "MHC class I antigen presentation: learning from viral evasion strategies," Nat. Rev. Immunol., Jul. 2009, pp. 503-513, vol. 9.
Heaton, K. et al., "Characterization of Lymphokine-Activated Killing by Human Peripheral Blood Mononuclear Cells Stimulated with Interleukin 2 (IL-2) Analogs Specific for the Intermediate Affinity IL-2 Receptor," Cellular Immunol., Mar. 1993, pp. 167-179, vol. 147, No. 1.
Heaton, K. et al., "Human Interleukin 2 Analogues That Preferentially Bind the Intermediate-Affinity Interleukin 2 Receptor Lead to Reduced Secondary Cytokine Secretion: Implications for the Use of These Interleukin 2 Analogues in Cancer Immunotherapy," Cancer Res., Jun. 1, 1993, pp. 2597-2602, vol. 53.
Hersey, P. et al., "Low natural-killer-cell activity in familial melanoma patients and their relatives," Br. J. Cancer, 1979, pp. 113-122, vol. 40.
Ho, E. et al., "Costimulation of Multiple NK Cell Activation Receptors by NKG2D," J. Immunol., 2002, pp. 3667-3675, vol. 169, The American Association of Immunologists, Inc.
Horng, T. et al., "NKG2D signaling is coupled to the interleukin 15 receptor signaling pathway," Nat. Immunol., Dec. 2007, pp. 1345-1352, vol. 8, No. 12, Nature Publishing Group.
Hue, S. et al., "A Direct Role for NKG2D/MICA Interaction in Villous Atrophy During Celiac Disease," Immunity, Sep. 2004, pp. 367-377, vol. 21, Cell Press.
Imai, K. et al., "Natural cytotoxic activity of peripheral-blood lymphocytes and cancer incidence: an 11-year follow-up study of a general population," Lancet, Nov. 25, 2000, pp. 1795-1799, vol. 356, No. 9244.
International Search Report and Written Opinion dated Apr. 26, 2018 from related International Patent Application No. PCT/US2017/016688; 17 pgs.

International Search Report and Written Opinion dated May 2, 2016 from related International Patent Application No. PCT/US2015/065872; 19 pgs.
Ji, Q. et al., "Provision of Granulocyte-Macrophage Colony-Stimulating Factor Converts an Autoimmune Response to a Self-Antigen into an Antitumor Response," J. Immunol., 2005, pp. 1456-1463, vol. 175.
Kang, T. et al., "Tumor-Targeted Delivery of IL-2 by NKG2D Leads to Accumulation of Antigen-Specific CD8+ T Cells In the Tumor Loci and Enhanced Anti-Tumor Effects," PLoS One, Apr. 2012, pp. 1-9, vol. 7, No. 4, e35141.
Karlin, S. et al., "Applications and statistics for multiple high-scoring segments in molecular sequences," PNAS, Jun. 1993, pp. 5873-5877, vol. 90.
Karlin, S. et al., "Methods for assessing the statistical significance of molecular sequence features by using general scoring schemes," PNAS, Mar. 1990, pp. 2264-2268, vol. 87.
Karre, K. et al., "Selective rejection of H-2-deficient lymphoma variants suggests alternative immune defence strategy," Nature, Feb. 1986, pp. 675-678, vol. 319, Nature Publishing Group.
Kim, H., "Antibody-based depletion of Foxp3+ T cells potentiates antitumor immune memory stimulated by mTOR inhibition," Oncoimmunology, Jun. 2014, pp. e29081-1 to e29081-3, vol. 3, Landes Bioscience.
Nellev, S. et al., "Inhibition of NKG2D receptor function by antibody therapy attenuates transfer-induced colitis in SCID mice," Eur. J. Immunol., 2007, pp. 1397-1406, vol. 37, Wiley-VCH Verlag GmbH & Co.
Klein, O., et al,. "Melan-A-specific Cytotoxic T Cells are Associated with Tumor Regression and Autoimmunity Following Treatment with Anti-CTLA-4," Clinical Cancer Res., Apr. 1, 2009, pp. 2507-2513, vol. 15, No. 7.
Kolate, A. et al., "PEG—A versatile conjugating ligand for drugs and drug delivery systems," J. Controlled Release, Oct. 28, 2014, pp. 67-81, vol. 192, Elsevier, B.V.
Kolitz, J. et al., "Recombinant Interleukin-2 in Patients Aged Younger Than 60 Years With Acute Myeloid Leukemia in First Complete Remission," Cancer, Apr. 1, 2014, pp. 1010-1017, vol. 120.
Konjevic, G. et al., "In-vitro IL-2 or IFN-alpha-induced NKG2D and CD161 NK cell receptor expression indicates novel aspects of NK cell activation in metastatic melanoma patients," Melanoma Res., 2010, pp. 459-467, vol. 20.
Kreisel, D. et al,. "Strain-Specific Variation in Murine Natural Killer Gene Complex Contributes to Differences in Immunosurveillance for Urethane-Induced Lung Cancer," Cancer Res., Jun. 29, 2012, Author Manuscript, 20 pgs.
Krieg, C. et al., "Improved IL-2 immunotherapy by selective stimulation of IL-2 receptors on lymphocytes and endothelial cells," PNAS, Jun. 29, 2010, pp. 11906-11911, vol. 107, No. 26, with Correction, 1 pg.
Krissinel, E. et al., "Inference of Macromolecular Assemblies from Crystalline State," J. Mol. Biol., Sep. 21, 2007, pp. 774-797, vol. 372, No. 3.
Krmpotic, A. et al., "NK cell activation through the NKG2D ligand MULT-1 is selectively prevented by the glycoprotein encoded by mouse cytomegalovirus gene m145," J. Exp. Med., Jan. 17, 2005, pp. 211-220, vol. 201, No. 2, The Rockefeller University Press.
Kwong, K. et al., "Generation, affinity maturation, and characterization of a human anti-human NKG2D monoclonal antibody with dual antagonistic and agonistic activity," NIH Public Access Author Manuscript, Dec. 31, 2009, pp. 1-25, published in final edited form as: J. Mol. Biol., Dec. 31, 2008, pp. 1143-1156, vol. 384, No. 5.
Landau, M. et al., "ConSurf 2005: the projection of evolutionary conservation scores of residues on protein structures," Nucl. Acids Res., 2005, pp. W299-W302, vol. 33, Oxford University Press.
Lanier, L., "NKG2D receptor and its ligands in host defense," HHS Public Access Author Manuscript, Jun. 1, 2016, pp. 1-14, published in final edited form as: Cancer Immunol. Res., Jun. 2015, pp. 575-582, vol. 3, No. 6.
Laskowski, R. et al., "LigPlot+: Multiple Ligand-Protein Interaction Diagrams for Drug Discovery," J. Chem. Inf. Model., 2011, pp. 2778-2786, vol. 51, American Chemical Society.

(56) References Cited

OTHER PUBLICATIONS

Lawrence, M. et al., "Shape Complementarity at Protein/Protein Interfaces," J. Mol. Biol., Dec. 20, 1993, pp. 946-950, vol. 234, No. 4.

Lazear, E. et al., "Cowpox virus OMCP antagonizes NKG2D via an unexpected binding orientation," PLoS Pathogens, unpublished, under review 2014, pp. 1-28 with Figs. 1-5 and Supplementary Fig. 1.

Lazear, E. et al., "Crystal Structure of the Cowpox Virus-Encoded NKG2D Ligand OMCP," J. Virol., Jan. 2013, pp. 840-850, vol. 87, No. 2.

Lefkowitz, E. et al., "Poxvirus Bioinformatics Resource Center: a comprehensive Poxviridae informational and analytical resource," Nucl. Acids Res., 2005, pp. D311-D316, vol. 33, Oxford University Press.

Lenac, T. et al., "The herpesviral Fc receptor fcr-1 down-regulates the NKG2D ligands MULT-1 and H60," J. Exp. Med., Aug. 7, 2006, pp. 1843-1850, vol. 203, No. 8, The Rockefeller University Press.

Letourneau, S. et al., "IL-2/anti-IL-2 antibody complexes show strong biological activity by avoiding interaction with IL-2 receptor alpha subunit CD25," PNAS, Feb. 2, 2010, pp. 2171-2176, vol. 107, No. 5.

Levin, A. et al., "Exploiting a natural conformational switch to engineer an Interleukin-2 superkine," HHS Public Access Author Manuscript, available in PMC Oct. 26, 2012, pp. 1-12, published in final form as: Nature, 2012, pp. 529-533, vol. 484, No. 7395.

Li, P. et al., "Crystal Structure of the MHC class I homolog MIC-A, a gammadelta T Cell Ligand," Immunity, May 1999, pp. 577-584, vol. 10, Cell Press.

Li, P. et al., "Crystal Structures of RAE-1beta and Its Complex with the Activating Immunoreceptor NKG2D," Immunity, Jan. 2002, pp. 77-86, vol. 16, Cell Press.

Li, Y. et al., "Structural and biophysical insights into the role of CD4 and CD8 in T cell activation," Front. Immunol., Jul. 2013, pp. 1-11, vol. 4, No. 206.

Li, Y. et al., "Structural basis for recognition of cellular and viral ligands by NK cell receptors," Front. Immunol., Mar. 2014, pp. 1-20, vol. 5, No. 123.

Li. P. et al., "Complex structure of the activating immunoreceptor NKG2D and its MHC class I-like ligand MICA," Nat. Immunol., May 2001, pp. 443-451, vol. 2, No. 5, Nature Publishing Group.

Lisnic, V. et al., "Modulation of natural killer cell activity by viruses," Curr. Opin. Microbiol., 2010, pp. 530-539, vol. 13.

Liu, K. et al., "Janus kinases in interleukin-2-mediated signaling: JAK1 and JAK3 are differentially regulated by tyrosine phosphorylation," Curr. Biol., 1997, pp. 817-826, vol. 7.

Lodoen, M. et al., "NKG2D-mediated Natural Killer Cell Protection Against Cytomegalovirus Is Impaired by Viral gp40 Modulation of Retinoic Acid Early Inducible 1 Gene Molecules," J. Exp. Med., May 19, 2003, pp. 1245-1253, vol. 197, No. 10, The Rockefeller University Press.

Lodoen, M. et al., "The Cytomegalovirus m155 Gene Product Subverts Natural Killer Cell Antiviral Protection by Disruption of H60-NKG2D Interactions," J. Exp. Med., Oct. 18, 2004, pp. 1075-1081, vol. 200, No. 8, The Rockefeller University Press.

Rossi, A. et al., "Analysis of protein-ligand interactions by fluorescence polarization," Europe PMC Funders Group, Author Manuscript, available in PMC Sep. 3, 2011, published in final form as: Nat. Protoc., Mar. 2011, pp. 365-387, vol. 6, No. 3.

Ryu, M., et al., "Accumulation of cytolytic CD8+ T cells in B16-melanoma and proliferation of mature T cells in TIS21-knockout mice after T cell receptor stimulation," Exp. Cell Res., Oct. 1, 2014, pp. 209-221, vol. 327, No. 2, Elsevier, Inc.

Sallusto, F. et al., "Two subsets of memory T lymphocytes with distinct homing potentials and effector functions," Nature, Oct. 14, 1999, pp. 708-712, vol. 401, Macmillan Magazines Ltd.

Sauve, K. et al., "Localization in human interleukin 2 of the binding site to the alpha chain (p55) of the interleukin 2 receptor," PNAS, Jun. 1991, pp. 4636-4640, vol. 88.

Schubert, D. et al., "Self-reactive human CD4 T cell clones form unusual immunological synapses," J. Exp. Med., Feb. 6, 2012, pp. 335-352, vol. 209, No. 2, The Rockefeller University Press.

Sethi, D. et al., "A highly tilted binding mode by a self-reactive T cell receptor results in altered engagement of peptide and MHC," J. Exp. Med., 2011, pp. 91-102, vol. 208, No. 1, The Rockefeller University Press.

Shane, H. et al., "Every breath you take: the impact of environment on resident memory CD8 T cells in the lung," Frontiers Immunol., Jul. 2014, pp. 1-10, vol. 5, No. 320.

Siiman, O. et al., "Cell Surface Receptor—Antibody Association Constants and Enumeration of Receptor Sites for Monoclonal Antibodies," Cytometry, 2000, pp. 316-326, vol. 40, Wiley-Liss, Inc.

Sim, G. et al., "IL-2 therapy promotes suppressive ICOS+ Treg expansion in melanoma patients," J. Clin. Invest., Jan. 2014, pp. 99-110, vol. 124, No. 1.

Smyth, M. et al., "CD4+CD25+ T Regulatory Cells Suppress NK Cell-Mediated Immunotherapy of Cancer," J. Immunol., 2006, pp. 1582-1587, vol. 176.

Song H, et al., "Monkeypox Virus Infection of Rhesus Macaques Induces Massive Expansion of Natural Killer Cells but Suppresses Natural Killer Cell Functions," PLoS One, Oct. 2013, pp. 1-15, vol. 8, No. 10, e77804.

Spangler, J. et al., "Antibodies to Interleukin-2 Elicit Selective T Cell Subset Potentiation through Distinct Conformational Mechanisms," Immunity, May 19, 2015, pp. 815-825, vol. 42, Elsevier Inc.

Stemberger, C. et al., "A Single Naive CD8+ T Cell Precursor Can Develop into Diverse Effector and Memory Subsets," Immunity, Dec. 2007, pp. 985-997, vol. 27, Elsevier Inc.

Stern-Ginossar, N. et al., "Host Immune System Gene Targeting by a Viral miRNA," Science, Jul. 20, 2007, pp. 376-381, vol. 317, No. 5836.

Stewart, D. et al., "Occurrence and Role of Cis Peptide Bonds in Protein Structures," J. Mol. Biol., Jul. 5, 1990, pp. 253-260, vol. 214, No. 1, Academic Press Limited.

Strausberg, R., "Generation and initial analysis of more than 15,000 full-length human and mouse cDNA sequenes," PNAS, Dec. 24, 2002, pp. 16899-16903, vol. 99, No. 26, with GenBank AAH66254.1 supplement, Mar. 6, 2007, 2 pgs.

Strong, R. et al., "NKG2D and Related Immunoreceptors," Adv. Protein Chem., 2004, pp. 281-312, vol. 68.

Strong, R., "Asymmetric ligand recognition by the activating natural killer cell receptor NKG2D, a symmetric homodimer," Mol. Immunol., 2001, pp. 1029-1037, vol. 38, Elsevier Science Ltd.

Tam, S. et al., "Abciximab (ReoPro, Chimeric 7E3 Fab) Demonstrates Equivalent Affinity and Functional Blockade of Glycoprotein IIb/IIIa and alpha(v)beta(3) Integrins," Circulation, 1998, pp. 1085-1091, vol. 98.

Thomas, M. et al., "Down-regulation of NKG2D and NKp80 ligands by Kaposi's sarcoma-associated herpesvirus K5 protects against NK cell cytotoxicity," PNAS, Feb. 5, 2008, pp. 1656-1661, vol. 105, No. 5.

Tietje, A. et al., "MULT1E/mIL-12: a novel bifunctional protein for natural killer cell activation," Gene Therapy, 2014, pp. 468-475, vol. 21, Macmillan Publishers Limited.

Tomala, J. et al., "Chimera of IL-2 Linked to Light Chain of anti-IL-2 mAb Mimics IL-2/anti-IL-2 mAb Complexes Both Structurally and Functionally," ACS Chem. Biol., May 17, 2013, pp. 871-876, vol. 8, No. 5.

Trikha, M. et al., "CNTO 95, a fully human monoclonal antibody that inhibits alphav integrins, has antitumor and antiangiogenic activity in vivo," Int. J. Cancer, 2004, pp. 326-335, vol. 110, Wiley-Liss, Inc.

Tsao, P. et al., "Type-specific Sorting of G Protein-coupled Receptors after Endocytosis," J. Biol. Chem., Apr. 14, 2000, pp. 11130-11140, vol. 275, No. 15.

Tzeng, A. et al., "Antigen specificity can be irrelevant to immunocytokine efficacy and biodistribution," PNAS, Mar. 17, 2015, pp. 3320-3325, vol. 112, No. 11.

Ullrich, E. et al., "New prospects on the NKG2D/NKG2DL system for oncology," OncoImmunology, Oct. 2013, pp. e26097-1-e26097-9, vol. 2, No. 10, Taylor & Francis Group.

(56) References Cited

OTHER PUBLICATIONS

UniProtKB/Swiss-Prot Accession Q15116.3, Jan. 16, 2019; 7 pgs.
Vadstrup, K. et al., "Anti-NKG2D mAb: A New Treatment for Crohn's Disease," Int. J. Mol. Sci., 2017, pp. 1-18, vol. 18, No. 1997.
Wang, Y. et al., "Foxp3+ T Cells Inhibit Antitumor Immune Memory Modulated by mTOR Inhibition," Cancer Res., Feb. 26, 2014, pp. 2217-2228, vol. 74, No. 8.
Ward, J. et al., "HIV modulates the expression of ligands important in triggering natural killer cell cytotoxic responses on infected primary T-cell blasts," Blood, Aug. 15, 2007, pp. 1207-1214, vol. 110, No. 4.
Welte, S. et al., "Selective intracellular retention of virally induced NKG2D ligands by the human cytomegalovirus UL16 glycoprotein," Eur. J. Immunol., 2003, pp. 194-203, vol. 33, Wiley-VCH Verlag GmbH & Co. KGaA, Weinheim.
Wen, C. et al., "Hepatitis C Virus Infection Downregulates the Ligands of the Activating Receptor NKG2D," Cell. Mol. Immunol., Dec. 2008, pp. 475-478, vol. 5, No. 6.
Wu, X. et al., "Myosin-Reactive Autoantibodies in Rheumatic Carditis and Normal Fetus," Clinical Immunology and Immunopathology, May 1998, pp. 184-192, vol. 87, No. 2, with GenBank AAD56260.1 supplement, Jul. 26, 2016, 2 pgs.
Wucherpfennig, K. et al., "Structural Alterations in peptide-MHC Recognition by Self-reactive T cell Receptors," NIH Public Access Author Manuscript, available in PMC Dec. 1, 2010, pp. 1-12, published in final edited form as: Curr. Opin. Immunol., Dec. 2009, pp. 590-595, vol. 21, No. 6.
Yamane, B. et al., "The development of antibody-based immunotherapy with (EMD-273063) Hu14.18-IL2 in melanoma and neuroblastoma," NIH Public Access Author Manuscript, available in PMC Oct. 10, 2010, pp. 1-15, published in final edited form as: Expert Opin. Investig. Drugs, Jul. 2009, pp. 991-1000, vol. 18, No. 7.
Ye, L. et al., "Tumor necrosis therapy antibody interleukin-2 fusion protein elicits prolonged and targeted antitumor effects in vivo," Appl. Microbiol. Biotechnol., May 2014, pp. 4053-4061, vol. 98, No. 9, Springer-Verlag Berlin, Heidelberg.
Yin, Y. et al., "Structural basis for self-recognition by autoimmune T-cell receptors," Immunol. Rev., Nov. 2012, pp. 32-48, vol. 250, No. 1, John Wiley & Sons A/S, Singapore.
Zafirova, B. et al., "Regulation of immune cell function and differentiation by the NKG2D receptor," Cell. Mol. Life Sci., 2011, pp. 3519-3529, vol. 68, Springer.
Zhao, L., et al., "5-Fluorouracil and Interleukin-2 Immunochemotherapy Enhances Immunogenicity of Non-Small Cell Lung Cancer A549 Cells through Upregulation of NKG2D Ligands," Asian Pac. J. Cancer Prev., 2014, pp. 4039-4044, vol. 15, No. 9.
Zhou, Y-J., et al., "Distinct tyrosine phosphorylation sites in JAK3 kinase domain positively and negatively regulate its enzymatic activity," PNAS, Dec. 1997, pp. 13850-13855, vol. 94.
Zhu, Z., et al., "High-Avidity T Cells Are Preferentially Tolerized in the Tumor Microenvironment," Cancer Res., Jan. 5, 2013, pp. 595-604, vol. 73, No. 2.
Zou, W. et al., "DAP12 Couples c-Fms Activation to the Osteoclast Cytoskeleton by Recruitment of Syk," Mol. Cell, Aug. 8, 2008, pp. 422-431, vol. 31, Elsevier Inc.
Australian Application No. 2017213659, Australian Examination Report No. 1 dated Mar. 30, 2023.
UK Application No. GB2112934.1, Examination Report under section 18(3) dated Apr. 11, 2023.
Gainey, M. et al., "Viral MHC class I inhibition evades CD8+ T-cell effector responses in vivo but not CD8+ T-cell priming," PNAS, Oct. 29, 2012, pp. E3260-3267, vol. 109.
Gately, M. et al., "Role of asialo-GM1-positive lymphoid cells in mediating the toxic effects of recombinant IL-2 in mice," J. Immunol., Jul. 1, 1988, pp. 189-200, vol. 141, No. 1.
GenBank accession No. 4FFE_X, dated Jan. 9, 2013, 2 pgs.
GenBank accession No. 4FFE_Y, dated Jan. 9, 2013, 2 pgs.
GenBank accession No. 4FFE_Z, dated Jan. 9, 2013, 2 pgs.
GenBank accession No. AAA59140.1, dated Jan. 6, 1995, 2 pgs.
GenBank accession No. AAA68969.1, dated Jun. 29, 1995, 2 pgs.
GenBank accession No. AAC23838.1, dated Jun. 8, 2000, 2 pgs.
GenBank accession No. AAH70338.1, dated Mar. 6, 2007, 2 pgs.
GenBank accession No. AAI00962.1, dated Oct. 4, 2006, 2 pgs.
GenBank accession No. AAI00963.1, dated Oct. 4, 2006, 2 pgs.
GenBank accession No. AAI16874.1, dated Jun. 29, 2006, 2 pgs.
GenBank accession No. AAP13470.1, dated Apr. 23, 2003; 1 pg.
GenBank accession No. AAQ10670.1, dated Jul. 7, 2005, 2 pgs.
GenBank accession No. AAQ10671.1, dated Jul. 7, 2005, 2 pgs.
GenBank accession No. AAV35056.1, dated Oct. 30, 2004, 2 pgs.
GenBank accession No. AAY97396, dated Sep. 28, 2005, 2 pgs.
GenBank accession No. ABK41601.1, dated Nov. 12, 2006, 2 pgs.
GenBank accession No. BC070338.1, dated Mar. 6, 2007, 3 pgs.
GenBank accession No. CAG46771.1, dated Oct. 16, 2008, 2 pgs.
GenBank accession No. CAG46777.1, dated Oct. 16, 2008, 2 pgs.
GenBank accession No. CR541973.1, dated Oct. 16, 2008, 2 pgs.
GenBank accession No. CR541980.1, dated Oct. 16, 2008, 2 pgs.
GenBank accession No. CR542001.1, dated Jul. 26, 2016, 2 pgs.
GenBank accession No. CR542007.1, dated Jul. 26, 2016, 2 pgs.
GenBank accession No. EDM01295.1, dated Jul. 26, 2016, 2 pgs.
GenBank accession No. ERE88380.1, dated Mar. 22, 2015, 2 pgs.
GenBank accession No. KJ891469.1, dated Mar. 19, 2015, 2 pgs.
GenBank accession No. KJ897054.1, dated Mar. 19, 2015, 2 pgs.
GenBank accession No. KR710147.1, dated Jun. 1, 2015, 2 pgs.
GenBank accession No. M22005.1, dated Jan. 6, 1995, 2 pgs.
GenBank accession No. NM_000585.4, dated Oct. 3, 2017, 2 pgs.
GenBank accession No. NM_001297562.1, dated Jan. 6, 2019; 5 pgs.
GenBank accession No. NM_003326.4, dated Oct. 21, 2018; 5 pgs.
GenBank accession No. NM_003811.3, dated Jun. 11, 2018; 4 pgs.
GenBank accession No. NM_172175.2, dated Oct. 3, 2017, 2 pgs.
GenBank accession No. NP_001020388.1, dated Mar. 4, 2017; 1 pg.
GenBank accession No. NP_001075454.1, dated Sep. 16, 2018; 2 pgs.
GenBank accession No. NP_001192644.1, dated May 30, 2018; 2 pgs.
GenBank accession No. NP_001284491.1, dated Jan. 6, 2019; 3 pgs.
GenBank accession No. NP_001306831.1, May 14, 2018; 2 pgs.
GenBank accession No. NP_003317.1, Jan. 6, 2019; 3 pgs.
GenBank accession No. NP_003802.1, Nov. 22, 2018; 3 pgs.
GenBank accession No. NP_033430.1, Jan. 20, 2019; 3 pgs.
GenBank accession No. NP_033478.1, Oct. 28, 2018; 3 pgs.
GenBank accession No. NP_446004.1, Jan. 19, 2019; 3 pgs.
GenBank accession No. NP_619807.1, dated Jan. 28, 2016, 2 pgs.
GenBank accession No. NP_852049.1, May 27, 2018; 3 pgs.
GenBank accession No. NP_999026.1, dated Oct. 1, 2017, 2 pgs.
GenBank accession No. XM_011509964.2, Mar. 26, 2018; 3 pgs.
GenBank accession No. XM_017002228.1, Mar. 26, 2018; 3 pgs.
GenBank accession No. XM_017002229.1, Mar. 26, 2018; 4 pgs.
GenBank accession No. XM_017002230.1, Mar. 26, 2018; 3 pgs.
GenBank accession No. XP_003480863.1, May 13, 2017; 2 pgs.
GenBank accession No. XP_003639215.1, Sep. 5, 2017; 2 pgs.
GenBank accession No. XP_005633029.1, Sep. 17, 2015; 1 pg.
GenBank accession No. XP_007610839.1, May 27, 2016; 2 pgs.
GenBank accession No. XP_007627369.1, May 27, 2016; 2 pgs.
GenBank accession No. XP_008251123.1, Jun. 13, 2014; 2 pgs.
GenBank accession No. XP_011508266.2, Mar. 26, 2018; 1 pg.
GenBank accession No. XP_012042680.1, Feb. 6, 2019; 2 pgs.
GenBank accession No. XP_013820683.1, Sep. 10, 2015; 2 pgs.
GenBank accession No. XP_013825644.1, Sep. 10, 2015; 2 pgs.
GenBank accession No. XP_014951136.1, Dec. 17, 2015; 2 pgs.
GenBank accession No. XP_016857717.1, Mar. 26, 2018; 1 pg.
GenBank accession No. XP_016857718.1, Mar. 26, 2018; 1 pg.
GenBank accession No. XP_016857719.1, Mar. 26, 2018; 1 pg.
GenBank accession No. XP_430147.2, May 17, 2018; 1 pg.
GenBank accession No. XR_001737393.1, Jun. 6, 2016; 4 pgs.
GenBank accession No. XR_001737394.1, Jun. 6, 2016; 4 pgs.
GenBank accession No. XR_001737395.1, Jun. 6, 2016; 4 pgs.
GenBank accession No. XR_001737396.1, Jun. 6, 2016; 2 pgs.
GenBank No. 148667521 (EDK99937.1), dated Jul. 26, 2016, 3 pgs.
GenBank No. 149049263 (EDM01717.1), dated Jul. 26, 2016, 2 pgs.

(56) References Cited

OTHER PUBLICATIONS

GenBank No. 21902299, dated Jul. 18, 2002, 2 pgs.
GenBank No. 30749494, dated Dec. 27, 2012, 3 pgs.
GenBank No. 332232684 (XP_003265533.1), dated May 13, 2015, 2 pgs.
GenBank No. 348569092 (XP_003470332.2), dated Jul. 14, 2015, 2 pgs.
GenBank No. 355785888 (EHH66071.1), dated Mar. 17, 2015, 2 pgs.
GenBank No. 380848799 (NP_001244177.1), dated Sep. 7, 2014, 2 pgs.
GenBank No. 410963826 (XP_003988460.2), dated Dec. 29, 2016, 2 pgs.
GenBank No. 505834608 (XP_004611478.1), dated May 20, 201, 2 pgs.
GenBank No. 507978716 (XP_004693215.1), dated Jun. 10, 2015, 2 pgs.
GenBank No. 512868733 (XP_004891778.1, dated Jun. 18, 2013, 2 pgs.
GenBank No. 532053033 (XP_005369262.1), dated Aug. 7, 2015, 2 pgs.
GenBank No. 532114387 (XP_005341860.1), dated Aug. 21, 2013, 2 pgs.
GenBank No. 537136230 (ERE66429.1), dated Mar. 22, 2015, 2 pgs.
GenBank No. 57113989 (NP_001009059.1), dated Oct. 1, 2017, 2 pgs.
GenBank No. 589967905 (XP_006996451.1), dated Mar. 21, 2016, 2 pgs.
GenBank No. 635063485 (XP_007965810.1), dated May 14, 2014, 2 pgs.
Germain, C. et al., "Redirecting NK cells mediated tumor cell lysis by a new recombinant bifunctional protein," Protein Eng. Des. Sel., 2008, pp. 665-672, vol. 21, No. 11, Oxford University Press.
Ghasemi, R. et al., "Selective targeting of IL-2 to NKG2D bearing cells for improved immunotherapy," Nat. Commun., 2016, pp. 1-15, vol. 7, No. 12878.
Ghiringhelli, F. et al., "The role of regulatory T cells in the control of natural killer cells: relevance during tumor progression," Immunol. Rev., 2006, pp. 229-238, vol. 214, Blackwell Munksgaard, Singapore.
Gilfillan, S. et al., "NKG2D recruits two distinct adapters to trigger NK cell activation and costimulation," Nature Immunol., Dec. 2002, pp. 1150-1155, vol. 3, No. 12, Nature Publishing Group.
Giuliani, E. et al., "Release of Soluble Ligands for the Activating NKG2D Receptor: One More Immune Evasion Strategy Evolved by HIV-1?," Current Drug Targets, Jan. 2016, pp. 54-64, vol. 17, No. 1, Bentham Science Publishers.
Glaser, F. et al., "ConSurf: Identification of Functional Regions in Proteins by Surface-Mapping of Phylogenetic Information," Bioinformatics, 2003, pp. 163-164, vol. 19, No. 1, Oxford University Press.
Glasner, A. et al., "Recognition and Prevention of Tumor Metastasis by the NK Receptor NKp46/NCR1," J. Immunol., 2012, pp. 2509-2515, vol. 188, The American Association of Immunologists, Inc.
Gorelik, E. et al., "Susceptibility of Various Strains of Mice to Urethan-Induced Lung Tumors and Depressed Natural Killer Cell Activity," J. Natl. Cancer Inst., Dec. 1981, pp. 1317-1322, vol. 67, No. 6.
Graham, D. et al., "Vav1 Controls DAP10-Mediated Natural Cytotoxicity by Regulating Actin and Microtubule Dynamics," J. Immunol., 2006, pp. 2349-2355, vol. 177, The American Association of Immunologists, Inc.
Graham, J. et al., "Regulatory T Cells Shape the Resident Memory T Cell Response to Virus Infection in the Tissues," J. Immunol., 2014, pp. 683-690, vol. 192, The American Association of Immunologists, Inc.

Adams, E. et al., "The Adaptable Major Histocompatibility Complex (MHC) Fold: Structure and Function of Nonclassical and MHC Class I-Like Molecules," Annu. Rev. Immunol., 2013, p. 529-561, vol. 31.
Adams, J. et al., "T cell receptor signaling is limited by docking geometry to peptide—Major Histocompatibility Complex," NIH Public Access, Author Manuscript, available in PMC May 23, 2013, pp. 1-22, published in final edited form as: Immunity, Nov. 23, 2011, pp. 681-693, vol. 35, No. 5.
Adams, P. et al., "PHENIX: building new software for automated crystallographic structure determination," Acta Crystallographica Section D Biological Crystallography, 2002, pp. 1948-1954, vol. D58, International Union of Crystallography, Denmark.
Altschul, S. et al., "Basic Local Alignment Search Tool," J. Mol. Biol., 1990, pp. 403-410, vol. 215, Academic Press Limited.
Altschul, S. et al., "Gapped BLAST and PSI-BLAST: a new generation of protein database search programs," Nucleic Acids Res., 1997, pp. 3389-3402, vol. 25, No. 17, Oxford University Press.
Alzhanova, D. et al., "Cowpox Virus Inhibits the Transporter Associated with Antigen Processing to Evade T Cell Recognition," Cell Host Microbe, Nov. 19, 2009, pp. 433-445, vol. 6, with Supplemental Data, 12 pgs., Elsevier Inc.
Anichini, A., et al., "Tumor-Reactive CD8+ Early Effector T Cells Identified at Tumor Site in Primary and Metastatic Melanoma," Cancer Res., Nov. 1, 2010, pp. 8378-8387, vol. 70, No. 21.
Araki, K., et al., "mTOR regulates memory CD8 T cell differentiation," NIH Public Access, Author Manuscript, available in PMC Jan. 2, 2010, pp. 1-13, published in final edited form as Nature, Jul. 2, 2009, pp. 108-112, vol. 460, No. 7251.
Ashkenazy, H. et al., "ConSurf 2010: calculating evolutionary conservation in sequence and structure of proteins and nucleic acids," Nucl. Acids Res., 2010, pp. W529-W533, vol. 38, Oxford University Press.
Atkins, M. et al., "High-Dose Recombinant Interleukin 2 Therapy for Patients With Metastatic Melanoma: Analysis of 270 Patients Treated Between 1985 and 1993," J. Clin. Oncol., Jul. 1999, pp. 2105-2116, vol. 17, No. 7.
Atomic Coordinates accession code 4PDC Protein Data Bank, Research Collaboratory for Structural Bioinformatics, Apr. 17, 2014, 10 pgs.
Bauman, Y. et al., "An Identical miRNA of the Human JC and BK Polyoma Viruses Targets the Stress-Induced Ligand ULBP3 to Escape Immune Elimination," Cell Host Microbe, Feb. 17, 2011, pp. 93-102, vol. 9, Elsevier Inc.
Becker, J. et al., "T Cell-mediated Eradication of Murine Metastatic Melanoma Induced by Targeted Interleukin 2 Therapy," J. Exp. Med., May 1996, pp. 2361-2366, vol. 183, The Rockefeller University Press.
Biolegend, "APC anti-human CD314 (NKG2D) Antibody," Nov. 30, 2012, 6 pgs., Version 1.
Boyman, O. et al., "Selective Stimulation of T Cell Subsets With Antibody-Cytokine Immune Complexes," Science, Mar. 31, 2006, pp. 1924-1927, vol. 311, No. 5769.
Boyman, O. et al., "Selectively Expanding Subsets of T Cells in Mice by Injection of Interleukin-2/Antibody Complexes: Implications for Transplantation Tolerance," Transplantation Proceedings, May 2012, pp. 1032-1034, vol. 44, No. 4, Elsevier Inc.
Bui, J. et al., "Comparative Analysis of Regulatory and Effector T Cells in Progressively Growing versus Rejecting Tumors of Similar Origins," Cancer Res., Jul. 15, 2006, pp. 7301-7309, vol. 66, No. 14.
Byun, M. et al., "Cowpox Virus Exploits the Endoplasmic Reticulum Retention Pathway to Inhibit MHC Class I Transport to the Cell Surface," Cell Host Microbe, Nov. 2007, pp. 306-315, vol. 2, Elsevier Inc.
Byun, M. et al., "Two mechanistically distinct immune evasion proteins of cowpox virus combine to avoid antiviral CD8 T cells," NIH Public Access, Author Manuscript, available in PMC May 19, 2010, pp. 1-20, published in final form as: Cell Host Microbe, Nov. 19, 2009, pp. 422-432, vol. 6, No. 5.

(56) References Cited

OTHER PUBLICATIONS

Campbell, J. et al., "Cutting Edge: FcR-Like 5 on Innate B Cells Is Targeted by a Poxvirus MHC Class I-Like Immunoevasin," J. Immunol., 2010, pp. 28-32, vol. 185, The American Association of Immunologists, Inc.
Campbell, J. et al., "Zoonotic orthopoxviruses encode a high-affinity antagonist of NKG2D," JEM, Jun. 11, 2007, pp. 1311-1317, vol. 204, No. 6, The Rockefeller University Press.
Carayannopoulos, L. et al., "Ligands for murine NKG2D display heterogeneous binding behavior," Eur. J. Immunol., 2002, pp. 597-605, vol. 32, Wiley-VCH Verlag, Germany.
Carmenate, T. et al., "Human IL-2 Mutein with Higher Antitumor Efficacy Than Wild Type IL-2," J. Immunol., 2013, pp. 6230-6238, vol. 190, The American Association of Immunologists, Inc.
Celniker, G. et al., "ConSurf: Using Evolutionary Data to Raise Testable Hypotheses about Protein Function," Isr. J. Chem., 2013, pp. 199-206, vol. 53, Wiley-VCH Verlag GmbH & Co. KGaA, Germany.
Cerboni, C. et al., "Human immunodeficiency virus 1 Nef protein downmodulates the ligands of the activating receptor NKG2D and inhibits natural killer cell-mediated cytotoxicity," J. Gen. Virol., 2007, pp. 242-250, vol. 88, SGM, Great Britain.
Chalupny, N. et al., "Down-regulation of the NKG2D ligand MICA by the human cytomegalovirus glycoprotein UL142," Biochem. Biophys. Res. Commun., Jul. 21, 2006, pp. 175-181, vol. 346, No. 1, Elsevier Inc.
Chang, S. et al., "Unique pulmonary antigen presentation may call for an alternative approach toward lung cancer immunotherapy," Oncoimmunology, Mar. 2013, pp. pp. e23563-1 to e23563-5, vol. 2, No. 3, Landes Bioscience.
Chen, V. et al., "MolProbity: all-atom structure validation for macromolecular crystallography," Acta Crystallogr. D Biol. Crystallogr., 2010, p. 12-21, vol. D66.
Copeland, R. et al., "Drug-target residence time and its implications for lead optimization," Nat. Rev. Drug Discov., Sep. 2006, pp. 730-739, vol. 5, with Corrigendum, 1 pg., Nature Publishing Group.
Correia, D. et al., "Differentiation of human peripheral blood Vdelta1+ T cells expressing the natural cytotoxicity receptor NKp30 for recognition of lymphoid leukemia cells," Blood, 2011, pp. 992-1001, vol. 118, No. 4.
Cosman, D. et al., "ULBPs, Novel MHC Class I-Related Molecules, Bind to CMV Glycoprotein UL16 and Stimulate NK Cytotoxicity through the NKG2D Receptor," Immunity, Feb. 2001, pp. 123-133, vol. 14, Cell Press.
Coudert, J. et al., "The role of the NKG2D receptor for tumor immunity," Seminars in Cancer Biol., 2006, pp. 333-343, vol. 16.
Craveur, P. et al., "Cis-trans isomerization of omega dihedrals in proteins," Amino Acids, 2013, pp. 279-289, vol. 45, Springer.
Dandamudi, U. et al., "A Phase II Study of Bevacizumab and High-dose Interleukin-2 in Patients With Metastatic Renal Cell Carcinoma: A Cytokine Working Group (CWG) Study," J. Immunother., Nov./Dec. 2013, pp. 490-495, vol. 36, No. 9.
Dasgupta, A. et al., "Cowpox Virus Evades CTL Recognition and Inhibits the Intracellular Transport of MHC Class I Molecules," J. Immunol., 2007, 1654-1661, vol. 178, The American Association of Immunologists, Inc.
De Goer De Herve, M. et al., "FoxP3(+) regulatory CD4 T cells control the generation of functional CD8 memory," Nature Commun., 2012, pp. 1-10, vol. 3, No. 986, Macmillan Publishers Limited.
Debbia, M. et al., "Measurement of anti-D intrinsic affinity with unlabeled antibodies," Transfusion, Mar. 2004, pp. 399-406, vol. 44, Wiley-Blackwell.
Deng, L. et al., "Structural basis for recognition of MHC and MHC-like ligands by natural killer cell receptors," NIH Public Access Author Manuscript, available in PMC Aug. 25, 2008, pp. 1-15, published in final edited form as: Semin. Immunol., Jun. 2006, pp. 159-166, vol. 18, No. 3.
Deng, W. et al., "A shed NKG2D ligand that promotes natural killer cell activation and tumor rejection," Science, Apr. 3, 2015, pp. 136-139, vol. 348, No. 6230.
Dokun, A. et al., "Specific and nonspecific NK cell activation during virus infection," Nat. Immunol., Oct. 2001, pp. 951-956, vol. 2, No. 10, Nature Publishing Group.
Draghi, M. et al., "NKp46 and NKG2D Recognition of Infected Dendritic Cells Is Necessary for NK Cell Activation in the Human Response to Influenza Infection," J. Immunol., 2007, pp. 2688-2698, vol. 178.
Drake, A.et al., "Characterizing high-affinity antigen/antibody complexes by kinetic- and equilibrium-based methods," Anal. Biochem., 2004, pp. 35-43, vol. 328, Elsevier Inc.
Eagle, R. et al., "Promiscuity and the single receptor: NKG2D," Nat. Rev. Immunol., Sep. 2007, pp. 737-744, vol. 7, Nature Publishing Group.
Emsley, P. et al., "Coot: model-building tools for molecular graphics," Acta Crystallogr. D Biol. Crystallogr., 2004, pp. 2126-2132, vol. D60, International Union of Crystallography, Denmark.
Extended European Search Report dated Mar. 2, 2018 from related European Patent Application No. 15870897.4; 7 pgs.
Extended European Search Report dated Sep. 23, 2019 from related European Patent Application No. 17748340.1; 9 pgs.
Fang M. et al., "A role for NKG2D in NK Cell-Mediated Resistance to Poxvirus Disease," PLoS Pathog., Feb. 2008, pp. 0001-0011, vol. 4, No. 2, e30.
Finton ,K. et al., "Structural insights into activation of antiviral NK cell responses," NIH Public Access Author Manuscript, available in PMC Nov. 1, 2013, pp. 1-29, published in final edited form as: Immunol. Rev., Nov. 2012, pp. 239-257, vol. 250, No. 1.
French, A. et al., "DAP12 Signaling Directly Augments Proproliferative Cytokine Stimulation of NK Cells during Viral Infections," J. Immunol., 2006, pp. 4981-4990, vol. 177, American Association of Immunologists, Inc.
Frese-Schaper, M. et al., "Influence of natural killer cells and perforin-mediated cytolysis on the development of chemically induced lung cancer in A/J mice," Cancer Immunol. Immunother., 2014, pp. 571-580, vol. 63, Springer.
GB2112934.1 Examination Report under Section 18(3) dated Jun. 22, 2023, 5 pgs.
GB2112934.1 Examination Report under Section 18(3) dated Jul. 21, 2023, 5 pgs.
Canadian Application No. 3,011,374 Jul. 19, 2018; Office Action dated Feb. 15, 2023; 3 pages.
European Application No. 17748340.1 filed Sep. 3, 2018; Examination Report dated Feb. 17, 2023; 6 pages.
Kwong, et al., Generation, affinity maturation, and characterization of a human anti-human NKG2D monoclonal antibody with dual antagonistic and agonistic activity, J. Mol Bio., Dec. 31, 2008, vol. 384(5), 25 pages.

\* cited by examiner

OMCP-mutIL-2, wild-type IL-2, mutIL-2, Saline

OMCP-mutIL-2, wild-type IL-2, mutIL-2, Saline 750,000IUe wtIL-2

--- +rabbit IgG
— +anti-asialoGM

OMCP-mutIL-2, wtIL-2, mutIL-2

Saline, wtIL-2, mutIL-2, OMCP-mutIL-2,

Saline, wtIL-2, mutIL-2, OMCP-mutIL-2, saline, wtIL-2, mutIL-2, OMCP-mutIL-2

1. PD1 ligand + cytokine

2. PDL1/PDL2 peptide + cytokine 3. pegylation and/or bi-functional
PEG linker
+/- PEG 4. engineered glycans N-glycan 5. linker length/composition ... etc 6. PD1 antibody + cytokine Fab specific for PD1

7. alternate PD1 ligands via structure- or selection-
based mutagenesis 8. mutant cytokines

COMPOSITIONS AND METHODS FOR TARGETED CYTOKINE DELIVERY

CROSS REFERENCE TO RELATED APPLICATIONS

This application claims the benefit of U.S. application Ser. No. 16/075,069, filed Aug. 2, 2018, PCT application number PCT/US2017/016688, filed Feb. 6, 2017, U.S. Provisional Application No. 62/292,046, filed Feb. 5, 2016, U.S. Provisional Application No. 62/342,630, filed May 27, 2016, U.S. Provisional Application No. 62/350,056, filed Jun. 14, 2016, and U.S. Provisional Application No. 62/419,146, filed Nov. 8, 2016, each of the disclosures of which is hereby incorporated by reference in its entirety.

GOVERNMENTAL RIGHTS

This invention was made with government support under AI073552, AI019687, AI109948, HHSN272201200026C and HL113931 awarded by the National Institutes of Health. The government has certain rights in the invention.

FIELD OF THE INVENTION

The present disclosure encompasses compositions and methods for targeted delivery of cytokines and for recruiting immune cells to target cells. Through specific delivery of cytokines and other agents, the compositions disclosed herein may improve immunotherapy and in some instances, limit side effects associated with immunotherapy.

BACKGROUND OF THE INVENTION

Systemic administration of high dose interleukin 2 (IL2) is one of the most potent forms of immunotherapy and is currently approved by the FDA for treatment of several malignancies. Efficacy of this treatment depends on activating cytotoxic lymphocytes (CTLs) such as natural killer cells (NK) and CD8$^+$ T lymphocytes (CD8$^+$ CTLs). Clinical trials have demonstrated approximately 15% partial or complete tumor responses, with up to 5% of patients having a durable long-lasting response resembling a cure. Despite these encouraging results in a minority of patients, most do not achieve a benefit or stop IL2 therapy prematurely due to complications such as blood pressure changes and pulmonary or systemic capillary leak. It is thought that the direct action of IL2 on vascular endothelium contributes to the majority of these side effects. The efficacy of IL2 is also limited by preferential activation of CD4$^+$Foxp3+ regulatory T cells ($T_{regs}$), which decrease the tumor immune response. For these reasons treatment with high-dose IL2 has fallen out of favor clinically.

Side effects and deceased efficacy of IL2 therapy occur due to the high affinity trimeric αβγ IL2 receptor (IL2R), which is expressed by vascular endothelial cells and $T_{regs}$ at baseline. Thus CD4$^+$Foxp3$^+$ $T_{regs}$ and vascular endothelium are activated at much lower doses of IL2 than NK cells, which express the lower affinity βγ chains of the IL2R at rest. NK cells do express the high affinity α chain of IL2R after activation and depend on this trimeric receptor for peak cytolytic capacity. Mutant forms of IL2 with decreased affinity for IL2Rα have been described and offer a more favorable side effect profile. However, they also result in lower efficacy and decreased therapeutic potential due to decreased CTL activation. Therefore, there is a need in the art for a form of IL2 that could preferentially bind to and activate CTLs without activating $T_{regs}$ and endothelial cells. Such an IL2 derivative might overcome such clinical barriers and result in more efficacious immunotherapy with fewer side effects.

SUMMARY OF THE INVENTION

In an aspect, the disclosure provides a composition comprising a cytokine linked to a NKG2D ligand. In one particular embodiment, the NKG2D ligand is an anti-NKG2D antibody.

In another aspect, the disclosure provides a composition comprising a ligand to the NKG2D receptor and a targeting molecule. The targeting molecule directs the composition to a binding partner on a target cell and recruits an immune cell upon the ligand specifically binding to the NKG2D receptor on the immune cell. In one instance, the ligand is orthopoxvirus major histocompatibility complex class I-like protein (OMCP). The targeting molecule can be linked to the ligand or unlinked and presented together in a single composition with the ligand or administered concurrently in separate compositions.

In another aspect, the disclosure provides a method to deliver a cytokine to a target cell comprising contacting a target cell with a composition comprising a cytokine linked to a NKG2D ligand. In still another aspect, the disclosure provides a method to activate immune cells comprising contacting an immune cell with a composition comprising a proinflammatory cytokine linked to a NKG2D ligand. The ligand specifically binds to a receptor on the immune cell thereby activating the cell.

In still another aspect, the disclosure provides a method to recruit and activate immune cells at a particular target cell comprising providing a composition comprising a ligand to an NKG2D receptor and a targeting molecule.

In still yet another aspect, the disclosure provides a method to treat a tumor comprising identifying a subject with a tumor and administering to the subject a therapeutically effective amount of a composition comprising a proinflammatory cytokine linked to a NKG2D ligand.

In a different aspect, the disclosure provides a method to treat a viral infection comprising administering to the subject a therapeutically effective amount of a composition comprising a proinflammatory cytokine linked to a NKG2D ligand. In other aspects, the disclosure provides a chimeric peptide comprising a cytokine peptide and a NKG2D ligand peptide.

In certain aspects, the disclosure provides a chimeric peptide comprising a cytokine peptide and an anti-NKG2D antibody.

In another aspect, the disclosure provides a composition comprising a cytokine linked to a programmed cell death protein 1 (PD1) ligand. In one particular embodiment, the PD1 ligand is programmed cell death ligand 1 (PDL1). In another particular embodiment, the PD1 ligand is programmed cell death ligand 2 (PDL2).

In another aspect, the disclosure provides a method to deliver a cytokine to a target cell comprising contacting a target cell with a composition comprising a cytokine linked to a PD1 ligand. In still another aspect, the disclosure provides a method to activate immune cells comprising contacting an immune cell with a composition comprising a proinflammatory cytokine linked to a PD1 ligand. The ligand specifically binds to a receptor on the immune cell thereby activating the cell.

In still yet another aspect, the disclosure provides a method to treat a tumor comprising identifying a subject with a tumor and administering to the subject a therapeutically effective amount of a composition comprising a proinflammatory cytokine linked to a PD1 ligand.

In a different aspect, the disclosure provides a method to treat a viral infection comprising administering to the subject a therapeutically effective amount of a composition comprising a proinflammatory cytokine linked to a PD1 ligand. In other aspects, the disclosure provides a chimeric peptide comprising a cytokine peptide and a PD1 ligand peptide.

In certain aspects, the disclosure provides a chimeric peptide comprising a cytokine peptide and an anti-PD1 antibody.

In another different aspect, the disclosure provides a nucleic acid molecule comprising a sequence encoding a chimeric peptide of the disclosure.

In yet another different aspect, the disclosure provides a pharmaceutical composition comprising a chimeric peptide of the disclosure.

In still yet another different aspect, the disclosure provides a method of treating a subject diagnosed with cancer comprising administering to the subject a pharmaceutical composition of the disclosure.

In another aspect is a method to treat a tumor by (1) identifying a subject with a tumor; and (2) administering to the subject a therapeutically effective amount of a combination therapy described herein.

In another aspect is a method for treating a viral infection, by administering to the subject a therapeutically effective amount of a combination therapy described herein.

In some embodiments of the various methods provided herein, a pharmaceutical composition of the disclosure is administered in combination with a PD-1 inhibitor. In certain embodiments, the PD-1 inhibitor is an anti-PD-1 antibody. In some embodiments, the anti-PD-1 antibody is an antagonistic antibody. In some embodiments, the PD-1 inhibitor is selected from the group consisting of nivolumab, pembrolizumab, pidilizumab, REGN2810, PDR 001, and MEDI0680.

In other embodiments, of the various methods provided herein, a pharmaceutical composition of the disclosure is administered in combination with a PD-L1 inhibitor. In certain embodiments, the PD-L1 inhibitor is an anti-PD-L1 antibody. In some embodiments, the anti-PD-L1 antibody is an antagonistic antibody. In some embodiments, the PD-L1 inhibitor is selected from the group consisting of durvalumab, avelumab, atezolizumab, or BMS-936559, STI-A1010, STI-A1011, STI-A1012, STI-A1013, STI-A1014, and STI-A1015.

BRIEF DESCRIPTION OF THE FIGURES

The application file contains at least one drawing executed in color. Copies of this patent application publication with color drawing(s) will be provided by the Office upon request and payment of the necessary fee.

FIG. 1A, FIG. 1B, FIG. 1C, FIG. 1D, FIG. 1E and FIG. 1F depict a diagram, immunoblot and graphs showing the generation and in vitro evaluation of OMCP-mutIL2. (FIG. 1A) Schematic structure of OMCP-mutIL2. (FIG. 1B) Molecular weight of OMCP-mutIL2 compared to mutIL2 and wild-type IL2. IL2, mutIL2, and OMCP-mutIL2 were produced in mammalian cells and have higher molecular weights due to glycosylation. The lower migrating band for mutIL2 corresponds to unglycosylated protein, likely due to lysis of the producing cells. Based on differences in molecular weight all cytokines and construct were administered on a molar basis with 1 μl of 4.4 μM solution defined as 1000 IU equivalents (IUe) herein. This effectively allows for equimolar comparison between IL2, mutIL2 and OMCP-mutIL2 despite different molecular weights. (FIG. 1C, FIG. 1D) In vitro activation of NJ lymphocyte subsets after 36 hours of culture in 100 IUe of cytokines or OMCP-mutIL2 construct. (FIG. 1E, FIG. 1F) Proliferation of B6 lymphocyte subsets after 5-day culture in 1000 IUe/ml of cytokines or OMCP-mutIL2 construct. Graphs representative of 3-6 replicates per condition. black=saline; blue=wtIL2, red=OMCP-mutIL2, green=mutIL2.

FIG. 2A, FIG. 2B, FIG. 2C, FIG. 2D, FIG. 2E, FIG. 2F, FIG. 2G, FIG. 2H, FIG. 2I, FIG. 2J, FIG. 2K, FIG. 2L, FIG. 2M, FIG. 2N and FIG. 2O depict graphs and images showing in vivo dosing of IL2 and IL2 constructs. Animal mortality (FIG. 2A) and morbidity assessed by weight loss (FIG. 2B) accumulation of ascites and pleural fluid (representative syringe-FIG. 2C; average from all mice in the group-FIG. 2D) and (FIG. 2E) organ inflammation after administration of wtIL2. Animal mortality (FIG. 2F, FIG. 2H, FIG. 2J) and morbidity as assessed by weight loss (FIG. 2G, FIG. 2I, FIG. 2K) after administration of high dose wtIL2 (FIG. 2F, FIG. 2G), OMCP-mutIL2 (FIG. 2H, FIG. 2I) and mutIL2 (FIG. 2J, FIG. 2K) in anti-AsialoGM1 (solid line) or rabbit IgG-treated (dotted line) in A/J mice. Weight loss (FIG. 2L), ascites (representative syringe-FIG. 2M; average from all mice in the group-FIG. 2N) and organ inflammation (FIG. 2O) in mice treated with 200,000 IUe of either wt IL2, OMCP-mutIL2 or mutIL2. All graphs represent 46 animals per treatment condition. ns $p>0.05$; $*p<0.05$; $p<0.01$; $*p<0.001$; black=saline; blue=wtIL2, red=OMCP-mutIL2, green=mutIL2.

FIG. 3A, FIG. 3B, FIG. 3C, FIG. 3D, FIG. 3E, FIG. 3F, FIG. 3G, FIG. 3H, FIG. 3I and FIG. 3J depict graphs and images showing immunologic changes associated with IL2 and IL2 construct administration in vivo. (FIG. 3A, FIG. 3B) Total splenocyte counts after a five-day course of 200,000 IUe of IL2 (blue), mutIL2 (green) and OMCP-mutIL2 (red). (FIG. 3C) NK cell expansion and activation after IL2, mutIL2, OMCP-mutIL2, high dose IL2, high dose mutIL2 and IL2/anti-IL2 complexes measured by cell counts in the spleen (top) and KLRG1 upregulation (bottom). (FIG. 3D) $CD4^+Foxp3^+$ $T_{reg}$ expansion and activation as measured by cell counts in the spleen (top) and ICOS upregulation (bottom) as well as (FIG. 3E) NK/$T_{reg}$ ratio in the spleen. Expansion of splenocytes (FIG. 3F, FIG. 3G) and NK cells (FIG. 3H) in B6 mice treated with 750,000 IUe of cytokine or construct. $T_{reg}$ expansion and activation (FIG. 3I) as well as NK:$T_{reg}$ ratio (FIG. 3J) in the spleen of B6 mice. All graphs represent an average cell count±SEM from 5-10 mice per group. ns $p>0.05$; $*p<0.05$; $p<0.01$; $*p<0.001$; black=saline; blue=wtIL2, red=OMCP-mutIL2, green=mutIL2.

FIG. 4A, FIG. 4B, FIG. 4C, FIG. 4D and FIG. 4E depict graphs and images showing cytokine-mediated tumor immunotherapy. (FIG. 4A) In vivo cytotoxicity for YAC-1 lymphoma after intravenous injection. (FIG. 4B, FIG. 4C) LLC tumor growth after a five-day course of 750,000 IUe of cytokine treatment given as ten doses on days 5-10 post tumor injection. LLC tumor growth in mice depleted on NK cells (FIG. 4D) or mutant mice deficient in NKG2D (FIG. 4E). Data represents 5-6 mice per group. ns $p>0.05$; $*p<0.05$; $p<0.01$; $*p<0.001$; black=saline; blue=wtlL2, red=OMCP-mutIL2, green=mutIL2.

FIG. 5A, FIG. 5B, FIG. 5C, FIG. 5D, FIG. 5E, FIG. 5F, FIG. 5G, FIG. 5H, FIG. 5I, FIG. 5J and FIG. 5K depict graphs and a schematic showing IL2 signaling in NK cells.

(FIG. 5A, FIG. 5B) Serum levels after injection of 1×10$^6$ IUe of fluorochrome-labeled cytokine or construct i.v. (FIG. 5C) Degranulation of NK cells in the presence of cytokines and pentameric OMCP-mediated crosslinking of NKG2D as measured by surface CD107a expression at 1000 IUe/ml. STAT5 phosphorylation in isolated NK cells from NJ (FIG. 5D) or B6 mice (FIG. 5E) by increasing doses of cytokine. Decay in STAT5 phosphorylation after a 15 minute stimulation by 1000 IUe/ml (FIG. 5F) or 100 IUe/ml (FIG. 5G) of IL2 or OMCP-mutIL2. (FIG. 5H) Proposed model of competition between NK cells and stromal cells for IL2. (FIG. 5I) STAT5 phosphorylation of B6 NK cells in the presence of other splenocytes by wtIL2 and OMCP-mutIL2. (FIG. 5J) STAT5 phosphorylation of wild-type or NKG2D$^{-/-}$ NK cells by wtIL2 and OMCP-mutIL2 in the presence of competing splenocytes. (FIG. 5K) STAT5 phosphorylation, as measured by fold change over saline-treated controls, of wild-type NK cells in the presence of competing splenocytes treated with saturating concentrations of rat anti-mouse CD25 (clone 3C7) or rat IgG isotype control.

FIG. 6 depicts graphs showing B6 NK cells are preferentially activated by low dose OMCP-mutIL2 but this selectivity disappears at the highest doses of cytokine or in the absence of NKG2D expression by NK cells. Left two graphs show B6 NK cells and right two graphs show BK NKG2D$^{-/-}$ NK cells.

FIG. 7A, FIG. 7B and FIG. 7C depict imaging showing that inspection of the viscera demonstrates limited food consumption after a 5-day course of 200,000 or 750,000 IUe of wtIL2. FIG. 7D depicts a graph showing that unlike the A/J strain, B6 mice are able to tolerate higher doses of wtIL2 with only moderate weight loss after 750,000 IUe. Higher doses of 1,500,000 IUe IL2 resulted in increased weight loss. Doses above this regimen led to animal death.

FIG. 8A depicts a graph showing that NJ mice treated with IL2/anti-IL2 antibodies or high dose mutIL2 lost significant weight during treatment. The majority of IL2/anti-IL2 treated mice could not survive the full 200,000 IUe dosing and were sacrificed four days after starting treatment thus receiving 160,000-180,000 IUe. FIG. 8B depicts a graph and flow cytometric plot showing NK expansion with ULBP3-mutIL2 and lower doses of OMCP-mutIL2 in NJ spleen (top). NK activation, as measured by surface KLRG1 expression on NK cells treated with 200,000 IUe of mutIL2 (green) or ULBP3-mutIL2 (purple) in NJ spleen (bottom). FIG. 8C and FIG. 8D depict graphs showing that unlike the case for NK cells, little expansion of CD8$^+$ or CD4$^+$Foxp3$^-$ T cells was evident in either IL2, OMCP-mut-IL2, or mutIL2 treated mice. FIG. 8E depicts a graph showing weight loss in B6 mice treated with high dose mutIL2 or IL2/anti-IL2 antibody complex. FIG. 8F and FIG. 8G depict graphs showing expansion of CD8$^+$ or CD4$^+$Foxp3$^-$ T cells in cytokine treated B6 mice. Graphs represent 5-10 mice per group.

Figure 11A:
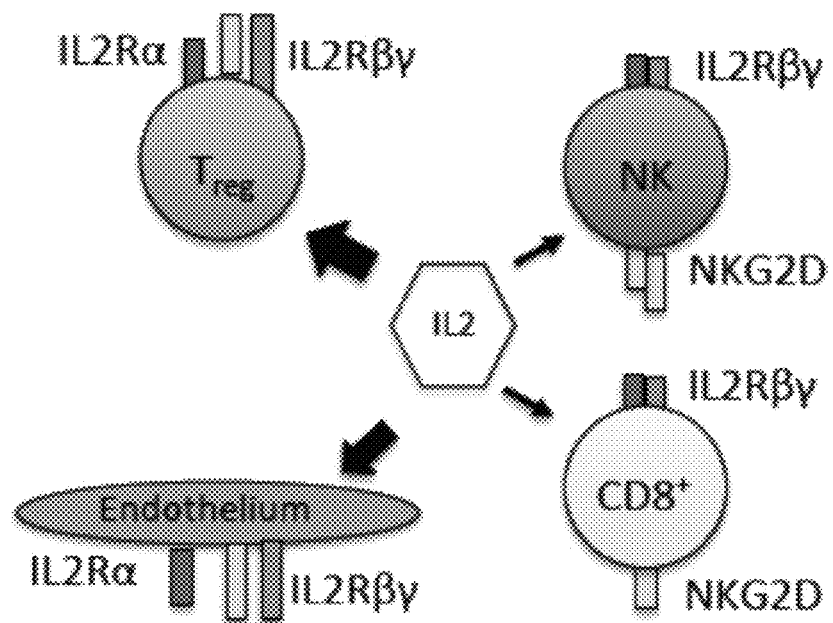
Figure 11B:
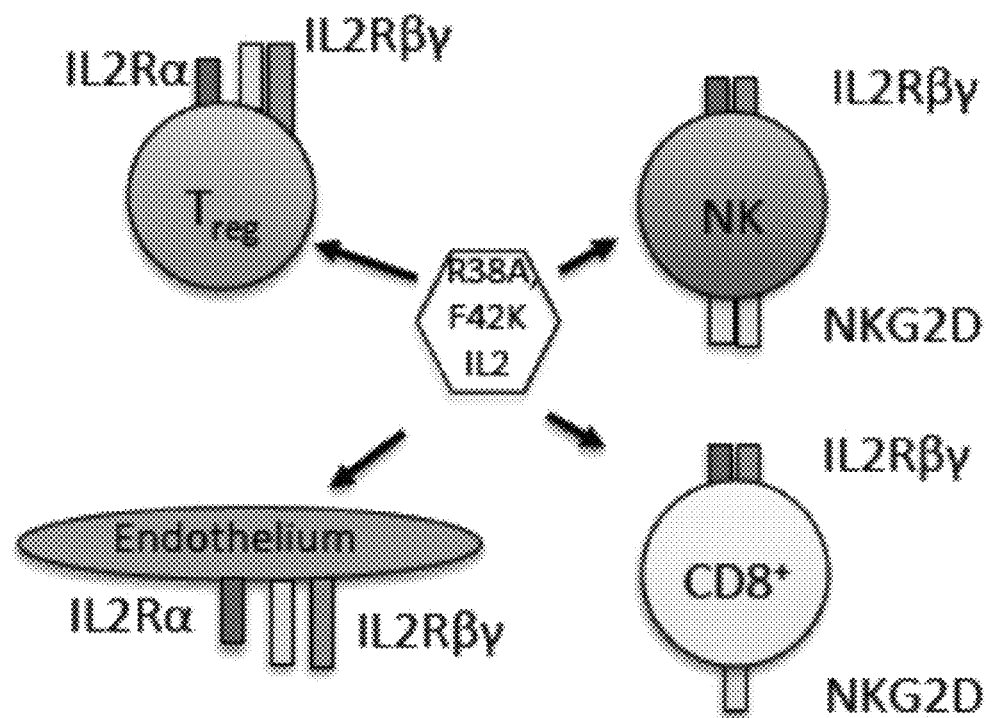
Figure 11C:
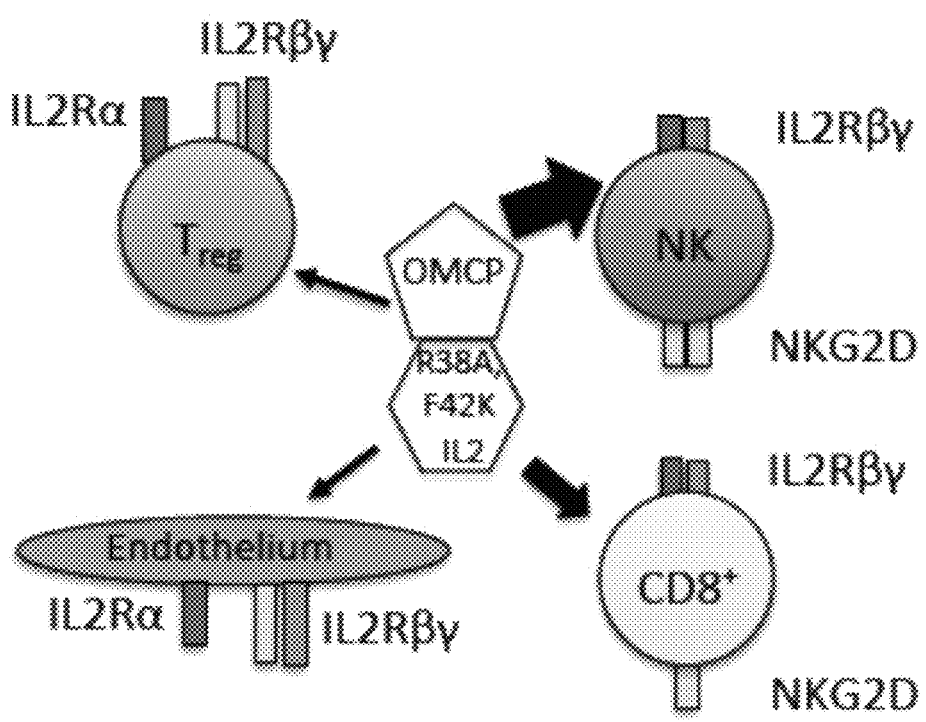

FIG. 11A, FIG. 11B and FIG. 11C depict a schematic of the differential IL2 binding and activation in vivo. (FIG. 11A) Regular wild-type IL2 preferentially binds to cells such as CD4$^+$Foxp3$^+$ T$_{regs}$ and vascular endothelium, both of which express the high affinity α chain along with the signaling β and γ chains of the IL2 receptor. (FIG. 11B) The R38A and F42K mutations in IL2 decrease affinity for the α chain of the IL2 receptor. (FIG. 11C) By linking R38A/F42K IL2 to the high affinity NKG2D ligand OMCP delivery and binding of this cytokine to NKG2D-expressing CTLs such as NK cells and activated CD8$^+$ T cells is increased. Width of arrows indicates proposed strength of IL2 binding and/or signaling.

Figure 12:
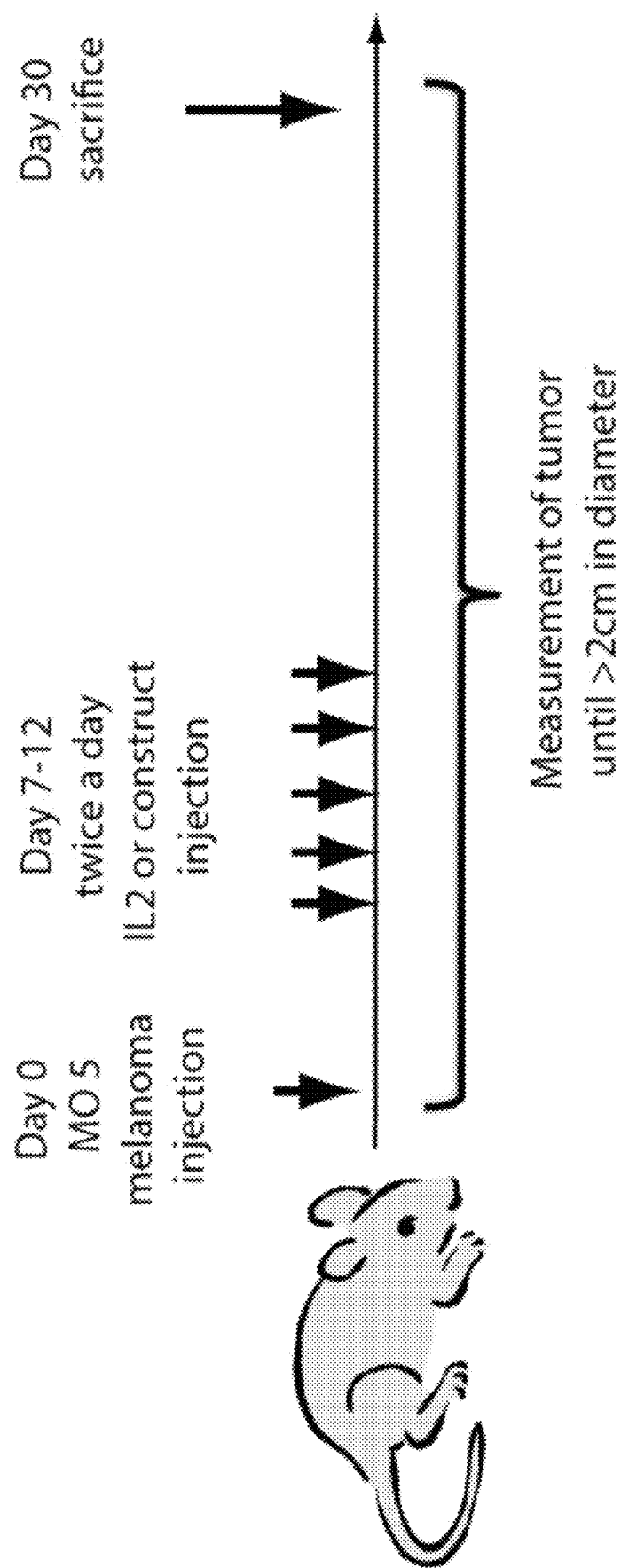

FIG. 12 depicts a schematic of the experimental design of immunotherapy experiments.

Figure 13:
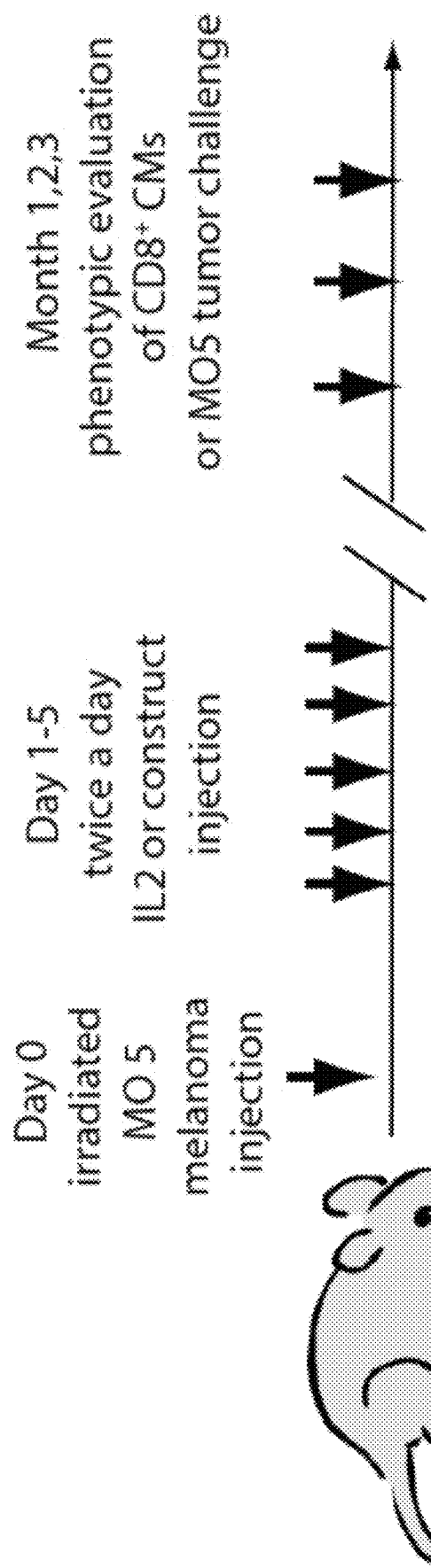

FIG. 13 depicts a schematic of the experimental design of vaccination experiments.

Figure 14A:
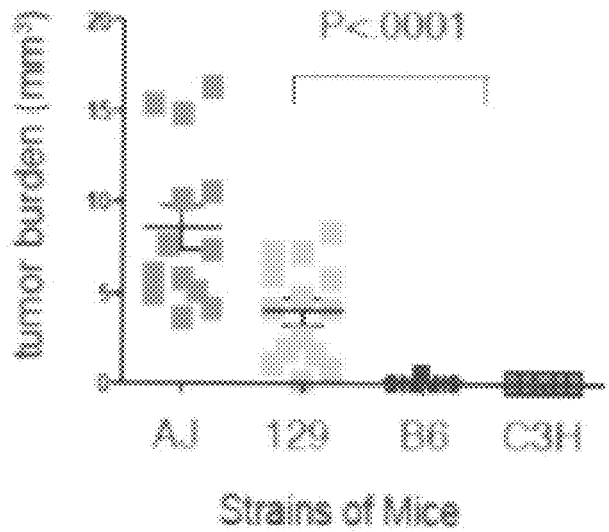
Figure 14B:
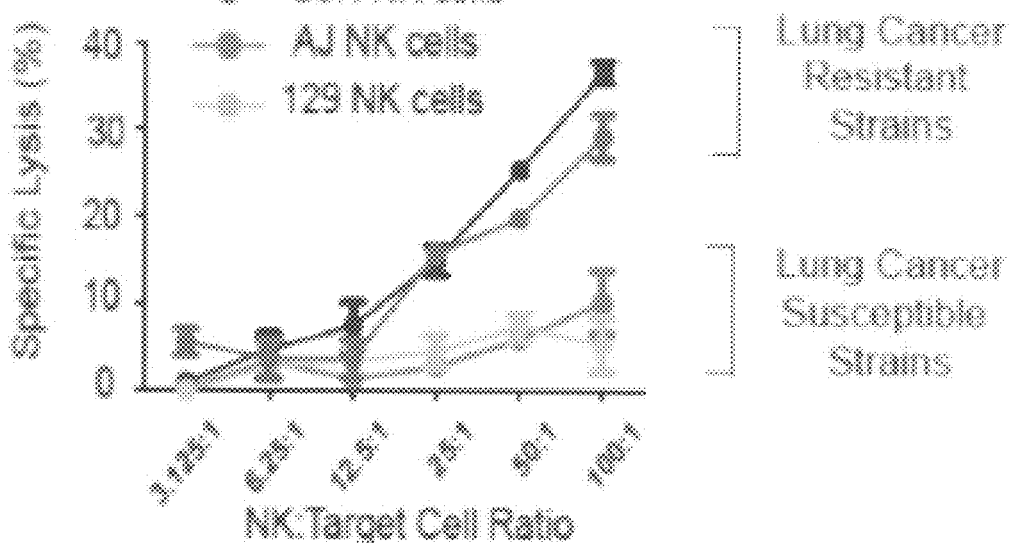

FIG. 14A and FIG. 14B depict graphs showing lung cancer susceptible and resistant strains of mice. (FIG. 14A) AJ and 129 mouse strains are susceptible to lung cancer as evidenced by tumor burden whereas B6 and C3H mouse strains are resistant to lung cancer as evidenced by tumor burden. (FIG. 14B) Upon incubation with freshly isolated NK cells from the various mouse strains, B6 and C3H NK cells result in significantly more LM2 lung carcinoma cell lysis than AJ and 129 NK cells.

Figure 15:
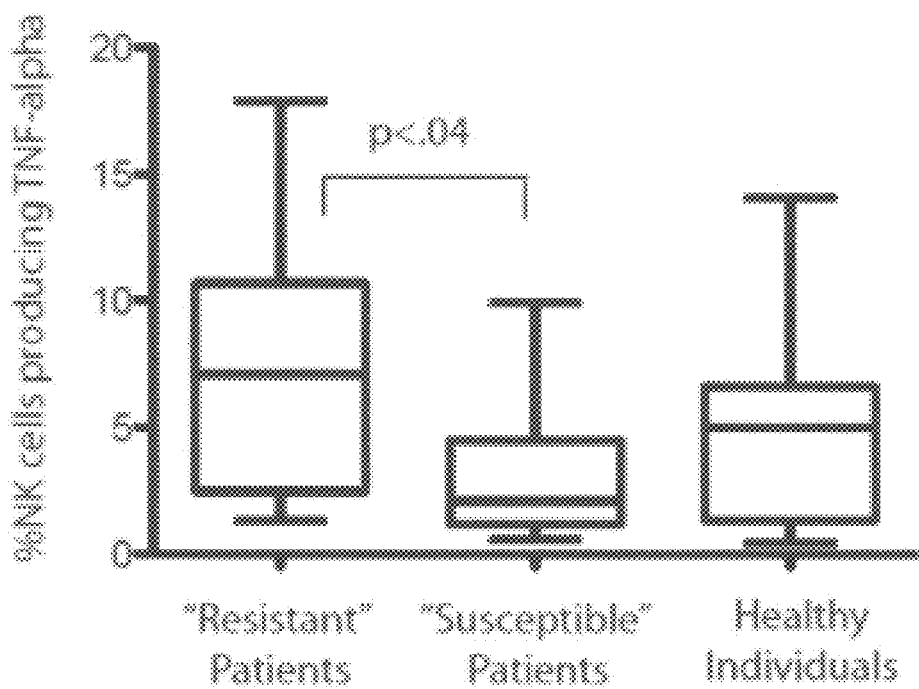

FIG. 15 depicts a graph showing that in human men, a greater percentage of NK cells appear to produce TNFα in "resistant" patients versus "susceptible" patients.

Figure 16:
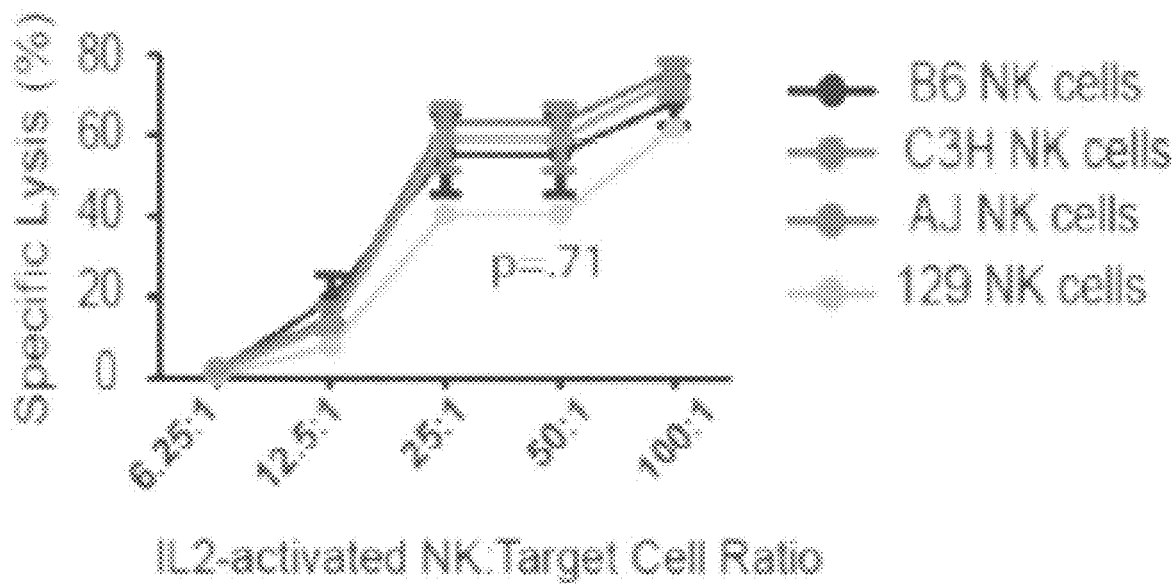
Figure 17A:
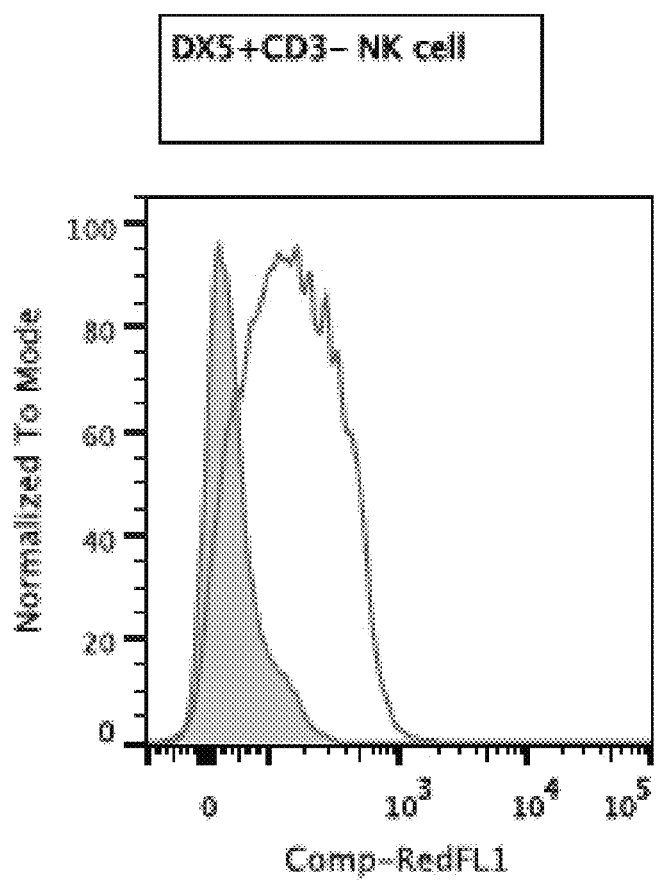
Figure 17B:
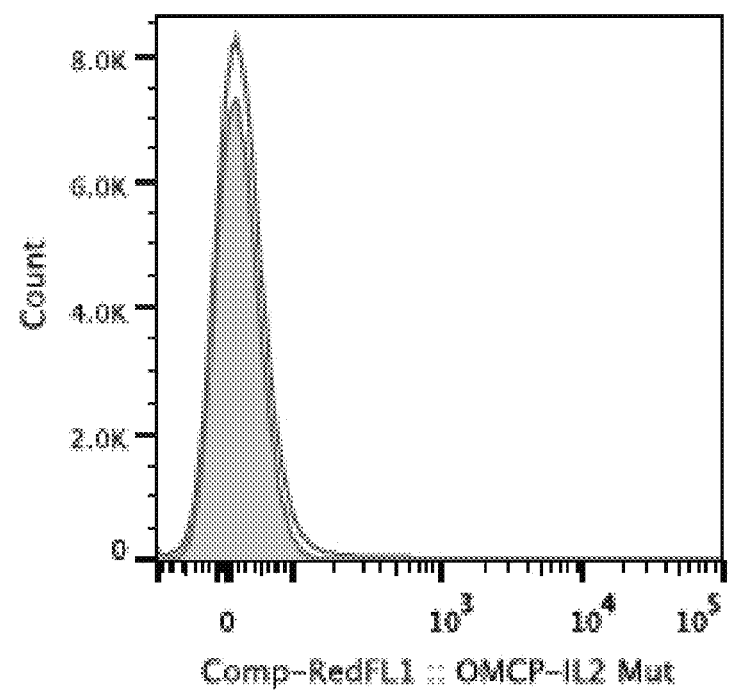
Figure 17C:
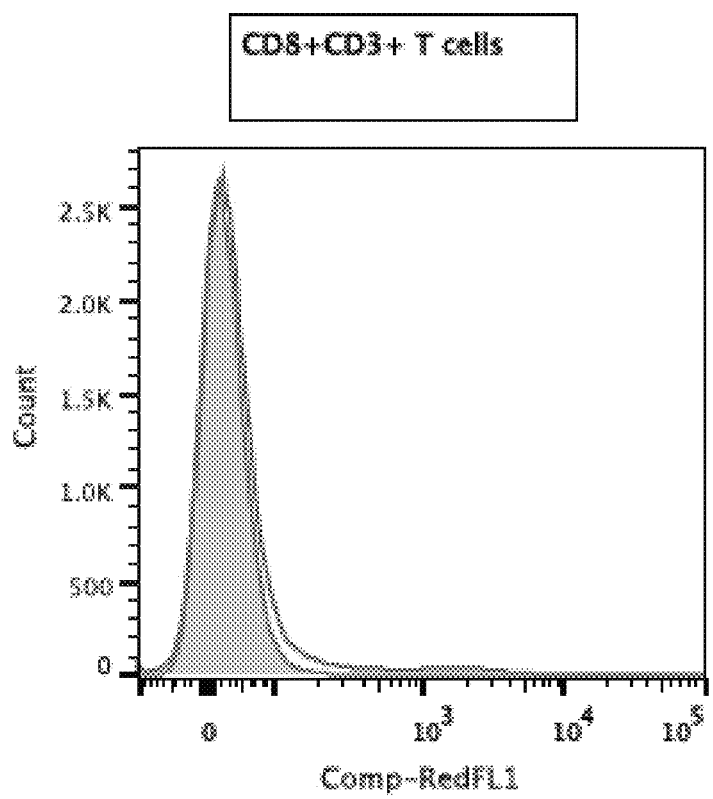
Figure 17D:
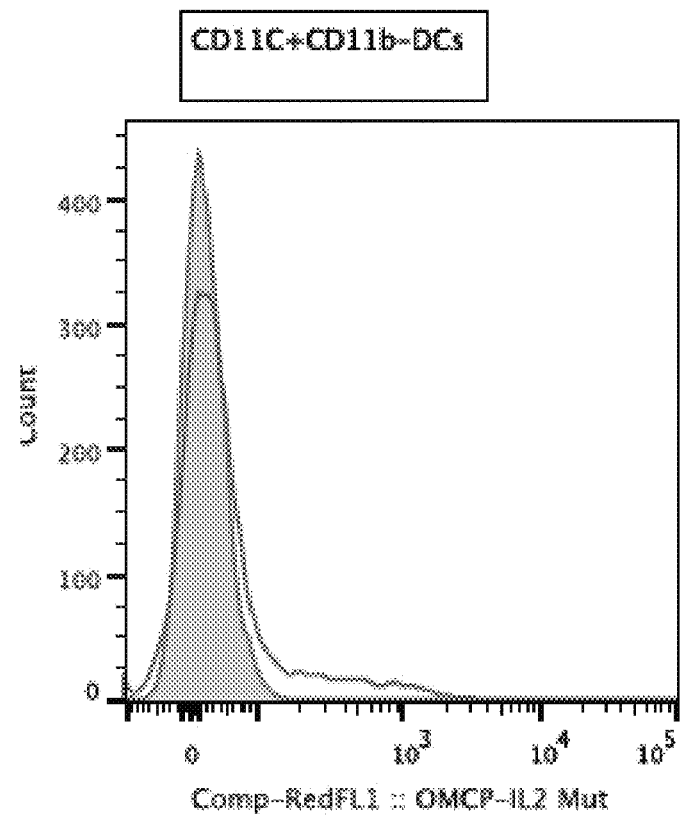
Figure 17E:
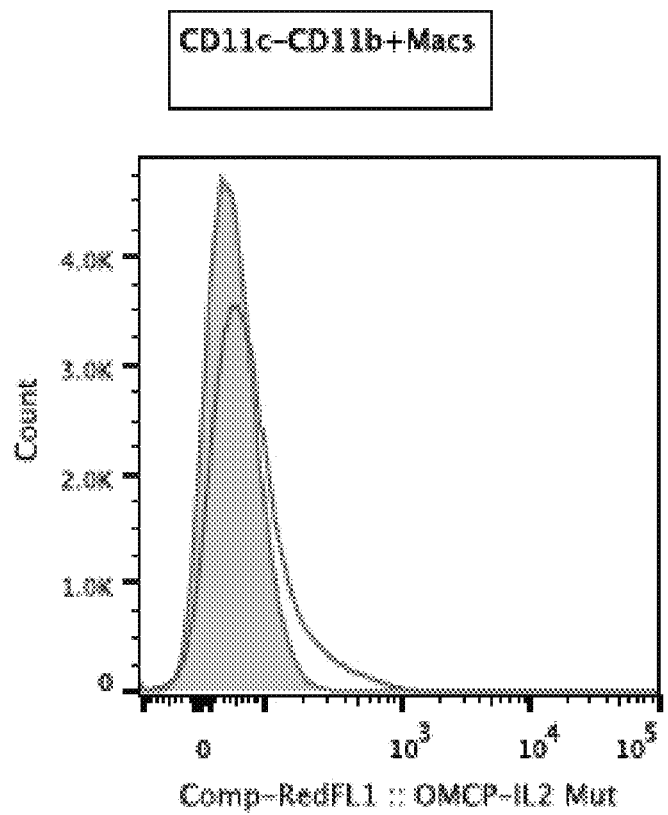
Figure 17F:
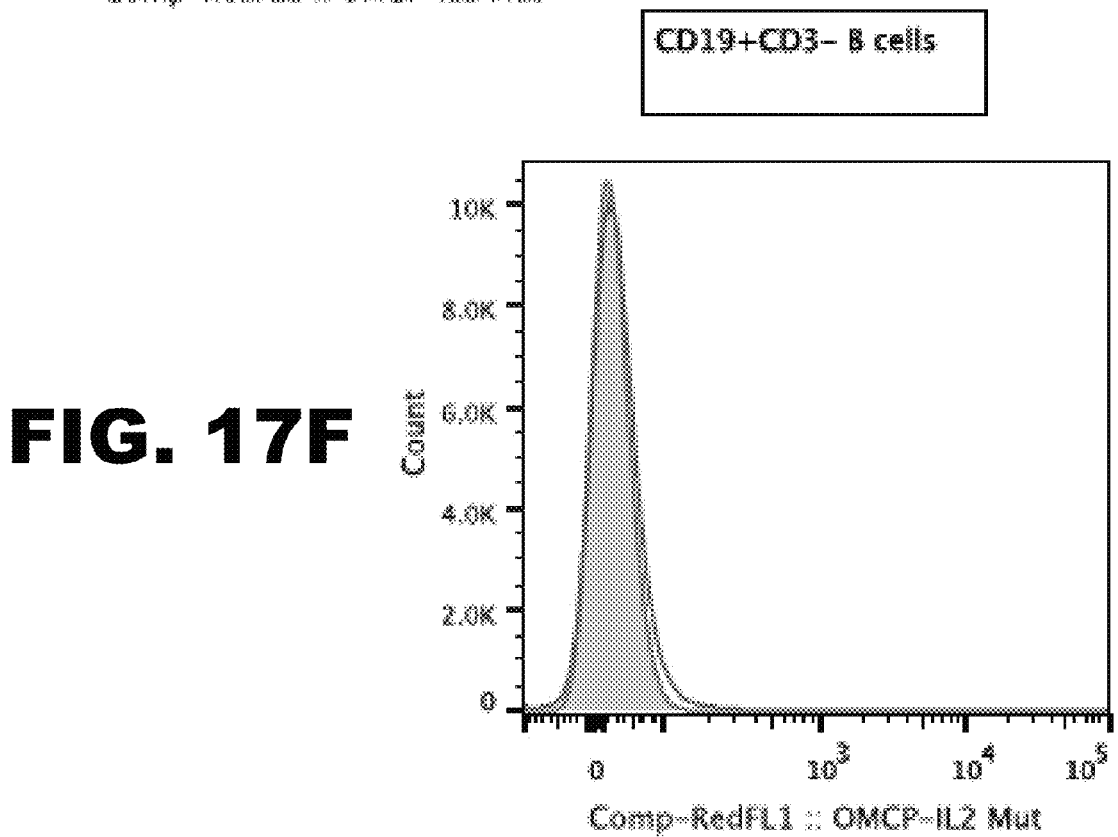

FIG. 16 depicts a graph showing that ex vivo cytokine activation can reverse natural killer cell dysfunction. Mouse NK Cells that did not show significant lysis of cancer cells (NK cells from 129 & AJ strains) were much more effective at lysis when treated with IL2. NK cells from cancer-resistant strains also showed increase % of specific lysis.

FIG. 17A, FIG. 17B, FIG. 17C, FIG. 17D, FIG. 17E and FIG. 17F depict graphs showing binding of fluorescently labeled construct tested in vitro at 37 degrees in bulk splenocytes. The construct appears to only bind to NK cells (express NKG2D). Red line is OMCP-IL2 construct. (FIG. 17A) DX5+CD3− NK cell; (FIG. 17B) CD4+CD3+ T cells; (FIG. 17C) CD8$^+$ CD3+ T cells; (FIG. 17D) CD11C+ CD11b− DCs; (FIG. 17E) CD11c−CD11b+ Macs; (FIG. 17F) CD19+CD3− B cells.

Figure 18:
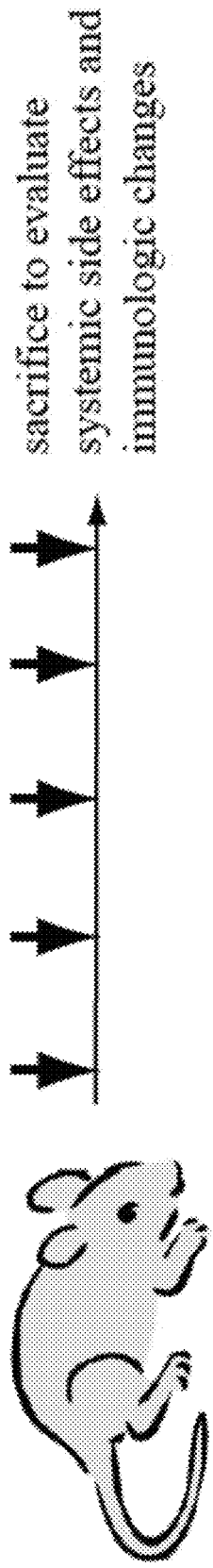

FIG. 18 depicts a schematic dosing regimen for IL2 or IL2 constructs.

Figure 19:
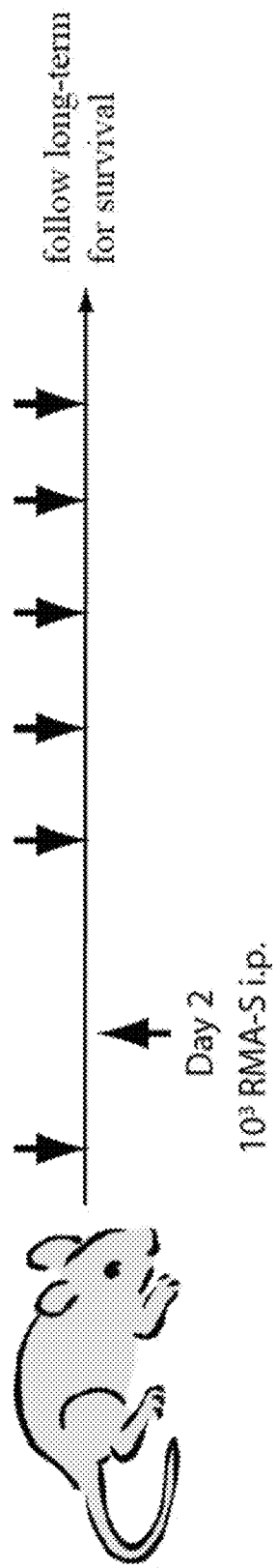

FIG. 19 depicts a schematic dosing regimen for IL2 or IL2 constructs after irradiation.

Figure 20A:
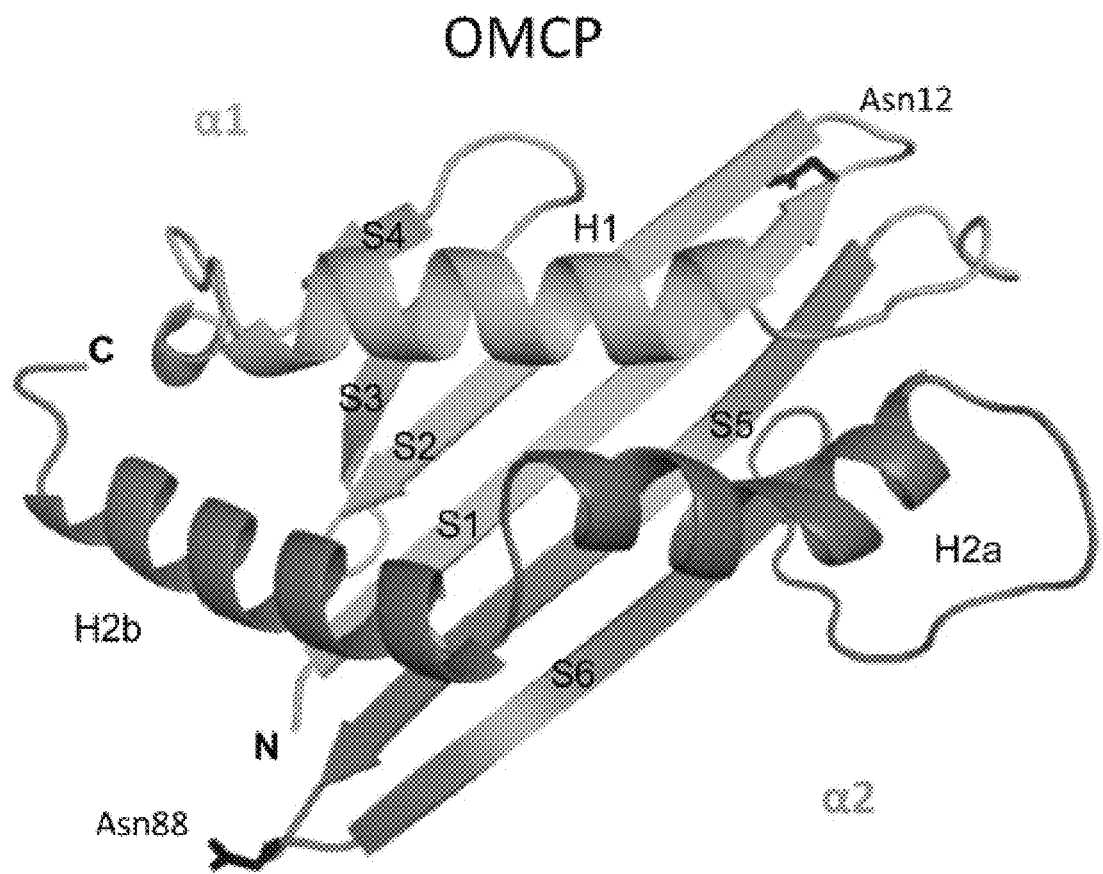
Figure 20B:
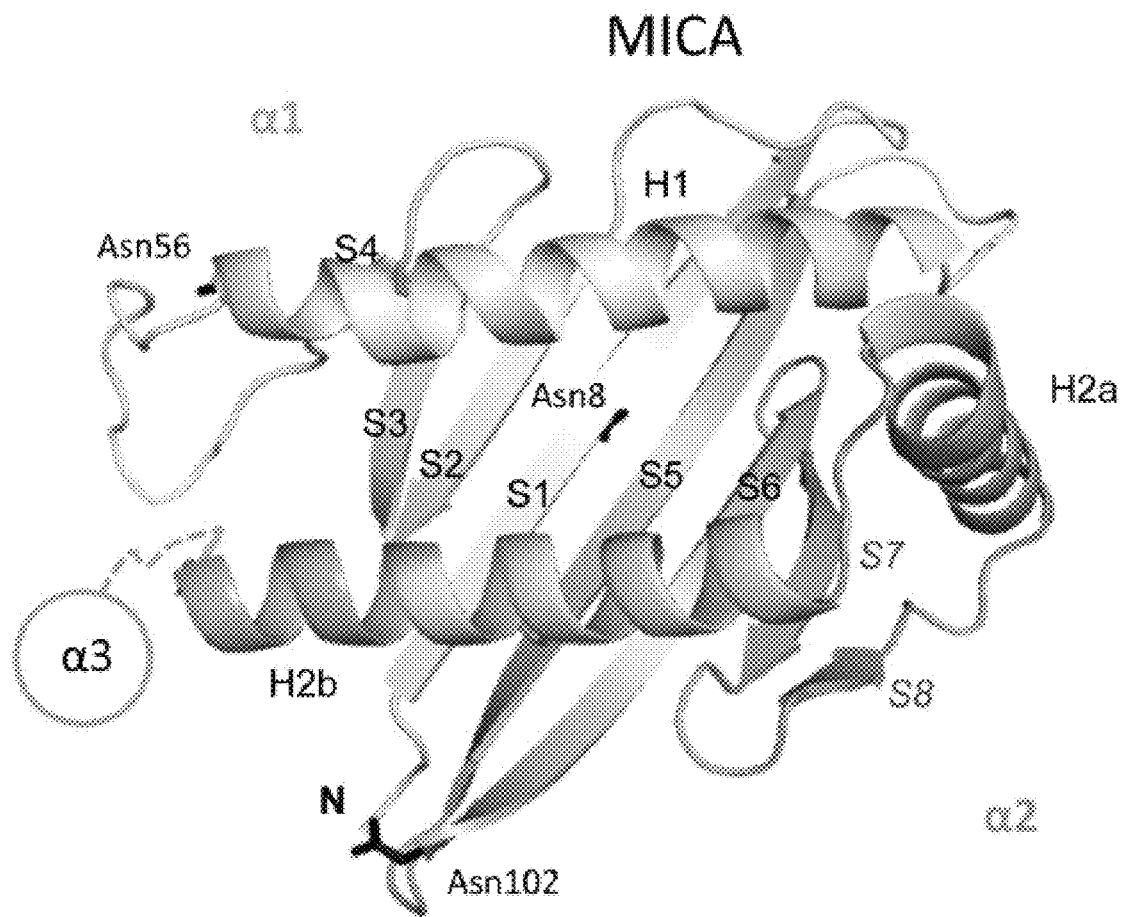
Figure 20C:
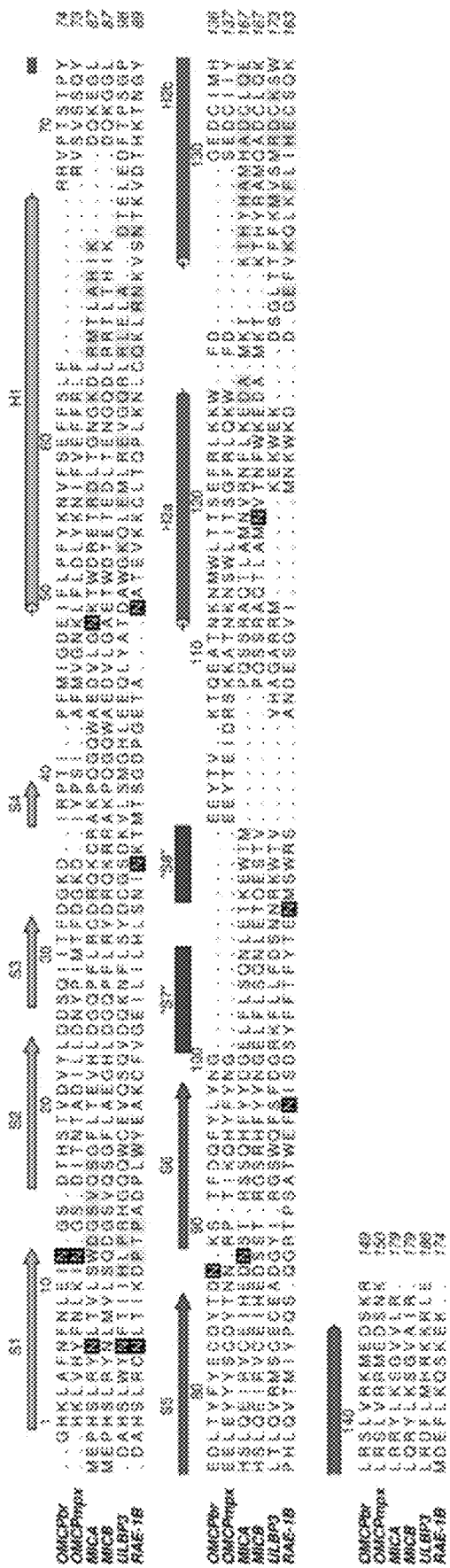

FIG. 20A, FIG. 20B and FIG. 20C depict images and alignments of the OMCP structure. (FIG. 20A) Ribbon diagram of CPXV OMCP. Secondary structure elements are noted, S for beta strands and H for helix. The α1/α2 portions of the platform domain are indicated in cyan and magenta, respectively. (FIG. 20B) Ribbon diagram of the α1/α2 domain of MICA (PDB identifier 1 HYR), with the α3 domain removed for clarity. Residues that contact NKG2D are colored yellow. (FIG. 20C) Structure alignment of OMCP with NKG2DLs. The mature sequences of OMCP$_{BR}$ (CPXV-BR-018; GenBank accession number NP_619807; PDB identifier 4FFE) and OMCP$_{MPX}$ (MPXV-ZAR_1979_005-198; N3R; GenBank accession number AAY97396) are aligned with the ectodomain sequences of MICA (1HYR), MICB (1JE6), ULBP3 (1KCG), and RAE-1β (1JFM). Known NKG2D contact residues for NKG2DLs are indicated in yellow. Asn residues likely to be glycosylated are noted by black boxes in panel C and as black side chains in panels A and B. OMCPbr=SEQ ID NO:13;

OMCPmpx=SEQ ID NO:14; MICA=SEQ ID NO:15; MICB=SEQ ID NO:16; ULBP3=SEQ ID NO:17; and RAE-1B=SEQ ID NO:18

Figure 21:
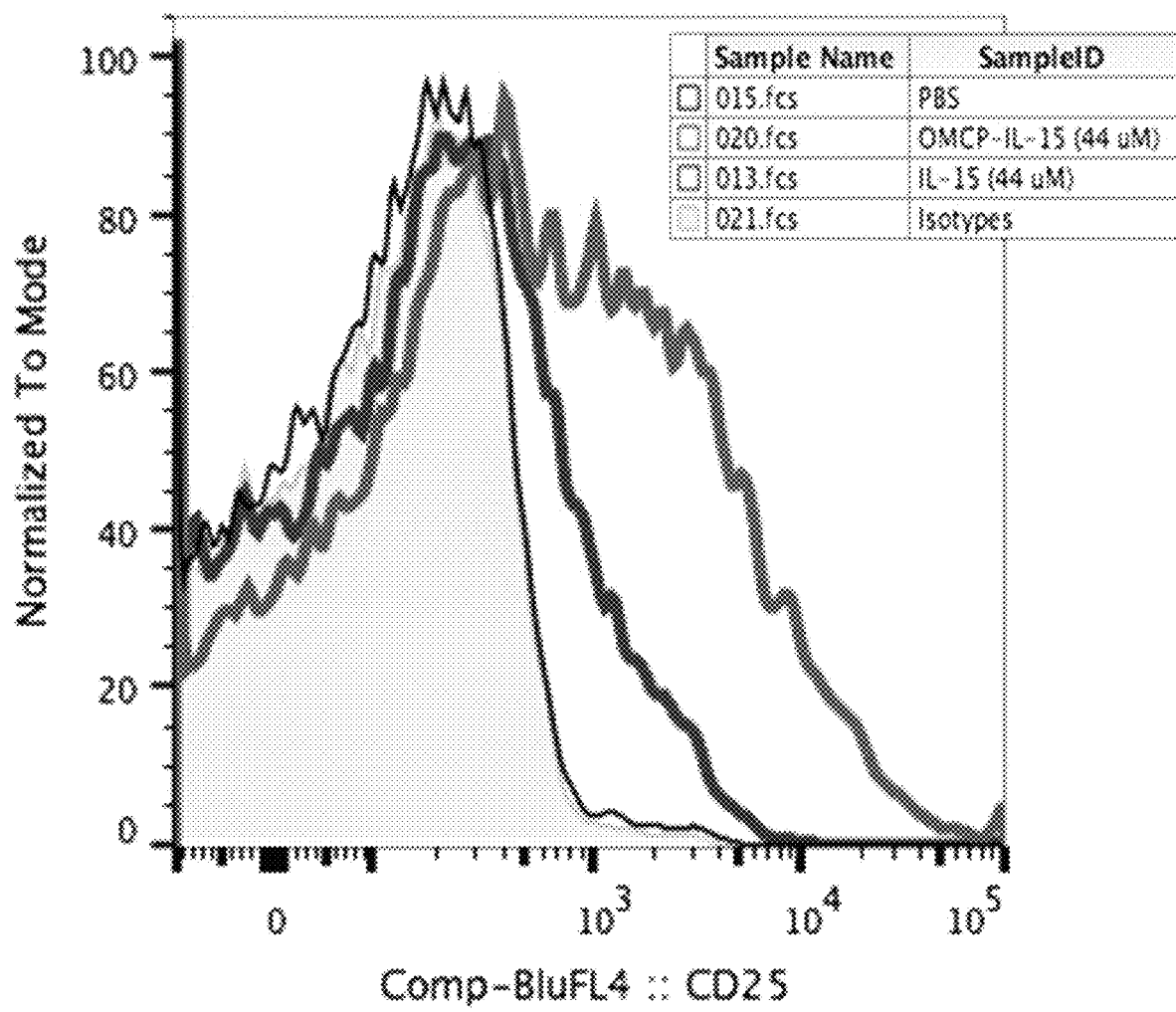

FIG. 21 depicts a graph showing OMCP-targeted delivery of IL15. Higher levels of CD25 are evident when IL15 is delivered by OMCP vs naked cytokine alone in equimolar doses.

Figure 22:
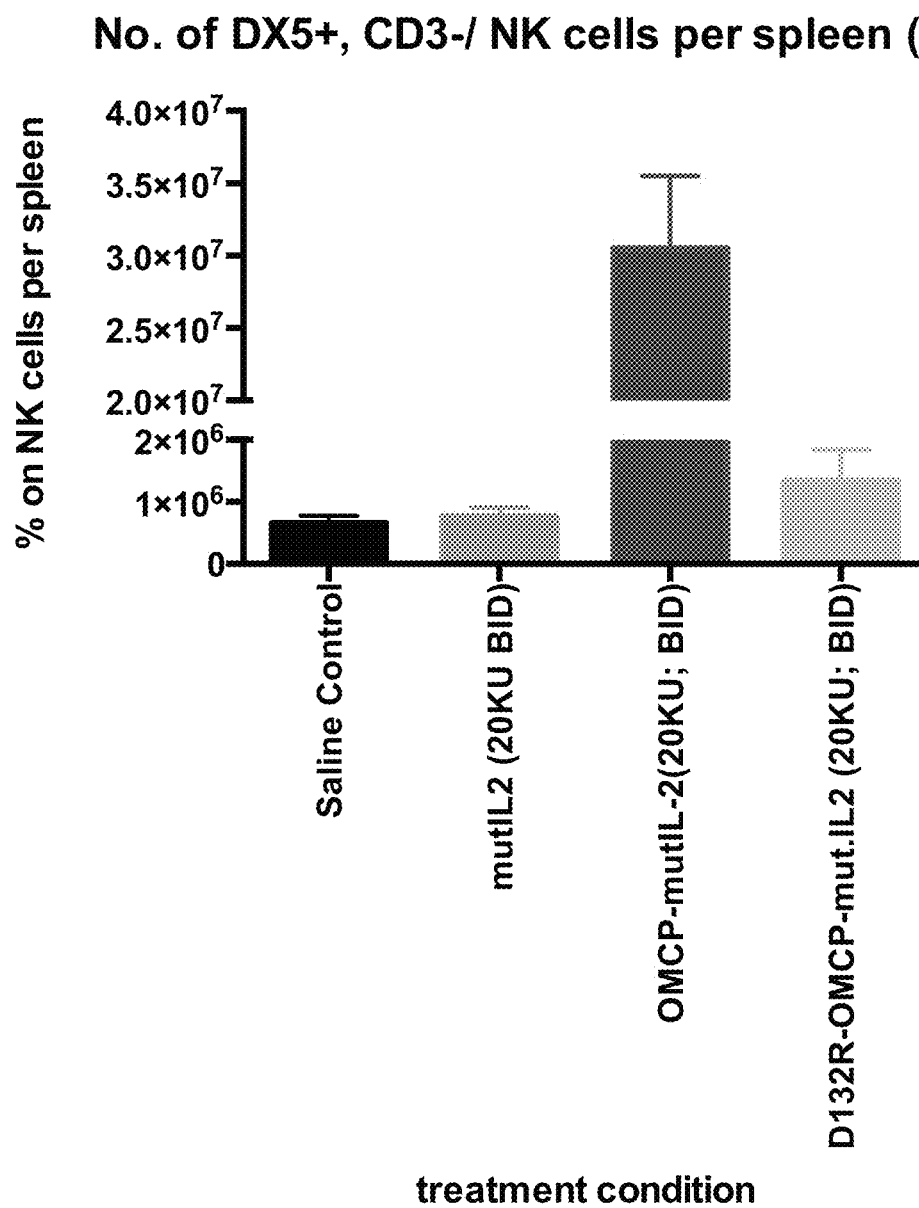

FIG. 22 depicts a graph showing that the D132R mutation in OMCP significantly decreases its NKG2D binding. NK expansion and activation in the presence of mutIL2, OMCP-mutIL2, and D132ROMCP-mutIL2 was tested. The D132R mutation ameliorated the superiority of natural killer cell activation over cytokine alone.

Figure 23:
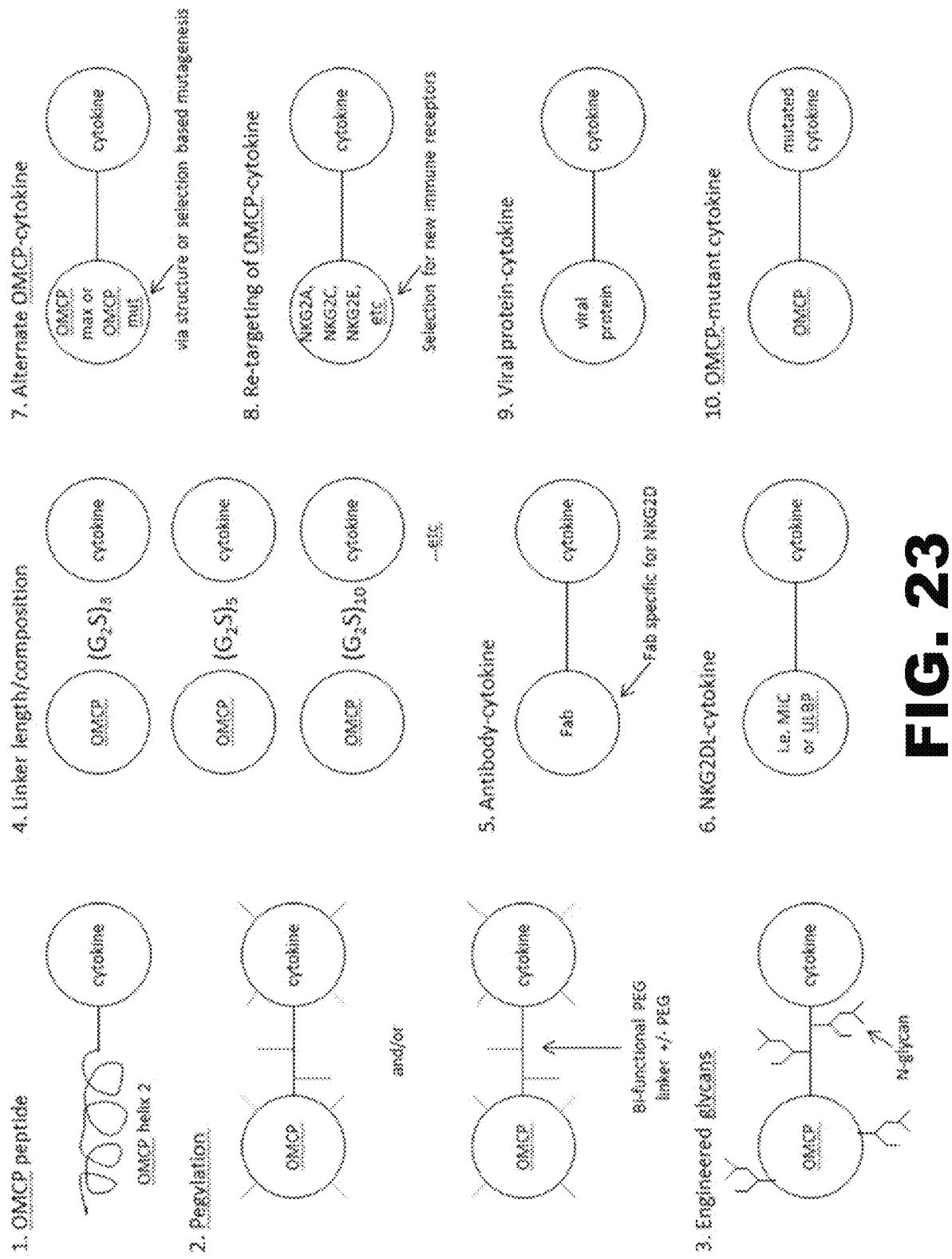

FIG. 23 depicts various embodiments of the invention. 1. depicts OMCP helix 2 linked to cytokine. 2. depicts pegylation of the composition. 3. depicts a composition comprising engineered glycans. 4. depicts various linker lengths and compositions. 5. depicts an antibody linked to a cytokine. For example a Fab specific NKG2D antibody. 6. depicts a NKG2DL linked to a cytokine. For example, MIC or ULBP. 7 depicts an alternative OMCP linked to a cytokine. For example, OMCP max could represent gain of function for NKG2D binding and mutant OMCP could represent loss of function for NKG2D binding. 8. depicts re-targeting of the OMCP in a composition. For example, the OMCP may be directed to NKG2A, NKG2C, NKG2E, etc. 9. depicts other viral protein liked to a cytokine. For example, the other viral protein may also bind to receptors on immune cells. 10. depicts OMCP linked to mutant cytokines. It is understood that the OMCP sequence could be from various sources such as cowpox or monkeypox. Also, Fc-chimeras of OMCP and IL2, and variants thereof may be used.

Figure 24A:
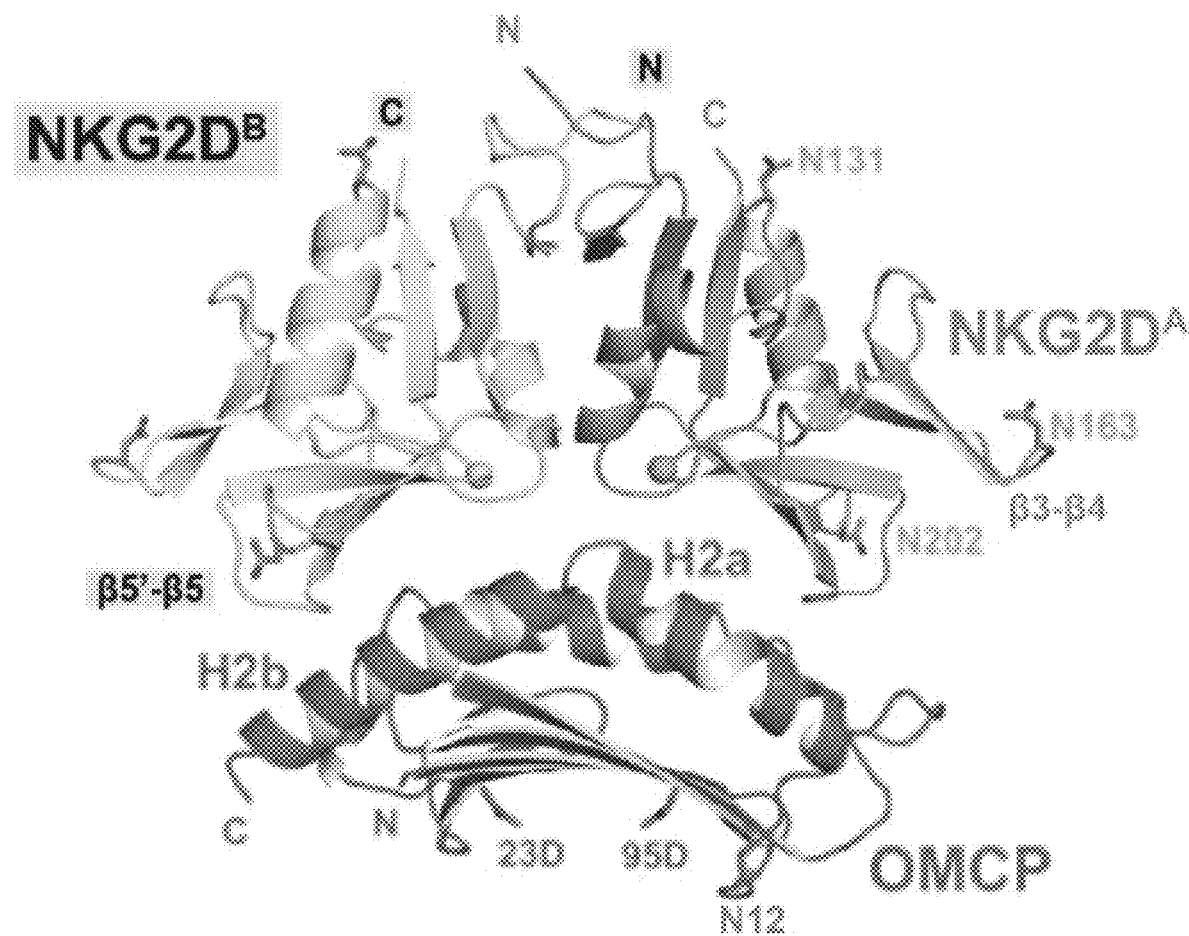
Figure 24B:
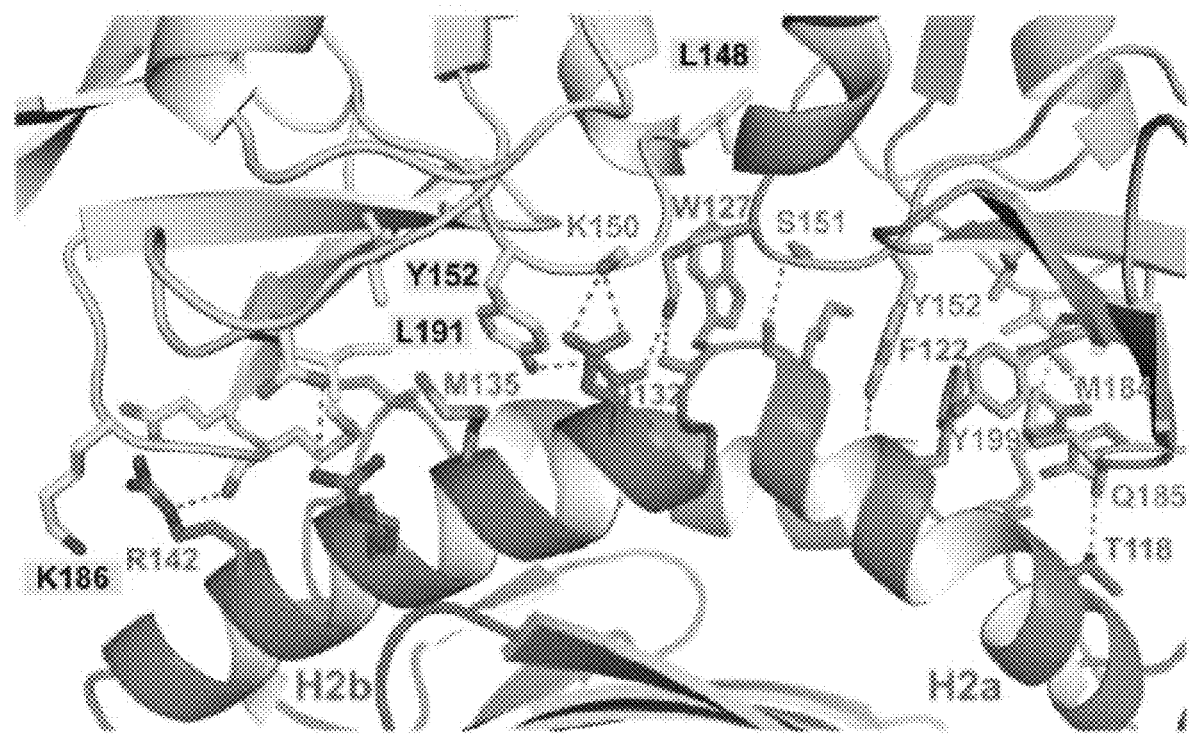

FIG. 24A and FIG. 24B depict the structure of OMCP in complex with NKG2D. (FIG. 24A) OMCP bound to NKG2D. OMCP is colored magenta and the protomers of NKG2D are colored cyan ("A") and yellow ("B"). $NKG2D^A$ makes contacts primarily with the H2a helix and $NKG2D^B$ with H2b. Mutations introduced to facilitate alternate crystal packing are shown in red. The S193-S194 bond is shown as a ball on each NKG2D protomer. The asparagines of putative hNKG2D glycosylation sites are shown in orange. The asparagine of the confirmed N-glycan site of OMCP is shown green (data not shown) (FIG. 24B) View of the interface between OMCP-NKG2D. The α2 domain of OMCP is shown in the front with the α1 domain behind. OMCP and NKG2D are shown with cartoon representations for the main chain, with the side chains of contact residues shown as sticks. Hydrogen bonds and salt bridges are indicated with green dotted lines.

Figure 25A:
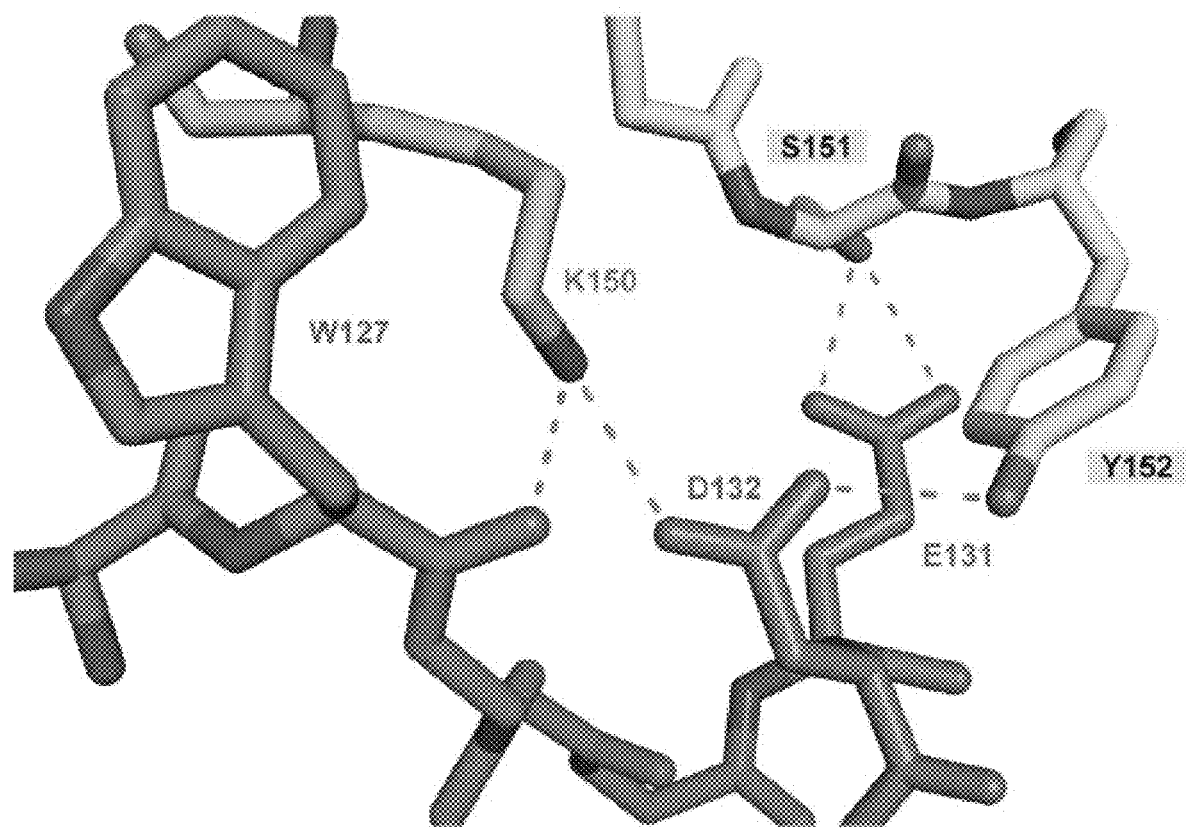
Figure 25B:
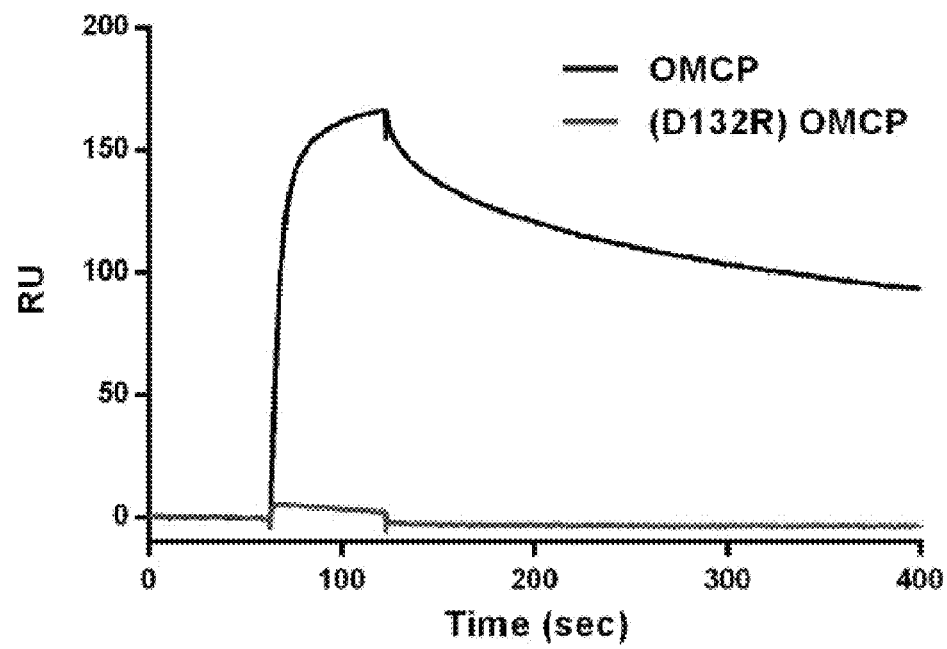
Figure 25C:
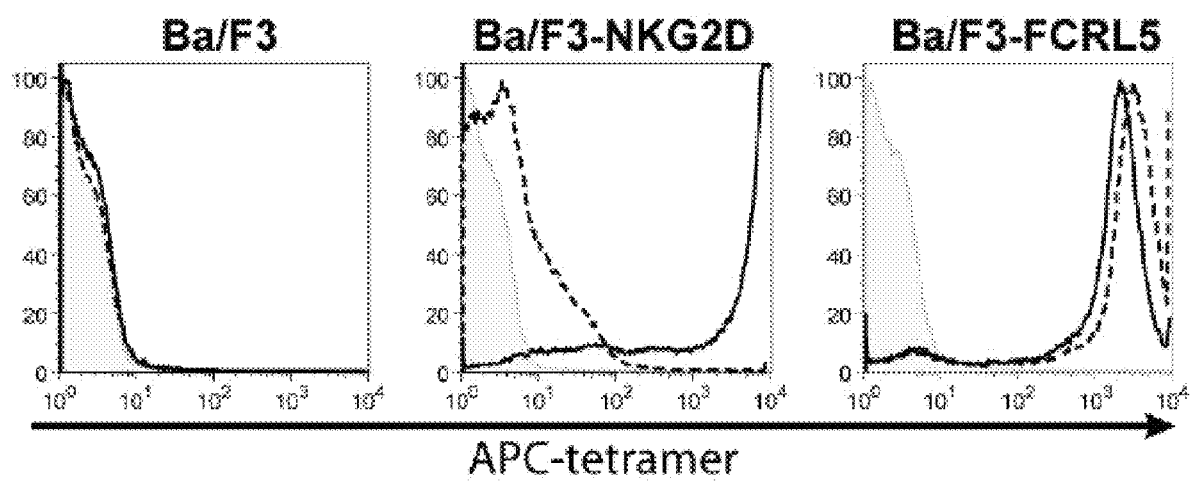

FIG. 25A, FIG. 25B and FIG. 25C depicts the interface of OMCP and NKG2D. (FIG. 25A) The local environment of the OMCP-NKG2D binding interface surrounding the D132R residue. The D132R mutation ablates OMCP-NKG2D binding. (FIG. 25B) A representative experiment for binding of WT and (D132R) OMCP to NKG2D by SPR. 100 nM of OMCP or (D132R) OMCP were injected at 50 µl/min over flowcells containing immobilized biotinylated murine NKG2D. (FIG. 25C) Ba/F3 cells transduced with NKG2D, FCRL5, or empty vector were stained with OMCP tetramers (solid line), D132R tetramers (dashed line), or WNV DIII tetramer control (gray histogram). Representative results from three independent experiments.

FIG. 26A, FIG. 26B, FIG. 26C and FIG. 26D depict the differences in the β5'-β5 loop (L2) of human and murine NKG2D. (FIG. 26A, FIG. 26B) Superimposition of mNKG2D (grey) (PDB ID: 1HQ8) with the structure of OMCP-hNKG2D (yellow and cyan). Core binding residues Y152 (Y168) and Y199 (Y215) are positionally conserved, while core binding residue M184 (1200) is not. (FIG. 26C) Surface representation of OMCP (magenta) interacting with the β5'-β5 loop. (FIG. 26D) Conservation of M184 and Q185. Only the NKG2D of mice, rats, guinea pigs, and flying foxes (not shown) differ. Conservation score is as computed by the ConSurf server. Human, organgutan, chimpanzee, gibbon, macaque-SEQ ID NO:19; Green monkey-SEQ ID NO:20; Marmoset-SEQ ID NO:21; Mouse-SEQ ID NO:22; Rat-SEQ ID NO:23; Guinea pig-SEQ ID NO:24; Ground squirrel-SEQ ID NO:25; Deer mouse-SEQ ID NO:26; Naked mole rat-SEQ ID NO:27; Prairie vole-SEQ ID NO:28; European shrew-SEQ ID NO:29; Star-nosed mole-SEQ ID NO:30; Chinese hamster-SEQ ID NO:31; Cat-SEQ ID NO:32.

Figure 27A:
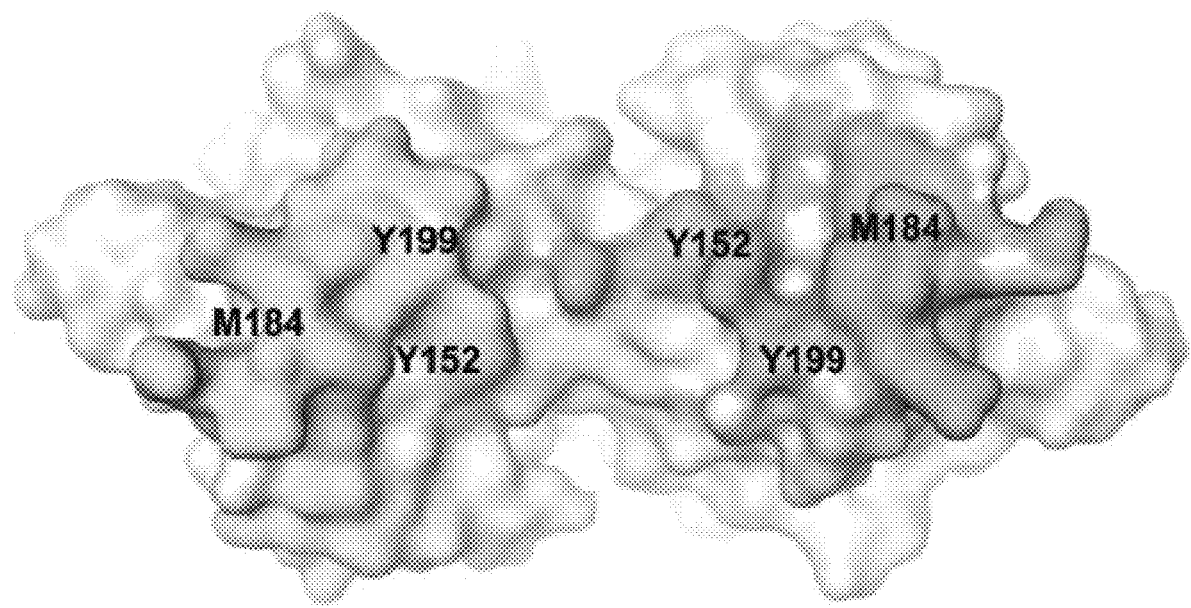
Figure 27B:
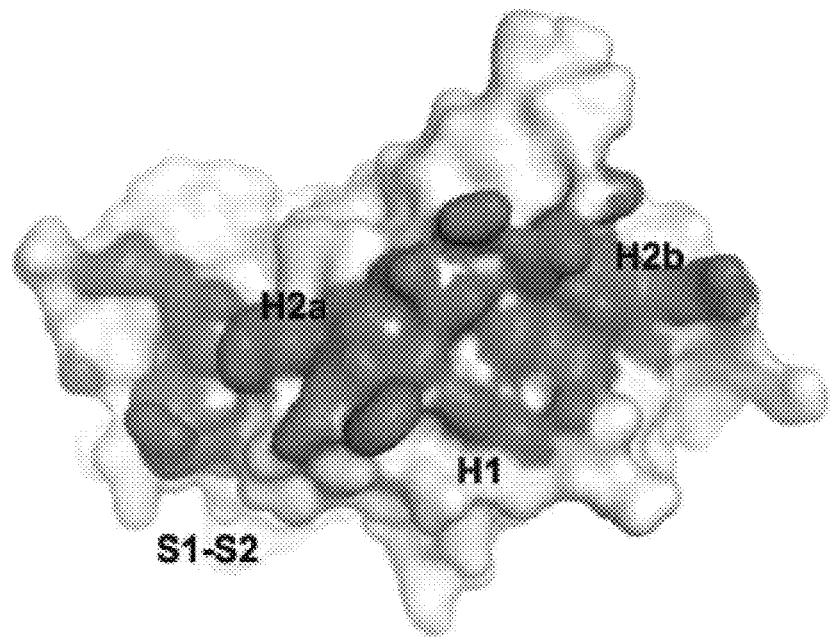
Figure 27C:
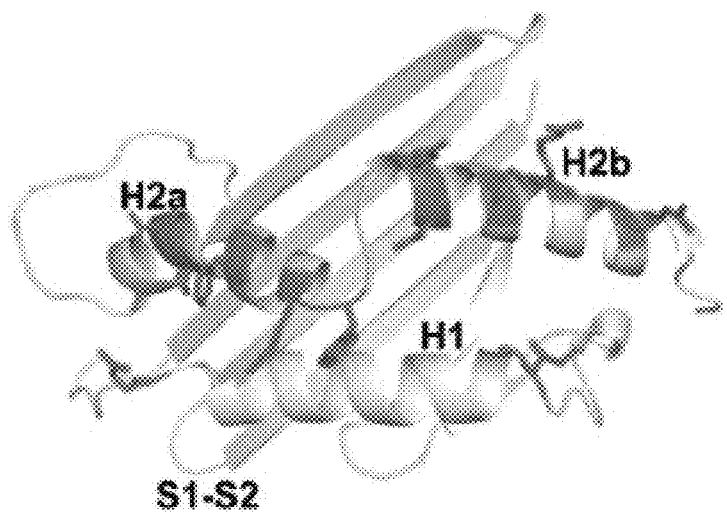
Figure 27D:
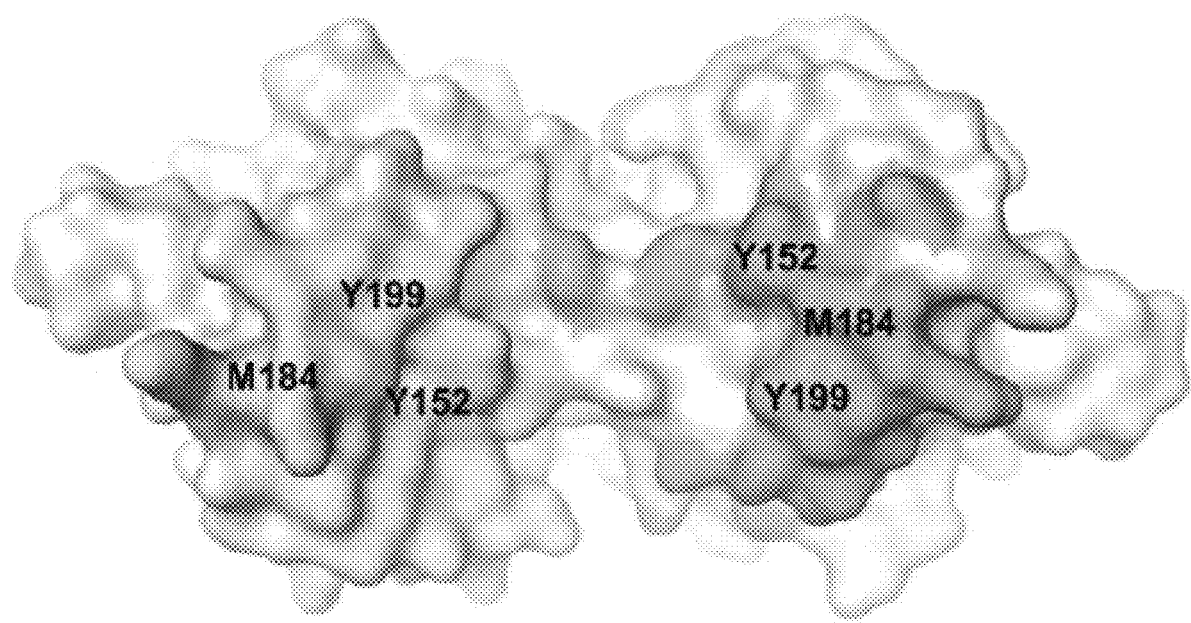
Figure 27E:
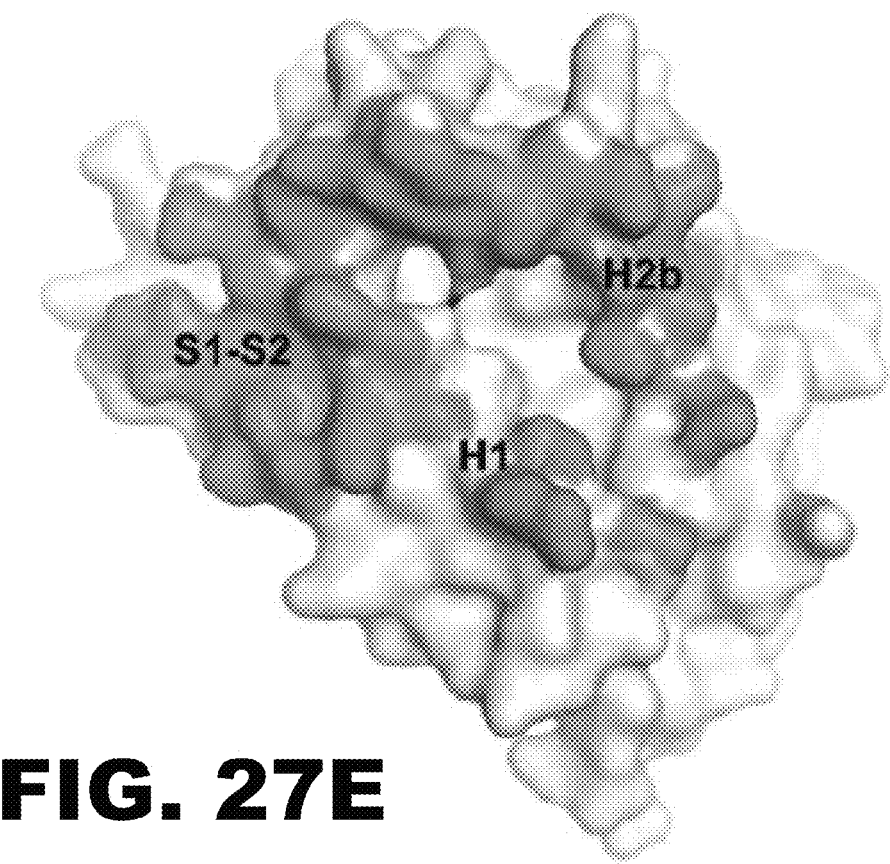
Figure 27F:
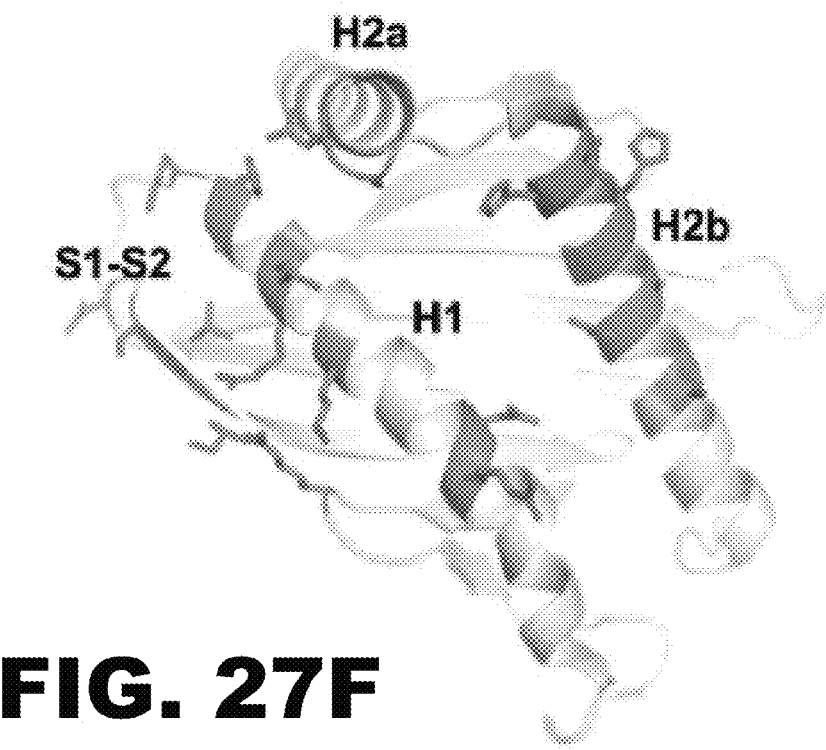
Figure 27G:
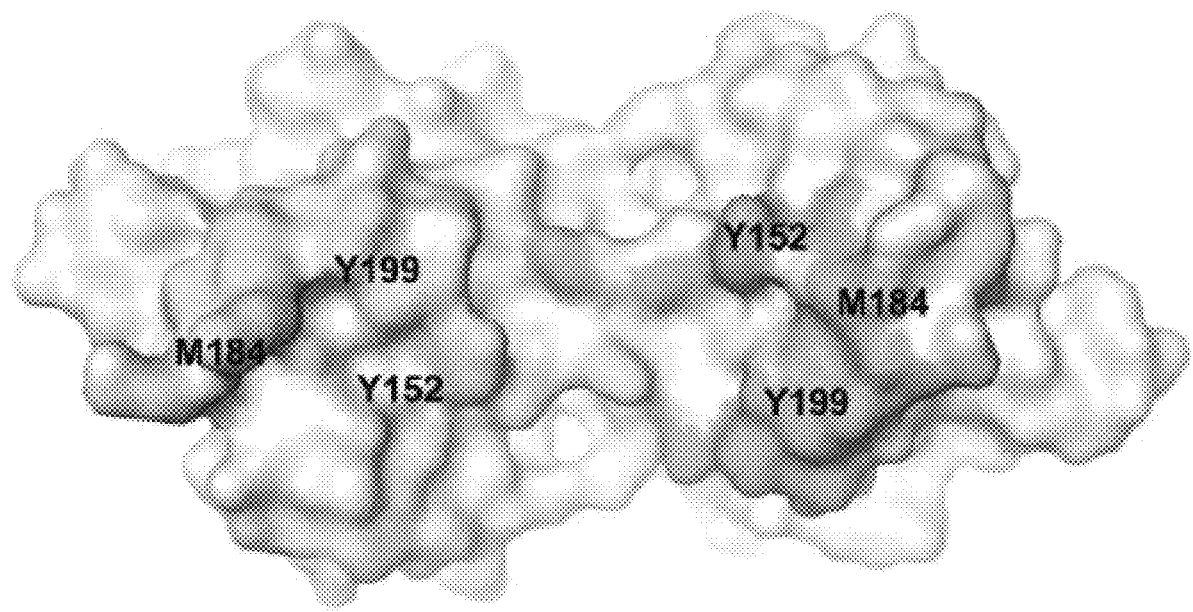
Figure 27H:
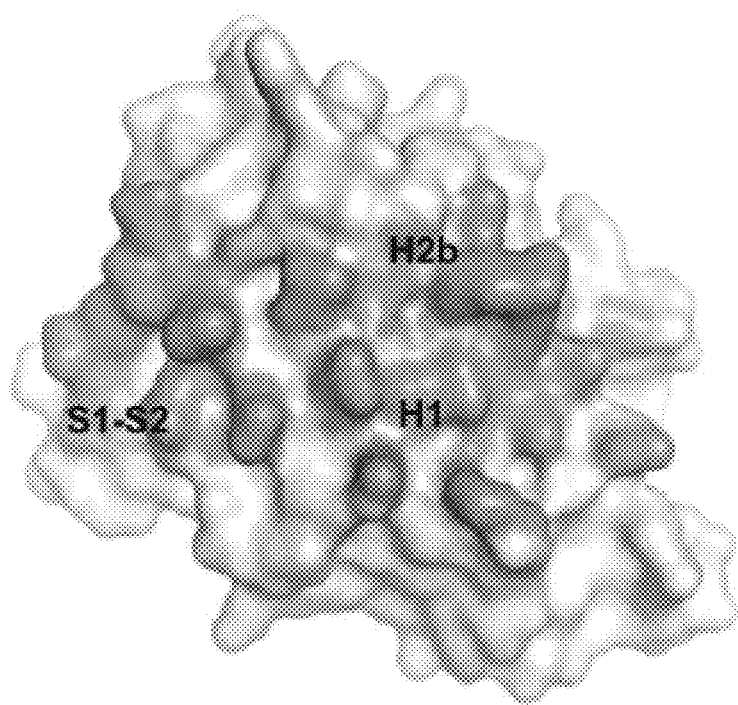
Figure 27I:
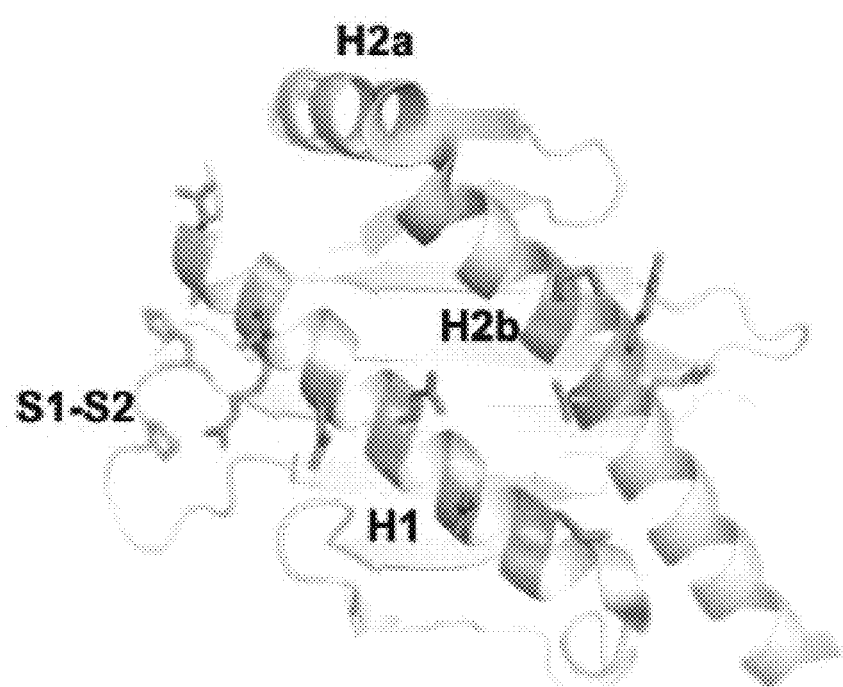
Figure 27J:
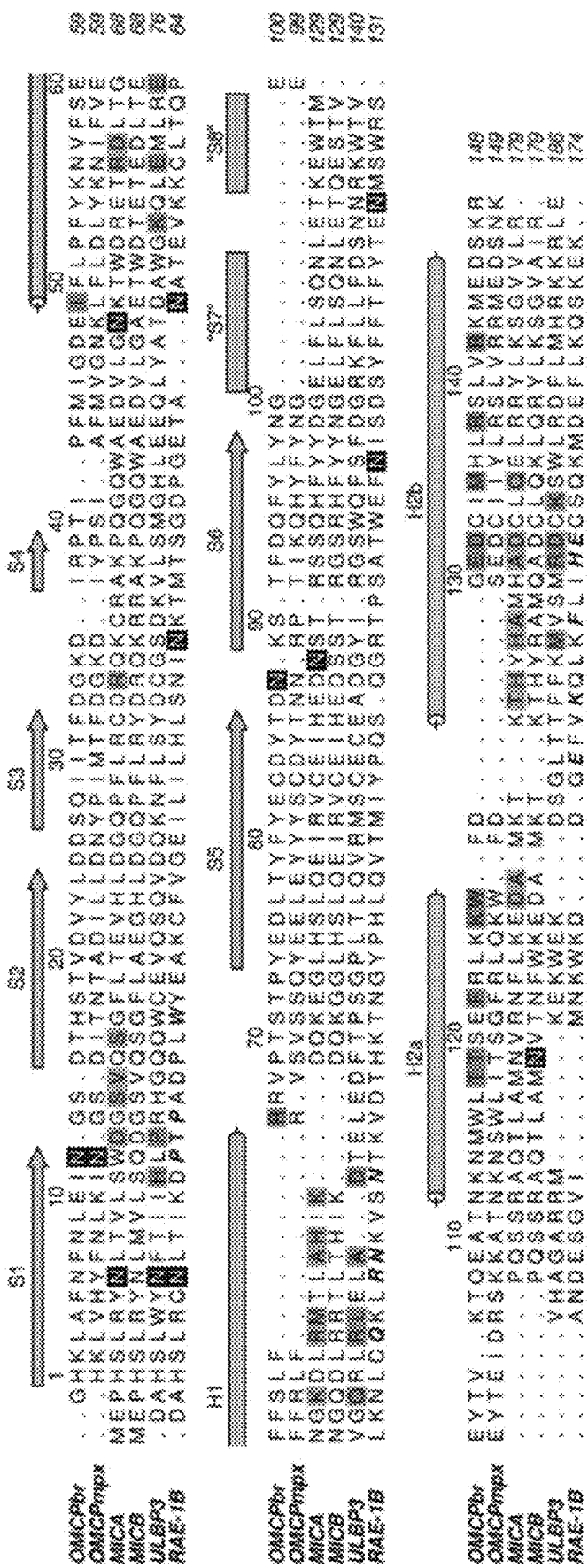

FIG. 27A, FIG. 27B, FIG. 27C, FIG. 27D, FIG. 27E, FIG. 27F, FIG. 27G, FIG. 27H and FIG. 27I depict a novel NKG2D binding adaptation and FIG. 27J depicts secondary structure alignment of various NKG2DLs. Surface representation of NKG2D and surface and cartoon representations of OMCP, MICA and ULBP3. Buried surface areas for $NKG2D^A$ and $NKG2D^B$ are indicated in cyan and yellow, respectively. Buried surface area by NKG2D is indicated for OMCP (magenta), MICA (green), and ULBP3 (orange). The core binding residues of NKG2D and NKG2D-binding elements of NKG2DLs are indicated. NKG2D (FIG. 27A) and OMCP (FIG. 27B, FIG. 27C) binding interactions. NKG2D (FIG. 27D) and MICA (FIG. 27E, FIG. 27F) binding interactions. NKG2D (FIG. 27G) and ULBP3 (FIG. 27H, FIG. 27I) binding interactions. (FIG. 27J) Alignment by secondary structure of NKG2DLs (PDB ID: OMCP (4FFE), MICA (1HYR), MICB (1JE6), ULBP3 (1KCG) and RAE-1β (1JSK)). Contact residues are indicated for OMCP (magenta), MICA (green), ULBP3 (orange) and RAE-1β (bold and italics). Secondary structure elements are noted above the sequence (arrow for beta sheets, cylinders for alpha helices). Predicted glycan sites are highlighted in black. OMCPbr=SEQ ID NO:13; OMCPmpx=SEQ ID NO:14; MICA=SEQ ID NO:15; MICB=SEQ ID NO:16; ULBP3=SEQ ID NO:17; and RAE-1B=SEQ ID NO:18

Figure 28A:
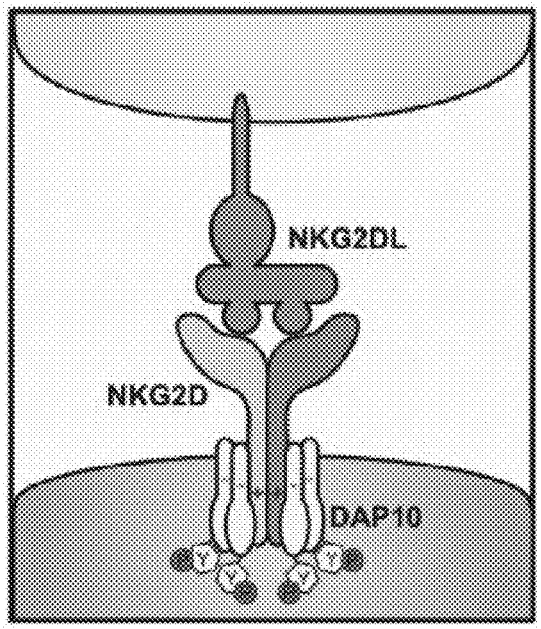
Figure 28B:
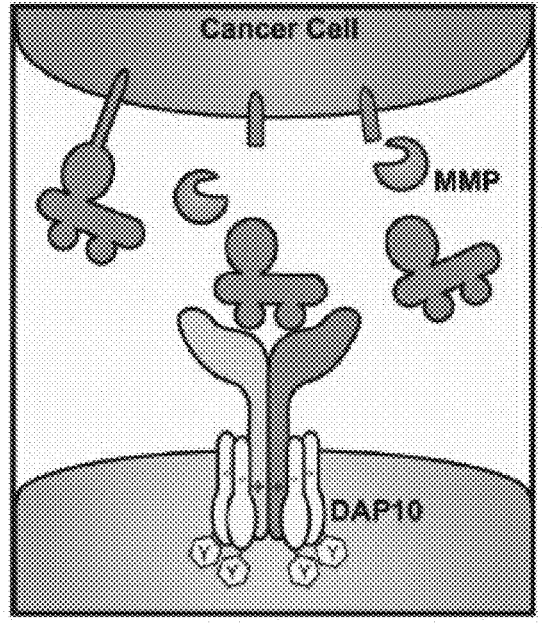
Figure 28C:
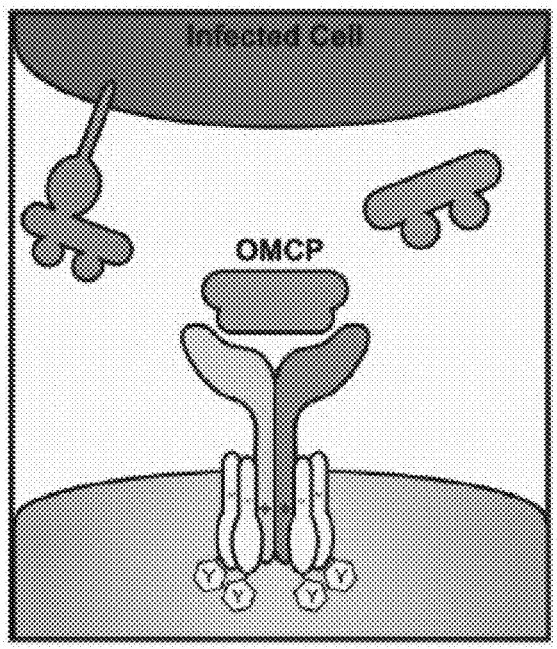
Figure 28D:
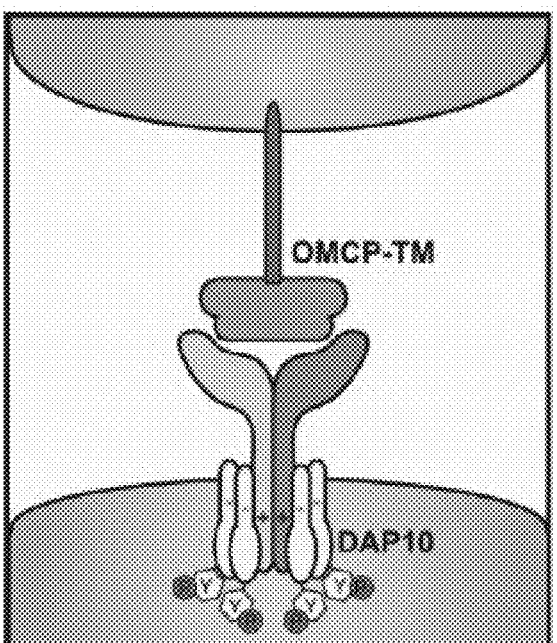
Figure 28E:
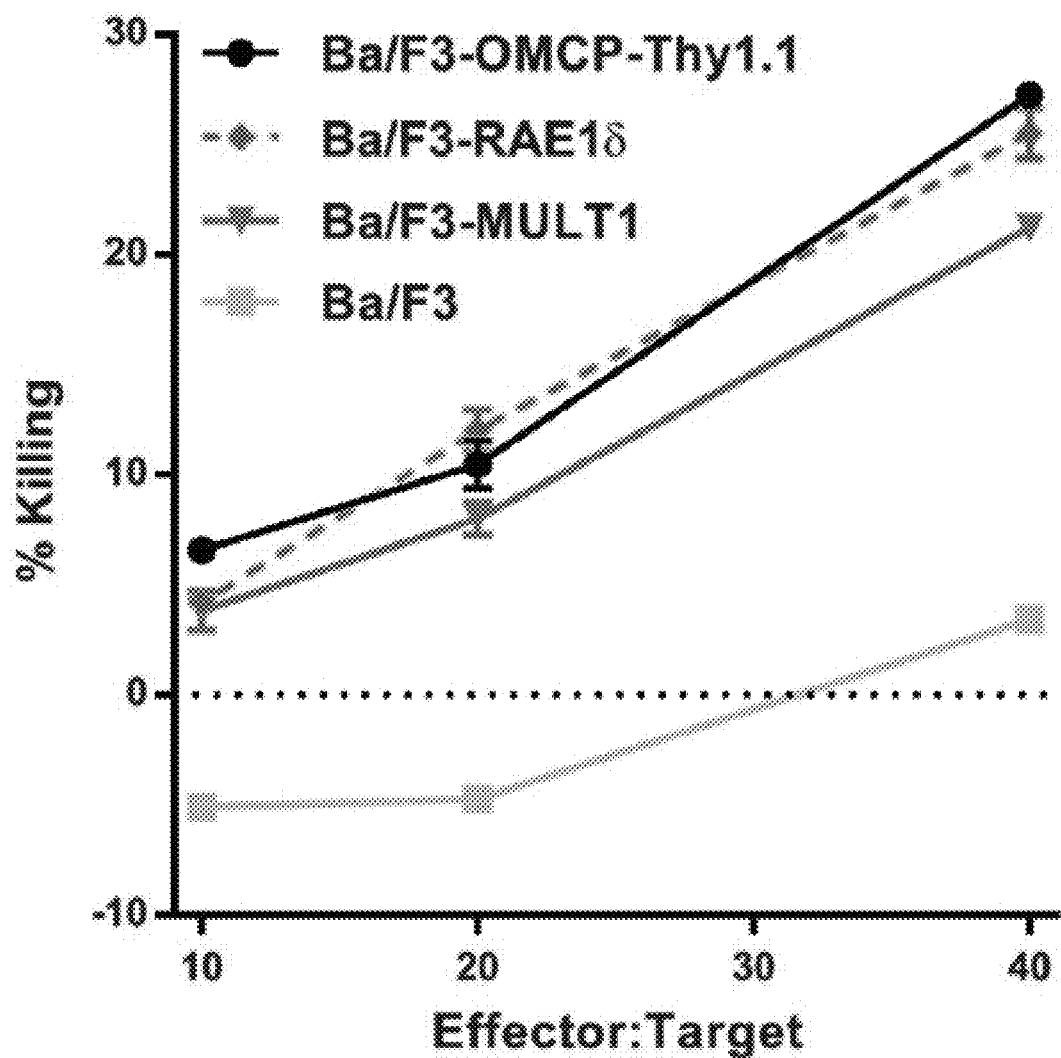
Figure 29A:
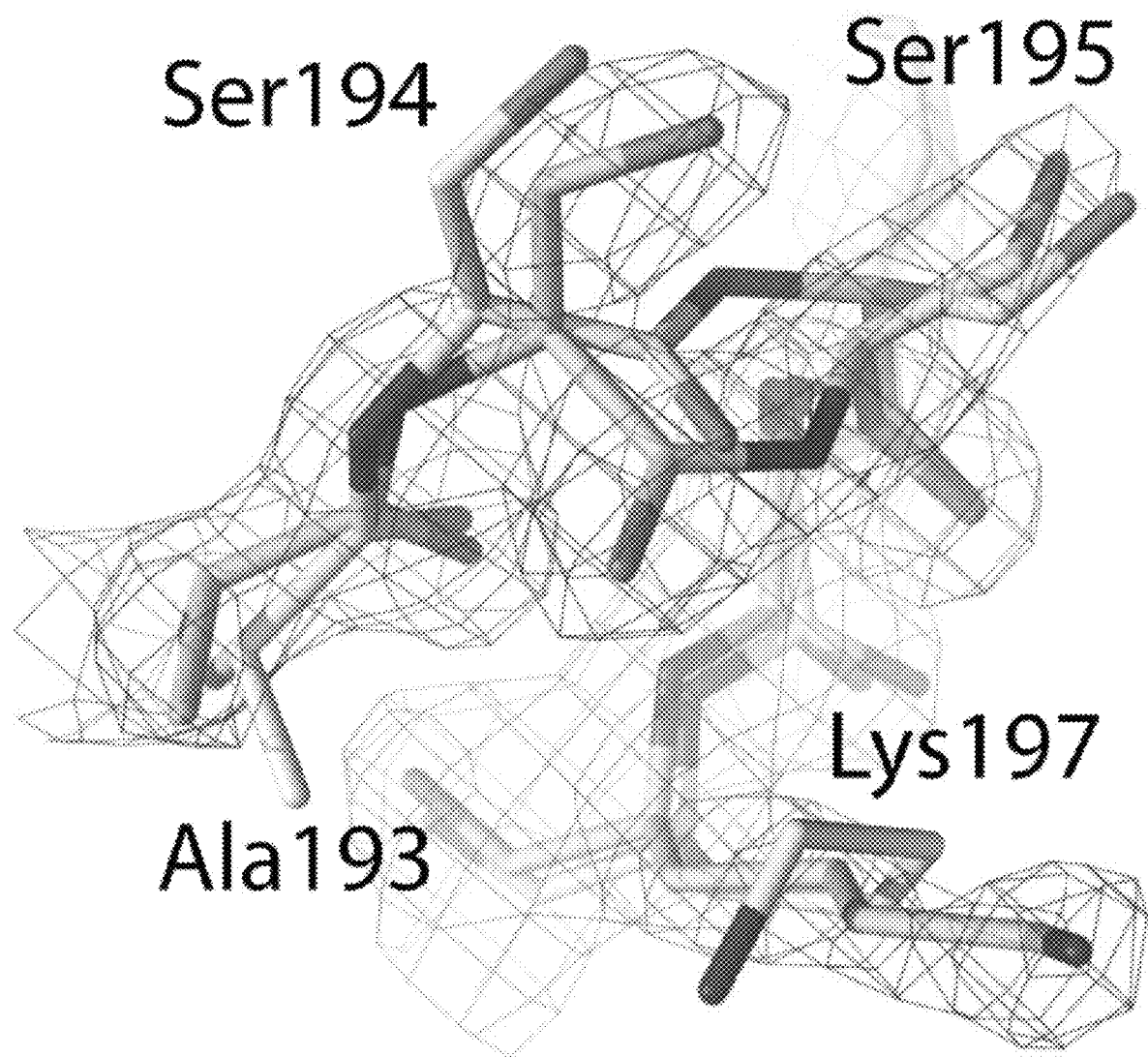
Figure 29B:
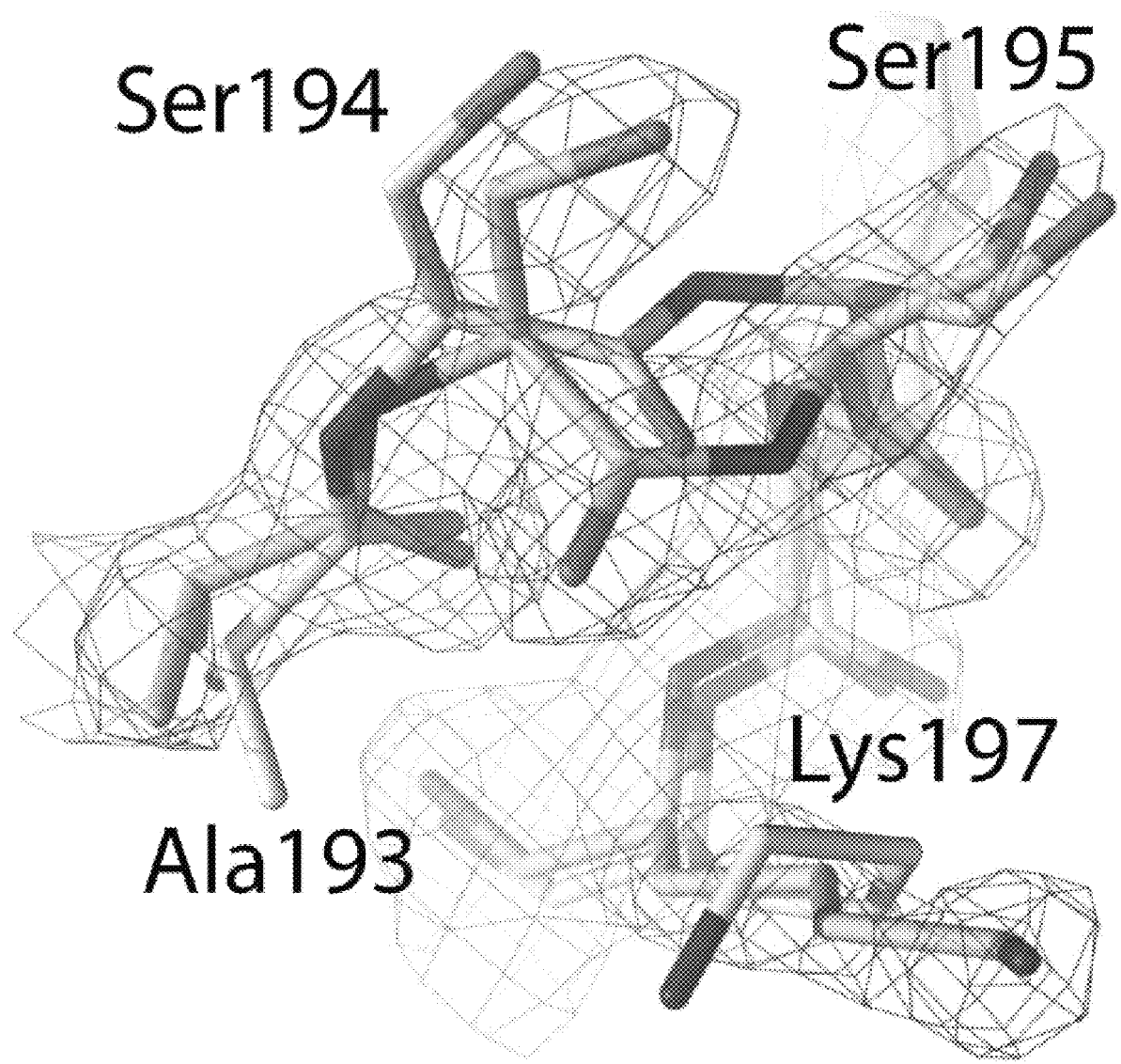

FIG. 28A, FIG. 28B, FIG. 28C, FIG. 28D and FIG. 28E depict activation of NK cells by cell-associated OMCP. Model depicting NKG2D interaction with (FIG. 28A) host, (FIG. 28B) cancer-induced, (FIG. 28C) viral, or (FIG. 28D) chimeric ligands. Binding interactions that lead to NKG2D-mediated signaling are indicated by DAP10 tyrosine phosphorylation (red filled circles). (FIG. 28E) IL2-activated splenocytes were used as cytotoxic effectors against stably transduced Ba/F3 cell lines. Splenocytes were activated with 200 U/ml of IL2 for 24 hours. Labeled target cells were co-incubated with activated splenocytes for 4 hours at effector:target ratios of 10:1, 20:1, and 40:1. Killing was measured by incorporation of 7AAD by CFSE-labeled target cells using flow cytometry. Representative data from five independent experiments is shown FIG. 29A and FIG. 29B depict the electron density supporting a cis peptide conformation. Stereo view of the β5-β6 loop of hNKG2D. Residues 193-Ala-Ser-Ser-Phe-Lys-197 (SEQ ID NO:33) is displayed for the OMCP-hNKG2D structure (yellow) and the structure of hNKG2D alone (grey). The 2Fo-Fc map for OMCP-hNKG2D is displayed at 2a.

Figure 30A:
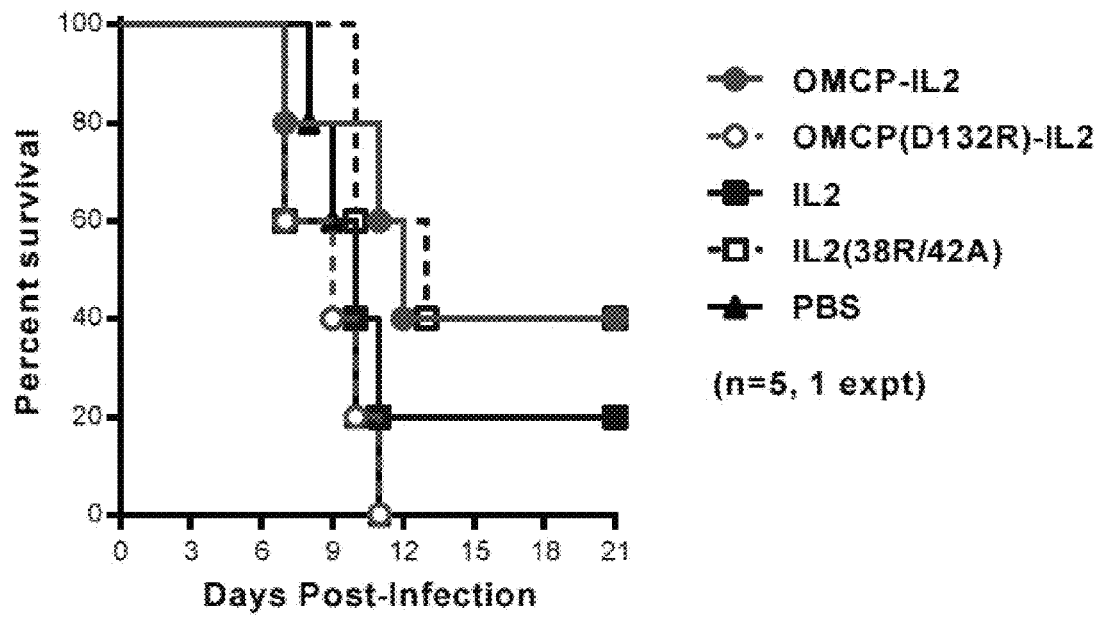
Figure 30B:
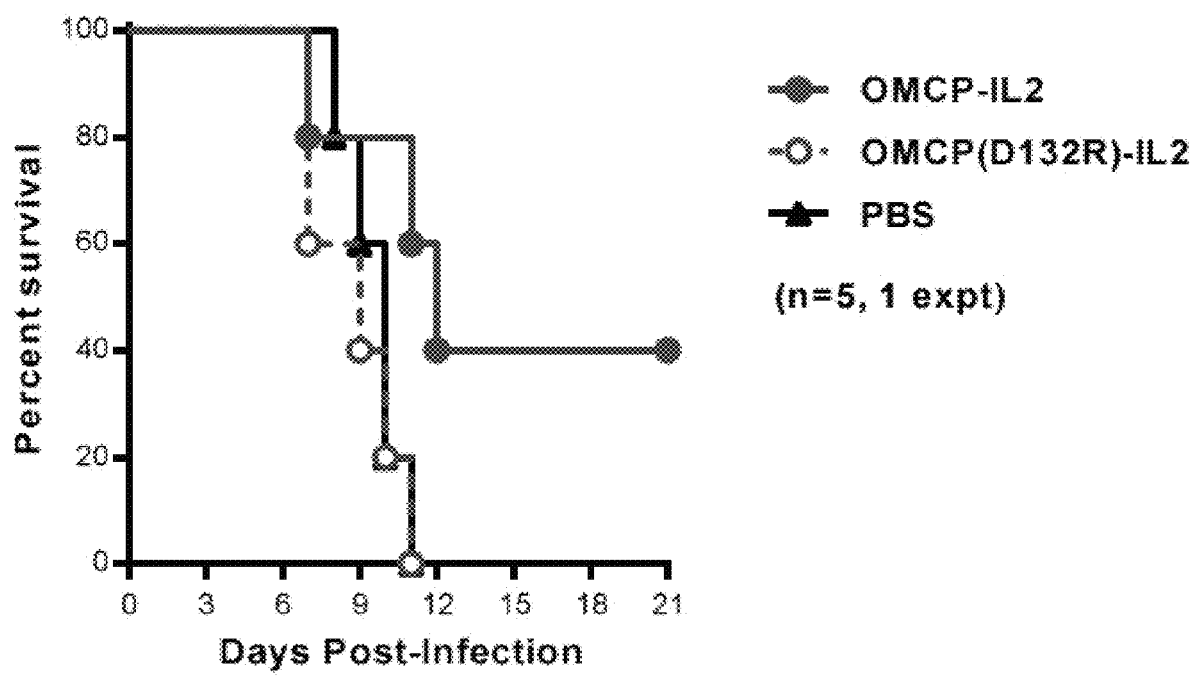

FIG. 30A and FIG. 30B depicts graphs showing survival curves of C57Bl/6J mice following infection with West Nile Virus (WNV). Mice were treated with OMCP-IL2, OMCP (D132R)-IL2, IL2, IL(38R/42A) or PBS after infection with WNV. Infection with OMCP-IL2 and IL2(38R/42A)

resulted in survival beyond 21 days in 40% of mice compared to 0 mice following treatment with PBS or OMCP (D132R)-IL2.

Figure 31A:
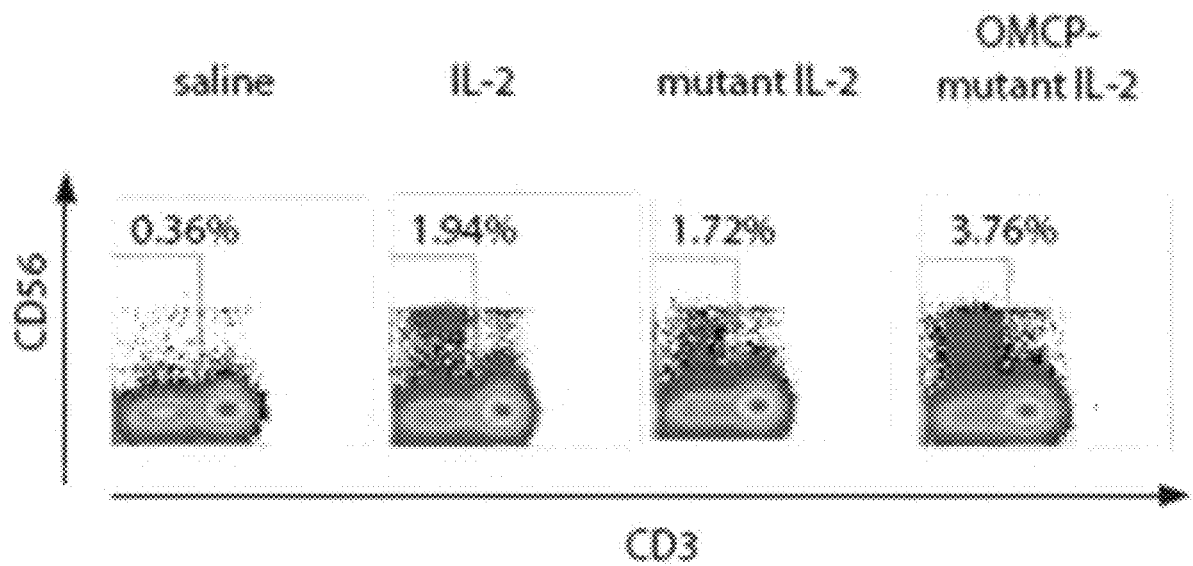
Figure 31B:
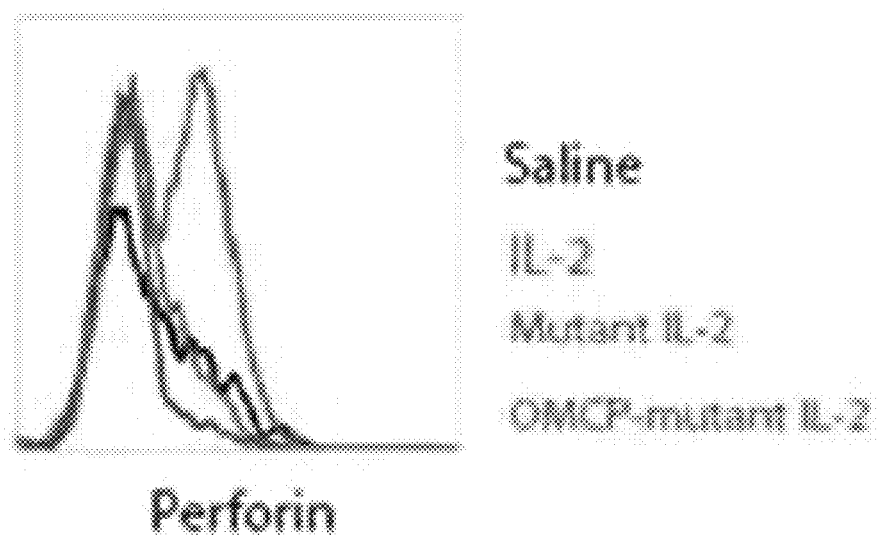
Figure 31C:
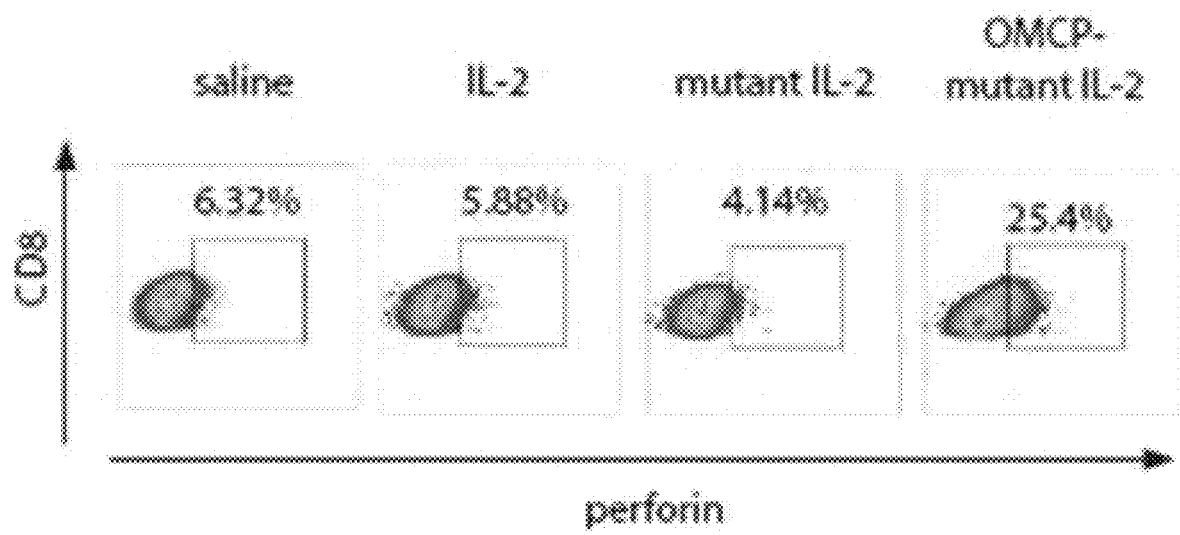
Figure 31D:
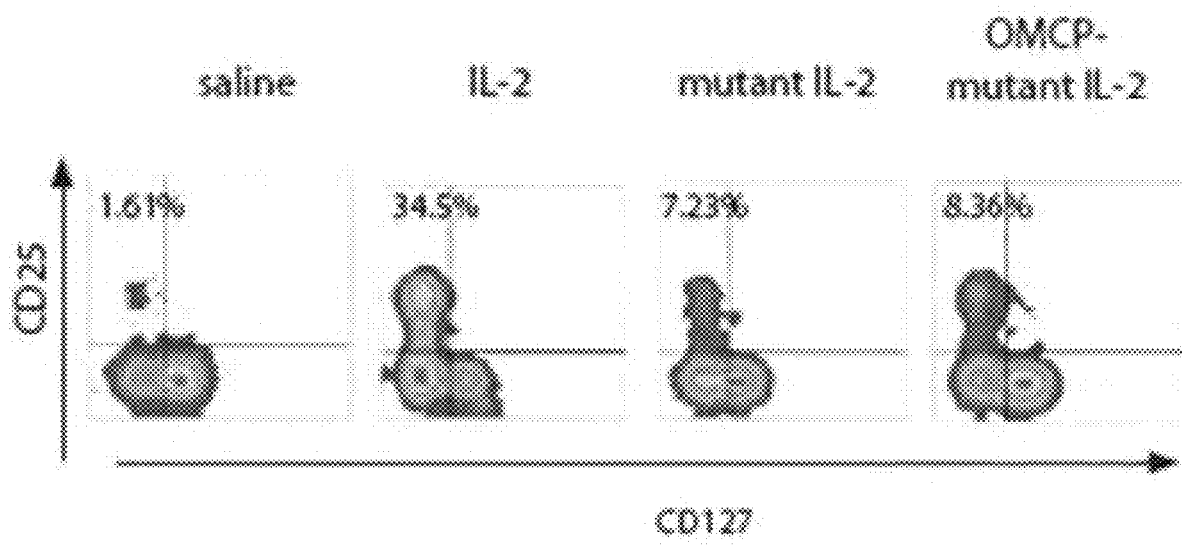

FIG. 31A, FIG. 31B, FIG. 31C and FIG. 31D depicts flow cytometry data showing that OMCP-Mutant IL2 activates NK and CD8+ T cells. FIG. 31A shows that a relatively higher proportion of NK cells was evident in the OMCP-mutant IL2 group. FIG. 31B shows that perforin levels were higher in OMCP-mutant IL2 treated NK cells (red) compared to saline (black), IL2 (blue) or mutant IL2 (green) treated ones. FIG. 31C shows that similar to NK cells, higher intracellular levels of perforin were evident in CD8+ T cells treated with OMCP-mutant IL2 compared to other conditions. FIG. 31D shows that when gating on CD4+Foxp3+CD45RA− T cells a relatively higher proportion of activated CD25+CD127− regulatory T cells was evident in IL2 treated peripheral blood lymphocyte cultures compared to other conditions.

Figure 32:
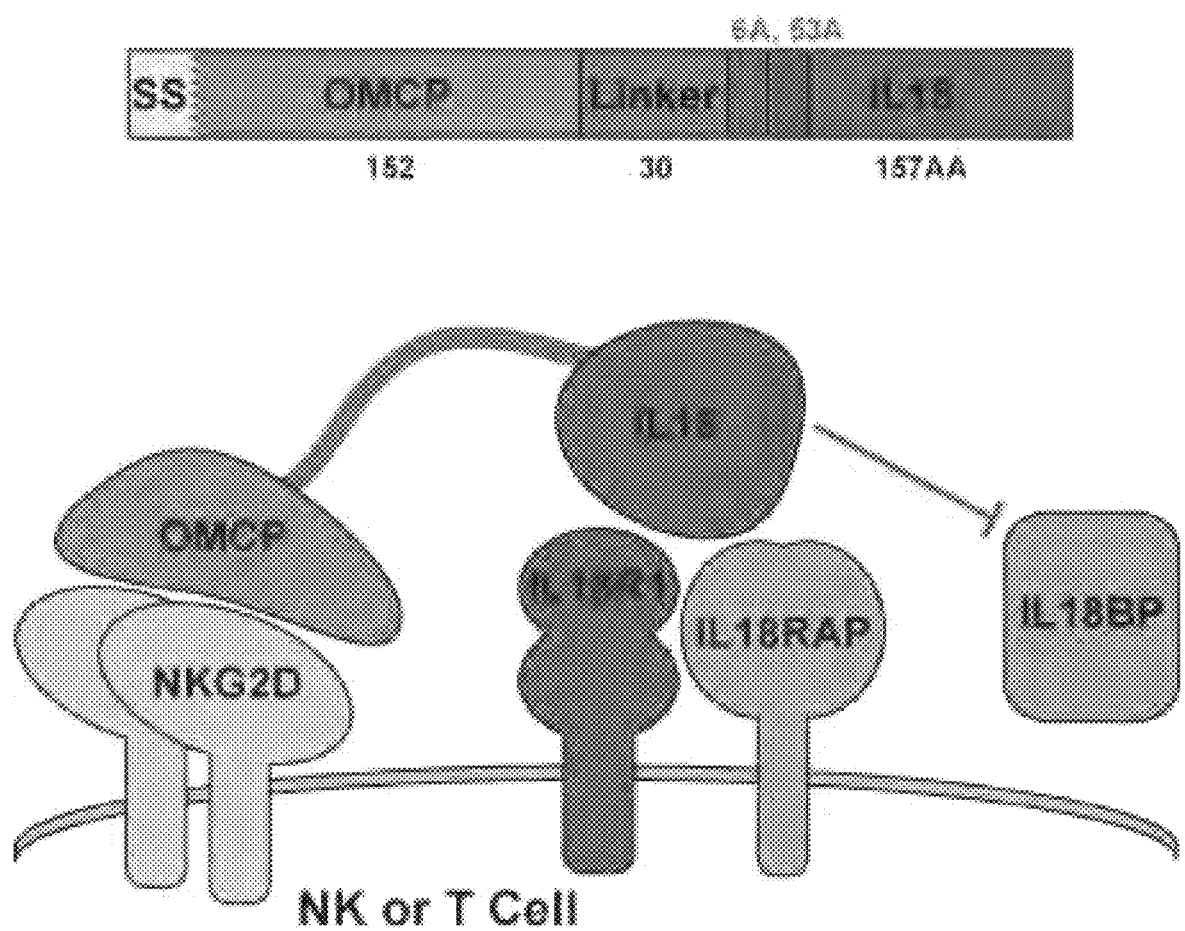

FIG. 32 depicts a schematic of the various IL18-OMCP constructs. Three versions were made, each having OMCP attached to either WT human IL-18, WT murine IL-18, or mutant human IL-18 (which inhibits its interaction with IL-18BP).

Figure 33:
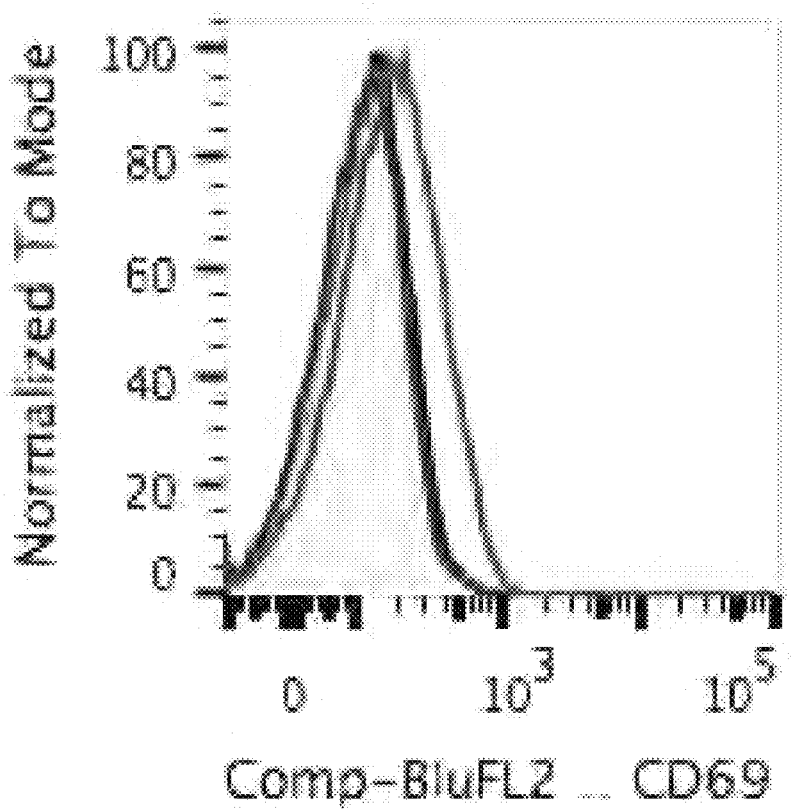

FIG. 33 depicts a flow cytometry plot showing that IL18-OMCP activates NK cells. Peripheral blood lymphocytes were cultured for 48 hours in 4.4 µM of either wild-type IL18 (blue), OMCP-IL18 (red) or saline (black). Activation of CD56+CD3-Natural killer cells, as measured by surface CD69 expression, was superior by OMCP-IL18 compared to wild-type IL18.

Figure 34:
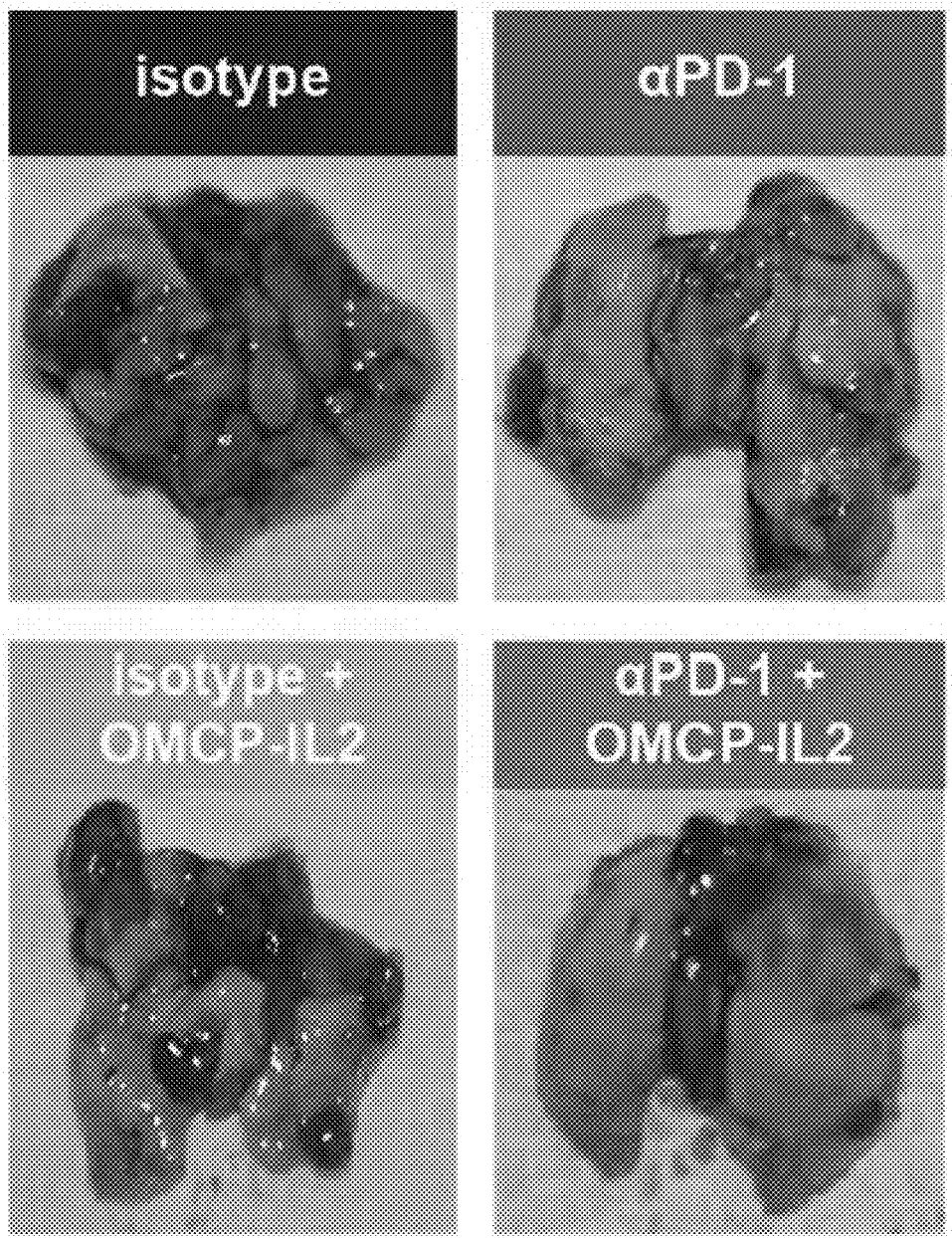

FIG. 34 depicts lungs of mice cohorts treated with isotype antibody, anti-PD-1 antibody, OMCP-IL2 and isotype antibody, and anti-PD-1 antibody and OMCP.

Figure 35:
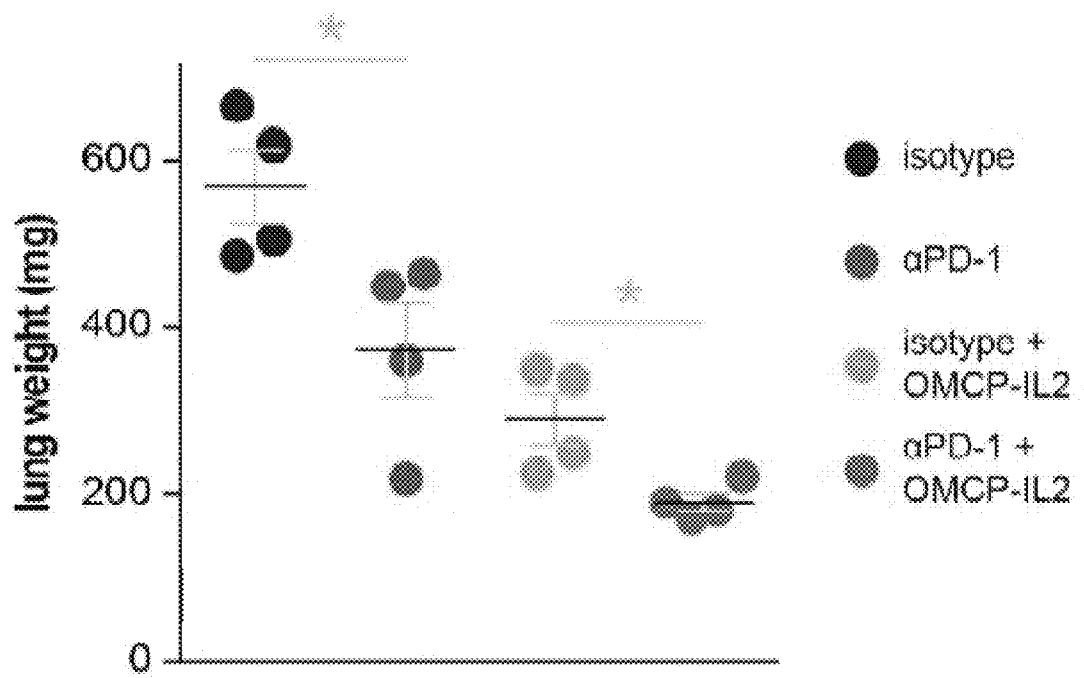

FIG. 35 shows lung weights as measured from the lungs from the mice cohorts of FIG. 34.

Figure 36:
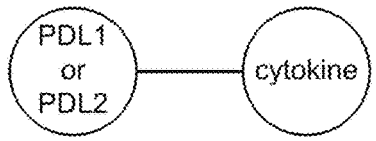
Figure 36:
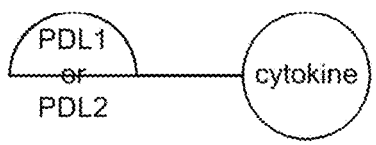
Figure 36:
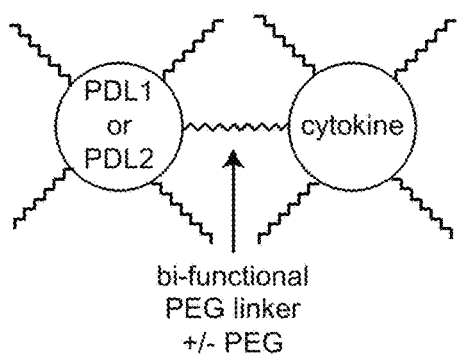
Figure 36:
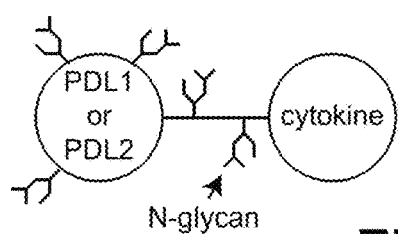
Figure 36:
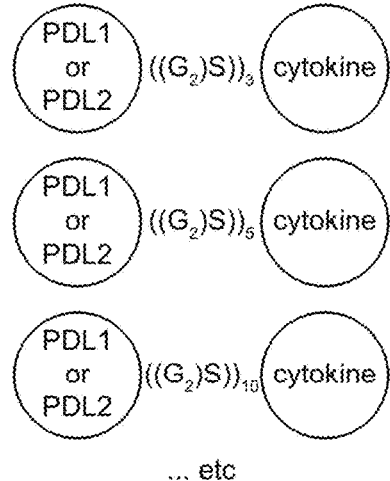
Figure 36:
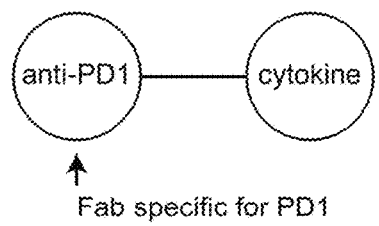
Figure 36:
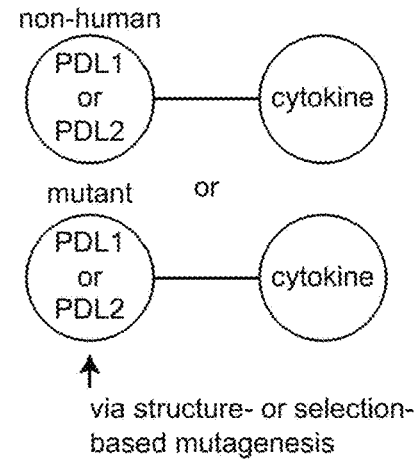
Figure 36:
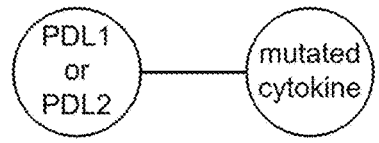

FIG. 36 depicts various embodiments of the invention. 1. A composition is depicted comprising full-length PDL1 or PDL2 linked to a cytokine. 2. A composition is depicted comprising a PDL1 or PDL2 derived peptide linked to a cytokine. 3. A composition is depicted comprising PDL1 or PDL2 linked to a cytokine, wherein the composition is pegylated. 4. A composition is depicted comprising PDL1 or PDL2 linked to a cytokine, wherein the composition comprises N-glycan. 5. A composition is depicted comprising PDL1 or PDL2 linked to a cytokine, wherein the linker comprises various sequences and various lengths. 6. A composition is depicted comprising a Fab specific antibody for PD1 linked to a cytokine. 7. A composition is depicted comprising various PD1 ligands, including mutated versions of PDL1 or PDL2, linked to a cytokine. PDL1 or PDL2 may be mutated to have improved binding affinity or weaker binding affinity. 8 A composition is depicted comprising PDL1 or PDL2 linked to a mutated cytokine. It is understood that the PDL1 and PDL2 sequence could be from various sources such as human, mouse, or monkey. Also, Fc-chimeras of PDL1 or PDL2 and IL2, and variants thereof may be used.

Figure 37A:
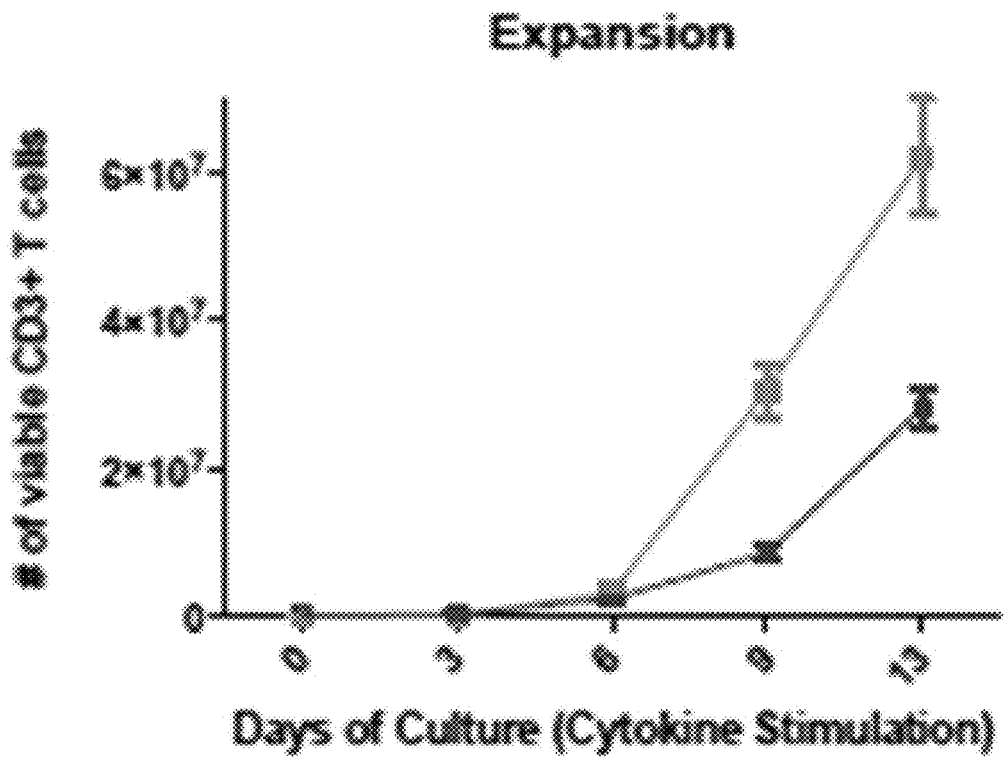
Figure 37B:
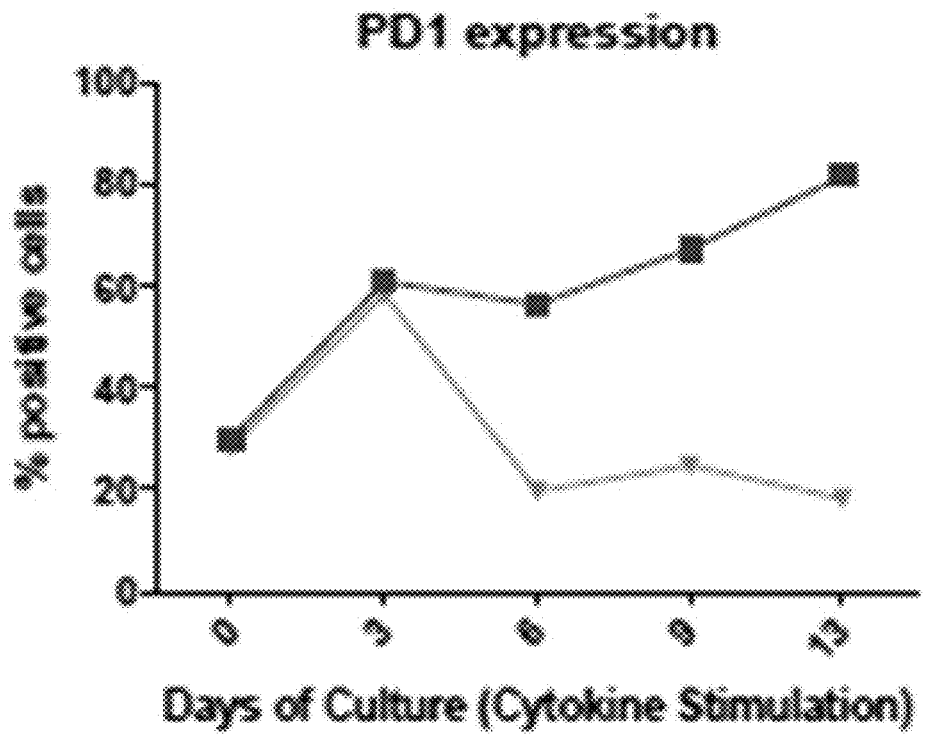
Figure 37C:
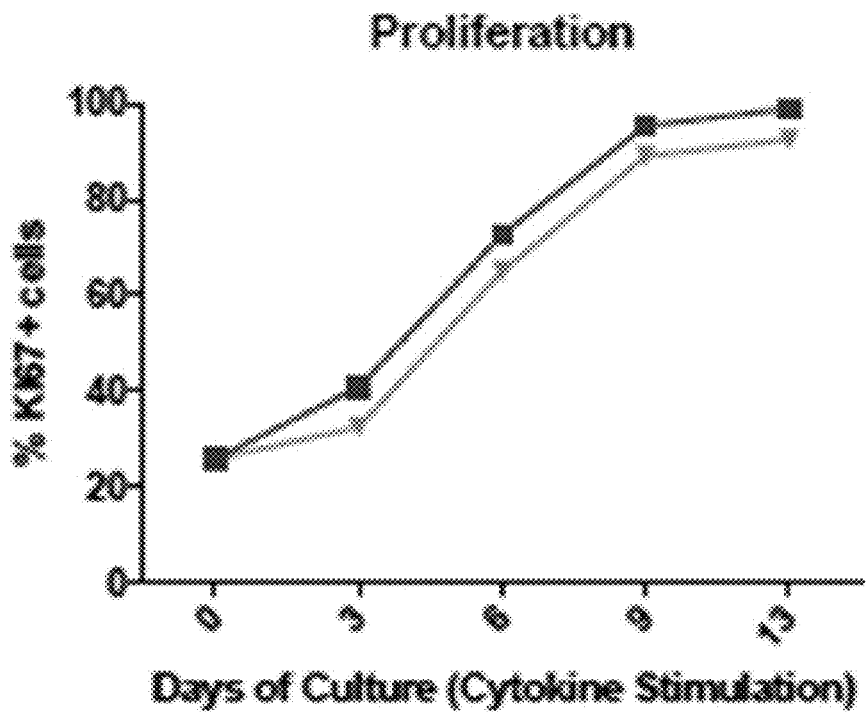
Figure 37D:
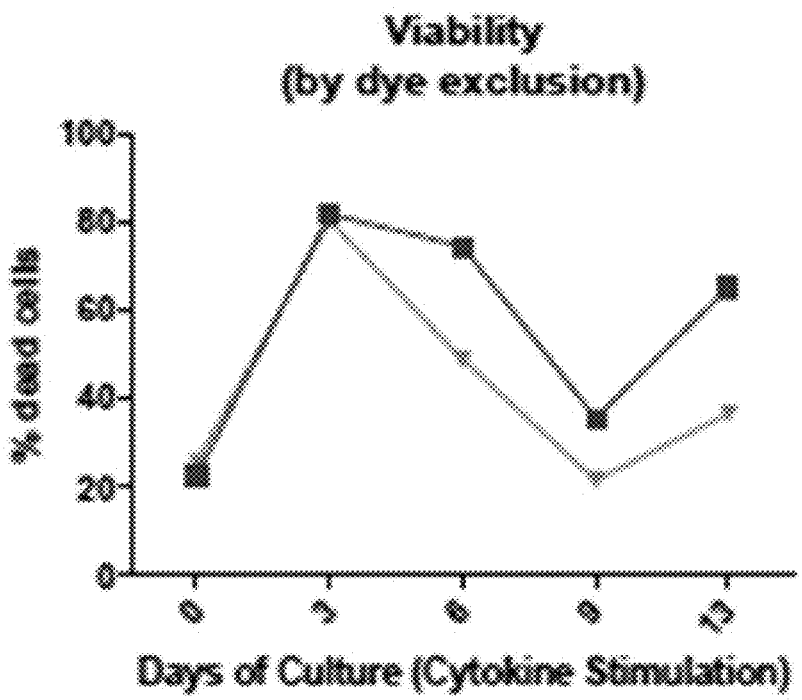
Figure 37E:
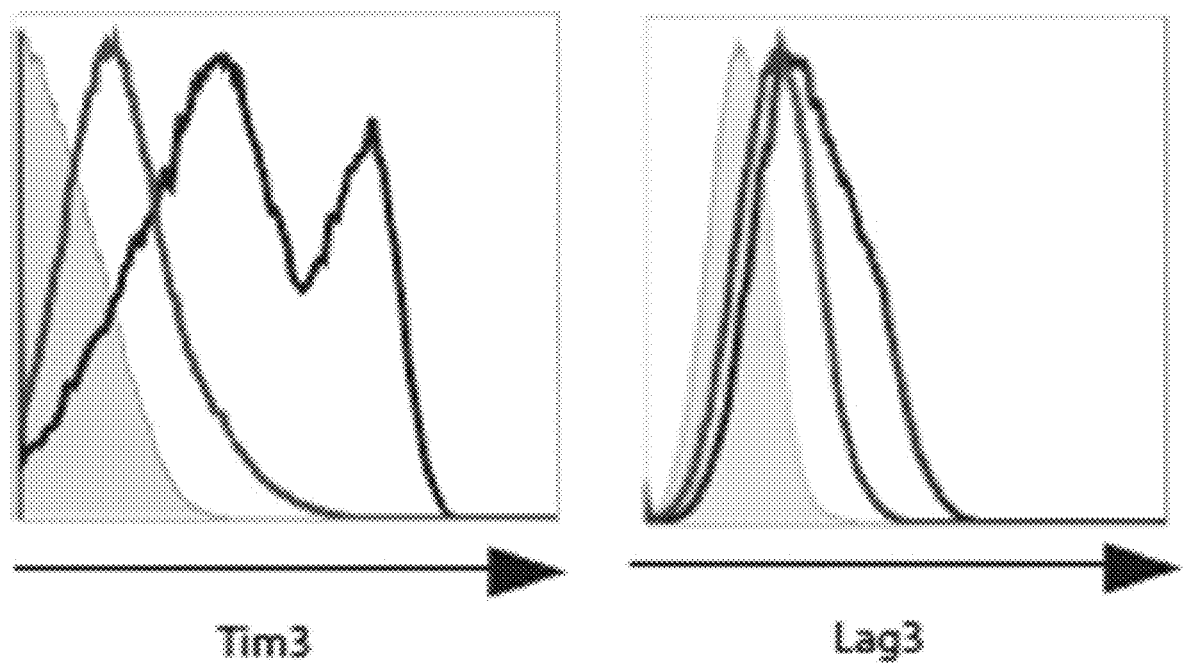

FIG. 37A, FIG. 37B, FIG. 37C, FIG. 37D and FIG. 37E depict graphs showing NK cell physiology after in vitro expansion with either wild-type IL-2 (blue) or OMCP-mutIL-2 (red). FIG. 37A depicts expansion of NK cells. FIG. 37B depicts PD1 expression on NK cells. FIG. 37C depicts NK cell proliferation. FIG. 37C depicts viability of NK cells. FIG. 37E depicts flow cytometry plots of Tim3 and Lag3 expression on NK cells.

Figure 38A:
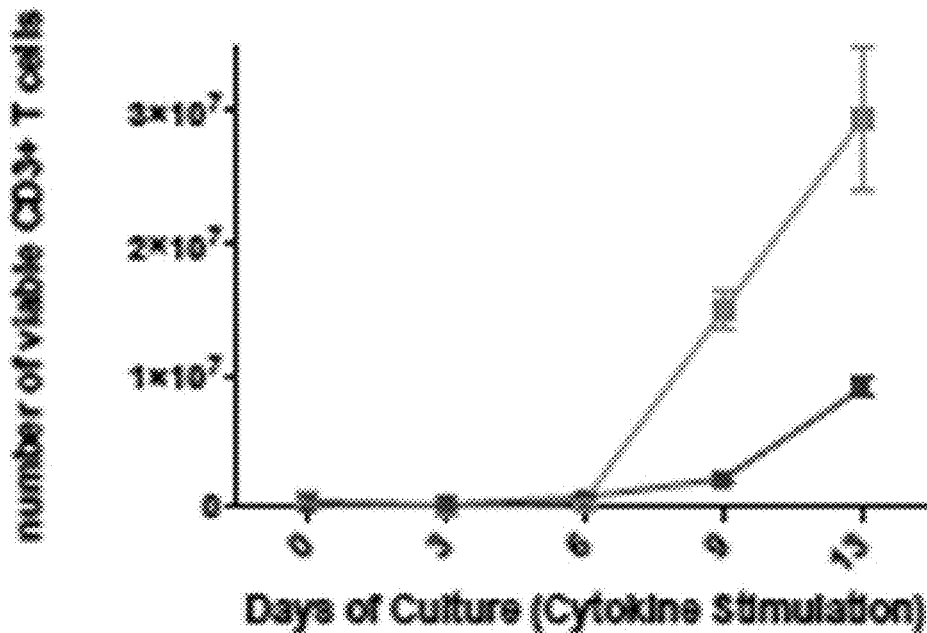
Figure 38B:
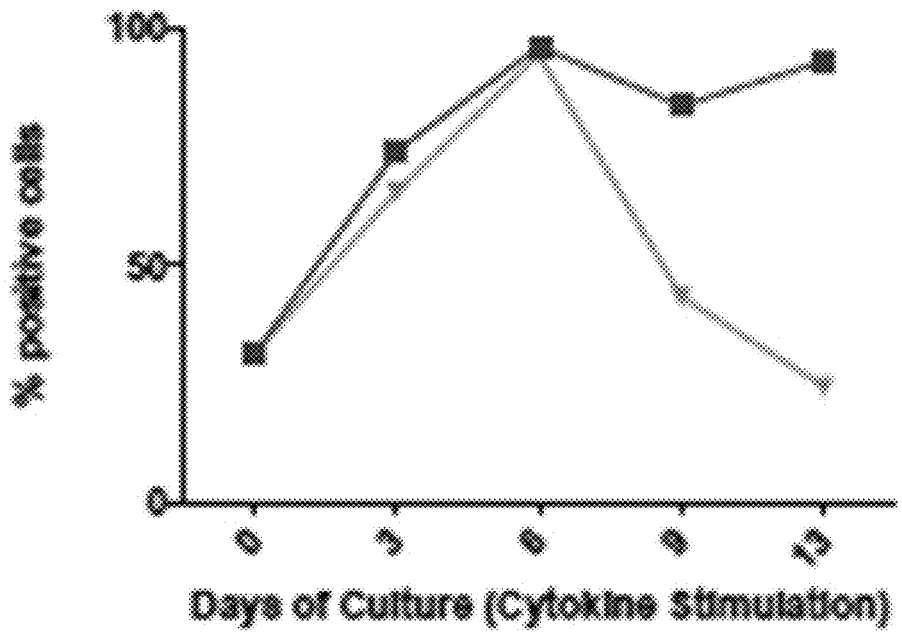
Figure 38C:
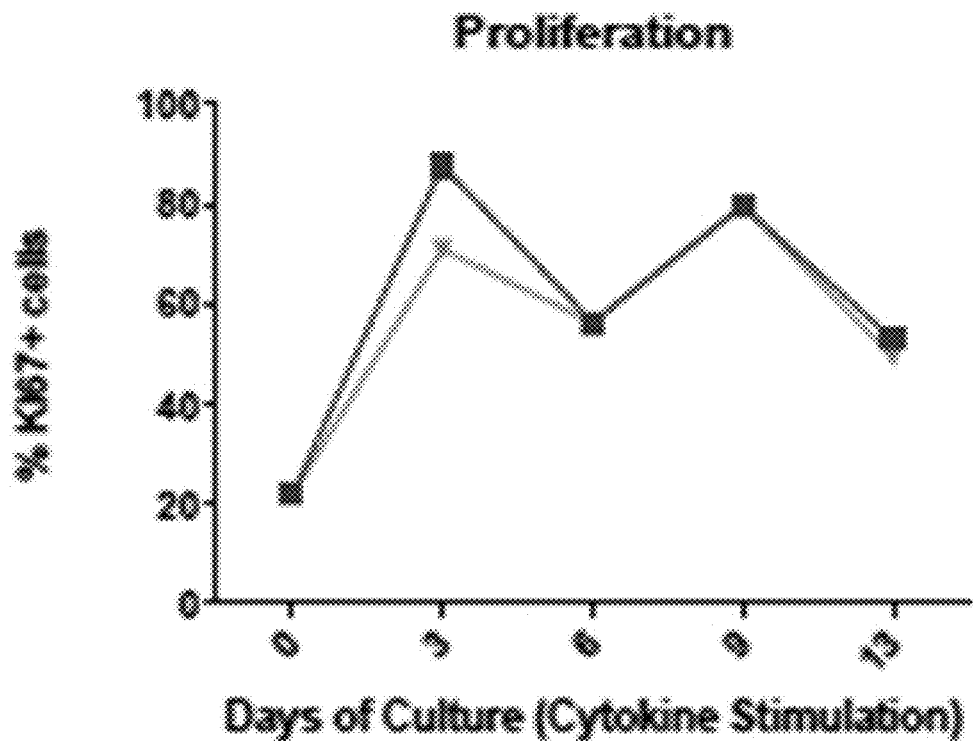
Figure 38D:
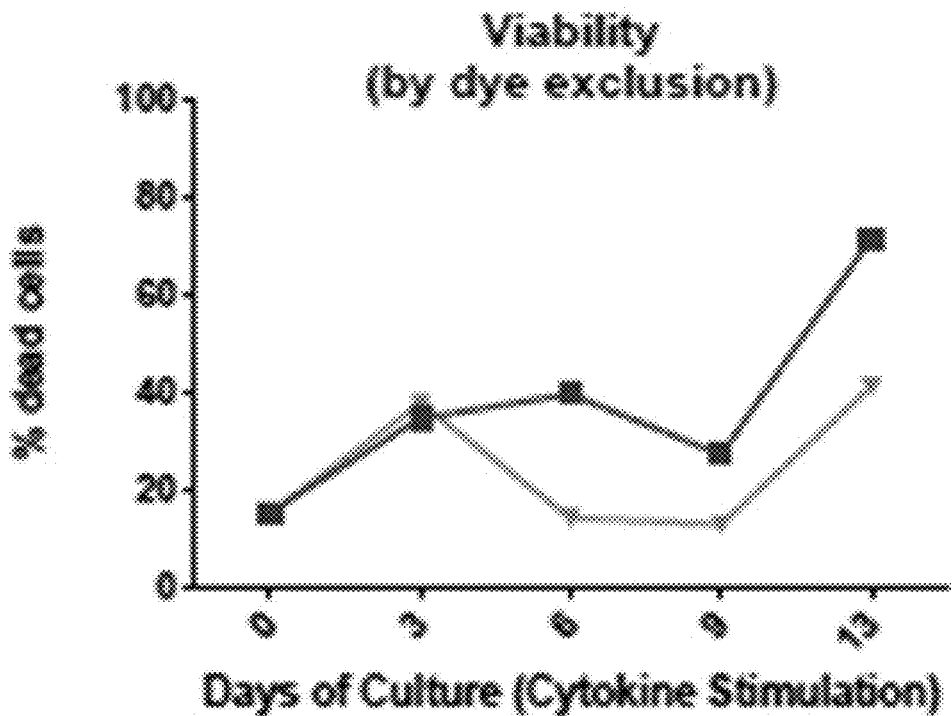
Figure 38E:
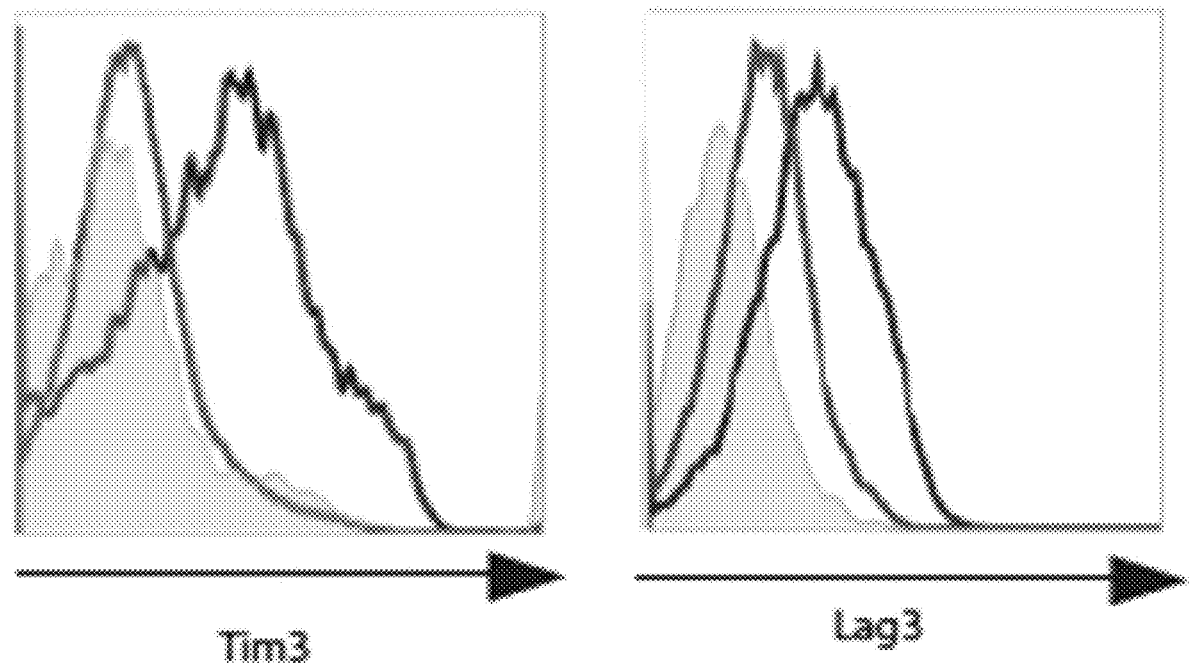

FIG. 38A, FIG. 38B, FIG. 38C, FIG. 38D and FIG. 38E depict graphs showing T cell physiology after in vitro expansion with either wild-type IL-2 (blue) or OMCP-mutIL-2 (red). FIG. 38A depicts expansion of T cells. FIG. 38B depicts PD1 expression on T cells. FIG. 38C depicts T cell proliferation. FIG. 38C depicts viability of T cells. FIG. 38E depicts flow cytometry plots of Tim3 and Lag3 expression on T cells.

Figure 39A:
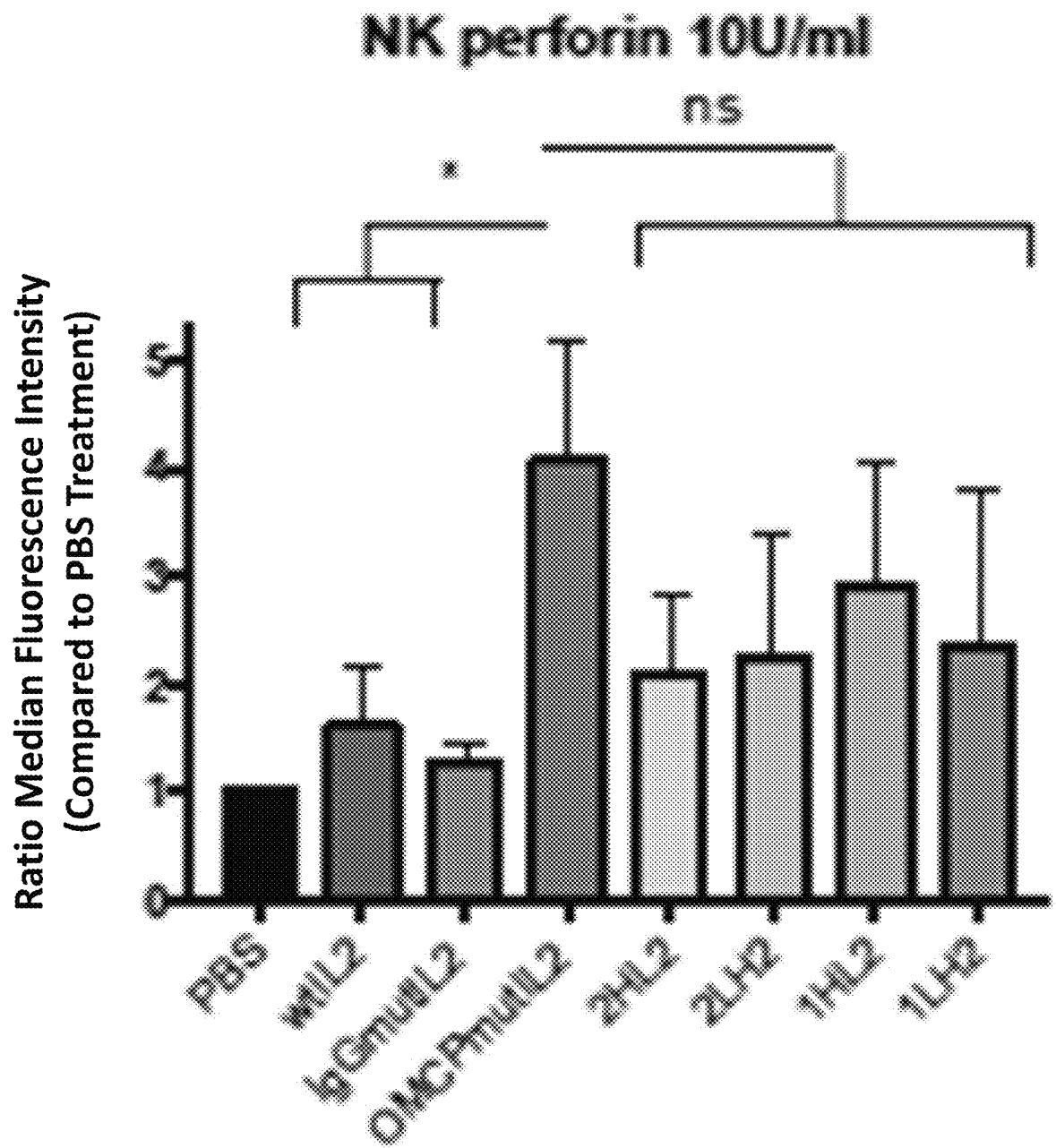
Figure 39B:
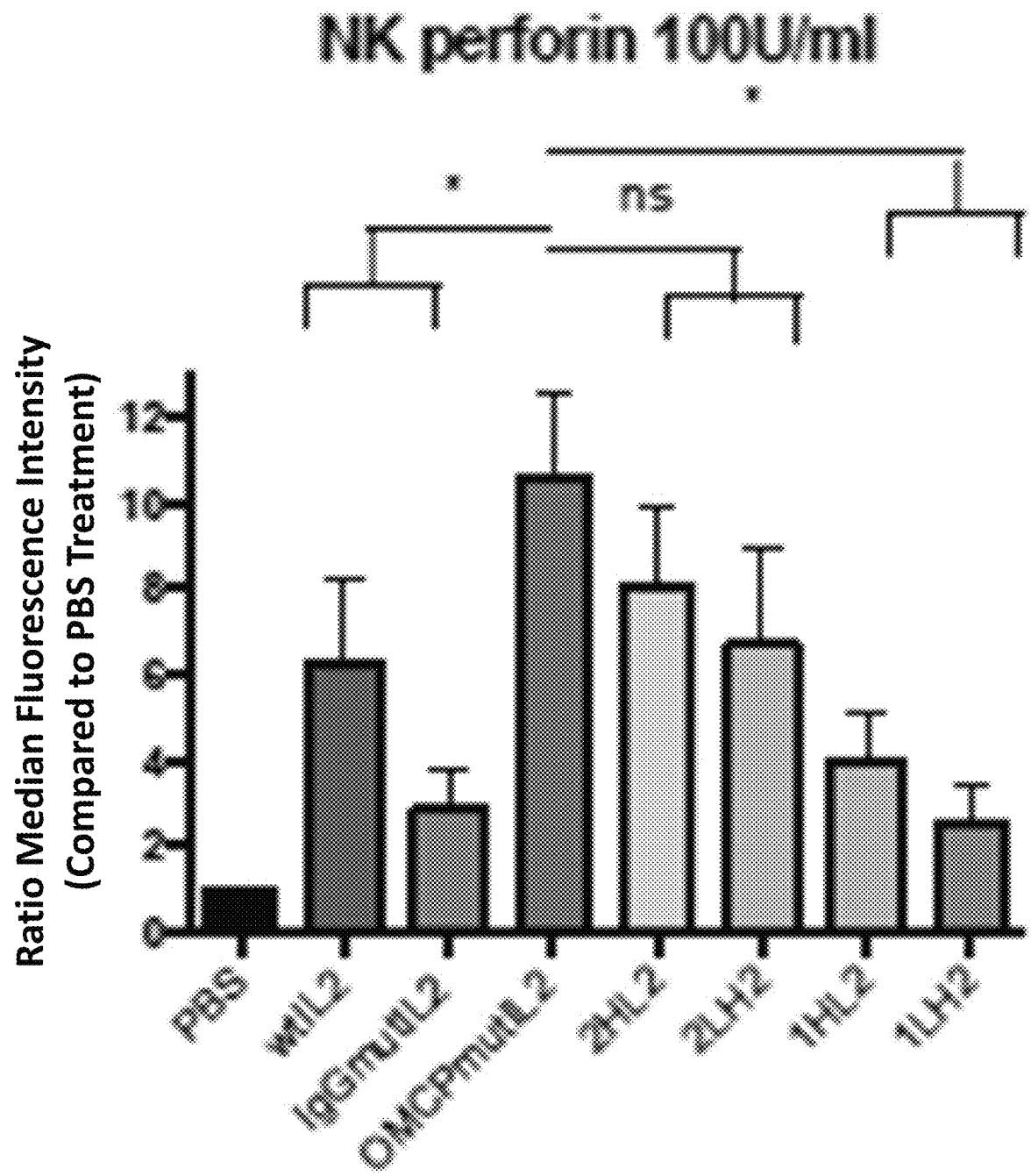
Figure 39C:
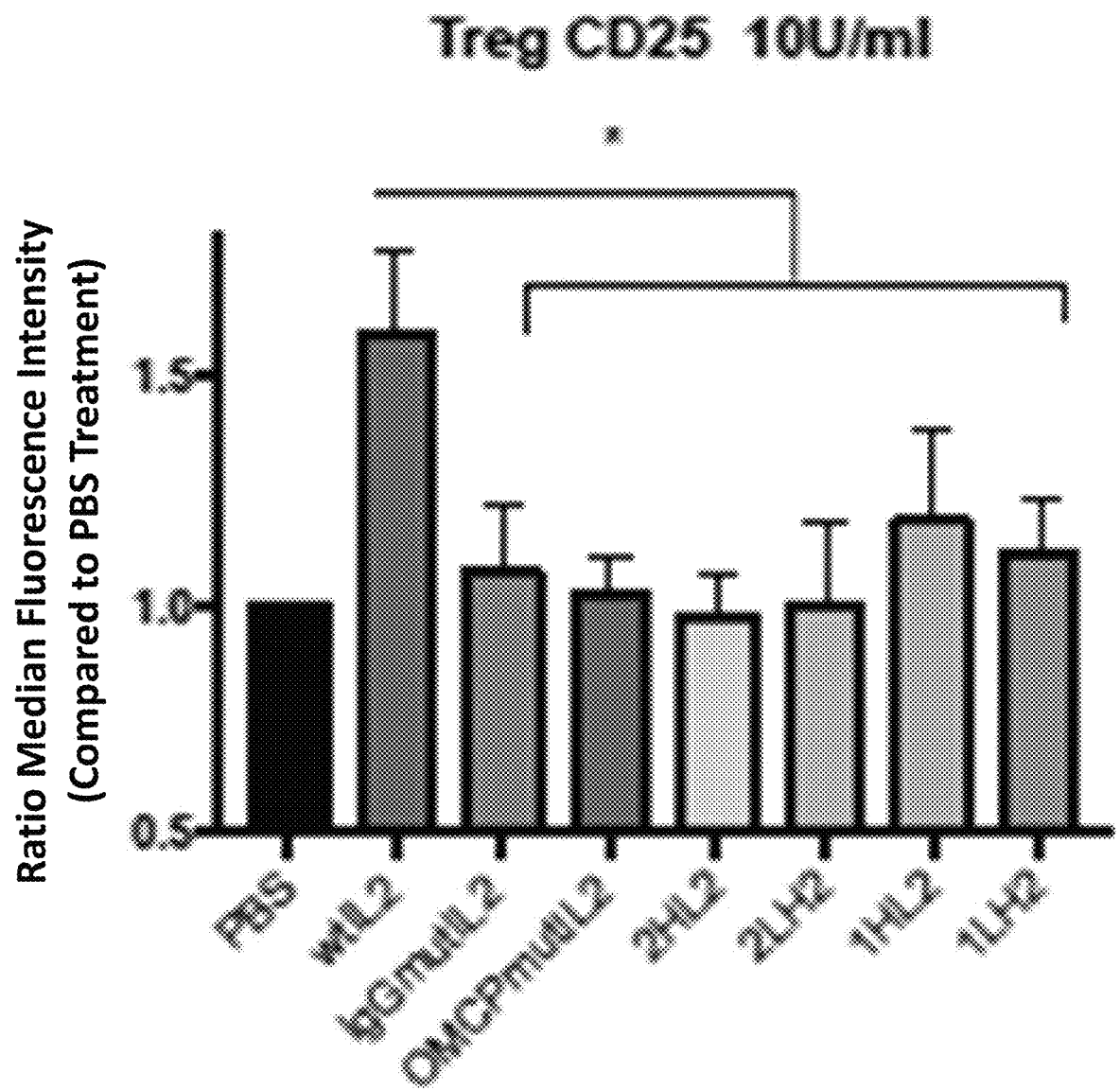
Figure 39D:
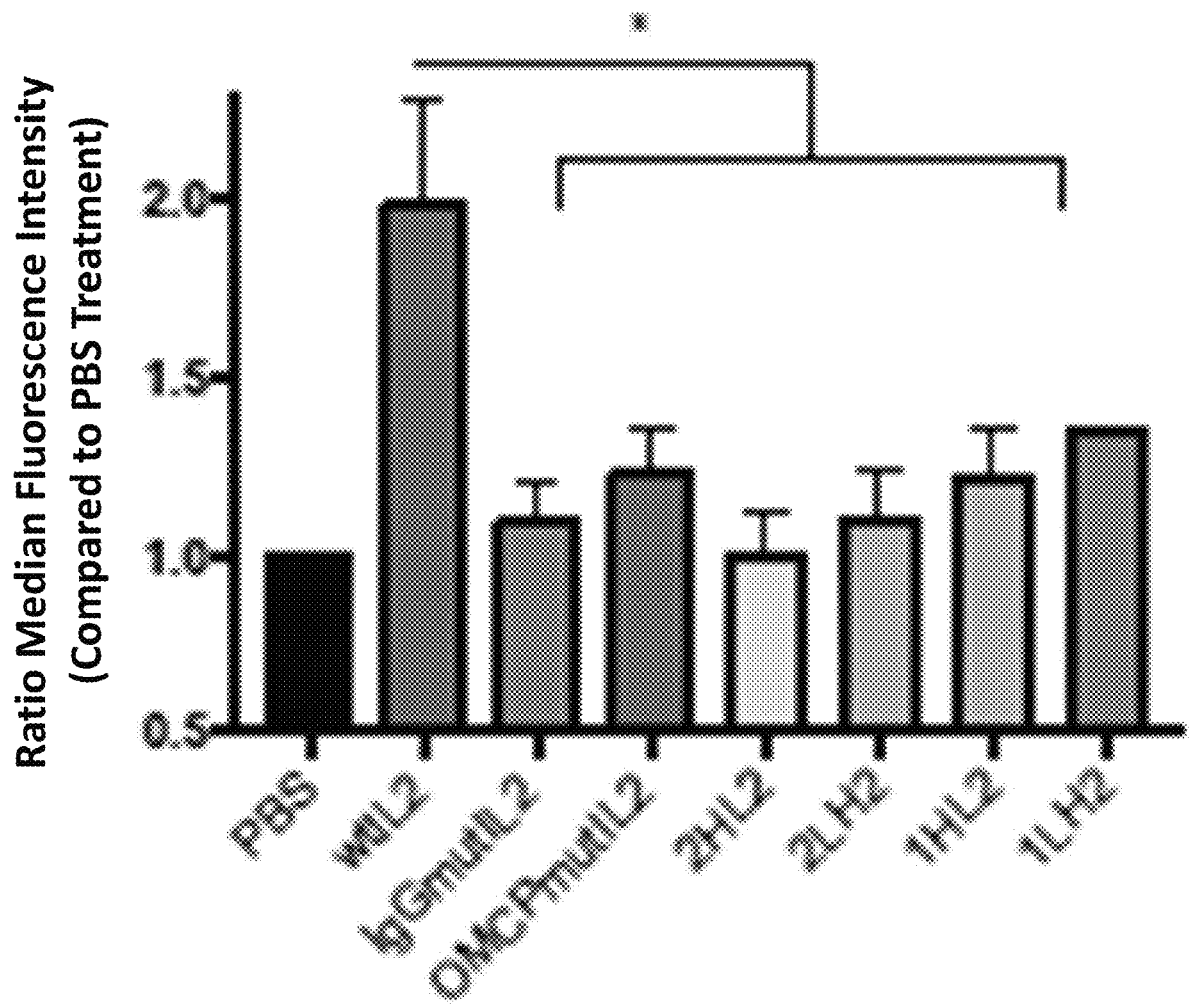

FIG. 39A, FIG. 39B, FIG. 39C and FIG. 39D depict graphs showing anti-NKG2D antibody-mediated delivery of R38A/F42K mutant IL-2. At 10 U/ml OMCP-mutant IL-2 demonstrated a trend toward increased perforin levels over antibody-mediated delivery but it did not reach statistical significance (FIG. 39A). At 100 U/ml NK cells treated with 2HL2 and 2LH2 antibodies synthesized as much perforin as OMCP-mutIL-2 treated cells but lower levels of perforin were evident in 1HL2 and 1LH2 treated NK cells (FIG. 39B). Higher levels of CD25 were evident in wild-type IL-2 treated cultures over all constructs (FIG. 39C, FIG. 39D). Data representative of 4-7 separate experiments. *=p<0.05 and ns=p>0.05.

DETAILED DESCRIPTION OF THE INVENTION

Certain compositions and methods described herein provide for delivery of cytokines to a defined cell via a NKG2D ligand. The fusion of a cytokine to a NKG2D ligand which specifically binds to the NKG2D receptor on the target cell creates an "address" for delivery of the cytokine. Specifically, using the invention disclosed herein, IL2 is directly targeted to lymphocytes, such as natural killer (NK) cells and CD8+ cytotoxic T lymphocytes (CTLs), via an anti-NKG2D antibody. However other NKG2D ligands, including but not limited to the OMCP ligand, ULBP1, ULBP2, ULBP3, H60, Rae-1α, Rae-1β, Rae-1δ, Rae-1γ, MICA, MICB, h-HLA-A, could also be used instead of an anti-NKG2D antibody. Specific delivery of IL2 to lymphocytes will enhance the efficacy of IL2, which could lead to reduced dosages and a significant decrease in associated toxicity. This methodology may be used for other cytokines, including, but not limited to, IL15, IL18, interferons, and members of the tumor necrosis family including, but not limited to TNF-alpha, OX40L, a 4-1BB ligand, TRAIL, Fas ligand, lymphotoxin-alpha, lymphotoxin-beta, CD30L, CD40L, CD27L and RANKL.

Other compositions and methods described herein provide for the activation and recruitment of NK cells and CTLs to a particular cell or tissue via the combination of a ligand to the NKG2D receptor and a targeting molecule. Specifically, in certain aspects, using the invention disclosed herein, NK cells and CTLs are recruited to a target cell via a composition comprising the OMCP ligand or a portion thereof and a targeting molecule. The targeting molecule permits recruitment of the NK cells and CTLs to the particular target cell wherein the OMCP ligand or a portion thereof provides for recruitment, and in some instance, activation, of the NK cells and CTLs resulting in a site-specific response. Targeting molecules may include any molecule that is capable of binding to a target specific to a cell in a disease state or to the extracellular matrix surrounding the diseased cell including, but not limited to, receptor ligands and antibodies. Specific aspects of the invention are described in detail below.

I. Composition

In an aspect, the invention encompasses a composition comprising a cytokine linked to an immune cell surface protein targeting ligand. In a specific aspect, the cytokine is linked to an NKG2D ligand. In another aspect, the cytokine is linked to a ligand targeting the PD1 surface protein. The composition may further comprise a linker to connect the cytokine to the ligand. The cytokine, ligand and linker are described in greater detail below. It should be understood that any of the cytokines described in detail below can be linked to any of the ligands described in detail below in the absence or presence of any of the linkers described below. In another aspect, the invention provides a nucleic acid molecule encoding a cytokine, a ligand, and optionally a linker.

(a) Cytokine

As used herein, a "cytokine" is a small protein (~5-20 kDa) that is important in cell signaling. Cytokines are released by cells and affect the behavior of other cells and/or the cells that release the cytokine. Non-limiting examples of cytokines include chemokines, interferons, interleukins, lymphokines, tumor necrosis factor, monokines, and colony stimulating factors. Cytokines may be produced by a broad range of cells including, but not limited to, immune cells such as macrophages, B lymphocytes, T lymphocytes, mast cells and monocytes, endothelial cells, fibroblasts and stromal cells. A cytokine may be produced by more than one type of cell. Cytokines act through receptors and are especially important in the immune system, modulate the balance between humoral and cell-based immune responses, and regulate maturation, growth and responsiveness of cell populations. Cytokines are important in host responses to infection, immune responses, inflammation, trauma, sepsis, cancer and reproduction. A cytokine of the invention may be a naturally occurring cytokine or may be a mutated version of a naturally occurring cytokine. As used herein, "naturally occurring", which may also be referred to as wild-type, includes allelic variances. A mutated version or "mutant" of a naturally occurring cytokine refers to specific mutations that have been made to the naturally occurring sequence to alter the function, activity and/or specificity of the cytokine. In one embodiment, the mutations may enhance the function, activity and/or specificity of the cytokine. In another embodiment, the mutations may decrease the function, activity and/or specificity of the cytokine. The mutation may include deletions or additions of one or more amino acid residues of the cytokine.

Cytokines may be classified based on structure. For example, cytokines may be classified into four types: the four-α-helix bundle family, the IL1 family, the IL17 family and the cysteine-knot cytokines. Members of the four-α-helix bundle family have three-dimensional structures with four bundles of α-helices. This family is further divided into three sub-families: the IL2 subfamily, the interferon (IFN) subfamily and the IL10 subfamily. The IL2 subfamily is the largest and comprises several non-immunological cytokines including, but not limited to, erythropoietin (EPO) and thrombopoietin (TPO). In certain embodiments, a cytokine of the composition is a cytokine from the four-α-helix bundle family or a mutant thereof. A skilled artisan would be able to determine cytokines within the four-α-helix bundle family. In other embodiments, a cytokine of the composition is an IL2 subfamily cytokine or a mutant thereof. Non-limiting examples of members of the IL2 subfamily include IL2, IL4, IL7, IL9, IL15 and IL21. In a specific embodiment, a cytokine of the composition is IL2 or a mutant thereof. In certain embodiments, a cytokine of the composition is IL15 or a mutant thereof. The sequence information for the full length human IL15 amino acid sequence can be found using, for example, the GenBank accession number CAG46777.1, AAI00962.1 or AAI00963.1. The sequence information for the full length human IL15 mRNA sequence can be found using, for example, the GenBank accession number CR542007.1, KJ891469.1, NM_172175.2, NM_000585.4 or CR541980.1. A skilled artisan will appreciate that IL15 may be found in a variety of species and methods of identifying analogs or homologs of IL15 are known in the art as described in detail below.

In another embodiment, a cytokine of the invention is an IL1 family cytokine or a mutant thereof. The IL1 family is a group of 11 cytokines, which plays a central role in the regulation of immune and inflammatory responses. Generally, the IL1 family of cytokines are proinflammatory cytokines that regulate and initiate inflammatory responses. Non-limiting examples of IL1 family cytokines include IL1α, IL1β, IL1Ra, IL18, IL36Ra, IL36α, IL37, IL36β, IL36γ, IL38, and IL33. IL1 family members have a similar gene structure. A skilled artisan would be able to determine cytokines within the IL1 family. In certain embodiments, a cytokine of the composition is IL18 or a mutant thereof. The sequence information for the full length human IL18 amino acid sequence can be found using, for example, the GenBank accession number CAG46771.1. The sequence information for the full length human IL18 mRNA sequence can be found using, for example, the GenBank accession number KR710147.1, CR542001.1, CR541973.1 or KJ897054.1. A skilled artisan will appreciate that IL18 may be found in a variety of species and methods of identifying analogs or homologs of IL18 are known in the art as described in detail below.

In other embodiments, a cytokine of the composition is an interferon subfamily cytokine or a mutant thereof. Interferons are named for their ability to "interfere" with viral replication by protecting cells from virus infection. IFNs also have other functions: they activate immune cells, such as natural killer cells and macrophages; they increase host defenses by up-regulating antigen presentation by virtue of increasing the expression of major histocompatibility complex (MHC) antigens. Based on the type of receptor through which they signal, human interferons have been classified into three major types: Type I IFN, Type II IFN, and Type III IFN. Type I IFNs bind to a specific cell surface receptor complex known as the IFN-α/β receptor (IFNAR) that consists of IFNAR1 and IFNAR2 chains. Non-limiting examples of type I interferons present in humans are IFN-α, IFN-β, IFN-ε, IFN-κ and IFN-ω. Thus, in certain embodiments, a cytokine of the composition is a Type 1 IFN cytokine or a mutant thereof, including, but not limited to wild-type and mutant forms of IFN-α, IFN-β, IFN-ε, IFN-κ and IFN-ω. Type II IFNs bind to IFNGR that consists of IFNGR1 and IFNGR2 chains. Non-limiting examples of type II interferons present in humans is IFN-γ. Thus, in certain embodiments, a cytokine of the composition is a Type II IFN cytokine or a mutant thereof, including, but not limited to wild-type and mutant forms of IFN-γ. Type III IFNs signal through a receptor complex consisting of IL10R2 (also called CRF2-4) and IFNLR1 (also called CRF2-12). Non-limiting examples of type III interferons include IFN-λ1, IFN-λ2 and IFN-λ3 (also called IL29, IL28A and IL28B respectively). Thus, in certain embodiments, a cytokine of the composition is a Type III IFN cytokine or a mutant thereof, including, but not limited to wild-type and mutant forms of IFN-λ1, IFN-λ2 and IFN-λ3.

In other embodiments, a cytokine of the composition is a member of the tumor necrosis factor superfamily (TNFSF), or a mutant thereof. TNFSF members are pro-inflammatory cytokines mainly expressed by immune cells which induce an inflammatory state and stimulate immune cell function.

At least 18 TNFSF homologues exist, including but not limited to, TNF (TNFalpha), CD40L (TNFSF5), CD70 (TNFSF7; CD27L), EDA, FASL (TNFSF6; Fas ligand), LTA (TNFSF1; lymphotoxin-alpha), LTB (TNFSF3; lymphotoxin-beta), TNFSF4 (OX40L), TNFSF8 (CD153), TNFSF9 (4-1BBL), TNFSF10 (TRAIL), TNFSF11 (RANKL; receptor activator of nuclear factor kappa-B ligand), TNFSF12 (TWEAK), TNFSF13, TNFSF13B, TNFSF14, TNFSF15, TNFSF18. Thus, in certain embodiments, a cytokine of the composition is a member of the tumor necrosis factor superfamily or a mutant thereof, including, but not limited to TNF (TNFalpha), CD40L (TNFSF5), CD70 (TNFSF7; CD27L), EDA, FASL (TNFSF6), LTA (TNFSF1), LTB (TNFSF3), TNFSF4 (OX40L), TNFSF8 (CD153), TNFSF9 (4-1BBL), TNFSF10 (TRAIL), TNFSF11 (RANKL), TNFSF12 (TWEAK), TNFSF13, TNFSF13B, TNFSF14, TNFSF15, TNFSF18.

In certain embodiments, a cytokine of the composition is OX40L, a fragment thereof, or a mutant thereof. The sequence information for the full length human OX40L amino acid sequence can be found using, for example, the GenBank accession number XP_016857719.1, XP_016857718.1, XP_016857717.1, XP_011508266.2, NP_001284491.1, NP_003317.1, CAG46830.1. The sequence information for the full length human OX40L mRNA sequence can be found using, for example, the GenBank accession number XR_001737396.1, XR_001737395.1, XR_001737394.1, XR_001737393.1, XM_017002230.1, XM_017002229.1, XM_017002228.1, XM_011509964.2, NM_001297562.1, NM_003326.4. A skilled artisan will appreciate that OX40L may be found in a variety of species and methods of identifying analogs or homologs of OX40L are known in the art as described in detail below.

A skilled artisan will appreciate that OX40L may be found in a variety of species. Non-limiting examples include mouse (NP_033478.1), pig (NP_001020388.1), cattle (NP_001192644.1), rat (NP_446004.1), rabbit (NP_001075454.1), goat (XP_013825644.1), sheep (XP_012042680.1), chicken (XP_430147.2), hamster (XP_007610839.1), and dog (XP_003639215.1). It is appreciated that the present invention is directed to analogs of OX40L in other organisms and is not limited to the human analog. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally, a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to OX40L.

In a specific embodiment, a cytokine of the composition is a wildtype sequence of OX40L. In a specific embodiment, the cytokine may contain the wild-type OX40L fragments such as the sequence set forth in

SEQ ID NO: 57
(QVSHRYPRIQSIKVQFTEYKKEKGFILTSQKEDEIMKVQNNSVIINCDG

FYLISLKGYFSQEVNISLHYQKDEEPLFQLKKVRSVNSLMVASLTYKDKV

YLNVTTDNTSLDDFHVNGGELILIHQNPGEFCVL).

In certain embodiments, these fragments may be connected into a continuous peptide via linker fragments. In a specific embodiment, a cytokine may be the OX40L fragments connected via linker peptides such as the sequence set forth in

SEQ ID NO: 58
(QVSHRYPRIQSIKVQFTEYKKEKGFILTSQKEDEIMKVQNNSVIINCD

GFYLISLKGYFSQEVNISLHYQKDEEPLFQLKKVRSVNSLMVASLTYKD

KVYLNVTTDNTSLDDFHVNGGELILIHQNPGEFCVLGGSGGGSGGGSGQ

VSHRYPRIQSIKVQFTEYKKEKGFILTSQKEDEIMKVQNNSVIINCDGF

YLISLKGYFSQEVNISLHYQKDEEPLFQLKKVRSVNSLMVASLTYKDKV

YLNVTTDNTSLDDFHVNGGELILIHQNPGEFCVLGGSGGGSGGGSGQVS

HRYPRIQSIKVQFTEYKKEKGFILTSQKEDEIMKVQNNSVIINCDGFYL

ISLKGYFSQEVNISLHYQKDEEPLFQLKKVRSVNSLMVASLTYKDKVYL

NVTTDNTSLDDFHVNGGELILIHQNPGEFCVL).

In an alternate embodiment, a cytokine of the composition is a mutated sequence of OX40L. In an embodiment, a mutation is a mutation that causes OX40L to bind to but inhibit signaling of the tumor necrosis factor receptor superfamily, member 4 (TNFRSF4, also known as OX40, also known as CD134). For example, a mutation may be one or more mutations selected from the group of N166A and F180A relative to the full length OX40L sequence in SEQ ID NO:56. In a specific embodiment, a mutated version of OX40L comprises at least one mutation selected from the group consisting of N166A and F180A relative to the full length OX40L sequence in SEQ ID NO:56. In a specific embodiment, a cytokine may contain the mutated OX40L fragments such as the sequence set forth in

SEQ ID NO: 59
(QVSHRYPRIQSIKVQFTEYKKEKGFILTSQKEDEIMKVQNNSVIINCDG

FYLISLKGYFSQEVNISLHYQKDEEPLFQLKKVRSVNSLMVASLTYKDKV

YLNVTTDNTSLDDFHVAGGELILIHQNPGEACVL).

In certain embodiments, these fragments may be connected into a continuous peptide via linker fragments. In a specific embodiment, a cyotokine may be mutated and unmutated OX40L fragments connected via linker peptides such as the sequence set forth in

SEQ ID NO: 60
(QVSHRYPRIQSIKVQFTEYKKEKGFILTSQKEDEIMKVQNNSVIINCDG

FYLISLKGYFSQEVNISLHYQKDEEPLFQLKKVRSVNSLMVASLTYKDKV

YLNVTTDNTSLDDFHVAGGELILIHQNPGEACVLGGSGGGSGGGSGQVSH

RYPRIQSIKVQFTEYKKEKGFILTSQKEDEIMKVQNNSVIINCDGFYLIS

LKGYFSQEVNISLHYQKDEEPLFQLKKVRSVNSLMVASLTYKDKVYLNVT

TDNTSLDDFHVAGGELILIHQNPGEACVLGGSGGGSGGGSGQVSHRYPRI

QSIKVQFTEYKKEKGFILTSQKEDEIMKVQNNSVIINCDGFYLISLKGYF

SQEVNISLHYQKDEEPLFQLKKVRSVNSLMVASLTYKDKVYLNVTTDNTS

LDDFHVNGGELILIHQNPGEFCVL).

In another specific embodiment, a cyotokine may be mutated and unmutated OX40L fragments connected via linker peptides such as the sequence set forth in

SEQ ID NO: 61
(QVSHRYPRIQSIKVQFTEYKKEKGFILTSQKEDEIMKVQNNSVIINCDG

FYLISLKGYFSQEVNISLHYQKDEEPLFQLKKVRSVNSLMVASLTYKDKV

YLNVTTDNTSLDDFHVAGGELILIHQNPGEACVLGGSGGGSGGGSGQVSH

RYPRIQSIKVQFTEYKKEKGFILTSQKEDEIMKVQNNSVIINCDGFYLIS

LKGYFSQEVNISLHYQKDEEPLFQLKKVRSVNSLMVASLTYKDKVYLNVT

TDNTSLDDFHVNGGELILIHQNPGEFCVLGGSGGGSGGGSGQVSHRYPRI

QSIKVQFTEYKKEKGFILTSQKEDEIMKVQNNSVIINCDGFYLISLKGYF

SQEVNISLHYQKDEEPLFQLKKVRSVNSLMVASLTYKDKVYLNVTTDNTS

LDDFHVNGGELILIHQNPGEFCVL).

In certain embodiments, a cytokine of the composition is 4-1BBL, a fragment thereof, or a mutant thereof. The sequence information for the full length human 4-1BBL amino acid sequence can be found using, for example, the GenBank accession number NP_003802.1. The sequence information for the full length human 4-1BBL mRNA sequence can be found using, for example, the GenBank accession number NM_003811.3. A skilled artisan will appreciate that 4-1BBL may be found in a variety of species and methods of identifying analogs or homologs of 4-1BBL are known in the art as described in detail below.

A skilled artisan will appreciate that 4-1BBL may be found in a variety of species. Non-limiting examples include mouse (NP_033430.1), pig (XP_003480863.1), cattle (NP_001306831.1), rat (NP_852049.1), rabbit (XP_008251123.1), goat (XP_013820683.1), sheep (XP_014951136.1), hamster (XP_007627369.1), and dog (XP_005633029.1). It is appreciated that the present invention is directed to analogs of 4-1BBL in other organisms and is not limited to the human analog. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215: 403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally, a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to 4-1BBL.

In a specific embodiment, a cytokine of the composition is a wildtype sequence of 4-1BBL. In a specific embodiment, the cytokine may contain the wild-type 4-1BBL fragments such as the sequence set forth in

SEQ ID NO: 65
(ACPWAVSGARASPGSAASPRLREGPELSPDDPAGLLDLRQGMFAQLVAQ

NVLLIDGPLSWYSDPGLAGVSLTGGLSYKEDTKELVVAKAGVYYVFFQLE

LRRVVAGEGSGSVSLALHLQPLRSAAGAAALALTVDLPPASSEARNSAFG

FQGRLLHLSAGQRLGVHLHTEARARHAWQLTQGATVLGLFRVTPEIPAGL

PSPRSE).

In certain embodiments, these fragments may be connected into a continuous peptide via linker fragments. In a specific embodiment, a cytokine may be the 4-1BBL fragments connected via linker peptides such as the sequence set forth in

SEQ ID NO: 66
(ACPWAVSGARASPGSAASPRLREGPELSPDDPAGLLDLRQGMFAQLVAQ

NVLLIDGPLSWYSDPGLAGVSLTGGLSYKEDTKELVVAKAGVYYVFFQLE

LRRVVAGEGSGSVSLALHLQPLRSAAGAAALALTVDLPPASSEARNSAFG

FQGRLLHLSAGQRLGVHLHTEARARHAWQLTQGATVLGLFRVTPEIPAGL

PSPRSEGGSGGGSGGGSGACPWAVSGARASPGSAASPRLREGPELSPDDP

AGLLDLRQGMFAQLVAQNVLLIDGPLSWYSDPGLAGVSLTGGLSYKEDTK

ELVVAKAGVYYVFFQLELRRVVAGEGSGSVSLALHLQPLRSAAGAAALAL

TVDLPPASSEARNSAFGFQGRLLHLSAGQRLGVHLHTEARARHAWQLTQG

ATVLGLFRVTPEIPAGLPSPRSEGGSGGGSGGGSGACPWAVSGARASPGS

AASPRLREGPELSPDDPAGLLDLRQGMFAQLVAQNVLLIDGPLSWYSDPG

LAGVSLTGGLSYKEDTKELVVAKAGVYYVFFQLELRRVVAGEGSGSVSLA

LHLQPLRSAAGAAALALTVDLPPASSEARNSAFGFQGRLLHLSAGQRLGV

HLHTEARARHAWQLTQGATVLGLFRVTPEIPAGLPSPRSE).

In an alternate embodiment, a cytokine of the composition is a mutated sequence of 4-1BBL. In an embodiment, a mutation is a mutation that affects the binding affinity between 4-1BBL and its receptor the tumor necrosis factor receptor superfamily, member 9 (TNFRSF9, also known as 4-1BB, also known as CD137).

In certain embodiments, a cytokine of the invention is an interleukin or mutant thereof. The majority of interleukins are synthesized by helper CD4 T lymphocytes, as well as through monocytes, macrophages, and endothelial cells. Interleukins may promote the development and differentiation of T and B lymphocytes and hematopoietic cells. Non-limiting examples of interleukins include IL1, IL2, IL3, IL4, IL5, IL6, IL7, IL8 (CXCL8), IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL35, or IL36. Thus, in certain embodiments, a cytokine of the composition is an interleukin or a mutant thereof, including, but not limited to wild-type and mutant forms of IL1, IL2, IL3, IL4, IL5, IL6, IL7, IL8 (CXCL8), IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL35, or IL36. In a specific embodiment, a cytokine of the composition is IL2 or a mutant thereof. IL2 is a lymphokine that induces the proliferation of responsive T cells. In addition, it acts on some B cells, via receptor-specific binding, as a growth factor and antibody production stimulant. The IL2 protein is secreted as a single glycosylated polypeptide, and cleavage of a signal sequence is required for its activity. The structure of IL2 comprises a bundle of 4 helices (termed A-D), flanked by 2 shorter helices and several poorly defined loops. Residues in helix A, and in the loop region between helices A and B, are important for receptor binding. Secondary structure analysis suggests similarity to IL4 and granulocyte-macrophage colony stimulating factor (GMCSF). In a specific embodiment, a cytokine of the composition is IL2 or a variant thereof. A variant may be a truncated or mutated IL2. The sequence information for the full length human IL2 amino acid sequence can be found using, for example, the GenBank accession number AAA59140.1 or AAH70338.1. The sequence information for the full length human IL2 mRNA sequence can be found using, for example, the GenBank accession number BC070338.1 or M22005.1.

A skilled artisan will appreciate that IL2 may be found in a variety of species. Non-limiting examples include mouse (AAI16874.1), pig (NP_999026.1), cattle (AAQ10670.1), rat (EDM01295.1), rabbit (AAC23838.1), goat (AAQ10671.1), sheep (ABK41601.1), chicken (AAV35056.1), hamster (ERE88380.1), and dog (AAA68969.1). It is appreciated that the present invention is directed to analogs of IL2 in other organisms and is not limited to the human analog. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215: 403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to IL2.

In a specific embodiment, a cytokine of the composition is a wildtype sequence of IL2 such as the sequence set forth in

SEQ ID NO: 5
(APTSSSTKKTQLQLEHLLLDLQMILNGINNYKNPKLTRMLTFKFYMPKK

ATELKHLQCLEEELKPLEEVLNLAQSKNFHLRPRDLISNINVIVLELKGS

ETTFMCEYADETATIVEFLNRWITFCQSIISTLT).

In an alternative embodiment, a cytokine is a mutated version of IL2. In an embodiment, a mutation is a mutation that causes IL2 to preferentially bind the receptor IL2βγ. In another embodiment, a mutation is a mutation that alters the function of IL2 such that IL2 has a decreased affinity for the IL2 receptor alpha (IL2Rα). For example, a mutation may be one or more mutations selected from the group consisting of R38A, F42K and/or C125S relative to SEQ ID NO:5. The C125S mutation may be included to reduce protein aggregation. In a specific embodiment, a mutated version of IL2 comprises at least one mutation selected from the group consisting of R38A, F42K and C125S relative to SEQ ID NO:5. In another specific embodiment, a mutated version of IL2 comprises the mutations R38A, F42K and C125S relative to SEQ ID NO:5. In a specific embodiment, a cytokine of the composition is a mutated sequence of IL2 such as the sequence set forth in

SEQ ID NO: 6
(APTSSSTKKTQLQLEHLLLDLQMILNGINNYKNPKLTAMLTKKFYMPKK

ATELKHLQCLEEELKPLEEVLNLAQSKNFHLRPRDLISNINVIVLELKGS

ETTFMCEYADETATIVEFLNRWITFSQSIISTLT).

In an alternative aspect, a toxin is substituted for a cytokine. The term "toxin" means the toxic material or product of plants, animals, microorganisms (including, but not limited to, bacteria, viruses, fungi, rickettsiae or protozoa), or infectious substances, or a recombinant or synthesized molecule, whatever their origin and method of production. A toxin may be a small molecule, peptide, or protein that is capable of causing disease on contact with or absorption by body tissues interacting with biological macromolecules such as enzymes or cellular receptors. A toxin may be a "biotoxin" which is used to explicitly identify the toxin as from biological origin. Biotoxins may be further classified into fungal biotoxins, or short mycotoxins, microbial biotoxins, plant biotoxins, short phytotoxins and animal biotoxins. Non-limiting examples of biotoxins include: cyanotoxins, produced by cyanobacteria, such as microcystins, nodularins, anatoxin-a, cylindrospermopsins, lyngbyatoxin-a, saxitoxin, lipopolysaccharides, aplysiatoxins, BMAA; dinotoxins, produced by dinoflagellates, such as saxitoxins and gonyautoxins; necrotoxins produced by, for example, the brown recluse or "fiddle back" spider, most rattlesnakes and vipers, the puff adder, Streptococcus pyogenes; neurotoxins, produced by, for example, the black widow spider, most scorpions, the box jellyfish, elapid snakes, the cone snail, the Blue-ringed octopus, venomous fish, frogs, palythoa coral, various different types of algae, cyanobacteria and dinoflagellates, such as botulinum toxin (e.g. Botox), tetanus toxin, tetrodotoxin, chlorotoxin, conotoxin, anatoxin-a, bungarotoxin, caramboxin, curare; myotoxins, found in, for example, snake and lizard venoms; and cytotoxins such as ricin, from castor beans, apitoxin, from honey bees, and T-2 mycotoxin, from certain toxic mushrooms. In certain embodiments, a toxin is a cytotoxin. In an embodiment, a cytotoxin is selected from the group consisting of ricin, apitoxin, and T-2 mycotoxin. In a specific embodiment, a toxin is ricin.

In certain embodiments, a cytokine or toxin of the invention may be PEGylated for improved systemic half-life and reduced dosage frequency. In an embodiment, PEG may be added to a cytokine or toxin. As such, a composition of the invention may comprise a cytokine or toxin comprising PEG. In an embodiment, PEG may be selected from the group consisting of PEG-10K, PEG-20K and PEG-40K. Methods of conjugating PEG to a protein are standard in the art. For example, see Kolate et al, *Journal of Controlled Release* 2014; 192(28): 67-81, which is hereby incorporated by reference in its entirety. Still further, a cytokine or toxin of the invention may be modified to remove T cell epitopes. T cell epitopes can be the cause of an immunogenicity issue upon administration of a composition to a subject. Through their presentation to T cells, they activate the process of anti-drug antibody development. Preclinical screening for T cell epitopes may be performed in silico, followed by in vitro and in vivo validation. T cell epitope-mapping tools such as EpiMatrix can be highly accurate predictors of immune response. Deliberate removal of T cell epitopes may reduce immunogenicity. Other means of improving the safety and efficacy of a composition of the invention by reducing their immunogenicity include humanization and PEGylation.

(b) Ligand

As used herein, a "ligand" is a protein that specifically binds to a receptor on a target cell and is not the corresponding binding partner to the cytokine linked to the ligand. A ligand may be from a eukaryote, a prokaryote or a virus. In certain embodiments, a ligand may be from a virus. The phrase "specifically binds" herein means ligands bind to the target protein with an affinity ($K_d$) in the range of at least 0.1 mM to 1 pM, or in the range of at least 0.1 pM to 200 nM, or in the range of at least 0.1 pM to 10 nM. A dissociation constant ($K_d$) measures the propensity of a larger object to separate (dissociate) reversibly into smaller components. The dissociation constant is the inverse of the association constant. The dissociation constant may be used to describe the affinity between a ligand (L) and a target protein (P). As such, $K_d=([P]\times[L])/[C]$, wherein C is a ligand-target protein complex and wherein [P], [L] and [C] represent molar concentrations of the protein, ligand and complex, respectively. Methods of determining whether a ligand binds to a target protein are known in the art. For instance, see the Rossi and Taylor, *Nature Protocols* 2011; 6: 365-387.

A ligand may trigger a signal through its binding to a receptor on a target cell. A receptor is a protein molecule that may be embedded within the plasma membrane surface of a cell that receives chemical signals from outside the cell. When such chemical signals bind to a receptor, they cause some form of cellular/tissue response. In preferred embodiments, a target cell is an immune cell. Accordingly, a ligand of the composition binds to a receptor expressed on immune cells. Non-limiting example of immune cells include macrophages, B lymphocytes, T lymphocytes, mast cells, monocytes, dendritic cells, eosinophils, natural killer cells, basophils, neutrophils. Thus, in certain embodiments, immune cells include, but are not limited to, macrophages, B lymphocytes, T lymphocytes, mast cells, monocytes, dendritic cells, eosinophils, natural killer cells, basophils, neutrophils. In a specific embodiment, an immune cell is a natural killer cell or a T lymphocyte. Non-limiting examples of receptors expressed on immune cells include major histocompatibility complex (MHC; e.g. MHCI, MHCII, and MHCIII), toll-like receptors (TLRs; e.g. TLR1, TLR2, TLR3, TLR4, TLR5, TLR6, TLR7, TLR8, TLR9, TLR10, TLR11, TLR12, and TLR13), CD94/NKG2 family receptor, endothelin receptors, signaling lymphocytic activation molecule (SLAM) family of receptors. Thus, in certain embodiments, a receptor on a target cell includes, but is not limited to, major histocompatibility complex (MHC; e.g. MHCI, MHCII, and MHCIII), toll-like receptors (TLRs; e.g. TLR1, TLR2, TLR3, TLR4, TLR5, TLR6, TLR7, TLR8, TLR9, TLR10, TLR11, TLR12, and TLR13), CD94/NKG2 family receptor, endothelin receptors, signaling lymphocytic activation molecule (SLAM) family of receptors. In a specific embodiment, the receptor on a target cell is a CD94/NKG2 family receptor. In another specific embodiment, a ligand of the composition specifically binds to a receptor expressed on natural killer (NK) cells and CD8$^+$ cytotoxic T lymphocytes (CTLs). In preferred embodiments, a ligand of the composition does not specifically bind to a receptor on vascular endothelial cells or regulatory T cells ($T_{regs}$).

A receptor expressed on NK cells and CTLs may be a CD94/NKG2 family receptor or KLRG1. KLRG1 (Killer cell lectin-like receptor subfamily G member 1) is a protein that in humans is encoded by the KLRG1 gene. CD94/NKG2 family receptors are a family of C-type lectin receptors which are expressed predominantly on the surface of NK cells and a subset of CD8+ T-lymphocyte. These receptors stimulate or inhibit cytotoxic activity of NK cells, therefore they are divided into activating and inhibitory receptors according to their function. CD94/NKG2 recognize MHC class I-related glycoproteins. CD94/NKG2 family includes seven members: NKG2A, NKG2B, NKG2C, NKG2D, NKG2E, NKG2F and NKG2H. Thus, in certain embodiments, a ligand of the invention specifically binds to a receptor selected from the group consisting of NKG2A, NKG2B, NKG2C, NKG2D, NKG2E, NKG2F and NKG2H. NKG2 receptors are transmembrane proteins type II which dimerize with CD94 molecule. CD94 contains a short cytoplasmic domain and it is responsible for signal transduction. Therefore NKG2 receptors form disulfide bonded heterodimers. NKG2D represents an exception, it is a homodimer. NKG2A and NKG2B receptors transmit inhibitory signal. NKG2C, NKG2E and NKG2H are activating receptors. NKG2D is activating receptor as well but it couples with adaptor protein DAP10 which carries signaling motif YINM (SEQ ID NO:34). Src or Jak kinases phosphorylate DAP10, which can then associate with p85 subunit of PI(3)K or adaptor molecule Grb2. This signaling triggers actin reorganization (cell polarization) and degranulation. NKG2F receptor function has not been clarified yet.

In a specific embodiment, a ligand of the composition specifically binds to the NKG2D receptor. NKG2D is an activating receptor found on NK cells and CD8$^+$ T cells (both αβ and γδ). The structure of NKG2D consists of two disulphide-linked type II transmembrane proteins with short intracellular domains incapable of transducing signals. The function of NKG2D on CD8$^+$ T cells is to send co-stimulatory signals to activate them. In an embodiment, a ligand that binds to NKG2D may be an anti-NKG2D antibody. An "anti-NKG2D" includes all antibodies that specifically bind an epitope within NKG2D. The term "antibody" includes the term "monoclonal antibody". "Monoclonal antibody" refers to an antibody that is derived from a single copy or clone, including e.g., any eukaryotic, prokaryotic, or phage clone. Monoclonal antibodies can be produced using e.g., hybridoma techniques well known in the art, as well as recombinant technologies, phage display technologies, synthetic technologies or combinations of such technologies and other technologies readily known in the art. Further by "antibody" is meant a functional monoclonal antibody, or an immunologically effective fragment thereof; such as an Fab, Fab', or F(ab')2 fragment thereof. As long as the protein retains the ability specifically to bind its intended target, it is included within the term "antibody." Also included within the definition "antibody" for example are single chain forms, generally designated Fv, regions, of antibodies with this specificity. These scFvs are comprised of the heavy and light chain variable regions connected by a linker. Methods of making and using scFvs are known in the art. Additionally, included within the definition "antibody" are single-domain antibodies, generally designated sdAb, which is an antibody fragment consisting of a single monomeric variable antibody domain. A sdAb antibody may be derived from camelids (VHH fragments) or cartilaginous fishes (V$_{NAR}$ fragments). As used herein "humanized antibody" includes an anti-NKG2D antibody that is composed partially or fully of amino acid sequence sequences derived from a human antibody germ line by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for NKG2D is maintained or enhanced in the context of fully human germ line framework regions or framework regions that are substantially human. In certain embodiments, an anti-NKG2D antibody is a Fab, Fab', or F(ab')2 fragment.

In one particular embodiment, the anti-NKG2D antibody is KYK-1 or KYK-2 as described in Kwong, et al, *J Mol Biol*. 2008 Dec. 31; 384(5):1143-56. The light chain of KYK-1 comprises the amino acid sequence set forth in

SEQ ID NO: 35
(QPVLTQPSSVSVAPGETARIPCGGDDIETKSVHWYQQKPGQAPVLVIYD

DDDRPSGIPERFFGSNSGNTATLSISRVEAGDEADYYCQVWDDNNDEWVF

GGGTQLTVL)

and the heavy chain of the KYK-1 comprises the amino acid sequence set forth in

SEQ ID NO: 36
(EVQLVESGGGVVQPGGSLRLSCAASGFTFSSYGMHWVRQAPGKGLEWVA

FIRYDGSNKYYADSVKGRFTISRDNSKNTLYLQMNSLRAEDTAVYYCAKD

RFGYYLDYWGQGTLVTVSS).

The light chain of KYK-2 comprises the amino acid sequence set forth in

SEQ ID NO: 37
(QSALTQPASVSGSPGQSITISCSGSSSNIGNNAVNWYQQLPGKAPKLLI

YYDDLLPSGVSDRFSGSKSGTSAFLAISGLQSEDEADYYCAAWDDSLNGP

VFGGGTKLTVL)

and the heavy chain of the KYK-2 comprises the amino acid sequence set forth in

SEQ ID NO: 38
(QVQLVESGGGLVKPGGSLRLSCAASGFTFSSYGMHWVRQAPGKGLEWVA

FIRYDGSNKYYADSVKGRFTISRDNSKNTLYLQMNSLRAEDTAVYYCAKD

RGLGDGTYFDYWGQGTTVTVSS).

In another particular embodiment, the anti-NKG2D antibody is an scFv derived from KYK-1. For example, the KYK-1 scFv comprises the amino acid sequence set forth in

SEQ ID NO: 39
(QPVLTQPSSVSVAPGETARIPCGGDDIETKSVHWYQQKPGQAPVLVIYD

DDDRPSGIPERFFGSNSGNTATLSISRVEAGDEADYYCQVWDDNNDEWVF

GGGTQLTVLGGGGSGGGGSGGGGSGGGGSEVQLVESGGGVVQPGGSLRLS

CAASGFTFSSYGMHWVRQAPGKGLEWVAFIRYDGSNKYYADSVKGRFTIS

RDNSKNTLYLQMNSLRAEDTAVYYCAKDRFGYYLDYWGQGTLVTVSS).

Alternatively, the KYK-1 scFv comprises the amino acid sequence set forth in

SEQ ID NO: 40
(EVQLVESGGGVVQPGGSLRLSCAASGFTFSSYGMHWVRQAPGKGLEWVA

FIRYDGSNKYYADSVKGRFTISRDNSKNTLYLQMNSLRAEDTAVYYCAKD

RFGYYLDYWGQGTLVTVSSGGGGSGGGGSGGGGSGGGGSQPVLTQPSSVS

VAPGETARIPCGGDDIETKSVHWYQQKPGQAPVLVIYDDDDRPSGIPERF

FGSNSGNTATLSISRVEAGDEADYYCQVWDDNNDEWVFGGGTQLTVL).

In another particular embodiment, the anti-NKG2D antibody is an scFv derived from KYK-2. For example, the KYK-2 scFv comprises the amino acid sequence set forth in

SEQ ID NO: 41
(QSALTQPASVSGSPGQSITISCSGSSSNIGNNAVNWYQQLPGKAPKLLI

YYDDLLPSGVSDRFSGSKSGTSAFLAISGLQSEDEADYYCAAWDDSLNGP

VFGGGTKLTVLGGGGSGGGGSGGGGSGGGGSQVQLVESGGGLVKPGGSLR

LSCAASGFTFSSYGMHWVRQAPGKGLEWVAFIRYDGSNKYYADSVKGRFT

ISRDNSKNTLYLQMNSLRAEDTAVYYCAKDRGLGDGTYFDYWGQGTTVTV

SS).

Alternatively, the KYK-2 scFv comprises the amino acid sequence set forth in

SEQ ID NO: 42
(QVQLVESGGGLVKPGGSLRLSCAASGFTFSSYGMHWVRQAPGKGLEWVA

FIRYDGSNKYYADSVKGRFTISRDNSKNTLYLQMNSLRAEDTAVYYCAKD

RGLGDGTYFDYWGQGTTVTV).

As stated above, the various KYK-1 and KYK-2 antibodies or scFv thereof may be combined with any of the cytokines disclosed herein, in the absence or presence of any of the linkers described herein to provide the compositions or chimeric peptides of the present invention. It should also be understood that the KYK-1 and KYK-2 antibodies are examples of antibodies suitable for use in the present compositions and one of skill in the art, based on this disclosure, will understand that other anti-NKG2D antibodies will be suitable as well.

In another embodiment, ligands that bind to NKG2D share an MHC class I-related α1α2 superdomain that constitutes the common site for interaction with NKG2D. Non-limiting examples of ligands that bind to NKG2D include MHC class I-related glycoproteins such as MIC family proteins (i.e., MICA, MICB), UL16-binding family proteins (i.e., ULBP1, ULBP2, ULPB3, ULBP4, ULBP5, ULBP6), retinoid acid early induce gene 1 (Rae1)-like proteins (i.e., Rae1α, Rae1β, Rae1γ, Rae1δ, Rae1ε), members of the H60 protein family (i.e., H60a, H60b, H60c), h-HLA-A, as well as Multi in mice and OMCP. In certain embodiments, a ligand is a MHC class-I-related glycoprotein. In other embodiments, a ligand of the invention is selected from the group consisting of MICA, MICB, ULBP1, ULBP2, ULBP3, ULBP4, ULBP5, ULBP6, Rae1α, Rae1β, Rae1γ, Rae1δ, Rae1ε, H60a, H60b, H60c, h-HLA-A, Multi and OMCP. In an embodiment, a ligand is a UL16-binding family protein or a MIC family protein. In a specific embodiment, a ligand is selected from the group consisting of ULBP1, ULBP2, ULBP3, ULBP4, ULBP5, and ULBP6. In another specific embodiment, a ligand is ULBP3. In a specific embodiment, a ligand is OMCP or a variant thereof. A variant may be a truncated or mutated OMCP that has about the same binding affinity of the full length OMCP. In an embodiment, a variant may be a truncated or mutated OMCP that has a slightly lower binding affinity relative to the binding affinity of the full length OMCP. In another embodiment, a variant is a truncated or mutated OMCP that has a slightly higher binding affinity relative to the binding affinity of the full length OMCP. Methods to determine binding affinity of a ligand to target protein are known in the art and described above. OMCP specifically binds to NKG2D with a binding affinity of about 0.1 to about 5 nM. For example, OMCP specially binds to human NKG2D with a binding affinity of about 0.2 nM and mouse NKG2D with a binding affinity of about 3 nM. In a preferred embodiment, OMCP or a variant thereof binds to human NKG2D with a binding affinity of about 1000 nM to about 0.1 nM. In certain embodiments, OMCP or a variant thereof binds to human NKG2D with a binding affinity of about 100 nM to about 0.1 nM, about 10 nM to about 0.1 nM, or about 1 nM to about 0.1 nM. In other embodiments, OMCP or a variant thereof binds to human NKG2D with a binding affinity of about 1000 nM to about 1 nM, or about 1000 nM to about 10 nM, or about 1000 nM to about 100 nM. In still other embodiments, OMCP or a variant thereof binds to human NKG2D with a binding affinity of about 100 nM to about 1 nM, or about 100 nM to 10 nM. For example, OMCP or a variant thereof binds to human NKG2D with a binding affinity of about 1000 nM, about 500 nM, about 100 nM, about 50 nM, about 10 nM, about 9 nM, about 8 nM, about 7 nM, about 6 nM about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM or about 0.1 nM. In another embodiment, a variant is a truncated or mutated OMCP that has binding affinity for one or more NKG2 family receptors other than NKG2D. For example, a variant is a truncated or mutated OMCP that has binding affinity for one or more NKG2 family receptors selected from the group consisting of NKG2A, NKG2B, NKG2C, NKG2E, NKG2F and NKG2H. Mutations to OMCP may be rationally selected via structure-based knowledge or mutations to OMCP may be identified via selection-based mutagenesis. In certain embodiments, mutations may be rationally selected to occur in the OMCP-NKG2D interface to either enhance or reduce binding affinity. Amino acids involved in binding at the OMCP-NKG2D interface are described in the Examples.

The structure of OMCP consists of an MHCI-like α1/α2 platform domain (FIG. 20A). The platform domain of OMCP has been trimmed to have only a six-stranded beta sheet with shorter flanking helices. The helix of the OMCP α1 domain (H1) is continuous, while the helix of the α2 domain is broken into two regions (H2a and H2b). The helices flank a six-stranded beta sheet and together form the characteristic platform that defines MHC proteins. Like other NKG2DLs (FIG. 20B), the alpha helices of OMCP are close together and thus have no groove for binding peptides or other ligands like antigen-presenting MHC platform domains. OMCP contains one disulfide bond between S5 and H2b, and this disulfide bond is conserved in most NKG2DLs (FIG. 20C). In certain embodiments, a ligand of the invention comprises one or more of the α helices of a MHC class I-related glycoprotein. In other embodiments, a ligand of the invention consists of one or more of the α helices of a MHC class I-related glycoprotein. More specifically, a ligand of the invention comprises the α1 domain (H1), α2 domain (H2), H2a, H2b, or combinations thereof of a MHC class I-related glycoprotein. Or, a ligand of the invention consists of the α1 domain (H1), α2 domain (H2), H2a, H2b, or combinations thereof of a MHC class I-related glycoprotein. In a specific embodiment, a ligand of the invention comprises the α2 domain (H2) of a MHC class I-related glycoprotein. In another specific embodiment, a ligand of the invention consists of the α2 domain (H2) of a MHC class I-related glycoprotein. A skilled artisan would be able to determine the location of the α helices in other MHC class I-related glycoproteins, for example, using sequence alignment (see FIG. 20C, which is reproduced from Lazear et al. *J Virol* 2013; 87(2): 840-850, which is hereby incorporated by reference in its entirety). In an embodiment, a ligand of the invention comprises one or more of the α helices of OMCP. In another embodiment, a ligand of the invention comprises the α1 domain (H1), α2 domain (H2), H2a, H2b, or combinations thereof of OMCP. In still another embodiment, a ligand of the invention comprises the α2 domain (H2) of OMCP. In a specific embodiment, a ligand of the invention consists of one or more of the α helices of OMCP. In another specific embodiment, a ligand of the invention consists of the α1 domain (H1), α2 domain (H2), H2a, H2b, or combinations thereof of OMCP. In still another specific embodiment, a ligand of the invention consists of the α2 domain (H2) of OMCP.

The sequence information for the full length OMCP amino acid sequence can be found using, for example, the GenBank accession number 4FFE_Z, 4FFE_Y or 4FFE_X. A skilled artisan will appreciate that homologs of OMCP may be found in other species or viruses. For example, see Lefkowitz et al, *Nucleic Acids Res* 2005; 33: D311-316, which is herein incorporated by reference in its entirety, which describes eighteen OMCP variants between cowpox and monkeypox virus strains. In an embodiment, OMCP is from an orthopoxvirus. In a specific embodiment, OMCP is from a cowpox virus or a monkeypox virus. In another specific embodiment, OMCP is from the Brighton Red strain of cowpoxvirus. Homologs can be found in other species by methods known in the art. For example, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details. Generally a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to OMCP.

A skilled artisan will appreciate that structural homologs of OMCP may be found in other species or viruses. A structural homolog may be a protein that is structurally related but the sequence is a distal homolog. For example, OMCP has low sequence identity for endogenous NKG2D however it was discovered that OMCP would bind to NKG2D based on structural homology. Structural homologs can be found in other species by methods known in the art. For example, protein structure prediction may be determined by various databases, such as Phyre and Phyre2. Such databases generate reliable protein models that may be used to determine structural homologs. The main results table in Phyre2 provides confidence estimates, images and links to the three-dimensional predicted models and information derived from either Structural Classification of Proteins database (SCOP) or the Protein Data Bank (PDB) depending on the source of the detected template. For each match a link takes the user to a detailed view of the alignment between the user sequence and the sequence of known three-dimensional structure. See www.sbg.bio.ic.ac.uk/phyre2/ for more details. Generally, a structural homolog will have a least 50, 51, 52, 53, 54, 55, 56, 57, 58, or 59% confidence with OMCP. In an embodiment, a structural homolog will have a least 60, 61, 62, 63, 64, 65, 66, 67, 68, or 69% confidence with OMCP. In another embodiment, a structural homolog will have a least 70, 71, 72, 73, 74, 75, 76, 77, 78, or 79% confidence with OMCP. In still another embodiment, a structural homolog will have a least 80, 81, 82, 83, 64, 85, 86, 87, 88, or 89% confidence with OMCP. In still yet another embodiment, a structural homolog may have at least 90, 91, 92, 93, 94, 95, 96, 97, 98, 99, or 100% confidence with OMCP. The structural information for OMCP-human NKG2D may be found using the PDB ID: 4PDC.

In a specific embodiment, a ligand of the composition is a sequence of OMCP such as the sequence set forth in

SEQ ID NO: 7

(HKLAFNFNLEINGSDTHSTVDVYLDDSQIITFDGKDIRPTIPFMIGDEI

FLPFYKNVFSEFFSLFRRVPTSTPYEDLTYFYECDYTDNKSTFDQFYLYN

GEEYTVKTQEATNKNMWLTTSEFRLKKWFDGEDCIMHLRSLVRKMEDSKR

NTG).

In an embodiment, a ligand of the composition is a sequence of OMCP comprising at least 80% identity to SEQ ID NO:7. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:7.

In another specific embodiment, a ligand of the composition is a sequence of OMCP such as the sequence set forth in

SEQ ID NO: 13

(GHKLAFNFNLEINGSDTHSTVDVYLDDSQIITFDGKDIRPTIPFMIGDE

IFLPFYKNVFSEFFSLFRRVPTSTPYEDLTYFYECDYTDNKSTFDQFYLY

NGEEYTVKTQEATNKNMWLTTSEFRLKKWFDGEDCIMHLRSLVRKMEDSK

R).

In an embodiment, a ligand of the composition is a sequence of OMCP comprising at least 80% identity to SEQ ID NO:13. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:13.

In still another specific embodiment, a ligand of the composition is a sequence of OMCP such as the sequence set forth in

SEQ ID NO: 14

(HKLVHYFNLKINGSDITNTADILLDNYPIMTFDGKDIYPSIAFMVGNKL

FLDLYKNIFVEFFRLFRVSVSSQYEELEYYYSCDYTNNRPTIKQHYFYNG

EEYTEIDRSKKATNKNSWLITSGFRLQKWFDSEDCIIYLRSLVRRMEDSN

K).

In an embodiment, a ligand of the composition is a sequence of OMCP comprising at least 80% identity to SEQ ID NO:14. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:14.

In an alternative aspect, a receptor expressed on immune cells may be PD1. PD1, also known as programmed cell death protein 1 and CD279 (cluster of differentiation 279), is a protein that in humans is encoded by the PDCD1 gene.

PD1 is a cell surface receptor that belongs to the immunoglobulin superfamily and is expressed on T cells and pro-B cells. PD1 binds two ligands, PDL1 and PDL2. PD1, functioning as an immune checkpoint, plays an important role in down regulating the immune system by preventing the activation of T-cells. In certain embodiments, a ligand of the composition specifically binds to PD1. In an embodiment, a ligand that specifically binds to PD1 may be an anti-PD1 antibody. An "anti-PD1" includes all antibodies that specifically bind an epitope within PD1. The term "antibody" is described above. In another embodiment, a ligand that specifically binds to PD1 may be PDL1 or PDL2. PDL1 (programmed death-ligand 1 also known as cluster of differentiation 274 (CD274)) or B7 homolog 1 (B7-H1), is a protein that in humans is encoded by the CD274 gene. PDL1 binds to its receptor, PD1, found on activated T cells, B cells, and myeloid cells, to modulate activation or inhibition. The affinity between PDL1 and PD1, as defined by the dissociation constant $K_d$, is 770 nM. PDL2 (programmed death ligand 2 also known as cluster of differentiation 273 (CD273) or B7DC) is a protein that in humans is encoded by the PDCD1LG2 gene. PDL2 also binds to the PD1 receptor. The affinity between PDL2 and PD1, as defined by the dissociation constant $K_d$, is 590 nM The sequence information for full length PDL1 mRNA can be found, for example, using the NCBI accession number NM_014143, NM_001267706, NR_052005, NM_001314029, and the full length amino acid sequence can be found using, for example, the NCBI accession number NP_001300958, NP_001254635, NP_054862. A skilled artisan will appreciate that homologs of PDL1 may be found in other species. In a particular embodiment, PDL1 is derived from *Homo sapiens*. Sequence similarity may be determined via conventional algorithms, such as described herein above for OMCP. Specifically, "percent identity" of two polypeptides or two nucleic acid sequences Is determined using the BLASTN, BLASTX, and Gapped BLAST programs using the default parameters. See www.ncbi.nlm.nih.gov for more details. Generally, a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to PDL1.

In a specific embodiment, a ligand of the composition is a sequence of PDL1 such as the sequence set forth in

SEQ ID NO: 51
(MRIFAVFIFMTYWHLLNAFTVTVPKDLYVVEYGSNMTIECKFPVEKQLD

LAALIVYWEMEDKNIIQFVHGEEDLKVQHSSYRQRARLLKDQLSLGNAAL

QITDVKLQDAGVYRCMISYGGADYKRITVKVNAPYNKINQRILVVDPVTS

EHELTCQAEGYPKAEVIWTSSDHQVLSGKTTTTNSKREEKLFNVTSTLRI

NTTTNEIFYCTFRRLDPEENHTAELVIPGNILNVSIKICLTLSPST).

In an embodiment, a ligand of the composition is a sequence of PDL1 comprising at least 80% identity to SEQ ID NO:51. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:51.

In still another specific embodiment, a ligand of the composition is a sequence of PDL1 such as the sequence set forth in

SEQ ID NO: 52
(MRIFAVFIFMTYWHLLNAPYNKINQRILVVDPVTSEHELTCQAEGYPKA

EVIWTSSDHQVLSGKTTTTNSKREEKLFNVTSTLRINTTTNEIFYCTFRR

LDPEENHTAELVIPELPLAHPPNERTHLVILGAILLCLGVALTFIFRLRK

GRMMDVKKCGIQDTNSKKQSDTHLEET).

In an embodiment, a ligand of the composition is a sequence of PDL1 comprising at least 80% identity to SEQ ID NO:52. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:52.

In still another specific embodiment, a ligand of the composition is a sequence of PDL1 such as the sequence set forth in

SEQ ID NO: 53
(MRIFAVFIFMTYWHLLNAFTVTVPKDLYVVEYGSNMTIECKFPVEKQLD

LAALIVYWEMEDKNIIQFVHGEEDLKVQHSSYRQRARLLKDQLSLGNAAL

QITDVKLQDAGVYRCMISYGGADYKRITVKVNAPYNKINQRILVVDPVTS

EHELTCQAEGYPKAEVIWTSSDHQVLSGKTTTTNSKREEKLFNVTSTLRI

NTTTNEIFYCTFRRLDPEENHTAELVIPELPLAHPPNERTHLVILGAILL

CLGVALTFIFRLRKGRMMDVKKCGIQDTNSKKQSDTHLEET).

In an embodiment, a ligand of the composition is a sequence of PDL1 comprising at least 80% identity to SEQ ID NO:53. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:53.

The sequence information for full length PDL2 mRNA can be found for example, using the NCBI accession number NM_025239 and XM_005251600, and the full length amino acid sequence can be found using, for example, the NCBI accession number NP_079515 and XP_005251657. A skilled artisan will appreciate that homologs of PDL1 may be found in other species. In a particular embodiment, PDL2 is derived from *Homo sapiens*. Sequence similarity may be determined via conventional algorithms, such as described herein above for OMCP. Specifically, "percent identity" of two polypeptides or two nucleic acid sequences Is determined using the BLASTN, BLASTX, and Gapped BLAST programs using the default parameters. See www.ncbi.nlm.nih.gov for more details. Generally, a homolog will have a least 80, 81, 82, 83, 84, 85, 86, 87, 88, or 89% homology. In another embodiment, the sequence may be at least 90, 91, 92, 93, 94, 95, 96, 97, 98, 99, or 100% homologous to PDL2.

In a specific embodiment, a ligand of the composition is a sequence of PDL2 such as the sequence set forth in

SEQ ID NO: 54
(IFLLLMLSLELQLHQIAALFTVTVPKELYIIEHGSNVTLECNFDTGSHV

NLGAITASLQKVENDTSPHRERATLLEEQLPLGKASFHIPQVQVRDEGQY

QCIIIYGVAWDYKYLTLKVKASYRKINTHILKVPETDEVELTCQATGYPL

```
-continued
AEVSWPNVSVPANTSHSRTPEGLYQVTSVLRLKPPPGRNFSCVFWNTHVR

ELTLASIDLQSQMEPRTHPTWLLHIFIPFCIIAFIFIATVIALRKQLCQK

LYSSKDTTKRPVTTTKREVNSAI).
```

In an embodiment, a ligand of the composition is a sequence of PDL2 comprising at least 80% identity to SEQ ID NO:54. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:54.

In another specific embodiment, a ligand of the composition is a sequence of PDL2 such as the sequence set forth in

```
                                           SEQ ID NO: 54
(MIFLLLMLSLELQLHQIAALFTVTVPKELYIIEHGSNVTLECNFDTGSH

VNLGAITASLQKVENDTSPHRERATLLEEQLPLGKASFHIPQVQVRDEGQ

YQCIIYGVAWDYKYLTLKVKASYRKINTHILKVPETDEVELTCQATGYP

LAEVSWPNVSVPANTSHSRTPEGLYQVTSVLRLKPPPGRNFSCVFWNTHV

RELTLASIDLQSQMEPRTHPTWLLHIFIPFCIIAFIFIATVIALRKQLCQ

KLYSSKDTTKRPVTTTKREVNSAVNLNLWSWEPG).
```

In an embodiment, a ligand of the composition is a sequence of PDL2 comprising at least 80% identity to SEQ ID NO:54. For example, the ligand may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:54.

In another aspect, a ligand of the composition may be Glucocorticoid-induced TNFR-related (GITR) ligand (GITRL). GITR activation by GITRL influences the activity of effector and regulatory T cells, thus participating in the development of immune response against tumors and infectious agents, as well as in autoimmune and inflammatory diseases. GITR triggering stimulates T effector activity and inhibits Treg activity. GITR inhibition may ameliorate autoimmune/inflammatory diseases whereas GITR activation may treat viral, bacterial and parasitic infections, as well as boost immune responses against tumors. GITRL is a type II transmembrane protein expressed at high levels on antigen presenting cells (APC) and endothelial cells.

In certain embodiments, a ligand of the invention is modified for improved systemic half-life and reduced dosage frequency. In an embodiment, N-glycans may be added to a ligand. While the biological function is typically determined by the protein component, carbohydrate can play a role in molecular stability, solubility, in vivo activity, serum half-life, and immunogenicity. The sialic acid component of carbohydrate in particular, can extend the serum half-life of protein therapeutics. Accordingly, new N-linked glycosylation consensus sequences may be introduced into desirable positions in the peptide backbone to generate proteins with increased sialic acid containing carbohydrate, thereby increasing in vivo activity due to a longer serum half-life. In another embodiment, PEG may be added to a ligand. Methods of conjugating PEG to a protein are standard in the art. For example, see Kolate et al, *Journal of Controlled Release* 2014; 192(28): 67-81, which is hereby incorporated by reference in its entirety. In an embodiment, a composition of the invention may comprise a ligand comprising PEG and/or one or more N-glycans. In an embodiment, PEG is selected from the group consisting of PEG-10K, PEG-20K and PEG-40K. Still further, a ligand of the invention may be modified to remove T cell epitopes. T cell epitopes can be the cause of an immunogenicity issue upon administration of a composition to a subject. Through their presentation to T cells, they activate the process of anti-drug antibody development. Preclinical screening for T cell epitopes may be performed in silico, followed by in vitro and in vivo validation. T cell epitope-mapping tools such as EpiMatrix can be highly accurate predictors of immune response. Deliberate removal of T cell epitopes may reduce immunogenicity. Other means of improving the safety and efficacy of a composition of the invention by reducing their immunogenicity include humanization and PEGylation.

(c) Linker

In an aspect, a composition of the invention further comprises a linker. The linker may be used to connect the cytokine to the ligand. It is to be understood that linking the cytokine to the ligand will not adversely affect the function of the cytokine or the ligand. Suitable linkers include amino acid chains and alkyl chains functionalized with reactive groups for coupling to both the cytokine and the ligand or combinations thereof.

In an embodiment, the linker may include amino acid side chains, referred to as a peptide linker. Amino acid residue linkers are usually at least one residue and can be 50 or more residues, but alone do not specifically bind to the target protein. In an embodiment, a linker may be about 1 to about 10 amino acids. In another embodiment, a linker may be about 10 to about 20 amino acids. In still another embodiment, a linker may be about 20 to about 30 amino acids. In still yet another embodiment, a linker may be about 30 to about 40 amino acids. In different embodiments, a linker may be about 40 to about 50 amino acids. In other embodiments, a linker may be more than 50 amino acids. For instance, a linker may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids. In a specific embodiment, a linker is about 20 to about 30 amino acids. In another specific embodiment, a linker is about 26 amino acids.

Any amino acid residue may be used for the linker provided the linker does not specifically bind to the target protein. Typical amino acid residues used for linking are glycine, serine, alanine, leucine, tyrosine, cysteine, lysine, glutamic and aspartic acid, or the like. For example, a linker may be $(AAS)_n$, $(AAAL)_n$ (SEQ ID NO:68), $(G_nS)_n$ or $(G_2S)_n$, wherein A is alanine, S is serine, L is leucine, and G is glycine and wherein n is an integer from 1-20, or 1-10, or 3-10. Accordingly, n may be 1, 2, 3, 4, 5, 6, 7, 8, 9, 10, 11, 12, 13, 14, 15, 16, 17, 18, 19 or 20. Thus, in certain embodiments, a linker includes, but is not limited to, $(AAS)_n$, $(AAAL)_n$ (SEQ ID NO:68), $(G_nS)_n$ or $(G_2S)_n$, wherein A is alanine, S is serine, L is leucine, and G is glycine and wherein n is an integer from 1-20, or 1-10, or 3-10. A linker may comprise one or more epitope tags. For instance, a linker may comprise 1, 2, 3, 4, 5, 6, 7 or 8 epitope tags. In a specific embodiment, a linker comprises 2 epitope tags. Non-limiting examples of epitope tags include FLAG tag (DYKDDDK epitope (SEQ ID NO:9)), HA tag (YPYDVPDYA epitope (SEQ ID NO:10)), His tag (6×-His or 8×-His), Myc tag (EQKLISEEDL epitope (SEQ ID NO:11)) and V5 tag (GKPIPNPLLGLDST epitope (SEQ ID NO:12)). In an embodiment, a linker may comprise at least one tag selected from the group consisting of a FLAG tag and a His tag. In a specific embodiment, a linker comprises a FLAG tag and a His tag. In another specific embodiment, a linker comprises the sequence set forth in SEQ ID NO:8 (GSSGSSDYKDDDDKHHHHHHHHGSSGSS).

In another embodiment, an alkyl chain linking group may be coupled to the cytokine by reacting the terminal amino group or the terminal carboxyl group with a functional group on the alkyl chain, such as a carboxyl group or an activated ester. Subsequently the ligand is attached to the alkyl chain to complete the formation of the complex by reacting a second functional group on the alkyl chain with an appropriate group on the ligand. The second functional group on the alkyl chain is selected from substituents that are reactive with a functional group on the ligand while not being reactive with the cytokine. For example, when the ligand incorporates a functional group, such as a carboxyl group or an activated ester, the second functional group of the alkyl chain linking group can be an amino group or vice versa. It will be appreciated that formation of the conjugate may require protection and deprotection of the functional groups present in order to avoid formation of undesired products. Protection and deprotection are accomplished using protecting groups, reagents, and protocols common in the art of organic synthesis. Particularly, protection and deprotection techniques employed in solid phase peptide synthesis may be used. It will be appreciated that linking groups may alternatively be coupled first to the ligand and then to the cytokine.

An alternative chemical linking group to an alkyl chain is polyethylene glycol (PEG), which is functionalized in the same manner as the alkyl chain described above. Such a linker may be referred to as a heterobifunctional PEG linker or a homobifunctional PEG linker. Non-limiting examples of heterobifunctional PEG linkers include: O-(2-Aminoethyl)-O'-[2-(biotinylamino)ethyl]octaethylene glycol; O-(2-Aminoethyl)-O'-(2-carboxyethyl)polyethylene glycol hydrochloride $M_p$ 3000; O-(2-Aminoethyl)-O'-(2-carboxyethyl)polyethylene glycol 5,000 hydrochloride $M_p$ 5,000; O-(2-Aminoethyl)polyethylene glycol 3,000 Mp 3,000; O-(2-Aminoethyl)-O'-(2-(succinylamino)ethyl)polyethylene glycol hydrochloride Mp 10,000; O-(2-Azidoethyl)heptaethylene glycol; O-[2-(Biotinylamino)ethyl]-O'-(2-carboxyethyl)undecaethylene glycol; 21-[D(+)-Biotinylamino]-4,7,10,13,16,19-hexaoxaheneicosanoic acid; O-(2-Carboxyethyl)-O'-[2-(Fmoc-amino)-ethyl]heptacosaethylene glycol; O-(2-Carboxyethyl)-O'-(2-mercaptoethyl)heptaethylene glycol; O-(3-Carboxypropyl)-O'-[2-(3-mercaptopropionylamino)ethyl]-polyethylene glycol $M_w$ 3000; O-(3-Carboxypropyl)-O'-[2-(3-mercaptopropionylamino)ethyl]-polyethylene glycol $M_w$ 5000; O—[N-(3-Maleimidopropionyl)aminoethyl]-O'-[3-(N-succinimidyloxy)-3-oxopropyl]heptacosaethylene glycol; and O-[2-(3-Tritylthiopropionylamino)ethyl]polyethylene glycol $M_p$ 3,000. Non-limiting examples of homobifunctional PEG linkers include: MAL-PEG-MAL (Bifunctional Maleimide PEG Maleimide); OPSS-PEG-OPSS (OPSS: orthopyridyl disulfide; PDP-PEG-PDP); HS-PEG-SH (Bifunctional Thiol PEG Thiol); SG-PEG-SG (Bifunctional PEG Succinimidyl Glutarate NHS ester); SS-PEG-SS (Bifunctional PEG Succinimidyl Succinate NHS ester); GAS-PEG-GAS (Bifunctional PEG Succinimidyl ester NHS-PEG-NHS); SAS-PEG-SAS (Bifunctional PEG Succinimidyl ester NHS-PEG-NHS); Amine-PEG-Amine (Bifunctional PEG Amine NH2-PEG-NH2); AC-PEG-AC (Bifunctional Acrylate PEG Acrylate); ACA-PEG-ACA (Bifunctional Polymerizable PEG Acrylate Acrylamide); Epoxide-PEG-Epoxide (Bifunctional PEG Epoxide or EP); NPC-PEG-NPC (Bifunctional NPC PEG, Nitrophenyl Carbonate); Aldehyde-PEG-Aldehyde (ALD-PEG-ALD, bifunctional PEG propionaldehyde); AA-PEG-AA (Acid-PEG-Acid, AA—acetic acid or carboxyl methyl); GA-PEG-GA (Acid-PEG-Acid, GA: Glutaric acid); SA-PEG-SA (Bifunctional PEG carboxylic acid-Succinic Acid); GAA-PEG-GAA (Bifunctional PEG carboxylic acid, Glutaramide Acid); SAA-PEG-SAA (Bifunctional PEG carboxylic acid, Succinamide Acid); Azide-PEG-Azide (Bifunctional PEG azide, N3-PEG-N3); Alkyne-PEG-Alkyne (Bifunctional alkyne or acetylene PEG); Biotin-PEG-Biotin (Bifunctional biotin PEG linker); Silane-PEG-Silane (Bifunctional silane PEG); Hydrazide-PEG-Hydrazide (Bifunctional PEG Hydrazide); Tosylate-PEG-Tosylate (Bifunctional PEG Tosyl); and Chloride-PEG-Chloride (Bifunctional PEG Halide).

In certain embodiments, a linker of the invention may be modified for improved systemic half-life and reduced dosage frequency. In an embodiment, N-glycans are added to a linker. While the biological function is typically determined by the protein component, carbohydrates can play a role in molecular stability, solubility, in vivo activity, serum half-life, and immunogenicity. The sialic acid component of carbohydrate in particular, can extend the serum half-life of protein therapeutics. Accordingly, new N-linked glycosylation consensus sequences may be introduced into desirable positions in the peptide backbone to generate proteins with increased sialic acid containing carbohydrate, thereby increasing in vivo activity due to a longer serum half-life. In another embodiment, PEG is added to a linker. Methods of conjugating PEG to a protein are standard in the art. For example, see Kolate et al, *Journal of Controlled Release* 2014; 192(28): 67-81, which is hereby incorporated by reference in its entirety. In an embodiment, a composition of the invention comprises a ligand comprising PEG and/or one or more N-glycans. In an embodiment, PEG is selected from the group consisting of PEG-10K, PEG-20K and PEG-40K.

Another aspect of the invention involves cross-linking the peptides of the invention to improve their pharmacokinetic, immunogenic, diagnostic, and/or therapeutic attributes. Cross-linking involves joining two molecules by a covalent bond through a chemical reaction at suitable site(s) (e.g., primary amines, sulfhydryls) on the cytokine and ligand of the invention. In an embodiment, the cytokine and ligand may be cross-linked together. The cross-linking agents may form a cleavable or non-cleavable linker between the cytokine and the ligand. Cross-linking agents that form non-cleavable linkers between the cytokine and the ligand may comprise a maleimido- or haloacetyl-based moiety. According to the present invention, such non-cleavable linkers are said to be derived from maleimido- or haloacetyl-based moiety. Cross-linking agents comprising a maleimido-based moiety include N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester [AMAS], succinimidyl-6-(β-maleimidopropionamido) hexanoate (SMPH), N-succinimidyl 4-(p-maleimidophenyl)-butyrate (SMPB), and N-(p-maleimidophenyl)isocyanate (PMPI). These cross-linking agents form non-cleavable linkers derived from maleimido-based moieties. Cross-linking agents comprising a haloacetyl-based moiety include N-succinimidyl-4-(iodoacetyl)-aminobenzoate (SIAB), N-succinimidyl iodoacetate (SIA), N-succinimidyl bromoacetate (SBA) and N-succinimidyl 3-(bromoacetamido)propionate (SBAP). These cross-linking agents form non-cleavable linkers derived from haloacetyl-based moieties. Cross-linking agents that form non-cleavable linkers between the cytokine and the ligand may comprise N-succinimidyl 3-(2-pyridyldithio)propionate, 4-succinimidyl-oxycarbonyl-α-methyl-alpha-(2-pyridyldithio)-toluene (SMPT), N-succinimidyl-3-(2-pyridyldithio)-butyrate (SDPB), 2-iminothiolane, or acetylsuccinic anhydride.

(d) Chimeric Peptide

In another aspect, the invention encompasses a chimeric peptide comprising a cytokine peptide and a NKG2D ligand peptide. In an alternate aspect, the invention encompasses a chimeric peptide comprising a cytokine peptide and a PD1 ligand peptide. It should be understood that "ligand peptide" is used interchangeably with "ligand" and "cytokine peptide" is used interchangeably with "cytokine" for purposes of descriptions herein of various cytokines and ligands that are suitable for use in the present compositions and methods. In certain embodiments, the cytokine peptide is in the IL2 subfamily. More specifically, the cytokine peptide is selected from the group consisting of IL2, IL7, IL15 and IL21. In a specific embodiment, the cytokine peptide is IL15 or a mutant thereof. In another specific embodiment, the cytokine peptide is IL2 or a mutant thereof. In another embodiment, the cytokine peptide is mutant IL2 comprising at least one mutation selected from the group consisting of R38A, F42K and C125S. In a specific embodiment, the cytokine peptide comprises the amino acid sequence set forth in SEQ ID NO:5 or SEQ ID NO:6. In other embodiments, the cytokine peptide is in the IL1 family. More specifically, the cytokine peptide is selected from the group consisting of IL1α, IL1β, IL1Ra, IL18, IL36Ra, IL36α, IL37, IL36β, IL36γ, IL38, and IL33. In a specific embodiment, the cytokine peptide is IL18 or a mutant thereof.

In certain embodiments, the cytokine peptide is in the tumor necrosis factor ligand superfamily (TNFSF). More specifically, the cytokine peptide is selected from the group consisting of TNF-alpha, OX40L, a 4-1BB ligand, TRAIL, Fas ligand, lymphotoxin-alpha, lymphotoxin-beta, CD30L, CD40L, CD27L and RANKL. In a specific embodiment, the cytokine peptide is OX40L, or a mutant thereof. In another specific embodiment, the cytokine peptide contains an OX40L fragment. In a specific embodiment, the OX40L fragment comprises the amino acid sequence set forth in SEQ ID NO:57. In certain specific embodiments, the OX40L fragments may be connected into a continuous construct via linker peptides. In a specific embodiment, the construct containing the OX40L fragments comprises the amino acid sequence set forth in SEQ ID NO:58. In certain embodiments, the cytokine peptide is a mutant OX40L comprising at least one mutant selected from the group N166A and F180A. In a specific embodiment, the cytokine contains a mutant OX40L fragment containing at least one mutant selected from the group N166A and F180A. In a specific embodiment, the mutant OX40L fragment comprises the amino acid sequence set forth in SEQ ID NO:59. In certain specific embodiments, mutant OX40L fragments or mutant and unmutated OX40L fragments may be connected into a continuous construct via linker peptides. In a specific embodiment, the construct containing the mutant and unmutated OX40L fragments comprises the amino acid sequence set forth in SEQ ID NO:60 or SEQ ID NO:61. In an alternate specific embodiment, the cytokine peptide is 4-1BBL, or a mutant thereof. In another specific embodiment, the cytokine peptide contains a 4-1BBL fragment. In a specific embodiment, the 4-1BBL fragment comprises the amino acid sequence set forth in SEQ ID NO:65. In certain specific embodiments, the 4-1BBL fragments may be connected into a continuous construct via linker peptides. In a specific embodiment, the construct containing the 4-1BBL fragments comprises the amino acid sequence set forth in SEQ ID NO:66. In certain embodiments, the cytokine peptide is a mutant 4-1BBL. In certain embodiments, the cytokine contains a mutant 4-1BBL fragment. In certain embodiments, mutant 4-1BBL fragments or mutant and unmutated 4-1BBL fragments may be connected into a continuous construct via linker peptides.

In certain embodiments, the NKG2D ligand peptide is an anti-NKG2D antibody. In another embodiment, the NKG2D ligand peptide is a MHC class-I-related glycoprotein. In another embodiment, the ligand peptide is OMCP, a portion thereof, or a mutant thereof. In an embodiment, the ligand peptide binds to a receptor expressed on NK cells and CD8+ CTLs. In a specific embodiment, the ligand peptide binds to an NKG2D receptor. In certain embodiments, the ligand peptide comprises the amino acid sequence set forth in SEQ ID NO:7 or a portion thereof that is capable of binding to the NKG2D receptor.

In certain embodiments, the PD1 ligand peptide is an anti-PD1 antibody. In another embodiment, the PD1 ligand peptide is PDL1, a portion thereof, or a mutant thereof. In yet another embodiment, the PD1 ligand peptide is PDL2, a portion thereof, or a mutant thereof. In an embodiment, the ligand peptide binds to a receptor expressed on T cells, NK cells, and macrophages. In a specific embodiment, the ligand peptide binds to a PD1 receptor. In certain embodiments, the ligand peptide comprises the amino acid sequence set forth in SEQ ID NO:48 or SEQ ID NO:50 or a portion thereof that is capable of binding to the PD1 receptor.

In other embodiments, a chimeric peptide further comprises a linker peptide. In certain embodiments, a linker peptide comprises the amino acid sequence selected from the group consisting of $(AAS)_n$, $(AAAL)_n$ (SEQ ID NO:68), $(G_nS)_n$ or $(G_2S)_n$, wherein A is alanine, S is serine, L is leucine, and G is glycine and wherein n is an integer from 1-20, or 1-10, or 3-10. In a different embodiment, a linker peptide comprises at least one tag selected from the group consisting of a FLAG tag and a His tag. In an embodiment, a linker peptide is about 20 to about 30 amino acids. In a specific embodiment, a linker peptide comprises the amino acid sequence set forth in SEQ ID NO:8.

The invention also encompasses a nucleic acid molecule encoding a chimeric peptide as described herein. Additionally, the invention encompasses a pharmaceutical composition comprising a chimeric peptide as described herein. Pharmaceutical compositions are described in more detail in Section I(h).

A chimeric peptide of the disclosure may optionally comprise a signal peptide and/or a purification moiety. When present, typically the signal peptide is at the N-terminus of the chimeric peptide and the purification moiety is at the C-terminus of the chimeric peptide. Alternatively, the signal peptide and the purification moiety are both at the N-terminus of the chimeric peptide. The choice of signal peptide can and will vary depending on a variety factors including, but not limited to, the desired cellular location and type of cell. Suitable polynucleotide sequence encoding signal peptides are known in the art, as are polypeptide sequences encoded therefrom. In a specific embodiment, the signal peptide comprises SEQ ID NO:69 (MGILPSPGM-PALLSLVSLLSVLLMGCVAETG). Similarly, the choice of purification moiety can and will vary. Suitable purification moieties are known in the art, as are the polynucleotide sequences encoding them. In general, signal peptides and/or purification moieties are cleaved off during processing and not included in the final chimeric peptide for use in a pharmaceutical composition.

The disclosure also encompasses a vector comprising a nucleic acid sequence capable of encoding a chimeric peptide of the disclosure. As used herein, a "vector" is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors. An expression vector encoding a chimeric peptide of the disclosure may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding a chimeric peptide of the disclosure that is introduced to the cell may be linear or circular, may be single-stranded or double-stranded, and may be DNA, RNA, or any modification or combination thereof. The disclosure also encompasses a cell line comprising a vector comprising a nucleic acid sequence capable of encoding a chimeric peptide of the disclosure. In some embodiments, the cell line is an immortalized cell line.

(e) Targeting Molecule

As used herein, a "targeting molecule" is a molecule that is capable of binding to a target specific to a cell in a disease state or to the extracellular matrix surrounding the diseased cell. In some instances, the targeting molecule binds a target molecular entity expressed on a cell. The targeting molecule may be any molecule capable of such association or binding including, but not limited to, receptor ligands and antibodies. Various types of targeting molecules will be known to one of skill in the art. For example, receptor ligands bind to target receptors expressed on the surface of a cell. Targeting molecules may also include other molecules such as interferons alpha, beta and gamma. Other examples of targeting molecules include antibodies, including agonist and antagonist antibodies to TNF receptors, antibodies to antigens present in a tumor stroma, antibodies to mesothelin and antibodies carcinoembryonic antigen. Antibodies to particular antigen targets may be generated by means known to those skilled in the art, including those methods discussed previously in this disclosure. In certain aspects, a targeting molecule may include only a portion of a molecule such as the binding portion of a ligand or antibody. The targeting molecule may be linked to the ligand by a linker as discussed in this disclosure. The targeting molecules of the present invention may be produced by means known to those of skill in the art.

(f) Combination Therapies

As used herein, "combination" is meant to include therapies that can be administered separately, for example, formulated separately for separate administration (e.g., as can be provided in a kit), and therapies that can be administered together in a single formulation (i.e., a "co-formulation"). Combinations of the polypeptides provided herein with one or more active therapeutic agents can be administered or applied sequentially (e.g., where one agent is administered prior to one or more other agents) or simultaneously (e.g., where two or more agents are administered at or about the same time). In some embodiments, administration is sequential. In other embodiments, administration is simultaneous. Regardless of whether the two or more agents are administered sequentially or simultaneously, they are considered to be administered in combination for purposes of the present disclosure.

Accordingly, methods and uses of the polypeptides described herein can be practiced prior to, substantially contemporaneously with or following another treatment, and can be supplemented with other forms of therapy.

In an aspect, provided herein are combination therapies that include a composition as described herein and a PD-1 inhibitor. A "PD-1 inhibitor" refers to a moiety (e.g., compound, nucleic acid, polypeptide, antibody) that decreases, inhibits, blocks, abrogates or interferes with the activity or expression of PD-1 (e.g., Programmed Cell Death Protein 1; PD-1 (CD279); GI: 145559515), including variants, isoforms, species homologs of human PD-1 (e.g., mouse) and analogues that have at least one common epitope with PD-1. A PD-1 inhibitor includes molecules and macromolecules such as, for example, compounds, nucleic acids, polypeptides, antibodies, peptibodies, diabodies, minibodies, nanobodies, single-chain variable fragments (scFv), and functional fragments or variants thereof. In particular embodiments described herein, a PD-1 inhibitor is an anti-PD-1 antibody. A PD-1 inhibitor (including an anti-PD-1 antibody) can antagonize PD-1 activity or expression. An anti-PD-1 antibody can be a monoclonal or polyclonal antibody as described herein. In some embodiments, the anti-PD-1 antibody is a monoclonal antibody. In other embodiments, the anti-PD-1 antibody is a polyclonal antibody. 0).

In one embodiment, the PD-1 inhibitor is selected from the group consisting of nivolumab, pembrolizumab, pidilizumab, AMP-224, REGN2810, PDR 001, and MEDI0680. In some embodiments, the PD-1 inhibitor is nivolumab. In some embodiments, the PD-1 inhibitor is pembrolizumab. In some embodiments, the PD-1 inhibitor is pidilizumab. In some embodiments, the PD-1 inhibitor is AMP-224. In some embodiments, the PD-1 inhibitor is REGN2810. In some embodiments, the PD-1 inhibitor is PDR 001. In some embodiments, the PD-1 inhibitor is MEDI0680.

In an aspect, the invention encompasses a combination therapy that includes a PD-1 inhibitor described herein and a composition comprising a cytokine as provided herein linked to a NKG2D ligand provided herein. The composition may further comprise a linker as described herein to connect the cytokine to the ligand as provided herein. For example, the cytokine can be an IL1 family cytokine, including those described herein (e.g., IL1α, IL1β, IL1 Ra, IL18, IL36Ra, IL36α, IL37, IL36β, IL36γ, IL38, and IL33. For example, the cytokine can be an IL2 subfamily cytokine such as IL2, IL4, IL7, IL9, IL15 and IL21. In some embodiments, the cytokine is IL2. In other embodiments, the cytokine is a mutant R38A/F42K form of IL2. For example, the cytokine can be an interferon as described herein (e.g., IFN-α, IFN-β, IFN-ε, IFN-κ, IFN-ω, IL10R2, or IFNLR1). In another example the cytokine is an interleukin such as, but not limited to, IL1, IL2, IL3, IL4, IL5, IL6, IL7, IL8 (CXCL8), IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL35, or IL36. In another example, the cytokine is a member of the TNFSF family such as, but not limited to TNF (TNFalpha), CD40L (TNFSF5), CD70 (TNFSF7), EDA, FASLG (TNFSF6), LTA (TNFSF1), LTB (TNFSF3), TNFSF4 (OX40L), TNFSF8 (CD153), TNFSF9 (4-1BBL), TNFSF10 (TRAIL), TNFSF11 (RANKL), TNFSF12 (TWEAK), TNFSF13, TNFSF13B, TNFSF14, TNFSF15, TNFSF18. For example, the NKG2D ligand can be NKG2A, NKG2B, NKG2C, NKG2D, NKG2E, NKG2F or NKG2H as described herein. The ligand can be selected from the group consisting of MICA, MICB, ULBP1, ULBP2, ULBP3, ULBP4, ULBP5, ULBP6, Rae1, H60a, H60b, H60c, h-HLA-A, Multi or OMCP. In certain embodiments, the NKG2D ligand is OMCP (e.g., SEQ ID NOs: 7, 13, or 14) as described herein.

In one embodiment, the combination therapy includes a PD-1 inhibitor described herein and a composition that includes OMCP or a portion thereof as provided herein and a targeting molecule. The OMCP can be linked to the targeting molecule or a portion of OMCP can be linked to the targeting molecule. In one embodiment, the combination therapy includes a PD-1 inhibitor described herein and a composition comprising OMCP or a portion thereof as provided herein and a tumor necrosis factor (TNF) family member. In one embodiment, the combination therapy includes a PD-1 inhibitor described herein and a composition comprising OMCP or a portion thereof as provided herein and TNF-related apoptosis-inducing targeting molecule. In one embodiment, the combination therapy includes a PD-1 inhibitor described herein and a composition comprising OMCP or a portion thereof as provided herein and a 4-1BB ligand. In one embodiment, the combination therapy includes a PD-1 inhibitor described herein and a composition comprising OMCP or a portion thereof as provided herein and a 4-1BB agonist. In one embodiment, the combination therapy includes a PD-1 inhibitor described herein and a composition comprising OMCP or a portion thereof as provided herein and TNF-alpha. In one embodiment, the combination therapy includes a PD-1 inhibitor described herein and a composition comprising OMCP or a portion thereof as provided herein and OX40L. In one embodiment, the combination therapy includes a PD-1 inhibitor described herein and a composition comprising OMCP or a portion thereof as provided herein and Fas ligand. In one embodiment, the combination therapy includes a PD-1 inhibitor described herein and a composition comprising OMCP or a portion thereof as provided herein and lymphotoxin-alpha (LT-a). In one embodiment, the combination therapy includes a PD-1 inhibitor described herein and a composition comprising OMCP or a portion thereof as provided herein and lymphotoxin-beta (LT-b). In one embodiment, the combination therapy includes a PD-1 inhibitor described herein and a composition comprising OMCP or a portion thereof as provided herein and CD40L. In one embodiment, the combination therapy includes a PD-1 inhibitor described herein and a composition comprising OMCP or a portion thereof as provided herein and CD27L. In one embodiment, the combination therapy includes a PD-1 inhibitor described herein and a composition comprising OMCP and receptor activator of nuclear factor kappa-B targeting molecule (RANKL).

In one embodiment, the combination therapy includes a PD-1 inhibitor described herein and a cytokine linked to an NKG2D ligand (e.g., KYK-1, an scFv of KYK-1, KYK-2 or an scFv of KYK-2). In one embodiment, the combination therapy includes a PD-1 inhibitor described herein and a cytokine linked to an NKG2D ligand, where the NKG2D ligand has the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In one embodiment, the combination therapy includes a PD-1 inhibitor described herein and a fusion protein described herein (e.g. a NKG2D ligand and a cytokine). The combination therapy can include a PD-1 inhibitor described herein and a fusion protein having the amino acid sequence set forth in SEQ ID NO:43, SEQ ID NO:44, SEQ ID NO:45, or SEQ ID NO:46.

Further provided herein are combination therapies that include a PD-1 inhibitor and a chimeric peptide described herein. In one embodiment, the combination therapy includes a PD-1 inhibitor described herein and a chimeric peptide that includes a cytokine peptide as described herein and a NKG2D ligand peptide as described herein. In certain instances, the cytokine peptide can be selected from the group consisting of IL2, IL7, IL15, IL18, IL21, and mutants thereof. In one embodiment, the cytokine peptide of the combination therapy is IL or a mutant thereof (e.g., SEQ ID NO:5 or 6). The NKG2D ligand of the chimeric peptide in the combination therapies described herein includes those ligands provided herein (e.g. KYK-1, an scFv of KYK-1, KYK-2, or an scFv of KYK-2). In another example, the NKG2D ligand of the chimeric peptide of the combination therapy has the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In another embodiment provided herein is a combination therapy that includes a PD-1 inhibitor provided herein and a chimeric peptide that includes a cytokine peptide and an anti-NKG2D antibody. The cytokine peptide is a cytokine as described hereinabove. The anti-NKG2D antibody is as described hereinabove.

In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In some embodiments, the IL2 is a mutant R38A/F42K form of IL2.

In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In some embodiments, the IL2 is a mutant R38A/F42K form of IL2.

In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the IL2 is a mutant R38A/F42K form of IL2.

In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2.

In another aspect of the invention provided herein are combination therapies that include a composition as described herein and a PD-L1 inhibitor. The term "PD-L1 inhibitor" refers to a moiety (e.g., compound, nucleic acid, polypeptide, antibody) that decreases, inhibits, blocks, abrogates or interferes with the activity, binding of PD-L1 to its receptor, PD-L1, or expression of PD-L1 (e.g., Programmed Cell Death 1 Ligand; PD-L1 (CD274); GI: 30088843), including variants, isoforms, species homologs of human PD-L1 (e.g., mouse) and analogues that have at least one common epitope with PD-L1. A PD-L1 inhibitor includes molecules and macromolecules such as, for example, compounds (small molecule compounds), nucleic acids, polypeptides, antibodies, peptibodies, diabodies, minibodies, single-domain antibodies or nanobodies, single-chain variable fragments (ScFv), and fragments or variants thereof. In particular embodiments, a PD-L1 inhibitor is an anti-PD-L1 antibody. A PD-L1 inhibitor (including an anti-PD-L1 antibody) can antagonize PD-L1 activity, its binding to PD-1, or its expression. Exemplary PD-L1 inhibitors include, but are not limited to, durvalumab, avelumab, atezolizumab, BMS-936559, STI-A1010, STI-A1011, STI-A1012, STI-A1013, STI-A1014, and STI-A1015.

In an aspect, the invention encompasses a combination therapy that includes a PD-L1 inhibitor described herein and a composition comprising a cytokine as provided herein linked to a NKG2D ligand provided herein. In some embodiments, the PD-L1 inhibitor is durvalumab. In some embodiments, the PD-L1 inhibitor is avelumab. In some embodiments, the PD-L1 inhibitor is atezolizumab. In some embodiments, the PD-L1 inhibitor is BMS-936559. In some embodiments, the PD-L1 inhibitor is STI-A1010, STI-A1011, STI-A1012, STI-A1013, STI-A1014, or STI-A1015.

The composition may further comprise a linker as described herein to connect the cytokine to the ligand as provided herein. The cytokine is a cytokine described herein. For example, the cytokine can be an IL1 family cytokine, including those described herein (e.g., IL1α, IL1β, IL1 Ra, IL18, IL36Ra, IL36α, IL37, IL36β, IL36γ, IL38, and IL33. For example, the cytokine can be an IL2 subfamily cytokine such as IL2, IL4, IL7, IL9, IL15 and IL21. In some embodiments, the cytokine is IL2. In other embodiments, the cytokine is a mutant R38A/F42K form of IL2. For example, the cytokine can be an interferon as described herein (e.g., IFN-α, IFN-β, IFN-ε, IFN-κ, IFN-ω, IL10R2, or IFNLR1). In another example the cytokine is an interleukin such as, but not limited to, IL1, IL2, IL3, IL4, IL5, IL6, IL7, IL8 (CXCL8), IL9, IL10, IL11, IL12, IL13, IL14, IL15, IL16, IL17, IL18, IL19, IL20, IL21, IL22, IL23, IL24, IL25, IL26, IL27, IL28, IL29, IL30, IL31, IL32, IL33, IL35, or IL36. In another example, the cytokine is a member of the TNFSF family such as, but not limited to TNF (TNFalpha), CD40L (TNFSF5), CD70 (TNFSF7), EDA, FASLG (TNFSF6), LTA (TNFSF1), LTB (TNFSF3), TNFSF4 (OX40L), TNFSF8 (CD153), TNFSF9 (4-1BBL), TNFSF10 (TRAIL), TNFSF11 (RANKL), TNFSF12 (TWEAK), TNFSF13, TNFSF13B, TNFSF14, TNFSF15, TNFSF18. The NKG2D ligand is as described above. For example, the ligand can be NKG2A, NKG2B, NKG2C, NKG2D, NKG2E, NKG2F or NKG2H as described herein. The ligand can be selected from the group consisting of MICA, MICB, ULBP1, ULBP2, ULBP3, ULBP4, ULBP5, ULBP6, Rae1, H60a, H60b, H60c, h-HLA-A, Multi or OMCP. In certain instances the NKG2D ligand is OMCP (e.g., SEQ ID NOs: 7, 13, or 14) as described herein.

In one embodiment, the combination therapy includes a PD-L1 inhibitor described herein and a composition that includes OMCP or a portion thereof as provided herein and a targeting molecule. The OMCP can be linked to the targeting molecule or a portion of OMCP can be linked to the targeting molecule. In one embodiment, the combination therapy includes a PD-L1 inhibitor described herein and a composition comprising OMCP or a portion thereof as provided herein and a tumor necrosis factor (TNF) family member. In one embodiment, the combination therapy includes a PD-L1 inhibitor described herein and a composition comprising OMCP or a portion thereof as provided herein and TNF-related apoptosis-inducing targeting molecule. In one embodiment, the combination therapy includes a PD-L1 inhibitor described herein and a composition comprising OMCP or a portion thereof as provided herein and a 4-1BB ligand. In one embodiment, the combination therapy includes a PD-L1 inhibitor described herein and a composition comprising OMCP or a portion thereof as provided herein and a 4-1BB agonist. In one embodiment, the combination therapy includes a PD-L1 inhibitor described herein and a composition comprising OMCP or a portion thereof as provided herein and TNF-alpha. In one embodiment, the combination therapy includes a PD-L1 inhibitor described herein and a composition comprising OMCP or a portion thereof as provided herein and OX40L. In one embodiment, the combination therapy includes a PD-L1 inhibitor described herein and a composition comprising OMCP or a portion thereof as provided herein and Fas ligand. In one embodiment, the combination therapy includes a PD-L1 inhibitor described herein and a composition comprising OMCP or a portion thereof as provided herein and lymphotoxin-alpha (LT-a). In one embodiment, the combination therapy includes a PD-L1 inhibitor described herein and a composition comprising OMCP or a portion thereof as provided herein and lymphotoxin-beta (LT-b). In one embodiment, the combination therapy includes a PD-L1 inhibitor described herein and a composition comprising OMCP or a portion thereof as provided herein and CD40L. In one embodiment, the combination therapy includes a PD-L1 inhibitor described herein and a composition comprising OMCP or a portion thereof as provided herein and CD27L. In one embodiment, the combination therapy includes a PD-L1 inhibitor described herein and a composition comprising OMCP and receptor activator of nuclear factor kappa-B targeting molecule (RANKL).

In one embodiment, the combination therapy includes a PD-L1 inhibitor described herein and a cytokine linked to an NKG2D ligand (e.g., KYK-1, an scFv of KYK-1, KYK-2 or an scFv of KYK-2). In one embodiment, the combination therapy includes a PD-L1 inhibitor described herein and a cytokine linked to an NKG2D ligand, where the NKG2D ligand has the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In one embodiment, the combination therapy includes a PD-L1 inhibitor described herein and a fusion protein described herein (e.g. a NKG2D ligand and a cytokine). The combination therapy can include a PD-L1 inhibitor described herein and a fusion protein having the amino acid sequence set forth in SEQ ID NO:43, SEQ ID NO:44, SEQ ID NO:45, or SEQ ID NO:46.

Further provided herein are combination therapies that include a PD-L1 inhibitor and a chimeric peptide described herein. In one embodiment, the combination therapy includes a PD-L1 inhibitor described herein and a chimeric peptide that includes a cytokine peptide as described herein and a NKG2D ligand peptide as described herein. In certain instances, the cytokine peptide can be selected from the group consisting of IL2, IL7, IL15, IL18, IL21, and mutants thereof. In one embodiment, the cytokine peptide of the combination therapy is IL or a mutant thereof (e.g., SEQ ID NO:5 or 6). The NKG2D ligand of the chimeric peptide in the combination therapies described herein includes those ligands provided herein (e.g. KYK-1, an scFv of KYK-1, KYK-2, or an scFv of KYK-2. In another example, the NKG2D ligand of the chimeric peptide of the combination therapy has the amino acid sequence set forth in SEQ ID NO: 35, SEQ ID NO: 36, SEQ ID NO: 37, SEQ ID NO: 38, SEQ ID NO: 39, SEQ ID NO: 40, SEQ ID NO: 41, or SEQ ID NO: 42.

In another embodiment provided herein is a combination therapy that includes a PD-L1 inhibitor provided herein and a chimeric peptide that includes a cytokine peptide and an anti-NKG2D antibody. The cytokine peptide is a cytokine as described hereinabove. The anti-NKG2D antibody is as described hereinabove.

In another embodiment provided herein is a combination therapy that includes a PD-L1 inhibitor provided herein and a chimeric peptide that includes a cytokine peptide and an anti-NKG2D antibody. The cytokine peptide is a cytokine as described hereinabove. The anti-NKG2D antibody is as described hereinabove.

In one embodiment, the combination therapy comprises an OMCP-IL2 fusion protein and a PD-L1 inhibitor. In another embodiment, the combination therapy comprises an OMCP-IL2 fusion protein and an anti-PD-L1 antibody. In some embodiments, the fusion protein further comprises a linker. In some embodiments, the IL2 is a mutant R38A/F42K form of IL2.

In one embodiment, the combination therapy comprises an OMCP-IL2 chimeric protein and a PD-L1 inhibitor. In another embodiment, the combination therapy comprises an OMCP-IL2 chimeric protein and an anti-PD-L1 antibody. In some embodiments, the chimeric protein further comprises a linker. In some embodiments, the IL2 is a mutant R38A/F42K form of IL2.

In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-L1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the IL2 is a mutant R38A/F42K form of IL2.

In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-L1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2.

(g) Preferred Embodiments

By way of non-limiting example, several preferred compositions of the invention are depicted in FIG. 23. 1. depicts a composition comprising α2 domain (H2) of OMCP linked to a cytokine. 2. depicts a composition comprising OMCP linked to a cytokine, wherein the composition is pegylated. 3. depicts a composition comprising OMCP linked to a cytokine, wherein the composition comprises N-glycan. 4. depicts a composition comprising, OMCP linked to a cytokine, wherein the linker comprises various sequences and various lengths. 5. depicts a composition comprising a Fab specific antibody for NKG2D linked to a cytokine. 6. depicts a composition comprising various NKG2D ligands linked to a cytokine. 7. depicts a composition comprising a mutated version of OMCP linked to a cytokine, wherein the OMCP may be mutated to have improved binding affinity or weaker binding affinity. 8. depicts a composition comprising a mutated version of OMCP linked to a cytokine, wherein the OMCP may be mutated to have binding affinity for other NKG2 receptors. 9. depicts a composition comprising a viral protein liked to a cytokine. For example, OMCP binds to NKG2D. Additionally, CPXV203 binds to MHCI. 10. depicts a composition comprising OMCP linked to a mutated cytokine. It is understood that the OMCP sequence could be from various sources such as cowpox or monkeypox. Also, Fc-chimeras of OMCP and IL2, and variants thereof may be used.

In a preferred embodiment, the composition comprises IL2, IL15 or IL18 linked to OMCP. In another preferred embodiment, the composition comprises IL2, IL15 or IL18 linked to OMCP via a peptide linker. In still another preferred embodiment, the composition comprises IL2, IL15 or IL18 linked to OMCP via a peptide linker comprising about 20 to about 30 amino acids. In still yet another preferred embodiment, the composition comprises IL2, IL15 or IL18 linked to OMCP via a peptide linker comprising a FLAG tag and a His tag. In each of the foregoing embodiments, the IL2 may be a mutated version of IL2 comprising the mutations R38A and F42K.

In a preferred embodiment, the composition comprises IL2, IL15 or IL18 linked to an anti-NKG2D antibody. In another preferred embodiment, the composition comprises IL2, IL15 or IL18 linked to an anti-NKG2D antibody via a peptide linker. In still another preferred embodiment, the composition comprises IL2, IL15 or IL18 linked to an anti-NKG2D antibody via a peptide linker comprising about 20 to about 30 amino acids. In still yet another preferred embodiment, the composition comprises IL2, IL15 or IL18 linked to an anti-NKG2D antibody via a peptide linker comprising a FLAG tag and a His tag. In each of the foregoing embodiments, the IL2 may be a mutated version of IL2 comprising the mutations R38A and F42K.

In a different preferred embodiment, the composition comprises IL2 linked to OMCP. In another preferred embodiment, the composition comprises IL2 linked to OMCP via a peptide linker. In still another preferred embodiment, the composition comprises IL2 linked to OMCP via a peptide linker comprising about 20 to about 30 amino acids. In still yet another preferred embodiment, the composition comprises IL2 linked to OMCP via a peptide linker comprising a FLAG tag and a His tag. In each of the foregoing embodiments, the IL2 may be a mutated version of IL2 comprising the mutations R38A and F42K.

In a different preferred embodiment, the composition comprises IL2 linked to an anti-NKG2D antibody. In another preferred embodiment, the composition comprises IL2 linked to an anti-NKG2D antibody via a peptide linker. In still another preferred embodiment, the composition comprises IL2 linked to an anti-NKG2D antibody via a peptide linker comprising about 20 to about 30 amino acids. In still yet another preferred embodiment, the composition comprises IL2 linked to an anti-NKG2D antibody via a peptide linker comprising a FLAG tag and a His tag. In each of the foregoing embodiments, the IL2 may be a mutated version of IL2 comprising the mutations R38A and F42K.

In an exemplary embodiment, the NKG2D ligand is an anti-NKG2D antibody or a scFv thereof, such as KYK-1 antibody, KYK-2 antibody, KYK-1 scFv, or KYK-2 scFv. In one particular exemplary embodiment, a chimeric peptide is provided wherein the anti-NKG2D antibody is KYK-1 linked to mutIL2 and comprises the amino acid sequence set forth in

SEQ ID NO: 43
(QPVLTQPSSVSVAPGETARIPCGGDDIETKSVHWYQQKPGQAPVLVIYD
DDDRPSGIPERFFGSNSGNTATLSISRVEAGDEADYYCQVWDDNNDEWVF
GGGTQLTVLGGGGSGGGGSGGGGSGGGGSEVQLVESGGGVVQPGGSLRLS
CAASGFTFSSYGMHWVRQAPGKGLEWVAFIRYDGSNKYYADSVKGRFTIS
RDNSKNTLYLQMNSLRAEDTAVYYCAKDRFGYYLDYWGQGTLVTVSSGGS
SGSSGSSHHHHHHHHGGSSGSSGSSAPTSSSTKKTQLQLEHLLLDLQMIL
NGINNYKNPKLTAMLTKKFYMPKKATELKHLQCLEEELKPLEEVLNLAQS
KNFHLRPRDLISNINVIVLELKGSETTFMCEYADETATIVEFLNRWITFS
QSIISTLT), or alternatively, comprises the amino acid sequence set forth in

SEQ ID NO: 44

(EVQLVESGGGVVQPGGSLRLSCAASGFTFSSYGMHWVRQAPGKGLEWVA
FIRYDGSNKYYADSVKGRFTISRDNSKNTLYLQMNSLRAEDTAVYYCAKD

-continued

RFGYYLDYWGQGTLVTVSSGGGGSGGGGSGGGGSGGGGSQPVLTQPSSVS
VAPGETARIPCGGDDIETKSVHWYQQKPGQAPVLVIYDDDDRPSGIPERF
FGSNSGNTATLSISRVEAGDEADYYCQVWDDNNDEWVFGGGTQLTVLGGS
SGSSGSSHHHHHHHHGGSSGSSGSSAPTSSSTKKTQLQLEHLLLDLQMIL
NGINNYKNPKLTAMLTKKFYMPKKATELKHLQCLEEELKPLEEVLNLAQS
KNFHLRPRDLISNINVIVLELKGSETTFMCEYADETATIVEFLNRWITFS
QSIISTLT).

In another particular exemplary embodiment, a chimeric peptide is provided wherein the anti-NKG2D antibody is KYK-2 linked to mutIL2 and comprises the amino acid sequence set forth in

SEQ ID NO: 45

(QSALTQPASVSGSPGQSITISCSGSSSNIGNNAVNWYQQLPGKAPKLLI
YYDDLLPSGVSDRFSGSKSGTSAFLAISGLQSEDEADYYCAAWDDSLNGP
VFGGGTKLTVLGGGGSGGGGSGGGGSGGGGSQVQLVESGGGLVKPGGSLR
LSCAASGFTFSSYGMHWVRQAPGKGLEWVAFIRYDGSNKYYADSVKGRFT
ISRDNSKNTLYLQMNSLRAEDTAVYYCAKDRGLGDGTYFDYWGQGTTVTV
SSGGSSGSSGSSHHHHHHHHGGSSGSSGSSAPTSSSTKKTQLQLEHLLLD
LQMILNGINNYKNPKLTAMLTKKFYMPKKATELKHLQCLEEELKPLEEVL
NLAQSKNFHLRPRDLISNINVIVLELKGSETTFMCEYADETATIVEFLNR
WITFSQSIISTLT), or alternatively, comprises the amino acid sequence set forth in

SEQ ID NO: 46

(QVQLVESGGGLVKPGGSLRLSCAASGFTFSSYGMHWVRQAPGKGLEWVA
FIRYDGSNKYYADSVKGRFTISRDNSKNTLYLQMNSLRAEDTAVYYCAKD
RGLGDGTYFDYWGQGTTVTVSSGGGGSGGGGSGGGGSGGGGSQSALTQPA
SVSGSPGQSITISCSGSSSNIGNNAVNWYQQLPGKAPKLLIYYDDLLPSG
VSDRFSGSKSGTSAFLAISGLQSEDEADYYCAAWDDSLNGPVFGGGTKLT
VLGGSSGSSGSSHHHHHHHHGGSSGSSGSSAPTSSSTKKTQLQLEHLLLD
LQMILNGINNYKNPKLTAMLTKKFYMPKKATELKHLQCLEEELKPLEEVL
NLAQSKNFHLRPRDLISNINVIVLELKGSETTFMCEYADETATIVEFLNR
WITFSQSIISTLT).

In an exemplary embodiment, the composition comprises the DNA sequence set forth in

SEQ ID NO: 10)

(CACAAACTCGCATTCAACTTCAATCTAGAAATAAATGGCAGTGATACAC
ATTCTACAGTAGATGTATATCTTGATGATTCTCAAATTATAACGTTTGAT
GGAAAAGATATCCGTCCAACCATCCCGTTCATGATAGGTGATGAAATTTT
CTTACCGTTTTATAAAAATGTGTTTAGTGAGTTTTTCTCTCTGTTTAGAA

-continued

```
GAGTTCCTACAAGTACTCCATATGAAGACTTGACATATTTTTATGAATGC

GACTATACAGACAATAAATCTACATTTGATCAGTTTTATCTTTATAATGG

CGAAGAATATACTGTCAAAACACAGGAGGCCACTAATAAAAATATGTGGC

TAACTACTTCCGAGTTTAGACTAAAAAAATGGTTCGATGGCGAAGATTGT

ATAATGCATCTTAGATCGTTAGTTAGAAAAATGGAGGACAGTAAACGAAA

CACTGGTGGTACCGGAAGTAGCGGTAGTAGTGATTACAAGGACGATGACG

ACAAGCACCACCATCATCATCACCACGGTAGCAGCGGCAGCAGTGCC

CCCACCTCTAGCAGCACAAAGAAGACCCAGCTGCAACTGGAACACCTCCT

GCTGGACCTGCAGATGATCCTGAACGGCATCAACAACTACAAGAACCCCA

AGCTGACCGCCATGCTGACCAAAAAGTTTTACATGCCCAAGAAGGCCACC

GAGCTTAAACACCTGCAATGCCTTGAGGAGGAGCTGAAGCCCTGGAGGAG

GTACTGAACCTGGCCCAGAGCAAGAACTTTCATCTGAGGCCCAGGGACCT

GATTAGCAACATCAACGTGATCGTGTTGGAGTTGAAGGGCAGCGAGACCA

CGTTCATGTGCGAGTACGCCGACGAGACGGCCACCATAGTGGAGTTTCTT

AACAGGTGGATCACCTTCTCACAGTCTATCATCAGCACCCTGACC).
```

In another exemplary embodiment, the composition comprises the amino acid sequence set forth in

```
                                      SEQ ID NO: 20)
(HKLAFNFNLEINGSDTHSTVDVYLDDSQIITFDGKDIRPTIPFMIGDEI

FLPFYKNVFSEFFSLFRRVPTSTPYEDLTYFYECDYTDNKSTFDQFYLYN

GEEYTVKTQEATNKNMWLTTSEFRLKKWFDGEDCIMHLRSLVRKMEDSKR

NTGGTGSSGSSDYKDDDDKHHHHHHHGSSGSSAPTSSSTKKTQLQLEHL

LLDLQMILNGINNYKNPKLTAMLTKKFYMPKKATELKHLQCLEEELKPLE

EVLNLAQSKNFHLRPRDLISNINVIVLELKGSETTFMCEYADETATIVEF

LNRWITFSQSIISTLT).
```

In a preferred embodiment, the composition comprises OX40L or 4-1BBL, or fragment constructs thereof, linked to OMCP. In another preferred embodiment, the composition comprises OX40L or 4-1BBL, or fragment constructs thereof, linked to OMCP via a peptide linker. In still another preferred embodiment, the composition comprises OX40L or 4-1BBL, or fragment constructs thereof, linked to OMCP via a peptide linker comprising about 20 to about 30 amino acids. In still yet another preferred embodiment, the composition comprises OX40L or 4-1BBL, or fragment constructs thereof, linked to OMCP via a peptide linker comprising a FLAG tag and a His tag. In each of the foregoing embodiments, the OX40L, or fragment constructs thereof, may be a mutated version of OX40L comprising the mutations N166A and F180A.

In a preferred embodiment, the composition comprises OX40L or 4-1BBL, or fragment constructs thereof, linked to an anti-NKG2D antibody. In another preferred embodiment, the composition comprises OX40L or 4-1BBL, or fragment constructs thereof, linked to an anti-NKG2D antibody via a peptide linker. In still another preferred embodiment, the composition comprises OX40L or 4-1BBL, or fragment constructs thereof, linked to an anti-NKG2D antibody via a peptide linker comprising about 20 to about 30 amino acids. In still yet another preferred embodiment, the composition comprises OX40L or 4-1BBL, or fragment constructs thereof, linked to an anti-NKG2D antibody via a peptide linker comprising a FLAG tag and a His tag. In each of the foregoing embodiments, the OX40L, or fragment constructs thereof, may be a mutated version of OX40L comprising the mutations N166A and F180A.

In a different preferred embodiment, the composition comprises OX40L, or fragment constructs thereof, linked to OMCP. In another preferred embodiment, the composition comprises OX40L, or fragment constructs thereof, linked to OMCP via a peptide linker. In still another preferred embodiment, the composition comprises OX40L, or fragment constructs thereof, linked to OMCP via a peptide linker comprising about 20 to about 30 amino acids. In still yet another preferred embodiment, the composition comprises OX40L, or fragment constructs thereof, linked to OMCP via a peptide linker comprising a FLAG tag and a His tag. In each of the foregoing embodiments, the OX40L, or fragment constructs thereof, may be a mutated version of OX40L comprising the mutations N166A and F180A.

In a preferred embodiment, the composition comprises OX40L, or fragment constructs thereof, linked to an anti-NKG2D antibody. In another preferred embodiment, the composition comprises OX40L, or fragment constructs thereof, linked to an anti-NKG2D antibody via a peptide linker. In still another preferred embodiment, the composition comprises OX40L, or fragment constructs thereof, linked to an anti-NKG2D antibody via a peptide linker comprising about 20 to about 30 amino acids. In still yet another preferred embodiment, the composition comprises OX40L, or fragment constructs thereof, linked to an anti-NKG2D antibody via a peptide linker comprising a FLAG tag and a His tag. In each of the foregoing embodiments, the OX40L, or fragment constructs thereof, may be a mutated version of OX40L comprising the mutations N166A and F180A.

In an exemplary embodiment, the NKG2D ligand is OMCP. In an exemplary embodiment, the cytokine is OX40L. In a particular exemplary embodiment, the cytokine is a construct comprising OX40L fragments. In a particular exemplary embodiment, the OX40L fragments are combined into a continuous construct. In one particular exemplary embodiment, a chimeric peptide is provided wherein OMCP is linked to an OX40L construct via a linker peptide and comprises the amino acid sequence set forth in

```
                                      SEQ ID NO: 62
(HKLAFNFNLEINGSDTHSTVDVYLDDSQIITFDGKDIRPTIPFMIGDEIF

LPFYKNVFSEFFSLFRRVPTSTPYEDLTYFYECDYTDNKSTFDQFYLYNGE

EYTVKTQEATNKNMWLTTSEFRLKKWFDGEDCIMHLRSLVRKMEDSKRNTG

GGSSGSSGSSHHHHHHHGGSSGSSGSSGGQVSHRYPRIQSIKVQFTEYKK

EKGFILTSQKEDEIMKVQNNSVIINCDGFYLISLKGYFSQEVNISLHYQKD

EEPLFQLKKVRSVNSLMVASLTYKDKVYLNVTTDNTSLDDFHVNGGELILI

HQNPGEFCV

In a particular exemplary embodiment, the cytokine is a construct comprising mutated OX40L fragments containing mutations at amino acid positions N166A and F180A. In a particular exemplary embodiment, the mutated OX40L fragments are combined into a continuous construct, with or without unmutated OX40L fragments. In one particular exemplary embodiment, a chimeric peptide is provided wherein OMCP is linked to a mutated OX40L construct via a linker peptide and comprises the amino acid sequence set forth in

SEQ ID NO: 63
(HKLAFNFNLEINGSDTHSTVDVYLDDSQIITFDGKDIRPTIPFMIGDEIF

LPFYKNVFSEFFSLFRRVPTSTPYEDLTYFYECDYTDNKSTFDQFYLYNGE

EYTVKTQEATNKNMWLTTSEFRLKKWFDGEDCIMHLRSLVRKMEDSKRNTG

GGSSGSSGSSHHHHHHHHGGSSGSSGSSGGQVSHRYPRIQSIKVQFTEYKK

EKGFILTSQKEDEIMKVQNNSVIINCDGFYLISLKGYFSQEVNISLHYQKD

EEPLFQLKKVRSVNSLMVASLTYKDKVYLNVTTDNTSLDDFHVAGGELILI

HQNPGEACVLGGSGGGSGGGSGQVSHRYPRIQSIKVQFTEYKKEKGFILTS

QKEDEIMKVQNNSVIINCDGFYLISLKGYFSQEVNISLHYQKDEEPLFQLK

KVRSVNSLMVASLTYKDKVYLNVTTDNTSLDDFHVAGGELILIHQNPGEAC

VLGGSGGGSGGGSGQVSHRYPRIQSIKVQFTEYKKEKGFILTSQKEDEIMK

VQNNSVIINCDGFYLISLKGYFSQEVNISLHYQKDEEPLFQLKKVRSVNSL

MVASLTYKDKVYLNVTTDNTSLDDFHVNGGELILIHQNPGEFCVL)
or

SEQ ID NO: 64
(HKLAFNFNLEINGSDTHSTVDVYLDDSQIITFDGKDIRPTIPFMIGDEIF

LPFYKNVFSEFFSLFRRVPTSTPYEDLTYFYECDYTDNKSTFDQFYLYNGE

EYTVKTQEATNKNMWLTTSEFRLKKWFDGEDCIMHLRSLVRKMEDSKRNTG

GGSSGSSGSSHHHHHHHHGGSSGSSGSSGGQVSHRYPRIQSIKVQFTEYKK

EKGFILTSQKEDEIMKVQNNSVIINCDGFYLISLKGYFSQEVNISLHYQKD

EEPLFQLKKVRSVNSLMVASLTYKDKVYLNVTTDNTSLDDFHVAGGELILI

HQNPGEACVLGGSGGGSGGGSGQVSHRYPRIQSIKVQFTEYKKEKGFILTS

QKEDEIMKVQNNSVIINCDGFYLISLKGYFSQEVNISLHYQKDEEPLFQLK

KVRSVNSLMVASLTYKDKVYLNVTTDNTSLDDFHVNGGELILIHQNPGEFC

VLGGSGGGSGGGSGQVSHRYPRIQSIKVQFTEYKKEKGFILTSQKEDEIMK

VQNNSVIINCDGFYLISLKGYFSQEVNISLHYQKDEEPLFQLKKVRSVNSL

MVASLTYKDKVYLNVTTDNTSLDDFHVNGGELILIHQNPGEFCVL).

In a different preferred embodiment, the composition comprises 4-1BBL, or fragment constructs thereof, linked to OMCP. In another preferred embodiment, the composition comprises 4-1BBL, or fragment constructs thereof, linked to OMCP via a peptide linker. In still another preferred embodiment, the composition comprises 4-1BBL, or fragment constructs thereof, linked to OMCP via a peptide linker comprising about 20 to about 30 amino acids. In still yet another preferred embodiment, the composition comprises 4-1BBL, or fragment constructs thereof, linked to OMCP via a peptide linker comprising a FLAG tag and a His tag.

In a different preferred embodiment, the composition comprises 4-1BBL, or fragment constructs thereof, linked to an anti-NKG2D antibody. In another preferred embodiment, the composition comprises 4-1BBL, or fragment constructs thereof, linked to an anti-NKG2D antibody via a peptide linker. In still another preferred embodiment, the composition comprises 4-1BBL, or fragment constructs thereof, linked to an anti-NKG2D antibody via a peptide linker comprising about 20 to about 30 amino acids. In still yet another preferred embodiment, the composition comprises 4-1BBL, or fragment constructs thereof, linked to an anti-NKG2D antibody via a peptide linker comprising a FLAG tag and a His tag.

In an exemplary embodiment, the NKG2D ligand is OMCP. In an exemplary embodiment, the cytokine is 4-1BBL. In a particular exemplary embodiment, the cytokine is a construct comprising 4-1BBL fragments. In a particular exemplary embodiment, the 4-1BBL fragments are combined into a continuous construct. In one particular exemplary embodiment, a chimeric peptide is provided wherein OMCP is linked to an 4-1BBL construct via a linker peptide and comprises the amino acid sequence set forth in

SEQ ID NO: 67
(HKLAFNFNLEINGSDTHSTVDVYLDDSQIITFDGKDIRPTIPFMIGDEIF

LPFYKNVFSEFFSLFRRVPTSTPYEDLTYFYECDYTDNKSTFDQFYLYNGE

EYTVKTQEATNKNMWLTTSEFRLKKWFDGEDCIMHLRSLVRKMEDSKRNTG

GGSSGSSGSSHHHHHHHHGGSSGSSGSSGGACPWAVSGARASPGSAASPRL

REGPELSPDDPAGLLDLRQGMFAQLVAQNVLLIDGPLSWYSDPGLAGVSLT

GGLSYKEDTKELVVAKAGVYYVFFQLELRRVVAGEGSGSVSLALHLQPLRS

AAGAAALALTVDLPPASSEARNSAFGFQGRLLHLSAGQRLGVHLHTEARAR

HAWQLTQGATVLGLFRVTPEIPAGLPSPRSEGGSGGGSGGGSGACPWAVSG

ARASPGSAASPRLREGPELSPDDPAGLLDLRQGMFAQLVAQNVLLIDGPLS

WYSDPGLAGVSLTGGLSYKEDTKELVVAKAGVYYVFFQLELRRVVAGEGSG

SVSLALHLQPLRSAAGAAALALTVDLPPASSEARNSAFGFQGRLLHLSAGQ

RLGVHLHTEARARHAWQLTQGATVLGLFRVTPEIPAGLPSPRSEGGSGGGS

GGGSGACPWAVSGARASPGSAASPRLREGPELSPDDPAGLLDLRQGMFAQL

VAQNVLLIDGPLSWYSDPGLAGVSLTGGLSYKEDTKELVVAKAGVYYVFFQ

LELRRVVAGEGSGSVSLALHLQPLRSAAGAAALALTVDLPPASSEARNSAF

GFQGRLLHLSAGQRLGVHLHTEARARHAWQLTQGATVLGLFRVTPEIPAGL

PSPRSE).

In another preferred embodiment, a composition comprises OMCP or a portion thereof and a targeting molecule. In another preferred embodiment, the OMCP or a portion thereof is linked to the targeting molecule via a linker. In still yet another preferred embodiment, the portion of OMCP comprises the H2b an activating portion of OMCP. In particular preferred embodiments, the activating portion of OMCP comprises the H2B helix.

In another non-limiting example, several preferred compositions of the invention binding the PD1 receptor are depicted in FIG. 36.

In a preferred embodiment, the composition comprises IL2, IL15 or IL18 linked to PDL1. In another preferred embodiment, the composition comprises IL2, IL15 or IL18 linked to PDL1 via a peptide linker. In still another preferred embodiment, the composition comprises IL2, IL15 or IL18 linked to PDL1 via a peptide linker comprising about 20 to about 30 amino acids. In still yet another preferred embodiment, the composition comprises IL2, IL15 or IL18 linked to PDL1 via a peptide linker comprising a FLAG tag and a His tag. In each of the foregoing embodiments, the IL2 may be a mutated version of IL2 comprising the mutations R38A and F42K.

In another preferred embodiment, the composition comprises IL2, IL15 or IL18 linked to PDL2. In another preferred embodiment, the composition comprises IL2, IL15 or IL18 linked to PDL2 via a peptide linker. In still another preferred embodiment, the composition comprises IL2, IL15 or IL18 linked to PDL2 via a peptide linker comprising about 20 to about 30 amino acids. In still yet another preferred embodiment, the composition comprises IL2, IL15 or IL18 linked to PDL2 via a peptide linker comprising a FLAG tag and a His tag. In each of the foregoing embodiments, the IL2 may be a mutated version of IL2 comprising the mutations R38A and F42K.

In yet another preferred embodiment, the composition comprises IL2, IL15 or IL18 linked to an anti-PD1 antibody. In another preferred embodiment, the composition comprises IL2, IL15 or IL18 linked to an anti-PD1 antibody via a peptide linker. In still another preferred embodiment, the composition comprises IL2, IL15 or IL18 linked to an anti-PD1 antibody via a peptide linker comprising about 20 to about 30 amino acids. In still yet another preferred embodiment, the composition comprises IL2, IL15 or IL18 linked to an anti-PD1 antibody via a peptide linker comprising a FLAG tag and a His tag. In each of the foregoing embodiments, the IL2 may be a mutated version of IL2 comprising the mutations R38A and F42K.

In an exemplary embodiment, the PD1 ligand is PDL1. In one particular exemplary embodiment, a chimeric peptide is provided wherein the PD1 ligand is PDL1 linked to mutIL2 and comprises the amino acid sequence set forth in SEQ ID NO: 48
(AFTVTVPKDLYVVEYGSNMTIECKFPVEKQLDLAALIVYWEMEDKNIIQF
VHGEEDLKVQHSSYRQRARLLKDQLSLGNAALQITDVKLQDAGVYRCMISY
GGADYKRITVKVNAPYGGSSGSSGSSHHHHHHHGGSSGSSGSSGGAPTSS
STKKTQLQLEHLLLDLQMILNGINNYKNPKLTAMLTKKFYMPKKATELKHL
QCLEEELKPLEEVLNLAQSKNFHLRPRDLISNINVIVLELKGSETTFMCEY
ADETATIVEFLNRWITFSQSIISTLT).

In a particular exemplary embodiment, the composition comprises the DNA sequence set forth in SEQ ID NO: 47
(GCCTTCACCGTGACTGTGCCCAAGGATCTGTACGTCGTGGAGTACGGCTC
CAACATGACAATCGAGTGCAAGTTCCCCGTGGAGAAGCAGCTGGACCTGGC
GGCACTGATCGTGTACTGGGAGATGGAGGACAAGAACATCATCCAGTTCGT
TCATGGCGAAGAGGATCTCAAGGTGCAGCACAGCAGCTACAGGCAGAGGGC
CCGACTGCTGAAGGACCAGCTGAGCCTGGGCAACGCCGCACTGCAAATCAC
CGACGTGAAGCTGCAGGACGCTGGCGTGTACAGGTGTATGATAAGCTACGG
CGGAGCTGACTACAAGAGAATCACGGTTAAGGTAAACGCCCCCTACGGGGG
CAGTAGCGGAAGCTCCGGCTCAAGCCACCACCATCATCATCATCACCACGG
CGGCAGCAGCGGGAGCTCAGGTAGCAGTGGTGGGCACCTACCTCTTCCAG
CACCAAGAAGACGCAGCTCCAGTTGGAACACCTTCTCCTTGACCTCCAGAT
GATCCTGAACGGCATCAACAACTACAAAAATCCCAAGCTGACCGCGATGCT
GACGAAGAAATTCTACATGCCAAAGAAGGCCACCGAGCTGAAACACCTGCA
GTGTCTTGAGGAGGAACTTAAGCCGCTCGAGGAGGTACTGAACCTGGCCCA
GAGTAAGAACTTCCACCTGAGGCCCAGGGACCTCATCAGCAACATCAATGT
GATCGTCCTTGAGCTTAAGGGCAGCGAGACCACCTTCATGTGCGAGTATGC
GGACGAAACGGCCACAATCGTCGAGTTTCTGAATAGGTGGATCACTTTCAG
CCAGAGCATCATCTCTACCCTGACC).

In an exemplary embodiment, the PD1 ligand is PDL2. In one particular exemplary embodiment, a chimeric peptide is provided wherein the PD1 ligand is PDL2 linked to mutIL2 and comprises the amino acid sequence set forth in SEQ ID NO: 50
(LYIIEHGSNVTLECNFDTGSHVNLGAITASLQKVENDTSPHRERATLLEE
QLPLGKASFHIPQVQVRDEGQYQCIIIYGVAWDYKYLTLKVKASGGSSGSS
GSSHHHHHHHGGSSGSSGSSGGAPTSSSTKKTQLQLEHLLLDLQMILNGI
NNYKNPKLTAMLTKKFYMPKKATELKHLQCLEEELKPLEEVLNLAQSKNFH
LRPRDLISNINVIVLELKGSETTFMCEYADETATIVEFLNRWITFSQSIIS
TLT).

In a particular exemplary embodiment, the composition comprises the DNA sequence set forth in SEQ ID NO: 49
(CTGTACATCATCGAGCACGGCAGTAACGTGACCCTGGAGTGCAACTTCGA
CACCGGCAGCCACGTGAATCTGGGCGCCATCACAGCTTCACTGCAGAAGGT
GGAGAATGACACCTCTCCCCACAGGGAGCGAGCCACCCTGCTTGAGGAACA
ACTGCCTCTCGGCAAGGCCAGCTTCCACATCCCCCAGGTGCAGGTGAGGGA
CGAGGGCCAGTACCAGTGCATAATCATCTACGGCGTGGCCTGGGACTACAA
GTACCTGACACTTAAGGTGAAAGCCTCCGGCGGTTCTTCCGGCTCTTCAGG
CAGCTCACACCATCATCATCATCACCACCATGGCGGCAGCAGCGGGAGCTC
TGGTAGCAGTGGCGGTGCCCCCACCAGCAGTAGCACTAAGAAGACCCAGCT
GCAACTGGAGCACTTGCTCCTGGACCTGCAAATGATCCTCAACGGCATCAA
CAACTATAAGAACCCCAAGCTGACGGCCATGCTGACCAAAAAGTTCTACAT
GCCCAAGAAGGCCACCGAGTTGAAACACTTGCAGTGCCTGGAGGAGGAGCT
GAAGCCCCTGGAAGAGGTGCTGAACCTGGCCCAGAGCAAGAATTTTCATCT
GAGGCCTAGGGACCTGATTAGCAACATCAACGTGATCGTGTTGGAGCTTAA
AGGCTCCGAGACCACCTTTATGTGCGAGTACGCCGACGAGACCGCGACTAT
CGTGGAGTTCCTGAACAGGTGGATCACCTTTTCACAGAGCATCATAAGCAC
ACTGACC).

(h) Pharmaceutical Compositions

The present disclosure also provides pharmaceutical compositions. The pharmaceutical composition can include a composition of the invention which is detailed above, as an active ingredient and at least one pharmaceutically acceptable excipient. The pharmaceutical compositions provided herein can also include a combination therapy as described herein. In some embodiments, the combination therapy comprises a PD-1 inhibitor. In other embodiments, the combination therapy comprises a PD-L1 inhibitor.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methyl-cellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In yet another embodiment, the excipient may be a taste-masking agent. Taste-masking materials include cellulose ethers; polyethylene glycols; polyvinyl alcohol; polyvinyl alcohol and polyethylene glycol copolymers; mono-glycerides or triglycerides; acrylic polymers; mixtures of acrylic polymers with cellulose ethers; cellulose acetate phthalate; and combinations thereof.

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered by a number of different means that will deliver a therapeutically effective amount of the active ingredient. Such compositions can be administered orally, parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Gennaro, A. R., Remington's Pharmaceutical Sciences, Mack Publishing Co., Easton, Pa. ($18^{th}$ ed, 1995), and Liberman, H. A. and Lachman, L., Eds., Pharmaceutical Dosage Forms, Marcel Dekker Inc., New York, N.Y. (1980).

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

For parenteral administration (including subcutaneous, intradermal, intravenous, intramuscular, and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

For topical (e.g., transdermal or transmucosal) administration, penetrants appropriate to the barrier to be permeated are generally included in the preparation. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound of the invention is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of the compound of the invention in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the compound of the invention may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally, contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying the compound of the invention (i.e., having at least one methionine compound) may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The composition of the invention may be encapsulated in a microemulsion by any method generally known in the art.

In yet another embodiment, a composition of the invention may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm II. Methods In an aspect, the invention encompasses a method to deliver a cytokine to a target cell. The method comprises contacting a target cell with a composition comprising a cytokine linked to a ligand, wherein the ligand specifically binds to a receptor on the target cell. Additionally, the method comprises contacting a target cell with a composition comprising a chimeric peptide as described in Section I. A target cell may be any cell comprising a target receptor for which the ligand specifically binds to. The ligand and specific binding are described in Section I. In certain embodiments, a target cell may be an immune cell. Non-limiting example of immune cells include macrophages, B lymphocytes, T lymphocytes, mast cells, monocytes, dendritic cells, eosinophils, natural killer cells, basophils, neutrophils. In certain embodiments, an immune cell is selected from the group consisting of a macrophage, B lymphocyte, T lymphocyte, mast cell, monocyte, dendritic cell, eosinophil, natural killer cell, basophil, and neutrophil. In a specific embodiment, a target cell is a natural killer (NK) cell and/or a CD8+ T cell. In other embodiments, a target cell is a NKG2D-expressing cell. Non-limiting examples of NKG2D-expressing cell include natural killer (NK) cells and CD8+ T cells (both αβ and γδ). In still other embodiments, a target cell is a PD1-expressing cell. Non-limiting examples of PD1-expressing cells include NK cells, CD8+ T cells, and myeloid cells. In some embodiments, the method of therapy comprises a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In some embodiments, the method further comprises administering a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody. In one embodiment, provided herein is a method to deliver a cytokine to a target cell comprising administration of a composition provided herein. In one embodiment, provided herein is a method to deliver a cytokine to a target cell comprising administration of a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In some embodiments, the target cell is a target cell of a subject. In certain embodiments, the subject is in need thereof. In certain embodiments, the subject is administered an effective amount of the combination therapy. The term "effective amount" as used herein refers to the amount of a pharmaceutical composition provided herein which is sufficient to result in the desired outcome. In specific embodiments, the subject is a human. In certain embodiments, the subject is a subject having a cancer or tumor. In specific embodiments, the cancer or tumor is a lung cancer or tumor.

In another aspect, the invention encompasses a method to activate immune cells. The method comprises contacting an immune cell with a composition comprising a cytokine linked to a ligand, wherein the ligand specifically binds to a receptor on the immune cell thereby activating the cell. Additionally, in some embodiments, the method comprises contacting an immune cell with a composition comprising a chimeric peptide as described in Section I. Non-limiting example of immune cells include macrophages, B lymphocytes, T lymphocytes, mast cells, monocytes, dendritic cells, eosinophils, natural killer cells, basophils, neutrophils. In certain embodiments, an immune cell is selected from the group consisting of a macrophage, B lymphocyte, T lymphocyte, mast cell, monocyte, dendritic cell, eosinophil, natural killer cell, basophil, and neutrophil. In a specific embodiment, an immune cell is a natural killer (NK) cell and/or a CD8$^+$ T cell. In still other embodiments, a target cell is a PD1-expressing cell. Non-limiting examples of PD1-expressing cells include NK cells, CD8$^+$ T cells, and myeloid cells. To facilitate activation of immune cells, a cytokine may be a proinflammatory cytokine. The term "proinflammatory cytokine" is a cytokine which promotes systemic inflammation. A skilled artisan would be able to determine those cytokines that are proinflammatory. In certain embodiments, a proinflammatory cytokine is IL1α, IL1β, IL2, IL3, IL6, IL7, IL9, IL12, IL15, IL17, IL18, IL21, IFNα, IFNγ, TNFα, MIF, G-CSF, GM-CSF, TNFalpha, CD40L, 4-1BBL, OX40L, RANKL, or mutants thereof. In an embodiment, a proinflammatory cytokine is an IL1 family cytokine. In certain embodiments, an IL1 family cytokine is selected from the group consisting of IL1α, IL1β, IL1Ra, IL18, IL36Ra, IL36α, IL37, IL36β, IL36γ, IL38, IL33 and mutants thereof. In a specific embodiment, a proinflammatory cytokine is selected from the group consisting of IL2, IL7, IL15, IL18, IL21 and mutants thereof. In another specific embodiment, a proinflammatory cytokine is selected from the group consisting of IL2, IL15, IL18, and mutants thereof. In an exemplary embodiment, a proinflammatory cytokine is IL2 or a mutant thereof. In other certain embodiments, a proinflammatory cytokine is a TNFSF family cytokine. In certain embodiments, the TNFSF family cytokine is selected from a group containing TNFalpha, CD40L, 4-1BBL, OX40L, or RANKL. In another specific embodiment, the proinflammatory cytokine is selected from either OX40L or 4-1BBL. In an exemplary embodiment, a proinflammatory cytokine is OX40L or a mutant thereof. In another exemplary embodiment, a proinflammatory cytokine is 4-1BBL or a mutant thereof. Activation of the immune cells may result in lysis of tumor cells. Accordingly, activation of immune cells may be measured by determining the amount of tumor cell lysis. In an embodiment, activation of the immune cells may result in about 10% to about 100% lysis of tumor cells. In another embodiment, activation of the immune cells may result in about 20% to about 80% lysis of tumor cells. In still another embodiment, activation of the immune cells may result in greater than 40% lysis of tumor cells. For example, activation of the immune cells may result in greater than 40%, greater than 45%, greater than 50%, greater than 55%, greater than 60%, greater than 65%, greater than 70%, greater than 75%, greater than 80%, greater than 85%, greater than 90%, greater than 95%, or greater than 99% lysis of tumor cells. The lysis of tumor cells may be measured using any standard assay (e.g., caspase assays, TUNEL and DNA fragmentation assays, cell permeability assays, and Annexin V assays). In some embodiments, the method of therapy comprises a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In some embodiments, the method further comprises administering a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody. In one embodiment, provided herein is a method to activate immune cells, comprising administration of a composition provided herein. In one embodiment, provided herein is a method to activate immune cells, comprising administration of a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In some embodiments, the immune cells are immune cells of a subject. In certain embodiments, the subject is in need thereof. In certain embodiments, the subject is administered an effective amount of the combination therapy. In specific embodiments, the subject is a human. In certain embodiments, the subject is a subject having a cancer or tumor. In specific embodiments, the cancer or tumor is a lung cancer or tumor.

In still another aspect, the invention encompasses a method to treat a tumor. The method comprises identifying a subject with a tumor and administering to the subject a composition comprising a cytokine linked to a ligand, wherein the ligand specifically binds to a receptor on a target cell. Additionally, the method comprises administering to the subject a composition comprising a chimeric peptide as described in Section I. Specifically, the inventors have shown that delivering a cytokine to a target cell activates the cells bound by the composition, wherein the activated cells specifically lyse tumor cells thereby reducing the amount of cancer cells. In a specific embodiment, a cytokine is a proinflammatory cytokine as described in the preceding paragraph. Accordingly, a composition of the present invention, may be used in treating, stabilizing and preventing cancer and associated diseases in a subject. By "treating, stabilizing, or preventing cancer" is meant causing a reduction in the size of a tumor or in the number of cancer cells, slowing or preventing an increase in the size of a tumor or cancer cell proliferation, increasing the disease-free survival time between the disappearance of a tumor or other cancer and its reappearance, preventing an initial or subsequent occurrence of a tumor or other cancer, or reducing an adverse symptom associated with a tumor or other cancer. The inventors have shown that a composition of the invention activates natural killer (NK) cells bound by the composition, wherein the activated NK cells specifically lyse tumor cells thereby reducing the amount of tumor cells. For example, as cancerous cells are "stressed", NKG2D ligands become upregulated, rendering the cell susceptible to NK cell-mediated lysis. In a desired embodiment, the percent of tumor or cancerous cells surviving the treatment is at least 20, 30, 40, 50, 60, 70, 80, 90 or 100% lower than the initial number of tumor or cancerous cells, as measured using any standard assay (e.g., caspase assays, TUNEL and DNA fragmentation assays, cell permeability assays, and Annexin V assays). Desirably, the decrease in the number of tumor or cancerous cells induced by administration of a composition of the invention is at least 2, 5, 10, 15, 20, 25, 30, 35, 40, 45 or 50-fold greater than the decrease in the number of non-tumor or non-cancerous cells. Desirably, the methods of the present invention result in a decrease of 20, 30, 40, 50, 60, 50, 80, 90 or 100% in the size of a tumor or in the number of cancerous cells, as determined using standard methods. Desirably, at least 20, 30, 40, 50, 60, 70, 80, 90, or 95% of the treated subjects have a complete remission in which all evidence of the tumor or cancer disappears. Desirably, the tumor or cancer does not reappear or reappears after at least 1, 2, 3, 4, 5, 10, 15, or 20 years. In some embodiments, the method further comprises administering a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In some embodiments, the method further comprises administering a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody. In one embodiment, provided herein is a method to treat a tumor in a subject, comprising administering to the subject a composition provided herein. In one embodiment, provided herein is a method to treat a tumor in a subject, comprising administering to the subject a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In certain embodiments, the subject is in need thereof. In certain embodiments, the subject is administered an effective amount of the combination therapy. In specific embodiments, the subject is a human. In specific embodiments, the tumor is a lung tumor.

In another aspect, the invention encompasses a method to suppress immune cells. The method comprises contacting an immune cell with a composition comprising a cytokine linked to a ligand, wherein the ligand specifically binds to a receptor on the immune cell thereby suppressing the cell. Additionally, the method comprises contacting an immune cells with a composition comprising a chimeric peptide as described in Section I. Non-limiting example of immune cells include macrophages, B lymphocytes, T lymphocytes, mast cells, monocytes, dendritic cells, eosinophils, natural killer cells, basophils, neutrophils. In certain embodiments, an immune cell is selected from the group consisting of a macrophage, B lymphocyte, T lymphocyte, mast cell, monocyte, dendritic cell, eosinophil, natural killer cell, basophil, and neutrophil. In a specific embodiment, an immune cell is a natural killer (NK) cell and/or a CD8+ T cell. In a specific embodiment, the immune cell expresses NKG2D. In an alternate specific embodiment, the immune cell expresses PD1. To facilitate suppression of immune cells, a cytokine may be an anti-inflammatory cytokine. The term "anti-inflammatory cytokine" is a cytokine that counteracts various aspects of inflammation, for example cell activation or the production of proinflammatory cytokines, and thus contributes to the control of the magnitude of the inflammatory response. A skilled artisan would be able to determine those cytokines that are anti-inflammatory. In certain embodiments, an anti-inflammatory cytokine is IL4, IL5, IL10, IL11, IL13, IL16, IL35, IFNα, TGFβ, G-CSF or a mutant thereof. In a specific embodiment, an anti-inflammatory cytokine is IL10 or a mutant thereof. In another embodiment, the invention encompasses a method to kill immune cells. The method comprises contacting an immune cell with a composition comprising a toxin linked to a ligand, wherein the ligand specifically binds to a receptor on the immune cell thereby killing the cell. Suppression or killing of the immune cells may result in treatment, stabilization and prevention of autoimmune diseases caused by overactive immune cells. NKG2D-expressing cells and/or aberrant expression of host NKG2DLs have been implicated in diabetes, celiac disease and rheumatoid arthritis. For example, NK cells can recognize pancreatic beta cells and destroy them. The destruction of pancreatic beta cells may lead to type 1 diabetes. By way of another example, overactive immune cells are involved in transplant/graft rejection. Accordingly, a composition of the present invention, may be used in treating, stabilizing and preventing an autoimmune disease in a subject. In a specific embodiment, the autoimmune disease is type 1 diabetes. In another specific embodiment, the autoimmune disease is transplant or graft rejection. In still another specific embodiment, the autoimmune disease is rheumatoid arthritis. In some embodiments, the method further comprises administering a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody. In one embodiment, provided herein is a method to suppress immune cells in a subject, comprising administering to the subject a composition provided herein. In one embodiment, provided herein is a method to suppress immune cells in a subject, comprising administering to the subject a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In some embodiments, the chimeric protein further comprises a linker. In some embodiment, the anti-PD-1 antibody is an antagonistic antibody. In certain embodiments, the anti-NKG2D antibody is KYK-1. In other embodiments, the anti-NKG2D antibody is KYK-2. In certain embodiments, the subject is in need thereof. In certain embodiments, the subject is administered an effective amount of the combination therapy. In specific embodiments, the subject is a human. In certain embodiments, the subject is a subject having a cancer or tumor. In specific embodiments, the cancer or tumor is a lung cancer or tumor.

In still yet another aspect, the invention encompasses a method to treat an infection comprising administering a composition comprising a cytokine linked to a ligand. For example, a composition comprising a cytokine linked to a ligand may specifically bind an immune cell that is then activated to target and lyse the infected host cell. Additionally, the method comprises administering to the subject a composition comprising a chimeric peptide as described in Section I. The term "infection" as used herein includes the presence of pathogens in or on a subject, which, if its growth were inhibited, would result in a benefit to the subject. As such, the term "infection" in addition to referring to the presence of pathogens also refers to normal flora which are not desirable. The term "pathogen" as used herein refers to an infectious agent that can produce disease. Non-limiting examples of an infectious agent include virus, bacterium, prion, fungus, viroid, or parasite that cause disease in a subject. In a specific embodiment, an infection is caused by pathogens such as bacteria or viruses. In certain embodiments, the infection is an intracellular infection. In an embodiment, the infection is a viral infection. In another embodiment, the viral infection is caused by a flavivirus. Flavivirus is a genus of viruses in the family Flaviviridae. Non-limiting examples of flaviviruses include Gadget's Gully virus, Kadam virus, Kyasanur Forrest disease virus, Langat virus, Omsk hemorrhagic fever virus, Tick-borne encephalitis virus, Louping ill virus, Aroa virus, Dengue viruses 1-4, Kedougou virus, Cacipacore virus, Koutango virus, Murray Valley encephalitis virus, St. Louis encephalitis virus, Usutu virus, West Nile virus, Yaounde virus, Kokobera virus group, Kokobera virus, Bagaza virus, Ilheus virus, Israel turkey meningoencephalomyelitis virus, Ntaya virus, Tembusu virus, Zika virus, Banzi virus, Bouboui virus, Edge Hill virus, Jugra virus, Saboya virus, Sepik virus, Uganda S virus, Wesselsbron virus, Yellow fever virus, Entebbe bat virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Phnom Penh bat virus, Rio Bravo virus, hepatitis C virus, e.g., hepatitis C virus genotypes 1-6, and GB virus A and B. In a certain embodiment, the flavivirus may be selected from the group consisting of West Nile virus, dengue virus, Japanese encephalitis virus, and yellow fever virus. In a specific embodiment, the viral infection is caused by West Nile virus. In certain embodiments, a pathogen, more specifically a virus, can induce the expression of proteins for which NKG2D binds. Accordingly, a composition comprising a cytokine linked to a ligand may specifically bind a NK cell that is then activated to target and lyse the infected host cell expressing NKG2D. In another embodiment, a composition comprising a cytokine linked to a ligand may activate cytotoxic T lymphocytes that recognize infected cells via other mechanisms for targeted killing. In some embodiments, the method further comprises administering a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In some other embodiments, the method further comprises administering a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody. In one embodiment, provided herein is a method to treat an infection in a subject, comprising administering to the subject a composition provided herein. In one embodiment, provided herein is a method to treat an infection in a subject, comprising administering to the subject a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In certain embodiments, the subject is in need thereof. In certain embodiments, the subject is administered an effective amount of the combination therapy. In specific embodiments, the subject is a human.

In a different aspect, the invention encompasses a method to alleviate immunosuppression related to radiation exposure or lymphotoxic substances comprising administering a composition comprising a cytokine linked to a ligand. Additionally, the method comprises administering a composition comprising a chimeric peptide as described in Section I. Additionally, a composition of the invention may be used to raise CD4 counts in HIV positive subjects. For example, a composition of the invention may be used to activate immune cells which can help restore the immune system of the subject. In some embodiments, the method further comprises administering a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In some embodiments, the method further comprises administering a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody. In one embodiment, provided herein is a method to alleviate immunosuppression related to radiation exposure or lymphotoxic substances in a subject, comprising administering to the subject a composition provided herein. In one embodiment, provided herein is a method to alleviate immunosuppression related to radiation exposure or lymphotoxic substances in a subject, comprising administering to the subject a combination therapy provided herein. In one embodiment, the immunosuppression is related to radiation exposure. In another embodiment, the immunosuppression is related to lympotoxic substances. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In certain embodiments, the subject is in need thereof. In certain embodiments, the subject is administered an effective amount of the combination therapy. In specific embodiments, the subject is a human. In certain embodiments, the subject is a subject having a cancer or tumor. In specific embodiments, the cancer or tumor is a lung cancer or tumor.

In an alternative aspect, the invention encompasses a method of use as an adjuvant in a vaccine composition. In one embodiment, provided herein is a method of vaccination in a subject, comprising administering to the subject a composition provided herein. In some embodiments, the method of vaccination in a subject comprises administering a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In one embodiment, provided herein is a method of vaccination in a subject, comprising administering to the subject a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In certain embodiments, the subject is in need thereof. In certain embodiments, the subject is administered an effective amount of the combination therapy. In specific embodiments, the subject is a human.

In other aspects, provided herein is a composition of the invention for use in expanding CD8+ memory cells. In one embodiment, provided herein is a method to expand CD8+ T cells in a subject, comprising administering to the subject a composition provided herein. In one embodiment, provided herein is a method to expand CD8+ T cells in a subject, the method further comprises administering a chimeric peptide comprising a PD1 ligand and a cytokine. In another embodiment, the chimeric peptide further comprises a linker. In one embodiment, the PD1 ligand is PDL1. In another embodiment, the PD1 ligand is PDL2. In still another embodiment, the PD1 ligand is an antibody specific to PD1. In another embodiment, the cytokine is IL2. In some embodiments, the IL2 is a mutant R38A/F42K form of IL2. In one embodiment, provided herein is a method to expand CD8+ T cells in a subject, comprising administering to the subject a combination therapy provided herein. In some embodiments, the combination therapy includes a PD-1 inhibitor provided herein and a chimeric peptide that includes a cytokine peptide and an anti-NKG2D antibody. In certain embodiments, the cytokine peptide is a cytokine as described hereinabove. In some embodiments, the anti-NKG2D antibody is as described hereinabove. In one embodiment, the combination therapy comprises an OMCP-IL2 fusion protein and a PD-1 inhibitor. In another embodiment, the combination therapy comprises an OMCP-IL2 fusion protein and an anti-PD-1 antibody. In some embodiments, the fusion protein further comprises a linker. In one embodiment, the combination therapy comprises an OMCP-IL2 chimeric protein and a PD-1 inhibitor. In another embodiment, the combination therapy comprises an OMCP-IL2 chimeric protein and an anti-PD-1 antibody. In some embodiments, the chimeric protein further comprises a linker. In other embodiments, the combination therapy comprises an anti-NKG2D antibody, IL2 and a PD1 inhibitor. In some embodiments, the combination therapy comprises an anti-NKG2D antibody, IL2 and an anti-PD1 antibody. In some embodiment, the anti-PD-1 antibody is an antagonistic antibody. In certain embodiments, the anti-NKG2D antibody is KYK-1. In other embodiments, the anti-NKG2D antibody is KYK-2. In some embodiments, the anti-NKG2D antibody and the IL2 are provided as a chimeric polypeptide. In some embodiments, the chimeric polypeptide further comprises a linker. In some embodiments, the anti-NKG2D antibody and the IL2 are provided as a fusion protein. In some embodiments, the fusion protein further comprises a linker. In some embodiments, the combination therapy comprises an anti-NKG2D scFv, IL2 and a PD1 inhibitor. In some embodiments, the combination therapy comprises an anti-NKG2D scFv, IL2 and an anti-PD1 antibody. In some embodiment, the anti-PD-1 antibody is an antagonistic antibody. In certain embodiments, the anti-NKG2D scFv is a KYK-1 scFv. In other embodiments, the anti-NKG2D scFv is a KYK-2 scFv. In some embodiments, the anti-NKG2D scFv and the IL2 are provided as a chimeric polypeptide. In some embodiments, the chimeric polypeptide further comprises a linker. In some embodiments, the anti-NKG2D scFv and the IL2 are provided as a fusion protein. In some embodiments, the fusion protein further comprises a linker. In some embodiments, the IL2 is a mutant R38A/F42K form of IL2. In certain embodiments, the subject is in need thereof. In certain embodiments, the subject is administered an effective amount of the combination therapy. In specific embodiments, the subject is a human. In certain embodiments, the subject is a subject having a cancer or tumor. In specific embodiments, the cancer or tumor is a lung cancer or tumor.

In other aspects, the disclosure provides a method to expand cytotoxic lympocytes ex vivo. The method comprises culturing lymphocytes in the presence of a composition provided herein. Lymphocytes may be derived from a publically available cell line, such as an ATCC™ cell line. Alternatively, lymphocytes may be isolated from a subject. The lymphocytes may be obtained from a single subject, or a plurality of subjects. A plurality refers to at least two (e.g., more than one) subjects. When lymphocytes obtained are from a plurality of subjects, their relationships may be autologous, syngeneic, allogeneic, or xenogeneic. Specifically, the lymphocytes may be cultured in the presence of a chimeric peptide described in Section I. In certain embodiments, the chimeric peptide comprises OMCP or a fragment thereof linked to IL2 or a mutant thereof. In other embodiments, the chimeric peptide comprises OMCP linked to mutant IL2. In another aspect, the disclosure provides a method to improve adoptive cellular immunotherapy in a subject. The method comprises administering to a subject a therapeutic composition comprising isolated cytotoxic lymphocytes that have been cultured in the presence of a composition provided herein. As used herein, "adoptive cellular immunotherapy", also referred to as "ACI", is a lymphocyte based immunotherapy whereby lympocytes are taken from a subject and stimulated and/or genetically manipulated. Following population expansion, the lymphocytes are then transferred back into the subject. Accordingly, the methods of the disclosure may be used to treat a disease or disorder in which it is desirable to increase the number of lymphocytes. For example, cancer and chronic viral infections. Regarding viral infections, ACI of virus-specific T cells may restore virus-specific immunity in a subject to prevent or treat viral diseases. Accordingly, virus-specific T cells may be used to reconstitute antiviral immunity after transplantation and/or to treat active viral infections. In an embodiment, a subject receiving T cells for treatment or prevention of a viral infection may be immunodeficient.

(a) Administration

In certain aspects, a pharmacologically effective amount of a composition of the invention may be administered to a subject. Administration is performed using standard effective techniques, including peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. Pheresis may be used to deliver a composition of the invention. In certain embodiments, a composition of the invention may be administered via an infusion (continuous or bolus).

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

Effective peripheral systemic delivery by intravenous or intraperitoneal or subcutaneous injection is a preferred method of administration to a living patient. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl]-N,N,N-trimethyl ammonium chloride (DOTMA) or various compounds such as cholesterol hemisuccinate, phosphatidyl glycerols and the like.

For therapeutic applications, a therapeutically effective amount of a composition of the invention is administered to a subject. A "therapeutically effective amount" is an amount of the therapeutic composition sufficient to produce a measurable response (e.g., an immunostimulatory, an anti-angiogenic response, a cytotoxic response, tumor regression, immunoinhibitory, immunosuppression, infection reduction). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, the autoimmune disease, infection, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In an aspect, a typical dose contains from about 10 IU/kg to about 1,000,000 IU/kg of a cytokine described herein. In an embodiment, a typical dose contains from about 10 IU/kg to about 100 IU/kg. In another embodiment, a typical dose contains about 100 IU/kg to about 1,000 IU/kg. In still another embodiment, a typical dose contains about 1,000 IU/kg to about 10,000 IU/kg. In yet still another embodiment, a typical dose contains about 10,000 IU/kg to about 100,000 IU/kg. In a different embodiment, a typical dose contains about 100,000 IU/kg to about 1,000,000 IU/kg. In certain embodiments, a typical dose contains about 500,000 IU/kg to about 1,000,000 IU/kg. In other embodiments, a typical dose contains about 100,000 IU/kg to about 500,000 IU/kg. Alternatively, a typical dose contains about 50,000 IU/kg to about 100,000 IU/kg. In another embodiment, a typical dose contains about 10,000 IU/kg to about 50,000 IU/kg. In still another embodiment, a typical dose contains about 5,000 IU/kg to about 10,000 IU/kg. In a specific embodiment, a typical dose contains about 5,000 IU/kg to about 200,000 IU/kg. In another specific embodiment, a typical dose contains about 5,000 IU/kg to about 500,000 IU/kg. In still another specific embodiment, a typical dose contains about 50,000 IU/kg to about 500,000 IU/kg. In still yet another specific embodiment, a typical dose contains about 250,000 IU/kg to about 750,000 IU/kg.

The frequency of dosing may be once, twice, three times or more daily or once, twice, three times or more per week or per month, as needed as to effectively treat the symptoms or disease. In certain embodiments, the frequency of dosing may be once, twice or three times daily. For example, a dose may be administered every 24 hours, every 12 hours, or every 8 hours. In a specific embodiment, the frequency of dosing may be twice daily.

Duration of treatment could range from a single dose administered on a one-time basis to a life-long course of therapeutic treatments. The duration of treatment can and will vary depending on the subject and the cancer or autoimmune disease or infection to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, or 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The timing of administration of the treatment relative to the disease itself and duration of treatment will be determined by the circumstances surrounding the case. Treatment could begin immediately, such as at the time of diagnosis, or treatment could begin following surgery. Treatment could begin in a hospital or clinic itself, or at a later time after discharge from the hospital or after being seen in an outpatient clinic.

Furthermore, treatment with a composition as described above can begin in an administration regimen together (e.g., sequentially or simultaneously) with administration of a PD-1 inhibitor or PD-L1 inhibitor described herein. In some embodiments, the PD-L1 inhibitor is present in an amount as a measure with regards to the weight of the patient in need thereof. For example, in some embodiments, the PD-L1 inhibitor is present in an amount of about: 0.1 mg/kg to about 50 mg/kg, 0.1 mg/kg to about 40 mg/kg, 0.1 mg/kg to about 30 mg/kg, 0.1 mg/kg to about 25 mg/kg, 0.1 mg/kg to about 20 mg/kg, 0.1 mg/kg to about 15 mg/kg, 0.1 mg/kg to about 10 mg/kg, 0.1 mg/kg to about 7.5 mg/kg, 0.1 mg/kg to about 5 mg/kg, 0.1 mg/kg to about 2.5 mg/kg, or about 0.1 mg/kg to about 1 mg/kg. In some embodiments, the PD-L1 inhibitor is present in an amount of about: 0.5 mg/kg to about 50 mg/kg, 0.5 mg/kg to about 40 mg/kg, 0.5 mg/kg to about 30 mg/kg, 0.5 mg/kg to about 25 mg/kg, 0.5 mg/kg to about 20 mg/kg, 0.5 mg/kg to about 15 mg/kg, 0.5 mg/kg to about 10 mg/kg, 0.5 mg/kg to about 7.5 mg/kg, 0.5 mg/kg to about 5 mg/kg, 0.5 mg/kg to about 2.5 mg/kg, or about 0.5 mg/kg to about 1 mg/kg. In some embodiments, the PD-L1 inhibitor is present in an amount of about 0.5 mg/kg to about 5 mg/kg or about 0.1 mg/kg to about 10 mg/kg. In some embodiments, the PD-L1 inhibitor is present in an amount of about 0.1 mg/kg to about 20 mg/kg or about 0.1 mg/kg to about 30 mg/kg.

In still other embodiments, In some embodiments, the PD-L1 inhibitor is present at an amount of about: 0.1 mg/kg, 0.5 mg/kg, 1 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, or 50 mg/kg. The PD-L1 antibody can be present at an amount of about: 1 mg/kg, 2 mg/kg, 3 mg/kg, 5 mg/kg, 10 mg/kg, 15 mg/kg, 20 mg/kg, 25 mg/kg, or 30 mg/kg. In some embodiments, the PD-L1 inhibitor is present at an amount of about: 3 mg/kg, 10 mg/kg, 20 mg/kg, or 30 mg/kg.

In some embodiments, the PD-L1 inhibitor is present in the combination therapy at an amount of about: 1 mg, 5 mg, 10 mg, 15 mg, 20 mg, 25 mg, 30 mg, 40 mg, 50 mg, 60 mg, 70 mg, 75 mg, 80 mg, 90 mg, 100 mg, 150 mg, or 200 mg. In some embodiments, the PD-L1 inhibitor is present in the combination therapy at an amount of about: 250 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg. In some embodiments, the PD-L1 inhibitor is present in the combination therapy at an amount of about 1000 mg to about 2000 mg. In some embodiments, the PD-L1 inhibitor is present in the combination therapy at an amount of about: 1 mg to about 10 mg, 10 mg to about 20 mg, 25 mg to about 50 mg, 30 mg to about 60 mg, 40 mg to about 50 mg, 50 mg to about 100 mg, 75 mg to about 150 mg, 100 mg to about 200 mg, 200 mg to about 500 mg, 500 mg to about 1000 mg, 1000 mg to about 1200 mg, 1000 mg to about 1500 mg, 1200 mg to about 1500 mg, or 1500 to about 2000 mg.

In some embodiments, the PD-L1 inhibitor is present in the combination therapy in an amount of about 0.1 mg/mL, 0.5 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, 100 mg/mL, 150 mg/mL, 200 mg/mL, 250 mg/mL, 300 mg/mL, 400 mg/mL, or 500 mg/mL. In one embodiment, the PD-L1 inhibitor is present in the combination therapy in an amount of about: 1 mg/mL to about 10 mg/mL, 5 mg/mL to about 10 mg/mL, 5 mg/mL to about 15 mg/mL, 10 mg/mL to about 25 mg/mL; 20 mg/mL to about 30 mg/mL; 25 mg/mL to about 50 mg/mL, or 50 mg/mL to about 100 mg/mL.

In certain instances the therapeutically effective amount of a PD-L1 inhibitor is determined as an amount provided in a package insert provided with the PD-L1 inhibitor. The term package insert refers to instructions customarily included in commercial packages of medicaments approved by the FDA or a similar regulatory agency of a country other than the USA, which contains information about, for example, the usage, dosage, administration, contraindications, and/or warnings concerning the use of such medicaments.

In some embodiments, the PD-1 inhibitor is present in an amount as a measure with regards to the weight of the patient in need thereof. For example, in some embodiments, the PD-1 inhibitor is present in an amount of about: 0.1 mg/kg to about 30 mg/kg, 0.1 mg/kg to about 25 mg/kg, 0.1 mg/kg to about 20 mg/kg, 0.1 mg/kg to about 15 mg/kg, 0.1 mg/kg to about 10 mg/kg, 0.1 mg/kg to about 7.5 mg/kg, 0.1 mg/kg to about 5 mg/kg, 0.1 mg/kg to about 2.5 mg/kg, or about 0.1 mg/kg to about 1 mg/kg. In some embodiments, the PD-1 inhibitor is present in an amount of about: 0.5 mg/kg to about 30 mg/kg, 0.5 mg/kg to about 25 mg/kg, 0.5 mg/kg to about 20 mg/kg, 0.5 mg/kg to about 15 mg/kg, 0.5 mg/kg to about 10 mg/kg, 0.5 mg/kg to about 7.5 mg/kg, 0.5 mg/kg to about 5 mg/kg, 0.5 mg/kg to about 2.5 mg/kg, or about 0.5 mg/kg to about 1 mg/kg. In some embodiments, the PD-1 inhibitor is present in an amount of about 0.5 mg/kg to about 5 mg/kg or about 0.1 mg/kg to about 10 mg/kg. In some embodiments, the PD-1 inhibitor is present in an amount of about 0.5 mg/kg to about 15 mg/kg or about 0.1 mg/kg to about 20 mg/kg.

In some embodiments, the PD-1 inhibitor is present at an amount of about: 0.1 mg/kg, 0.5 mg/kg, 1 mg/kg, 2 mg/kg, 3 mg/kg, 4 mg/kg, 5 mg/kg, 10 mg/kg, 15 mg/kg, 20 mg/kg or 30 mg/kg. In some embodiments, the PD-1 inhibitor is present at an amount of about: 1 mg/kg, 2 mg/kg, 3 mg/kg, or 5 mg/kg.

In some embodiments, the PD-1 inhibitor is present in the combination therapy at an amount of about: 1 mg, 5 mg, 10 mg, 15 mg, 20 mg, 25 mg, 30 mg, 40 mg, 50 mg, 60 mg, 70 mg, 75 mg, 80 mg, 90 mg, 100 mg, 150 mg, 200 mg, 250 mg, 300 mg, 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, or 2000 mg. In some embodiments, the PD-1 inhibitor is present in the combination therapy at an amount of about: 1 mg to about 10 mg, 10 mg to about 20 mg, 25 mg to about 50 mg, 30 mg to about 60 mg, 40 mg to about 50 mg, 50 mg to about 100 mg, 75 mg to about 150 mg, 100 mg to about 200 mg, 200 mg to about 500 mg, 500 mg to about 1000 mg, 1000 mg to about 1200 mg, 1000 mg to about 1500 mg, 1200 mg to about 1500 mg, or 1500 mg to about 2000 mg.

In some embodiments, the PD-1 inhibitor is present in the combination therapy in an amount of about: 0.1 mg/mL, 0.5 mg/mL, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 15 mg/mL, 20 mg/mL, 25 mg/mL, 30 mg/mL, 40 mg/mL, 50 mg/mL, 60 mg/mL, 70 mg/mL, 80 mg/mL, 90 mg/mL, 100 mg/mL, 150 mg/mL, 200 mg/mL, 250 mg/mL, 300 mg/mL, 400 mg/mL, or 500 mg/mL. In one embodiment, the PD-1 inhibitor is present in the combination therapy in an amount of about: 1 mg/mL to about 10 mg/mL, 5 mg/mL to about 10 mg/mL, 5 mg/mL to about 15 mg/mL, 10 mg/mL to about 25 mg/mL; 20 mg/mL to about 30 mg/mL; 25 mg/mL to about 50 mg/mL, or 50 mg/mL to about 100 mg/mL.

In certain instances the therapeutically effective amount of a PD-1 inhibitor is determined as an amount provided in a package insert provided with the PD-1 inhibitor.

A synergistic effect of a combination therapy described herein can permit the use of lower dosages of one or more of the components of the combination (e.g., a composition described herein and a PD-1 or PD-L1 inhibitor). A synergistic effect can permit less frequent administration of at least one of the administered therapies (e.g., a composition described herein and a PD-1 or PD-L1 inhibitor) to a subject with a disease, disorder, or condition described herein. Such lower dosages and reduced frequency of administration can reduce the toxicity associated with the administration of at least one of the therapies (e.g., a composition described herein and a PD-1 or PD-L1 inhibitor) to a subject without reducing the efficacy of the treatment. A synergistic effect as described herein can avoid or reduce adverse or unwanted side effects associated with the use of either of the therapies described herein.

Although the foregoing methods appear the most convenient and most appropriate and effective for administration of a composition or a combination therapy of the invention, by suitable adaptation, other effective techniques for administration, such as intraventricular administration, transdermal administration and oral administration may be employed provided proper formulation is utilized herein.

In addition, it may be desirable to employ controlled release formulations using biodegradable films and matrices, or osmotic mini-pumps, or delivery systems based on dextran beads, alginate, or collagen.

(b) Tumor

A composition of the invention may be used in a method to treat or recognize a tumor derived from a neoplasm or a cancer. The neoplasm may be malignant or benign, the cancer may be primary or metastatic; the neoplasm or cancer may be early stage or late stage. Non-limiting examples of neoplasms or cancers that may be treated include acute lymphoblastic leukemia, acute myeloid leukemia, adrenocortical carcinoma, AIDS-related cancers, AIDS-related lymphoma, anal cancer, appendix cancer, astrocytomas (childhood cerebellar or cerebral), basal cell carcinoma, bile duct cancer, bladder cancer, bone cancer, brainstem glioma, brain tumors (cerebellar astrocytoma, cerebral astrocytoma/malignant glioma, ependymoma, medulloblastoma, supratentorial primitive neuroectodermal tumors, visual pathway and hypothalamic gliomas), breast cancer, bronchial adenomas/carcinoids, Burkitt lymphoma, carcinoid tumors (childhood, gastrointestinal), carcinoma of unknown primary, central nervous system lymphoma (primary), cerebellar astrocytoma, cerebral astrocytoma/malignant glioma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma in the Ewing family of tumors, extracranial germ cell tumor (childhood), extragonadal germ cell tumor, extrahepatic bile duct cancer, eye cancers (intraocular melanoma, retinoblastoma), gallbladder cancer, gastric (stomach) cancer, gastrointestinal carcinoid tumor, gastrointestinal stromal tumor, germ cell tumors (childhood extracranial, extragonadal, ovarian), gestational trophoblastic tumor, gliomas (adult, childhood brain stem, childhood cerebral astrocytoma, childhood visual pathway and hypothalamic), gastric carcinoid, hairy cell leukemia, head and neck cancer, hepatocellular (liver) cancer, Hodgkin lymphoma, hypopharyngeal cancer, hypothalamic and visual pathway glioma (childhood), intraocular melanoma, islet cell carcinoma, Kaposi sarcoma, kidney cancer (renal cell cancer), laryngeal cancer, leukemias (acute lymphoblastic, acute myeloid, chronic lymphocytic, chronic myelogenous, hairy cell), lip and oral cavity cancer, liver cancer (primary), lung cancers (non-small cell, small cell), lymphomas (AIDS-related, Burkitt, cutaneous T-cell, Hodgkin, non-Hodgkin, primary central nervous system), macroglobulinemia (Waldenström), malignant fibrous histiocytoma of bone/osteosarcoma, medulloblastoma (childhood), melanoma, intraocular melanoma, Merkel cell carcinoma, mesotheliomas (adult malignant, childhood), metastatic squamous neck cancer with occult primary, mouth cancer, multiple endocrine neoplasia syndrome (childhood), multiple myeloma/plasma cell neoplasm, mycosis fungoides, myelodysplastic syndromes, myelodysplastic/myeloproliferative diseases, myelogenous leukemia (chronic), myeloid leukemias (adult acute, childhood acute), multiple myeloma, myeloproliferative disorders (chronic), nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer (surface epithelial-stromal tumor), ovarian germ cell tumor, ovarian low malignant potential tumor, pancreatic cancer, pancreatic cancer (islet cell), paranasal sinus and nasal cavity cancer, parathyroid cancer, penile cancer, pharyngeal cancer, pheochromocytoma, pineal astrocytoma, pineal germinoma, pineoblastoma and supratentorial primitive neuroectodermal tumors (childhood), pituitary adenoma, plasma cell neoplasia, pleuropulmonary blastoma, primary central nervous system lymphoma, prostate cancer, rectal cancer, renal cell carcinoma (kidney cancer), renal pelvis and ureter transitional cell cancer, retinoblastoma, rhabdomyosarcoma (childhood), salivary gland cancer, sarcoma (Ewing family of tumors, Kaposi, soft tissue, uterine), Sezary syndrome, skin cancers (nonmelanoma, melanoma), skin carcinoma (Merkel cell), small cell lung cancer, small intestine cancer, soft tissue sarcoma, squamous cell carcinoma, squamous neck cancer with occult primary (metastatic), stomach cancer, supratentorial primitive neuroectodermal tumor (childhood), T-Cell lymphoma (cutaneous), testicular cancer, throat cancer, thymoma (childhood), thymoma and thymic carcinoma, thyroid cancer, thyroid cancer (childhood), transitional cell cancer of the renal pelvis and ureter, trophoblastic tumor (gestational), unknown primary site (adult, childhood), ureter and renal pelvis transitional cell cancer, urethral cancer, uterine cancer (endometrial), uterine sarcoma, vaginal cancer, visual pathway and hypothalamic glioma (childhood), vulvar cancer, Waldenström macroglobulinemia, and Wilms tumor (childhood). In certain embodiments, the neoplasm or cancer may be selected from the group consisting of melanoma, renal cell carcinoma, lung cancer and blood cancer. In one embodiment, the tumor is melanoma. In another embodiment, the tumor is renal cell carcinoma. In one embodiment, the tumor is lung cancer (e.g., NSCLC). In another embodiment, the tumor is a blood cancer described herein. As used herein, a "blood cancer" is a cancer that affects the blood, bone marrow and lymphatic system. There are three main groups of blood cancer: leukemia, lymphoma and myeloma. The four broad classification of leukemia are: acute lymphocytic leukemia (ALL), acute myelogenous leukemia (AML), chronic lymphocytic leukemia (CLL) and chronic myelogenous leukemia (CML). Lymphomas are divided into two categories: Hodgkin lymphoma and non-Hodgkin lymphoma. Most non-Hodgkin lymphomas are B-cell lymphomas, and either grow quickly (high-grade) or slowly (low-grade). There are 14 types of B-cell non-Hodgkin lymphomas. The rest are T-cell lymphomas, named after a different cancerous white blood cell, or lymphocyte. Because myeloma frequently occurs at many sites in the bone marrow, it is often referred to as multiple myeloma. In some embodiments, the method comprises administration of a combination therapy as provided herein. In some embodiments, the combination therapy comprises a PD-1 inhibitor. In other embodiments, the PD-1 inhibitor is an anti-PD-1 antibody. In some embodiments, the combination therapy comprises a PD-L1 inhibitor. In other embodiments, the PD-L1 inhibitor is an anti-PD-L1 antibody.

(c) Subject

A suitable subject includes a human, a livestock animal, a companion animal, a lab animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

TABLE A

| SEQ ID NO | Name | Sequence | Source |
|---|---|---|---|
| 1 | R38A, F42K, C125S IL2-OMCP construct | CACAAACTCGCATTCAACTTCAATCTAGAAATAAATGGCAG TGATACACATTCTACAGTAGATGTATATCTTGATGATTCT CAAATTATAACGTTTGATGGAAAAGATATCCGTCCAA CCATCCCGTTCATGATAGGTGATGAAATTTTCTTACCGTTT TATAAAAATGTGTTTAGTGAGTTTTTCTCTCTGTTTAGAAGA GTTCCTACAAGTACTCCATATGAAGACTTGACATATTTTTAT GAATGCGACTATACAGACAATAAATCTACATTTGATCAGTT TTATCTTTATAATGGCGAAGAATATACTGTCAAAACACAGG AGGCCACTAATAAAAATATGTGGCTAACTACTTCCGAGTTT AGACTAAAAAAATGGTTCGATGGCGAAGATTGTATAATGCA TCTTAGATCGTTAGTTAGAAAAATGGAGGACAGTAAACGAA ACACTGGTGGTACCGGAAGTAGCGGTAGTAGTGATTACAA GGACGATGACGACAAGCACCACCATCATCATCATCACCAC GGTAGCAGCGGCAGCAGTGCCCCCACCTCTAGCAGCACA AAGAAGACCCAGCTGCAACTGGAACACCTCCTGCTGGACC TGCAGATGATCCTGAACGGCATCAACAACTACAAGAACCC CAAGCTGACCGCCATGCTGACCAAAAAGTTTTACATGCCC AAGAAGGCCACCGAGCTTAAACACCTGCAATGCCTTGAGG AGGAGCTGAAGCCCTGGAGGAGGTACTGAACCTGGCCCA GAGCAAGAACTTTCATCTGAGGCCCAGGGACCTGATTAGC AACATCAACGTGATCGTGTTGGAGTTGAAGGGCAGCGAGA | Synthesized |

TABLE A-continued

Sequences

| SEQ ID NO | Name | Sequence | Source |
|---|---|---|---|
| | | CCACGTTCATGTGCGAGTACGCCGACGAGACGGCCACCA TAGTGGAGTTTCTTAACAGGTGGATCACCTTCTCACAGTCT ATCATCAGCACCCTGACC | |
| 2 | R38A, F42K, C125S IL2-OMCP construct | HKLAFNFNLEINGSDTHSTVDVYLDDSQIITFDGKDIRPTIPFMI GDEIFLPFYKNVFSEFFSLFRRVPTSTPYEDLTYFYECDYTDN KSTFDQFYLYNGEEYTVKTQEATNKNMWLTTSEFRLKKWFD GEDCIMHLRSLVRKMEDSKRNTGGTGSSGSSDYKDDDDKH HHHHHHGSSGSSAPTSSSTKKTQLQLEHLLLDLQMILNGIN NYKNPKLTAMLTKKFYMPKKATELKHLQCLEE TABLE A-continued Sequences

| SEQ ID NO | Name | Sequence | Source |
|---|---|---|---|
| 17 | ULBP3 | DAHSLWYNFTIIHLPRHGQQWCEVQSQVDQKNFLSYDCGSD KVLSMGHLEEQLYATDAWGKQLEMLREVGQRLRLELADTEL EDFTPSGPLTLQVRMSCECEADGYIRGSWQFSFDGRKFLLF DSNNRKWTVVHAGARRMKEKWEKDSGLTTFFKMVSMRDCK SWLRDFLMHRKKRLE | *Homo sapiens* |
| 18 | RAE-1B | DAHSLRCNLTIKDPTPADPLWYEAKCFVGEILILHLSNINKTMT SGDPGETANATEVKKCLTQPLKNLCQKLRNKVSNTKVDTHK TNGYPHLQVTMIYPQSQGRTPSATWEFNISDSYFFTFYTENM SWRSANDESGVIMNKWKDDGEFVKQLKFLIHECSQKMDEFL KQSKEK | *Homo sapiens* |
| 19 | NKG2D portion | LTIIEMQKGDCALYAS | *Homo sapiens* |
| 20 | NKG2D portion | LTIIEMQKGECALYAS | Green monkey |
| 21 | NKG2D portion | LTIIEMQKGDCAVYAS | Marmoset |
| 22 | NKG2D portion | LTLVEIPKGSCAVYGS | Mouse |
| 23 | NKG2D portion | LTLVKTPSGTCAVYGS | Rat |
| 24 | NKG2D portion | LTLMDTQNGKCALYGS | Guinea pig |
| 25 | NKG2D portion | LTLVEMQNGTCIVYGS | Ground squirrel |
| 26 | NKG2D portion | LTVVEMQSGSCAVYGS | Deer mouse |
| 27 | NKG2D portion | LSMVEMQNGTCAVYAS | Naked mole rat |
| 28 | NKG2D portion | LTLVEMQRGSCAVYGS | Prairie vole |
| 29 | NKG2D portion | VSIVEMQGGNCAVYGS | European shrew |
| 30 | NKG2D portion | VTVYEMQNGSCAVYGS | Star-nosed mole |
| 31 | NKG2D portion | LTLVEMQNGSCAVYGS | Chinese hamster |
| 32 | NKG2D portion | LTMVDMQNGTCAVYGS | Cat |
| 33 | OMCP portion | ASSFK | Cowpox virus |
| 34 | DAP10 signaling motif | YINM | Synthesized |
| 35 | KYK-1 antibody (light chain) | QPVLTQPSSVSVAPGETARIPCGGDDIETKSVHWYQQKPGQ APVLVIYDDDDRPSGIPERFFGSNSGNTATLSISRVEAGDEAD YYC QVWDDNNDEWV FGGGTQLTVL | Synthesized |
| 36 | KYK-1 antibody (heavy chain) | EVQLVESGGGVVQPGGSLRLSCAASGFTFSSYGMHWVRQA PGKGLEWVAFIRYDGSNKYYADSVKGRFTISRDNSKNTLYLQ MNSLRAEDTAVYYCAK DRFGYYLDY WGQGTLVTVSS | Synthesized |
| 37 | KYK-2 antibody (light chain) | QSALTQPASVSGSPGQSITISCSGSSSNIGNNAVNWYQQLP GKAPKLLIYYDDLLPSGVSDRFSGSKSGTSAFLAISGLQSEDE ADYYC AAWDDSLNGPV FGGGTKLTVL | Synthesized |

TABLE A-continued

Sequences

| SEQ ID NO | Name | Sequence | Source |
|---|---|---|---|
| 38 | KYK-2 antibody (heavy chain) | QVQLVESGGGLVKPGGSLRLSCAASGFTFSSYGMHWRQA PGKGLEWVAFIRYDGSNKYYADSVKGRFTISRDNSKNTLYLQ MNSLRAEDTAVYYCAK DRGLGDGTYFDYWGQGTTVTVSS | Synthesized |
| 39 | KYK-1 scFv 1 | QPVLTQPSSVSVAPGETARIPCGGDDIETKSVHWYQQKPGQ APVLVIYDDDDRPSGIPERFFGSNSGNTATLSISRVEAGDEAD YYCQVWDDNNDEWVFGGGTQLTVLGGGGSGGGGSGGGG SGGGGSEVQLVESGGGVVQPGGSLRLSCAASGFTFSSYGM HWVRQAPGKGLEWVAFIRYDGSNKYYADSVKGRFTISRDNS KNTLYLQMNSLRAEDTAVYYCAKDRFGYYLDYWGQGTLVTV SS | Synthesized |
| 40 | KYK-1 scFv 2 | EVQLVESGGGVVQPGGSLRLSCAASGFTFSSYGMHWRQA PGKGLEWVAFIRYDGSNKYYADSVKGRFTISRDNSKNTLYLQ MNSLRAEDTAVYYCAKDRFGYYLDYWGQGTLVTVSSGGGG SGGGGSGGGGSGGGGSQPVLTQPSSVSVAPGETARIPCGG DDIETKSVHWYQQKPGQAPVLVIYDDDDRPSGIPERFFGSNS GNTATLSISRVEAGDEADYYCQVWDDNNDEWVFGGGTQLT VL | Synthesized |
| 41 | KYK-2 scFv 1 | QSALTQPASVSGSPGQSITISCSGSSSNIGNNAVNWYQQLP GKAPKLLIYYDDLLPSGVSDRFSGSKSGTSAFLAISGLQSEDE ADYYCAAWDDSLNGPVFGGGTKLTVLGGGGSGGGGSGGG GSGGGGSQVQLVESGGGLVKPGGSLRLSCAASGFTFSSYG MHWVRQAPGKGLEWVAFIRYDGSNKYYADSVKGRFTISRDN SKNTLYLQMNSLRAEDTAVYYCAKDRGLGDGTYFDYWGQG TTVTVSS | Synthesized |
| 42 | KYK-2 scFv 2 | QVQLVESGGGLVKPGGSLRLSCAASGFTFSSYGMHWRQA PGKGLEWVAFIRYDGSNKYYADSVKGRFTISRDNSKNTLYLQ MNSLRAEDTAVYYCAKDRGLGDGTYFDYWGQGTTVTV | Synthesized |
| 43 | R38A, F42K, C125S IL2-KYK-1 (light-heavy) construct | QPVLTQPSSVSVAPGETARIPCGGDDIETKSVHWYQQKPGQ APVLVIYDDDDRPSGIPERFFGSNSGNTATLSISRVEAGDEAD YYCQVWDDNNDEWVFGGGTQLTVLGGGGSGGGGSGGGG SGGGGSEVQLVESGGGVVQPGGSLRLSCAASGFTFSSYGM HWVRQAPGKGLEWVAFIRYDGSNKYYADSVKGRFTISRDNS KNTLYLQMNSLRAEDTAVYYCAKDRFGYYLDYWGQGTLVTV SSGGSSGSGSSHHHHHHHHGGSSGSSGSSAPTSSSTKKT QLQLEHLLLDLQMILNGINNYKNPKLTAMLTKKFYMPKKATEL KHLQCLEEELKPLEEVLNLAQSKNFHLRPRDLISNINVIVLELK GSETTFMCEYADETATIVEFLNRWITFSQSIISTLT | Synthesized |
| 44 | R38A, F42K, C125S IL2-KYK-1 (heavy-light) construct | EVQLVESGGGVVQPGGSLRLSCAASGFTFSSYGMHWVRQ APGKGLEWVAFIRYDGSNKYYADSVKGRFTISRDNSKNTLY LQMNSLRAEDTAVYYCAKDRFGYYLDYWGQGTLVTVSSGG GGSGGGGSGGGGSGGGGSQPVLTQPSSVSVAPGETARIP CGGDDIETKSVHWYQQKPGQAPVLVIYDDDDRPSGIPERFF GSNSGNTATLSISRVEAGDEADYYCQVWDDNNDEWVFGGG TQLTVLGGSSGSSGSSHHHHHHHHGGSSGSSGSSAPTSSS TKKTQLQLEHLLLDLQMILNGINNYKNPKLTAMLTKKFYMPKK ATELKHLQCLEEELKPLEEVLNLAQSKNFHLRPRDLISNINVIV LELKGSETTFMCEYADETATIVEFLNRWITFSQSIISTLT | Synthesized |
| 45 | R38A, F42K, C125S IL2-KYK-2 (light-heavy) construct | QSALTQPASVSGSPGQSITISCSGSSSNIGNNAVNWYQQLP GKAPKLLIYYDDLLPSGVSDRFSGSKSGTSAFLAISGLQSED EADYYCAAWDDSLNGPVFGGGTKLTVLGGGGSGGGGSGG GGSGGGGSQVQLVESGGGLVKPGGSLRLSCAASGFTFSSY GMHWVRQAPGKGLEWVAFIRYDGSNKYYADSVKGRFTISR DNSKNTLYLQMNSLRAEDTAVYYCAKDRGLGDGTYFDYWG QGTTVTVSSGGSSGSSGSSHHHHHHHHGGSSGSSGSSAPT SSSTKKTQLQLEHLLLDLQMILNGINNYKNPKLTAMLTKKFYM PKKATELKHLQCLEEELKPLEEVLNLAQSKNFHLRPRDLISNI NVIVLELKGSETTFMCEYADETATIVEFLNRWITFSQSIISTLT | Synthesized |
| 46 | R38A, F42K, C125S IL2-KYK-2 (heavy-light) construct | QVQLVESGGGLVKPGGSLRLSCAASGFTFSSYGMHWVRQ APGKGLEWVAFIRYDGSNKYYADSVKGRFTISRDNSKNTLY LQMNSLRAEDTAVYYCAKDRGLGDGTYFDYWGQGTTVTVS SGGGGSGGGGSGGGGSGGGGSQSALTQPASVSGSPGQSI TISCSGSSSNIGNNAVNWYQQLPGKAPKLLIYYDDLLPSGVS DRFSGSKSGTSAFLAISGLQSEDEADYYCAAWDDSLNGPVF GGGTKLTVLGGSSGSSGSSHHHHHHHHGGSSGSSGSSAPT | Synthesized |

… TABLE A-continued

Sequences

| SEQ ID NO | Name | Sequence | Source |
|---|---|---|---|
| | | SSSTKKTQLQLEHLLLDLQMILNGINNYKNPKLTAMLTKKFYM PKKATELKHLQCLEEELKPLEEVLNLAQSKNFHLRPRDLISNI NVIVLELKGSETTFMCEYADETATIVEFLNRWITFSQSIISTLT | |
| 47 | R38A, F42K, C125S IL2-PDL1 construct | GCCTTCACCGTGACTGTGCCCAAGGATCTGTACGTCGTGG AGTACGGCTCCAACATGACAATCGAGTGCAAGTTCCCCGT GGGAGAAGCAGCTGGACCTGGCGGCACTGATCGTGTACTG GGAGATGGAGGACAAGAACATCATCCAGTTCGTTCATGGC GAAGAGGATCTCAAGGTGCAGCACAGCAGCTACAGGCAG AGGGCCCGACTGCTGAAGGACCAGCTGAGCCTGGGCAAC GCCGCACTGCAAATCACCGACGTGAAGCTGCAGGACGCT GGCGTGTACAGGTGTATGATAAGCTACGGCGGAGCTGAC TACAAGAGAATCACGGTTAAGGTAAACGCCCCCTACGGGG GCAGTAGCGGAAGCTCCGGCTCAAGCCACCACCATCATC ATCATCACCGGCGGCAGCAGCGGGAGCTCAGGTAGCA GTGGTGGGCACCTACCTCTTCCAGCACCAAGAAGACGC AGCTCCAGTTGGAACACCTTCTCCTTGACCTCCAGATGAT CCTGAACGGCATCAACAACTACAAAAATCCCAAGCTGACC GCGATGCTGACGAAGAAATTCTACATGCCAAAGAAGGCCA CCGAGCTGAAACACCTGCAGTGTCTTGAGGAGGAACTTAA GCCGCTCGAGGAGGTACTGAACCTGGCCCAGAGTAAGAA CTTCCACCTGAGGCCCAGGGACCTCATCAGCAACATCAAT GTGATCGTCCTTGAGCTTAAGGGCAGCGAGACCACCTTCA TGTGCGAGTATGCGGACGAAACGGCCACAATCGTCGAGTT TCTGAATAGGTGGATCACTTTCAGCCAGAGCATCATCTCTA CCCTGACC | Synthesized |
| 48 | R38A, F42K, C125S IL2-PDL1 construct | AFTVTVPKDLYVVEYGSNMTIECKFPVEKQLDLAALIVYWEM EDKNIIQFVHGEEDLKVQHSSYRQRARLLKDQLSLGNAALQIT DVKLQDAGVYRCMISYGGADYKRITVKVNAPYGGSSGSSGS SHHHHHHHGGSSGSSGSSGGAPTSSSTKKTQLQLEHLLLD LQMILNGINNYKNPKLTAMLTKKFYMPKKATELKHLQCLEEEL KPLEEVLNLAQSKNFHLRPRDLISNINVIVLELKGSETTFMCEY ADETATIVEFLNRWITFSQSIISTLT | Synthesized |
| 49 | R38A, F42K, C125S IL2-PDL2 construct | CTGTACATCATCGAGCACGGCAGTAACGTGACCCTGGAGT GCAACTTCGACACCGGCAGCCACGTGAATCTGGGCGCCA TCACAGCTTCACTGCAGAAGGTGGAGAATGACACCTCTCC CCACAGGGAGCGAGCCACCCTGCTTGAGGAACAACTGCC TCTCGGCAAGGCCAGCTTCCACATCCCCCAGGTGCAGGT GAGGGACGAGGGCCAGTACCAGTGCATAATCATCTACGG CGTGGCCTGGGACTACAAGTACCTGACACTTAAGGTGAAA GCCTCCGGCGGTTCTTCCGGCTCTTCAGGCAGCTCACAC CATCATCATCATCACCACCATGGCGGCAGCAGCGGGAGC TCTGGTAGCAGTGGCGGTGCCCCCACCAGCAGTACT AAGAAGACCCAGCTGCAACTGGAGCACTTGCTCCTGGACC TGCAAATGATCCTCAACGGCATCAACAACTATAAGAACCC CAAGCTGACGGCCATGCTGACCAAAAAGTTCTACATGCCC AAGAAGGCCACCGAGTTGAAACACTTGCAGTGCCTGGAG GAGGAGCTGAAGCCCCTGGAAGAGGTGCTGAACCTGGCC CAGAGCAAGAATTTTCATCTGAGGCCTAGGGACCTGATTA GCAACATCAACGTGATCGTGTTGGAGCTTAAAGGCTCCGA GACCACCTTTATGTGCGAGTACGCCGACGAGACCGCGAC TATCGTGGAGTTCCTGAACAGGTGGATCACCTTTTCACAG AGCATCATAAGCACACTGACC | Synthesized |
| 50 | R38A, F42K, C125S IL2-PDL2 construct | LYIIEHGSNVTLECNFDTGSHVNLGAITASLQKVENDTSPHRE RATLLEEQLPLGKASFHIPQVQVRDEGQYQCIIIYGVAWDYKY LTLKVKASGGSSGSSGSSHHHHHHHGGSSGSSGSSGGAP TSSSTKKTQLQLEHLLLDLQMILNGINNYKNPKLTAMLTKKFY MPKKATELKHLQCLEEELKPLEEVLNLAQSKNFHLRPRDLISN INVIVLELKGSETTFMCEYADETATIVEFLNRWITFSQSIISTLT | Synthesized |
| 51 | PDL1 | MRIFAVFIFMTYWHLLNAFTVTVPKDLYVVEYGSNMTIECKFP VEKQLDLAALIVYWEMEDKNIIQFVHGEEDLKVQHSSYRQRA RLLKDQLSLGNAALQITDVKLQDAGVYRCMISYGGADYKRIT VKVNAPYNKINQRILVVDPVTSEHELTCQAEGYPKAEVIWTSS DHQVLSGKTTTTNSKREEKLFNVTSTLRINTTTNEIFYCTFRR LDPEENHTAELVIPGNILNVSIKICLTLSPST | Homo sapiens |
| 52 | PDL1 | MRIFAVFIFMTYWHLLNAPYNKINQRILVVDPVTSEHELTCQA EGYPKAEVIWTSSDHQVLSGKTTTTNSKREEKLFNVTSTLRIN TTTNEIFYCTFRRLDPEENHTAELVIPELPLAHPPNERTHLVIL GAILLCLGVALTFIFRLKGRMMDVKKCGIQDTNSKKQSDTHL EET | Homo sapiens |

TABLE A-continued

Sequences

| SEQ ID NO | Name | Sequence | Source |
|---|---|---|---|
| 53 | PDL1 | MRIFAVFIFMTYWHLLNAFTVTVPKDLYVVEYGSNMTIECKFP VEKQLDLAALIVYWEMEDKNIIQFVHGEEDLKVQHSSYRQRA RLLKDQLSLGNAALQITDVKLQDAGVYRCMISYGGADYKRIT VKVNAPYNKINQRILVVDPVTSEHELTCQAEGYPKAEVIWTSS DHQVLSGKTTTTNSKREEKLFNVTSTLRINTTTNEIFYCTFRR LDPEENHTAELVIPELPLAHPPNERTHLVILGAILLCLGVALTFI FRLRKGRMMDVKKCGIQDTNSKKQSDTHLEET | Homo sapiens |
| 54 | PDL2 | IFLLLMLSLELQLHQIAALFTVTVPKELYIIEHGSNVTLECNFDT GSHVNLGAITASLQKVENDTSPHRERATLLEEQLPLGKASFHI PQVQVRDEGQYQCIIIYGVAWDYKYLTLKVKASYRKINTHILK VPETDEVELTCQATGYPLAEVSWPNVSVPANTSHSRTPEGL YQVTSVLRLKPPPGRNFSCVFWNTHVRELTLASIDLQSQMEP RTHPTWLLHIFIPFCIIAFIFIATVIALRKQLCQKLYSSKDTTKRP VTTTKREVNSAI | Homo sapiens |
| 55 | PDL2 | MIFLLLMLSLELQLHQIAALFTVTVPKELYIIEHGSNVTLECNFD TGSHVNLGAITASLQKVENDTSPHRERATLLEEQLPLGKASF HIPQVQVRDEGQYQCIIIYGVAWDYKYLTLKVKASYRKINTHIL KVPETDEVELTCQATGYPLAEVSWPNVSVPANTSHSRTPEG LYQVTSVLRLKPPPGRNFSCVFWNTHVRELTLASIDLQSQME PRTHPTWLLHIFIPFCIIAFIFIATVIALRKQLCQKLYSSKDTTKR PVTTTKREVNSAVNLNLWSWEPG | Homo sapiens |
| 56 | OX40L | MERVQPLEENVGNAARPRFERNKLLLVASVIQGLGLLLCFTYI CLHFSTLQVSHRYPRIQSIKVQFTEYKKEKGFILTSQKEDEIM KVQNNSVIINCDGFYLISLKGYFSQEVNISLHYQKDEEPLFQL KKVRSVNSLMVASLTYKDKVYLNVTTDNTSLDDFHVNGGELI LIHQNPGEFCVL | Homo sapiens |
| 57 | OX40L portion | QVSHRYPRIQSIKVQFTEYKKEKGFILTSQKEDEIMKVQNNSV IINCDGFYLISLKGYFSQEVNISLHYQKDEEPLFQLKKVRSVNS LMVASLTYKDKVYLNVTTDNTSLDDFHVNGGELILIHQNPGEF CVL | Homo sapiens |
| 58 | OX40L construct | QVSHRYPRIQSIKVQFTEYKKEKGFILTSQKEDEIMKVQNNSV IINCDGFYLISLKGYFSQEVNISLHYQKDEEPLFQLKKVRSVNS LMVASLTYKDKVYLNVTTDNTSLDDFHVNGGELILIHQNPGEF CVLGGSGGGSGGGSGQVSHRYPRIQSIKVQFTEYKKEKGFIL TSQKEDEIMKVQNNSVIINCDGFYLISLKGYFSQEVNISLHYQ KDEEPLFQLKKVRSVNSLMVASLTYKDKVYLNVTTDNTSLDD FHVNGGELILIHQNPGEFCVLGGSGGGSGGGSGQVSHRYPR IQSIKVQFTEYKKEKGFILTSQKEDEIMKVQNNSVIINCDGFYLI SLKGYFSQEVNISLHYQKDEEPLFQLKKVRSVNSLMVASLTY KDKVYLNVTTDNTSLDDFHVNGGELILIHQNPGEFCVL | Synthesized |
| 59 | OX40L N166A, F180A portion | QVSHRYPRIQSIKVQFTEYKKEKGFILTSQKEDEIMKVQNNSV IINCDGFYLISLKGYFSQEVNISLHYQKDEEPLFQLKKVRSVNS LMVASLTYKDKVYLNVTTDNTSLDDFHVAGGELILIHQNPGEA CVL | Synthesized |
| 60 | OX40L N166A, F180A construct | QVSHRYPRIQSIKVQFTEYKKEKGFILTSQKEDEIMKVQNNSV IINCDGFYLISLKGYFSQEVNISLHYQKDEEPLFQLKKVRSVNS LMVASLTYKDKVYLNVTTDNTSLDDFHVAGGELILIHQNPGEA CVLGGSGGGSGGGSGQVSHRYPRIQSIKVQFTEYKKEKGFIL TSQKEDEIMKVQNNSVIINCDGFYLISLKGYFSQEVNISLHYQ KDEEPLFQLKKVRSVNSLMVASLTYKDKVYLNVTTDNTSLDD FHVAGGELILIHQNPGEACVLGGSGGGSGGGSGQVSHRYPR IQSIKVQFTEYKKEKGFILTSQKEDEIMKVQNNSVIINCDGFYLI SLKGYFSQEVNISLHYQKDEEPLFQLKKVRSVNSLMVASLTY KDKVYLNVTTDNTSLDDFHVNGGELILIHQNPGEFCVL | Synthesized |
| 61 | OX40L N166A, F180A construct 2 | QVSHRYPRIQSIKVQFTEYKKEKGFILTSQKEDEIMKVQNNSV IINCDGFYLISLKGYFSQEVNISLHYQKDEEPLFQLKKVRSVNS LMVASLTYKDKVYLNVTTDNTSLDDFHVAGGELILIHQNPGEA CVLGGSGGGSGGGSGQVSHRYPRIQSIKVQFTEYKKEKGFIL TSQKEDEIMKVQNNSVIINCDGFYLISLKGYFSQEVNISLHYQ KDEEPLFQLKKVRSVNSLMVASLTYKDKVYLNVTTDNTSLDD FHVNGGELILIHQNPGEFCVLGGSGGGSGGGSGQVSHRYPR IQSIKVQFTEYKKEKGFILTSQKEDEIMKVQNNSVIINCDGFYLI SLKGYFSQEVNISLHYQKDEEPLFQLKKVRSVNSLMVASLTY KDKVYLNVTTDNTSLDDFHVNGGELILIHQNPGEFCVL | Synthesized |

TABLE A-continued

Sequences

| SEQ ID NO | Name | Sequence | Source |
|---|---|---|---|
| 62 | OMCP-OX40L construct | HKLAFNFNLEINGSDTHSTVDVYLDDSQIITFDGKDIRPTIPFMI GDEIFLPFYKNVFSEFFSLFRRVPTSTPYEDLTYFYECDYTDN KSTFDQFYLYNGEEYTVKTQEATNKNMWLTTSEFRLKKWFD GEDCIMHLRSLVRKMEDSKRNTGGGSSGSSGSSHHHHHHH HGGSSGSSGSSGGQVSHRYPRIQSIKVQFTEYKKEKGFILTS QKEDEIMKVQNNSVIINCDGFYLISLKGYFSQEVNISLHYQKD EEPLFQLKKVRSVNSLMVASLTYKDKVYLNVTTDNTSLDDFH VNGGELILIHQNPGEFCVLGGSGGGSGGGSGQVSHRYPRIQ SIKVQFTEYKKEKGFILTSQKEDEIMKVQNNSVIINCDGFYLISL KGYFSQEVNISLHYQKDEEPLFQLKKVRSVNSLMVASLTYKD KVYLNVTTDNTSLDDFHVNGGELILIHQNPGEFCVLGGSGGG SGGGSGQVSHRYPRIQSIKVQFTEYKKEKGFILTSQKEDEIM KVQNNSVIINCDGFYLISLKGYFSQEVNISLHYQKDEEPLFQL KKVRSVNSLMVASLTYKDKVYLNVTTDNTSLDDFHVNGGELI LIHQNPGEFCVL | Synthesized |
| 63 | OMCP-OX40L N166A, F180A construct | HKLAFNFNLEINGSDTHSTVDVYLDDSQIITFDGKDIRPTIPFMI GDEIFLPFYKNVFSEFFSLFRRVPTSTPYEDLTYFYECDYTDN KSTFDQFYLYNGEEYTVKTQEATNKNMWLTTSEFRLKKWFD GEDCIMHLRSLVRKMEDSKRNTGGGSSGSSGSSHHHHHHH HGGSSGSSGSSGGQVSHRYPRIQSIKVQFTEYKKEKGFILTS QKEDEIMKVQNNSVIINCDGFYLISLKGYFSQEVNISLHYQKD EEPLFQLKKVRSVNSLMVASLTYKDKVYLNVTTDNTSLDDFH VAGGELILIHQNPGEACVLGGSGGGSGGGSGQVSHRYPRIQ SIKVQFTEYKKEKGFILTSQKEDEIMKVQNNSVIINCDGFYLISL KGYFSQEVNISLHYQKDEEPLFQLKKVRSVNSLMVASLTYKD KVYLNVTTDNTSLDDFHVAGGELILIHQNPGEACVLGGSGGG SGGGSGQVSHRYPRIQSIKVQFTEYKKEKGFILTSQKEDEIM KVQNNSVIINCDGFYLISLKGYFSQEVNISLHYQKDEEPLFQL KKVRSVNSLMVASLTYKDKVYLNVTTDNTSLDDFHVNGGELI LIHQNPGEFCVL | Synthesized |
| 64 | OMCP-OX40L N166A, F180A construct 2 | HKLAFNFNLEINGSDTHSTVDVYLDDSQIITFDGKDIRPTIPFMI GDEIFLPFYKNVFSEFFSLFRRVPTSTPYEDLTYFYECDYTDN KSTFDQFYLYNGEEYTVKTQEATNKNMWLTTSEFRLKKWFD GEDCIMHLRSLVRKMEDSKRNTGGGSSGSSGSSHHHHHHH HGGSSGSSGSSGGQVSHRYPRIQSIKVQFTEYKKEKGFILTS QKEDEIMKVQNNSVIINCDGFYLISLKGYFSQEVNISLHYQKD EEPLFQLKKVRSVNSLMVASLTYKDKVYLNVTTDNTSLDDFH VAGGELILIHQNPGEACVLGGSGGGSGGGSGQVSHRYPRIQ SIKVQFTEYKKEKGFILTSQKEDEIMKVQNNSVIINCDGFYLISL KGYFSQEVNISLHYQKDEEPLFQLKKVRSVNSLMVASLTYKD KVYLNVTTDNTSLDDFHVNGGELILIHQNPGEFCVLGGSGGG SGGGSGQVSHRYPRIQSIKVQFTEYKKEKGFILTSQKEDEIM KVQNNSVIINCDGFYLISLKGYFSQEVNISLHYQKDEEPLFQL KKVRSVNSLMVASLTYKDKVYLNVTTDNTSLDDFHVNGGELI LIHQNPGEFCVL | Synthesized |
| 65 | 4-1BBL portion | ACPWAVSGARASPGSAASPRLREGPELSPDDPAGLLDLRQ GMFAQLVAQNVLLIDGPLSWYSDPGLAGVSLTGGLSYKEDT KELVVAKAGVYYVFFQLELRRVVAGEGSGSVSLALHLQPLRS AAGAAALALTVDLPPASSEARNSAFGFQGRLLHLSAGQRLG VHLHTEARARHAWQLTQGATVLGLFRVTPEIPAGLPSPRSE | *Homo sapiens* |
| 66 | 4-1BBL construct | ACPWAVSGARASPGSAASPRLREGPELSPDDPAGLLDLRQ GMFAQLVAQNVLLIDGPLSWYSDPGLAGVSLTGGLSYKEDT KELVVAKAGVYYVFFQLELRRVVAGEGSGSVSLALHLQPLRS AAGAAALALTVDLPPASSEARNSAFGFQGRLLHLSAGQRLG VHLHTEARARHAWQLTQGATVLGLFRVTPEIPAGLPSPRSEG GSGGGSGGGSGACPWAVSGARASPGSAASPRLREGPELS PDDPAGLLDLRQGMFAQLVAQNVLLIDGPLSWYSDPGLAGV SLTGGLSYKEDTKELVVAKAGVYYVFFQLELRRVVAGEGSG SVSLALHLQPLRSAAGAAALALTVDLPPASSEARNSAFGFQG RLLHLSAGQRLGVHLHTEARARHAWQLTQGATVLGLFRVTP EIPAGLPSPRSEGGSGGGSGGGSGACPWAVSGARASPGSA ASPRLREGPELSPDDPAGLLDLRQGMFAQLVAQNVLLIDGPL SWYSDPGLAGVSLTGGLSYKEDTKELVVAKAGVYYVFFQLE LRRVVAGEGSGSVSLALHLQPLRSAAGAAALALTVDLPPASS EARNSAFGFQGRLLHLSAGQRLGVHLHTEARARHAWQLTQ GATVLGLFRVTPEIPAGLPSPRSE | Synthesized |
| 67 | OMCP-41BBL construct | HKLAFNFNLEINGSDTHSTVDVYLDDSQIITFDGKDIRPTIPFMI GDEIFLPFYKNVFSEFFSLFRRVPTSTPYEDLTYFYECDYTDN KSTFDQFYLYNGEEYTVKTQEATNKNMWLTTSEFRLKKWFD | Synthesized |

TABLE A-continued

Sequences

| SEQ ID NO | Name | Sequence | Source |
|---|---|---|---|
| | | GEDCIMHLRSLVRKMEDSKRNTGGGSSGSSGSSHHHHHHH HGGSSGSSGSSGGACPWAVSGARASPGSAASPRLREGPEL SPDDPAGLLDLRQGMFAQLVAQNVLLIDGPLSWYSDPGLAG VSLTGGLSYKEDTKELVVAKAGVYYVFFQLELRRVVAGEGS GSVSLALHLQPLRSAAGAAALALTVDLPPASSEARNSAFGFQ GRLLHLSAGQRLGVHLHTEARARHAWQLTQGATVLGLFRVT PEIPAGLPSPRSEGGSGGGSGGGSGACPWAVSGARASPGS AASPRLREGPELSPDDPAGLLDLRQGMFAQLVAQNVLLIDGP LSWYSDPGLAGVSLTGGLSYKEDTKELVVAKAGVYYVFFQL ELRRVVAGEGSGSVSLALHLQPLRSAAGAAALALTVDLPPAS SEARNSAFGFQGRLLHLSAGQRLGVHLHTEARARHAWQLT QGATVLGLFRVTPEIPAGLPSPRSEGGSGGGSGGGSGACP WAVSGARASPGSAASPRLREGPELSPDDPAGLLDLRQGMF AQLVAQNVLLIDGPLSWYSDPGLAGVSLTGGLSYKEDTKELV VAKAGVYYVFFQLELRRVVAGEGSGSVSLALHLQPLRSAAG AAALALTVDLPPASSEARNSAFGFQGRLLHLSAGQRLGVHLH TEARARHAWQLTQGATVLGLFRVTPEIPAGLPSPRSE | |

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to Examples 1-6

The IL2Rα chain serves to capture IL2 at the cell surface to facilitate subsequent binding to the signaling part of the receptor, namely the IL2Rβγ chains. Resting cytotoxic lymphocytes, such as natural killer (NK) and CD8+ T cells, do not express appreciable IL2Rα at the cell surface and are thus not activated by low levels of IL2[1]. IL2Rα is expressed on this population after initial activation, however, and is required for maximum cytotoxic lymphocyte expansion[2]. High dose IL2 can induce the activation of all cytotoxic lymphocytes and is approved for treatment of several malignancies with an approximately 15% partial or complete tumor response[3-5]. Most patients do not benefit from such therapy due to activation of regulatory T cell ($T_{regs}$) and complications such as severe blood pressure alteration, generalized capillary leak, and end organ failure due to activation of vascular endothelium[6, 3, 7]. Both vascular endothelium and $T_{regs}$ express IL2Rα and are thus preferentially activated by IL2 over cytotoxic lymphocytes[8]. Lowering the IL2 dose can ameliorate side effects but also decreases efficacy. Mutant forms of IL2, such as those with substitutions of alanine for arginine at the 38 position (R38A) and/or lysine for phenylalanine at the 42 position (F42K), decrease the affinity of IL2 for IL2Rα and thus eliminate many side effects[9]. Such IL2a mutants may also decrease the efficacy of immunotherapy[2]. A form of IL2 that could preferentially activate cytotoxic lymphocytes in the absence of IL2Rα reactivity would be highly advantageous for clinical applications.

NKG2D recognizes MHC class-I-related stress ligands expressed by malignant or virally-transformed cells[10]. Of all the activating immunoreceptors NKG2D has the highest specificity for cytotoxic lymphocytes as it is constitutively expressed on both murine and human NK cells as well as activated CD8+ T cells[11]. Consequentially it has been argued that tumors and virally infected cells utilize shed NKG2D ligands as a mechanism of immune evasion[12, 13]. Orthopox major histocompatibility complex class I-like protein, or OMCP, is an NKG2D ligand decoy shed by monkeypox and cowpox virus infected cells. It is not expressed by small pox or vaccinia virus and thus not recognized by those immunized with small pox vaccine. As OMCP binds to both human and murine NKG2D with the highest affinity of any known ligand we thought it might function as an ideal targeting vector to optimally deliver IL2 to cytotoxic lymphocytes[14, 15]. Here we describe the construction and function of a fusion protein designed to deliver an IL2Rα mutant to NKG2D-expressing lymphocytes[15]. We demonstrate that this construct overcomes decreased efficacy associated with mutations in the IL2Rα binding region while retaining a favorable safety profile. Systemic administration of this fusion protein improves immunotherapy against both solid and liquid tumors. Targeted delivery of IL2 can thus be safely used to maximally activate NKG2D-expressing lymphocytes, such as NK cells, to optimize immunotherapy without systemic side effects.

Example 1. NKG2D-Targeted Delivery of an IL2 Mutant Preferentially Activates Cytotoxic Lymphocytes In Vitro To overcome the preferential activation of IL2Rα-expressing cells, we designed an IL2 fusion protein that would target cytotoxic lymphocytes directly via the NKG2D receptor. This fusion protein combines the high affinity NKG2D ligand OMCP with an IL2 mutated to reduce IL2Rα reactivity. Our construct, termed OMCP-mutIL2, consists of the 152 residue OMCP protein fused to the N-terminus of the 133 amino acid R38A/F42K mutant form of human IL2 (mutIL2) via a flexible 30 residue linker (FIG. 1A-B). The construct was first assessed for its in vitro binding ability. Binding of fluorescently labeled construct was tested in vitro at 37° C. in bulk splenocytes. FIG. 17 shows that the construct appears to only bind to NK cells which express NKG2D. The construct does not show binding to CD4+ CD3+ T cells, CD8+ CD3+ T cells, CD11C+CD11b− DCs, CD11c−CD11b+ Macs or CD19+CD3− B cells.

Figure 1A:
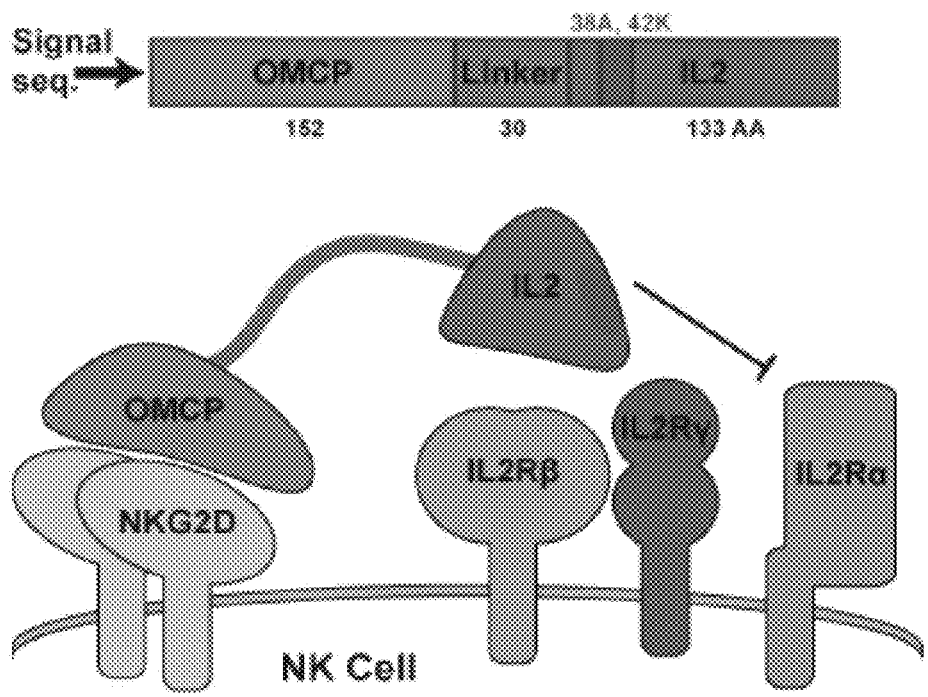
Figure 1B:
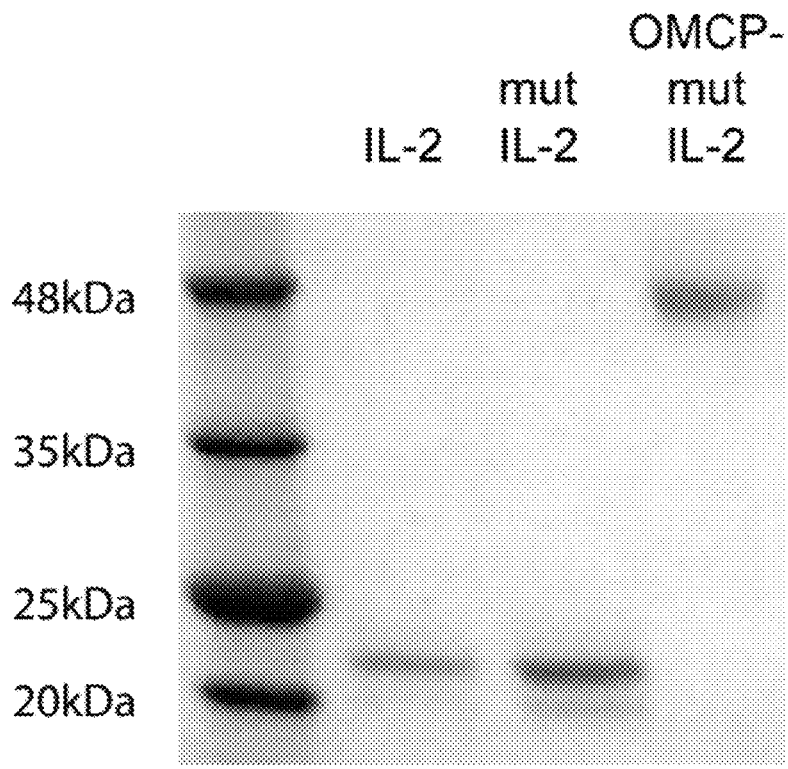
Figure 1C:
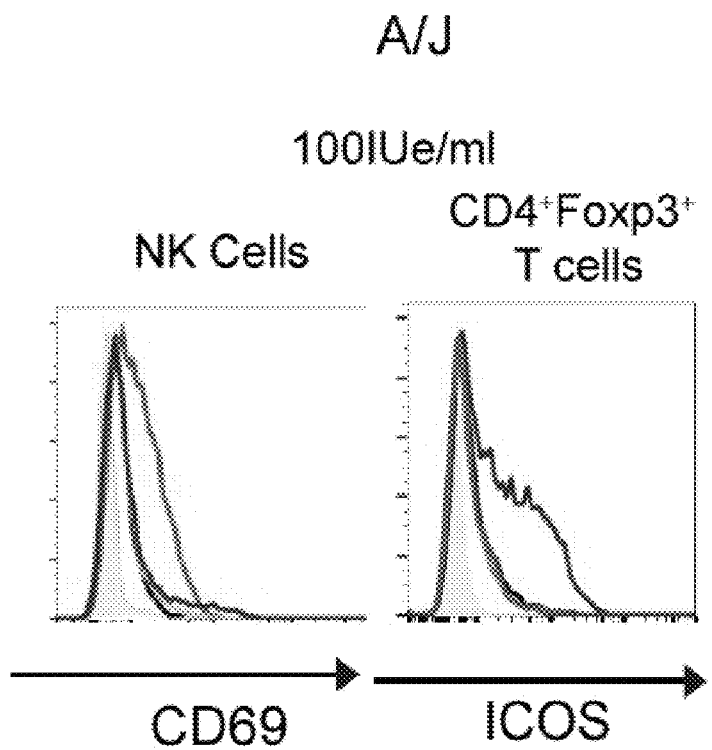
Figure 1D:
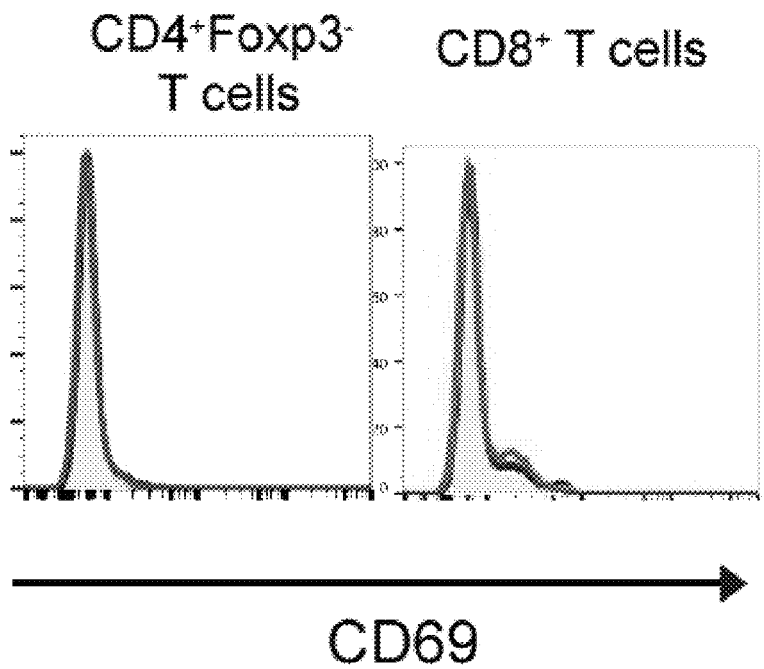
Figure 1E:
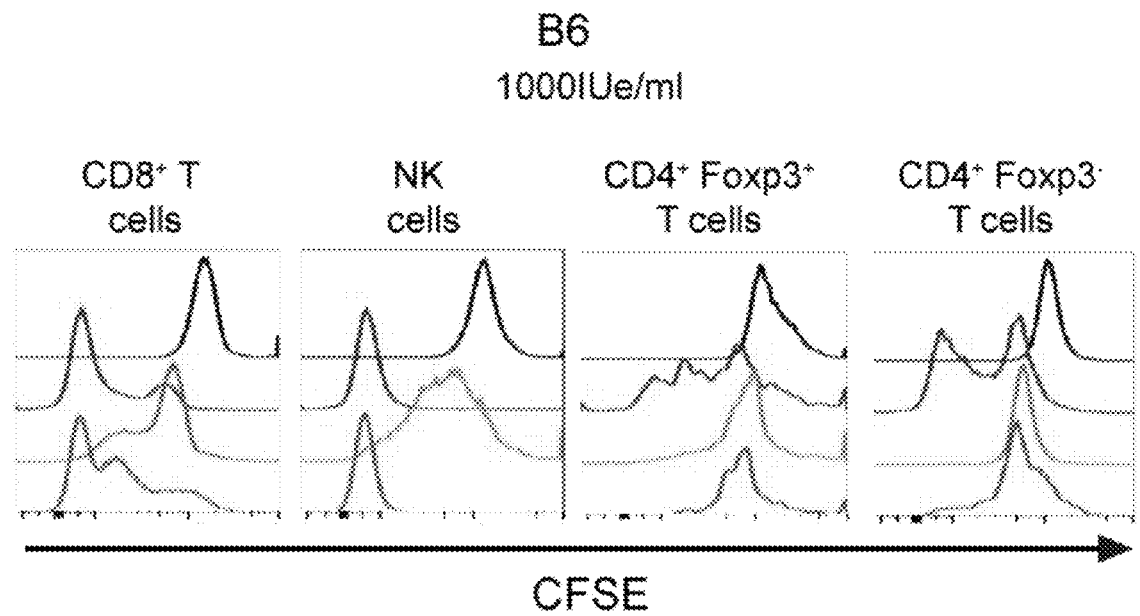
Figure 1F:
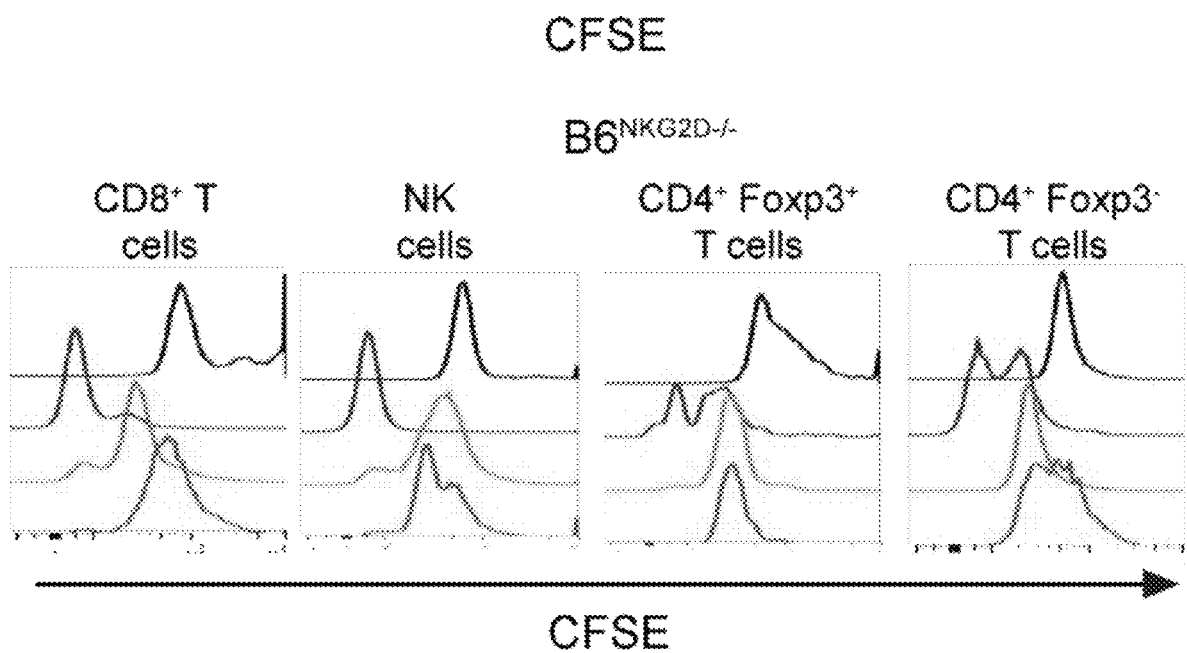
Figure 6:
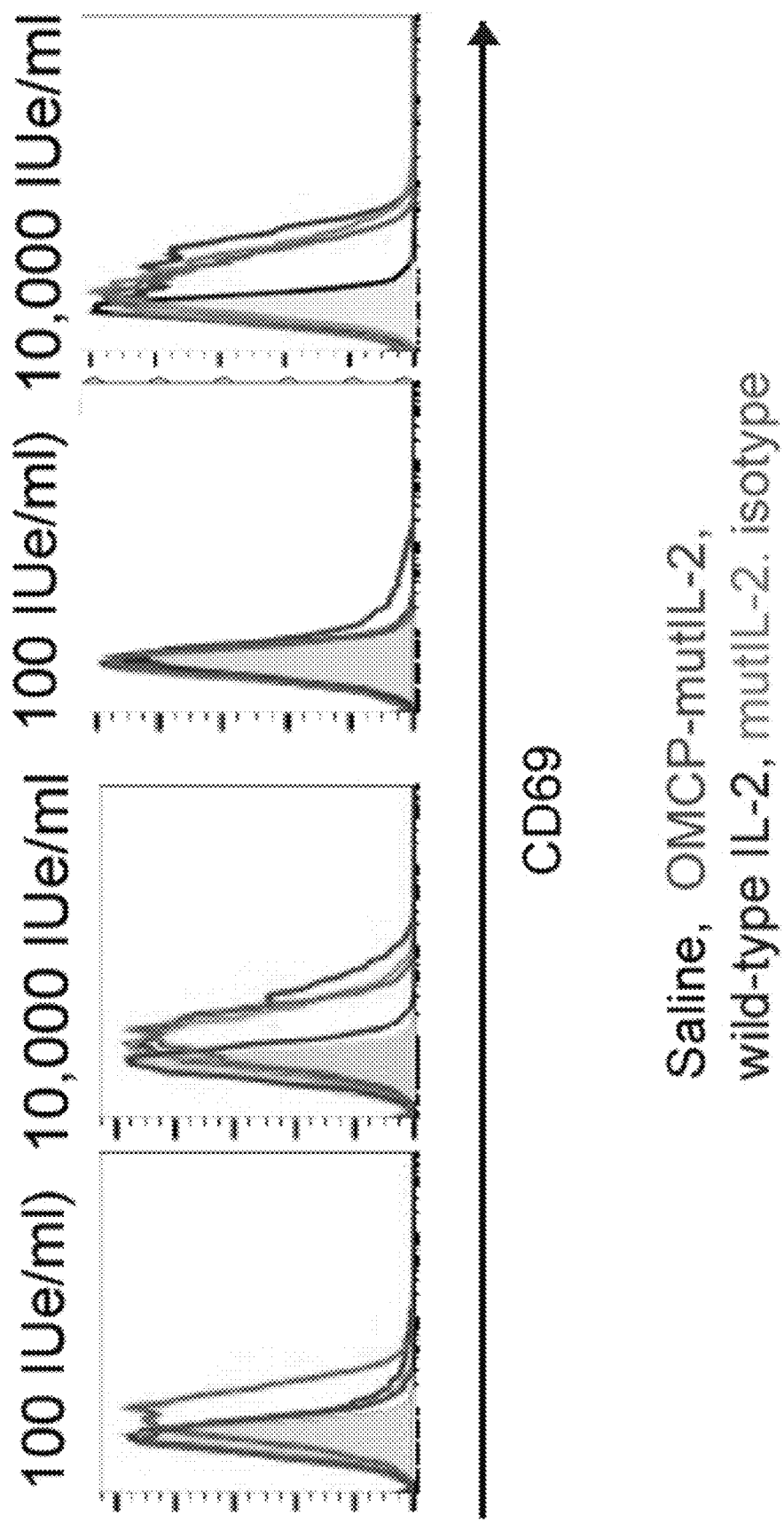

We have previously demonstrated strain-specific differences in murine NK cell cytotoxicity and lung cancer immunosurveillance[16] (and Example 7). Therefore, we set out to examine the efficacy of OMCP-mut-IL2 in activation of NK cells from two different strains of mice, namely A/J and B6 with poor and robust NK function, respectively. Compared to wild-type IL2 (wtIL2) or mutIL2, OMCP-mutIL2 strongly upregulated CD69 on NK cells of both strains after 36-hour co-culture with 100 IUe/ml of cytokine (FIG. 1C, left; FIG. 6, left two graphs)[16, 17]. At high concentrations a similar increase in CD69 expression was observed with OMCP-mut-IL2, wtIL2 or mutIL2 (FIG. 6). Activation of CD4+Foxp3+ $T_{regs}$, as measured by upregulation of ICOS, was evident with wtIL2 only, but not with mutIL2 or OMCP-mutIL2 (FIG. 1C-D). CD8+ and CD4+ Foxp3− effector T cells, on the other hand, demonstrated no upregulation of CD69 after 36 hours, even at highest doses of cytokines (FIG. 1C-D and data not shown). Longer exposure over a period of five days led to proliferation of both NK and CD8+ T cells exposed to wtIL2 and OMCP-mutIL2 (FIG. 1E-F). Importantly, OMCP-mutIL2 activated CD8+ T cells and NK cells equivalently to mutIL2 in NKG2D−/− splenocytes, indicating that the increased activation was due to the effect of OMCP targeting upon NKG2D-bearing cells (FIG. 1F; FIG. 6, right two graphs). Only incubation with wtIL2 led to CD4+Foxp3+ $T_{regs}$ and CD4+Foxp3− effector cell proliferation (FIG. 1E-F). Thus exposure to OMCP-mutIL2 results in preferential NK activation that is superior or equivalent to wtIL2 in a dose-dependent manner. CD8+ T cells can also be activated but require prolonged exposure to higher doses of OMCP-mutIL2.

Example 2. Low-Dose Cytokine Therapy Offers a Favorable Safety Profile

Figure 2A:
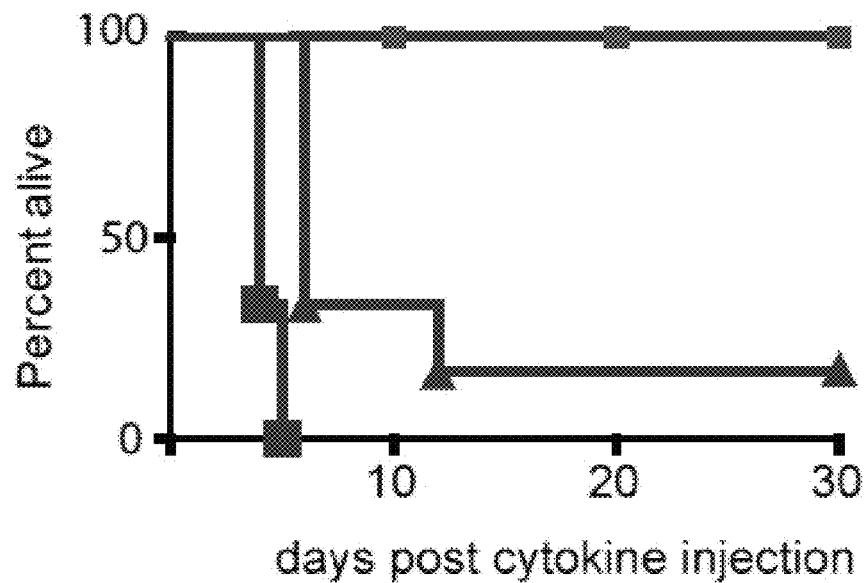
Figure 2B:
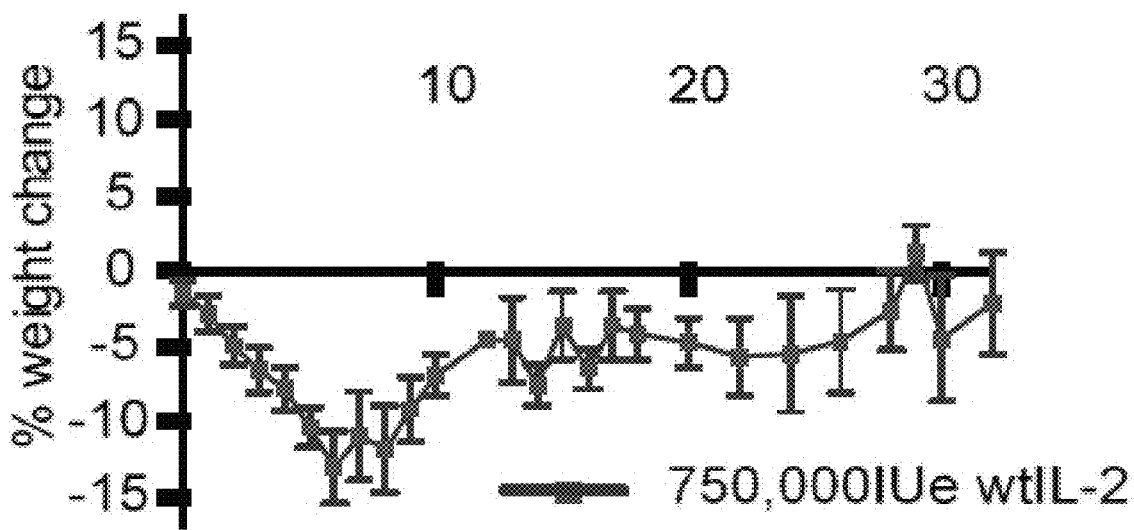
Figure 2C:
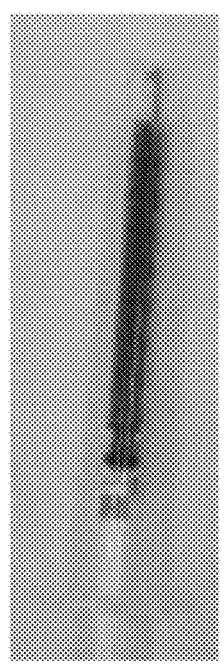
Figure 2D:
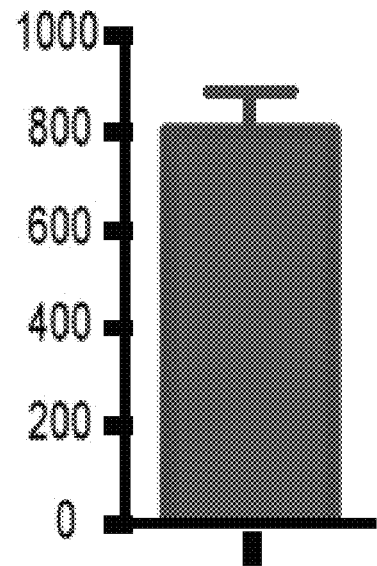
Figure 2E:
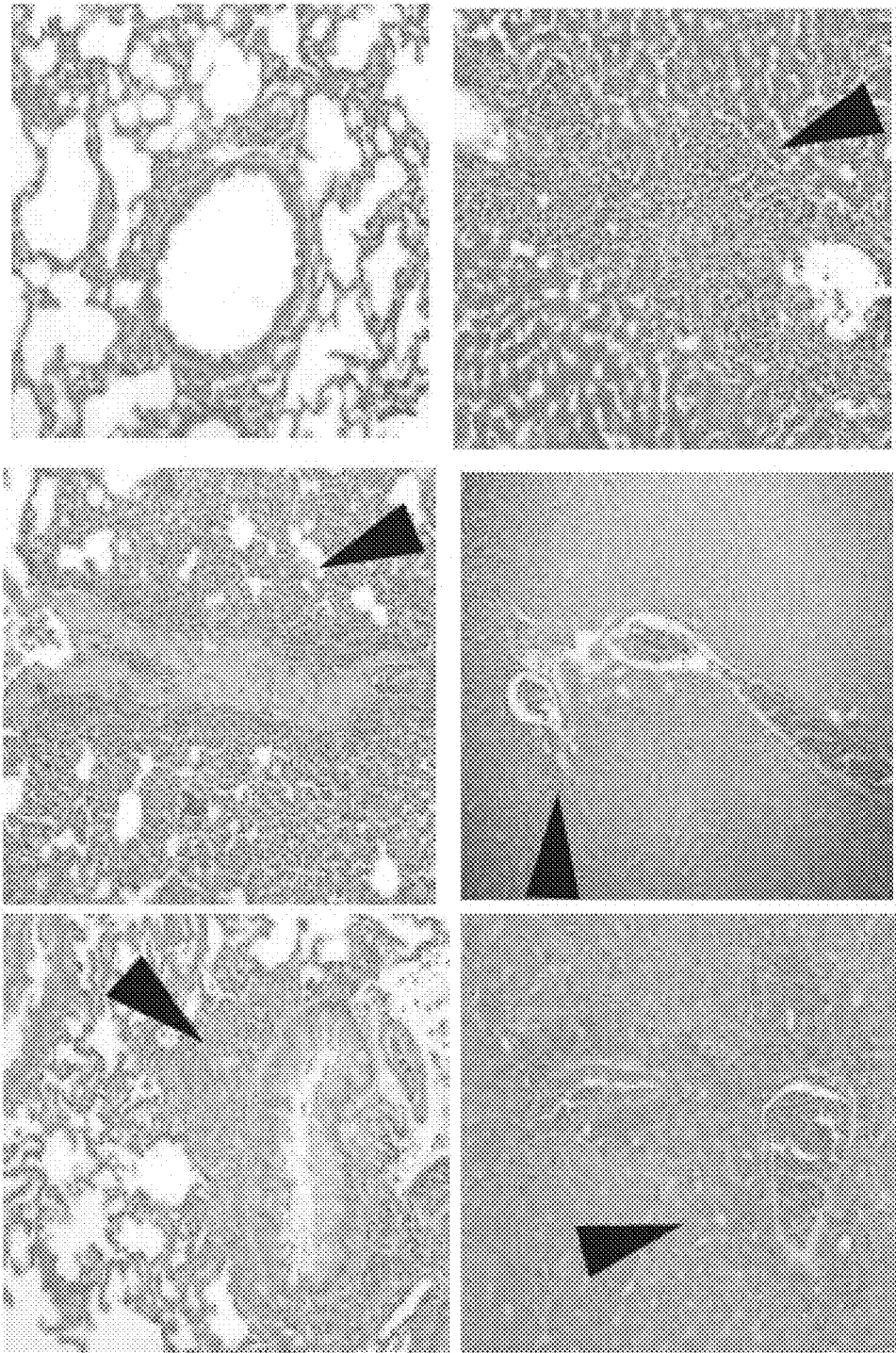
Figure 2F:
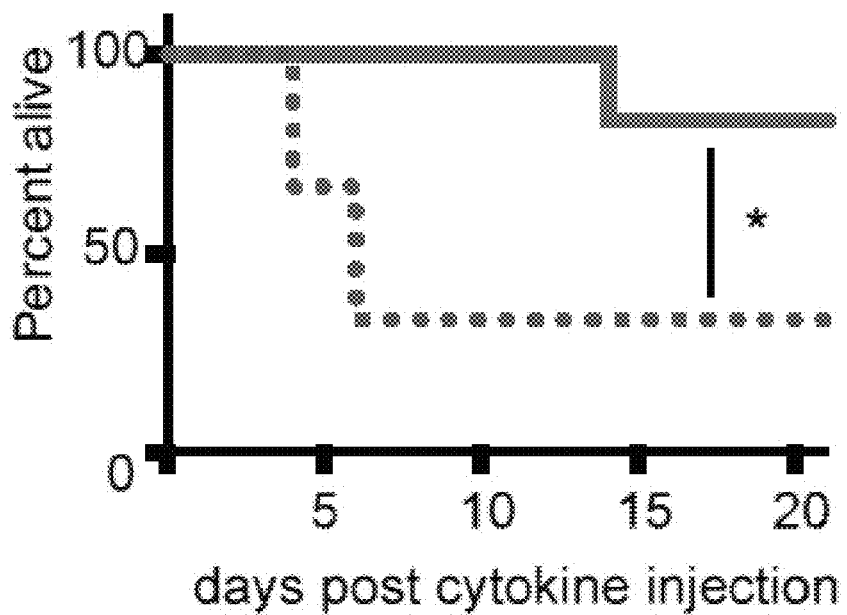
Figure 2G:
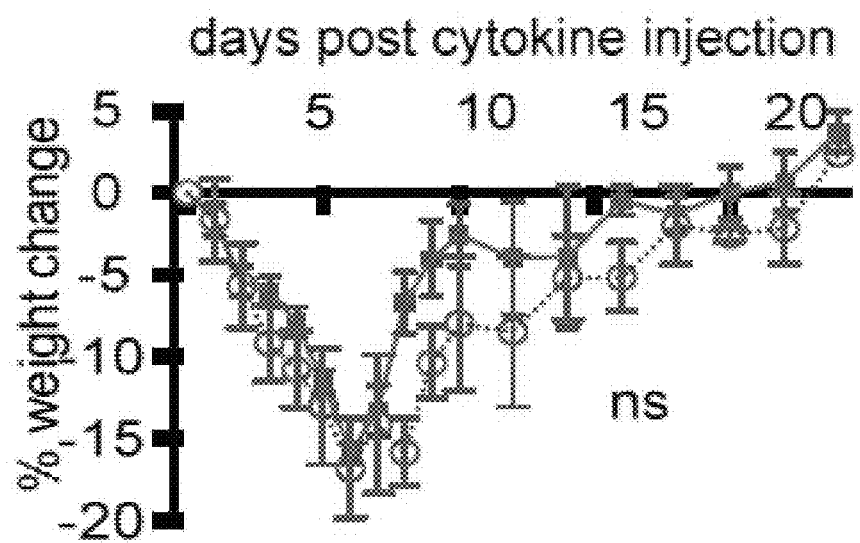
Figure 2H:
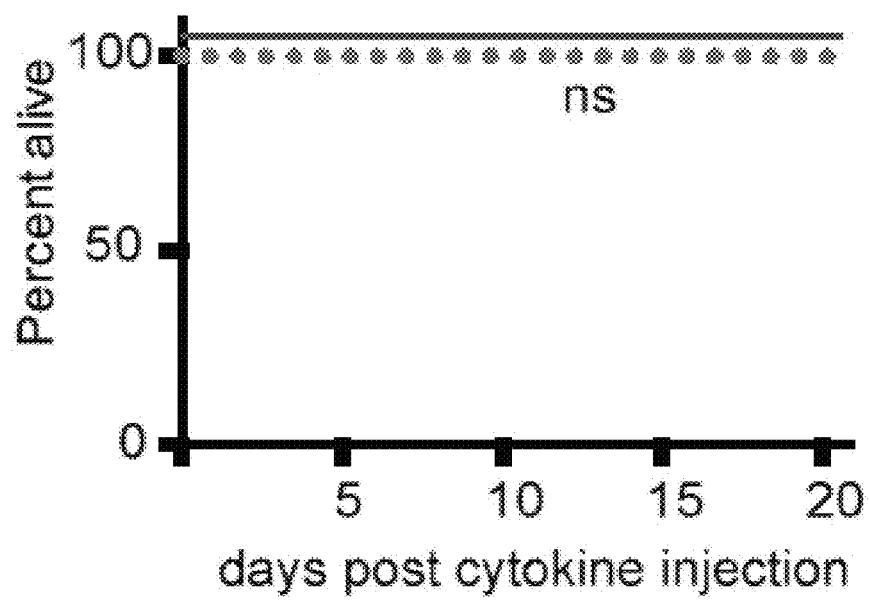
Figure 2I:
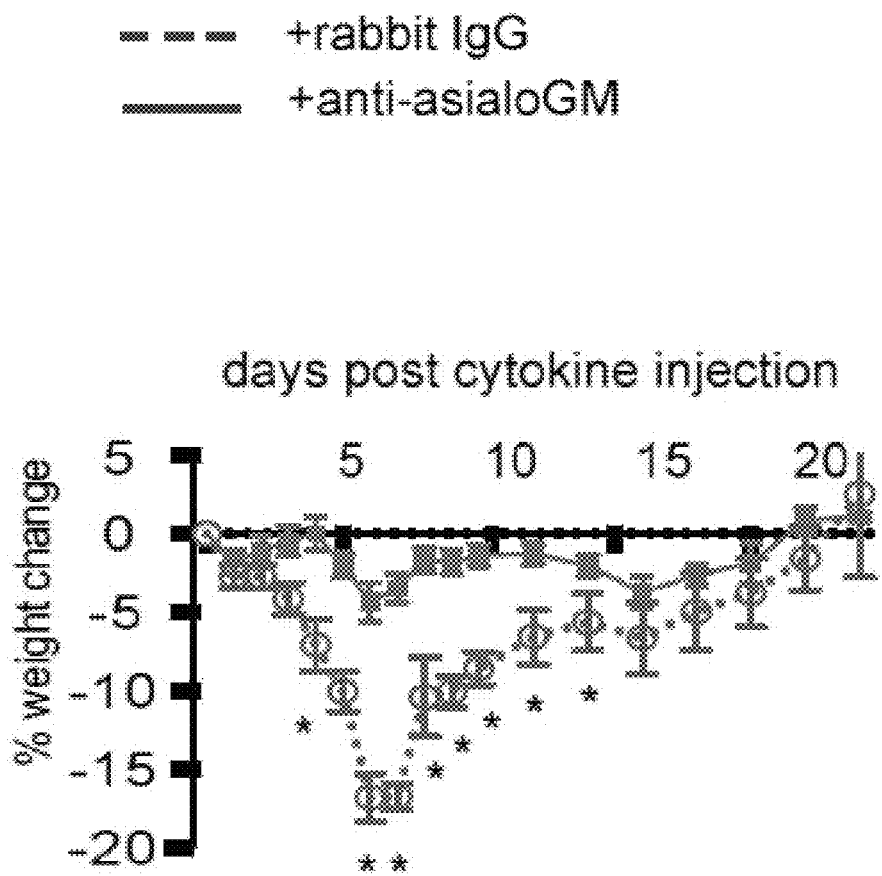
Figure 2J:
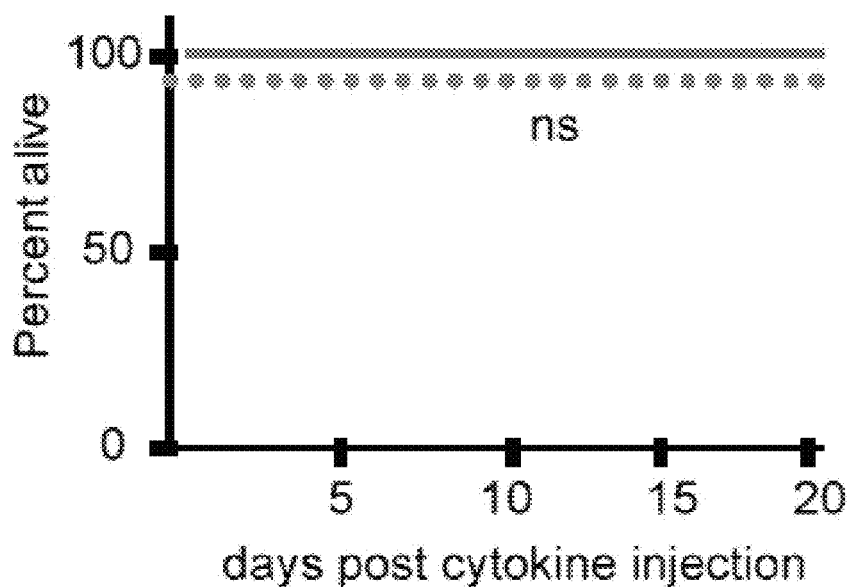
Figure 2K:
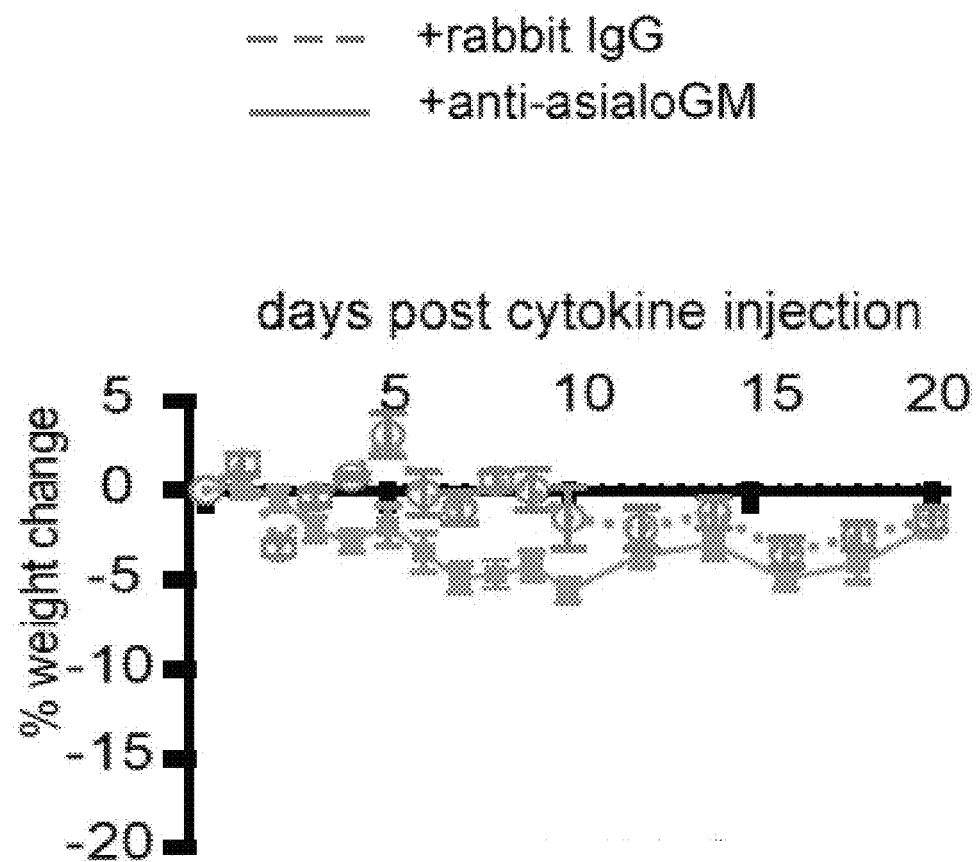
Figure 2L:
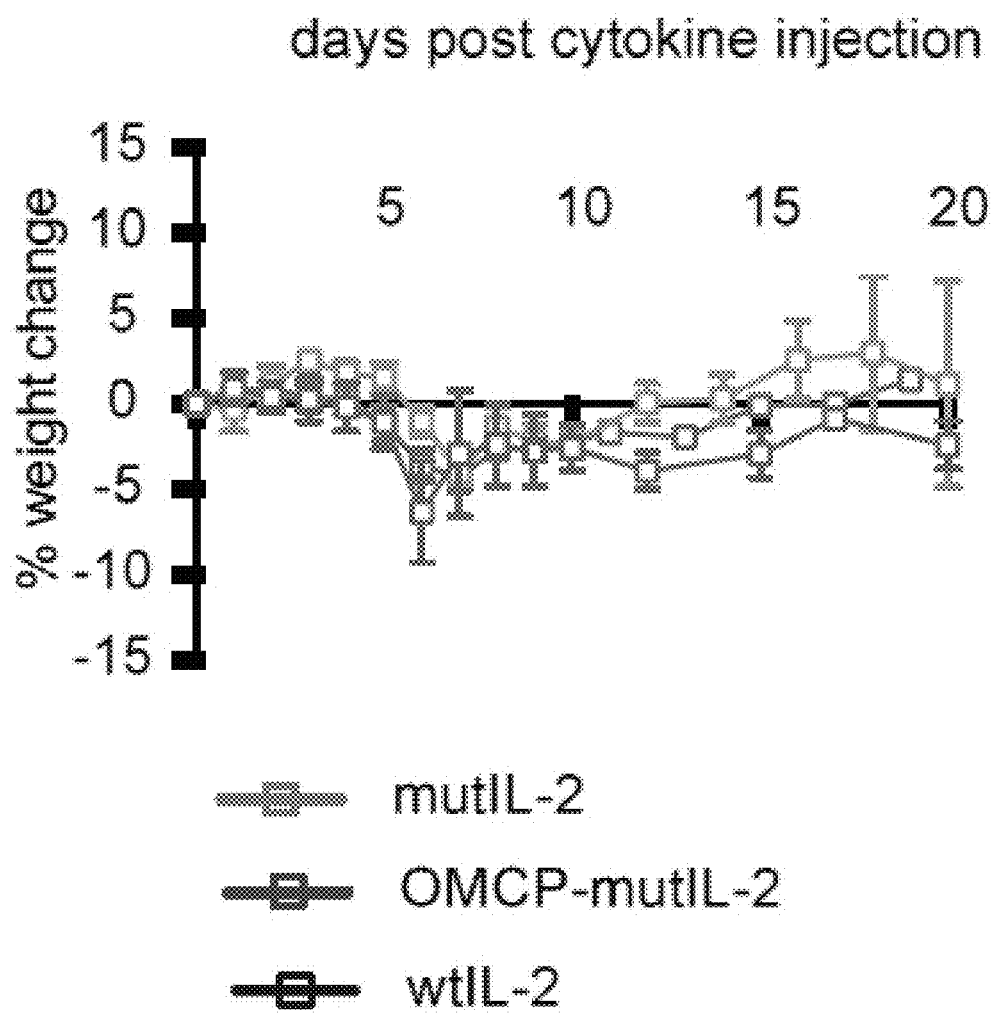
Figure 2M:
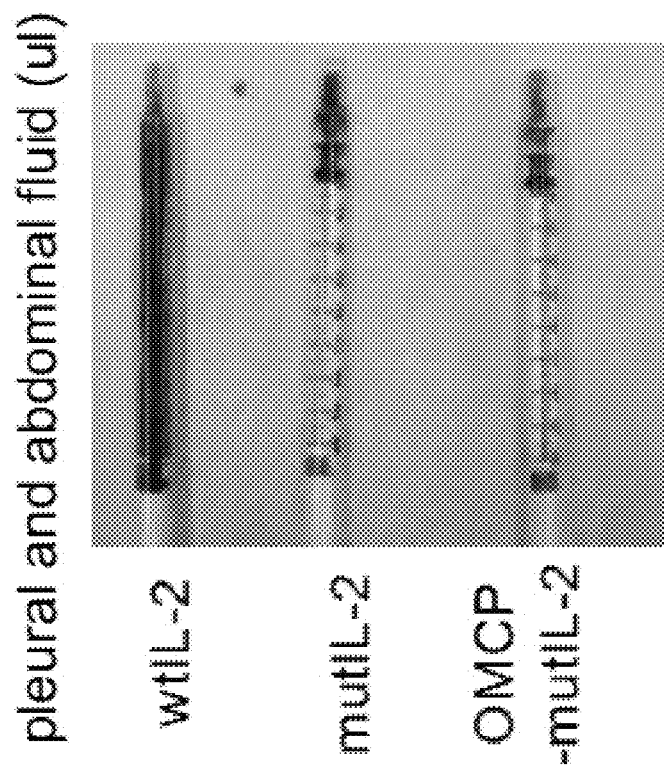
Figure 2N:
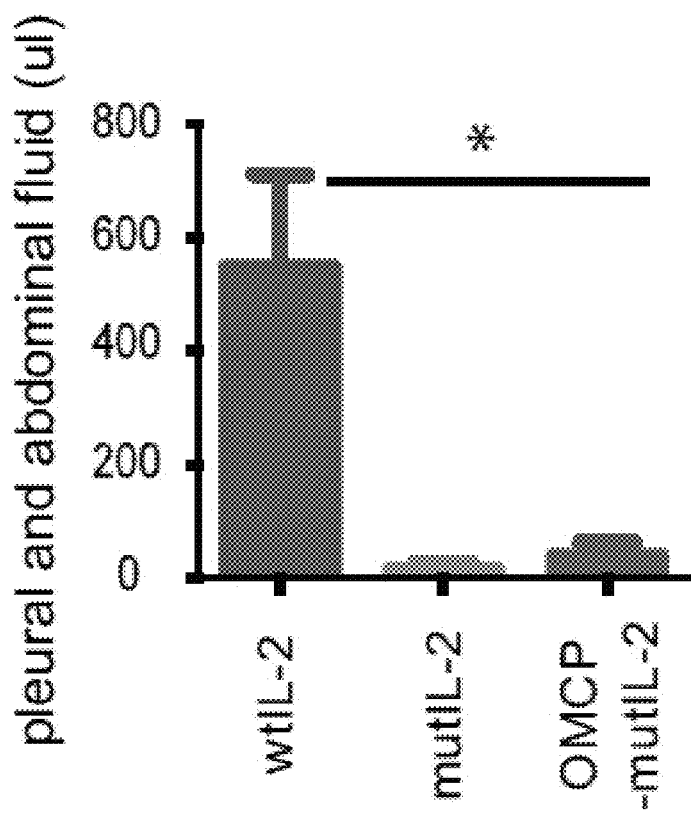
Figure 20:
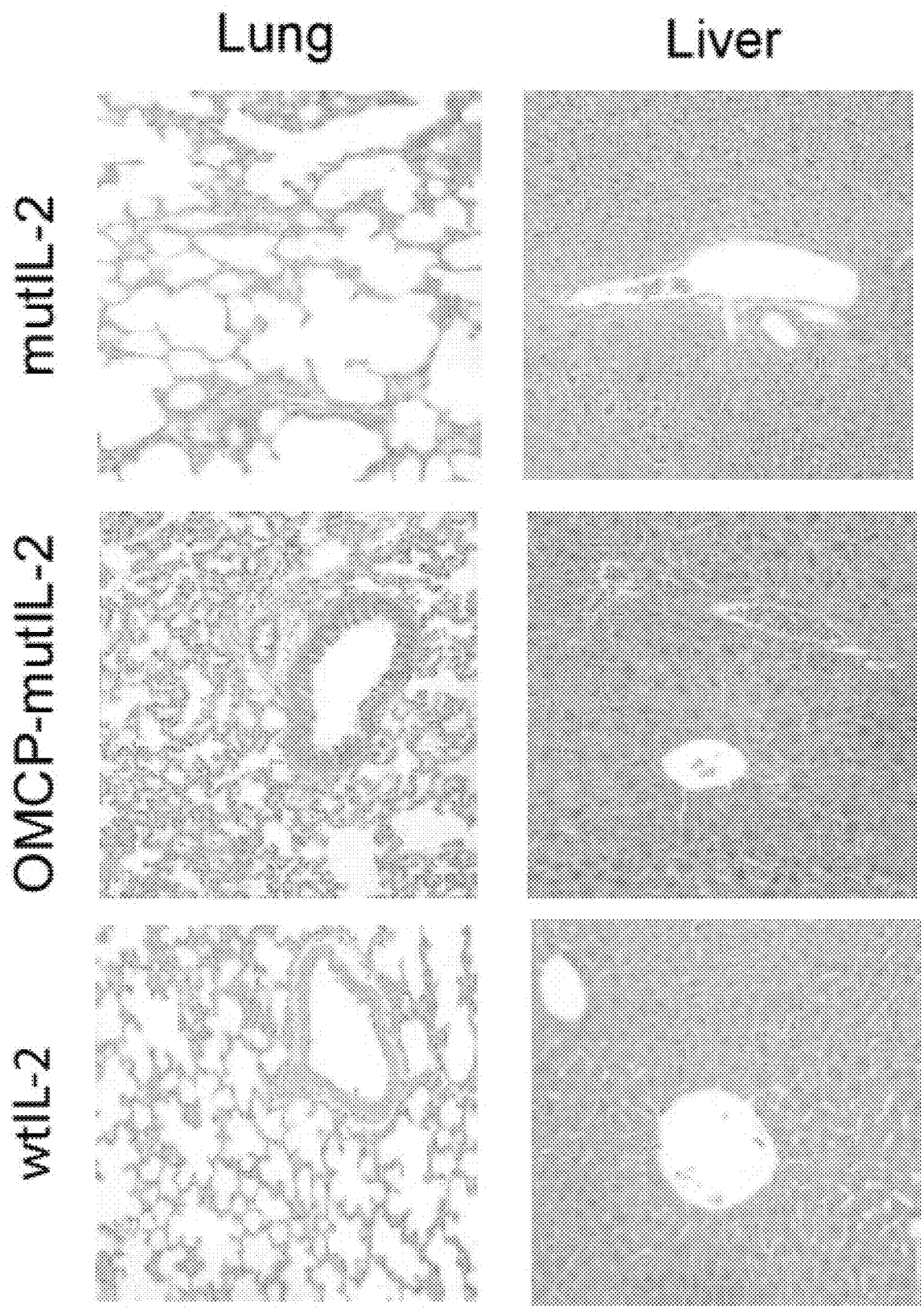
Figures 7A, 7B, 7C:
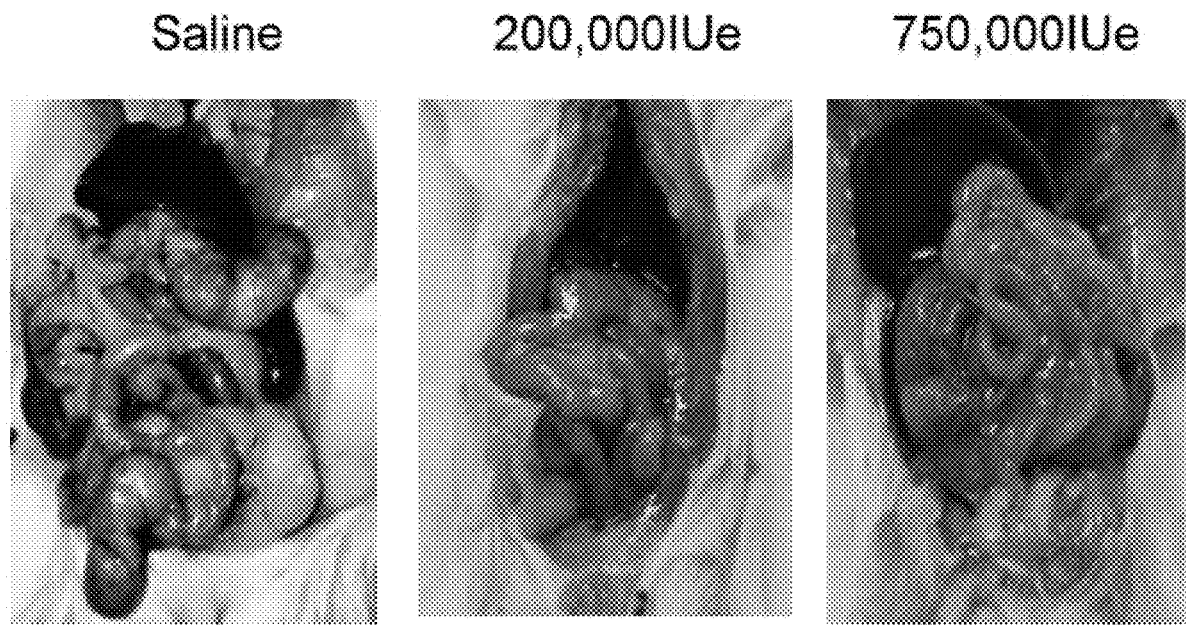
Figure 7D:
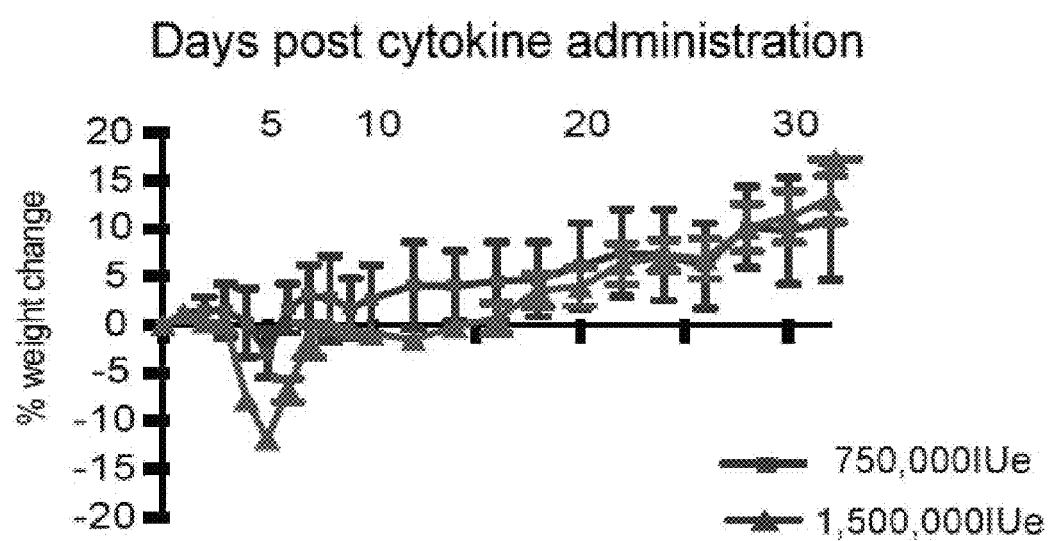

Dose-dependent toxicity can limit cytokine administration in vivo. To model human immunotherapy protocols we next treated NJ mice with wtIL2 given as ten doses over a five day cycle[18]. While A/J mice tolerated 750,000 IUe of wtIL2, significant mortality was evident at higher doses (FIG. 2A-B). Even after a 750,000 IUe dose mice demonstrated extreme distress, weight loss, decreased food consumption, ascites and hepatic inflammation (FIG. 2A-E; FIG. 7A-C). These side-effects mirror the capillary leak and distress associated with high dose IL2 therapy in humans[7]. Treatment with anti-Asialo-GM1 ameliorated mortality, but not weight loss, induced by high dose wtIL2 (1,500,000 IUe) in A/J mice, confirming that side effects of such therapy can occur independent of NK cells (FIG. 2F-K). Unlike the case for wtIL2 no animal death was evident after 1,500,000 IUe of OMCP-mutIL2 or mutIL2 in the presence or absence of NK cells. Animal weight loss after 1,500,000 IUe of OMCP-mutIL2 occurred only in NK-sufficient mice suggesting that toxicity of our construct was solely due to immunoactivation (FIG. 2F-K). A regimen of 200,000 IUe was well tolerated in A/J mice with minimal weight loss, distress, or organ inflammation for all cytokines (FIG. 2L-O). Capillary leak, however, was still evident by accumulation of pleural effusion and ascites after wtIL2, but not OMCP-mutIL2 or mutIL2, at this dose. B6 mice were able to tolerate higher doses of wtIL2 but still suffered significant morbidity over 750,000 IUe (FIG. 7D).

Example 3. OMCP-mutIL2 Preferentially Expands and Activates NK Cells In Vivo Compared to wtIL2 or mutIL2

Figure 3A:
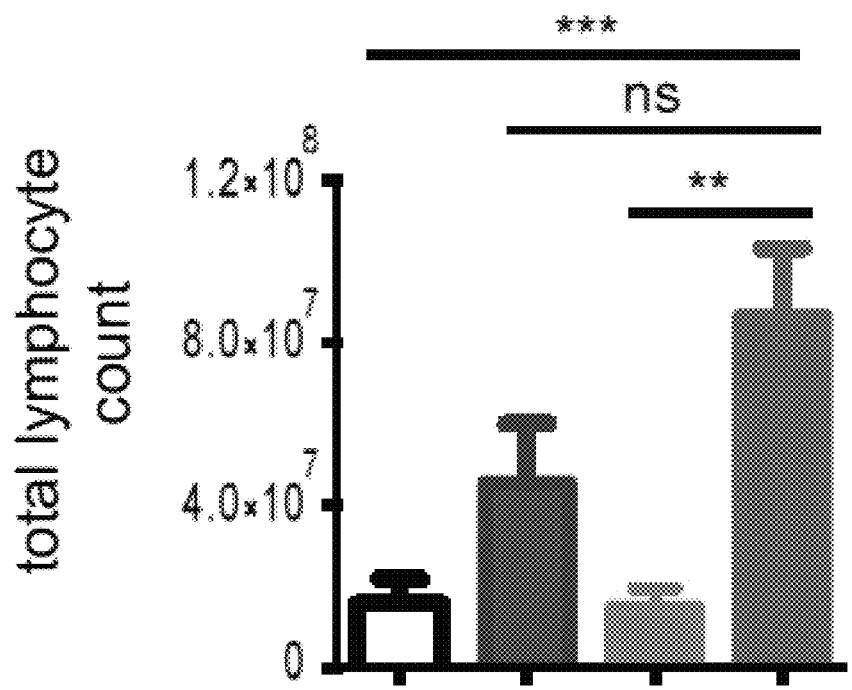
Figure 3B:
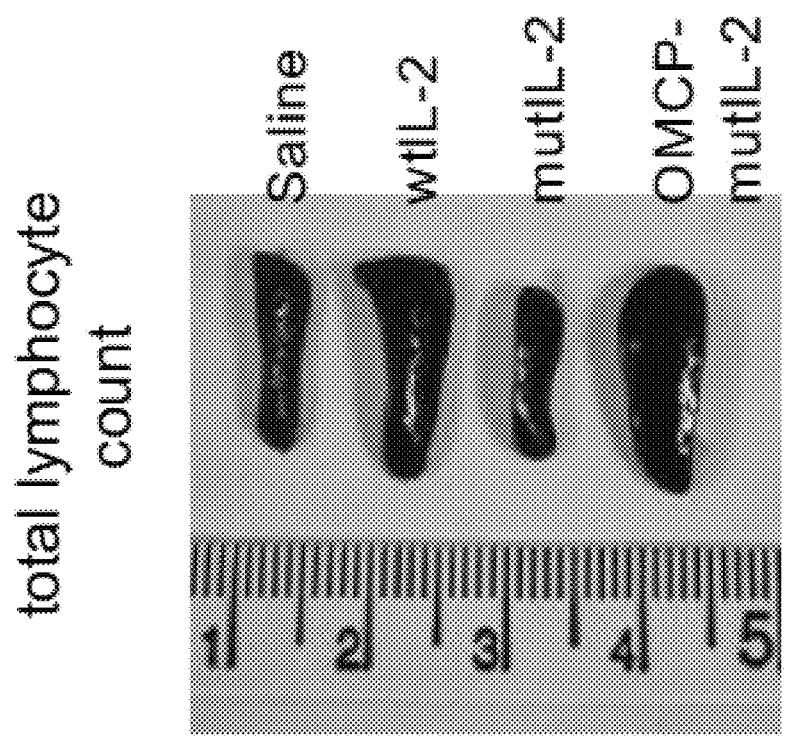
Figure 3C:
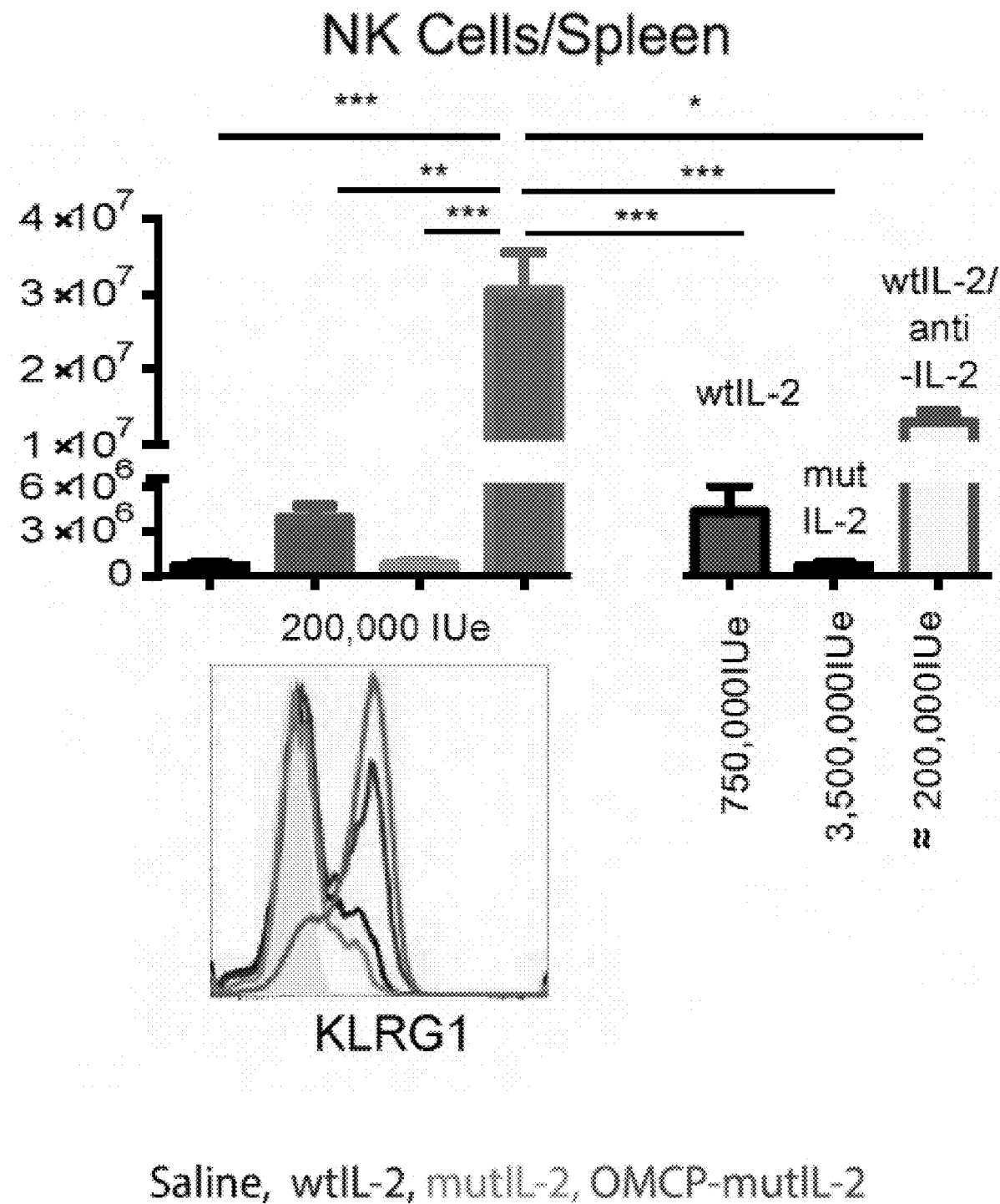
Figure 3D:
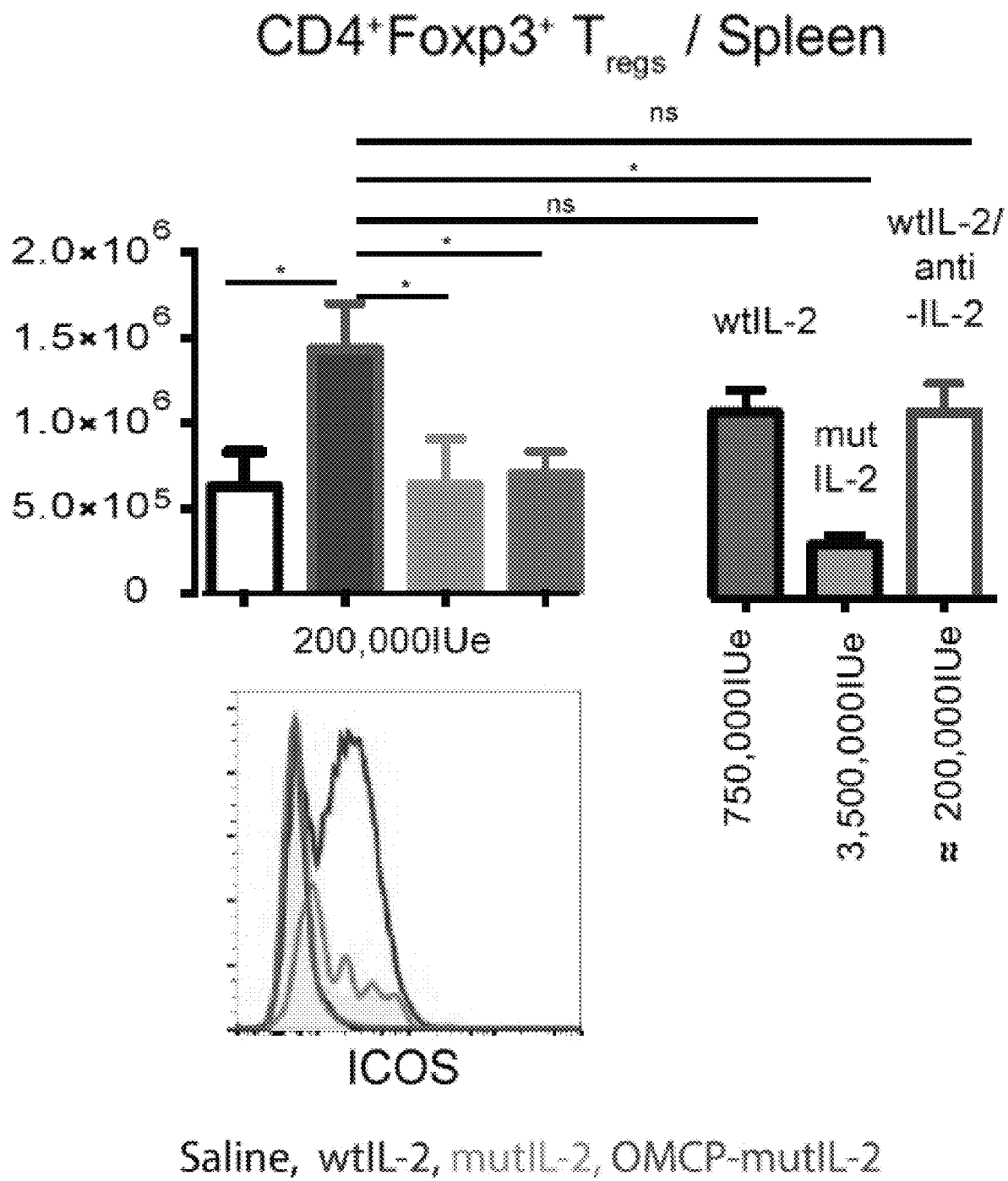
Figure 3E:
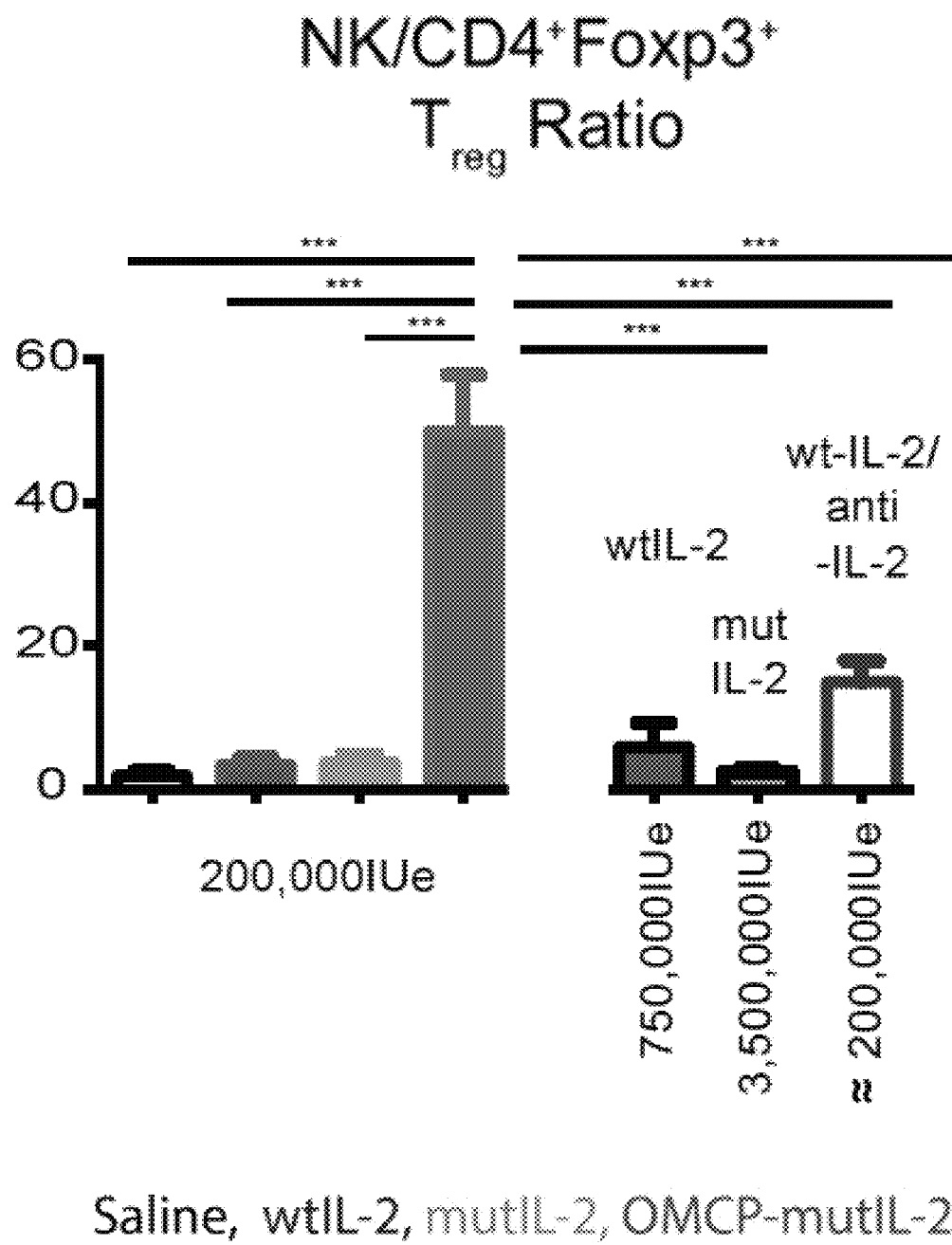
Figure 8A:
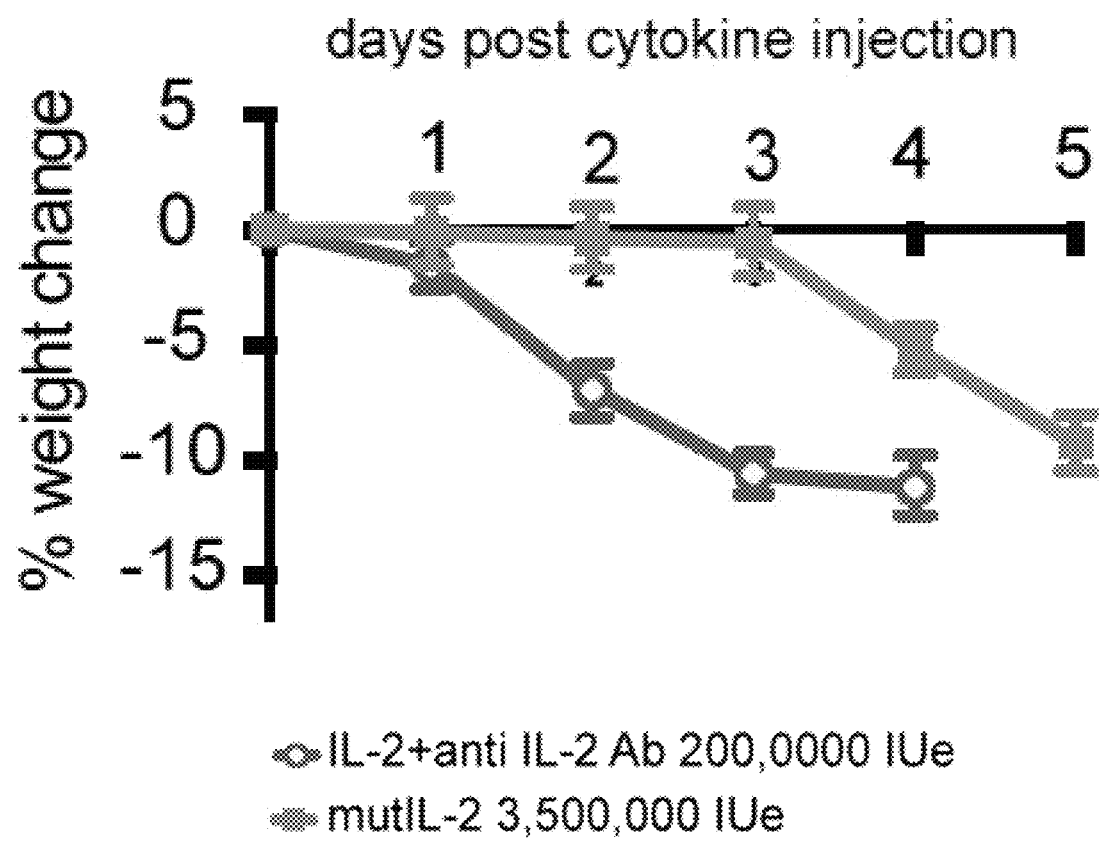
Figure 8B:
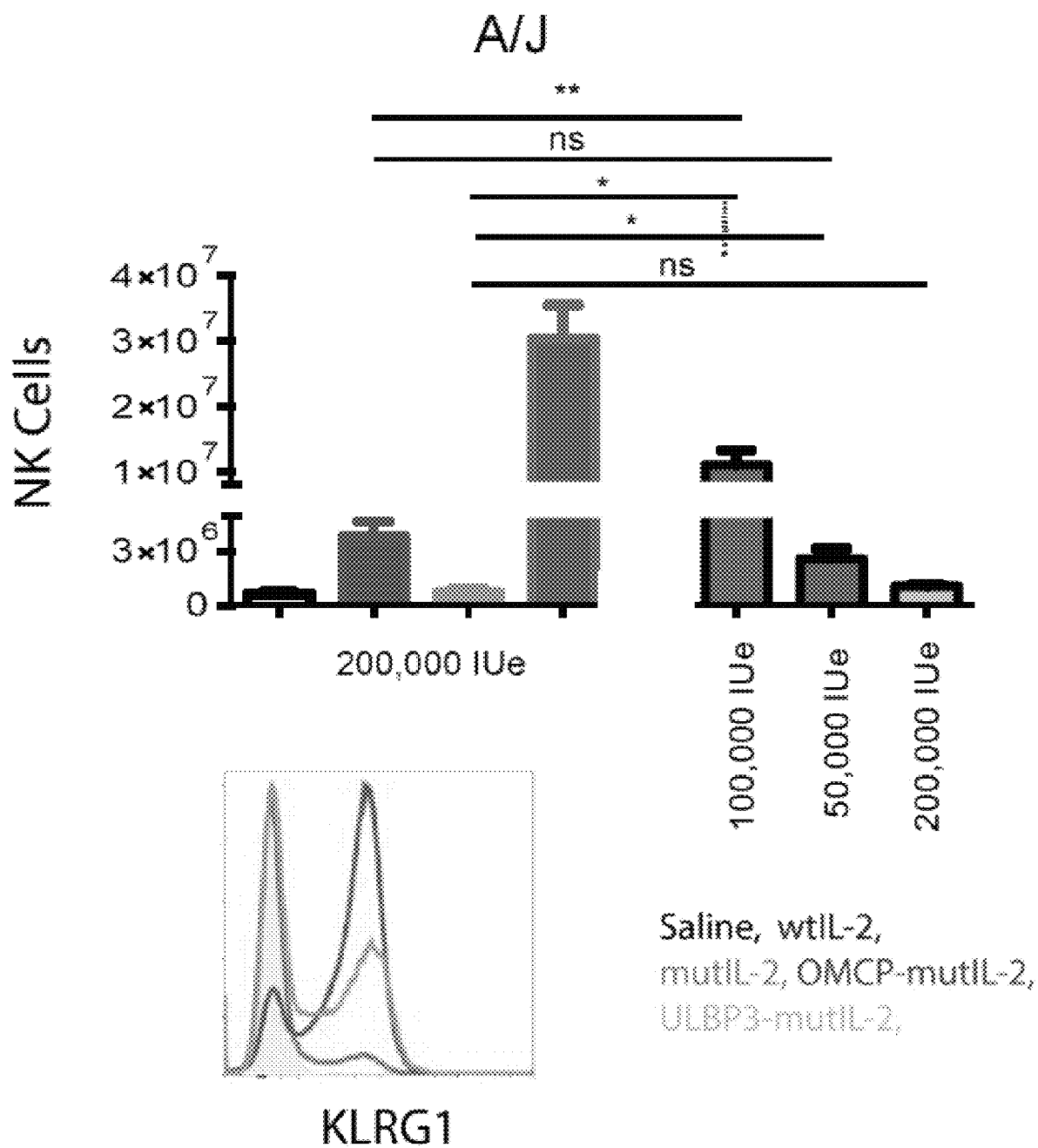
Figure 8C:
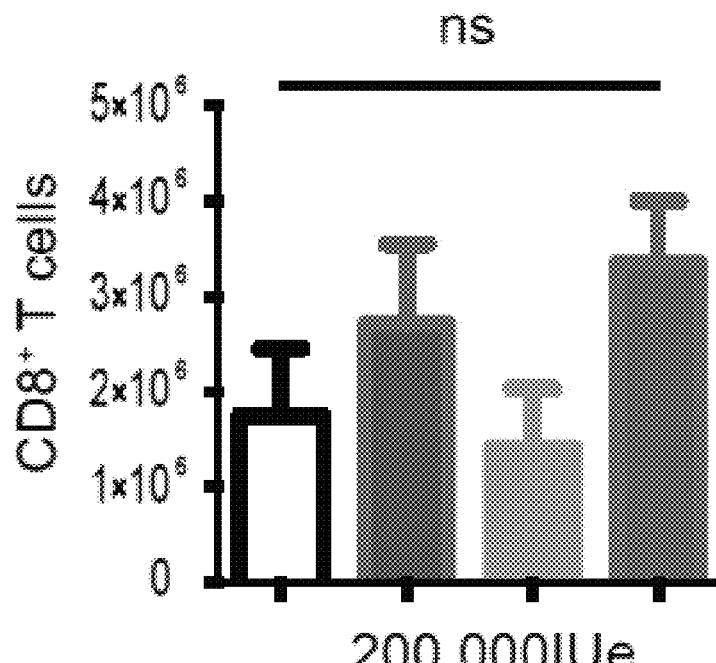
Figure 8D:
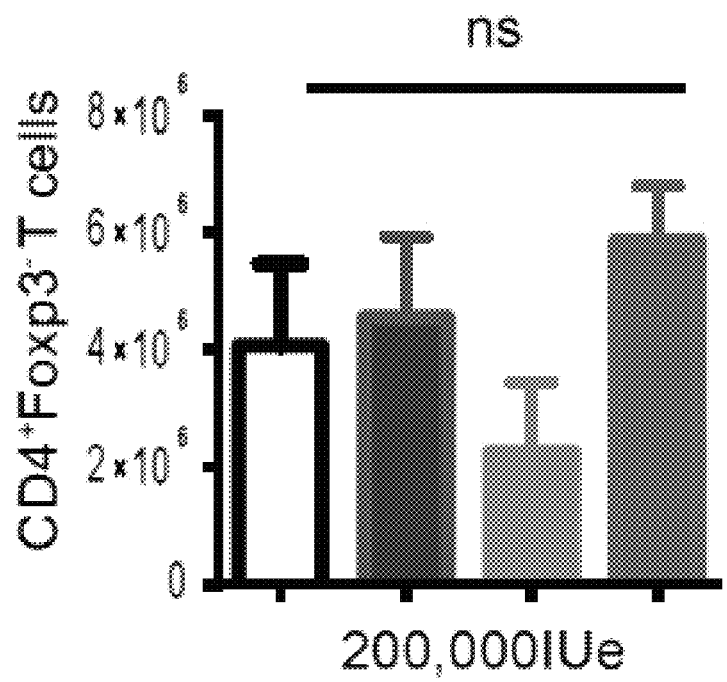
Figure 8E:
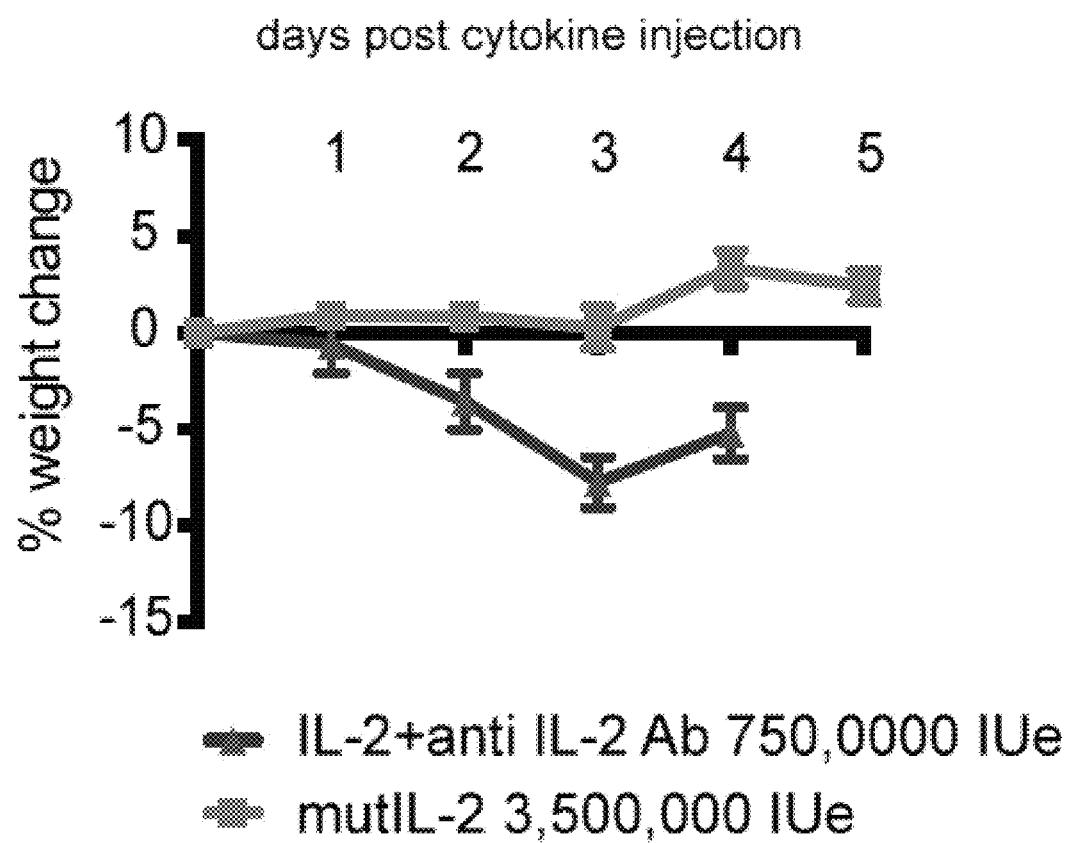

To evaluate immunologic changes associated with cytokine treatment, NJ mice received 200,000 IUe of cytokine or construct given as ten equal doses over five days. Splenic lymphocytes were evaluated flow cytometrically on day six. Both wtIL2 and OMCP-mutIL2 increased lymphocyte content and splenic size over saline-treated controls (FIG. 3A-B). OMCP-mutIL2 led to a substantial expansion and activation of NK cells measured by cellularity and surface KLRG1 levels (FIG. 3C). In OMCP-mutIL2 treated mice NK cells comprised close to half of all splenic lymphocytes, paralleling or even surpassing the total lymphocyte counts of saline or mutIL2-treated mice (FIG. 3A vs. FIG. 3C). NK expansion by 200,000 IUe of OMCP-mutIL2 was superior to near toxic doses of wtIL2 (750,000 IU), high dose mutIL2 (3,500,000 IUe), or wtIL2 complexed to anti-IL2 antibody (clone MA6602)[19] (FIG. 3C). In fact, the majority of mice could not tolerate the full 200,000 IUe of wtIL2/anti-IL2 antibody and injections had to be terminated at 160,000 or 180,000 IUe with requisite animal sacrifice due to animal distress and rapid weight loss (FIG. 8A). WtIL2 led to a significant expansion of CD4+Foxp3+ $T_{regs}$, specifically the ICOS+ subset[6] in NJ mice even when complexed to anti-IL2 antibodies (FIG. 3D). Importantly the NK/$T_{reg}$ ratio, which has been described as a predictive factor for success of immunotherapy[20], was dramatically increased in OMCP-mutIL2 treated mice compared to all other treatment conditions (FIG. 3E). Superior expansion of NK cells by OMCP-mutIL2 was even possible at doses 2-fold lower than wtIL2 (FIG. 8B). However, targeting NKG2D with a ~500-fold lower affinity NKG2D ligand, ULBP3, ameliorated efficacy of the fusion construct for expansion but still offered superior NK activation compared to mutIL2 alone (FIG. 8B). No statistically significant increase in CD4+Foxp3− or CD8+ T lymphocytes was evident after wtIL2 or OMCP-mutIL2 treatment, although a trend for CD8+ T cell expansion was evident (FIG. 8C-D). Such data is consistent with the prevalence of naïve T lymphocytes, expressing low levels of IL2 receptors and NKG2D in specific pathogen-free mice.

Figure 3F:
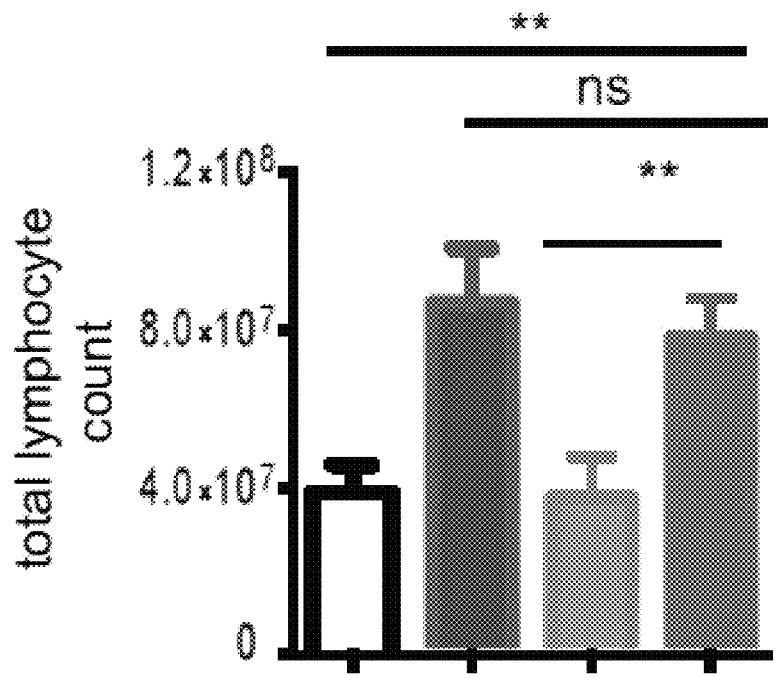
Figure 3G:
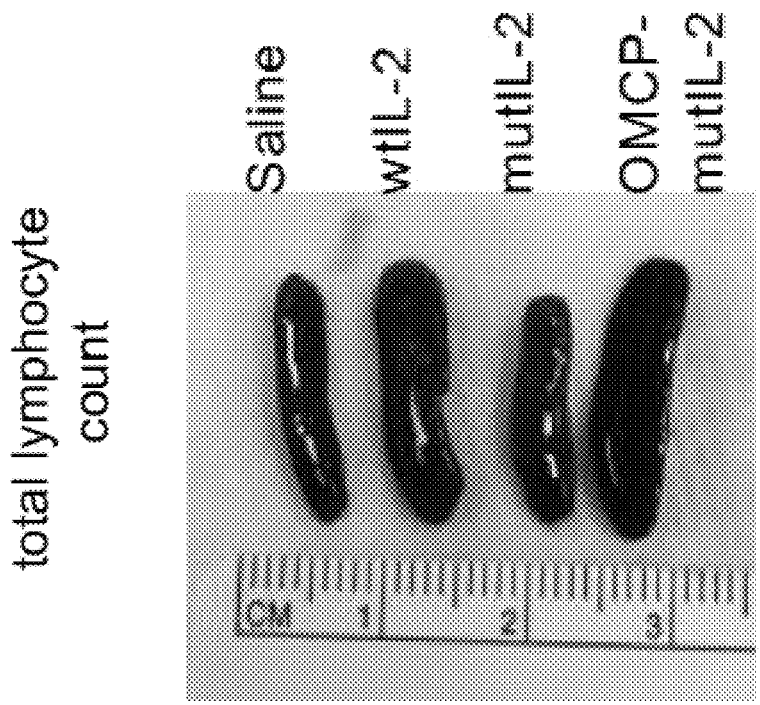
Figure 3H:
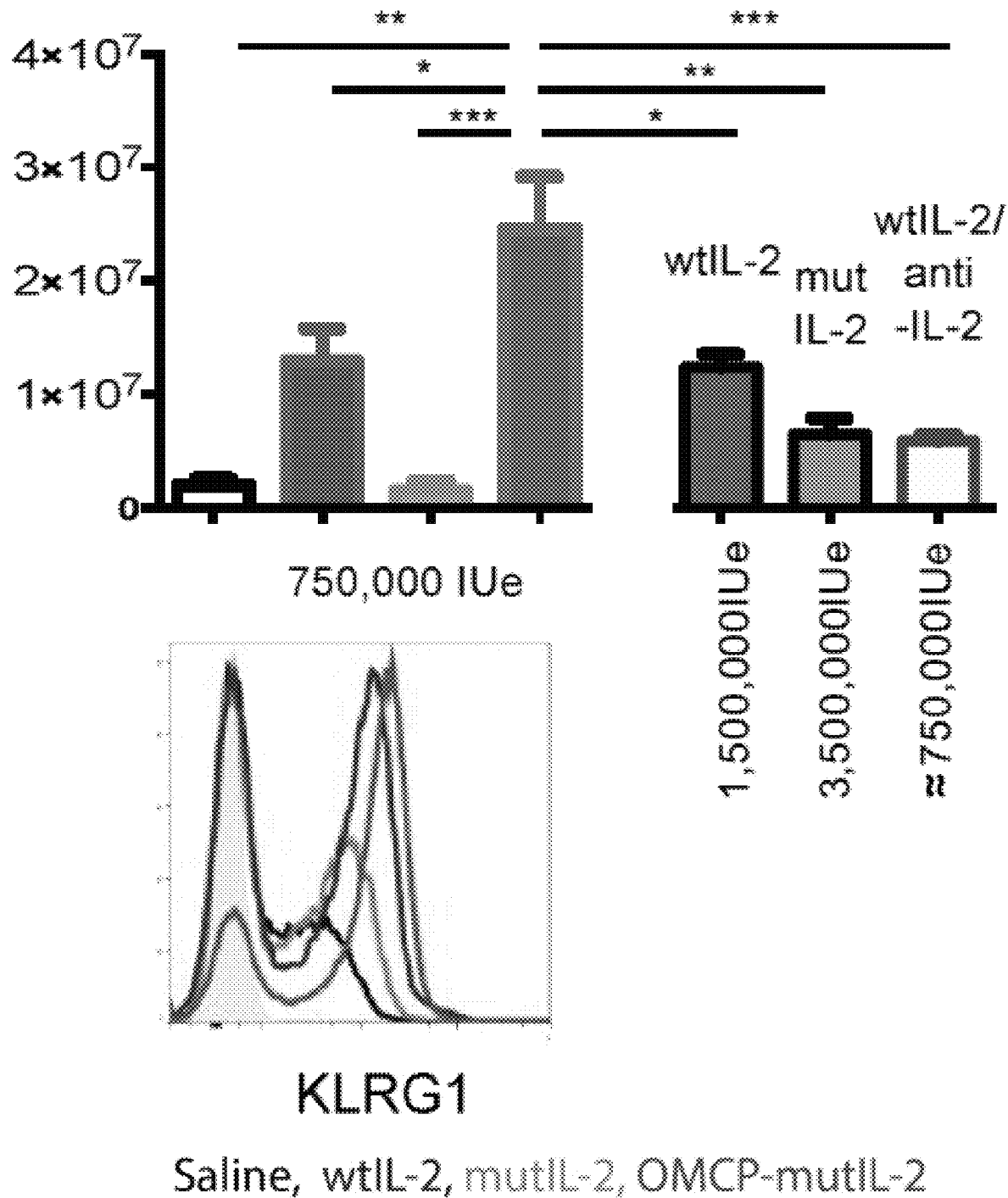
Figure 3I:
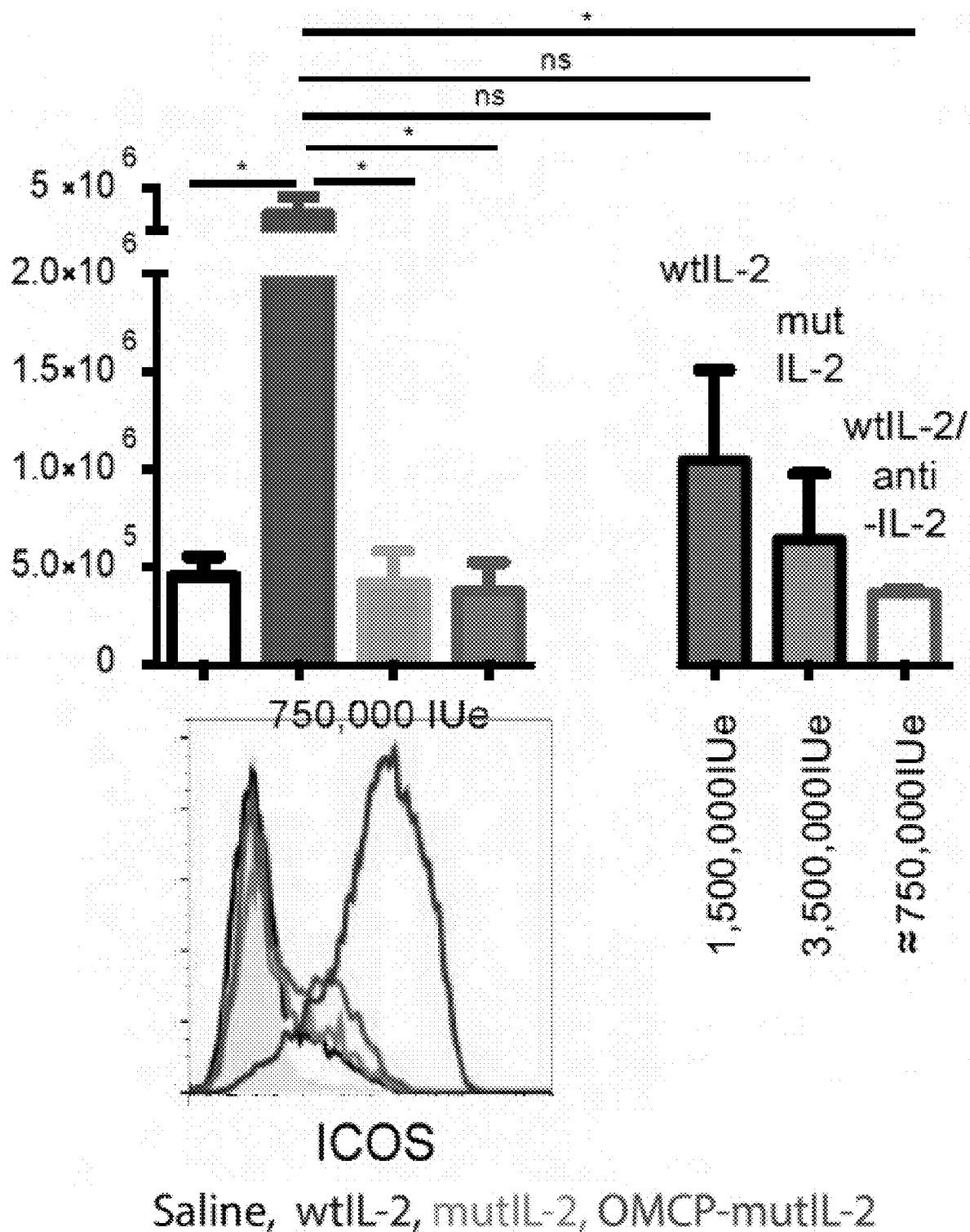
Figure 3J:
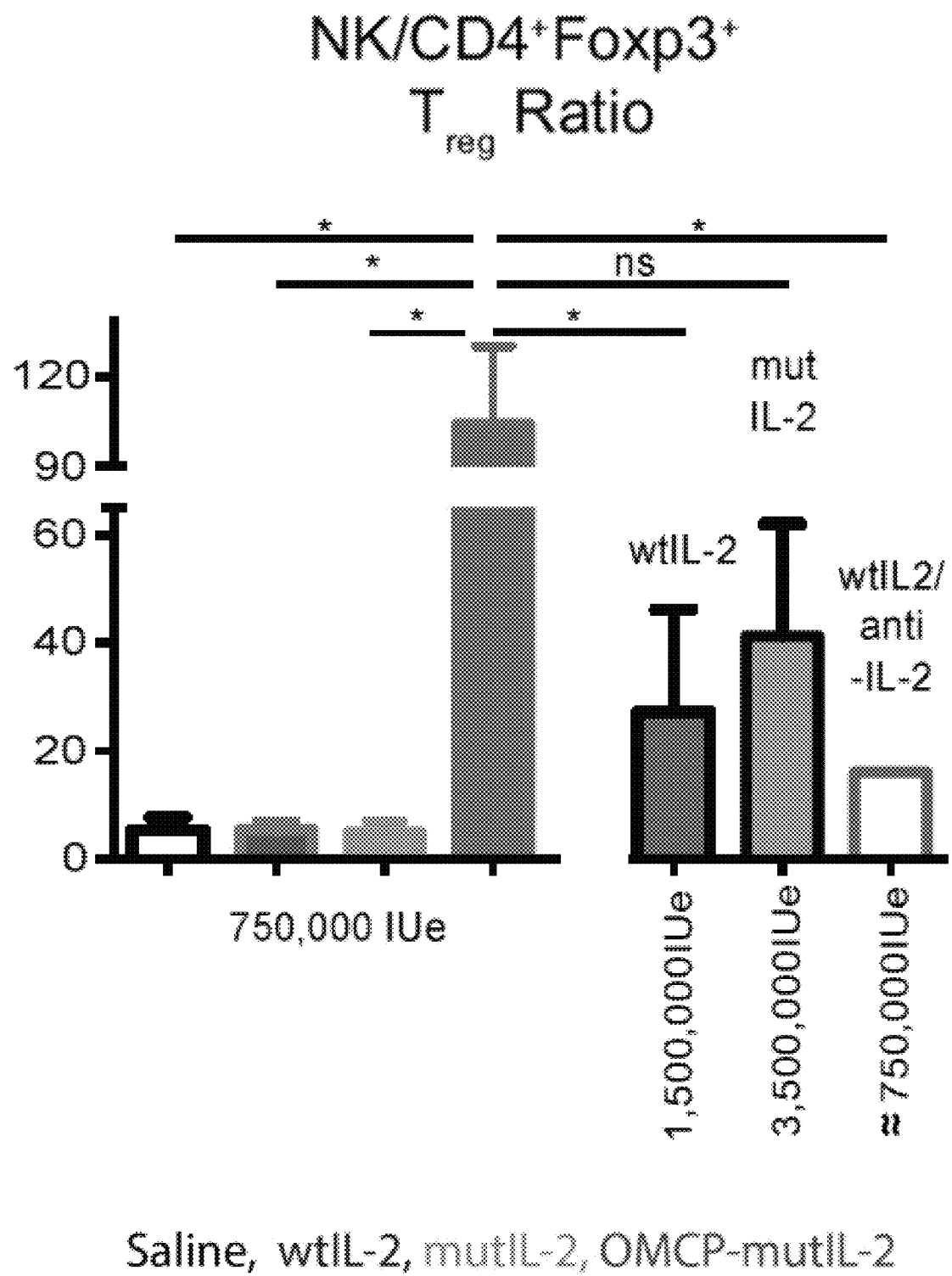
Figure 8F:
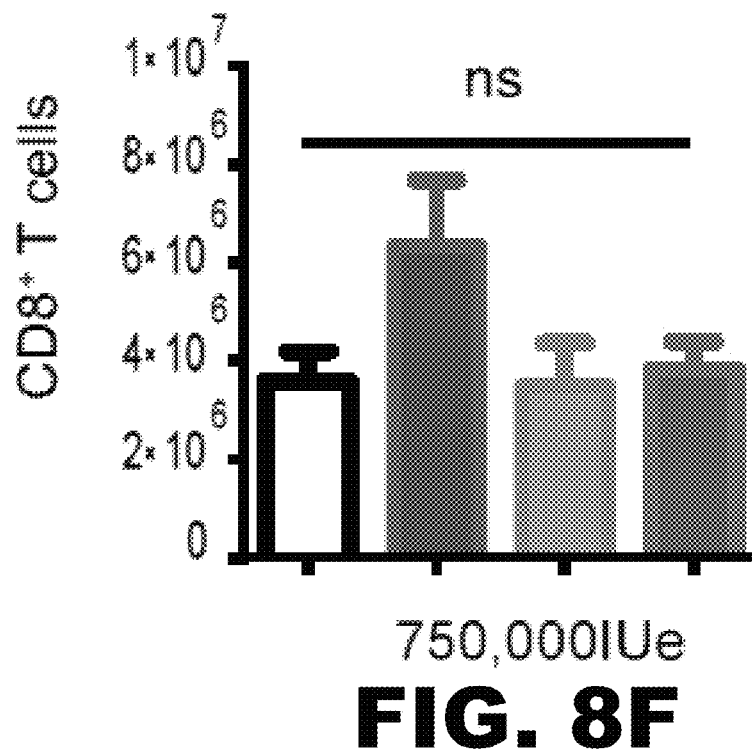
Figure 8G:
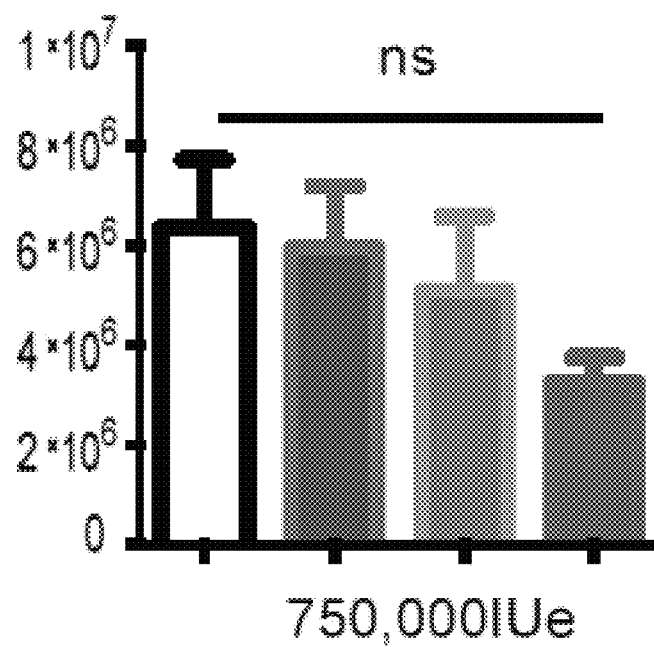

Unlike the A/J strain little immunoactivation of lymphocytes was evident in B6 mice treated with 200,000 IUe of wtIL2 (data not shown). At higher doses of 750,000 IUe OMCP-mutIL2 expanded NK cells more robustly than wtIL2 in this strain (FIG. 3F-H). IL2/anti-IL2 antibody complexes prevented $T_{reg}$ expansion but, similar to the A/J strain, such treatment had toxicity and the majority of B6 mice could not tolerate the full 750,000 IUe dose (FIG. 3I). OMCP-mutIL2, however, was well tolerated at this dose and led to a high NK/$T_{reg}$ ratio (FIG. 3J). No expansion of NK cells was evident in OMCP-mutIL2 treated B6 NKG2D−/− mutants, confirming the requirement for NKG2D in the function of our construct (data not shown). No statistically significant expansion of B6 CD8+ or CD4+Foxp3− T cells was evident in any treatment group although a trend for CD8+ T cell expansion was evident after wtIL2 administration (FIG. 8F-G). Identical data was obtained for lung resident lymphocytes in both the NJ and B6 strains (data not shown).

Example 4. OMCP-mutIL2 Preferentially Expands and Activates NK Cells in Human Peripheral Blood Lymphocytes Compared to wtIL2 or mutIL2

To demonstrate the effectiveness of OMCP-mutIL2 in human lymphocytes, human peripheral blood lymphocytes were co-cultured for 36 hours in 100 IUe of either wild-type IL2, R38A/F42K mutant form of IL2 or OMCP-mutant IL2.

NK Cells:

The cells were flow cytometrically analyzed and relative prevalence of CD56+CD3− NK cells compared between conditions. A relatively higher proportion of NK cells was evident in the OMCP-mutant IL2 group (FIG. 31A). Perforin levels were higher in OMCP-mutant IL2 treated NK cells (red) compared to saline (black), IL2 (blue) or mutant IL2 (green) treated ones (FIG. 31B).

CD8+ T Cells:

Similar to NK cells, higher intracellular levels of perforin were evident in CD8+ T cells treated with OMCP-mutant IL2 compared to other conditions (FIG. 31C).

Tregs:

When gating on CD4+Foxp3+CD45RA− T cells a relatively higher proportion of activated CD25+CD127− regulatory T cells was evident in IL2 treated peripheral blood lymphocyte cultures compared to other conditions (FIG. 31D). Taken together this data suggests that OMCP-mutIL2 preferentially expands and activates NK cells and CD8+ cells in human peripheral blood lymphocytes compared to wtIL2 or mutIL2. Importantly, OMCP-mutIL2 does not activated regulatory T cells significantly relative to IL2.

Figure 4A:
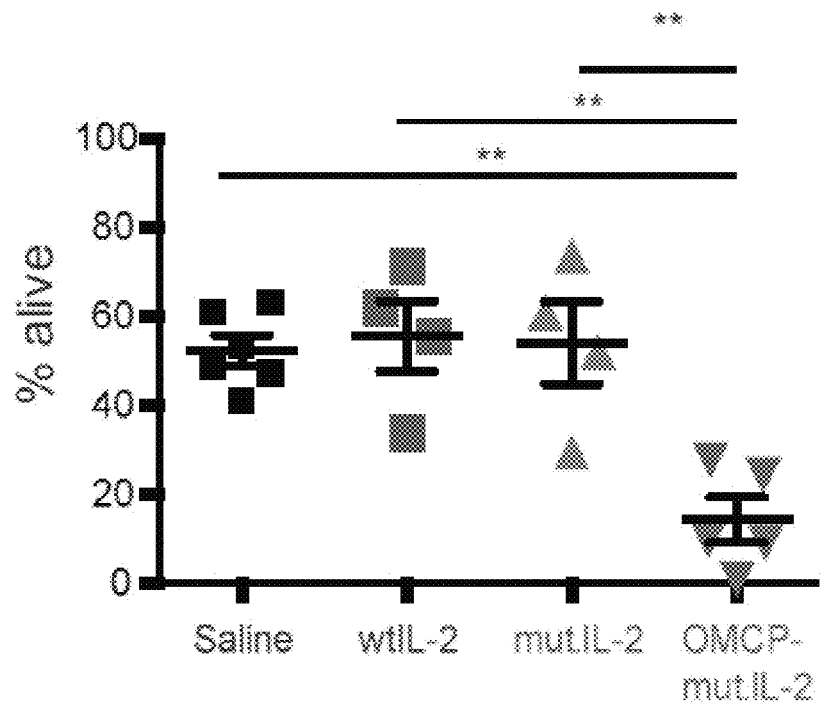
Figure 4B:
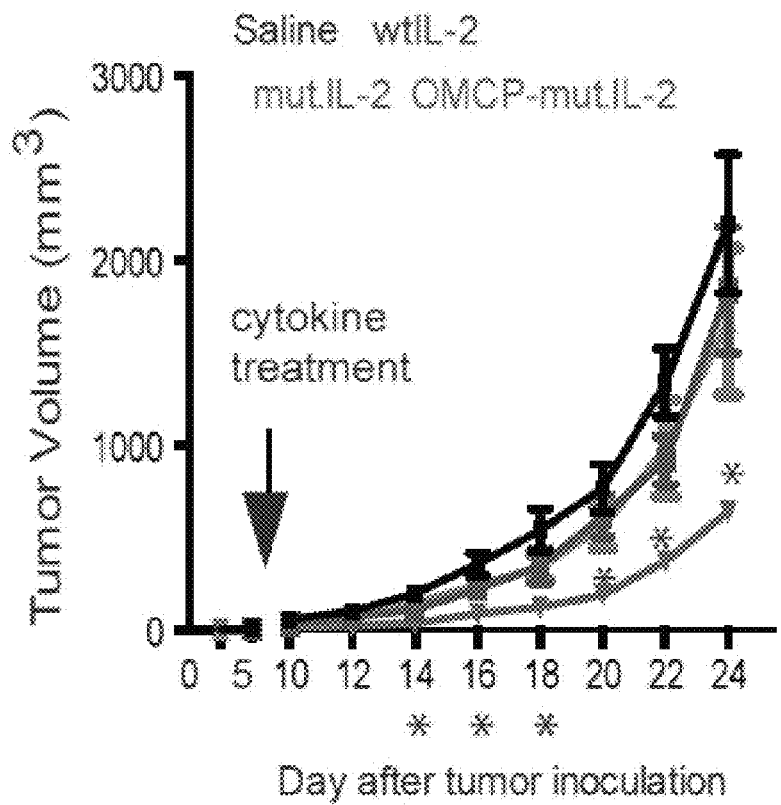
Figure 4C:
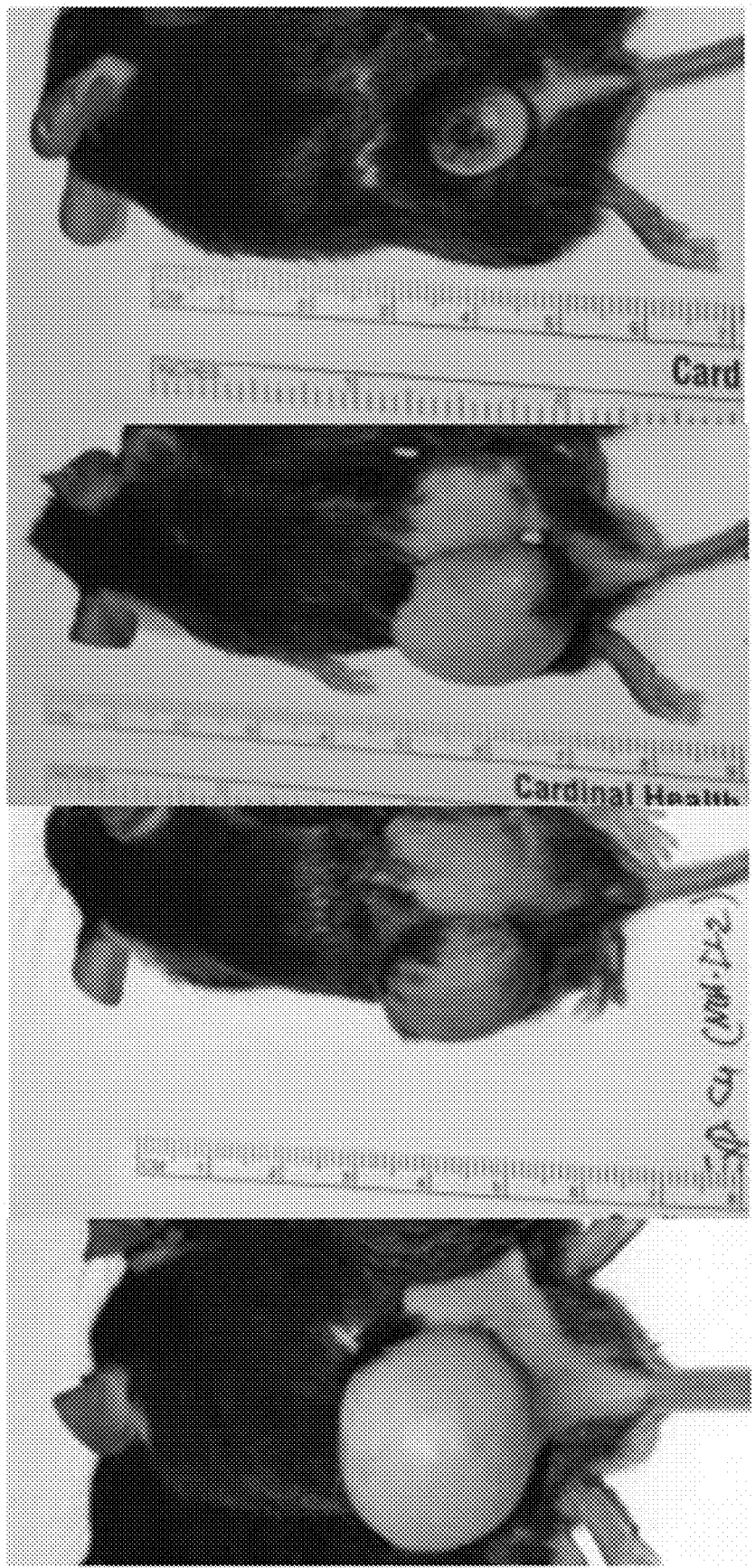
Figure 4D:
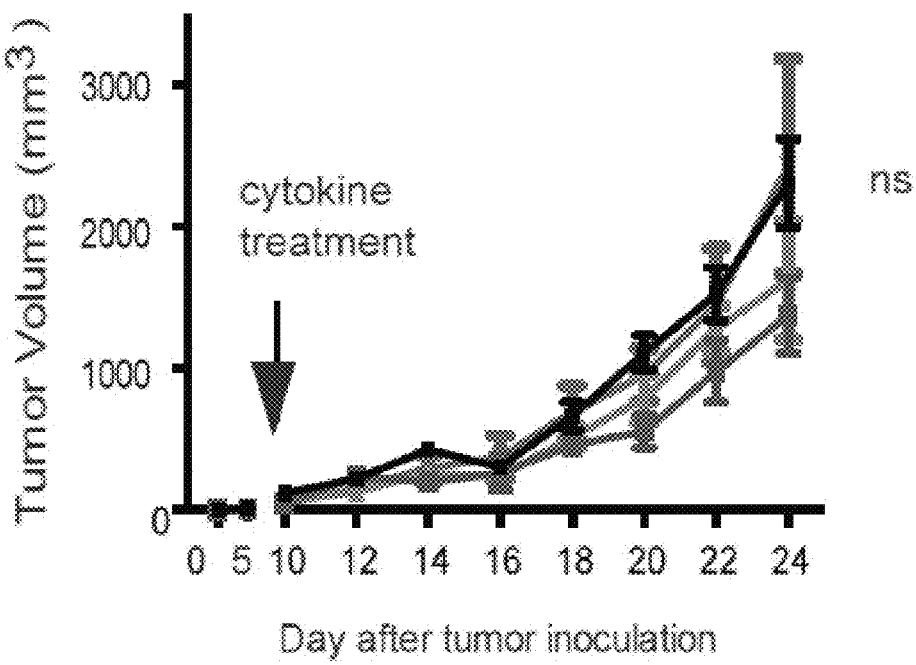
Figure 4E:
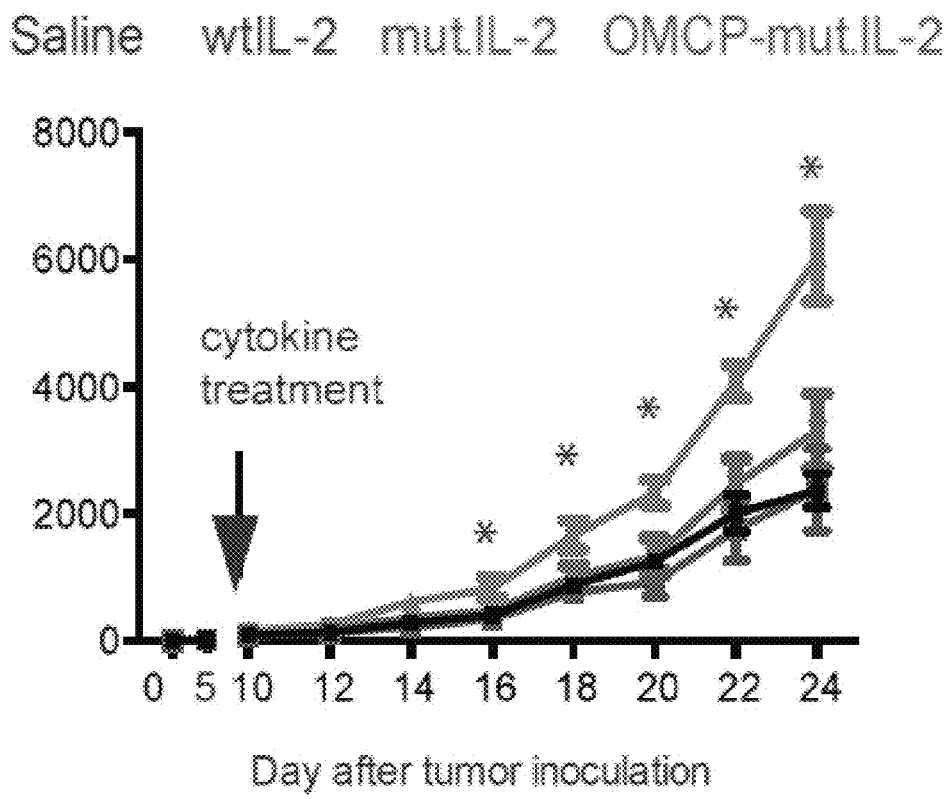
Figure 9A:
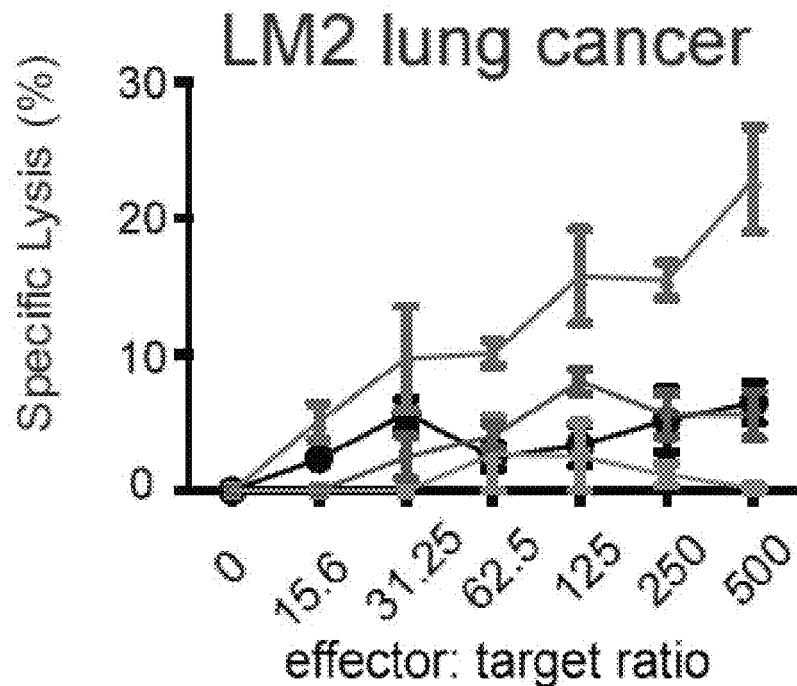
FIG. 9A and FIG. 9B depict graphs showing in vitro lysis of NJ tumors, such as LM2 lung adenocarcinoma (FIG. 9A) or YAC-1 lymphoma (FIG. 9B) by bulk splenocytes after a five day course of 200,000 IUe of cytokine given over ten doses.
Figure 9B:
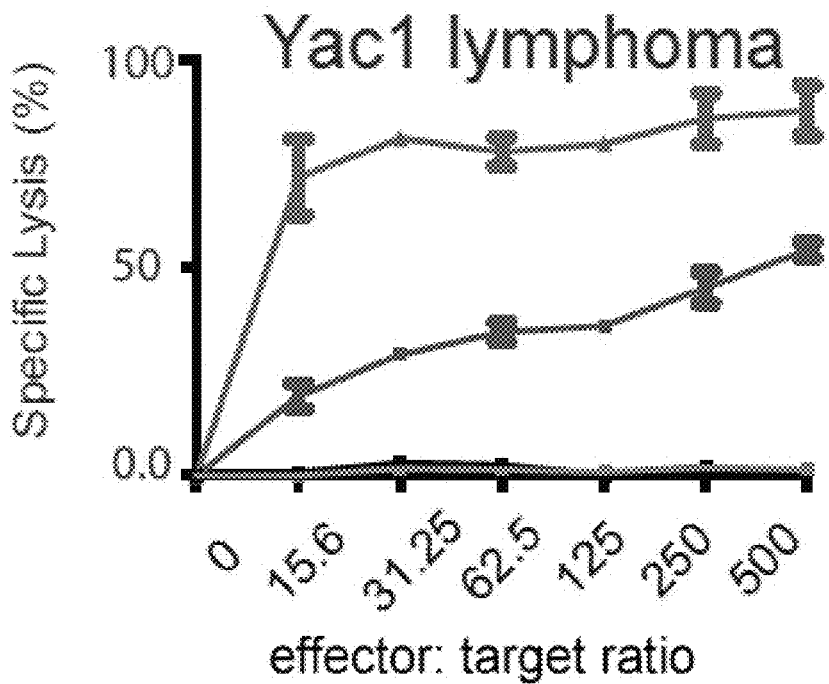
Figure 9C:
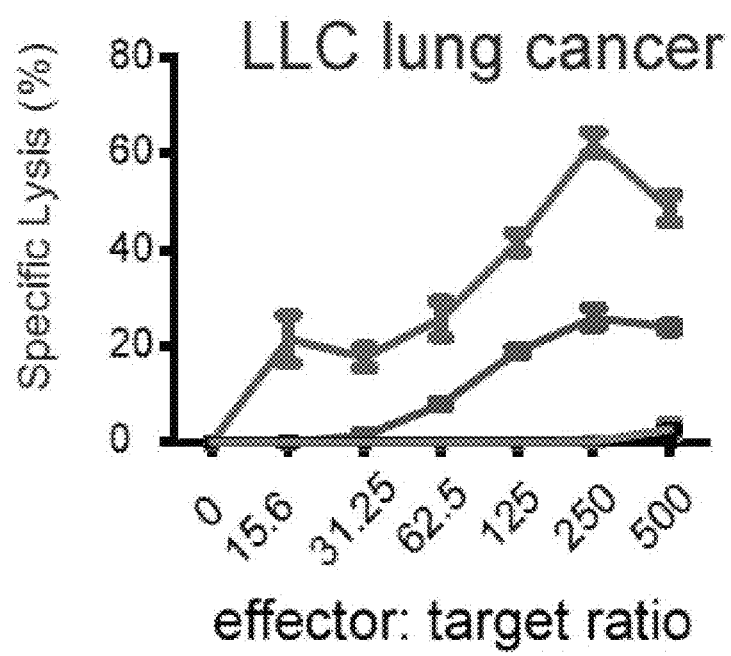
FIG. 9C shows in vitro lysis of LLC lung cancer by B6 splenocytes treated with 750,000 IUe of cytokines or constructs given over five days in ten doses.

Example 5. Treatment with OMCP-mutIL2 Offers Superior Immunologic Control of Malignancies In Vivo Unlike T lymphocytes, which require prior antigen encounter for optimal antigen-specific tumor cytotoxicity, NK cells can mediate natural cytotoxicity without prior sensitization. NK cells also form the primary barrier for expansion of select malignancies, such as lymphoma and lung cancer[16, 17, 21, 22]. Treatment of NJ mice with OMCP-mutIL2, compared to wtIL2 or mutIL2, led to enhanced in vivo clearance and in vitro lysis of YAC-1 cells by bulk splenocytes (FIG. 4A, FIG. 9A-B). Decreased growth of the highly aggressive Lewis Lung Carcinoma (LLC) cell line was evident in B6 mice after 750,000 IUe of OMCP-mutIL2 compared to wtIL2 or mutIL2. Increased cytotoxicity was evident in OMCP-mutIL2 treated splenocytes for the LLC cell line as well (FIG. 4B-C; FIG. 9A-C). Enhanced immunotherapy was lost in NKG2D−/− mice or following NK depletion (FIG. 4D-E). In the absence of host NKG2D mutIL2 actually increased the rate of LLC growth. Thus OMCP-mediated targeting of mutIL2 offers a safer and more efficacious form of immunotherapy for both solid and liquid tumors in various strains of mice.

Example 6. Impact of NKG2D Targeting on IL2 Signaling

Figure 5A:
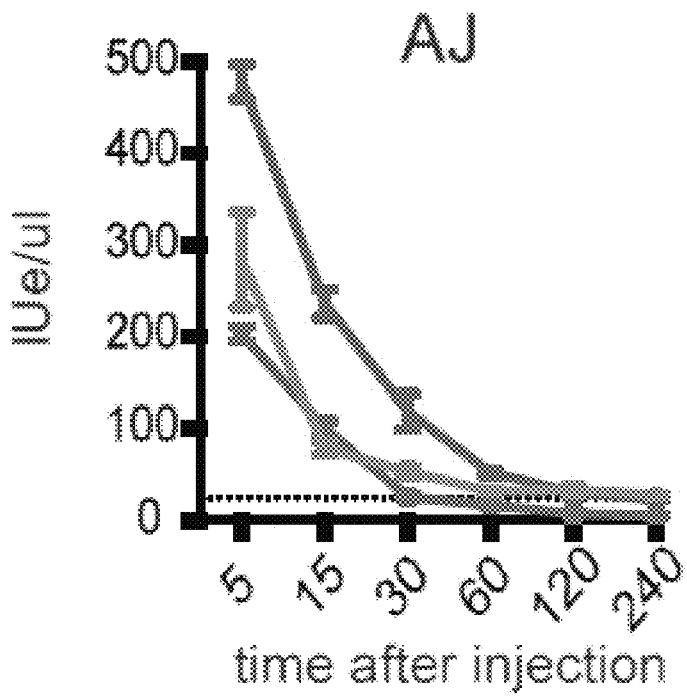
Figure 5B:
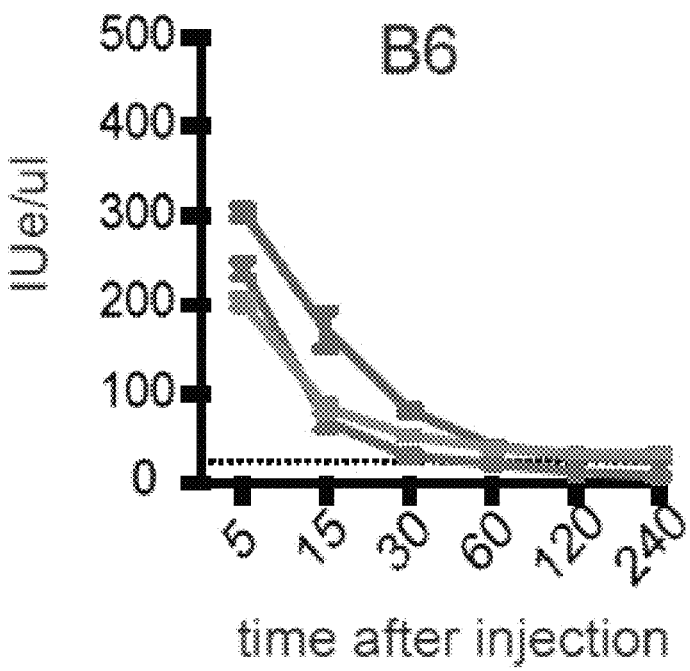

Antibody-IL2 conjugates, or IL2/anti-IL2 antibody complexes demonstrate improved biologic activity over purified cytokine by extending the duration of serum half-life[23, 24]. To investigate whether linking IL2 to OMCP increased serum half-life, we injected 500,000 IUe of fluorescently-labeled wtIL2, mutIL2 or OMCP-mutIL2 into A/J and B6 mice and monitored serum clearance by serial blood draws. While OMCP-mutIL2 had a slightly higher serum concentration at early time points, all constructs were undetectable in the blood one hour post-injection (FIG. 5A-B). This is significantly shorter than the described 11-14 hour serum half-life of antibody-IL2 conjugates[23]. Interestingly, despite the injection of identical amount of cytokine, lower cytokine levels were detected in B6 mice compared to A/J mice at all time points. Such data points to strain-specific differences in clearance of IL2 and may explain why B6 mice are able to both tolerate and require higher doses of cytokine for NK expansion. Nevertheless, based on this data it is unlikely that prolonged circulation of construct was responsible for the increased activity of OMCP-mutIL2 over wtIL2.

Figure 5C:
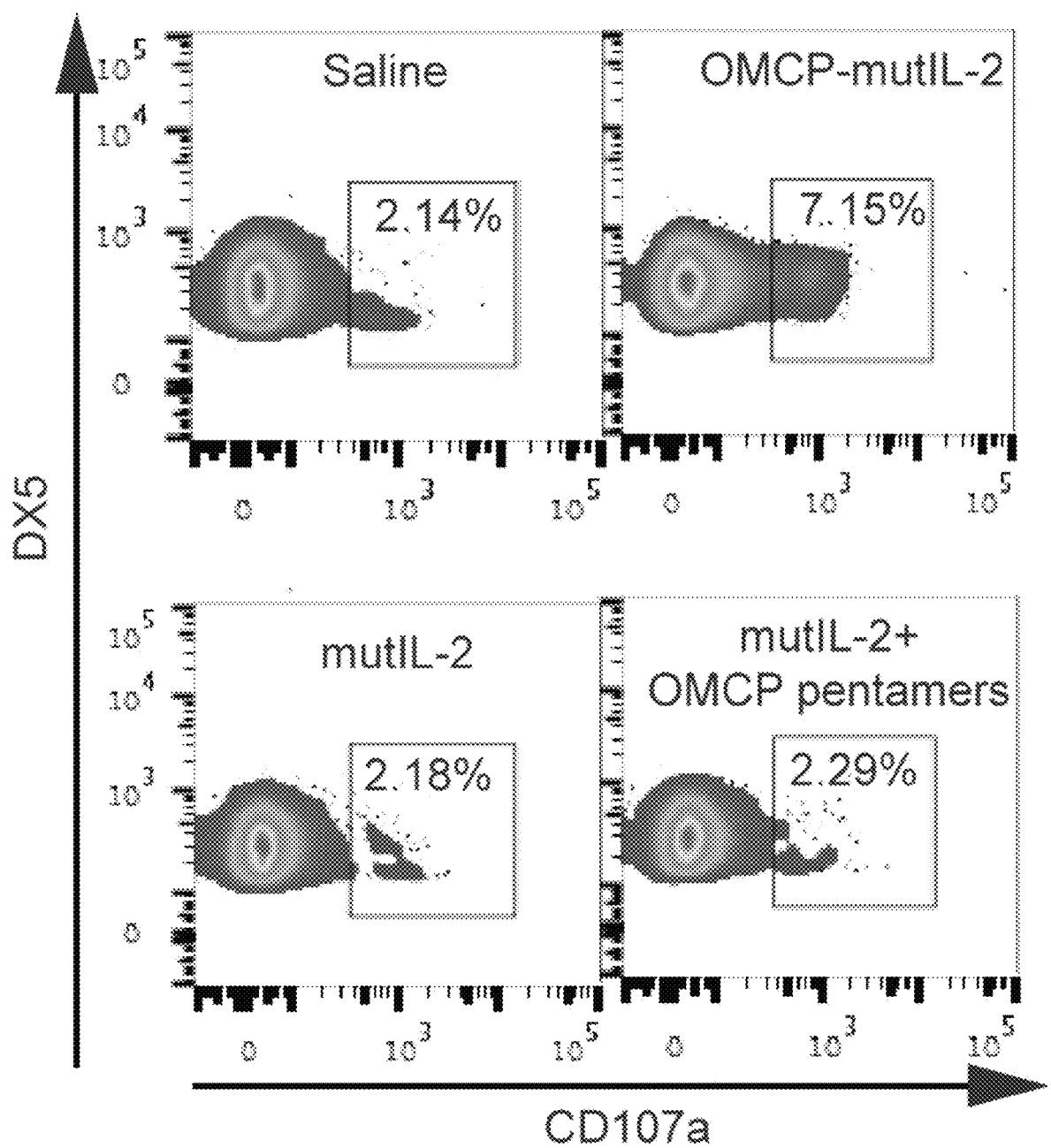
Figure 10A:
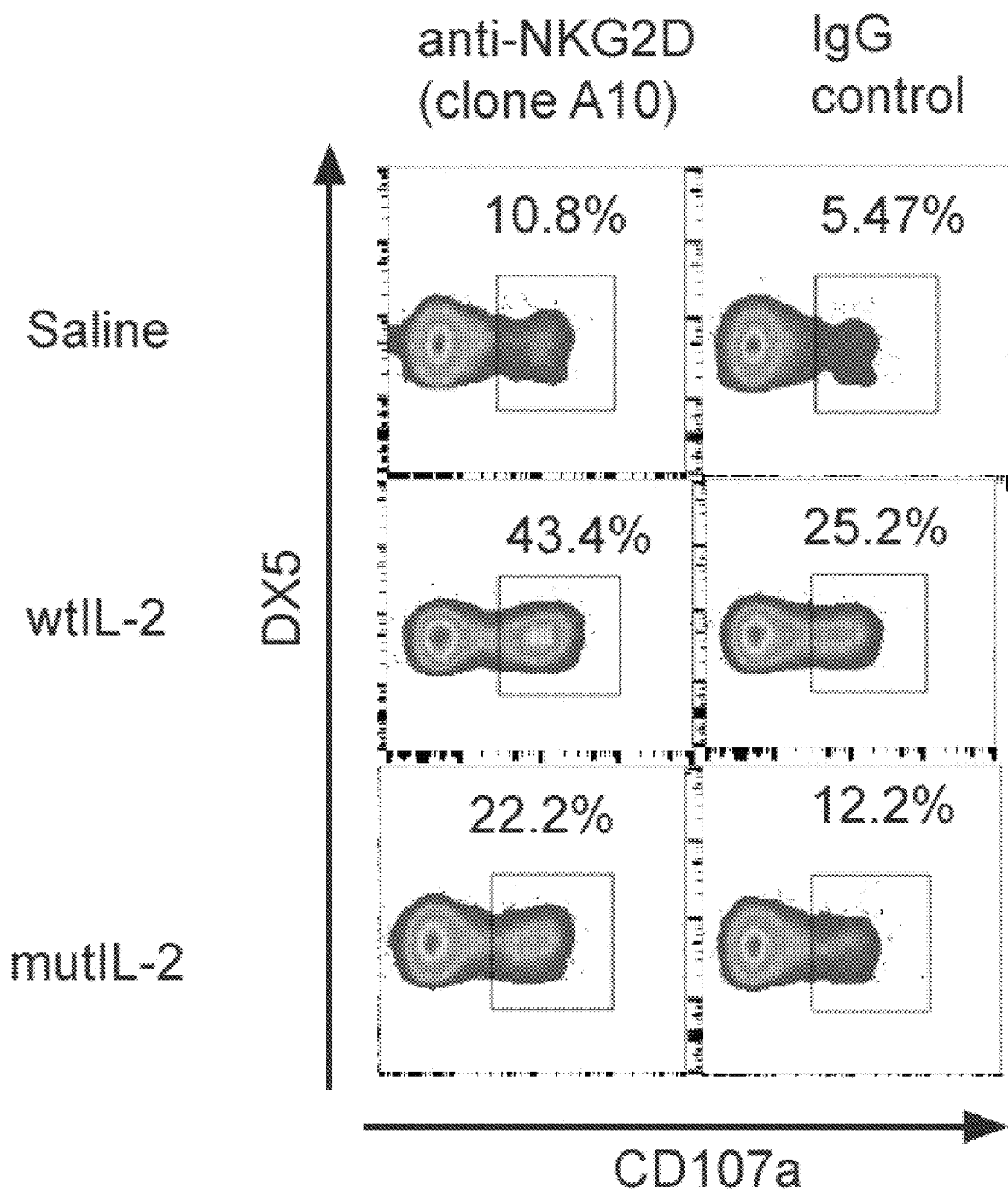
FIG. 10A depicts flow cytometric plots showing that plate bound anti-NKG2D antibody (clone A10)-mediated augmentation of NK degranulation with cytokines added at 1000 IUe/ml.
Figure 10B:
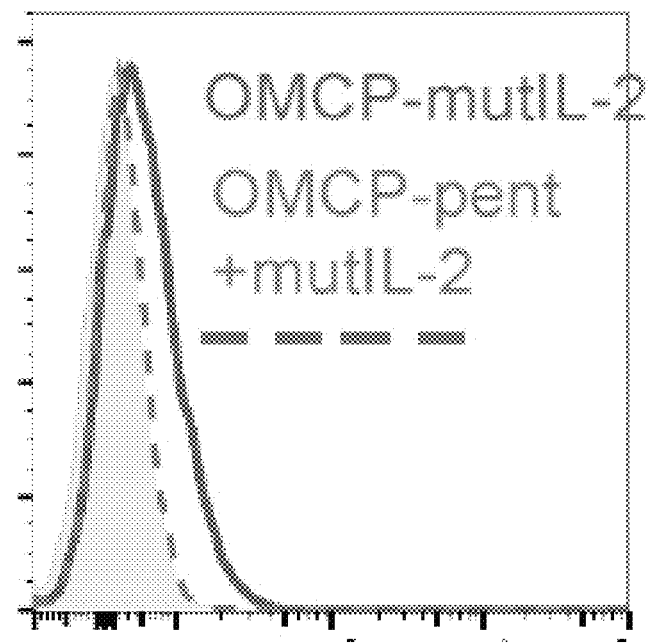
FIG. 10B depicts a flow cytometric plot showing CD69 levels on NK cells cultured at 100 IUe/ml of OMCP-mut-IL2 or mutIL2 with pentameric OMCP.

We next considered the possibility that the superiority of OMCP-mutIL2 was the result of signaling through NKG2D as antibody-mediated crosslinking of this receptor can activate NK cells (FIG. 10A)[25]. While the addition of purified OMCP to mutIL2 did not augment NK activation or expansion in vitro or in vivo (data not shown) we would not expect a monomeric ligand to crosslink NKG2D. We thus directly compared NK cell activation in the presence of 1000 IUe of OMCP-mutIL2, mutIL2 and mutIL2 combined with equimolar concentration of pentamerized OMCP. No increase in NK activation, as measured by CD69 upregulation or degranulation, was evident in the presence of pentamerized OMCP (FIG. 5C, FIG. 10B). This suggests that NKG2D crosslinking is not responsible for augmented NK cell activation by OMCP-mutIL2 at physiologic concentrations.

Figure 5D:
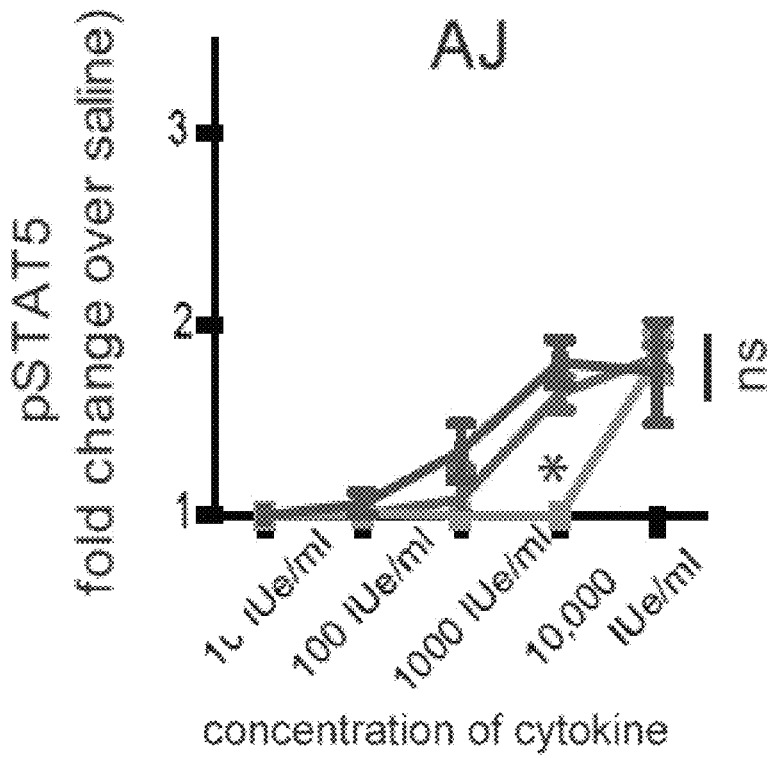
Figure 5E:
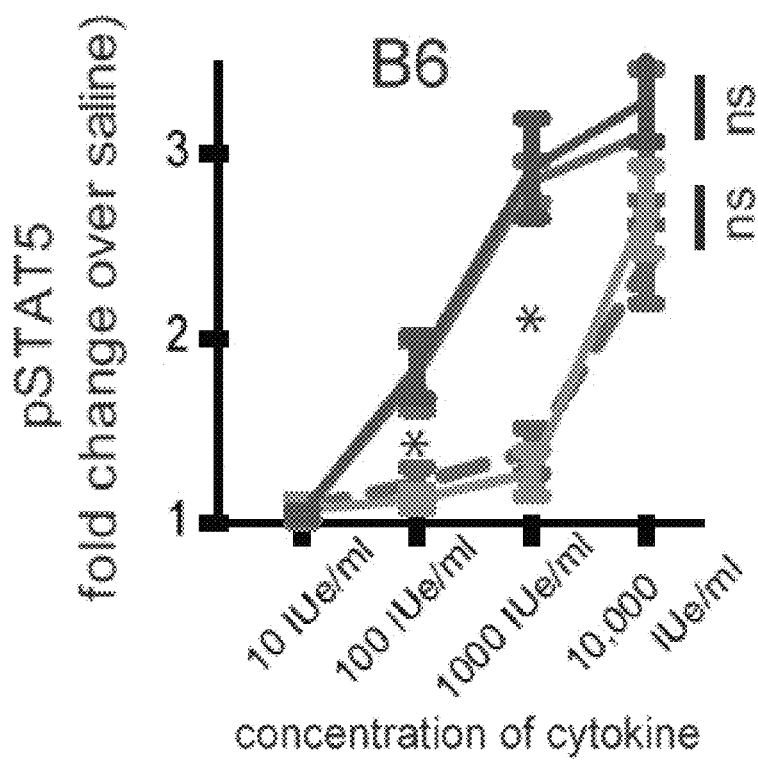

To evaluate IL2 signaling we next quantitated STAT5 phosphorylation after a 15 minute cytokine stimulation of freshly isolated NK cells in vitro. Lower levels of STAT5 phosphorylation were evident in NJ compared to B6 NK cells at all concentrations tested (FIG. 5D-E) suggesting that lymphocyte dysfunction of NJ mice may at least partially be the result of inefficient IL2 signal transduction. Surprisingly, for both B6 and A/J NK cells wtIL2 and OMCP-mutIL2 demonstrated an identical dose-dependent pattern of STAT5 phosphorylation (FIG. 5D-E). In the absence of NKG2D reactivity OMCP-mutIL2 failed to increase STAT5 phosphorylation over mutIL2 alone. Taken together these data suggested that IL2a reactivity is important for peak IL2 signaling in resting NK cells, and that NKG2D-binding may effectively substitute for IL2Rα-binding in IL2-mediated signal transduction. Such data, however, failed to explain the superior NK activation by OMCP-mutIL2 in vivo or in bulk splenocyte cultures (FIG. 1C-D, FIG. 3).

Figure 5F:
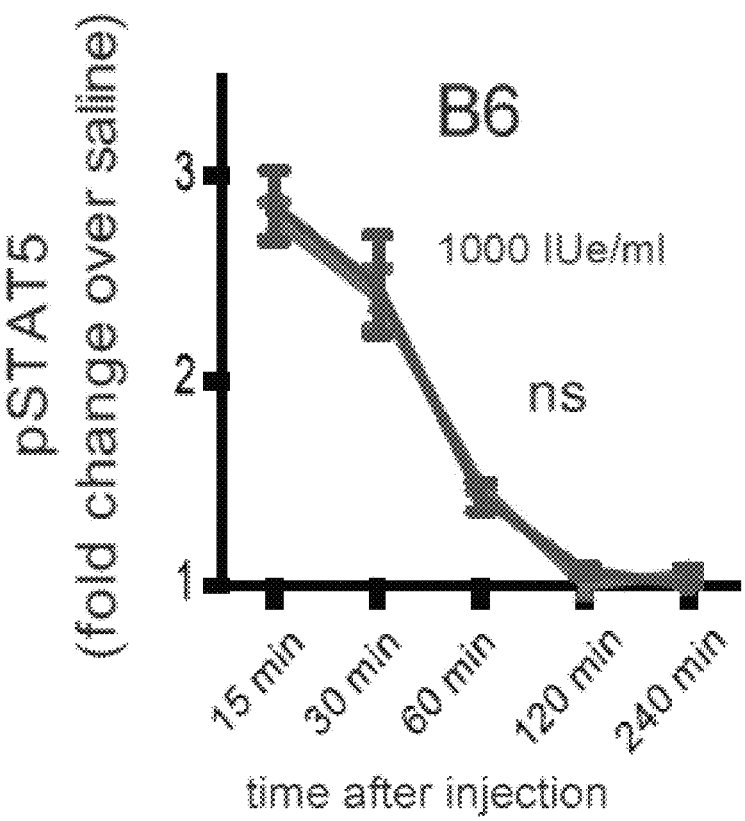
Figure 5G:
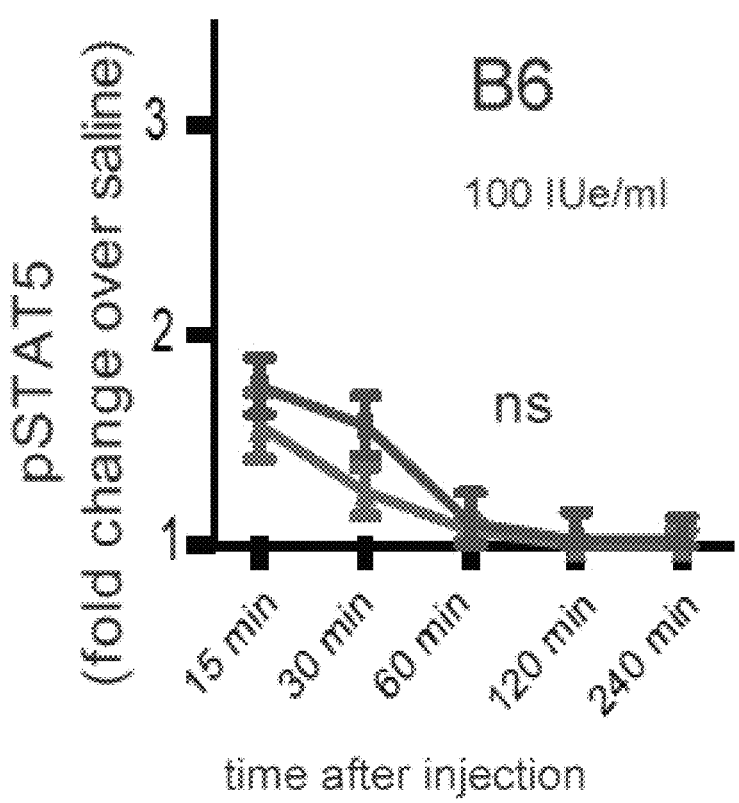

IL2 signaling results in the internalization of IL2/IL2R, with subsequent degradation of IL2 and IL2Rβγ. The binding of OMCP-mutIL2 to both the IL2 receptor and NKG2D could thus lead to altered internalization and enhanced NK cell activation by prolonging IL2 signaling. To test this we stimulated freshly isolated NK cells for 15 minutes, replaced the culture media with cytokine free media, and monitored STAT5 phosphorylation for four hours. Identical decay of phospho-STAT5 was evident for both wtIL2 and OMCP-mutIL2 (FIG. 5F-G). Thus altering duration of IL2 signaling is not responsible for superior NK activation by OMCP-mutIL2.

Figure 5H:
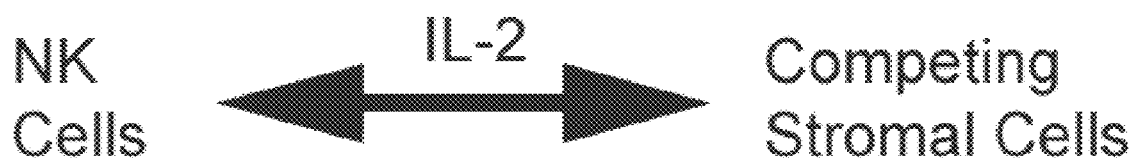
Figure 5I:
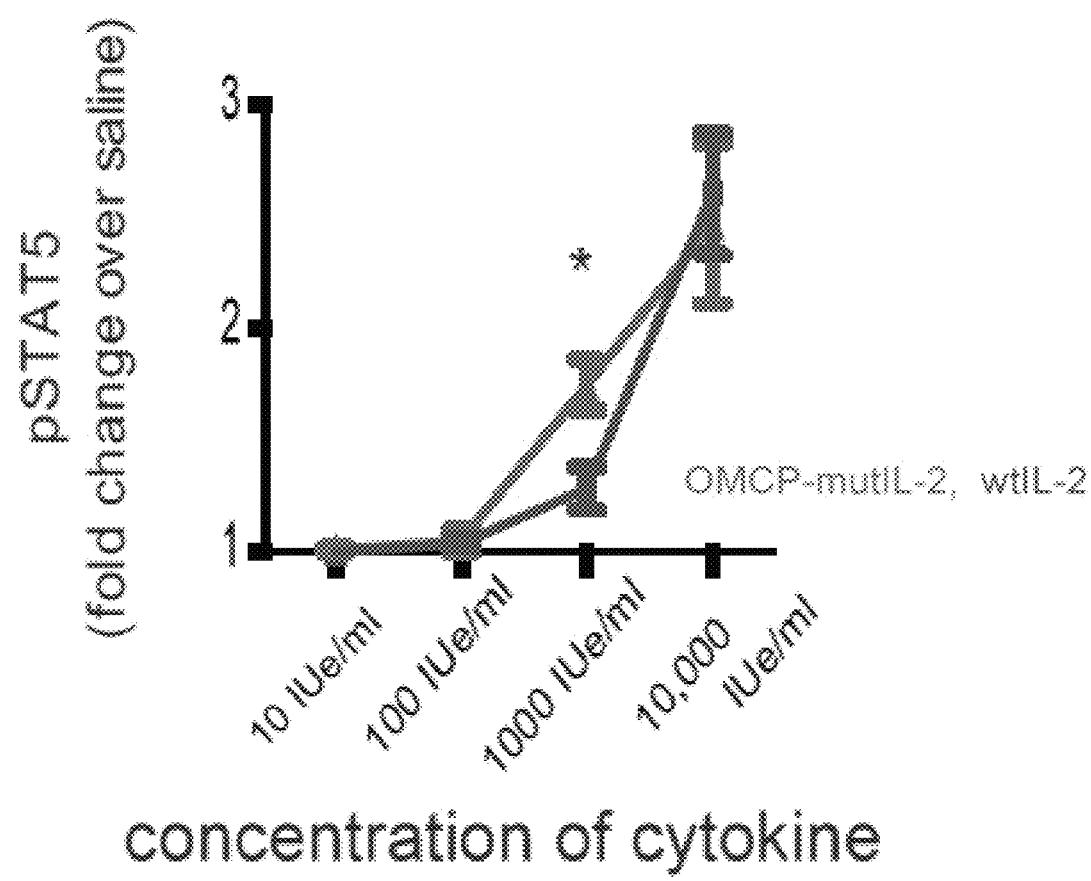

We next considered the possibility that superior NK activation by OMCP-mutIL2 may be the result of altered cytokine interaction with competing stromal cells (FIG. 5H). Indeed, in the presence of other splenocytes OMCP-mutIL2 demonstrated a dose-dependent enhancement in NK STAT5 phosphorylation over wtIL2 (FIG. 5I). We next explored the interplay between IL2Rα expression by stromal cells and NKG2D expression by NK cells on IL2 signal transduction. To accomplish this we isolated splenic NK cells from either wild-type or NKG2D−/− B6 mice and combined them with wild-type splenocytes depleted of NK cells. Cultures were recombined in a 1:20 NK:splenocyte ratio, resembling the proportion normally present in resting wild-type B6 mice. For some cultures NK cell depleted splenocytes were treated with saturating concentrations of IL2Rα-blocking antibody (clone 3C7) prior to recombining with wild-type NK cells.

Figure 5J:
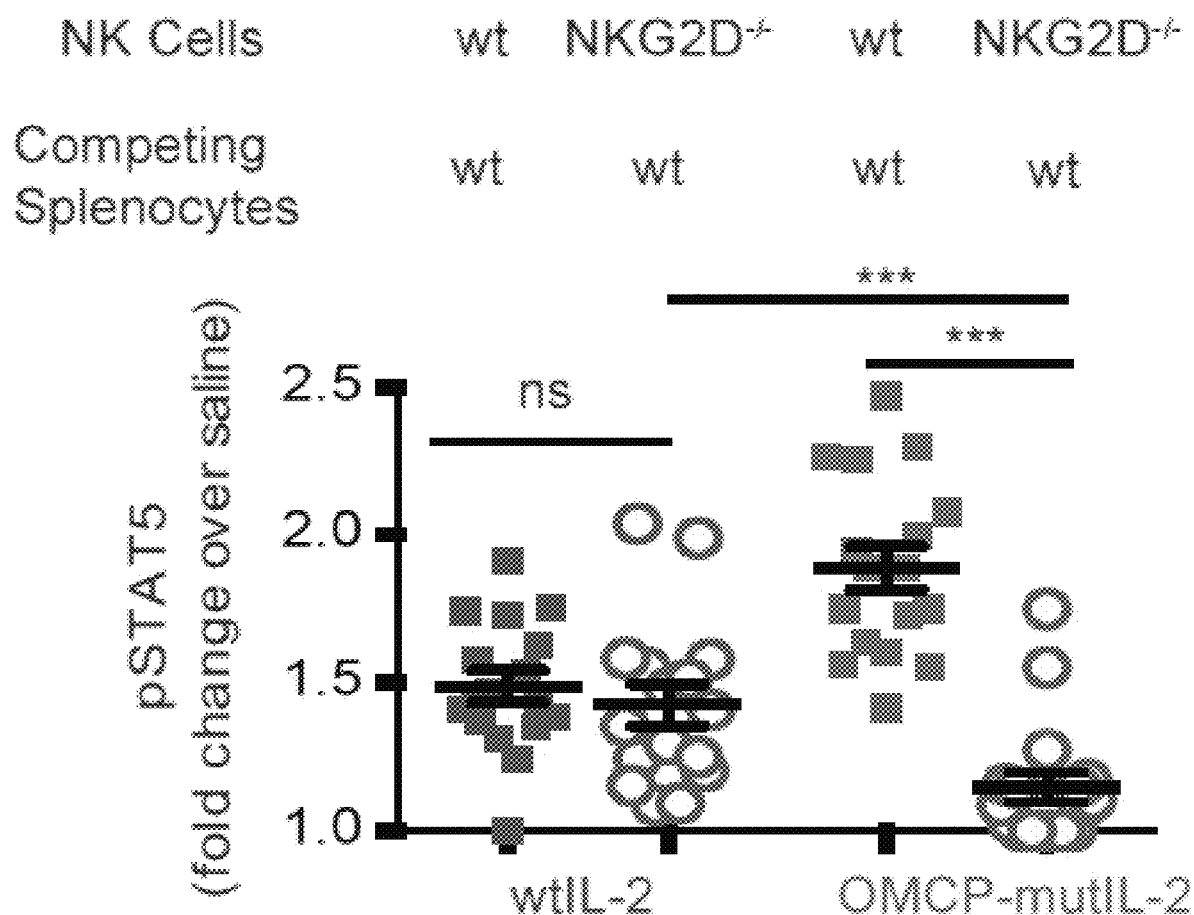
Figure 5K:
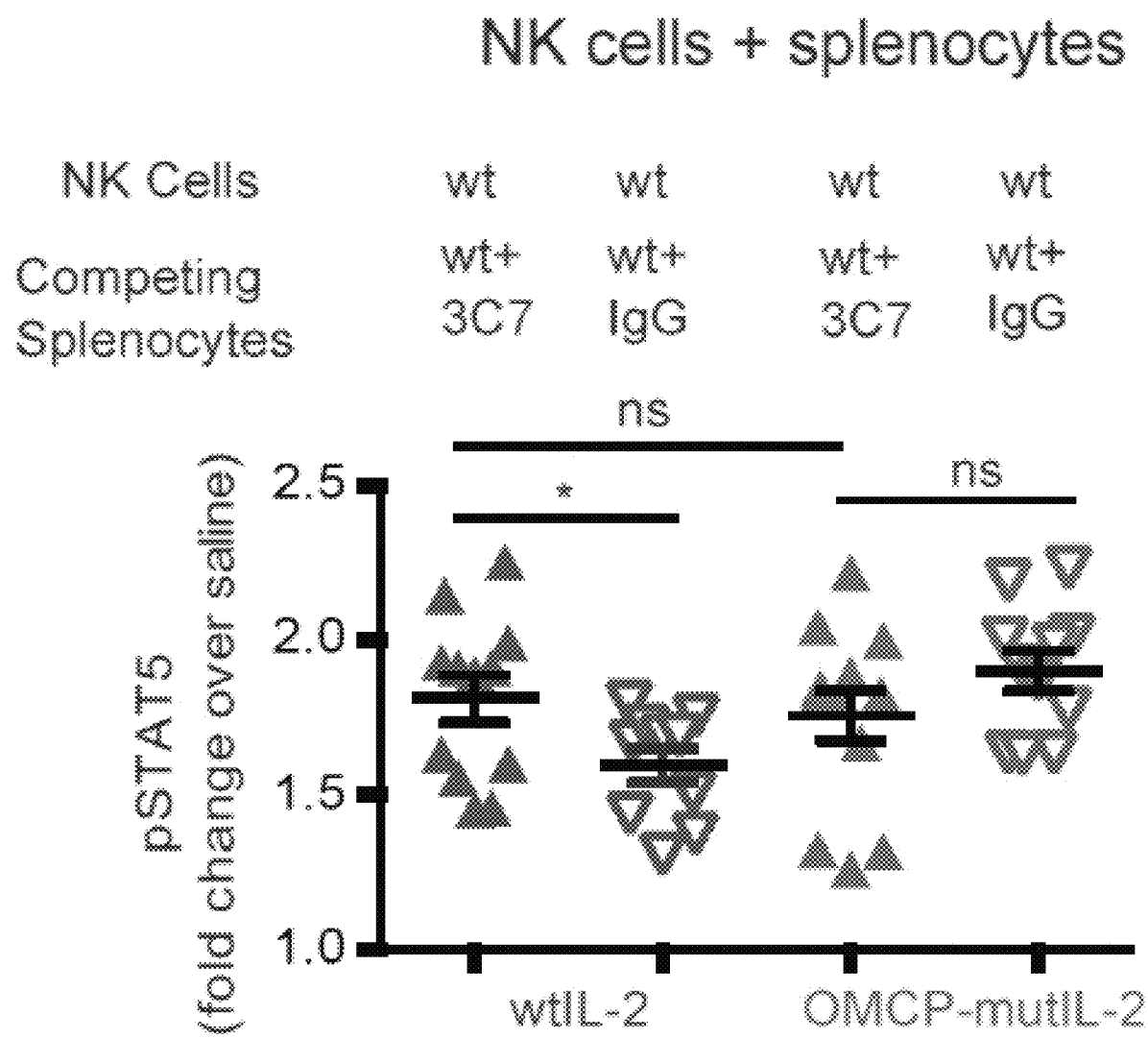

The cultures were then stimulated with 1000 IUe of either wtIL2 or OMCP-mutIL2 for 15 minutes. STAT5 phosphorylation was identical in NKG2D$^{-/-}$ or wild type NK cells in the presence of wtIL2 (FIG. 5J, left two columns). Wild-type NK cells cultured with OMCP-mutIL2 demonstrated superior STAT5 phosphorylation to cultures with wtIL2. Little STAT5 phosphorylation was evident in NKG2D$^{-/-}$ NK cells cultured with OMCP-mutIL2 (FIG. 5J, right two columns). In the presence of IL2Rα-blockade of competing splenocyte stromal cells, NK cell STAT5 phosphorylation by wtIL2 increased to levels comparable to OMCP-mutIL2 (FIG. 5K). Taken together these data demonstrate that IL2-Ra expression by "competing" stromal cells limits NK cell activation by wtIL2 and this competition can be eliminated by the NKG2D-targeted, IL2Rα-binding impaired OMCP-mutIL2 construct.

Discussion for Examples 1-6

While IL2 therapy initially showed great promise, it has been limited by activation of $T_{regs}$ and toxic side effects associated with activation of vascular endothelium. Several strategies have been proposed to preferentially activate cytotoxic lymphocytes. One strategy has been to create mutants with increased affinity for IL2Rβ to remove the preference for IL2Rα[26, 27]. Importantly, these IL2 mutants retain wild type binding for IL2Rα, and would therefore still be recognized by $T_{reg}$ cells and vascular endothelium. Our results also suggest that competition with IL2-$R\alpha^{+}$-expressing cells limits bioavailability of wtIL2 to cytotoxic lymphocytes.

Another promising therapy involves anti-IL2 antibodies that sterically inhibit wtIL2 binding to IL2Rα[1, 28, 29]. Such treatment can extend serum half-life[24] due to the Fc region of the antibody and potentially due to reduced competition for wtIL2 from IL2Rα-expressing cells. Antibody-IL2 fusion proteins have also been designed to target IL2 to specific tumor antigens[30, 31]. While offering the potential for personalized therapy such antibody-mediated delivery of IL2 to the tumor depends on the expression of a known tumor associated antigen, a situation that often does not exist. This approach could potentially be further limited by tumor-mediated alteration of the targeted antigen.

Finally, IL2 mutants with reduced affinity for IL2Rα have been tested extensively. Compared to wtIL2 these mutants can be administered in supratherapeutic doses without IL2Rα-mediated capillary leak or systemic toxicity[32]. While these mutants have excellent safety profiles, they activate cytotoxic lymphocytes poorly (FIG. 5C-E)[33]. Our approach combines several of the concepts above to target a safe form of IL2 directly to cytotoxic lymphocytes, instead of tumors. This is accomplished by replacing the normal targeting of IL2 to IL2Rα with NKG2D. The combination of an IL2Rα-deficient IL2 fused to a high affinity NKG2D-ligand improves upon previous strategies by specifically expanding NK cells without any apparent activation of $T_{regs}$ or capillary leak. These findings offer the promise of a potentially safe and highly efficacious form of IL2.

One limitation in translating results from inbred lab animals to humans is the natural diversity in cytokine reactivity and environmentally dependent threshold for lymphocyte activation. Previous studies have demonstrated a correlation between ex vivo killing of tumor cells and enhanced long-term cancer immunity[34]. Therefore, any potential therapy needs to account for a population that has differential levels of cytotoxic lymphocyte activity. We have thus attempted to model this natural variation by using two strains of mice known to be highly resistant (B6) or susceptible (NJ) to carcinogenesis. For example, NK cells from B6 mice, are activated by wtIL2 and extreme doses of mutIL2. In contrast, IL2/anti-IL2 antibody complexes resulted in expansion of NK cells in NJ but not in B6 mice. Such variations highlight the limitations of translating results derived from a single strain of mice to immunologically diverse humans. Importantly, the OMCP-mutIL2 construct was able to expand NK cells in both strains of mice, indicating that this therapy could be efficacious in populations with diverse NK function and cytokine reactivity.

Since OMCP has been described as an evolutionary antagonist of NKG2D[35] blockade of this immunoreceptor at the time of tumor therapy may be construed as counterproductive. Nevertheless, natural cytotoxicity and tumor clearance was augmented in OMCP-mutIL2-treated mice even in the presence of established tumors. This suggests minimal or transient NKG2D receptor occupancy and preservation of function. Alternatively recent reports have demonstrated that shed NKG2D ligands may actually promote tumor immunity through reversal of NK desensitization imposed by chronic agonistic engagement[36]. While we did not detect NK activation or expansion by monomeric or even pentameric OMCP, it is possible that within the tumor bed such competitive antagonism plays a paradoxical role in NK activation. In addition, IL2 may upregulate receptors necessary for NK migration and tumor infiltration. It is thus possible that anti-tumor immunity mediated by OMCP-mutIL2 may depend on NK cells located outside the tumor bed and not subject to local tumor-specific tolerance or anergy. Furthermore, OMCP may be the ideal "targeting vector" due to its high affinity and long half-life of binding to human NKG2D.

While NK cells from two separate strains of mice were activated by OMCP-mutIL2 we did not detect global expansion of activation of $CD8^{+}$ T cells by our construct. This is most likely due to the fact that NKG2D is expressed only on select subsets of $CD8^{+}$ T cells, namely memory or activated cytotoxic lymphocytes. Based on the paucity of this cell population in mice raised in specific pathogen-free environment, OMCP-mutIL2-mediated activation was limited in our system to NK cells. To this end we focused on immunotherapy for lung cancer and lymphoma, whose growth is regulated primarily by NK cells[16, 17, 22, 37]. Nevertheless OMCP-mutIL2 was able to expand $CD8^{+}$ T cells when administered in high concentrations in vitro (FIG. 1E-F). Thus, it may be possible that NKG2D-targeted delivery of immunostimulatory cytokines may lead to the expansion and/or activation of antigen-specific $CD8^{+}$ memory cells for long-term tumor immunity under normal immunologic conditions.

Methods for Examples 1-6

Cytokine and Construct Generation:

The sequences encoding human IL2 (1-133; C125S) and mutant IL2 (1-133; R38A, F42K, C125S) were cloned into the pFM1.2R[38] with an N-terminal FLAG/hexahistidine tag. The chimeric OMCP-mutIL2 molecule comprises the full-length OMCP (1-152) coding sequence cloned in frame with a C-terminal FLAG/hexahistidine tag-mutant IL2 (1-133; R38A, F42k, C125S) cloned into the pFM1.2R vector. Proteins were expressed by transient transfection into HEK293F (Life Technologies). Supernatant was recovered at 72 h and 144 h post-transfection. Supernatants were supplemented with 5 mM imidazole and 0.02% sodium azide and purified by nickel-nitrilotriacetic acid (Ni-NTA)

chromatography (Qiagen). Purified proteins were buffer exchanged into saline and flash frozen in liquid nitrogen. Equivalent in vitro and in vivo activity was documented for wild-type IL2 generated in house and Teceleukin (Tecin™) available from the NCI repository (Frederick National Laboratory for Cancer Research). Thus for some experiments these two preparations of IL2 were used interchangeably.

Wild-type IL2 has a specific activity of $15 \times 10^6$ IU/mg[39]. Thus, based on the molecular weight of 15.5 kDa a 4.4 µM solution is equivalent to 1000 Based on this calculation all cytokines and construct were administered on a molar basis with 1 µl of 4.4 µM solution defined as 1000 IU equivalents (IUe from here on). Such a system allows for equimolar comparison between IL2, mutIL2 and OMCP-mutIL2 despite difference in molecular weight.

Animals:

NJ (8-12 weeks) and C57BL/6J (6-9 weeks) strains of mice were purchased from the Jackson Laboratory (Bar Harbor, Me.). NKG2D$^{-/-}$ mice on the B6 background were kindly provided by Wayne Yokoyama and bred in house (Howard Hughes Institute of Medicine at Washington University in St. Louis). Animals were housed in a barrier facility in air-filtered cages and allowed free access to food and water. For some experiments NJ mice were treated with depleting concentrations of anti-Asialo-GM1 (50 µl day −2; 25 µl day −1) or control rabbit IgG (Wako Chemical Company). Animal procedures were approved by the animal studies committee of Washington University School of Medicine, St. Louis, Mo.

Tissue Harvest and In Vitro Cultures:

Single cell suspension of splenocytes were obtained by crushing whole spleens through 70 µm cell strainers prior to RBC lysis by ACK buffer (Lonza, Walkersville, Md.) and re-filtration through a 40 µm filter. Lungs were digested for 90 minutes at 37° C. in 1 mg/ml collagenase II (Fisher Scientific), and 5 U/ml DNase I (Sigma-Aldridge) prior to processing in an identical fashion to spleens.

For in vitro cultures splenocytes from either A/J, B6, or NKG2D$^{-/-}$ mice were extracted in a sterile fashion and seeded in 12-well plates in complete media (RPMI 1640 supplemented with 10% FBS, 100 U/ml Penicillin and Streptomycin, 2 mM L-glutamine and 50 µM 2-Mercaptoethanol) at 5 million cells per ml per well. The cells were treated with increasing doses of human recombinant IL2, mutIL2, OMCP-mutIL2, or OMCP for 36 hours as described in the manuscript. For some experiments bulk splenocytes were labeled with CFSE and cultured in 1000 IUe/ml of cytokine for 5 days prior to flow cytometric analysis. For NK isolation experiments bulk splenocytes were processed using either the NK cell isolation kit II or CD49b (DX5) positive magnetic bead selection (both from Miltenyi Biotech). For STAT5 phosphorylation experiments, isolated NK cells were stimulated in increasing concentrations of IL2 or construct at 100,000 cells/500 µl for 15 minutes. For experiments evaluating the interaction of NK cells with splenic stroma, DX5 positively selected NK cells were labeled with CFSE (for identification after fixation and permeabilization) and recombined with NK depleted stromal cells. As described in the manuscript, for some studies NKG2D$^{-/-}$ NK cells were combined with wild-type splenocyte stromal cells. For other experiments, NK-depleted splenocytes from wild-type B6 mice were treated with saturating concentrations of anti-IL2a blocking antibody (clone 3C7) or isotype control (both from Biolegend) prior to recombining with NK cells. For such competitive STAT5 phosphorylation experiments 100,000 cells were resuspended into 2 µl complete media containing 1,000 IU/ml of either wtIL2, mutIL2 or OMCP-mut-IL2 (freshly prepared and pre-warmed). The cells were then incubated at 37° C. for 15 minutes Flow Cytometry:

All flow cytometric analysis was performed using saturating concentrations of fluorochrome-conjugated antibodies at 4° C. in FACS buffer consisting of PBS with 2% FBS and 0.4% EDTA. All antibodies were anti-mouse and purchased from BD Bioscience or eBioscience and consisted of anti-CD4 (clones GK1.5 or RM4-5), anti-CD8 (clone 53-6.7), anti-CD278 (ICOS) (clone: 7E.17G9), anti-CD25 (clone PC61), anti-KLRG1 (clone 2F1), CD49b (Integrin alpha 2) (clone DX5), anti-CD3e (clone 1452C11), anti-CD45 (clone 30-F11), anti-CD69 PE (clone H1.2F3), anti-GITR (clone DTA-1), anti-Foxp3 (clone: FJK-16s) and Anti-Stat5 (clone 47/Stat5; pY694). Antibodies were conjugated to either FITC, PE, PerCP-Cy™5.5, PE-Cyanine7, APC, APC-eFluor® 780, eFluor® 450, or Alexa Fluor® 647.

Phospho-STAT5 evaluation was performed by paraformaldehyde fixation, methanol permeabilization and staining with AlexaFluor488-conjugated Anti-Stat5 (pY694) (BD Pharmingen; clone 612599). To accomplish this isolated NK cells or NK cells combined with NK-depleted splenocyte stromal cells were fixed in 2% paraformaldehyde (PFA) at 37° C. for 10 minutes after IL2 stimulation for 15 minutes. The cells were then washed once with ice-cold PBS and permeabilized by adding 0.5 ml/tube of 90% Methanol on ice for 1 hour. The cells were washed once with ice-cold PBS (to remove methanol), and stained for 1 hour with anti-Stat5 (pY694) antibody at room temperature followed by one wash in PBS/0.5% fetal calf serum.

In Vitro Cytotoxicity:

$^{51}$Chromium release was conducted by incubating the target cells with 100 mCi sodium $^{51}$chromate (PerkinElmer) for 1 hour. Bulk splenocytes were used as effector cells and incubated with targets at defined effector:target ratios for 4 hours at 37° C. in round bottom 96 well plates. Specific lysis was expressed as (experimental release−spontaneous release)/(maximum release−spontaneous release)×100% with 0% specific lysis as lowest expressed value.

In Vivo Cytokine Injections:

For select experiment, the mice received intraperitoneal injections of cytokines in 200 µl volume given as ten equal doses given twice a day over a period of five days. As described above all cytokines were normalized to IUe on a molar basis. For select experiments, the mice were then sacrificed on day 6 and organs were fixed in 10% buffered formalin for histological analyses. For other experiments splenocyte and lung lymphocyte populations were analyzed flow cytometrically. For all the in vivo cytokine treatment experiments, animals were weighed (daily or every other day) and expressed as % change from start of cytokine therapy.

For evaluation of serum concentration wtIL2, mutIL2 or OMCP-mutIL2 were labeled with Alexa Fluor® 647 (LifeTechnologies Inc.) according to manufacturer instructions. Serum was collected at times specified and concentration of cytokine determined fluoroscopically according to a standard curve.

In Vivo Tumor Studies:

Lewis lung carcinoma (LLC) cells were subcutaneously injected into B6 or B6 NKG2D$^{-/-}$ mice at $1 \times 10^5$ cells per mouse in 100 µl of sterile saline. Once visible tumors were evident, day 5 post-injection, a five day course of cytokine treatment was started as described above. Measurement of cross sectional tumor diameter was performed using calipers and tumor volume estimated as $4/3\pi r^3$. The mice were sacrificed on day 24 post injection or once they reached a maximal tumor diameter of 20 mm. For NK cell depletion, mice were treated with anti-NK1.1 antibody (clone PK136) or mouse IgG isotype control (both from BioXcell) at 500 µg day −2, 250 µg day −1 and 250 µg weekly for the duration of the experiment. For lymphoma clearance experiments NJ mice were treated with ten doses of cytokine over a period of five days as described above and on day #6 injected intravenously with YAC-1 cells that were labeled with CFSE at $5\times10^6$ cells/mouse. Mice were sacrificed 4 hours later, lungs were digested and viability of YAC-1 determined by forward and side scatter analysis of $CFSE^+$ cells.

Statistics:

Comparison of splenic and lung-resident lymphocytes between various cytokine treatment conditions was performed by unpaired T-test with Welch's correction to account for unequal variance or unequal sample size. Tumor growth between different cytokine conditions was compared by multiple unpaired-T tests performed between various conditions at various time points using the Sidak-Bonferroni correction. Fold change in STAT5 phosphorylation was evaluated by unpaired T-test with Welch's correction in a similar fashion.

REFERENCES FOR EXAMPLES 1-6

1. Spangler, J. B. et al. Antibodies to Interleukin-2 Elicit Selective T Cell Subset Potentiation through Distinct Conformational Mechanisms. *Immunity* 42, 815-825 (2015).
2. French, A. R. et al. DAP12 signaling directly augments proproliferative cytokine stimulation of NK cells during viral infections. *J Immunol* 177, 49814990 (2006).
3. Rosenberg, S. A. et al. Experience with the use of high-dose interleukin-2 in the treatment of 652 cancer patients. *Annals of surgery* 210, 474-484; discussion 484-475 (1989).
4. Rosenberg, S. A. IL2: the first effective immunotherapy for human cancer. J *Immunol* 192, 5451-5458 (2014).
5. Atkins, M. B. et al. High-dose recombinant interleukin 2 therapy for patients with metastatic melanoma: analysis of 270 patients treated between 1985 and 1993. *J Clin Oncol* 17, 2105-2116 (1999).
6. Sim, G. C. et al. IL2 therapy promotes suppressive $ICOS^+$ Treg expansion in melanoma patients. *J Clin Invest* 124, 99-110 (2014).
7. Kolitz, J. E. et al. Recombinant interleukin-2 in patients aged younger than 60 years with acute myeloid leukemia in first complete remission: results from Cancer and Leukemia Group B 19808. *Cancer* 120, 1010-1017 (2014).
8. Krieg, C., Letourneau, S., Pantaleo, G. & Boyman, O. Improved IL2 immunotherapy by selective stimulation of IL2 receptors on lymphocytes and endothelial cells. *Proc Natl Acad Sci USA* 107, 11906-11911 (2010).
9. Heaton, K. M., Ju, G. & Grimm, E. A. Human interleukin 2 analogues that preferentially bind the intermediate-affinity interleukin 2 receptor lead to reduced secondary cytokine secretion: implications for the use of these interleukin 2 analogues in cancer immunotherapy. *Cancer Res* 53, 2597-2602 (1993).
10. Ullrich, E., Koch, J., Cerwenka, A. & Steinle, A. New prospects on the NKG2D/NKG2DL system for oncology. *Oncoimmunology* 2, e26097 (2013).
11. Raulet, D. H. Roles of the NKG2D immunoreceptor and its ligands. *Nat Rev Immunol* 3, 781-790 (2003).
12. Raulet, D. H., Gasser, S., Gowen, B. G., Deng, W. & Jung, H. Regulation of ligands for the NKG2D activating receptor. *Annu Rev Immunol* 31, 413-441 (2013).
13. Giuliani, E., Vassena, L., Cerboni, C. & Doria, M. Release of Soluble Ligands for the Activating NKG2D Receptor: One More Immune Evasion Strategy Evolved by HIV-1 ? *Current drug targets* (2015).
14. Campbell, J. A., Trossman, D. S., Yokoyama, W. M. & Carayannopoulos, L. N. Zoonotic orthopoxviruses encode a high-affinity antagonist of NKG2D. *J Exp Med* 204, 1311-1317 (2007).
15. Lazear, E., Peterson, L. W., Nelson, C. A. & Fremont, D. H. Crystal structure of the cowpox virus-encoded NKG2D ligand OMCP. *J Virol* 87, 840-850 (2013).
16. Kreisel, D. et al. Strain-specific variation in murine natural killer gene complex contributes to differences in immunosurveillance for urethane-induced lung cancer. *Cancer Res* 72, 4311-4317 (2012).
17. Frese-Schaper, M. et al. Influence of natural killer cells and perforinmediated cytolysis on the development of chemically induced lung cancer in NJ mice. *Cancer Immunol Immunother* 63, 571-580 (2014).
18. Dandamudi, U. B. et al. A phase II study of bevacizumab and high-dose interleukin-2 in patients with metastatic renal cell carcinoma: a Cytokine Working Group (CWG) study. *J Immunother* 36, 490-495 (2013).
19. Boyman, O., Kovar, M., Rubinstein, M. P., Surh, C. D. & Sprent, J. Selective stimulation of T cell subsets with antibody-cytokine immune complexes. *Science* 311, 1924-1927 (2006).
20. Smyth, M. J. et al. CD4+CD25+ T regulatory cells suppress NK cell-mediated immunotherapy of cancer. *J Immunol* 176, 1582-1587 (2006).
21. Chang, S. et al. Unique pulmonary antigen presentation may call for an alternative approach toward lung cancer immunotherapy. *Oncoimmunology* 2, e23563 (2013).
22. Plonquet, A. et al. Peripheral blood natural killer cell count is associated with clinical outcome in patients with aaIPI 2-3 diffuse large B-cell lymphoma. *Annals of oncology: official journal of the European Society for Medical Oncology/ESMO* 18, 1209-1215 (2007).
23. Tzeng, A., Kwan, B. H., Opel, C. F., Navaratna, T. & Wittrup, K. D. Antigen specificity can be irrelevant to immunocytokine efficacy and biodistribution. *Proc Natl Acad Sci USA* 112, 3320-3325 (2015).
24. Letourneau, S. et al. IL2/anti-IL2 antibody complexes show strong biological activity by avoiding interaction with IL2 receptor alpha subunit CD25. *Proc Natl Acad Sci USA* 107, 2171-2176 (2010).
25. Ho, E. L. et al. *Costimulation of multiple NK cell activation receptors by* NKG2D. *J Immunol* 169, 3667-3675 (2002).
26. Levin, A. M. et al. Exploiting a natural conformational switch to engineer an interleukin-2 'superkine'. *Nature* 484, 529-533 (2012).
27. Mitra, S. et al. Interleukin-2 activity can be fine tuned with engineered receptor signaling clamps. *Immunity* 42, 826-838 (2015).
28. Boyman, O. et al. Selectively expanding subsets of T cells in mice by injection of interleukin-2/antibody complexes: implications for transplantation tolerance. *Transplantation proceedings* 44, 1032-1034 (2012).
29. Tomala, J. et al. Chimera of IL2 linked to light chain of anti-IL2 mAb mimics IL2/anti-IL2 mAb complexes both structurally and functionally. *ACS chemical biology* 8, 871-876 (2013).

30. Gutbrodt, K. L., Casi, G. & Neri, D. Antibody-based delivery of IL2 and cytotoxics eradicates tumors in immunocompetent mice. *Molecular cancer therapeutics* 13, 1772-1776 (2014).
32. Yamane, B. H., Hank, J. A., Albertini, M. R. & Sondel, P. M. The development of antibody-IL2 based immunotherapy with hu14.18-IL2 (EMD-273063) in melanoma and neuroblastoma. *Expert opinion on investigational drugs* 18, 991-1000 (2009).
33. Carmenate, T. et al. Human IL2 mutein with higher antitumor efficacy than wild type IL2. *J Immunol* 190, 6230-6238 (2013).
34. Heaton, K. M. et al. Characterization of lymphokine-activated killing by human peripheral blood mononuclear cells stimulated with interleukin 2 (IL2) analogs specific for the intermediate affinity IL2 receptor. *Cellular immunology* 147, 167-179 (1993).
35. Imai, K., Matsuyama, S., Miyake, S., Suga, K. & Nakachi, K. Natural cytotoxic activity of peripheral-blood lymphocytes and cancer incidence: an 11-year follow-up study of a general population. *Lancet* 356, 1795-1799 (2000).
36. Lazear, E. et al. Cowpox virus OMCP antagonizes NKG2D via an unexpected binding orientation. *PLos Pathogen* In revision (2014).
37. Deng, W. et al. Antitumor immunity. A shed NKG2D ligand that promotes natural killer cell activation and tumor rejection. *Science* 348, 136-139 (2015).
38. Gorelik, E. & Herberman, R. B. Susceptibility of various strains of mice to urethan-induced lung tumors and depressed natural killer cell activity. *J Natl Cancer Inst* 67, 1317-1322 (1981).
39. Mancia, F. et al. Optimization of protein production in mammalian cells with a coexpressed fluorescent marker. *Structure* 12, 1355-1360 (2004).
40. Hank, J. A. et al. Distinct clinical and laboratory activity of two recombinant interleukin-2 preparations. *Clin Cancer Res* 5, 281-289 (1999).

Introduction to Examples 7-10

Intracellular surveillance mediated by MHC class I (MHCI) is a critical host immune function and as such MHCI molecules are frequently targeted for destruction or intracellular retention by viruses [1]. Many herpesviruses encode at least one protein that prevents the cell surface expression of MHCI [1,2]. However, this immune evasion strategy renders the infected cell susceptible to NK cell-mediated lysis due to loss of inhibitory signals [3]. Viral infection also leads to cell surface display of NKG2D ligands (NKG2DLs) recognized by the activating receptor NKG2D, further predisposing the infected cell towards NK cell-mediated lysis. Therefore, viruses that target MHCI expression often also sabotage NKG2D-mediated cell responses by targeting NKG2DLs on the infected cell [4-7].

NKG2DLs are not normally expressed on the cell surface but can be induced by cellular stress [8]. The specific trigger for NKG2DL expression is not known but NKG2DLs are upregulated in response to several viral infections [9-12]. NKG2DLs comprise a large group of proteins all recognized by NKG2D, despite having low sequence identity. NKG2DLs include the MIC (A and B) and ULBP (1-6) families in humans as well as MULTI and the RAE-1 ($\alpha$-$\epsilon$) and H60 (a-c) families in mice [13]. The redundancy in NKG2DLs is likely due to a combination of tissue specific expression patterns of the ligands and the need to counter viral NKG2D evasion strategies [14]. Many viruses have evolved mechanisms to inhibit the cell surface expression of NKG2DLs as a means of interfering with NKG2D surveillance of viral infection. This strategy is most apparent among $\beta$- and $\gamma$-herpesviruses, in which four murine cytomegalovirus proteins (m138, m145, m152, m155) [15-18], two human cytomegalovirus proteins (UL16, UL142) [19, 20] and one Kaposi's sarcoma-associated herpesvirus protein (K5) [21] have been demonstrated to block NKG2DL surface expression. This evasion strategy is also found in RNA viruses, as hepatitis C virus NS3/4a and human immunodeficiency virus Nef proteins also block the expression of a subset of NKG2DLs [22,23]. Additionally, human cytomegalovirus, herpes simplex virus type 1 and Epstein-Barr virus each also encode at least one miRNA that prevents translation of MICB [24,25]. Similarly, JCV and BKV polyoma viruses target ULBP3 with miRNAs [26]. However, blocking NKG2DL expression on the infected cell is an imperfect evasion strategy, since no single viral protein or miRNA has been shown to block the expression of all NKG2DLs.

Like several herpesviruses, cowpoxvirus (CPXV) also sabotages MHCI expression. CPXV expresses CPXV012 and CPXV203, two proteins that prevent TAP-mediated peptide transport and MHCI trafficking to the cell surface, respectively [27-34]. Ectromelia virus, a related orthopoxvirus, induces NKG2DL expression and NKG2D is critical for the control of ectomelia virus pathogensis [35]. Infection with another orthopoxvirus, monkeypox virus, leads to dramatic expansion of NK cells but impaired NK cell function [36]. Together this suggests that CPXV infected cells would be sensitive to NK cell-mediated lysis.

Unlike herpesviruses, CPXV does not target NKG2DLs. Instead this virus targets NKG2D directly by encoding a competitive inhibitor of NKG2DLs, orthopoxvirus MHC class I-like protein (OMCP) [37,38]. OMCP is a 152 residue protein that is secreted from infected cells and antagonizes the NKG2D-mediated killing of NKG2DL-expressing target cells [37]. OMCP also plays an important role in vivo, with OMCP-null CPXV attenuated in mouse models of infection (M. Sun et al, personal communication). OMCP binds to murine NKG2D with an affinity equal or greater than all tested murine NKG2DLs, and to human NKG2D with an affinity ~5,000-fold higher than human NKG2DLs [37-40].

Despite their divergence in sequence identity, all known host NKG2DLs share common structural features [41,42]. NKG2DLs contain an MHCI-like platform domain composed of an eight-stranded beta sheet with two helices [43-47]. The platform domain is subdivided into $\alpha$1 and $\alpha$2 domains, with each domain containing four beta strands and an alpha helix. Unlike MHCI, the groove between the helices of the NKG2DL platform domain is closed and therefore NKG2DLs do not bind peptides.

Like host NKG2DLs, OMCP also adopts an MHCI-like platform domain [38]. However, the platform domain of OMCP has been trimmed to have only a six-stranded beta sheet with shorter flanking helices. We termed the helix of the $\alpha$1 domain H1 and the discontinuous helix of the $\alpha$2 domain is termed H2a and H2b. The H2a and H2b helices of OMCP are also rearranged to be flatter against the beta sheet and to be splayed apart from each other. These differences in the OMCP structure were hypothesized to be important for the high affinity binding of OMCP to NKG2D. However, OMCP was still expected to bind to NKG2D in the same orientation as host NKG2DLs, i.e. with the alpha helices oriented diagonally within the symmetric NKG2D binding groove.

Here we report the 2.0 Å-resolution structure of human NKG2D bound to OMCP of the Brighton Red strain of cowpoxvirus. The structure reveals a significant reorientation of OMCP in the NKG2D binding groove relative to host NKG2DLs. The interface of OMCP with NKG2D is highly complementary, buries a significantly larger surface area than host NKG2DLs, and remains continuous across the entire NKG2D binding groove. This novel binding adaptation and high affinity allows OMCP to compete with the high local concentration of membrane-associated host NKG2DLs. We further show that the mechanism of NKG2D antagonism requires OMCP to be secreted, lest it lead to NKG2D signaling.

Example 7. Structure Determination of OMCP-NKG2D

We had previously solved the structure of OMCP alone and shown that, similar to host NKG2DLs, OMCP adopts an MHCI-like platform domain [38]. Despite the overall similarity of the domain structure of OMCP to host NKG2DLs, OMCP had several notable deviations in the putative NKG2D-binding site that were hypothesized to be important for the high affinity binding of OMCP to NKG2D. To further understand the unusually high affinity of OMCP for NKG2D, we crystallized and solved the structure of OMCP bound to human NKG2D.

Initial crystallization trials with OMCP and NKG2D yielded ~30 different crystallization conditions. Subsequent data collection and molecular replacement of multiple low-resolution crystal forms all yielded similar partial solutions, with alternating sheets of OMCP-NKG2D complexes separated by undefined density. In the original structure of OMCP alone, the beta sheets packed to form a trimer with the alpha helices oriented away from the center [38]. An identical OMCP trimer formed in the OMCP-NKG2D partial solutions, with NKG2D now bound to the outward facing helices (data not shown). In an attempt to change the lattice packing, we introduced mutations into the beta sheet of OMCP that were designed to break the trimeric interface. These mutations were on the opposite face of OMCP from the NKG2D binding site to avoid disrupting OMCP-NKG2D binding. A mutant form of OMCP (Y23D, F95D) crystallized with NKG2D in a new space group and the crystals diffracted to 2.0 Å (Table 1)(FIG. 24A).

The electron density map was continuous and unambiguous throughout all chains of the structure, with the exception of Q108 in OMCP. This residue was situated in the center of the largest loop of OMCP and unambiguous density for this residue was also absent from the structure of OMCP alone [38]. The structure of OMCP bound to NKG2D showed no major differences from our previous structure of OMCP alone, with an RMSD for all atoms of 0.8 Å. Likewise, NKG2D was also similar to previous NKG2D structures with RMSDs ranging from 0.5-0.9 Å. The β3-β4 loop of NKG2D is the only region of either OMCP or NKG2D that displayed above-average B factors. This loop is thought to be flexible and has had above average B factors in all previous NKG2D structures [48]. Interestingly, the peptide bond between S193-S194 in our NKG2D structure had a cis conformation not described in other NKG2D structures (FIG. 29).

Example 8. The Interface Between OMCP and NKG2D

OMCP was hypothesized to bind to the same surface of NKG2D used by host NKG2DLs because (i) OMCP competed with host NKG2DLs for NKG2D and (ii) mutations within the NKG2DL-binding pocket of NKG2D altered OMCP binding affinity [38]. OMCP does bind NKG2D using the same concave binding pocket as host NKG2DLs (FIG. 24A). OMCP binds primarily using the discontinuous helices of its a2 domain, H2a and H2b. The position of the H2a and H2b helices is such that every surface exposed side chain of both helices within the binding site directly contacts NKG2D (FIG. 24B). Only two contacts are found outside of H2a and H2b, Ile49 and Arg66. Both of these residues are within the α1 domain but lie outside of the H1 helix.

Twelve OMCP residues contact eighteen NKG2D residues to form a mixture of bond types (Table 2). Three residues in each NKG2D half-site are known as core binding residues because they make contacts with all known host NKG2DLs. The core residues of NKG2D subunit A ($NKG2D^A$) (Tyr152, Tyr199, Met184) form two hydrogen bonds and make extensive hydrophobic contacts with OMCP residues. The core residues of $NKG2D^A$ contact four OMCP residues and the most critical of these residues is Phe122. Phe122 makes multiple hydrophobic contacts with all three $NKG2D^A$ core residues, including pi-stacking with Tyr152. Phe122 also forms a backbone-to-sidechain hydrogen bond with Tyr152. Interestingly, OMCP is the first NKG2D ligand not to utilize all six NKG2D core-binding residues, with only Met184 and Tyr152 of NKG2D subunit B ($NKG2D^B$) contacting OMCP. $NKG2D^B$ Met184 and Tyr152 each make a single hydrogen bond and hydrophobic contacts with OMCP residues. Two OMCP residues, Trp127 and Asp132, make contacts with both NKG2D protomers. OMCP Trp127 forms a hydrogen bond to Lys150 of $NKG2D^A$ and makes several hydrophobic contacts with Leu148 of $NKG2D^B$, Lys150 and Ser151 of $NKG2D^A$. OMCP Asp132 forms a hydrogen bond with Tyr152 of $NKG2D^B$ and a salt bridge with Lys150 of $NKG2D^A$ (FIG. 25A).

Due to the high affinity of the OMCP-NKG2D interaction we harnessed a high throughput in vitro selection approach to find NKG2D-binding null mutants (Table 3). The results of the screen identified D132 as an important residue for disrupting NKG2D binding. We then generated the mutation D132R in attempt to completely ablate NKG2D binding. Surprisingly, the D132R mutant alone was unable to bind to NKG2D at concentrations 35-fold above the $K_D$ (FIG. 25B), but did not affect binding of OMCP to FcRL5-expressing cells (FIG. 25C). This mutation is likely to cause significant steric clashes, as well as disrupting both interactions made by Asp132 to $NKG2D^A$ Lys150 and $NKG2D^B$ Tyr152 (FIG. 25A).

Figure 26A:
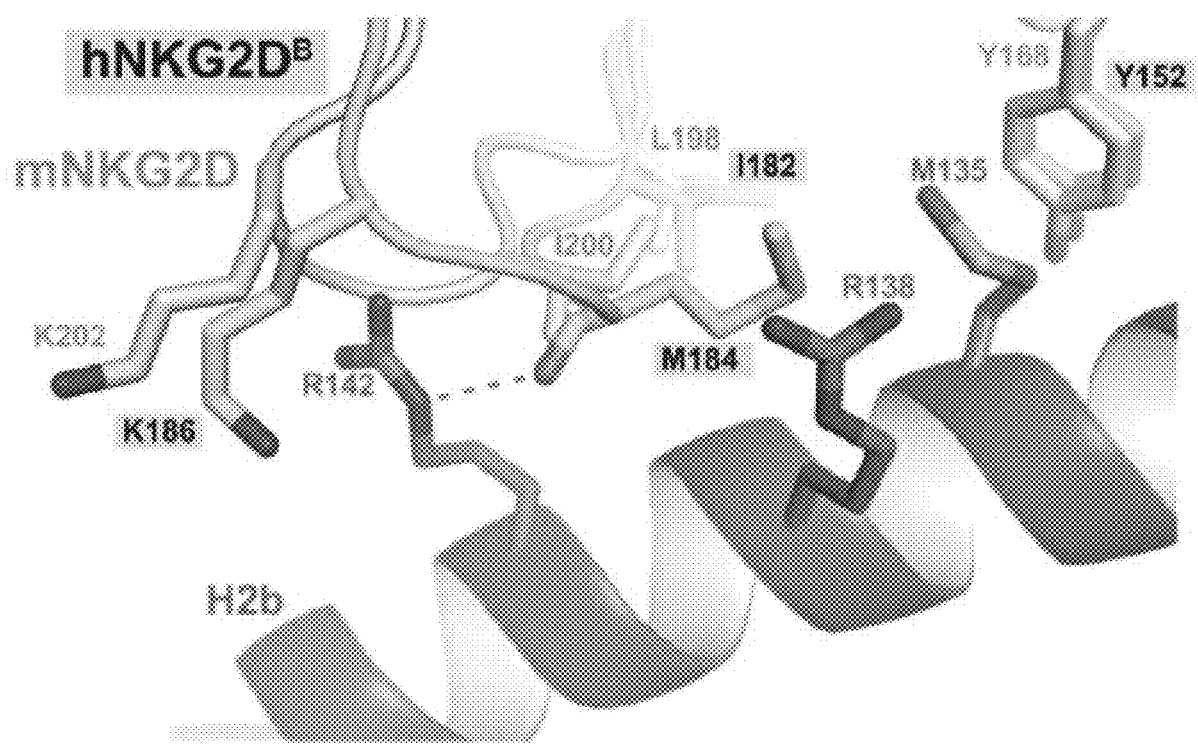
Figure 26B:
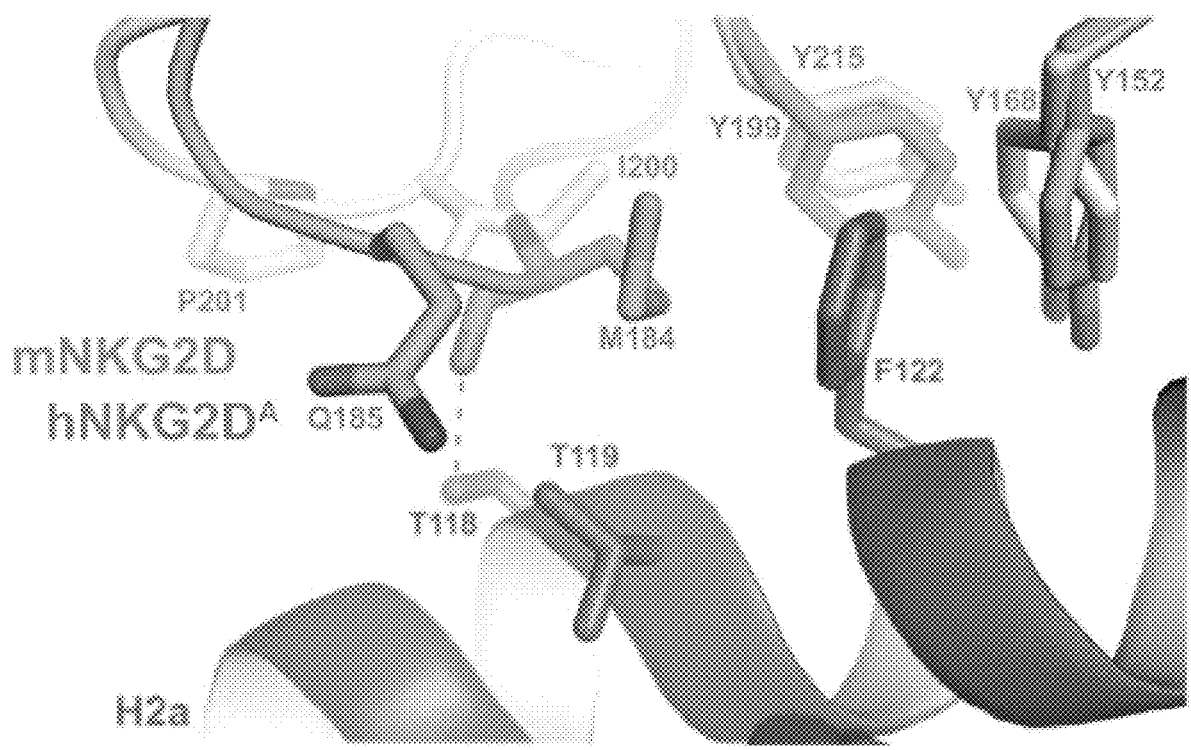
Figure 26C:
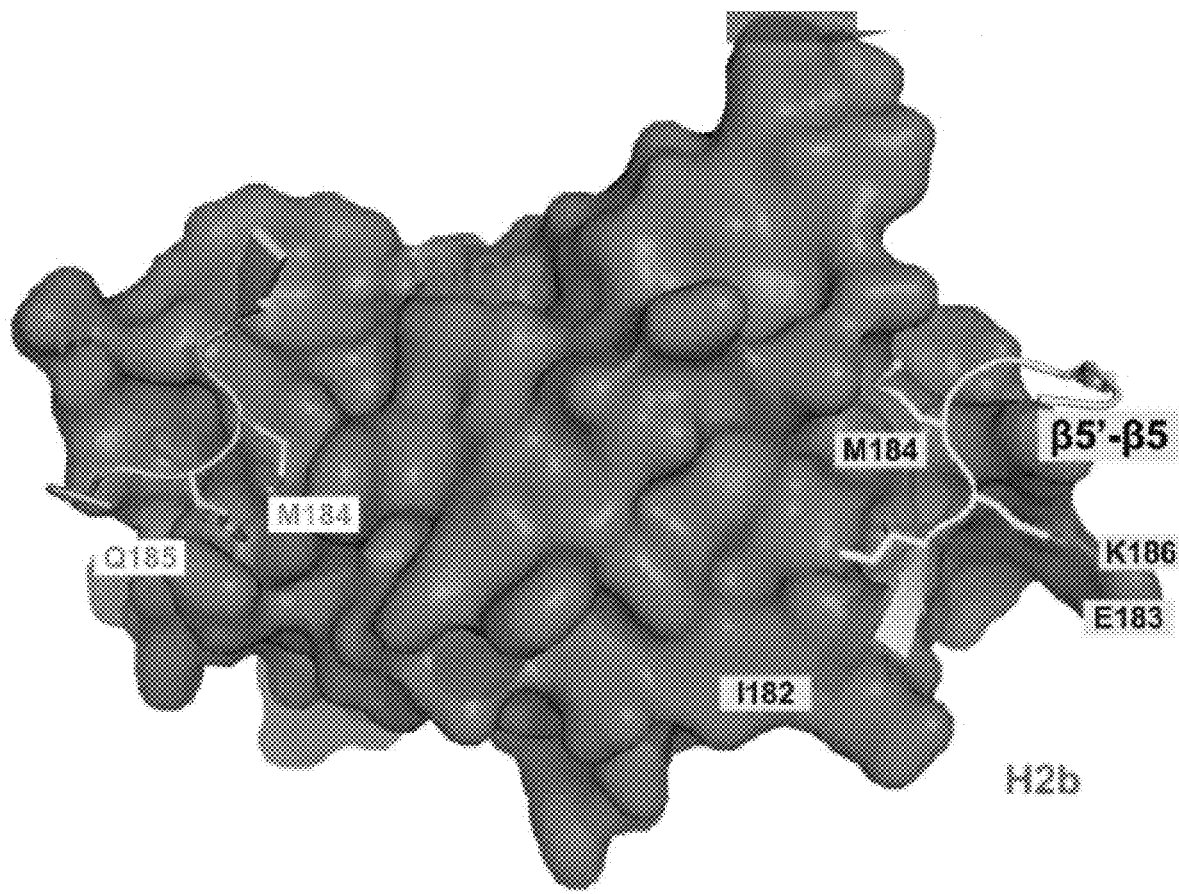
Figure 26D:
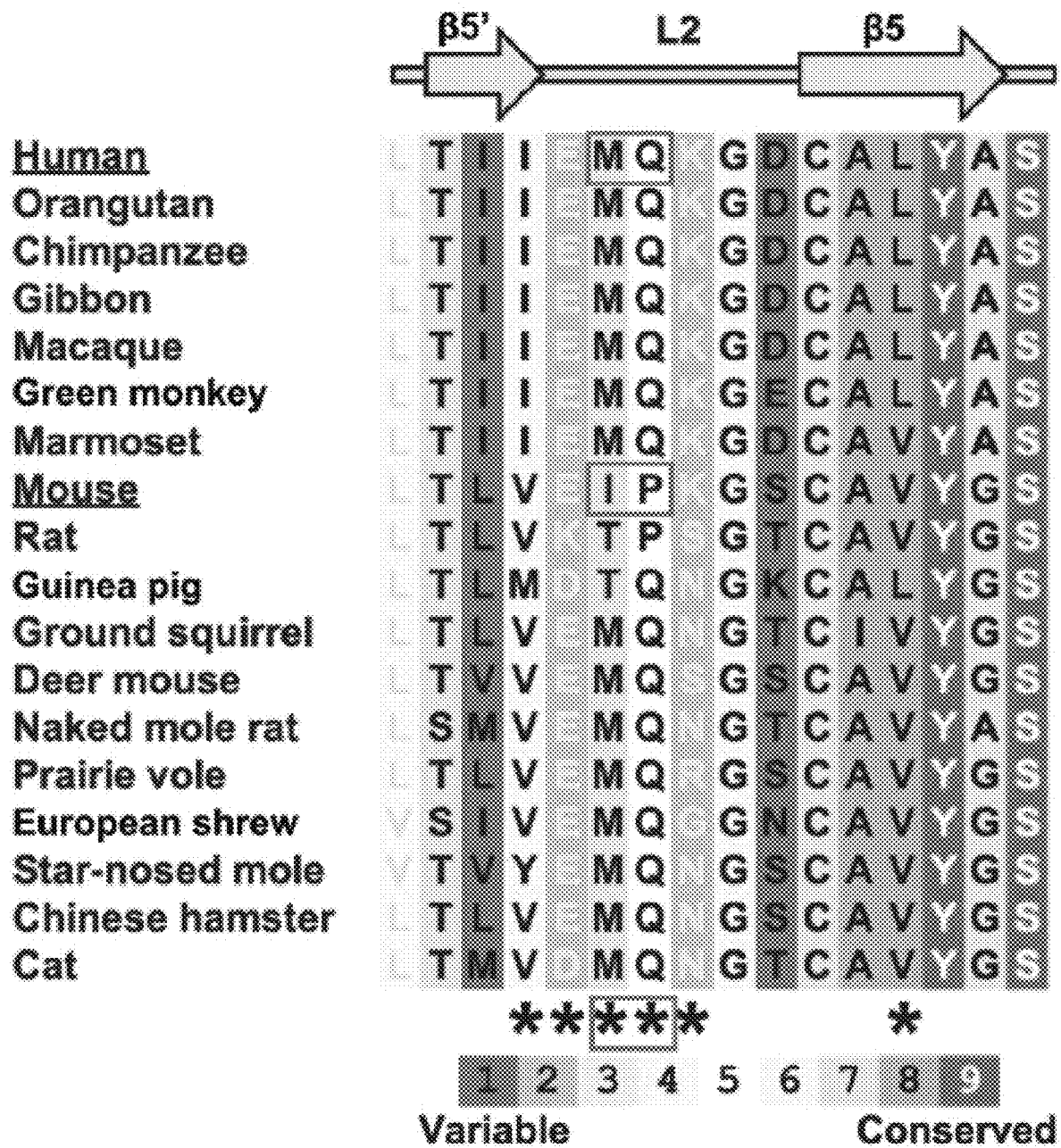

Previously, the 14-fold higher affinity of OMCP for human vs murine NKG2D was mapped to three amino acid substitutions in the β5'-β5 loop of NKG2D, abbreviated L2 [38]. In addition to the substitutions themselves (I182V, M184I and Q185P), the position of the loop between NKG2D orthologs differs. L2 in human NKG2D is bent towards the center of the concave binding cavity compared to L2 of murine NKG2D. Superimposition of murine NKG2D onto the human NKG2D-OMCP structure reveals that the contacts between OMCP and Met184 (mNKG2D residue 1200) in $NKG2D^B$ and between Met184 (1200) and Glu 85 (P201) in $NKG2D^A$ would be altered due to the different position of the murine (β5'-β5 loop (FIG. 26A-B). This alteration would disrupt contacts with three residues in OMCP H2a, three residues in H2b and Arg66 within the α1 domain. Of the contact residues of L2, Met184 makes the most significant contacts in both NKG2Ds (Table 2)(FIG. 26C). Critically, of the 58 NKG2D sequences available in GenBank, 54 conserve the Met184 and Glu185 found in the high affinity human NKG2D (FIG. 26D).

Eighteen OMCP variants have been described between different CPXV and MPXV strains [51]. In this study we have crystallized OMCP from the Brighton Red strain of CPXV which has >60% sequence identity with the highly conserved sequence of the other 17 OMCP variants, collectively termed $OMCP_{mpx}$. Of the 12 OMCP contact residues observed, 9 are identical to $OMCP_{mpx}$. Of the remaining contacts, all three are conservative hydrophobic substitutions (I49L, T1181 and M1351) (FIG. 27). $OMCP_{mpx}$ binds to NKG2D and the substitutions in the NKG2D contact residues are unlikely to grossly affect the affinity of $OMCP_{mpx}$ for NKG2D [37].

Example 9. A Novel NKG2D-Binding Adaptation

Host NKG2DLs have low sequence identity but overall similar structures, with MHCI-like platform domains binding diagonally across the symmetric binding groove created by the NKG2D homodimer [13,41,52]. Host ligands contact one NKG2D half site with H1 and the S1-S2 loop, and contact the second NKG2D half site with H2b. Despite the similar MHCI-like fold, OMCP binds the NKG2D binding groove in a novel orientation, rotating ~45° relative to host NKG2DLs (FIG. 27). Instead of using H1 and S1-S2 loop like host ligands, OMCP has replaced these contacts with H2a. This rotation leads to the helices of OMCP being perpendicular to the NKG2D binding groove, instead of lying diagonally across it.

Two unique rearrangements of H2a and H2b make the OMCP orientation possible. The α2 helices of OMCP and host NKG2DLs are discontinuous, with the two shorter helices hinged relative to each other. For host ligands, the angle between H2a and H2b is ~90°, positioning H2a away from the NKG2D interface. In contrast, OMCP has increased the hinge angle between the helices by ~20°, leading to a α2 helix that is flatter relative to the beta sheet of OMCP. The flattening of the α2 helix allows H2a and H2b to closely complement the concave binding groove of the NKG2D homodimer (FIG. 24B). The tight fit of the α2 helix for NKG2D is reflected in the high shape complementarity (0.77) and buried surface area (2,612 Å$^2$). In contrast, host NKG2DLs have shape complementarity ranging from 0.63-0.72 and buried surface areas ranging from 1,700-2,180 Å$^2$ [43,44,46].

The second unique feature of the α2 helix is the separation of H2a and H2b relative to each other. This region also contains a translation that completely separates H2a and H2b into two distinct helices. This translation is critical for NKG2D binding because it allows each helix to be directly centered on the core binding sites of each NKG2D monomer (FIG. 27). This creates a symmetric binding site on OMCP that recognizes the symmetric binding groove created by the NKG2D dimer. The symmetry between OMCP and NKG2D binding is in stark contrast to the canonical binding of an asymmetric host ligand to the symmetric NKG2D binding groove [52]. However, one element of asymmetry remains in the OMCP-NKG2D interaction because each NKG2D half-site recognizes an OMCP helix in a different N- to C-terminal orientation, demonstrating again the flexibility of NKG2Ds rigid adaptation recognition [41,53].

The contact sites between NKG2D and host NKG2DLs are made up of two patches centered on the core binding sites of NKG2D and H1/S1-S2 loop and H2b of NKG2DLs [41]. As a result, the interface of NKG2D with NKG2DLs is discontinuous, particularly in the center of the NKG2D binding groove (FIG. 27). Due to the unique orientation of OMCP, H2a and H2b make continuous contacts along the entire NKG2D binding groove (FIG. 27). The sidechains of OMCP Lys126, Trp127, Glu131 and Asp132 make contacts with residues in the center of the NKG2D binding groove and bridge the core binding sites on each NKG2D monomer (FIG. 24B). In particular, OMCP Trp127 is directed towards the center of the NKG2D dimer and makes hydrophobic contacts with residues on both NKG2D monomers, effectively closing any gaps in the binding interface.

Example 10. Signaling of NKG2D Upon Ligand Engagement

CPXV and MPXV-infected cells secrete OMCP, which can act as an NKG2D-antagonist [37]. This immune evasion strategy is reminiscent of cancer induced-NKG2DL shedding. Some cancer cells proteolytically cleave NKG2DLs from the cell surface using matrix metalloproteinases (MMPs), simultaneously preventing NKG2D-bearing lymphocytes from targeting the cancer cell, as well as creating soluble NKG2DLs to inhibit NKG2D in trans. Cell-associated NKG2DLs trigger NKG2D effector functions (FIG. 28A), while cancer-induced, soluble NKG2DLs block NKG2D function (FIG. 28B). Like shed NKG2DLs, OMCP is soluble and blocks NKG2D function in trans [37] (FIG. 28C). Unlike host NKG2DLs, OMCP binds NKG2D with a novel orientation. We therefore asked whether OMCP could serve as a NKG2D agonist in the context of the cell membrane, analogously to host NKG2D ligands. Since OMCP is a secreted protein, an artificially cell-associated OMCP was constructed by using a heterologous transmembrane domain from Thy1.1 [37] (FIG. 28D). To measure NKG2D-mediated cell killing, we stably transduced Ba/F3 cells with retroviral vectors expressing either the OMCP-Thy1.1 construct or host NKG2DLs. OMCP-Thy1.1-expressing target cells were killed equivalently to host NKG2DL-transduced target cells, indicating that despite its altered binding orientation, cell-associated OMCP was able to activate NKG2D signaling (FIG. 28E). Thus, OMCP must be secreted lest it active NKG2D-effector functions itself, despite potential loss of efficacy due to diffusion.

Discussion for Examples 7-10

While many viruses have adopted a general mechanism of NKG2D-sabotage by trying to retain multiple host-encoded NKG2D ligands within the infected cell, CPXV and MPXV take the very different approach of targeting NKG2D directly. Since NKG2D is monomorphic, this mechanism has the significant advantage of requiring a single protein to prevent NKG2D recognition of the infected cell. The large number of sequence-divergent host NKG2DLs and their associated polymorphisms are thought to be driven by selection from pathogen-encoded NKG2DL antagonists [14]. Likewise, viral NKG2L antagonists are under selective pressure from the diverse host NKG2DLs in a continual cycle of adaptation. Due to the need to recognize multiple NKG2DLs, NKG2D has a limited mutational space to adapt. The limited ability of NKG2D to mutate is yet another advantage of OMCP directly targeting NKG2D, instead of NKG2DLs.

Similarly to OMCP, some cancer cells shed host NKG2DLs to create their own soluble NKG2D antagonists. However, this strategy has the additional benefit of removing host NKG2DL from the surface of cancer cells. In contrast, CPXV and MPXV lack a known mechanism of blocking host NKG2DL surface expression. Secreted OMCP must then be able to compete efficiently against the high local concentration of multiple host NKG2DLs on the infected cell, as well as against diffusion away from the infected cell. One possible way to increase OMCP's ability to compete with host ligands would be to increase the avidity of OMCP by having multiple NKG2D-binding domains. However, a multimeric OMCP could crosslink NKG2D and potentially trigger NKG2D-mediated killing. Therefore, secreted OMCP must be monomeric to prevent aberrant NKG2D signaling. Thus to compensate for these deficiencies, OMCP must have the highest affinity possible to effectively compete against cell-associated host NKG2DLs [37,38]. The half-life of ligand-receptor interactions correlate well with physiological competitiveness [55]. OMCP binds human and murine NKG2D with half-lives of 348 and 54 seconds, respectively, compared to half-lives of 1.5-18 seconds for most NKG2DLs [38,44,56]. Indeed, the increased half-life for NKG2D allows OMCP to effectively antagonize NKG2D-mediated immunity in a murine infection model (M. Sun et al, personal communication).

To understand the molecular basis for the long half-life of OMCP for NKG2D, we previously determined the structure of OMCP alone, and here, we report the structure of OMCP bound to NKG2D. The structure of OMCP alone was grossly similar to that of host NKG2D ligands, containing an atypical MHCI-like platform domain. Host NKG2D ligands bind with the helices of their platform domains oriented diagonally within the symmetric binding groove of NKG2D. Thus it was expected that OMCP was a viral mimic of host NKG2D ligands and would interact with NKG2D analogously.

The structure of OMCP-NKG2D instead revealed a novel orientation for an NKG2D ligand in the NKG2D binding groove. Alterations within the α2 domain helix allow OMCP to arrange its helices perpendicularly within the binding groove. This reorientation places the H2a and H2b helices directly in contact with the core binding sites of NKG2D and also forms the largest and most continuous binding interface with NKG2D. Because the forces (hydrogen bonds, van der Waals, hydrophobic interactions) that mediate protein-protein interactions are individually weak, a large, continuous interface with high shape complementary allows for a cumulatively strong interaction between proteins. This change in the binding orientation of OMCP reveals how the MHCI-like platform used by host ligands can be adapted by a pathogen to enhance NKG2D binding.

Since host NKG2DLs and OMCP have a similar MHCI-like platform, it is reasonable to wonder why no host ligand has evolved an analogous high-affinity interaction with NKG2D. One likely reason is that the host immune response must be carefully calibrated to balance the need for protection against the threat of autoimmunity. Since the expression of NKG2DLs on the cell surface signals for effector functions, even a small amount of high affinity host ligand on the cell surface could trigger an immune response, and the resulting tissue damage could be deleterious for the host. Indeed, NKG2D-expressing cells and/or aberrant expression of host NKG2DLs have been implicated in diabetes, celiac disease and rheumatoid arthritis [57-60]. Viruses are not constrained by autoimmune selective pressures. Therefore, CPXV and MPXV were free to evolve a viral NKG2DL with the highest possible affinity to maximize immune evasion potential.

Interestingly, OMCP triggers NKG2D signaling when attached to a target cell membrane, despite the novel orientation of OMCP relative to host NKG2DLs. The interaction of host NKG2DLs with the dimeric NKG2D bears broad structural similarity to the interaction between MHC molecules with their cognate T cell receptors (TCRs). In both cases, the NKG2DL/MHC lies diagonally across the surface created by the dimeric NKG2D/TCR. However, there are several examples of MHC-TCR complexes that, like OMCP-NKG2D, interact with unconventional orientations [61-65]. Several of these complexes involved autoimmune MHC-TCR complexes that were tilted or rotated outside of the normal range for MHC-TCR complexes [61,65]. While these receptors could induce TCR signaling at high MHC concentrations, they failed to assemble characteristic immunological synapses [66]. A striking example of unconventional binding was found when an in vitro peptide library-MHC-TCR (H2-$L^d$-42F3) screen produced a p3A1-H2-$L^d$-42F3 complex with an interface rotated ~40° relative to other H2-$L^d$-42F3 complexes. This rotation places the TCR nearly parallel with the MHC peptide-binding groove and shifted the interface center almost entirely on one of the MHC α helices—an orientation strikingly similar to the interface of OMCP-NKG2D [65]. Interestingly, the p3A1-H2-$L^d$-42F3 complex failed to induce TCR signaling [65]. Thus, unlike OMCP/NKG2D, the orientation of MHC relative to TCR is an important factor for signaling.

OMCP-NKG2D and p3A1-H2-$L^d$-42F3 have opposite signaling outcomes, despite having very similar orientations. TCR signaling requires co-receptor binding to either the α2/β2 or α3 domains of MHCII or MHCI, respectively. The failure of p3A1-H2-$L^d$-42F3 to signal, and of other unconventional MHC-TCR complexes to form true immunological synapses, is potentially due to the inability of co-receptors to form correct quaternary structures for signaling [64,65,67]. Signaling by NKG2D is not known to require co-receptor stimulation and the majority of NKG2DLs lack the co-receptor binding α2/β2 or α3 domains of true MHC molecules. This difference in co-receptor dependency likely explains why OMCP (when attached via transmembrane) is still competent to stimulate NKG2D-signaling compared to MHC-TCR complexes with unconventional binding orientations. Further, it suggests that clustering of NKG2D on the cell surface is the major determinant of NKG2D-mediated activation.

Methods for Examples 7-10

Identification of NKG2D-Binding Null Mutant D132R.

A high throughput in vitro selection approach based on combinatorial cell surface display was utilized to identify NKG2D-binding null mutants. The sequence of OMCP was globally mutagenized using error-prone PCR, and the mutated amplicons were spliced to a signal-less Thy1.1 cDNA via overlap extension PCR. This library of mutated OMCPs fused to unmutated Thy1.1 was cloned into the pMXs-IRES-EGFP retroviral transfer vector (kind gift of Toshio Kitamura, University of Tokyo) to generate a molecular library for transduction into Ba/F3 cells. The transductants were then sorted for green fluorescence and anti-Thy1.1 expression to yield a cellular library whose members all had surface expression of OMCP, filtering out mutations giving frameshifts, premature stop codons, and folding-incompetent OMCP. This OMCP library was sorted for NKG2D binding using NKG2D-tetramers. Sorted cells were cloned by limiting dilution and analyzed. The retroviral cassettes of cells lacking or having reduced NKG2D-binding activity were amplified and sequenced. Utilizing this approach, we identified Asp132 as a critical residue for NKG2D binding.

Protein Expression and Purification.

$OMCP_{BR}$ and human NKG2D expression constructs were previously described [38]. The (D132R) $OMCP_{BR}$ protein was prepared identically to WT $OMCP_{BR}$. (23D/95D)

OMCP-NKG2D complex was reconstituted by oxidative co-refolding from purified inclusion bodies, as described previously [38]. Refolded protein was slowly diluted 10-fold with water and captured on a 5 ml HiTrap Q HP column (GE Healthcare) using a Profinia instrument (Bio-Rad). The captured protein was washed with 50 mM Tris, pH 8.5, 20 mM NaCl and bulk eluted with 50 mM Tris, pH 8.5, 250 mM NaCl. The eluted protein was then concentrated and further purified by gel filtration chromatography on a Superdex S75 column (16/60; Amersham Biosciences). Fractions containing mono-dispersed OMCP-NKG2D complex (~50 KDa) were pooled and buffer exchanged into 25 mM Ammonium acetate pH 7.4.

Crystallization, Data Collection and Processing.

Native protein crystals were grown by hanging drop vapor diffusion at 20° C. by streak seeding into a well solution containing 15% PEG 3350, 0.2M MgCl2, 0.1M Bis-Tris pH 6.75. Crystals were cryoprotected with well solution containing 15% glycerol before flash freezing directly in a liquid nitrogen bath. Diffraction data were collected at the Advanced Light Source synchrotron (beam line 4.2.2). Native (23D/95D) OMCP-hNKG2D crystal diffraction data were collected at 100 K and at a wavelength of 1.00004 Å. Additional diffraction data statistics are summarized in Table 1. Data processing with HKL2000 [68] showed the crystals belonged to the primitive monoclinic space group $P2_1$ (space group #4). The asymmetric unit of the crystal contained two copies of the (23D/95D) OMCP-hNKG2D complex.

Model Building and Refinement.

The structures of human NKG2D (1MPU) [48] and OMCP (4FFE) [38] were used as search models for molecular replacement through Phenix [69]. Reiterative refinement and manual rebuilding were performed using Phenix and Coot [70], respectively. Both 2Fo-Fc and Fo-Fc maps were used for manual building and to place solvent molecules. The final model yielded an $R_{work}$ of 16.6% and $R_{free}$ of 21.4%, with 4% of all reflections set aside for free R factor cross-validation. Progress in refinement was also measured using the MOLPROBITY webserver [71]. The final Ramachandran statistics for the model were 98% favored and 0% outliers. Additional refinement statistics are summarized in Table 1. Images of structures were produced using the program PyMol [72].

Structure Analysis.

Analysis of the contact residues, buried surface area and shape complementarity of the OMCP-NKG2D interface were carried out using the programs Ligplot+ [73], PISA [74] and SC [75]. Structural programs as compiled by the SBGrid consortium [76]. Analysis of NKG2D conservation was performed using the ConSurf server [77-80]. GenBank numbers for species used in Consurf analysis are: Humans (30749494), Borean orangutan (21902299), Chimpanzee (57113989), Gibbon (332232684), Macaque (355785888), Green Monkey (63/506,3485), Common marmoset (380848799), Mouse (148667521), Brown rat (149049263), Guinea Pig (348569092), Ground squirrel (532114387), Deer mouse (589967905), Naked mole rat (512868733), Prairie vole (532053033), European Shrew (505834608), Star-nosed mole (507978716), Chinese hamster (537136230), and Cat (410963826).

Atomic Coordinates.

The atomic coordinates (accession code 4PDC) have been deposited in the Protein Data Bank, Research Collaboratory for Structural Bioinformatics (Rutgers University, New Brunswick, N.J.)

In Vitro NK Cell Killing Assays.

Splenocytes from C57BL/6 mice were preactivated with 200 U/ml IL2 for 24 hours and used as cytotoxic effectors against stably transduced Ba/F3 cell lines in standard killing assays. Target cells were carboxyfluorescein succinimidyl ester (CFSE) labeled and co-incubated with activated splenocytes at 37° C., 5% CO2 for 4 hours at effector:target ratios of 10:1, 20:1, and 40:1. Killing percentage was determined by incorporation of the dead cell exclusion dye 7-amino-actinomycin D (7AAD) in the CFSE+ target population as assessed by flow cytometry. Percent specific lysis was calculated using the formula [(experimental dead %−background dead %)/(maximum release dead %−background dead %)]×100. C57BL/6 mice were obtained from the National Cancer Institute (Charles River, Mass.). Mice were maintained under specific pathogen-free conditions and used between 8 and 12 weeks of age. Single cell suspensions of splenocytes used in killing assays were generated using standard protocols [81].

TABLE 1

Data collection and refinement statistics

| Data collection | $OMCP_{BR}$-hNKG2D |
|---|---|
| Space group | $P2_1$ |
| Cell dimensions | |
| a, b, c (Å) | 43.3, 101.1, 91.4 |
| α, β, γ (°) | 90.0, 91.6, 90.0 |
| Resolution (Å) | 50-2.0 (2.07-2.00) |
| $R_{sym}$ | 11.8 (48.5) |
| I/σ | 14.5 (3.8) |
| Completeness (%) | 93.5 (91.5) |
| Redundancy | 6.2 (5.3) |
| Refinement | |
| Resolution (Å) | 44-2.0 |
| Total reflections | 309693 |
| Unique reflection | 50139 |
| $R_{work}$ | 16.6% (21.0%) |
| $R_{free}$ | 21.4% (29.5%) |
| Wilson B-factor | 21.62 |
| Protein residues | 791 |
| Water molecules | 524 |
| R.M.S. deviations | 0.003 |
| Bond lengths (Å) | |
| Bond angles (°) | 0.79 |

[a] As defined by PHENIX [69]

TABLE 2

Interface contacts between NKG2D and OMCP

| NKG2D-A | OMCP | Bond type |
|---|---|---|
| Lys150 | Asp132 | Salt bridge |
| Lys150 | Trp127 | H bond |
| Lys150 | Trp127 | φ (3) |
| Ser151 | Lys126 | H bond |
| Ser151 | Trp127 | φ (1) |
| Tyr152 | Phe122 | H bond |
| Tyr152 | Phe122 | φ (9) |
| Tyr152 | Lys126 | φ (5) |
| Met184 | Thr118 | H bond |
| Met184 | Thr119 | φ (1) |
| Met184 | Phe122 | φ (5) |
| Gln185 | Arg66 | φ (1) |
| Leu191 | Phe122 | φ (1) |
| Tyr199 | Phe122 | φ (4) |
| Glu201 | Arg66 | Salt bridge |
| Thr205 | Arg66 | H bond |

TABLE 2-continued

Interface contacts between NKG2D and OMCP

| NKG2D-B | OMCP | Bond type |
|---|---|---|
| Leu148 | Trp127 | φ (1) |
| Ser151 | Glu131 | H bond |
| Tyr152 | Asp132 | H bond |
| Tyr152 | Glu131 | φ (3) |
| Tyr152 | Met135 | φ (5) |
| Ile182 | Ile49 | φ (2) |
| Glu183 | Arg142 | Salt bridge |
| Met184 | Met135 | φ (1) |
| Met184 | Arg138 | φ (2) |
| Met184 | Arg142 | H bond |
| Lys186 | Arg142 | φ (1) |
| Leu191 | Met135 | φ (1) |
| Glu201 | Arg138 | Salt bridge |

Hydrogen bonds (H bonds), salt bridges and carbon-to-carbon hydrophobic interactions (φ) are shown for each contact residue. The number of hydrophobic interactions between contact residues is designated in parenthesis.

TABLE 3

NKG2D binding mutations identified through global

| Amino Acid | Frequency of Mutation | Associated Mutations | Solvent Accessible |
|---|---|---|---|
| D132 | 4 | D132N | ++ |
| | | D132N, T31S, V68A | |
| | | D132G, K126N, D76V | |
| | | D132G, K126N, D76V | |
| K126 | 4 | K126N | ++ |
| | | K126N, S71G | |
| | | K126N, D132G, D76V | |
| | | K126N, D132G, D76V | |
| K125 | 2 | K125E, F65C | − |
| | | K125E, F92V | |
| S120 | 2 | S120Y | − |
| | | S120Y, E10A, N56K | |
| D76 | 2 | D76V, D132G, K126N | ++ |
| | | D76V, D132G, K126N | |
| W116 | 2 | W116R | − |
| | | W116R, K113Q | |
| R123 | 2 | R123G, D26G, F50L | − |
| | | R123G, D21V, F128L | |
| E75 | 1 | E75D | − |
| S71 | 1 | S71G, K126N | ++ |
| F92 | 1 | F92V, K125E | + |
| F65 | 1 | F65C, K125E | − |
| K113 | 1 | K113Q, W116R | + |
| E10 | 1 | E10A, N56K, S120Y | ++ |
| N56 | 1 | E10A, N56K, S120Y | ++ |
| D21 | 1 | D21V, R123G, F128L | ++ |
| F128 | 1 | D21V, R123G, F128L | − |
| D26 | 1 | D26G, F50L, R123G | ++ |
| F50 | 1 | D26G, F50L, R123G | − |
| T31 | 1 | T31S, V68A, D132N | ++ |
| V68 | 1 | T31S, V68A, D132N | − |
| I30 | 1 | I30L, L51F, L64P, M135T | − |
| L51 | 1 | I30L, L51F, L64P, M135T | − |
| L64 | 1 | I30L, L51F, L64P, M135T | ++ |
| M135 | 1 | I30L, L51F, L64P, M135T | ++ |
| R67 | 1 | R67S, L117P, T119N, F122L | + |
| L117 | 1 | R67S, L117P, T119N, F122L | − |
| T119 | 1 | R67S, L117P, T119N, F122L | ++ |
| F122 | 1 | R67S, L117P, T119N, F122L | ++ |

Mutations were sequenced from 17 clones expressing mutagenized OMCP-Thy1.1. Clones were selected for reduced binding to NKG2D tetramers. The selected clones showed variable deficits in NKG2D binding. Each clone had 1-4 mutations in the amino acid sequence of OMCP (5 clones with 1 mutation; 4 clones with 2 mutations; 6 clones with 3 mutations; 2 clones with 4 mutations). Silent mutations are not indicated. Mutations are listed in the order of frequency sequenced from the selected clones, and mutations that occurred together within individual clones are listed where applicable. Clones highlighted in grey have at least one mutation in a solvent inaccessible residue that may alter the overall stability of OMCP.

REFERENCES FOR EXAMPLES 7-10

1. Hansen T H, Bouvier M (2009) MHC class I antigen presentation: learning from viral evasion strategies. Nat Rev Immunol 9: 503-513.
2. Griffin B D, Verweij M C, Wiertz E J (2010) Herpesviruses and immunity: the art of evasion. Vet Microbiol 143: 89-100.
3. Karre K, Ljunggren H G, Piontek G, Kiessling R (1986) Selective rejection of H-2-deficient lymphoma variants suggests alternative immune defence strategy. Nature 319: 675-678.
4. Orange J S, Fassett M S, Koopman L A, Boyson J E, Strominger J L (2002) Viral evasion of natural killer cells. Nat Immunol 3: 1006-1012.
5. Lisnic V J, Krmpotic A, Jonjic S (2010) Modulation of natural killer cell activity by viruses. Curr Opin Microbiol 13: 530-539.
6. Finton K A, Strong R K (2012) Structural insights into activation of antiviral NK cell responses. Immunol Rev 250: 239-257.
7. Li Y, Mariuzza R A (2014) Structural Basis for Recognition of Cellular and Viral Ligands by NK Cell Receptors. Front Immunol 5: 123.
8. Raulet D H (2003) Roles of the NKG2D immunoreceptor and its ligands. Nat Rev Immunol 3: 781-790.
9. Draghi M, Pashine A, Sanjanwala B, Gendzekhadze K, Cantoni C, et al. (2007) NKp46 and NKG2D recognition of infected dendritic cells is necessary for NK cell activation in the human response to influenza infection. J Immunol 178: 2688-2698.
10. Pappworth I Y, Wang E C, Rowe M (2007) The switch from latent to productive infection in epstein-barr virus-infected B cells is associated with sensitization to NK cell killing. J Virol 81: 474-482.
11. Welte S A, Sinzger C, Lutz S Z, Singh-Jasuja H, Sampaio K L, et al. (2003) Selective intracellular retention of virally induced NKG2D ligands by the human cytomegalovirus UL16 glycoprotein. Eur J Immunol 33: 194-203.
12. Ward J, Bonaparte M, Sacks J, Guterman J, Fogli M, et al. (2007) HIV modulates the expression of ligands important in triggering natural killer cell cytotoxic responses on infected primary T-cell blasts. Blood 110: 1207-1214.
13. Obeidy P, Sharland A F (2009) NKG2D and its ligands. Int J Biochem Cell Biol 41: 2364-2367.
14. Eagle R A, Trowsdale J (2007) Promiscuity and the single receptor: NKG2D. Nat Rev Immunol 7: 737-744.
15. Lodoen M, Ogasawara K, Hamerman J A, Arase H, Houchins J P, et al. (2003) NKG2D-mediated natural killer cell protection against cytomegalovirus is impaired by viral gp40 modulation of retinoic acid early inducible 1 gene molecules. J Exp Med 197: 1245-1253.
16. Lodoen M B, Abenes G, Umamoto S, Houchins J P, Liu F, et al. (2004) The cytomegalovirus m155 gene product subverts natural killer cell antiviral protection by disruption of H60-NKG2D interactions. J Exp Med 200: 1075-1081.
17. Krmpotic A, Hasan M, Loewendorf A, Saulig T, Halenius A, et al. (2005) NK cell activation through the NKG2D ligand MULT-1 is selectively prevented by the glycoprotein encoded by mouse cytomegalovirus gene m145. J Exp Med 201: 211-220.
18. Lenac T, Budt M, Arapovic J, Hasan M, Zimmermann A, et al. (2006) The herpesviral Fc receptor fcr-1 down-regulates the NKG2D ligands MULT-1 and H60. J Exp Med 203: 1843-1850.

19. Cosman D, Mullberg J, Sutherland C L, Chin W, Armitage R, et al. (2001) ULBPs, novel MHC class I-related molecules, bind to CMV glycoprotein UL16 and stimulate NK cytotoxicity through the NKG2D receptor. Immunity 14: 123-133.
20. Chalupny N J, Rein-Weston A, Dosch S, Cosman D (2006) Down-regulation of the NKG2D ligand MICA by the human cytomegalovirus glycoprotein UL142. Biochem Biophys Res Commun 346: 175-181.
21. Thomas M, Boname J M, Field S, Nejentsev S, Salio M, et al. (2008) Down-regulation of NKG2D and NKp80 ligands by Kaposi's sarcoma-associated herpesvirus K5 protects against NK cell cytotoxicity. Proc Natl Acad Sci USA 105: 1656-1661.
22. Cerboni C, Neri F, Casartelli N, Zingoni A, Cosman D, et al. (2007) Human immunodeficiency virus 1 Nef protein downmodulates the ligands of the activating receptor NKG2D and inhibits natural killer cell-mediated cytotoxicity. J Gen Virol 88: 242-250.
23. Wen C, He X, Ma H, Hou N, Wei C, et al. (2008) Hepatitis C virus infection downregulates the ligands of the activating receptor NKG2D. Cell Mol Immunol 5: 475-478.
24. Stern-Ginossar N, Elefant N, Zimmermann A, Wolf D G, Saleh N, et al. (2007) Host immune system gene targeting by a viral miRNA. Science 317: 376-381.
25. Nachmani D, Stern-Ginossar N, Sarid R, Mandelboim O (2009) Diverse herpesvirus microRNAs target the stress-induced immune ligand MICB to escape recognition by natural killer cells. Cell Host Microbe 5: 376-385.
26. Bauman Y, Nachmani D, Vitenshtein A, Tsukerman P, Drayman N, et al. (2011) An identical miRNA of the human JC and BK polyoma viruses targets the stress-induced ligand ULBP3 to escape immune elimination. Cell Host Microbe 9: 93-102.
27. Gainey M D, Rivenbark J G, Cho H, Yang L, Yokoyama W M (2012) Viral MHC class I inhibition evades CD8+ T-cell effector responses in vivo but not CD8+ T-cell priming. Proc Natl Acad Sci USA 109: E3260-3267.
28. Byun M, Verweij M C, Pickup D J, Wiertz E J, Hansen T H, et al. (2009) Two mechanistically distinct immune evasion proteins of cowpox virus combine to avoid antiviral CD8 T cells. Cell Host Microbe 6: 422-432.
29. Byun M, Wang X, Pak M, Hansen T H, Yokoyama W M (2007) Cowpox virus exploits the endoplasmic reticulum retention pathway to inhibit MHC class I transport to the cell surface. Cell Host Microbe 2: 306-315.
30. McCoy WHt, Wang X, Yokoyama W M, Hansen T H, Fremont D H (2013) Cowpox virus employs a two-pronged strategy to outflank MHCI antigen presentation. Mol Immunol.
31. McCoy WHt, Wang X, Yokoyama W M, Hansen T H, Fremont D H (2012) Structural mechanism of ER retrieval of MHC class I by cowpox. PLoS Biol 10: e1001432.
32. Alzhanova D, Edwards D M, Hammarlund E, Scholz I G, Horst D, et al. (2009) Cowpox virus inhibits the transporter associated with antigen processing to evade T cell recognition. Cell Host Microbe 6: 433-445.
33. Dasgupta A, Hammarlund E, Slifka M K, Fruh K (2007) Cowpox virus evades CTL recognition and inhibits the intracellular transport of MHC class I molecules. J Immunol 178: 1654-1661.
34. Luteijn R D, Hoelen H, Kruse E, van Leeuwen W F, Grootens J, et al. (2014) Cowpox Virus Protein CPXV012 Eludes CTLs by Blocking ATP Binding to TAP. J Immunol 193: 1578-1589.
35. Fang M, Lanier L L, Sigal L J (2008) A role for NKG2D in NK cell-mediated resistance to poxvirus disease. PLoS Pathog 4: e30.
36. Song H, Josleyn N, Janosko K, Skinner J, Reeves R K, et al. (2013) Monkeypox virus infection of rhesus macaques induces massive expansion of natural killer cells but suppresses natural killer cell functions. PLoS One 8: e77804.
37. Campbell J A, Trossman D S, Yokoyama W M, Carayannopoulos L N (2007) Zoonotic orthopoxviruses encode a high-affinity antagonist of NKG2D. J Exp Med 204: 1311-1317.
38. Lazear E, Peterson L W, Nelson C A, Fremont D H (2013) Crystal structure of the cowpox virus-encoded NKG2D ligand OMCP. J Virol 87: 840-850.
39. Carayannopoulos L N, Naidenko O V, Kinder J, Ho E L, Fremont D H, et al. (2002) Ligands for murine NKG2D display heterogeneous binding behavior. Eur J Immunol 32: 597-605.
40. Mistry A R, O'Callaghan C A (2007) Regulation of ligands for the activating receptor NKG2D. Immunology 121: 439-447.
41. Strong R K, McFarland B J (2004) NKG2D and Related Immunoreceptors. Adv Protein Chem 68: 281-312.
42. Deng L, Mariuzza R A (2006) Structural basis for recognition of MHC and MHC-like ligands by natural killer cell receptors. Semin Immunol 18: 159-166.
43. Li P, McDermott G, Strong R K (2002) Crystal structures of RAE-1beta and its complex with the activating immunoreceptor NKG2D. Immunity 16: 77-86.
44. Li P, Morris D L, Willcox B E, Steinle A, Spies T, et al. (2001) Complex structure of the activating immunoreceptor NKG2D and its MHC class I-like ligand MICA. Nat Immunol 2: 443-451.
45. Li P, Willie S T, Bauer S, Morris D L, Spies T, et al. (1999) Crystal structure of the MHC class I homolog MIC-A, a gammadelta T cell ligand. Immunity 10: 577-584.
46. Radaev S, Rostro B, Brooks A G, Colonna M, Sun P D (2001) Conformational plasticity revealed by the cocrystal structure of NKG2D and its class I MHC-like ligand ULBP3. Immunity 15: 1039-1049.
47. Adams E J, Luoma A M (2013) The adaptable major histocompatibility complex (MHC) fold: structure and function of nonclassical and MHC class I-like molecules. Annu Rev Immunol 31: 529-561.
48. McFarland B J, Kortemme T, Yu S F, Baker D, Strong R K (2003) Symmetry recognizing asymmetry: analysis of the interactions between the C-type lectin-like immunoreceptor NKG2D and MHC class I-like ligands. Structure 11: 411-422.
49. Stewart D E, Sarkar A, Wampler J E (1990) Occurrence and role of cis peptide bonds in protein structures. J Mol Biol 214: 253-260.
50. Craveur P, Joseph A P, Poulain P, de Brevern A G, Rebehmed J (2013) Cis-trans isomerization of omega dihedrals in proteins. Amino Acids 45: 279-289.
51. Lefkowitz E J, Upton C, Changayil S S, Buck C, Traktman P, et al. (2005) Poxvirus Bioinformatics Resource Center: a comprehensive Poxviridae informational and analytical resource. Nucleic Acids Res 33: D311-316.
52. Strong R K (2002) Asymmetric ligand recognition by the activating natural killer cell receptor NKG2D, a symmetric homodimer. Mol Immunol 38: 1029-1037.

53. Radaev S, Sun P D (2003) Structure and function of natural killer cell surface receptors. Annu Rev Biophys Biomol Struct 32: 93-114.
54. Campbell J A, Davis R S, Lilly L M, Fremont D H, French A R, et al. (2010) Cutting edge: FcR-like 5 on innate B cells is targeted by a poxvirus MHC class I-like immunoevasin. J Immunol 185: 28-32.
55. Copeland R A, Pompliano D L, Meek T D (2006) Drug-target residence time and its implications for lead optimization. Nat Rev Drug Discov 5: 730-739.
56. O'Callaghan C A, Cerwenka A, Willcox B E, Lanier L L, Bjorkman P J (2001) Molecular competition for NKG2D: H60 and RAE1 compete unequally for NKG2D with dominance of H60. Immunity 15: 201-211.
57. Groh V, Bruhl A, EI-Gabalawy H, Nelson J L, Spies T (2003) Stimulation of T cell autoreactivity by anomalous expression of NKG2D and its MIC ligands in rheumatoid arthritis. Proc Natl Acad Sci USA 100: 9452-9457.
58. Hue S, Mention J J, Monteiro R C, Zhang S, Cellier C, et al. (2004) A direct role for NKG2D/MICA interaction in villous atrophy during celiac disease. Immunity 21: 367-377.
59. Meresse B, Chen Z, Ciszewski C, Tretiakova M, Bhagat G, et al. (2004) Coordinated induction by IL15 of a TCR-independent NKG2D signaling pathway converts CTL into lymphokine-activated killer cells in celiac disease. Immunity 21: 357-366.
60. Ogasawara K, Hamerman J A, Hsin H, Chikuma S, Bour-Jordan H, et al. (2003) Impairment of NK cell function by NKG2D modulation in NOD mice. Immunity 18: 41-51.
61. Hahn M, Nicholson M J, Pyrdol J, Wucherpfennig K W (2005) Unconventional topology of self peptide-major histocompatibility complex binding by a human autoimmune T cell receptor. Nat Immunol 6: 490-496.
62. Sethi D K, Schubert D[4], Anders A K, Heroux A, Bonsor D[4], et al. (2011) A highly tilted binding mode by a self-reactive T cell receptor results in altered engagement of peptide and MHC. J Exp Med 208: 91-102.
63. Wucherpfennig K W, Call M J, Deng L, Mariuzza R (2009) Structural alterations in peptide-MHC recognition by self-reactive T cell receptors. Curr Opin Immunol 21: 590-595.
64. Yin Y, Li Y, Mariuzza R A (2012) Structural basis for self-recognition by autoimmune T-cell receptors. Immunol Rev 250: 32-48.
65. Adams J J, Narayanan S, Liu B, Birnbaum M E, Kruse A C, et al. (2011) T cell receptor signaling is limited by docking geometry to peptide-major histocompatibility complex. Immunity 35: 681-693.
66. Schubert D[4], Gordo S, Sabatino J J, Jr., Vardhana S, Gagnon E, et al. (2012) Self-reactive human CD4 T cell clones form unusual immunological synapses. J Exp Med 209: 335-352.
67. Li Y, Yin Y, Mariuzza R A (2013) Structural and biophysical insights into the role of CD4 and CD8 in T cell activation. Front Immunol 4: 206.
68. Otwinowski Z, Minor W (1997) Processing of X-ray diffraction data collected in oscillation mode. Macromolecular Crystallography, Pt A 276: 307-326.
69. Adams P D, Grosse-Kunstleve R W, Hung L W, Ioerger T R, McCoy A J, et al. (2002) PHENIX: building new software for automated crystallographic structure determination. Acta Crystallogr D Biol Crystallogr 58: 1948-1954.
70. Emsley P, Cowtan K (2004) Coot: model-building tools for molecular graphics. Acta Crystallogr D Biol Crystallogr 60: 2126-2132.
71. Chen V B, Arendall W B, 3rd, Headd J J, Keedy D A, Immormino R M, et al. (2010) MolProbity: all-atom structure validation for macromolecular crystallography. Acta Crystallogr D Biol Crystallogr 66: 12-21.
72. Schrodinger, LLC (2010) The PyMOL Molecular Graphics System, Version 1.3r1.
73. Laskowski R A, Swindells M B (2011) LigPlot+: multiple ligand-protein interaction diagrams for drug discovery. J Chem Inf Model 51: 2778-2786.
74. Krissinel E, Henrick K (2007) Inference of macromolecular assemblies from crystalline state. J Mol Biol 372: 774-797.
75. Lawrence M C, Colman P M (1993) Shape complementarity at protein/protein interfaces. J Mol Biol 234: 946-950.
76. Morin A, Eisenbraun B, Key J, Sanschagrin P C, Timony M A, et al. (2013) Collaboration gets the most out of software. Elife 2: e01456.
77. Ashkenazy H, Erez E, Martz E, Pupko T, Ben-Tal N (2010) ConSurf 2010: calculating evolutionary conservation in sequence and structure of proteins and nucleic acids. Nucleic Acids Res 38: W529-533.
78. Landau M, Mayrose I, Rosenberg Y, Glaser F, Martz E, et al. (2005) ConSurf 2005: the projection of evolutionary conservation scores of residues on protein structures. Nucleic Acids Res 33: W299-302.
79. Glaser F, Pupko T, Paz I, Bell R E, Bechor-Shental D, et al. (2003) ConSurf: identification of functional regions in proteins by surface-mapping of phylogenetic information. Bioinformatics 19: 163-164.
80. Celniker G, Nimrod G, Ashkenazy H, Glaser F, Martz E, et al. (2013) ConSurf: Using Evolutionary Data to Raise Testable Hypotheses about Protein Function. Israel Journal of Chemistry 53: 199-206.
81. Dokun A O, Kim S, Smith H R, Kang H S, Chu D T, et al. (2001) Specific and nonspecific NK cell activation during virus infection. Nat Immunol 2: 951-956.

Example 11. Individuals with Poorly Functioning Natural Killer Cells are More Susceptible to Malignancies FIG. 14A shows that AJ and 129 are lung cancer susceptible strain of mice and B6 and C3H are lung cancer resistant strains of mice based on the larger tumor burden found in AJ and 129 mice. FIG. 14B shows that when NK cells from the various mouse strains were incubated with LM2 lung carcinoma cells at varying ratios, the NK cells freshly isolated from B6 and C3H mice (lung cancer resistant strains) resulted in significantly more lysis of LM2 lung carcinoma cells than the NK cells freshly isolated from AJ and 129 mice (lung cancer susceptible strains). Taken together these data show that strains of mice that are resistant to lung cancer have NK cells that more effectively lyse lung carcinoma cells. Further, susceptible strains have poorly functioning NK cells.

That data also correlates with human data. FIG. 15 shows that a greater percentage of NK cells appear to produce TNFα in "resistant" patients versus "susceptible" patients. Further, it has been shown that tumors downregulate the lytic capacity of NK cells, even if they were highly functional before.[53] Thus, even individuals with highly functioning NK cells may benefit from therapy to enhance NK cell function.

Notably, ex vivo cytokine activation can reverse natural killer cell dysfuction. FIG. 16 shows that IL2 activated NK cells from both resistant (B6 and C3H) and susceptible (AJ and 129) mouse strains can lyse LM2 lung cancer cells. Accordingly, mouse NK Cells that did not show significant lysis of cancer cells (NK cells from 129 & AJ strains) were much more effective at lysis when treated with IL2. NK cells from cancer-resistant strains also showed increase % of specific lysis.

Example 12. OMCP-mutIL2 Mediated Immunotherapy In Vivo

Immunoregulation of malignancies involves an intricate interplay of multiple cellular components. $CD4^+Foxp3^+$ $T_{regs}$ have been shown in multiple models to contribute to tumor-specific tolerance and facilitate tumor growth[4, 16, 17]. NK cells and $CD8^+$ CTLs contribute to immunoregulation of multiple tumors, such as melanoma[12, 18]. Other tumors, such as lung cancer, are controlled almost exclusively by NK cells with little contribution by the adaptive immune system[19, 20] (and unpublished data AS. Krupnick). In order to test OMCP-mutIL2 mediated immunotherapy we will rely on B16 melanoma expressing the model tumor antigen ovalbumin (MO5 tumor cell line)[21]. Multiple studies have demonstrated a role for both NK cells and $CD8^+$ CTLs in controlling melanoma growth[22-24]. Thus the melanoma model offers an experimental advantage in studying OMCP-mutIL2, which can activate both types of cells (FIG. 1E-F). Reagents specific to this tumor, such as tetramers for the MHC Class I-restricted $CD8^+$ T cell receptor specific for the melanoma tumor associated antigen tyrosinase-related protein 2 peptide SVYDFFVWL (SEQ ID NO:3), can be readily purchased commercially (Proimmune, Sarasota, Fl.). The use of an ovalbum in-expressing cell line also offers the advantage of studying the immune response to a the highly immunogenic peptide SIINFEKL (SEQ ID NO:4) in addition to naturally occurring tumor associated antigens such as tyrosinase-related protein 2 which generally expands T cells with low avidity[25, 26].

In order to perform the studies B6 mice will be injected subcutaneously with $1 \times 10^6$ MO5 melanoma cells. One week after tumor injection mice will be divided into 4 groups (10 mice per group) and treated with ten twice a day injections of either: wild type IL2 (group #1); mutIL2 (group #2); OMCP-mutIL2 (group #3) or; saline (group #4) (FIG. 12). Tumor growth will be followed by daily measurements of diameter for 4 weeks, or until one of the groups develops tumors >2 cm in diameter. At that point mice in all groups will be sacrificed for analysis. In addition to tumor growth, lymphocyte infiltration of both the tumor and draining inguinal lymph node will be evaluated by flow cytometry. We will quantitate the total number and activation status of $CD4^+Foxp3+$ $T_{regs}$ (evaluated by ICOS and GITR upregulation). We will also evaluate NK cell number and activation as measured by IFN-γ production and CD69 upregulation. Antigen-specific CTL generation will be evaluated by quantitating both $CD8^+$ T cells and $CD8^+CD44^{hi}CD62^{low}$ effector cells (ECs) that are primarily responsible for tumor clearance[22, 27, 28]. Antigen specificity will be determined by identifying $CD8^+$ CTLs with T cell receptor specific for either the ovalbumin peptide SIINFEKL (SEQ ID NO:4) or melanoma specific tyrosinase-related protein 2 peptide SVYDFFVWL (SEQ ID NO:3) (both tetramers from Proimmune, Sarasota, Fl.). Tumor apoptosis will be quantitated by TUNEL staining.

Based on our in vitro tumor data and in vivo phenotypic analysis we suspect that the OMCP-mutIL2 group will demonstrate attenuation in tumor growth with high number of NK cells, antigen-specific CTLs, specifically $CD8^+$ ECs, and fewer $CD4^+Foxp3^+$ $T_{regs}$. If this turns out to be the case we would determine the relative role for $CD8^+$ or NK CTLs by depletion experiments. Even if CTLs increase it is possible that M05 growth will not be altered. If that turns out to be the case we would look in closer detail at the $CD4^+Foxp3^+$ $T_{regs}$ or in the presence and activation of myeloid-derived suppressor cells in OMCP-mutIL2 treated mice. Based on melanoma data additional tumors will be tested using similar methods.

Example 13. $CD8^+$ Memory T Cell Generation after Treatment with OMCP-mutIL2 Fusion Construct Once activation through their T cell receptor, naive $CD8^+$ T cells primarily differentiate into short-lived $CD44^{hi}CD62^{low}$ effector cells (ECs) with cytolytic potential. A portion of activated cells, however, differentiate to long-lived $CD44^{hi}CD62L^{hi}$ central memory T cells ($CD8^+$ CMs)[29-31]. $CD8^+$ CMs act as an antigen specific reservoir for cellular protection and upon restimulation differentiate into $CD8^+$ ECs with cytolytic function. The durability of $CD8^+$ CMs makes them an ideal target for ex vivo generation and adoptive transfer for long-term protection[31]. The possibility of generating this cell population in vivo offers multiple advantages over an ex vivo system, including establishing a polyclonal population reactive to multiple tumor associated antigens and avoidance of costs associated with donor pheresis and ex vivo expansion. In vivo expansion of tumor antigen specific $CD8^+$ CMs could also eliminate the need for frequent pheresis and cell readministration.

High dose IL2 therapy results in activation of both $CD4^+Foxp3^+$ $T_{regs}$ and $CD8^+$ T cells but its effect on tumor associated antigen specific $CD8^+$ CM generation is unknown. Some have demonstrated, using antibody depletion, that $CD4^+Foxp3^+$ $T_{regs}$ interfere with tumor specific $CD8^+$ CM generation[17, 32] while others, using different models, have demonstrated that $CD4^+Foxp3^+$ $T_{reg}$ depletion impairs $CD8^+$ memory formation[33, 34]. OMCP-mutIL2 creates a unique immunologic environment where $CD4^+$ $Foxp3^+$ $T_{regs}$ are maintained but not actively expanded (FIG. 3). While NKG2D is not expressed on resting $CD8^+$ T cells, it is induced on this population upon activation[35]. Thus, unlike mutIL2, OMCP-mutIL2 results in $CD8^+$ T cell proliferation at levels comparable to wild-type IL2 in NKG2D-sufficient mice (FIG. 1E-F). The effect of OMCP-mutIl2 on $CD8^+$ T cell memory formation, however, is unknown but is critical to decipher based on the long-term tumor specific immunity that this cell population can confer.

In order to test long-term memory formation after cytokine stimulation in vivo we will utilize a model of irradiated tumor cell vaccination and cytokine treatment. In order to accomplish this we will subcutaneously inject $1 \times 10^7$ lethally irradiated (10 Gy) M05 melanoma cells into C57131/6 mice. The recipient mice will then be treated either regular IL2 (group #1), mutIL2 (group #2), OMCP-mutIL2 (group #3) or saline (group #4) in twice daily doses over a course of 5 days (FIG. 13). The mice will be sacrificed at various time points ranging from one to three months post infection (FIG. 13). Antigen-specific $CD8^+$ CM formation will be assessed by phenotypic analysis of splenic, peripheral lymph node, lung, and liver-resident $CD8^+$ $CD44^{hi}CD62L^{hi}$ CMs. Antigen specificity will be determined by MHC Class I staining for either the ovalbumin peptide, SIINFEKL (SEQ ID NO:4), or melanoma specific tyrosinase-related protein 2 peptide SVYDFFVWL (SEQ ID NO:3) (both from Proimmune, Sarasota, Fl.).

In order to test the functional protection of such vaccination protocols in a separate set of experiments mice from the four groups described above will not be sacrificed for phenotypic analysis and will be reinjected with live M05 melanoma ($1 \times 10^6$ cells/mouse subcutaneously). Melanoma growth will be assessed by serial measurement of tumor diameter. Contribution of $CD8^+$ T cells to any immunologic protection will be assessed by CD8-specific antibody depletion in a portion of mice (clone YTS 169.4, BioXcell Inc., West Lebanon, NH).

Example 14. Mechanism of CTL Activation by OMCP-mutIL2 Fusion Construct

A mechanistic understanding of the enhanced activation of effector cell function by the OMCP-mutIL2 chimera will be critical for optimizing this therapeutic agent. The interaction of the fusion protein with IL2R and NKG2D are likely to be dependent on several factors including the length of the linker peptide (FIG. 1E-F). Therefore, it is critical to understand the mechanism of OMCP-mutIL2 chimera mediated CTL activation in order to allow for optimization of the construct and design of future immunotherapy protocols. The two-domain chimeric protein could potentially increase the activation of NKG2D-expressing cells by three non-mutually exclusive mechanisms. First and foremost the OMCP-mutIL2 construct could increase the avidity of mutIL2 binding to targeted cells. This could lead to an increase in the number of receptors occupied and increased signaling intensity compared to mutIL2. Additionally dual binding to both NKG2D and IL2R could decrease the rate of receptor internalization and increase the duration of signaling by IL2. It is also possible that the OMCP-mutIL2 construct alters the signaling profile by the target cell by activating both the IL2 and NKG2D stimulatory pathways. These three non-mutually exclusive effects could explain the increase in activation of our construct of CTLs in an NKG2D-mediated fashion.

There are several methods for determining the avidity of a protein for a cell, either directly (radiolabeled, fluorescent) or indirectly (antigen exclusion)[38, 39]. We plan to determine the avidity of wild-type IL2, mutIL2, or OMCP-mutIL2 for $CD4^+Foxp3+$ $T_{regs}$, NK cells, and $CD8^+$ T lymphocytes using KinExA[40]. To accomplish this we will isolate cells from splenocytes of either wild-type C57Bl/6 or $NKG2D^{-/-}$ mice on a C57Bl/6 background using a magnetic bead isolation kit (Miltenyi Biotech, San Diego, Calif.). Target cells will be serially diluted by a factor of 2 in 11 falcon tubes in media containing 0.05% $NaN_3$. The 12th tube will contain just the media. OMCP-mutIL2 or mutIL2 alone will then be added to each tube of either wild-type or $NKG2D^{-/-}$ cells and the cells with cytokine will be rotated at 4° C. for 36 h. At the end of 36 h, the cells were centrifuged at 2400 rpm for 4 min and the free construct present in the supernatant will be measured by an anti-IL2 ELISA. The equilibrium dissociation constant (Kd) will then be calculated[41]. This approach has the advantage of measuring the avidity of cell surface molecules at physiologic densities and obviates the need for labeling, which can artificially lower the affinity of antibodies for their antigens[42, 43].

The two-domain structure of the fusion protein is likely to significantly increase the half-life of the protein on the surface of $NKG2D^+$ and $IL2R^+$ cells. Any increase in surface half-life likely affects both the internalization of the bound receptors and signaling intensity and duration. To address the internalization of receptors, we will incubate each construct with the above mentioned cell types over a range of times and monitor the change in cell surface expression of IL2Rβγ and NKG2D using flow cytometry as previously described[44]. Of key interest will be the signaling profile of each construct. IL2-IL2R engagement signals through JAK-STAT pathways, while NKG2D signals through DAP10/12 pathways. While monomeric, soluble OMCP does not induce NKG2D signaling, OMCP can signal when concentrated locally on the cell surface[45]. Therefore, it is critical to determine whether the chimera is capable of inducing dual signaling through IL2R and NKG2D. IL2-mediated signaling will be assessed by Western blot for phosphorylated JAK1 and JAK3 in freshly isolated $CD4^+Foxp3^+$ $T_{regs}$, NK cells or $CD8^+$ T cells incubated in vitro with the construct[46, 47]. NKG2D-mediated signaling will be assessed by immunoprecipitation of DAP10 or DAP12 followed by Western blotting for phosphotyrosine as previously described[48, 49].

Both IL2 and OMCP interact with their cognate receptors with high affinity; the fusion of the two proteins is anticipated to greatly enhance the avidity of the chimeric construct for cells expressing both IL2R and NKG2D. As a consequence, the tethering of the construct to two cell surface receptors may lead to reduced internalization and increased duration of signaling. Combined these two phenomena represent the most likely mechanism for increased proliferation of NK cells in vivo. The signaling via NKG2D relies upon receptor clustering[45]. Since the construct is soluble it is possible, though unlikely, that the chimera will cluster NKG2D and induce DAP10/12 signaling. However, should DAP10/12 signaling be detected, we will then investigate the importance of this signaling in the expansion of NK cells using cells derived from Vav1 knockout mice. Vav1 is a signal mediator downstream of DAP10[50]. Using a Vav1 knockout has the advantage of leaving NKG2D expression intact, in contrast to DAP knockouts[50]. This will remove the NKG2D signaling component while leaving the NKG2D-dependent targeting intact. A clearer understanding of the mechanism of action for OMCP-IL2 chimera dependent expansion will be crucial for further refinements of the therapeutic agent. Understanding these parameters will allow for testing of different construct designs, primarily in the length of the linker between OMCP and IL2, to calibrate the effects of the chimera.

Example 15. In Vivo Immunotherapy with IL2, R38A/F42K IL2 or OMCP Targeted IL2 Constructs In order to determine if our construct plays a role in immunoregulation of malignancies as well as viral infections we will rely on in vivo models of B16 melanoma and mouse cytomegalovirus (MCMV). In one set of experiments B6 mice will be injected subcutaneously with $1\times10^6$ cells of the poorly immunogenic B16 melanoma cell line. One week after tumor injection mice will be divided into 13 groups (5 mice per group) and treated with five daily injections of IL2, R38A/F42K IL2, OMCP fusion constructs or saline as described in FIG. 18 and Table 4. Tumor growth will be followed by daily measurements of diameter for 4 weeks or until one of the groups develops tumors >2 cm in diameter. At that point mice in all groups will be sacrificed for analysis. In addition to tumor growth lymphocyte infiltration of both the tumor and draining inguinal lymph node will be evaluated by flow cytometry. We will quantitate the total number and activation status of $CD4^+Foxp3^+$ $T_{regs}$ (expressed as % of tumor infiltrating lymphocytes and % ICOS+). We will also evaluate NK cell number and activation as measured by IFN-γ production and CD69 upregulation. Tumor apoptosis will be evaluated by TUNEL staining.

TABLE 4

Experimental Design for Dosing for IL2, R38A/F42K IL2, OMCP-R38A/F42K IL2 or OMCP linked IL2 constructs

| Dose Cytokine | LOW DOSE | INTERMEDIATE DOSE | HIGH DOSE |
|---|---|---|---|
| IL2 | Group 1 | Group 2 | Group 3 |
| R38A/F42K IL2 | Group 4 | Group 5 | Group 6 |
| OMCP-wild-type IL2 | Group 7 | Group 8 | Group 9 |
| OMCP-R38A/F42K IL2 | Group 10 | Group 11 | Group 12 |
| Saline | Group 13 | | |

In order to evaluate the therapeutic potential of IL2 in an infectious disease model, B6 mice will be infected with a sublethal dose of MCMV ($5\times10^4$) particle forming units (PFUs) as previously described[29]. Day 1 post infection the mice will be divided into 13 groups (5 mice per group) and treated with five daily injections of IL2, R38A/F42K IL2, OMCP fusion constructs or saline as described in FIG. 18 and Table 4. On post-infection day #6 the mice will be sacrificed and splenic and pulmonary viral load determined by standard plaque assay.

Potential outcomes include a finding that treatment with pure IL2 will have little effect on tumor growth or viral load as we expect to see preferential activation of $T_{regs}$ over CTLs. We suspect that administration of the mutant R38A/F42K form of IL2 will result a lower tumor and viral burden compared to wild-type IL2 due to less activation of CD4+ Foxp3+ $T_{regs}$. Nevertheless it is possible that despite lower levels of $T_{reg}$ activation the tumor burden will be identical between IL2 and R38A/F42K IL2 due to decreased NK activation by the mutant form of IL2 as well. Potential outcomes include a finding that OMCP IL2 construct-treated mice will have lower tumor burden compared to pure cytokine and predict that OMCP-R38A/F42K IL2 will demonstrate the best efficacy for immunotherapy with the most favorable side effect profile.

If we do not see an effect of OMCP expressing IL2 constructs we will closely evaluate our data for confounding factors such as excessive CTL death due to extreme stimulation as well as possible sequestration of CTLs in systemic organs such as the liver and lungs. If our hypothesis is supported and NK cells are activated and tumor growth ameliorated after OMCP-construct treatment we would repeat these experiments after NK depletion (using anti-NK1.1 clone PK136, mouse anti-mouse depleting antibody) and CD8 depletion (clone YTS169, rat anti-mouse CD8+ T cell-depleting antibody) (both from BioXcell, West Lebanon, NH). Based on these results future work will focus on immunotherapy in primary carcinogenesis models.

Example 16. The Effects of IL2, R38A/F42K IL2 or OMCP Targeted IL2 Constructs on Immunosuppression after Radiation Exposure Sublethal radiation exposure is a constant risk to those involved in combat duty. In addition to the direct carcinogenic effects of radiation-induced DNA damage, sublethal irradiation results in immunologic damage due to selective death of lymphocyte subsets. CD8+ T cells and CD44I° naïve T cells are specifically sensitive to radiation-induced death while NK cell function significantly declines after irradiation. CD4+25+ T cells as well as $CD44^{hi}$ memory-like T cells, however, have a survival advantage after radiation. Both CD4+25+ T cells and CD8+ $CD44^{hi}$ T cells can downregulate immune responses, explaining why even limited exposure to radiation can result in significant immunosuppression. Pharmacologic interventions to restore the immune system can alleviate morbidity and mortality of radiation poisoning. Surprisingly the role of IL2 in alleviating radiation-induced changes has never been studied. The low affinity IL2 receptor is expressed on bone marrow-resident hematopoietic stem cells and committed NK progenitors. NK cells, in turn, can secrete granulocyte-macrophage colony-stimulating factor (GM-CSF) upon stimulation, a cytokine that can assist with hematopoietic recovery. Based on these data in this aim we plan to test the hypothesis that IL2 or OMCP-IL2 constructs can assist with hematopoietic recovery after sublethal and lethal irradiation.

Based on previously described models of radiation-induced hematopoietic damage and recovery we will irradiate B6 mice with either sublethal 4.5 or lethal 7.5 Gy from a cesium source. Within one hour of exposure mice in both radiation doses will be randomly divided into 13 groups as described in Table 4 and treated for five days with low, intermediate or high dose IL2, R38A/F42K IL2 or OMCP expressing IL2 constructs (FIG. 18). A portion of the mice will be injected with saline after irradiation (group 13) (Table 4) and unirradiated untreated B6 mice will be included as a control as well (group 14). On day 6 hematopoietic recovery will be monitored by flow cytometric analysis of peripheral blood obtained by superficial mandibular vein sampling. The sample will be analyzed for total number of NK cells, T cells, B cells, granulocytes, as well as monocytes and macrophages per ml of blood. Since 90% of untreated mice die 15-25 days after exposure to 7.5 Gy, mice will be followed daily and survival curves in each treatment group will be compared by Kaplan-Meier analysis. Moribund mice in the 7.5 Gy group will be carefully analyzed for cause of death evaluating the bone marrow, spleen and peripheral organs for both infection as well as hematopoietic failure by flow cytometry and tissue culture. Since mice in the sublethal 4.5 Gy group are expected to survive long term, they will be sacrificed one month after exposure and peripheral lymphoid organs as well as bone marrow evaluated for hematopoietic recovery by flow cytometric analysis.

Radiation related DNA damage results in malignant transformation. Hematopoietic malignancies are especially prominent after radiation exposure. In order to evaluate the ability of IL2 or OMCP linked IL2 constructs to facilitate in clearing hematopoietic malignancies after radiation exposure we will treat B6 mice with sublethal exposure to 4.5 Gy from a cesium source. Two days after irradiation the mice will be injected with $10^3$ RMA-S lymphoma cells i.p. and three days later treated for a five day course with low, intermediate or high dose IL2, R38A/F42K IL2 or OMCP expressing IL2 constructs (Table 4, FIG. 19). Unirradiated B6 mice will be included as a control (group 14) as well. The mice will be followed for survival.

We anticipate that wild-type IL2 alone will have a negligible effect on immunorestoration since it will most likely result in preferential expansion of CD4+Foxp3+ $T_{regs}$, which are already preserved after irradiation. We suspect, however, that R38A/F42K IL2 as well as OMCP expressing IL2 constructs will expand the NK fraction in the peripheral blood and will contribute to broad hematopoietic recovery, albeit indirectly through secretion of homeostatic cytokines such as GM-CSF. If we detect no differences in hematopoietic recovery between IL2 and saline-treated groups, we will examine other confounding factors, such as homeostatic proliferation induced alteration of the immune system and the effect of IL2 or OMCP expressing IL2 constructs on such proliferation. While 200,000 IU of IL2 administered daily to B6 mice is not lethal, we realize that in the face of irradiation the mice might be weaker. It is thus possible that dosing might need to be adjusted. For the "functional" part of this experiment we plan to specifically utilize the well-established model of RMA-S lymphoma challenge due to the role of NK cells in controlling hematologic malignancies. This established assay will allow us to gain rapid experimental data to advance this aim. Based on this data we would extend this aim in the future utilizing a primary carcinogenesis model as well.

Example 17. OMCP-Targeted Delivery of IL15 Enhances CD25 Upregulation

Interleukin 15 (IL15) is a cytokine with structural similarity to IL2. Like IL2, IL15 binds to and signals through a complex composed of IL2/IL15 receptor beta chain (CD122) and the common gamma chain (gamma-C, CD132). IL15 is secreted by mononuclear phagocytes (and some other cells) following infection by viruses. IL15 regulates T and natural killer (NK) cell activation and proliferation. Survival signals that maintain memory T cells in the absence of antigen are provided by IL15. This cytokine is also implicated in NK cell development. IL-15 belongs to the four α-helix bundle family of cytokine.

OMCP was linked to the cytokine IL15 and its ability to active NK cells compared to IL15 alone was examined. NK cell activation was measured by CD25 upregulation. As demonstrated in FIG. 21, higher levels of CD25 are evident when IL15 is delivered by OMCP vs naked cytokine alone in equimolar doses.

Example 18. OMCP-Targeted Delivery of IL18 Enhances NK Cell Activation

OMCP was linked to WT human IL18, WT murine IL18 or mutant human IL18 (which inhibits its interaction with IL18BP) and its ability to active NK cells was examined (FIG. 32). Peripheral blood lymphocytes were cultured for 48 hours in 4.4 µM of either wild-type IL18 (blue), OMCP-IL18 (red) or saline (black). Activation of CD56+CD3− natural killer cells, as measured by surface CD69 expression, was superior by OMCP-IL18 compared to wild-type IL18 (FIG. 33). This data demonstrates that linking OMCP to IL18 also enhances NK cell activation relative to IL18 without OMCP.

Example 19. The D132R Mutation in OMCP Significantly Decreases its NKG2D Binding To further test the necessity of NKG2D binding in targeted delivery of IL2, we tested NK expansion and activation in the presence of mutIL2, OMCP-mutIL2, and (D132R) OMCP-mutIL2. The D132R mutation ameliorated the superiority of natural killer cell activation over cytokine alone (FIG. 22). Thus high affinity NKG2D binding is critical for targeted delivery and lymphocyte activation by IL2.

Example 20. OMCP-IL2 Effectively Treats Infection Caused by West Nile Virus (WNV)

The ability of various constructs of the invention to treat infection caused by West Nile Virus (WNV) was evaluated. Mice were given OMCP-IL2, the binding null mutant of OMCP, OMCP(D132R)-IL2, IL2 alone, IL2(38R/42A) alone and PBS. Upon treatment with OMCP(D132R)-IL2 and PBS all mice succumbed to infection by about day 11. Following treatment with IL2 alone, approximately 20% of mice survived until day 21. However, treatment with IL2 (38R/42A) and OMCP-IL2 resulted in about 40% of mice surviving beyond 21 days (FIG. 30A). These results were consistently repeatable as demonstrated in FIG. 30B.

REFERENCES FOR EXAMPLE 11-20

1. Rosenberg, S. A. IL2: the first effective immunotherapy for human cancer. *J Immunol* 192, 5451-5458 (2014).
2. Atkins, M. B., et al. High-dose recombinant interleukin 2 therapy for patients with metastatic melanoma: analysis of 270 patients treated between 1985 and 1993. *J Clin Oncol* 17, 2105-2116 (1999).
3. Krieg, C., Letourneau, S., Pantaleo, G. & Boyman, O. Improved IL2 immunotherapy by selective stimulation of IL2 receptors on lymphocytes and endothelial cells. *Proc Natl Acad Sci USA* 107, 11906-11911 (2010).
4. Ghiringhelli, F., Menard, C., Martin, F. & Zitvogel, L. The role of regulatory T cells in the control of natural killer cells: relevance during tumor progression. *Immunol Rev* 214, 229-238 (2006).
5. French, A. R., et al. DAP12 signaling directly augments proproliferative cytokine stimulation of NK cells during viral infections. *J Immunol* 177, 4981-4990 (2006).
6. Heaton, K. M., Ju, G. & Grimm, E. A. Human interleukin 2 analogues that preferentially bind the intermediate-affinity interleukin 2 receptor lead to reduced secondary cytokine secretion: implications for the use of these interleukin 2 analogues in cancer immunotherapy. *Cancer Res* 53, 2597-2602 (1993).
7. Heaton, K. M., et al. Characterization of lymphokine-activated killing by human peripheral blood mononuclear cells stimulated with interleukin 2 (IL2) analogs specific for the intermediate affinity IL2 receptor. *Cellular immunology* 147, 167-179 (1993).
8. Levin, A. M., et al. Exploiting a natural conformational switch to engineer an interleukin-2 'superkine'. *Nature* 484, 529-533 (2012).
9. Campbell, J. A., Trossman, D. S., Yokoyama, W. M. & Carayannopoulos, L. N. Zoonotic orthopoxviruses encode a high-affinity antagonist of NKG2D. *J Exp Med* 204, 1311-1317 (2007).
10. Rosenberg, S. A., et al. Experience with the use of high-dose interleukin-2 in the treatment of 652 cancer patients. *Annals of surgery* 210, 474-484; discussion 484-475 (1989).
11. Gately, M. K., Anderson, T. D. & Hayes, T. J. Role of asialo-GM1-positive lymphoid cells in mediating the toxic effects of recombinant IL2 in mice. *J Immunol* 141, 189-200 (1988).
12. Sim, G. C., et al. IL2 therapy promotes suppressive ICOS+ Treg expansion in melanoma patients. *J Clin Invest* 124, 99-110 (2014).
13. Raulet, D. H. Roles of the NKG2D immunoreceptor and its ligands. *Nat Rev Immunol* 3, 781-790 (2003).
14. Ullrich, E., Koch, J., Cerwenka, A. & Steinle, A. New prospects on the NKG2D/NKG2DL system for oncology. *Oncoimmunology* 2, e26097 (2013).
15. Lazear, E., Peterson, L. W., Nelson, C. A. & Fremont, D. H. Crystal structure of the cowpox virus-encoded NKG2D ligand OMCP. *J Virol* 87, 840-850 (2013).

16. Bui, J. D., Uppaluri, R., Hsieh, C. S. & Schreiber, R. D. Comparative analysis of regulatory and effector T cells in progressively growing versus rejecting tumors of similar origins. *Cancer Res* 66, 7301-7309 (2006).
17. Wang, Y., Sparwasser, T., Figlin, R. & Kim, H. L. Foxp3+ T cells inhibit antitumor immune memory modulated by mTOR inhibition. *Cancer Res* 74, 2217-2228 (2014).
18. Poschke, I., et al. A phase I clinical trial combining dendritic cell vaccination with adoptive T cell transfer in patients with stage IV melanoma. *Cancer immunology, immunotherapy: CII* 63, 1061-1071 (2014).
19. Kreisel, D., et al. Strain-specific variation in murine natural killer gene complex contributes to differences in immunosurveillance for urethane-induced lung cancer. *Cancer Res* 72, 4311-4317 (2012).
20. Frese-Schaper, M., et al. Influence of natural killer cells and perforinmediated cytolysis on the development of chemically induced lung cancer in NJ mice. *Cancer immunology, immunotherapy: CII* 63, 571-580 (2014).
21. Ryu, M. S., et al. Accumulation of cytolytic CD8(+) T cells in B16-melanoma and proliferation of mature T cells in TIS21-knockout mice after T cell receptor stimulation. *Experimental cell research* 327, 209221 (2014).
22. Anichini, A., et al. Tumor-reactive CD8$^+$ early effector T cells identified at tumor site in primary and metastatic melanoma. *Cancer Res* 70, 8378-8387 (2010).
23. Glasner, A., et al. Recognition and prevention of tumor metastasis by the NK receptor NKp46/NCR1. *J Immunol* 188, 2509-2515 (2012).
24. Hersey, P., Edwards, A., Honeyman, M. & McCarthy, W. H. Low natural-killer-cell activity in familial melanoma patients and their relatives. *Br J Cancer* 40, 113-122 (1979).
25. Ji, Q., Gondek, D. & Hurwitz, A. A. Provision of granulocyte-macrophage colony-stimulating factor converts an autoimmune response to a self-antigen into an antitumor response. *J Immunol* 175, 14561463 (2005).
26. Zhu, Z., et al. High-avidity T cells are preferentially tolerized in the tumor microenvironment. *Cancer Res* 73, 595-604 (2013).
27. Klein, O., et al. Melan-A-specific cytotoxic T cells are associated with tumor regression and autoimmunity following treatment with anti-CTLA-4. *Clinical cancer research: an official journal of the American Association for Cancer Research* 15, 2507-2513 (2009).
28. Meiraz, A., Garber, O. G., Harari, S., Hassin, D. & Berke, G. Switch from perforin-expressing to perforin-deficient CD8(+) T cells accounts for two distinct types of effector cytotoxic T lymphocytes in vivo. *Immunology* 128, 69-82 (2009).
29. Stemberger, C., et al. A single naive CD8$^+$ T cell precursor can develop into diverse effector and memory subsets. *Immunity* 27, 985-997 (2007).
30. Sallusto, F., Lenig, D., Forster, R., Lipp, M. & Lanzavecchia, A. Two subsets of memory T lymphocytes with distinct homing potentials and effector functions. *Nature* 401, 708-712 (1999).
31. Araki, K., et al. mTOR regulates memory CD8 T-cell differentiation. *Nature* 460, 108-112 (2009).
32. Kim, H. L. Antibody-based depletion of Foxp3+ T cells potentiates antitumor immune memory stimulated by mTOR inhibition. *Oncoimmunology* 3, e29081 (2014).
33. Graham, J. B., Da Costa, A. & Lund, J. M. Regulatory T cells shape the resident memory T cell response to virus infection in the tissues. *J Immunol* 192, 683-690 (2014).
34. de Goer de Herve, M. G., Jaafoura, S., Vallee, M. & Taoufik, Y. FoxP3(+) regulatory CD4 T cells control the generation of functional CD8 memory. *Nature communications* 3, 986 (2012).
35. Gilfillan, S., Ho, E. L., Cella, M., Yokoyama, W. M. & Colonna, M. NKG2D recruits two distinct adapters to trigger NK cell activation and costimulation. *Nature immunology* 3, 1150-1155 (2002).
36. Shane, H. L. & Klonowski, K. D. Every breath you take: the impact of environment on resident memory CD8 T cells in the lung. *Frontiers in immunology* 5, 320 (2014).
37. Marcus, A. & Raulet, D. H. Evidence for natural killer cell memory. *Current biology: CB* 23, R817-820 (2013).
38. Tam, S. H., Sassoli, P. M., Jordan, R. E. & Nakada, M. T. Abciximab (ReoPro, chimeric 7E3 Fab) demonstrates equivalent affinity and functional blockade of glycoprotein IIb/IIIa and alpha(v)beta3 integrins. *Circulation* 98, 1085-1091 (1998).
39. Trikha, M., et al. CNTO 95, a fully human monoclonal antibody that inhibits alphav integrins, has antitumor and antiangiogenic activity in vivo. *International journal of cancer. Journal international du cancer* 110, 326-335 (2004).
40. Rathanaswami, P., Babcook, J. & Gallo, M. High-affinity binding measurements of antibodies to cell-surface-expressed antigens. *Anal Biochem* 373, 52-60 (2008).
41. Drake, A. W., Myszka, D. G. & Klakamp, S. L. Characterizing high-affinity antigen/antibody complexes by kinetic- and equilibrium-based methods. *Anal Biochem* 328, 35-43 (2004).
42. Siiman, 0. & Burshteyn, A. Cell surface receptor-antibody association constants and enumeration of receptor sites for monoclonal antibodies. *Cytometry* 40, 316-326 (2000).
43. Debbia, M. & Lambin, P. Measurement of anti-D intrinsic affinity with unlabeled antibodies. *Transfusion* 44, 399-406 (2004).
44. Tsao, P. I. & von Zastrow, M. Type-specific sorting of G protein-coupled receptors after endocytosis. *The Journal of biological chemistry* 275, 11130-11140 (2000).
45. Lazear, E., et al. Cowpox virus OMCP antagonizes NKG2D via an unexpected binding orientation. *PLos Pathogen* Under review(2014).
46. Liu, K. D., Gaffen, S. L., Goldsmith, M. A. & Greene, W. C. Janus kinases in interleukin-2-mediated signaling: JAK1 and JAK3 are differentially regulated by tyrosine phosphorylation. *Current biology: CB* 7, 817-826 (1997).
47. Zhou, Y. J., et al. Distinct tyrosine phosphorylation sites in JAK3 kinase domain positively and negatively regulate its enzymatic activity. *Proc Natl Acad Sci USA* 94, 13850-13855 (1997).
48. Horng, T., Bezbradica, J. S. & Medzhitov, R. NKG2D signaling is coupled to the interleukin 15 receptor signaling pathway. *Nature immunology* 8, 1345-1352 (2007).
49. Zou, W., Reeve, J. L., Liu, Y., Teitelbaum, S. L. & Ross, F. P. DAP12 couples c-Fms activation to the osteoclast cytoskeleton by recruitment of Syk. *Molecular cell* 31, 422-431 (2008).
50. Graham, D. B., et al. Vav1 controls DAP10-mediated natural cytotoxicity by regulating actin and microtubule dynamics. *J Immunol* 177, 2349-2355 (2006).
51. Yamane, B. H., Hank, J. A., Albertini, M. R. & Sondel, P. M. The development of antibody-IL2 based immunotherapy with hu14.18-IL2 (EMD-273063) in melanoma and neuroblastoma. *Expert opinion on investigational drugs* 18, 991-1000 (2009).

52. Becker, J. C., Pancook, J. D., Gillies, S. D., Furukawa, K. & Reisfeld, R. A. T cell-mediated eradication of murine metastatic melanoma induced by targeted interleukin 2 therapy. *J Exp Med* 183, 2361-2366 (1996).
53. Lundholm et al., Prostate tumor-derived exosomes down-regulate NKG2D expression on natural killer cells and CD8+ T cells: mechanism of immune evasion. *PLoS One* 2014; 9(9):e108925.

Example 21. Anti-NKG2D Antibody-Mediated Delivery of R38A/F42K Mutant IL-2

In order to compare antibody-mediated delivery of mutIL-2 to OMCP-mediated delivery of mutIL-2, 4 anti-human NKG2D single chain variable fragment domains were engineered based on the described sequence of the KYK1 and KYK2 antibodies (*J Mol Biol* 2008, 384(5), 1143-1156). 1HL2 and are 1LH2 derived from the kyk1 antibody and 2HL2 and 2LH2 from the kyk2 antibody. The binding coefficients of OMCP, KYK1 and KYK2 are 0.1 nM, 27 nM and 6 nM, respectively.

Antibodies linked to OMCP-mutant IL-2, IgG-mutant IL-2, wild type IL-2 and PBS control were co-cultured with $2.5 \times 10^6$ peripheral blood lymphocytes in 500 µl of media in either 10 U/ml or 100 U/ml final concentration of cytokine or construct. Forty-eight hours later NK activation was evaluated as relative median fluorescence intensity of intracellular perforin compared to PBS control. $CD4^+CD45RA^-Foxp3^+$ activation was evaluated as relative median fluorescence intensity of surface CD25 compared to PBS control.

At 10 U/ml OMCP-mutant IL-2 demonstrated a trend toward increased perforin levels over antibody-mediated delivery but it did not reach statistical significance (FIG. 39). At 100 U/ml NK cells treated with 2HL2 and 2LH2 antibodies synthesized as much perforin as OMCP-mutIL-2 treated cells but lower levels of perforin were evident in 1HL2 and 1LH2 treated NK cells. Higher levels of CD25 were evident in wild-type IL-2 treated cultures over all constructs. Accordingly, the results demonstrate that mutant IL-2 linked to NKG2D antibodies performs comparably to OMCP linked to mutant IL-2.

Example 22. Combination Therapy with an OMCP-IL2 and PD-1 Inhibitor

This example describes in vivo testing of combination therapies of OMCP-IL2 in combination with a PD-1 antibody.

A total of 16 C57131/6 mice 6-9 weeks of age were seeded with 100,000 Lewis Lung Carcinoma cells per mouse via tail vein injection to induce seeding of the tumor cells into the lungs. Mice were subsequently randomized into four groups to receive the following therapies, which were initiated 5 days post-cell seeding:

Group 1—antibody isotype control,
Group 2—anti-PD-1 antibody therapy,
Group 3—antibody isotype control plus OMCP-IL2,
Group 4—anti-PD-1 antibody plus OMCP-IL2.
Group 1—The mice were intraperitoneally (i.p.) administered 250 µg isotype control antibody (Bioxcell clone no. 2A3, cat no. BP0089) twice weekly for two weeks for a total of 4 doses (1000 µg total) of antibody.
Group 2—The mice were administered i.p. 250 µg of an anti-PD-1 antibody (Bioxcell clone no. RMP1-14, cat. no. BP0146) twice weekly for two weeks for a total of 4 doses (1000 µg total) of antibody.
Group 3—The mice were administered i.p. (i) 75,000 IUe OMCP-IL2 fusion protein twice daily for five days for a total of ten doses (750,000 IUe) of OMCP-IL2 fusion protein; and (ii) 250 µg isotype control antibody (Bioxcell clone no. 2A3, cat no. BP0089) twice weekly for two weeks for a total of 4 doses (1000 µg total) of antibody.
Group 4—The mice were administered i.p. (i) 75,000 IUe OMCP-IL2 fusion protein twice daily for five days for a total of ten doses (750,000 IUe) of OMCP-IL2 fusion protein; and (ii) 250 µg of an anti-PD-1 antibody (Bioxcell clone no. RMP1-14, cat. no. BP0146) twice weekly for two weeks for a total of 4 doses (1000 µg total) of antibody.

Mice were retained for three weeks after the completion of the respective therapy, at which time they were euthanized.

Because tumor burden measurably increases the weight of the lungs, lung weight was used as a primary measurement for therapy efficacy. FIG. 34 depicts photographs of lungs of the Groups 1-4 mice cohorts and FIG. 35 depicts lung weights as measured from the lungs from the Group 1-4 mice cohorts. As shown in FIGS. 34 and 35, the combination of an anti-PD-1 antibody and OMCP-IL2 (Group 4) was found to virtually eliminate tumor growth in the lung, and synergistically decreases tumor burden over either OMCP-IL2 therapy alone (Group 3) or anti-PD-1 antibody therapy alone (Group 2). Thus, the combination therapy demonstrated surprisingly greater efficacy than each component administered alone.

Example 23. PD1-Targeted Delivery of an IL2 Mutant Preferentially Activates Cytotoxic Lymphocytes In Vitro This example describes in vitro testing of PD1 ligand therapies. Specifically, this example will demonstrate improved immune cell activation of PDL1-mutIL2 and PDL2-mutIL2 fusion proteins over purified cytokine.

A total of 4 C57131/6 mice 6-9 weeks of age will be utilized to prepare a fresh splenocyte culture. Splenocytes will be cultured in triplicate for 36 hours according to the following groups: Group 1—saline control, Group 2—100 IUe/mL wt IL2, Group 3—100 IUe/mL mut IL2, Group 4—100 IUe/mL PDL1, Group 5—100 IUe/mL PDL2, Group 6—100 IUe/mL PDL1-mutIL2, Group 7—100 IUe/mL PDL2-mutIL2. After the 36-hour culture period, cells will be stained for flow cytometry according to standard protocols, and cellular activation will be evaluated.

Cellular populations will be defined via the following gating strategies: $T_{regs}$—CD45+CD3+CD4+Foxp3+, NK cells—CD45+CD3−CD49b+CD335+, Teff—CD45+CD3+CD8+. Cellular activation will be further defined via evaluation whether the following markers are upergulated: $T_{regs}$—ICOS, NK cells—CD69 and KLRG1, Teff—CD69.

Potential outcomes include a finding that NK cells are significantly activated by treatment with wtIL2, PDL1-mutIL2, and PDL2-mutIL2. Teff cells may also be activated by treatment with wtIL2, PDL1-mutIL2, and PDL2-mutIL2. This is in contrast with $T_{regs}$, which should be activated by treatment with wtIL2 but not with PDL1-mutIL2 or PDL2-mutIL2.

These results would suggest that targeting IL2 therapy to PD1 cells via a PD1 ligand fusion protein significantly enhances the efficacy of IL2 therapy in anti-tumor cell populations such as NK cells and Teff cells, while avoiding activation of immunotolerant populations such as Treg cells.

Example 24. PD1-Targeted Delivery of an IL2 Mutant Induces Proliferation of Cytotoxic Lymphocytes In Vitro This example describes in vitro testing of PD1 ligand therapies. Specifically, this example will demonstrate improved cytotoxic immune cell expansion by PDL1-mutIL2 and PDL2-mutIL2 fusion proteins over purified cytokine.

A total of 4 C57Bl/6 mice 6-9 weeks of age will be utilized to prepare a fresh splenocyte culture. Splenocytes will be stained with CFSE prior to culture. CFSE permanently binds DNA, and provides an indication of cellular proliferation via reduced fluorescence with subsequent cellular divisions. Stained splenocytes will be subsequently cultured in triplicate for 6 days according to the following groups: Group 1 saline control, Group 2—1000 IUe/mL wt IL2, Group 3—1000 IUe/mL mut IL2, Group 4—1000 IUe/mL PDL1, Group 5—1000 IUe/mL PDL2, Group 6—1000 IUe/mL PDL1-mutIL2, Group 7—1000 IUe/mL PDL2-mutIL2. After the 6-day culture period, cells will be stained for flow cytometry according to standard protocols, and cellular proliferation will be evaluated.

Cellular populations will be defined via the following gating strategies: $T_{regs}$—CD45+CD3+CD4+Foxp3+, NK cells—CD45+CD3−CD49b+CD335+, Teff—CD45+CD3+CD8+.

Potential outcomes include a finding that wtIL2, PDL1-mutIL2, and PDL2-mutIL2 will induce significant proliferation in the NK cell population. We may also find that Teff cells are induced to proliferate via these same treatment groups. However, Treg cells will only be induced to proliferate by the wtIL2 treatment, and will remain relatively quiescent with PDL1-mutIL2 and PDL2-mutIL2 treatment. Therefore, the NK cell to Treg cell ratio, a marker for immune cell activation and prognostic for cancer therapeutic responses, will be significantly enhanced by PDL1-mutIL2 and PDL2-mutIL2 treatment over the wtIL2 treatment alone.

These results would suggest that targeting IL2 therapy to PD1 cells via a PD1 ligand fusion protein significantly enhances the proliferative capacity of anti-tumor cell populations such as NK cells and Teff cells, while avoiding activation of immunotolerant populations such as Treg cells.

Example 25. Lymphocyte Cytotoxicity is Enhanced by PD1 Targeted Delivery of Mutant IL2

This example describes in vitro testing of PD1 ligand therapies. Specifically, this example will demonstrate improved cytotoxic immune cell response after treatment with PDL1-mutIL2 and PDL2-mutIL2 fusion proteins over purified cytokine.

A total of 6 C57131/6 mice 6-9 weeks of age will be utilized to prepare a fresh splenocyte culture. Bulk splenocytes will be cultured for 6 days according to the following groups: Group 1—saline control, Group 2—1000 IUe/mL wt IL2, Group 3—1000 IUe/mL mut IL2, Group 4—1000 IUe/mL PDL1, Group 5—1000 IUe/mL PDL2, Group 6—1000 IUe/mL PDL1-mutIL2, Group 7—1000 IUe/mL PDL2-mutIL2. After the 6-day culture period, cells will be prepared for a 7-AAD/CFSE cytotoxicity assay against K562 cells using a kit according to the manufacturer's protocols (Cayman Chemical, 7-AAD/CFSE Cell-Mediated Cytotoxicity Assay Kit, Item No. 600120). Splenocytes from each group will be seeded with target K562 cells in triplicate at the following ratios: no target cells, 15.6:1, 31.25:1, 62.5:1, 125:1, 250:1, 500:1. After 4 hours, the live versus dead target cell ratio will be evaluated via flow cytometry.

Potential outcomes include a finding that splenocytes incubated with wtIL2 will have enhanced cytotoxic function against the target cells versus saline controls. We further expect to find that PDL1-mutIL2 and PDL2-mutIL2 treatment will further enhance the cytotoxicity of the splenocytes.

These results would suggest that PD1 ligand IL2 fusion proteins increase splenocyte cytotoxic activity over wtIL2 therapy. This may be a function of decreased Treg activation within the splenocyte population. This may further be a function of enhanced binding and signaling of the mutIL2 portion of the fusion proteins through the IL2 receptor on T and NK cells.

Example 26. Tumor Growth and Survival after In Vivo Treatment with PD1 Targeted Therapies This example describes in vivo proof of concept that PD1 ligand therapies inhibit tumor or cancer progression. Specifically, this example will demonstrate improved tumor growth and overall survival metrics after in vivo treatment with PDL1-mutIL2 and PDL2-mutIL2 fusion proteins over purified cytokine.

A total of 50 C57Bl/6 mice 6-9 weeks of age will be utilized. Mice will be injected with Lewis Lung Carcinoma subcutaneously at the flank with 1×105 cells per mouse. Treatment will begin 5 days later, when tumors have grown sufficiently to become visible and measurable. Initial tumor sizes and mouse weights will be taken, and mice will be randomized into groups of 10 mice such that the initial tumor sizes and mouse weights are similar between groups. The treatment groups are as follows: Group 1—saline control, Group 2—wt IL2, Group 3—mut IL2, Group 4—PDL1-mutIL2, Group 5—PDL2-mutIL2.

All mice will be treated according to their groups twice daily in 12 hour intervals for 5 days, a total of 10 doses. Group 1—The mice will be intraperitoneally (i.p.) administered 200 μL saline for all treatments as a negative control. Group 2—The mice will be i.p. administered 75,000 IUe wt IL2 for each dose, for a total of 750,000 IUe wt IL2 after treatment. Group 3—The mice will be i.p. administered 75,000 IUe mut IL2 for each dose, for a total of 750,000 IUe mut IL2 after treatment. Group 4—The mice will be i.p. administered 75,000 IUe PDL1-mutIL2 for each dose, for a total of 750,000 IUe PDL1-mutIL2 after treatment. Group 5—The mice will be i.p. administered 75,000 IUe PDL2-mutIL2 for each dose, for a total of 750,000 IUe PDL2-mutIL2 after treatment.

All tumors will be measured via caliper measurements and mouse weights measured every day during treatment. After the completion of the therapeutic course, mouse weights and tumors will be measured thrice weekly. Mice will be monitored throughout the study for signs of distress or other effects of the therapeutic treatment All mice will be euthanized at a maximum tumor diameter of 20 mm, and tumors will be reserved for later analysis. Any mice that die prematurely from known or unknown causes will have a final measurement taken and tissues collected as soon as is possible.

Potential outcomes include a finding that mice treated with wt IL2 will exhibit considerable physiological distress compared to saline controls, and may even die prematurely from the treatment itself due to vascular leak syndrome (VLS). Those mice that survive the treatment may have some attenuated tumor growth and increased survival compared to saline controls. Potential outcomes further include a finding that mice treated with mut IL2 will not have VLS and the associated physiological stresses, but will have little or no attenuation of tumor growth compared with the saline control mice. In comparison, potential outcomes may include a finding that treatment with PDL1-mutIL2 and PDL2-mutIL2 will significantly attenuate tumor growth and increase survival over both the saline control and the wt IL2 group.

We will further analyze residual tumors for lymphocyte infiltration via immunohistochemistry. Specifically, we will evaluate the intratumoral infiltration of CD8+ Teff cells and NK cells. Further, we will evaluate the apoptotic levels via a TUNEL assay (Millipore ApopTag Peroxidase In Situ Apoptosis Detection Kit, Cat No. S7100). Potential outcomes include a finding that treatment with PDL1-mutIL2 and PDL2-mutIL2 increases CD8$^+$ Teff an NK cell intratumoral infiltration significantly over either saline control mice or wt IL2 treated mice.

These results would suggest that PD1 ligand IL2 fusion proteins, specifically PDL1-mutIL2 and PDL2-mutIL2, have an increased therapeutic benefit as compared to wt IL2 or mut IL2 cytokine treatment alone. By targeting the IL2 treatment to PD1 expressing cells, unintended toxicities and side effects will be reduced as compared to wt IL2 treatment. Further, intratumoral infiltration of cytotoxic lymphocytes is enhanced by the PD1 ligand IL2 fusion proteins, suggesting that targeted activation of these cellular populations increases the capacity of these cells to overcome the immunosuppression of the tumor cells.

Example 27. NKG2D Targeted Delivery of OX40L Preferentially Activates Cytotoxic Lymphocytes In Vitro This example describes in vitro testing of NKG2D targeted delivery of OX40L therapies. Specifically, this example will demonstrate improved immune cell activation of OMCP-OX40L over purified cytokine. This example will further demonstrate inhibition of OX40L signaling by OMCP-OX40L mutt and OMCP-OX40L mut2.

A total of 4 C57Bl/6 mice 6-9 weeks of age will be utilized to prepare a fresh splenocyte culture. Splenocytes will be cultured in triplicate for 36 hours according to the following groups: Group 1—saline control, Group 2—100 IUe/mL OX40L, Group 3—100 IUe/mL OX40L mut1, Group 4—100 IUe/mL OX40L mut2, Group 5—100 IUe/mL OMCP-OX40L, Group 6—100 IUe/mL OMCP-OX40L mutt, Group 7—100 IUe/mL OMCP-OX40L mut2. After the 36-hour culture period, cells will be stained for flow cytometry according to standard protocols, and cellular activation will be evaluated.

Cellular populations will be defined via the following gating strategies: $T_{regs}$—CD45+CD3+CD4+Foxp3+, NK cells—CD45+CD3-CD49b+CD335+, Teff—CD45+CD3+CD8+. Cellular activation will be further defined via evaluation whether the following markers are upergulated: $T_{regs}$—ICOS, NK cells—CD69 and KLRG1, Teff—CD69.

Potential outcomes include a finding that NK cells are significantly activated by treatment with OX40L and OMCP-OX40L. Teff cells may also be activated by treatment with OX40L, and OMCP-OX40L. This is in contrast with OX40L mutt, OX40L mut2, OMCP-OX40L mutt, and OMCP-OX40L mut2, which should inhibit NK cell activation. Further, Teff cells may also be inhibited by treatment with OX40L mutt, OX40L mut2, OMCP-OX40L mutt, and OMCP-OX40L mut2, which should inhibit NK cell activation.

These results would suggest that targeting OX40L therapy to NKG2D expressing cells via OMCP ligand fusion protein significantly enhances the efficacy of OX40L therapy in anti-tumor cell populations such as NK cells and Teff cells.

Example 28. NKG2D Targeted Delivery of OX40L Induces Proliferation of Cytotoxic Lymphocytes In Vitro This example describes in vitro testing of NKG2D targeted delivery of OX40L therapies. Specifically, this example will demonstrate improved cytotoxic immune cell expansion by OMCP-OX40L over purified cytokine.

A total of 4 C57Bl/6 mice 6-9 weeks of age will be utilized to prepare a fresh splenocyte culture. Splenocytes will be stained with CFSE prior to culture. CFSE permanently binds DNA, and provides an indication of cellular proliferation via reduced fluorescence with subsequent cellular divisions. Stained splenocytes will be subsequently cultured in triplicate for 6 days according to the following groups: Group 1—saline control, Group 2—1000 IUe/mL OX40L, Group 3—1000 IUe/mL OX40L mutt, Group 4—1000 IUe/mL OX40L mut2, Group 5—1000 IUe/mL OMCP-OX40L, Group 6—1000 IUe/mL OMCP-OX40L mutt, Group 7—1000 IUe/mL OMCP-OX40L mut2. After the 6-day culture period, cells will be stained for flow cytometry according to standard protocols, and cellular proliferation will be evaluated.

Cellular populations will be defined via the following gating strategies: $T_{regs}$—CD45+CD3+CD4+Foxp3+, NK cells—CD45+CD3-CD49b+CD335+, Teff—CD45+CD3+CD8+.

Potential outcomes include a finding that OX40L and OMCP-OX40L will induce significant proliferation in the NK cell population. We may also find that Teff cells are induced to proliferate via these same treatment groups. However, potential outcomes may include a finding that treatment with OX40L mutt, OX40L mut2, OMCP-OX40L mutt, and OMCP-OX40L mut2 will not induce either NK cell or Teff cell expansion. The NK cell to Treg cell ratio, a marker for immune cell activation and prognostic for cancer therapeutic responses, will be significantly enhanced by OMCP-OX40L treatment over the OX40L treatment alone.

These results would suggest that targeting OX40L therapy to NKG2D expressing cells via a NKG2D ligand fusion protein significantly enhances the proliferative capacity of anti-tumor cell populations such as NK cells and Teff cells.

Example 29. Lymphocyte Cytotoxicity is Enhanced by NKG2D Targeted Delivery of OX40L This example describes in vitro testing of NKG2D targeted delivery of OX40L therapies. Specifically, this example will demonstrate improved cytotoxic immune cell response after treatment with OMCP-OX40L over purified cytokine.

A total of 6 C57131/6 mice 6-9 weeks of age will be utilized to prepare a fresh splenocyte culture. Bulk splenocytes will be cultured for 6 days according to the following groups: Group 1—saline control, Group 2—1000 IUe/mL OX40L, Group 3—1000 IUe/mL OX40L mutt, Group 4—1000 IUe/mL OX40L mut2, Group 5—1000 IUe/mL OMCP-OX40L, Group 6—1000 IUe/mL OMCP-OX40L mutt, Group 7—1000 IUe/mL OMCP-OX40L mut2. After the 6-day culture period, cells will be prepared for a 7-AAD/CFSE cytotoxicity assay against K562 cells using a kit according to the manufacturer's protocols (Cayman Chemical, 7-AAD/CFSE Cell-Mediated Cytotoxicity Assay Kit, Item No. 600120). Splenocytes from each group will be seeded with target K562 cells in triplicate at the following ratios: no target cells, 15.6:1, 31.25:1, 62.5:1, 125:1, 250:1, 500:1. After 4 hours, the live versus dead target cell ratio will be evaluated via flow cytometry.

Potential outcomes include a finding that splenocytes incubated with OX40L, will have enhanced cytotoxic function against the target cells versus saline, OX40L mutt, and OX40L mut2 controls. Potential outcomes further include a finding that OMCP-OX40L treatment will further enhance the cytotoxicity of the splenocytes.

These results would suggest that NKG2D ligand OX40L fusion proteins increase splenocyte cytotoxic activity over OX40L therapy. This may be a function of enhanced binding and signaling of the OX40L portion of the fusion proteins through the OX40 receptor on T and NK cells.

Example 30. Tumor Growth and Survival after In Vivo Treatment with OMCP-OX40L Targeted Therapies This example describes in vivo proof of concept that OMCP-OX40L therapies inhibit tumor or cancer progression. Specifically, this example will demonstrate improved tumor growth and overall survival metrics after in vivo treatment with OMCP-OX40L fusion proteins over purified cytokine.

A total of 70 C57Bl/6 mice 6-9 weeks of age will be utilized. Mice will be injected with Lewis Lung Carcinoma subcutaneously at the flank with 1×105 cells per mouse. Treatment will begin 5 days later, when tumors have grown sufficiently to become visible and measurable. Initial tumor sizes and mouse weights will be taken, and mice will be randomized into groups of 10 mice such that the initial tumor sizes and mouse weights are similar between groups. The treatment groups are as follows: Group 1—saline control, Group 2—OX40L, Group 3—OX40L mutt, Group 4—OX40L mut2, Group 5—OMCP-OX40L, Group 6—OMCP-OX40L mutt, Group 7—OMCP-OX40L mut2.

All mice will be treated according to their groups twice daily in 12 hour intervals for 5 days, a total of 10 doses. Group 1—The mice will be intraperitoneally (i.p.) administered 200 μL saline for all treatments as a negative control. Group 2—The mice will be i.p. administered 75,000 IUe OX40L for each dose, for a total of 750,000 IUe OX40L after treatment. Group 3—The mice will be i.p. administered 75,000 IUe OX40L mut 1 for each dose, for a total of 750,000 IUe OX40L mut 1 after treatment. Group 4—The mice will be i.p. administered 75,000 IUe OX40L mut 2 for each dose, for a total of 750,000 IUe OX40L mut 2 after treatment. Group 5—The mice will be i.p. administered 75,000 IUe OMCP-OX40L for each dose, for a total of 750,000 IUe OMCP-OX40L after treatment. Group 6—The mice will be i.p. administered 75,000 IUe OMCP-OX40L mutt for each dose, for a total of 750,000 IUe OMCP-OX40L mutt after treatment. The mice will be i.p. administered 75,000 IUe OMCP-OX40L mut 2 for each dose, for a total of 750,000 IUe OMCP-OX40L mut 2 after treatment.

All tumors will be measured via caliper measurements and mouse weights measured every day during treatment. After the completion of the therapeutic course, mouse weights and tumors will be measured thrice weekly. Mice will be monitored throughout the study for signs of distress or other effects of the therapeutic treatment All mice will be euthanized at a maximum tumor diameter of 20 mm, and tumors will be reserved for later analysis. Any mice that die prematurely from known or unknown causes will have a final measurement taken and tissues collected as soon as is possible.

Potential outcomes include a finding that mice treated with OX40L may have some attenuated tumor growth and increased survival compared to saline controls. Potential outcomes further include a finding that mice treated with OX40L mut 1 or OX40L mut 2 will have little or no attenuation of tumor growth compared with the saline control mice. In comparison, potential outcomes may include a finding that treatment with OMCP-OX40L will significantly attenuate tumor growth and increase survival over both the saline, OMCP-OX40L mutt, and OMCP-OX40L mut 2 controls, as well as the OX40L group.

We will further analyze residual tumors for lymphocyte infiltration via immunohistochemistry. Specifically, we will evaluate the intratumoral infiltration of CD8+ Teff cells and NK cells. Further, we will evaluate the apoptotic levels via a TUNEL assay (Millipore ApopTag Peroxidase In Situ Apoptosis Detection Kit, Cat No. S7100). Potential outcomes include a finding that treatment with OMCP-OX40L increases CD8+ Teff an NK cell intratumoral infiltration significantly over either saline control mice or OX40L treated mice.

These results would suggest that NKG2D ligand OX40L fusion proteins, specifically OMCP-OX40L, has an increased therapeutic benefit as compared to OX40L treatment alone. Further, intratumoral infiltration of cytotoxic lymphocytes should be enhanced by the NKG2D ligand OX40L fusion protein, suggesting that targeted activation of these cellular populations increases the capacity of these cells to overcome the immunosuppression of the tumor cells.

Example 31. NKG2D Targeted Delivery of 4-1BBL Preferentially Activates Cytotoxic Lymphocytes In Vitro This example describes in vitro testing of NKG2D targeted delivery of 4-1BBL therapies. Specifically, this example will demonstrate improved immune cell activation of OMCP-4-1BBL over purified cytokine.

A total of 4 C57131/6 mice 6-9 weeks of age will be utilized to prepare a fresh splenocyte culture. Splenocytes will be cultured in triplicate for 36 hours according to the following groups: Group 1—saline control, Group 2—100 IUe/mL 4-1BBL, Group 3—100 IUe/mL OMCP-4-1BBL. After the 36-hour culture period, cells will be stained for flow cytometry according to standard protocols, and cellular activation will be evaluated.

Cellular populations will be defined via the following gating strategies: $T_{regs}$—CD45+CD3+CD4+Foxp3+, NK cells—CD45+CD3−CD49b+CD335+, Teff—CD45+CD3+CD8+. Cellular activation will be further defined via evaluation whether the following markers are upergulated: $T_{regs}$—ICOS, NK cells—CD69 and KLRG1, Teff—CD69.

Potential outcomes include a finding that NK cells are significantly activated by treatment with 4-1BBL and OMCP-4-1BBL. Teff cells may also be activated by treatment with -1BBL and OMCP-4-1BBL. Potential outcomes further include a finding that the OMCP-4-1BBL will show greater activation of NK, and potentially Teff cells, over the 4-1BBL ligand alone.

These results would suggest that targeting 4-1BBL therapy to NKG2D expressing cells via OMCP ligand fusion protein significantly enhances the efficacy of 4-1BBL therapy in anti-tumor cell populations such as NK cells and Teff cells.

Example 32. NKG2D Targeted Delivery of 4-1BBL Induces Proliferation of Cytotoxic Lymphocytes In Vitro This example describes in vitro testing of NKG2D targeted delivery of 4-1BBL therapies. Specifically, this example will demonstrate improved cytotoxic immune cell expansion by OMCP-4-1BBL over purified cytokine.

A total of 4 C57131/6 mice 6-9 weeks of age will be utilized to prepare a fresh splenocyte culture. Splenocytes will be stained with CFSE prior to culture. CFSE permanently binds DNA, and provides an indication of cellular proliferation via reduced fluorescence with subsequent cellular divisions. Stained splenocytes will be subsequently cultured in triplicate for 6 days according to the following groups: Group 1—saline control, Group 2—1000 IUe/mL 4-1BBL, Group 3—1000 IUe/mL OMCP-4-1BBL. After the 6-day culture period, cells will be stained for flow cytometry according to standard protocols, and cellular proliferation will be evaluated.

Cellular populations will be defined via the following gating strategies: $T_{regs}$—CD45+CD3+CD4+Foxp3+, NK cells—CD45+CD3−CD49b+CD335+, Teff—CD45+CD3+CD8+.

Potential outcomes include a finding that 4-1BBL and OMCP-4-1BBL will induce significant proliferation in the NK cell population. We may also find that Teff cells are induced to proliferate via these same treatment groups. Potential outcomes further include a finding that the NK cell to Treg cell ratio, a marker for immune cell activation and prognostic for cancer therapeutic responses, will be significantly enhanced by OMCP-4-1BBL treatment over the 4-1BBL treatment alone.

These results would suggest that targeting 4-1BBL therapy to NKG2D expressing cells via a NKG2D ligand fusion protein significantly enhances the proliferative capacity of anti-tumor cell populations such as NK cells and Teff cells.

Example 33. Lymphocyte Cytotoxicity is Enhanced by NKG2D Targeted Delivery of 4-1 BBL This example describes in vitro testing of NKG2D targeted delivery of 4-1BBL therapies. Specifically, this example will demonstrate improved cytotoxic immune cell response after treatment with OMCP-4-1BBL over purified cytokine.

A total of 6 C57131/6 mice 6-9 weeks of age will be utilized to prepare a fresh splenocyte culture. Bulk splenocytes will be cultured for 6 days according to the following groups: Group 1—saline control, Group 2—1000 IUe/mL 4-1BBL, Group 3—1000 IUe/mL OMCP-4-1BBL. After the 6-day culture period, cells will be prepared for a 7-AAD/CFSE cytotoxicity assay against K562 cells using a kit according to the manufacturer's protocols (Cayman Chemical, 7-AAD/CFSE Cell-Mediated Cytotoxicity Assay Kit, Item No. 600120). Splenocytes from each group will be seeded with target K562 cells in triplicate at the following ratios: no target cells, 15.6:1, 31.25:1, 62.5:1, 125:1, 250:1, 500:1. After 4 hours, the live versus dead target cell ratio will be evaluated via flow cytometry.

Potential outcomes include a finding that splenocytes incubated with 4-1BBL, will have enhanced cytotoxic function against the target cells versus saline control. Potential outcomes further include a finding that OMCP-4-1BBL treatment will further enhance the cytotoxicity of the splenocytes.

These results would suggest that NKG2D ligand 4-1BBL fusion proteins increase splenocyte cytotoxic activity over 4-1BBL therapy. This may be a function of enhanced binding and signaling of the 4-1BBL portion of the fusion proteins through the 4-1BB receptor on T and NK cells.

Example 34. Tumor Growth and Survival after In Vivo Treatment with OMCP-4-1BBL Targeted Therapies This example describes in vivo proof of concept that OMCP-4-1BBL therapies inhibit tumor or cancer progression. Specifically, this example will demonstrate improved tumor growth and overall survival metrics after in vivo treatment with OMCP-4-1 BBL fusion proteins over purified cytokine.

A total of 30 C57131/6 mice 6-9 weeks of age will be utilized. Mice will be injected with Lewis Lung Carcinoma subcutaneously at the flank with 1×105 cells per mouse. Treatment will begin 5 days later, when tumors have grown sufficiently to become visible and measurable. Initial tumor sizes and mouse weights will be taken, and mice will be randomized into groups of 10 mice such that the initial tumor sizes and mouse weights are similar between groups. The treatment groups are as follows: Group 1—saline control, Group 2—4-1BBL, Group 3—OMCP-4-1BBL.

All mice will be treated according to their groups twice daily in 12 hour intervals for 5 days, a total of 10 doses. Group 1—The mice will be intraperitoneally (i.p.) administered 200 μL saline for all treatments as a negative control. Group 2—The mice will be i.p. administered 75,000 IUe 4-1BBL for each dose, for a total of 750,000 IUe 4-1BBL after treatment. Group 3—The mice will be i.p. administered 75,000 IUe OMCP-4-1BBL for each dose, for a total of 750,000 IUe OMCP-4-1BBL after treatment.

All tumors will be measured via caliper measurements and mouse weights measured every day during treatment. After the completion of the therapeutic course, mouse weights and tumors will be measured thrice weekly. Mice will be monitored throughout the study for signs of distress or other effects of the therapeutic treatment All mice will be euthanized at a maximum tumor diameter of 20 mm, and tumors will be reserved for later analysis. Any mice that die prematurely from known or unknown causes will have a final measurement taken and tissues collected as soon as is possible.

Potential outcomes include a finding that mice treated with 4-1BBL may have some attenuated tumor growth and increased survival compared to saline controls. In comparison, Potential outcomes further include a finding that treatment with OMCP-4-1BBL will significantly attenuate tumor growth and increase survival over both the saline controls, as well as the 4-1BBL group.

We will further analyze residual tumors for lymphocyte infiltration via immunohistochemistry. Specifically, we will evaluate the intratumoral infiltration of CD8+ Teff cells and NK cells. Further, we will evaluate the apoptotic levels via a TUNEL assay (Millipore ApopTag Peroxidase In Situ Apoptosis Detection Kit, Cat No. S7100). Potential outcomes include a finding that treatment with OMCP-4-1BBL increases CD8+ Teff an NK cell intratumoral infiltration significantly over either saline control mice or 4-1BBL treated mice.

These results would suggest that NKG2D ligand 4-1BBL fusion proteins, specifically OMCP-4-1BBL, has an increased therapeutic benefit as compared to 4-1BBL treatment alone. Further, intratumoral infiltration of cytotoxic lymphocytes should be enhanced by the NKG2D ligand 4-1BBL fusion protein, suggesting that targeted activation of these cellular populations increases the capacity of these cells to overcome the immunosuppression of the tumor cells.

Example 35. OMCP-IL2 for Expanding Ex Vivo Cell Therapy Cultures

An experiment was conducted to evaluate the utility of targeted cytokine delivery on in vitro cytotoxic lymphocyte expansion. The disclosed chimeric peptides, specifically OMCP-IL2, may be used to expand T cells such as CAR-T cells or tumor infiltrating lymphocytes (TIL). These therapies are typically cultured ex vivo in the presence of IL2 to facilitate their expansion. Experiments were conducted to determine if OMCP-IL2 would expand ex vivo cultured lymphocytes better than IL2 alone.

In this study, $2.5 \times 10^6$ C57BL/6 splenocytes were cultured in the presence of plate bound anti-CD3 and either wild-type IL-2 or OMCP-mutIL-2 at 1000 IUe/ml. The CD3 stimulation was removed after 72 hours and cytokine containing media was replenished every other day to avoid media exhaustion. The total number of CD3+ T cells and well as NK1.1$^+$CD3$^-$ NK cells was counted flow cytometrically over the course of 2 weeks and phenotypic markers of proliferation (KI67 expression), viability (staining by the exclusion of viability dye L34959) and exhaustion (surface PD1 expression). At the completion of the experiment (day 13) the cells were evaluated for other markers of exhaustion such as Lag3 and Tim3.

The results demonstrated that an increased number of both T and NK cells was evident in cultures expanded with OMCP-mutIL-2 over wild type IL-2 (FIG. 37, FIG. 38). A similar level of proliferation was evident between the two cultures but viability of OMCP-mutIL-2 treated cells was higher, possibly explaining the increase in cell number. PD-1 levels increased in both NK and CD3+ T cells but decreased significantly by day 6-9 of culture in OMCP-mutIL-2 treated cells but not wild-type IL-2 treated cells. Other markers of exhaustion, such as Tim-2 and Lag-3 were increased in wild-type IL-2 treated cultures as well. Accordingly, these results demonstrate that OMCP-mutIL2 is more effective than wild-type IL2 at ex vivo expansion of lymphocytes. This has important implications for therapies such as adoptive cellular immunotherapies. Adoptive cellular immunotherapy is a T cell based immunotherapy whereby T cells are taken from a subject and stimulated and/or genetically manipulated in vitro and then transferred back into a patient to fight against a tumor or infection.

TABLE 5

Atomic Coordinates for OMCP-NKG2D (4PDC).

```
HEADER    IMMUNE SYSTEM/VIRAL PROTEIN 17-APR-14 4PDC
TITLE     CRYSTAL STRUCTURE OF COWPOX VIRUS CPXV018 (OMCP) BOUND TO HUMAN NKG2D
COMPND    MOL_ID: 1;
COMPND   2 MOLECULE: NKG2-D TYPE II INTEGRAL MEMBRANE PROTEIN;
COMPND   3 CHAIN: A, B, C, D;
COMPND   4 FRAGMENT: UNP RESIDUES 93-215;
COMPND   5 SYNONYM: KILLER CELL LECTIN-LIKE RECEPTOR SUBFAMILY K MEMBER 1, NK
COMPND   6 CELL RECEPTOR D, NKG2-D-ACTIVATING NK RECEPTOR;
COMPND   7 ENGINEERED: YES;
COMPND   8 MOL_ID: 2;
COMPND   9 MOLECULE: CPXV018 PROTEIN;
COMPND  10 CHAIN: E, F;
COMPND  11 FRAGMENT: UNP RESIDUES 20-168;
COMPND  12 ENGINEERED: YES;
COMPND  13 MUTATION: YES
SOURCE    MOL_ID: 1;
SOURCE   2 ORGANISM_SCIENTIFIC: HOMO SAPIENS;
SOURCE   3 ORGANISM_TAXID: 9606;
SOURCE   4 GENE: KLRK1, D12S2489E, NKG2D;
SOURCE   5 EXPRESSION_SYSTEM: ESCHERICHIA COLI;
SOURCE   6 EXPRESSION_SYSTEM_TAXID: 469008;
SOURCE   7 EXPRESSION_SYSTEM_STRAIN: BL21(DE3)RIL;
SOURCE   8 EXPRESSION_SYSTEM_VECTOR_TYPE: PLASMID;
SOURCE   9 EXPRESSION_SYSTEM_PLASMID: PET21A(+);
SOURCE  10 MOL_ID: 2;
SOURCE  11 ORGANISM_SCIENTIFIC: COWPOX VIRUS;
SOURCE  12 ORGANISM_COMMON: CPV;
SOURCE  13 ORGANISM_TAXID: 10243;
SOURCE  14 GENE: CPXV018 CDS;
SOURCE  15 EXPRESSION_SYSTEM: ESCHERICHIA COLI;
SOURCE  16 EXPRESSION_SYSTEM_TAXID: 469008;
SOURCE  17 EXPRESSION_SYSTEM_STRAIN: BL21(DE3)RIL;
SOURCE  18 EXPRESSION_SYSTEM_VECTOR_TYPE: PLASMID;
SOURCE  19 EXPRESSION_SYSTEM_PLASMID: PET21A(+)
KEYWDS    SECRETED VIRAL PROTEIN, IMMUNE EVASION, ORTHOPOXVIRUS, MHC-LIKE FOLD,
KEYWDS   2 NK CELL RECEPTOR LIGAND, STRUCTURAL GENOMICS, CENTER FOR STRUCTURAL
KEYWDS   3 GENOMICS OF INFECTIOUS DISEASES, CSGID, IMMUNE SYSTEM-VIRAL PROTEIN
KEYWDS   4 COMPLEX
EXPDTA    X-RAY DIFFRACTION
AUTHOR    E. LAZEAR, C. A. NELSON, D. H. FREMONT, CENTER FOR STRUCTURAL GENOMICS OF
AUTHOR   2 INFECTIOUS DISEASES (CSGID)
REVDAT    30-JUL-14 4PDC 1 JRNL
REVDAT  1 21-MAY-14 4PDC 0
JRNL      AUTH E. LAZEAR, M. SUN, C. A. NELSON, J. A. CAMPBELL, L. N. CARAYANNOPOULOS,
JRNL      AUTH 2 A. R. FRENCH, D. H. FREMONT,
JRNL      AUTH 3 CENTER FOR STRUCTURAL GENOMICS OF INFECTIOUS DISEASES
JRNL      AUTH 4 (CSGID)
JRNL      TITL COWPOX VIRUS OMCP ANTAGONIZES NKG2D VIA AN UNEXPECTED
JRNL      TITL 2 BINDING ORIENTATION
```

TABLE 5-continued

Atomic Coordinates for OMCP-NKG2D (4PDC).

| | | |
|---|---|---|
| JRNL | | REF TO BE PUBLISHED |
| REMARK | 2 | RESOLUTION. 1.99 ANGSTROMS. |
| REMARK | 3 | REFINEMENT. |
| REMARK | 3 | PROGRAM: PHENIX (PHENIX.REFINE: 1.8.4_1496) |
| REMARK | 3 | AUTHORS: PAUL ADAMS, PAVEL AFONINE, VINCENT CHEN, IAN |
| REMARK | 3 | REFINEMENT TARGET: ML |
| REMARK | 3 | DATA USED IN REFINEMENT. |
| REMARK | 3 | RESOLUTION RANGE HIGH (ANGSTROMS): 1.99 |
| REMARK | 3 | RESOLUTION RANGE LOW (ANGSTROMS): 45.67 |
| REMARK | 3 | MIN(FOBS/SIGMA_FOBS): 1.380 |
| REMARK | 3 | COMPLETENESS FOR RANGE (%): 92.9 |
| REMARK | 3 | NUMBER OF REFLECTIONS: 50042 |
| REMARK | 3 | FIT TO DATA USED IN REFINEMENT. |
| REMARK | 3 | R VALUE (WORKING + TEST SET): 0.168 |
| REMARK | 3 | R VALUE (WORKING SET): 0.166 |
| REMARK | 3 | FREE R VALUE: 0.214 |
| REMARK | 3 | FREE R VALUE TEST SET SIZE (%): 3.980 |
| REMARK | 3 | FREE R VALUE TEST SET COUNT: 1994 |
| REMARK | 3 | FIT TO DATA USED IN REFINEMENT (IN BINS). |

| | | BIN | RESOLUTION RANGE | COMPL. | NWORK | NFREE | RWORK | RFREE |
|---|---|---|---|---|---|---|---|---|
| REMARK | 3 | 1 | 45.6774 -4.7969 | 1.00 | 3740 | 160 | 0.1646 | 0.1709 |
| REMARK | 3 | 2 | 4.7969 -3.808 | 1.00 | 3733 | 155 | 0.1289 | 0.1960 |
| REMARK | 3 | 3 | 3.8080 -3.3268 | 1.00 | 3673 | 151 | 0.1493 | 0.1701 |
| REMARK | 3 | 4 | 3.3268 -3.0227 | 0.99 | 3700 | 158 | 0.1688 | 0.2284 |
| REMARK | 3 | 5 | 3.0227 -2.8061 | 0.95 | 3529 | 151 | 0.1864 | 0.2352 |
| REMARK | 3 | 6 | 2.8061 -2.6407 | 0.91 | 3353 | 142 | 0.1826 | 0.2189 |
| REMARK | 3 | 7 | 2.6407 -2.5084 | 0.90 | 3309 | 133 | 0.1790 | 0.2297 |
| REMARK | 3 | 8 | 2.5084 -2.3993 | 0.89 | 3281 | 134 | 0.1744 | 0.2545 |
| REMARK | 3 | 9 | 2.3993 -2.3069 | 0.89 | 3285 | 132 | 0.1778 | 0.2825 |
| REMARK | 3 | 10 | 2.3069 -2.2273 | 0.90 | 3327 | 131 | 0.1764 | 0.2197 |
| REMARK | 3 | 11 | 2.2273 -2.1577 | 0.90 | 3302 | 127 | 0.1777 | 0.2202 |
| REMARK | 3 | 12 | 2.1577 -2.096 | 0.91 | 3328 | 152 | 0.1834 | 0.2460 |
| REMARK | 3 | 13 | 2.0960 -2.0408 | 0.91 | 3341 | 145 | 0.2098 | 0.2812 |
| REMARK | 3 | 14 | 2.0408 -1.991 | 0.85 | 3147 | 123 | 0.2098 | 0.2951 |

| | | |
|---|---|---|
| REMARK | 3 | BULK SOLVENT MODELLING. |
| REMARK | 3 | METHOD USED: FLAT BULK SOLVENT MODEL |
| REMARK | 3 | SOLVENT RADIUS: 1.11 |
| REMARK | 3 | SHRINKAGE RADIUS: 0.90 |
| REMARK | 3 | K_SOL: NULL |
| REMARK | 3 | B_SOL: NULL |
| REMARK | 3 | ERROR ESTIMATES. |
| REMARK | 3 | COORDINATE ERROR (MAXIMUM-LIKELIHOOD BASED): 0.230 |
| REMARK | 3 | PHASE ERROR (DEGREES, MAXIMUM-LIKELIHOOD BASED): 20.990 |
| REMARK | 3 | B VALUES. |
| REMARK | 3 | FROM WILSON PLOT (A**2): 21.62 |
| REMARK | 3 | MEAN B VALUE (OVERALL, A**2): NULL |
| REMARK | 3 | OVERALL ANISOTROPIC B VALUE. |
| REMARK | 3 | B11 (A**2): NULL |
| REMARK | 3 | B22 (A**2): NULL |
| REMARK | 3 | B33 (A**2): NULL |
| REMARK | 3 | B12 (A**2): NULL |

TABLE 5-continued

Atomic Coordinates for OMCP-NKG2D (4PDC).

```
REMARK   3  B13 (A**2): NULL
REMARK   3  B23 (A**2): NULL
REMARK   3  TWINNING INFORMATION.
REMARK   3   FRACTION: NULL
REMARK   3   OPERATOR: NULL
REMARK   3  DEVIATIONS FROM IDEAL VALUES.              RMSD     COUNT
REMARK   3              BOND:                          0.003     6687
REMARK   3              ANGLE:                         0.786     9030
REMARK   3              CHIRALITY:                     0.031      933
REMARK   3              PLANARITY:                     0.003     1150
REMARK   3              DIHEDRAL:                     13.423     2426
REMARK   3  TLS DETAILS
REMARK   3   NUMBER OF TLS GROUPS: NULL
REMARK   3  NCS DETAILS
REMARK   3   NUMBER OF NCS GROUPS: NULL
REMARK   3  OTHER REFINEMENT REMARKS: NULL
REMARK   4  4PDC COMPLIES WITH FORMAT V. 3.30, 13-JUL-11
REMARK 100  THIS ENTRY HAS BEEN PROCESSED BY RCSB ON 21-APR-14.
REMARK 100  THE DEPOSITION ID IS D_1000201141.
REMARK 200  EXPERIMENTAL DETAILS
REMARK 200   EXPERIMENT TYPE: X-RAY DIFFRACTION
REMARK 200   DATE OF DATA COLLECTION: 19-OCT-10
REMARK 200   TEMPERATURE (KELVIN): 100
REMARK 200   PH: 6.75
REMARK 200   NUMBER OF CRYSTALS USED: 1
REMARK 200   SYNCHROTRON (Y/N): Y
REMARK 200   RADIATION SOURCE: ALS
REMARK 200   BEAMLINE: 4.2.2
REMARK 200   X-RAY GENERATOR MODEL: NULL
REMARK 200   MONOCHROMATIC OR LAUE (M/L): M
REMARK 200   WAVELENGTH OR RANGE (A): 1.00004
REMARK 200   MONOCHROMATOR: NULL
REMARK 200   OPTICS: NULL
REMARK 200   DETECTOR TYPE: CCD
REMARK 200   DETECTOR MANUFACTURER: NOIR-1
REMARK 200   INTENSITY-INTEGRATION SOFTWARE: HKL
REMARK 200   DATA SCALING SOFTWARE: HKL
REMARK 200   NUMBER OF UNIQUE REFLECTIONS: 50139
REMARK 200   RESOLUTION RANGE HIGH (A): 1.991
REMARK 200   RESOLUTION RANGE LOW  (A): 50.000
REMARK 200   REJECTION CRITERIA (SIGMA(I)): NULL
REMARK 200  OVERALL.
REMARK 200   COMPLETENESS FOR RANGE (%): 93.5
REMARK 200   DATA REDUNDANCY: 6.200
REMARK 200   R MERGE      (I): 0.11800
REMARK 200   R SYM        (I): NULL
REMARK 200   <I/SIGMA(I)> FOR THE DATA SET: 12.7000
REMARK 200  IN THE HIGHEST RESOLUTION SHELL.
REMARK 200   HIGHEST RESOLUTION SHELL, RANGE HIGH (A): 2.00
REMARK 200   HIGHEST RESOLUTION SHELL, RANGE LOW  (A): 2.07
```

TABLE 5-continued

Atomic Coordinates for OMCP-NKG2D (4PDC).

| | | | | | |
|---|---|---|---|---|---|
| REMARK | 200 | COMPLETENESS FOR SHELL (%): 91.5 | | | |
| REMARK | 200 | DATA REDUNDANCY IN SHELL: 5.30 | | | |
| REMARK | 200 | R MERGE FOR SHELL (I): 0.48500 | | | |
| REMARK | 200 | R SYM FOR SHELL (I): NULL | | | |
| REMARK | 200 | <I/SIGMA(I)> FOR SHELL: NULL | | | |
| REMARK | 200 | DIFFRACTION PROTOCOL: SINGLE WAVELENGTH | | | |
| REMARK | 200 | METHOD USED TO DETERMINE THE STRUCTURE: MOLECULAR REPLACEMENT | | | |
| REMARK | 200 | SOFTWARE USED: PHASER | | | |
| REMARK | 200 | STARTING MODEL: 1MPU, 4FFE | | | |
| REMARK | 200 | REMARK: NULL | | | |
| REMARK | 280 | CRYSTAL | | | |
| REMARK | 280 | SOLVENT CONTENT, VS (%): 42.94 | | | |
| REMARK | 280 | MATTHEWS COEFFICIENT, VM (ANGSTROMS**3/DA): 2.16 | | | |
| REMARK | 280 | CRYSTALLIZATION CONDITIONS: 15% PEG 3350, 0.2M MGCL2, 0.1M BIS | | | |
| REMARK | 280 | -TRIS | | | |
| REMARK | 290 | CRYSTALLOGRAPHIC SYMMETRY | | | |
| REMARK | 290 | SYMMETRY OPERATORS FOR SPACE GROUP: P 1 21 1 | | | |
| REMARK | 290 | SYMOP SYMMETRY | | | |
| REMARK | 290 | NNNMMM OPERATOR | | | |
| REMARK | 290 | 1555 X,Y,Z | | | |
| REMARK | 290 | 2555 -X, Y +1/2, -Z | | | |
| REMARK | 290 | WHERE NNN -> OPERATOR NUMBER | | | |
| REMARK | 290 | MMM -> TRANSLATION VECTOR | | | |
| REMARK | 290 | CRYSTALLOGRAPHIC SYMMETRY TRANSFORMATIONS | | | |
| REMARK | 290 | THE FOLLOWING TRANSFORMATIONS OPERATE ON THE ATOM/HETATM | | | |
| REMARK | 290 | RECORDS IN THIS ENTRY TO PRODUCE CRYSTALLOGRAPHICALLY | | | |
| REMARK | 290 | RELATED MOLECULES. | | | |
| REMARK | 290 | SMTRY1 1 | 1.000000 | 0.000000 | 0.000000 | 0.000000 |
| REMARK | 290 | SMTRY2 1 | 0.000000 | 1.000000 | 0.000000 | 0.000000 |
| REMARK | 290 | SMTRY3 1 | 0.000000 | 0.000000 | 1.000000 | 0.000000 |
| REMARK | 290 | SMTRY1 2 | -1.000000 | 0.000000 | 0.000000 | 0.000000 |
| REMARK | 290 | SMTRY2 2 | 0.000000 | 1.000000 | 0.000000 | 50.55500 |
| REMARK | 290 | SMTRY3 2 | 0.000000 | 0.000000 | -1.000000 | 0.000000 |
| REMARK | 290 | REMARK: NULL | | | |
| REMARK | 300 | BIOMOLECULE: 1, 2 | | | |
| REMARK | 300 | SEE REMARK 350 FOR THE AUTHOR PROVIDED AND/OR PROGRAM | | | |
| REMARK | 300 | GENERATED ASSEMBLY INFORMATION FOR THE STRUCTURE IN | | | |
| REMARK | 300 | THIS ENTRY. THE REMARK MAY ALSO PROVIDE INFORMATION ON | | | |
| REMARK | 300 | BURIED SURFACE AREA. | | | |
| REMARK | 300 | REMARK: THE BIOLOGICAL UNIT OF HNKG2D IS A DIMER (CHAINS A & B AND | | | |
| REMARK | 300 | CHAINS C & D | | | |
| REMARK | 300 | COORDINATES FOR A COMPLETE MULTIMER REPRESENTING THE KNOWN | | | |
| REMARK | 350 | BIOLOGICALLY SIGNIFICANT OLIGOMERIZATION STATE OF THE | | | |
| REMARK | 350 | MOLECULE CAN BE GENERATED BY APPLYING BIOMT TRANSFORMATIONS | | | |
| REMARK | 350 | GIVEN BELOW. BOTH NON-CRYSTALLOGRAPHIC AND | | | |
| REMARK | 350 | CRYSTALLOGRAPHIC OPERATIONS ARE GIVEN. | | | |
| REMARK | 350 | BIOMOLECULE: 1 | | | |
| REMARK | 350 | AUTHOR DETERMINED BIOLOGICAL UNIT: TRIMERIC | | | |
| REMARK | 350 | APPLY THE FOLLOWING TO CHAINS: A, B, E | | | |
| REMARK | 350 | BIOMT1 1 | 1.000000 | 0.000000 | 0.000000 | 0.000000 |
| REMARK | 350 | BIOMT2 1 | 0.000000 | 1.000000 | 0.000000 | 0.000000 |

TABLE 5-continued

Atomic Coordinates for OMCP-NKG2D (4PDC).

| REMARK | | | | | | | | |
|---|---|---|---|---|---|---|---|---|
| REMARK | 350 | BIOMT3 | | 0.000000 | 0.000000 | 1.000000 | | 0.000000 |
| REMARK | 350 | BIOMOLECULE: 2 | | | | | | |
| REMARK | 350 | AUTHOR DETERMINED BIOLOGICAL UNIT: TRIMERIC | | | | | | |
| REMARK | 350 | APPLY THE FOLLOWING TO CHAINS: C, D, F | | | | | | |
| REMARK | 350 | BIOMT1 | | 1.000000 | 0.000000 | 0.000000 | | 0.000000 |
| REMARK | 350 | BIOMT2 | | 0.000000 | 1.000000 | 0.000000 | | 0.000000 |
| REMARK | 350 | BIOMT3 | | 0.000000 | 0.000000 | 1.000000 | | 0.000000 |
| REMARK | 465 | MISSING RESIDUES | | | | | | |
| REMARK | 465 | THE FOLLOWING RESIDUES WERE NOT LOCATED IN THE | | | | | | |
| REMARK | 465 | EXPERIMENT. (M = MODEL NUMBER; RES = RESIDUE NAME; C = CHAIN | | | | | | |
| REMARK | 465 | IDENTIFIER; SSSEQ = SEQUENCE NUMBER; I = INSERTION CODE.) | | | | | | |
| REMARK | 465 | M RES C SSSEQI | | | | | | |
| REMARK | 465 | GLU B 93 | | | | | | |
| REMARK | 500 | GEOMETRY AND STEREOCHEMISTRY | | | | | | |
| REMARK | 500 | SUBTOPIC: CLOSE CONTACTS IN SAME ASYMMETRIC UNIT | | | | | | |
| REMARK | 500 | THE FOLLOWING ATOMS ARE IN CLOSE CONTACT. | | | | | | |
| REMARK | 500 | ATM1 | RES C | SSEQI | ATM2 | RES C | SSEQI | DISTANCE |
| REMARK | 500 | O | HOH F | 293 | O | HOH F | 324 | 2.19 |
| REMARK | 500 | REMARK: NULL | | | | | | |
| REMARK | 500 | GEOMETRY AND STEREOCHEMISTRY | | | | | | |
| REMARK | 500 | SUBTOPIC: CLOSE CONTACTS | | | | | | |
| REMARK | 500 | THE FOLLOWING ATOMS THAT ARE RELATED BY CRYSTALLOGRAPHIC | | | | | | |
| REMARK | 500 | SYMMETRY ARE IN CLOSE CONTACT. AN ATOM LOCATED WITHIN 0.15 | | | | | | |
| REMARK | 500 | ANGSTROMS OF A SYMMETRY RELATED ATOM IS ASSUMED TO BE ON A | | | | | | |
| REMARK | 500 | SPECIAL POSITION AND IS, THEREFORE, LISTED IN REMARK 375 | | | | | | |
| REMARK | 500 | INSTEAD OF REMARK 500. ATOMS WITH NON-BLANK ALTERNATE | | | | | | |
| REMARK | 500 | LOCATION INDICATORS ARE NOT INCLUDED IN THE CALCULATIONS. | | | | | | |
| REMARK | 500 | DISTANCE CUTOFF: | | | | | | |
| REMARK | 500 | 2.2 ANGSTROMS FOR CONTACTS NOT INVOLVING HYDROGEN ATOMS | | | | | | |
| REMARK | 500 | 1.6 ANGSTROMS FOR CONTACTS INVOLVING HYDROGEN ATOMS | | | | | | |
| REMARK | 500 | ATM1 | RES C | SSEQI | ATM2 | RES C | SSYMOP | DISTANCE |
| REMARK | 500 | O | HOH C | 301 | O | HOH D | 1655 | 2.15 |
| REMARK | 500 | O | HOH C | 318 | O | HOH D | 1655 | 2.19 |
| REMARK | 500 | REMARK: NULL | | | | | | |
| REMARK | 500 | GEOMETRY AND STEREOCHEMISTRY | | | | | | |
| REMARK | 500 | SUBTOPIC: TORSION ANGLES | | | | | | |
| REMARK | 500 | TORSION ANGLES OUTSIDE THE EXPECTED RAMACHANDRAN REGIONS: | | | | | | |
| REMARK | 500 | (M = MODEL NUMBER; RES = RESIDUE NAME; C = CHAIN IDENTIFIER; | | | | | | |
| REMARK | 500 | SSEQ = SEQUENCE NUMBER; I = INSERTION CODE). | | | | | | |
| REMARK | 500 | STANDARD TABLE: | | | | | | |
| REMARK | 500 | FORMAT: (10X, I3, 1X, A3, 1X, A1, I4, A1, 4X, F7.2, 3X, F7.2) | | | | | | |
| REMARK | 500 | EXPECTED VALUES: GJ KLEYWEGT AND TA JONES (1996). PHI/PSI- | | | | | | |
| REMARK | 500 | CHOLOGY: RAMACHANDRAN REVISITED. STRUCTURE 4, 1395-1400 | | | | | | |
| REMARK | 500 | M RES | CSSEQI | | | PSI | | PHI |
| REMARK | 500 | SER A | 151 | | | -170.24 | | 71.72 |
| REMARK | 500 | THR A | 162 | | | -74.87 | | -58.64 |
| REMARK | 500 | MET A | 184 | | | -75.63 | | -143.50 |
| REMARK | 500 | TYR B | 106 | | | 114.87 | | -162.70 |
| REMARK | 500 | SER B | 151 | | | -171.27 | | 67.58 |
| REMARK | 500 | THR B | 162 | | | -35.85 | | 164.34 |
| REMARK | 500 | MET B | 184 | | | -59.05 | | -140.78 |

TABLE 5-continued

Atomic Coordinates for OMCP-NKG2D (4PDC).

```
REMARK 500                        SER C   151              -172.20    65.21
REMARK 500                        MET C   184               -64.72  -143.36
REMARK 500                        SER D   151              -170.57    74.89
REMARK 500                        MET D   184               -66.96  -138.40
REMARK 500                        ASN E    88                16.97    57.97
REMARK 500                        THR E   104               -12.21  -141.68
REMARK 500                        LYS F    35               -52.70  -131.11
REMARK 500                        THR F   104                -6.09  -145.54
REMARK 500
REMARK 500 REMARK: NULL
REMARK 525
REMARK 525 SOLVENT
REMARK 525
REMARK 525 THE SOLVENT MOLECULES HAVE CHAIN IDENTIFIERS THAT
REMARK 525 INDICATE THE POLYMER CHAIN WITH WHICH THEY ARE MOST
REMARK 525 CLOSELY ASSOCIATED. THE REMARK LISTS ALL THE SOLVENT
REMARK 525 MOLECULES WHICH ARE MORE THAN 5A AWAY FROM THE
REMARK 525 NEAREST POLYMER CHAIN (M = MODEL NUMBER;
REMARK 525 RES = RESIDUE NAME; C = CHAIN IDENTIFIER; SSEQ = SEQUENCE
REMARK 525 NUMBER; I = INSERTION CODE):
REMARK 525                                                  CSSEQI
REMARK 525  M RES
REMARK 525    HOH A                                         385 DISTANCE =  6.57 ANGSTROMS
REMARK 525    HOH A                                         387 DISTANCE =  6.32 ANGSTROMS
REMARK 525    HOH F                                         337 DISTANCE =  5.90 ANGSTROMS
REMARK 900
REMARK 900 RELATED ENTRIES
REMARK 900 RELATED ID: 4FFE  RELATED DB: PDB
REMARK 900 4FFE IS THE STRUCTURE OF FREE COWPOX VIRUS CPXV018 (OMCP)
REMARK 900 RELATED ID: 1MPU  RELATED DB: PDB
REMARK 900 1MPU IS THE STRUCTURE OF FREE HUMAN NKG2D IMMUNORECEPTOR.
REMARK 900 RELATED ID: 1HYR  RELATED DB: PDB
REMARK 900 HUMAN NKG2D IN COMPLEX WITH MIC-A
REMARK 900 RELATED ID: 1JSK  RELATED DB: PDB
REMARK 900 HUMAN NKG2D IN COMPLEX WITH RAE-1BETA
REMARK 900 RELATED ID: 1KCG  RELATED DB: PDB
REMARK 900 MOUSE NKG2D IN COMPLEX WITH ULBP3
REMARK 900 RELATED ID: CSGID-IDP00259 RELATED DB: TARGETTRACK
DBREF  4PDC A    1     215  UNP    P26718   NKG2D_HUMAN     93    215
DBREF  4PDC B    1     215  UNP    P26718   NKG2D_HUMAN     93    215
DBREF  4PDC C    1     215  UNP    P26718   NKG2D_HUMAN     93    215
DBREF  4PDC D    1     215  UNP    P26718   NKG2D_HUMAN     93    215
DBREF  4PDC E    1     149  UNP    Q8QN43   Q8QN43_COWPX    20    168
DBREF  4PDC F    1     149  UNP    Q8QN43   Q8QN43_COWPX    20    168
SEQADV 4PDC     GLY E     0  UNP    Q8QN43                          EXPRESSION TAG
SEQADV 4PDC     ASP E    23  UNP    Q8QN43                42  TYR   ENGINEERED MUTATION
SEQADV 4PDC     ASP E    95  UNP    Q8QN43               114  PHE   ENGINEERED MUTATION
SEQADV 4PDC     GLY F     0  UNP    Q8QN43                          EXPRESSION TAG
SEQADV 4PDC     ASP F    23  UNP    Q8QN43                42  TYR   ENGINEERED MUTATION
SEQADV 4PDC     ASP F    95  UNP    Q8QN43               114  PHE   ENGINEERED MUTATION
SEQRES   1 A  123  GLU SER TYR CYS GLY PRO CYS PRO LYS ASN TRP ILE CYS
SEQRES   2 A  123  TYR LYS ASN CYS TYR GLN PHE PHE ASP GLU SER LYS
SEQRES   3 A  123  ASN TRP TYR GLU SER GLN ALA SER MET SER GLN ASN
SEQRES   4 A  123  ALA SER LEU LEU LYS VAL TYR SER LYS SER GLU GLN ASP
SEQRES   5 A  123  LEU LEU LYS LEU VAL LYS SER TYR HIS TRP MET GLY LEU
SEQRES   6 A  123  VAL HIS ILE PRO THR ASN GLY SER TRP GLN TRP GLU ASP
```

TABLE 5-continued

Atomic Coordinates for OMCP-NKG2D (4PDC).

| | | | | | | | | | | | | | | | | |
|---|---|---|---|---|---|---|---|---|---|---|---|---|---|---|---|---|
| SEQRES | 7 | A | 123 | GLY | SER | ILE | LEU | SER | PRO | ASN | LEU | LEU | THR | ILE | ILE | GLU |
| SEQRES | 8 | A | 123 | MET | GLN | LYS | ASP | CYS | ALA | LEU | TYR | ALA | SER | PHE |
| SEQRES | 9 | A | 123 | LYS | GLY | TYR | ILE | GLU | ASN | CYS | SER | THR | PRO | ASN | THR | TYR |
| SEQRES | 10 | A | 123 | ILE | CYS | MET | GLN | ARG | THR |
| SEQRES | 1 | B | 123 | GLU | SER | TYR | CYS | GLY | PRO | CYS | PRO | LYS | ASN | TRP | ILE | CYS |
| SEQRES | 2 | B | 123 | TYR | LYS | ASN | ASN | CYS | TYR | GLN | PHE | PHE | ASP | GLU | SER | LYS |
| SEQRES | 3 | B | 123 | ASN | TRP | TYR | GLU | SER | GLN | ALA | SER | CYS | MET | SER | GLN | ASN |
| SEQRES | 4 | B | 123 | ALA | SER | LEU | LEU | LYS | VAL | TYR | SER | LYS | GLU | ASP | GLN | ASP |
| SEQRES | 5 | B | 123 | LEU | LEU | LYS | LEU | VAL | LYS | SER | TYR | HIS | TRP | MET | GLY | LEU |
| SEQRES | 6 | B | 123 | VAL | HIS | ILE | PRO | THR | ASN | GLY | SER | TRP | GLN | TRP | GLU | ASP |
| SEQRES | 7 | B | 123 | GLY | SER | ILE | LEU | SER | PRO | ASN | LEU | LEU | THR | ILE | ILE | GLU |
| SEQRES | 8 | B | 123 | MET | GLN | LYS | GLY | ASP | CYS | ALA | LEU | TYR | ALA | SER | PHE |
| SEQRES | 9 | B | 123 | LYS | GLY | TYR | ILE | GLU | ASN | CYS | SER | THR | PRO | ASN | THR | TYR |
| SEQRES | 10 | B | 123 | ILE | CYS | MET | GLN | ARG | THR |
| SEQRES | 1 | C | 123 | GLU | SER | TYR | CYS | GLY | PRO | CYS | PRO | LYS | ASN | TRP | ILE | CYS |
| SEQRES | 2 | C | 123 | TYR | LYS | ASN | ASN | CYS | TYR | GLN | PHE | PHE | ASP | GLU | SER | LYS |
| SEQRES | 3 | C | 123 | ASN | TRP | TYR | GLU | SER | GLN | ALA | SER | CYS | MET | SER | GLN | ASN |
| SEQRES | 4 | C | 123 | ALA | SER | LEU | LEU | LYS | VAL | TYR | SER | LYS | GLU | ASP | GLN | ASP |
| SEQRES | 5 | C | 123 | LEU | LEU | LYS | LEU | VAL | LYS | SER | TYR | HIS | TRP | MET | GLY | LEU |
| SEQRES | 6 | C | 123 | VAL | HIS | ILE | PRO | THR | ASN | GLY | SER | TRP | GLN | TRP | GLU | ASP |
| SEQRES | 7 | C | 123 | GLY | SER | ILE | LEU | SER | PRO | ASN | LEU | LEU | THR | ILE | ILE | GLU |
| SEQRES | 8 | C | 123 | MET | GLN | LYS | GLY | ASP | CYS | ALA | LEU | TYR | ALA | SER | PHE |
| SEQRES | 9 | C | 123 | LYS | GLY | TYR | ILE | GLU | ASN | CYS | SER | THR | PRO | ASN | THR | TYR |
| SEQRES | 10 | C | 123 | ILE | CYS | MET | GLN | ARG | THR |
| SEQRES | 1 | D | 123 | GLU | SER | TYR | CYS | GLY | PRO | CYS | PRO | LYS | ASN | TRP | ILE | CYS |
| SEQRES | 2 | D | 123 | TYR | LYS | ASN | ASN | CYS | TYR | GLN | PHE | PHE | ASP | GLU | SER | LYS |
| SEQRES | 3 | D | 123 | ASN | TRP | TYR | GLU | SER | GLN | ALA | SER | CYS | MET | SER | GLN | ASN |
| SEQRES | 4 | D | 123 | ALA | SER | LEU | LEU | LYS | VAL | TYR | SER | LYS | GLU | ASP | GLN | ASP |
| SEQRES | 5 | D | 123 | LEU | LEU | LYS | LEU | VAL | LYS | SER | TYR | HIS | TRP | MET | GLY | LEU |
| SEQRES | 6 | D | 123 | VAL | HIS | ILE | PRO | THR | ASN | GLY | SER | TRP | GLN | TRP | GLU | ASP |
| SEQRES | 7 | D | 123 | GLY | SER | ILE | LEU | SER | PRO | ASN | LEU | LEU | THR | ILE | ILE | GLU |
| SEQRES | 8 | D | 123 | MET | GLN | LYS | GLY | ASP | CYS | ALA | LEU | TYR | ALA | SER | PHE |
| SEQRES | 9 | D | 123 | LYS | GLY | TYR | ILE | GLU | ASN | CYS | SER | THR | PRO | ASN | THR | TYR |
| SEQRES | 10 | D | 123 | ILE | CYS | MET | GLN | ARG | THR |
| SEQRES | 1 | E | 150 | GLY | HIS | LYS | LEU | ALA | PHE | ASN | PHE | ASN | LEU | GLU | ILE | ASN |
| SEQRES | 2 | E | 150 | GLY | SER | ASP | THR | HIS | SER | THR | VAL | ASP | VAL | ASP | LEU | ASP |
| SEQRES | 3 | E | 150 | ASP | SER | GLN | ILE | ILE | THR | PHE | ALA | GLY | LYS | ASP | ILE | ARG |
| SEQRES | 4 | E | 150 | PRO | THR | ILE | PHE | MET | ILE | GLY | ASP | GLU | ILE | PHE | LEU |
| SEQRES | 5 | E | 150 | PRO | PHE | TYR | LYS | ASN | VAL | PHE | SER | GLU | GLU | PHE | SER | LEU |
| SEQRES | 6 | E | 150 | PHE | ARG | ARG | VAL | PRO | THR | SER | ASP | PRO | TYR | GLU | LYS | SER |
| SEQRES | 7 | E | 150 | THR | TYR | PHE | ASP | CYS | TYR | LEU | TYR | ASN | GLY | GLU | GLY | TYR |
| SEQRES | 8 | E | 150 | THR | PHE | VAL | LYS | THR | GLN | ALA | THR | ASN | LYS | ASN | MET | TRP |
| SEQRES | 9 | E | 150 | LEU | THR | THR | SER | GLU | PHE | ARG | LEU | LYS | TRP | PHE | ASP |
| SEQRES | 10 | E | 150 | GLY | GLU | GLN | CYS | ILE | MET | LYS | ASN | HIS | LEU | ARG | SER | LEU | VAL | ARG |
| SEQRES | 11 | E | 150 |
| SEQRES | 12 | E | 150 |
| SEQRES | 1 | F | 150 | GLY | HIS | LYS | LEU | ALA | PHE | ASN | PHE | ASN | LEU | GLU | ILE | ASN |
| SEQRES | 2 | F | 150 | GLY | SER | ASP | THR | HIS | SER | THR | VAL | ASP | VAL | ASP | LEU | ASP |
| SEQRES | 3 | F | 150 | ASP | SER | GLN | ILE | ILE | THR | PHE | ALA | GLY | LYS | ASP | ILE | ARG |
| SEQRES | 4 | F | 150 | PRO | THR | ILE | PHE | MET | ILE | PRO | PHE | ILE | GLY | ASP | PHE | LEU |
| SEQRES | 5 | F | 150 | PRO | PHE | TYR | ASN | VAL | PHE | SER | GLU | GLU | PHE | SER | LEU |

TABLE 5-continued

Atomic Coordinates for OMCP-NKG2D (4PDC).

| | | | | | | | | | | | | | | |
|---|---|---|---|---|---|---|---|---|---|---|---|---|---|---|
| SEQRES | 6 | F | 150 | PHE | ARG | ARG | VAL | PRO | THR | SER | THR | PRO | TYR | GLU | ASP | LEU |
| SEQRES | 7 | F | 150 | THR | TYR | PHE | ASP | CYS | TYR | LEU | TYR | ASP | GLY | ASN | LYS | SER |
| SEQRES | 8 | F | 150 | THR | PHE | ASP | GLN | ASP | TYR | LEU | TYR | ASN | GLY | GLU | GLU | TYR |
| SEQRES | 9 | F | 150 | THR | VAL | LYS | THR | GLN | GLU | ALA | THR | ASN | LYS | ASN | MET | TRP |
| SEQRES | 10 | F | 150 | LEU | THR | THR | SER | GLU | PHE | ARG | LEU | LYS | LYS | TRP | PHE | ASP |
| SEQRES | 11 | F | 150 | GLY | GLU | ASP | CYS | ILE | MET | HIS | LEU | ARG | SER | LEU | VAL | ARG |
| SEQRES | 12 | F | 150 | LYS | MET | GLU | ASP | SER | LYS | ARG | | | | | | |
| FORMUL | 7 | HOH | *660(H2 O) | | | | | | | | | | | | | |
| HELIX | 1 | AA1 | ASN | A | 119 | SER | A | 129 | 1 | | | | | | | 11 |
| HELIX | 2 | AA2 | GLN | B | 143 | VAL | A | 149 | 5 | | | | | | | 7 |
| HELIX | 3 | AA3 | ASN | B | 119 | SER | B | 129 | 1 | | | | | | | 11 |
| HELIX | 4 | AA4 | GLN | B | 143 | VAL | B | 149 | 5 | | | | | | | 7 |
| HELIX | 5 | AA5 | ASN | C | 119 | SER | C | 129 | 1 | | | | | | | 11 |
| HELIX | 6 | AA6 | GLN | C | 143 | VAL | C | 149 | 5 | | | | | | | 7 |
| HELIX | 7 | AA7 | ASN | D | 119 | GLN | D | 130 | 1 | | | | | | | 12 |
| HELIX | 8 | AA8 | GLN | D | 143 | VAL | D | 149 | 5 | | | | | | | 7 |
| HELIX | 9 | AA9 | ILE | E | 41 | ILE | E | 45 | 1 | | | | | | | 5 |
| HELIX | 10 | AB1 | ILE | E | 49 | LEU | E | 64 | 1 | | | | | | | 16 |
| HELIX | 11 | AB2 | THR | E | 111 | LYS | E | 126 | 1 | | | | | | | 16 |
| HELIX | 12 | AB3 | ASP | E | 129 | ASP | E | 146 | 1 | | | | | | | 18 |
| HELIX | 13 | AB4 | ILE | F | 41 | ILE | F | 45 | 1 | | | | | | | 5 |
| HELIX | 14 | AB5 | ILE | F | 49 | LEU | F | 64 | 1 | | | | | | | 16 |
| HELIX | 15 | AB6 | THR | F | 111 | LYS | F | 125 | 1 | | | | | | | 16 |
| HELIX | 16 | AB7 | ASP | F | 129 | ASP | F | 146 | 1 | | | | | | | 18 |
| Sheet1 | AA1 | 2 | SER | A | 94 | CYS | A | 96 | 0 | | | | | | | |
| Sheet2 | AA1 | 2 | CYS | B | 96 | CYS | B | 99-10 | 99N | SER | A | 94 | | | | |
| Sheet1 | AA2 | 4 | ILE | A | 104 | TYR | A | 10 | 6 | 0 | | | | | | |
| Sheet2 | AA2 | 4 | ASN | A | 109 | LYS | A | 11 | 8-10 | 111 | N | ILE | A | 104 | | |
| Sheet3 | AA2 | 4 | ASN | A | 207 | GLN | A | 21 | 3-10 | 213 | N | CYS | A | 110 | | |
| Sheet4 | AA2 | 4 | SER | A | 133 | LEU | A | 13 | 4-1N | 133 | O | MET | A | 212 | | |
| Sheet1 | AA3 | 4 | HIS | A | 153 | TRP | A | 15 | 4 | 0 | | | | | | |
| Sheet2 | AA3 | 4 | CYS | A | 189 | ALA | A | 19 | 3-10 | 192 | N | HIS | A | 153 | | |
| Sheet3 | AA3 | 4 | LYS | A | 197 | GLU | A | 20 | 1-10 | 201 | N | CYS | A | 189 | | |
| Sheet4 | AA3 | 4 | THR | A | 180 | ILE | A | 18 | 2 | 1N | 182 | N | GLY | A | 198 | |
| Sheet1 | AA4 | 2 | LEU | A | 157 | HIS | A | 15 | 9 | 0 | | | | | | |
| Sheet2 | AA4 | 2 | TRP | A | 166 | TYR | A | 16 | 8-10 | 167 | N | VAL | A | 158 | | |
| Sheet1 | AA5 | 5 | ILE | B | 104 | TYR | B | 10 | 6 | 0 | | | | | | |
| Sheet2 | AA5 | 5 | ASN | B | 109 | LYS | B | 11 | 8-10 | 111 | N | ILE | B | 104 | | |
| Sheet3 | AA5 | 5 | ASN | B | 207 | ARG | B | 21 | 4-10 | 207 | O | LYS | B | 118 | | |
| Sheet4 | AA5 | 5 | HIS | B | 153 | HIS | B | 15 | 9 | 1N | 154 | O | THR | B | 208 | |
| Sheet5 | AA5 | 5 | TRP | B | 166 | GLN | B | 16 | 8-10 | 167 | N | VAL | B | 158 | | |
| Sheet1 | AA6 | 6 | SER | B | 133 | LEU | B | 13 | 4 | 0 | | | | | | |
| Sheet2 | AA6 | 6 | ASN | B | 207 | ARG | B | 21 | 4-10 | 212 | N | SER | B | 133 | | |
| Sheet3 | AA6 | 6 | HIS | B | 153 | HIS | B | 15 | 9 | 1N | 154 | O | THR | B | 208 | |
| Sheet4 | AA6 | 6 | CYS | B | 189 | ALA | B | 19 | 3-10 | 192 | N | HIS | B | 153 | | |
| Sheet5 | AA6 | 6 | LYS | B | 197 | GLU | B | 20 | 1-10 | 197 | N | ALA | B | 193 | | |
| Sheet6 | AA6 | 6 | THR | B | 180 | ILE | B | 18 | 2 | 1N | 182 | O | GLY | B | 198 | |
| Sheet1 | AA7 | 2 | CYS | C | 96 | CYS | C | 99 | 0 | | | | | | | |
| Sheet2 | AA7 | 2 | SER | D | 94 | SER | D | 96-10 | 94 | N | CYS | C | 99 | | | |
| Sheet1 | AA8 | 8 | LEU | C | 133 | LEU | C | 13 | 4 | 0 | | | | | | |
| Sheet2 | AA8 | 8 | ASN | C | 207 | ARG | C | 21 | 4-10 | 212 | N | SER | C | 133 | | |

TABLE 5-continued

Atomic Coordinates for OMCP-NKG2D (4PDC).

| | | | | | | | | | | | | | |
|---|---|---|---|---|---|---|---|---|---|---|---|---|---|
| Sheet3 | AA8 | 8 | ASN C | 109 | LYS C | 109 | 11 | 8 | -1N | 110 | O | GLN C | 1555 | 213 |
| Sheet4 | AA8 | 8 | ILE C | 104 | TYR C | 104 | 10 | 6 | -1N | 104 | O | TYR C | 1555 | 111 |
| Sheet5 | AA8 | 8 | ILE D | 104 | TYR D | 104 | 106 | -10 | | 105 | N | CYS C | 1555 | 105 |
| Sheet6 | AA8 | 8 | ASN D | 109 | LYS D | 109 | 118 | -10 | | 111 | N | ILE D | 1555 | 104 |
| Sheet7 | AA8 | 8 | ASN D | 207 | GLN D | 207 | 213 | -10 | | 207 | N | LYS D | 1555 | 118 |
| Sheet8 | AA8 | 8 | SER D | 133 | LEU D | 133 | 134 | -1N | | 133 | O | MET D | 1555 | 212 |
| Sheet1 | AA9 | 5 | SER C | 165 | TRP C | 165 | 168 | O | | | | | | |
| Sheet2 | AA9 | 5 | HIS C | 153 | ILE C | 153 | 160 | -1N | | 158 | O | GLN C | 1555 | 167 |
| Sheet3 | AA9 | 5 | CYS C | 189 | ALA C | 189 | 193 | -10 | | 192 | N | HIS C | 1555 | 153 |
| Sheet4 | AA9 | 5 | LYS C | 197 | GLU C | 197 | 201 | -10 | | 201 | N | CYS C | 1555 | 189 |
| Sheet5 | AA9 | 5 | THR C | 180 | ILE C | 180 | 182 | 1N | | 182 | O | GLY C | 1555 | 198 |
| Sheet1 | AB1 | 5 | TRP D | 166 | TRP D | 166 | 168 | O | | | | | | |
| Sheet2 | AB1 | 5 | HIS D | 153 | HIS D | 153 | 159 | -1N | | 158 | O | GLN D | 1555 | 167 |
| Sheet3 | AB1 | 5 | CYS D | 189 | ALA D | 189 | 193 | -10 | | 192 | N | HIS D | 1555 | 153 |
| Sheet4 | AB1 | 5 | LYS D | 197 | GLU D | 197 | 201 | -10 | | 201 | N | CYS D | 1555 | 189 |
| Sheet5 | AB1 | 5 | THR D | 180 | ILE D | 180 | 182 | 1N | | 182 | O | GLY D | 1555 | 198 |
| Sheet1 | AB2 | 7 | ILE E | 37 | PRO E | 37 | 39 | O | | | | | | |
| Sheet2 | AB2 | 7 | GLN E | 28 | PHE E | 28 | 32 | -1N | | 31 | O | ARG E | 1555 | 38 |
| Sheet3 | AB2 | 7 | ASP E | 15 | LEU E | 15 | 24 | -1N | | 22 | O | ILE E | 1555 | 29 |
| Sheet4 | AB2 | 7 | HIS E | 1 | ASN E | 1 | 12 | -1N | | 4 | O | ASP E | 1555 | 23 |
| Sheet5 | AB2 | 7 | TYR E | 74 | THR E | 74 | 86 | -10 | | 75 | N | ILE E | 1555 | 11 |
| Sheet6 | AB2 | 7 | LYS E | 89 | TYR E | 89 | 98 | -10 | | 93 | N | GLU E | 1555 | 82 |
| Sheet7 | AB2 | 7 | GLU E | 101 | TYR E | 101 | 103 | -10 | | 101 | N | TYR E | 1555 | 98 |
| Sheet1 | AB3 | 7 | ILE F | 37 | PRO F | 37 | 39 | O | | | | | | |
| Sheet2 | AB3 | 7 | SER F | 27 | PHE F | 27 | 32 | -1N | | 31 | O | ARG F | 1555 | 38 |
| Sheet3 | AB3 | 7 | ASP F | 15 | LEU F | 15 | 24 | -1N | | 24 | O | SER F | 1555 | 27 |
| Sheet4 | AB3 | 7 | HIS F | 1 | ASN F | 1 | 12 | -10 | | 12 | O | ASP F | 1555 | 15 |
| Sheet5 | AB3 | 7 | GLU F | 75 | THR F | 75 | 86 | -10 | | 81 | N | PHE F | 1555 | 5 |
| Sheet6 | AB3 | 7 | LYS F | 89 | TYR F | 89 | 98 | -10 | | 91 | N | ASP F | 1555 | 84 |
| Sheet7 | AB3 | 7 | GLU F | 101 | TYR F | 101 | 103 | -10 | | 101 | N | TYR F | 1555 | 98 |
| SSBOND | 1 | | CYS A | 96 | | | CYS A | 105 | | 1555 | 1555 | | | 2.05 |
| SSBOND | 2 | | CYS A | 99 | | | CYS A | 110 | | 1555 | 1555 | | | 2.03 |
| SSBOND | 3 | | CYS A | 127 | | | CYS A | 211 | | 1555 | 1555 | | | 2.04 |
| SSBOND | 4 | | CYS A | 189 | | | CYS A | 203 | | 1555 | 1555 | | | 2.03 |
| SSBOND | 5 | | CYS B | 96 | | | CYS B | 105 | | 1555 | 1555 | | | 2.03 |
| SSBOND | 6 | | CYS B | 99 | | | CYS B | 110 | | 1555 | 1555 | | | 2.04 |
| SSBOND | 7 | | CYS B | 127 | | | CYS B | 211 | | 1555 | 1555 | | | 2.04 |
| SSBOND | 8 | | CYS B | 189 | | | CYS B | 203 | | 1555 | 1555 | | | 2.03 |
| SSBOND | 9 | | CYS C | 96 | | | CYS C | 105 | | 1555 | 1555 | | | 2.03 |
| SSBOND | 10 | | CYS C | 99 | | | CYS C | 110 | | 1555 | 1555 | | | 2.03 |
| SSBOND | 11 | | CYS C | 127 | | | CYS C | 211 | | 1555 | 1555 | | | 2.04 |
| SSBOND | 12 | | CYS C | 189 | | | CYS C | 203 | | 1555 | 1555 | | | 2.04 |
| SSBOND | 13 | | CYS D | 96 | | | CYS D | 105 | | 1555 | 1555 | | | 2.03 |
| SSBOND | 14 | | CYS D | 99 | | | CYS D | 110 | | 1555 | 1555 | | | 2.04 |
| SSBOND | 15 | | CYS D | 127 | | | CYS D | 211 | | 1555 | 1555 | | | 2.04 |
| SSBOND | 16 | | CYS D | 189 | | | CYS D | 203 | | 1555 | 1555 | | | 2.04 |
| SSBOND | 17 | | CYS E | 83 | | | CYS E | 133 | | 1555 | 1555 | | | 2.06 |
| SSBOND | 18 | | CYS F | 83 | | | CYS F | 133 | | 1555 | 1555 | | | 2.06 |
| CISPEP | 1 | | GLY A | 97 | | | PRO A | 98 | | 0 | | | | 1.2 |
| CISPEP | 2 | | SER A | 194 | | | SER A | 195 | | 0 | | | | -3.36 |
| CISPEP | 3 | | GLY B | 97 | | | PRO B | 98 | | 0 | | | | 1.05 |

TABLE 5-continued

Atomic Coordinates for OMCP-NKG2D (4PDC).

| | | | | | | | | | | | | |
|---|---|---|---|---|---|---|---|---|---|---|---|---|
| CISPEP | 4 | SER | B | 194 | SER | B | 195 | | | | -1.59 | |
| CISPEP | 5 | GLY | C | 97 | PRO | C | 98 | | | | 2.4 | |
| CISPEP | 6 | SER | C | 194 | SER | C | 195 | | | | 1.38 | |
| CISPEP | 7 | GLY | D | 97 | PRO | D | 98 | | | | 0.65 | |
| CISPEP | 8 | SER | D | 194 | SER | D | 195 | | | | -3.12 | |
| CRYST1 | 43.315 | | 101.11 | 91.368 | 90 | 91.63 | 90 | P | 1 | 21 | | 8 |
| ORIGX1 | | | 1.000000 | 0.000000 | | 0.000000 | | 0.00000 | | | | |
| ORIGX2 | | | 0.000000 | 1.000000 | | 0.000000 | | 0.00000 | | | | |
| ORIGX3 | | | 0.000000 | 0.000000 | | 1.000000 | | 0.00000 | | | | |
| SCALE1 | | | 0.023087 | 0.000000 | | 0.000659 | | 0.00000 | | | | |
| SCALE2 | | | 0.000000 | 0.009890 | | 0.000000 | | 0.00000 | | | | |
| SCALE3 | | | 0.000000 | 0.000000 | | 0.010949 | | 0.00000 | | | | |
| ATOM | 1 | N | | GLU A | 93 | | -14.924 | -22.137 | 7.066 | 1 | 59.38 | N |
| ATOM | 2 | CA | | GLU A | 93 | | -14.415 | -23.496 | 6.924 | 1 | 58.81 | C |
| ATOM | 3 | C | | GLU A | 93 | | -15.44 | -24.389 | 6.231 | 1 | 56.95 | C |
| ATOM | 4 | O | | GLU A | 93 | | -16.124 | -23.956 | 5.303 | 1 | 61.11 | O |
| ATOM | 5 | CB | | GLU A | 93 | | -13.098 | -23.497 | 6.143 | 1 | 60 | C |
| ATOM | 6 | CG | | GLU A | 93 | | -13.22 | -22.996 | 4.711 | 1 | 72.71 | C |
| ATOM | 7 | CD | | GLU A | 93 | | -11.88 | -22.928 | 3.998 | 1 | 80.57 | C |
| ATOM | 8 | OE1 | | GLU A | 93 | | -10.846 | -23.211 | 4.64 | 1 | 79.10 | O |
| ATOM | 9 | OE2 | | GLU A | 93 | | -11.862 | -22.593 | 2.794 | 1 | 85.72 | O1- |
| ATOM | 10 | HA | | GLU A | 93 | | -14.242 | -23.864 | 7.805 | 1 | 70.57 | H |
| ATOM | 11 | HB2 | | GLU A | 93 | | -12.756 | -24.404 | 6.11 | 1 | 72 | H |
| ATOM | 12 | HB3 | | GLU A | 93 | | -12.464 | -22.925 | 6.603 | 1 | 72 | H |
| ATOM | 13 | HG2 | | GLU A | 93 | | -13.601 | -22.104 | 4.719 | 1 | 87.25 | H |
| ATOM | 14 | HG3 | | GLU A | 93 | | -13.794 | -23.598 | 4.213 | 1 | 87.25 | H |
| ATOM | 15 | N | | SER A | 94 | | -15.537 | -25.634 | 6.687 | 1 | 47.51 | N |
| ATOM | 16 | CA | | SER A | 94 | | -16.522 | -26.571 | 6.163 | 1 | 43.6 | C |
| ATOM | 17 | C | | SER A | 94 | | -15.911 | -27.937 | 5.889 | 1 | 40.17 | C |
| ATOM | 18 | O | | SER A | 94 | | -14.793 | -28.231 | 6.312 | 1 | 42.4 | O |
| ATOM | 19 | CB | | SER A | 94 | | -17.684 | -26.716 | 7.143 | 1 | 50.65 | C |
| ATOM | 20 | OG | | SER A | 94 | | -17.227 | -27.207 | 8.391 | 1 | 53.61 | O |
| ATOM | 21 | H | | SER A | 94 | | -15.038 | -25.963 | 7.306 | 1 | 57.02 | H |
| ATOM | 22 | HA | | SER A | 94 | | -16.874 | -26.226 | 5.328 | 1 | 52.32 | H |
| ATOM | 23 | HB2 | | SER A | 94 | | -18.332 | -27.339 | 6.777 | 1 | 60.78 | H |
| ATOM | 24 | HB3 | | SER A | 94 | | -18.096 | -25.848 | 7.276 | 1 | 60.78 | H |
| ATOM | 25 | HG | | SER A | 94 | | -17.873 | -27.284 | 8.923 | 1 | 64.33 | H |
| ATOM | 26 | N | | TYR A | 95 | | -16.662 | -28.766 | 5.174 | 1 | 37.41 | N |
| ATOM | 27 | CA | | TYR A | 95 | | -16.245 | -30.126 | 4.875 | 1 | 36.16 | C |
| ATOM | 28 | C | | TYR A | 95 | | -16.815 | -31.089 | 5.907 | 1 | 32.15 | C |
| ATOM | 29 | O | | TYR A | 95 | | -17.812 | -30.789 | 6.566 | 1 | 28.55 | O |
| ATOM | 30 | CB | | TYR A | 95 | | -16.696 | -30.528 | 3.473 | 1 | 35.46 | C |
| ATOM | 31 | CG | | TYR A | 95 | | -15.877 | -29.913 | 2.361 | 1 | 39.96 | C |
| ATOM | 32 | CD1 | | TYR A | 95 | | -16.234 | -28.694 | 1.797 | 1 | 39.91 | C |
| ATOM | 33 | CD2 | | TYR A | 95 | | -14.75 | -30.557 | 1.87 | 1 | 39.04 | C |
| ATOM | 34 | CE1 | | TYR A | 95 | | -15.488 | -28.135 | 0.775 | 1 | 45.29 | C |
| ATOM | 35 | CE2 | | TYR A | 95 | | -13.998 | -30.006 | 0.85 | 1 | 44.91 | C |
| ATOM | 36 | CZ | | TYR A | 95 | | -14.37 | -28.795 | 0.306 | 1 | 46.64 | C |
| ATOM | 37 | OH | | TYR A | 95 | | -13.617 | -28.249 | -0.71 | 1 | 43.67 | O |
| ATOM | 38 | H | | TYR A | 95 | | -17.43 | -28.559 | 4.846 | 1 | 44.89 | H |
| ATOM | 39 | HA | | TYR A | 95 | | -15.278 | -30.179 | 4.91 | 1 | 43.39 | H |

TABLE 5-continued

Atomic Coordinates for OMCP-NKG2D (4PDC).

| ATOM | 40 | HB2 | TYR | A | 95 | -17.617 | 3.35 | -30.25 | 1 | 42.56 | H |
|---|---|---|---|---|---|---|---|---|---|---|---|
| ATOM | 41 | HB3 | TYR | A | 95 | -16.63 | 3.389 | -31.492 | 1 | 42.56 | H |
| ATOM | 42 | HD1 | TYR | A | 95 | -16.988 | 2.111 | -28.248 | 1 | 46.85 | H |
| ATOM | 43 | HD2 | TYR | A | 95 | -14.496 | 2.234 | -31.374 | 1 | 47.89 | H |
| ATOM | 44 | HE1 | TYR | A | 95 | -15.737 | 0.407 | -27.318 | 1 | 54.35 | H |
| ATOM | 45 | HE2 | TYR | A | 95 | -13.244 | 0.533 | -30.449 | 1 | 53.9 | H |
| ATOM | 46 | HH | TYR | A | 95 | -13.948 | -0.951 | -27.516 | 1 | 52.4 | H |
| ATOM | 47 | N | CYS | A | 96 | -16.167 | 6.043 | -32.241 | 1 | 28.25 | N |
| ATOM | 48 | CA | CYS | A | 96 | -16.597 | 6.969 | -33.278 | 1 | 23.26 | C |
| ATOM | 49 | C | CYS | A | 96 | -16.818 | 6.214 | -34.584 | 1 | 27.35 | C |
| ATOM | 50 | O | CYS | A | 96 | -15.989 | 5.397 | -34.985 | 1 | 25.95 | O |
| ATOM | 51 | CB | CYS | A | 96 | -15.561 | 8.079 | -33.472 | 1 | 25.56 | C |
| ATOM | 52 | SG | CYS | A | 96 | -16.018 | 9.334 | -34.695 | 1 | 27.03 | S |
| ATOM | 53 | H | CYS | A | 96 | -15.46 | 5.599 | -32.448 | 1 | 33.9 | H |
| ATOM | 54 | HA | CYS | A | 96 | -17.437 | 7.378 | -33.016 | 1 | 27.92 | H |
| ATOM | 55 | HB2 | CYS | A | 96 | -15.428 | 8.53 | -32.624 | 1 | 30.68 | H |
| ATOM | 56 | HB3 | CYS | A | 96 | -14.727 | 7.677 | -33.761 | 1 | 30.68 | H |
| ATOM | 57 | N | GLY | A | 97 | -17.937 | 6.497 | -35.244 | 1 | 24.78 | N |
| ATOM | 58 | CA | GLY | A | 97 | -18.277 | 5.84 | -36.491 | 1 | 28.73 | C |
| ATOM | 59 | C | GLY | A | 97 | -19.711 | 5.345 | -36.494 | 1 | 30.42 | C |
| ATOM | 60 | O | GLY | A | 97 | -20.56 | 5.912 | -35.807 | 1 | 28.09 | O |
| ATOM | 61 | H | GLY | A | 97 | -18.52 | 7.074 | -34.984 | 1 | 29.73 | H |
| ATOM | 62 | HA2 | GLY | A | 97 | -18.162 | 6.46 | -37.228 | 1 | 34.47 | H |
| ATOM | 63 | HA3 | GLY | A | 97 | -17.688 | 5.082 | -36.63 | 1 | 34.47 | H |
| ATOM | 64 | N | PRO | A | 98 | -19.994 | 4.281 | -37.266 | 1 | 30.69 | N |
| ATOM | 65 | CA | PRO | A | 98 | -19.033 | 3.536 | -38.091 | 1 | 29.74 | C |
| ATOM | 66 | C | PRO | A | 98 | -18.509 | 4.341 | -39.28 | 1 | 26.22 | C |
| ATOM | 67 | O | PRO | A | 98 | -19.241 | 5.13 | -39.878 | 1 | 28.36 | O |
| ATOM | 68 | CB | PRO | A | 98 | -19.843 | 2.324 | -38.566 | 1 | 27.73 | C |
| ATOM | 69 | CG | PRO | A | 98 | -21.247 | 2.772 | -38.528 | 1 | 29.99 | C |
| ATOM | 70 | CD | PRO | A | 98 | -21.353 | 3.723 | -37.371 | 1 | 26.89 | C |
| ATOM | 71 | HA | PRO | A | 98 | -18.286 | 3.234 | -37.551 | 1 | 35.69 | H |
| ATOM | 72 | HB2 | PRO | A | 98 | -19.581 | 2.088 | -39.469 | 1 | 33.28 | H |
| ATOM | 73 | HB3 | PRO | A | 98 | -19.703 | 1.579 | -37.96 | 1 | 33.28 | H |
| ATOM | 74 | HG2 | PRO | A | 98 | -21.466 | 3.222 | -39.358 | 1 | 35.98 | H |
| ATOM | 75 | HG3 | PRO | A | 98 | -21.827 | 2.006 | -38.392 | 1 | 35.98 | H |
| ATOM | 76 | HD2 | PRO | A | 98 | -21.993 | 4.424 | -37.567 | 1 | 32.27 | H |
| ATOM | 77 | HD3 | PRO | A | 98 | -21.585 | 3.244 | -36.559 | 1 | 32.27 | H |
| ATOM | 78 | N | CYS | A | 99 | -17.232 | 4.142 | -39.591 | 1 | 22.72 | N |
| ATOM | 79 | CA | CYS | A | 99 | -16.582 | 4.768 | -40.737 | 1 | 27.89 | C |
| ATOM | 80 | C | CYS | A | 99 | -15.575 | 3.793 | -41.326 | 1 | 21.11 | C |
| ATOM | 81 | O | CYS | A | 99 | -15.165 | 2.848 | -40.653 | 1 | 25.21 | O |
| ATOM | 82 | CB | CYS | A | 99 | -15.865 | 6.062 | -40.337 | 1 | 25.67 | C |
| ATOM | 83 | SG | CYS | A | 99 | -16.919 | 7.351 | -39.649 | 1 | 24.92 | S |
| ATOM | 84 | H | CYS | A | 99 | -16.707 | 3.634 | -39.138 | 1 | 27.26 | H |
| ATOM | 85 | HA | CYS | A | 99 | -17.245 | 4.977 | -41.414 | 1 | 33.47 | H |
| ATOM | 86 | HB2 | CYS | A | 99 | -15.194 | 5.847 | -39.67 | 1 | 30.81 | H |
| ATOM | 87 | HB3 | CYS | A | 99 | -15.433 | 6.429 | -41.124 | 1 | 30.81 | H |
| ATOM | 88 | N | PRO | A | 100 | -15.165 | 4.018 | -42.583 | 1 | 24.66 | N |
| ATOM | 89 | CA | PRO | A | 100 | -14.053 | 3.244 | -43.146 | 1 | 24.78 | C |
| ATOM | 90 | C | PRO | A | 100 | -12.777 | 3.4 | -42.312 | 1 | 27.64 | C |

TABLE 5-continued

Atomic Coordinates for OMCP-NKG2D (4PDC).

| | | | | | | | | | | |
|---|---|---|---|---|---|---|---|---|---|---|
| ATOM | 91 | O | PRO | A | 100 | -12.552 | 4.46 | -41.723 | 1 | 21.92 | O |
| ATOM | 92 | CB | PRO | A | 100 | -13.882 | 3.841 | -44.546 | 1 | 25.09 | C |
| ATOM | 93 | CG | PRO | A | 100 | -15.217 | 4.427 | -44.874 | 1 | 26.97 | C |
| ATOM | 94 | CD | PRO | A | 100 | -15.757 | 4.935 | -43.574 | 1 | 24.88 | C |
| ATOM | 95 | HA | PRO | A | 100 | -14.288 | 2.306 | -43.216 | 1 | 29.73 | H |
| ATOM | 96 | HB2 | PRO | A | 100 | -13.199 | 4.53 | -44.527 | 1 | 30.11 | H |
| ATOM | 97 | HB3 | PRO | A | 100 | -13.649 | 3.141 | -45.175 | 1 | 30.11 | H |
| ATOM | 98 | HG2 | PRO | A | 100 | -15.108 | 5.153 | -45.507 | 1 | 32.37 | H |
| ATOM | 99 | HG3 | PRO | A | 100 | -15.795 | 3.738 | -45.239 | 1 | 32.37 | H |
| ATOM | 100 | HD2 | PRO | A | 100 | -15.458 | 5.844 | -43.415 | 1 | 29.86 | H |
| ATOM | 101 | HD3 | PRO | A | 100 | -16.725 | 4.87 | -43.56 | 1 | 29.86 | H |
| ATOM | 102 | N | LYS | A | 101 | -11.958 | 2.356 | -42.268 | 1 | 25.51 | N |
| ATOM | 103 | CA | LYS | A | 101 | -10.803 | 2.317 | -41.372 | 1 | 31.26 | C |
| ATOM | 104 | C | LYS | A | 101 | -9.762 | 3.391 | -41.68 | 1 | 29.73 | C |
| ATOM | 105 | O | LYS | A | 101 | -9.072 | 3.864 | -40.778 | 1 | 35.56 | O |
| ATOM | 106 | CB | LYS | A | 101 | -10.142 | 0.936 | -41.429 | 1 | 34.82 | C |
| ATOM | 107 | CG | LYS | A | 101 | -10.941 | -0.169 | -40.743 | 1 | 42.12 | C |
| ATOM | 108 | CD | LYS | A | 101 | -10.935 | -0.038 | -39.222 | 1 | 53.27 | C |
| ATOM | 109 | CE | LYS | A | 101 | -9.57 | -0.367 | -38.628 | 1 | 64.08 | C |
| ATOM | 110 | NZ | LYS | A | 101 | -9.569 | -0.299 | -37.138 | 1 | 67.45 | + |
| ATOM | 111 | H | LYS | A | 101 | -12.048 | 1.65 | -42.75 | 1 | 30.62 | H |
| ATOM | 112 | HA | LYS | A | 101 | -11.111 | 2.46 | -40.464 | 1 | 37.51 | H |
| ATOM | 113 | HB2 | LYS | A | 101 | -10.027 | 0.684 | -42.358 | 1 | 41.79 | H |
| ATOM | 114 | HB3 | LYS | A | 101 | -9.276 | 0.988 | -40.994 | 1 | 41.79 | H |
| ATOM | 115 | HG2 | LYS | A | 101 | -11.862 | -0.127 | -41.045 | 1 | 50.54 | H |
| ATOM | 116 | HG3 | LYS | A | 101 | -10.554 | -1.028 | -40.973 | 1 | 50.54 | H |
| ATOM | 117 | HD2 | LYS | A | 101 | -11.158 | 0.874 | -38.979 | 1 | 63.92 | H |
| ATOM | 118 | HD3 | LYS | A | 101 | -11.585 | -0.652 | -38.846 | 1 | 63.92 | H |
| ATOM | 119 | HE2 | LYS | A | 101 | -9.319 | -1.267 | -38.889 | 1 | 76.89 | H |
| ATOM | 120 | HE3 | LYS | A | 101 | -8.917 | 0.27 | -38.959 | 1 | 76.89 | H |
| ATOM | 121 | HZ1 | LYS | A | 101 | -8.759 | -0.496 | -36.825 | 1 | 80.94 | H |
| ATOM | 122 | HZ2 | LYS | A | 101 | -9.791 | 0.52 | -36.87 | 1 | 80.94 | H |
| ATOM | 123 | HZ3 | LYS | A | 101 | -10.156 | -0.88 | -36.807 | 1 | 80.94 | H |
| ATOM | 124 | N | ASN | A | 102 | -9.648 | 3.77 | -42.949 | 1 | 25.43 | N |
| ATOM | 125 | CA | ASN | A | 102 | -8.65 | 4.749 | -43.37 | 1 | 29.54 | C |
| ATOM | 126 | C | ASN | A | 102 | -9.227 | 6.159 | -43.532 | 1 | 27.18 | C |
| ATOM | 127 | O | ASN | A | 102 | -8.621 | 7.013 | -44.18 | 1 | 24.09 | O |
| ATOM | 128 | CB | ASN | A | 102 | -7.995 | 4.294 | -44.68 | 1 | 34.94 | C |
| ATOM | 129 | CG | ASN | A | 102 | -9.006 | 3.828 | -45.715 | 1 | 30.75 | C |
| ATOM | 130 | OD1 | ASN | A | 102 | -10.215 | 3.951 | -45.52 | 1 | 34.9 | O |
| ATOM | 131 | ND2 | ASN | A | 102 | -8.512 | 3.285 | -46.823 | 1 | 37.11 | N |
| ATOM | 132 | H | ASN | A | 102 | -10.139 | 3.473 | -43.589 | 1 | 30.52 | H |
| ATOM | 133 | HA | ASN | A | 102 | -7.956 | 4.793 | -42.695 | 1 | 35.45 | H |
| ATOM | 134 | HB2 | ASN | A | 102 | -7.498 | 5.035 | -45.06 | 1 | 41.92 | H |
| ATOM | 135 | HB3 | ASN | A | 102 | -7.396 | 3.554 | -44.493 | 1 | 41.92 | H |
| ATOM | 136 | HD21 | ASN | A | 102 | -9.043 | 3.006 | -47.439 | 1 | 44.53 | H |
| ATOM | 137 | HD22 | ASN | A | 102 | -7.661 | 3.213 | -46.923 | 1 | 44.53 | H |
| ATOM | 138 | N | TRP | A | 103 | -10.392 | 6.399 | -42.932 | 1 | 22.81 | N |
| ATOM | 139 | CA | TRP | A | 103 | -11.038 | 7.712 | -42.979 | 1 | 22.94 | C |
| ATOM | 140 | C | TRP | A | 103 | -11.012 | 8.411 | -41.623 | 1 | 21.34 | C |
| ATOM | 141 | O | TRP | A | 103 | -10.915 | 7.764 | -40.583 | 1 | 18.27 | O |

TABLE 5-continued

Atomic Coordinates for OMCP-NKG2D (4PDC).

| ATOM | 142 | CB | TRP | A | 103 | -12.492 | 7.586 | -43.443 | 1 | 21.32 | C |
| --- | --- | --- | --- | --- | --- | --- | --- | --- | --- | --- | --- |
| ATOM | 143 | CG | TRP | A | 103 | -12.658 | 7.417 | -44.919 | 1 | 26.61 | C |
| ATOM | 144 | CD1 | TRP | A | 103 | -11.883 | 6.664 | -45.755 | 1 | 30.04 | C |
| ATOM | 145 | CD2 | TRP | A | 103 | -13.663 | 8.023 | -45.738 | 1 | 23.17 | C |
| ATOM | 146 | NE1 | TRP | A | 103 | -12.351 | 6.759 | -47.044 | 1 | 29.11 | N |
| ATOM | 147 | CE2 | TRP | A | 103 | -13.442 | 7.588 | -47.061 | 1 | 26.93 | C |
| ATOM | 148 | CE3 | TRP | A | 103 | -14.731 | 8.887 | -45.481 | 1 | 20.7 | C |
| ATOM | 149 | CZ2 | ARP | A | 103 | -14.249 | 7.99 | -48.123 | 1 | 28.53 | C |
| ATOM | 150 | CZ3 | TRP | A | 103 | -15.53 | 9.286 | -46.534 | 1 | 24.02 | C |
| ATOM | 151 | CH2 | TRP | A | 103 | -15.285 | 8.837 | -47.841 | 1 | 22.8 | C |
| ATOM | 152 | H | TRP | A | 103 | -10.834 | 5.812 | -42.486 | 1 | 27.37 | H |
| ATOM | 153 | HA | TRP | A | 103 | -10.568 | 8.273 | -43.616 | 1 | 27.52 | H |
| ATOM | 154 | HB2 | TRP | A | 103 | -12.889 | 6.814 | -43.011 | 1 | 25.59 | H |
| ATOM | 155 | HB3 | TRP | A | 103 | -12.971 | 8.389 | -43.183 | 1 | 25.59 | H |
| ATOM | 156 | HD1 | TRP | A | 103 | -11.15 | 6.157 | -45.49 | 1 | 36.05 | H |
| ATOM | 157 | HE1 | TRP | A | 103 | -12.012 | 6.365 | -47.729 | 1 | 34.93 | H |
| ATOM | 158 | HE3 | TRP | A | 103 | -14.9 | 9.188 | -44.618 | 1 | 24.84 | H |
| ATOM | 159 | HZ2 | TRP | A | 103 | -14.088 | 7.695 | -48.99 | 1 | 34.23 | H |
| ATOM | 160 | HZ3 | TRP | A | 103 | -16.243 | 9.861 | -46.374 | 1 | 28.82 | H |
| ATOM | 161 | HH2 | TRP | A | 103 | -15.84 | 9.122 | -48.531 | 1 | 27.37 | H |
| ATOM | 162 | N | ILE | A | 104 | -11.122 | 9.737 | -41.653 | 1 | 15.59 | N |
| ATOM | 163 | CA | ILE | A | 104 | -11.21 | 10.546 | -40.444 | 1 | 17.76 | C |
| ATOM | 164 | C | ILE | A | 104 | -12.621 | 10.491 | -39.868 | 1 | 21.68 | C |
| ATOM | 165 | O | ILE | A | 104 | -13.587 | 10.764 | -40.577 | 1 | 20.98 | O |
| ATOM | 166 | CB | ILE | A | 104 | -10.853 | 12.022 | -40.718 | 1 | 19.18 | C |
| ATOM | 167 | CG1 | ILE | A | 104 | -12.139 | 12.835 | -41.368 | 1 | 22.53 | C |
| ATOM | 168 | CG2 | ILE | A | 104 | -9.47 | 10.91 | -39.425 | 1 | 20.64 | C |
| ATOM | 169 | CD1 | ILE | A | 104 | -9.156 | 13.53 | -41.903 | 1 | 18.1 | C |
| ATOM | 170 | H | ILE | A | 104 | -11.147 | 10.199 | -42.378 | 1 | 18.71 | H |
| ATOM | 171 | HA | ILE | A | 104 | -10.594 | 10.201 | -39.779 | 1 | 21.31 | H |
| ATOM | 172 | HB | ILE | A | 104 | -11.51 | 12.384 | -41.333 | 1 | 23.02 | H |
| ATOM | 173 | HG12 | ILE | A | 104 | -8.795 | 11.917 | -40.708 | 1 | 27.03 | H |
| ATOM | 174 | HG13 | ILE | A | 104 | -9.421 | 11.518 | -42.111 | 1 | 27.03 | H |
| ATOM | 175 | HG21 | ILE | A | 104 | -10.683 | 13.757 | -39.622 | 1 | 24.77 | H |
| ATOM | 176 | HG22 | ILE | A | 104 | -11.808 | 12.785 | -39.061 | 1 | 24.77 | H |
| ATOM | 177 | HG23 | ILE | A | 104 | -10.275 | 12.465 | -38.792 | 1 | 24.77 | H |
| ATOM | 178 | HD11 | ILE | A | 104 | -8.27 | 13.523 | -42.297 | 1 | 21.72 | H |
| ATOM | 179 | HD12 | ILE | A | 104 | -9.815 | 13.765 | -42.575 | 1 | 21.72 | H |
| ATOM | 180 | HD13 | ILE | A | 104 | -9.189 | 14.164 | -41.171 | 1 | 21.72 | H |
| ATOM | 181 | N | CYS | A | 105 | -12.734 | 10.151 | -38.587 | 1 | 19.34 | N |
| ATOM | 182 | CA | CYS | A | 105 | -14.026 | 10.133 | -37.909 | 1 | 18.07 | C |
| ATOM | 183 | C | CYS | A | 105 | -14.117 | 11.285 | -36.914 | 1 | 21.22 | C |
| ATOM | 184 | O | CYS | A | 105 | -13.216 | 11.497 | -36.102 | 1 | 21.2 | O |
| ATOM | 185 | CB | CYS | A | 105 | -14.249 | 8.8 | -37.196 | 1 | 23.12 | C |
| ATOM | 186 | SG | CYS | A | 105 | -15.944 | 8.565 | -36.591 | 1 | 26.35 | S |
| ATOM | 187 | H | CYS | A | 105 | -12.073 | 9.926 | -38.085 | 1 | 23.2 | H |
| ATOM | 188 | HA | CYS | A | 105 | -14.731 | 10.246 | -38.566 | 1 | 21.68 | H |
| ATOM | 189 | HB2 | CYS | A | 105 | -14.053 | 8.079 | -37.814 | 1 | 27.74 | H |
| ATOM | 190 | HB3 | CYS | A | 105 | -13.653 | 8.75 | -36.433 | 1 | 27.74 | H |
| ATOM | 191 | N | TYR | A | 106 | -15.207 | 12.035 | -37 | 1 | 17.94 | N |
| ATOM | 192 | CA | TYR | A | 106 | -15.451 | 13.148 | -36.097 | 1 | 18.87 | C |

TABLE 5-continued

Atomic Coordinates for OMCP-NKG2D (4PDC).

| | | | | | | | | | | |
|---|---|---|---|---|---|---|---|---|---|---|
| ATOM | 193 | C | TYR | A | 106 | -16.943 | 13.284 | -35.857 | 1 | 20.09 | C |
| ATOM | 194 | O | TYR | A | 106 | -17.711 | 13.548 | -36.785 | 1 | 17.41 | O |
| ATOM | 195 | CB | TYR | A | 106 | -14.881 | 14.452 | -36.659 | 1 | 17.9 | C |
| ATOM | 196 | CG | TYR | A | 106 | -14.966 | 15.613 | -35.696 | 1 | 17.46 | C |
| ATOM | 197 | CD1 | TYR | A | 106 | -14.351 | 15.552 | -34.452 | 1 | 24.97 | C |
| ATOM | 198 | CD2 | TYR | A | 106 | -15.651 | 16.774 | -36.031 | 1 | 21.85 | C |
| ATOM | 199 | CE1 | TYR | A | 106 | -14.424 | 16.61 | -33.562 | 1 | 22.33 | C |
| ATOM | 200 | CE2 | TYR | A | 106 | -15.726 | 17.841 | -35.148 | 1 | 20.74 | C |
| ATOM | 201 | CZ | TYR | A | 106 | -15.112 | 17.752 | -33.915 | 1 | 22.72 | C |
| ATOM | 202 | OH | TYR | A | 106 | -15.177 | 18.806 | -33.03 | 1 | 19.96 | O |
| ATOM | 203 | H | TYR | A | 106 | -15.829 | 11.918 | -37.582 | 1 | 21.53 | H |
| ATOM | 204 | HA | TYR | A | 106 | -15.021 | 12.971 | 35.245 | 1 | 22.65 | H |
| ATOM | 205 | HB2 | TYR | A | 106 | -13.947 | 14.316 | -36.88 | 1 | 21.49 | H |
| ATOM | 206 | HB3 | TYR | A | 106 | -15.377 | 14.692 | -37.458 | 1 | 21.49 | H |
| ATOM | 207 | HD1 | TYR | A | 106 | -13.888 | 14.783 | -34.209 | 1 | 29.97 | H |
| ATOM | 208 | HD2 | TYR | A | 106 | -16.068 | 16.836 | -36.88 | 1 | 26.22 | H |
| ATOM | 209 | HE1 | TYR | A | 106 | -14.008 | 16.553 | -32.732 | 1 | 26.79 | H |
| ATOM | 210 | HE2 | TYR | A | 106 | -16.19 | 18.611 | -35.385 | 1 | 24.89 | H |
| ATOM | 211 | HH | TYR | A | 106 | -15.622 | 19.435 | -33.364 | 1 | 23.95 | H |
| ATOM | 212 | N | LYS | A | 107 | -17.336 | 13.091 | -34.602 | 1 | 16.9 | N |
| ATOM | 213 | CA | LYS | A | 107 | -18.732 | 13.154 | -34.19 | 1 | 20.74 | C |
| ATOM | 214 | C | LYS | A | 107 | -19.605 | 12.235 | -35.048 | 1 | 17.68 | C |
| ATOM | 215 | O | LYS | A | 107 | -20.703 | 12.597 | -35.458 | 1 | 16.31 | O |
| ATOM | 216 | CB | LYS | A | 107 | -19.221 | 14.602 | -34.239 | 1 | 23.06 | C |
| ATOM | 217 | CG | LYS | A | 107 | -18.453 | 15.502 | -33.268 | 1 | 17.83 | C |
| ATOM | 218 | CD | LYS | A | 107 | -18.965 | 16.932 | -33.266 | 1 | 24.69 | C |
| ATOM | 219 | CE | LYS | A | 107 | -18.353 | 17.73 | -32.122 | 1 | 26.16 | C |
| ATOM | 220 | NZ | LYS | A | 107 | -18.797 | 19.153 | -32.118 | 1 | 29.75 | N1+ |
| ATOM | 221 | H | LYS | A | 107 | -16.797 | 12.917 | -33.955 | 1 | 20.28 | H |
| ATOM | 222 | HA | LYS | A | 107 | -18.8 | 12.851 | -33.271 | 1 | 24.89 | H |
| ATOM | 223 | HB2 | LYS | A | 107 | -19.096 | 14.949 | -35.136 | 1 | 27.68 | H |
| ATOM | 224 | HB3 | LYS | A | 107 | -20.16 | 14.629 | -33.998 | 1 | 27.68 | H |
| ATOM | 225 | HG2 | LYS | A | 107 | -18.545 | 15.149 | -32.369 | 1 | 21.4 | H |
| ATOM | 226 | HG3 | LYS | A | 107 | -17.518 | 15.519 | -33.524 | 1 | 21.4 | H |
| ATOM | 227 | HD2 | LYS | A | 107 | -18.723 | 17.362 | -34.102 | 1 | 29.63 | H |
| ATOM | 228 | HD3 | LYS | A | 107 | -19.929 | 16.929 | -33.155 | 1 | 29.63 | H |
| ATOM | 229 | HE2 | LYS | A | 107 | -18.618 | 17.329 | -31.279 | 1 | 31.4 | H |
| ATOM | 230 | HE3 | LYS | A | 107 | -17.387 | 17.716 | -32.208 | 1 | 31.4 | H |
| ATOM | 231 | HZ1 | LYS | A | 107 | -18.421 | 19.587 | -31.438 | 1 | 35.7 | H |
| ATOM | 232 | HZ2 | LYS | A | 107 | -18.56 | 19.548 | -32.88 | 1 | 35.7 | H |
| ATOM | 233 | HZ3 | LYS | A | 107 | -19.682 | 19.195 | -32.034 | 1 | 35.7 | H |
| ATOM | 234 | N | ASN | A | 108 | -19.079 | 11.04 | -35.303 | 1 | 22.6 | N |
| ATOM | 235 | CA | ASN | A | 108 | -19.77 | 9.979 | -36.04 | 1 | 25.82 | C |
| ATOM | 236 | C | ASN | A | 108 | -20.056 | 10.31 | -37.506 | 1 | 27.7 | C |
| ATOM | 237 | O | ASN | A | 108 | -20.822 | 9.609 | -38.164 | 1 | 25.85 | O |
| ATOM | 238 | CB | ASN | A | 108 | -21.069 | 9.606 | -35.324 | 1 | 25.22 | C |
| ATOM | 239 | CG | ASN | A | 108 | -20.816 | 8.947 | -33.984 | 1 | 29.09 | C |
| ATOM | 240 | OD1 | ASN | A | 108 | -19.803 | 8.274 | -33.796 | 1 | 25.84 | O |
| ATOM | 241 | ND2 | ASN | A | 108 | -21.733 | 9.139 | -33.043 | 1 | 32.94 | N |
| ATOM | 242 | H | ASN | A | 108 | -18.29 | 10.81 | -35.05 | 1 | 27.12 | H |
| ATOM | 243 | HA | ASN | A | 108 | -19.204 | 9.191 | -36.033 | 1 | 30.98 | H |

TABLE 5-continued

Atomic Coordinates for OMCP-NKG2D (4PDC).

| | | | | | | | | | |
|---|---|---|---|---|---|---|---|---|---|
| ATOM | 244 | HB2 | ASN | A | 108 | -21.59 | -35.172 | 10.41 | 1 | 30.27 | H |
| ATOM | 245 | HB3 | ASN | A | 108 | -21.569 | -35.876 | 8.984 | 1 | 30.27 | H |
| ATOM | 246 | HD21 | ASN | A | 108 | -21.632 | -32.266 | 8.784 | 1 | 39.52 | H |
| ATOM | 247 | HD22 | ASN | A | 108 | -22.427 | -33.21 | 9.617 | 1 | 39.52 | H |
| ATOM | 248 | N | ASN | A | 109 | -19.429 | -38.013 | 11.369 | 1 | 18.88 | N |
| ATOM | 249 | CA | ASN | A | 109 | -19.347 | -39.45 | 11.605 | 1 | 16.87 | C |
| ATOM | 250 | C | ASN | A | 109 | -17.968 | -39.936 | 11.166 | 1 | 20.87 | C |
| ATOM | 251 | O | ASN | A | 109 | -17.001 | -39.174 | 11.227 | 1 | 18.96 | O |
| ATOM | 252 | CB | ASN | A | 109 | -19.587 | -39.786 | 13.078 | 1 | 18.38 | C |
| ATOM | 253 | CG | ASN | A | 109 | -21.004 | -39.487 | 13.525 | 1 | 25.45 | C |
| ATOM | 254 | OD1 | ASN | A | 109 | -21.96 | -39.697 | 12.779 | 1 | 23.05 | O |
| ATOM | 255 | ND2 | ASN | A | 109 | -21.145 | -38.994 | 14.749 | 1 | 21.26 | N |
| ATOM | 256 | H | ASN | A | 109 | -19.038 | -37.539 | 11.971 | 1 | 22.66 | H |
| ATOM | 257 | HA | ASN | A | 109 | -20.019 | -39.905 | 11.072 | 1 | 20.25 | H |
| ATOM | 258 | HB2 | ASN | A | 109 | -18.983 | -39.259 | 13.625 | 1 | 22.05 | H |
| ATOM | 259 | HB3 | ASN | A | 109 | -19.422 | -40.731 | 13.218 | 1 | 22.05 | H |
| ATOM | 260 | HD21 | ASN | A | 109 | -21.929 | -38.808 | 15.05 | 1 | 25.51 | H |
| ATOM | 261 | HD22 | ASN | A | 109 | -20.453 | -38.862 | 15.242 | 1 | 25.51 | H |
| ATOM | 262 | N | CYS | A | 110 | -17.878 | -41.188 | 10.721 | 1 | 16.93 | N |
| ATOM | 263 | CA | CYS | A | 110 | -16.608 | -41.76 | 10.264 | 1 | 16.78 | C |
| ATOM | 264 | C | CYS | A | 110 | -16.142 | -42.866 | 11.205 | 1 | 19.88 | C |
| ATOM | 265 | O | CYS | A | 110 | -16.951 | -43.665 | 11.666 | 1 | 18.76 | O |
| ATOM | 266 | CB | CYS | A | 110 | -16.748 | -42.312 | 8.846 | 1 | 23.56 | C |
| ATOM | 267 | SG | CYS | A | 110 | -17.888 | -41.378 | 7.805 | 1 | 24.98 | S |
| ATOM | 268 | H | CYS | A | 110 | -18.543 | -41.732 | 10.673 | 1 | 20.32 | H |
| ATOM | 269 | HA | CYS | A | 110 | -15.931 | -41.065 | 10.253 | 1 | 20.14 | H |
| ATOM | 270 | HB2 | CYS | A | 110 | -17.074 | -43.224 | 8.898 | 1 | 28.27 | H |
| ATOM | 271 | HB3 | CYS | A | 110 | -15.878 | -42.297 | 8.419 | 1 | 28.27 | H |
| ATOM | 272 | N | TYR | A | 111 | -14.842 | -42.904 | 11.489 | 1 | 14.28 | N |
| ATOM | 273 | CA | TYR | A | 111 | -14.262 | -43.921 | 12.364 | 1 | 17.86 | C |
| ATOM | 274 | C | TYR | A | 111 | -12.987 | -44.505 | 11.787 | 1 | 17.19 | C |
| ATOM | 275 | O | TYR | A | 111 | -12.298 | -43.866 | 10.99 | 1 | 20.29 | O |
| ATOM | 276 | CB | TYR | A | 111 | -13.932 | -43.342 | 13.74 | 1 | 15.15 | C |
| ATOM | 277 | CG | TYR | A | 111 | -15.08 | -42.669 | 14.434 | 1 | 16.62 | C |
| ATOM | 278 | CD1 | TYR | A | 111 | -15.332 | -41.317 | 14.246 | 1 | 16.48 | C |
| ATOM | 279 | CD2 | TYR | A | 111 | -15.907 | -43.381 | 15.292 | 1 | 18.87 | C |
| ATOM | 280 | CE1 | TYR | A | 111 | -16.382 | -40.694 | 14.887 | 1 | 16.82 | C |
| ATOM | 281 | CE2 | TYR | A | 111 | -16.956 | -42.77 | 15.935 | 1 | 19.83 | C |
| ATOM | 282 | CZ | TYR | A | 111 | -17.191 | -41.425 | 15.73 | 1 | 18.41 | C |
| ATOM | 283 | OH | TYR | A | 111 | -18.242 | -40.816 | 16.373 | 1 | 19.61 | O |
| ATOM | 284 | H | TYR | A | 111 | -14.266 | -42.343 | 11.182 | 1 | 17.13 | H |
| ATOM | 285 | HA | TYR | A | 111 | -14.901 | -44.642 | 12.482 | 1 | 21.43 | H |
| ATOM | 286 | HB2 | TYR | A | 111 | -13.226 | -44.063 | 13.638 | 1 | 18.18 | H |
| ATOM | 287 | HB3 | TYR | A | 111 | -13.625 | -42.685 | 14.313 | 1 | 18.18 | H |
| ATOM | 288 | HD1 | TYR | A | 111 | -14.786 | -40.825 | 13.677 | 1 | 19.77 | H |
| ATOM | 289 | HD2 | TYR | A | 111 | -15.751 | -44.287 | 15.431 | 1 | 22.65 | H |
| ATOM | 290 | HE1 | TYR | A | 111 | -16.543 | -39.788 | 14.75 | 1 | 20.19 | H |
| ATOM | 291 | HE2 | TYR | A | 111 | -17.505 | -43.259 | 16.505 | 1 | 23.79 | H |
| ATOM | 292 | HH | TYR | A | 111 | -18.275 | -40.004 | 16.163 | 1 | 23.53 | H |
| ATOM | 293 | N | GLN | A | 112 | -12.659 | -45.716 | 12.214 | 1 | 18.48 | N |
| ATOM | 294 | CA | GLN | A | 112 | -11.331 | -46.254 | 11.972 | 1 | 20.7 | C |

TABLE 5-continued

Atomic Coordinates for OMCP-NKG2D (4PDC).

| | | | | | | | | | | |
|---|---|---|---|---|---|---|---|---|---|---|
| ATOM | 295 | C | GLN | A | 112 | -10.973 | 13.053 | -47.256 | 1 | 20.13 | C |
| ATOM | 296 | O | GLN | A | 112 | -11.806 | 13.479 | -48.055 | 1 | 20.24 | O |
| ATOM | 297 | CB | GLN | A | 112 | -11.233 | 10.591 | -46.905 | 1 | 24.04 | C |
| ATOM | 298 | CG | GLN | A | 112 | -9.818 | 10.232 | -47.369 | 1 | 23.23 | C |
| ATOM | 299 | CD | GLN | A | 112 | -8.771 | 10.4 | -46.272 | 1 | 29.49 | C |
| ATOM | 300 | OE1 | GLN | A | 112 | -8.311 | 11.511 | -45.994 | 1 | 31.23 | O |
| ATOM | 301 | NE2 | GLN | A | 112 | -8.392 | 9.296 | -45.645 | 1 | 30.5 | N |
| ATOM | 302 | H | GLN | A | 112 | -13.184 | 12.644 | -46.244 | 1 | 22.17 | H |
| ATOM | 303 | HA | GLN | A | 112 | -10.687 | 12.008 | -45.53 | 1 | 24.84 | H |
| ATOM | 304 | HB2 | GLN | A | 112 | -11.513 | 9.921 | -46.262 | 1 | 28.85 | H |
| ATOM | 305 | HB3 | GLN | A | 112 | -11.815 | 10.567 | -47.68 | 1 | 28.85 | H |
| ATOM | 306 | HG2 | GLN | A | 112 | -9.806 | 9.306 | -47.655 | 1 | 27.88 | H |
| ATOM | 307 | HG3 | GLN | A | 112 | -9.573 | 10.811 | -48.108 | 1 | 27.88 | H |
| ATOM | 308 | HE21 | GLN | A | 112 | -7.804 | 9.338 | -45.018 | 1 | 36.6 | H |
| ATOM | 309 | HE22 | GLN | A | 112 | -8.733 | 8.538 | -45.864 | 1 | 36.6 | H |
| ATOM | 310 | N | PHE | A | 113 | -9.722 | 13.492 | -47.189 | 1 | 18.31 | N |
| ATOM | 311 | CA | PHE | A | 113 | -9.211 | 14.536 | -48.062 | 1 | 22.45 | C |
| ATOM | 312 | C | PHE | A | 113 | -8.399 | 13.908 | -49.187 | 1 | 18.61 | C |
| ATOM | 313 | O | PHE | A | 113 | -7.556 | 13.051 | -48.936 | 1 | 23.89 | O |
| ATOM | 314 | CB | PHE | A | 113 | -8.36 | 15.523 | -47.259 | 1 | 23.17 | C |
| ATOM | 315 | CG | PHE | A | 113 | -9.135 | 16.272 | -46.211 | 1 | 24.24 | C |
| ATOM | 316 | CD1 | PHE | A | 113 | -9.569 | 15.633 | -45.06 | 1 | 29.05 | C |
| ATOM | 317 | CD2 | PHE | A | 113 | -9.431 | 17.615 | -46.375 | 1 | 27.58 | C |
| ATOM | 318 | CE1 | PHE | A | 113 | -10.287 | 16.317 | -44.096 | 1 | 26.86 | C |
| ATOM | 319 | CE2 | PHE | A | 113 | -10.149 | 18.306 | -45.412 | 1 | 28.41 | C |
| ATOM | 320 | CZ | PHE | A | 113 | -10.574 | 17.655 | -44.272 | 1 | 30.18 | C |
| ATOM | 321 | H | PHE | A | 113 | -9.138 | 13.192 | -46.634 | 1 | 21.97 | H |
| ATOM | 322 | HA | PHE | A | 113 | -9.954 | 15.021 | -48.454 | 1 | 26.94 | H |
| ATOM | 323 | HB2 | PHE | A | 113 | -7.651 | 15.034 | -46.812 | 1 | 27.81 | H |
| ATOM | 324 | HB3 | PHE | A | 113 | -7.977 | 16.174 | -47.868 | 1 | 27.81 | H |
| ATOM | 325 | HD1 | PHE | A | 113 | -9.379 | 14.731 | -44.936 | 1 | 34.86 | H |
| ATOM | 326 | HD2 | PHE | A | 113 | -9.147 | 18.058 | -47.142 | 1 | 33.09 | H |
| ATOM | 327 | HE1 | PHE | A | 113 | -10.572 | 15.877 | -43.328 | 1 | 32.23 | H |
| ATOM | 328 | HE2 | PHE | A | 113 | -10.342 | 19.208 | -45.533 | 1 | 34.1 | H |
| ATOM | 329 | HZ | PHE | A | 113 | -11.055 | 18.118 | -43.624 | 1 | 36.22 | H |
| ATOM | 330 | N | PHE | A | 114 | -8.669 | 14.324 | -50.42 | 1 | 16.59 | N |
| ATOM | 331 | CA | PHE | A | 114 | -7.977 | 13.782 | -51.589 | 1 | 20.44 | C |
| ATOM | 332 | C | PHE | A | 114 | -7.12 | 14.85 | -52.25 | 1 | 23.27 | C |
| ATOM | 333 | O | PHE | A | 114 | -7.637 | 15.86 | -52.728 | 1 | 21.65 | O |
| ATOM | 334 | CB | PHE | A | 114 | -8.987 | 13.208 | -52.582 | 1 | 23.69 | C |
| ATOM | 335 | CG | PHE | A | 114 | -9.683 | 11.983 | -52.077 | 1 | 18.44 | C |
| ATOM | 336 | CD1 | PHE | A | 114 | -10.811 | 12.092 | -51.285 | 1 | 22.02 | C |
| ATOM | 337 | CD2 | PHE | A | 114 | -9.19 | 10.723 | -52.366 | 1 | 25.83 | C |
| ATOM | 338 | CE1 | PHE | A | 114 | -11.447 | 10.964 | -50.805 | 1 | 26.42 | C |
| ATOM | 339 | CE2 | PHE | A | 114 | -9.821 | 9.592 | -51.89 | 1 | 23.08 | C |
| ATOM | 340 | CZ | PHE | A | 114 | -10.949 | 9.712 | -51.107 | 1 | 25.76 | C |
| ATOM | 341 | H | PHE | A | 114 | -9.255 | 14.925 | -50.61 | 1 | 19.91 | H |
| ATOM | 342 | HA | PHE | A | 114 | -7.393 | 13.062 | -51.305 | 1 | 24.52 | H |
| ATOM | 343 | HB2 | PHE | A | 114 | -9.662 | 13.88 | -52.767 | 1 | 28.43 | H |
| ATOM | 344 | HB3 | PHE | A | 114 | -8.524 | 12.972 | -53.401 | 1 | 28.43 | H |
| ATOM | 345 | HD1 | PHE | A | 114 | -11.149 | 12.933 | -51.079 | 1 | 26.43 | H |

TABLE 5-continued

Atomic Coordinates for OMCP-NKG2D (4PDC).

| ATOM | 346 | HD2 | PHE | A | 114 | -8.428 | 10.637 | -52.893 | 1 | 31 | H |
|---|---|---|---|---|---|---|---|---|---|---|---|
| ATOM | 347 | HE1 | PHE | A | 114 | -12.209 | 11.047 | -50.278 | 1 | 31.7 | H |
| ATOM | 348 | HE2 | PHE | A | 114 | -9.485 | 8.749 | -52.095 | 1 | 27.69 | H |
| ATOM | 349 | HZ | PHE | A | 114 | -11.377 | 8.951 | -50.787 | 1 | 30.91 | H |
| ATOM | 350 | N | ASP | A | 115 | -5.81 | 14.617 | -52.275 | 1 | 21.39 | N |
| ATOM | 351 | CA | ASP | A | 115 | -4.861 | 15.629 | -52.727 | 1 | 28.87 | C |
| ATOM | 352 | C | ASP | A | 115 | -4.607 | 15.563 | -54.233 | 1 | 29.39 | C |
| ATOM | 353 | O | ASP | A | 115 | -3.87 | 16.383 | -54.778 | 1 | 29.44 | O |
| ATOM | 354 | CB | ASP | A | 115 | -3.541 | 15.496 | -51.959 | 1 | 30.8 | C |
| ATOM | 355 | G | ASP | A | 115 | -2.889 | 14.136 | -52.135 | 1 | 36.31 | C |
| ATOM | 356 | OD1 | ASP | A | 115 | -3.559 | 13.199 | -52.615 | 1 | 34.47 | O |
| ATOM | 357 | OD2 | ASP | A | 115 | -1.698 | 14.005 | -51.78 | 1 | 46.52 | O1- |
| ATOM | 358 | H | ASP | A | 115 | -5.444 | 13.877 | -52.034 | 1 | 25.67 | H |
| ATOM | 359 | HA | ASP | A | 115 | -5.228 | 16.505 | -52.53 | 1 | 34.65 | H |
| ATOM | 360 | HB2 | ASP | A | 115 | -2.921 | 16.169 | -52.278 | 1 | 36.95 | H |
| ATOM | 361 | HB3 | ASP | A | 115 | -3.713 | 15.625 | -51.013 | 1 | 36.95 | H |
| ATOM | 362 | N | GLU | A | 116 | -5.226 | 14.596 | -54.903 | 1 | 28.73 | N |
| ATOM | 363 | CA | GLU | A | 116 | -5.17 | 14.52 | -56.362 | 1 | 33.21 | C |
| ATOM | 364 | C | GLU | A | 116 | -6.288 | 15.378 | -56.938 | 1 | 33.91 | C |
| ATOM | 365 | O | GLU | A | 116 | -7.466 | 15.116 | -56.699 | 1 | 38.64 | O |
| ATOM | 366 | CB | GLU | A | 116 | -5.287 | 13.075 | -56.86 | 1 | 37.54 | C |
| ATOM | 367 | CG | GLU | A | 116 | -6.251 | 12.196 | -56.072 | 1 | 39.66 | C |
| ATOM | 368 | CD | GLU | A | 116 | -5.606 | 11.573 | -54.842 | 1 | 41.78 | C |
| ATOM | 369 | OE1 | GLU | A | 116 | -4.525 | 10.959 | -54.979 | 1 | 47.28 | O |
| ATOM | 370 | OE2 | GLU | A | 116 | -6.177 | 11.707 | -53.737 | 1 | 32.41 | O1- |
| ATOM | 371 | H | GLU | A | 116 | -5.687 | 13.969 | -54.536 | 1 | 34.48 | H |
| ATOM | 372 | HA | GLU | A | 116 | -4.323 | 14.88 | -56.669 | 1 | 39.85 | H |
| ATOM | 373 | HB2 | GLU | A | 116 | -5.592 | 13.09 | -57.781 | 1 | 45.05 | H |
| ATOM | 374 | HB3 | GLU | A | 116 | -4.411 | 12.662 | -56.815 | 1 | 45.05 | H |
| ATOM | 375 | HG2 | GLU | A | 116 | -7.001 | 12.735 | -55.777 | 1 | 47.6 | H |
| ATOM | 376 | HG3 | GLU | A | 116 | -6.563 | 11.477 | -56.643 | 1 | 47.6 | H |
| ATOM | 377 | N | SER | A | 117 | -5.915 | 16.408 | -57.69 | 1 | 24.41 | N |
| ATOM | 378 | CA | SER | A | 117 | -6.878 | 17.401 | -58.14 | 1 | 29.4 | C |
| ATOM | 379 | C | SER | A | 117 | -7.682 | 16.92 | -59.344 | 1 | 31.91 | C |
| ATOM | 380 | O | SER | A | 117 | -7.135 | 16.366 | -60.296 | 1 | 31.79 | O |
| ATOM | 381 | CB | SER | A | 117 | -6.169 | 18.715 | -58.475 | 1 | 29.88 | C |
| ATOM | 382 | OG | SER | A | 117 | -5.324 | 18.57 | -59.597 | 1 | 37.03 | O |
| ATOM | 383 | H | SER | A | 117 | -5.109 | 16.553 | -57.953 | 1 | 29.3 | H |
| ATOM | 384 | HA | SER | A | 117 | -7.502 | 17.578 | -57.419 | 1 | 35.28 | H |
| ATOM | 385 | HB2 | SER | A | 117 | -6.836 | 19.392 | -58.669 | 1 | 35.86 | H |
| ATOM | 386 | HB3 | SER | A | 117 | -5.634 | 18.987 | -57.712 | 1 | 35.86 | H |
| ATOM | 387 | HG | SER | A | 117 | -4.943 | 19.299 | -59.767 | 1 | 44.43 | H |
| ATOM | 388 | N | LYS | A | 118 | -8.992 | 17.136 | -59.276 | 1 | 27.54 | N |
| ATOM | 389 | CA | LYS | A | 118 | -9.912 | 16.776 | -60.348 | 1 | 27.36 | C |
| ATOM | 390 | C | LYS | A | 118 | -10.967 | 17.859 | -60.482 | 1 | 25.25 | C |
| ATOM | 391 | O | LYS | A | 118 | -11.153 | 18.661 | -59.564 | 1 | 21.89 | O |
| ATOM | 392 | CB | LYS | A | 118 | -10.586 | 15.433 | -60.07 | 1 | 24.18 | C |
| ATOM | 393 | CG | LYS | A | 118 | -9.635 | 14.268 | -59.906 | 1 | 30.02 | C |
| ATOM | 394 | CD | LYS | A | 118 | -10.378 | 12.951 | -60.041 | 1 | 32.21 | C |
| ATOM | 395 | CE | LYS | A | 118 | -9.457 | 11.767 | -59.823 | 1 | 34.89 | C |
| ATOM | 396 | NZ | LYS | A | 118 | -9.058 | 11.664 | -58.403 | 1 | 38.04 | N1+ |

TABLE 5-continued

Atomic Coordinates for OMCP-NKG2D (4PDC).

| ATOM | 397 | H | LYS | A | 118 | -9.381 | 17.499 | -58.6 | 1 | 33.04 | H |
|------|-----|------|-----|---|-----|--------|--------|---------|---|-------|---|
| ATOM | 398 | HA | LYS | A | 118 | -9.427 | 16.712 | -61.185 | 1 | 32.84 | H |
| ATOM | 399 | HB2 | LYS | A | 118 | -11.1 | 15.508 | -59.252 | 1 | 29.02 | H |
| ATOM | 400 | HB3 | LYS | A | 118 | -11.178 | 15.225 | -60.81 | 1 | 29.02 | H |
| ATOM | 401 | HG2 | LYS | A | 118 | -8.953 | 14.308 | -60.595 | 1 | 36.02 | H |
| ATOM | 402 | HG3 | LYS | A | 118 | -9.23 | 14.303 | -59.025 | 1 | 36.02 | H |
| ATOM | 403 | HD2 | LYS | A | 118 | -11.085 | 12.913 | -59.378 | 1 | 38.65 | H |
| ATOM | 404 | HD3 | LYS | A | 118 | -10.752 | 12.885 | -60.934 | 1 | 38.65 | H |
| ATOM | 405 | HE2 | LYS | A | 118 | -9.918 | 10.95 | -60.071 | 1 | 41.87 | H |
| ATOM | 406 | HE3 | LYS | A | 118 | -8.656 | 11.879 | -60.358 | 1 | 41.87 | H |
| ATOM | 407 | HZ1 | LYS | A | 118 | -9.779 | 11.559 | -57.891 | 1 | 45.64 | H |
| ATOM | 408 | HZ2 | LYS | A | 118 | -8.518 | 10.966 | -58.288 | 1 | 45.64 | H |
| ATOM | 409 | HZ3 | LYS | A | 118 | -8.631 | 12.404 | -58.152 | 1 | 45.64 | H |
| ATOM | 410 | N | ASN | A | 119 | -11.664 | 17.885 | -61.612 | 1 | 23.33 | N |
| ATOM | 411 | CA | ASN | A | 119 | -12.769 | 18.818 | -61.77 | 1 | 22.32 | C |
| ATOM | 412 | C | ASN | A | 119 | -13.904 | 18.37 | -60.861 | 1 | 18.79 | C |
| ATOM | 413 | O | ASN | A | 119 | -13.846 | 17.281 | -60.292 | 1 | 20.16 | O |
| ATOM | 414 | CB | ASN | A | 119 | -13.213 | 18.92 | -63.235 | 1 | 26.91 | C |
| ATOM | 415 | CG | ASN | A | 119 | -13.744 | 17.612 | -63.795 | 1 | 27.14 | C |
| ATOM | 416 | OD1 | ASN | A | 119 | -14.413 | 16.842 | -63.11 | 1 | 23.11 | O |
| ATOM | 417 | ND2 | ASN | A | 119 | -13.453 | 17.366 | -65.066 | 1 | 29.78 | N |
| ATOM | 418 | H | ASN | A | 119 | -11.52 | 17.38 | -62.293 | 1 | 27.99 | H |
| ATOM | 419 | HA | ASN | A | 119 | -12.483 | 19.699 | -61.481 | 1 | 26.78 | H |
| ATOM | 420 | HB2 | ASN | A | 119 | -13.919 | 19.582 | -63.304 | 1 | 32.29 | H |
| ATOM | 421 | HB3 | ASN | A | 119 | -12.454 | 19.189 | -63.775 | 1 | 32.29 | H |
| ATOM | 422 | HD21 | ASN | A | 119 | -13.728 | 16.641 | -65.437 | 1 | 35.74 | H |
| ATOM | 423 | HD22 | ASN | A | 119 | -12.99 | 17.932 | -65.518 | 1 | 35.74 | H |
| ATOM | 424 | N | TRP | A | 120 | -14.925 | 19.204 | -60.713 | 1 | 19 | N |
| ATOM | 425 | CA | TRP | A | 120 | -15.991 | 18.921 | -59.76 | 1 | 20.49 | C |
| ATOM | 426 | C | TRP | A | 120 | -16.696 | 17.599 | -60.061 | 1 | 22.8 | C |
| ATOM | 427 | O | TRP | A | 120 | -16.99 | 16.822 | -59.15 | 1 | 19.34 | O |
| ATOM | 428 | CB | TRP | A | 120 | -17.014 | 20.055 | -59.746 | 1 | 21.71 | C |
| ATOM | 429 | CG | TRP | A | 120 | -18.043 | 19.878 | -58.679 | 1 | 20.57 | C |
| ATOM | 430 | CD1 | TRP | A | 120 | -17.954 | 20.29 | -57.382 | 1 | 20.1 | C |
| ATOM | 431 | CD2 | TRP | A | 120 | -19.313 | 19.229 | -58.808 | 1 | 20.41 | C |
| ATOM | 432 | NE1 | TRP | A | 120 | -19.092 | 19.944 | -56.696 | 1 | 18.87 | N |
| ATOM | 433 | CE2 | TRP | A | 120 | -19.942 | 19.29 | -57.548 | 1 | 21.17 | C |
| ATOM | 434 | CE3 | TRP | A | 120 | -19.978 | 18.602 | -59.865 | 1 | 22.6 | C |
| ATOM | 435 | CZ2 | TRP | A | 120 | -21.205 | 18.749 | -57.316 | 1 | 22.12 | C |
| ATOM | 436 | CZ3 | TRP | A | 120 | -21.23 | 18.065 | -59.635 | 1 | 20.75 | C |
| ATOM | 437 | CH2 | TRP | A | 120 | -21.832 | 18.142 | -58.371 | 1 | 28.09 | C |
| ATOM | 438 | H | TRP | A | 120 | -15.025 | 19.938 | -61.149 | 1 | 22.8 | H |
| ATOM | 439 | HA | TRP | A | 120 | -15.606 | 18.856 | -58.872 | 1 | 24.58 | H |
| ATOM | 440 | HB2 | TRP | A | 120 | -16.555 | 20.894 | -59.586 | 1 | 26.06 | H |
| ATOM | 441 | HB3 | TRP | A | 120 | -17.47 | 20.082 | -60.602 | 1 | 26.06 | H |
| ATOM | 442 | HD1 | TRP | A | 120 | -17.23 | 20.744 | -57.017 | 1 | 24.12 | H |
| ATOM | 443 | HE1 | TRP | A | 120 | -19.246 | 20.11 | -55.866 | 1 | 22.64 | H |
| ATOM | 444 | HE3 | TRP | A | 120 | -19.585 | 18.546 | -60.706 | 1 | 27.12 | H |
| ATOM | 445 | HZ2 | TRP | A | 120 | -21.607 | 18.799 | -56.479 | 1 | 26.54 | H |
| ATOM | 446 | HZ3 | TRP | A | 120 | -21.683 | 17.647 | -60.331 | 1 | 24.9 | H |
| ATOM | 447 | HH2 | TRP | A | 120 | -22.677 | 17.774 | -58.246 | 1 | 33.71 | H |

TABLE 5-continued

Atomic Coordinates for OMCP-NKG2D (4PDC).

| ATOM | 448 | N | TYR | A | 121 | -16.96 | 17.346 | -61.339 | 1 | 21.32 | N |
| --- | --- | --- | --- | --- | --- | --- | --- | --- | --- | --- | --- |
| ATOM | 449 | CA | TYR | A | 121 | -17.709 | 16.158 | -61.743 | 1 | 25.07 | C |
| ATOM | 450 | C | TYR | A | 121 | -16.927 | 14.885 | -61.415 | 1 | 20.81 | C |
| ATOM | 451 | O | TYR | A | 121 | -17.473 | 13.937 | -60.848 | 1 | 21.52 | O |
| ATOM | 452 | CB | TYR | A | 121 | -18.037 | 16.221 | -63.238 | 1 | 23.23 | C |
| ATOM | 453 | CG | TYR | A | 121 | -18.622 | 17.55 | -63.662 | 1 | 26.15 | C |
| ATOM | 454 | CD1 | TYR | A | 121 | -19.935 | 17.885 | -63.353 | 1 | 33.8 | C |
| ATOM | 455 | CD2 | TYR | A | 121 | -17.859 | 18.473 | -64.363 | 1 | 24.99 | C |
| ATOM | 456 | CE1 | TYR | A | 121 | -20.471 | 19.105 | -63.734 | 1 | 30.23 | C |
| ATOM | 457 | CE2 | TYR | A | 121 | -18.386 | 19.693 | -64.748 | 1 | 33.24 | C |
| ATOM | 458 | CZ | TYR | A | 121 | -19.689 | 20.003 | -64.431 | 1 | 29.9 | C |
| ATOM | 459 | OH | TYR | A | 121 | -20.21 | 21.217 | -64.815 | 1 | 39.68 | O |
| ATOM | 460 | H | TYR | A | 121 | -16.717 | 17.848 | -61.993 | 1 | 25.59 | H |
| ATOM | 461 | HA | TYR | A | 121 | -18.546 | 16.13 | -61.254 | 1 | 30.08 | H |
| ATOM | 462 | HB2 | TYR | A | 121 | -17.222 | 16.079 | -63.745 | 1 | 27.87 | H |
| ATOM | 463 | HB3 | TYR | A | 121 | -18.683 | 15.529 | -63.448 | 1 | 27.87 | H |
| ATOM | 464 | HD1 | TYR | A | 121 | -20.462 | 17.281 | -62.882 | 1 | 40.56 | H |
| ATOM | 465 | HD2 | TYR | A | 121 | -16.978 | 18.268 | -64.578 | 1 | 29.99 | H |
| ATOM | 466 | HE1 | TYR | A | 121 | -21.351 | 19.317 | -63.521 | 1 | 36.27 | H |
| ATOM | 467 | HE2 | TYR | A | 121 | -17.862 | 20.301 | -65.218 | 1 | 39.89 | H |
| ATOM | 468 | HH | TYR | A | 121 | -21.008 | 21.28 | -64.562 | 1 | 47.62 | H |
| ATOM | 469 | N | GLU | A | 122 | -15.645 | 14.883 | -61.76 | 1 | 20.76 | N |
| ATOM | 470 | CA | GLU | A | 122 | -14.76 | 13.767 | -61.449 | 1 | 22.88 | C |
| ATOM | 471 | C | GLU | A | 122 | -14.653 | 13.563 | -59.938 | 1 | 22.74 | C |
| ATOM | 472 | O | GLU | A | 122 | -14.647 | 12.432 | -59.451 | 1 | 21.61 | O |
| ATOM | 473 | CB | GLU | A | 122 | -13.374 | 14.011 | -62.049 | 1 | 30.2 | C |
| ATOM | 474 | CG | GLU | A | 122 | -13.32 | 13.954 | -63.575 | 1 | 37.52 | C |
| ATOM | 475 | CD | GLU | A | 122 | -11.969 | 14.386 | -64.136 | 1 | 47.14 | C |
| ATOM | 476 | OE1 | GLU | A | 122 | -11.248 | 15.152 | -63.458 | 1 | 45.66 | O |
| ATOM | 477 | OE2 | GLU | A | 122 | -11.625 | 13.956 | -65.257 | 1 | 59.27 | O1- |
| ATOM | 478 | H | GLU | A | 122 | -15.258 | 15.525 | -62.18 | 1 | 24.92 | H |
| ATOM | 479 | HA | GLU | A | 122 | -15.121 | 12.956 | -61.839 | 1 | 27.46 | H |
| ATOM | 480 | HB2 | GLU | A | 122 | -13.07 | 14.891 | -61.777 | 1 | 36.24 | H |
| ATOM | 481 | HB3 | GLU | A | 122 | -12.766 | 13.337 | -61.708 | 1 | 36.24 | H |
| ATOM | 482 | HG2 | GLU | A | 122 | -13.487 | 13.042 | -63.863 | 1 | 45.03 | H |
| ATOM | 483 | HG3 | GLU | A | 122 | -13.998 | 14.545 | -63.937 | 1 | 45.03 | H |
| ATOM | 484 | N | SER | A | 123 | -14.565 | 14.666 | -59.202 | 1 | 22.3 | N |
| ATOM | 485 | CA | SER | A | 123 | -14.528 | 14.613 | -57.745 | 1 | 20.93 | C |
| ATOM | 486 | C | SER | A | 123 | -15.806 | 13.978 | -57.214 | 1 | 20.42 | C |
| ATOM | 487 | O | SER | A | 123 | -15.762 | 13.104 | -56.344 | 1 | 18.79 | O |
| ATOM | 488 | CB | SER | A | 123 | -14.345 | 16.015 | -57.155 | 1 | 20.25 | C |
| ATOM | 489 | OG | SER | A | 123 | -13.11 | 16.585 | -57.557 | 1 | 15.46 | O |
| ATOM | 490 | H | SER | A | 123 | -14.526 | 15.463 | -59.524 | 1 | 26.76 | H |
| ATOM | 491 | HA | SER | A | 123 | -13.778 | 14.066 | -57.465 | 1 | 25.12 | H |
| ATOM | 492 | HB2 | SER | A | 123 | -15.069 | 16.583 | -57.463 | 1 | 24.31 | H |
| ATOM | 493 | HB3 | SER | A | 123 | -14.363 | 15.953 | -56.187 | 1 | 24.31 | H |
| ATOM | 494 | HG | SER | A | 123 | -13.08 | 16.645 | -58.395 | 1 | 18.56 | H |
| ATOM | 495 | N | GLN | A | 124 | -16.941 | 14.421 | -57.749 | 1 | 19.5 | N |
| ATOM | 496 | CA | GLN | A | 124 | -18.241 | 13.88 | -57.365 | 1 | 18.56 | C |
| ATOM | 497 | C | GLN | A | 124 | -18.3 | 12.38 | -57.618 | 1 | 21.42 | C |
| ATOM | 498 | O | GLN | A | 124 | -18.736 | 11.612 | -56.758 | 1 | 18.75 | O |

TABLE 5-continued

Atomic Coordinates for OMCP-NKG2D (4PDC).

| | | | | | | | | | | |
|---|---|---|---|---|---|---|---|---|---|---|
| ATOM | 499 | CB | GLN | A | 124 | -19.363 | 14.585 | -58.134 | 1 | 22.37 | C |
| ATOM | 500 | CG | GLN | A | 124 | -20.744 | 13.971 | -57.944 | 1 | 25.68 | C |
| ATOM | 501 | CD | GLN | A | 124 | -21.805 | 14.643 | -58.8 | 1 | 30.6 | C |
| ATOM | 502 | OE1 | GLN | A | 124 | -21.672 | 14.729 | -60.023 | 1 | 32.6 | O |
| ATOM | 503 | NE2 | GLN | A | 124 | -22.862 | 15.13 | -58.159 | 1 | 27.2 | N |
| ATOM | 504 | H | GLN | A | 124 | -16.985 | 15.041 | -58.344 | 1 | 23.4 | H |
| ATOM | 505 | HA | GLN | A | 124 | -18.382 | 14.033 | -56.418 | 1 | 22.27 | H |
| ATOM | 506 | HB2 | GLN | A | 124 | -19.408 | 15.508 | -57.839 | 1 | 26.84 | H |
| ATOM | 507 | HB3 | GLN | A | 124 | -19.156 | 14.555 | -59.082 | 1 | 26.84 | H |
| ATOM | 508 | HG2 | GLN | A | 124 | -20.71 | 13.033 | -58.189 | 1 | 30.82 | H |
| ATOM | 509 | HG3 | GLN | A | 124 | -21.006 | 14.062 | -57.014 | 1 | 30.82 | H |
| ATOM | 510 | HE21 | GLN | A | 124 | -23.489 | 15.52 | -58.599 | 1 | 32.63 | H |
| ATOM | 511 | HE22 | GLN | A | 124 | -22.918 | 15.055 | -57.305 | 1 | 32.63 | H |
| ATOM | 512 | N | ALA | A | 125 | -17.868 | 11.972 | -58.807 | 1 | 21.97 | N |
| ATOM | 513 | CA | ALA | A | 125 | -17.868 | 10.561 | -59.176 | 1 | 20.84 | C |
| ATOM | 514 | C | ALA | A | 125 | -16.946 | 9.762 | -58.26 | 1 | 21.56 | C |
| ATOM | 515 | O | ALA | A | 125 | -17.233 | 8.613 | -57.929 | 1 | 23.96 | O |
| ATOM | 516 | CB | ALA | A | 125 | -17.448 | 10.394 | -60.623 | 1 | 22.81 | C |
| ATOM | 517 | H | ALA | A | 125 | -17.569 | 12.494 | -59.42 | 1 | 26.37 | H |
| ATOM | 518 | HA | ALA | A | 125 | -18.767 | 10.208 | -59.081 | 1 | 25.01 | H |
| ATOM | 519 | HB1 | ALA | A | 125 | -17.455 | 9.45 | -60.846 | 1 | 27.37 | H |
| ATOM | 520 | HB2 | ALA | A | 125 | -18.072 | 10.873 | -61.19 | 1 | 27.37 | H |
| ATOM | 521 | HB3 | ALA | A | 125 | -16.554 | 10.754 | -60.735 | 1 | 27.37 | H |
| ATOM | 522 | N | SER | A | 126 | -15.841 | 10.38 | -57.85 | 1 | 19.66 | N |
| ATOM | 523 | CA | SER | A | 126 | -14.891 | 9.726 | -56.96 | 1 | 21.36 | C |
| ATOM | 524 | C | SER | A | 126 | -15.526 | 9.424 | -55.597 | 1 | 20.78 | C |
| ATOM | 525 | O | SER | A | 126 | -15.4 | 8.316 | -55.079 | 1 | 20.5 | O |
| ATOM | 526 | CB | SER | A | 126 | -13.644 | 10.595 | -56.782 | 1 | 21.76 | C |
| ATOM | 527 | OG | SER | A | 126 | -12.641 | 9.91 | -56.052 | 1 | 22.07 | O |
| ATOM | 528 | H | SER | A | 126 | -15.619 | 11.18 | -58.074 | 1 | 23.59 | H |
| ATOM | 529 | HA | SER | A | 126 | -14.615 | 8.884 | -57.355 | 1 | 25.64 | H |
| ATOM | 530 | HB2 | SER | A | 126 | -13.294 | 10.826 | -57.657 | 1 | 26.11 | H |
| ATOM | 531 | HB3 | SER | A | 126 | -13.888 | 11.401 | -56.301 | 1 | 26.11 | H |
| ATOM | 532 | HG | SER | A | 126 | -11.965 | 10.401 | -55.964 | 1 | 26.49 | H |
| ATOM | 533 | N | CYS | A | 127 | -16.208 | 10.408 | -55.018 | 1 | 17.68 | N |
| ATOM | 534 | CA | CYS | A | 127 | -16.855 | 10.214 | -53.722 | 1 | 20.49 | C |
| ATOM | 535 | C | CYS | A | 127 | -17.995 | 9.206 | -53.839 | 1 | 20.57 | C |
| ATOM | 536 | O | CYS | A | 127 | -18.171 | 8.348 | -52.973 | 1 | 19.87 | O |
| ATOM | 537 | CB | CYS | A | 127 | -17.379 | 11.542 | -53.174 | 1 | 18.87 | C |
| ATOM | 538 | SG | CYS | A | 127 | -16.086 | 12.764 | -52.854 | 1 | 19.71 | S |
| ATOM | 539 | H | CYS | A | 127 | -16.312 | 11.193 | -55.352 | 1 | 21.21 | H |
| ATOM | 540 | HA | CYS | A | 127 | -16.206 | 9.863 | -53.092 | 1 | 24.59 | H |
| ATOM | 541 | HB2 | CYS | A | 127 | -17.995 | 11.925 | -53.818 | 1 | 22.65 | H |
| ATOM | 542 | HB3 | CYS | A | 127 | -17.842 | 11.374 | -52.337 | 1 | 22.65 | H |
| ATOM | 543 | N | MET | A | 128 | -18.765 | 9.315 | -54.918 | 1 | 17.8 | N |
| ATOM | 544 | CA | MET | A | 128 | -19.856 | 8.382 | -55.179 | 1 | 25.06 | C |
| ATOM | 545 | C | MET | A | 128 | -19.319 | 6.961 | -55.283 | 1 | 22.86 | C |
| ATOM | 546 | O | MET | A | 128 | -19.956 | 6.008 | -54.835 | 1 | 25.41 | O |
| ATOM | 547 | CB | MET | A | 128 | -20.593 | 8.754 | -56.464 | 1 | 28.91 | C |
| ATOM | 548 | CG | MET | A | 128 | -22.085 | 8.97 | -56.28 | 1 | 40.17 | C |
| ATOM | 549 | SD | MET | A | 128 | -22.957 | 9.136 | -57.85 | 1 | 65.5 | S |

TABLE 5-continued

Atomic Coordinates for OMCP-NKG2D (4PDC).

| ATOM | 550 | CE | MET | A | 128 | -22.156 | 10.582 | -58.544 | 1 | 43.48 | C |
| --- | --- | --- | --- | --- | --- | --- | --- | --- | --- | --- | --- |
| ATOM | 551 | H | MET | A | 128 | -18.675 | 9.925 | -55.518 | 1 | 21.37 | H |
| ATOM | 552 | HA | MET | A | 128 | -20.49 | 8.426 | -54.447 | 1 | 30.08 | H |
| ATOM | 553 | HB2 | MET | A | 128 | -20.216 | 9.577 | -56.812 | 1 | 34.7 | H |
| ATOM | 554 | HB3 | MET | A | 128 | -20.474 | 8.04 | -57.11 | 1 | 34.7 | H |
| ATOM | 555 | HG2 | MET | A | 128 | -22.459 | 8.21 | -55.808 | 1 | 48.2 | H |
| ATOM | 556 | HG3 | MET | A | 128 | -22.227 | 9.782 | -55.769 | 1 | 48.2 | H |
| ATOM | 557 | HE1 | MET | A | 128 | -22.549 | 10.776 | -59.41 | 1 | 52.17 | H |
| ATOM | 558 | HE2 | MET | A | 128 | -22.288 | 11.334 | -57.945 | 1 | 52.17 | H |
| ATOM | 559 | HE3 | MET | A | 128 | -21.208 | 10.401 | -58.644 | 1 | 52.17 | H |
| ATOM | 560 | N | SER | A | 129 | -18.133 | 6.833 | -55.865 | 1 | 22.61 | N |
| ATOM | 561 | CA | SER | A | 129 | -17.491 | 5.535 | -56.033 | 1 | 26.16 | C |
| ATOM | 562 | C | SER | A | 129 | -17.085 | 4.913 | -54.697 | 1 | 25.71 | C |
| ATOM | 563 | O | SER | A | 129 | -16.695 | 3.745 | -54.645 | 1 | 24.09 | O |
| ATOM | 564 | CB | SER | A | 129 | -16.261 | 5.674 | -56.935 | 1 | 25.52 | C |
| ATOM | 565 | OG | SER | A | 129 | -15.546 | 4.455 | -57.022 | 1 | 33.82 | O |
| ATOM | 566 | H | SER | A | 129 | -17.673 | 7.491 | -56.175 | 1 | 27.13 | H |
| ATOM | 567 | HA | SER | A | 129 | -18.113 | 4.93 | -56.467 | 1 | 31.39 | H |
| ATOM | 568 | HB2 | SER | A | 129 | -16.551 | 5.932 | -57.824 | 1 | 30.62 | H |
| ATOM | 569 | HB3 | SER | A | 129 | -15.677 | 6.355 | -56.567 | 1 | 30.62 | H |
| ATOM | 570 | HG | SER | A | 129 | -16.039 | 3.855 | -57.341 | 1 | 40.59 | H |
| ATOM | 571 | N | GLN | A | 130 | -17.171 | 5.694 | -53.623 | 1 | 20.18 | N |
| ATOM | 572 | CA | GLN | A | 130 | -16.753 | 5.233 | -52.303 | 1 | 22.43 | C |
| ATOM | 573 | C | GLN | A | 130 | -17.916 | 5.241 | -51.317 | 1 | 24.16 | C |
| ATOM | 574 | O | GLN | A | 130 | -17.715 | 5.372 | -50.111 | 1 | 27.76 | O |
| ATOM | 575 | CB | GLN | A | 130 | -15.612 | 6.103 | -51.779 | 1 | 23.18 | C |
| ATOM | 576 | CG | GLN | A | 130 | -14.386 | 6.095 | -52.674 | 1 | 25.86 | C |
| ATOM | 577 | CD | GLN | A | 130 | -13.321 | 7.067 | -52.215 | 1 | 22.81 | C |
| ATOM | 578 | OE1 | GLN | A | 130 | -12.837 | 6.988 | -51.087 | 1 | 19.87 | O |
| ATOM | 579 | NE2 | GLN | A | 130 | -12.951 | 7.993 | -53.091 | 1 | 20.58 | N |
| ATOM | 580 | H | GLN | A | 130 | -17.47 | 6.5 | -53.634 | 1 | 24.21 | H |
| ATOM | 581 | HA | GLN | A | 130 | -16.427 | 4.322 | -52.375 | 1 | 26.92 | H |
| ATOM | 582 | HB2 | GLN | A | 130 | -15.923 | 7.019 | -51.709 | 1 | 27.81 | H |
| ATOM | 583 | HB3 | GLN | A | 130 | -15.345 | 5.778 | -50.905 | 1 | 27.81 | H |
| ATOM | 584 | HG2 | GLN | A | 130 | -14.001 | 5.205 | -52.674 | 1 | 31.04 | H |
| ATOM | 585 | HG3 | GLN | A | 130 | -14.65 | 6.342 | -53.574 | 1 | 31.04 | H |
| ATOM | 586 | HE21 | GLN | A | 130 | -12.349 | 8.569 | -52.879 | 1 | 24.7 | H |
| ATOM | 587 | HE22 | GLN | A | 130 | -13.313 | 8.016 | -53.871 | 1 | 24.7 | H |
| ATOM | 588 | N | ASN | A | 131 | -19.127 | 5.083 | -51.839 | 1 | 23.03 | N |
| ATOM | 589 | CA | ASN | A | 131 | -20.331 | 5.118 | -51.016 | 1 | 28.97 | C |
| ATOM | 590 | C | ASN | A | 131 | -20.37 | 6.396 | -50.19 | 1 | 27.25 | C |
| ATOM | 591 | O | ASN | A | 131 | -20.655 | 6.375 | -48.992 | 1 | 24.85 | O |
| ATOM | 592 | CB | ASN | A | 131 | -20.396 | 3.89 | -50.104 | 1 | 30.97 | C |
| ATOM | 593 | CG | ASN | A | 131 | -21.744 | 3.736 | -49.429 | 1 | 34.4 | C |
| ATOM | 594 | OD1 | ASN | A | 131 | -22.772 | 4.158 | -49.962 | 1 | 38.37 | O |
| ATOM | 595 | ND2 | ASN | A | 131 | -21.745 | 3.139 | -48.241 | 1 | 40.3 | N |
| ATOM | 596 | H | ASN | A | 131 | -19.28 | 4.953 | -52.676 | 1 | 27.63 | H |
| ATOM | 597 | HA | ASN | A | 131 | -21.111 | 5.107 | -51.593 | 1 | 34.76 | H |
| ATOM | 598 | HB2 | ASN | A | 131 | -20.232 | 3.093 | -50.633 | 1 | 37.17 | H |
| ATOM | 599 | HB3 | ASN | A | 131 | -19.721 | 3.973 | -49.413 | 1 | 37.17 | H |
| ATOM | 600 | HD21 | ASN | A | 131 | -22.485 | 3.028 | -47.817 | 1 | 48.35 | H |

TABLE 5-continued

Atomic Coordinates for OMCP-NKG2D (4PDC).

| | | | | | | | | | | |
|---|---|---|---|---|---|---|---|---|---|---|
| ATOM | 601 | HD22 | ASN | A | 131 | -21.006 | 2.864 | -47.897 | 1 | 48.35 | H |
| ATOM | 602 | N | ALA | A | 132 | -20.066 | 7.51 | -50.846 | 1 | 25.64 | N |
| ATOM | 603 | CA | ALA | A | 132 | -19.98 | 8.8 | -50.181 | 1 | 21.88 | C |
| ATOM | 604 | C | ALA | A | 132 | -20.378 | 9.915 | -51.139 | 1 | 21.78 | C |
| ATOM | 605 | O | ALA | A | 132 | -20.768 | 9.663 | -52.277 | 1 | 22.4 | O |
| ATOM | 606 | CB | ALA | A | 132 | -18.57 | 9.026 | -49.656 | 1 | 20.15 | C |
| ATOM | 607 | H | ALA | A | 132 | -19.903 | 7.543 | -51.69 | 1 | 30.77 | H |
| ATOM | 608 | HA | ALA | A | 132 | -20.591 | 8.813 | -49.428 | 1 | 26.25 | H |
| ATOM | 609 | HB1 | ALA | A | 132 | -18.531 | 9.89 | -49.217 | 1 | 24.18 | H |
| ATOM | 610 | HB2 | ALA | A | 132 | -18.352 | 8.323 | -49.025 | 1 | 24.18 | H |
| ATOM | 611 | HB3 | ALA | A | 132 | -17.949 | 9.006 | -50.401 | 1 | 24.18 | H |
| ATOM | 612 | N | SER | A | 133 | -20.27 | 11.151 | -50.672 | 1 | 18.84 | N |
| ATOM | 613 | CA | SER | A | 133 | -20.529 | 12.309 | -51.509 | 1 | 21.81 | C |
| ATOM | 614 | C | SER | A | 133 | -19.499 | 13.378 | -51.19 | 1 | 19.07 | C |
| ATOM | 615 | O | SER | A | 133 | -18.693 | 13.211 | -50.276 | 1 | 17.95 | O |
| ATOM | 616 | CB | SER | A | 133 | -21.945 | 12.833 | -51.281 | 1 | 25.17 | C |
| ATOM | 617 | OG | SER | A | 133 | -22.071 | 13.372 | -49.979 | 1 | 30.73 | O |
| ATOM | 618 | H | SER | A | 133 | -20.045 | 11.346 | -49.865 | 1 | 22.61 | H |
| ATOM | 619 | HA | SER | A | 133 | -20.438 | 12.061 | -52.442 | 1 | 26.18 | H |
| ATOM | 620 | HB2 | SER | A | 133 | -22.134 | 13.528 | -51.931 | 1 | 30.2 | H |
| ATOM | 621 | HB3 | SER | A | 133 | -22.574 | 12.102 | -51.384 | 1 | 30.2 | H |
| ATOM | 622 | HG | SER | A | 133 | -21.908 | 12.78 | -49.406 | 1 | 36.88 | H |
| ATOM | 623 | N | LEU | A | 134 | -19.516 | 14.469 | -51.947 | 1 | 18.66 | N |
| ATOM | 624 | CA | LEU | A | 134 | -18.644 | 15.594 | -51.646 | 1 | 18.37 | C |
| ATOM | 625 | C | LEU | A | 134 | -19.076 | 16.218 | -50.327 | 1 | 17.9 | C |
| ATOM | 626 | O | LEU | A | 134 | -20.216 | 16.046 | -49.898 | 1 | 17.3 | O |
| ATOM | 627 | CB | LEU | A | 134 | -18.675 | 16.627 | -52.772 | 1 | 17.75 | C |
| ATOM | 628 | CG | LEU | A | 134 | -17.977 | 16.21 | -54.067 | 1 | 16.83 | C |
| ATOM | 629 | CD1 | LEU | A | 134 | -18.32 | 17.168 | -55.192 | 1 | 18.55 | C |
| ATOM | 630 | CD2 | LEU | A | 134 | -16.469 | 16.142 | -53.878 | 1 | 18.53 | C |
| ATOM | 631 | H | LEU | A | 134 | -20.019 | 14.581 | -52.635 | 1 | 22.4 | H |
| ATOM | 632 | HA | LEU | A | 134 | -17.733 | 15.276 | -51.549 | 1 | 22.05 | H |
| ATOM | 633 | HB2 | LEU | A | 134 | -19.601 | 16.817 | -52.988 | 1 | 21.31 | H |
| ATOM | 634 | HB3 | LEU | A | 134 | -18.243 | 17.436 | -52.457 | 1 | 21.31 | H |
| ATOM | 635 | HG | LEU | A | 134 | -18.287 | 15.327 | -54.322 | 1 | 20.2 | H |
| ATOM | 636 | HD11 | LEU | A | 134 | -18.028 | 18.06 | -54.946 | 1 | 22.26 | H |
| ATOM | 637 | HD12 | LEU | A | 134 | -17.866 | 16.882 | -56 | 1 | 22.26 | H |
| ATOM | 638 | HD13 | LEU | A | 134 | -19.28 | 17.161 | -55.331 | 1 | 22.26 | H |
| ATOM | 639 | HD21 | LEU | A | 134 | -16.266 | 15.491 | -53.188 | 1 | 22.24 | H |
| ATOM | 640 | HD22 | LEU | A | 134 | -16.058 | 15.876 | -54.716 | 1 | 22.24 | H |
| ATOM | 641 | HD23 | LEU | A | 134 | -16.144 | 17.017 | -53.613 | 1 | 22.24 | H |
| ATOM | 642 | N | LEU | A | 135 | -18.157 | 16.926 | -49.681 | 1 | 15.27 | N |
| ATOM | 643 | CA | LEU | A | 135 | -18.428 | 17.543 | -48.386 | 1 | 14.24 | C |
| ATOM | 644 | C | LEU | A | 135 | -19.756 | 18.295 | -48.351 | 1 | 13.72 | C |
| ATOM | 645 | O | LEU | A | 135 | -20.021 | 19.141 | -49.207 | 1 | 14.87 | O |
| ATOM | 646 | CB | LEU | A | 135 | -17.299 | 18.503 | -48.018 | 1 | 11.92 | C |
| ATOM | 647 | CG | LEU | A | 135 | -17.524 | 19.369 | -46.773 | 1 | 13.8 | C |
| ATOM | 648 | CD1 | LEU | A | 135 | -17.707 | 18.499 | -45.536 | 1 | 16.19 | C |
| ATOM | 649 | CD2 | LEU | A | 135 | -16.366 | 20.34 | -46.586 | 1 | 15.37 | C |
| ATOM | 650 | H | LEU | A | 135 | -17.361 | 17.065 | -49.975 | 1 | 18.33 | H |
| ATOM | 651 | HA | LEU | A | 135 | -18.461 | 16.848 | -47.71 | 1 | 17.09 | H |

TABLE 5-continued

Atomic Coordinates for OMCP-NKG2D (4PDC).

| ATOM | 652 | HB2 | LEU | A | 135 | -16.495 | 17.982 | -47.865 | 1 | 14.3 | H |
|---|---|---|---|---|---|---|---|---|---|---|---|
| ATOM | 653 | HB3 | LEU | A | 135 | -17.156 | 19.104 | -48.765 | 1 | 14.3 | H |
| ATOM | 654 | HG | LEU | A | 135 | -18.333 | 19.889 | -46.894 | 1 | 16.56 | H |
| ATOM | 655 | HD11 | LEU | A | 135 | -17.846 | 19.072 | -44.766 | 1 | 19.43 | H |
| ATOM | 656 | HD12 | LEU | A | 135 | -18.477 | 17.924 | -45.666 | 1 | 19.43 | H |
| ATOM | 657 | HD13 | LEU | A | 135 | -16.91 | 17.961 | -45.409 | 1 | 19.43 | H |
| ATOM | 658 | HD21 | LEU | A | 135 | -16.529 | 20.877 | -45.795 | 1 | 18.45 | H |
| ATOM | 659 | HD22 | LEU | A | 135 | -15.545 | 19.835 | -46.48 | 1 | 18.45 | H |
| ATOM | 660 | HD23 | LEU | A | 135 | -16.305 | 20.912 | -47.367 | 1 | 18.45 | H |
| ATOM | 661 | N | LYS | A | 135 | -20.583 | 17.967 | -47.359 | 1 | 11.97 | N |
| ATOM | 662 | CA | LYS | A | 136 | -21.789 | 18.732 | -47.064 | 1 | 19.27 | C |
| ATOM | 663 | C | LYS | A | 136 | -21.649 | 19.428 | -45.714 | 1 | 16.87 | C |
| ATOM | 664 | O | LYS | A | 136 | -21.409 | 18.784 | -44.691 | 1 | 16.35 | O |
| ATOM | 665 | CB | LYS | A | 136 | -23.029 | 17.836 | -47.062 | 1 | 20.92 | C |
| ATOM | 666 | CG | LYS | A | 136 | -24.294 | 18.572 | -46.624 | 1 | 23.85 | C |
| ATOM | 667 | CD | LYS | A | 136 | -25.542 | 17.721 | -46.767 | 1 | 27.86 | C |
| ATOM | 668 | CE | LYS | A | 136 | -26.766 | 18.475 | -46.263 | 1 | 36.34 | C |
| ATOM | 669 | NZ | LYS | A | 136 | -28.041 | 17.844 | -46.689 | 1 | 34.12 | N1+ |
| ATOM | 670 | H | LYS | A | 136 | -20.463 | 17.295 | -46.836 | 1 | 14.37 | H |
| ATOM | 671 | HA | LYS | A | 136 | -21.908 | 19.412 | -47.745 | 1 | 23.12 | H |
| ATOM | 672 | HB2 | LYS | A | 136 | -23.176 | 17.498 | -47.959 | 1 | 25.11 | H |
| ATOM | 673 | HB3 | LYS | A | 136 | -22.885 | 17.099 | -46.448 | 1 | 25.11 | H |
| ATOM | 674 | HG2 | LYS | A | 136 | -24.207 | 18.824 | -45.691 | 1 | 28.62 | H |
| ATOM | 675 | HG3 | LYS | A | 136 | -24.406 | 19.364 | -47.172 | 1 | 28.62 | H |
| ATOM | 676 | HD2 | LYS | A | 136 | -25.679 | 17.503 | -47.702 | 1 | 33.44 | H |
| ATOM | 677 | HD3 | LYS | A | 136 | -25.443 | 16.912 | -46.241 | 1 | 33.44 | H |
| ATOM | 678 | HE2 | LYS | A | 136 | -26.749 | 18.494 | -45.294 | 1 | 43.61 | H |
| ATOM | 679 | HE3 | LYS | A | 136 | -26.746 | 19.379 | -46.614 | 1 | 43.61 | H |
| ATOM | 680 | HZ1 | LYS | A | 136 | -28.73 | 18.312 | -46.377 | 1 | 40.94 | H |
| ATOM | 681 | HZ2 | LYS | A | 136 | -28.086 | 17.82 | -47.577 | 1 | 40.94 | H |
| ATOM | 682 | HZ3 | LYS | A | 136 | -28.088 | 17.013 | -46.374 | 1 | 40.94 | H |
| ATOM | 683 | N | VAL | A | 137 | -21.807 | 20.746 | -45.726 | 1 | 17.32 | N |
| ATOM | 684 | CA | VAL | A | 137 | -21.728 | 21.552 | -44.516 | 1 | 16.33 | C |
| ATOM | 685 | C | VAL | A | 137 | -23.137 | 21.792 | -43.974 | 1 | 18.35 | C |
| ATOM | 686 | O | VAL | A | 137 | -23.93 | 22.488 | -44.603 | 1 | 20.87 | O |
| ATOM | 687 | CB | VAL | A | 137 | -21.028 | 22.895 | -44.788 | 1 | 17.82 | C |
| ATOM | 688 | CG1 | VAL | A | 137 | -20.955 | 23.732 | -43.518 | 1 | 22.96 | C |
| ATOM | 689 | CG2 | VAL | A | 137 | -19.627 | 22.656 | -45.354 | 1 | 18.45 | C |
| ATOM | 690 | H | VAL | A | 137 | -21.964 | 21.205 | -46.436 | 1 | 20.78 | H |
| ATOM | 691 | HA | VAL | A | 137 | -21.22 | 21.073 | -43.843 | 1 | 19.6 | H |
| ATOM | 692 | HB | VAL | A | 137 | -21.539 | 23.391 | -45.447 | 1 | 21.39 | H |
| ATOM | 693 | HG11 | VAL | A | 137 | -20.51 | 24.571 | -43.719 | 1 | 27.55 | H |
| ATOM | 694 | HG12 | VAL | A | 137 | -21.856 | 23.903 | -43.201 | 1 | 27.55 | H |
| ATOM | 695 | HG13 | VAL | A | 137 | -20.454 | 23.244 | -42.847 | 1 | 27.55 | H |
| ATOM | 696 | HG21 | VAL | A | 137 | -19.203 | 23.513 | -45.519 | 1 | 22.14 | H |
| ATOM | 697 | HG22 | VAL | A | 137 | -19.109 | 22.148 | -44.711 | 1 | 22.14 | H |
| ATOM | 698 | HG23 | VAL | A | 137 | -19.703 | 22.159 | -46.184 | 1 | 22.14 | H |
| ATOM | 699 | N | TYR | A | 138 | -23.437 | 21.22 | -42.81 | 1 | 19.32 | N |
| ATOM | 700 | CA | TYR | A | 138 | -24.792 | 21.266 | -42.259 | 1 | 24.49 | C |
| ATOM | 701 | C | TYR | A | 138 | -24.832 | 21.797 | -40.83 | 1 | 24.58 | C |
| ATOM | 702 | O | TYR | A | 138 | -25.909 | 22.078 | -40.302 | 1 | 22.3 | O |

TABLE 5-continued

Atomic Coordinates for OMCP-NKG2D (4PDC).

| | | | | | | | | | | |
|---|---|---|---|---|---|---|---|---|---|---|
| ATOM | 703 | CB | TYR | A | 138 | -25.423 | 19.871 | -42.295 | 1 | 21.46 | C |
| ATOM | 704 | CG | TYR | A | 138 | -24.849 | 18.919 | -41.271 | 1 | 22.69 | C |
| ATOM | 705 | CD1 | TYR | A | 138 | -23.689 | 18.203 | -41.533 | 1 | 21.21 | C |
| ATOM | 706 | CD2 | TYR | A | 138 | -25.463 | 18.742 | -40.037 | 1 | 22.66 | C |
| ATOM | 707 | CE1 | TYR | A | 138 | -23.16 | 17.331 | -40.598 | 1 | 19.74 | C |
| ATOM | 708 | CE2 | TYR | A | 138 | -24.94 | 17.874 | -39.095 | 1 | 23.87 | C |
| ATOM | 709 | CZ | TYR | A | 138 | -23.788 | 17.172 | -39.38 | 1 | 23.25 | C |
| ATOM | 710 | OH | TYR | A | 138 | -23.263 | 16.308 | -38.446 | 1 | 19.45 | O |
| ATOM | 711 | H | TYR | A | 138 | -22.873 | 20.797 | -42.318 | 1 | 23.18 | H |
| ATOM | 712 | HA | TYR | A | 138 | -25.334 | 21.853 | -42.809 | 1 | 29.39 | H |
| ATOM | 713 | HB2 | TYR | A | 138 | -26.374 | 19.954 | -42.123 | 1 | 25.75 | H |
| ATOM | 714 | HB3 | TYR | A | 138 | -25.279 | 19.485 | -43.173 | 1 | 25.75 | H |
| ATOM | 715 | HD1 | TYR | A | 138 | -23.263 | 18.308 | -42.353 | 1 | 25.45 | H |
| ATOM | 716 | HD2 | TYR | A | 138 | -26.239 | 19.214 | -39.842 | 1 | 27.2 | H |
| ATOM | 717 | HE1 | TYR | A | 138 | -22.383 | 16.857 | -40.788 | 1 | 23.69 | H |
| ATOM | 718 | HE2 | TYR | A | 138 | -25.363 | 17.766 | -38.274 | 1 | 28.64 | H |
| ATOM | 719 | HH | TYR | A | 138 | -23.74 | 16.308 | -37.755 | 1 | 23.34 | H |
| ATOM | 720 | N | SER | A | 139 | -23.668 | 21.933 | -40.202 | 1 | 16.32 | N |
| ATOM | 721 | CA | SER | A | 139 | -23.62 | 22.342 | -38.802 | 1 | 22.45 | C |
| ATOM | 722 | C | SER | A | 139 | -22.28 | 22.946 | -38.399 | 1 | 21.92 | C |
| ATOM | 723 | O | SER | A | 139 | -21.243 | 22.31 | -38.547 | 1 | 20.19 | O |
| ATOM | 724 | CB | SER | A | 139 | -23.922 | 21.142 | -37.908 | 1 | 20.56 | C |
| ATOM | 725 | OG | SER | A | 139 | -23.63 | 21.435 | -36.555 | 1 | 23.25 | O |
| ATOM | 726 | H | SER | A | 139 | -22.899 | 21.796 | -40.56 | 1 | 19.58 | H |
| ATOM | 727 | HA | SER | A | 139 | -24.306 | 23.01 | -38.646 | 1 | 26.94 | H |
| ATOM | 728 | HB2 | SER | A | 139 | -24.862 | 20.918 | -37.987 | 1 | 24.67 | H |
| ATOM | 729 | HB3 | SER | A | 139 | -23.377 | 20.391 | -38.193 | 1 | 24.67 | H |
| ATOM | 730 | HG | SER | A | 139 | -23.799 | 20.768 | -36.073 | 1 | 27.89 | H |
| ATOM | 731 | N | LYS | A | 140 | -22.304 | 24.164 | -37.869 | 1 | 21.91 | N |
| ATOM | 732 | CA | LYS | A | 140 | -21.074 | 24.803 | -37.417 | 1 | 22.19 | C |
| ATOM | 733 | C | LYS | A | 140 | -20.566 | 24.16 | -36.132 | 1 | 22.96 | C |
| ATOM | 734 | O | LYS | A | 140 | -19.382 | 24.24 | -35.823 | 1 | 23.93 | O |
| ATOM | 735 | CB | LYS | A | 140 | -21.28 | 26.304 | -37.215 | 1 | 25.51 | C |
| ATOM | 736 | CG | LYS | A | 140 | -21.119 | 27.111 | -38.497 | 1 | 26.71 | C |
| ATOM | 737 | CD | LYS | A | 140 | -21.243 | 28.605 | -38.258 | 1 | 29.71 | C |
| ATOM | 738 | CE | LYS | A | 140 | -20.959 | 29.383 | -39.534 | 1 | 30.52 | C |
| ATOM | 739 | NZ | LYS | A | 140 | -21.099 | 30.852 | -39.352 | 1 | 46.5 | N1+ |
| ATOM | 740 | H | LYS | A | 140 | -23.013 | 24.638 | -37.76 | 1 | 26.29 | H |
| ATOM | 741 | HA | LYS | A | 140 | -20.392 | 24.686 | -38.097 | 1 | 26.63 | H |
| ATOM | 742 | HB2 | LYS | A | 140 | -22.177 | 26.456 | -36.877 | 1 | 30.61 | H |
| ATOM | 743 | HB3 | LYS | A | 140 | -20.627 | 26.628 | -36.574 | 1 | 30.61 | H |
| ATOM | 744 | HG2 | LYS | A | 140 | -20.242 | 26.938 | -38.873 | 1 | 32.06 | H |
| ATOM | 745 | HG3 | LYS | A | 140 | -21.809 | 26.848 | -39.126 | 1 | 32.06 | H |
| ATOM | 746 | HD2 | LYS | A | 140 | -22.145 | 28.811 | -37.969 | 1 | 35.66 | H |
| ATOM | 747 | HD3 | LYS | A | 140 | -20.601 | 28.877 | -37.584 | 1 | 35.66 | H |
| ATOM | 748 | HE2 | LYS | A | 140 | -20.049 | 29.201 | -39.819 | 1 | 36.62 | H |
| ATOM | 749 | HE3 | LYS | A | 140 | -21.584 | 29.104 | -40.22 | 1 | 36.62 | H |
| ATOM | 750 | HZ1 | LYS | A | 140 | -20.925 | 31.271 | -40.118 | 1 | 55.8 | H |
| ATOM | 751 | HZ2 | LYS | A | 140 | -21.928 | 31.049 | -39.097 | 1 | 55.8 | H |
| ATOM | 752 | HZ3 | LYS | A | 140 | -20.529 | 31.138 | -38.731 | 1 | 55.8 | H |
| ATOM | 753 | N | GLU | A | 141 | -21.459 | 23.513 | -35.39 | 1 | 22.3 | N |

TABLE 5-continued

Atomic Coordinates for OMCP-NKG2D (4PDC).

| ATOM | 754 | CA | GLU | A | 141 | -21.065 | 22.818 | -34.17 | 1 | 22.51 | C |
|------|-----|-----|-----|---|-----|---------|--------|---------|---|-------|---|
| ATOM | 755 | C | GLU | A | 141 | -20.504 | 21.427 | -34.473 | 1 | 23.38 | C |
| ATOM | 756 | O | GLU | A | 141 | -19.397 | 21.093 | -34.048 | 1 | 20.37 | O |
| ATOM | 757 | CB | GLU | A | 141 | -22.25 | 22.705 | -33.215 | 1 | 27.68 | C |
| ATOM | 758 | CG | GLU | A | 141 | -21.925 | 22.006 | -31.91 | 1 | 37.33 | C |
| ATOM | 759 | CD | GLU | A | 141 | -23.137 | 21.869 | -31.013 | 1 | 48.81 | C |
| ATOM | 760 | OE1 | GLU | A | 141 | -23.28 | 22.685 | -30.079 | 1 | 53.5 | O |
| ATOM | 761 | OE2 | GLU | A | 141 | -23.95 | 20.947 | -31.241 | 1 | 51.65 | O1- |
| ATOM | 762 | H | GLU | A | 141 | -22.298 | 23.461 | -35.571 | 1 | 26.77 | H |
| ATOM | 763 | HA | GLU | A | 141 | -20.37 | 23.33 | -33.727 | 1 | 27.01 | H |
| ATOM | 764 | HB2 | GLU | A | 141 | -22.565 | 23.598 | -33.003 | 1 | 33.21 | H |
| ATOM | 765 | HB3 | GLU | A | 141 | -22.956 | 22.203 | -33.652 | 1 | 33.21 | H |
| ATOM | 766 | HG2 | GLU | A | 141 | -21.589 | 21.116 | -32.101 | 1 | 44.8 | H |
| ATOM | 767 | HG3 | GLU | A | 141 | -21.254 | 22.52 | -31.433 | 1 | 44.8 | H |
| ATOM | 768 | N | ASP | A | 142 | -21.273 | 20.619 | -35.2 | 1 | 22.34 | N |
| ATOM | 769 | CA | ASP | A | 142 | -20.873 | 19.244 | -35.515 | 1 | 21.81 | C |
| ATOM | 770 | C | ASP | A | 142 | -19.649 | 19.185 | -36.433 | 1 | 18.46 | C |
| ATOM | 771 | O | ASP | A | 142 | -20.37 | 18.171 | -36.48 | 1 | 19.9 | O |
| ATOM | 772 | CB | ASP | A | 142 | -21.254 | 18.486 | -36.178 | 1 | 21.93 | C |
| ATOM | 773 | CG | ASP | A | 142 | -22.029 | 17.966 | -35.18 | 1 | 25.65 | C |
| ATOM | 774 | OD1 | ASP | A | 142 | -23.054 | 18.415 | -34.015 | 1 | 31.16 | O |
| ATOM | 775 | OD2 | ASP | A | 142 | -23.865 | 17.101 | -35.576 | 1 | 29.49 | O1- |
| ATOM | 776 | H | ASP | A | 142 | -22.037 | 20.843 | -35.526 | 1 | 26.8 | H |
| ATOM | 777 | HA | ASP | A | 142 | -20.649 | 18.786 | -34.69 | 1 | 26.17 | H |
| ATOM | 778 | HB2 | ASP | A | 142 | -22.485 | 19.082 | -36.792 | 1 | 26.32 | H |
| ATOM | 779 | HB3 | ASP | A | 142 | -21.67 | 17.725 | -36.661 | 1 | 26.32 | H |
| ATOM | 780 | N | GLN | A | 143 | -19.407 | 20.265 | -37.169 | 1 | 17.54 | N |
| ATOM | 781 | CA | GLN | A | 143 | -18.302 | 20.325 | -38.124 | 1 | 18.55 | C |
| ATOM | 782 | C | GLN | A | 143 | -17.408 | 21.528 | -37.839 | 1 | 21.09 | C |
| ATOM | 783 | O | GLN | A | 143 | -16.838 | 22.123 | -38.756 | 1 | 15.66 | O |
| ATOM | 784 | CB | GLN | A | 143 | -18.842 | 20.393 | -39.553 | 1 | 17.56 | C |
| ATOM | 785 | CG | GLN | A | 143 | -19.803 | 19.267 | -39.896 | 1 | 20.23 | C |
| ATOM | 786 | CD | GLN | A | 143 | -20.459 | 19.445 | -41.251 | 1 | 20.71 | C |
| ATOM | 787 | OE1 | GLN | A | 143 | -21.171 | 20.425 | -41.486 | 1 | 19.03 | O |
| ATOM | 788 | NE2 | GLN | A | 143 | -20.225 | 18.496 | -42.152 | 1 | 18.38 | N |
| ATOM | 789 | H | GLN | A | 143 | -19.874 | 20.986 | -37.134 | 1 | 21.05 | H |
| ATOM | 790 | HA | GLN | A | 143 | -17.765 | 19.521 | -38.041 | 1 | 22.26 | H |
| ATOM | 791 | HB2 | GLN | A | 143 | -19.314 | 21.232 | -39.67 | 1 | 21.08 | H |
| ATOM | 792 | HB3 | GLN | A | 143 | -18.096 | 20.345 | -40.172 | 1 | 21.08 | H |
| ATOM | 793 | HG2 | GLN | A | 143 | -19.315 | 18.428 | -39.907 | 1 | 24.27 | H |
| ATOM | 794 | HG3 | GLN | A | 143 | -20.503 | 19.234 | -39.226 | 1 | 24.27 | H |
| ATOM | 795 | HE21 | GLN | A | 143 | -18.552 | 18.552 | -42.935 | 1 | 22.06 | H |
| ATOM | 796 | HE22 | GLN | A | 143 | -19.724 | 17.827 | -41.95 | 1 | 22.06 | H |
| ATOM | 797 | N | ASP | A | 144 | -17.288 | 21.876 | -36.561 | 1 | 17.64 | N |
| ATOM | 798 | CA | ASP | A | 144 | -16.568 | 23.078 | -36.157 | 1 | 19.87 | C |
| ATOM | 799 | C | ASP | A | 144 | -15.114 | 23.071 | -36.621 | 1 | 19.55 | C |
| ATOM | 800 | O | ASP | A | 144 | -14.547 | 24.122 | -36.92 | 1 | 19.43 | O |
| ATOM | 801 | CB | ASP | A | 144 | -16.632 | 23.247 | -34.636 | 1 | 21.16 | C |
| ATOM | 802 | CG | ASP | A | 144 | -16.132 | 22.027 | -33.882 | 1 | 25.44 | C |
| ATOM | 803 | OD1 | ASP | A | 144 | -16.127 | 20.917 | -34.455 | 1 | 24.83 | O |
| ATOM | 804 | OD2 | ASP | A | 144 | -15.753 | 22.181 | -32.702 | 1 | 30.53 | O1- |

TABLE 5-continued

Atomic Coordinates for OMCP-NKG2D (4PDC).

| | | | | | | | | | | |
|---|---|---|---|---|---|---|---|---|---|---|
| ATOM | 805 | H | ASP | A | 144 | -17.618 | 21.429 | -35.904 | 1 | 21.16 | H |
| ATOM | 806 | HA | ASP | A | 144 | -17.001 | 23.848 | -36.558 | 1 | 23.85 | H |
| ATOM | 807 | HB2 | ASP | A | 144 | -16.081 | 24.004 | -34.38 | 1 | 25.4 | H |
| ATOM | 808 | HB3 | ASP | A | 144 | -17.552 | 23.405 | -34.374 | 1 | 25.4 | H |
| ATOM | 809 | N | LEU | A | 145 | -14.516 | 21.891 | -36.711 | 1 | 17.05 | N |
| ATOM | 810 | CA | LEU | A | 145 | -13.098 | 21.807 | -37.047 | 1 | 17.13 | C |
| ATOM | 811 | C | LEU | A | 145 | -12.832 | 22.091 | -38.531 | 1 | 17.51 | C |
| ATOM | 812 | O | LEU | A | 145 | -11.681 | 22.142 | -38.963 | 1 | 18.01 | O |
| ATOM | 813 | CB | LEU | A | 145 | -12.549 | 20.442 | -36.639 | 1 | 22.72 | C |
| ATOM | 814 | CG | LEU | A | 145 | -12.526 | 20.245 | -35.115 | 1 | 27.83 | C |
| ATOM | 815 | CD1 | LEU | A | 145 | -12.087 | 18.841 | -34.761 | 1 | 30.89 | C |
| ATOM | 816 | CD2 | LEU | A | 145 | -11.61 | 21.254 | -34.415 | 1 | 26.54 | C |
| ATOM | 817 | H | LEU | A | 145 | -14.9 | 21.132 | -36.585 | 1 | 20.46 | H |
| ATOM | 818 | HA | LEU | A | 145 | -12.621 | 22.478 | -36.533 | 1 | 20.56 | H |
| ATOM | 819 | HB2 | LEU | A | 145 | -13.109 | 19.748 | -37.023 | 1 | 27.26 | H |
| ATOM | 820 | HB3 | LEU | A | 145 | -11.641 | 20.355 | -36.967 | 1 | 27.26 | H |
| ATOM | 821 | HG | LEU | A | 145 | -13.424 | 20.371 | -34.77 | 1 | 33.39 | H |
| ATOM | 822 | HD11 | LEU | A | 145 | -12.082 | 18.746 | -33.795 | 1 | 37.07 | H |
| ATOM | 823 | HD12 | LEU | A | 145 | -12.709 | 18.208 | -35.152 | 1 | 37.07 | H |
| ATOM | 824 | HD13 | LEU | A | 145 | -11.196 | 18.691 | -35.113 | 1 | 37.07 | H |
| ATOM | 825 | HD21 | LEU | A | 145 | -11.63 | 21.089 | -33.459 | 1 | 31.85 | H |
| ATOM | 826 | HD22 | LEU | A | 145 | -10.706 | 21.145 | -34.75 | 1 | 31.85 | H |
| ATOM | 827 | HD23 | LEU | A | 145 | -11.927 | 22.151 | -34.602 | 1 | 31.85 | H |
| ATOM | 828 | N | LEU | A | 146 | -13.892 | 22.317 | -39.3 | 1 | 14.54 | N |
| ATOM | 829 | CA | LEU | A | 146 | -13.741 | 22.812 | -40.663 | 1 | 17.73 | C |
| ATOM | 830 | C | LEU | A | 146 | -13.1 | 24.2 | -40.661 | 1 | 13.72 | C |
| ATOM | 831 | O | LEU | A | 146 | -12.574 | 24.65 | -41.679 | 1 | 14.63 | O |
| ATOM | 832 | CB | LEU | A | 146 | -15.093 | 22.857 | -41.382 | 1 | 16.27 | C |
| ATOM | 833 | CG | LEU | A | 146 | -15.734 | 21.525 | -41.77 | 1 | 19.7 | C |
| ATOM | 834 | CD1 | LEU | A | 146 | -17.09 | 21.764 | -42.414 | 1 | 16.79 | C |
| ATOM | 835 | CD2 | LEU | A | 146 | -14.839 | 20.74 | -42.715 | 1 | 17.92 | C |
| ATOM | 836 | H | LEU | A | 146 | -14.708 | 22.193 | -39.057 | 1 | 17.45 | H |
| ATOM | 837 | HA | LEU | A | 146 | -13.158 | 22.212 | -41.155 | 1 | 21.28 | H |
| ATOM | 838 | HB2 | LEU | A | 146 | -15.723 | 23.318 | -40.806 | 1 | 19.52 | H |
| ATOM | 839 | HB3 | LEU | A | 146 | -14.98 | 23.366 | -42.2 | 1 | 19.52 | H |
| ATOM | 840 | HG | LEU | A | 146 | -15.869 | 20.992 | -40.971 | 1 | 23.64 | H |
| ATOM | 841 | HD11 | LEU | A | 146 | -17.481 | 20.909 | -42.653 | 1 | 20.15 | H |
| ATOM | 842 | HD12 | LEU | A | 146 | -17.663 | 22.224 | -41.782 | 1 | 20.15 | H |
| ATOM | 843 | HD13 | LEU | A | 146 | -16.97 | 22.307 | -43.209 | 1 | 20.15 | H |
| ATOM | 844 | HD21 | LEU | A | 146 | -15.275 | 19.903 | -42.94 | 1 | 21.5 | H |
| ATOM | 845 | HD22 | LEU | A | 146 | -14.692 | 21.264 | -43.518 | 1 | 21.28 | H |
| ATOM | 846 | HD23 | LEU | A | 146 | -13.992 | 20.565 | -42.275 | 1 | 21.5 | H |
| ATOM | 847 | N | LYS | A | 147 | -13.14 | 24.875 | -39.517 | 1 | 15.29 | N |
| ATOM | 848 | CA | LYS | A | 147 | -12.485 | 26.173 | -39.36 | 1 | 18.16 | C |
| ATOM | 849 | C | LYS | A | 147 | -10.973 | 26.053 | -39.545 | 1 | 16.32 | C |
| ATOM | 850 | O | LYS | A | 147 | -10.321 | 26.979 | -40.029 | 1 | 15.57 | O |
| ATOM | 851 | CB | LYS | A | 147 | -12.798 | 26.763 | -37.981 | 1 | 22.56 | C |
| ATOM | 852 | CG | LYS | A | 147 | -12.018 | 28.031 | -37.645 | 1 | 33.54 | C |
| ATOM | 853 | CD | LYS | A | 147 | -12.43 | 28.588 | -36.287 | 1 | 49.3 | C |
| ATOM | 854 | CE | LYS | A | 147 | -11.588 | 29.796 | -35.894 | 1 | 57.42 | C |
| ATOM | 855 | NZ | LYS | A | 147 | -11.76 | 30.941 | -36.829 | 1 | 59.81 | N1+ |

TABLE 5-continued

Atomic Coordinates for OMCP-NKG2D (4PDC).

| | | | | | | | | | | |
|---|---|---|---|---|---|---|---|---|---|---|
| ATOM | 856 | H | LYS | A | 147 | -13.544 | 24.601 | -38.808 | 1 | 18.35 | H |
| ATOM | 857 | HA | LYS | A | 147 | -12.824 | 26.783 | -40.034 | 1 | 21.79 | H |
| ATOM | 858 | HB2 | LYS | A | 147 | -13.742 | 26.98 | -37.943 | 1 | 27.07 | H |
| ATOM | 859 | HB3 | LYS | A | 147 | -12.587 | 26.1 | -37.305 | 1 | 27.07 | H |
| ATOM | 860 | HG2 | LYS | A | 147 | -11.07 | 27.826 | -37.616 | 1 | 40.24 | H |
| ATOM | 861 | HG3 | LYS | A | 147 | -12.197 | 28.705 | -38.318 | 1 | 40.24 | H |
| ATOM | 862 | HD2 | LYS | A | 147 | -13.359 | 28.864 | -36.324 | 1 | 59.16 | H |
| ATOM | 863 | HD3 | LYS | A | 147 | -12.31 | 27.902 | -35.612 | 1 | 59.16 | H |
| ATOM | 864 | HE2 | LYS | A | 147 | -11.851 | 30.089 | -35.008 | 1 | 68.91 | H |
| ATOM | 865 | HE3 | LYS | A | 147 | -10.652 | 29.543 | -35.897 | 1 | 68.91 | H |
| ATOM | 866 | HZ1 | LYS | A | 147 | -11.255 | 31.626 | -36.567 | 1 | 71.78 | H |
| ATOM | 867 | HZ2 | LYS | A | 147 | -11.519 | 30.701 | -37.652 | 1 | 71.78 | H |
| ATOM | 868 | HZ3 | LYS | A | 147 | -12.612 | 31.199 | -36.841 | 1 | 71.78 | H |
| ATOM | 869 | N | LEU | A | 148 | -10.426 | 24.903 | -39.166 | 1 | 13.11 | N |
| ATOM | 870 | CA | LEU | A | 148 | -8.984 | 24.68 | -39.204 | 1 | 13.14 | C |
| ATOM | 871 | C | LEU | A | 148 | -8.491 | 24.075 | -40.519 | 1 | 13.81 | C |
| ATOM | 872 | O | LEU | A | 148 | -7.296 | 23.812 | -40.667 | 1 | 17.85 | O |
| ATOM | 873 | CB | LEU | A | 148 | -8.568 | 23.765 | -38.052 | 1 | 15.95 | C |
| ATOM | 874 | CG | LEU | A | 148 | -8.725 | 24.317 | -36.634 | 1 | 20.41 | C |
| ATOM | 875 | CD1 | LEU | A | 148 | -8.325 | 23.25 | -35.63 | 1 | 17.28 | C |
| ATOM | 876 | CD2 | LEU | A | 148 | -7.903 | 25.578 | -36.435 | 1 | 21.97 | C |
| ATOM | 877 | H | LEU | A | 148 | -10.875 | 24.228 | -38.879 | 1 | 15.73 | H |
| ATOM | 878 | HA | LEU | A | 148 | -8.534 | 25.531 | -39.084 | 1 | 15.77 | H |
| ATOM | 879 | HB2 | LEU | A | 148 | -9.099 | 22.954 | -38.103 | 1 | 19.14 | H |
| ATOM | 880 | HB3 | LEU | A | 148 | -7.631 | 23.54 | -38.169 | 1 | 19.14 | H |
| ATOM | 881 | HG | LEU | A | 148 | -9.657 | 24.538 | -36.482 | 1 | 24.49 | H |
| ATOM | 882 | HD11 | LEU | A | 148 | -8.427 | 23.607 | -34.733 | 1 | 20.73 | H |
| ATOM | 883 | HD12 | LEU | A | 148 | -8.898 | 22.477 | -35.746 | 1 | 20.73 | H |
| ATOM | 884 | HD13 | LEU | A | 148 | 7.4 | 23.003 | -35.784 | 1 | 20.73 | H |
| ATOM | 885 | HD21 | LEU | A | 148 | -8.028 | 25.897 | -35.527 | 1 | 26.36 | H |
| ATOM | 886 | HD22 | LEU | A | 148 | -6.967 | 25.372 | -36.587 | 1 | 26.36 | H |
| ATOM | 887 | HD23 | LEU | A | 148 | -8.2 | 26.252 | -37.066 | 1 | 14.39 | H |
| ATOM | 888 | N | VAL | A | 149 | -9.396 | 23.849 | -41.467 | 1 | 13.95 | N |
| ATOM | 889 | CA | VAL | A | 149 | -9.009 | 23.24 | -42.738 | 1 | 15.01 | C |
| ATOM | 890 | C | VAL | A | 149 | -8.252 | 24.22 | -43.624 | 1 | 13.43 | C |
| ATOM | 891 | O | VAL | A | 149 | -8.734 | 25.307 | -43.936 | 1 | 13.62 | O |
| ATOM | 892 | CB | VAL | A | 149 | -10.234 | 22.703 | -43.505 | 1 | 18.07 | C |
| ATOM | 893 | CG1 | VAL | A | 149 | -9.869 | 22.333 | -44.945 | 1 | 13.27 | C |
| ATOM | 894 | CG2 | VAL | A | 149 | -10.796 | 21.498 | -42.787 | 1 | 17.27 | C |
| ATOM | 895 | H | VAL | A | 149 | -10.233 | 24.036 | -41.401 | 1 | 16.74 | H |
| ATOM | 896 | HA | VAL | A | 149 | -8.422 | 22.49 | -42.557 | 1 | 16.34 | H |
| ATOM | 897 | HB | VAL | A | 149 | -10.92 | 23.388 | -43.532 | 1 | 21.68 | H |
| ATOM | 898 | HG11 | VAL | A | 149 | -10.661 | 22 | -45.396 | 1 | 21.68 | H |
| ATOM | 899 | HG12 | VAL | A | 149 | -9.537 | 23.123 | -45.4 | 1 | 15.93 | H |
| ATOM | 900 | HG13 | VAL | A | 149 | -9.184 | 21.646 | -44.93 | 1 | 15.93 | H |
| ATOM | 901 | HG21 | VAL | A | 149 | -11.566 | 21.169 | -43.278 | 1 | 18.07 | H |
| ATOM | 902 | HG22 | VAL | A | 149 | -10.234 | 20.811 | -42.742 | 1 | 15.93 | H |
| ATOM | 903 | HG23 | VAL | A | 149 | -11.062 | 21.76 | -41.892 | 1 | 15.93 | H |
| ATOM | 904 | N | LYS | A | 150 | -7.063 | 23.797 | -44.032 | 1 | 13.03 | N |
| ATOM | 905 | CA | LYS | A | 150 | -6.189 | 24.572 | -44.898 | 1 | 14.72 | C |
| ATOM | 906 | C | LYS | A | 150 | -6.493 | 24.295 | -46.366 | 1 | 13.85 | C |

TABLE 5-continued

Atomic Coordinates for OMCP-NKG2D (4PDC).

| ATOM | 907 | O | LYS | A | 150 | -6.988 | 23.224 | -46.705 | 1 | 15.19 | O |
|------|-----|-----|-----|---|-----|--------|--------|---------|---|-------|-----|
| ATOM | 908 | CB | LYS | A | 150 | -4.73 | 24.229 | -44.589 | 1 | 17.03 | C |
| ATOM | 909 | CG | LYS | A | 150 | -3.696 | 25.097 | -45.282 | 1 | 16.21 | C |
| ATOM | 910 | CD | LYS | A | 150 | -2.302 | 24.647 | -44.88 | 1 | 15.63 | C |
| ATOM | 911 | CE | LYS | A | 150 | -1.224 | 25.608 | -45.344 | 1 | 20.81 | C |
| ATOM | 912 | NZ | LYS | A | 150 | 0.121 | 25.154 | -44.907 | 1 | 24.83 | N1+ |
| ATOM | 913 | H | LYS | A | 150 | -6.729 | 23.036 | -43.81 | 1 | 15.64 | H |
| ATOM | 914 | HA | LYS | A | 150 | -6.324 | 25.518 | -44.73 | 1 | 17.66 | H |
| ATOM | 915 | HB2 | LYS | A | 150 | -4.59 | 24.317 | -43.633 | 1 | 20.44 | H |
| ATOM | 916 | HB3 | LYS | A | 150 | -4.567 | 23.312 | -44.857 | 1 | 20.44 | H |
| ATOM | 917 | HG2 | LYS | A | 150 | -3.786 | 25.006 | -46.243 | 1 | 19.45 | H |
| ATOM | 918 | HG3 | LYS | A | 150 | -3.813 | 26.021 | -45.013 | 1 | 19.45 | H |
| ATOM | 919 | HD2 | LYS | A | 150 | -2.255 | 24.587 | -43.913 | 1 | 18.76 | H |
| ATOM | 920 | HD3 | LYS | A | 150 | -2.122 | 23.78 | -45.276 | 1 | 18.76 | H |
| ATOM | 921 | HE2 | LYS | A | 150 | -1.23 | 25.654 | -46.313 | 1 | 24.98 | H |
| ATOM | 922 | HE3 | LYS | A | 150 | -1.389 | 26.484 | -44.964 | 1 | 24.98 | H |
| ATOM | 923 | HZ1 | LYS | A | 150 | 0.296 | 24.35 | -45.246 | 1 | 29.79 | H |
| ATOM | 924 | HZ2 | LYS | A | 150 | 0.741 | 25.728 | -45.186 | 1 | 29.79 | H |
| ATOM | 925 | HZ3 | LYS | A | 150 | 0.151 | 25.106 | -44.018 | 1 | 29.79 | H |
| ATOM | 926 | N | SER | A | 151 | -6.191 | 25.271 | -47.219 | 1 | 11.64 | N |
| ATOM | 927 | CA | SER | A | 151 | -6.34 | 25.146 | -48.669 | 1 | 12 | C |
| ATOM | 928 | C | SER | A | 151 | -7.809 | 25.15 | -49.09 | 1 | 15.77 | C |
| ATOM | 929 | O | SER | A | 151 | -8.698 | 25.423 | -48.283 | 1 | 13.47 | O |
| ATOM | 930 | CB | SER | A | 151 | -5.657 | 23.875 | -49.185 | 1 | 15.08 | C |
| ATOM | 931 | OG | SER | A | 151 | -5.545 | 23.9 | -50.6 | 1 | 18.05 | O |
| ATOM | 932 | H | SER | A | 151 | -5.889 | 26.038 | -46.975 | 1 | 13.97 | H |
| ATOM | 933 | HA | SER | A | 151 | -5.91 | 25.905 | -49.092 | 1 | 14.4 | H |
| ATOM | 934 | HB2 | SER | A | 151 | -4.769 | 23.815 | -48.8 | 1 | 18.09 | H |
| ATOM | 935 | HB3 | SER | A | 151 | -6.184 | 23.104 | -48.924 | 1 | 18.09 | H |
| ATOM | 936 | HG | SER | A | 151 | -5.169 | 23.2 | -50.871 | 1 | 21.66 | H |
| ATOM | 937 | N | TYR | A | 152 | -8.034 | 24.838 | -50.363 | 1 | 15.37 | N |
| ATOM | 938 | CA | TYR | A | 152 | -9.332 | 24.985 | -51.015 | 1 | 14.25 | C |
| ATOM | 939 | C | TYR | A | 152 | -9.729 | 23.674 | -51.687 | 1 | 16.05 | C |
| ATOM | 940 | O | TYR | A | 152 | -8.929 | 23.071 | -52.401 | 1 | 15.6 | O |
| ATOM | 941 | CB | TYR | A | 152 | -9.27 | 26.138 | -52.025 | 1 | 15.37 | C |
| ATOM | 942 | CG | TYR | A | 152 | -8.986 | 27.455 | -51.343 | 1 | 16.48 | C |
| ATOM | 943 | CD1 | TYR | A | 152 | -7.721 | 27.747 | -50.853 | 1 | 14.01 | C |
| ATOM | 944 | CD2 | TYR | A | 152 | -9.991 | 28.393 | -51.161 | 1 | 18.15 | C |
| ATOM | 945 | CE1 | TYR | A | 152 | -7.464 | 28.935 | -50.202 | 1 | 15.58 | C |
| ATOM | 946 | CE2 | TYR | A | 152 | -9.745 | 29.584 | -50.511 | 1 | 16.03 | C |
| ATOM | 947 | CZ | TYR | A | 152 | -8.48 | 29.85 | -50.032 | 1 | 17.68 | C |
| ATOM | 948 | OH | TYR | A | 152 | -8.237 | 31.038 | -49.385 | 1 | 16.49 | O |
| ATOM | 949 | H | TYR | A | 152 | -7.428 | 24.528 | -50.888 | 1 | 18.44 | H |
| ATOM | 950 | HA | TYR | A | 152 | -10.003 | 25.2 | -50.348 | 1 | 17.09 | H |
| ATOM | 951 | HB2 | TYR | A | 152 | -8.56 | 25.967 | -52.663 | 1 | 18.44 | H |
| ATOM | 952 | HB3 | TYR | A | 152 | -10.123 | 26.21 | -52.482 | 1 | 18.44 | H |
| ATOM | 953 | HD1 | TYR | A | 152 | -10.847 | 27.127 | -50.958 | 1 | 16.82 | H |
| ATOM | 954 | HD2 | TYR | A | 152 | -7.036 | 28.212 | -51.474 | 1 | 21.78 | H |
| ATOM | 955 | HE1 | TYR | A | 152 | -6.611 | 29.117 | -50.032 | 1 | 18.7 | H |
| ATOM | 956 | HE2 | TYR | A | 152 | -10.428 | 30.204 | -50.396 | 1 | 19.23 | H |
| ATOM | 957 | HH | TYR | A | 152 | -8.94 | 31.496 | -49.353 | 1 | 19.79 | H |

TABLE 5-continued

Atomic Coordinates for OMCP-NKG2D (4PDC).

| | | | | | | | | | | |
|---|---|---|---|---|---|---|---|---|---|---|
| ATOM | 958 | N | HIS | A | 153 | -10.959 | 23.228 | -51.441 | 1 | 16.84 | N |
| ATOM | 959 | CA | HIS | A | 153 | -11.394 | 21.895 | -51.859 | 1 | 17.66 | C |
| ATOM | 960 | C | HIS | A | 153 | -12.829 | 21.891 | -52.367 | 1 | 16.44 | C |
| ATOM | 961 | O | HIS | A | 153 | -13.682 | 22.586 | -51.821 | 1 | 13.76 | O |
| ATOM | 962 | CB | HIS | A | 153 | -11.271 | 20.913 | -50.69 | 1 | 13.32 | C |
| ATOM | 963 | CG | HIS | A | 153 | -10.048 | 21.124 | -49.856 | 1 | 19.37 | C |
| ATOM | 964 | ND1 | HIS | A | 153 | -8.865 | 20.454 | -50.086 | 1 | 19.53 | N |
| ATOM | 965 | CD2 | HIS | A | 153 | -9.819 | 21.941 | -48.801 | 1 | 16.93 | C |
| ATOM | 966 | CE1 | HIS | A | 153 | -7.963 | 20.843 | -49.203 | 1 | 16.06 | C |
| ATOM | 967 | NE2 | HIS | A | 153 | -8.516 | 21.746 | -48.413 | 1 | 15.08 | N |
| ATOM | 968 | H | HIS | A | 153 | -11.565 | 23.68 | -51.031 | 1 | 20.2 | H |
| ATOM | 969 | HA | HIS | A | 153 | -10.819 | 21.584 | -52.576 | 1 | 21.19 | H |
| ATOM | 970 | HB2 | HIS | A | 153 | -12.044 | 21.015 | -50.113 | 1 | 15.98 | H |
| ATOM | 971 | HB3 | HIS | A | 153 | -11.239 | 20.01 | -51.041 | 1 | 15.98 | H |
| ATOM | 972 | HD1 | HIS | A | 153 | -8.736 | 19.87 | -50.705 | 1 | 23.43 | H |
| ATOM | 973 | HD2 | HIS | A | 153 | -10.43 | 22.523 | -48.411 | 1 | 20.31 | H |
| ATOM | 974 | HE1 | HIS | A | 153 | -7.087 | 20.535 | -49.149 | 1 | 19.27 | H |
| ATOM | 975 | HE2 | HIS | A | 153 | 8.124 | 22.146 | -47.76 | 1 | 18.09 | H |
| ATOM | 976 | N | TRP | A | 154 | -13.094 | 21.106 | -53.409 | 1 | 16.17 | N |
| ATOM | 977 | CA | TRP | A | 154 | -14.461 | 20.939 | -53.897 | 1 | 16.21 | C |
| ATOM | 978 | C | TRP | A | 154 | -15.351 | 20.404 | -52.787 | 1 | 14.86 | C |
| ATOM | 979 | O | TRP | A | 154 | -14.984 | 19.458 | -52.093 | 1 | 13.34 | O |
| ATOM | 980 | CB | TRP | A | 154 | -14.523 | 19.976 | -55.092 | 1 | 15.43 | C |
| ATOM | 981 | CG | TRP | A | 154 | -14.018 | 20.527 | -56.39 | 1 | 17.31 | C |
| ATOM | 982 | CD1 | TRP | A | 154 | -13.089 | 19.957 | -57.21 | 1 | 18.38 | C |
| ATOM | 983 | CD2 | TRP | A | 154 | -14.421 | 21.746 | -57.029 | 1 | 22.3 | C |
| ATOM | 984 | NE1 | TRP | A | 154 | -12.884 | 20.744 | -58.317 | 1 | 20.02 | N |
| ATOM | 985 | CE2 | TRP | A | 154 | -13.687 | 21.85 | -58.23 | 1 | 22.6 | C |
| ATOM | 986 | CE3 | TRP | A | 154 | -15.326 | 22.761 | -56.702 | 1 | 18.3 | C |
| ATOM | 987 | CZ2 | TRP | A | 154 | -13.831 | 22.927 | -59.104 | 1 | 22.55 | C |
| ATOM | 988 | CZ3 | TRP | A | 154 | -15.464 | 23.831 | -57.568 | 1 | 19.05 | C |
| ATOM | 989 | CH2 | TRP | A | 154 | -14.723 | 23.904 | -58.757 | 1 | 23.4 | C |
| ATOM | 990 | H | TRP | A | 154 | -12.504 | 20.661 | -53.848 | 1 | 19.4 | H |
| ATOM | 991 | HA | TRP | A | 154 | -14.808 | 21.799 | -54.179 | 1 | 19.45 | H |
| ATOM | 992 | HB2 | TRP | A | 154 | -13.992 | 19.192 | -54.882 | 1 | 18.52 | H |
| ATOM | 993 | HB3 | TRP | A | 154 | -15.447 | 19.714 | -55.226 | 1 | 18.52 | H |
| ATOM | 994 | HD1 | TRP | A | 154 | -12.657 | 19.15 | -57.044 | 1 | 22.06 | H |
| ATOM | 995 | HE1 | TRP | A | 154 | -12.338 | 20.572 | -58.959 | 1 | 24.02 | H |
| ATOM | 996 | HE3 | TRP | A | 154 | -15.821 | 22.72 | -55.916 | 1 | 21.96 | H |
| ATOM | 997 | HZ2 | TRP | A | 154 | -13.339 | 22.979 | -59.891 | 1 | 27.07 | H |
| ATOM | 998 | HZ3 | TRP | A | 154 | -16.064 | 24.511 | -57.361 | 1 | 22.86 | H |
| ATOM | 999 | HH2 | TRP | A | 154 | -14.838 | 24.635 | -59.321 | 1 | 28.08 | H |
| ATOM | 1000 | N | MET | A | 155 | -16.514 | 21.022 | -52.612 | 1 | 17.17 | N |
| ATOM | 1001 | CA | MET | A | 155 | -17.553 | 20.465 | -51.758 | 1 | 15.84 | C |
| ATOM | 1002 | C | MET | A | 155 | -18.796 | 20.242 | -52.615 | 1 | 16.3 | C |
| ATOM | 1003 | O | MET | A | 155 | -18.784 | 20.513 | -53.816 | 1 | 19.47 | O |
| ATOM | 1004 | CB | MET | A | 155 | -17.852 | 21.382 | -50.569 | 1 | 15.2 | C |
| ATOM | 1005 | CG | MET | A | 155 | -18.223 | 22.801 | -50.94 | 1 | 12.06 | C |
| ATOM | 1006 | SD | MET | A | 155 | -18.683 | 23.761 | -49.486 | 1 | 15.98 | S |
| ATOM | 1007 | CE | MET | A | 155 | -18.393 | 25.415 | -50.109 | 1 | 15.7 | C |
| ATOM | 1008 | H | MET | A | 155 | -16.726 | 21.77 | -52.98 | 1 | 20.6 | H |

TABLE 5-continued

Atomic Coordinates for OMCP-NKG2D (4PDC).

| ATOM | 1009 | HA | MET A | 155 | -17.252 | 19.612 | -51.41 | 1 | 19.01 | H |
|------|------|-----|-------|-----|---------|--------|--------|---|-------|---|
| ATOM | 1010 | HB2 | MET A | 155 | -18.592 | 21.006 | -50.068 | 1 | 18.23 | H |
| ATOM | 1011 | HB3 | MET A | 155 | -17.064 | 21.423 | -50.005 | 1 | 18.23 | H |
| ATOM | 1012 | HG2 | MET A | 155 | -17.463 | 23.231 | -51.362 | 1 | 14.47 | H |
| ATOM | 1013 | HG3 | MET A | 155 | -18.98 | 22.785 | -51.547 | 1 | 14.47 | H |
| ATOM | 1014 | HE1 | MET A | 155 | -18.606 | 26.056 | -49.412 | 1 | 18.84 | H |
| ATOM | 1015 | HE2 | MET A | 155 | -17.461 | 25.498 | -50.362 | 1 | 18.84 | H |
| ATOM | 1016 | HE3 | MET A | 155 | -18.961 | 25.565 | -50.881 | 1 | 18.84 | H |
| ATOM | 1017 | N | GLY A | 156 | -19.859 | 19.739 | -52 | 1 | 16.55 | N |
| ATOM | 1018 | CA | GLY A | 156 | -19.008 | 19.259 | -52.744 | 1 | 17.95 | C |
| ATOM | 1019 | C | GLY A | 156 | -21.008 | 20.285 | -53.069 | 1 | 23.68 | C |
| ATOM | 1020 | O | GLY A | 156 | -22.078 | 19.911 | -53.339 | 1 | 23.71 | O |
| ATOM | 1021 | H | GLY A | 156 | -23.217 | 19.667 | -51.147 | 1 | 19.86 | H |
| ATOM | 1022 | HA2 | GLY A | 156 | -19.937 | 20.698 | -53.582 | 1 | 21.54 | H |
| ATOM | 1023 | HA3 | GLY A | 156 | -20.698 | 18.882 | -52.237 | 1 | 21.54 | H |
| ATOM | 1024 | N | LEU A | 157 | -21.428 | 18.546 | -53.048 | 1 | 20.6 | N |
| ATOM | 1025 | CA | LEU A | 157 | -21.732 | 21.569 | -53.407 | 1 | 26.74 | C |
| ATOM | 1026 | C | LEU A | 157 | -22.694 | 22.607 | -54.914 | 1 | 32.2 | C |
| ATOM | 1027 | O | LEU A | 157 | -22.917 | 22.621 | -55.695 | 1 | 30.5 | O |
| ATOM | 1028 | CB | LEU A | 157 | -21.984 | 22.421 | -52.945 | 1 | 23.22 | C |
| ATOM | 1029 | CG | LEU A | 157 | -22.23 | 23.992 | -54.455 | 1 | 27.17 | C |
| ATOM | 1030 | CD1 | LEU A | 157 | -22.516 | 25.924 | -51.512 | 1 | 29.03 | C |
| ATOM | 1031 | CD2 | LEU A | 157 | -22.148 | 24.244 | -51.377 | 1 | 26.6 | C |
| ATOM | 1032 | H | LEU A | 157 | -23.963 | 21.864 | -51.093 | 1 | 24.72 | H |
| ATOM | 1033 | HA | LEU A | 157 | -20.953 | 22.415 | -52.831 | 1 | 32.08 | H |
| ATOM | 1034 | HB2 | LEU A | 157 | -23.543 | 24.03 | -52.978 | 1 | 27.87 | H |
| ATOM | 1035 | HB3 | LEU A | 157 | -21.268 | 24.647 | -53.059 | 1 | 27.87 | H |
| ATOM | 1036 | HG | LEU A | 157 | -22.639 | 23.951 | -53.532 | 1 | 32.6 | H |
| ATOM | 1037 | HD11 | LEU A | 157 | -21.954 | 26.212 | -50.903 | 1 | 34.83 | H |
| ATOM | 1038 | HD12 | LEU A | 157 | -22.331 | 26.033 | -50.469 | 1 | 34.83 | H |
| ATOM | 1039 | HD13 | LEU A | 157 | -21.205 | 26.44 | -51.576 | 1 | 34.83 | H |
| ATOM | 1040 | HD21 | LEU A | 157 | -22.681 | 24.556 | -52.002 | 1 | 31.92 | H |
| ATOM | 1041 | HD22 | LEU A | 157 | -24.076 | 24.747 | -50.181 | 1 | 31.92 | H |
| ATOM | 1042 | HD23 | LEU A | 157 | -24.54 | 23.299 | -51.689 | 1 | 31.92 | H |
| ATOM | 1043 | N | VAL A | 158 | -24.173 | 22.86 | -51.148 | 1 | 35.94 | N |
| ATOM | 1044 | CA | VAL A | 158 | -24.164 | 22.891 | -55.306 | 1 | 35.15 | C |
| ATOM | 1045 | C | VAL A | 158 | -24.554 | 24.154 | -56.709 | 1 | 41.48 | C |
| ATOM | 1046 | O | VAL A | 158 | -25.361 | 24.493 | -56.983 | 1 | 36.73 | O |
| ATOM | 1047 | CB | VAL A | 158 | -26.272 | 21.662 | -56.226 | 1 | 38.21 | C |
| ATOM | 1048 | CG1 | VAL A | 158 | -25.393 | 21.504 | -57.097 | 1 | 49.98 | C |
| ATOM | 1049 | CG2 | VAL A | 158 | -25.423 | 20.401 | -58.607 | 1 | 39.33 | C |
| ATOM | 1050 | H | VAL A | 158 | -24.839 | 23.011 | -56.443 | 1 | 43.13 | H |
| ATOM | 1051 | HA | VAL A | 158 | -24.816 | 22.908 | -54.765 | 1 | 42.18 | H |
| ATOM | 1052 | HB | VAL A | 158 | -23.759 | 21.787 | -57.265 | 1 | 45.85 | H |
| ATOM | 1053 | HG11 | VAL A | 158 | -26.303 | 20.725 | -56.788 | 1 | 59.98 | H |
| ATOM | 1054 | HG12 | VAL A | 158 | -25.955 | 22.299 | -58.832 | 1 | 59.98 | H |
| ATOM | 1055 | HG13 | VAL A | 158 | -25.816 | 21.389 | -58.999 | 1 | 59.98 | H |
| ATOM | 1056 | HG21 | VAL A | 158 | -25.386 | 19.644 | -58.93 | 1 | 47.2 | H |
| ATOM | 1057 | HG22 | VAL A | 158 | -23.925 | 20.267 | -56.704 | 1 | 47.2 | H |
| ATOM | 1058 | HG23 | VAL A | 158 | -24.863 | 20.51 | -56.739 | 1 | 47.2 | H |
| ATOM | 1059 | N | HIS A | 159 | -25.018 | 24.849 | -58.062 | 1 | 40.87 | N |

TABLE 5-continued

Atomic Coordinates for OMCP-NKG2D (4PDC).

| | | | | | | | | | |
|---|---|---|---|---|---|---|---|---|---|
| ATOM | 1060 | CA | HIS A | 159 | -25.71 | 26.078 | -58.427 | 1 | 49.33 C |
| ATOM | 1061 | C | HIS A | 159 | -26.895 | 25.782 | -59.331 | 1 | 56.17 C |
| ATOM | 1062 | O | HIS A | 159 | -26.738 | 25.178 | -60.39 | 1 | 50.22 O |
| ATOM | 1063 | CB | HIS A | 159 | -24.759 | 27.046 | -59.131 | 1 | 49.48 C |
| ATOM | 1064 | CG | HIS A | 159 | -25.285 | 28.444 | -59.229 | 1 | 56.01 C |
| ATOM | 1065 | ND1 | HIS A | 159 | -24.876 | 29.324 | -60.207 | 1 | 66.11 N |
| ATOM | 1066 | CD2 | HIS A | 159 | -26.184 | 29.115 | -58.47 | 1 | 57.64 C |
| ATOM | 1067 | CE1 | HIS A | 159 | -25.502 | 30.477 | -60.048 | 1 | 76.9 C |
| ATOM | 1068 | NE2 | HIS A | 159 | -26.301 | 30.377 | -59.001 | 1 | 68.99 N |
| ATOM | 1069 | H | HIS A | 159 | -24.386 | 24.629 | -58.601 | 1 | 49.05 H |
| ATOM | 1070 | HA | HIS A | 159 | -26.041 | 26.509 | -57.624 | 1 | 59.2 H |
| ATOM | 1071 | HB2 | HIS A | 159 | -23.924 | 27.077 | -58.639 | 1 | 59.38 H |
| ATOM | 1072 | HB3 | HIS A | 159 | -24.598 | 26.726 | -60.032 | 1 | 59.38 H |
| ATOM | 1073 | HD1 | HIS A | 159 | -24.304 | 29.15 | -60.825 | 1 | 79.33 H |
| ATOM | 1074 | HD2 | HIS A | 159 | -26.637 | 28.784 | -57.729 | 1 | 69.17 H |
| ATOM | 1075 | HE1 | HIS A | 159 | -25.397 | 31.231 | -60.582 | 1 | 92.28 H |
| ATOM | 1076 | HE2 | HIS A | 159 | -26.811 | 31 | -58.701 | 1 | 82.79 H |
| ATOM | 1077 | N | ILE A | 160 | -28.078 | 26.209 | -58.904 | 1 | 63.42 N |
| ATOM | 1078 | CA | ILE A | 160 | -29.278 | 26.111 | -59.725 | 1 | 74.82 C |
| ATOM | 1079 | C | ILE A | 160 | -29.379 | 27.349 | -60.618 | 1 | 81.75 C |
| ATOM | 1080 | O | ILE A | 160 | -29.585 | 28.452 | -60.113 | 1 | 78.84 O |
| ATOM | 1081 | CB | ILE A | 160 | -30.549 | 25.992 | -58.859 | 1 | 74.4 C |
| ATOM | 1082 | CG1 | ILE A | 160 | -30.45 | 24.786 | -57.917 | 1 | 65.58 C |
| ATOM | 1083 | CG2 | ILE A | 160 | -31.79 | 25.885 | -59.736 | 1 | 81.67 C |
| ATOM | 1084 | CD1 | ILE A | 160 | -30.357 | 23.442 | -58.622 | 1 | 62.63 C |
| ATOM | 1085 | H | ILE A | 160 | -28.213 | 26.565 | -58.132 | 1 | 76.11 H |
| ATOM | 1086 | HA | ILE A | 160 | -29.219 | 25.326 | -60.292 | 1 | 89.78 H |
| ATOM | 1087 | HB | ILE A | 160 | -30.626 | 26.794 | -58.319 | 1 | 89.28 H |
| ATOM | 1088 | HG12 | ILE A | 160 | -29.657 | 24.886 | -57.368 | 1 | 78.7 H |
| ATOM | 1089 | HG13 | ILE A | 160 | -31.238 | 24.768 | -57.352 | 1 | 78.7 H |
| ATOM | 1090 | HG21 | ILE A | 160 | -32.573 | 25.811 | -59.168 | 1 | 98 H |
| ATOM | 1091 | HG22 | ILE A | 160 | -31.856 | 26.68 | -60.288 | 1 | 98 H |
| ATOM | 1092 | HG23 | ILE A | 160 | -31.713 | 25.097 | -60.297 | 1 | 98 H |
| ATOM | 1093 | HD11 | ILE A | 160 | -30.298 | 22.74 | -57.955 | 1 | 75.15 H |
| ATOM | 1094 | HD12 | ILE A | 160 | -31.15 | 23.316 | -59.166 | 1 | 75.15 H |
| ATOM | 1095 | HD13 | ILE A | 160 | -29.565 | 23.434 | -59.182 | 1 | 75.15 H |
| ATOM | 1096 | N | PRO A | 161 | -29.227 | 27.178 | -61.946 | 1 | 91.79 N |
| ATOM | 1097 | CA | PRO A | 161 | -29.299 | 28.358 | -62.819 | 1 | 98.12 C |
| ATOM | 1098 | C | PRO A | 161 | -30.683 | 29.003 | -62.824 | 1 | 100.1 C |
| ATOM | 1099 | O | PRO A | 161 | -30.811 | 30.182 | -63.157 | 1 | 100.43 O |
| ATOM | 1100 | CB | PRO A | 161 | -28.959 | 27.797 | -64.208 | 1 | 103.41 C |
| ATOM | 1101 | CG | PRO A | 161 | -28.314 | 26.477 | -63.957 | 1 | 98.76 C |
| ATOM | 1102 | CD | PRO A | 161 | -28.948 | 25.953 | -62.715 | 1 | 93.32 C |
| ATOM | 1103 | HA | PRO A | 161 | -28.634 | 29.015 | -62.561 | 1 | 117.74 H |
| ATOM | 1104 | HB2 | PRO A | 161 | -29.774 | 27.687 | -64.723 | 1 | 124.09 H |
| ATOM | 1105 | HB3 | PRO A | 161 | -28.346 | 28.398 | -64.66 | 1 | 124.09 H |
| ATOM | 1106 | HG2 | PRO A | 161 | -28.485 | 25.884 | -64.705 | 1 | 118.52 H |
| ATOM | 1107 | HG3 | PRO A | 161 | -27.36 | 26.6 | -63.829 | 1 | 118.52 H |
| ATOM | 1108 | HD2 | PRO A | 161 | -29.774 | 25.489 | -62.925 | 1 | 111.99 H |
| ATOM | 1109 | HD3 | PRO A | 161 | -28.33 | 25.383 | -62.232 | 1 | 111.99 H |
| ATOM | 1110 | N | THR A | 162 | -31.699 | 28.227 | -62.458 | 1 | 100.32 N |

TABLE 5-continued

Atomic Coordinates for OMCP-NKG2D (4PDC).

| ATOM | 1111 | CA | THR | A | 162 | -33.074 | 28.712 | -62.425 | 1 | 102.58 | C |
| ATOM | 1112 | C | THR | A | 162 | -33.221 | 29.911 | -61.488 | 1 | 98.89 | C |
| ATOM | 1113 | O | THR | A | 162 | -33.339 | 31.051 | -61.94 | 1 | 100.64 | O |
| ATOM | 1114 | CB | THR | A | 162 | -34.048 | 27.597 | -61.978 | 1 | 103.4 | C |
| ATOM | 1115 | OG1 | THR | A | 162 | -33.897 | 26.454 | -62.828 | 1 | 102.81 | O |
| ATOM | 1116 | CG2 | THR | A | 162 | -35.492 | 28.078 | -62.034 | 1 | 106.25 | C |
| ATOM | 1117 | H | THR | A | 162 | -31.616 | 27.405 | -62.222 | 1 | 120.38 | H |
| ATOM | 1118 | HA | THR | A | 162 | -33.331 | 28.995 | -63.316 | 1 | 123.09 | H |
| ATOM | 1119 | HB | THR | A | 162 | -33.847 | 27.345 | -61.063 | 1 | 124.08 | H |
| ATOM | 1120 | HG1 | THR | A | 162 | -34.066 | 26.664 | -63.624 | 1 | 123.38 | H |
| ATOM | 1121 | HG21 | THR | A | 162 | -36.089 | 27.368 | -61.751 | 1 | 127.5 | H |
| ATOM | 1122 | HG22 | THR | A | 162 | -35.61 | 28.842 | -61.447 | 1 | 127.5 | H |
| ATOM | 1123 | HG23 | THR | A | 162 | -35.719 | 28.339 | -62.94 | 1 | 127.5 | H |
| ATOM | 1124 | N | ASN | A | 163 | -33.204 | 29.643 | -60.185 | 1 | 94.97 | N |
| ATOM | 1125 | CA | ASN | A | 163 | -33.435 | 30.674 | -59.178 | 1 | 91.11 | C |
| ATOM | 1126 | C | ASN | A | 163 | -32.14 | 31.232 | -58.589 | 1 | 85.58 | C |
| ATOM | 1127 | O | ASN | A | 163 | -32.03 | 32.03 | -57.651 | 1 | 80.37 | O |
| ATOM | 1128 | CB | ASN | A | 163 | -34.319 | 30.117 | -58.057 | 1 | 85.28 | C |
| ATOM | 1129 | CG | ASN | A | 163 | -33.748 | 28.858 | -57.431 | 1 | 81.5 | C |
| ATOM | 1130 | OD1 | ASN | A | 163 | -32.899 | 28.188 | -58.018 | 1 | 80.62 | O |
| ATOM | 1131 | ND2 | ASN | A | 163 | -34.221 | 28.525 | -56.236 | 1 | 76.73 | N |
| ATOM | 1132 | H | ASN | A | 163 | -33.06 | 28.862 | -59.856 | 1 | 113.96 | H |
| ATOM | 1133 | HA | ASN | A | 163 | -33.912 | 31.411 | -59.591 | 1 | 109.34 | H |
| ATOM | 1134 | HB2 | ASN | A | 163 | -34.404 | 30.787 | -57.36 | 1 | 102.34 | H |
| ATOM | 1135 | HB3 | ASN | A | 163 | -35.192 | 29.903 | -58.42 | 1 | 102.34 | H |
| ATOM | 1136 | HD21 | ASN | A | 163 | -33.93 | 27.82 | -55.839 | 1 | 92.07 | H |
| ATOM | 1137 | HD22 | ASN | A | 163 | -34.819 | 29.015 | -55.858 | 1 | 92.07 | H |
| ATOM | 1138 | N | GLY | A | 164 | -31.005 | 30.815 | -59.141 | 1 | 84.69 | N |
| ATOM | 1139 | CA | GLY | A | 164 | -29.712 | 31.301 | -58.69 | 1 | 79.34 | C |
| ATOM | 1140 | C | GLY | A | 164 | -29.381 | 30.898 | -57.264 | 1 | 74.41 | C |
| ATOM | 1141 | O | GLY | A | 164 | -28.51 | 31.495 | -56.63 | 1 | 68.03 | O |
| ATOM | 1142 | H | GLY | A | 164 | -30.959 | 30.245 | -59.784 | 1 | 101.63 | H |
| ATOM | 1143 | HA2 | GLY | A | 164 | -29.019 | 30.953 | -59.273 | 1 | 95.2 | H |
| ATOM | 1144 | HA3 | GLY | A | 164 | -29.556 | 32.269 | -58.744 | 1 | 95.2 | H |
| ATOM | 1145 | N | SER | A | 165 | -30.073 | 29.88 | -56.761 | 1 | 71.84 | N |
| ATOM | 1146 | CA | SER | A | 165 | -29.858 | 29.399 | -55.402 | 1 | 60.5 | C |
| ATOM | 1147 | C | SER | A | 165 | -28.787 | 28.313 | -55.373 | 1 | 53.12 | C |
| ATOM | 1148 | O | SER | A | 165 | -28.365 | 27.818 | -56.418 | 1 | 52.63 | O |
| ATOM | 1149 | CB | SER | A | 165 | -31.163 | 28.861 | -54.811 | 1 | 63.49 | C |
| ATOM | 1150 | OG | SER | A | 165 | -31.594 | 27.699 | -55.498 | 1 | 66.5 | O |
| ATOM | 1151 | H | SER | A | 165 | -30.679 | 29.448 | -57.192 | 1 | 86.21 | H |
| ATOM | 1152 | HA | SER | A | 165 | -29.556 | 30.135 | -54.847 | 1 | 72.59 | H |
| ATOM | 1153 | HB2 | SER | A | 165 | -31.018 | 28.639 | -53.878 | 1 | 76.19 | H |
| ATOM | 1154 | HB3 | SER | A | 165 | -31.848 | 29.544 | -54.886 | 1 | 76.19 | H |
| ATOM | 1155 | HG | SER | A | 165 | -31.724 | 27.876 | -56.309 | 1 | 79.8 | H |
| ATOM | 1156 | N | TRP | A | 166 | -28.355 | 27.956 | -54.167 | 1 | 44.12 | N |
| ATOM | 1157 | CA | TRP | A | 166 | -27.377 | 26.893 | -53.971 | 1 | 38.56 | C |
| ATOM | 1158 | C | TRP | A | 166 | -27.987 | 25.748 | -53.173 | 1 | 36.68 | C |
| ATOM | 1159 | O | TRP | A | 166 | -28.722 | 25.969 | -52.211 | 1 | 33.26 | O |
| ATOM | 1160 | CB | TRP | A | 166 | -26.135 | 27.424 | -53.25 | 1 | 32.81 | C |
| ATOM | 1161 | CG | TRP | A | 166 | -25.29 | 28.347 | -54.08 | 1 | 38.99 | C |

TABLE 5-continued

Atomic Coordinates for OMCP-NKG2D (4PDC).

| | | | | | | | | | | | |
|---|---|---|---|---|---|---|---|---|---|---|---|
| ATOM | 1162 | CD1 | TRP | A | 166 | -25.364 | 29.709 | -54.125 | 1 | 41.82 | C |
| ATOM | 1163 | CD2 | TRP | A | 166 | -24.237 | 27.973 | -54.978 | 1 | 38.51 | C |
| ATOM | 1164 | NE1 | TRP | A | 166 | -24.424 | 30.207 | -54.996 | 1 | 39.58 | N |
| ATOM | 1165 | CE2 | TRP | A | 166 | -23.72 | 29.162 | -55.533 | 1 | 36.7 | C |
| ATOM | 1166 | CE3 | TRP | A | 166 | -23.682 | 26.751 | -55.366 | 1 | 35.41 | C |
| ATOM | 1167 | CZ2 | TRP | A | 166 | -22.678 | 29.163 | -56.458 | 1 | 35.25 | C |
| ATOM | 1168 | CZ3 | TRP | A | 166 | -22.646 | 26.753 | -56.282 | 1 | 32.08 | C |
| ATOM | 1169 | CH2 | TRP | A | 166 | -22.154 | 27.952 | -56.817 | 1 | 33.54 | C |
| ATOM | 1170 | H | TRP | A | 166 | -28.62 | 28.321 | -53.435 | 1 | 52.94 | H |
| ATOM | 1171 | HA | TRP | A | 166 | -27.102 | 26.548 | -54.835 | 1 | 46.28 | H |
| ATOM | 1172 | HB2 | TRP | A | 166 | -26.418 | 27.912 | -52.461 | 1 | 39.37 | H |
| ATOM | 1173 | HB3 | TRP | A | 166 | -25.581 | 26.672 | -52.989 | 1 | 39.37 | H |
| ATOM | 1174 | HD1 | TRP | A | 166 | -25.964 | 30.226 | -53.637 | 1 | 50.18 | H |
| ATOM | 1175 | HE1 | TRP | A | 166 | -24.3 | 31.039 | -55.177 | 1 | 47.49 | H |
| ATOM | 1176 | HE3 | TRP | A | 166 | -24.003 | 25.951 | -55.015 | 1 | 42.49 | H |
| ATOM | 1177 | HZ2 | TRP | A | 166 | -22.348 | 29.956 | -56.813 | 1 | 42.3 | H |
| ATOM | 1178 | HZ3 | TRP | A | 166 | -22.27 | 25.946 | -56.548 | 1 | 38.5 | H |
| ATOM | 1179 | HH2 | TRP | A | 166 | -21.457 | 27.923 | -57.432 | 1 | 40.24 | H |
| ATOM | 1180 | N | GLN | A | 167 | -27.678 | 24.524 | -53.583 | 1 | 31.8 | N |
| ATOM | 1181 | CA | GLN | A | 167 | -28.116 | 23.343 | -52.859 | 1 | 37.87 | C |
| ATOM | 1182 | C | GLN | A | 167 | -27.035 | 22.268 | -52.901 | 1 | 26.79 | C |
| ATOM | 1183 | O | GLN | A | 167 | -26.107 | 22.337 | -53.706 | 1 | 25.74 | O |
| ATOM | 1184 | CB | GLN | A | 167 | -29.425 | 22.807 | -53.444 | 1 | 40.72 | C |
| ATOM | 1185 | CG | GLN | A | 167 | -29.394 | 22.6 | -54.947 | 1 | 46.08 | C |
| ATOM | 1186 | CD | GLN | A | 167 | -30.494 | 21.674 | -55.428 | 1 | 45.1 | C |
| ATOM | 1187 | OE1 | GLN | A | 167 | -30.226 | 20.635 | -56.033 | 1 | 47.82 | O |
| ATOM | 1188 | NE2 | GLN | A | 167 | -31.737 | 22.046 | -55.162 | 1 | 41.89 | N |
| ATOM | 1189 | H | GLN | A | 167 | -27.212 | 24.352 | -54.285 | 1 | 38.17 | H |
| ATOM | 1190 | HA | GLN | A | 167 | -28.273 | 23.578 | -51.932 | 1 | 45.44 | H |
| ATOM | 1191 | HB2 | GLN | A | 167 | -29.623 | 21.952 | -53.032 | 1 | 48.87 | H |
| ATOM | 1192 | HB3 | GLN | A | 167 | -30.135 | 23.438 | -53.248 | 1 | 48.87 | H |
| ATOM | 1193 | HG2 | GLN | A | 167 | -29.507 | 23.457 | -55.387 | 1 | 55.29 | H |
| ATOM | 1194 | HG3 | GLN | A | 167 | -28.541 | 22.209 | -55.195 | 1 | 55.29 | H |
| ATOM | 1195 | HE21 | GLN | A | 167 | -32.397 | 21.555 | -55.414 | 1 | 50.26 | H |
| ATOM | 1196 | HE22 | GLN | A | 167 | -31.885 | 22.779 | -54.737 | 1 | 50.26 | H |
| ATOM | 1197 | N | TRP | A | 168 | -27.159 | 21.284 | -52.019 | 1 | 29 | N |
| ATOM | 1198 | CA | TRP | A | 168 | -26.234 | 20.16 | -51.988 | 1 | 25.2 | C |
| ATOM | 1199 | C | TRP | A | 168 | -26.642 | 19.126 | -53.024 | 1 | 33.37 | C |
| ATOM | 1200 | O | TRP | A | 168 | -27.778 | 19.137 | -53.5 | 1 | 26.7 | O |
| ATOM | 1201 | CB | TRP | A | 168 | -26.194 | 19.554 | -50.59 | 1 | 25.54 | C |
| ATOM | 1202 | CG | TRP | A | 168 | -25.774 | 20.563 | -49.587 | 1 | 26.46 | C |
| ATOM | 1203 | CD1 | TRP | A | 168 | -26.564 | 21.196 | -48.677 | 1 | 29.23 | C |
| ATOM | 1204 | CD2 | TRP | A | 168 | -24.458 | 21.094 | -49.417 | 1 | 24.51 | C |
| ATOM | 1205 | NE1 | TRP | A | 168 | -25.818 | 22.082 | -47.938 | 1 | 25.79 | N |
| ATOM | 1206 | CE2 | TRP | A | 168 | -24.52 | 22.038 | -48.376 | 1 | 20.96 | C |
| ATOM | 1207 | CE3 | TRP | A | 168 | -23.231 | 20.858 | -50.044 | 1 | 20.74 | C |
| ATOM | 1208 | CZ2 | TRP | A | 168 | -23.402 | 22.746 | -47.944 | 1 | 18.61 | C |
| ATOM | 1209 | CZ3 | TRP | A | 168 | -22.122 | 21.558 | -49.613 | 1 | 18.82 | C |
| ATOM | 1210 | CH2 | TRP | A | 168 | -22.215 | 22.493 | -48.573 | 1 | 19.65 | C |
| ATOM | 1211 | H | TRP | A | 168 | -27.777 | 21.244 | -51.423 | 1 | 34.8 | H |
| ATOM | 1212 | HA | TRP | A | 168 | -25.343 | 20.474 | -52.207 | 1 | 30.24 | H |

TABLE 5-continued

Atomic Coordinates for OMCP-NKG2D (4PDC).

| ATOM | 1213 | HB2 | TRP | A | 168 | -27.078 | 19.235 | -50.351 | 1 | 30.65 | H |
| --- | --- | --- | --- | --- | --- | --- | --- | --- | --- | --- | --- |
| ATOM | 1214 | HB3 | TRP | A | 168 | -25.556 | 18.823 | -50.573 | 1 | 30.65 | H |
| ATOM | 1215 | HD1 | TRP | A | 168 | -27.476 | 21.048 | -48.569 | 1 | 35.07 | H |
| ATOM | 1216 | HE1 | TRP | A | 168 | -26.116 | 22.582 | -47.306 | 1 | 30.95 | H |
| ATOM | 1217 | HE3 | TRP | A | 168 | -23.162 | 20.241 | -50.736 | 1 | 24.89 | H |
| ATOM | 1218 | HZ2 | TRP | A | 168 | -23.459 | 23.364 | -47.251 | 1 | 22.33 | H |
| ATOM | 1219 | HZ3 | TRP | A | 168 | -21.3 | 21.41 | -50.023 | 1 | 22.59 | H |
| ATOM | 1220 | HH2 | TRP | A | 168 | -21.451 | 22.949 | -48.303 | 1 | 23.58 | H |
| ATOM | 1221 | N | GLU | A | 169 | -25.718 | 18.238 | -53.379 | 1 | 30.13 | N |
| ATOM | 1222 | CA | GLU | A | 169 | -25.959 | 17.297 | -54.468 | 1 | 31.2 | C |
| ATOM | 1223 | C | GLU | A | 169 | -27.056 | 16.293 | -54.122 | 1 | 30.15 | C |
| ATOM | 1224 | O | GLU | A | 169 | -27.646 | 15.685 | -55.013 | 1 | 35.52 | O |
| ATOM | 1225 | CB | GLU | A | 169 | -24.668 | 16.564 | -54.842 | 1 | 34.22 | C |
| ATOM | 1226 | CG | GLU | A | 169 | -24.055 | 15.756 | -53.726 | 1 | 30.07 | C |
| ATOM | 1227 | CD | GLU | A | 169 | -22.585 | 15.446 | -53.98 | 1 | 32.91 | C |
| ATOM | 1228 | OE1 | GLU | A | 169 | -22.224 | 15.153 | -55.14 | 1 | 30.13 | O |
| ATOM | 1229 | OE2 | GLU | A | 169 | -21.789 | 15.504 | -53.021 | 1 | 27.4 | O1- |
| ATOM | 1230 | H | GLU | A | 169 | -24.947 | 18.16 | -53.007 | 1 | 36.15 | H |
| ATOM | 1231 | HA | GLU | A | 169 | -26.252 | 17.794 | -55.248 | 1 | 37.44 | H |
| ATOM | 1232 | HB2 | GLU | A | 169 | -24.858 | 15.957 | -55.574 | 1 | 41.07 | H |
| ATOM | 1233 | HB3 | GLU | A | 169 | -24.011 | 17.219 | -55.125 | 1 | 41.07 | H |
| ATOM | 1234 | HG2 | GLU | A | 169 | -24.119 | 16.257 | -52.898 | 1 | 36.08 | H |
| ATOM | 1235 | HG3 | GLU | A | 169 | -24.531 | 14.914 | -53.644 | 1 | 36.08 | H |
| ATOM | 1236 | N | ASP | A | 170 | -27.342 | 16.132 | -52.834 | 1 | 31.34 | N |
| ATOM | 1237 | CA | ASP | A | 170 | -28.442 | 15.27 | -52.412 | 1 | 30.16 | C |
| ATOM | 1238 | C | ASP | A | 170 | -29.781 | 15.998 | -52.539 | 1 | 31.43 | C |
| ATOM | 1239 | O | ASP | A | 170 | -30.818 | 15.485 | -52.124 | 1 | 29.59 | O |
| ATOM | 1240 | CB | ASP | A | 170 | -28.229 | 14.785 | -50.974 | 1 | 32.21 | C |
| ATOM | 1241 | CG | ASP | A | 170 | -28.404 | 15.887 | -49.939 | 1 | 31.98 | C |
| ATOM | 1242 | OD1 | ASP | A | 170 | -28.531 | 17.071 | -50.314 | 1 | 33.58 | O |
| ATOM | 1243 | OD2 | ASP | A | 170 | -28.398 | 15.562 | -48.733 | 1 | 27.25 | O1- |
| ATOM | 1244 | H | ASP | A | 170 | -26.918 | 16.508 | -52.187 | 1 | 37.61 | H |
| ATOM | 1245 | HA | ASP | A | 170 | -28.47 | 14.491 | -52.989 | 1 | 36.19 | H |
| ATOM | 1246 | HB2 | ASP | A | 170 | -28.874 | 14.087 | -50.779 | 1 | 38.65 | H |
| ATOM | 1247 | HB3 | ASP | A | 170 | -27.328 | 14.435 | -50.89 | 1 | 38.65 | H |
| ATOM | 1248 | N | GLY | A | 171 | -29.741 | 17.204 | -53.098 | 1 | 35.35 | N |
| ATOM | 1249 | CA | GLY | A | 171 | -30.939 | 17.987 | -53.336 | 1 | 37.34 | C |
| ATOM | 1250 | C | GLY | A | 171 | -31.329 | 18.85 | -52.152 | 1 | 34.83 | C |
| ATOM | 1251 | O | GLY | A | 171 | -32.126 | 19.779 | -52.294 | 1 | 36.63 | O |
| ATOM | 1252 | H | GLY | A | 171 | -29.017 | 17.594 | -53.351 | 1 | 42.42 | H |
| ATOM | 1253 | HA2 | GLY | A | 171 | -30.798 | 18.565 | -54.102 | 1 | 44.81 | H |
| ATOM | 1254 | HA3 | GLY | A | 171 | -31.678 | 17.39 | -53.535 | 1 | 44.81 | H |
| ATOM | 1255 | N | SER | A | 172 | -30.76 | 18.555 | -50.987 | 1 | 33.06 | N |
| ATOM | 1256 | CA | SER | A | 172 | -31.137 | 19.238 | -49.752 | 1 | 34.83 | C |
| ATOM | 1257 | C | SER | A | 172 | -30.789 | 20.72 | -49.789 | 1 | 39 | C |
| ATOM | 1258 | O | SER | A | 172 | -30.003 | 21.17 | -50.623 | 1 | 36.04 | O |
| ATOM | 1259 | CB | SER | A | 172 | -30.454 | 18.589 | -48.551 | 1 | 37.68 | C |
| ATOM | 1260 | OG | SER | A | 172 | -29.067 | 18.869 | -48.56 | 1 | 31.69 | O |
| ATOM | 1261 | H | SER | A | 172 | -30.149 | 17.959 | -50.883 | 1 | 39.68 | H |
| ATOM | 1262 | HA | SER | A | 172 | -32.096 | 19.16 | -49.63 | 1 | 41.8 | H |
| ATOM | 1263 | HB2 | SER | A | 172 | -30.844 | 18.943 | -47.736 | 1 | 45.22 | H |

TABLE 5-continued

Atomic Coordinates for OMCP-NKG2D (4PDC).

| | | | | | | | | | | |
|---|---|---|---|---|---|---|---|---|---|---|
| ATOM | 1264 | HB3 | SER A | 172 | -30.584 | 17.629 | -48.593 | 1 | 45.22 | H |
| ATOM | 1265 | HG | SER A | 172 | -28.718 | 18.569 | -49.263 | 1 | 38.03 | H |
| ATOM | 1266 | N | ILE A | 173 | -31.374 | 21.467 | -48.859 | 1 | 40.76 | N |
| ATOM | 1267 | CA | ILE A | 173 | -31.214 | 22.915 | -48.809 | 1 | 44.21 | C |
| ATOM | 1268 | C | ILE A | 173 | -29.943 | 23.328 | -48.07 | 1 | 35.14 | C |
| ATOM | 1269 | O | ILE A | 173 | -29.563 | 22.716 | -47.069 | 1 | 35.11 | O |
| ATOM | 1270 | CB | ILE A | 173 | -32.431 | 23.587 | -48.128 | 1 | 50.72 | C |
| ATOM | 1271 | CG1 | ILE A | 173 | -32.642 | 23.026 | -46.711 | 1 | 49.11 | C |
| ATOM | 1272 | CG2 | ILE A | 173 | -33.678 | 23.388 | -48.982 | 1 | 62.02 | C |
| ATOM | 1273 | CD1 | ILE A | 173 | -33.764 | 23.689 | -45.932 | 1 | 53.43 | C |
| ATOM | 1274 | H | ILE A | 173 | -31.876 | 21.153 | -48.236 | 1 | 48.91 | H |
| ATOM | 1275 | HA | ILE A | 173 | -31.154 | 23.254 | -49.716 | 1 | 53.05 | H |
| ATOM | 1276 | HB | ILE A | 173 | -32.256 | 24.538 | -48.058 | 1 | 60.86 | H |
| ATOM | 1277 | HG12 | ILE A | 173 | -32.849 | 22.081 | -46.779 | 1 | 58.93 | H |
| ATOM | 1278 | HG13 | ILE A | 173 | -31.822 | 23.145 | -46.205 | 1 | 58.93 | H |
| ATOM | 1279 | HG21 | ILE A | 173 | -34.431 | 23.814 | -48.543 | 1 | 74.42 | H |
| ATOM | 1280 | HG22 | ILE A | 173 | -33.532 | 23.79 | -49.852 | 1 | 74.42 | H |
| ATOM | 1281 | HG23 | ILE A | 173 | -33.845 | 22.438 | -49.079 | 1 | 74.42 | H |
| ATOM | 1282 | HD11 | ILE A | 173 | -33.826 | 23.276 | -45.056 | 1 | 64.11 | H |
| ATOM | 1283 | HD12 | ILE A | 173 | -33.568 | 24.634 | -45.84 | 1 | 64.11 | H |
| ATOM | 1284 | HD13 | ILE A | 173 | -34.596 | 23.568 | -46.415 | 1 | 64.11 | H |
| ATOM | 1285 | N | LEU A | 174 | -29.284 | 24.363 | -48.579 | 1 | 36.19 | N |
| ATOM | 1286 | CA | LEU A | 174 | -28.194 | 25.002 | -47.854 | 1 | 33.01 | C |
| ATOM | 1287 | C | LEU A | 174 | -28.785 | 25.874 | -46.762 | 1 | 25.23 | C |
| ATOM | 1288 | O | LEU A | 174 | -29.378 | 26.91 | -47.051 | 1 | 35.07 | O |
| ATOM | 1289 | CB | LEU A | 174 | -27.317 | 25.839 | -48.788 | 1 | 28.79 | C |
| ATOM | 1290 | CG | LEU A | 174 | -26.268 | 26.722 | -48.096 | 1 | 30.47 | C |
| ATOM | 1291 | CD1 | LEU A | 174 | -25.235 | 25.873 | -47.369 | 1 | 28.59 | C |
| ATOM | 1292 | CD2 | LEU A | 174 | -25.593 | 27.65 | -49.086 | 1 | 23.68 | C |
| ATOM | 1293 | H | LEU A | 174 | -29.449 | 24.715 | -49.346 | 1 | 43.42 | H |
| ATOM | 1294 | HA | LEU A | 174 | -27.64 | 24.322 | -47.438 | 1 | 39.62 | H |
| ATOM | 1295 | HB2 | LEU A | 174 | -26.843 | 25.238 | -49.385 | 1 | 34.54 | H |
| ATOM | 1296 | HB3 | LEU A | 174 | -27.892 | 26.422 | -49.307 | 1 | 34.54 | H |
| ATOM | 1297 | HG | LEU A | 174 | -26.715 | 27.273 | -47.434 | 1 | 36.57 | H |
| ATOM | 1298 | HD11 | LEU A | 174 | -24.589 | 26.458 | -46.944 | 1 | 34.31 | H |
| ATOM | 1299 | HD12 | LEU A | 174 | -25.685 | 25.334 | -46.699 | 1 | 34.31 | H |
| ATOM | 1300 | HD13 | LEU A | 174 | -24.79 | 25.299 | -48.012 | 1 | 34.31 | H |
| ATOM | 1301 | HD21 | LEU A | 174 | -24.939 | 28.191 | -48.616 | 1 | 28.42 | H |
| ATOM | 1302 | HD22 | LEU A | 174 | -25.154 | 27.119 | -49.768 | 1 | 28.42 | H |
| ATOM | 1303 | HD23 | LEU A | 174 | -26.265 | 28.221 | -49.492 | 1 | 28.42 | H |
| ATOM | 1304 | N | SER A | 175 | -28.63 | 25.45 | -45.513 | 1 | 30.51 | N |
| ATOM | 1305 | CA | SER A | 175 | -29.152 | 26.205 | -44.382 | 1 | 30.76 | C |
| ATOM | 1306 | C | SER A | 175 | -28.581 | 27.619 | -44.38 | 1 | 30.6 | C |
| ATOM | 1307 | O | SER A | 175 | -27.82 | 27.82 | -44.727 | 1 | 29.98 | O |
| ATOM | 1308 | CB | SER A | 175 | -28.819 | 25.511 | -43.063 | 1 | 29.16 | C |
| ATOM | 1309 | OG | SER A | 175 | -29.013 | 24.111 | -43.155 | 1 | 41.38 | O |
| ATOM | 1310 | H | SER A | 175 | -28.224 | 24.724 | -45.293 | 1 | 36.61 | H |
| ATOM | 1311 | HA | SER A | 175 | -30.117 | 26.267 | -44.458 | 1 | 36.91 | H |
| ATOM | 1312 | HB2 | SER A | 175 | -27.891 | 25.686 | -42.842 | 1 | 35 | H |
| ATOM | 1313 | HB3 | SER A | 175 | -29.396 | 25.863 | -42.368 | 1 | 35 | H |
| ATOM | 1314 | HG | SER A | 175 | -28.825 | 23.746 | -42.422 | 1 | 49.66 | H |

TABLE 5-continued

Atomic Coordinates for OMCP-NKG2D (4PDC).

| | | | | | | | | | | | |
|---|---|---|---|---|---|---|---|---|---|---|---|
| ATOM | 1315 | N | PRO | A | 176 | -29.399 | 28.608 | -43.989 | 1 | 27.59 | N |
| ATOM | 1316 | CA | PRO | A | 176 | -28.904 | 29.986 | -43.961 | 1 | 27.04 | C |
| ATOM | 1317 | C | PRO | A | 176 | -27.802 | 30.194 | -42.923 | 1 | 27.52 | C |
| ATOM | 1318 | O | PRO | A | 176 | -27.783 | 29.514 | -41.898 | 1 | 28.41 | O |
| ATOM | 1319 | CB | PRO | A | 176 | -30.154 | 30.8 | -43.603 | 1 | 27.57 | C |
| ATOM | 1320 | CG | PRO | A | 176 | -31.03 | 29.849 | -42.883 | 1 | 31.89 | C |
| ATOM | 1321 | CD | PRO | A | 176 | -30.791 | 28.51 | -43.515 | 1 | 24.67 | C |
| ATOM | 1322 | HA | PRO | A | 176 | -28.583 | 30.252 | -44.837 | 1 | 32.45 | H |
| ATOM | 1323 | HB2 | PRO | A | 176 | -29.908 | 31.544 | -43.03 | 1 | 33.08 | H |
| ATOM | 1324 | HB3 | PRO | A | 176 | -30.583 | 31.117 | -44.414 | 1 | 33.08 | H |
| ATOM | 1325 | HG2 | PRO | A | 176 | -30.787 | 29.831 | -41.944 | 1 | 38.27 | H |
| ATOM | 1326 | HG3 | PRO | A | 176 | -31.957 | 30.116 | -42.99 | 1 | 38.27 | H |
| ATOM | 1327 | HD2 | PRO | A | 176 | -30.876 | 27.804 | -42.856 | 1 | 29.6 | H |
| ATOM | 1328 | HD3 | PRO | A | 176 | -31.394 | 28.376 | -44.262 | 1 | 29.6 | H |
| ATOM | 1329 | N | ASN | A | 177 | -26.89 | 31.117 | -43.213 | 1 | 26.69 | N |
| ATOM | 1330 | CA | ASN | A | 177 | -25.849 | 31.524 | -42.273 | 1 | 28.9 | C |
| ATOM | 1331 | C | ASN | A | 177 | -24.926 | 30.384 | -41.861 | 1 | 30.53 | C |
| ATOM | 1332 | O | ASN | A | 177 | -24.475 | 30.324 | -40.719 | 1 | 37.62 | O |
| ATOM | 1333 | CB | ASN | A | 177 | -26.488 | 32.149 | -41.034 | 1 | 32.1 | C |
| ATOM | 1334 | CG | ASN | A | 177 | -27.336 | 33.353 | -41.374 | 1 | 27.74 | C |
| ATOM | 1335 | OD1 | ASN | A | 177 | -26.88 | 34.275 | -42.05 | 1 | 29.89 | O |
| ATOM | 1336 | ND2 | ASN | A | 177 | -28.585 | 33.345 | -40.927 | 1 | 27.4 | N |
| ATOM | 1337 | H | ASN | A | 177 | -26.853 | 31.532 | -43.965 | 1 | 32.03 | H |
| ATOM | 1338 | HA | ASN | A | 177 | -25.302 | 32.204 | -42.696 | 1 | 34.68 | H |
| ATOM | 1339 | HB2 | ASN | A | 177 | -27.057 | 31.492 | -40.604 | 1 | 38.52 | H |
| ATOM | 1340 | HB3 | ASN | A | 177 | -25.789 | 32.435 | -40.426 | 1 | 38.52 | H |
| ATOM | 1341 | HD21 | ASN | A | 177 | -29.106 | 34.008 | -41.095 | 1 | 32.88 | H |
| ATOM | 1342 | HD22 | ASN | A | 177 | -28.873 | 32.676 | -40.469 | 1 | 32.88 | H |
| ATOM | 1343 | N | LEU | A | 178 | -24.646 | 29.488 | -42.802 | 1 | 23.55 | N |
| ATOM | 1344 | CA | LEU | A | 178 | -23.682 | 28.417 | -42.587 | 1 | 26.07 | C |
| ATOM | 1345 | C | LEU | A | 178 | -22.392 | 28.718 | -43.335 | 1 | 25.37 | C |
| ATOM | 1346 | O | LEU | A | 178 | -21.299 | 28.646 | -42.771 | 1 | 26.43 | O |
| ATOM | 1347 | CB | LEU | A | 178 | -24.243 | 27.071 | -43.052 | 1 | 27.18 | C |
| ATOM | 1348 | CG | LEU | A | 178 | -24.863 | 26.136 | -42.012 | 1 | 31.75 | C |
| ATOM | 1349 | CD1 | LEU | A | 178 | -25.286 | 24.847 | -42.694 | 1 | 32.44 | C |
| ATOM | 1350 | CD2 | LEU | A | 178 | -23.906 | 25.83 | -40.869 | 1 | 27.31 | C |
| ATOM | 1351 | H | LEU | A | 178 | -25.006 | 29.479 | -43.583 | 1 | 28.26 | H |
| ATOM | 1352 | HA | LEU | A | 178 | -23.478 | 28.353 | -41.641 | 1 | 31.28 | H |
| ATOM | 1353 | HB2 | LEU | A | 178 | -24.931 | 27.249 | -43.712 | 1 | 32.62 | H |
| ATOM | 1354 | HB3 | LEU | A | 178 | -23.522 | 26.579 | -43.475 | 1 | 32.62 | H |
| ATOM | 1355 | HG | LEU | A | 178 | -25.655 | 26.555 | -41.639 | 1 | 38.1 | H |
| ATOM | 1356 | HD11 | LEU | A | 178 | -25.679 | 24.255 | -42.034 | 1 | 38.93 | H |
| ATOM | 1357 | HD12 | LEU | A | 178 | -25.937 | 25.054 | -43.383 | 1 | 38.93 | H |
| ATOM | 1358 | HD13 | LEU | A | 178 | -24.505 | 24.43 | -43.091 | 1 | 38.93 | H |
| ATOM | 1359 | HD21 | LEU | A | 178 | -24.345 | 25.236 | -40.24 | 1 | 32.77 | H |
| ATOM | 1360 | HD22 | LEU | A | 178 | -23.113 | 25.403 | -41.228 | 1 | 32.77 | H |
| ATOM | 1361 | HD23 | LEU | A | 178 | -23.665 | 26.66 | -40.428 | 1 | 32.77 | H |
| ATOM | 1362 | N | LEU | A | 179 | -22.536 | 29.044 | -44.614 | 1 | 21.47 | N |
| ATOM | 1363 | CA | LEU | A | 179 | -21.403 | 29.358 | -45.471 | 1 | 22.73 | C |
| ATOM | 1364 | C | LEU | A | 179 | -21.496 | 30.785 | -45.977 | 1 | 24.99 | C |
| ATOM | 1365 | O | LEU | A | 179 | -22.58 | 31.279 | -46.292 | 1 | 21.88 | O |

TABLE 5-continued

Atomic Coordinates for OMCP-NKG2D (4PDC).

| ATOM | 1366 | CB | LEU | A | 179 | -21.34 | 28.399 | -46.66 | 1 | 20.75 | C |
|---|---|---|---|---|---|---|---|---|---|---|---|
| ATOM | 1367 | CG | LEU | A | 179 | -21.094 | 26.923 | -46.352 | 1 | 20.55 | C |
| ATOM | 1368 | CD1 | LEU | A | 179 | -21.138 | 26.111 | -47.637 | 1 | 23.59 | C |
| ATOM | 1369 | CD2 | LEU | A | 179 | -19.764 | 26.739 | -45.65 | 1 | 20.81 | C |
| ATOM | 1370 | H | LEU | A | 179 | -23.295 | 29.09 | -45.015 | 1 | 25.76 | H |
| ATOM | 1371 | HA | LEU | A | 179 | -20.582 | 29.267 | -44.963 | 1 | 27.27 | H |
| ATOM | 1372 | HB2 | LEU | A | 179 | -22.182 | 28.454 | -47.137 | 1 | 24.9 | H |
| ATOM | 1373 | HB3 | LEU | A | 179 | -20.623 | 28.691 | -47.245 | 1 | 24.9 | H |
| ATOM | 1374 | HG | LEU | A | 179 | -21.795 | 26.598 | -45.764 | 1 | 24.66 | H |
| ATOM | 1375 | HD11 | LEU | A | 179 | -20.98 | 25.178 | -47.426 | 1 | 28.3 | H |
| ATOM | 1376 | HD12 | LEU | A | 179 | -20.449 | 26.216 | -48.047 | 1 | 28.3 | H |
| ATOM | 1377 | HD13 | LEU | A | 179 | -22.011 | 26.436 | -48.238 | 1 | 28.3 | H |
| ATOM | 1378 | HD21 | LEU | A | 179 | -19.632 | 25.796 | -45.465 | 1 | 24.97 | H |
| ATOM | 1379 | HD22 | LEU | A | 179 | -19.055 | 27.066 | -46.226 | 1 | 24.97 | H |
| ATOM | 1380 | HD23 | LEU | A | 179 | -19.773 | 27.241 | -44.82 | 1 | 24.97 | H |
| ATOM | 1381 | N | THR | A | 180 | -20.347 | 31.443 | -46.038 | 1 | 21.26 | N |
| ATOM | 1382 | CA | THR | A | 180 | -20.231 | 32.721 | -46.711 | 1 | 19.84 | C |
| ATOM | 1383 | C | THR | A | 180 | -19.779 | 32.441 | -48.136 | 1 | 21.52 | C |
| ATOM | 1384 | O | THR | A | 180 | -18.64 | 32.036 | -48.366 | 1 | 23.27 | O |
| ATOM | 1385 | CB | THR | A | 180 | -19.238 | 33.651 | -45.993 | 1 | 24.67 | C |
| ATOM | 1386 | OG1 | THR | A | 180 | -19.714 | 33.921 | -44.669 | 1 | 25.74 | O |
| ATOM | 1387 | CG2 | THR | A | 180 | -19.074 | 34.963 | -46.744 | 1 | 25.66 | C |
| ATOM | 1388 | H | THR | A | 180 | -19.612 | 31.164 | -45.691 | 1 | 25.51 | H |
| ATOM | 1389 | HA | THR | A | 180 | -21.098 | 33.155 | -46.74 | 1 | 23.81 | H |
| ATOM | 1390 | HB | THR | A | 180 | -18.372 | 33.218 | -45.942 | 1 | 29.61 | H |
| ATOM | 1391 | HG1 | THR | A | 180 | -19.784 | 33.203 | -44.237 | 1 | 30.89 | H |
| ATOM | 1392 | HG21 | THR | A | 180 | -18.445 | 35.535 | -46.276 | 1 | 30.8 | H |
| ATOM | 1393 | HG22 | THR | A | 180 | -18.741 | 34.793 | -47.639 | 1 | 30.8 | H |
| ATOM | 1394 | HG23 | THR | A | 180 | -19.928 | 35.418 | -46.806 | 1 | 30.8 | H |
| ATOM | 1395 | N | ILE | A | 181 | -20.683 | 32.633 | -49.089 | 1 | 22.03 | N |
| ATOM | 1396 | CA | ILE | A | 181 | -20.372 | 32.385 | -50.49 | 1 | 21.98 | C |
| ATOM | 1397 | C | ILE | A | 181 | -19.733 | 33.621 | -51.1 | 1 | 25.54 | C |
| ATOM | 1398 | O | ILE | A | 181 | -20.283 | 34.72 | -51.025 | 1 | 23.45 | O |
| ATOM | 1399 | CB | ILE | A | 181 | -21.623 | 31.998 | -51.297 | 1 | 25.31 | C |
| ATOM | 1400 | CG1 | ILE | A | 181 | -22.295 | 30.767 | -50.684 | 1 | 27.58 | C |
| ATOM | 1401 | CG2 | ILE | A | 181 | -21.257 | 31.731 | -52.759 | 1 | 29.37 | C |
| ATOM | 1402 | CD1 | ILE | A | 181 | -21.409 | 29.523 | -50.619 | 1 | 25.67 | C |
| ATOM | 1403 | H | ILE | A | 181 | -21.487 | 32.906 | -48.95 | 1 | 26.43 | H |
| ATOM | 1404 | HA | ILE | A | 181 | -19.736 | 31.655 | -50.55 | 1 | 26.37 | H |
| ATOM | 1405 | HB | ILE | A | 181 | -22.249 | 32.738 | -51.267 | 1 | 30.37 | H |
| ATOM | 1406 | HG12 | ILE | A | 181 | -22.567 | 30.982 | -49.778 | 1 | 30.81 | H |
| ATOM | 1407 | HG13 | ILE | A | 181 | -23.076 | 30.544 | -51.215 | 1 | 33.09 | H |
| ATOM | 1408 | HG21 | ILE | A | 181 | -22.061 | 31.489 | -53.246 | 1 | 35.24 | H |
| ATOM | 1409 | HG22 | ILE | A | 181 | -20.869 | 32.534 | -53.139 | 1 | 35.24 | H |
| ATOM | 1410 | HG23 | ILE | A | 181 | -20.617 | 31.003 | -52.796 | 1 | 35.24 | H |
| ATOM | 1411 | HD11 | ILE | A | 181 | -21.913 | 28.797 | -50.219 | 1 | 30.81 | H |
| ATOM | 1412 | HD12 | ILE | A | 181 | -21.138 | 29.282 | -51.519 | 1 | 30.81 | H |
| ATOM | 1413 | HD13 | ILE | A | 181 | -20.628 | 29.72 | -50.079 | 1 | 30.81 | H |
| ATOM | 1414 | N | ILE | A | 182 | -18.567 | 33.418 | -51.706 | 1 | 21.72 | N |
| ATOM | 1415 | CA | ILE | A | 182 | -17.765 | 34.497 | -52.261 | 1 | 20.53 | C |
| ATOM | 1416 | C | ILE | A | 182 | -17.654 | 34.34 | -53.767 | 1 | 23.4 | C |

TABLE 5-continued

Atomic Coordinates for OMCP-NKG2D (4PDC).

| | | | | | | | | | | |
|---|---|---|---|---|---|---|---|---|---|---|
| ATOM | 1417 | O | ILE | A | 182 | -17.226 | 33.296 | -54.256 | 1 | 22.37 | O |
| ATOM | 1418 | CB | ILE | A | 182 | -16.346 | 34.515 | -51.649 | 1 | 20.38 | C |
| ATOM | 1419 | CG1 | ILE | A | 182 | -16.43 | 34.684 | -50.132 | 1 | 20.79 | C |
| ATOM | 1420 | CG2 | ILE | A | 182 | -15.494 | 35.626 | -52.271 | 1 | 21.86 | C |
| ATOM | 1421 | CD1 | ILE | A | 182 | -15.132 | 34.434 | -49.414 | 1 | 22.03 | C |
| ATOM | 1422 | H | ILE | A | 182 | -18.211 | 32.641 | -51.808 | 1 | 26.06 | H |
| ATOM | 1423 | HA | ILE | A | 182 | -18.192 | 35.347 | -52.072 | 1 | 24.63 | H |
| ATOM | 1424 | HB | ILE | A | 182 | -15.922 | 33.664 | -51.838 | 1 | 24.45 | H |
| ATOM | 1425 | HG12 | ILE | A | 182 | -16.706 | 35.593 | -49.934 | 1 | 24.95 | H |
| ATOM | 1426 | HG13 | ILE | A | 182 | -17.085 | 34.059 | -49.784 | 1 | 24.95 | H |
| ATOM | 1427 | HG21 | ILE | A | 182 | -14.613 | 35.611 | -51.867 | 1 | 26.24 | H |
| ATOM | 1428 | HG22 | ILE | A | 182 | -15.424 | 35.472 | -53.226 | 1 | 26.24 | H |
| ATOM | 1429 | HG23 | ILE | A | 182 | -15.921 | 36.481 | -52.104 | 1 | 26.24 | H |
| ATOM | 1430 | HD11 | ILE | A | 182 | -15.269 | 34.561 | -48.462 | 1 | 26.43 | H |
| ATOM | 1431 | HD12 | ILE | A | 182 | -14.845 | 33.524 | -49.589 | 1 | 26.43 | H |
| ATOM | 1432 | HD13 | ILE | A | 182 | -14.466 | 35.06 | -49.74 | 1 | 26.43 | H |
| ATOM | 1433 | N | GLU | A | 183 | -18.035 | 35.379 | -54.5 | 1 | 21.68 | N |
| ATOM | 1434 | CA | GLU | A | 183 | -17.855 | 35.391 | -55.943 | 1 | 27.56 | C |
| ATOM | 1435 | C | GLU | A | 183 | -16.373 | 35.527 | -56.271 | 1 | 29.48 | C |
| ATOM | 1436 | O | GLU | A | 183 | -15.667 | 36.337 | -55.67 | 1 | 31.01 | O |
| ATOM | 1437 | CB | GLU | A | 183 | -18.648 | 36.533 | -56.582 | 1 | 39.38 | C |
| ATOM | 1438 | CG | GLU | A | 183 | -20.154 | 36.416 | -56.407 | 1 | 45.85 | C |
| ATOM | 1439 | CD | GLU | A | 183 | -20.911 | 37.55 | -57.074 | 1 | 71.49 | C |
| ATOM | 1440 | OE1 | GLU | A | 183 | -20.297 | 38.607 | -57.336 | 1 | 65.31 | O |
| ATOM | 1441 | OE2 | GLU | A | 183 | -22.12 | 37.382 | -57.34 | 1 | 84.35 | O1- |
| ATOM | 1442 | H | GLU | A | 183 | -18.402 | 36.09 | -54.184 | 1 | 26.02 | H |
| ATOM | 1443 | HA | GLU | A | 183 | -18.174 | 34.553 | -56.314 | 1 | 33.07 | H |
| ATOM | 1444 | HB2 | GLU | A | 183 | -18.368 | 37.37 | -56.18 | 1 | 47.25 | H |
| ATOM | 1445 | HB3 | GLU | A | 183 | -18.461 | 36.548 | -57.534 | 1 | 47.25 | H |
| ATOM | 1446 | HG2 | GLU | A | 183 | -20.454 | 35.582 | -56.802 | 1 | 55.02 | H |
| ATOM | 1447 | HG3 | GLU | A | 183 | -20.364 | 36.43 | -55.461 | 1 | 55.02 | H |
| ATOM | 1448 | N | MET | A | 184 | -15.908 | 34.723 | -57.219 | 1 | 27.36 | N |
| ATOM | 1449 | CA | MET | A | 184 | -14.52 | 34.765 | -57.655 | 1 | 30.39 | C |
| ATOM | 1450 | C | MET | A | 184 | -14.461 | 34.514 | -59.154 | 1 | 36.58 | C |
| ATOM | 1451 | O | MET | A | 184 | -14.269 | 35.441 | -59.942 | 1 | 34.99 | O |
| ATOM | 1452 | CB | MET | A | 184 | -13.684 | 33.732 | -56.895 | 1 | 28.2 | C |
| ATOM | 1453 | CG | MET | A | 184 | -12.2 | 33.78 | -57.213 | 1 | 26.4 | C |
| ATOM | 1454 | SD | MET | A | 184 | -11.3 | 32.412 | -56.469 | 1 | 27.32 | S |
| ATOM | 1455 | CE | MET | A | 184 | -11.827 | 31.057 | -57.524 | 1 | 31.27 | C |
| ATOM | 1456 | H | MET | A | 184 | -16.384 | 34.136 | -57.631 | 1 | 32.83 | H |
| ATOM | 1457 | HA | MET | A | 184 | -14.155 | 35.644 | -57.466 | 1 | 36.47 | H |
| ATOM | 1458 | HB2 | MET | A | 184 | -13.788 | 33.887 | -55.943 | 1 | 33.85 | H |
| ATOM | 1459 | HB3 | MET | A | 184 | -14.006 | 32.845 | -57.12 | 1 | 33.85 | H |
| ATOM | 1460 | HG2 | MET | A | 184 | -12.08 | 33.732 | -58.175 | 1 | 31.68 | H |
| ATOM | 1461 | HG3 | MET | A | 184 | -11.828 | 34.607 | -56.871 | 1 | 31.68 | H |
| ATOM | 1462 | HE1 | MET | A | 184 | -11.402 | 30.239 | -57.223 | 1 | 37.53 | H |
| ATOM | 1463 | HE2 | MET | A | 184 | -12.791 | 30.969 | -57.468 | 1 | 37.53 | H |
| ATOM | 1464 | HE3 | MET | A | 184 | -11.565 | 31.248 | -58.439 | 1 | 37.53 | H |
| ATOM | 1465 | N | GLN | A | 185 | -14.639 | 33.253 | -59.535 | 1 | 34.02 | N |
| ATOM | 1466 | CA | GLN | A | 185 | -14.708 | 32.865 | -60.935 | 1 | 39.99 | C |
| ATOM | 1467 | C | GLN | A | 185 | -16.136 | 32.439 | -61.257 | 1 | 36.81 | C |

TABLE 5-continued

Atomic Coordinates for OMCP-NKG2D (4PDC).

| ATOM | 1468 | O    | GLN | A | 185 | -16.749 | 31.687 | -60.498 | 1 | 32.57  | O   |
|------|------|------|-----|---|-----|---------|--------|---------|---|--------|-----|
| ATOM | 1469 | CB   | GLN | A | 185 | -13.724 | 31.732 | -61.23  | 1 | 31.78  | C   |
| ATOM | 1470 | CG   | GLN | A | 185 | -13.525 | 31.454 | -62.708 | 1 | 37.09  | C   |
| ATOM | 1471 | CD   | GLN | A | 185 | -12.853 | 32.606 | -63.427 | 1 | 49.35  | C   |
| ATOM | 1472 | OE1  | GLN | A | 185 | -11.834 | 33.129 | -62.972 | 1 | 44.78  | O   |
| ATOM | 1473 | NE2  | GLN | A | 185 | -13.427 | 33.014 | -64.554 | 1 | 50.69  | N   |
| ATOM | 1474 | H    | GLN | A | 185 | -14.723 | 32.593 | -58.99  | 1 | 40.83  | H   |
| ATOM | 1475 | HA   | GLN | A | 185 | -14.48  | 33.624 | -61.494 | 1 | 47.99  | H   |
| ATOM | 1476 | HB2  | GLN | A | 185 | -12.86  | 31.964 | -60.855 | 1 | 38.14  | H   |
| ATOM | 1477 | HB3  | GLN | A | 185 | -14.053 | 30.918 | -60.818 | 1 | 38.14  | H   |
| ATOM | 1478 | HG2  | GLN | A | 185 | -12.966 | 30.668 | -62.81  | 1 | 44.51  | H   |
| ATOM | 1479 | HG3  | GLN | A | 185 | -14.39  | 31.304 | -63.121 | 1 | 44.51  | H   |
| ATOM | 1480 | HE21 | GLN | A | 185 | -13.084 | 33.665 | -64.999 | 1 | 60.83  | H   |
| ATOM | 1481 | HE22 | GLN | A | 185 | -14.141 | 32.629 | -64.837 | 1 | 60.83  | H   |
| ATOM | 1482 | N    | LYS | A | 186 | -16.669 | 32.933 | -62.37  | 1 | 41.91  | N   |
| ATOM | 1483 | CA   | LYS | A | 186 | -18.026 | 32.585 | -62.779 | 1 | 44.77  | C   |
| ATOM | 1484 | C    | LYS | A | 186 | -18.149 | 31.085 | -63.028 | 1 | 32.82  | C   |
| ATOM | 1485 | O    | LYS | A | 186 | -17.492 | 30.537 | -63.913 | 1 | 41.23  | O   |
| ATOM | 1486 | CB   | LYS | A | 186 | -18.427 | 33.361 | -64.033 | 1 | 55.29  | C   |
| ATOM | 1487 | CG   | LYS | A | 186 | -18.429 | 34.868 | -63.851 | 1 | 69.71  | C   |
| ATOM | 1488 | CD   | LYS | A | 186 | -18.935 | 35.578 | -65.096 | 1 | 87.98  | C   |
| ATOM | 1489 | CE   | LYS | A | 186 | -18.822 | 37.087 | -64.961 | 1 | 90.78  | C   |
| ATOM | 1490 | NZ   | LYS | A | 186 | -17.407 | 37.529 | -64.823 | 1 | 89.35  | N1+ |
| ATOM | 1491 | H    | LYS | A | 186 | -16.266 | 33.47  | -62.907 | 1 | 50.3   | H   |
| ATOM | 1492 | HA   | LYS | A | 186 | -18.642 | 32.823 | -62.068 | 1 | 53.72  | H   |
| ATOM | 1493 | HB2  | LYS | A | 186 | -17.802 | 33.15  | -64.744 | 1 | 66.35  | H   |
| ATOM | 1494 | HB3  | LYS | A | 186 | -19.323 | 33.093 | -64.293 | 1 | 66.35  | H   |
| ATOM | 1495 | HG2  | LYS | A | 186 | -19.012 | 35.1   | -63.11  | 1 | 83.65  | H   |
| ATOM | 1496 | HG3  | LYS | A | 186 | -17.525 | 35.171 | -63.674 | 1 | 83.65  | H   |
| ATOM | 1497 | HD2  | LYS | A | 186 | -18.406 | 35.301 | -65.86  | 1 | 105.57 | H   |
| ATOM | 1498 | HD3  | LYS | A | 186 | -19.869 | 35.354 | -65.235 | 1 | 105.57 | H   |
| ATOM | 1499 | HE2  | LYS | A | 186 | -19.194 | 37.507 | -65.753 | 1 | 108.94 | H   |
| ATOM | 1500 | HE3  | LYS | A | 186 | -19.307 | 37.374 | -64.172 | 1 | 108.94 | H   |
| ATOM | 1501 | HZ1  | LYS | A | 186 | -16.94  | 37.281 | -65.54  | 1 | 107.22 | H   |
| ATOM | 1502 | HZ2  | LYS | A | 186 | -17.371 | 38.415 | -64.747 | 1 | 107.22 | H   |
| ATOM | 1503 | HZ3  | LYS | A | 186 | -17.043 | 37.16  | -64.1   | 1 | 107.22 | H   |
| ATOM | 1504 | N    | GLY | A | 187 | -18.991 | 30.427 | -62.239 | 1 | 31.79  | N   |
| ATOM | 1505 | CA   | GLY | A | 187 | -19.178 | 28.993 | -62.35  | 1 | 33.62  | C   |
| ATOM | 1506 | C    | GLY | A | 187 | -20.338 | 28.512 | -61.506 | 1 | 28.83  | C   |
| ATOM | 1507 | O    | GLY | A | 187 | -20.967 | 29.303 | -60.803 | 1 | 31.67  | O   |
| ATOM | 1508 | H    | GLY | A | 187 | -19.468 | 30.795 | -61.626 | 1 | 38.15  | H   |
| ATOM | 1509 | HA2  | GLY | A | 187 | -19.35  | 28.758 | -63.276 | 1 | 40.35  | H   |
| ATOM | 1510 | HA3  | GLY | A | 187 | -18.373 | 28.536 | -62.06  | 1 | 40.35  | H   |
| ATOM | 1511 | N    | ASP | A | 188 | -20.613 | 27.211 | -61.571 | 1 | 26.78  | N   |
| ATOM | 1512 | CA   | ASP | A | 188 | -21.741 | 26.613 | -60.86  | 1 | 29.71  | C   |
| ATOM | 1513 | C    | ASP | A | 188 | -21.302 | 25.691 | -59.721 | 1 | 27.78  | C   |
| ATOM | 1514 | O    | ASP | A | 188 | -22.11  | 24.929 | -59.185 | 1 | 26.36  | O   |
| ATOM | 1515 | CB   | ASP | A | 188 | -22.617 | 25.84  | -61.843 | 1 | 34.87  | C   |
| ATOM | 1516 | CG   | ASP | A | 188 | -23.227 | 26.735 | -62.901 | 1 | 39.7   | C   |
| ATOM | 1517 | OD1  | ASP | A | 188 | -23.676 | 27.848 | -62.551 | 1 | 38.4   | O   |
| ATOM | 1518 | OD2  | ASP | A | 188 | -23.248 | 26.332 | -64.083 | 1 | 40.4   | O1- |

TABLE 5-continued

Atomic Coordinates for OMCP-NKG2D (4PDC).

| ATOM | 1519 | H | ASP A | 188 | -20.154 | 26.645 | -62.028 | 1 | 32.14 | H |
|---|---|---|---|---|---|---|---|---|---|---|
| ATOM | 1520 | HA | ASP A | 188 | -22.28 | 27.322 | -60.476 | 1 | 35.65 | H |
| ATOM | 1521 | HB2 | ASP A | 188 | -22.077 | 25.17 | -62.291 | 1 | 41.85 | H |
| ATOM | 1522 | HB3 | ASP A | 188 | -23.34 | 25.413 | -61.357 | 1 | 41.85 | H |
| ATOM | 1523 | N | CYS A | 189 | -20.027 | 25.772 | -59.349 | 1 | 25.17 | N |
| ATOM | 1524 | CA | CYS A | 189 | -19.485 | 24.978 | -58.248 | 1 | 21.3 | C |
| ATOM | 1525 | C | CYS A | 189 | -18.739 | 25.877 | -57.264 | 1 | 22.52 | C |
| ATOM | 1526 | O | CYS A | 189 | -18.363 | 27.001 | -57.605 | 1 | 24.18 | O |
| ATOM | 1527 | CB | CYS A | 189 | -18.546 | 23.887 | -58.776 | 1 | 24.76 | C |
| ATOM | 1528 | SG | CYS A | 189 | -19.31 | 22.735 | -59.952 | 1 | 29.58 | S |
| ATOM | 1529 | H | CYS A | 189 | -19.448 | 26.286 | -59.723 | 1 | 30.21 | H |
| ATOM | 1530 | HA | CYS A | 189 | -20.214 | 24.548 | -57.774 | 1 | 25.56 | H |
| ATOM | 1531 | HB2 | CYS A | 189 | -17.799 | 24.312 | -59.224 | 1 | 29.72 | H |
| ATOM | 1532 | HB3 | CYS A | 189 | -18.222 | 23.367 | -58.024 | 1 | 29.72 | H |
| ATOM | 1533 | N | ALA A | 190 | -18.52 | 25.374 | -56.053 | 1 | 21.28 | N |
| ATOM | 1534 | CA | ALA A | 190 | -17.838 | 26.14 | -55.015 | 1 | 21.57 | C |
| ATOM | 1535 | C | ALA A | 190 | -16.767 | 25.316 | -54.311 | 1 | 18.66 | C |
| ATOM | 1536 | O | ALA A | 190 | -16.936 | 24.118 | -54.073 | 1 | 17.27 | O |
| ATOM | 1537 | CB | ALA A | 190 | -18.838 | 26.661 | -54.007 | 1 | 20.73 | C |
| ATOM | 1538 | H | ALA A | 190 | -18.759 | 24.585 | -55.805 | 1 | 25.54 | H |
| ATOM | 1539 | HA | ALA A | 190 | -17.403 | 26.904 | -55.425 | 1 | 25.89 | H |
| ATOM | 1540 | HB1 | ALA A | 190 | -18.366 | 27.166 | -53.327 | 1 | 24.88 | H |
| ATOM | 1541 | HB2 | ALA A | 190 | -19.476 | 27.232 | -54.462 | 1 | 24.88 | H |
| ATOM | 1542 | HB3 | ALA A | 190 | -19.298 | 25.909 | -53.602 | 1 | 24.88 | H |
| ATOM | 1543 | N | LEU A | 191 | -15.664 | 25.981 | -53.984 | 1 | 20.48 | N |
| ATOM | 1544 | CA | LEU A | 191 | -14.578 | 25.382 | -53.216 | 1 | 18.02 | C |
| ATOM | 1545 | C | LEU A | 191 | -14.722 | 25.748 | -51.745 | 1 | 17.63 | C |
| ATOM | 1546 | O | LEU A | 191 | -14.852 | 26.927 | -51.421 | 1 | 16.65 | O |
| ATOM | 1547 | CB | LEU A | 191 | -13.226 | 25.869 | -53.737 | 1 | 15.13 | C |
| ATOM | 1548 | CG | LEU A | 191 | -12.856 | 25.493 | -55.171 | 1 | 21.15 | C |
| ATOM | 1549 | CD1 | LEU A | 191 | -11.76 | 26.409 | -55.687 | 1 | 23.95 | C |
| ATOM | 1550 | CD2 | LEU A | 191 | -12.414 | 24.04 | -55.236 | 1 | 19.16 | C |
| ATOM | 1551 | H | LEU A | 191 | -15.518 | 26.8 | -54.2 | 1 | 24.57 | H |
| ATOM | 1552 | HA | LEU A | 191 | -14.613 | 24.416 | -53.3 | 1 | 21.63 | H |
| ATOM | 1553 | HB2 | LEU A | 191 | -13.213 | 26.837 | -53.683 | 1 | 18.15 | H |
| ATOM | 1554 | HB3 | LEU A | 191 | -12.533 | 25.509 | -53.16 | 1 | 18.15 | H |
| ATOM | 1555 | HG | LEU A | 191 | -13.634 | 25.6 | -55.741 | 1 | 25.38 | H |
| ATOM | 1556 | HD11 | LEU A | 191 | -11.54 | 26.155 | -56.597 | 1 | 28.74 | H |
| ATOM | 1557 | HD12 | LEU A | 191 | -12.079 | 27.324 | -55.667 | 1 | 28.74 | H |
| ATOM | 1558 | HD13 | LEU A | 191 | -10.979 | 26.317 | -55.119 | 1 | 28.74 | H |
| ATOM | 1559 | HD21 | LEU A | 191 | -12.183 | 23.821 | -56.153 | 1 | 22.99 | H |
| ATOM | 1560 | HD22 | LEU A | 191 | -11.641 | 23.919 | -54.663 | 1 | 22.99 | H |
| ATOM | 1561 | HD23 | LEU A | 191 | -13.142 | 23.475 | -54.934 | 1 | 22.99 | H |
| ATOM | 1562 | N | TYR A | 192 | -14.703 | 24.757 | -50.855 | 1 | 15.23 | N |
| ATOM | 1563 | CA | TYR A | 192 | -13.365 | 25.056 | -49.43 | 1 | 14.68 | C |
| ATOM | 1564 | C | TYR A | 192 | -13.365 | 25.597 | -48.98 | 1 | 17.4 | C |
| ATOM | 1565 | O | TYR A | 192 | -12.324 | 25.129 | -49.427 | 1 | 12.57 | O |
| ATOM | 1566 | CB | TYR A | 192 | -15.055 | 23.831 | -48.568 | 1 | 16.6 | C |
| ATOM | 1567 | CG | TYR A | 192 | -14.916 | 24.199 | -47.115 | 1 | 16.87 | C |
| ATOM | 1568 | CD1 | TYR A | 192 | -15.948 | 24.847 | -46.45 | 1 | 14.23 | C |
| ATOM | 1569 | CD2 | TYR A | 192 | -13.724 | 23.981 | -46.428 | 1 | 17.91 | C |

TABLE 5-continued

Atomic Coordinates for OMCP-NKG2D (4PDC).

| ATOM | 1570 | CE1 | TYR | A | 192 | -15.817 | 25.235 | -45.14 | 1 | 15.45 | C |
|------|------|-----|-----|---|-----|---------|--------|--------|---|-------|---|
| ATOM | 1571 | CE2 | TYR | A | 192 | -13.584 | 24.368 | -45.111 | 1 | 16.81 | C |
| ATOM | 1572 | CZ | TYR | A | 192 | -14.637 | 24.997 | -44.473 | 1 | 17.95 | C |
| ATOM | 1573 | OH | TYR | A | 192 | -14.514 | 25.401 | -43.164 | 1 | 18.94 | O |
| ATOM | 1574 | H | TYR | A | 192 | -14.683 | 23.919 | -51.048 | 1 | 18.28 | H |
| ATOM | 1575 | HA | TYR | A | 192 | -15.386 | 25.737 | -49.257 | 1 | 17.62 | H |
| ATOM | 1576 | HB2 | TYR | A | 192 | -15.97 | 23.556 | -48.734 | 1 | 19.92 | H |
| ATOM | 1577 | HB3 | TYR | A | 192 | -14.437 | 23.11 | -48.768 | 1 | 19.92 | H |
| ATOM | 1578 | HD1 | TYR | A | 192 | -16.745 | 25.017 | -46.898 | 1 | 17.07 | H |
| ATOM | 1579 | HD2 | TYR | A | 192 | -13.015 | 23.564 | -46.861 | 1 | 21.49 | H |
| ATOM | 1580 | HE1 | TYR | A | 192 | -16.521 | 25.66 | -44.706 | 1 | 18.54 | H |
| ATOM | 1581 | HE2 | TYR | A | 192 | -12.788 | 24.21 | -44.657 | 1 | 20.17 | H |
| ATOM | 1582 | HH | TYR | A | 192 | -13.753 | 25.2 | -42.872 | 1 | 22.72 | H |
| ATOM | 1583 | N | ALA | A | 193 | -13.392 | 26.573 | -48.078 | 1 | 14.04 | N |
| ATOM | 1584 | CA | ALA | A | 193 | -12.184 | 27.021 | -47.395 | 1 | 14.46 | C |
| ATOM | 1585 | C | ALA | A | 193 | -12.528 | 27.614 | -46.037 | 1 | 14.85 | C |
| ATOM | 1586 | O | ALA | A | 193 | -13.669 | 28.005 | -45.784 | 1 | 16.32 | O |
| ATOM | 1587 | CB | ALA | A | 193 | -11.44 | 28.029 | -48.233 | 1 | 16.01 | C |
| ATOM | 1588 | H | ALA | A | 193 | -14.103 | 26.995 | -47.843 | 1 | 16.85 | H |
| ATOM | 1589 | HA | ALA | A | 193 | -11.6 | 26.26 | -47.251 | 1 | 17.35 | H |
| ATOM | 1590 | HB1 | ALA | A | 193 | -10.644 | 28.309 | -47.756 | 1 | 19.22 | H |
| ATOM | 1591 | HB2 | ALA | A | 193 | -11.194 | 27.617 | -49.076 | 1 | 19.22 | H |
| ATOM | 1592 | HB3 | ALA | A | 193 | -12.017 | 28.792 | -48.393 | 1 | 19.22 | H |
| ATOM | 1593 | N | SER | A | 194 | -11.534 | 27.675 | -45.162 | 1 | 13.15 | N |
| ATOM | 1594 | CA | SER | A | 194 | -11.726 | 28.278 | -43.857 | 1 | 12.99 | C |
| ATOM | 1595 | C | SER | A | 194 | -11.964 | 29.777 | -44.025 | 1 | 15.13 | C |
| ATOM | 1596 | O | SER | A | 194 | -11.387 | 30.378 | -44.93 | 1 | 16.35 | O |
| ATOM | 1597 | CB | SER | A | 194 | -10.507 | 28.029 | -42.963 | 1 | 15.47 | C |
| ATOM | 1598 | OG | SER | A | 194 | -10.547 | 28.856 | -41.815 | 1 | 15.91 | O |
| ATOM | 1599 | H | SER | A | 194 | -10.741 | 27.374 | -45.301 | 1 | 15.78 | H |
| ATOM | 1600 | HA | SER | A | 194 | -12.505 | 27.888 | -43.431 | 1 | 15.59 | H |
| ATOM | 1601 | HB2 | SER | A | 194 | -10.506 | 27.1 | -42.684 | 1 | 18.57 | H |
| ATOM | 1602 | HB3 | SER | A | 194 | -9.701 | 28.226 | -43.466 | 1 | 18.57 | H |
| ATOM | 1603 | HG | SER | A | 194 | -9.875 | 28.71 | -41.333 | 1 | 19.09 | H |
| ATOM | 1604 | N | SER | A | 195 | -12.803 | 30.394 | -43.191 | 1 | 13.88 | N |
| ATOM | 1605 | CA | SER | A | 195 | -13.586 | 29.735 | -42.148 | 1 | 14.38 | C |
| ATOM | 1606 | C | SER | A | 195 | -15.056 | 29.686 | -42.571 | 1 | 18.17 | C |
| ATOM | 1607 | O | SER | A | 195 | -15.731 | 30.717 | -42.606 | 1 | 15.7 | O |
| ATOM | 1608 | CB | SER | A | 195 | -13.442 | 30.477 | -40.821 | 1 | 15.67 | C |
| ATOM | 1609 | OG | SER | A | 195 | -14.164 | 29.81 | -39.798 | 1 | 20.71 | O |
| ATOM | 1610 | H | SER | A | 195 | -12.941 | 31.242 | -43.215 | 1 | 16.65 | H |
| ATOM | 1611 | HA | SER | A | 195 | -13.268 | 28.826 | -42.029 | 1 | 17.26 | H |
| ATOM | 1612 | HB2 | SER | A | 195 | -12.503 | 30.51 | -40.577 | 1 | 18.81 | H |
| ATOM | 1613 | HB3 | SER | A | 195 | -13.791 | 31.376 | -40.922 | 1 | 18.81 | H |
| ATOM | 1614 | HG | SER | A | 195 | -14.08 | 30.224 | -39.071 | 1 | 24.86 | H |
| ATOM | 1615 | N | PHE | A | 196 | -15.542 | 28.492 | -42.898 | 1 | 14.12 | N |
| ATOM | 1616 | CA | PHE | A | 196 | -16.912 | 28.314 | -43.376 | 1 | 16.5 | C |
| ATOM | 1617 | C | PHE | A | 196 | -17.212 | 29.262 | -44.53 | 1 | 16.82 | C |
| ATOM | 1618 | O | PHE | A | 196 | -18.205 | 29.992 | -44.522 | 1 | 15.43 | O |
| ATOM | 1619 | CB | PHE | A | 196 | -17.909 | 28.514 | -42.233 | 1 | 19.48 | C |
| ATOM | 1620 | CG | PHE | A | 196 | -17.9 | 27.392 | -41.233 | 1 | 20.88 | C |

TABLE 5-continued

Atomic Coordinates for OMCP-NKG2D (4PDC).

| ATOM | 1621 | CD1 | PHE | A | 196 | -17.045 | 27.42 | -40.146 | 1 | 19.36 | C |
|------|------|-----|-----|---|-----|---------|-------|---------|---|-------|---|
| ATOM | 1622 | CD2 | PHE | A | 196 | -18.734 | 26.3 | -41.395 | 1 | 21 | C |
| ATOM | 1623 | CE1 | PHE | A | 196 | -17.028 | 26.381 | -39.233 | 1 | 22.54 | C |
| ATOM | 1624 | CE2 | PHE | A | 196 | -18.722 | 25.259 | -40.489 | 1 | 24.48 | C |
| ATOM | 1625 | CZ | PHE | A | 196 | -17.868 | 25.297 | -39.409 | 1 | 23.71 | C |
| ATOM | 1626 | H | PHE | A | 196 | -15.093 | 27.76 | -42.851 | 1 | 16.94 | H |
| ATOM | 1627 | HA | PHE | A | 196 | -17.014 | 27.407 | -43.703 | 1 | 19.8 | H |
| ATOM | 1628 | HB2 | PHE | A | 196 | -17.689 | 29.334 | -41.763 | 1 | 23.38 | H |
| ATOM | 1629 | HB3 | PHE | A | 196 | -18.803 | 28.576 | -42.603 | 1 | 23.38 | H |
| ATOM | 1630 | HD1 | PHE | A | 196 | -16.476 | 28.146 | -40.027 | 1 | 23.23 | H |
| ATOM | 1631 | HD2 | PHE | A | 196 | -19.31 | 26.267 | -42.125 | 1 | 25.2 | H |
| ATOM | 1632 | HE1 | PHE | A | 196 | -16.451 | 26.41 | -38.504 | 1 | 27.05 | H |
| ATOM | 1633 | HE2 | PHE | A | 196 | -19.29 | 24.532 | -40.608 | 1 | 29.38 | H |
| ATOM | 1634 | HZ | PHE | A | 196 | -17.862 | 24.598 | -38.795 | 1 | 28.45 | H |
| ATOM | 1635 | N | LYS | A | 197 | -16.328 | 29.24 | -45.519 | 1 | 12.88 | N |
| ATOM | 1636 | CA | LYS | A | 197 | -16.488 | 30.028 | -46.726 | 1 | 14.65 | C |
| ATOM | 1637 | C | LYS | A | 197 | -16.602 | 29.102 | -47.924 | 1 | 20.06 | C |
| ATOM | 1638 | O | LYS | A | 197 | -16.201 | 27.937 | -47.864 | 1 | 15.47 | O |
| ATOM | 1639 | CB | LYS | A | 197 | -15.316 | 30.995 | -46.902 | 1 | 17.78 | C |
| ATOM | 1640 | CG | LYS | A | 197 | -15.28 | 32.1 | -45.858 | 1 | 18.13 | C |
| ATOM | 1641 | CD | LYS | A | 197 | -14.046 | 32.976 | -45.998 | 1 | 21.25 | C |
| ATOM | 1642 | CE | LYS | A | 197 | -14.128 | 34.17 | -45.061 | 1 | 21.78 | C |
| ATOM | 1643 | NZ | LYS | A | 197 | -12.877 | 34.972 | -45.042 | 1 | 22.18 | N1+ |
| ATOM | 1644 | H | LYS | A | 197 | -15.612 | 28.764 | -45.511 | 1 | 15.45 | H |
| ATOM | 1645 | HA | LYS | A | 197 | -17.305 | 30.547 | -46.664 | 1 | 17.58 | H |
| ATOM | 1646 | HB2 | LYS | A | 197 | -14.486 | 30.497 | -46.837 | 1 | 21.34 | H |
| ATOM | 1647 | HB3 | LYS | A | 197 | -15.382 | 31.413 | -47.775 | 1 | 21.34 | H |
| ATOM | 1648 | HG2 | LYS | A | 197 | -16.063 | 32.662 | -45.962 | 1 | 21.75 | H |
| ATOM | 1649 | HG3 | LYS | A | 197 | -15.267 | 31.702 | -44.973 | 1 | 21.75 | H |
| ATOM | 1650 | HD2 | LYS | A | 197 | -13.257 | 32.461 | -45.77 | 1 | 25.49 | H |
| ATOM | 1651 | HD3 | LYS | A | 197 | -13.985 | 33.305 | -46.908 | 1 | 25.49 | H |
| ATOM | 1652 | HE2 | LYS | A | 197 | -14.851 | 34.749 | -45.349 | 1 | 26.13 | H |
| ATOM | 1653 | HE3 | LYS | A | 197 | -14.295 | 33.854 | -44.159 | 1 | 26.13 | H |
| ATOM | 1654 | HZ1 | LYS | A | 197 | -12.703 | 35.282 | -45.858 | 1 | 26.61 | H |
| ATOM | 1655 | HZ2 | LYS | A | 197 | -12.965 | 35.659 | -44.484 | 1 | 26.61 | H |
| ATOM | 1656 | HZ3 | LYS | A | 197 | -12.196 | 34.466 | -44.774 | 1 | 26.61 | H |
| ATOM | 1657 | N | GLY | A | 198 | -17.172 | 29.632 | -49.001 | 1 | 21.19 | N |
| ATOM | 1658 | CA | GLY | A | 198 | -17.291 | 28.916 | -50.256 | 1 | 20.02 | C |
| ATOM | 1659 | C | GLY | A | 198 | -16.977 | 29.862 | -51.394 | 1 | 18.77 | C |
| ATOM | 1660 | O | GLY | A | 198 | -17.644 | 30.88 | -51.561 | 1 | 21.65 | O |
| ATOM | 1661 | H | GLY | A | 198 | -17.505 | 30.424 | -49.026 | 1 | 25.43 | H |
| ATOM | 1662 | HA2 | GLY | A | 198 | -16.667 | 28.173 | -50.278 | 1 | 24.02 | H |
| ATOM | 1663 | HA3 | GLY | A | 198 | -18.193 | 28.577 | -50.364 | 1 | 24.02 | H |
| ATOM | 1664 | N | TYR | A | 199 | -15.942 | 29.535 | -52.16 | 1 | 17.44 | N |
| ATOM | 1665 | CA | TYR | A | 199 | -15.521 | 30.351 | -53.289 | 1 | 16.54 | C |
| ATOM | 1666 | C | TYR | A | 199 | -16.048 | 29.768 | -54.591 | 1 | 23.54 | C |
| ATOM | 1667 | O | TYR | A | 199 | -15.735 | 28.63 | -54.944 | 1 | 19 | O |
| ATOM | 1668 | CB | TYR | A | 199 | -13.997 | 30.446 | -53.349 | 1 | 17.44 | C |
| ATOM | 1669 | CG | TYR | A | 199 | -13.376 | 31.238 | -52.222 | 1 | 14.05 | C |
| ATOM | 1670 | CD1 | TYR | A | 199 | -13.236 | 30.689 | -50.958 | 1 | 15.06 | C |
| ATOM | 1671 | CD2 | TYR | A | 199 | -12.912 | 32.529 | -52.432 | 1 | 17.4 | C |

TABLE 5-continued

Atomic Coordinates for OMCP-NKG2D (4PDC).

| ATOM | 1672 | CE1 | TYR | A | 199 | -12.663 | 31.41 | -49.926 | 1 | 17.88 | C |
|------|------|-----|-----|---|-----|---------|-------|---------|---|-------|---|
| ATOM | 1673 | CE2 | TYR | A | 199 | -12.332 | 33.255 | -51.409 | 1 | 15.39 | C |
| ATOM | 1674 | CZ | TYR | A | 199 | -12.213 | 32.69 | -50.156 | 1 | 15.83 | C |
| ATOM | 1675 | OH | TYR | A | 199 | -11.637 | 33.406 | -49.131 | 1 | 18.67 | O |
| ATOM | 1676 | H | TYR | A | 199 | -15.461 | 28.832 | -52.043 | 1 | 20.93 | H |
| ATOM | 1677 | HA | TYR | A | 199 | -15.878 | 31.247 | -53.189 | 1 | 19.84 | H |
| ATOM | 1678 | HB2 | TYR | A | 199 | -13.629 | 29.549 | -53.316 | 1 | 20.92 | H |
| ATOM | 1679 | HB3 | TYR | A | 199 | -13.745 | 30.872 | -54.183 | 1 | 20.92 | H |
| ATOM | 1680 | HD1 | TYR | A | 199 | -13.541 | 29.825 | -50.798 | 1 | 18.08 | H |
| ATOM | 1681 | HD2 | TYR | A | 199 | -12.992 | 32.912 | -53.275 | 1 | 20.88 | H |
| ATOM | 1682 | HE1 | TYR | A | 199 | -12.579 | 31.03 | -49.082 | 1 | 21.46 | H |
| ATOM | 1683 | HE2 | TYR | A | 199 | -12.029 | 34.12 | -51.564 | 1 | 18.47 | H |
| ATOM | 1684 | HH | TYR | A | 199 | -11.626 | 32.945 | -48.429 | 1 | 22.4 | H |
| ATOM | 1685 | N | ILE | A | 200 | -16.841 | 30.552 | -55.309 | 1 | 22.64 | N |
| ATOM | 1686 | CA | ILE | A | 200 | -17.424 | 30.09 | -56.558 | 1 | 23.49 | C |
| ATOM | 1687 | C | ILE | A | 200 | -16.323 | 29.921 | -57.6 | 1 | 24.43 | C |
| ATOM | 1688 | O | ILE | A | 200 | -15.491 | 30.808 | -57.79 | 1 | 21.73 | O |
| ATOM | 1689 | CB | ILE | A | 200 | -18.499 | 31.059 | -57.068 | 1 | 24.34 | C |
| ATOM | 1690 | CG1 | ILE | A | 200 | -19.571 | 31.263 | -55.989 | 1 | 24.68 | C |
| ATOM | 1691 | CG2 | ILE | A | 200 | -19.121 | 30.526 | -58.354 | 1 | 27.39 | C |
| ATOM | 1692 | CD1 | ILE | A | 200 | -20.587 | 32.342 | -56.308 | 1 | 32.82 | C |
| ATOM | 1693 | H | ILE | A | 200 | -17.058 | 31.356 | -55.094 | 1 | 27.17 | H |
| ATOM | 1694 | HA | ILE | A | 200 | -17.84 | 29.226 | -56.415 | 1 | 28.19 | H |
| ATOM | 1695 | HB | ILE | A | 200 | -18.082 | 31.915 | -57.257 | 1 | 29.21 | H |
| ATOM | 1696 | HG12 | ILE | A | 200 | -20.054 | 30.43 | -55.87 | 1 | 29.61 | H |
| ATOM | 1697 | HG13 | ILE | A | 200 | -19.133 | 31.508 | -55.158 | 1 | 29.61 | H |
| ATOM | 1698 | HG21 | ILE | A | 200 | -19.797 | 31.151 | -58.66 | 1 | 32.86 | H |
| ATOM | 1699 | HG22 | ILE | A | 200 | -18.427 | 30.433 | -59.025 | 1 | 32.86 | H |
| ATOM | 1700 | HG23 | ILE | A | 200 | -19.525 | 29.663 | -58.174 | 1 | 32.86 | H |
| ATOM | 1701 | HD11 | ILE | A | 200 | -21.223 | 32.403 | -55.578 | 1 | 39.38 | H |
| ATOM | 1702 | HD12 | ILE | A | 200 | -20.125 | 33.188 | -56.417 | 1 | 39.38 | H |
| ATOM | 1703 | HD13 | ILE | A | 200 | -21.048 | 32.108 | -57.129 | 1 | 39.38 | H |
| ATOM | 1704 | N | GLU | A | 201 | -16.33 | 28.769 | -58.264 | 1 | 22.73 | N |
| ATOM | 1705 | CA | GLU | A | 201 | -15.255 | 28.388 | -59.169 | 1 | 24 | C |
| ATOM | 1706 | C | GLU | A | 201 | -15.8 | 27.657 | -60.392 | 1 | 25.5 | C |
| ATOM | 1707 | O | GLU | A | 201 | -16.887 | 27.076 | -60.35 | 1 | 22.4 | O |
| ATOM | 1708 | CB | GLU | A | 201 | -14.244 | 27.508 | -58.425 | 1 | 23.12 | C |
| ATOM | 1709 | CG | GLU | A | 201 | -13.104 | 26.959 | -59.269 | 1 | 25.67 | C |
| ATOM | 1710 | CD | GLU | A | 201 | -12.274 | 28.048 | -59.917 | 1 | 31.64 | C |
| ATOM | 1711 | OE1 | GLU | A | 201 | -11.116 | 28.247 | -59.49 | 1 | 34.45 | O |
| ATOM | 1712 | OE2 | GLU | A | 201 | -12.777 | 28.7 | -60.856 | 1 | 31.63 | O1- |
| ATOM | 1713 | H | GLU | A | 201 | -16.957 | 28.184 | -58.206 | 1 | 27.27 | H |
| ATOM | 1714 | HA | GLU | A | 201 | -14.797 | 29.186 | -59.473 | 1 | 28.8 | H |
| ATOM | 1715 | HB2 | GLU | A | 201 | -13.849 | 28.032 | -57.71 | 1 | 27.75 | H |
| ATOM | 1716 | HB3 | GLU | A | 201 | -14.716 | 26.75 | -58.047 | 1 | 27.75 | H |
| ATOM | 1717 | HG2 | GLU | A | 201 | -12.518 | 26.432 | -58.704 | 1 | 30.81 | H |
| ATOM | 1718 | HG3 | GLU | A | 201 | -13.472 | 26.404 | -59.974 | 1 | 30.81 | H |
| ATOM | 1719 | N | ASN | A | 202 | -15.04 | 27.709 | -61.48 | 1 | 26.48 | N |
| ATOM | 1720 | CA | ASN | A | 202 | -15.344 | 26.948 | -62.684 | 1 | 25.56 | C |
| ATOM | 1721 | C | ASN | A | 202 | -15.316 | 25.452 | -62.389 | 1 | 24.34 | C |
| ATOM | 1722 | O | ASN | A | 202 | -14.295 | 24.914 | -61.967 | 1 | 26.28 | O |

TABLE 5-continued

Atomic Coordinates for OMCP-NKG2D (4PDC).

| ATOM | 1723 | CB | ASN | A | 202 | -14.343 | 27.294 | -63.788 | 1 | 29.63 | C |
| ATOM | 1724 | CG | ASN | A | 202 | -14.689 | 26.66 | -65.123 | 1 | 31.7 | C |
| ATOM | 1725 | OD1 | ASN | A | 202 | -15.292 | 25.589 | -65.187 | 1 | 30.51 | O |
| ATOM | 1726 | ND2 | ASN | A | 202 | -14.297 | 27.323 | -66.203 | 1 | 38.46 | N |
| ATOM | 1727 | H | ASN | A | 202 | -14.328 | 28.187 | -61.546 | 1 | 31.77 | H |
| ATOM | 1728 | HA | ASN | A | 202 | -16.234 | 27.18 | -62.994 | 1 | 30.67 | H |
| ATOM | 1729 | HB2 | ASN | A | 202 | -14.329 | 28.256 | -63.91 | 1 | 35.55 | H |
| ATOM | 1730 | HB3 | ASN | A | 202 | -13.464 | 26.98 | -63.526 | 1 | 35.55 | H |
| ATOM | 1731 | HD21 | ASN | A | 202 | -14.466 | 27.009 | -66.985 | 1 | 46.15 | H |
| ATOM | 1732 | HD22 | ASN | A | 202 | -13.873 | 28.067 | -66.121 | 1 | 46.15 | H |
| ATOM | 1733 | N | CYS | A | 203 | -16.44 | 24.785 | -62.627 | 1 | 28.75 | N |
| ATOM | 1734 | CA | CYS | A | 203 | -16.574 | 23.364 | -62.325 | 1 | 25.56 | C |
| ATOM | 1735 | C | CYS | A | 203 | -15.508 | 22.513 | -63.014 | 1 | 26.17 | C |
| ATOM | 1736 | O | CYS | A | 203 | -15.174 | 21.43 | -62.539 | 1 | 23.9 | O |
| ATOM | 1737 | CB | CYS | A | 203 | -17.967 | 22.874 | -62.726 | 1 | 25.82 | C |
| ATOM | 1738 | SG | CYS | A | 203 | -19.313 | 23.627 | -61.778 | 1 | 33.04 | S |
| ATOM | 1739 | H | CYS | A | 203 | -17.148 | 25.136 | -62.966 | 1 | 34.5 | H |
| ATOM | 1740 | HA | CYS | A | 203 | -16.479 | 23.238 | -61.368 | 1 | 30.67 | H |
| ATOM | 1741 | HB2 | CYS | A | 203 | -18.112 | 23.081 | -63.663 | 1 | 30.99 | H |
| ATOM | 1742 | HB3 | CYS | A | 203 | -18.011 | 21.914 | -62.592 | 1 | 30.99 | H |
| ATOM | 1743 | N | SER | A | 204 | -14.962 | 23.015 | -64.118 | 1 | 26.58 | N |
| ATOM | 1744 | CA | SER | A | 204 | -14.011 | 22.25 | -64.918 | 1 | 28.83 | C |
| ATOM | 1745 | C | SER | A | 204 | -12.568 | 22.426 | -64.464 | 1 | 29.48 | C |
| ATOM | 1746 | O | SER | A | 204 | -11.67 | 21.765 | -64.98 | 1 | 30.84 | O |
| ATOM | 1747 | CB | SER | A | 204 | -14.13 | 22.646 | -66.391 | 1 | 34.76 | C |
| ATOM | 1748 | OG | SER | A | 204 | -15.399 | 22.282 | -66.905 | 1 | 36.78 | O |
| ATOM | 1749 | H | SER | A | 204 | -15.127 | 23.801 | -64.426 | 1 | 31.89 | H |
| ATOM | 1750 | HA | SER | A | 204 | -14.23 | 21.308 | -64.847 | 1 | 34.6 | H |
| ATOM | 1751 | HB2 | SER | A | 204 | -14.02 | 23.607 | -66.47 | 1 | 41.72 | H |
| ATOM | 1752 | HB3 | SER | A | 204 | -13.44 | 22.19 | -66.898 | 1 | 41.72 | H |
| ATOM | 1753 | HG | SER | A | 204 | -15.456 | 22.503 | -67.713 | 1 | 44.13 | H |
| ATOM | 1754 | N | THR | A | 205 | -12.342 | 23.313 | -63.501 | 1 | 30.18 | N |
| ATOM | 1755 | CA | THR | A | 205 | -10.991 | 23.564 | -63.01 | 1 | 31.93 | C |
| ATOM | 1756 | C | THR | A | 205 | -10.595 | 22.49 | -62.002 | 1 | 26.32 | C |
| ATOM | 1757 | O | THR | A | 205 | -11.3 | 22.28 | -61.017 | 1 | 27.11 | O |
| ATOM | 1758 | CB | THR | A | 205 | -10.88 | 24.953 | -62.354 | 1 | 30.33 | C |
| ATOM | 1759 | OG1 | THR | A | 205 | -11.195 | 25.962 | -63.322 | 1 | 32.74 | O |
| ATOM | 1760 | CG2 | THR | A | 205 | -9.473 | 25.195 | -61.822 | 1 | 28.31 | C |
| ATOM | 1761 | H | THR | A | 205 | -12.951 | 23.783 | -63.117 | 1 | 36.22 | H |
| ATOM | 1762 | HA | THR | A | 205 | -10.369 | 23.528 | -63.753 | 1 | 38.32 | H |
| ATOM | 1763 | HB | THR | A | 205 | -11.503 | 25.011 | -61.613 | 1 | 36.4 | H |
| ATOM | 1764 | HG1 | THR | A | 205 | -10.66 | 25.917 | -63.968 | 1 | 39.29 | H |
| ATOM | 1765 | HG21 | THR | A | 205 | -9.42 | 26.073 | -61.413 | 1 | 33.97 | H |
| ATOM | 1766 | HG22 | THR | A | 205 | -9.25 | 24.524 | -61.158 | 1 | 33.97 | H |
| ATOM | 1767 | HG23 | THR | A | 205 | -8.831 | 25.146 | -62.547 | 1 | 33.97 | H |
| ATOM | 1768 | N | PRO | A | 206 | -9.462 | 21.808 | -62.235 | 1 | 25.18 | N |
| ATOM | 1769 | CA | PRO | A | 206 | -9.108 | 20.744 | -61.29 | 1 | 27.92 | C |
| ATOM | 1770 | C | PRO | A | 206 | -8.728 | 21.285 | -59.913 | 1 | 27.31 | C |
| ATOM | 1771 | O | PRO | A | 206 | -8.02 | 22.285 | -59.806 | 1 | 24.19 | O |
| ATOM | 1772 | CB | PRO | A | 206 | -7.918 | 20.051 | -61.963 | 1 | 27.16 | C |
| ATOM | 1773 | CG | PRO | A | 206 | -7.34 | 21.073 | -62.876 | 1 | 35.92 | C |

TABLE 5-continued

Atomic Coordinates for OMCP-NKG2D (4PDC).

| ATOM | 1774 | CD | PRO | A | 206 | -8.479 | 21.937 | -63.326 | 1 | 32.59 | C |
| ATOM | 1775 | HA | PRO | A | 206 | -9.839 | 20.113 | -61.199 | 1 | 33.5 | H |
| ATOM | 1776 | HB2 | PRO | A | 206 | -7.271 | 19.786 | -61.29 | 1 | 32.59 | H |
| ATOM | 1777 | HB3 | PRO | A | 206 | -8.229 | 19.28 | -62.463 | 1 | 32.59 | H |
| ATOM | 1778 | HG2 | PRO | A | 206 | -6.683 | 21.6 | -62.396 | 1 | 43.11 | H |
| ATOM | 1779 | HG3 | PRO | A | 206 | -6.93 | 20.631 | -63.636 | 1 | 43.11 | H |
| ATOM | 1780 | HD2 | PRO | A | 206 | -8.189 | 22.859 | -63.411 | 1 | 39.11 | H |
| ATOM | 1781 | HD3 | PRO | A | 206 | -8.85 | 21.602 | -64.157 | 1 | 39.11 | H |
| ATOM | 1782 | N | ASN | A | 207 | -9.223 | 20.624 | -58.873 | 1 | 24.26 | N |
| ATOM | 1783 | CA | ASN | A | 207 | -8.923 | 20.983 | -57.492 | 1 | 25.76 | C |
| ATOM | 1784 | C | ASN | A | 207 | -8.955 | 19.741 | -56.616 | 1 | 23.33 | C |
| ATOM | 1785 | O | ASN | A | 207 | -9.56 | 18.734 | -56.988 | 1 | 20.6 | O |
| ATOM | 1786 | CB | ASN | A | 207 | -9.927 | 22.01 | -56.957 | 1 | 23.82 | C |
| ATOM | 1787 | CG | ASN | A | 207 | -9.62 | 23.423 | -57.405 | 1 | 27.43 | C |
| ATOM | 1788 | OD1 | ASN | A | 207 | -8.771 | 24.097 | -56.822 | 1 | 28.42 | O |
| ATOM | 1789 | ND2 | ASN | A | 207 | -10.327 | 23.889 | -58.43 | 1 | 23.94 | N |
| ATOM | 1790 | H | ASN | A | 207 | -9.749 | 19.947 | -58.944 | 1 | 29.12 | H |
| ATOM | 1791 | HA | ASN | A | 207 | -8.034 | 21.369 | -57.444 | 1 | 30.91 | H |
| ATOM | 1792 | HB2 | ASN | A | 207 | -10.813 | 21.78 | -57.276 | 1 | 28.58 | H |
| ATOM | 1793 | HB3 | ASN | A | 207 | -9.909 | 21.993 | -55.987 | 1 | 28.58 | H |
| ATOM | 1794 | HD21 | ASN | A | 207 | -10.189 | 24.687 | -58.721 | 1 | 28.73 | H |
| ATOM | 1795 | HD22 | ASN | A | 207 | -10.923 | 23.393 | -58.803 | 1 | 28.73 | H |
| ATOM | 1796 | N | THR | A | 208 | -8.312 | 19.815 | -55.454 | 1 | 22.57 | N |
| ATOM | 1797 | CA | THR | A | 208 | -8.444 | 18.773 | -54.443 | 1 | 19.78 | C |
| ATOM | 1798 | C | THR | A | 208 | -9.888 | 18.768 | -53.954 | 1 | 16.39 | C |
| ATOM | 1799 | O | THR | A | 208 | -10.62 | 19.723 | -54.195 | 1 | 15.26 | O |
| ATOM | 1800 | CB | THR | A | 208 | -7.479 | 18.998 | -53.26 | 1 | 20.25 | C |
| ATOM | 1801 | OG1 | THR | A | 208 | -7.743 | 20.271 | -52.655 | 1 | 17.1 | O |
| ATOM | 1802 | CG2 | THR | A | 208 | -6.032 | 18.957 | -53.738 | 1 | 20.83 | C |
| ATOM | 1803 | H | THR | A | 208 | -7.792 | 20.461 | -55.227 | 1 | 27.08 | H |
| ATOM | 1804 | HA | THR | A | 208 | -8.249 | 17.909 | -54.84 | 1 | 23.73 | H |
| ATOM | 1805 | HB | THR | A | 208 | -7.605 | 18.296 | -52.603 | 1 | 24.3 | H |
| ATOM | 1806 | HG1 | THR | A | 208 | -7.219 | 20.397 | -52.01 | 1 | 20.52 | H |
| ATOM | 1807 | HG21 | THR | A | 208 | -5.432 | 19.099 | -52.989 | 1 | 24.99 | H |
| ATOM | 1808 | HG22 | THR | A | 208 | -5.839 | 18.094 | -54.137 | 1 | 24.99 | H |
| ATOM | 1809 | HG23 | THR | A | 208 | -5.881 | 19.65 | -54.399 | 1 | 24.99 | H |
| ATOM | 1810 | N | TYR | A | 209 | -10.303 | 17.702 | -53.277 | 1 | 16.05 | N |
| ATOM | 1811 | CA | TYR | A | 209 | -11.692 | 17.583 | -52.843 | 1 | 17.55 | C |
| ATOM | 1812 | C | TYR | A | 209 | -11.836 | 16.812 | -51.533 | 1 | 16.31 | C |
| ATOM | 1813 | O | TYR | A | 209 | -10.928 | 16.09 | -51.112 | 1 | 16.24 | O |
| ATOM | 1814 | CB | TYR | A | 209 | -12.534 | 16.92 | -53.941 | 1 | 17.25 | C |
| ATOM | 1815 | CG | TYR | A | 209 | -12.03 | 15.571 | -54.393 | 1 | 14.62 | C |
| ATOM | 1816 | CD1 | TYR | A | 209 | -10.964 | 15.467 | -55.276 | 1 | 19.2 | C |
| ATOM | 1817 | CD2 | TYR | A | 209 | -12.633 | 14.401 | -53.955 | 1 | 18.23 | C |
| ATOM | 1818 | CE1 | TYR | A | 209 | -10.499 | 14.234 | -55.695 | 1 | 22.13 | C |
| ATOM | 1819 | CE2 | TYR | A | 209 | -11.692 | 13.16 | -54.372 | 1 | 21.56 | C |
| ATOM | 1820 | CZ | TYR | A | 209 | -11.107 | 13.085 | -55.243 | 1 | 22.08 | C |
| ATOM | 1821 | OH | TYR | A | 209 | -10.644 | 11.857 | -55.664 | 1 | 21.65 | O |
| ATOM | 1822 | H | TYR | A | 209 | -9.804 | 17.037 | -53.057 | 1 | 19.26 | H |
| ATOM | 1823 | HA | TYR | A | 209 | -12.048 | 18.474 | -52.698 | 1 | 21.06 | H |
| ATOM | 1824 | HB2 | TYR | A | 209 | -13.437 | 16.8 | -53.608 | 1 | 20.7 | H |

TABLE 5-continued

Atomic Coordinates for OMCP-NKG2D (4PDC).

| ATOM | 1825 | HB3 | TYR | A | 209 | -12.547 | 17.504 | -54.716 | 1 | 20.7 | H |
|---|---|---|---|---|---|---|---|---|---|---|---|
| ATOM | 1826 | HD1 | TYR | A | 209 | -10.548 | 16.24 | -55.582 | 1 | 23.04 | H |
| ATOM | 1827 | HD2 | TYR | A | 209 | -13.351 | 14.449 | -53.366 | 1 | 21.87 | H |
| ATOM | 1828 | HE1 | TYR | A | 209 | -9.78 | 14.182 | -56.283 | 1 | 26.56 | H |
| ATOM | 1829 | HE2 | TYR | A | 209 | -12.585 | 12.383 | -54.067 | 1 | 25.87 | H |
| ATOM | 1830 | HH | TYR | A | 209 | -9.994 | 11.959 | -56.187 | 1 | 25.99 | H |
| ATOM | 1831 | N | ILE | A | 210 | -12.986 | 16.991 | -50.892 | 1 | 14.44 | N |
| ATOM | 1832 | CA | ILE | A | 210 | -13.276 | 16.355 | -49.617 | 1 | 13.02 | C |
| ATOM | 1833 | C | ILE | A | 210 | -14.502 | 15.475 | -49.75 | 1 | 14.98 | C |
| ATOM | 1834 | O | ILE | A | 210 | -15.563 | 15.937 | -50.175 | 1 | 15.19 | O |
| ATOM | 1835 | CB | ILE | A | 210 | -13.52 | 17.394 | -48.506 | 1 | 15.09 | C |
| ATOM | 1836 | CG1 | ILE | A | 210 | -12.293 | 18.294 | -48.337 | 1 | 18.45 | C |
| ATOM | 1837 | CG2 | ILE | A | 210 | -13.86 | 16.695 | -47.19 | 1 | 15.58 | C |
| ATOM | 1838 | CD1 | ILE | A | 210 | -12.516 | 19.483 | -47.404 | 1 | 16.93 | C |
| ATOM | 1839 | H | ILE | A | 210 | -13.625 | 17.487 | -51.184 | 1 | 17.32 | H |
| ATOM | 1840 | HA | ILE | A | 210 | -12.526 | 15.798 | -49.356 | 1 | 15.62 | H |
| ATOM | 1841 | HB | ILE | A | 210 | -14.274 | 17.948 | -48.763 | 1 | 18.1 | H |
| ATOM | 1842 | HG12 | ILE | A | 210 | -11.566 | 17.764 | -47.974 | 1 | 22.14 | H |
| ATOM | 1843 | HG13 | ILE | A | 210 | -12.042 | 18.643 | -49.207 | 1 | 22.14 | H |
| ATOM | 1844 | HG21 | ILE | A | 210 | -14.01 | 17.366 | -46.506 | 1 | 18.7 | H |
| ATOM | 1845 | HG22 | ILE | A | 210 | -14.662 | 16.164 | -47.313 | 1 | 18.7 | H |
| ATOM | 1846 | HG23 | ILE | A | 210 | -13.119 | 16.123 | -46.936 | 1 | 18.7 | H |
| ATOM | 1847 | HD11 | ILE | A | 210 | -11.697 | 20 | -47.351 | 1 | 20.32 | H |
| ATOM | 1848 | HD12 | ILE | A | 210 | -13.232 | 20.033 | -47.758 | 1 | 20.32 | H |
| ATOM | 1849 | HD13 | ILE | A | 210 | -12.756 | 19.153 | -46.524 | 1 | 20.32 | H |
| ATOM | 1850 | N | CYS | A | 211 | -14.352 | 14.207 | -49.383 | 1 | 13.79 | N |
| ATOM | 1851 | CA | CYS | A | 211 | -15.472 | 13.276 | -49.363 | 1 | 18.54 | C |
| ATOM | 1852 | C | CYS | A | 211 | -15.996 | 13.147 | -47.94 | 1 | 18.83 | C |
| ATOM | 1853 | O | CYS | A | 211 | -15.243 | 13.306 | -46.976 | 1 | 15.68 | O |
| ATOM | 1854 | CB | CYS | A | 211 | -15.057 | 11.909 | -49.912 | 1 | 19.87 | C |
| ATOM | 1855 | SG | CYS | A | 211 | -14.655 | 11.923 | -51.673 | 1 | 23.9 | S |
| ATOM | 1856 | H | CYS | A | 211 | -13.604 | 13.859 | -49.139 | 1 | 16.55 | H |
| ATOM | 1857 | HA | CYS | A | 211 | -16.186 | 13.623 | -49.92 | 1 | 22.25 | H |
| ATOM | 1858 | HB2 | CYS | A | 211 | -14.272 | 11.605 | -49.431 | 1 | 23.84 | H |
| ATOM | 1859 | HB3 | CYS | A | 211 | -15.787 | 11.284 | -49.779 | 1 | 23.84 | H |
| ATOM | 1860 | N | MET | A | 212 | -17.29 | 12.865 | -47.821 | 1 | 16.73 | N |
| ATOM | 1861 | CA | MET | A | 212 | -17.952 | 12.779 | -46.527 | 1 | 19.25 | C |
| ATOM | 1862 | C | MET | A | 212 | -19.005 | 11.671 | -46.513 | 1 | 21.41 | C |
| ATOM | 1863 | O | MET | A | 212 | -19.713 | 11.464 | -47.5 | 1 | 24.33 | O |
| ATOM | 1864 | CB | MET | A | 212 | -18.598 | 14.124 | -46.181 | 1 | 15.5 | C |
| ATOM | 1865 | CG | MET | A | 212 | -19.443 | 14.128 | -44.912 | 1 | 19.16 | C |
| ATOM | 1866 | SD | MET | A | 212 | -20.263 | 15.719 | -44.644 | 1 | 21.71 | S |
| ATOM | 1867 | CE | MET | A | 212 | -21.41 | 15.313 | -43.333 | 1 | 26.47 | C |
| ATOM | 1868 | H | MET | A | 212 | -17.813 | 12.717 | -48.487 | 1 | 20.08 | H |
| ATOM | 1869 | HA | MET | A | 212 | -17.286 | 12.586 | -45.848 | 1 | 23.1 | H |
| ATOM | 1870 | HB2 | MET | A | 212 | -17.896 | 14.783 | -46.066 | 1 | 18.61 | H |
| ATOM | 1871 | HB3 | MET | A | 212 | -19.174 | 14.388 | -46.916 | 1 | 18.61 | H |
| ATOM | 1872 | HG2 | MET | A | 212 | -20.127 | 13.444 | -44.983 | 1 | 22.99 | H |
| ATOM | 1873 | HG3 | MET | A | 212 | -18.871 | 13.951 | -44.148 | 1 | 22.99 | H |
| ATOM | 1874 | HE1 | MET | A | 212 | -21.917 | 16.107 | -43.101 | 1 | 31.76 | H |
| ATOM | 1875 | HE2 | MET | A | 212 | -22.009 | 14.616 | -43.643 | 1 | 31.76 | H |

TABLE 5-continued

Atomic Coordinates for OMCP-NKG2D (4PDC).

| | | | | | | | | | | | |
|---|---|---|---|---|---|---|---|---|---|---|---|
| ATOM | 1876 | HE3 | MET | A | 212 | -20.91 | 15.002 | -42.562 | 1 | 31.76 | H |
| ATOM | 1877 | N | GLN | A | 213 | -19.09 | 10.969 | -45.385 | 1 | 18.51 | N |
| ATOM | 1878 | CA | GLN | A | 213 | -20.142 | 9.985 | -45.123 | 1 | 26.68 | C |
| ATOM | 1879 | C | GLN | A | 213 | -20.849 | 10.345 | -43.823 | 1 | 25.55 | C |
| ATOM | 1880 | O | GLN | A | 213 | -20.203 | 10.47 | -42.781 | 1 | 22.83 | O |
| ATOM | 1881 | CB | GLN | A | 213 | -19.567 | 8.571 | -45.017 | 1 | 26.14 | C |
| ATOM | 1882 | CG | GLN | A | 213 | -19.588 | 7.762 | -46.297 | 1 | 36.07 | C |
| ATOM | 1883 | CD | GLN | A | 213 | -19.101 | 6.337 | -46.08 | 1 | 35.95 | C |
| ATOM | 1884 | OE1 | GLN | A | 213 | -19.101 | 5.856 | -44.949 | 1 | 38.02 | O |
| ATOM | 1885 | NE2 | GLN | A | 213 | -18.738 | 5.658 | -47.164 | 1 | 33.49 | N |
| ATOM | 1886 | H | GLN | A | 213 | -18.531 | 11.047 | -44.735 | 1 | 22.21 | H |
| ATOM | 1887 | HA | GLN | A | 213 | -20.79 | 10.003 | -45.844 | 1 | 32.01 | H |
| ATOM | 1888 | HB2 | GLN | A | 213 | -18.643 | 8.636 | -44.729 | 1 | 31.37 | H |
| ATOM | 1889 | HB3 | GLN | A | 213 | -20.079 | 8.081 | -44.354 | 1 | 31.37 | H |
| ATOM | 1890 | HG2 | GLN | A | 213 | -20.497 | 7.722 | -46.634 | 1 | 43.28 | H |
| ATOM | 1891 | HG3 | GLN | A | 213 | -19.008 | 8.184 | -46.95 | 1 | 43.28 | H |
| ATOM | 1892 | HE21 | GLN | A | 213 | -18.786 | 6.028 | -47.939 | 1 | 40.19 | H |
| ATOM | 1893 | HE22 | GLN | A | 213 | -18.456 | 4.849 | -47.09 | 1 | 40.19 | H |
| ATOM | 1894 | N | ARG | A | 214 | -22.169 | 10.497 | -43.875 | 1 | 30.78 | N |
| ATOM | 1895 | CA | ARG | A | 214 | -22.922 | 10.975 | -42.717 | 1 | 39 | C |
| ATOM | 1896 | C | ARG | A | 214 | -23.6 | 9.833 | -41.967 | 1 | 50.04 | C |
| ATOM | 1897 | O | ARG | A | 214 | -23.446 | 9.709 | -40.749 | 1 | 47.2 | O |
| ATOM | 1898 | CB | ARG | A | 214 | -23.958 | 12.01 | -43.156 | 1 | 48.11 | C |
| ATOM | 1899 | CG | ARG | A | 214 | -24.524 | 12.838 | -42.013 | 1 | 41.27 | C |
| ATOM | 1900 | CD | ARG | A | 214 | -24.916 | 14.231 | -42.48 | 1 | 41.95 | C |
| ATOM | 1901 | NE | ARG | A | 214 | -25.794 | 14.187 | -43.648 | 1 | 45.75 | N |
| ATOM | 1902 | CZ | ARG | A | 214 | -26.622 | 15.164 | -44.006 | 1 | 46.72 | C |
| ATOM | 1903 | NH1 | ARG | A | 214 | -26.706 | 16.278 | -43.285 | 1 | 46.09 | N |
| ATOM | 1904 | NH2 | ARG | A | 214 | -27.378 | 15.022 | -45.084 | 1 | 46.67 | N |
| ATOM | 1905 | H | ARG | A | 214 | -22.653 | 10.331 | -44.566 | 1 | 36.93 | H |
| ATOM | 1906 | HA | ARG | A | 214 | -22.31 | 11.41 | -42.104 | 1 | 46.8 | H |
| ATOM | 1907 | HB2 | ARG | A | 214 | -23.543 | 12.619 | -43.786 | 1 | 57.73 | H |
| ATOM | 1908 | HB3 | ARG | A | 214 | -24.698 | 11.55 | -43.582 | 1 | 57.73 | H |
| ATOM | 1909 | HG2 | ARG | A | 214 | -25.315 | 12.401 | -41.661 | 1 | 49.52 | H |
| ATOM | 1910 | HG3 | ARG | A | 214 | -23.852 | 12.928 | -41.319 | 1 | 49.52 | H |
| ATOM | 1911 | HD2 | ARG | A | 214 | -25.387 | 14.686 | -41.765 | 1 | 50.35 | H |
| ATOM | 1912 | HD3 | ARG | A | 214 | -24.116 | 14.723 | -42.721 | 1 | 50.35 | H |
| ATOM | 1913 | HE | ARG | A | 214 | -25.774 | 13.48 | -44.137 | 1 | 54.9 | H |
| ATOM | 1914 | HH11 | ARG | A | 214 | -26.219 | 16.374 | -42.584 | 1 | 55.31 | H |
| ATOM | 1915 | HH12 | ARG | A | 214 | -27.246 | 16.904 | -43.523 | 1 | 55.31 | H |
| ATOM | 1916 | HH21 | ARG | A | 214 | -27.328 | 14.302 | -45.553 | 1 | 56.01 | H |
| ATOM | 1917 | HH22 | ARG | A | 214 | -27.916 | 15.651 | -45.318 | 1 | 56.01 | H |
| ATOM | 1918 | N | THR | A | 215 | -24.349 | 9.007 | -42.691 | 1 | 58.9 | N |
| ATOM | 1919 | CA | THR | A | 215 | -24.978 | 7.827 | -42.103 | 1 | 68.61 | C |
| ATOM | 1920 | C | THR | A | 215 | -25.559 | 6.955 | -43.21 | 1 | 64.97 | C |
| ATOM | 1921 | O | THR | A | 215 | -26.049 | 7.466 | -44.216 | 1 | 62.09 | O |
| ATOM | 1922 | CB | THR | A | 215 | -26.083 | 8.217 | -41.083 | 1 | 70.62 | C |
| ATOM | 1923 | OG1 | THR | A | 215 | -25.689 | 7.809 | -39.767 | 1 | 63.52 | O |
| ATOM | 1924 | CG2 | THR | A | 215 | -27.433 | 7.574 | -41.417 | 1 | 62.01 | C |
| ATOM | 1925 | H | THR | A | 215 | -24.51 | 9.108 | -43.53 | 1 | 70.68 | H |
| ATOM | 1926 | HA | THR | A | 215 | -24.304 | 7.31 | -41.635 | 1 | 82.33 | H |

TABLE 5-continued

Atomic Coordinates for OMCP-NKG2D (4PDC).

| | | | | | | | | | | | |
|---|---|---|---|---|---|---|---|---|---|---|---|
| ATOM | 1927 | HB | THR | A | 215 | -26.198 | 9.18 | -41.094 | 1 | 84.75 | H |
| ATOM | 1928 | HG1 | THR | A | 215 | -26.283 | 8.018 | -39.211 | 1 | 76.23 | H |
| ATOM | 1929 | HG21 | THR | A | 215 | -27.35 | 6.608 | -41.411 | 1 | 74.41 | H |
| ATOM | 1930 | HG22 | THR | A | 215 | -28.097 | 7.839 | -40.761 | 1 | 74.41 | H |
| ATOM | 1931 | HG23 | THR | A | 215 | -27.727 | 7.86 | -42.296 | 1 | 74.41 | H |
| TER | 1932 | | THR | A | 215 | | | | | | |
| ATOM | 1933 | N | SER | B | 94 | -17.256 | -1.068 | -39.057 | 1 | 38.91 | N |
| ATOM | 1934 | CA | SER | B | 94 | -16.499 | -1.068 | -37.812 | 1 | 42.58 | C |
| ATOM | 1935 | C | SER | B | 94 | -16.281 | 0.359 | -37.313 | 1 | 42.15 | C |
| ATOM | 1936 | O | SER | B | 94 | -16.626 | 1.322 | -37.999 | 1 | 37.44 | O |
| ATOM | 1937 | CB | SER | B | 94 | -15.156 | -1.775 | -37.999 | 1 | 45.61 | C |
| ATOM | 1938 | OG | SER | B | 94 | -14.385 | -1.141 | -39.004 | 1 | 54.06 | O |
| ATOM | 1939 | HA | SER | B | 94 | -17.001 | -1.549 | -37.136 | 1 | 51.1 | H |
| ATOM | 1940 | HB2 | SER | B | 94 | -14.667 | -1.748 | -37.162 | 1 | 54.73 | H |
| ATOM | 1941 | HB3 | SER | B | 94 | -15.318 | -2.695 | -38.259 | 1 | 54.73 | H |
| ATOM | 1942 | HG | SER | B | 94 | -14.237 | -0.342 | -38.791 | 1 | 64.88 | H |
| ATOM | 1943 | N | TYR | B | 95 | -15.698 | 0.478 | -36.122 | 1 | 37.34 | N |
| ATOM | 1944 | CA | TYR | B | 95 | -15.564 | 1.76 | -35.437 | 1 | 35.53 | C |
| ATOM | 1945 | C | TYR | B | 95 | -14.114 | 2.137 | -35.164 | 1 | 36.3 | C |
| ATOM | 1946 | O | TYR | B | 95 | -13.233 | 1.279 | -35.095 | 1 | 36.5 | O |
| ATOM | 1947 | CB | TYR | B | 95 | -16.332 | 1.732 | -34.113 | 1 | 34.25 | C |
| ATOM | 1948 | CG | TYR | B | 95 | -17.832 | 1.686 | -34.273 | 1 | 32.06 | C |
| ATOM | 1949 | CD1 | TYR | B | 95 | -18.476 | 0.505 | -34.615 | 1 | 35.96 | C |
| ATOM | 1950 | CD2 | TYR | B | 95 | -18.604 | 2.822 | -34.078 | 1 | 33.01 | C |
| ATOM | 1951 | CE1 | TYR | B | 95 | -19.848 | 0.458 | -34.761 | 1 | 34.2 | C |
| ATOM | 1952 | CE2 | TYR | B | 95 | -19.976 | 2.784 | -34.22 | 1 | 40.01 | C |
| ATOM | 1953 | CZ | TYR | B | 95 | -20.593 | 1.601 | -34.563 | 1 | 39.11 | C |
| ATOM | 1954 | OH | TYR | B | 95 | -21.96 | 1.564 | -34.706 | 1 | 42 | O |
| ATOM | 1955 | H | TYR | B | 95 | -15.367 | -0.183 | -35.682 | 1 | 44.8 | H |
| ATOM | 1956 | HA | TYR | B | 95 | -15.953 | 2.454 | -35.992 | 1 | 42.63 | H |
| ATOM | 1957 | HB2 | TYR | B | 95 | -16.063 | 0.945 | -33.614 | 1 | 41.11 | H |
| ATOM | 1958 | HB3 | TYR | B | 95 | -16.113 | 2.531 | -33.608 | 1 | 41.11 | H |
| ATOM | 1959 | HD1 | TYR | B | 95 | -17.975 | -0.267 | -34.749 | 1 | 43.16 | H |
| ATOM | 1960 | HD2 | TYR | B | 95 | -18.191 | 3.622 | -33.847 | 1 | 39.62 | H |
| ATOM | 1961 | HE1 | TYR | B | 95 | -20.267 | -0.339 | -34.991 | 1 | 41.04 | H |
| ATOM | 1962 | HE2 | TYR | B | 95 | -20.482 | 3.554 | -34.088 | 1 | 48.01 | H |
| ATOM | 1963 | HH | TYR | B | 95 | -22.285 | 2.324 | -34.558 | 1 | 50.4 | H |
| ATOM | 1964 | N | CYS | B | 96 | -13.888 | 3.438 | -35.01 | 1 | 30.02 | N |
| ATOM | 1965 | CA | CYS | B | 96 | -12.593 | 3.973 | -34.613 | 1 | 34.28 | C |
| ATOM | 1966 | C | CYS | B | 96 | -12.642 | 4.321 | -33.129 | 1 | 32.78 | C |
| ATOM | 1967 | O | CYS | B | 96 | -13.603 | 4.937 | -32.669 | 1 | 31.3 | O |
| ATOM | 1968 | CB | CYS | B | 96 | -12.247 | 5.206 | -35.453 | 1 | 31.86 | C |
| ATOM | 1969 | SG | CYS | B | 96 | -10.576 | 5.848 | -35.221 | 1 | 33.72 | S |
| ATOM | 1970 | H | CYS | B | 96 | -14.485 | 4.044 | -35.133 | 1 | 36.02 | H |
| ATOM | 1971 | HA | CYS | B | 96 | -11.907 | 3.302 | -34.752 | 1 | 41.13 | H |
| ATOM | 1972 | HB2 | CYS | B | 96 | -12.345 | 4.977 | -36.391 | 1 | 38.23 | H |
| ATOM | 1973 | HB3 | CYS | B | 96 | -12.867 | 5.917 | -35.227 | 1 | 38.23 | H |
| ATOM | 1974 | N | GLY | B | 97 | -11.618 | 3.918 | -32.381 | 1 | 33.09 | N |
| ATOM | 1975 | CA | GLY | B | 97 | -11.554 | 4.204 | -30.957 | 1 | 31.22 | C |
| ATOM | 1976 | C | GLY | B | 97 | -11.135 | 2.998 | -30.132 | 1 | 35.55 | C |
| ATOM | 1977 | O | GLY | B | 97 | -10.551 | 2.054 | -30.663 | 1 | 39.96 | O |

TABLE 5-continued

Atomic Coordinates for OMCP-NKG2D (4PDC).

| ATOM | 1978 | H | GLY | B | 97 | -10.944 | 3.474 | -32.68 | 1 | 39.71 | H |
|------|------|------|-----|---|-----|---------|--------|---------|---|--------|----|
| ATOM | 1979 | HA2 | GLY | B | 97 | -10.917 | 4.918 | -30.8 | 1 | 37.46 | H |
| ATOM | 1980 | HA3 | GLY | B | 97 | -12.426 | 4.497 | -30.648 | 1 | 37.46 | H |
| ATOM | 1981 | N | PRO | B | 98 | -11.429 | 3.019 | -28.821 | 1 | 38.2 | N |
| ATOM | 1982 | CA | PRO | B | 98 | -12.139 | 4.096 | -28.12 | 1 | 36.03 | C |
| ATOM | 1983 | C | PRO | B | 98 | -11.312 | 5.373 | -27.973 | 1 | 35.11 | C |
| ATOM | 1984 | O | PRO | B | 98 | -10.086 | 5.318 | -27.863 | 1 | 34.34 | O |
| ATOM | 1985 | CB | PRO | B | 98 | -12.439 | 3.48 | -26.749 | 1 | 43.03 | C |
| ATOM | 1986 | CG | PRO | B | 98 | -11.379 | 2.466 | -26.551 | 1 | 44.9 | C |
| ATOM | 1987 | CD | PRO | B | 98 | -11.075 | 1.914 | -27.912 | 1 | 43.35 | C |
| ATOM | 1988 | HA | PRO | B | 98 | -12.973 | 4.301 | -28.57 | 1 | 43.23 | H |
| ATOM | 1989 | HB2 | PRO | B | 98 | -12.392 | 4.165 | -26.065 | 1 | 51.64 | H |
| ATOM | 1990 | HB3 | PRO | B | 98 | -13.315 | 3.064 | -26.761 | 1 | 51.64 | H |
| ATOM | 1991 | HG2 | PRO | B | 98 | -10.593 | 2.888 | -26.172 | 1 | 53.88 | H |
| ATOM | 1992 | HG3 | PRO | B | 98 | -11.706 | 1.765 | -25.965 | 1 | 53.88 | H |
| ATOM | 1993 | HD2 | PRO | B | 98 | -10.131 | 1.703 | -27.988 | 1 | 52.02 | H |
| ATOM | 1994 | HD3 | PRO | B | 98 | -11.628 | 1.138 | -28.093 | 1 | 52.02 | H |
| ATOM | 1995 | N | CYS | B | 99 | -11.999 | 6.51 | -27.991 | 1 | 28.31 | N |
| ATOM | 1996 | CA | CYS | B | 99 | -11.382 | 7.814 | -27.782 | 1 | 31.04 | C |
| ATOM | 1997 | C | CYS | B | 99 | -12.176 | 8.587 | -26.75 | 1 | 29.57 | C |
| ATOM | 1998 | O | CYS | B | 99 | -13.297 | 8.207 | -26.419 | 1 | 34.43 | O |
| ATOM | 1999 | CB | CYS | B | 99 | -11.33 | 8.62 | -29.08 | 1 | 22.49 | C |
| ATOM | 2000 | SG | CYS | B | 99 | -10.222 | 7.973 | -30.33 | 1 | 25.81 | S |
| ATOM | 2001 | H | CYS | B | 99 | -12.847 | 6.552 | -28.127 | 1 | 33.97 | H |
| ATOM | 2002 | HA | CYS | B | 99 | -10.477 | 7.697 | -27.453 | 1 | 37.25 | H |
| ATOM | 2003 | HB2 | CYS | B | 99 | -12.22 | 8.645 | -29.464 | 1 | 26.99 | H |
| ATOM | 2004 | HB3 | CYS | B | 99 | -11.04 | 9.522 | -28.872 | 1 | 26.99 | H |
| ATOM | 2005 | N | PRO | B | 100 | -11.599 | 9.682 | -26.237 | 1 | 32.75 | N |
| ATOM | 2006 | CA | PRO | B | 100 | -12.421 | 10.607 | -25.458 | 1 | 27.02 | C |
| ATOM | 2007 | C | PRO | B | 100 | -13.576 | 11.111 | -26.308 | 1 | 29.55 | C |
| ATOM | 2008 | O | PRO | B | 100 | -13.455 | 11.152 | -27.535 | 1 | 23.9 | O |
| ATOM | 2009 | CB | PRO | B | 100 | -11.45 | 11.733 | -25.099 | 1 | 26.53 | C |
| ATOM | 2010 | CG | PRO | B | 100 | -10.094 | 11.101 | -25.168 | 1 | 24.03 | C |
| ATOM | 2011 | CD | PRO | B | 100 | -10.181 | 10.084 | -26.262 | 1 | 29.2 | C |
| ATOM | 2012 | HA | PRO | B | 100 | -12.756 | 10.184 | -24.652 | 1 | 32.42 | H |
| ATOM | 2013 | HB2 | PRO | B | 100 | -11.528 | 12.452 | -25.745 | 1 | 31.83 | H |
| ATOM | 2014 | HB3 | PRO | B | 100 | -11.635 | 12.053 | -24.202 | 1 | 31.83 | H |
| ATOM | 2015 | HG2 | PRO | B | 100 | -9.431 | 11.776 | -25.381 | 1 | 28.84 | H |
| ATOM | 2016 | HG3 | PRO | B | 100 | -9.89 | 10.676 | -24.321 | 1 | 28.84 | H |
| ATOM | 2017 | HD2 | PRO | B | 100 | -9.957 | 10.486 | -27.116 | 1 | 35.04 | H |
| ATOM | 2018 | HD3 | PRO | B | 100 | -9.61 | 9.325 | -26.064 | 1 | 35.04 | H |
| ATOM | 2019 | N | LYS | B | 101 | -14.678 | 11.479 | -25.668 | 1 | 32.78 | N |
| ATOM | 2020 | CA | LYS | B | 101 | -15.875 | 11.896 | -26.387 | 1 | 39.36 | C |
| ATOM | 2021 | C | LYS | B | 101 | -15.597 | 13.072 | -27.325 | 1 | 32.37 | C |
| ATOM | 2022 | O | LYS | B | 101 | -14.877 | 14.005 | -26.97 | 1 | 30.08 | O |
| ATOM | 2023 | CB | LYS | B | 101 | -16.984 | 12.266 | -25.396 | 1 | 44.44 | C |
| ATOM | 2024 | CG | LYS | B | 101 | -18.332 | 12.57 | -26.041 | 1 | 61.82 | C |
| ATOM | 2025 | CD | LYS | B | 101 | -18.865 | 11.378 | -26.824 | 1 | 74.76 | C |
| ATOM | 2026 | CE | LYS | B | 101 | -20.227 | 11.667 | -27.429 | 1 | 100.45 | C |
| ATOM | 2027 | NZ | LYS | B | 101 | -20.686 | 10.552 | -28.301 | 1 | 117.51 | N1+ |
| ATOM | 2028 | H | LYS | B | 101 | -14.76 | 11.497 | -24.812 | 1 | 39.34 | H |

TABLE 5-continued

Atomic Coordinates for OMCP-NKG2D (4PDC).

| ATOM | 2029 | HA   | LYS | B | 101 | -16.192 | 11.153 | -26.926 | 1 | 47.24  | H |
|------|------|------|-----|---|-----|---------|--------|---------|---|--------|---|
| ATOM | 2030 | HB2  | LYS | B | 101 | -17.111 | 11.525 | -24.782 | 1 | 53.33  | H |
| ATOM | 2031 | HB3  | LYS | B | 101 | -16.709 | 13.054 | -24.903 | 1 | 53.33  | H |
| ATOM | 2032 | HG2  | LYS | B | 101 | -18.975 | 12.79  | -25.348 | 1 | 74.18  | H |
| ATOM | 2033 | HG3  | LYS | B | 101 | -18.232 | 13.315 | -26.654 | 1 | 74.18  | H |
| ATOM | 2034 | HD2  | LYS | B | 101 | -18.251 | 11.169 | -27.546 | 1 | 89.71  | H |
| ATOM | 2035 | HD3  | LYS | B | 101 | -18.953 | 10.617 | -26.228 | 1 | 89.71  | H |
| ATOM | 2036 | HE2  | LYS | B | 101 | -20.876 | 11.782 | -26.716 | 1 | 120.53 | H |
| ATOM | 2037 | HE3  | LYS | B | 101 | -20.174 | 12.472 | -27.967 | 1 | 120.53 | H |
| ATOM | 2038 | HZ1  | LYS | B | 101 | -21.485 | 10.743 | -28.644 | 1 | 141.01 | H |
| ATOM | 2039 | HZ2  | LYS | B | 101 | -20.108 | 10.429 | -28.967 | 1 | 141.01 | H |
| ATOM | 2040 | HZ3  | LYS | B | 101 | -20.747 | 9.8    | -27.828 | 1 | 141.01 | H |
| ATOM | 2041 | N    | ASN | B | 102 | -16.163 | 12.996 | -28.527 | 1 | 30.16  | N |
| ATOM | 2042 | CA   | ASN | B | 102 | -16.115 | 14.077 | -29.514 | 1 | 31.24  | C |
| ATOM | 2043 | C    | ASN | B | 102 | -14.712 | 14.442 | -30.002 | 1 | 27.87  | C |
| ATOM | 2044 | O    | ASN | B | 102 | -14.519 | 15.491 | -30.613 | 1 | 26.23  | O |
| ATOM | 2045 | CB   | ASN | B | 102 | -16.798 | 15.329 | -28.954 | 1 | 34.75  | C |
| ATOM | 2046 | CG   | ASN | B | 102 | -18.292 | 15.143 | -28.774 | 1 | 42.54  | C |
| ATOM | 2047 | OD1  | ASN | B | 102 | -18.922 | 14.366 | -29.491 | 1 | 45.19  | O |
| ATOM | 2048 | ND2  | ASN | B | 102 | -18.866 | 15.857 | -27.814 | 1 | 46.35  | N |
| ATOM | 2049 | H    | ASN | B | 102 | -16.596 | 12.306 | -28.804 | 1 | 36.19  | H |
| ATOM | 2050 | HA   | ASN | B | 102 | -16.623 | 13.797 | -30.292 | 1 | 37.49  | H |
| ATOM | 2051 | HB2  | ASN | B | 102 | -16.414 | 15.538 | -28.088 | 1 | 41.7   | H |
| ATOM | 2052 | HB3  | ASN | B | 102 | -16.659 | 16.067 | -29.567 | 1 | 41.7   | H |
| ATOM | 2053 | HD21 | ASN | B | 102 | -19.712 | 15.786 | -27.673 | 1 | 55.63  | H |
| ATOM | 2054 | HD22 | ASN | B | 102 | -18.394 | 16.391 | -27.333 | 1 | 55.63  | H |
| ATOM | 2055 | N    | TRP | B | 103 | -13.737 | 13.577 | -29.751 | 1 | 23.28  | N |
| ATOM | 2056 | CA   | TRP | B | 103 | -12.41  | 13.762 | -30.328 | 1 | 23.16  | C |
| ATOM | 2057 | C    | TRP | B | 103 | -12.392 | 13.237 | -31.763 | 1 | 23.53  | C |
| ATOM | 2058 | O    | TRP | B | 103 | -13.233 | 12.419 | -32.14  | 1 | 22.63  | O |
| ATOM | 2059 | CB   | TRP | B | 103 | -11.343 | 13.049 | -29.491 | 1 | 21.69  | C |
| ATOM | 2060 | CG   | TRP | B | 103 | -10.963 | 13.783 | -28.236 | 1 | 23.99  | C |
| ATOM | 2061 | CD1  | TRP | B | 103 | -11.76  | 14.599 | -27.485 | 1 | 23.75  | C |
| ATOM | 2062 | CD2  | TRP | B | 103 | -9.679  | 13.777 | -27.595 | 1 | 20.75  | C |
| ATOM | 2063 | NE1  | TRP | B | 103 | -11.054 | 15.094 | -26.413 | 1 | 20.78  | N |
| ATOM | 2064 | CE2  | TRP | B | 103 | -9.775  | 14.606 | -26.459 | 1 | 20.29  | C |
| ATOM | 2065 | CE3  | TRP | B | 103 | -8.461  | 13.15  | -27.871 | 1 | 21.26  | C |
| ATOM | 2066 | CZ2  | TRP | B | 103 | -8.699  | 14.823 | -25.6   | 1 | 21.46  | C |
| ATOM | 2067 | CZ3  | TRP | B | 103 | -7.394  | 13.365 | -27.015 | 1 | 25.01  | C |
| ATOM | 2068 | CH2  | TRP | B | 103 | -7.521  | 14.195 | -25.893 | 1 | 17.81  | C |
| ATOM | 2069 | H    | TRP | B | 103 | -13.815 | 12.881 | -29.253 | 1 | 27.94  | H |
| ATOM | 2070 | HA   | TRP | B | 103 | -12.198 | 14.708 | -30.348 | 1 | 27.79  | H |
| ATOM | 2071 | HB2  | TRP | B | 103 | -11.68  | 12.176 | -29.233 | 1 | 26.03  | H |
| ATOM | 2072 | HB3  | TRP | B | 103 | -10.542 | 12.946 | -30.028 | 1 | 26.03  | H |
| ATOM | 2073 | HD1  | TRP | B | 103 | -12.652 | 14.789 | -27.67  | 1 | 28.5   | H |
| ATOM | 2074 | HE1  | TRP | B | 103 | -11.365 | 15.626 | -25.813 | 1 | 24.94  | H |
| ATOM | 2075 | HE3  | TRP | B | 103 | -8.37   | 12.597 | -28.613 | 1 | 25.51  | H |
| ATOM | 2076 | HZ2  | TRP | B | 103 | -8.781  | 15.373 | -24.854 | 1 | 25.75  | H |
| ATOM | 2077 | HZ3  | TRP | B | 103 | -6.578  | 12.953 | -27.188 | 1 | 30.01  | H |
| ATOM | 2078 | HH2  | TRP | B | 103 | -6.787  | 14.323 | -25.336 | 1 | 21.37  | H |
| ATOM | 2079 | N    | ILE | B | 104 | -11.452 | 13.725 | -32.566 | 1 | 17.2   | N |

TABLE 5-continued

Atomic Coordinates for OMCP-NKG2D (4PDC).

| | | | | | | | | | | |
|---|---|---|---|---|---|---|---|---|---|---|
| ATOM | 2080 | CA | ILE | B | 104 | -11.198 | 13.133 | -33.873 | 1 | 21.24 | C |
| ATOM | 2081 | C | ILE | B | 104 | -10.616 | 11.753 | -33.647 | 1 | 24.16 | C |
| ATOM | 2082 | O | ILE | B | 104 | -9.835 | 11.559 | -32.719 | 1 | 23.98 | O |
| ATOM | 2083 | CB | ILE | B | 104 | -10.215 | 13.966 | -34.726 | 1 | 21.34 | C |
| ATOM | 2084 | CG1 | ILE | B | 104 | -10.796 | 15.348 | -35.026 | 1 | 22.32 | C |
| ATOM | 2085 | CG2 | ILE | B | 104 | -9.876 | 13.23 | -36.033 | 1 | 24.29 | C |
| ATOM | 2086 | CD1 | ILE | B | 104 | -9.849 | 16.253 | -35.781 | 1 | 28.99 | C |
| ATOM | 2087 | H | ILE | B | 104 | -10.949 | 14.396 | -32.377 | 1 | 20.64 | H |
| ATOM | 2088 | HA | ILE | B | 104 | -12.032 | 13.044 | -34.359 | 1 | 25.48 | H |
| ATOM | 2089 | HB | ILE | B | 104 | -9.395 | 14.083 | -34.221 | 1 | 25.61 | H |
| ATOM | 2090 | HG12 | ILE | B | 104 | -11.597 | 15.241 | -35.564 | 1 | 26.78 | H |
| ATOM | 2091 | HG13 | ILE | B | 104 | -11.018 | 15.783 | -34.188 | 1 | 26.78 | H |
| ATOM | 2092 | HG21 | ILE | B | 104 | -9.259 | 13.772 | -36.55 | 1 | 29.15 | H |
| ATOM | 2093 | HG22 | ILE | B | 104 | -9.467 | 12.377 | -35.818 | 1 | 29.15 | H |
| ATOM | 2094 | HG23 | ILE | B | 104 | -10.693 | 13.088 | -36.536 | 1 | 29.15 | H |
| ATOM | 2095 | HD11 | ILE | B | 104 | -10.283 | 17.107 | -35.934 | 1 | 34.79 | H |
| ATOM | 2096 | HD12 | ILE | B | 104 | -9.046 | 16.381 | -35.252 | 1 | 34.79 | H |
| ATOM | 2097 | HD13 | ILE | B | 104 | -9.624 | 15.839 | -36.628 | 1 | 34.79 | H |
| ATOM | 2098 | N | CYS | B | 105 | -11.001 | 10.8 | -34.489 | 1 | 22.22 | N |
| ATOM | 2099 | CA | CYS | B | 105 | -10.421 | 9.462 | -34.455 | 1 | 24.13 | C |
| ATOM | 2100 | C | CYS | B | 105 | -9.93 | 9.12 | -35.853 | 1 | 25.68 | C |
| ATOM | 2101 | O | CYS | B | 105 | -10.66 | 9.288 | -36.83 | 1 | 25.12 | O |
| ATOM | 2102 | CB | CYS | B | 105 | -11.44 | 8.433 | -33.962 | 1 | 25.61 | C |
| ATOM | 2103 | SG | CYS | B | 105 | -10.702 | 6.857 | -33.461 | 1 | 33.63 | S |
| ATOM | 2104 | H | CYS | B | 105 | -11.602 | 10.904 | -35.096 | 1 | 26.67 | H |
| ATOM | 2105 | HA | CYS | B | 105 | -9.661 | 9.455 | -33.852 | 1 | 28.95 | H |
| ATOM | 2106 | HB2 | CYS | B | 105 | -11.908 | 8.799 | -33.195 | 1 | 30.73 | H |
| ATOM | 2107 | HB3 | CYS | B | 105 | -12.071 | 8.251 | -34.676 | 1 | 30.73 | H |
| ATOM | 2108 | N | TYR | B | 106 | -8.689 | 8.653 | -35.949 | 1 | 22.66 | N |
| ATOM | 2109 | CA | TYR | B | 106 | -8.061 | 8.421 | -37.245 | 1 | 21.9 | C |
| ATOM | 2110 | C | TYR | B | 106 | 6.84 | 7.512 | -37.14 | 1 | 29.8 | C |
| ATOM | 2111 | O | TYR | B | 106 | -5.832 | 7.876 | -36.531 | 1 | 19.08 | O |
| ATOM | 2112 | CB | TYR | B | 106 | -7.656 | 9.754 | -37.874 | 1 | 22.79 | C |
| ATOM | 2113 | CG | TYR | B | 106 | -7.09 | 9.639 | -39.271 | 1 | 21.75 | C |
| ATOM | 2114 | CD1 | TYR | B | 106 | -7.886 | 9.228 | -40.333 | 1 | 23 | C |
| ATOM | 2115 | CD2 | TYR | B | 106 | -5.766 | 9.961 | -39.532 | 1 | 22.3 | C |
| ATOM | 2116 | CE1 | TYR | B | 106 | -7.375 | 9.131 | -41.614 | 1 | 22.33 | C |
| ATOM | 2117 | CE2 | TYR | B | 106 | -5.247 | 9.871 | -40.811 | 1 | 23.29 | C |
| ATOM | 2118 | CZ | TYR | B | 106 | -6.056 | 9.455 | -41.846 | 1 | 24.28 | C |
| ATOM | 2119 | OH | TYR | B | 106 | -5.543 | 9.363 | -43.116 | 1 | 28.23 | O |
| ATOM | 2120 | H | TYR | B | 106 | -8.188 | 8.462 | -35.277 | 1 | 27.19 | H |
| ATOM | 2121 | HA | TYR | B | 106 | -8.703 | 7.995 | -37.834 | 1 | 26.28 | H |
| ATOM | 2122 | HB2 | TYR | B | 106 | -8.438 | 10.326 | -37.919 | 1 | 27.35 | H |
| ATOM | 2123 | HB3 | TYR | B | 106 | -6.98 | 10.168 | -37.315 | 1 | 27.35 | H |
| ATOM | 2124 | HD1 | TYR | B | 106 | -8.777 | 9.01 | -40.179 | 1 | 27.6 | H |
| ATOM | 2125 | HD2 | TYR | B | 106 | -5.218 | 10.244 | -38.836 | 1 | 26.77 | H |
| ATOM | 2126 | HE1 | TYR | B | 106 | -7.919 | 8.852 | -42.315 | 1 | 26.8 | H |
| ATOM | 2127 | HE2 | TYR | B | 106 | -5.247 | 10.087 | -40.97 | 1 | 27.94 | H |
| ATOM | 2128 | HH | TYR | B | 106 | -4.357 | 9.588 | -43.115 | 1 | 33.88 | H |
| ATOM | 2129 | N | LYS | B | 107 | 6.944 | 6.335 | -37.75 | 1 | 26.75 | N |
| ATOM | 2130 | CA | LYS | B | 107 | -5.852 | 5.367 | -37.787 | 1 | 26.22 | C |

TABLE 5-continued

Atomic Coordinates for OMCP-NKG2D (4PDC).

| ATOM | 2131 | C | LYS | B | 107 | -5.272 | 5.107 | -36.397 | 1 | 26.74 | C |
|---|---|---|---|---|---|---|---|---|---|---|---|
| ATOM | 2132 | O | LYS | B | 107 | -4.095 | 5.36 | -36.145 | 1 | 26.52 | O |
| ATOM | 2133 | CB | LYS | B | 107 | -4.763 | 5.846 | -38.749 | 1 | 24.14 | C |
| ATOM | 2134 | CG | LYS | B | 107 | -5.256 | 5.963 | -40.189 | 1 | 25.22 | C |
| ATOM | 2135 | CD | LYS | B | 107 | -4.169 | 6.41 | -41.147 | 1 | 30.82 | C |
| ATOM | 2136 | CE | LYS | B | 107 | -4.65 | 6.327 | -42.592 | 1 | 28.59 | C |
| ATOM | 2137 | NZ | LYS | B | 107 | -3.633 | 6.838 | -43.557 | 1 | 32.24 | N1+ |
| ATOM | 2138 | H | LYS | B | 107 | -7.653 | 6.068 | -38.157 | 1 | 32.1 | H |
| ATOM | 2139 | HA | LYS | B | 107 | -6.195 | 4.525 | -38.126 | 1 | 31.46 | H |
| ATOM | 2140 | HB2 | LYS | B | 107 | -4.453 | 6.721 | -38.466 | 1 | 28.97 | H |
| ATOM | 2141 | HB3 | LYS | B | 107 | -4.027 | 5.214 | -38.734 | 1 | 28.97 | H |
| ATOM | 2142 | HG2 | LYS | B | 107 | -5.578 | 5.097 | -40.483 | 1 | 30.27 | H |
| ATOM | 2143 | HG3 | LYS | B | 107 | -5.974 | 6.614 | -40.224 | 1 | 30.27 | H |
| ATOM | 2144 | HD2 | LYS | B | 107 | -3.93 | 7.331 | -40.957 | 1 | 36.98 | H |
| ATOM | 2145 | HD3 | LYS | B | 107 | -3.395 | 5.834 | -41.049 | 1 | 36.98 | H |
| ATOM | 2146 | HE2 | LYS | B | 107 | -4.836 | 5.401 | -42.812 | 1 | 34.3 | H |
| ATOM | 2147 | HE3 | LYS | B | 107 | -5.453 | 6.861 | -42.69 | 1 | 34.3 | H |
| ATOM | 2148 | HZ1 | LYS | B | 107 | -3.448 | 7.69 | -43.381 | 1 | 38.69 | H |
| ATOM | 2149 | HZ2 | LYS | B | 107 | -2.885 | 6.36 | -43.491 | 1 | 38.69 | H |
| ATOM | 2150 | HZ3 | LYS | B | 107 | -3.944 | 6.775 | -44.388 | 1 | 38.69 | H |
| ATOM | 2151 | N | ASN | B | 108 | -6.125 | 4.609 | -35.505 | 1 | 28.96 | N |
| ATOM | 2152 | CA | ASN | B | 108 | -5.729 | 4.193 | -34.16 | 1 | 35.2 | C |
| ATOM | 2153 | C | ASN | B | 108 | 5.175 | 5.334 | -33.306 | 1 | 33.16 | C |
| ATOM | 2154 | O | ASN | B | 108 | -4.472 | 5.094 | -32.324 | 1 | 35.7 | O |
| ATOM | 2155 | CB | ASN | B | 108 | -4.701 | 3.058 | -34.243 | 1 | 34 | C |
| ATOM | 2156 | CG | ASN | B | 108 | -5.251 | 1.82 | -34.927 | 1 | 38.47 | C |
| ATOM | 2157 | OD1 | ASN | B | 108 | -6.448 | 1.54 | -34.861 | 1 | 40.72 | O |
| ATOM | 2158 | ND2 | ASN | B | 108 | 4.377 | 1.071 | -35.589 | 1 | 50.98 | N |
| ATOM | 2159 | H | ASN | B | 108 | -6.964 | 4.5 | -35.66 | 1 | 34.75 | H |
| ATOM | 2160 | HA | ASN | B | 108 | -6.512 | 3.844 | -33.705 | 1 | 42.24 | H |
| ATOM | 2161 | HB2 | ASN | B | 108 | -3.932 | 3.364 | -34.749 | 1 | 40.8 | H |
| ATOM | 2162 | HB3 | ASN | B | 108 | -4.43 | 2.81 | -33.345 | 1 | 40.8 | H |
| ATOM | 2163 | HD21 | ASN | B | 108 | -3.548 | 0.359 | -35.993 | 1 | 61.17 | H |
| ATOM | 2164 | HD22 | ASN | B | 108 | -5.499 | 1.298 | -35.613 | 1 | 61.17 | H |
| ATOM | 2165 | N | ASN | B | 109 | -5.125 | 6.57 | -33.679 | 1 | 26.48 | N |
| ATOM | 2166 | CA | ASN | B | 109 | -6.311 | 7.739 | -32.888 | 1 | 25.08 | C |
| ATOM | 2167 | C | ASN | B | 109 | -7.165 | 8.665 | -32.655 | 1 | 23.92 | C |
| ATOM | 2168 | O | ASN | B | 109 | -3.994 | 8.828 | -33.526 | 1 | 25.78 | O |
| ATOM | 2169 | CB | ASN | B | 109 | -2.706 | 8.508 | -33.571 | 1 | 25.68 | C |
| ATOM | 2170 | CG | ASN | B | 109 | -2.107 | 7.718 | -33.624 | 1 | 28.52 | C |
| ATOM | 2171 | OD1 | ASN | B | 109 | -2.278 | 7.55 | -34.686 | 1 | 29.25 | O |
| ATOM | 2172 | ND2 | ASN | B | 109 | -5.94 | 7.221 | -32.474 | 1 | 28.6 | N |
| ATOM | 2173 | H | ASN | B | 109 | -4.804 | 6.759 | -34.393 | 1 | 31.78 | H |
| ATOM | 2174 | HA | ASN | B | 109 | -4.257 | 7.442 | -32.022 | 1 | 30.1 | H |
| ATOM | 2175 | HB2 | ASN | B | 109 | -3.825 | 8.715 | -34.482 | 1 | 30.82 | H |
| ATOM | 2176 | HB3 | ASN | B | 109 | -1.551 | 9.326 | -33.079 | 1 | 30.82 | H |
| ATOM | 2177 | HD21 | ASN | B | 109 | 2.728 | 6.763 | -32.448 | 1 | 34.32 | H |
| ATOM | 2178 | HD22 | ASN | B | 109 | -6.355 | 7.355 | -31.753 | 1 | 34.32 | H |
| ATOM | 2179 | N | CYS | B | 110 | -7.381 | 10.236 | -31.467 | 1 | 21.75 | N |
| ATOM | 2180 | CA | CYS | B | 110 | -6.754 | 11.621 | -31.115 | 1 | 19.96 | C |
| ATOM | 2181 | C | CYS | B | 110 | | | -31.065 | 1 | 20.85 | C |

TABLE 5-continued

Atomic Coordinates for OMCP-NKG2D (4PDC).

| | | | | | | | | | | |
|---|---|---|---|---|---|---|---|---|---|---|
| ATOM | 2182 | O | CYS | B | 110 | -5.632 | -30.591 | 11.768 | 1 | 18.06 | O |
| ATOM | 2183 | CB | CYS | B | 110 | -8.015 | -29.766 | 9.899 | 1 | 23.36 | C |
| ATOM | 2184 | SG | CYS | B | 110 | -8.365 | -29.523 | 8.144 | 1 | 28.07 | S |
| ATOM | 2185 | H | CYS | B | 110 | -5.789 | -30.836 | 9.116 | 1 | 26.1 | H |
| ATOM | 2186 | HA | CYS | B | 110 | -8.076 | -31.792 | 10.235 | 1 | 23.95 | H |
| ATOM | 2187 | HB2 | CYS | B | 110 | -7.411 | -29.061 | 10.18 | 1 | 28.03 | H |
| ATOM | 2188 | HB3 | CYS | B | 110 | -8.854 | -29.689 | 10.38 | 1 | 28.03 | H |
| ATOM | 2189 | N | TYR | B | 111 | -7.475 | -31.554 | 12.626 | 1 | 18.22 | N |
| ATOM | 2190 | CA | TYR | B | 111 | -6.973 | -31.572 | 13.997 | 1 | 16.26 | C |
| ATOM | 2191 | C | TYR | B | 111 | -8.02 | -31.11 | 14.998 | 1 | 18.87 | C |
| ATOM | 2192 | O | TYR | B | 111 | -9.212 | -31.37 | 14.83 | 1 | 17.84 | O |
| ATOM | 2193 | CB | TYR | B | 111 | -6.517 | -32.977 | 14.392 | 1 | 16.69 | C |
| ATOM | 2194 | CG | TYR | B | 111 | -5.434 | -33.571 | 13.532 | 1 | 17.24 | C |
| ATOM | 2195 | CD1 | TYR | B | 111 | -4.095 | -33.292 | 13.773 | 1 | 20.23 | C |
| ATOM | 2196 | CD2 | TYR | B | 111 | -5.747 | -34.436 | 12.493 | 1 | 19.87 | C |
| ATOM | 2197 | CE1 | TYR | B | 111 | -3.102 | -33.843 | 12.992 | 1 | 17.86 | C |
| ATOM | 2198 | CE2 | TYR | B | 111 | -4.763 | -34.994 | 11.71 | 1 | 19.29 | C |
| ATOM | 2199 | CZ | TYR | B | 111 | -3.443 | -34.696 | 11.962 | 1 | 19.83 | C |
| ATOM | 2200 | OH | TYR | B | 111 | -2.463 | -35.251 | 11.177 | 1 | 21.43 | O |
| ATOM | 2201 | H | TYR | B | 111 | -8.264 | -31.884 | 12.539 | 1 | 21.87 | H |
| ATOM | 2202 | HA | TYR | B | 111 | -6.209 | -30.977 | 14.064 | 1 | 19.51 | H |
| ATOM | 2203 | HB2 | TYR | B | 111 | -7.282 | -33.571 | 14.349 | 1 | 20.03 | H |
| ATOM | 2204 | HB3 | TYR | B | 111 | -6.181 | -32.947 | 15.302 | 1 | 20.03 | H |
| ATOM | 2205 | HD1 | TYR | B | 111 | -3.865 | -32.717 | 14.467 | 1 | 24.28 | H |
| ATOM | 2206 | HD2 | TYR | B | 111 | -6.638 | -34.639 | 12.321 | 1 | 23.85 | H |
| ATOM | 2207 | HE1 | TYR | B | 111 | -2.21 | -33.644 | 13.16 | 1 | 21.44 | H |
| ATOM | 2208 | HE2 | TYR | B | 111 | -4.988 | -35.568 | 11.013 | 1 | 23.14 | H |
| ATOM | 2209 | HH | TYR | B | 111 | -2.809 | -35.746 | 10.593 | 1 | 25.72 | H |
| ATOM | 2210 | N | GLN | B | 112 | -7.573 | -30.444 | 16.055 | 1 | 16.37 | N |
| ATOM | 2211 | CA | GLN | B | 112 | -8.44 | -30.183 | 17.199 | 1 | 18.53 | C |
| ATOM | 2212 | C | GLN | B | 112 | -7.66 | -30.315 | 18.496 | 1 | 18.9 | C |
| ATOM | 2213 | O | GLN | B | 112 | -6.506 | -29.89 | 18.591 | 1 | 13.32 | O |
| ATOM | 2214 | CB | GLN | B | 112 | -9.083 | -28.798 | 17.104 | 1 | 18.31 | C |
| ATOM | 2215 | CG | GLN | B | 112 | -10.016 | -28.458 | 18.266 | 1 | 20.42 | C |
| ATOM | 2216 | CD | GLN | B | 112 | -11.205 | -29.402 | 18.373 | 1 | 22.22 | C |
| ATOM | 2217 | OE1 | GLN | B | 112 | -11.057 | -30.575 | 18.71 | 1 | 23.6 | O |
| ATOM | 2218 | NE2 | GLN | B | 112 | -12.395 | -28.886 | 18.088 | 1 | 27.09 | N |
| ATOM | 2219 | H | GLN | B | 112 | -6.638 | -30.133 | 16.136 | 1 | 19.65 | H |
| ATOM | 2220 | HA | GLN | B | 112 | -9.152 | -30.842 | 17.21 | 1 | 22.24 | H |
| ATOM | 2221 | HB2 | GLN | B | 112 | -9.601 | -28.751 | 16.285 | 1 | 21.98 | H |
| ATOM | 2222 | HB3 | GLN | B | 112 | -8.38 | -28.13 | 17.085 | 1 | 21.98 | H |
| ATOM | 2223 | HG2 | GLN | B | 112 | -10.359 | -27.559 | 18.142 | 1 | 24.51 | H |
| ATOM | 2224 | HG3 | GLN | B | 112 | -9.517 | -28.511 | 19.096 | 1 | 24.51 | H |
| ATOM | 2225 | HE21 | GLN | B | 112 | -13.099 | -29.378 | 18.134 | 1 | 32.51 | H |
| ATOM | 2226 | HE22 | GLN | B | 112 | -12.462 | -28.06 | 17.858 | 1 | 32.51 | H |
| ATOM | 2227 | N | PHE | B | 113 | -8.309 | -30.923 | 19.484 | 1 | 17.31 | N |
| ATOM | 2228 | CA | PHE | B | 113 | -7.731 | -31.141 | 20.801 | 1 | 18.02 | C |
| ATOM | 2229 | C | PHE | B | 113 | -8.352 | -30.178 | 21.798 | 1 | 19.91 | C |
| ATOM | 2230 | O | PHE | B | 113 | -9.508 | -32.583 | 21.259 | 1 | 25.64 | O |
| ATOM | 2231 | CB | PHE | B | 113 | -7.961 | -32.583 | 21.259 | 1 | 16.63 | C |
| ATOM | 2232 | CG | PHE | B | 113 | -7.265 | -33.612 | 20.414 | 1 | 20.32 | C |

TABLE 5-continued

Atomic Coordinates for OMCP-NKG2D (4PDC).

| | | | | | | | | | |
|---|---|---|---|---|---|---|---|---|---|
| ATOM | 2233 | CD1 | PHE | B | 113 | -7.73 | -33.92 | 19.144 | 1 | 23.5 | C |
| ATOM | 2234 | CD2 | PHE | B | 113 | -6.158 | -34.285 | 20.898 | 1 | 20.35 | C |
| ATOM | 2235 | CE1 | PHE | B | 113 | 7.092 | -34.87 | 18.371 | 1 | 25.58 | C |
| ATOM | 2236 | CE2 | PHE | B | 113 | -5.515 | -35.235 | 20.128 | 1 | 24.89 | C |
| ATOM | 2237 | CZ | PHE | B | 113 | -5.984 | -35.529 | 18.863 | 1 | 28.96 | C |
| ATOM | 2238 | H | PHE | B | 113 | -9.11 | -31.227 | 19.41 | 1 | 20.77 | H |
| ATOM | 2239 | HA | PHE | B | 113 | -6.775 | -30.977 | 20.767 | 1 | 21.62 | H |
| ATOM | 2240 | HB2 | PHE | B | 113 | 8.913 | -32.77 | 21.23 | 1 | 19.95 | H |
| ATOM | 2241 | HB3 | PHE | B | 113 | -7.636 | -32.677 | 22.168 | 1 | 19.95 | H |
| ATOM | 2242 | HD1 | PHE | B | 113 | -8.475 | -33.478 | 18.807 | 1 | 28.2 | H |
| ATOM | 2243 | HD2 | PHE | B | 113 | -5.837 | -34.09 | 21.749 | 1 | 24.42 | H |
| ATOM | 2244 | HE1 | PHE | B | 113 | -7.41 | -35.066 | 17.519 | 1 | 30.7 | H |
| ATOM | 2245 | HE2 | PHE | B | 113 | -4.769 | -35.678 | 20.463 | 1 | 29.86 | H |
| ATOM | 2246 | HZ | PHE | B | 113 | -5.554 | -36.17 | 18.344 | 1 | 34.75 | H |
| ATOM | 2247 | N | PHE | B | 113 | -7.589 | -29.173 | 22.215 | 1 | 18.14 | N |
| ATOM | 2248 | CA | PHE | B | 114 | -8.09 | -28.167 | 23.146 | 1 | 16.48 | C |
| ATOM | 2249 | C | PHE | B | 114 | -7.775 | -28.554 | 24.587 | 1 | 19.56 | C |
| ATOM | 2250 | O | PHE | B | 114 | -6.611 | -28.675 | 24.962 | 1 | 18.71 | O |
| ATOM | 2251 | CB | PHE | B | 114 | -7.496 | -26.799 | 22.821 | 1 | 19.55 | C |
| ATOM | 2252 | CG | PHE | B | 114 | -7.961 | -26.237 | 21.508 | 1 | 21.13 | C |
| ATOM | 2253 | CD1 | PHE | B | 114 | -7.233 | -26.45 | 20.352 | 1 | 21.85 | C |
| ATOM | 2254 | CD2 | PHE | B | 114 | -9.132 | -25.501 | 21.429 | 1 | 27.16 | C |
| ATOM | 2255 | CE1 | PHE | B | 114 | -7.658 | -25.935 | 19.14 | 1 | 21.25 | C |
| ATOM | 2256 | CE2 | PHE | B | 114 | -9.564 | -24.984 | 20.218 | 1 | 27.33 | C |
| ATOM | 2257 | CZ | PHE | B | 114 | -8.824 | -25.202 | 19.074 | 1 | 22.66 | C |
| ATOM | 2258 | H | PHE | B | 114 | -6.773 | -29.05 | 21.972 | 1 | 21.76 | H |
| ATOM | 2259 | HA | PHE | B | 114 | -9.054 | -28.105 | 23.056 | 1 | 19.78 | H |
| ATOM | 2260 | HB2 | PHE | B | 114 | -6.53 | -26.878 | 22.785 | 1 | 23.47 | H |
| ATOM | 2261 | HB3 | PHE | B | 114 | -7.75 | -26.174 | 23.518 | 1 | 23.47 | H |
| ATOM | 2262 | HD1 | PHE | B | 114 | -6.445 | -26.942 | 20.391 | 1 | 26.22 | H |
| ATOM | 2263 | HD2 | PHE | B | 114 | -9.633 | -25.351 | 22.198 | 1 | 32.6 | H |
| ATOM | 2264 | HE1 | PHE | B | 114 | -7.158 | -26.084 | 18.37 | 1 | 25.5 | H |
| ATOM | 2265 | HE2 | PHE | B | 114 | -10.351 | -24.49 | 20.176 | 1 | 32.79 | H |
| ATOM | 2266 | HZ | PHE | B | 114 | -9.111 | -24.856 | 18.26 | 1 | 27.2 | H |
| ATOM | 2267 | N | ASP | B | 115 | -8.82 | -28.738 | 25.391 | 1 | 19.34 | N |
| ATOM | 2268 | CA | ASP | B | 115 | -8.666 | -29.234 | 26.759 | 1 | 22.18 | C |
| ATOM | 2269 | C | ASP | B | 115 | -8.421 | -28.121 | 27.778 | 1 | 22.24 | C |
| ATOM | 2270 | O | ASP | B | 115 | -8.374 | -28.375 | 28.983 | 1 | 23.21 | O |
| ATOM | 2271 | CB | ASP | B | 115 | -9.896 | -30.053 | 27.172 | 1 | 28.95 | C |
| ATOM | 2272 | CG | ASP | B | 115 | -11.204 | -29.31 | 26.959 | 1 | 30.69 | C |
| ATOM | 2273 | OD1 | ASP | B | 115 | -11.201 | -28.06 | 26.953 | 1 | 36.27 | O |
| ATOM | 2274 | OD2 | ASP | B | 115 | -12.244 | -29.985 | 26.8 | 1 | 43.5 | O1- |
| ATOM | 2275 | H | ASP | B | 115 | -9.636 | -28.582 | 25.167 | 1 | 23.21 | H |
| ATOM | 2276 | HA | ASP | B | 115 | -7.898 | -29.826 | 26.786 | 1 | 26.62 | H |
| ATOM | 2277 | HB2 | ASP | B | 115 | 9.827 | -30.272 | 28.115 | 1 | 34.74 | H |
| ATOM | 2278 | HB3 | ASP | B | 115 | -9.925 | -30.866 | 26.645 | 1 | 21.76 | H |
| ATOM | 2279 | N | GLU | B | 116 | -8.267 | -26.892 | 27.295 | 1 | 25.37 | N |
| ATOM | 2280 | CA | GLU | B | 116 | -7.861 | -25.782 | 28.151 | 1 | 26.04 | C |
| ATOM | 2281 | C | GLU | B | 116 | -6.344 | -25.771 | 28.309 | 1 | 26.31 | C |
| ATOM | 2282 | O | GLU | B | 116 | -5.61 | -25.778 | 27.323 | 1 | 26.31 | O |
| ATOM | 2283 | CB | GLU | B | 116 | -8.34 | -24.447 | 27.578 | 1 | 30.28 | C |

TABLE 5-continued

Atomic Coordinates for OMCP-NKG2D (4PDC).

| ATOM | 2284 | CG | GLU | B | 116 | -9.811 | 27.839 | -24.153 | 1 | 43.86 | C |
|---|---|---|---|---|---|---|---|---|---|---|---|
| ATOM | 2285 | CD | GLU | B | 116 | -10.256 | 27.25 | -22.827 | 1 | 59.8 | C |
| ATOM | 2286 | OE1 | GLU | B | 116 | -9.383 | 26.828 | -22.037 | 1 | 55.77 | O |
| ATOM | 2287 | OE2 | GLU | B | 116 | -11.48 | 27.208 | -22.576 | 1 | 69.76 | O1- |
| ATOM | 2288 | H | GLU | B | 116 | -8.391 | 26.473 | -26.674 | 1 | 26.11 | H |
| ATOM | 2289 | HA | GLU | B | 116 | -8.256 | 29.029 | -25.895 | 1 | 30.45 | H |
| ATOM | 2290 | HB2 | GLU | B | 116 | -8.205 | 26.618 | -24.453 | 1 | 36.34 | H |
| ATOM | 2291 | HB3 | GLU | B | 116 | -7.82 | 27.978 | -23.732 | 1 | 36.34 | H |
| ATOM | 2292 | HG2 | GLU | B | 116 | -9.963 | 28.796 | -24.123 | 1 | 52.63 | H |
| ATOM | 2293 | HG3 | GLU | B | 116 | -10.349 | 27.439 | -24.855 | 1 | 52.63 | H |
| ATOM | 2294 | N | SER | B | 117 | -5.878 | 29.551 | -25.757 | 1 | 24.25 | N |
| ATOM | 2295 | CA | SER | B | 117 | -4.446 | 29.825 | -25.766 | 1 | 24.22 | C |
| ATOM | 2296 | C | SER | B | 117 | -3.832 | 29.548 | -24.401 | 1 | 24.91 | C |
| ATOM | 2297 | O | SER | B | 117 | -4.271 | 30.095 | -23.39 | 1 | 25.88 | O |
| ATOM | 2298 | CB | SER | B | 117 | -4.179 | 31.275 | -26.178 | 1 | 25.72 | C |
| ATOM | 2299 | OG | SER | B | 117 | -4.568 | 31.501 | -27.519 | 1 | 35.43 | O |
| ATOM | 2300 | H | SER | B | 117 | -6.371 | 30.256 | -25.743 | 1 | 29.1 | H |
| ATOM | 2301 | HA | SER | B | 117 | -4.017 | 29.244 | -26.413 | 1 | 29.07 | H |
| ATOM | 2302 | HB2 | SER | B | 117 | -4.687 | 31.865 | -25.599 | 1 | 30.86 | H |
| ATOM | 2303 | HB3 | SER | B | 117 | -3.231 | 31.458 | -26.089 | 1 | 30.86 | H |
| ATOM | 2304 | HG | SER | B | 117 | -4.416 | 32.299 | -27.731 | 1 | 42.52 | H |
| ATOM | 2305 | N | LYS | B | 118 | -2.815 | 28.692 | -24.384 | 1 | 17.66 | N |
| ATOM | 2306 | CA | LYS | B | 118 | -2.093 | 28.355 | -23.163 | 1 | 23.06 | C |
| ATOM | 2307 | C | LYS | B | 118 | -0.612 | 28.252 | -23.478 | 1 | 21.34 | C |
| ATOM | 2308 | O | LYS | B | 118 | -0.238 | 27.982 | -24.623 | 1 | 18.83 | O |
| ATOM | 2309 | CB | LYS | B | 118 | -2.597 | 27.035 | -22.571 | 1 | 22.84 | C |
| ATOM | 2310 | CG | LYS | B | 118 | -4.06 | 27.046 | -22.162 | 1 | 24.02 | C |
| ATOM | 2311 | CD | LYS | B | 118 | -4.473 | 25.704 | -21.567 | 1 | 26.42 | C |
| ATOM | 2312 | CE | LYS | B | 118 | -5.958 | 25.669 | -21.232 | 1 | 32.25 | C |
| ATOM | 2313 | NZ | LYS | B | 118 | -6.343 | 26.77 | -20.307 | 1 | 35.19 | N1+ |
| ATOM | 2314 | H | LYS | B | 118 | -2.518 | 28.286 | -25.082 | 1 | 21.19 | H |
| ATOM | 2315 | HA | LYS | B | 118 | -2.222 | 29.057 | -22.506 | 1 | 27.68 | H |
| ATOM | 2316 | HB2 | LYS | B | 118 | -2.481 | 26.335 | -23.231 | 1 | 27.41 | H |
| ATOM | 2317 | HB3 | LYS | B | 118 | -2.072 | 26.83 | -21.781 | 1 | 27.41 | H |
| ATOM | 2318 | HG2 | LYS | B | 118 | -4.202 | 27.733 | -21.492 | 1 | 28.83 | H |
| ATOM | 2319 | HG3 | LYS | B | 118 | -4.611 | 27.216 | -22.942 | 1 | 28.83 | H |
| ATOM | 2320 | HD2 | LYS | B | 118 | -4.29 | 25 | -22.209 | 1 | 31.7 | H |
| ATOM | 2321 | HD3 | LYS | B | 118 | -3.974 | 25.55 | -20.749 | 1 | 31.7 | H |
| ATOM | 2322 | HE2 | LYS | B | 118 | -6.471 | 25.767 | -22.049 | 1 | 38.7 | H |
| ATOM | 2323 | HE3 | LYS | B | 118 | -6.168 | 24.825 | -20.803 | 1 | 38.7 | H |
| ATOM | 2324 | HZ1 | LYS | B | 118 | -5.888 | 26.7 | -19.545 | 1 | 42.23 | H |
| ATOM | 2325 | HZ2 | LYS | B | 118 | -6.164 | 27.557 | -20.68 | 1 | 42.23 | H |
| ATOM | 2326 | HZ3 | LYS | B | 118 | -7.214 | 26.726 | -20.129 | 1 | 42.23 | H |
| ATOM | 2327 | N | ASN | B | 119 | 0.236 | 28.473 | -22.478 | 1 | 16.27 | N |
| ATOM | 2328 | CA | ASN | B | 119 | 1.659 | 28.241 | -22.668 | 1 | 20.3 | C |
| ATOM | 2329 | C | ASN | B | 119 | 1.878 | 26.738 | -22.763 | 1 | 16.48 | C |
| ATOM | 2330 | O | ASN | B | 119 | 0.946 | 25.951 | -22.569 | 1 | 17.62 | O |
| ATOM | 2331 | CB | ASN | B | 119 | 2.499 | 28.869 | -21.542 | 1 | 19.64 | C |
| ATOM | 2332 | CG | ASN | B | 119 | 2.262 | 28.228 | -20.183 | 1 | 20.65 | C |
| ATOM | 2333 | OD1 | ASN | B | 119 | 2.498 | 27.035 | -19.986 | 1 | 17.21 | O |
| ATOM | 2334 | ND2 | ASN | B | 119 | 1.823 | 29.036 | -19.224 | 1 | 20.04 | N |

TABLE 5-continued

Atomic Coordinates for OMCP-NKG2D (4PDC).

| ATOM | 2335 | H | ASN | B | 119 | 0.016 | 28.753 | -21.695 | 1 | 19.52 | H |
|---|---|---|---|---|---|---|---|---|---|---|---|
| ATOM | 2336 | HA | ASN | B | 119 | 1.936 | 28.639 | -23.508 | 1 | 24.36 | H |
| ATOM | 2337 | HB2 | ASN | B | 119 | 3.439 | 28.769 | -21.759 | 1 | 23.57 | H |
| ATOM | 2338 | HB3 | ASN | B | 119 | 2.275 | 29.81 | -21.471 | 1 | 23.57 | H |
| ATOM | 2339 | HD21 | ASN | B | 119 | 1.673 | 28.726 | -18.436 | 1 | 24.05 | H |
| ATOM | 2340 | HD22 | ASN | B | 119 | 1.691 | 29.869 | -19.391 | 1 | 24.05 | H |
| ATOM | 2341 | N | TRP | B | 120 | 3.102 | 26.333 | -19.067 | 1 | 15.24 | N |
| ATOM | 2342 | CA | TRP | B | 120 | 3.362 | 24.93 | -23.348 | 1 | 16.04 | C |
| ATOM | 2343 | C | TRP | B | 120 | 3.052 | 24.039 | -22.148 | 1 | 19.13 | C |
| ATOM | 2344 | O | TRP | B | 120 | 2.588 | 22.909 | -22.313 | 1 | 15.63 | O |
| ATOM | 2345 | CB | TRP | B | 120 | 4.813 | 24.733 | -23.779 | 1 | 16.87 | C |
| ATOM | 2346 | CG | TRP | B | 120 | 5.085 | 23.34 | -24.242 | 1 | 15.71 | C |
| ATOM | 2347 | CD1 | TRP | B | 120 | 5.006 | 22.874 | -25.52 | 1 | 15.03 | C |
| ATOM | 2348 | CD2 | TRP | B | 120 | 5.465 | 22.226 | -23.431 | 1 | 19.26 | C |
| ATOM | 2349 | NE1 | TRP | B | 120 | 5.318 | 21.54 | -25.558 | 1 | 16.56 | N |
| ATOM | 2350 | CE2 | TRP | B | 120 | 5.604 | 21.116 | -24.288 | 1 | 19.91 | C |
| ATOM | 2351 | CE3 | TRP | B | 120 | 5.703 | 22.059 | -22.064 | 1 | 20.14 | C |
| ATOM | 2352 | CZ2 | TRP | B | 120 | 5.972 | 19.856 | -23.823 | 1 | 20.45 | C |
| ATOM | 2353 | CZ3 | TRP | B | 120 | 6.068 | 20.807 | -21.604 | 1 | 24 | C |
| ATOM | 2354 | CH2 | TRP | B | 120 | 6.199 | 19.721 | -22.482 | 1 | 20.1 | C |
| ATOM | 2355 | H | TRP | B | 120 | 3.792 | 26.844 | -23.117 | 1 | 18.29 | H |
| ATOM | 2356 | HA | TRP | B | 120 | 2.793 | 24.648 | -24.082 | 1 | 19.25 | H |
| ATOM | 2357 | HB2 | TRP | B | 120 | 5.012 | 25.338 | -24.51 | 1 | 20.25 | H |
| ATOM | 2358 | HB3 | TRP | B | 120 | 5.395 | 24.918 | -23.025 | 1 | 20.25 | H |
| ATOM | 2359 | HD1 | TRP | B | 120 | 4.775 | 23.387 | -26.261 | 1 | 18.03 | H |
| ATOM | 2360 | HE1 | TRP | B | 120 | 5.332 | 21.049 | -26.264 | 1 | 19.88 | H |
| ATOM | 2361 | HE3 | TRP | B | 120 | 5.618 | 22.775 | -21.476 | 1 | 24.16 | H |
| ATOM | 2362 | HZ2 | TRP | B | 120 | 6.06 | 19.134 | -24.403 | 1 | 24.54 | H |
| ATOM | 2363 | HZ3 | TRP | B | 120 | 6.23 | 20.683 | -20.697 | 1 | 28.8 | H |
| ATOM | 2364 | HH2 | TRP | B | 120 | 6.446 | 18.891 | -22.144 | 1 | 24.12 | H |
| ATOM | 2365 | N | TYR | B | 121 | 3.297 | 24.553 | -20.946 | 1 | 20.9 | N |
| ATOM | 2366 | CA | TYR | B | 121 | 3.179 | 23.75 | -19.733 | 1 | 19.53 | C |
| ATOM | 2367 | C | TYR | B | 121 | 1.735 | 23.563 | -19.268 | 1 | 17.33 | C |
| ATOM | 2368 | O | TYR | B | 121 | 1.386 | 22.498 | -18.763 | 1 | 20.12 | O |
| ATOM | 2369 | CB | TYR | B | 121 | 4.006 | 24.375 | -18.612 | 1 | 20.76 | C |
| ATOM | 2370 | CG | TYR | B | 121 | 5.479 | 24.438 | -18.945 | 1 | 27.57 | C |
| ATOM | 2371 | CD1 | TYR | B | 121 | 6.266 | 23.294 | -18.909 | 1 | 26.72 | C |
| ATOM | 2372 | CD2 | TYR | B | 121 | 6.077 | 25.635 | -19.312 | 1 | 22 | C |
| ATOM | 2373 | CE1 | TYR | B | 121 | 7.607 | 23.343 | -19.222 | 1 | 27.02 | C |
| ATOM | 2374 | CE2 | TYR | B | 121 | 7.416 | 25.693 | -19.623 | 1 | 29.21 | C |
| ATOM | 2375 | CZ | TYR | B | 121 | 8.175 | 24.544 | -19.578 | 1 | 30.61 | C |
| ATOM | 2376 | OH | TYR | B | 121 | 9.511 | 24.599 | -19.891 | 1 | 42.9 | O |
| ATOM | 2377 | H | TYR | B | 121 | 3.533 | 25.368 | -20.805 | 1 | 25.08 | H |
| ATOM | 2378 | HA | TYR | B | 121 | 3.545 | 22.869 | -19.911 | 1 | 23.43 | H |
| ATOM | 2379 | HB2 | TYR | B | 121 | 3.694 | 25.28 | -18.455 | 1 | 24.91 | H |
| ATOM | 2380 | HB3 | TYR | B | 121 | 3.902 | 23.843 | -17.807 | 1 | 24.91 | H |
| ATOM | 2381 | HD1 | TYR | B | 121 | 5.882 | 22.481 | -18.67 | 1 | 32.06 | H |
| ATOM | 2382 | HD2 | TYR | B | 121 | 5.565 | 26.411 | -19.344 | 1 | 26.41 | H |
| ATOM | 2383 | HE1 | TYR | B | 121 | 8.124 | 22.57 | -19.192 | 1 | 32.42 | H |
| ATOM | 2384 | HE2 | TYR | B | 121 | 7.805 | 26.502 | -19.866 | 1 | 35.05 | H |
| ATOM | 2385 | HH | TYR | B | 121 | 9.728 | 25.386 | -20.088 | 1 | 51.48 | H |

TABLE 5-continued

Atomic Coordinates for OMCP-NKG2D (4PDC).

| | | | | | | | | | | |
|---|---|---|---|---|---|---|---|---|---|---|
| ATOM | 2386 | N | GLU | B | 122 | 0.899 | -19.418 | 24.586 | 1 | 19.17 | N |
| ATOM | 2387 | CA | GLU | B | 122 | -0.514 | -19.074 | 24.422 | 1 | 20.84 | C |
| ATOM | 2388 | C | GLU | B | 122 | -1.187 | -20.161 | 23.598 | 1 | 20.4 | C |
| ATOM | 2389 | O | GLU | B | 122 | -2.164 | -19.895 | 22.904 | 1 | 23.74 | O |
| ATOM | 2390 | CB | GLU | B | 122 | -1.24 | -18.887 | 25.765 | 1 | 25.11 | C |
| ATOM | 2391 | CG | GLU | B | 122 | -0.55 | -19.475 | 26.974 | 1 | 30.11 | C |
| ATOM | 2392 | CD | GLU | B | 122 | -1.378 | -19.377 | 28.248 | 1 | 32.89 | C |
| ATOM | 2393 | OE1 | GLU | B | 122 | -2.424 | -18.687 | 28.235 | 1 | 36.08 | O |
| ATOM | 2394 | OE2 | GLU | B | 122 | -0.975 | -19.988 | 29.264 | 1 | 26.01 | O1- |
| ATOM | 2395 | H | GLU | B | 122 | 1.114 | -19.709 | 25.366 | 1 | 23.01 | H |
| ATOM | 2396 | HA | GLU | B | 122 | -0.58 | -18.241 | 23.929 | 1 | 25 | H |
| ATOM | 2397 | HB2 | GLU | B | 122 | -2.114 | -19.303 | 25.699 | 1 | 30.13 | H |
| ATOM | 2398 | HB3 | GLU | B | 122 | -1.346 | -17.937 | 25.925 | 1 | 30.13 | H |
| ATOM | 2399 | HG2 | GLU | B | 122 | 0.283 | -19 | 27.123 | 1 | 36.13 | H |
| ATOM | 2400 | HG3 | GLU | B | 122 | -0.369 | -20.414 | 26.807 | 1 | 36.13 | H |
| ATOM | 2401 | N | SER | B | 123 | -0.657 | -21.382 | 23.676 | 1 | 17.88 | N |
| ATOM | 2402 | CA | SER | B | 123 | -1.132 | -22.477 | 22.838 | 1 | 18.47 | C |
| ATOM | 2403 | C | SER | B | 123 | -0.844 | -22.16 | 21.374 | 1 | 17.37 | C |
| ATOM | 2404 | O | SER | B | 123 | -1.706 | -22.321 | 20.515 | 1 | 17.15 | O |
| ATOM | 2405 | CB | SER | B | 123 | -0.472 | -23.805 | 23.23 | 1 | 17.79 | C |
| ATOM | 2406 | OG | SER | B | 123 | -0.916 | -24.251 | 24.501 | 1 | 16.72 | O |
| ATOM | 2407 | H | SER | B | 123 | -0.019 | -21.6 | 24.209 | 1 | 21.45 | H |
| ATOM | 2408 | HA | SER | B | 123 | -2.091 | -22.571 | 22.946 | 1 | 22.17 | H |
| ATOM | 2409 | HB2 | SER | B | 123 | 0.49 | -23.68 | 23.261 | 1 | 21.34 | H |
| ATOM | 2410 | HB3 | SER | B | 123 | -0.697 | -24.475 | 22.567 | 1 | 21.34 | H |
| ATOM | 2411 | HG | SER | B | 123 | -0.727 | -23.681 | 25.088 | 1 | 20.06 | H |
| ATOM | 2412 | N | GLN | B | 124 | 0.376 | -21.709 | 21.105 | 1 | 17.12 | N |
| ATOM | 2413 | CA | GLN | B | 124 | 0.765 | -21.286 | 19.765 | 1 | 19.26 | C |
| ATOM | 2414 | C | GLN | B | 124 | -0.119 | -20.156 | 19.251 | 1 | 17.95 | C |
| ATOM | 2415 | O | GLN | B | 124 | -0.516 | -20.153 | 18.086 | 1 | 18.47 | O |
| ATOM | 2416 | CB | GLN | B | 124 | 2.225 | -20.831 | 19.751 | 1 | 19.97 | C |
| ATOM | 2417 | CG | GLN | B | 124 | 2.631 | -20.125 | 18.463 | 1 | 20.4 | C |
| ATOM | 2418 | CD | GLN | B | 124 | 4.098 | -19.763 | 18.437 | 1 | 25.03 | C |
| ATOM | 2419 | OE1 | GLN | B | 124 | 4.522 | -18.811 | 19.09 | 1 | 29 | O |
| ATOM | 2420 | NE2 | GLN | B | 124 | 4.884 | -20.523 | 17.686 | 1 | 22.34 | N |
| ATOM | 2421 | H | GLN | B | 124 | 1.004 | -21.639 | 21.688 | 1 | 20.54 | H |
| ATOM | 2422 | HA | GLN | B | 124 | 0.678 | -22.037 | 19.158 | 1 | 23.11 | H |
| ATOM | 2423 | HB2 | GLN | B | 124 | 2.797 | -21.607 | 19.856 | 1 | 23.97 | H |
| ATOM | 2424 | HB3 | GLN | B | 124 | 2.369 | -20.214 | 20.485 | 1 | 23.97 | H |
| ATOM | 2425 | HG2 | GLN | B | 124 | 2.118 | -19.307 | 18.376 | 1 | 24.48 | H |
| ATOM | 2426 | HG3 | GLN | B | 124 | 2.452 | -20.711 | 17.711 | 1 | 24.48 | H |
| ATOM | 2427 | HE21 | GLN | B | 124 | 5.726 | -20.356 | 17.639 | 1 | 26.81 | H |
| ATOM | 2428 | HE22 | GLN | B | 124 | 4.551 | -21.183 | 17.246 | 1 | 26.81 | H |
| ATOM | 2429 | N | ALA | B | 125 | -0.397 | -19.186 | 20.118 | 1 | 19.16 | N |
| ATOM | 2430 | CA | ALA | B | 125 | -1.234 | -18.05 | 19.754 | 1 | 21.66 | C |
| ATOM | 2431 | C | ALA | B | 125 | -2.65 | -18.513 | 19.437 | 1 | 22.92 | C |
| ATOM | 2432 | O | ALA | B | 125 | -3.292 | -17.996 | 18.528 | 1 | 22.29 | O |
| ATOM | 2433 | CB | ALA | B | 125 | -1.251 | -17.021 | 20.873 | 1 | 21.65 | C |
| ATOM | 2434 | H | ALA | B | 125 | -0.111 | -19.164 | 20.928 | 1 | 23 | H |
| ATOM | 2435 | HA | ALA | B | 125 | -0.87 | -17.627 | 18.961 | 1 | 26 | H |
| ATOM | 2436 | HB1 | ALA | B | 125 | -1.813 | -16.276 | 20.609 | 1 | 25.98 | H |

TABLE 5-continued

Atomic Coordinates for OMCP-NKG2D (4PDC).

| | | | | | | | | | | |
|---|---|---|---|---|---|---|---|---|---|---|
| ATOM | 2437 | HB2 | ALA | B | 125 | -0.345 | -16.712 | 21.032 | 1 | 25.98 | H |
| ATOM | 2438 | HB3 | ALA | B | 125 | -1.605 | -17.434 | 21.676 | 1 | 25.98 | H |
| ATOM | 2439 | N | SER | B | 126 | -3.129 | -19.491 | 20.199 | 1 | 19.48 | N |
| ATOM | 2440 | CA | SER | B | 126 | -4.467 | -20.035 | 20.008 | 1 | 22.96 | C |
| ATOM | 2441 | C | SER | B | 126 | -4.622 | -20.696 | 18.638 | 1 | 24.3 | C |
| ATOM | 2442 | O | SER | B | 126 | -5.617 | -20.474 | 17.945 | 1 | 23.17 | O |
| ATOM | 2443 | CB | SER | B | 126 | -4.79 | -21.042 | 21.113 | 1 | 21.51 | C |
| ATOM | 2444 | OG | SER | B | 126 | -6.033 | -21.679 | 20.874 | 1 | 26.37 | O |
| ATOM | 2445 | H | SER | B | 126 | -2.692 | -19.861 | 20.841 | 1 | 23.37 | H |
| ATOM | 2446 | HA | SER | B | 126 | -5.111 | -19.311 | 20.065 | 1 | 27.56 | H |
| ATOM | 2447 | HB2 | SER | B | 126 | -4.833 | -20.575 | 21.962 | 1 | 25.81 | H |
| ATOM | 2448 | HB3 | SER | B | 126 | -4.091 | -21.714 | 21.14 | 1 | 25.81 | H |
| ATOM | 2449 | HG | SER | B | 126 | -6.197 | -22.228 | 21.488 | 1 | 31.64 | H |
| ATOM | 2450 | N | CYS | B | 127 | -3.646 | -21.511 | 18.251 | 1 | 19.38 | N |
| ATOM | 2451 | CA | CYS | B | 127 | -3.696 | -22.182 | 16.956 | 1 | 17.72 | C |
| ATOM | 2452 | C | CYS | B | 127 | -3.596 | -21.158 | 15.833 | 1 | 23.86 | C |
| ATOM | 2453 | O | CYS | B | 127 | -4.292 | -21.262 | 14.824 | 1 | 24.87 | O |
| ATOM | 2454 | CB | CYS | B | 127 | -2.574 | -23.215 | 16.829 | 1 | 16.67 | C |
| ATOM | 2455 | SG | CYS | B | 127 | -2.664 | -24.573 | 18.028 | 1 | 18.01 | S |
| ATOM | 2456 | H | CYS | B | 127 | -2.946 | -21.692 | 18.717 | 1 | 23.26 | H |
| ATOM | 2457 | HA | CYS | B | 127 | -4.544 | -22.644 | 16.869 | 1 | 21.26 | H |
| ATOM | 2458 | HB2 | CYS | B | 127 | -1.724 | -22.766 | 16.956 | 1 | 20.01 | H |
| ATOM | 2459 | HB3 | CYS | B | 127 | -2.61 | -23.603 | 15.941 | 1 | 20.01 | H |
| ATOM | 2460 | N | MET | B | 128 | -2.728 | -20.169 | 16.014 | 1 | 21.99 | N |
| ATOM | 2461 | CA | MET | B | 128 | -2.562 | -19.119 | 15.018 | 1 | 30.3 | C |
| ATOM | 2462 | C | MET | B | 128 | -3.878 | -18.387 | 14.767 | 1 | 27.68 | C |
| ATOM | 2463 | O | MET | B | 128 | -4.261 | -18.166 | 13.62 | 1 | 33.94 | O |
| ATOM | 2464 | CB | MET | B | 128 | -1.491 | -18.115 | 15.452 | 1 | 27.2 | C |
| ATOM | 2465 | CG | MET | B | 128 | -1.259 | -17.019 | 14.418 | 1 | 33.45 | C |
| ATOM | 2466 | SD | MET | B | 128 | 0.009 | -15.796 | 14.851 | 1 | 47.54 | S |
| ATOM | 2467 | CE | MET | B | 128 | -0.094 | -14.801 | 13.355 | 1 | 39.77 | C |
| ATOM | 2468 | H | MET | B | 128 | -2.224 | -20.083 | 16.706 | 1 | 26.39 | H |
| ATOM | 2469 | HA | MET | B | 128 | -2.267 | -19.523 | 14.187 | 1 | 36.36 | H |
| ATOM | 2470 | HB2 | MET | B | 128 | -0.652 | -18.584 | 15.585 | 1 | 32.64 | H |
| ATOM | 2471 | HB3 | MET | B | 128 | -1.77 | -17.692 | 16.279 | 1 | 32.64 | H |
| ATOM | 2472 | HG2 | MET | B | 128 | -2.094 | -16.545 | 14.281 | 1 | 40.14 | H |
| ATOM | 2473 | HG3 | MET | B | 128 | -0.983 | -17.435 | 13.587 | 1 | 40.14 | H |
| ATOM | 2474 | HE1 | MET | B | 128 | -0.994 | -14.451 | 13.26 | 1 | 47.73 | H |
| ATOM | 2475 | HE2 | MET | B | 128 | 0.126 | -15.359 | 12.593 | 1 | 47.73 | H |
| ATOM | 2476 | HE3 | MET | B | 128 | 0.54 | -14.071 | 13.426 | 1 | 47.73 | H |
| ATOM | 2477 | N | SER | B | 129 | -4.573 | -18.029 | 15.842 | 1 | 29.26 | N |
| ATOM | 2478 | CA | SER | B | 129 | -5.795 | -17.233 | 15.737 | 1 | 32.8 | C |
| ATOM | 2479 | C | SER | B | 129 | -6.901 | -17.968 | 14.984 | 1 | 29.82 | C |
| ATOM | 2480 | O | SER | B | 129 | -7.932 | -17.381 | 14.658 | 1 | 30.42 | O |
| ATOM | 2481 | CB | SER | B | 129 | -6.296 | -16.839 | 17.127 | 1 | 32.72 | C |
| ATOM | 2482 | OG | SER | B | 129 | -6.872 | -17.945 | 17.799 | 1 | 38.37 | O |
| ATOM | 2483 | H | SER | B | 129 | -4.358 | -18.235 | 16.649 | 1 | 35.11 | H |
| ATOM | 2484 | HA | SER | B | 129 | -5.596 | -16.418 | 15.25 | 1 | 39.36 | H |
| ATOM | 2485 | HB2 | SER | B | 129 | -6.966 | -16.144 | 17.034 | 1 | 39.26 | H |
| ATOM | 2486 | HB3 | SER | B | 129 | -5.548 | -16.509 | 17.649 | 1 | 39.26 | H |
| ATOM | 2487 | HG | SER | B | 129 | -6.302 | -18.556 | 17.888 | 1 | 46.05 | H |

TABLE 5-continued

Atomic Coordinates for OMCP-NKG2D (4PDC).

| ATOM | 2488 | N | GLN | B | 130 | -6.682 | 14.717 | -19.251 | 1 | 32.61 | N |
| --- | --- | --- | --- | --- | --- | --- | --- | --- | --- | --- | --- |
| ATOM | 2489 | CA | GLN | B | 130 | -7.63 | 13.962 | -20.059 | 1 | 32.51 | C |
| ATOM | 2490 | C | GLN | B | 130 | -7.007 | 12.648 | -20.517 | 1 | 30.71 | C |
| ATOM | 2491 | O | GLN | B | 130 | -7.402 | 12.083 | -21.536 | 1 | 31.54 | O |
| ATOM | 2492 | CB | GLN | B | 130 | -8.082 | 14.801 | -21.255 | 1 | 34.47 | C |
| ATOM | 2493 | CG | GLN | B | 130 | -8.648 | 16.155 | -20.845 | 1 | 35.04 | C |
| ATOM | 2494 | CD | GLN | B | 130 | -8.999 | 17.038 | -22.023 | 1 | 35.73 | C |
| ATOM | 2495 | OE1 | GLN | B | 130 | -9.762 | 16.647 | -22.906 | 1 | 32.33 | O |
| ATOM | 2496 | NE2 | GLN | B | 130 | -8.442 | 18.245 | -22.04 | 1 | 42.1 | N |
| ATOM | 2497 | H | GLN | B | 130 | -5.981 | 14.966 | -19.681 | 1 | 39.14 | H |
| ATOM | 2498 | HA | GLN | B | 130 | -8.411 | 13.755 | -19.523 | 1 | 39.01 | H |
| ATOM | 2499 | HB2 | GLN | B | 130 | -7.322 | 14.957 | -21.837 | 1 | 41.37 | H |
| ATOM | 2500 | HB3 | GLN | B | 130 | -8.774 | 14.319 | -21.735 | 1 | 41.37 | H |
| ATOM | 2501 | HG2 | GLN | B | 130 | -9.456 | 16.015 | -20.327 | 1 | 42.05 | H |
| ATOM | 2502 | HG3 | GLN | B | 130 | -7.988 | 16.622 | -20.309 | 1 | 42.05 | H |
| ATOM | 2503 | HE21 | GLN | B | 130 | -8.608 | 18.786 | -22.687 | 1 | 50.53 | H |
| ATOM | 2504 | HE22 | GLN | B | 130 | -7.915 | 18.484 | -21.404 | 1 | 50.53 | H |
| ATOM | 2505 | N | ASN | B | 131 | -6.032 | 12.168 | -19.75 | 1 | 31.89 | N |
| ATOM | 2506 | CA | ASN | B | 131 | -5.372 | 10.896 | -20.028 | 1 | 35.86 | C |
| ATOM | 2507 | C | ASN | B | 131 | 4.77 | 10.869 | -21.431 | 1 | 35.32 | C |
| ATOM | 2508 | O | ASN | B | 131 | 4.818 | 9.852 | -22.125 | 1 | 31.56 | O |
| ATOM | 2509 | CB | ASN | B | 131 | -6.358 | 9.74 | -19.852 | 1 | 44.38 | C |
| ATOM | 2510 | CG | ASN | B | 131 | -5.665 | 8.403 | -19.679 | 1 | 65.46 | C |
| ATOM | 2511 | OD1 | ASN | B | 131 | -5.153 | 8.093 | -18.604 | 1 | 82.44 | O |
| ATOM | 2512 | ND2 | ASN | B | 131 | -5.648 | 7.603 | -20.737 | 1 | 73.37 | N |
| ATOM | 2513 | H | ASN | B | 131 | -5.73 | 12.567 | -19.05 | 1 | 38.26 | H |
| ATOM | 2514 | HA | ASN | B | 131 | -4.65 | 10.772 | -19.392 | 1 | 43.03 | H |
| ATOM | 2515 | HB2 | ASN | B | 131 | -6.899 | 9.903 | -19.063 | 1 | 53.26 | H |
| ATOM | 2516 | HB3 | ASN | B | 131 | -6.925 | 9.685 | -20.638 | 1 | 53.26 | H |
| ATOM | 2517 | HD21 | ASN | B | 131 | -5.267 | 6.833 | -20.689 | 1 | 88.04 | H |
| ATOM | 2518 | HD22 | ASN | B | 131 | -6.019 | 7.853 | -21.472 | 1 | 88.04 | H |
| ATOM | 2519 | N | ALA | B | 132 | -4.206 | 12.001 | -21.838 | 1 | 25.52 | N |
| ATOM | 2520 | C | ALA | B | 132 | -3.593 | 12.132 | -23.153 | 1 | 27.44 | C |
| ATOM | 2521 | C | ALA | B | 132 | -2.264 | 12.868 | -23.05 | 1 | 26.46 | C |
| ATOM | 2522 | O | ALA | B | 132 | -1.802 | 13.178 | -21.954 | 1 | 24.84 | O |
| ATOM | 2523 | CB | ALA | B | 132 | -4.533 | 12.86 | -24.1 | 1 | 24.28 | C |
| ATOM | 2524 | H | ALA | B | 132 | -4.166 | 12.717 | -21.364 | 1 | 30.62 | H |
| ATOM | 2525 | HA | ALA | B | 132 | -3.422 | 11.248 | -23.515 | 1 | 32.93 | H |
| ATOM | 2526 | HB1 | ALA | B | 132 | -4.107 | 12.937 | -24.969 | 1 | 29.14 | H |
| ATOM | 2527 | HB2 | ALA | B | 132 | -5.356 | 12.353 | -24.179 | 1 | 29.14 | H |
| ATOM | 2528 | HB3 | ALA | B | 132 | -4.719 | 13.742 | -23.743 | 1 | 29.14 | H |
| ATOM | 2529 | N | SER | B | 133 | -1.657 | 13.137 | -24.201 | 1 | 21.19 | N |
| ATOM | 2530 | CA | SER | B | 133 | -0.426 | 13.913 | -24.27 | 1 | 20.84 | C |
| ATOM | 2531 | C | SER | B | 133 | -0.54 | 14.942 | -25.383 | 1 | 21.2 | C |
| ATOM | 2532 | O | SER | B | 133 | -1.48 | 14.903 | -26.177 | 1 | 19.82 | O |
| ATOM | 2533 | CB | SER | B | 133 | 0.776 | 13.001 | -24.514 | 1 | 26.77 | C |
| ATOM | 2534 | OG | SER | B | 133 | 0.841 | 11.979 | -23.535 | 1 | 32.82 | O |
| ATOM | 2535 | H | SER | B | 133 | -1.944 | 12.875 | -24.968 | 1 | 25.43 | H |
| ATOM | 2536 | HA | SER | B | 133 | -0.292 | 14.381 | -23.431 | 1 | 25.01 | H |
| ATOM | 2537 | HB2 | SER | B | 133 | 0.691 | 12.594 | -25.39 | 1 | 32.13 | H |
| ATOM | 2538 | HB3 | SER | B | 133 | 1.588 | 13.53 | -24.472 | 1 | 32.13 | H |

TABLE 5-continued

Atomic Coordinates for OMCP-NKG2D (4PDC).

| ATOM | 2539 | HG | SER B | 133 | 0.914 | 12.318 | -22.77 | 1 | 39.39 | H |
|------|------|-----|-------|-----|--------|--------|---------|---|-------|---|
| ATOM | 2540 | N | LEU B | 134 | 0.404 | 15.873 | -25.431 | 1 | 18.46 | N |
| ATOM | 2541 | CA | LEU B | 134 | 0.479 | 16.796 | -26.55 | 1 | 18.04 | C |
| ATOM | 2542 | C | LEU B | 134 | 0.794 | 15.995 | -27.806 | 1 | 21 | C |
| ATOM | 2543 | O | LEU B | 134 | 1.303 | 14.877 | -27.723 | 1 | 18.42 | O |
| ATOM | 2544 | CB | LEU B | 134 | 1.54 | 17.869 | -26.311 | 1 | 20.17 | C |
| ATOM | 2545 | CG | LEU B | 134 | 1.167 | 18.973 | -25.319 | 1 | 19.25 | C |
| ATOM | 2546 | CD1 | LEU B | 134 | 2.4 | 19.78 | -24.937 | 1 | 19.48 | C |
| ATOM | 2547 | CD2 | LEU B | 134 | 0.096 | 19.889 | -25.898 | 1 | 16.17 | C |
| ATOM | 2548 | H | LEU B | 134 | 1.01 | 15.99 | -24.831 | 1 | 22.15 | H |
| ATOM | 2549 | HA | LEU B | 134 | -0.379 | 17.231 | -26.669 | 1 | 21.65 | H |
| ATOM | 2550 | HB2 | LEU B | 134 | 2.341 | 17.437 | -25.976 | 1 | 24.2 | H |
| ATOM | 2551 | HB3 | LEU B | 134 | 1.736 | 18.298 | -27.159 | 1 | 24.2 | H |
| ATOM | 2552 | HG | LEU B | 134 | 0.812 | 18.567 | -24.513 | 1 | 23.1 | H |
| ATOM | 2553 | HD11 | LEU B | 134 | 2.142 | 20.472 | -24.308 | 1 | 23.37 | H |
| ATOM | 2554 | HD12 | LEU B | 134 | 3.05 | 19.187 | -24.528 | 1 | 23.37 | H |
| ATOM | 2555 | HD13 | LEU B | 134 | 2.775 | 20.181 | -25.736 | 1 | 23.37 | H |
| ATOM | 2556 | HD21 | LEU B | 134 | -0.117 | 20.576 | -25.247 | 1 | 19.4 | H |
| ATOM | 2557 | HD22 | LEU B | 134 | -0.435 | 20.297 | -26.71 | 1 | 19.4 | H |
| ATOM | 2558 | HD23 | LEU B | 134 | -0.695 | 19.363 | -26.097 | 1 | 19.4 | H |
| ATOM | 2559 | N | LEU B | 135 | 0.486 | 16.57 | -28.963 | 1 | 15.7 | N |
| ATOM | 2560 | CA | LEU B | 135 | 0.693 | 15.894 | -30.236 | 1 | 15.71 | C |
| ATOM | 2561 | C | LEU B | 135 | 2.099 | 15.32 | -30.37 | 1 | 16.68 | C |
| ATOM | 2562 | O | LEU B | 135 | 3.084 | 16.02 | -30.142 | 1 | 15.25 | O |
| ATOM | 2563 | CB | LEU B | 135 | 0.43 | 16.862 | -31.388 | 1 | 13.32 | C |
| ATOM | 2564 | CG | LEU B | 135 | 0.715 | 16.342 | -32.793 | 1 | 13.52 | C |
| ATOM | 2565 | CD1 | LEU B | 135 | -0.22 | 15.193 | -33.142 | 1 | 16.61 | C |
| ATOM | 2566 | CD2 | LEU B | 135 | 0.582 | 17.468 | -33.796 | 1 | 13.74 | C |
| ATOM | 2567 | H | LEU B | 135 | 0.152 | 17.359 | -29.037 | 1 | 18.84 | H |
| ATOM | 2568 | HA | LEU B | 135 | 0.062 | 15.161 | -30.31 | 1 | 18.85 | H |
| ATOM | 2569 | HB2 | LEU B | 135 | -0.505 | 17.12 | -31.36 | 1 | 15.99 | H |
| ATOM | 2570 | HB3 | LEU B | 135 | 0.983 | 17.648 | -31.255 | 1 | 15.99 | H |
| ATOM | 2571 | HG | LEU B | 135 | 1.626 | 16.011 | -32.831 | 1 | 16.22 | H |
| ATOM | 2572 | HD11 | LEU B | 135 | -0.017 | 14.882 | -34.038 | 1 | 19.93 | H |
| ATOM | 2573 | HD12 | LEU B | 135 | -0.087 | 14.474 | -32.504 | 1 | 19.93 | H |
| ATOM | 2574 | HD13 | LEU B | 135 | -1.136 | 15.508 | -33.099 | 1 | 19.93 | H |
| ATOM | 2575 | HD21 | LEU B | 135 | 0.765 | 17.123 | -34.684 | 1 | 16.49 | H |
| ATOM | 2576 | HD22 | LEU B | 135 | -0.321 | 17.82 | -33.758 | 1 | 16.49 | H |
| ATOM | 2577 | HD23 | LEU B | 135 | 1.219 | 18.165 | -33.574 | 1 | 16.49 | H |
| ATOM | 2578 | N | LYS B | 136 | 2.178 | 14.042 | -30.735 | 1 | 16.35 | N |
| ATOM | 2579 | CA | LYS B | 136 | 3.437 | 13.426 | -31.139 | 1 | 16.55 | C |
| ATOM | 2580 | C | LYS B | 136 | 3.381 | 13.084 | -32.624 | 1 | 17.63 | C |
| ATOM | 2581 | O | LYS B | 136 | 2.532 | 12.309 | -33.055 | 1 | 21.03 | O |
| ATOM | 2582 | CB | LYS B | 136 | 3.728 | 12.163 | -30.323 | 1 | 19.4 | C |
| ATOM | 2583 | CG | LYS B | 136 | 4.973 | 11.413 | -30.793 | 1 | 19.92 | C |
| ATOM | 2584 | CD | LYS B | 136 | 5.2 | 10.114 | -30.027 | 1 | 27.62 | C |
| ATOM | 2585 | CE | LYS B | 136 | 6.484 | 9.429 | -30.494 | 1 | 26.76 | C |
| ATOM | 2586 | NZ | LYS B | 136 | 6.768 | 8.164 | -29.765 | 1 | 29.82 | N1+ |
| ATOM | 2587 | H | LYS B | 136 | 1.507 | 13.505 | -30.757 | 1 | 19.62 | H |
| ATOM | 2588 | HA | LYS B | 136 | 4.162 | 14.054 | -30.998 | 1 | 19.86 | H |
| ATOM | 2589 | HB2 | LYS B | 136 | 3.863 | 12.413 | -29.395 | 1 | 23.28 | H |

TABLE 5-continued

Atomic Coordinates for OMCP-NKG2D (4PDC).

| | | | | | | | | | | |
|---|---|---|---|---|---|---|---|---|---|---|
| ATOM | 2590 | HB3 | LYS | B | 136 | 2.972 | 11.56 | -30.396 | 1 | 23.28 | H |
| ATOM | 2591 | HG2 | LYS | B | 136 | 4.875 | 11.194 | -31.733 | 1 | 23.9 | H |
| ATOM | 2592 | HG3 | LYS | B | 136 | 5.751 | 11.978 | -30.663 | 1 | 23.9 | H |
| ATOM | 2593 | HD2 | LYS | B | 136 | 5.283 | 10.307 | -29.08 | 1 | 33.15 | H |
| ATOM | 2594 | HD3 | LYS | B | 136 | 4.457 | 9.511 | -30.186 | 1 | 33.15 | H |
| ATOM | 2595 | HE2 | LYS | B | 136 | 6.403 | 9.219 | -31.437 | 1 | 32.11 | H |
| ATOM | 2596 | HE3 | LYS | B | 136 | 7.231 | 10.031 | -30.351 | 1 | 32.11 | H |
| ATOM | 2597 | HZ1 | LYS | B | 136 | 6.101 | 7.588 | -29.885 | 1 | 35.78 | H |
| ATOM | 2598 | HZ2 | LYS | B | 136 | 7.522 | 7.802 | -30.069 | 1 | 35.78 | H |
| ATOM | 2599 | HZ3 | LYS | B | 136 | 6.856 | 8.328 | -28.895 | 1 | 35.78 | H |
| ATOM | 2600 | N | VAL | B | 137 | 4.281 | 13.676 | -33.401 | 1 | 17.2 | N |
| ATOM | 2601 | CA | VAL | B | 137 | 4.399 | 13.367 | -34.822 | 1 | 17.92 | C |
| ATOM | 2602 | C | VAL | B | 137 | 5.388 | 12.221 | -34.998 | 1 | 22.09 | C |
| ATOM | 2603 | O | VAL | B | 137 | 6.556 | 12.346 | -34.63 | 1 | 20.93 | O |
| ATOM | 2604 | CB | VAL | B | 137 | 4.868 | 14.59 | -35.643 | 1 | 23.08 | C |
| ATOM | 2605 | CG1 | VAL | B | 137 | 5.015 | 14.234 | -37.124 | 1 | 22.11 | C |
| ATOM | 2606 | CG2 | VAL | B | 137 | 3.896 | 15.744 | -35.477 | 1 | 15.93 | C |
| ATOM | 2607 | H | VAL | B | 137 | 4.842 | 14.268 | -33.126 | 1 | 20.64 | H |
| ATOM | 2608 | HA | VAL | B | 137 | 3.537 | 13.082 | -35.162 | 1 | 21.51 | H |
| ATOM | 2609 | HB | VAL | B | 137 | 5.734 | 14.878 | -35.316 | 1 | 27.69 | H |
| ATOM | 2610 | HG11 | VAL | B | 137 | 5.309 | 15.02 | -37.61 | 1 | 26.53 | H |
| ATOM | 2611 | HG12 | VAL | B | 137 | 5.67 | 13.525 | -37.214 | 1 | 26.53 | H |
| ATOM | 2612 | HG13 | VAL | B | 137 | 4.156 | 13.937 | -37.464 | 1 | 26.53 | H |
| ATOM | 2613 | HG21 | VAL | B | 137 | 4.21 | 16.499 | -36 | 1 | 19.12 | H |
| ATOM | 2614 | HG22 | VAL | B | 137 | 3.021 | 15.467 | -35.789 | 1 | 19.12 | H |
| ATOM | 2615 | HG23 | VAL | B | 137 | 3.852 | 15.987 | -34.539 | 1 | 19.12 | H |
| ATOM | 2616 | N | TYR | B | 138 | 4.915 | 11.113 | -35.563 | 1 | 20.52 | N |
| ATOM | 2617 | CA | TYR | B | 138 | 5.748 | 9.928 | -35.754 | 1 | 25.3 | C |
| ATOM | 2618 | C | TYR | B | 138 | 5.614 | 9.342 | -37.163 | 1 | 26.25 | C |
| ATOM | 2619 | O | TYR | B | 138 | 6.481 | 8.587 | -37.601 | 1 | 27.44 | O |
| ATOM | 2620 | CB | TYR | B | 138 | 5.393 | 8.861 | -34.713 | 1 | 26.97 | C |
| ATOM | 2621 | CG | TYR | B | 138 | 4.047 | 8.217 | -34.94 | 1 | 23.68 | C |
| ATOM | 2622 | CD1 | TYR | B | 138 | 2.886 | 8.797 | -34.451 | 1 | 23.08 | C |
| ATOM | 2623 | CD2 | TYR | B | 138 | 3.938 | 7.028 | -35.65 | 1 | 27.12 | C |
| ATOM | 2624 | CE1 | TYR | B | 138 | 1.654 | 8.212 | -34.661 | 1 | 25.34 | C |
| ATOM | 2625 | CE2 | TYR | B | 138 | 2.709 | 6.437 | -35.867 | 1 | 26.65 | C |
| ATOM | 2626 | CZ | TYR | B | 138 | 1.572 | 7.033 | -35.371 | 1 | 28.22 | C |
| ATOM | 2627 | OH | TYR | B | 138 | 0.347 | 6.447 | -35.581 | 1 | 30.35 | O |
| ATOM | 2628 | H | TYR | B | 138 | 4.108 | 11.021 | -35.847 | 1 | 24.63 | H |
| ATOM | 2629 | HA | TYR | B | 138 | 6.676 | 10.175 | -35.623 | 1 | 30.36 | H |
| ATOM | 2630 | HB2 | TYR | B | 138 | 6.066 | 8.163 | -34.74 | 1 | 32.36 | H |
| ATOM | 2631 | HB3 | TYR | B | 138 | 5.381 | 9.273 | -33.835 | 1 | 32.36 | H |
| ATOM | 2632 | HD1 | TYR | B | 138 | 2.939 | 9.593 | -33.974 | 1 | 27.7 | H |
| ATOM | 2633 | HD2 | TYR | B | 138 | 4.705 | 6.626 | -35.988 | 1 | 32.54 | H |
| ATOM | 2634 | HE1 | TYR | B | 138 | 0.883 | 8.612 | -34.327 | 1 | 30.41 | H |
| ATOM | 2635 | HE2 | TYR | B | 138 | 2.65 | 5.641 | -36.344 | 1 | 31.98 | H |
| ATOM | 2636 | HH | TYR | B | 138 | -0.257 | 6.909 | -35.225 | 1 | 36.42 | H |
| ATOM | 2637 | N | SER | B | 139 | 4.538 | 9.689 | -37.87 | 1 | 26.36 | N |
| ATOM | 2638 | CA | SER | B | 139 | 4.288 | 9.139 | -39.207 | 1 | 27.55 | C |
| ATOM | 2639 | C | SER | B | 139 | 3.526 | 10.099 | -40.119 | 1 | 23.78 | C |
| ATOM | 2640 | O | SER | B | 139 | 2.379 | 10.447 | -39.841 | 1 | 22.07 | O |

TABLE 5-continued

Atomic Coordinates for OMCP-NKG2D (4PDC).

| | | | | | | | | | | |
|---|---|---|---|---|---|---|---|---|---|---|
| ATOM | 2641 | CB | SER | B | 139 | 3.507 | -39.099 | 7.826 | 1 | 25.84 | C |
| ATOM | 2642 | OG | SER | B | 139 | 3.173 | -40.386 | 7.324 | 1 | 25.64 | O |
| ATOM | 2643 | H | SER | B | 139 | 3.936 | -37.6 | 10.241 | 1 | 31.64 | H |
| ATOM | 2644 | HA | SER | B | 139 | 5.14 | -39.628 | 8.944 | 1 | 33.05 | H |
| ATOM | 2645 | HB2 | SER | B | 139 | 4.054 | -38.638 | 7.171 | 1 | 31.01 | H |
| ATOM | 2646 | HB3 | SER | B | 139 | 2.69 | -38.601 | 7.985 | 1 | 31.01 | H |
| ATOM | 2647 | HG | SER | B | 139 | 3.872 | -40.829 | 7.181 | 1 | 30.77 | H |
| ATOM | 2648 | N | LYS | B | 140 | 4.161 | -41.215 | 10.507 | 1 | 23.74 | N |
| ATOM | 2649 | CA | LYS | B | 140 | 3.52 | -42.19 | 11.383 | 1 | 25.13 | C |
| ATOM | 2650 | C | LYS | B | 140 | 2.262 | -42.772 | 10.751 | 1 | 27.27 | C |
| ATOM | 2651 | O | LYS | B | 140 | 1.31 | -43.124 | 11.446 | 1 | 23.6 | O |
| ATOM | 2652 | CB | LYS | B | 140 | 4.479 | -43.332 | 11.725 | 1 | 33.45 | C |
| ATOM | 2653 | CG | LYS | B | 140 | 5.508 | -43.013 | 12.792 | 1 | 30.77 | C |
| ATOM | 2654 | CD | LYS | B | 140 | 6.309 | -44.257 | 13.145 | 1 | 35.69 | C |
| ATOM | 2655 | CE | LYS | B | 140 | 7.517 | -43.925 | 13.999 | 1 | 38.62 | C |
| ATOM | 2656 | NZ | LYS | B | 140 | 7.166 | -43.646 | 15.412 | 1 | 40.07 | N1+ |
| ATOM | 2657 | H | LYS | B | 140 | 4.968 | -41.417 | 10.29 | 1 | 28.48 | H |
| ATOM | 2658 | HA | LYS | B | 140 | 3.265 | -41.753 | 12.211 | 1 | 30.15 | H |
| ATOM | 2659 | HB2 | LYS | B | 140 | 4.961 | -43.581 | 10.921 | 1 | 40.14 | H |
| ATOM | 2660 | HB3 | LYS | B | 140 | 3.959 | -44.088 | 12.039 | 1 | 40.14 | H |
| ATOM | 2661 | HG2 | LYS | B | 140 | 5.058 | -42.699 | 13.592 | 1 | 36.92 | H |
| ATOM | 2662 | HG3 | LYS | B | 140 | 6.119 | -42.337 | 12.46 | 1 | 36.92 | H |
| ATOM | 2663 | HD2 | LYS | B | 140 | 6.621 | -44.678 | 12.329 | 1 | 42.82 | H |
| ATOM | 2664 | HD3 | LYS | B | 140 | 5.745 | -44.869 | 13.643 | 1 | 42.82 | H |
| ATOM | 2665 | HE2 | LYS | B | 140 | 7.953 | -43.512 | 13.637 | 1 | 46.34 | H |
| ATOM | 2666 | HE3 | LYS | B | 140 | 8.129 | -44.678 | 13.985 | 1 | 46.34 | H |
| ATOM | 2667 | HZ1 | LYS | B | 140 | 7.902 | -43.456 | 15.876 | 1 | 48.08 | H |
| ATOM | 2668 | HZ2 | LYS | B | 140 | 6.771 | -44.357 | 15.773 | 1 | 48.08 | H |
| ATOM | 2669 | HZ3 | LYS | B | 140 | 6.61 | -42.952 | 15.455 | 1 | 48.08 | H |
| ATOM | 2670 | N | GLU | B | 141 | 2.267 | -42.874 | 9.427 | 1 | 25 | N |
| ATOM | 2671 | CA | GLU | B | 141 | 1.193 | -43.544 | 8.708 | 1 | 27.84 | C |
| ATOM | 2672 | C | GLU | B | 141 | 0.014 | -42.607 | 8.489 | 1 | 25.06 | C |
| ATOM | 2673 | O | GLU | B | 141 | -1.123 | -42.942 | 8.813 | 1 | 27.37 | O |
| ATOM | 2674 | CB | GLU | B | 141 | 1.7 | -44.078 | 7.367 | 1 | 34.11 | C |
| ATOM | 2675 | CG | GLU | B | 141 | 2.769 | -45.16 | 7.49 | 1 | 36.43 | C |
| ATOM | 2676 | CD | GLU | B | 141 | 4.098 | -44.638 | 8.026 | 1 | 46.4 | C |
| ATOM | 2677 | OE1 | GLU | B | 141 | 4.499 | -43.512 | 7.656 | 1 | 42.36 | O |
| ATOM | 2678 | OE2 | GLU | B | 141 | 4.74 | -45.356 | 8.824 | 1 | 49.27 | O1- |
| ATOM | 2679 | H | GLU | B | 141 | 2.886 | -42.561 | 8.919 | 1 | 30 | H |
| ATOM | 2680 | HA | GLU | B | 141 | 0.883 | -44.298 | 9.233 | 1 | 33.41 | H |
| ATOM | 2681 | HB2 | GLU | B | 141 | 2.082 | -43.342 | 6.864 | 1 | 40.93 | H |
| ATOM | 2682 | HB3 | GLU | B | 141 | 0.952 | -44.455 | 6.879 | 1 | 40.93 | H |
| ATOM | 2683 | HG2 | GLU | B | 141 | 2.932 | -45.543 | 6.613 | 1 | 43.71 | H |
| ATOM | 2684 | HG3 | GLU | B | 141 | 2.452 | -45.847 | 8.097 | 1 | 43.71 | H |
| ATOM | 2685 | N | ASP | B | 142 | 0.29 | -41.429 | 7.943 | 1 | 28.26 | N |
| ATOM | 2686 | CA | ASP | B | 142 | -0.758 | -40.452 | 7.684 | 1 | 24.57 | C |
| ATOM | 2687 | C | ASP | B | 142 | -1.332 | -39.892 | 8.975 | 1 | 20.54 | C |
| ATOM | 2688 | O | ASP | B | 142 | -2.446 | -39.375 | 8.987 | 1 | 22.29 | O |
| ATOM | 2689 | CB | ASP | B | 142 | -0.226 | -39.31 | 6.82 | 1 | 25.59 | C |
| ATOM | 2690 | CG | ASP | B | 142 | 0.03 | -39.737 | 5.39 | 1 | 31.43 | C |
| ATOM | 2691 | OD1 | ASP | B | 142 | -0.408 | -40.844 | 5.011 | 1 | 33.75 | O |

TABLE 5-continued

Atomic Coordinates for OMCP-NKG2D (4PDC).

| ATOM | 2692 | OD2  | ASP | B | 142 | 0.658  | -38.96  | 4.641  | 1 | 36.61 | O1- |
| ---- | ---- | ---- | --- | - | --- | ------ | ------- | ------ | - | ----- | --- |
| ATOM | 2693 | H    | ASP | B | 142 | 1.077  | -41.171 | 7.713  | 1 | 33.91 | H   |
| ATOM | 2694 | HA   | ASP | B | 142 | -1.479 | -40.884 | 7.199  | 1 | 29.48 | H   |
| ATOM | 2695 | HB2  | ASP | B | 142 | 0.612  | -38.994 | 7.194  | 1 | 30.71 | H   |
| ATOM | 2696 | HB3  | ASP | B | 142 | -0.877 | -38.592 | 6.807  | 1 | 30.71 | H   |
| ATOM | 2697 | N    | GLN | B | 143 | -0.567 | -39.996 | 10.057 | 1 | 21.57 | N   |
| ATOM | 2698 | CA   | GLN | B | 143 | -1.007 | -39.489 | 11.352 | 1 | 22.32 | C   |
| ATOM | 2699 | C    | GLN | B | 143 | -1.076 | -40.617 | 12.372 | 1 | 21.14 | C   |
| ATOM | 2700 | O    | GLN | B | 143 | -0.821 | -40.412 | 13.555 | 1 | 19.64 | O   |
| ATOM | 2701 | CB   | GLN | B | 143 | -0.069 | -38.383 | 11.831 | 1 | 16.49 | C   |
| ATOM | 2702 | CG   | GLN | B | 143 | 0.132  | -37.295 | 10.792 | 1 | 21.19 | C   |
| ATOM | 2703 | CD   | GLN | B | 143 | 1.05   | -36.196 | 11.269 | 1 | 21.57 | C   |
| ATOM | 2704 | OE1  | GLN | B | 143 | 2.263  | -36.384 | 11.355 | 1 | 19.08 | O   |
| ATOM | 2705 | NE2  | GLN | B | 143 | 0.478  | -35.039 | 11.581 | 1 | 19.58 | N   |
| ATOM | 2706 | H    | GLN | B | 143 | -0.213 | -40.356 | 10.068 | 1 | 25.88 | H   |
| ATOM | 2707 | HA   | GLN | B | 143 | -1.896 | -39.112 | 11.26  | 1 | 26.78 | H   |
| ATOM | 2708 | HB2  | GLN | B | 143 | 0.798  | -38.769 | 12.032 | 1 | 19.78 | H   |
| ATOM | 2709 | HB3  | GLN | B | 143 | -0.443 | -37.974 | 12.626 | 1 | 19.78 | H   |
| ATOM | 2710 | HG2  | GLN | B | 143 | -0.727 | -36.897 | 10.581 | 1 | 25.43 | H   |
| ATOM | 2711 | HG3  | GLN | B | 143 | 0.521  | -37.686 | 9.995  | 1 | 25.43 | H   |
| ATOM | 2712 | HE21 | GLN | B | 143 | 0.96   | -34.382 | 11.858 | 1 | 23.5  | H   |
| ATOM | 2713 | HE22 | GLN | B | 143 | -0.374 | -34.946 | 11.507 | 1 | 23.5  | H   |
| ATOM | 2714 | N    | ASP | B | 144 | -1.441 | -41.808 | 11.906 | 1 | 23.98 | N   |
| ATOM | 2715 | CA   | ASP | B | 144 | -1.449 | -42.986 | 12.764 | 1 | 24.23 | C   |
| ATOM | 2716 | C    | ASP | B | 144 | -2.493 | -43.879 | 12.881 | 1 | 22.36 | C   |
| ATOM | 2717 | O    | ASP | B | 144 | -2.389 | -44.374 | 14.881 | 1 | 21.23 | O   |
| ATOM | 2718 | CB   | ASP | B | 144 | -1.678 | -43.582 | 11.933 | 1 | 28.7  | C   |
| ATOM | 2719 | CG   | ASP | B | 144 | -2.948 | -44.256 | 11.106 | 1 | 27.6  | C   |
| ATOM | 2720 | OD1  | ASP | B | 144 | -3.543 | -44.203 | 10.979 | 1 | 24.37 | O   |
| ATOM | 2721 | OD2  | ASP | B | 144 | -3.344 | -45.113 | 10.567 | 1 | 40.47 | O1- |
| ATOM | 2722 | H    | ASP | B | 144 | -1.689 | -45.258 | 11.096 | 1 | 28.78 | H   |
| ATOM | 2723 | HA   | ASP | B | 144 | -0.579 | -41.96  | 13.185 | 1 | 29.08 | H   |
| ATOM | 2724 | HB2  | ASP | B | 144 | -1.742 | -43.065 | 12.532 | 1 | 34.44 | H   |
| ATOM | 2725 | HB3  | ASP | B | 144 | -0.93  | -45.016 | 11.326 | 1 | 34.44 | H   |
| ATOM | 2726 | N    | LEU | B | 145 | -3.477 | -44.374 | 13.728 | 1 | 19.04 | N   |
| ATOM | 2727 | CA   | LEU | B | 145 | -4.471 | -41.996 | 14.785 | 1 | 22.41 | C   |
| ATOM | 2728 | C    | LEU | B | 145 | -4.471 | -41.804 | 16.062 | 1 | 23.21 | C   |
| ATOM | 2729 | O    | LEU | B | 145 | -4.353 | -41.284 | 17.157 | 1 | 16.02 | O   |
| ATOM | 2730 | CB   | LEU | B | 145 | -5.59  | -41.44  | 14.338 | 1 | 23.82 | C   |
| ATOM | 2731 | CG   | LEU | B | 145 | -5.318 | -40.849 | 14.061 | 1 | 27.11 | C   |
| ATOM | 2732 | CD1  | LEU | B | 145 | -5.111 | -39.362 | 15.321 | 1 | 36.24 | C   |
| ATOM | 2733 | CD2  | LEU | B | 145 | -6.485 | -38.53  | 13.274 | 1 | 26.9  | C   |
| ATOM | 2734 | H    | LEU | B | 145 | -3.591 | -38.783 | 13.034 | 1 | 22.85 | H   |
| ATOM | 2735 | HA   | LEU | B | 145 | -4.878 | -41.501 | 14.99  | 1 | 26.9  | H   |
| ATOM | 2736 | HB2  | LEU | B | 145 | -6.276 | -42.661 | 15.024 | 1 | 28.59 | H   |
| ATOM | 2737 | HB3  | LEU | B | 145 | -5.962 | -40.873 | 13.519 | 1 | 28.59 | H   |
| ATOM | 2738 | HG   | LEU | B | 145 | -4.52  | -41.211 | 13.515 | 1 | 32.54 | H   |
| ATOM | 2739 | HD11 | LEU | B | 145 | -4.946 | -39.283 | 15.068 | 1 | 43.49 | H   |
| ATOM | 2740 | HD12 | LEU | B | 145 | -4.349 | -37.609 | 15.809 | 1 | 43.49 | H   |
| ATOM | 2741 | HD13 | LEU | B | 145 | -5.909 | -38.881 | 15.87  | 1 | 43.49 | H   |
| ATOM | 2742 | HD21 | LEU | B | 145 | -6.571 | -38.585 | 12.437 | 1 | 32.28 | H   |

TABLE 5-continued

Atomic Coordinates for OMCP-NKG2D (4PDC).

| ATOM | 2743 | HD22 | LEU | B | 145 | -6.313 | 13.1 | -37.845 | 1 | 32.28 | H |
|---|---|---|---|---|---|---|---|---|---|---|---|
| ATOM | 2744 | HD23 | LEU | B | 145 | -7.296 | 13.797 | -38.88 | 1 | 32.28 | H |
| ATOM | 2745 | N | LEU | B | 146 | -2.641 | 15.917 | -40.669 | 1 | 18.69 | N |
| ATOM | 2746 | CA | LEU | B | 146 | -1.906 | 17.067 | -40.147 | 1 | 20.59 | C |
| ATOM | 2747 | C | LEU | B | 146 | -1.461 | 18.011 | -41.261 | 1 | 22.13 | C |
| ATOM | 2748 | O | LEU | B | 146 | -1.05 | 19.139 | -40.994 | 1 | 20.52 | O |
| ATOM | 2749 | CB | LEU | B | 146 | -0.687 | 16.603 | -39.346 | 1 | 17.78 | C |
| ATOM | 2750 | CG | LEU | B | 146 | -0.968 | 15.902 | -38.018 | 1 | 17.5 | C |
| ATOM | 2751 | CD1 | LEU | B | 146 | 0.325 | 15.414 | -37.395 | 1 | 17.27 | C |
| ATOM | 2752 | CD2 | LEU | B | 146 | -1.696 | 16.837 | -37.055 | 1 | 20.64 | C |
| ATOM | 2753 | H | LEU | B | 146 | -2.25 | 15.162 | -40.542 | 1 | 22.42 | H |
| ATOM | 2754 | HA | LEU | B | 146 | -2.485 | 17.564 | -39.548 | 1 | 24.71 | H |
| ATOM | 2755 | HB2 | LEU | B | 146 | -0.181 | 15.984 | -39.896 | 1 | 21.34 | H |
| ATOM | 2756 | HB3 | LEU | B | 146 | -0.14 | 17.38 | -39.151 | 1 | 21.34 | H |
| ATOM | 2757 | HG | LEU | B | 146 | -1.536 | 15.132 | -38.178 | 1 | 21 | H |
| ATOM | 2758 | HD11 | LEU | B | 146 | 0.123 | 14.973 | -36.555 | 1 | 20.72 | H |
| ATOM | 2759 | HD12 | LEU | B | 146 | 0.751 | 14.789 | -38.003 | 1 | 20.72 | H |
| ATOM | 2760 | HD13 | LEU | B | 146 | 0.907 | 16.174 | -37.239 | 1 | 20.72 | H |
| ATOM | 2761 | HD21 | LEU | B | 146 | -1.861 | 16.367 | -36.223 | 1 | 24.77 | H |
| ATOM | 2762 | HD22 | LEU | B | 146 | -1.142 | 17.615 | -36.892 | 1 | 24.77 | H |
| ATOM | 2763 | HD23 | LEU | B | 146 | -2.538 | 17.108 | -37.455 | 1 | 24.77 | H |
| ATOM | 2764 | N | LYS | B | 147 | -1.546 | 17.549 | -42.505 | 1 | 18.08 | N |
| ATOM | 2765 | CA | LYS | B | 147 | -1.162 | 18.363 | -43.656 | 1 | 21.55 | C |
| ATOM | 2766 | C | LYS | B | 147 | -2.1 | 19.543 | -43.918 | 1 | 18.51 | C |
| ATOM | 2767 | O | LYS | B | 147 | -1.684 | 20.547 | -44.493 | 1 | 21.96 | O |
| ATOM | 2768 | CB | LYS | B | 147 | -1.098 | 17.501 | -44.915 | 1 | 21.16 | C |
| ATOM | 2769 | CG | LYS | B | 147 | 0.074 | 16.547 | -44.957 | 1 | 30.69 | C |
| ATOM | 2770 | CD | LYS | B | 147 | 0.195 | 15.878 | -46.321 | 1 | 36.31 | C |
| ATOM | 2771 | CE | LYS | B | 147 | -0.442 | 14.498 | -46.326 | 1 | 47.69 | C |
| ATOM | 2772 | NZ | LYS | B | 147 | -0.373 | 13.845 | -47.665 | 1 | 54.63 | N1+ |
| ATOM | 2773 | H | LYS | B | 147 | -1.824 | 16.762 | -42.711 | 1 | 21.7 | H |
| ATOM | 2774 | HA | LYS | B | 147 | -0.275 | 18.723 | -43.499 | 1 | 25.85 | H |
| ATOM | 2775 | HB2 | LYS | B | 147 | -1.91 | 16.973 | -44.972 | 1 | 25.39 | H |
| ATOM | 2776 | HB3 | LYS | B | 147 | -1.032 | 18.084 | -45.688 | 1 | 25.39 | H |
| ATOM | 2777 | HG2 | LYS | B | 147 | 0.893 | 17.037 | -44.784 | 1 | 36.83 | H |
| ATOM | 2778 | HG3 | LYS | B | 147 | -0.052 | 15.855 | -44.289 | 1 | 36.83 | H |
| ATOM | 2779 | HD2 | LYS | B | 147 | -0.255 | 16.423 | -46.986 | 1 | 43.57 | H |
| ATOM | 2780 | HD3 | LYS | B | 147 | 1.134 | 15.78 | -46.547 | 1 | 43.57 | H |
| ATOM | 2781 | HE2 | LYS | B | 147 | 0.023 | 13.931 | -45.691 | 1 | 57.23 | H |
| ATOM | 2782 | HE3 | LYS | B | 147 | -1.376 | 14.579 | -46.078 | 1 | 57.23 | H |
| ATOM | 2783 | HZ1 | LYS | B | 147 | 0.476 | 13.753 | -47.915 | 1 | 65.55 | H |
| ATOM | 2784 | HZ2 | LYS | B | 147 | -0.754 | 13.042 | -47.632 | 1 | 65.55 | H |
| ATOM | 2785 | HZ3 | LYS | B | 147 | -0.799 | 14.343 | -48.268 | 1 | 65.55 | H |
| ATOM | 2786 | N | LEU | B | 148 | -3.362 | 19.42 | -43.518 | 1 | 18.78 | N |
| ATOM | 2787 | CA | LEU | B | 148 | -4.353 | 20.45 | -43.829 | 1 | 22.97 | C |
| ATOM | 2788 | C | LEU | B | 148 | -4.868 | 21.167 | -42.585 | 1 | 14.82 | C |
| ATOM | 2789 | O | LEU | B | 148 | -6.011 | 21.617 | -42.541 | 1 | 14.64 | O |
| ATOM | 2790 | CB | LEU | B | 148 | -5.517 | 19.832 | -44.607 | 1 | 26 | C |
| ATOM | 2791 | CG | LEU | B | 148 | -5.16 | 19.38 | -46.029 | 1 | 31.59 | C |
| ATOM | 2792 | CD1 | LEU | B | 148 | -6.356 | 18.716 | -46.679 | 1 | 33.85 | C |
| ATOM | 2793 | CD2 | LEU | B | 148 | -4.67 | 20.547 | -46.891 | 1 | 31.17 | C |

TABLE 5-continued

Atomic Coordinates for OMCP-NKG2D (4PDC).

| | | | | | | | | | | |
|---|---|---|---|---|---|---|---|---|---|---|
| ATOM | 2794 | H | LEU | B | 148 | -3.67 | 18.755 | -43.068 | 1 | 22.53 | H |
| ATOM | 2795 | HA | LEU | B | 148 | -3.939 | 21.115 | -44.401 | 1 | 27.56 | H |
| ATOM | 2796 | HB2 | LEU | B | 148 | -5.837 | 19.055 | -44.123 | 1 | 31.2 | H |
| ATOM | 2797 | HB3 | LEU | B | 148 | -6.228 | 20.489 | -44.677 | 1 | 31.2 | H |
| ATOM | 2798 | HG | LEU | B | 148 | -4.446 | 18.725 | -45.98 | 1 | 37.91 | H |
| ATOM | 2799 | HD11 | LEU | B | 148 | -6.113 | 18.437 | -47.575 | 1 | 40.61 | H |
| ATOM | 2800 | HD12 | LEU | B | 148 | -6.614 | 17.944 | -46.15 | 1 | 40.61 | H |
| ATOM | 2801 | HD13 | LEU | B | 148 | -7.088 | 19.351 | -46.716 | 1 | 40.61 | H |
| ATOM | 2802 | HD21 | LEU | B | 148 | -3.878 | 20.931 | -46.481 | 1 | 37.4 | H |
| ATOM | 2803 | HD22 | LEU | B | 148 | -4.456 | 20.216 | -47.778 | 1 | 37.4 | H |
| ATOM | 2804 | HD23 | LEU | B | 148 | -5.371 | 21.215 | -46.946 | 1 | 37.4 | H |
| ATOM | 2805 | N | VAL | B | 149 | -4 | 21.295 | -41.587 | 1 | 21.37 | N |
| ATOM | 2806 | CA | VAL | B | 149 | -4.324 | 22.025 | -40.365 | 1 | 16 | C |
| ATOM | 2807 | C | VAL | B | 149 | -3.814 | 23.459 | -40.465 | 1 | 15.16 | C |
| ATOM | 2808 | O | VAL | B | 149 | -2.619 | 23.685 | -40.651 | 1 | 17.77 | O |
| ATOM | 2809 | CB | VAL | B | 149 | -3.708 | 21.343 | -39.13 | 1 | 15.06 | C |
| ATOM | 2810 | CG1 | VAL | B | 149 | -4.064 | 22.1 | -37.853 | 1 | 19.91 | C |
| ATOM | 2811 | CG2 | VAL | B | 149 | -4.179 | 19.899 | -39.037 | 1 | 22.08 | C |
| ATOM | 2812 | H | VAL | B | 149 | -3.206 | 20.964 | -41.594 | 1 | 25.65 | H |
| ATOM | 2813 | HA | VAL | B | 149 | -5.287 | 22.05 | -40.252 | 1 | 19.19 | H |
| ATOM | 2814 | HB | VAL | B | 149 | -2.742 | 21.34 | -39.219 | 1 | 18.07 | H |
| ATOM | 2815 | HG11 | VAL | B | 149 | -3.662 | 21.646 | -37.096 | 1 | 23.89 | H |
| ATOM | 2816 | HG12 | VAL | B | 149 | -3.721 | 23.005 | -37.917 | 1 | 23.89 | H |
| ATOM | 2817 | HG13 | VAL | B | 149 | -5.028 | 22.118 | -37.755 | 1 | 23.89 | H |
| ATOM | 2818 | HG21 | VAL | B | 149 | -3.781 | 19.488 | -38.254 | 1 | 26.49 | H |
| ATOM | 2819 | HG22 | VAL | B | 149 | -5.146 | 19.886 | -38.963 | 1 | 26.49 | H |
| ATOM | 2820 | HG23 | VAL | B | 149 | -3.902 | 19.425 | -39.837 | 1 | 26.49 | H |
| ATOM | 2821 | N | LYS | B | 150 | -4.723 | 24.422 | -40.354 | 1 | 13.81 | N |
| ATOM | 2822 | CA | LYS | B | 150 | -4.346 | 25.833 | -40.34 | 1 | 15.89 | C |
| ATOM | 2823 | C | LYS | B | 150 | -3.784 | 26.238 | -38.987 | 1 | 14.81 | C |
| ATOM | 2824 | O | LYS | B | 150 | -3.953 | 25.531 | -37.996 | 1 | 17.84 | O |
| ATOM | 2825 | CB | LYS | B | 150 | -5.542 | 26.729 | -40.663 | 1 | 19.83 | C |
| ATOM | 2826 | CG | LYS | B | 150 | -5.939 | 26.78 | -42.121 | 1 | 18.05 | C |
| ATOM | 2827 | CD | LYS | B | 150 | -6.947 | 27.893 | -42.372 | 1 | 16 | C |
| ATOM | 2828 | CE | LYS | B | 150 | -6.287 | 29.264 | -42.452 | 1 | 20.31 | C |
| ATOM | 2829 | NZ | LYS | B | 150 | -5.422 | 29.408 | -43.661 | 1 | 20.83 | N1+ |
| ATOM | 2830 | H | LYS | B | 150 | -5.569 | 24.285 | -40.285 | 1 | 16.58 | H |
| ATOM | 2831 | HA | LYS | B | 150 | -3.663 | 25.986 | -41.011 | 1 | 19.07 | H |
| ATOM | 2832 | HB2 | LYS | B | 150 | -6.31 | 26.409 | -40.163 | 1 | 23.79 | H |
| ATOM | 2833 | HB3 | LYS | B | 150 | -5.331 | 27.634 | -40.386 | 1 | 23.79 | H |
| ATOM | 2834 | HG2 | LYS | B | 150 | -5.153 | 26.952 | -42.662 | 1 | 21.66 | H |
| ATOM | 2835 | HG3 | LYS | B | 150 | -6.346 | 25.937 | -42.373 | 1 | 21.66 | H |
| ATOM | 2836 | HD2 | LYS | B | 150 | -7.4 | 27.728 | -43.214 | 1 | 19.21 | H |
| ATOM | 2837 | HD3 | LYS | B | 150 | -7.589 | 27.91 | -41.645 | 1 | 19.21 | H |
| ATOM | 2838 | HE2 | LYS | B | 150 | -6.976 | 29.946 | -42.491 | 1 | 24.37 | H |
| ATOM | 2839 | HE3 | LYS | B | 150 | -5.732 | 29.395 | -41.667 | 1 | 24.37 | H |
| ATOM | 2840 | HZ1 | LYS | B | 150 | -5.053 | 30.217 | -43.676 | 1 | 25 | H |
| ATOM | 2841 | HZ2 | LYS | B | 150 | -4.776 | 28.796 | -43.647 | 1 | 25 | H |
| ATOM | 2842 | HZ3 | LYS | B | 150 | -5.908 | 29.297 | -44.398 | 1 | 25 | H |
| ATOM | 2843 | N | SER | B | 151 | -3.129 | 27.394 | -38.963 | 1 | 16.36 | N |
| ATOM | 2844 | CA | SER | B | 151 | -2.654 | 28.008 | -37.729 | 1 | 15.93 | C |

TABLE 5-continued

Atomic Coordinates for OMCP-NKG2D (4PDC).

| | | | | | | | | | | |
|---|---|---|---|---|---|---|---|---|---|---|
| ATOM | 2845 | C | SER | B | 151 | -1.536 | 27.201 | -37.075 | 1 | 14.66 C |
| ATOM | 2846 | O | SER | B | 151 | -1.004 | 26.253 | -37.656 | 1 | 15.81 O |
| ATOM | 2847 | CB | SER | B | 151 | -3.817 | 28.195 | -36.746 | 1 | 16.71 C |
| ATOM | 2848 | OG | SER | B | 151 | -3.442 | 29.042 | -35.672 | 1 | 18.88 O |
| ATOM | 2849 | H | SER | B | 151 | -2.944 | 27.853 | -39.666 | 1 | 19.63 H |
| ATOM | 2850 | HA | SER | B | 151 | -2.3 | 28.887 | -37.937 | 1 | 19.12 H |
| ATOM | 2851 | HB2 | SER | B | 151 | -4.566 | 28.593 | -37.215 | 1 | 20.05 H |
| ATOM | 2852 | HB3 | SER | B | 151 | -4.071 | 27.329 | -36.39 | 1 | 20.05 H |
| ATOM | 2853 | HG | SER | B | 151 | -4.087 | 29.136 | -35.142 | 1 | 22.66 H |
| ATOM | 2854 | N | TYR | B | 152 | -1.184 | 27.604 | -35.862 | 1 | 13.42 N |
| ATOM | 2855 | CA | TYR | B | 152 | -0.041 | 27.051 | -35.15 | 1 | 12.43 C |
| ATOM | 2856 | C | TYR | B | 152 | -0.498 | 26.485 | -33.816 | 1 | 12.59 C |
| ATOM | 2857 | O | TYR | B | 152 | -1.349 | 27.075 | -33.152 | 1 | 14.9 O |
| ATOM | 2858 | CB | TYR | B | 152 | 1.015 | 28.128 | -34.925 | 1 | 11.01 C |
| ATOM | 2859 | CG | TYR | B | 152 | 1.401 | 28.904 | -36.165 | 1 | 14.74 C |
| ATOM | 2860 | CD1 | TYR | B | 152 | 1.697 | 28.254 | -37.356 | 1 | 14.53 C |
| ATOM | 2861 | CD2 | TYR | B | 152 | 1.476 | 30.291 | -36.14 | 1 | 16.11 C |
| ATOM | 2862 | CE1 | TYR | B | 152 | 2.063 | 28.964 | -38.488 | 1 | 19.24 C |
| ATOM | 2863 | CE2 | TYR | B | 152 | 1.837 | 31.011 | -37.265 | 1 | 13.65 C |
| ATOM | 2864 | CZ | TYR | B | 152 | 2.132 | 30.343 | -38.436 | 1 | 18.79 C |
| ATOM | 2865 | OH | TYR | B | 152 | 2.492 | 31.058 | -39.558 | 1 | 16.6 O |
| ATOM | 2866 | H | TYR | B | 152 | -1.602 | 28.212 | -35.42 | 1 | 16.1 H |
| ATOM | 2867 | HA | TYR | B | 152 | 0.353 | 26.334 | -35.672 | 1 | 14.92 H |
| ATOM | 2868 | HB2 | TYR | B | 152 | 0.676 | 28.764 | -34.276 | 1 | 13.21 H |
| ATOM | 2869 | HB3 | TYR | B | 152 | 1.818 | 27.708 | -34.581 | 1 | 13.21 H |
| ATOM | 2870 | HD1 | TYR | B | 152 | 1.656 | 27.325 | -37.393 | 1 | 17.43 H |
| ATOM | 2871 | HD2 | TYR | B | 152 | 1.283 | 30.744 | -35.351 | 1 | 19.33 H |
| ATOM | 2872 | HE1 | TYR | B | 152 | 2.259 | 28.516 | -39.278 | 1 | 23.09 H |
| ATOM | 2873 | HE2 | TYR | B | 152 | 1.884 | 31.939 | -37.231 | 1 | 16.38 H |
| ATOM | 2874 | HH | TYR | B | 152 | 2.493 | 31.88 | -39.386 | 1 | 19.92 H |
| ATOM | 2875 | N | HIS | B | 153 | 0.066 | 25.347 | -33.423 | 1 | 12.19 N |
| ATOM | 2876 | CA | HIS | B | 153 | -0.389 | 24.651 | -32.228 | 1 | 14.36 C |
| ATOM | 2877 | C | HIS | B | 153 | 0.758 | 23.957 | -31.495 | 1 | 13.41 C |
| ATOM | 2878 | O | HIS | B | 153 | 1.626 | 23.342 | -32.118 | 1 | 12.89 O |
| ATOM | 2879 | CB | HIS | B | 153 | 1.464 | 23.627 | -32.601 | 1 | 15.15 C |
| ATOM | 2880 | CG | HIS | B | 153 | -2.473 | 24.146 | -33.578 | 1 | 14.4 C |
| ATOM | 2881 | ND1 | HIS | B | 153 | -3.664 | 24.719 | -33.187 | 1 | 12.28 N |
| ATOM | 2882 | CD2 | HIS | B | 153 | -2.459 | 24.195 | -34.932 | 1 | 15.15 C |
| ATOM | 2883 | CE1 | HIS | B | 153 | -4.344 | 25.088 | -34.257 | 1 | 14.83 C |
| ATOM | 2884 | NE2 | HIS | B | 153 | -3.635 | 24.783 | -35.329 | 1 | 14.05 N |
| ATOM | 2885 | H | HIS | B | 153 | 0.714 | 24.958 | -33.833 | 1 | 14.63 H |
| ATOM | 2886 | HA | HIS | B | 153 | -0.787 | 25.294 | -31.621 | 1 | 17.23 H |
| ATOM | 2887 | HB2 | HIS | B | 153 | -1.035 | 22.854 | -32.999 | 1 | 18.18 H |
| ATOM | 2888 | HB3 | HIS | B | 153 | -1.937 | 23.364 | -31.796 | 1 | 18.18 H |
| ATOM | 2889 | HD1 | HIS | B | 153 | -3.926 | 24.816 | -32.373 | 1 | 14.73 H |
| ATOM | 2890 | HD2 | HIS | B | 153 | -1.781 | 23.885 | -35.488 | 1 | 18.18 H |
| ATOM | 2891 | HE1 | HIS | B | 153 | -5.18 | 25.496 | -34.257 | 1 | 17.79 H |
| ATOM | 2892 | HE2 | HIS | B | 153 | -3.871 | 24.928 | -36.143 | 1 | 16.86 H |
| ATOM | 2893 | N | TRP | B | 154 | 0.757 | 24.065 | -30.169 | 1 | 14.83 N |
| ATOM | 2894 | CA | TRP | B | 154 | 1.722 | 23.341 | -29.353 | 1 | 15.59 C |
| ATOM | 2895 | C | TRP | B | 154 | 1.638 | 21.838 | -29.612 | 1 | 15.56 C |

TABLE 5-continued

Atomic Coordinates for OMCP-NKG2D (4PDC).

| | | | | | | | | | |
|---|---|---|---|---|---|---|---|---|---|
| ATOM | 2896 | O | TRP | B | 154 | 0.546 | 21.257 | -29.644 | 1 | 12.57 | O |
| ATOM | 2897 | CB | TRP | B | 154 | 1.497 | 23.599 | -27.86 | 1 | 17.58 | C |
| ATOM | 2898 | CG | TRP | B | 154 | 1.962 | 24.933 | -27.34 | 1 | 16.06 | C |
| ATOM | 2899 | CD1 | TRP | B | 154 | 1.23 | 25.821 | -26.606 | 1 | 18.33 | C |
| ATOM | 2900 | CD2 | TRP | B | 154 | 3.265 | 25.515 | -27.489 | 1 | 12.92 | C |
| ATOM | 2901 | NE1 | TRP | B | 154 | 1.993 | 26.922 | -26.293 | 1 | 15.98 | N |
| ATOM | 2902 | CE2 | TRP | B | 154 | 3.244 | 26.76 | -26.825 | 1 | 16.75 | C |
| ATOM | 2903 | CE3 | TRP | B | 154 | 4.441 | 25.112 | -28.125 | 1 | 14.07 | C |
| ATOM | 2904 | CZ2 | TRP | B | 154 | 4.357 | 27.6 | -26.777 | 1 | 16.96 | C |
| ATOM | 2905 | CZ3 | TRP | B | 154 | 5.543 | 25.946 | -28.075 | 1 | 13.07 | C |
| ATOM | 2906 | CH2 | TRP | B | 154 | 5.493 | 27.176 | -27.407 | 1 | 16.27 | C |
| ATOM | 2907 | H | TRP | B | 154 | 0.208 | 24.551 | -29.72 | 1 | 17.8 | H |
| ATOM | 2908 | HA | TRP | B | 154 | 2.617 | 23.638 | -29.58 | 1 | 18.71 | H |
| ATOM | 2909 | HB2 | TRP | B | 154 | 0.546 | 23.535 | -27.681 | 1 | 21.1 | H |
| ATOM | 2910 | HB3 | TRP | B | 154 | 1.966 | 22.914 | -27.359 | 1 | 21.1 | H |
| ATOM | 2911 | HD1 | TRP | B | 154 | 0.345 | 25.698 | -26.35 | 1 | 22 | H |
| ATOM | 2912 | HE1 | TRP | B | 154 | 1.726 | 27.602 | -25.839 | 1 | 19.17 | H |
| ATOM | 2913 | HE3 | TRP | B | 154 | 4.484 | 24.295 | -28.568 | 1 | 16.88 | H |
| ATOM | 2914 | HZ2 | TRP | B | 154 | 4.325 | 28.418 | -26.337 | 1 | 20.35 | H |
| ATOM | 2915 | HZ3 | TRP | B | 154 | 6.332 | 25.686 | -28.493 | 1 | 15.69 | H |
| ATOM | 2916 | HH2 | TRP | B | 154 | 6.249 | 27.717 | -27.393 | 1 | 19.52 | H |
| ATOM | 2917 | N | MET | B | 155 | 2.802 | 21.229 | -29.81 | 1 | 9.94 | N |
| ATOM | 2918 | CA | MET | B | 155 | 2.946 | 19.779 | -29.802 | 1 | 14.74 | C |
| ATOM | 2919 | C | MET | B | 155 | 3.944 | 19.396 | -28.711 | 1 | 16.06 | C |
| ATOM | 2920 | O | MET | B | 155 | 4.555 | 20.265 | -28.092 | 1 | 15.26 | O |
| ATOM | 2921 | CB | MET | B | 155 | 3.401 | 19.261 | -31.167 | 1 | 14.63 | C |
| ATOM | 2922 | CG | MET | B | 155 | 4.639 | 19.948 | -31.731 | 1 | 14.92 | C |
| ATOM | 2923 | SD | MET | B | 155 | 5.043 | 19.295 | -33.366 | 1 | 14.73 | S |
| ATOM | 2924 | CE | MET | B | 155 | 6.245 | 20.481 | -33.946 | 1 | 14.31 | C |
| ATOM | 2925 | H | MET | B | 155 | 3.541 | 21.645 | -29.955 | 1 | 11.93 | H |
| ATOM | 2926 | HA | MET | B | 155 | 2.086 | 19.377 | -29.6 | 1 | 17.69 | H |
| ATOM | 2927 | HB2 | MET | B | 155 | 3.601 | 18.315 | -31.088 | 1 | 17.56 | H |
| ATOM | 2928 | HB3 | MET | B | 155 | 2.68 | 19.389 | -31.803 | 1 | 17.56 | H |
| ATOM | 2929 | HG2 | MET | B | 155 | 4.47 | 20.9 | -31.814 | 1 | 17.9 | H |
| ATOM | 2930 | HG3 | MET | B | 155 | 5.393 | 19.789 | -31.142 | 1 | 17.9 | H |
| ATOM | 2931 | HE1 | MET | B | 155 | 6.539 | 20.224 | -34.834 | 1 | 17.17 | H |
| ATOM | 2932 | HE2 | MET | B | 155 | 5.834 | 21.359 | -33.973 | 1 | 17.17 | H |
| ATOM | 2933 | HE3 | MET | B | 155 | 7 | 20.487 | -33.337 | 1 | 17.17 | H |
| ATOM | 2934 | N | GLY | B | 156 | 4.118 | 18.098 | -28.488 | 1 | 16.14 | N |
| ATOM | 2935 | CA | GLY | B | 156 | 4.866 | 17.615 | -27.341 | 1 | 17.15 | C |
| ATOM | 2936 | C | GLY | B | 156 | 6.372 | 17.566 | -27.518 | 1 | 20.32 | C |
| ATOM | 2937 | O | GLY | B | 156 | 7.04 | 16.765 | -26.871 | 1 | 22.44 | O |
| ATOM | 2938 | H | GLY | B | 156 | 3.809 | 17.474 | -28.993 | 1 | 19.37 | H |
| ATOM | 2939 | HA2 | GLY | B | 156 | 4.674 | 18.186 | -26.58 | 1 | 20.58 | H |
| ATOM | 2940 | HA3 | GLY | B | 156 | 4.563 | 16.719 | -27.125 | 1 | 20.58 | H |
| ATOM | 2941 | N | LEU | B | 157 | 6.907 | 18.425 | -28.379 | 1 | 19.69 | N |
| ATOM | 2942 | CA | LEU | B | 157 | 8.338 | 18.436 | -28.667 | 1 | 18.9 | C |
| ATOM | 2943 | C | LEU | B | 157 | 9.056 | 19.485 | -27.826 | 1 | 26.5 | C |
| ATOM | 2944 | O | LEU | B | 157 | 8.641 | 20.647 | -27.784 | 1 | 20.35 | O |
| ATOM | 2945 | CB | LEU | B | 157 | 8.575 | 18.704 | -30.151 | 1 | 21.54 | C |
| ATOM | 2946 | CG | LEU | B | 157 | 9.956 | 18.345 | -30.698 | 1 | 24.32 | C |

TABLE 5-continued

Atomic Coordinates for OMCP-NKG2D (4PDC).

| ATOM | 2947 | CD1 | LEU | B | 157 | 10.18 | 16.839 | -30.673 | 1 | 23 | C |
|------|------|-----|-----|---|-----|-------|--------|---------|---|-------|---|
| ATOM | 2948 | CD2 | LEU | B | 157 | 10.107 | 18.882 | -32.106 | 1 | 21.66 | C |
| ATOM | 2949 | H | LEU | B | 157 | 6.459 | 19.017 | -28.813 | 1 | 23.63 | H |
| ATOM | 2950 | HA | LEU | B | 157 | 8.713 | 17.567 | -28.453 | 1 | 22.67 | H |
| ATOM | 2951 | HB2 | LEU | B | 157 | 7.924 | 18.195 | -30.659 | 1 | 25.85 | H |
| ATOM | 2952 | HB3 | LEU | B | 157 | B.44 | 19.651 | -30.313 | 1 | 25.85 | H |
| ATOM | 2953 | HG | LEU | B | 157 | 10.635 | 18.76 | -30.143 | 1 | 29.18 | H |
| ATOM | 2954 | HD11 | LEU | B | 157 | 11.063 | 16.646 | -31.026 | 1 | 27.6 | H |
| ATOM | 2955 | HD12 | LEU | B | 157 | 10.114 | 16.526 | -29.757 | 1 | 27.6 | H |
| ATOM | 2956 | HD13 | LEU | B | 157 | 9.504 | 16.411 | -31.22 | 1 | 27.6 | H |
| ATOM | 2957 | HD21 | LEU | B | 157 | 10.986 | 18.647 | -32.441 | 1 | 25.99 | H |
| ATOM | 2958 | HD22 | LEU | B | 157 | 9.422 | 18.488 | -32.669 | 1 | 25.99 | H |
| ATOM | 2959 | HD23 | LEU | B | 157 | 10.006 | 19.847 | -32.088 | 1 | 25.99 | H |
| ATOM | 2960 | N | VAL | B | 158 | 10.131 | 19.072 | -27.16 | 1 | 22.65 | N |
| ATOM | 2961 | CA | VAL | B | 158 | 10.884 | 19.968 | -26.289 | 1 | 21.67 | C |
| ATOM | 2962 | C | VAL | B | 158 | 12.384 | 19.821 | -26.504 | 1 | 23.85 | C |
| ATOM | 2963 | O | VAL | B | 158 | 12.879 | 18.732 | -26.798 | 1 | 21.21 | O |
| ATOM | 2964 | CB | VAL | B | 158 | 10.56 | 19.711 | -24.804 | 1 | 27.43 | C |
| ATOM | 2965 | CG1 | VAL | B | 158 | 9.115 | 20.099 | -24.502 | 1 | 26.57 | C |
| ATOM | 2966 | CG2 | VAL | B | 158 | 10.814 | 18.253 | -24.446 | 1 | 29.47 | C |
| ATOM | 2967 | H | VAL | B | 158 | 10.447 | 18.273 | -27.197 | 1 | 27.18 | H |
| ATOM | 2968 | HA | VAL | B | 158 | 10.641 | 20.885 | -26.494 | 1 | 26.01 | H |
| ATOM | 2969 | HB | VAL | B | 158 | 11.139 | 20.261 | -24.254 | 1 | 32.92 | H |
| ATOM | 2970 | HG11 | VAL | B | 158 | 8.933 | 19.929 | -23.565 | 1 | 31.88 | H |
| ATOM | 2971 | HG12 | VAL | B | 158 | 8.995 | 21.041 | -24.698 | 1 | 31.88 | H |
| ATOM | 2972 | HG13 | VAL | B | 158 | 8.524 | 19.567 | -25.056 | 1 | 31.88 | H |
| ATOM | 2973 | HG21 | VAL | B | 158 | 10.602 | 18.117 | -23.509 | 1 | 35.36 | H |
| ATOM | 2974 | HG22 | VAL | B | 158 | 10.249 | 17.689 | -24.998 | 1 | 35.36 | H |
| ATOM | 2975 | HG23 | VAL | B | 158 | 11.747 | 18.046 | -24.608 | 1 | 35.36 | H |
| ATOM | 2976 | N | HIS | B | 159 | 13.096 | 20.933 | -26.357 | 1 | 22.33 | N |
| ATOM | 2977 | CA | HIS | B | 159 | 14.541 | 20.959 | -26.523 | 1 | 29.47 | C |
| ATOM | 2978 | C | HIS | B | 159 | 15.215 | 20.956 | -25.158 | 1 | 41.69 | C |
| ATOM | 2979 | O | HIS | B | 159 | 14.926 | 21.802 | -24.315 | 1 | 37.55 | O |
| ATOM | 2980 | CB | HIS | B | 159 | 14.961 | 22.189 | -27.327 | 1 | 33.99 | C |
| ATOM | 2981 | CG | HIS | B | 159 | 16.43 | 22.259 | -27.601 | 1 | 41.87 | C |
| ATOM | 2982 | ND1 | HIS | B | 159 | 17.272 | 23.12 | -26.929 | 1 | 45.71 | N |
| ATOM | 2983 | CD2 | HIS | B | 159 | 17.207 | 21.576 | -28.474 | 1 | 42.1 | C |
| ATOM | 2984 | CE1 | HIS | B | 159 | 18.505 | 22.962 | -27.377 | 1 | 52.16 | C |
| ATOM | 2985 | NE2 | HIS | B | 159 | 18.492 | 22.032 | -28.314 | 1 | 50.26 | N |
| ATOM | 2986 | H | HIS | B | 159 | 12.757 | 21.698 | -26.158 | 1 | 26.8 | H |
| ATOM | 2987 | HA | HIS | B | 159 | 14.824 | 20.167 | -27.006 | 1 | 35.36 | H |
| ATOM | 2988 | HB2 | HIS | B | 159 | 14.501 | 22.177 | -28.18 | 1 | 40.79 | H |
| ATOM | 2989 | HB3 | HIS | B | 159 | 14.714 | 22.985 | -26.831 | 1 | 40.79 | H |
| ATOM | 2990 | HD1 | HIS | B | 159 | 17.033 | 23.672 | -26.315 | 1 | 54.85 | H |
| ATOM | 2991 | HD2 | HIS | B | 159 | 16.923 | 20.92 | -29.07 | 1 | 50.52 | H |
| ATOM | 2992 | HE1 | HIS | B | 159 | 19.255 | 23.428 | -27.083 | 1 | 62.6 | H |
| ATOM | 2993 | HE2 | HIS | B | 159 | 19.178 | 21.757 | -28.754 | 1 | 60.31 | H |
| ATOM | 2994 | N | ILE | B | 160 | 16.102 | 19.991 | -24.944 | 1 | 47.95 | N |
| ATOM | 2995 | CA | ILE | B | 160 | 16.84 | 19.885 | -23.692 | 1 | 58.27 | C |
| ATOM | 2996 | C | ILE | B | 160 | 18.248 | 20.455 | -23.88 | 1 | 66.09 | C |
| ATOM | 2997 | O | ILE | B | 160 | 19.148 | 19.743 | -24.324 | 1 | 70.94 | O |

TABLE 5-continued

Atomic Coordinates for OMCP-NKG2D (4PDC).

| ATOM | 2998 | CB | ILE | B | 160 | 16.936 | 18.419 | -23.208 | 1 | 63.95 | C |
|---|---|---|---|---|---|---|---|---|---|---|---|
| ATOM | 2999 | CG1 | ILE | B | 160 | 15.588 | 17.704 | -23.348 | 1 | 56.29 | C |
| ATOM | 3000 | CG2 | ILE | B | 160 | 17.414 | 18.368 | -21.768 | 1 | 67.71 | C |
| ATOM | 3001 | CD1 | ILE | B | 160 | 14.461 | 18.326 | -22.545 | 1 | 48.29 | C |
| ATOM | 3002 | H | ILE | B | 160 | 16.295 | 19.377 | -25.514 | 1 | 57.54 | H |
| ATOM | 3003 | HA | ILE | B | 160 | 16.389 | 20.404 | -23.007 | 1 | 69.92 | H |
| ATOM | 3004 | HB | ILE | B | 160 | 17.585 | 17.958 | -23.761 | 1 | 76.73 | H |
| ATOM | 3005 | HG12 | ILE | B | 160 | 15.326 | 17.717 | -24.282 | 1 | 67.54 | H |
| ATOM | 3006 | HG13 | ILE | B | 160 | 15.69 | 16.787 | -23.05 | 1 | 67.54 | H |
| ATOM | 3007 | HG21 | ILE | B | 160 | 17.467 | 17.442 | -21.486 | 1 | 81.25 | H |
| ATOM | 3008 | HG22 | ILE | B | 160 | 18.29 | 18.782 | -21.712 | 1 | 81.25 | H |
| ATOM | 3009 | HG23 | ILE | B | 160 | 16.784 | 18.849 | -21.209 | 1 | 81.25 | H |
| ATOM | 3010 | HD11 | ILE | B | 160 | 13.65 | 17.815 | -22.691 | 1 | 57.95 | H |
| ATOM | 3011 | HD12 | ILE | B | 160 | 14.698 | 18.311 | -21.605 | 1 | 57.95 | H |
| ATOM | 3012 | HD13 | ILE | B | 160 | 14.332 | 19.242 | -22.839 | 1 | 57.95 | H |
| ATOM | 3013 | N | PRO | B | 161 | 18.448 | 21.748 | -23.558 | 1 | 69.7 | N |
| ATOM | 3014 | CA | PRO | B | 161 | 19.784 | 22.316 | -23.778 | 1 | 73.07 | C |
| ATOM | 3015 | C | PRO | B | 161 | 20.833 | 21.764 | -22.813 | 1 | 80.56 | C |
| ATOM | 3016 | O | PRO | B | 161 | 20.862 | 22.147 | -21.644 | 1 | 84.37 | O |
| ATOM | 3017 | CB | PRO | B | 161 | 19.57 | 23.817 | -23.556 | 1 | 69.03 | C |
| ATOM | 3018 | CG | PRO | B | 161 | 18.392 | 23.902 | -22.659 | 1 | 63.55 | C |
| ATOM | 3019 | CD | PRO | B | 161 | 17.503 | 22.758 | -23.048 | 1 | 60.94 | C |
| ATOM | 3020 | HA | PRO | B | 161 | 20.072 | 22.162 | -24.692 | 1 | 87.68 | H |
| ATOM | 3021 | HB2 | PRO | B | 161 | 20.354 | 24.2 | -23.132 | 1 | 82.83 | H |
| ATOM | 3022 | HB3 | PRO | B | 161 | 19.39 | 24.251 | -24.404 | 1 | 82.83 | H |
| ATOM | 3023 | HG2 | PRO | B | 161 | 18.678 | 23.814 | -21.737 | 1 | 76.25 | H |
| ATOM | 3024 | HG3 | PRO | B | 161 | 17.939 | 24.749 | -22.798 | 1 | 76.25 | H |
| ATOM | 3025 | HD2 | PRO | B | 161 | 17.031 | 22.417 | -22.272 | 1 | 73.12 | H |
| ATOM | 3026 | HD3 | PRO | B | 161 | 16.888 | 23.029 | -23.748 | 1 | 73.12 | H |
| ATOM | 3027 | N | THR | B | 162 | 21.679 | 20.88 | -23.334 | 1 | 82.8 | N |
| ATOM | 3028 | CA | THR | B | 162 | 22.732 | 20.185 | -22.591 | 1 | 89.98 | C |
| ATOM | 3029 | C | THR | B | 162 | 23.165 | 19.019 | -23.47 | 1 | 91.72 | C |
| ATOM | 3030 | O | THR | B | 162 | 24.34 | 18.653 | -23.513 | 1 | 95.85 | O |
| ATOM | 3031 | CB | THR | B | 162 | 22.284 | 19.66 | -21.201 | 1 | 95.35 | C |
| ATOM | 3032 | OG1 | THR | B | 162 | 23.364 | 18.945 | -20.585 | 1 | 96.68 | O |
| ATOM | 3033 | CG2 | THR | B | 162 | 21.08 | 18.741 | -21.324 | 1 | 98.91 | C |
| ATOM | 3034 | H | THR | B | 162 | 21.661 | 20.654 | -24.164 | 1 | 99.36 | H |
| ATOM | 3035 | HA | THR | B | 162 | 23.49 | 20.778 | -22.468 | 1 | 107.98 | H |
| ATOM | 3036 | HB | THR | B | 162 | 22.037 | 20.412 | -20.64 | 1 | 114.42 | H |
| ATOM | 3037 | HG1 | THR | B | 162 | 23.588 | 18.294 | -21.066 | 1 | 116.01 | H |
| ATOM | 3038 | HG21 | THR | B | 162 | 20.815 | 18.424 | -20.446 | 1 | 118.69 | H |
| ATOM | 3039 | HG22 | THR | B | 162 | 20.337 | 19.22 | -21.724 | 1 | 118.69 | H |
| ATOM | 3040 | HG23 | THR | B | 162 | 21.301 | 17.979 | -21.881 | 1 | 118.69 | H |
| ATOM | 3041 | N | ASN | B | 163 | 22.186 | 18.447 | -24.166 | 1 | 91.1 | N |
| ATOM | 3042 | CA | ASN | B | 163 | 22.418 | 17.423 | -25.177 | 1 | 91.71 | C |
| ATOM | 3043 | C | ASN | B | 163 | 22.143 | 17.982 | -26.573 | 1 | 82.79 | C |
| ATOM | 3044 | O | ASN | B | 163 | 22.538 | 17.393 | -27.58 | 1 | 78.88 | O |
| ATOM | 3045 | CB | ASN | B | 163 | 21.543 | 16.19 | -24.907 | 1 | 94.16 | C |
| ATOM | 3046 | CG | ASN | B | 163 | 20.053 | 16.513 | -24.865 | 1 | 93.87 | C |
| ATOM | 3047 | OD1 | ASN | B | 163 | 19.539 | 17.272 | -25.687 | 1 | 91.61 | O |
| ATOM | 3048 | ND2 | ASN | B | 163 | 19.353 | 15.925 | -23.9 | 1 | 94.1 | N |

TABLE 5-continued

Atomic Coordinates for OMCP-NKG2D (4PDC).

| | | | | | | | | | | |
|---|---|---|---|---|---|---|---|---|---|---|
| ATOM | 3049 | H | ASN | B | 163 | 21.354 | 18.643 | -24.066 | 1 | 109.32 | H |
| ATOM | 3050 | HA | ASN | B | 163 | 23.347 | 17.147 | -25.141 | 1 | 110.05 | H |
| ATOM | 3051 | HB2 | ASN | B | 163 | 21.688 | 15.54 | -25.612 | 1 | 112.99 | H |
| ATOM | 3052 | HB3 | ASN | B | 163 | 21.791 | 15.81 | -24.05 | 1 | 112.99 | H |
| ATOM | 3053 | HD21 | ASN | B | 163 | 18.509 | 16.073 | -23.831 | 1 | 112.92 | H |
| ATOM | 3054 | HD22 | ASN | B | 163 | 19.744 | 15.398 | -23.345 | 1 | 112.92 | H |
| ATOM | 3055 | N | GLY | B | 164 | 21.463 | 19.124 | -26.622 | 1 | 81.6 | N |
| ATOM | 3056 | CA | GLY | B | 164 | 21.145 | 19.781 | -27.877 | 1 | 76.23 | C |
| ATOM | 3057 | C | GLY | B | 164 | 20.312 | 18.905 | -28.793 | 1 | 73.18 | C |
| ATOM | 3058 | O | GLY | B | 164 | 20.669 | 18.689 | -29.951 | 1 | 76.11 | O |
| ATOM | 3059 | H | GLY | B | 164 | 21.172 | 19.542 | -25.929 | 1 | 97.92 | H |
| ATOM | 3060 | HA2 | GLY | B | 164 | 20.652 | 20.597 | -27.7 | 1 | 91.48 | H |
| ATOM | 3061 | HA3 | GLY | B | 164 | 21.967 | 20.012 | -28.338 | 1 | 91.48 | H |
| ATOM | 3062 | N | SER | B | 165 | 19.2 | 18.399 | -28.269 | 1 | 64.95 | N |
| ATOM | 3063 | CA | SER | B | 165 | 18.326 | 17.518 | -29.031 | 1 | 57.43 | C |
| ATOM | 3064 | C | SER | B | 165 | 16.861 | 17.81 | -28.744 | 1 | 45.57 | C |
| ATOM | 3065 | O | SER | B | 165 | 16.511 | 18.287 | -27.663 | 1 | 44.26 | O |
| ATOM | 3066 | CB | SER | B | 165 | 18.635 | 16.056 | -28.711 | 1 | 62.72 | C |
| ATOM | 3067 | OG | SER | B | 165 | 18.321 | 15.754 | -27.362 | 1 | 67.74 | O |
| ATOM | 3068 | H | SER | B | 165 | 18.928 | 18.554 | -27.468 | 1 | 77.94 | H |
| ATOM | 3069 | HA | SER | B | 165 | 18.481 | 17.659 | -29.978 | 1 | 68.91 | H |
| ATOM | 3070 | HB2 | SER | B | 165 | 18.106 | 15.488 | -29.292 | 1 | 75.26 | H |
| ATOM | 3071 | HB3 | SER | B | 165 | 19.58 | 15.894 | -28.859 | 1 | 75.26 | H |
| ATOM | 3072 | HG | SER | B | 165 | 17.505 | 15.89 | -27.219 | 1 | 81.29 | H |
| ATOM | 3073 | N | TRP | B | 166 | 16.012 | 17.515 | -29.723 | 1 | 40.98 | N |
| ATOM | 3074 | CA | TRP | B | 166 | 14.569 | 17.656 | -29.572 | 1 | 34.55 | C |
| ATOM | 3075 | C | TRP | B | 166 | 13.945 | 16.298 | -29.288 | 1 | 31.08 | C |
| ATOM | 3076 | O | TRP | B | 166 | 14.212 | 15.33 | -29.999 | 1 | 34.34 | O |
| ATOM | 3077 | CB | TRP | B | 166 | 13.953 | 18.265 | -30.83 | 1 | 30.13 | C |
| ATOM | 3078 | CG | TRP | B | 166 | 14.302 | 19.703 | -31.041 | 1 | 30.81 | C |
| ATOM | 3079 | CD1 | TRP | B | 166 | 15.354 | 20.196 | -31.756 | 1 | 36.26 | C |
| ATOM | 3080 | CD2 | TRP | B | 166 | 13.591 | 20.841 | -30.538 | 1 | 28.21 | C |
| ATOM | 3081 | NE1 | TRP | B | 166 | 15.344 | 21.569 | -31.726 | 1 | 34.03 | N |
| ATOM | 3082 | CE2 | TRP | B | 166 | 14.272 | 21.99 | -30.984 | 1 | 27.63 | C |
| ATOM | 3083 | CE3 | TRP | B | 166 | 12.446 | 20.999 | -29.751 | 1 | 23.82 | C |
| ATOM | 3084 | CZ2 | TRP | B | 166 | 13.846 | 23.28 | -30.671 | 1 | 27.91 | C |
| ATOM | 3085 | CZ3 | TRP | B | 166 | 12.024 | 22.281 | -29.44 | 1 | 24.12 | C |
| ATOM | 3086 | CH2 | TRP | B | 166 | 12.722 | 23.405 | -29.901 | 1 | 25.08 | C |
| ATOM | 3087 | H | TRP | B | 166 | 16.252 | 17.226 | -30.496 | 1 | 49.18 | H |
| ATOM | 3088 | HA | TRP | B | 166 | 14.379 | 18.243 | -28.824 | 1 | 41.46 | H |
| ATOM | 3089 | HB2 | TRP | B | 166 | 14.265 | 17.769 | -31.603 | 1 | 36.16 | H |
| ATOM | 3090 | HB3 | TRP | B | 166 | 12.987 | 18.201 | -30.767 | 1 | 36.16 | H |
| ATOM | 3091 | HD1 | TRP | B | 166 | 15.987 | 19.677 | -32.198 | 1 | 43.51 | H |
| ATOM | 3092 | HE1 | TRP | B | 166 | 15.918 | 22.081 | -32.111 | 1 | 40.83 | H |
| ATOM | 3093 | HE3 | TRP | B | 166 | 11.977 | 20.257 | -29.442 | 1 | 28.59 | H |
| ATOM | 3094 | HZ2 | TRP | B | 166 | 14.308 | 24.028 | -30.975 | 1 | 33.49 | H |
| ATOM | 3095 | HZ3 | TRP | B | 166 | 11.263 | 22.398 | -28.918 | 1 | 28.94 | H |
| ATOM | 3096 | HH2 | TRP | B | 166 | 12.416 | 24.254 | -29.676 | 1 | 30.1 | H |
| ATOM | 3097 | N | GLN | B | 167 | 13.119 | 16.225 | -28.25 | 1 | 27.39 | N |
| ATOM | 3098 | CA | GLN | B | 167 | 12.485 | 14.965 | -27.879 | 1 | 30.85 | C |
| ATOM | 3099 | C | GLN | B | 167 | 11.02 | 15.147 | -27.492 | 1 | 26.83 | C |

TABLE 5-continued

Atomic Coordinates for OMCP-NKG2D (4PDC).

| | | | | | | | | | | |
|---|---|---|---|---|---|---|---|---|---|---|
| ATOM | 3100 | O | GLN | B | 167 | 10.604 | 16.219 | -27.048 | 1 | 24.25 | O |
| ATOM | 3101 | CB | GLN | B | 167 | 13.248 | 14.306 | -26.729 | 1 | 31.47 | C |
| ATOM | 3102 | CG | GLN | B | 167 | 13.319 | 15.142 | -25.462 | 1 | 39.54 | C |
| ATOM | 3103 | CD | GLN | B | 167 | 13.995 | 14.409 | -24.315 | 1 | 47.76 | C |
| ATOM | 3104 | OE1 | GLN | B | 167 | 13.559 | 14.498 | -23.168 | 1 | 47.44 | O |
| ATOM | 3105 | NE2 | GLN | B | 167 | 15.066 | 13.683 | -24.618 | 1 | 48.92 | N |
| ATOM | 3106 | H | GLN | B | 167 | 12.91 | 16.889 | -27.745 | 1 | 32.87 | H |
| ATOM | 3107 | HA | GLN | B | 167 | 12.517 | 14.364 | -28.639 | 1 | 37.02 | H |
| ATOM | 3108 | HB2 | GLN | B | 167 | 12.811 | 13.469 | -26.505 | 1 | 37.76 | H |
| ATOM | 3109 | HB3 | GLN | B | 167 | 14.157 | 14.132 | -27.018 | 1 | 37.76 | H |
| ATOM | 3110 | HG2 | GLN | B | 167 | 13.827 | 15.949 | -25.644 | 1 | 47.45 | H |
| ATOM | 3111 | HG3 | GLN | B | 167 | 12.419 | 15.371 | -25.183 | 1 | 47.45 | H |
| ATOM | 3112 | HE21 | GLN | B | 167 | 15.482 | 13.251 | -24.002 | 1 | 58.7 | H |
| ATOM | 3113 | HE22 | GLN | B | 167 | 15.344 | 13.645 | -25.431 | 1 | 58.7 | H |
| ATOM | 3114 | N | TRP | B | 168 | 10.249 | 14.079 | -27.668 | 1 | 23.01 | N |
| ATOM | 3115 | CA | TRP | B | 168 | 8.838 | 14.077 | -27.318 | 1 | 26.18 | C |
| ATOM | 3116 | C | TRP | B | 168 | 8.659 | 13.855 | -25.826 | 1 | 24.45 | C |
| ATOM | 3117 | O | TRP | B | 168 | 9.611 | 13.512 | -25.128 | 1 | 28.38 | O |
| ATOM | 3118 | CB | TRP | B | 168 | 8.1 | 13 | -28.108 | 1 | 25.3 | C |
| ATOM | 3119 | CG | TRP | B | 168 | 8.224 | 13.197 | -29.577 | 1 | 26.32 | C |
| ATOM | 3120 | CD1 | TRP | B | 168 | 8.994 | 12.476 | -30.439 | 1 | 25.09 | C |
| ATOM | 3121 | CD2 | TRP | B | 168 | 7.571 | 14.198 | -30.361 | 1 | 22.02 | C |
| ATOM | 3122 | NE1 | TRP | B | 168 | 8.856 | 12.963 | -31.716 | 1 | 23.33 | N |
| ATOM | 3123 | CE2 | TRP | B | 168 | 7.985 | 14.02 | -31.694 | 1 | 23.22 | C |
| ATOM | 3124 | CE3 | TRP | B | 168 | 6.67 | 15.228 | -30.064 | 1 | 25.48 | C |
| ATOM | 3125 | CZ2 | TRP | B | 168 | 7.532 | 14.832 | -32.731 | 1 | 20.73 | C |
| ATOM | 3126 | CZ3 | TRP | B | 168 | 6.22 | 16.029 | -31.093 | 1 | 20.54 | C |
| ATOM | 3127 | CH2 | TRP | B | 168 | 6.653 | 15.829 | -32.41 | 1 | 19.21 | C |
| ATOM | 3128 | H | TRP | B | 168 | 10.527 | 13.334 | -27.995 | 1 | 27.61 | H |
| ATOM | 3129 | HA | TRP | B | 168 | 8.452 | 14.937 | -27.544 | 1 | 31.42 | H |
| ATOM | 3130 | HB2 | TRP | B | 168 | 8.473 | 12.133 | -27.888 | 1 | 30.36 | H |
| ATOM | 3131 | HB3 | TRP | B | 168 | 7.158 | 13.027 | -27.879 | 1 | 30.36 | H |
| ATOM | 3132 | HD1 | TRP | B | 168 | 9.534 | 11.758 | -30.198 | 1 | 30.11 | H |
| ATOM | 3133 | HE1 | TRP | B | 168 | 9.25 | 12.653 | -32.415 | 1 | 28 | H |
| ATOM | 3134 | HE3 | TRP | B | 168 | 6.379 | 15.367 | -29.192 | 1 | 30.57 | H |
| ATOM | 3135 | HZ2 | TRP | B | 168 | 7.815 | 14.701 | -33.607 | 1 | 24.88 | H |
| ATOM | 3136 | HZ3 | TRP | B | 168 | 5.622 | 16.717 | -30.909 | 1 | 24.65 | H |
| ATOM | 3137 | HH2 | TRP | B | 168 | 6.332 | 16.385 | -33.082 | 1 | 23.05 | H |
| ATOM | 3138 | N | GLU | B | 169 | 7.44 | 14.052 | -25.341 | 1 | 23.03 | N |
| ATOM | 3139 | CA | GLU | B | 169 | 7.144 | 13.867 | -23.922 | 1 | 27.07 | C |
| ATOM | 3140 | C | GLU | B | 169 | 7.491 | 12.466 | -23.43 | 1 | 28.35 | C |
| ATOM | 3141 | O | GLU | B | 169 | 7.865 | 12.291 | -22.271 | 1 | 29.75 | O |
| ATOM | 3142 | CB | GLU | B | 169 | 5.67 | 14.146 | -23.646 | 1 | 26.09 | C |
| ATOM | 3143 | CG | GLU | B | 169 | 5.303 | 15.611 | -23.69 | 1 | 25.97 | C |
| ATOM | 3144 | CD | GLU | B | 169 | 3.812 | 15.826 | -23.565 | 1 | 24.5 | C |
| ATOM | 3145 | OE1 | GLU | B | 169 | 3.374 | 16.389 | -22.542 | 1 | 25.81 | O |
| ATOM | 3146 | OE2 | GLU | B | 169 | 3.078 | 15.423 | -24.491 | 1 | 26.86 | O1- |
| ATOM | 3147 | H | GLU | B | 169 | 6.762 | 14.294 | -25.812 | 1 | 27.63 | H |
| ATOM | 3148 | HA | GLU | B | 169 | 7.669 | 14.501 | -23.408 | 1 | 32.48 | H |
| ATOM | 3149 | HB2 | GLU | B | 169 | 5.135 | 13.687 | -24.312 | 1 | 31.3 | H |
| ATOM | 3150 | HB3 | GLU | B | 169 | 5.45 | 13.813 | -22.762 | 1 | 31.3 | H |

TABLE 5-continued

Atomic Coordinates for OMCP-NKG2D (4PDC).

| ATOM | 3151 | HG2 | GLU | B | 169 | 5.737 | -22.954 | 31.17 | 1 | H |
|------|------|-----|-----|---|-----|-------|---------|-------|---|---|
| ATOM | 3152 | HG3 | GLU | B | 169 | 5.593 | -24.536 | 31.17 | 1 | H |
| ATOM | 3153 | N | ASP | B | 170 | 7.365 | -24.307 | 30.2 | 1 | N |
| ATOM | 3154 | CA | ASP | B | 170 | 7.651 | -23.935 | 31.21 | 1 | C |
| ATOM | 3155 | C | ASP | B | 170 | 9.145 | -24.088 | 30.44 | 1 | C |
| ATOM | 3156 | O | ASP | B | 170 | 9.779 | -24.005 | 30.44 | 1 | O |
| ATOM | 3157 | CB | ASP | B | 170 | 8.62 | -23.93 | 33.82 | 1 | C |
| ATOM | 3158 | CG | ASP | B | 170 | 9.111 | -24.827 | 31.14 | 1 | C |
| ATOM | 3159 | OD1 | ASP | B | 170 | 9.188 | -26.297 | 28.8 | 1 | O |
| ATOM | 3160 | OD2 | ASP | B | 170 | 8.297 | -26.629 | 28.18 | 1 | O1- |
| ATOM | 3161 | H | ASP | B | 170 | 6.557 | -27.131 | 33.86 | 1 | H |
| ATOM | 3162 | HA | ASP | B | 170 | 7.116 | -25.124 | 36.24 | 1 | H |
| ATOM | 3163 | HB2 | ASP | B | 170 | 7.363 | -23.02 | 37.45 | 1 | H |
| ATOM | 3164 | HB3 | ASP | B | 170 | 7.036 | -24.52 | 37.37 | 1 | H |
| ATOM | 3165 | N | GLY | B | 170 | 5.926 | -24.766 | 37.37 | 1 | N |
| ATOM | 3166 | CA | GLY | B | 171 | 9.959 | -24.173 | 28.28 | 1 | C |
| ATOM | 3167 | C | GLY | B | 171 | 11.402 | -24.161 | 30.98 | 1 | C |
| ATOM | 3168 | O | GLY | B | 171 | 11.999 | -25.498 | 29.68 | 1 | O |
| ATOM | 3169 | H | GLY | B | 171 | 13.213 | -25.688 | 36.65 | 1 | H |
| ATOM | 3170 | HA2 | GLY | B | 171 | 9.693 | -24.296 | 33.93 | 1 | H |
| ATOM | 3171 | HA3 | GLY | B | 171 | 11.806 | -23.887 | 37.17 | 1 | H |
| ATOM | 3172 | N | SER | B | 171 | 11.644 | -23.511 | 37.17 | 1 | N |
| ATOM | 3173 | CA | SER | B | 172 | 11.159 | -26.428 | 28.25 | 1 | C |
| ATOM | 3174 | C | SER | B | 172 | 11.644 | -27.733 | 32.36 | 1 | C |
| ATOM | 3175 | O | SER | B | 172 | 12.201 | -28.513 | 30.64 | 1 | O |
| ATOM | 3176 | CB | SER | B | 172 | 11.694 | -28.417 | 29.69 | 1 | C |
| ATOM | 3177 | OG | SER | B | 172 | 10.531 | -28.527 | 30.14 | 1 | O |
| ATOM | 3178 | H | SER | B | 172 | 9.494 | -28.857 | 32.1 | 1 | H |
| ATOM | 3179 | HA | SER | B | 172 | 10.307 | -26.329 | 33.9 | 1 | H |
| ATOM | 3180 | HB2 | SER | B | 172 | 12.362 | -27.607 | 38.83 | 1 | H |
| ATOM | 3181 | HB3 | SER | B | 172 | 10.906 | -29.346 | 36.17 | 1 | H |
| ATOM | 3182 | HG | SER | B | 172 | 10.16 | -27.991 | 36.17 | 1 | H |
| ATOM | 3183 | N | ILE | B | 172 | 9.158 | -28.157 | 38.52 | 1 | N |
| ATOM | 3184 | CA | ILE | B | 173 | 9.939 | -29.274 | 33.34 | 1 | C |
| ATOM | 3185 | C | ILE | B | 173 | 13.257 | -30.055 | 36.79 | 1 | C |
| ATOM | 3186 | O | ILE | B | 173 | 13.897 | -31.284 | 34.73 | 1 | O |
| ATOM | 3187 | CB | ILE | B | 173 | 13.052 | -31.782 | 35.37 | 1 | C |
| ATOM | 3188 | CG1 | ILE | B | 173 | 12.329 | -30.48 | 41.45 | 1 | C |
| ATOM | 3189 | CG2 | ILE | B | 173 | 15.328 | -31.044 | 45.9 | 1 | C |
| ATOM | 3190 | CD1 | ILE | B | 173 | 16.111 | -31.487 | 41.81 | 1 | C |
| ATOM | 3191 | H | ILE | B | 173 | 15.285 | -29.995 | 47.62 | 1 | H |
| ATOM | 3192 | HA | ILE | B | 173 | 13.16 | -29.357 | 40.01 | 1 | H |
| ATOM | 3193 | HB | ILE | B | 173 | 13.625 | -29.518 | 44.15 | 1 | H |
| ATOM | 3194 | HG12 | ILE | B | 173 | 13.961 | -29.69 | 49.74 | 1 | H |
| ATOM | 3195 | HG13 | ILE | B | 173 | 15.794 | -31.483 | 55.09 | 1 | H |
| ATOM | 3196 | HG21 | ILE | B | 173 | 16.91 | -31.686 | 55.09 | 1 | H |
| ATOM | 3197 | HG22 | ILE | B | 173 | 15.553 | -31.734 | 50.17 | 1 | H |
| ATOM | 3198 | HG23 | ILE | B | 173 | 16.193 | -31.081 | 50.17 | 1 | H |
| ATOM | 3199 | HD11 | ILE | B | 173 | 14.843 | -32.272 | 45.9 | 1 | H |
| ATOM | 3200 | HD12 | ILE | B | 173 | 14.794 | -30.428 | 57.15 | 1 | H |
| ATOM | 3201 | HD13 | ILE | B | 173 | 17.029 | -29.553 | 57.15 | 1 | H |

TABLE 5-continued

Atomic Coordinates for OMCP-NKG2D (4PDC).

| ATOM | 3202 | N | LEU | B | 174 | 13.137 | 12.929 | -31.76 | 1 | 35.6 | N |
|---|---|---|---|---|---|---|---|---|---|---|---|
| ATOM | 3203 | CA | LEU | B | 174 | 12.474 | 13.322 | -32.997 | 1 | 31.48 | C |
| ATOM | 3204 | C | LEU | B | 174 | 13.053 | 12.55 | -34.174 | 1 | 35.42 | C |
| ATOM | 3205 | O | LEU | B | 174 | 14.217 | 12.734 | -34.531 | 1 | 33.32 | O |
| ATOM | 3206 | CB | LEU | B | 174 | 12.623 | 14.826 | -33.23 | 1 | 26.55 | C |
| ATOM | 3207 | CG | LEU | B | 174 | 12.246 | 15.348 | -34.619 | 1 | 31.49 | C |
| ATOM | 3208 | CD1 | LEU | B | 174 | 10.787 | 15.05 | -34.937 | 1 | 27.57 | C |
| ATOM | 3209 | CD2 | LEU | B | 174 | 12.528 | 16.84 | -34.714 | 1 | 29.29 | C |
| ATOM | 3210 | H | LEU | B | 174 | 13.576 | 13.564 | -31.382 | 1 | 42.72 | H |
| ATOM | 3211 | HA | LEU | B | 174 | 11.528 | 13.116 | -32.933 | 1 | 37.78 | H |
| ATOM | 3212 | HB2 | LEU | B | 174 | 12.063 | 15.289 | -32.588 | 1 | 31.86 | H |
| ATOM | 3213 | HB3 | LEU | B | 174 | 13.551 | 15.065 | -33.077 | 1 | 31.86 | H |
| ATOM | 3214 | HG | LEU | B | 174 | 12.793 | 14.899 | -35.282 | 1 | 37.79 | H |
| ATOM | 3215 | HD11 | LEU | B | 174 | 10.581 | 15.392 | -35.821 | 1 | 33.08 | H |
| ATOM | 3216 | HD12 | LEU | B | 174 | 10.649 | 14.09 | -34.913 | 1 | 33.08 | H |
| ATOM | 3217 | HD13 | LEU | B | 174 | 10.225 | 15.482 | -34.275 | 1 | 33.08 | H |
| ATOM | 3218 | HD21 | LEU | B | 174 | 12.283 | 17.151 | -35.599 | 1 | 35.15 | H |
| ATOM | 3219 | HD22 | LEU | B | 174 | 12.004 | 17.303 | -34.043 | 1 | 35.15 | H |
| ATOM | 3220 | HD23 | LEU | B | 174 | 13.474 | 16.992 | -34.56 | 1 | 35.15 | H |
| ATOM | 3221 | N | SER | B | 175 | 12.242 | 11.686 | -34.776 | 1 | 36.01 | N |
| ATOM | 3222 | CA | SER | B | 175 | 12.703 | 10.894 | -35.911 | 1 | 38.08 | C |
| ATOM | 3223 | C | SER | B | 175 | 12.978 | 11.796 | -37.114 | 1 | 39.53 | C |
| ATOM | 3224 | O | SER | B | 175 | 12.257 | 12.771 | -37.345 | 1 | 35.1 | O |
| ATOM | 3225 | CB | SER | B | 175 | 11.679 | 9.818 | -36.277 | 1 | 34.05 | C |
| ATOM | 3226 | OG | SER | B | 175 | 11.435 | 8.952 | -35.181 | 1 | 46.41 | O |
| ATOM | 3227 | H | SER | B | 175 | 11.426 | 11.54 | -34.548 | 1 | 43.22 | H |
| ATOM | 3228 | HA | SER | B | 175 | 13.532 | 10.451 | -35.672 | 1 | 45.7 | H |
| ATOM | 3229 | HB2 | SER | B | 175 | 10.847 | 10.248 | -36.53 | 1 | 40.86 | H |
| ATOM | 3230 | HB3 | SER | B | 175 | 12.022 | 9.297 | -37.02 | 1 | 40.86 | H |
| ATOM | 3231 | HG | SER | B | 175 | 10.872 | 8.368 | -35.397 | 1 | 55.69 | H |
| ATOM | 3232 | N | PRO | B | 176 | 14.024 | 11.475 | -37.89 | 1 | 37.56 | N |
| ATOM | 3233 | CA | PRO | B | 176 | 14.394 | 12.331 | -39.02 | 1 | 40.19 | C |
| ATOM | 3234 | C | PRO | B | 176 | 13.366 | 12.306 | -40.148 | 1 | 39.31 | C |
| ATOM | 3235 | O | PRO | B | 176 | 12.536 | 11.398 | -40.204 | 1 | 39.37 | O |
| ATOM | 3236 | CB | PRO | B | 176 | 15.725 | 11.738 | -39.482 | 1 | 42.21 | C |
| ATOM | 3237 | CG | PRO | B | 176 | 15.663 | 10.317 | -39.076 | 1 | 48.89 | C |
| ATOM | 3238 | CD | PRO | B | 176 | 14.882 | 10.281 | -37.799 | 1 | 40.78 | C |
| ATOM | 3239 | HA | PRO | B | 176 | 14.53 | 13.245 | -38.724 | 1 | 48.23 | H |
| ATOM | 3240 | HB2 | PRO | B | 176 | 15.803 | 11.818 | -40.446 | 1 | 50.65 | H |
| ATOM | 3241 | HB3 | PRO | B | 176 | 16.459 | 12.192 | -39.038 | 1 | 50.65 | H |
| ATOM | 3242 | HG2 | PRO | B | 176 | 15.212 | 9.803 | -39.764 | 1 | 58.67 | H |
| ATOM | 3243 | HG3 | PRO | B | 176 | 16.562 | 9.981 | -38.934 | 1 | 58.67 | H |
| ATOM | 3244 | HD2 | PRO | B | 176 | 14.341 | 9.477 | -37.757 | 1 | 48.94 | H |
| ATOM | 3245 | HD3 | PRO | B | 176 | 15.478 | 10.35 | -37.037 | 1 | 48.94 | H |
| ATOM | 3246 | N | ASN | B | 177 | 13.423 | 13.307 | -41.022 | 1 | 32.05 | N |
| ATOM | 3247 | CA | ASN | B | 177 | 12.551 | 13.372 | -42.192 | 1 | 37.49 | C |
| ATOM | 3248 | C | ASN | B | 177 | 11.058 | 13.384 | -41.853 | 1 | 32.07 | C |
| ATOM | 3249 | O | ASN | B | 177 | 10.227 | 13.073 | -42.704 | 1 | 32.22 | O |
| ATOM | 3250 | CB | ASN | B | 177 | 12.853 | 12.2 | -43.134 | 1 | 43.25 | C |
| ATOM | 3251 | CG | ASN | B | 177 | 14.279 | 12.223 | -43.656 | 1 | 42.46 | C |
| ATOM | 3252 | OD1 | ASN | B | 177 | 14.599 | 12.972 | -44.579 | 1 | 48.73 | O |

TABLE 5-continued

Atomic Coordinates for OMCP-NKG2D (4PDC).

| ATOM | 3253 | ND2 | ASN | B | 177 | 15.14 | 11.398 | -43.072 | 1 | 42.22 | N |
|---|---|---|---|---|---|---|---|---|---|---|---|
| ATOM | 3254 | H | ASN | B | 177 | 13.967 | 13.97 | -40.959 | 1 | 38.46 | H |
| ATOM | 3255 | HA | ASN | B | 177 | 12.746 | 14.191 | -42.674 | 1 | 44.99 | H |
| ATOM | 3256 | HB2 | ASN | B | 177 | 12.722 | 11.367 | -42.655 | 1 | 51.9 | H |
| ATOM | 3257 | HB3 | ASN | B | 177 | 12.253 | 12.243 | -43.895 | 1 | 51.9 | H |
| ATOM | 3258 | HD21 | ASN | B | 177 | 15.959 | 11.376 | -43.334 | 1 | 50.66 | H |
| ATOM | 3259 | HD22 | ASN | B | 177 | 14.879 | 10.886 | -42.432 | 1 | 50.66 | H |
| ATOM | 3260 | N | LEU | B | 178 | 10.722 | 13.744 | -40.615 | 1 | 29.94 | N |
| ATOM | 3261 | CA | LEU | B | 178 | 9.326 | 13.905 | -40.208 | 1 | 27.52 | C |
| ATOM | 3262 | C | LEU | B | 178 | 8.926 | 15.373 | -40.174 | 1 | 28.55 | C |
| ATOM | 3263 | O | LEU | B | 178 | 7.933 | 15.769 | -40.785 | 1 | 28.18 | O |
| ATOM | 3264 | CB | LEU | B | 178 | 9.082 | 13.284 | -38.831 | 1 | 25.65 | C |
| ATOM | 3265 | CG | LEU | B | 178 | 8.632 | 11.822 | -38.77 | 1 | 29.25 | C |
| ATOM | 3266 | CD1 | LEU | B | 178 | 8.419 | 11.427 | -37.326 | 1 | 30.04 | C |
| ATOM | 3267 | CD2 | LEU | B | 178 | 7.356 | 11.576 | -39.57 | 1 | 30.4 | C |
| ATOM | 3268 | H | LEU | B | 178 | 11.289 | 13.902 | -39.987 | 1 | 35.93 | H |
| ATOM | 3269 | HA | LEU | B | 178 | 8.755 | 13.452 | -40.848 | 1 | 33.02 | H |
| ATOM | 3270 | HB2 | LEU | B | 178 | 9.907 | 13.346 | -38.326 | 1 | 30.78 | H |
| ATOM | 3271 | HB3 | LEU | B | 178 | 8.398 | 13.808 | -38.385 | 1 | 30.78 | H |
| ATOM | 3272 | HG | LEU | B | 178 | 9.331 | 11.259 | -39.137 | 1 | 35.1 | H |
| ATOM | 3273 | HD11 | LEU | B | 178 | 8.134 | 10.5 | -37.292 | 1 | 36.05 | H |
| ATOM | 3274 | HD12 | LEU | B | 178 | 9.253 | 11.535 | -36.844 | 1 | 36.05 | H |
| ATOM | 3275 | HD13 | LEU | B | 178 | 7.736 | 11.998 | -36.94 | 1 | 36.05 | H |
| ATOM | 3276 | HD21 | LEU | B | 178 | 7.115 | 10.64 | -39.499 | 1 | 36.49 | H |
| ATOM | 3277 | HD22 | LEU | B | 178 | 6.646 | 12.129 | -39.209 | 1 | 36.49 | H |
| ATOM | 3278 | HD23 | LEU | B | 178 | 7.517 | 11.808 | -40.498 | 1 | 36.49 | H |
| ATOM | 3279 | N | LEU | B | 179 | 9.706 | 16.171 | -39.449 | 1 | 24.55 | N |
| ATOM | 3280 | CA | LEU | B | 179 | 9.42 | 17.591 | -39.277 | 1 | 21.87 | C |
| ATOM | 3281 | C | LEU | B | 179 | 10.57 | 18.473 | -39.737 | 1 | 24.32 | C |
| ATOM | 3282 | O | LEU | B | 179 | 11.735 | 18.189 | -39.457 | 1 | 23.82 | O |
| ATOM | 3283 | CB | LEU | B | 179 | 9.114 | 17.896 | -37.81 | 1 | 23.91 | C |
| ATOM | 3284 | CG | LEU | B | 179 | 7.814 | 17.348 | -37.224 | 1 | 22.72 | C |
| ATOM | 3285 | CD1 | LEU | B | 179 | 7.76 | 17.633 | -35.726 | 1 | 20.68 | C |
| ATOM | 3286 | CD2 | LEU | B | 179 | 6.602 | 17.946 | -37.927 | 1 | 23.32 | C |
| ATOM | 3287 | H | LEU | B | 179 | 10.416 | 15.909 | -39.041 | 1 | 29.47 | H |
| ATOM | 3288 | HA | LEU | B | 179 | 8.637 | 17.821 | -39.802 | 1 | 26.24 | H |
| ATOM | 3289 | HB2 | LEU | B | 179 | 9.839 | 17.539 | -37.273 | 1 | 28.7 | H |
| ATOM | 3290 | HB3 | LEU | B | 179 | 9.088 | 18.86 | -37.705 | 1 | 28.7 | H |
| ATOM | 3291 | HG | LEU | B | 179 | 7.791 | 16.387 | -37.349 | 1 | 27.27 | H |
| ATOM | 3292 | HD11 | LEU | B | 179 | 8.516 | 17.28 | -35.368 | 1 | 24.81 | H |
| ATOM | 3293 | HD12 | LEU | B | 179 | 7.8 | 18.592 | -35.296 | 1 | 24.81 | H |
| ATOM | 3294 | HD13 | LEU | B | 179 | 6.931 | 17.203 | -35.586 | 1 | 24.81 | H |
| ATOM | 3295 | HD21 | LEU | B | 179 | 5.795 | 17.579 | -37.533 | 1 | 27.98 | H |
| ATOM | 3296 | HD22 | LEU | B | 179 | 6.616 | 18.91 | -37.816 | 1 | 27.98 | H |
| ATOM | 3297 | HD23 | LEU | B | 179 | 6.642 | 17.721 | -38.87 | 1 | 27.98 | H |
| ATOM | 3298 | N | THR | B | 180 | 10.228 | 19.547 | -40.441 | 1 | 21.44 | N |
| ATOM | 3299 | CA | THR | B | 180 | 11.169 | 20.621 | -40.726 | 1 | 24.48 | C |
| ATOM | 3300 | C | THR | B | 180 | 11.15 | 21.596 | -39.556 | 1 | 24.18 | C |
| ATOM | 3301 | O | THR | B | 180 | 10.148 | 22.277 | -39.33 | 1 | 20.49 | O |
| ATOM | 3302 | CB | THR | B | 180 | 10.814 | 21.367 | -42.029 | 1 | 26.75 | C |
| ATOM | 3303 | OG1 | THR | B | 180 | 10.749 | 20.439 | -43.119 | 1 | 26.99 | O |

TABLE 5-continued

Atomic Coordinates for OMCP-NKG2D (4PDC).

| ATOM | 3304 | CG2 | THR | B | 180 | 11.848 | 22.444 | -42.342 | 1 | 29.06 | C |
|------|------|-----|-----|---|-----|--------|--------|---------|---|-------|---|
| ATOM | 3305 | H | THR | B | 180 | 9.444 | 19.678 | -40.769 | 1 | 25.72 | H |
| ATOM | 3306 | HA | THR | B | 180 | 12.063 | 20.256 | -40.812 | 1 | 29.38 | H |
| ATOM | 3307 | HB | THR | B | 180 | 11.798 | 21.798 | -41.926 | 1 | 32.1 | H |
| ATOM | 3308 | HG1 | THR | B | 180 | 9.951 | 19.858 | -42.966 | 1 | 32.39 | H |
| ATOM | 3309 | HG21 | THR | B | 180 | 10.161 | 22.903 | -43.163 | 1 | 34.88 | H |
| ATOM | 3310 | HG22 | THR | B | 180 | 11.611 | 23.09 | -41.619 | 1 | 34.88 | H |
| ATOM | 3311 | HG23 | THR | B | 180 | 11.883 | 22.041 | -42.448 | 1 | 34.88 | H |
| ATOM | 3312 | N | ILE | B | 181 | 12.724 | 21.645 | -38.804 | 1 | 23.05 | N |
| ATOM | 3313 | CA | ILE | B | 181 | 12.246 | 22.54 | -37.656 | 1 | 22.09 | C |
| ATOM | 3314 | C | ILE | B | 181 | 12.353 | 23.895 | -38.081 | 1 | 26.12 | C |
| ATOM | 3315 | O | ILE | B | 181 | 12.91 | 23.972 | -38.711 | 1 | 23.5 | O |
| ATOM | 3316 | CB | ILE | B | 181 | 13.964 | 21.948 | -36.557 | 1 | 23.97 | C |
| ATOM | 3317 | CG1 | ILE | B | 181 | 13.251 | 20.565 | -36.131 | 1 | 23.66 | C |
| ATOM | 3318 | CG2 | ILE | B | 181 | 12.745 | 22.885 | -35.356 | 1 | 22.95 | C |
| ATOM | 3319 | CD1 | ILE | B | 181 | 13.312 | 20.552 | -35.592 | 1 | 28.66 | C |
| ATOM | 3320 | H | ILE | B | 181 | 11.326 | 21.167 | -38.94 | 1 | 27.67 | H |
| ATOM | 3321 | HA | ILE | B | 181 | 12.947 | 22.681 | -37.281 | 1 | 26.51 | H |
| ATOM | 3322 | HB | ILE | B | 181 | 11.47 | 21.849 | -36.914 | 1 | 28.77 | H |
| ATOM | 3323 | HG12 | ILE | B | 181 | 14.147 | 19.974 | -36.899 | 1 | 28.39 | H |
| ATOM | 3324 | HG13 | ILE | B | 181 | 12.773 | 20.223 | -35.434 | 1 | 28.39 | H |
| ATOM | 3325 | HG21 | ILE | B | 181 | 13.327 | 22.492 | -34.677 | 1 | 27.55 | H |
| ATOM | 3326 | HG22 | ILE | B | 181 | 13.883 | 23.738 | -35.64 | 1 | 27.55 | H |
| ATOM | 3327 | HG23 | ILE | B | 181 | 13.676 | 23.008 | -35.005 | 1 | 27.55 | H |
| ATOM | 3328 | HD11 | ILE | B | 181 | 12.416 | 19.643 | -35.348 | 1 | 34.39 | H |
| ATOM | 3329 | HD12 | ILE | B | 181 | 11.089 | 21.126 | -34.812 | 1 | 34.39 | H |
| ATOM | 3330 | HD13 | ILE | B | 181 | 11.279 | 20.877 | -36.279 | 1 | 34.39 | H |
| ATOM | 3331 | N | ILE | B | 182 | 10.724 | 24.958 | -37.706 | 1 | 23.73 | N |
| ATOM | 3332 | CA | ILE | B | 182 | 12.203 | 26.304 | -38.171 | 1 | 20.26 | C |
| ATOM | 3333 | C | ILE | B | 182 | 12.514 | 27.254 | -36.992 | 1 | 23.35 | C |
| ATOM | 3334 | O | ILE | B | 182 | 12.68 | 27.378 | -36.163 | 1 | 18.77 | O |
| ATOM | 3335 | CB | ILE | B | 182 | 11.782 | 26.838 | -39.101 | 1 | 21.54 | C |
| ATOM | 3336 | CG1 | ILE | B | 182 | 11.154 | 25.858 | -40.255 | 1 | 22.95 | C |
| ATOM | 3337 | CG2 | ILE | B | 182 | 11.751 | 28.23 | -39.631 | 1 | 20.67 | C |
| ATOM | 3338 | CD1 | ILE | B | 182 | 9.889 | 26.137 | -41.035 | 1 | 27.62 | C |
| ATOM | 3339 | H | ILE | B | 182 | 11.528 | 24.923 | -37.174 | 1 | 28.48 | H |
| ATOM | 3340 | HA | ILE | B | 182 | 13.346 | 26.287 | -38.669 | 1 | 24.31 | H |
| ATOM | 3341 | HB | ILE | B | 182 | 10.582 | 26.908 | -38.585 | 1 | 25.85 | H |
| ATOM | 3342 | HG12 | ILE | B | 182 | 11.9 | 25.909 | -40.873 | 1 | 27.54 | H |
| ATOM | 3343 | HG13 | ILE | B | 182 | 11.087 | 24.96 | -39.894 | 1 | 27.54 | H |
| ATOM | 3344 | HG21 | ILE | B | 182 | 11.036 | 28.537 | -40.21 | 1 | 24.8 | H |
| ATOM | 3345 | HG22 | ILE | B | 182 | 11.854 | 28.836 | -38.881 | 1 | 24.8 | H |
| ATOM | 3346 | HG23 | ILE | B | 182 | 12.581 | 28.177 | -40.13 | 1 | 24.8 | H |
| ATOM | 3347 | HD11 | ILE | B | 182 | 9.803 | 25.48 | -41.743 | 1 | 33.14 | H |
| ATOM | 3348 | HD12 | ILE | B | 182 | 9.129 | 26.078 | -40.435 | 1 | 33.14 | H |
| ATOM | 3349 | HD13 | ILE | B | 182 | 9.942 | 27.028 | -41.415 | 1 | 33.14 | H |
| ATOM | 3350 | N | GLU | B | 183 | 13.821 | 27.934 | -36.916 | 1 | 24.54 | N |
| ATOM | 3351 | CA | GLU | B | 183 | 14.022 | 28.911 | -35.854 | 1 | 27.28 | C |
| ATOM | 3352 | C | GLU | B | 183 | 13.14 | 30.122 | -36.128 | 1 | 29.16 | C |
| ATOM | 3353 | O | GLU | B | 183 | 13.045 | 30.599 | -37.26 | 1 | 34.53 | O |
| ATOM | 3354 | CB | GLU | B | 183 | 15.494 | 29.314 | -35.73 | 1 | 36.17 | C |

TABLE 5-continued

Atomic Coordinates for OMCP-NKG2D (4PDC).

| ATOM | 3355 | CG | GLU | B | 183 | 16.063 | 30.065 | −36.915 | 1 | 45.13 | C |
|---|---|---|---|---|---|---|---|---|---|---|---|
| ATOM | 3356 | CD | GLU | B | 183 | 17.553 | 30.328 | −36.767 | 1 | 52.61 | C |
| ATOM | 3357 | OE1 | GLU | B | 183 | 18.036 | 30.396 | −35.616 | 1 | 55.37 | O |
| ATOM | 3358 | OE2 | GLU | B | 183 | 18.243 | 30.456 | −37.8 | 1 | 57.38 | O1− |
| ATOM | 3359 | H | GLU | B | 183 | 14.482 | 27.851 | −37.459 | 1 | 29.44 | H |
| ATOM | 3360 | HA | GLU | B | 183 | 13.745 | 28.522 | −35.01 | 1 | 32.74 | H |
| ATOM | 3361 | HB2 | GLU | B | 183 | 15.592 | 29.882 | −34.95 | 1 | 43.4 | H |
| ATOM | 3362 | HB3 | GLU | B | 183 | 16.024 | 28.51 | −35.613 | 1 | 43.4 | H |
| ATOM | 3363 | HG2 | GLU | B | 183 | 15.927 | 29.54 | −37.719 | 1 | 54.15 | H |
| ATOM | 3364 | HG3 | GLU | B | 183 | 15.612 | 30.92 | −36.995 | 1 | 54.15 | H |
| ATOM | 3365 | N | MET | B | 184 | 12.478 | 30.594 | −35.08 | 1 | 29.01 | N |
| ATOM | 3366 | CA | MET | B | 184 | 11.478 | 31.648 | −35.192 | 1 | 25.24 | C |
| ATOM | 3367 | C | MET | B | 184 | 11.643 | 32.571 | −33.986 | 1 | 34.39 | C |
| ATOM | 3368 | O | MET | B | 184 | 11.916 | 33.764 | −34.133 | 1 | 34.16 | O |
| ATOM | 3369 | CB | MET | B | 184 | 10.075 | 31.032 | −35.263 | 1 | 25.23 | C |
| ATOM | 3370 | CG | MET | B | 184 | 8.947 | 31.974 | −35.675 | 1 | 22.62 | C |
| ATOM | 3371 | SD | MET | B | 184 | 8.098 | 32.757 | −34.293 | 1 | 34.48 | S |
| ATOM | 3372 | CE | MET | B | 184 | 7.45 | 31.341 | −33.4 | 1 | 28.01 | C |
| ATOM | 3373 | H | MET | B | 184 | 12.592 | 30.314 | −34.275 | 1 | 34.81 | H |
| ATOM | 3374 | HA | MET | B | 184 | 11.631 | 32.152 | −36.006 | 1 | 30.28 | H |
| ATOM | 3375 | HB2 | MET | B | 184 | 10.093 | 30.305 | −35.905 | 1 | 30.28 | H |
| ATOM | 3376 | HB3 | MET | B | 184 | 9.852 | 30.681 | −34.386 | 1 | 30.28 | H |
| ATOM | 3377 | HG2 | MET | B | 184 | 9.317 | 32.677 | −36.231 | 1 | 27.15 | H |
| ATOM | 3378 | HG3 | MET | B | 184 | 8.289 | 31.47 | −36.179 | 1 | 27.15 | H |
| ATOM | 3379 | HE1 | MET | B | 184 | 6.964 | 31.655 | −32.621 | 1 | 33.61 | H |
| ATOM | 3380 | HE2 | MET | B | 184 | 6.855 | 30.845 | −33.984 | 1 | 33.61 | H |
| ATOM | 3381 | HE3 | MET | B | 184 | 8.189 | 30.777 | −33.124 | 1 | 33.61 | H |
| ATOM | 3382 | N | GLN | B | 185 | 11.505 | 31.998 | −32.794 | 1 | 32.9 | N |
| ATOM | 3383 | CA | GLN | B | 185 | 11.808 | 32.696 | −31.549 | 1 | 32.39 | C |
| ATOM | 3384 | C | GLN | B | 185 | 12.769 | 31.85 | −30.723 | 1 | 34.72 | C |
| ATOM | 3385 | O | GLN | B | 185 | 12.721 | 30.619 | −30.769 | 1 | 28.22 | O |
| ATOM | 3386 | CB | GLN | B | 185 | 10.531 | 32.976 | −30.754 | 1 | 29.62 | C |
| ATOM | 3387 | CG | GLN | B | 185 | 9.601 | 34 | −31.39 | 1 | 33.22 | C |
| ATOM | 3388 | CD | GLN | B | 185 | 9.964 | 35.435 | −31.046 | 1 | 40.19 | C |
| ATOM | 3389 | OE1 | GLN | B | 185 | 11.094 | 35.73 | −30.652 | 1 | 41.44 | O |
| ATOM | 3390 | NE2 | GLN | B | 185 | 8.997 | 36.337 | −31.188 | 1 | 34.22 | N |
| ATOM | 3391 | H | GLN | B | 185 | 11.232 | 31.19 | −32.679 | 1 | 39.48 | H |
| ATOM | 3392 | HA | GLN | B | 185 | 12.237 | 33.542 | −31.749 | 1 | 38.87 | H |
| ATOM | 3393 | HB2 | GLN | B | 185 | 10.036 | 32.148 | −30.659 | 1 | 35.55 | H |
| ATOM | 3394 | HB3 | GLN | B | 185 | 10.779 | 33.31 | −29.877 | 1 | 35.55 | H |
| ATOM | 3395 | HG2 | GLN | B | 185 | 9.641 | 33.905 | −32.355 | 1 | 39.87 | H |
| ATOM | 3396 | HG3 | GLN | B | 185 | 8.696 | 33.839 | −31.08 | 1 | 39.87 | H |
| ATOM | 3397 | HE21 | GLN | B | 185 | 9.15 | 37.164 | −31.007 | 1 | 41.06 | H |
| ATOM | 3398 | HE22 | GLN | B | 185 | 8.218 | 36.094 | −31.461 | 1 | 41.06 | H |
| ATOM | 3399 | N | LYS | B | 186 | 13.654 | 32.506 | −29.98 | 1 | 34.85 | N |
| ATOM | 3400 | CA | LYS | B | 186 | 14.542 | 31.796 | −29.071 | 1 | 34.85 | C |
| ATOM | 3401 | C | LYS | B | 186 | 13.694 | 31.086 | −28.016 | 1 | 28.04 | C |
| ATOM | 3402 | O | LYS | B | 186 | 12.924 | 31.726 | −27.301 | 1 | 27.27 | O |
| ATOM | 3403 | CB | LYS | B | 186 | 15.533 | 32.763 | −28.418 | 1 | 43.85 | C |
| ATOM | 3404 | CG | LYS | B | 186 | 16.859 | 32.136 | −28.014 | 1 | 64.98 | C |
| ATOM | 3405 | CD | LYS | B | 186 | 17.666 | 31.694 | −29.229 | 1 | 85.87 | C |

TABLE 5-continued

Atomic Coordinates for OMCP-NKG2D (4PDC).

| ATOM | 3406 | CE | LYS | B | 186 | 19.083 | -28.845 | 31.299 | 1 | 104.79 | C |
|---|---|---|---|---|---|---|---|---|---|---|---|
| ATOM | 3407 | NZ | LYS | B | 186 | 19.756 | -29.918 | 30.516 | 1 | 110.38 | N1+ |
| ATOM | 3408 | H | LYS | B | 186 | 13.758 | -29.984 | 33.359 | 1 | 41.82 | H |
| ATOM | 3409 | HA | LYS | B | 186 | 15.043 | -29.563 | 31.127 | 1 | 41.82 | H |
| ATOM | 3410 | HB2 | LYS | B | 186 | 15.725 | -29.044 | 33.478 | 1 | 52.62 | H |
| ATOM | 3411 | HB3 | LYS | B | 186 | 15.125 | -27.618 | 33.13 | 1 | 52.62 | H |
| ATOM | 3412 | HG2 | LYS | B | 186 | 17.383 | -27.523 | 32.788 | 1 | 77.98 | H |
| ATOM | 3413 | HG3 | LYS | B | 186 | 16.69 | -27.462 | 31.357 | 1 | 77.98 | H |
| ATOM | 3414 | HD2 | LYS | B | 186 | 17.236 | -29.635 | 30.925 | 1 | 103.05 | H |
| ATOM | 3415 | HD3 | LYS | B | 186 | 17.716 | -29.864 | 32.425 | 1 | 103.05 | H |
| ATOM | 3416 | HE2 | LYS | B | 186 | 19.604 | -28.684 | 32.101 | 1 | 125.75 | H |
| ATOM | 3417 | HE3 | LYS | B | 186 | 19.055 | -28.044 | 30.753 | 1 | 125.75 | H |
| ATOM | 3418 | HZ1 | LYS | B | 186 | 19.799 | -30.664 | 30.999 | 1 | 132.46 | H |
| ATOM | 3419 | HZ2 | LYS | B | 186 | 20.581 | -29.664 | 30.301 | 1 | 132.46 | H |
| ATOM | 3420 | HZ3 | LYS | B | 186 | 19.3 | -30.081 | 29.77 | 1 | 132.46 | H |
| ATOM | 3421 | N | GLY | B | 187 | 13.816 | -27.932 | 29.765 | 1 | 25.29 | N |
| ATOM | 3422 | CA | GLY | B | 187 | 13.002 | -27.007 | 28.997 | 1 | 25.76 | C |
| ATOM | 3423 | C | GLY | B | 187 | 13.264 | -27.086 | 27.506 | 1 | 23.48 | C |
| ATOM | 3424 | O | GLY | B | 187 | 14.02 | -27.944 | 27.05 | 1 | 19.67 | O |
| ATOM | 3425 | H | GLY | B | 187 | 14.362 | -28.4 | 29.294 | 1 | 30.35 | H |
| ATOM | 3426 | HA2 | GLY | B | 187 | 13.181 | -26.101 | 29.291 | 1 | 30.91 | H |
| ATOM | 3427 | HA3 | GLY | B | 187 | 12.064 | -27.2 | 29.152 | 1 | 30.91 | H |
| ATOM | 3428 | N | ASP | B | 188 | 12.629 | -26.19 | 26.752 | 1 | 17.61 | N |
| ATOM | 3429 | CA | ASP | B | 188 | 12.873 | -26.064 | 25.316 | 1 | 20.1 | C |
| ATOM | 3430 | C | ASP | B | 188 | 11.623 | -27.007 | 28.997 | 1 | 17.87 | C |
| ATOM | 3431 | O | ASP | B | 188 | 11.587 | -25.973 | 23.291 | 1 | 18.91 | O |
| ATOM | 3432 | CB | ASP | B | 188 | 13.42 | -24.673 | 25 | 1 | 22.84 | C |
| ATOM | 3433 | CG | ASP | B | 188 | 14.737 | -24.393 | 25.686 | 1 | 27 | C |
| ATOM | 3434 | OD1 | ASP | B | 188 | 15.629 | -25.265 | 25.638 | 1 | 28.51 | O |
| ATOM | 3435 | OD2 | ASP | B | 188 | 14.877 | -23.3 | 26.274 | 1 | 29.6 | O1- |
| ATOM | 3436 | H | ASP | B | 188 | 12.044 | -25.637 | 27.053 | 1 | 21.13 | H |
| ATOM | 3437 | HA | ASP | B | 188 | 13.544 | -26.714 | 25.055 | 1 | 24.12 | H |
| ATOM | 3438 | HB2 | ASP | B | 188 | 12.78 | -24.007 | 25.296 | 1 | 27.41 | H |
| ATOM | 3439 | HB3 | ASP | B | 188 | 13.559 | -24.598 | 24.043 | 1 | 27.41 | H |
| ATOM | 3440 | N | CYS | B | 189 | 10.597 | -26.901 | 25.079 | 1 | 15.55 | N |
| ATOM | 3441 | CA | CYS | B | 189 | 9.399 | -27.293 | 24.344 | 1 | 18.29 | C |
| ATOM | 3442 | C | CYS | B | 189 | 9.129 | -28.777 | 24.575 | 1 | 18.34 | C |
| ATOM | 3443 | O | CYS | B | 189 | 9.771 | -29.403 | 25.421 | 1 | 16.24 | O |
| ATOM | 3444 | CB | CYS | B | 189 | 8.202 | -26.437 | 24.763 | 1 | 21.42 | C |
| ATOM | 3445 | SG | CYS | B | 189 | 8.369 | -24.685 | 24.31 | 1 | 19.88 | S |
| ATOM | 3446 | H | CYS | B | 189 | 10.568 | -27.083 | 25.919 | 1 | 18.66 | H |
| ATOM | 3447 | HA | CYS | B | 189 | 9.549 | -27.158 | 23.395 | 1 | 21.95 | H |
| ATOM | 3448 | HB2 | CYS | B | 189 | 8.103 | -26.487 | 25.726 | 1 | 25.71 | H |
| ATOM | 3449 | HB3 | CYS | B | 189 | 7.404 | -26.781 | 24.331 | 1 | 25.71 | H |
| ATOM | 3450 | N | ALA | B | 190 | 8.195 | -29.337 | 23.813 | 1 | 17.84 | N |
| ATOM | 3451 | CA | ALA | B | 190 | 7.935 | -30.773 | 23.856 | 1 | 16.98 | C |
| ATOM | 3452 | C | ALA | B | 190 | 6.443 | -31.098 | 23.85 | 1 | 13.84 | C |
| ATOM | 3453 | O | ALA | B | 190 | 5.68 | -30.566 | 23.04 | 1 | 13.74 | O |
| ATOM | 3454 | CB | ALA | B | 190 | 8.622 | -31.461 | 22.686 | 1 | 18.2 | C |
| ATOM | 3455 | H | ALA | B | 190 | 7.697 | -28.907 | 23.26 | 1 | 21.4 | H |
| ATOM | 3456 | HA | ALA | B | 190 | 8.312 | -31.133 | 24.674 | 1 | 20.37 | H |

TABLE 5-continued

Atomic Coordinates for OMCP-NKG2D (4PDC).

| ATOM | 3457 | HB1 | ALA | B | 190 | 8.44 | 22.729 | -32.413 | 1 | 21.84 | H |
|---|---|---|---|---|---|---|---|---|---|---|---|
| ATOM | 3458 | HB2 | ALA | B | 190 | 9.577 | 22.744 | -31.303 | 1 | 21.84 | H |
| ATOM | 3459 | HB3 | ALA | B | 190 | 8.275 | 21.858 | -31.094 | 1 | 21.84 | H |
| ATOM | 3460 | N | LEU | B | 191 | 6.047 | 24.763 | -31.982 | 1 | 11.45 | N |
| ATOM | 3461 | CA | LEU | B | 191 | 4.68 | 24.829 | -32.492 | 1 | 14.13 | C |
| ATOM | 3462 | C | LEU | B | 191 | 4.554 | 23.994 | -33.749 | 1 | 16.78 | C |
| ATOM | 3463 | O | LEU | B | 191 | 5.395 | 24.1 | -34.642 | 1 | 15.41 | O |
| ATOM | 3464 | CB | LEU | B | 191 | 4.288 | 26.269 | -32.817 | 1 | 12.09 | C |
| ATOM | 3465 | CG | LEU | B | 191 | 4.165 | 27.255 | -31.659 | 1 | 14.17 | C |
| ATOM | 3466 | CD1 | LEU | B | 191 | 4.052 | 28.666 | -32.203 | 1 | 14.01 | C |
| ATOM | 3467 | CD2 | LEU | B | 191 | 2.958 | 26.915 | -30.798 | 1 | 16.56 | C |
| ATOM | 3468 | H | LEU | B | 191 | 6.564 | 25.368 | -32.309 | 1 | 13.74 | H |
| ATOM | 3469 | HA | LEU | B | 191 | 4.066 | 24.482 | -31.825 | 1 | 16.96 | H |
| ATOM | 3470 | HB2 | LEU | B | 191 | 4.953 | 26.629 | -33.424 | 1 | 14.51 | H |
| ATOM | 3471 | HB3 | LEU | B | 191 | 3.428 | 26.25 | -33.264 | 1 | 14.51 | H |
| ATOM | 3472 | HG | LEU | B | 191 | 4.959 | 27.203 | -31.105 | 1 | 17.01 | H |
| ATOM | 3473 | HD11 | LEU | B | 191 | 3.974 | 29.285 | -31.461 | 1 | 16.81 | H |
| ATOM | 3474 | HD12 | LEU | B | 191 | 4.847 | 28.868 | -32.721 | 1 | 16.81 | H |
| ATOM | 3475 | HD13 | LEU | B | 191 | 3.265 | 28.724 | -32.768 | 1 | 16.81 | H |
| ATOM | 3476 | HD21 | LEU | B | 191 | 2.9 | 27.553 | -30.07 | 1 | 19.87 | H |
| ATOM | 3477 | HD22 | LEU | B | 191 | 2.158 | 26.962 | -31.345 | 1 | 19.87 | H |
| ATOM | 3478 | HD23 | LEU | B | 191 | 3.065 | 26.018 | -30.445 | 1 | 19.87 | H |
| ATOM | 3479 | N | TYR | B | 192 | 3.513 | 23.172 | -33.834 | 1 | 16.15 | N |
| ATOM | 3480 | CA | TYR | B | 192 | 3.244 | 22.485 | -35.084 | 1 | 12.87 | C |
| ATOM | 3481 | C | TYR | B | 192 | 2.607 | 23.44 | -36.076 | 1 | 18.63 | C |
| ATOM | 3482 | O | TYR | B | 192 | 1.704 | 24.209 | -35.732 | 1 | 14.22 | O |
| ATOM | 3483 | CB | TYR | B | 192 | 2.322 | 21.279 | -34.921 | 1 | 17.45 | C |
| ATOM | 3484 | CG | TYR | B | 192 | 2.041 | 20.673 | -36.28 | 1 | 18.09 | C |
| ATOM | 3485 | CD1 | TYR | B | 192 | 2.958 | 19.818 | -36.876 | 1 | 18.3 | C |
| ATOM | 3486 | CD2 | TYR | B | 192 | 0.901 | 21.013 | -36.997 | 1 | 15.77 | C |
| ATOM | 3487 | CE1 | TYR | B | 192 | 2.731 | 19.287 | -38.131 | 1 | 17.41 | C |
| ATOM | 3488 | CE2 | TYR | B | 192 | 0.666 | 20.487 | -38.257 | 1 | 19.17 | C |
| ATOM | 3489 | CZ | TYR | B | 192 | 1.586 | 19.625 | -38.819 | 1 | 19.87 | C |
| ATOM | 3490 | OH | TYR | B | 192 | 1.361 | 19.098 | -40.072 | 1 | 20.58 | O |
| ATOM | 3491 | H | TYR | B | 192 | 2.962 | 22.999 | -33.197 | 1 | 19.37 | H |
| ATOM | 3492 | HA | TYR | B | 192 | 4.082 | 22.174 | -35.461 | 1 | 15.44 | H |
| ATOM | 3493 | HB2 | TYR | B | 192 | 2.753 | 20.611 | -34.366 | 1 | 20.94 | H |
| ATOM | 3494 | HB3 | TYR | B | 192 | 1.482 | 21.561 | -34.527 | 1 | 20.94 | H |
| ATOM | 3495 | HD1 | TYR | B | 192 | 3.734 | 19.589 | -36.417 | 1 | 21.96 | H |
| ATOM | 3496 | HD2 | TYR | B | 192 | 0.281 | 21.595 | -36.621 | 1 | 18.92 | H |
| ATOM | 3497 | HE1 | TYR | B | 192 | 3.351 | 18.706 | -38.512 | 1 | 20.89 | H |
| ATOM | 3498 | HE2 | TYR | B | 192 | -0.107 | 20.714 | -38.722 | 1 | 23 | H |
| ATOM | 3499 | HH | TYR | B | 192 | 0.633 | 19.384 | -40.377 | 1 | 24.69 | H |
| ATOM | 3500 | N | ALA | B | 193 | 3.077 | 23.36 | -37.315 | 1 | 12.79 | N |
| ATOM | 3501 | CA | ALA | B | 193 | 2.483 | 24.079 | -38.431 | 1 | 15.94 | C |
| ATOM | 3502 | C | ALA | B | 193 | 2.55 | 23.173 | -39.65 | 1 | 18.77 | C |
| ATOM | 3503 | O | ALA | B | 193 | 3.498 | 22.402 | -39.801 | 1 | 16.34 | O |
| ATOM | 3504 | CB | ALA | B | 193 | 3.211 | 25.385 | -38.685 | 1 | 17.09 | C |
| ATOM | 3505 | H | ALA | B | 193 | 3.756 | 22.883 | -37.538 | 1 | 15.35 | H |
| ATOM | 3506 | HA | ALA | B | 193 | 1.553 | 24.274 | -38.238 | 1 | 19.13 | H |
| ATOM | 3507 | HB1 | ALA | B | 193 | 2.792 | 25.839 | -39.433 | 1 | 20.5 | H |

TABLE 5-continued

Atomic Coordinates for OMCP-NKG2D (4PDC).

| | | | | | | | | | |
|---|---|---|---|---|---|---|---|---|---|
| ATOM | 3508 | HB2 | ALA | B | 193 | 3.156 | 25.937 | -37.89 | 1 | 20.5 | H |
| ATOM | 3509 | HB3 | ALA | B | 193 | 4.139 | 25.194 | -38.892 | 1 | 20.5 | H |
| ATOM | 3510 | N | SER | B | 194 | 1.543 | 23.243 | -40.509 | 1 | 15.79 | N |
| ATOM | 3511 | CA | SER | B | 194 | 1.535 | 22.414 | -41.708 | 1 | 21.22 | C |
| ATOM | 3512 | C | SER | B | 194 | 2.354 | 23.092 | -42.803 | 1 | 20.82 | C |
| ATOM | 3513 | O | SER | B | 194 | 2.449 | 24.317 | -42.813 | 1 | 23.78 | O |
| ATOM | 3514 | CB | SER | B | 194 | 0.109 | 22.172 | -42.191 | 1 | 20.14 | C |
| ATOM | 3515 | OG | SER | B | 194 | -0.41 | 23.338 | -42.795 | 1 | 26.86 | O |
| ATOM | 3516 | H | SER | B | 194 | 0.859 | 23.757 | -40.424 | 1 | 18.95 | H |
| ATOM | 3517 | HA | SER | B | 194 | 1.941 | 21.555 | -41.509 | 1 | 25.47 | H |
| ATOM | 3518 | HB2 | SER | B | 194 | 0.113 | 21.453 | -42.842 | 1 | 24.17 | H |
| ATOM | 3519 | HB3 | SER | B | 194 | -0.446 | 21.933 | -41.433 | 1 | 24.17 | H |
| ATOM | 3520 | HG | SER | B | 194 | -0.416 | 23.97 | -42.241 | 1 | 32.23 | H |
| ATOM | 3521 | N | SER | B | 195 | 2.948 | 22.328 | -43.72 | 1 | 22.26 | N |
| ATOM | 3522 | CA | SER | B | 195 | 2.901 | 20.869 | -43.738 | 1 | 19.41 | C |
| ATOM | 3523 | C | SER | B | 195 | 4.097 | 20.267 | -42.993 | 1 | 26.14 | C |
| ATOM | 3524 | O | SER | B | 195 | 5.234 | 20.349 | -43.461 | 1 | 25.77 | O |
| ATOM | 3525 | CB | SER | B | 195 | 2.879 | 20.368 | -45.182 | 1 | 28.07 | C |
| ATOM | 3526 | OG | SER | B | 195 | 2.594 | 18.984 | -45.234 | 1 | 34.28 | O |
| ATOM | 3527 | H | SER | B | 195 | 3.406 | 22.652 | -44.372 | 1 | 26.71 | H |
| ATOM | 3528 | HA | SER | B | 195 | 2.089 | 20.571 | -43.3 | 1 | 23.3 | H |
| ATOM | 3529 | HB2 | SER | B | 195 | 2.194 | 20.849 | -45.672 | 1 | 33.69 | H |
| ATOM | 3530 | HB3 | SER | B | 195 | 3.747 | 20.527 | -45.584 | 1 | 33.69 | H |
| ATOM | 3531 | HG | SER | B | 195 | 3.18 | 18.555 | -44.813 | 1 | 41.13 | H |
| ATOM | 3532 | N | PHE | B | 196 | 3.832 | 19.674 | -41.832 | 1 | 24.04 | N |
| ATOM | 3533 | CA | PHE | B | 196 | 4.858 | 19 | -41.029 | 1 | 22.02 | C |
| ATOM | 3534 | C | PHE | B | 196 | 6.07 | 19.879 | -40.731 | 1 | 23.97 | C |
| ATOM | 3535 | O | PHE | B | 196 | 7.214 | 19.502 | -40.988 | 1 | 20.66 | O |
| ATOM | 3536 | CB | PHE | B | 196 | 5.297 | 17.709 | -41.724 | 1 | 24 | C |
| ATOM | 3537 | CG | PHE | B | 196 | 4.251 | 16.638 | -41.695 | 1 | 22.78 | C |
| ATOM | 3538 | CD1 | PHE | B | 196 | 4.128 | 15.806 | -40.596 | 1 | 23.64 | C |
| ATOM | 3539 | CD2 | PHE | B | 196 | 3.373 | 16.477 | -42.751 | 1 | 28.16 | C |
| ATOM | 3540 | CE1 | PHE | B | 196 | 3.156 | 14.827 | -40.556 | 1 | 24.03 | C |
| ATOM | 3541 | CE2 | PHE | B | 196 | 2.399 | 15.5 | -42.716 | 1 | 29.08 | C |
| ATOM | 3542 | CZ | PHE | B | 196 | 2.288 | 14.675 | -41.617 | 1 | 25.46 | C |
| ATOM | 3543 | H | PHE | B | 196 | 3.048 | 19.646 | -41.479 | 1 | 28.84 | H |
| ATOM | 3544 | HA | PHE | B | 196 | 4.465 | 18.752 | -40.178 | 1 | 26.42 | H |
| ATOM | 3545 | HB2 | PHE | B | 196 | 5.499 | 17.904 | -42.652 | 1 | 28.8 | H |
| ATOM | 3546 | HB3 | PHE | B | 196 | 6.088 | 17.366 | -41.279 | 1 | 28.8 | H |
| ATOM | 3547 | HD1 | PHE | B | 196 | 4.709 | 15.907 | -39.877 | 1 | 28.37 | H |
| ATOM | 3548 | HD2 | PHE | B | 196 | 3.44 | 17.033 | -43.493 | 1 | 33.8 | H |
| ATOM | 3549 | HE1 | PHE | B | 196 | 3.086 | 14.271 | -39.814 | 1 | 28.83 | H |
| ATOM | 3550 | HE2 | PHE | B | 196 | 1.817 | 15.398 | -43.434 | 1 | 34.9 | H |
| ATOM | 3551 | HZ | PHE | B | 196 | 1.635 | 14.013 | -41.594 | 1 | 30.55 | H |
| ATOM | 3552 | N | LYS | B | 197 | 5.795 | 21.056 | -40.182 | 1 | 23.08 | N |
| ATOM | 3553 | CA | LYS | B | 197 | 6.829 | 21.97 | -39.726 | 1 | 20.49 | C |
| ATOM | 3554 | C | LYS | B | 197 | 6.749 | 22.119 | -38.22 | 1 | 18.79 | C |
| ATOM | 3555 | O | LYS | B | 197 | 5.683 | 21.951 | -37.624 | 1 | 16.31 | O |
| ATOM | 3556 | CB | LYS | B | 197 | 6.681 | 23.346 | -40.376 | 1 | 23.24 | C |
| ATOM | 3557 | CG | LYS | B | 197 | 6.695 | 23.349 | -41.889 | 1 | 26.94 | C |
| ATOM | 3558 | CD | LYS | B | 197 | 6.409 | 24.749 | -42.412 | 1 | 35.07 | C |

TABLE 5-continued

Atomic Coordinates for OMCP-NKG2D (4PDC).

| ATOM | 3559 | CE  | LYS | B | 197 | 6.323  | 24.784 | -43.924 | 1 | 45.32 | C   |
|------|------|-----|-----|---|-----|--------|--------|---------|---|-------|-----|
| ATOM | 3560 | NZ  | LYS | B | 197 | 6.012  | 26.155 | -44.422 | 1 | 56.39 | N1+ |
| ATOM | 3561 | H   | LYS | B | 197 | 4.998  | 21.354 | -40.061 | 1 | 27.7  | H   |
| ATOM | 3562 | HA  | LYS | B | 197 | 7.702  | 21.613 | -39.955 | 1 | 24.58 | H   |
| ATOM | 3563 | HB2 | LYS | B | 197 | 5.838  | 23.731 | -40.092 | 1 | 27.89 | H   |
| ATOM | 3564 | HB3 | LYS | B | 197 | 7.412  | 23.908 | -40.077 | 1 | 27.89 | H   |
| ATOM | 3565 | HG2 | LYS | B | 197 | 7.57   | 23.074 | -42.205 | 1 | 32.33 | H   |
| ATOM | 3566 | HG3 | LYS | B | 197 | 6.009  | 22.749 | -42.221 | 1 | 32.33 | H   |
| ATOM | 3567 | HD2 | LYS | B | 197 | 5.561  | 25.056 | -42.054 | 1 | 42.09 | H   |
| ATOM | 3568 | HD3 | LYS | B | 197 | 7.123  | 25.345 | -42.135 | 1 | 42.09 | H   |
| ATOM | 3569 | HE2 | LYS | B | 197 | 7.175  | 24.51  | -44.299 | 1 | 54.39 | H   |
| ATOM | 3570 | HE3 | LYS | B | 197 | 5.619  | 24.186 | -44.218 | 1 | 54.39 | H   |
| ATOM | 3571 | HZ1 | LYS | B | 197 | 5.967  | 26.152 | -45.311 | 1 | 67.66 | H   |
| ATOM | 3572 | HZ2 | LYS | B | 197 | 6.428  | 26.428 | -44.094 | 1 | 67.66 | H   |
| ATOM | 3573 | HZ3 | LYS | B | 197 | 6.648  | 26.723 | -44.167 | 1 | 67.66 | H   |
| ATOM | 3574 | N   | GLY | B | 198 | 7.886  | 22.439 | -37.617 | 1 | 17.88 | N   |
| ATOM | 3575 | CA  | GLY | B | 198 | 7.954  | 22.804 | -36.219 | 1 | 19.24 | C   |
| ATOM | 3576 | C   | GLY | B | 198 | 8.632  | 24.154 | -36.088 | 1 | 16.43 | C   |
| ATOM | 3577 | O   | GLY | B | 198 | 9.783  | 24.311 | -36.488 | 1 | 18.89 | O   |
| ATOM | 3578 | H   | GLY | B | 198 | 8.65   | 22.452 | -38.012 | 1 | 21.46 | H   |
| ATOM | 3579 | HA2 | GLY | B | 198 | 7.061  | 22.86  | -35.845 | 1 | 18.34 | H   |
| ATOM | 3580 | HA3 | GLY | B | 198 | 8.465  | 22.143 | -35.726 | 1 | 18.34 | H   |
| ATOM | 3581 | N   | TYR | B | 199 | 7.914  | 25.136 | -35.554 | 1 | 16    | N   |
| ATOM | 3582 | CA  | TYR | B | 199 | 8.489  | 26.452 | -35.299 | 1 | 17.75 | C   |
| ATOM | 3583 | C   | TYR | B | 199 | 8.943  | 26.544 | -33.849 | 1 | 19.24 | C   |
| ATOM | 3584 | O   | TYR | B | 199 | 8.155  | 26.33  | -32.932 | 1 | 16.43 | O   |
| ATOM | 3585 | CB  | TYR | B | 199 | 7.481  | 27.562 | -35.6   | 1 | 15.65 | C   |
| ATOM | 3586 | CG  | TYR | B | 199 | 7.254  | 27.819 | -37.072 | 1 | 15.66 | C   |
| ATOM | 3587 | CD1 | TYR | B | 199 | 8.128  | 28.612 | -37.801 | 1 | 17.35 | C   |
| ATOM | 3588 | CD2 | TYR | B | 199 | 6.151  | 27.285 | -37.728 | 1 | 22.19 | C   |
| ATOM | 3589 | CE1 | TYR | B | 199 | 7.918  | 28.856 | -39.15  | 1 | 24.18 | C   |
| ATOM | 3590 | CE2 | TYR | B | 199 | 5.931  | 27.523 | -39.074 | 1 | 19.74 | C   |
| ATOM | 3591 | CZ  | TYR | B | 199 | 6.817  | 28.308 | -39.78  | 1 | 27.19 | C   |
| ATOM | 3592 | OH  | TYR | B | 199 | 6.6    | 28.545 | -41.117 | 1 | 25.4  | O   |
| ATOM | 3593 | H   | TYR | B | 199 | 7.087  | 25.065 | -35.329 | 1 | 19.2  | H   |
| ATOM | 3594 | HA  | TYR | B | 199 | 9.262  | 26.58  | -35.869 | 1 | 21.3  | H   |
| ATOM | 3595 | HB2 | TYR | B | 199 | 6.628  | 27.321 | -35.208 | 1 | 18.77 | H   |
| ATOM | 3596 | HB3 | TYR | B | 199 | 7.801  | 28.387 | -35.204 | 1 | 18.77 | H   |
| ATOM | 3597 | HD1 | TYR | B | 199 | 8.871  | 28.981 | -37.38  | 1 | 20.82 | H   |
| ATOM | 3598 | HD2 | TYR | B | 199 | 5.552  | 26.754 | -37.255 | 1 | 26.63 | H   |
| ATOM | 3599 | HE1 | TYR | B | 199 | 8.515  | 29.386 | -39.628 | 1 | 29.02 | H   |
| ATOM | 3600 | HE2 | TYR | B | 199 | 5.191  | 27.155 | -39.499 | 1 | 23.69 | H   |
| ATOM | 3601 | HH  | TYR | B | 199 | 7.209  | 29.034 | -41.425 | 1 | 30.48 | H   |
| ATOM | 3602 | N   | ILE | B | 200 | 10.218 | 26.861 | -33.648 | 1 | 18.78 | N   |
| ATOM | 3603 | CA  | ILE | B | 200 | 10.764 | 27.005 | -32.305 | 1 | 20.57 | C   |
| ATOM | 3604 | C   | ILE | B | 200 | 10.151 | 28.24  | -31.654 | 1 | 22.09 | C   |
| ATOM | 3605 | O   | ILE | B | 200 | 10.139 | 29.323 | -32.242 | 1 | 21.41 | O   |
| ATOM | 3606 | CB  | ILE | B | 200 | 12.305 | 27.118 | -32.322 | 1 | 22.56 | C   |
| ATOM | 3607 | CG1 | ILE | B | 200 | 12.914 | 25.902 | -33.023 | 1 | 23.09 | C   |
| ATOM | 3608 | CG2 | ILE | B | 200 | 12.85  | 27.236 | -30.901 | 1 | 23.03 | C   |
| ATOM | 3609 | CD1 | ILE | B | 200 | 14.406 | 26.001 | -33.258 | 1 | 28.91 | C   |

TABLE 5-continued

Atomic Coordinates for OMCP-NKG2D (4PDC).

| ATOM | 3610 | H | ILE | B | 200 | 10.789 | 26.998 | −34.276 | 1 | 22.53 | H |
|------|------|------|------|---|-----|--------|--------|---------|---|-------|---|
| ATOM | 3611 | HA | ILE | B | 200 | 10.522 | 26.229 | −31.775 | 1 | 24.68 | H |
| ATOM | 3612 | HB | ILE | B | 200 | 12.551 | 27.916 | −32.816 | 1 | 27.07 | H |
| ATOM | 3613 | HG12 | ILE | B | 200 | 12.753 | 25.116 | −32.478 | 1 | 27.71 | H |
| ATOM | 3614 | HG13 | ILE | B | 200 | 12.486 | 25.794 | −33.887 | 1 | 27.71 | H |
| ATOM | 3615 | HG21 | ILE | B | 200 | 13.816 | 27.306 | −30.939 | 1 | 27.64 | H |
| ATOM | 3616 | HG22 | ILE | B | 200 | 12.476 | 28.029 | −30.485 | 1 | 27.64 | H |
| ATOM | 3617 | HG23 | ILE | B | 200 | 12.594 | 26.447 | −30.399 | 1 | 27.64 | H |
| ATOM | 3618 | HD11 | ILE | B | 200 | 14.709 | 25.194 | −33.704 | 1 | 34.69 | H |
| ATOM | 3619 | HD12 | ILE | B | 200 | 14.587 | 26.775 | −33.814 | 1 | 34.69 | H |
| ATOM | 3620 | HD13 | ILE | B | 200 | 14.854 | 26.095 | −32.403 | 1 | 34.69 | H |
| ATOM | 3621 | N | GLU | B | 201 | 9.629 | 28.066 | −30.445 | 1 | 18.17 | N |
| ATOM | 3622 | CA | GLU | B | 201 | 8.939 | 29.143 | −29.751 | 1 | 18.13 | C |
| ATOM | 3623 | C | GLU | B | 201 | 9.234 | 29.096 | −28.26 | 1 | 19.85 | C |
| ATOM | 3624 | O | GLU | B | 201 | 9.528 | 28.034 | −27.703 | 1 | 17.15 | O |
| ATOM | 3625 | CB | GLU | B | 201 | 7.428 | 29.05 | −30.006 | 1 | 16.42 | C |
| ATOM | 3626 | CG | GLU | B | 201 | 6.564 | 30.052 | −29.239 | 1 | 24.81 | C |
| ATOM | 3627 | CD | GLU | B | 201 | 6.879 | 31.502 | −29.577 | 1 | 29.39 | C |
| ATOM | 3628 | OE1 | GLU | B | 201 | 7.969 | 31.986 | −29.202 | 1 | 28.55 | O |
| ATOM | 3629 | OE2 | GLU | B | 201 | 6.028 | 32.161 | −30.213 | 1 | 33.83 | O1− |
| ATOM | 3630 | H | GLU | B | 201 | 9.663 | 27.329 | −21.8 | 1 | 21.8 | H |
| ATOM | 3631 | HA | GLU | B | 201 | 9.251 | 29.994 | −30.094 | 1 | 21.75 | H |
| ATOM | 3632 | HB2 | GLU | B | 201 | 7.268 | 29.193 | −30.952 | 1 | 19.7 | H |
| ATOM | 3633 | HB3 | GLU | B | 201 | 7.13 | 28.161 | −29.759 | 1 | 19.7 | H |
| ATOM | 3634 | HG2 | GLU | B | 201 | 5.632 | 29.892 | −29.453 | 1 | 29.77 | H |
| ATOM | 3635 | HG3 | GLU | B | 201 | 6.71 | 29.929 | −28.288 | 1 | 29.77 | H |
| ATOM | 3636 | N | ASN | B | 202 | 9.168 | 30.26 | −27.625 | 1 | 21.76 | N |
| ATOM | 3637 | CA | ASN | B | 202 | 9.292 | 30.361 | −26.179 | 1 | 22.4 | C |
| ATOM | 3638 | C | ASN | B | 202 | 8.163 | 29.592 | −25.495 | 1 | 18.61 | C |
| ATOM | 3639 | O | ASN | B | 202 | 6.984 | 29.863 | −25.726 | 1 | 17.6 | O |
| ATOM | 3640 | CB | ASN | B | 202 | 9.284 | 31.831 | −25.75 | 1 | 25.89 | C |
| ATOM | 3641 | CG | ASN | B | 202 | 9.627 | 32.019 | −24.284 | 1 | 30.35 | C |
| ATOM | 3642 | OD1 | ASN | B | 202 | 9.134 | 31.298 | −23.417 | 1 | 28.07 | O |
| ATOM | 3643 | ND2 | ASN | B | 202 | 10.484 | 32.995 | −24.002 | 1 | 32.66 | N |
| ATOM | 3644 | H | ASN | B | 202 | 9.049 | 31.017 | −28.017 | 1 | 26.11 | H |
| ATOM | 3645 | HA | ASN | B | 202 | 10.135 | 29.969 | −25.904 | 1 | 26.88 | H |
| ATOM | 3646 | HB2 | ASN | B | 202 | 9.938 | 32.317 | −26.276 | 1 | 31.07 | H |
| ATOM | 3647 | HB3 | ASN | B | 202 | 8.399 | 32.199 | −25.9 | 1 | 31.07 | H |
| ATOM | 3648 | HD21 | ASN | B | 202 | 10.713 | 33.144 | −23.187 | 1 | 39.19 | H |
| ATOM | 3649 | HD22 | ASN | B | 202 | 10.81 | 33.477 | −24.635 | 1 | 39.19 | H |
| ATOM | 3650 | N | CYS | B | 203 | 8.541 | 28.633 | −24.654 | 1 | 15.24 | N |
| ATOM | 3651 | CA | CYS | B | 203 | 7.584 | 27.779 | −23.962 | 1 | 18.87 | C |
| ATOM | 3652 | C | CYS | B | 203 | 6.517 | 28.573 | −23.207 | 1 | 18.33 | C |
| ATOM | 3653 | O | CYS | B | 203 | 5.426 | 28.065 | −22.954 | 1 | 20.66 | O |
| ATOM | 3654 | CB | CYS | B | 203 | 8.322 | 26.852 | −22.989 | 1 | 18.37 | C |
| ATOM | 3655 | SG | CYS | B | 203 | 9.514 | 25.728 | −23.774 | 1 | 24.48 | S |
| ATOM | 3656 | H | CYS | B | 203 | 9.361 | 28.456 | −24.465 | 1 | 18.29 | H |
| ATOM | 3657 | HA | CYS | B | 203 | 7.132 | 27.223 | −24.615 | 1 | 22.64 | H |
| ATOM | 3658 | HB2 | CYS | B | 203 | 8.809 | 27.397 | −22.351 | 1 | 22.04 | H |
| ATOM | 3659 | HB3 | CYS | B | 203 | 7.668 | 26.309 | −22.522 | 1 | 22.04 | H |
| ATOM | 3660 | N | SER | B | 204 | 6.83 | 29.819 | −22.859 | 1 | 17.86 | N |

TABLE 5-continued

Atomic Coordinates for OMCP-NKG2D (4PDC).

| ATOM | 3661 | CA | SER | B | 204 | 5.916 | -22.087 | 30.656 | 1 | 22.5 | C |
|------|------|------|-----|---|-----|--------|---------|--------|---|-------|---|
| ATOM | 3662 | C | SER | B | 204 | 4.864 | -22.948 | 31.354 | 1 | 20.68 | C |
| ATOM | 3663 | O | SER | B | 204 | 3.937 | -22.42 | 31.963 | 1 | 22.63 | O |
| ATOM | 3664 | CB | SER | B | 204 | 6.703 | -21.302 | 31.71 | 1 | 20.13 | C |
| ATOM | 3665 | OG | SER | B | 204 | 7.47 | -20.279 | 31.104 | 1 | 22.97 | O |
| ATOM | 3666 | H | SER | B | 204 | 7.571 | -23.061 | 30.206 | 1 | 21.43 | H |
| ATOM | 3667 | HA | SER | B | 204 | 5.449 | -21.446 | 30.098 | 1 | 27 | H |
| ATOM | 3668 | HB2 | SER | B | 204 | 7.298 | -21.909 | 32.177 | 1 | 24.15 | H |
| ATOM | 3669 | HB3 | SER | B | 204 | 6.08 | -20.901 | 32.335 | 1 | 24.15 | H |
| ATOM | 3670 | HG | SER | B | 204 | 7.898 | -19.855 | 31.69 | 1 | 27.57 | H |
| ATOM | 3671 | N | THR | B | 205 | 5.005 | -24.267 | 31.27 | 1 | 18.95 | N |
| ATOM | 3672 | CA | THR | B | 205 | 4.096 | -25.178 | 31.964 | 1 | 19.15 | C |
| ATOM | 3673 | C | THR | B | 205 | 2.756 | -25.307 | 31.236 | 1 | 18.16 | C |
| ATOM | 3674 | O | THR | B | 205 | 2.722 | -25.709 | 30.073 | 1 | 16.01 | O |
| ATOM | 3675 | CB | THR | B | 205 | 4.704 | -26.585 | 32.103 | 1 | 25.38 | C |
| ATOM | 3676 | OG1 | THR | B | 205 | 6.06 | -26.487 | 32.554 | 1 | 28.77 | O |
| ATOM | 3677 | CG2 | THR | B | 205 | 3.896 | -27.42 | 33.092 | 1 | 24.93 | C |
| ATOM | 3678 | H | THR | B | 205 | 5.621 | -24.661 | 30.817 | 1 | 22.74 | H |
| ATOM | 3679 | HA | THR | B | 205 | 3.924 | -24.835 | 32.855 | 1 | 22.99 | H |
| ATOM | 3680 | HB | THR | B | 205 | 4.684 | -27.03 | 31.241 | 1 | 30.45 | H |
| ATOM | 3681 | HG1 | THR | B | 205 | 6.087 | -26.103 | 33.3 | 1 | 34.52 | H |
| ATOM | 3682 | HG21 | THR | B | 205 | 4.286 | -28.305 | 33.174 | 1 | 29.92 | H |
| ATOM | 3683 | HG22 | THR | B | 205 | 2.981 | -27.506 | 32.784 | 1 | 29.92 | H |
| ATOM | 3684 | HG23 | THR | B | 205 | 3.897 | -26.994 | 33.964 | 1 | 29.92 | H |
| ATOM | 3685 | N | PRO | B | 206 | 1.645 | -24.977 | 31.917 | 1 | 18 | N |
| ATOM | 3686 | CA | PRO | B | 206 | 0.35 | -25.14 | 31.248 | 1 | 17.87 | C |
| ATOM | 3687 | C | PRO | B | 206 | 0.05 | -26.593 | 30.892 | 1 | 20.2 | C |
| ATOM | 3688 | O | PRO | B | 206 | 0.187 | -27.477 | 31.737 | 1 | 14.53 | O |
| ATOM | 3689 | CB | PRO | B | 206 | -0.655 | -24.621 | 32.286 | 1 | 22.87 | C |
| ATOM | 3690 | CG | PRO | B | 206 | 0.134 | -23.763 | 33.198 | 1 | 22.22 | C |
| ATOM | 3691 | CD | PRO | B | 206 | 1.494 | -24.382 | 33.257 | 1 | 21.86 | C |
| ATOM | 3692 | HA | PRO | B | 206 | 0.306 | -24.591 | 30.45 | 1 | 21.45 | H |
| ATOM | 3693 | HB2 | PRO | B | 206 | -1.042 | -25.369 | 32.767 | 1 | 27.45 | H |
| ATOM | 3694 | HB3 | PRO | B | 206 | -1.345 | -24.104 | 31.841 | 1 | 27.45 | H |
| ATOM | 3695 | HG2 | PRO | B | 206 | -0.277 | -23.758 | 34.077 | 1 | 26.66 | H |
| ATOM | 3696 | HG3 | PRO | B | 206 | 0.183 | -22.864 | 32.839 | 1 | 26.66 | H |
| ATOM | 3697 | HD2 | PRO | B | 206 | 1.525 | -25.071 | 33.939 | 1 | 26.23 | H |
| ATOM | 3698 | HD3 | PRO | B | 206 | 2.171 | -23.703 | 33.404 | 1 | 26.23 | H |
| ATOM | 3699 | N | ASN | B | 207 | -0.342 | -26.829 | 29.644 | 1 | 19.17 | N |
| ATOM | 3700 | CA | ASN | B | 207 | -0.792 | -28.146 | 29.207 | 1 | 16.49 | C |
| ATOM | 3701 | C | ASN | B | 207 | -1.897 | -28.01 | 28.165 | 1 | 19.54 | C |
| ATOM | 3702 | O | ASN | B | 207 | -2.061 | -26.95 | 27.557 | 1 | 15.66 | O |
| ATOM | 3703 | CB | ASN | B | 207 | 0.371 | -28.961 | 28.628 | 1 | 19.53 | C |
| ATOM | 3704 | CG | ASN | B | 207 | 1.225 | -29.62 | 29.702 | 1 | 16.92 | C |
| ATOM | 3705 | OD1 | ASN | B | 207 | 0.877 | -30.681 | 30.221 | 1 | 16.98 | O |
| ATOM | 3706 | ND2 | ASN | B | 207 | 2.356 | -29.002 | 30.023 | 1 | 17.66 | N |
| ATOM | 3707 | H | ASN | B | 207 | -0.356 | -26.235 | 29.022 | 1 | 23 | H |
| ATOM | 3708 | HA | ASN | B | 207 | -1.151 | -28.629 | 29.968 | 1 | 19.79 | H |
| ATOM | 3709 | HB2 | ASN | B | 207 | 0.943 | -28.372 | 28.111 | 1 | 23.43 | H |
| ATOM | 3710 | HB3 | ASN | B | 207 | 0.014 | -29.66 | 28.058 | 1 | 23.43 | H |
| ATOM | 3711 | HD21 | ASN | B | 207 | 2.872 | -29.336 | 30.625 | 1 | 21.19 | H |

TABLE 5-continued

Atomic Coordinates for OMCP-NKG2D (4PDC).

| | | | | | | | | | | |
|---|---|---|---|---|---|---|---|---|---|---|
| ATOM | 3712 | HD22 | ASN B | 207 | 2.572 | 29.63 | -28.268 | 1 | 21.19 | H |
| ATOM | 3713 | N | THR B | 208 | -2.662 | 27.961 | -29.077 | 1 | 16.41 | N |
| ATOM | 3714 | CA | THR B | 208 | -3.612 | 26.859 | -29.105 | 1 | 14.55 | C |
| ATOM | 3715 | C | THR B | 208 | -2.801 | 25.564 | -29.139 | 1 | 16.01 | C |
| ATOM | 3716 | O | THR B | 208 | -1.589 | 25.596 | -29.359 | 1 | 12.88 | O |
| ATOM | 3717 | CB | THR B | 208 | -4.568 | 26.951 | -30.307 | 1 | 14.56 | C |
| ATOM | 3718 | OG1 | THR B | 208 | -3.821 | 27.017 | -31.528 | 1 | 15.04 | O |
| ATOM | 3719 | CG2 | THR B | 208 | -5.45 | 28.186 | -30.187 | 1 | 15.59 | C |
| ATOM | 3720 | H | THR B | 208 | -2.65 | 28.442 | -29.79 | 1 | 19.7 | H |
| ATOM | 3721 | HA | THR B | 208 | -4.14 | 26.868 | -28.292 | 1 | 17.46 | H |
| ATOM | 3722 | HB | THR B | 208 | -5.141 | 26.168 | -30.322 | 1 | 17.48 | H |
| ATOM | 3723 | HG1 | THR B | 208 | -4.345 | 27.067 | -32.183 | 1 | 18.05 | H |
| ATOM | 3724 | HG21 | THR B | 208 | -6.051 | 28.239 | -30.947 | 1 | 18.71 | H |
| ATOM | 3725 | HG22 | THR B | 208 | -5.975 | 28.14 | -29.372 | 1 | 18.71 | H |
| ATOM | 3726 | HG23 | THR B | 208 | -4.9 | 28.984 | -30.164 | 1 | 18.71 | H |
| ATOM | 3727 | N | TYR B | 209 | -3.446 | 24.429 | -28.895 | 1 | 13.5 | N |
| ATOM | 3728 | CA | TYR B | 209 | -2.703 | 23.175 | -28.8 | 1 | 13 | C |
| ATOM | 3729 | C | TYR B | 209 | -3.513 | 21.958 | -29.226 | 1 | 14.49 | C |
| ATOM | 3730 | O | TYR B | 209 | -4.744 | 21.996 | -29.295 | 1 | 11.51 | O |
| ATOM | 3731 | CB | TYR B | 209 | -2.187 | 22.983 | -27.371 | 1 | 14 | C |
| ATOM | 3732 | CG | TYR B | 209 | -3.26 | 22.967 | -26.303 | 1 | 13.42 | C |
| ATOM | 3733 | CD1 | TYR B | 209 | -3.864 | 24.146 | -25.876 | 1 | 15.48 | C |
| ATOM | 3734 | CD2 | TYR B | 209 | -3.65 | 21.777 | -25.703 | 1 | 14.21 | C |
| ATOM | 3735 | CE1 | TYR B | 209 | -4.84 | 24.134 | -24.894 | 1 | 19.28 | C |
| ATOM | 3736 | CE2 | TYR B | 209 | -4.619 | 21.755 | -24.72 | 1 | 19.66 | C |
| ATOM | 3737 | CZ | TYR B | 209 | -5.211 | 22.935 | -24.319 | 1 | 20.66 | C |
| ATOM | 3738 | OH | TYR B | 209 | -6.178 | 22.907 | -23.343 | 1 | 19.94 | O |
| ATOM | 3739 | H | TYR B | 209 | -4.295 | 24.355 | -28.783 | 1 | 16.2 | H |
| ATOM | 3740 | HA | TYR B | 209 | -1.931 | 23.231 | -29.385 | 1 | 15.6 | H |
| ATOM | 3741 | HB2 | TYR B | 209 | -1.714 | 22.137 | -27.325 | 1 | 16.8 | H |
| ATOM | 3742 | HB3 | TYR B | 209 | -1.577 | 23.708 | -27.163 | 1 | 16.8 | H |
| ATOM | 3743 | HD1 | TYR B | 209 | -3.615 | 24.954 | -26.263 | 1 | 18.58 | H |
| ATOM | 3744 | HD2 | TYR B | 209 | -3.253 | 20.979 | -25.971 | 1 | 17.06 | H |
| ATOM | 3745 | HE1 | TYR B | 209 | -5.24 | 24.928 | -24.621 | 1 | 23.13 | H |
| ATOM | 3746 | HE2 | TYR B | 209 | -4.874 | 20.949 | -24.333 | 1 | 23.6 | H |
| ATOM | 3747 | HH | TYR B | 209 | -6.458 | 23.684 | -23.193 | 1 | 23.92 | H |
| ATOM | 3748 | N | ILE B | 210 | -2.782 | 20.885 | -29.516 | 1 | 14.8 | N |
| ATOM | 3749 | CA | ILE B | 210 | -3.348 | 19.627 | -29.975 | 1 | 18.21 | C |
| ATOM | 3750 | C | ILE B | 210 | -3.006 | 18.514 | -28.994 | 1 | 15.01 | C |
| ATOM | 3751 | O | ILE B | 210 | -1.834 | 18.276 | -28.705 | 1 | 15.25 | O |
| ATOM | 3752 | CB | ILE B | 210 | -2.818 | 19.246 | -31.373 | 1 | 15.54 | C |
| ATOM | 3753 | CG1 | ILE B | 210 | -3.11 | 20.366 | -32.375 | 1 | 15.83 | C |
| ATOM | 3754 | CG2 | ILE B | 210 | -3.438 | 17.936 | -31.837 | 1 | 14.28 | C |
| ATOM | 3755 | CD1 | ILE B | 210 | -2.421 | 20.193 | -33.707 | 1 | 18.37 | C |
| ATOM | 3756 | H | ILE B | 210 | -1.924 | 20.865 | -29.452 | 1 | 17.76 | H |
| ATOM | 3757 | HA | ILE B | 210 | -4.314 | 19.706 | -30.024 | 1 | 21.85 | H |
| ATOM | 3758 | HB | ILE B | 210 | -1.857 | 19.127 | -31.315 | 1 | 18.65 | H |
| ATOM | 3759 | HG12 | ILE B | 210 | -4.066 | 20.397 | -32.538 | 1 | 18.99 | H |
| ATOM | 3760 | HG13 | ILE B | 210 | -2.814 | 21.208 | -31.996 | 1 | 18.99 | H |
| ATOM | 3761 | HG21 | ILE B | 210 | -3.09 | 17.718 | -32.716 | 1 | 17.13 | H |
| ATOM | 3762 | HG22 | ILE B | 210 | -3.207 | 17.237 | -31.207 | 1 | 17.13 | H |

TABLE 5-continued

Atomic Coordinates for OMCP-NKG2D (4PDC).

| | | | | | | | | | | |
|---|---|---|---|---|---|---|---|---|---|---|
| ATOM | 3763 | HG23 | ILE | B | 210 | -4.401 | 18.041 | -31.879 | 1 | 17.13 | H |
| ATOM | 3764 | HD11 | ILE | B | 210 | -2.655 | 20.938 | -34.282 | 1 | 22.04 | H |
| ATOM | 3765 | HD12 | ILE | B | 210 | -1.461 | 20.172 | -33.565 | 1 | 22.04 | H |
| ATOM | 3766 | HD13 | ILE | B | 210 | -2.714 | 19.36 | -34.108 | 1 | 22.04 | H |
| ATOM | 3767 | N | CYS | B | 211 | -4.031 | 17.845 | -28.478 | 1 | 13.03 | N |
| ATOM | 3768 | CA | CYS | B | 211 | -3.838 | 16.677 | -27.628 | 1 | 16.24 | C |
| ATOM | 3769 | C | CYS | B | 211 | -3.968 | 15.42 | -28.469 | 1 | 20.33 | C |
| ATOM | 3770 | O | CYS | B | 211 | -4.712 | 15.394 | -29.452 | 1 | 17.44 | O |
| ATOM | 3771 | CB | CYS | B | 211 | -4.848 | 16.651 | -26.479 | 1 | 22.87 | C |
| ATOM | 3772 | SG | CYS | B | 211 | -4.586 | 17.937 | -25.24 | 1 | 32.56 | S |
| ATOM | 3773 | H | CYS | B | 211 | -4.856 | 18.049 | -28.607 | 1 | 15.64 | H |
| ATOM | 3774 | HA | CYS | B | 211 | -2.945 | 16.699 | -27.249 | 1 | 19.49 | H |
| ATOM | 3775 | HB2 | CYS | B | 211 | -5.739 | 16.77 | -26.844 | 1 | 27.44 | H |
| ATOM | 3776 | HB3 | CYS | B | 211 | -4.789 | 15.793 | -26.031 | 1 | 27.44 | H |
| ATOM | 3777 | N | MET | B | 212 | -3.236 | 14.385 | -28.075 | 1 | 20.62 | N |
| ATOM | 3778 | CA | MET | B | 212 | -3.224 | 13.123 | -28.796 | 1 | 19.04 | C |
| ATOM | 3779 | C | MET | B | 212 | -3.266 | 11.958 | -27.822 | 1 | 24.41 | C |
| ATOM | 3780 | O | MET | B | 212 | -2.621 | 11.994 | -26.773 | 1 | 20.8 | O |
| ATOM | 3781 | CB | MET | B | 212 | -1.982 | 13.025 | -29.676 | 1 | 22.84 | C |
| ATOM | 3782 | CG | MET | B | 212 | -1.792 | 11.672 | -30.333 | 1 | 22.92 | C |
| ATOM | 3783 | SD | MET | B | 212 | -0.403 | 11.689 | -31.475 | 1 | 24.54 | S |
| ATOM | 3784 | CE | MET | B | 212 | -0.348 | 9.97 | -31.974 | 1 | 31.53 | C |
| ATOM | 3785 | H | MET | B | 212 | -2.729 | 14.391 | -27.38 | 1 | 24.74 | H |
| ATOM | 3786 | HA | MET | B | 212 | -4.003 | 13.081 | -29.372 | 1 | 22.85 | H |
| ATOM | 3787 | HB2 | MET | B | 212 | -2.047 | 13.688 | -30.381 | 1 | 27.41 | H |
| ATOM | 3788 | HB3 | MET | B | 212 | -1.199 | 13.201 | -29.131 | 1 | 27.41 | H |
| ATOM | 3789 | HG2 | MET | B | 212 | -1.616 | 11.006 | -29.65 | 1 | 27.5 | H |
| ATOM | 3790 | HG3 | MET | B | 212 | -2.592 | 11.441 | -30.83 | 1 | 27.5 | H |
| ATOM | 3791 | HE1 | MET | B | 212 | 0.378 | 9.849 | -32.605 | 1 | 37.83 | H |
| ATOM | 3792 | HE2 | MET | B | 212 | -0.2 | 9.419 | -31.189 | 1 | 37.83 | H |
| ATOM | 3793 | HE3 | MET | B | 212 | -1.192 | 9.735 | -32.39 | 1 | 37.83 | H |
| ATOM | 3794 | N | GLN | B | 213 | -4.031 | 10.931 | -28.178 | 1 | 22.35 | N |
| ATOM | 3795 | CA | GLN | B | 213 | -4.116 | 9.713 | -27.386 | 1 | 24.56 | C |
| ATOM | 3796 | C | GLN | B | 213 | 4.148 | 8.501 | -28.309 | 1 | 31.59 | C |
| ATOM | 3797 | O | GLN | B | 213 | -5.071 | 8.346 | -29.111 | 1 | 28.14 | O |
| ATOM | 3798 | CB | GLN | B | 213 | -5.357 | 9.735 | -26.493 | 1 | 27.78 | C |
| ATOM | 3799 | CG | GLN | B | 213 | -5.48 | 8.534 | -25.565 | 1 | 30.43 | C |
| ATOM | 3800 | CD | GLN | B | 213 | -6.836 | 8.462 | -24.893 | 1 | 33.92 | C |
| ATOM | 3801 | OE1 | GLN | B | 213 | -7.736 | 7.766 | -25.363 | 1 | 34.06 | O |
| ATOM | 3802 | NE2 | GLN | B | 213 | -6.991 | 9.185 | -23.788 | 1 | 30.76 | N |
| ATOM | 3803 | H | GLN | B | 213 | -4.519 | 10.917 | -26.818 | 1 | 26.82 | H |
| ATOM | 3804 | HA | GLN | B | 213 | -3.333 | 9.644 | -26.818 | 1 | 29.47 | H |
| ATOM | 3805 | HB2 | GLN | B | 213 | -5.329 | 10.533 | -25.941 | 1 | 33.34 | H |
| ATOM | 3806 | HB3 | GLN | B | 213 | -6.145 | 9.755 | -27.057 | 1 | 33.34 | H |
| ATOM | 3807 | HG2 | GLN | B | 213 | -5.356 | 7.722 | -26.08 | 1 | 36.51 | H |
| ATOM | 3808 | HG3 | GLN | B | 213 | -4.803 | 8.597 | -24.873 | 1 | 36.51 | H |
| ATOM | 3809 | HE21 | GLN | B | 213 | -7.742 | 9.177 | -23.371 | 1 | 36.91 | H |
| ATOM | 3810 | HE22 | GLN | B | 213 | -6.339 | 9.661 | -23.491 | 1 | 36.91 | H |
| ATOM | 3811 | N | ARG | B | 214 | -3.137 | 7.645 | -28.192 | 1 | 26.52 | N |
| ATOM | 3812 | CA | ARG | B | 214 | -3.047 | 6.45 | -29.023 | 1 | 33.12 | C |
| ATOM | 3813 | C | ARG | B | 214 | -4.103 | 5.415 | -28.633 | 1 | 37.91 | C |

TABLE 5-continued

Atomic Coordinates for OMCP-NKG2D (4PDC).

| ATOM | 3814 | O | ARG | B | 214 | -4.624 | 5.431 | -27.514 | 1 | 34.52 | O |
|------|------|-----|-----|---|-----|--------|-------|---------|---|-------|---|
| ATOM | 3815 | CB | ARG | B | 214 | -1.646 | 5.838 | -28.929 | 1 | 42.25 | C |
| ATOM | 3816 | CG | ARG | B | 214 | -0.556 | 6.668 | -29.617 | 1 | 42.31 | C |
| ATOM | 3817 | CD | ARG | B | 214 | 0.652 | 5.824 | -30.026 | 1 | 42.8 | C |
| ATOM | 3818 | NE | ARG | B | 214 | 0.268 | 4.633 | -30.787 | 1 | 51.67 | N |
| ATOM | 3819 | CZ | ARG | B | 214 | 0.147 | 4.575 | -32.112 | 1 | 45.75 | C |
| ATOM | 3820 | NH1 | ARG | B | 214 | 0.385 | 5.64 | -32.865 | 1 | 40.29 | N |
| ATOM | 3821 | NH2 | ARG | B | 214 | -0.212 | 3.438 | -32.692 | 1 | 44.7 | N |
| ATOM | 3822 | H | ARG | B | 214 | -2.488 | 7.735 | -27.635 | 1 | 31.82 | H |
| ATOM | 3823 | HA | ARG | B | 214 | -3.201 | 6.699 | -29.947 | 1 | 39.74 | H |
| ATOM | 3824 | HB2 | ARG | B | 214 | -1.405 | 5.751 | -27.993 | 1 | 50.7 | H |
| ATOM | 3825 | HB3 | ARG | B | 214 | -1.659 | 4.963 | -29.347 | 1 | 50.7 | H |
| ATOM | 3826 | HG2 | ARG | B | 214 | -0.924 | 7.074 | -30.417 | 1 | 50.77 | H |
| ATOM | 3827 | HG3 | ARG | B | 214 | -0.248 | 7.356 | -29.006 | 1 | 50.77 | H |
| ATOM | 3828 | HD2 | ARG | B | 214 | 1.24 | 6.36 | -30.582 | 1 | 51.36 | H |
| ATOM | 3829 | HD3 | ARG | B | 214 | 1.122 | 5.534 | -29.228 | 1 | 51.36 | H |
| ATOM | 3830 | HE | ARG | B | 214 | 0.108 | 3.914 | -30.343 | 1 | 62 | H |
| ATOM | 3831 | HH11 | ARG | B | 214 | 0.617 | 6.382 | -32.498 | 1 | 48.35 | H |
| ATOM | 3832 | HH12 | ARG | B | 214 | 0.304 | 5.589 | -33.719 | 1 | 48.35 | H |
| ATOM | 3833 | HH21 | ARG | B | 214 | -0.367 | 2.741 | -32.213 | 1 | 53.64 | H |
| ATOM | 3834 | HH22 | ARG | B | 214 | -0.289 | 3.397 | -33.548 | 1 | 53.64 | H |
| ATOM | 3835 | N | THR | B | 215 | -4.411 | 4.526 | -29.575 | 1 | 42.55 | N |
| ATOM | 3836 | CA | THR | B | 215 | -5.441 | 3.504 | -29.396 | 1 | 47.95 | C |
| ATOM | 3837 | C | THR | B | 215 | -6.789 | 4.141 | -29.072 | 1 | 47.59 | C |
| ATOM | 3838 | O | THR | B | 215 | -7.69 | 4.169 | -29.914 | 1 | 48.2 | O |
| ATOM | 3839 | CB | THR | B | 215 | -5.061 | 2.502 | -28.283 | 1 | 45.58 | C |
| ATOM | 3840 | OG1 | THR | B | 215 | -3.858 | 1.816 | -28.651 | 1 | 50.86 | O |
| ATOM | 3841 | CG2 | THR | B | 215 | -6.166 | 1.475 | -28.071 | 1 | 55.86 | C |
| ATOM | 3842 | H | THR | B | 215 | -4.028 | 4.494 | -30.344 | 1 | 51.06 | H |
| ATOM | 3843 | HA | THR | B | 215 | -5.537 | 3.008 | -30.223 | 1 | 57.54 | H |
| ATOM | 3844 | HB | THR | B | 215 | -4.92 | 2.98 | -27.451 | 1 | 54.7 | H |
| ATOM | 3845 | HG1 | THR | B | 215 | -3.645 | 1.269 | -28.05 | 1 | 61.03 | H |
| ATOM | 3846 | HG21 | THR | B | 215 | -5.911 | 0.855 | -27.37 | 1 | 67.03 | H |
| ATOM | 3847 | HG22 | THR | B | 215 | -6.988 | 1.922 | -27.814 | 1 | 67.03 | H |
| ATOM | 3848 | HG23 | THR | B | 215 | -6.32 | 0.98 | -28.891 | 1 | 67.03 | H |
| TER | 3849 | | THR | B | 215 | | | | | | |
| ATOM | 3850 | N | GLU | C | 93 | -21.096 | 71.394 | -8.126 | 1 | 57.72 | N |
| ATOM | 3851 | CA | GLU | C | 93 | -19.991 | 72.179 | -7.586 | 1 | 64.4 | C |
| ATOM | 3852 | C | GLU | C | 93 | -18.719 | 71.951 | -8.396 | 1 | 60.46 | C |
| ATOM | 3853 | O | GLU | C | 93 | -18.309 | 72.806 | -9.183 | 1 | 62.51 | O |
| ATOM | 3854 | CB | GLU | C | 93 | -19.747 | 71.824 | -6.115 | 1 | 58.36 | C |
| ATOM | 3855 | CG | GLU | C | 93 | -18.795 | 72.76 | -5.383 | 1 | 58.1 | C |
| ATOM | 3856 | CD | GLU | C | 93 | -19.458 | 74.063 | -4.971 | 1 | 61.87 | C |
| ATOM | 3857 | OE1 | GLU | C | 93 | -20.558 | 74.362 | -5.481 | 1 | 60.81 | O |
| ATOM | 3858 | OE2 | GLU | C | 93 | -18.885 | 74.786 | -4.129 | 1 | 60.23 | O1- |
| ATOM | 3859 | HA | GLU | C | 93 | -20.216 | 73.122 | -7.636 | 1 | 77.28 | H |
| ATOM | 3860 | HB2 | GLU | C | 93 | -20.596 | 71.844 | -5.647 | 1 | 70.03 | H |
| ATOM | 3861 | HB3 | GLU | C | 93 | -19.371 | 70.93 | -6.071 | 1 | 70.03 | H |
| ATOM | 3862 | HG2 | GLU | C | 93 | -18.474 | 72.32 | -4.58 | 1 | 69.72 | H |
| ATOM | 3863 | HG3 | GLU | C | 93 | -18.05 | 72.973 | -5.966 | 1 | 69.72 | H |
| ATOM | 3864 | N | SER | C | 94 | -18.107 | 70.787 | -8.197 | 1 | 55.28 | N |

TABLE 5-continued

Atomic Coordinates for OMCP-NKG2D (4PDC).

| ATOM | 3865 | CA | SER | C | 94 | -16.857 | 70.437 | -8.856 | 1 | 48.47 | C |
|---|---|---|---|---|---|---|---|---|---|---|---|
| ATOM | 3866 | C | SER | C | 94 | -16.938 | 69.038 | -9.447 | 1 | 42.81 | C |
| ATOM | 3867 | O | SER | C | 94 | -17.428 | 68.105 | -8.805 | 1 | 35 | O |
| ATOM | 3868 | CB | SER | C | 94 | -15.69 | 70.525 | -7.872 | 1 | 51.57 | C |
| ATOM | 3869 | OG | SER | C | 94 | -15.518 | 71.852 | -7.409 | 1 | 59.31 | O |
| ATOM | 3870 | H | SER | C | 94 | -18.404 | 70.172 | -7.673 | 1 | 66.34 | H |
| ATOM | 3871 | HA | SER | C | 94 | -16.691 | 71.062 | -9.579 | 1 | 58.16 | H |
| ATOM | 3872 | HB2 | SER | C | 94 | -15.872 | 69.947 | -7.115 | 1 | 61.88 | H |
| ATOM | 3873 | HB3 | SER | C | 94 | -14.878 | 70.239 | -8.32 | 1 | 61.88 | H |
| ATOM | 3874 | HG | SER | C | 94 | -14.875 | 71.887 | -6.87 | 1 | 71.18 | H |
| ATOM | 3875 | N | TYR | C | 95 | -16.457 | 68.908 | -10.678 | 1 | 41.19 | N |
| ATOM | 3876 | CA | TYR | C | 95 | -16.444 | 67.634 | -11.379 | 1 | 38.72 | C |
| ATOM | 3877 | C | TYR | C | 95 | -15.019 | 67.168 | -11.629 | 1 | 38.41 | C |
| ATOM | 3878 | O | TYR | C | 95 | -14.099 | 67.975 | -11.764 | 1 | 32.89 | O |
| ATOM | 3879 | CB | TYR | C | 95 | -17.19 | 67.743 | -12.708 | 1 | 37.08 | C |
| ATOM | 3880 | CG | TYR | C | 95 | -18.693 | 67.809 | -12.573 | 1 | 37.6 | C |
| ATOM | 3881 | CD1 | TYR | C | 95 | -19.338 | 69.017 | -12.344 | 1 | 41.89 | C |
| ATOM | 3882 | CD2 | TYR | C | 95 | -19.469 | 66.663 | -12.685 | 1 | 34.68 | C |
| ATOM | 3883 | CE1 | TYR | C | 95 | -20.712 | 69.08 | -12.226 | 1 | 39.87 | C |
| ATOM | 3884 | CE2 | TYR | C | 95 | -20.842 | 66.716 | -12.569 | 1 | 36.52 | C |
| ATOM | 3885 | CZ | TYR | C | 95 | -21.459 | 67.926 | -12.34 | 1 | 40.73 | C |
| ATOM | 3886 | OH | TYR | C | 95 | -22.829 | 67.98 | -12.225 | 1 | 41.72 | O |
| ATOM | 3887 | H | TYR | C | 95 | -16.127 | 69.557 | -11.136 | 1 | 49.43 | H |
| ATOM | 3888 | HA | TYR | C | 95 | -16.89 | 66.966 | -10.835 | 1 | 46.47 | H |
| ATOM | 3889 | HB2 | TYR | C | 95 | -16.899 | 68.549 | -13.162 | 1 | 44.49 | H |
| ATOM | 3890 | HB3 | TYR | C | 95 | -16.976 | 66.967 | -13.249 | 1 | 44.49 | H |
| ATOM | 3891 | HD1 | TYR | C | 95 | -18.837 | 69.797 | -12.267 | 1 | 50.27 | H |
| ATOM | 3892 | HD2 | TYR | C | 95 | -19.055 | 65.845 | -12.84 | 1 | 41.62 | H |
| ATOM | 3893 | HE1 | TYR | C | 95 | -21.132 | 69.895 | -12.072 | 1 | 47.85 | H |
| ATOM | 3894 | HE2 | TYR | C | 95 | -21.348 | 65.94 | -12.645 | 1 | 43.82 | H |
| ATOM | 3895 | HH | TYR | C | 95 | -23.074 | 68.771 | -12.087 | 1 | 50.06 | H |
| ATOM | 3896 | N | CYS | C | 96 | -14.853 | 65.853 | -11.684 | 1 | 35.27 | N |
| ATOM | 3897 | CA | CYS | C | 96 | -13.59 | 65.246 | -12.064 | 1 | 33.31 | C |
| ATOM | 3898 | C | CYS | C | 96 | -13.632 | 64.911 | -13.55 | 1 | 27.94 | C |
| ATOM | 3899 | O | CYS | C | 96 | -14.616 | 64.36 | -14.036 | 1 | 24.96 | O |
| ATOM | 3900 | CB | CYS | C | 96 | -13.329 | 63.99 | -11.232 | 1 | 32.47 | C |
| ATOM | 3901 | SG | CYS | C | 96 | -11.682 | 63.299 | -11.433 | 1 | 36.22 | S |
| ATOM | 3902 | H | CYS | C | 96 | -15.47 | 65.283 | -11.503 | 1 | 42.33 | H |
| ATOM | 3903 | HA | CYS | C | 96 | -12.867 | 65.874 | -11.909 | 1 | 39.98 | H |
| ATOM | 3904 | HB2 | CYS | C | 96 | -13.445 | 64.208 | -10.294 | 1 | 38.96 | H |
| ATOM | 3905 | HB3 | CYS | C | 96 | -13.969 | 63.307 | -11.49 | 1 | 38.96 | H |
| ATOM | 3906 | N | GLY | C | 97 | -12.573 | 65.259 | -14.272 | 1 | 28.67 | N |
| ATOM | 3907 | CA | GLY | C | 97 | -12.49 | 64.946 | -15.687 | 1 | 31.01 | C |
| ATOM | 3908 | C | GLY | C | 97 | -12.065 | 66.13 | -16.535 | 1 | 33.85 | C |
| ATOM | 3909 | O | GLY | C | 97 | -11.45 | 67.067 | -16.028 | 1 | 35.84 | O |
| ATOM | 3910 | H | GLY | C | 97 | -11.888 | 65.677 | -13.962 | 1 | 34.4 | H |
| ATOM | 3911 | HA2 | GLY | C | 97 | -11.849 | 64.23 | -15.82 | 1 | 37.22 | H |
| ATOM | 3912 | HA3 | GLY | C | 97 | -13.357 | 64.643 | -16 | 1 | 37.22 | H |
| ATOM | 3913 | N | PRO | C | 98 | -12.391 | 66.097 | -17.837 | 1 | 33.61 | N |
| ATOM | 3914 | CA | PRO | C | 98 | -12.165 | 65.036 | -18.492 | 1 | 34.25 | C |
| ATOM | 3915 | C | PRO | C | 98 | -12.428 | 63.695 | -18.552 | 1 | 32.91 | C |

TABLE 5-continued

Atomic Coordinates for OMCP-NKG2D (4PDC).

| ATOM | 3916 | O | PRO | C | 98 | -11.2 | 63.661 | -18.522 | 1 | 33.58 | O |
|------|------|-----|-----|---|-----|---------|---------|---------|---|-------|----|
| ATOM | 3917 | CB | PRO | C | 98 | -13.4 | 65.596 | -19.897 | 1 | 43.48 | C |
| ATOM | 3918 | CG | PRO | C | 98 | -12.285 | 66.542 | -20.119 | 1 | 44.16 | C |
| ATOM | 3919 | CD | PRO | C | 98 | -11.991 | 67.149 | -18.785 | 1 | 39.32 | C |
| ATOM | 3920 | HA | PRO | C | 98 | -14.019 | 64.916 | -18.046 | 1 | 41.1 | H |
| ATOM | 3921 | HB2 | PRO | C | 98 | -13.374 | 64.875 | -20.546 | 1 | 52.18 | H |
| ATOM | 3922 | HB3 | PRO | C | 98 | -14.253 | 66.056 | -19.928 | 1 | 52.18 | H |
| ATOM | 3923 | HG2 | PRO | C | 98 | -11.512 | 66.06 | -20.452 | 1 | 52.99 | H |
| ATOM | 3924 | HG3 | PRO | C | 98 | -12.56 | 67.225 | -20.751 | 1 | 52.99 | H |
| ATOM | 3925 | HD2 | PRO | C | 98 | -11.043 | 67.337 | -18.701 | 1 | 47.19 | H |
| ATOM | 3926 | HD3 | PRO | C | 98 | -12.526 | 67.946 | -18.651 | 1 | 47.19 | H |
| ATOM | 3927 | N | CYS | C | 99 | -13.195 | 62.61 | -18.619 | 1 | 29.92 | N |
| ATOM | 3928 | CA | CYS | C | 99 | -12.656 | 61.259 | -18.747 | 1 | 30.84 | C |
| ATOM | 3929 | C | CYS | C | 9 | -13.492 | 60.459 | -19.732 | 1 | 33.78 | C |
| ATOM | 3930 | O | CYS | C | 99 | -14.602 | 60.863 | -20.076 | 1 | 29.2 | O |
| ATOM | 3931 | CB | CYS | C | 99 | -12.646 | 60.535 | -17.4 | 1 | 24.67 | C |
| ATOM | 3932 | SG | CYS | C | 99 | -11.422 | 61.121 | -16.229 | 1 | 27.04 | S |
| ATOM | 3933 | OH | CYS | C | 99 | -14.054 | 62.632 | -18.593 | 1 | 35.9 | H |
| ATOM | 3934 | HA | CYS | C | 99 | -11.746 | 61.303 | -19.079 | 1 | 37.01 | H |
| ATOM | 3935 | HB2 | CYS | C | 99 | -13.518 | 60.639 | -16.987 | 1 | 29.6 | H |
| ATOM | 3936 | HB3 | CYS | C | 99 | -12.473 | 59.593 | -17.557 | 1 | 29.6 | H |
| ATOM | 3937 | N | PRO | C | 100 | -12.963 | 59.314 | -20.19 | 1 | 30.07 | N |
| ATOM | 3938 | CA | PRO | C | 100 | -13.8 | 58.399 | -20.968 | 1 | 29.87 | C |
| ATOM | 3939 | C | PRO | C | 100 | -14.997 | 57.928 | -20.148 | 1 | 33.56 | C |
| ATOM | 3940 | O | PRO | C | 100 | -14.919 | 57.895 | -18.917 | 1 | 26.53 | O |
| ATOM | 3941 | CB | PRO | C | 100 | -12.852 | 57.239 | -21.291 | 1 | 30.74 | C |
| ATOM | 3942 | CG | PRO | C | 100 | -11.483 | 57.83 | -21.199 | 1 | 29.98 | C |
| ATOM | 3943 | CD | PRO | C | 100 | -11.566 | 58.853 | -20.11 | 1 | 28.76 | C |
| ATOM | 3944 | HA | PRO | C | 100 | -14.102 | 58.818 | -21.789 | 1 | 35.84 | H |
| ATOM | 3945 | HB2 | PRO | C | 100 | -12.965 | 56.531 | -20.638 | 1 | 36.89 | H |
| ATOM | 3946 | HB3 | PRO | C | 100 | -13.026 | 56.912 | -22.188 | 1 | 36.89 | H |
| ATOM | 3947 | HG2 | PRO | C | 100 | -10.843 | 57.138 | -20.971 | 1 | 35.98 | H |
| ATOM | 3948 | HG3 | PRO | C | 100 | -11.251 | 58.248 | -22.043 | 1 | 35.98 | H |
| ATOM | 3949 | HD2 | PRO | C | 100 | -11.393 | 58.444 | -19.247 | 1 | 34.51 | H |
| ATOM | 3950 | HD3 | PRO | C | 100 | -10.956 | 59.586 | -20.286 | 1 | 34.51 | H |
| ATOM | 3951 | N | LYS | C | 101 | -16.086 | 57.579 | -20.825 | 1 | 31.45 | N |
| ATOM | 3952 | CA | LYS | C | 101 | -17.315 | 57.171 | -20.154 | 1 | 38.12 | C |
| ATOM | 3953 | C | LYS | C | 101 | -17.066 | 56.015 | -19.182 | 1 | 30.89 | C |
| ATOM | 3954 | O | LYS | C | 101 | -16.41 | 55.034 | -19.529 | 1 | 28.71 | O |
| ATOM | 3955 | CB | LYS | C | 101 | -18.373 | 56.768 | -21.188 | 1 | 43.7 | C |
| ATOM | 3956 | CG | LYS | C | 101 | -19.776 | 56.557 | -20.62 | 1 | 55.1 | C |
| ATOM | 3957 | CD | LYS | C | 101 | -20.514 | 57.877 | -20.423 | 1 | 71.07 | C |
| ATOM | 3958 | CE | LYS | C | 101 | -21.918 | 57.662 | -19.866 | 1 | 83.53 | C |
| ATOM | 3959 | NZ | LYS | C | 101 | -22.935 | 57.438 | -20.932 | 1 | 96.55 | N1+ |
| ATOM | 3960 | H | LYS | C | 101 | -16.139 | 57.57 | -21.684 | 1 | 37.74 | H |
| ATOM | 3961 | HA | LYS | C | 101 | -17.662 | 57.921 | -19.645 | 1 | 45.75 | H |
| ATOM | 3962 | HB2 | LYS | C | 101 | -18.431 | 57.465 | -21.86 | 1 | 52.44 | H |
| ATOM | 3963 | HB3 | LYS | C | 101 | -18.098 | 55.936 | -21.605 | 1 | 52.44 | H |
| ATOM | 3964 | HG2 | LYS | C | 101 | -20.291 | 56.011 | -21.235 | 1 | 66.13 | H |
| ATOM | 3965 | HG3 | LYS | C | 101 | -19.708 | 56.117 | -19.758 | 1 | 66.13 | H |
| ATOM | 3966 | HD2 | LYS | C | 101 | -20.02 | 58.428 | -19.797 | 1 | 85.28 | H |

TABLE 5-continued

Atomic Coordinates for OMCP-NKG2D (4PDC).

| ATOM | 3967 | HD3 | LYS | C | 101 | -20.593 | 58.329 | -21.278 | 1 | 85.28 | H |
|------|------|-----|-----|---|-----|---------|--------|---------|---|-------|---|
| ATOM | 3968 | HE2 | LYS | C | 101 | -21.912 | 56.882 | -19.288 | 1 | 100.24 | H |
| ATOM | 3969 | HE3 | LYS | C | 101 | -22.18 | 58.447 | -19.36 | 1 | 100.24 | H |
| ATOM | 3970 | HZ1 | LYS | C | 101 | -23.738 | 57.318 | -20.567 | 1 | 115.86 | H |
| ATOM | 3971 | HZ2 | LYS | C | 101 | -22.967 | 58.143 | -21.474 | 1 | 115.86 | H |
| ATOM | 3972 | HZ3 | LYS | C | 101 | -22.723 | 56.717 | -21.409 | 1 | 115.86 | H |
| ATOM | 3973 | N | ASN | C | 102 | -17.578 | 56.16 | -17.962 | 1 | 29.4 | N |
| ATOM | 3974 | CA | ASN | C | 102 | -17.566 | 55.095 | -16.957 | 1 | 21.26 | C |
| ATOM | 3975 | C | ASN | C | 102 | -16.171 | 54.67 | -16.501 | 1 | 23.13 | C |
| ATOM | 3976 | O | ASN | C | 102 | -15.98 | 53.538 | -16.052 | 1 | 23.84 | O |
| ATOM | 3977 | CB | ASN | C | 102 | -18.317 | 53.871 | -17.484 | 1 | 26.84 | C |
| ATOM | 3978 | CG | ASN | C | 102 | -19.758 | 54.178 | -17.827 | 1 | 37.5 | C |
| ATOM | 3979 | OD1 | ASN | C | 102 | -20.39 | 55.027 | -17.198 | 1 | 35.99 | O |
| ATOM | 3980 | ND2 | ASN | C | 102 | -20.288 | 53.491 | -18.833 | 1 | 39.34 | N |
| ATOM | 3981 | H | ASN | C | 102 | -17.948 | 56.885 | -17.684 | 1 | 35.28 | H |
| ATOM | 3982 | HA | ASN | C | 102 | -18.042 | 55.411 | -16.173 | 1 | 25.51 | H |
| ATOM | 3983 | HB2 | ASN | C | 102 | -17.878 | 53.551 | -18.287 | 1 | 32.21 | H |
| ATOM | 3984 | HB3 | ASN | C | 102 | -18.311 | 53.179 | -16.804 | 1 | 32.21 | H |
| ATOM | 3985 | HD21 | ASN | C | 102 | -21.104 | 53.63 | -19.066 | 1 | 47.21 | H |
| ATOM | 3986 | HD22 | ASN | C | 102 | -19.814 | 52.907 | -19.251 | 1 | 47.21 | H |
| ATOM | 3987 | N | TRP | C | 103 | -15.202 | 55.573 | -16.611 | 1 | 20.5 | N |
| ATOM | 3988 | CA | TRP | C | 103 | -13.88 | 55.343 | -16.034 | 1 | 23.43 | C |
| ATOM | 3989 | C | TRP | C | 103 | -13.826 | 55.907 | -14.62 | 1 | 21.27 | C |
| ATOM | 3990 | O | TRP | C | 103 | -14.659 | 56.727 | -14.239 | 1 | 23.07 | O |
| ATOM | 3991 | CB | TRP | C | 103 | -12.785 | 55.984 | -16.889 | 1 | 21.36 | C |
| ATOM | 3992 | CG | TRP | C | 103 | -12.438 | 55.213 | -18.124 | 1 | 22.71 | C |
| ATOM | 3993 | CD1 | TRP | C | 103 | -13.27 | 54.42 | -18.857 | 1 | 24.15 | C |
| ATOM | 3994 | CD2 | TRP | C | 103 | -11.158 | 55.158 | -18.771 | 1 | 19.27 | C |
| ATOM | 3995 | NE1 | TRP | C | 103 | -12.591 | 53.88 | -19.923 | 1 | 20.72 | N |
| ATOM | 3996 | CE2 | TRP | C | 103 | -11.293 | 54.317 | -19.891 | 1 | 20.3 | C |
| ATOM | 3997 | CE3 | TRP | C | 103 | -9.914 | 55.737 | -18.508 | 1 | 20.4 | C |
| ATOM | 3998 | CZ2 | TRP | C | 103 | -10.23 | 54.042 | -20.751 | 1 | 24.78 | C |
| ATOM | 3999 | CZ3 | TRP | C | 103 | -8.862 | 55.465 | -19.36 | 1 | 20.79 | C |
| ATOM | 4000 | CH2 | TRP | C | 103 | -9.026 | 54.624 | -20.468 | 1 | 22.99 | C |
| ATOM | 4001 | H | TRP | C | 103 | -15.284 | 56.328 | -17.014 | 1 | 24.6 | H |
| ATOM | 4002 | HA | TRP | C | 103 | -13.712 | 54.389 | -15.989 | 1 | 28.12 | H |
| ATOM | 4003 | HB2 | TRP | C | 103 | -13.082 | 56.865 | -17.165 | 1 | 25.64 | H |
| ATOM | 4004 | HB3 | TRP | C | 103 | -11.979 | 56.063 | -16.355 | 1 | 25.64 | H |
| ATOM | 4005 | HD1 | TRP | C | 103 | -14.169 | 54.273 | -18.669 | 1 | 28.98 | H |
| ATOM | 4006 | HE1 | TRP | C | 103 | -12.926 | 53.352 | -20.514 | 1 | 24.87 | H |
| ATOM | 4007 | HE3 | TRP | C | 103 | -9.797 | 56.298 | -17.776 | 1 | 24.47 | H |
| ATOM | 4008 | HZ2 | TRP | C | 103 | -10.336 | 53.482 | -21.486 | 1 | 29.74 | H |
| ATOM | 4009 | HZ3 | TRP | C | 103 | -8.03 | 55.848 | -19.196 | 1 | 24.95 | H |
| ATOM | 4010 | HH2 | TRP | C | 103 | -8.299 | 54.458 | -21.025 | 1 | 27.58 | H |
| ATOM | 4011 | N | ILE | C | 104 | -12.852 | 55.455 | -13.838 | 1 | 21.47 | N |
| ATOM | 4012 | CA | ILE | C | 104 | -12.562 | 56.076 | -12.552 | 1 | 22.27 | C |
| ATOM | 4013 | C | ILE | C | 104 | -11.92 | 57.428 | -12.799 | 1 | 20.16 | C |
| ATOM | 4014 | O | ILE | C | 104 | -11.097 | 57.559 | -13.694 | 1 | 20.4 | O |
| ATOM | 4015 | CB | ILE | C | 104 | -11.618 | 55.218 | -11.691 | 1 | 20.98 | C |
| ATOM | 4016 | CG1 | ILE | C | 104 | -12.318 | 53.922 | -11.276 | 1 | 23.82 | C |
| ATOM | 4017 | CG2 | ILE | C | 104 | -11.151 | 56.005 | -10.452 | 1 | 22.89 | C |

TABLE 5-continued

Atomic Coordinates for OMCP-NKG2D (4PDC).

| ATOM | 4018 | CD1 | ILE | C | 104 | -11.469 | 53 | -10.418 | 1 | 32.17 | C |
| ATOM | 4019 | H | ILE | | 104 | -12.343 | 54.789 | -14.03 | 1 | 25.76 | H |
| ATOM | 4020 | HA | ILE | | 104 | -13.389 | 56.212 | -12.062 | 1 | 26.72 | H |
| ATOM | 4021 | HB | ILE | | 104 | -10.839 | 54.991 | -12.222 | 1 | 25.18 | H |
| ATOM | 4022 | HG12 | ILE | | 104 | -13.114 | 54.147 | -10.769 | 1 | 28.58 | H |
| ATOM | 4023 | HG13 | ILE | | 104 | -12.567 | 53.433 | -12.076 | 1 | 28.58 | H |
| ATOM | 4024 | HG21 | ILE | | 104 | -10.559 | 55.444 | -9.927 | 1 | 27.46 | H |
| ATOM | 4025 | HG22 | ILE | | 104 | -10.681 | 56.802 | -10.744 | 1 | 27.46 | H |
| ATOM | 4026 | HG23 | ILE | | 104 | -11.927 | 56.252 | -9.925 | 1 | 27.46 | H |
| ATOM | 4027 | HD11 | ILE | | 104 | -11.984 | 52.208 | -10.201 | 1 | 38.61 | H |
| ATOM | 4028 | HD12 | ILE | | 104 | -10.673 | 52.752 | -10.915 | 1 | 38.61 | H |
| ATOM | 4029 | HD13 | ILE | | 104 | -11.22 | 53.467 | -9.605 | 1 | 38.61 | H |
| ATOM | 4030 | N | CYS | C | 105 | -12.291 | 58.426 | -12.005 | 1 | 18.5 | N |
| ATOM | 4031 | CA | CYS | C | 105 | -11.642 | 59.73 | -12.068 | 1 | 21.47 | C |
| ATOM | 4032 | C | CYS | C | 105 | -11.168 | 60.124 | -10.673 | 1 | 24.11 | C |
| ATOM | 4033 | O | CYS | C | 105 | -11.949 | 60.137 | -9.72 | 1 | 22.75 | O |
| ATOM | 4034 | CB | CYS | C | 105 | -12.592 | 60.783 | -12.641 | 1 | 24.61 | C |
| ATOM | 4035 | SG | CYS | C | 105 | -11.757 | 62.29 | -13.195 | 1 | 30.83 | S |
| ATOM | 4036 | H | CYS | | 105 | -12.918 | 58.373 | -11.418 | 1 | 22.2 | H |
| ATOM | 4037 | HA | CYS | | 105 | -10.867 | 59.673 | -12.648 | 1 | 25.76 | H |
| ATOM | 4038 | HB2 | CYS | | 105 | -13.056 | 60.403 | -13.404 | 1 | 29.53 | H |
| ATOM | 4039 | HB3 | CYS | | 105 | -13.232 | 61.032 | -11.957 | 1 | 29.53 | H |
| ATOM | 4040 | N | TYR | C | 106 | -9.88 | 60.43 | -10.556 | 1 | 20.57 | N |
| ATOM | 4041 | CA | TYR | C | 106 | -9.279 | 60.704 | -9.259 | 1 | 19.53 | C |
| ATOM | 4042 | C | TYR | C | 106 | -8.063 | 61.607 | -9.395 | 1 | 24.23 | C |
| ATOM | 4043 | O | TYR | C | 106 | -7.074 | 61.243 | -10.036 | 1 | 18.6 | O |
| ATOM | 4044 | CB | TYR | C | 106 | -8.885 | 59.394 | -8.58 | 1 | 18.96 | C |
| ATOM | 4045 | CG | TYR | C | 106 | -8.336 | 59.537 | -7.183 | 1 | 17.51 | C |
| ATOM | 4046 | CD1 | TYR | C | 106 | -9.161 | 59.887 | -6.128 | 1 | 20.97 | C |
| ATOM | 4047 | CD2 | TYR | C | 106 | -6.995 | 59.293 | -6.912 | 1 | 20.26 | C |
| ATOM | 4048 | CE1 | TYR | C | 106 | -8.669 | 60.006 | -4.846 | 1 | 22.2 | C |
| ATOM | 4049 | CE2 | TYR | C | 106 | -6.494 | 59.405 | -5.629 | 1 | 20.01 | C |
| ATOM | 4050 | CZ | TYR | C | 106 | -7.339 | 59.764 | -4.599 | 1 | 22.79 | C |
| ATOM | 4051 | OH | TYR | C | 106 | -6.864 | 59.881 | -3.313 | 1 | 24.09 | O |
| ATOM | 4052 | H | TYR | | 106 | -9.332 | 60.486 | -11.217 | 1 | 24.68 | H |
| ATOM | 4053 | HA | TYR | | 106 | -9.928 | 61.153 | -8.696 | 1 | 23.44 | H |
| ATOM | 4054 | HB2 | TYR | | 106 | -9.67 | 58.826 | -8.529 | 1 | 22.75 | H |
| ATOM | 4055 | HB3 | TYR | | 106 | -8.205 | 58.96 | -9.119 | 1 | 22.75 | H |
| ATOM | 4056 | HD1 | TYR | | 106 | -10.062 | 60.051 | -6.288 | 1 | 25.17 | H |
| ATOM | 4057 | HD2 | TYR | | 106 | -6.425 | 59.049 | -7.606 | 1 | 24.31 | H |
| ATOM | 4058 | HE1 | TYR | | 106 | -9.237 | 60.246 | -4.149 | 1 | 26.64 | H |
| ATOM | 4059 | HE2 | TYR | | 106 | -5.594 | 59.243 | -5.461 | 1 | 24.02 | H |
| ATOM | 4060 | HH | TYR | | 106 | -6.042 | 59.709 | -3.293 | 1 | 28.9 | H |
| ATOM | 4061 | N | LYS | C | 107 | -8.157 | 62.784 | -8.783 | 1 | 23.77 | N |
| ATOM | 4062 | CA | LYS | C | 107 | -7.07 | 63.754 | -8.756 | 1 | 22.66 | C |
| ATOM | 4063 | C | LYS | C | 107 | -6.482 | 63.992 | -10.144 | 1 | 26.25 | C |
| ATOM | 4064 | O | LYS | C | 107 | -5.304 | 63.722 | -10.384 | 1 | 25.69 | O |
| ATOM | 4065 | CB | LYS | C | 107 | -5.982 | 63.288 | -7.786 | 1 | 23.7 | C |
| ATOM | 4066 | CG | LYS | C | 107 | -6.453 | 63.225 | -6.341 | 1 | 25.76 | C |
| ATOM | 4067 | CD | LYS | C | 107 | -5.337 | 62.83 | -5.392 | 1 | 24.07 | C |
| ATOM | 4068 | CE | LYS | C | 107 | -5.787 | 62.932 | -3.946 | 1 | 25.09 | C |

TABLE 5-continued

Atomic Coordinates for OMCP-NKG2D (4PDC).

| ATOM | 4069 | NZ | LYS | C | 107 | -4.764 | 62.412 | -3.002 | 1 | 28.21 | N1+ |
|---|---|---|---|---|---|---|---|---|---|---|---|
| ATOM | 4070 | H | LYS | C | 107 | -8.86 | 63.049 | -8.365 | 1 | 28.53 | H |
| ATOM | 4071 | HA | LYS | C | 107 | -7.415 | 64.6 | -8.431 | 1 | 27.19 | H |
| ATOM | 4072 | HB2 | LYS | C | 107 | -5.69 | 62.399 | -8.043 | 1 | 28.45 | H |
| ATOM | 4073 | HB3 | LYS | C | 107 | -5.236 | 63.906 | -7.83 | 1 | 28.45 | H |
| ATOM | 4074 | HG2 | LYS | C | 107 | -6.78 | 64.099 | -6.076 | 1 | 30.91 | H |
| ATOM | 4075 | HG3 | LYS | C | 107 | -7.161 | 62.567 | -6.266 | 1 | 30.91 | H |
| ATOM | 4076 | HD2 | LYS | C | 107 | -5.077 | 61.911 | -5.566 | 1 | 28.88 | H |
| ATOM | 4077 | HD3 | LYS | C | 107 | -4.581 | 63.424 | -5.519 | 1 | 28.88 | H |
| ATOM | 4078 | HE2 | LYS | C | 107 | -5.952 | 63.863 | -3.729 | 1 | 30.11 | H |
| ATOM | 4079 | HE3 | LYS | C | 107 | -6.599 | 62.414 | -3.828 | 1 | 30.11 | H |
| ATOM | 4080 | HZ1 | LYS | C | 107 | -4.009 | 62.875 | -3.086 | 1 | 33.85 | H |
| ATOM | 4081 | HZ2 | LYS | C | 107 | -5.058 | 62.486 | -2.165 | 1 | 33.85 | H |
| ATOM | 4082 | HZ3 | LYS | C | 107 | -4.598 | 61.555 | -3.175 | 1 | 33.85 | H |
| ATOM | 4083 | N | ASN | C | 108 | -7.324 | 64.477 | -11.052 | 1 | 24.3 | N |
| ATOM | 4084 | CA | ASN | C | 108 | -6.908 | 64.862 | -12.399 | 1 | 29.43 | C |
| ATOM | 4085 | C | ASN | C | 108 | -6.39 | 63.7 | -13.248 | 1 | 29.94 | C |
| ATOM | 4086 | O | ASN | C | 108 | -5.692 | 63.92 | -14.238 | 1 | 30.74 | O |
| ATOM | 4087 | CB | ASN | C | 108 | -5.834 | 65.95 | -12.322 | 1 | 37.42 | C |
| ATOM | 4088 | CG | ASN | C | 108 | -6.243 | 67.111 | -11.434 | 1 | 39.33 | C |
| ATOM | 4089 | OD1 | ASN | C | 108 | -7.357 | 67.623 | -11.536 | 1 | 36.77 | O |
| ATOM | 4090 | ND2 | ASN | C | 108 | -5.341 | 67.526 | -10.549 | 1 | 38.25 | N |
| ATOM | 4091 | H | ASN | C | 108 | -8.163 | 64.595 | -10.908 | 1 | 29.16 | H |
| ATOM | 4092 | HA | ASN | C | 108 | -7.674 | 65.239 | -12.859 | 1 | 35.31 | H |
| ATOM | 4093 | HB2 | ASN | C | 108 | -5.02 | 65.566 | -11.959 | 1 | 44.91 | H |
| ATOM | 4094 | HB3 | ASN | C | 108 | -5.67 | 66.296 | -13.213 | 1 | 44.91 | H |
| ATOM | 4095 | HD21 | ASN | C | 108 | -5.525 | 68.181 | -10.023 | 1 | 45.91 | H |
| ATOM | 4096 | HD22 | ASN | C | 108 | -4.574 | 67.14 | -10.503 | 1 | 45.91 | H |
| ATOM | 4097 | N | ASN | C | 109 | -6.729 | 62.472 | -12.863 | 1 | 22.35 | N |
| ATOM | 4098 | CA | ASN | C | 109 | -6.364 | 61.294 | -13.65 | 1 | 21.33 | C |
| ATOM | 4099 | C | ASN | C | 109 | -7.542 | 60.352 | -13.846 | 1 | 21.79 | C |
| ATOM | 4100 | O | ASN | C | 109 | -8.331 | 60.125 | -12.924 | 1 | 20.85 | O |
| ATOM | 4101 | CB | ASN | C | 109 | -5.211 | 60.538 | -12.986 | 1 | 24.32 | C |
| ATOM | 4102 | CG | ASN | C | 109 | -3.921 | 61.337 | -12.968 | 1 | 22.95 | C |
| ATOM | 4103 | OD1 | ASN | C | 109 | -3.364 | 61.656 | -14.015 | 1 | 30.85 | O |
| ATOM | 4104 | ND2 | ASN | C | 109 | -3.434 | 61.653 | -11.775 | 1 | 23.23 | N |
| ATOM | 4105 | H | ASN | C | 109 | -7.173 | 62.292 | -12.148 | 1 | 26.82 | H |
| ATOM | 4106 | HA | ASN | C | 109 | -6.065 | 61.583 | -14.526 | 1 | 25.6 | H |
| ATOM | 4107 | HB2 | ASN | C | 109 | -5.452 | 60.336 | -12.068 | 1 | 29.18 | H |
| ATOM | 4108 | HB3 | ASN | C | 109 | -5.049 | 59.716 | -13.475 | 1 | 29.18 | H |
| ATOM | 4109 | HD21 | ASN | C | 109 | -2.705 | 62.105 | -11.713 | 1 | 27.87 | H |
| ATOM | 4110 | HD22 | ASN | C | 109 | -3.848 | 61.405 | -11.062 | 1 | 27.87 | H |
| ATOM | 4111 | N | CYS | C | 110 | -7.646 | 59.804 | -15.053 | 1 | 16.78 | N |
| ATOM | 4112 | CA | CYS | C | 110 | -8.675 | 58.825 | -15.382 | 1 | 19.5 | C |
| ATOM | 4113 | C | CYS | C | 110 | -8.083 | 57.42 | -15.392 | 1 | 18.25 | C |
| ATOM | 4114 | O | CYS | C | 110 | -6.991 | 59.131 | -15.923 | 1 | 16.64 | O |
| ATOM | 4115 | CB | CYS | C | 110 | -9.296 | 60.882 | -16.745 | 1 | 22.08 | C |
| ATOM | 4116 | SG | CYS | C | 110 | -9.588 | 61.405 | -17.059 | 1 | 25.44 | S |
| ATOM | 4117 | H | CYS | C | 110 | -7.122 | 59.987 | -15.71 | 1 | 20.14 | H |
| ATOM | 4118 | HA | CYS | C | 110 | -9.376 | 58.857 | -14.712 | 1 | 23.4 | H |
| ATOM | 4119 | HB2 | CYS | C | 110 | -8.7 | 58.804 | -17.438 | 1 | 26.5 | H |

TABLE 5-continued

Atomic Coordinates for OMCP-NKG2D (4PDC).

| | | | | | | | | | |
|---|---|---|---|---|---|---|---|---|---|
| ATOM | 4120 | HB3 | CYS | C | 110 | -10.15 | 58.675 | -16.807 | 1 | 26.5 | H |
| ATOM | 4121 | N | TYR | C | 111 | -8.806 | 56.462 | -14.823 | 1 | 16.4 | N |
| ATOM | 4122 | CA | TYR | C | 111 | -8.35 | 55.074 | -14.793 | 1 | 16.58 | C |
| ATOM | 4123 | C | TYR | C | 111 | -9.442 | 54.103 | -15.219 | 1 | 18.92 | C |
| ATOM | 4124 | O | TYR | C | 111 | -10.626 | 54.362 | -15.018 | 1 | 17.47 | O |
| ATOM | 4125 | CB | TYR | C | 111 | -7.872 | 54.69 | -13.391 | 1 | 15.45 | C |
| ATOM | 4126 | CG | TYR | C | 111 | -6.797 | 55.583 | -12.823 | 1 | 14.27 | C |
| ATOM | 4127 | CD1 | TYR | C | 111 | -5.456 | 55.321 | -13.059 | 1 | 17.54 | C |
| ATOM | 4128 | CD2 | TYR | C | 111 | -7.124 | 56.68 | -12.039 | 1 | 17.77 | C |
| ATOM | 4129 | CE1 | TYR | C | 111 | -4.47 | 56.131 | -12.535 | 1 | 19.61 | C |
| ATOM | 4130 | CE2 | TYR | C | 111 | -6.148 | 57.495 | -11.509 | 1 | 15.51 | C |
| ATOM | 4131 | CZ | TYR | C | 111 | -4.822 | 57.216 | -11.76 | 1 | 17.01 | C |
| ATOM | 4132 | OH | TYR | C | 111 | -3.845 | 58.025 | -11.239 | 1 | 17.34 | O |
| ATOM | 4133 | H | TYR | C | 111 | -9.569 | 56.589 | -14.446 | 1 | 19.67 | H |
| ATOM | 4134 | HA | TYR | C | 111 | -7.603 | 54.973 | -15.404 | 1 | 19.9 | H |
| ATOM | 4135 | HB2 | TYR | C | 111 | -8.63 | 54.723 | -12.786 | 1 | 18.53 | H |
| ATOM | 4136 | HB3 | TYR | C | 111 | -7.518 | 53.788 | -13.421 | 1 | 18.53 | H |
| ATOM | 4137 | HD1 | TYR | C | 111 | -5.218 | 54.589 | -13.58 | 1 | 21.04 | H |
| ATOM | 4138 | HD2 | TYR | C | 111 | -8.019 | 56.868 | -11.868 | 1 | 21.32 | H |
| ATOM | 4139 | HE1 | TYR | C | 111 | -3.574 | 55.945 | -12.703 | 1 | 23.53 | H |
| ATOM | 4140 | HE2 | TYR | C | 111 | -6.382 | 58.229 | -10.987 | 1 | 18.62 | H |
| ATOM | 4141 | HH | TYR | C | 111 | -4.194 | 58.643 | -10.79 | 1 | 20.81 | H |
| ATOM | 4142 | N | GLN | C | 112 | -9.035 | 52.978 | -15.797 | 1 | 18.21 | N |
| ATOM | 4143 | CA | GLN | C | 112 | -9.954 | 51.869 | -16.025 | 1 | 19.09 | C |
| ATOM | 4144 | C | GLN | C | 112 | -9.246 | 50.536 | -15.845 | 1 | 17.43 | C |
| ATOM | 4145 | O | GLN | C | 112 | -8.135 | 50.33 | -16.337 | 1 | 15.67 | O |
| ATOM | 4146 | CB | GLN | C | 112 | -10.578 | 51.946 | -17.416 | 1 | 21.52 | C |
| ATOM | 4147 | CG | GLN | C | 112 | -11.604 | 50.841 | -17.706 | 1 | 22.47 | C |
| ATOM | 4148 | CD | GLN | C | 112 | -12.794 | 50.862 | -16.753 | 1 | 23.56 | C |
| ATOM | 4149 | OE1 | GLN | C | 112 | -12.685 | 50.483 | -15.585 | 1 | 22.27 | O |
| ATOM | 4150 | NE2 | GLN | C | 112 | -13.941 | 51.302 | -17.256 | 1 | 30.82 | N |
| ATOM | 4151 | H | GLN | C | 112 | -8.231 | 52.831 | -16.067 | 1 | 21.85 | H |
| ATOM | 4152 | HA | GLN | C | 112 | -10.671 | 51.917 | -15.373 | 1 | 22.91 | H |
| ATOM | 4153 | HB2 | GLN | C | 112 | -11.03 | 52.799 | -17.509 | 1 | 25.83 | H |
| ATOM | 4154 | HB3 | GLN | C | 112 | -9.873 | 51.875 | -18.079 | 1 | 25.83 | H |
| ATOM | 4155 | HG2 | GLN | C | 112 | -11.942 | 50.954 | -18.608 | 1 | 26.97 | H |
| ATOM | 4156 | HG3 | GLN | C | 112 | -11.17 | 49.978 | -17.621 | 1 | 26.97 | H |
| ATOM | 4157 | HE21 | GLN | C | 112 | -14.643 | 51.335 | -16.76 | 1 | 36.99 | H |
| ATOM | 4158 | HE22 | GLN | C | 112 | -13.982 | 51.555 | -18.077 | 1 | 36.99 | H |
| ATOM | 4159 | N | PHE | C | 113 | -9.911 | 49.643 | -15.122 | 1 | 16.74 | N |
| ATOM | 4160 | CA | PHE | C | 113 | -9.411 | 48.302 | -14.867 | 1 | 19.52 | C |
| ATOM | 4161 | C | PHE | C | 113 | -10.086 | 47.323 | -15.811 | 1 | 21.23 | C |
| ATOM | 4162 | O | PHE | C | 113 | -11.263 | 47.011 | -15.651 | 1 | 24.99 | O |
| ATOM | 4163 | CB | PHE | C | 113 | -9.663 | 47.898 | -13.415 | 1 | 17.97 | C |
| ATOM | 4164 | CG | PHE | C | 113 | -8.873 | 48.695 | -12.419 | 1 | 25.87 | C |
| ATOM | 4165 | CD1 | PHE | C | 113 | -9.189 | 50.019 | -12.163 | 1 | 23.02 | C |
| ATOM | 4166 | CD2 | PHE | C | 113 | -7.817 | 48.119 | -11.734 | 1 | 25.71 | C |
| ATOM | 4167 | CE1 | PHE | C | 113 | -8.466 | 50.751 | -11.248 | 1 | 25.64 | C |
| ATOM | 4168 | CE2 | PHE | C | 113 | -7.091 | 48.849 | -10.815 | 1 | 27.12 | C |
| ATOM | 4169 | CZ | PHE | C | 113 | -7.416 | 50.166 | -10.572 | 1 | 26.16 | C |
| ATOM | 4170 | H | PHE | C | 113 | -10.675 | 49.797 | -14.759 | 1 | 20.08 | H |

TABLE 5-continued

Atomic Coordinates for OMCP-NKG2D (4PDC).

| | | | | | | | | | | |
|---|---|---|---|---|---|---|---|---|---|---|
| ATOM | 4171 | HA | PHE | C | 113 | -8.455 | 48.277 | -15.031 | 1 | 23.43 | H |
| ATOM | 4172 | HB2 | PHE | C | 113 | -10.604 | 48.022 | -13.215 | 1 | 21.57 | H |
| ATOM | 4173 | HB3 | PHE | C | 113 | -9.423 | 46.964 | -13.305 | 1 | 21.57 | H |
| ATOM | 4174 | HD1 | PHE | C | 113 | -9.896 | 50.418 | -12.615 | 1 | 27.62 | H |
| ATOM | 4175 | HD2 | PHE | C | 113 | -7.594 | 47.231 | -11.895 | 1 | 30.85 | H |
| ATOM | 4176 | HE1 | PHE | C | 113 | -8.687 | 51.639 | -11.085 | 1 | 30.77 | H |
| ATOM | 4177 | HE2 | PHE | C | 113 | -6.382 | 48.452 | -10.361 | 1 | 32.55 | H |
| ATOM | 4178 | HZ | PHE | C | 113 | -6.927 | 50.66 | -9.953 | 1 | 31.39 | H |
| ATOM | 4179 | N | PHE | C | 114 | -9.339 | 46.858 | -16.805 | 1 | 16.23 | N |
| ATOM | 4180 | CA | PHE | C | 114 | -9.855 | 45.885 | -17.757 | 1 | 21.01 | C |
| ATOM | 4181 | C | PHE | C | 114 | -9.597 | 44.462 | -17.277 | 1 | 23.07 | C |
| ATOM | 4182 | O | PHE | C | 114 | -8.447 | 44.064 | -17.067 | 1 | 19.02 | O |
| ATOM | 4183 | CB | PHE | C | 114 | -9.229 | 46.114 | -19.132 | 1 | 22.6 | C |
| ATOM | 4184 | CG | PHE | C | 114 | -9.646 | 47.407 | -19.764 | 1 | 22.75 | C |
| ATOM | 4185 | CD1 | PHE | C | 114 | -10.804 | 47.479 | -20.517 | 1 | 26.86 | C |
| ATOM | 4186 | CD2 | PHE | C | 114 | -8.895 | 48.556 | -19.584 | 1 | 23.18 | C |
| ATOM | 4187 | CE1 | PHE | C | 114 | -11.197 | 48.673 | -21.094 | 1 | 30.06 | C |
| ATOM | 4188 | CE2 | PHE | C | 114 | -9.283 | 49.751 | -20.162 | 1 | 23.89 | C |
| ATOM | 4189 | CZ | PHE | C | 114 | -10.435 | 49.809 | -20.914 | 1 | 22.95 | C |
| ATOM | 4190 | H | PHE | C | 114 | -8.525 | 47.092 | -16.95 | 1 | 19.48 | H |
| ATOM | 4191 | HA | PHE | C | 114 | -10.815 | 46.003 | -17.841 | 1 | 25.21 | H |
| ATOM | 4192 | HB2 | PHE | C | 114 | -8.264 | 46.125 | -19.039 | 1 | 27.12 | H |
| ATOM | 4193 | HB3 | PHE | C | 114 | -9.496 | 45.393 | -19.723 | 1 | 27.12 | H |
| ATOM | 4194 | HD1 | PHE | C | 114 | -11.32 | 46.716 | -20.642 | 1 | 32.23 | H |
| ATOM | 4195 | HD2 | PHE | C | 114 | -8.116 | 48.521 | -19.078 | 1 | 27.81 | H |
| ATOM | 4196 | HE1 | PHE | C | 114 | -11.974 | 48.71 | -21.603 | 1 | 36.07 | H |
| ATOM | 4197 | HE2 | PHE | C | 114 | -8.769 | 50.517 | -20.039 | 1 | 28.67 | H |
| ATOM | 4198 | HZ | PHE | C | 114 | -10.698 | 50.612 | -21.303 | 1 | 27.54 | H |
| ATOM | 4199 | N | ASP | C | 115 | -10.676 | 43.702 | -17.113 | 1 | 17.95 | N |
| ATOM | 4200 | CA | ASP | C | 115 | -10.596 | 42.336 | -16.605 | 1 | 23.68 | C |
| ATOM | 4201 | C | ASP | C | 115 | -10.397 | 41.329 | -17.734 | 1 | 26.5 | C |
| ATOM | 4202 | O | ASP | C | 115 | -10.405 | 40.12 | -17.503 | 1 | 28.7 | O |
| ATOM | 4203 | CB | ASP | C | 115 | -11.856 | 41.988 | -15.81 | 1 | 32.14 | C |
| ATOM | 4204 | CG | ASP | C | 115 | -13.112 | 42.022 | -16.662 | 1 | 34.91 | C |
| ATOM | 4205 | OD1 | ASP | C | 115 | -13.093 | 42.679 | -17.724 | 1 | 35.65 | O |
| ATOM | 4206 | OD2 | ASP | C | 115 | -14.118 | 41.395 | -16.269 | 1 | 44.7 | O1- |
| ATOM | 4207 | H | ASP | C | 115 | -11.477 | 43.958 | -17.291 | 1 | 21.53 | H |
| ATOM | 4208 | HA | ASP | C | 115 | -9.836 | 42.267 | -16.006 | 1 | 28.42 | H |
| ATOM | 4209 | HB2 | ASP | C | 115 | -11.764 | 41.093 | -15.446 | 1 | 38.57 | H |
| ATOM | 4210 | HB3 | ASP | C | 115 | -11.964 | 42.629 | -15.09 | 1 | 38.57 | H |
| ATOM | 4211 | N | GLU | C | 116 | -10.227 | 41.832 | -18.952 | 1 | 22.96 | N |
| ATOM | 4212 | CA | GLU | C | 116 | -9.886 | 40.989 | -20.091 | 1 | 27.29 | C |
| ATOM | 4213 | C | GLU | C | 116 | -8.406 | 40.646 | -20.029 | 1 | 28.42 | C |
| ATOM | 4214 | O | GLU | C | 116 | -7.556 | 41.538 | -20.019 | 1 | 29.3 | O |
| ATOM | 4215 | CB | GLU | C | 116 | -10.212 | 41.689 | -21.415 | 1 | 32.71 | C |
| ATOM | 4216 | CG | GLU | C | 116 | -11.703 | 41.836 | -21.705 | 1 | 41.3 | C |
| ATOM | 4217 | CD | GLU | C | 116 | -12.404 | 42.802 | -20.764 | 1 | 43.24 | C |
| ATOM | 4218 | OE1 | GLU | C | 116 | -11.789 | 43.823 | -20.383 | 1 | 32.76 | O |
| ATOM | 4219 | OE2 | GLU | C | 116 | -13.572 | 42.536 | -20.403 | 1 | 49.42 | O1- |
| ATOM | 4220 | H | GLU | C | 116 | -10.304 | 42.667 | -19.146 | 1 | 27.55 | H |
| ATOM | 4221 | HA | GLU | C | 116 | -10.395 | 40.165 | -20.046 | 1 | 32.74 | H |

TABLE 5-continued

Atomic Coordinates for OMCP-NKG2D (4PDC).

| ATOM | 4222 | HB2 | GLU | C | 116 | -9.827 | 42.579 | -21.397 | 1 | 39.25 | H |
|------|------|-----|-----|---|-----|--------|--------|---------|---|-------|---|
| ATOM | 4223 | HB3 | GLU | C | 116 | -9.82 | 41.178 | -22.14 | 1 | 39.25 | H |
| ATOM | 4224 | HG2 | GLU | C | 116 | -11.816 | 42.166 | -22.61 | 1 | 49.56 | H |
| ATOM | 4225 | HG3 | GLU | C | 116 | -12.128 | 40.969 | -21.614 | 1 | 49.56 | H |
| ATOM | 4226 | N | SER | C | 117 | -8.096 | 39.357 | -19.979 | 1 | 18.99 | N |
| ATOM | 4227 | CA | SER | C | 117 | -6.709 | 38.922 | -19.893 | 1 | 24.06 | C |
| ATOM | 4228 | C | SER | C | 117 | -6.009 | 39.087 | -21.24 | 1 | 23.72 | C |
| ATOM | 4229 | O | SER | C | 117 | -6.42 | 38.498 | -22.238 | 1 | 23.97 | O |
| ATOM | 4230 | CB | SER | C | 117 | -6.636 | 37.47 | -19.425 | 1 | 24.23 | C |
| ATOM | 4231 | OG | SER | C | 117 | -5.313 | 37.131 | -19.059 | 1 | 33.7 | O |
| ATOM | 4232 | H | SER | C | 117 | -8.669 | 38.716 | -19.994 | 1 | 22.79 | H |
| ATOM | 4233 | HA | SER | C | 117 | -6.245 | 39.472 | -19.243 | 1 | 28.88 | H |
| ATOM | 4234 | HB2 | SER | C | 117 | -7.216 | 37.356 | -18.656 | 1 | 29.08 | H |
| ATOM | 4235 | HB3 | SER | C | 117 | -6.923 | 36.89 | -20.147 | 1 | 29.08 | H |
| ATOM | 4236 | HG | SER | C | 117 | -5.052 | 37.628 | -18.434 | 1 | 40.44 | H |
| ATOM | 4237 | N | LYS | C | 118 | -4.95 | 39.895 | -21.255 | 1 | 19.67 | N |
| ATOM | 4238 | CA | LYS | C | 118 | -4.202 | 40.183 | -22.476 | 1 | 18.97 | C |
| ATOM | 4239 | C | LYS | C | 118 | -2.705 | 40.264 | -22.19 | 1 | 19.32 | C |
| ATOM | 4240 | O | LYS | C | 118 | -2.304 | 40.608 | -21.081 | 1 | 17.06 | O |
| ATOM | 4241 | CB | LYS | C | 118 | -4.674 | 41.499 | -23.096 | 1 | 20.06 | C |
| ATOM | 4242 | CG | LYS | C | 118 | -6.039 | 41.439 | -23.756 | 1 | 24.89 | C |
| ATOM | 4243 | CD | LYS | C | 118 | -6.415 | 42.794 | -24.345 | 1 | 27.05 | C |
| ATOM | 4244 | CE | LYS | C | 118 | -7.689 | 42.712 | -25.171 | 1 | 30.29 | C |
| ATOM | 4245 | NZ | LYS | C | 118 | -8.838 | 42.217 | -24.367 | 1 | 41.79 | N1+ |
| ATOM | 4246 | H | LYS | C | 118 | -4.642 | 40.295 | -20.559 | 1 | 23.6 | H |
| ATOM | 4247 | HA | LYS | C | 118 | -4.351 | 39.472 | -23.119 | 1 | 22.76 | H |
| ATOM | 4248 | HB2 | LYS | C | 118 | -4.715 | 42.172 | -22.399 | 1 | 24.07 | H |
| ATOM | 4249 | HB3 | LYS | C | 118 | -4.034 | 41.769 | -23.773 | 1 | 24.07 | H |
| ATOM | 4250 | HG2 | LYS | C | 118 | -6.022 | 40.787 | -24.474 | 1 | 29.87 | H |
| ATOM | 4251 | HG3 | LYS | C | 118 | -6.706 | 41.196 | -23.095 | 1 | 29.87 | H |
| ATOM | 4252 | HD2 | LYS | C | 118 | -6.561 | 43.426 | -23.624 | 1 | 32.46 | H |
| ATOM | 4253 | HD3 | LYS | C | 118 | -5.699 | 43.102 | -24.921 | 1 | 32.46 | H |
| ATOM | 4254 | HE2 | LYS | C | 118 | -7.91 | 43.596 | -25.504 | 1 | 36.35 | H |
| ATOM | 4255 | HE3 | LYS | C | 118 | -7.55 | 42.1 | -25.91 | 1 | 36.35 | H |
| ATOM | 4256 | HZ1 | LYS | C | 118 | -8.661 | 41.403 | -24.053 | 1 | 50.14 | H |
| ATOM | 4257 | HZ2 | LYS | C | 118 | -8.988 | 42.765 | -23.682 | 1 | 50.14 | H |
| ATOM | 4258 | HZ3 | LYS | C | 118 | -9.569 | 42.179 | -24.873 | 1 | 50.14 | H |
| ATOM | 4259 | N | ASN | C | 119 | -1.876 | 39.965 | -23.186 | 1 | 16.38 | N |
| ATOM | 4260 | CA | ASN | C | 119 | -0.438 | 40.141 | -23.016 | 1 | 19.02 | C |
| ATOM | 4261 | C | ASN | C | 119 | -0.135 | 41.64 | -23.019 | 1 | 17.17 | C |
| ATOM | 4262 | O | ASN | C | 119 | -1.03 | 42.453 | -23.271 | 1 | 15.21 | O |
| ATOM | 4263 | CB | ASN | C | 119 | 0.354 | 39.374 | -24.095 | 1 | 16.08 | C |
| ATOM | 4264 | CG | ASN | C | 119 | 0.249 | 39.985 | -25.491 | 1 | 21.42 | C |
| ATOM | 4265 | OD1 | ASN | C | 119 | 0.176 | 41.202 | -25.669 | 1 | 20.88 | O |
| ATOM | 4266 | ND2 | ASN | C | 119 | 0.267 | 39.119 | -26.5 | 1 | 28.85 | N |
| ATOM | 4267 | H | ASN | C | 119 | -2.115 | 39.664 | -23.956 | 1 | 19.65 | H |
| ATOM | 4268 | HA | ASN | C | 119 | -0.179 | 39.788 | -22.151 | 1 | 22.82 | H |
| ATOM | 4269 | HB2 | ASN | C | 119 | 1.291 | 39.363 | -23.846 | 1 | 19.3 | H |
| ATOM | 4270 | HB3 | ASN | C | 119 | 0.016 | 38.466 | -24.144 | 1 | 19.3 | H |
| ATOM | 4271 | HD21 | ASN | C | 119 | 0.211 | 39.402 | -27.311 | 1 | 34.62 | H |
| ATOM | 4272 | HD22 | ASN | C | 119 | 0.334 | 38.276 | -26.343 | 1 | 34.62 | H |

TABLE 5-continued

Atomic Coordinates for OMCP-NKG2D (4PDC).

| | | | | | | | | | | |
|---|---|---|---|---|---|---|---|---|---|---|
| ATOM | 4273 | N | TRP | C | 120 | 1.108 | -22.734 | 42.013 | 1 | 17.45 | N |
| ATOM | 4274 | CA | TRP | C | 120 | 1.443 | -22.571 | 43.427 | 1 | 16.39 | C |
| ATOM | 4275 | C | TRP | C | 120 | 1.229 | -23.861 | 44.216 | 1 | 19.16 | C |
| ATOM | 4276 | O | TRP | C | 120 | 0.768 | -23.822 | 45.36 | 1 | 20.05 | O |
| ATOM | 4277 | CB | TRP | C | 120 | 2.888 | -22.098 | 43.592 | 1 | 15.72 | C |
| ATOM | 4278 | CG | TRP | C | 120 | 3.216 | -21.718 | 45.005 | 1 | 18.6 | C |
| ATOM | 4279 | CD1 | TRP | C | 120 | 3.152 | -20.47 | 45.554 | 1 | 18.56 | C |
| ATOM | 4280 | CD2 | TRP | C | 120 | 3.652 | -22.593 | 46.053 | 1 | 18.79 | C |
| ATOM | 4281 | NE1 | TRP | C | 120 | 3.518 | -20.514 | 46.876 | 1 | 17.94 | N |
| ATOM | 4282 | CE2 | TRP | C | 120 | 3.83 | -21.805 | 47.208 | 1 | 20.55 | C |
| ATOM | 4283 | CE3 | TRP | C | 120 | 3.903 | -23.966 | 46.128 | 1 | 23.33 | C |
| ATOM | 4284 | CZ2 | TRP | C | 120 | 4.251 | -22.342 | 48.42 | 1 | 21.4 | C |
| ATOM | 4285 | CZ3 | TRP | C | 120 | 4.321 | -24.497 | 47.334 | 1 | 19.62 | C |
| ATOM | 4286 | CH2 | TRP | C | 120 | 4.492 | -23.687 | 48.463 | 1 | 24.59 | C |
| ATOM | 4287 | H | TRP | C | 120 | 1.771 | -22.631 | 41.475 | 1 | 20.94 | H |
| ATOM | 4288 | HA | TRP | C | 120 | 0.864 | -21.892 | 43.807 | 1 | 19.67 | H |
| ATOM | 4289 | HB2 | TRP | C | 120 | 3.032 | -21.319 | 43.032 | 1 | 18.86 | H |
| ATOM | 4290 | HB3 | TRP | C | 120 | 3.487 | -22.813 | 43.327 | 1 | 18.86 | H |
| ATOM | 4291 | HD1 | TRP | C | 120 | 2.895 | -19.701 | 45.098 | 1 | 22.28 | H |
| ATOM | 4292 | HE1 | TRP | C | 120 | 3.55 | -19.839 | 47.408 | 1 | 21.53 | H |
| ATOM | 4293 | HE3 | TRP | C | 120 | 3.791 | -24.511 | 45.383 | 1 | 28 | H |
| ATOM | 4294 | HZ2 | TRP | C | 120 | 4.366 | -21.806 | 49.172 | 1 | 25.69 | H |
| ATOM | 4295 | HZ3 | TRP | C | 120 | 4.493 | -25.409 | 47.396 | 1 | 23.55 | H |
| ATOM | 4296 | HH2 | TRP | C | 120 | 4.776 | -24.072 | 49.26 | 1 | 29.5 | H |
| ATOM | 4297 | N | TYR | C | 121 | 1.555 | -24.998 | 43.605 | 1 | 17.25 | N |
| ATOM | 4298 | CA | TYR | C | 121 | 1.432 | -26.289 | 44.28 | 1 | 19.29 | C |
| ATOM | 4299 | C | TYR | C | 121 | -0.035 | -26.645 | 44.502 | 1 | 19.51 | C |
| ATOM | 4300 | O | TYR | C | 121 | -0.406 | -27.164 | 45.554 | 1 | 22.89 | O |
| ATOM | 4301 | CB | TYR | C | 121 | 2.124 | -27.392 | 43.472 | 1 | 22.07 | C |
| ATOM | 4302 | CG | TYR | C | 121 | 3.47 | -26.983 | 42.922 | 1 | 18.97 | C |
| ATOM | 4303 | CD1 | TYR | C | 121 | 4.582 | -26.897 | 43.748 | 1 | 21.63 | C |
| ATOM | 4304 | CD2 | TYR | C | 121 | 3.627 | -26.675 | 41.577 | 1 | 18.97 | C |
| ATOM | 4305 | CE1 | TYR | C | 121 | 5.812 | -26.517 | 43.25 | 1 | 22.33 | C |
| ATOM | 4306 | CE2 | TYR | C | 121 | 4.853 | -26.296 | 41.07 | 1 | 21.4 | C |
| ATOM | 4307 | CZ | TYR | C | 121 | 5.939 | -26.216 | 41.91 | 1 | 21.86 | C |
| ATOM | 4308 | OH | TYR | C | 121 | 7.161 | -25.84 | 41.408 | 1 | 22.74 | O |
| ATOM | 4309 | H | TYR | C | 121 | 1.85 | -25.049 | 42.799 | 1 | 20.71 | H |
| ATOM | 4310 | HA | TYR | C | 121 | 1.863 | -26.236 | 45.148 | 1 | 23.15 | H |
| ATOM | 4311 | HB2 | TYR | C | 121 | 1.558 | -27.633 | 42.722 | 1 | 26.49 | H |
| ATOM | 4312 | HB3 | TYR | C | 121 | 2.259 | -28.163 | 44.044 | 1 | 26.49 | H |
| ATOM | 4313 | HD1 | TYR | C | 121 | 4.496 | -27.097 | 44.652 | 1 | 25.95 | H |
| ATOM | 4314 | HD2 | TYR | C | 121 | 2.893 | -26.726 | 41.008 | 1 | 22.76 | H |
| ATOM | 4315 | HE1 | TYR | C | 121 | 6.55 | -26.464 | 43.815 | 1 | 26.8 | H |
| ATOM | 4316 | HE2 | TYR | C | 121 | 4.944 | -26.092 | 40.167 | 1 | 25.68 | H |
| ATOM | 4317 | HH | TYR | C | 121 | 7.734 | -25.835 | 42.021 | 1 | 27.29 | H |
| ATOM | 4318 | N | GLU | C | 122 | -0.864 | -26.363 | 43.503 | 1 | 19.03 | N |
| ATOM | 4319 | CA | GLU | C | 122 | -2.296 | -26.607 | 43.606 | 1 | 20.24 | C |
| ATOM | 4320 | C | GLU | C | 122 | -2.911 | -25.688 | 44.657 | 1 | 22.15 | C |
| ATOM | 4321 | O | GLU | C | 122 | -3.781 | -26.098 | 45.424 | 1 | 21.67 | O |
| ATOM | 4322 | CB | GLU | C | 122 | -2.969 | -26.399 | 42.249 | 1 | 23.32 | C |
| ATOM | 4323 | CG | GLU | C | 122 | -2.577 | -27.442 | 41.198 | 1 | 28.93 | C |

TABLE 5-continued

Atomic Coordinates for OMCP-NKG2D (4PDC).

| | | | | | | | | | | |
|---|---|---|---|---|---|---|---|---|---|---|
| ATOM | 4324 | CD | GLU | C | 122 | -3.051 | 39.794 | -27.089 | 1 | 31.55 | C |
| ATOM | 4325 | OE1 | GLU | C | 122 | -3.184 | 39.484 | -25.884 | 1 | 26.49 | O |
| ATOM | 4326 | OE2 | GLU | C | 122 | -3.289 | 38.996 | -28.023 | 1 | 36.3 | O1- |
| ATOM | 4327 | H | GLU | C | 122 | -0.619 | 42.75 | -26.028 | 1 | 22.84 | H |
| ATOM | 4328 | HA | GLU | C | 122 | -2.445 | 43.881 | -27.525 | 1 | 24.29 | H |
| ATOM | 4329 | HB2 | GLU | C | 122 | -2.72 | 41.907 | -27.98 | 1 | 27.98 | H |
| ATOM | 4330 | HB3 | GLU | C | 122 | -3.931 | 42.366 | -26.444 | 1 | 27.98 | H |
| ATOM | 4331 | HG2 | GLU | C | 122 | -2.97 | 41.44 | -28.295 | 1 | 34.71 | H |
| ATOM | 4332 | HG3 | GLU | C | 122 | -1.61 | 41.176 | -27.517 | 1 | 34.71 | H |
| ATOM | 4333 | N | SER | C | 123 | -2.442 | 44.696 | -24.446 | 1 | 20.16 | N |
| ATOM | 4334 | CA | SER | C | 123 | -2.934 | 45.664 | -23.473 | 1 | 21.59 | C |
| ATOM | 4335 | C | SER | C | 123 | -2.539 | 47.085 | -23.865 | 1 | 20.7 | C |
| ATOM | 4336 | O | SER | C | 123 | -3.328 | 48.019 | -23.717 | 1 | 19.9 | O |
| ATOM | 4337 | CB | SER | C | 123 | -2.405 | 45.335 | -22.08 | 1 | 19.87 | C |
| ATOM | 4338 | OG | SER | C | 123 | -2.871 | 44.07 | -21.655 | 1 | 17.57 | O |
| ATOM | 4339 | H | SER | C | 123 | -1.836 | 44.169 | -24.14 | 1 | 24.19 | H |
| ATOM | 4340 | HA | SER | C | 123 | -3.903 | 45.619 | -23.445 | 1 | 25.91 | H |
| ATOM | 4341 | HB2 | SER | C | 123 | -1.436 | 45.323 | -22.105 | 1 | 23.85 | H |
| ATOM | 4342 | HB3 | SER | C | 123 | -2.713 | 46.011 | -21.457 | 1 | 23.85 | H |
| ATOM | 4343 | HG | SER | C | 123 | -2.612 | 43.475 | -22.188 | 1 | 21.09 | H |
| ATOM | 4344 | N | GLN | C | 124 | -1.318 | 47.244 | -24.366 | 1 | 24.47 | N |
| ATOM | 4345 | CA | GLN | C | 124 | -0.843 | 48.55 | -24.805 | 1 | 22.72 | C |
| ATOM | 4346 | C | GLN | C | 124 | -1.706 | 49.08 | -25.946 | 1 | 24.57 | C |
| ATOM | 4347 | O | GLN | C | 124 | -2.072 | 50.256 | -25.962 | 1 | 20.57 | O |
| ATOM | 4348 | CB | GLN | C | 124 | 0.675 | 48.478 | -25.256 | 1 | 26.56 | C |
| ATOM | 4349 | CG | GLN | C | 124 | 1.218 | 49.843 | -25.591 | 1 | 36.95 | C |
| ATOM | 4350 | CD | GLN | C | 124 | 2.42 | 49.764 | -26.513 | 1 | 46.63 | C |
| ATOM | 4351 | OE1 | GLN | C | 124 | 2.512 | 48.882 | -27.367 | 1 | 51.66 | O |
| ATOM | 4352 | NE2 | GLN | C | 124 | 3.351 | 50.695 | -26.344 | 1 | 54.16 | N |
| ATOM | 4353 | H | GLN | C | 124 | -0.745 | 46.61 | -24.462 | 1 | 29.36 | H |
| ATOM | 4354 | HA | GLN | C | 124 | -0.901 | 49.176 | -24.066 | 1 | 27.27 | H |
| ATOM | 4355 | HB2 | GLN | C | 124 | 1.148 | 48.087 | -24.543 | 1 | 31.87 | H |
| ATOM | 4356 | HB3 | GLN | C | 124 | 0.675 | 47.925 | -26.05 | 1 | 31.87 | H |
| ATOM | 4357 | HG2 | GLN | C | 124 | 0.542 | 50.384 | -26.029 | 1 | 44.35 | H |
| ATOM | 4358 | HG3 | GLN | C | 124 | 1.501 | 50.272 | -24.769 | 1 | 44.35 | H |
| ATOM | 4359 | HE21 | GLN | C | 124 | 4.053 | 50.696 | -26.84 | 1 | 64.99 | H |
| ATOM | 4360 | HE22 | GLN | C | 124 | 3.253 | 51.297 | -25.737 | 1 | 64.99 | H |
| ATOM | 4361 | N | ALA | C | 125 | -2.013 | 48.209 | -26.905 | 1 | 22.47 | N |
| ATOM | 4362 | CA | ALA | C | 125 | -2.833 | 48.589 | -28.053 | 1 | 26.65 | C |
| ATOM | 4363 | C | ALA | C | 125 | -4.243 | 48.953 | -27.612 | 1 | 27.08 | C |
| ATOM | 4364 | O | ALA | C | 125 | -4.863 | 49.867 | -28.162 | 1 | 28.57 | O |
| ATOM | 4365 | CB | ALA | C | 125 | -2.877 | 47.464 | -29.074 | 1 | 20.86 | C |
| ATOM | 4366 | H | ALA | C | 125 | -1.758 | 47.388 | -26.914 | 1 | 26.96 | H |
| ATOM | 4367 | HA | ALA | C | 125 | -2.44 | 49.368 | -28.479 | 1 | 31.98 | H |
| ATOM | 4368 | HB1 | ALA | C | 125 | -3.426 | 47.741 | -29.825 | 1 | 25.03 | H |
| ATOM | 4369 | HB2 | ALA | C | 125 | -1.974 | 47.276 | -29.375 | 1 | 25.03 | H |
| ATOM | 4370 | HB3 | ALA | C | 125 | -3.258 | 46.676 | -28.658 | 1 | 25.03 | H |
| ATOM | 4371 | N | SER | C | 126 | -4.747 | 48.225 | -26.622 | 1 | 19.59 | N |
| ATOM | 4372 | CA | SER | C | 126 | -6.082 | 48.473 | -26.088 | 1 | 26.3 | C |
| ATOM | 4373 | C | SER | C | 126 | -6.193 | 49.891 | -25.531 | 1 | 26.98 | C |
| ATOM | 4374 | O | SER | C | 126 | -7.138 | 50.616 | -25.844 | 1 | 26.2 | O |

TABLE 5-continued

Atomic Coordinates for OMCP-NKG2D (4PDC).

| ATOM | 4375 | CB | SER | C | 126 | -6.419 | 47.449 | -25.003 | 1 | 24.52 | C |
| --- | --- | --- | --- | --- | --- | --- | --- | --- | --- | --- | --- |
| ATOM | 4376 | OG | SER | C | 126 | -7.657 | 47.745 | -24.384 | 1 | 25.71 | O |
| ATOM | 4377 | H | SER | C | 126 | -4.333 | 47.575 | -26.239 | 1 | 23.51 | H |
| ATOM | 4378 | HA | SER | C | 126 | -6.731 | 48.379 | -26.802 | 1 | 31.56 | H |
| ATOM | 4379 | HB2 | SER | C | 126 | -6.472 | 46.569 | -25.407 | 1 | 29.43 | H |
| ATOM | 4380 | HB3 | SER | C | 126 | -5.72 | 47.462 | -24.33 | 1 | 29.43 | H |
| ATOM | 4381 | HG | SER | C | 126 | -7.826 | 47.174 | -23.792 | 1 | 30.85 | H |
| ATOM | 4382 | N | CYS | C | 127 | -5.218 | 50.285 | -24.717 | 1 | 24.31 | N |
| ATOM | 4383 | CA | CYS | C | 127 | -5.209 | 51.616 | -24.121 | 1 | 23.85 | C |
| ATOM | 4384 | C | CYS | C | 127 | -5.053 | 52.705 | -25.182 | 1 | 28.4 | C |
| ATOM | 4385 | O | CYS | C | 127 | -5.731 | 53.734 | -25.127 | 1 | 25.1 | O |
| ATOM | 4386 | CB | CYS | C | 127 | -4.088 | 51.731 | -23.086 | 1 | 21.86 | C |
| ATOM | 4387 | SG | CYS | C | 127 | -4.254 | 50.602 | -21.682 | 1 | 18.33 | S |
| ATOM | 4388 | H | CYS | C | 127 | -4.546 | 49.796 | -24.493 | 1 | 29.17 | H |
| ATOM | 4389 | HA | CYS | C | 127 | -6.053 | 51.762 | -23.665 | 1 | 28.62 | H |
| ATOM | 4390 | HB2 | CYS | C | 127 | -3.243 | 51.539 | -23.521 | 1 | 26.23 | H |
| ATOM | 4391 | HB3 | CYS | C | 127 | -4.079 | 52.636 | -22.737 | 1 | 26.23 | H |
| ATOM | 4392 | N | MET | C | 128 | -4.159 | 52.476 | -26.142 | 1 | 24.31 | N |
| ATOM | 4393 | CA | MET | C | 128 | -3.917 | 53.445 | -27.21 | 1 | 28.72 | C |
| ATOM | 4394 | C | MET | C | 128 | -5.173 | 53.665 | -28.049 | 1 | 28.9 | C |
| ATOM | 4395 | O | MET | C | 128 | -5.436 | 54.776 | -28.504 | 1 | 34.94 | O |
| ATOM | 4396 | CB | MET | C | 128 | -2.77 | 52.985 | -28.114 | 1 | 29.76 | C |
| ATOM | 4397 | CG | MET | C | 128 | -1.377 | 53.258 | -27.565 | 1 | 41.22 | C |
| ATOM | 4398 | SD | MET | C | 128 | -0.084 | 53.092 | -28.823 | 1 | 57.79 | S |
| ATOM | 4399 | CE | MET | C | 128 | -0.259 | 51.366 | -29.269 | 1 | 79.41 | C |
| ATOM | 4400 | H | MET | C | 128 | -3.679 | 51.765 | -26.199 | 1 | 29.18 | H |
| ATOM | 4401 | HA | MET | C | 128 | -3.658 | 54.289 | -26.81 | 1 | 34.46 | H |
| ATOM | 4402 | HB2 | MET | C | 128 | -2.848 | 52.028 | -28.251 | 1 | 35.71 | H |
| ATOM | 4403 | HB3 | MET | C | 128 | -2.844 | 53.443 | -28.966 | 1 | 35.71 | H |
| ATOM | 4404 | HG2 | MET | C | 128 | -1.345 | 54.165 | -27.22 | 1 | 49.47 | H |
| ATOM | 4405 | HG3 | MET | C | 128 | -1.187 | 52.626 | -26.854 | 1 | 49.47 | H |
| ATOM | 4406 | HE1 | MET | C | 128 | 0.395 | 51.149 | -29.952 | 1 | 95.3 | H |
| ATOM | 4407 | HE2 | MET | C | 128 | -0.109 | 50.82 | -28.481 | 1 | 95.3 | H |
| ATOM | 4408 | HE3 | MET | C | 128 | -1.155 | 51.218 | -29.609 | 1 | 95.3 | H |
| ATOM | 4409 | N | SER | C | 129 | -5.945 | 52.601 | -28.246 | 1 | 29.07 | N |
| ATOM | 4410 | CA | SER | C | 129 | -7.157 | 52.672 | -29.055 | 1 | 32 | C |
| ATOM | 4411 | C | SER | C | 129 | -8.256 | 53.469 | -28.358 | 1 | 36.56 | C |
| ATOM | 4412 | O | SER | C | 129 | -9.307 | 53.735 | -28.945 | 1 | 32.22 | O |
| ATOM | 4413 | CB | SER | C | 129 | -7.669 | 51.267 | -29.377 | 1 | 33.16 | C |
| ATOM | 4414 | OG | SER | C | 129 | -8.267 | 50.67 | -28.237 | 1 | 33.58 | O |
| ATOM | 4415 | H | SER | C | 129 | -5.788 | 51.821 | -27.92 | 1 | 34.88 | H |
| ATOM | 4416 | HA | SER | C | 129 | -6.952 | 53.115 | -29.893 | 1 | 38.4 | H |
| ATOM | 4417 | HB2 | SER | C | 129 | -8.329 | 51.325 | -30.085 | 1 | 39.79 | H |
| ATOM | 4418 | HB3 | SER | C | 129 | -6.922 | 50.718 | -29.664 | 1 | 39.79 | H |
| ATOM | 4419 | HG | SER | C | 129 | -7.706 | 50.613 | -27.615 | 1 | 40.3 | H |
| ATOM | 4420 | N | GLN | C | 130 | -8.01 | 53.834 | -27.102 | 1 | 33.51 | N |
| ATOM | 4421 | CA | GLN | C | 130 | -8.946 | 54.642 | -26.331 | 1 | 30.27 | C |
| ATOM | 4422 | C | GLN | C | 130 | -8.314 | 55.976 | -25.955 | 1 | 26.64 | C |
| ATOM | 4423 | O | GLN | C | 130 | -8.73 | 56.622 | -24.995 | 1 | 31.87 | O |
| ATOM | 4424 | CB | GLN | C | 130 | -9.393 | 53.881 | -25.082 | 1 | 30.65 | C |
| ATOM | 4425 | CG | GLN | C | 130 | -10.037 | 52.545 | -25.414 | 1 | 34.01 | C |

TABLE 5-continued

Atomic Coordinates for OMCP-NKG2D (4PDC).

| ATOM | 4426 | CD | GLN | C | 130 | -10.477 | 51.776 | -24.191 | 1 | 33.95 | C |
|---|---|---|---|---|---|---|---|---|---|---|---|
| ATOM | 4427 | OE1 | GLN | C | 130 | -11.212 | 52.29 | -23.347 | 1 | 40.96 | O |
| ATOM | 4428 | NE2 | GLN | C | 130 | -10.033 | 50.529 | -24.089 | 1 | 34.2 | N |
| ATOM | 4429 | H | GLN | C | 130 | -7.297 | 53.622 | -26.67 | 1 | 40.22 | H |
| ATOM | 4430 | HA | GLN | C | 130 | -9.731 | 54.822 | -26.872 | 1 | 36.32 | H |
| ATOM | 4431 | HB2 | GLN | C | 130 | -8.62 | 53.711 | -24.521 | 1 | 36.78 | H |
| ATOM | 4432 | HB3 | GLN | C | 130 | -10.043 | 54.416 | -24.601 | 1 | 36.78 | H |
| ATOM | 4433 | HG2 | GLN | C | 130 | -10.819 | 52.701 | -25.966 | 1 | 40.81 | H |
| ATOM | 4434 | HG3 | GLN | C | 130 | -9.396 | 51.998 | -25.896 | 1 | 40.81 | H |
| ATOM | 4435 | HE21 | GLN | C | 130 | -10.254 | 50.047 | -23.411 | 1 | 41.04 | H |
| ATOM | 4436 | HE22 | GLN | C | 130 | -9.523 | 50.203 | -24.7 | 1 | 41.04 | H |
| ATOM | 4437 | N | ASN | C | 131 | -7.312 | 56.382 | -26.73 | 1 | 25.72 | N |
| ATOM | 4438 | CA | ASN | C | 131 | -6.593 | 57.631 | -26.495 | 1 | 31.52 | C |
| ATOM | 4439 | C | ASN | C | 131 | -6.008 | 57.676 | -25.091 | 1 | 30.51 | C |
| ATOM | 4440 | O | ASN | C | 131 | -5.996 | 58.719 | -24.433 | 1 | 30.75 | O |
| ATOM | 4441 | CB | ASN | C | 131 | -7.512 | 58.833 | -26.721 | 1 | 40 | C |
| ATOM | 4442 | CG | ASN | C | 131 | -6.739 | 60.121 | -26.931 | 1 | 45.49 | C |
| ATOM | 4443 | OD1 | ASN | C | 131 | -6.12 | 60.32 | -27.975 | 1 | 53.22 | O |
| ATOM | 4444 | ND2 | ASN | C | 131 | -6.769 | 61.001 | -25.937 | 1 | 44.21 | N |
| ATOM | 4445 | H | ASN | C | 131 | -7.025 | 55.944 | -27.412 | 1 | 30.86 | H |
| ATOM | 4446 | HA | ASN | C | 131 | -5.859 | 57.695 | -27.126 | 1 | 37.83 | H |
| ATOM | 4447 | HB2 | ASN | C | 131 | -8.053 | 58.675 | -27.511 | 1 | 48 | H |
| ATOM | 4448 | HB3 | ASN | C | 131 | -8.082 | 58.947 | -25.945 | 1 | 48 | H |
| ATOM | 4449 | HD21 | ASN | C | 131 | -6.346 | 61.746 | -26.009 | 1 | 53.05 | H |
| ATOM | 4450 | HD22 | ASN | C | 131 | -7.211 | 60.826 | -25.22 | 1 | 53.05 | H |
| ATOM | 4451 | N | ALA | C | 132 | -5.522 | 56.526 | -24.641 | 1 | 27.31 | N |
| ATOM | 4452 | CA | ALA | C | 132 | -4.952 | 56.397 | -23.311 | 1 | 24.35 | C |
| ATOM | 4453 | C | ALA | C | 132 | -3.654 | 55.604 | -23.376 | 1 | 22.93 | C |
| ATOM | 4454 | O | ALA | C | 132 | -3.175 | 55.264 | -24.456 | 1 | 22.28 | O |
| ATOM | 4455 | CB | ALA | C | 132 | -5.946 | 55.724 | -22.377 | 1 | 24.1 | C |
| ATOM | 4456 | H | ALA | C | 132 | -5.512 | 55.796 | -25.096 | 1 | 32.77 | H |
| ATOM | 4457 | HA | ALA | C | 132 | -4.753 | 57.279 | -22.96 | 1 | 29.22 | H |
| ATOM | 4458 | HB1 | ALA | C | 132 | -5.548 | 55.647 | -21.496 | 1 | 28.92 | H |
| ATOM | 4459 | HB2 | ALA | C | 132 | -6.75 | 56.264 | -22.331 | 1 | 28.92 | H |
| ATOM | 4460 | HB3 | ALA | C | 132 | -6.157 | 54.843 | -22.724 | 1 | 28.92 | H |
| ATOM | 4461 | N | SER | C | 133 | -3.086 | 55.317 | -22.211 | 1 | 23.85 | N |
| ATOM | 4462 | CA | SER | C | 133 | -1.908 | 54.47 | -22.123 | 1 | 19.49 | C |
| ATOM | 4463 | C | SER | C | 133 | -2.035 | 53.561 | -20.913 | 1 | 19.76 | C |
| ATOM | 4464 | O | SER | C | 133 | -2.954 | 53.714 | -20.106 | 1 | 21.65 | O |
| ATOM | 4465 | CB | SER | C | 133 | -0.637 | 55.315 | -22.035 | 1 | 28.62 | C |
| ATOM | 4466 | OG | SER | C | 133 | -0.593 | 56.041 | -20.822 | 1 | 30.86 | O |
| ATOM | 4467 | H | SER | C | 133 | -3.368 | 55.604 | -21.451 | 1 | 28.62 | H |
| ATOM | 4468 | HA | SER | C | 133 | -1.851 | 53.916 | -22.917 | 1 | 23.39 | H |
| ATOM | 4469 | HB2 | SER | C | 133 | 0.135 | 54.73 | -22.081 | 1 | 34.34 | H |
| ATOM | 4470 | HB3 | SER | C | 133 | -0.622 | 55.94 | -22.777 | 1 | 34.34 | H |
| ATOM | 4471 | HG | SER | C | 133 | -1.256 | 56.554 | -20.769 | 1 | 37.04 | H |
| ATOM | 4472 | N | LEU | C | 134 | -1.131 | 52.597 | -20.799 | 1 | 15.3 | N |
| ATOM | 4473 | CA | LEU | C | 134 | -1.085 | 51.753 | -19.618 | 1 | 16.31 | C |
| ATOM | 4474 | C | LEU | C | 134 | -0.722 | 52.605 | -18.413 | 1 | 18.61 | C |
| ATOM | 4475 | O | LEU | C | 134 | -0.102 | 53.66 | -18.558 | 1 | 17.38 | O |
| ATOM | 4476 | CB | LEU | C | 134 | -0.082 | 50.615 | -19.8 | 1 | 18.05 | C |

TABLE 5-continued

Atomic Coordinates for OMCP-NKG2D (4PDC).

| ATOM | 4477 | CG | LEU | C | 134 | -0.545 | -20.739 | 49.502 | 1 | 18.46 | C |
|---|---|---|---|---|---|---|---|---|---|---|---|
| ATOM | 4478 | CD1 | LEU | C | 134 | 0.622 | -21.151 | 48.613 | 1 | 18.54 | C |
| ATOM | 4479 | CD2 | LEU | C | 134 | -1.633 | -20.07 | 48.677 | 1 | 13.57 | C |
| ATOM | 4480 | H | LEU | C | 134 | -0.535 | -21.391 | 52.413 | 1 | 18.36 | H |
| ATOM | 4481 | HA | LEU | C | 134 | -1.961 | -19.465 | 51.366 | 1 | 19.57 | H |
| ATOM | 4482 | HB2 | LEU | C | 134 | 0.74 | -20.162 | 50.982 | 1 | 21.66 | H |
| ATOM | 4483 | HB3 | LEU | C | 134 | 0.094 | -18.934 | 50.215 | 1 | 21.66 | H |
| ATOM | 4484 | HG | LEU | C | 134 | -0.919 | -21.541 | 49.899 | 1 | 22.15 | H |
| ATOM | 4485 | HD11 | LEU | C | 134 | 0.296 | -21.745 | 47.919 | 1 | 22.25 | H |
| ATOM | 4486 | HD12 | LEU | C | 134 | 1.285 | -21.608 | 49.154 | 1 | 22.25 | H |
| ATOM | 4487 | HD13 | LEU | C | 134 | 1.011 | -20.357 | 48.214 | 1 | 22.25 | H |
| ATOM | 4488 | HD21 | LEU | C | 134 | -1.916 | -20.678 | 47.976 | 1 | 16.29 | H |
| ATOM | 4489 | HD22 | LEU | C | 134 | -1.278 | -19.256 | 48.287 | 1 | 16.29 | H |
| ATOM | 4490 | HD23 | LEU | C | 134 | -2.383 | -19.859 | 49.256 | 1 | 16.29 | H |
| ATOM | 4491 | N | LEU | C | 135 | -1.122 | -17.232 | 52.145 | 1 | 17.61 | N |
| ATOM | 4492 | CA | LEU | C | 135 | -0.861 | -15.99 | 52.863 | 1 | 16.82 | C |
| ATOM | 4493 | C | LEU | C | 135 | 0.574 | -15.907 | 53.365 | 1 | 17.04 | C |
| ATOM | 4494 | O | LEU | C | 135 | 1.521 | -16.145 | 52.614 | 1 | 17.43 | O |
| ATOM | 4495 | CB | LEU | C | 135 | -1.16 | -14.792 | 51.962 | 1 | 13.74 | C |
| ATOM | 4496 | CG | LEU | C | 135 | -0.816 | -13.409 | 52.517 | 1 | 13.56 | C |
| ATOM | 4497 | CD1 | LEU | C | 135 | -1.668 | -13.089 | 53.736 | 1 | 14.51 | C |
| ATOM | 4498 | CD2 | LEU | C | 135 | -0.994 | -12.348 | 51.438 | 1 | 14.41 | C |
| ATOM | 4499 | H | LEU | C | 135 | -1.553 | -17.123 | 51.409 | 1 | 21.14 | H |
| ATOM | 4500 | HA | LEU | C | 135 | -1.45 | -15.941 | 53.632 | 1 | 20.18 | H |
| ATOM | 4501 | HB2 | LEU | C | 135 | -2.109 | -14.793 | 51.762 | 1 | 16.49 | H |
| ATOM | 4502 | HB3 | LEU | C | 135 | -0.66 | -14.901 | 51.138 | 1 | 16.49 | H |
| ATOM | 4503 | HG | LEU | C | 135 | 0.114 | -13.402 | 52.793 | 1 | 16.27 | H |
| ATOM | 4504 | HD11 | LEU | C | 135 | -1.429 | -12.209 | 54.066 | 1 | 17.41 | H |
| ATOM | 4505 | HD12 | LEU | C | 135 | -1.502 | -13.756 | 54.421 | 1 | 17.41 | H |
| ATOM | 4506 | HD13 | LEU | C | 135 | -2.604 | -13.104 | 53.48 | 1 | 17.41 | H |
| ATOM | 4507 | HD21 | LEU | C | 135 | -0.772 | -11.48 | 51.81 | 1 | 17.29 | H |
| ATOM | 4508 | HD22 | LEU | C | 135 | -1.917 | -12.354 | 51.139 | 1 | 17.29 | H |
| ATOM | 4509 | HD23 | LEU | C | 135 | -0.404 | -12.551 | 50.695 | 1 | 17.29 | H |
| ATOM | 4510 | N | LYS | C | 136 | 0.716 | -15.601 | 54.65 | 1 | 17.22 | N |
| ATOM | 4511 | CA | LYS | C | 136 | 2 | -15.224 | 55.223 | 1 | 18.54 | C |
| ATOM | 4512 | C | LYS | C | 136 | 1.937 | -13.766 | 55.661 | 1 | 20.47 | C |
| ATOM | 4513 | O | LYS | C | 136 | 1.05 | -13.383 | 56.424 | 1 | 19.64 | O |
| ATOM | 4514 | CB | LYS | C | 136 | 2.365 | -16.117 | 56.409 | 1 | 20.46 | C |
| ATOM | 4515 | CG | LYS | C | 136 | 3.646 | -15.689 | 57.121 | 1 | 23.01 | C |
| ATOM | 4516 | CD | LYS | C | 136 | 3.99 | -16.612 | 58.278 | 1 | 23.3 | C |
| ATOM | 4517 | CE | LYS | C | 136 | 5.219 | -16.123 | 59.029 | 1 | 27.96 | C |
| ATOM | 4518 | NZ | LYS | C | 136 | 5.543 | -16.968 | 60.212 | 1 | 28.81 | N1+ |
| ATOM | 4519 | H | LYS | C | 136 | 0.072 | -15.605 | 55.219 | 1 | 20.67 | H |
| ATOM | 4520 | HA | LYS | C | 136 | 2.692 | -15.312 | 54.549 | 1 | 22.25 | H |
| ATOM | 4521 | HB2 | LYS | C | 136 | 2.49 | -17.025 | 56.091 | 1 | 24.55 | H |
| ATOM | 4522 | HB3 | LYS | C | 136 | 1.642 | -16.09 | 57.055 | 1 | 24.55 | H |
| ATOM | 4523 | HG2 | LYS | C | 136 | 3.53 | -14.792 | 57.473 | 1 | 27.61 | H |
| ATOM | 4524 | HG3 | LYS | C | 136 | 4.382 | -15.708 | 56.49 | 1 | 27.61 | H |
| ATOM | 4525 | HD2 | LYS | C | 136 | 4.175 | -17.5 | 57.936 | 1 | 27.96 | H |
| ATOM | 4526 | HD3 | LYS | C | 136 | 3.245 | -16.639 | 58.899 | 1 | 27.96 | H |
| ATOM | 4527 | HE2 | LYS | C | 136 | 5.061 | -15.218 | 59.341 | 1 | 33.55 | H |

TABLE 5-continued

Atomic Coordinates for OMCP-NKG2D (4PDC).

| ATOM | 4528 | HE3 | LYS | C | 5.983 | 58.431 | -16.14 | 1 | 33.55 | H |
|------|------|-----|-----|---|-------|--------|--------|---|-------|---|
| ATOM | 4529 | HZ1 | LYS | C | 5.701 | 59.954 | -17.805 | 1 | 34.57 | H |
| ATOM | 4530 | HZ2 | LYS | C | 4.86 | 60.783 | -16.965 | 1 | 34.57 | H |
| ATOM | 4531 | HZ3 | LYS | C | 6.265 | 60.623 | -16.65 | 1 | 34.57 | H |
| ATOM | 4532 | N | VAL | C | 2.879 | 55.174 | -12.962 | 1 | 17.55 | N |
| ATOM | 4533 | CA | VAL | C | 2.946 | 55.507 | -11.54 | 1 | 20.81 | C |
| ATOM | 4534 | C | VAL | C | 3.952 | 56.623 | -11.309 | 1 | 21.28 | C |
| ATOM | 4535 | O | VAL | C | 5.166 | 56.402 | -11.4 | 1 | 21.39 | O |
| ATOM | 4536 | CB | VAL | C | 3.34 | 54.286 | -10.685 | 1 | 17.34 | C |
| ATOM | 4537 | CG1 | VAL | C | 3.489 | 54.674 | -9.218 | 1 | 17.08 | C |
| ATOM | 4538 | CG2 | VAL | C | 2.308 | 53.18 | -10.832 | 1 | 19.83 | C |
| ATOM | 4539 | H | VAL | C | 3.501 | 54.639 | -13.221 | 1 | 21.06 | H |
| ATOM | 4540 | HA | VAL | C | 2.075 | 55.816 | -11.243 | 1 | 24.98 | H |
| ATOM | 4541 | HB | VAL | C | 4.194 | 53.945 | -10.994 | 1 | 20.81 | H |
| ATOM | 4542 | HG11 | VAL | C | 3.737 | 53.887 | -8.708 | 1 | 20.5 | H |
| ATOM | 4543 | HG12 | VAL | C | 4.179 | 55.351 | -9.14 | 1 | 20.5 | H |
| ATOM | 4544 | HG13 | VAL | C | 2.643 | 55.024 | -8.897 | 1 | 20.5 | H |
| ATOM | 4545 | HG21 | VAL | C | 2.576 | 52.424 | -10.287 | 1 | 23.8 | H |
| ATOM | 4546 | HG22 | VAL | C | 1.446 | 53.512 | -10.537 | 1 | 23.8 | H |
| ATOM | 4547 | HG23 | VAL | C | 2.26 | 52.915 | -11.764 | 1 | 23.8 | H |
| ATOM | 4548 | N | TYR | C | 3.447 | 57.812 | -10.992 | 1 | 20.38 | N |
| ATOM | 4549 | CA | TYR | C | 4.298 | 58.989 | -10.848 | 1 | 21.11 | C |
| ATOM | 4550 | C | TYR | C | 4.204 | 59.608 | -9.457 | 1 | 24.17 | C |
| ATOM | 4551 | O | TYR | C | 5.071 | 60.393 | -9.071 | 1 | 24.32 | O |
| ATOM | 4552 | CB | TYR | C | 3.94 | 60.037 | -11.906 | 1 | 22.43 | C |
| ATOM | 4553 | CG | TYR | C | 2.622 | 60.739 | -11.663 | 1 | 20.09 | C |
| ATOM | 4554 | CD1 | TYR | C | 1.442 | 60.245 | -12.197 | 1 | 21.54 | C |
| ATOM | 4555 | CD2 | TYR | C | 2.56 | 61.899 | -10.899 | 1 | 24.15 | C |
| ATOM | 4556 | CE1 | TYR | C | 0.238 | 60.882 | -11.978 | 1 | 23.42 | C |
| ATOM | 4557 | CE2 | TYR | C | 1.361 | 62.542 | -10.673 | 1 | 24.55 | C |
| ATOM | 4558 | CZ | TYR | C | 0.204 | 62.029 | -11.214 | 1 | 24.76 | C |
| ATOM | 4559 | OH | TYR | C | -0.991 | 62.663 | -10.994 | 1 | 25.68 | O |
| ATOM | 4560 | H | TYR | C | 2.612 | 57.965 | -10.855 | 1 | 24.46 | H |
| ATOM | 4561 | HA | TYR | C | 5.221 | 58.726 | -10.992 | 1 | 25.34 | H |
| ATOM | 4562 | HB2 | TYR | C | 4.636 | 60.712 | -11.923 | 1 | 26.92 | H |
| ATOM | 4563 | HB3 | TYR | C | 3.887 | 59.6 | -12.77 | 1 | 26.92 | H |
| ATOM | 4564 | HD1 | TYR | C | 1.462 | 59.471 | -12.712 | 1 | 25.85 | H |
| ATOM | 4565 | HD2 | TYR | C | 3.341 | 62.246 | -10.531 | 1 | 28.98 | H |
| ATOM | 4566 | HE1 | TYR | C | -0.546 | 60.538 | -12.342 | 1 | 28.11 | H |
| ATOM | 4567 | HE2 | TYR | C | 1.334 | 63.316 | -10.159 | 1 | 29.46 | H |
| ATOM | 4568 | HH | TYR | C | -0.872 | 63.344 | -10.517 | 1 | 30.82 | H |
| ATOM | 4569 | N | SER | C | 3.16 | 59.265 | -8.704 | 1 | 20.17 | N |
| ATOM | 4570 | CA | SER | C | 2.98 | 59.837 | -7.369 | 1 | 25.07 | C |
| ATOM | 4571 | C | SER | C | 2.203 | 58.946 | -6.407 | 1 | 22.13 | C |
| ATOM | 4572 | O | SER | C | 1.051 | 58.586 | -6.664 | 1 | 19.25 | O |
| ATOM | 4573 | CB | SER | C | 2.267 | 61.184 | -7.468 | 1 | 26.51 | C |
| ATOM | 4574 | OG | SER | C | 1.936 | 61.668 | -6.178 | 1 | 27.3 | O |
| ATOM | 4575 | H | SER | C | 2.547 | 58.709 | -8.939 | 1 | 24.21 | H |
| ATOM | 4576 | HA | SER | C | 3.854 | 59.995 | -6.98 | 1 | 30.08 | H |
| ATOM | 4577 | HB2 | SER | C | 2.854 | 61.821 | -7.905 | 1 | 31.82 | H |
| ATOM | 4578 | HB3 | SER | C | 1.453 | 61.074 | -7.984 | 1 | 31.82 | H |

TABLE 5-continued

Atomic Coordinates for OMCP-NKG2D (4PDC).

| | | | | | | | | | | |
|---|---|---|---|---|---|---|---|---|---|---|
| ATOM | 4579 | HG | SER C | 139 | 1.545 | 62.408 | -6.24 | 1 | 32.76 | H |
| ATOM | 4580 | N | LYS C | 140 | 2.828 | 58.62 | -5.28 | 1 | 15.89 | N |
| ATOM | 4581 | CA | LYS C | 140 | 2.167 | 57.822 | -4.254 | 1 | 23.7 | C |
| ATOM | 4582 | C | LYS C | 140 | 0.968 | 58.551 | -3.655 | 1 | 24.9 | C |
| ATOM | 4583 | O | LYS C | 140 | -0.012 | 57.922 | -3.258 | 1 | 26.09 | O |
| ATOM | 4584 | CB | LYS C | 140 | 3.15 | 57.456 | -3.142 | 1 | 28.92 | C |
| ATOM | 4585 | CG | LYS C | 140 | 4.057 | 56.282 | -3.47 | 1 | 29.54 | C |
| ATOM | 4586 | CD | LYS C | 140 | 4.867 | 55.875 | -2.252 | 1 | 37.47 | C |
| ATOM | 4587 | CE | LYS C | 140 | 5.648 | 54.596 | -2.489 | 1 | 37.64 | C |
| ATOM | 4588 | NZ | LYS C | 140 | 6.295 | 54.118 | -1.233 | 1 | 49.87 | N1+ |
| ATOM | 4589 | H | LYS C | 140 | 3.634 | 58.848 | -5.085 | 1 | 19.07 | H |
| ATOM | 4590 | HA | LYS C | 140 | 1.847 | 56.998 | -4.653 | 1 | 28.44 | H |
| ATOM | 4591 | HB2 | LYS C | 140 | 3.715 | 58.224 | -2.962 | 1 | 34.7 | H |
| ATOM | 4592 | HB3 | LYS C | 140 | 2.646 | 57.226 | -2.346 | 1 | 34.7 | H |
| ATOM | 4593 | HG2 | LYS C | 140 | 3.517 | 55.525 | -3.746 | 1 | 35.45 | H |
| ATOM | 4594 | HG3 | LYS C | 140 | 4.671 | 56.536 | -4.177 | 1 | 35.45 | H |
| ATOM | 4595 | HD2 | LYS C | 140 | 5.499 | 56.581 | -2.04 | 1 | 44.96 | H |
| ATOM | 4596 | HD3 | LYS C | 140 | 4.267 | 55.729 | -1.504 | 1 | 44.96 | H |
| ATOM | 4597 | HE2 | LYS C | 140 | 5.045 | 53.905 | -2.803 | 1 | 45.16 | H |
| ATOM | 4598 | HE3 | LYS C | 140 | 6.343 | 54.762 | -3.145 | 1 | 45.16 | H |
| ATOM | 4599 | HZ1 | LYS C | 140 | 6.748 | 53.368 | -1.391 | 1 | 59.85 | H |
| ATOM | 4600 | HZ2 | LYS C | 140 | 6.857 | 54.736 | -0.926 | 1 | 59.85 | H |
| ATOM | 4601 | HZ3 | LYS C | 140 | 5.676 | 53.957 | -0.614 | 1 | 59.85 | H |
| ATOM | 4602 | N | GLU C | 141 | 1.046 | 59.876 | -3.593 | 1 | 24.55 | N |
| ATOM | 4603 | CA | GLU C | 141 | -0.002 | 60.674 | -2.963 | 1 | 26.23 | C |
| ATOM | 4604 | C | GLU C | 141 | -1.169 | 60.917 | -3.914 | 1 | 24.95 | C |
| ATOM | 4605 | O | GLU C | 141 | -2.327 | 60.758 | -3.534 | 1 | 21.89 | O |
| ATOM | 4606 | CB | GLU C | 141 | 0.559 | 62.01 | -2.474 | 1 | 26.15 | C |
| ATOM | 4607 | CG | GLU C | 141 | 1.543 | 61.885 | -1.314 | 1 | 34.78 | C |
| ATOM | 4608 | CD | GLU C | 141 | 2.855 | 61.219 | -1.707 | 1 | 37.55 | C |
| ATOM | 4609 | OE1 | GLU C | 141 | 3.227 | 61.278 | -2.899 | 1 | 33.99 | O |
| ATOM | 4610 | OE2 | GLU C | 141 | 3.514 | 60.634 | -0.82 | 1 | 45.19 | O1- |
| ATOM | 4611 | H | GLU C | 141 | 1.698 | 60.339 | -3.91 | 1 | 29.46 | H |
| ATOM | 4612 | HA | GLU C | 141 | -0.342 | 60.193 | -2.192 | 1 | 31.47 | H |
| ATOM | 4613 | HB2 | GLU C | 141 | 1.022 | 62.442 | -3.209 | 1 | 31.39 | H |
| ATOM | 4614 | HB3 | GLU C | 141 | -0.178 | 62.568 | -2.178 | 1 | 31.39 | H |
| ATOM | 4615 | HG2 | GLU C | 141 | 1.747 | 62.772 | -0.978 | 1 | 41.74 | H |
| ATOM | 4616 | HG3 | GLU C | 141 | 1.136 | 61.352 | -0.613 | 1 | 41.74 | H |
| ATOM | 4617 | N | ASP C | 142 | -0.867 | 61.296 | -5.152 | 1 | 22.41 | N |
| ATOM | 4618 | CA | ASP C | 142 | -1.915 | 61.567 | -6.129 | 1 | 21.49 | C |
| ATOM | 4619 | C | ASP C | 142 | -2.56 | 60.282 | -6.633 | 1 | 21.91 | C |
| ATOM | 4620 | O | ASP C | 142 | -3.686 | 60.3 | -7.128 | 1 | 24.05 | O |
| ATOM | 4621 | CB | ASP C | 142 | -1.357 | 62.369 | -7.307 | 1 | 24.21 | C |
| ATOM | 4622 | CG | ASP C | 142 | -0.908 | 63.76 | -6.901 | 1 | 29.23 | C |
| ATOM | 4623 | OD1 | ASP C | 142 | -1.248 | 64.193 | -5.776 | 1 | 30.52 | O |
| ATOM | 4624 | OD2 | ASP C | 142 | -0.223 | 64.424 | -7.707 | 1 | 33.69 | O1- |
| ATOM | 4625 | H | ASP C | 142 | -0.067 | 61.403 | -5.45 | 1 | 26.89 | H |
| ATOM | 4626 | HA | ASP C | 142 | -2.606 | 62.101 | -5.707 | 1 | 25.79 | H |
| ATOM | 4627 | HB2 | ASP C | 142 | -0.59 | 61.901 | -7.674 | 1 | 29.05 | H |
| ATOM | 4628 | HB3 | ASP C | 142 | -2.046 | 62.46 | -7.983 | 1 | 29.05 | H |
| ATOM | 4629 | N | GLN C | 143 | -1.849 | 59.167 | -6.501 | 1 | 17.21 | N |

TABLE 5-continued

Atomic Coordinates for OMCP-NKG2D (4PDC).

| ATOM | 4630 | CA | GLN | C | 143 | -2.357 | 57.882 | -6.969 | 1 | 20.06 | C |
|---|---|---|---|---|---|---|---|---|---|---|---|
| ATOM | 4631 | C | GLN | C | 143 | -2.424 | 56.89 | -5.819 | 1 | 19.18 | C |
| ATOM | 4632 | O | GLN | C | 143 | -2.183 | 55.696 | -5.994 | 1 | 17.46 | O |
| ATOM | 4633 | CB | GLN | C | 143 | -1.479 | 57.342 | -8.097 | 1 | 18.97 | C |
| ATOM | 4634 | CG | GLN | C | 143 | -1.248 | 58.349 | 9.217 | 1 | 17.93 | C |
| ATOM | 4635 | CD | GLN | C | 143 | -0.285 | 57.837 | -10.27 | 1 | 21.93 | C |
| ATOM | 4636 | OE1 | GLN | C | 143 | -0.917 | 57.724 | -10.024 | 1 | 19.88 | O |
| ATOM | 4637 | NE2 | GLN | C | 143 | -0.808 | 57.52 | -11.45 | 1 | 17.07 | N |
| ATOM | 4638 | H | GLN | C | 143 | -1.069 | 59.128 | -6.143 | 1 | 20.65 | H |
| ATOM | 4639 | HA | GLN | C | 143 | -3.255 | 58.002 | -7.317 | 1 | 24.08 | H |
| ATOM | 4640 | HB2 | GLN | C | 143 | -0.614 | 57.098 | -7.732 | 1 | 22.76 | H |
| ATOM | 4641 | HB3 | GLN | C | 143 | -1.906 | 56.561 | -8.482 | 1 | 22.76 | H |
| ATOM | 4642 | HG2 | GLN | C | 143 | 2.094 | 58.54 | -9.651 | 1 | 21.52 | H |
| ATOM | 4643 | HG3 | GLN | C | 143 | -0.877 | 59.162 | -8.84 | 1 | 21.52 | H |
| ATOM | 4644 | HE21 | GLN | C | 143 | -0.302 | 57.225 | -12.079 | 1 | 20.49 | H |
| ATOM | 4645 | HE22 | GLN | C | 143 | -1.653 | 57.609 | -11.584 | 1 | 20.49 | H |
| ATOM | 4646 | N | ASP | C | 144 | -2.77 | 57.395 | -4.639 | 1 | 22.78 | N |
| ATOM | 4647 | CA | ASP | C | 144 | -2.791 | 56.572 | -3.438 | 1 | 23.8 | C |
| ATOM | 4648 | C | ASP | C | 144 | -3.893 | 55.512 | -3.492 | 1 | 19.24 | C |
| ATOM | 4649 | O | ASP | C | 144 | -3.854 | 54.538 | -2.74 | 1 | 21.24 | O |
| ATOM | 4650 | CB | ASP | C | 144 | -2.949 | 57.449 | -2.188 | 1 | 24.8 | C |
| ATOM | 4651 | CG | ASP | C | 144 | -4.205 | 58.296 | -2.215 | 1 | 24.61 | C |
| ATOM | 4652 | OD1 | ASP | C | 144 | -4.881 | 58.345 | -3.264 | 1 | 31.09 | O |
| ATOM | 4653 | OD2 | ASP | C | 144 | -4.511 | 58.927 | -1.183 | 1 | 34.04 | O1- |
| ATOM | 4654 | H | ASP | C | 144 | -2.998 | 58.214 | -4.509 | 1 | 27.33 | H |
| ATOM | 4655 | HA | ASP | C | 144 | -1.942 | 56.108 | -3.366 | 1 | 28.56 | H |
| ATOM | 4656 | HB2 | ASP | C | 144 | -2.991 | 56.878 | -1.405 | 1 | 29.76 | H |
| ATOM | 4657 | HB3 | ASP | C | 144 | -2.188 | 58.046 | -2.123 | 1 | 29.76 | H |
| ATOM | 4658 | N | LEU | C | 145 | -4.864 | 55.678 | -4.386 | 1 | 18.41 | N |
| ATOM | 4659 | CA | LEU | C | 145 | -5.892 | 54.652 | -4.544 | 1 | 19.62 | C |
| ATOM | 4660 | C | LEU | C | 145 | -5.274 | 53.321 | -4.976 | 1 | 20.78 | C |
| ATOM | 4661 | O | LEU | C | 145 | -5.893 | 52.27 | -4.826 | 1 | 14.96 | O |
| ATOM | 4662 | CB | LEU | C | 145 | -6.968 | 55.078 | -5.553 | 1 | 19.66 | C |
| ATOM | 4663 | CG | LEU | C | 145 | -6.615 | 55.709 | -6.908 | 1 | 27.1 | C |
| ATOM | 4664 | CD1 | LEU | C | 145 | -5.336 | 55.184 | -7.518 | 1 | 25.7 | C |
| ATOM | 4665 | CD2 | LEU | C | 145 | -7.776 | 55.498 | -7.879 | 1 | 21.56 | C |
| ATOM | 4666 | H | LEU | C | 145 | -4.95 | 56.36 | -4.903 | 1 | 22.09 | H |
| ATOM | 4667 | HA | LEU | C | 145 | -6.328 | 54.513 | -3.689 | 1 | 23.55 | H |
| ATOM | 4668 | HB2 | LEU | C | 145 | -7.493 | 54.288 | -5.756 | 1 | 23.59 | H |
| ATOM | 4669 | HB3 | LEU | C | 145 | -7.54 | 55.718 | -5.102 | 1 | 23.59 | H |
| ATOM | 4670 | HG | LEU | C | 145 | -6.508 | 56.665 | -6.784 | 1 | 32.52 | H |
| ATOM | 4671 | HD11 | LEU | C | 145 | -5.185 | 55.63 | -8.366 | 1 | 30.83 | H |
| ATOM | 4672 | HD12 | LEU | C | 145 | -4.6 | 55.366 | -6.913 | 1 | 30.83 | H |
| ATOM | 4673 | HD13 | LEU | C | 145 | -5.422 | 54.228 | -7.657 | 1 | 25.87 | H |
| ATOM | 4674 | HD21 | LEU | C | 145 | -7.55 | 55.898 | 8.734 | 1 | 22.09 | H |
| ATOM | 4675 | HD22 | LEU | C | 145 | -7.927 | 54.547 | -7.989 | 1 | 25.87 | H |
| ATOM | 4676 | HD23 | LEU | C | 145 | -8.571 | 55.92 | -7.517 | 1 | 25.87 | H |
| ATOM | 4677 | N | LEU | C | 146 | -4.048 | 53.365 | -5.494 | 1 | 16.14 | N |
| ATOM | 4678 | CA | LEU | C | 146 | -3.384 | 52.158 | -5.983 | 1 | 16.03 | C |
| ATOM | 4679 | C | LEU | C | 146 | -2.981 | 51.231 | -4.84 | 1 | 17.57 | C |
| ATOM | 4680 | O | LEU | C | 146 | -2.655 | 50.065 | -5.067 | 1 | 16.74 | O |

TABLE 5-continued

Atomic Coordinates for OMCP-NKG2D (4PDC).

| | | | | | | | | | | |
|---|---|---|---|---|---|---|---|---|---|---|
| ATOM | 4681 | CB   | LEU | C | 146 | -2.154 | 52.524 | -6.821 | 1 | 17.95 C |
| ATOM | 4682 | CG   | LEU | C | 146 | -2.41  | 53.275 | -8.132 | 1 | 15.53 C |
| ATOM | 4683 | CD1  | LEU | C | 146 | -1.089 | 53.618 | -8.817 | 1 | 16.96 C |
| ATOM | 4684 | CD2  | LEU | C | 146 | -3.292 | 52.46  | 9.064  | 1 | 19.12 C |
| ATOM | 4685 | H    | LEU | C | 146 | -3.579 | 54.081 | -5.574 | 1 | 19.36 H |
| ATOM | 4686 | HA   | LEU | C | 146 | -3.999 | 51.673 | -6.555 | 1 | 19.23 H |
| ATOM | 4687 | HB2  | LEU | C | 146 | -1.575 | 53.083 | -6.28  | 1 | 21.54 H |
| ATOM | 4688 | HB3  | LEU | C | 146 | -1.688 | 51.704 | -7.048 | 1 | 21.54 H |
| ATOM | 4689 | HG   | LEU | C | 146 | -2.87  | 54.106 | -7.935 | 1 | 18.63 H |
| ATOM | 4690 | HD11 | LEU | C | 146 | -1.276 | 54.092 | -9.642 | 1 | 20.36 H |
| ATOM | 4691 | HD12 | LEU | C | 146 | -0.564 | 54.179 | -8.225 | 1 | 20.36 H |
| ATOM | 4692 | HD13 | LEU | C | 146 | -0.61  | 52.797 | -9.007 | 1 | 20.36 H |
| ATOM | 4693 | HD21 | LEU | C | 146 | -3.435 | 52.962 | -9.882 | 1 | 22.95 H |
| ATOM | 4694 | HD22 | LEU | C | 146 | -2.85  | 51.621 | -9.264 | 1 | 22.95 H |
| ATOM | 4695 | HD23 | LEU | C | 146 | -4.142 | 52.291 | -8.627 | 1 | 19.33 H |
| ATOM | 4696 | N    | LYS | C | 147 | -3.014 | 51.744 | -3.613 | 1 | 19.87 N |
| ATOM | 4697 | CA   | LYS | C | 147 | -2.75  | 50.925 | -2.433 | 1 | 17.73 C |
| ATOM | 4698 | C    | LYS | C | 147 | -3.839 | 49.877 | -2.192 | 1 | 19.26 C |
| ATOM | 4699 | O    | LYS | C | 147 | -3.603 | 48.867 | -1.526 | 1 | 23.96 O |
| ATOM | 4700 | CB   | LYS | C | 147 | -2.628 | 51.807 | -1.188 | 1 | 34.05 C |
| ATOM | 4701 | CG   | LYS | C | 147 | -1.4   | 52.698 | -1.163 | 1 | 43.75 C |
| ATOM | 4702 | CD   | LYS | C | 147 | -1.286 | 53.467 | 0.152  | 1 | 52.91 C |
| ATOM | 4703 | CE   | LYS | C | 147 | -2.464 | 54.413 | 0.354  | 1 | 63.31 C |
| ATOM | 4704 | NZ   | LYS | C | 147 | -2.213 | 55.423 | 1.423  | 1 | 52.91 N1+ |
| ATOM | 4705 | H    | LYS | C | 147 | -3.187 | 52.568 | -3.436 | 1 | 23.19 H |
| ATOM | 4706 | HA   | LYS | C | 147 | -1.908 | 50.459 | -2.555 | 1 | 23.84 H |
| ATOM | 4707 | HB2  | LYS | C | 147 | -3.409 | 52.38  | -1.136 | 1 | 28.75 H |
| ATOM | 4708 | HB3  | LYS | C | 147 | -2.592 | 51.234 | -0.405 | 1 | 28.75 H |
| ATOM | 4709 | HG2  | LYS | C | 147 | -0.606 | 52.15  | -1.263 | 1 | 40.86 H |
| ATOM | 4710 | HG3  | LYS | C | 147 | -1.458 | 53.341 | -1.886 | 1 | 40.86 H |
| ATOM | 4711 | HD2  | LYS | C | 147 | -1.272 | 52.838 | 0.89   | 1 | 52.5 H |
| ATOM | 4712 | HD3  | LYS | C | 147 | -0.472 | 53.994 | 0.145  | 1 | 52.5 H |
| ATOM | 4713 | HE2  | LYS | C | 147 | -2.634 | 54.888 | -0.474 | 1 | 63.49 H |
| ATOM | 4714 | HE3  | LYS | C | 147 | -3.245 | 53.896 | 0.607  | 1 | 63.49 H |
| ATOM | 4715 | HZ1  | LYS | C | 147 | -2.921 | 55.955 | 1.511  | 1 | 75.97 H |
| ATOM | 4716 | HZ2  | LYS | C | 147 | -2.06  | 55.014 | 2.198  | 1 | 75.97 H |
| ATOM | 4717 | HZ3  | LYS | C | 147 | -1.504 | 55.918 | 1.213  | 1 | 75.97 H |
| ATOM | 4718 | N    | LEU | C | 148 | -5.028 | 50.122 | -2.732 | 1 | 15.82 N |
| ATOM | 4719 | CA   | LEU | C | 148 | -6.21  | 49.333 | -2.387 | 1 | 18.04 C |
| ATOM | 4720 | C    | LEU | C | 148 | -6.593 | 48.304 | -3.45  | 1 | 18.6 C |
| ATOM | 4721 | O    | LEU | C | 148 | -7.686 | 47.744 | -3.405 | 1 | 15.31 O |
| ATOM | 4722 | CB   | LEU | C | 148 | -7.395 | 50.269 | -2.151 | 1 | 23.06 C |
| ATOM | 4723 | CG   | LEU | C | 148 | -7.13  | 51.452 | -1.217 | 1 | 32.15 C |
| ATOM | 4724 | CD1  | LEU | C | 148 | -8.009 | 52.619 | -1.612 | 1 | 32.37 C |
| ATOM | 4725 | CD2  | LEU | C | 148 | -7.363 | 51.056 | 0.236  | 1 | 30.03 C |
| ATOM | 4726 | H    | LEU | C | 148 | -5.179 | 50.745 | -3.306 | 1 | 18.98 H |
| ATOM | 4727 | HA   | LEU | C | 148 | -6.038 | 48.856 | -1.56  | 1 | 21.65 H |
| ATOM | 4728 | HB2  | LEU | C | 148 | -7.674 | 50.632 | -3.007 | 1 | 27.68 H |
| ATOM | 4729 | HB3  | LEU | C | 148 | -8.122 | 49.753 | -1.768 | 1 | 27.68 H |
| ATOM | 4730 | HG   | LEU | C | 148 | -6.204 | 51.727 | -1.308 | 1 | 38.58 H |
| ATOM | 4731 | HD11 | LEU | C | 148 | -7.833 | 53.363 | -1.015 | 1 | 38.84 H |

TABLE 5-continued

Atomic Coordinates for OMCP-NKG2D (4PDC).

| ATOM | 4732 | HD12 | LEU | C | 148 | -7.804 | 52.873 | -2.526 | 1 | 38.84 | H |
|---|---|---|---|---|---|---|---|---|---|---|---|
| ATOM | 4733 | HD13 | LEU | C | 148 | -8.939 | 52.351 | -1.544 | 1 | 38.84 | H |
| ATOM | 4734 | HD21 | LEU | C | 148 | -7.188 | 51.822 | 0.804 | 1 | 36.04 | H |
| ATOM | 4735 | HD22 | LEU | C | 148 | -8.284 | 50.77 | 0.341 | 1 | 36.04 | H |
| ATOM | 4736 | HD23 | LEU | C | 148 | -6.763 | 50.329 | 0.466 | 1 | 36.04 | H |
| ATOM | 4737 | N | VAL | C | 149 | -5.697 | 48.054 | -4.398 | 1 | 16.71 | N |
| ATOM | 4738 | CA | VAL | C | 149 | -6.011 | 47.21 | -5.548 | 1 | 14.87 | C |
| ATOM | 4739 | C | VAL | C | 149 | 5.503 | 45.783 | -5.38 | 1 | 14.53 | C |
| ATOM | 4740 | O | VAL | C | 149 | -4.311 | 45.568 | -5.166 | 1 | 16.23 | O |
| ATOM | 4741 | CB | VAL | C | 149 | -5.409 | 47.803 | -6.833 | 1 | 18.92 | C |
| ATOM | 4742 | CG1 | VAL | C | 149 | -5.723 | 46.926 | -8.036 | 1 | 20.42 | C |
| ATOM | 4743 | CG2 | VAL | C | 149 | -5.93 | 49.222 | -7.054 | 1 | 20.99 | C |
| ATOM | 4744 | H | VAL | C | 149 | -4.894 | 48.363 | -4.399 | 1 | 20.06 | H |
| ATOM | 4745 | HA | VAL | C | 149 | -6.975 | 47.174 | -5.658 | 1 | 17.84 | H |
| ATOM | 4746 | HB | VAL | C | 149 | -4.445 | 47.849 | 6.738 | 1 | 22.71 | H |
| ATOM | 4747 | HG11 | VAL | C | 149 | -5.33 | 47.326 | -8.828 | 1 | 24.51 | H |
| ATOM | 4748 | HG12 | VAL | C | 149 | -5.347 | 46.044 | -7.89 | 1 | 24.51 | H |
| ATOM | 4749 | HG13 | VAL | C | 149 | -6.685 | 46.864 | -8.139 | 1 | 24.51 | H |
| ATOM | 4750 | HG21 | VAL | C | 149 | -5.539 | 49.577 | -7.868 | 1 | 25.18 | H |
| ATOM | 4751 | HG22 | VAL | C | 149 | -6.896 | 49.194 | -7.136 | 1 | 25.18 | H |
| ATOM | 4752 | HG23 | VAL | C | 149 | -5.677 | 49.772 | -6.297 | 1 | 25.18 | H |
| ATOM | 4753 | N | LYS | C | 150 | -6.408 | 44.816 | -5.5 | 1 | 13.93 | N |
| ATOM | 4754 | CA | LYS | C | 150 | -6.044 | 43.402 | -5.45 | 1 | 18.06 | C |
| ATOM | 4755 | C | LYS | C | 150 | -5.531 | 42.912 | -6.797 | 1 | 15.46 | C |
| ATOM | 4756 | O | LYS | C | 150 | -5.715 | 43.57 | -7.819 | 1 | 15.34 | O |
| ATOM | 4757 | CB | LYS | C | 150 | -7.238 | 42.538 | -5.03 | 1 | 16.72 | C |
| ATOM | 4758 | CG | LYS | C | 150 | -7.584 | 42.607 | -3.553 | 1 | 17.69 | C |
| ATOM | 4759 | CD | LYS | C | 150 | -8.705 | 41.641 | -3.194 | 1 | 15.55 | C |
| ATOM | 4760 | CE | LYS | C | 150 | -8.218 | 40.202 | -3.082 | 1 | 17.69 | C |
| ATOM | 4761 | NZ | LYS | C | 150 | -7.374 | 39.972 | -1.871 | 1 | 15.2 | N1+ |
| ATOM | 4762 | H | LYS | C | 150 | -7.249 | 44.953 | -5.613 | 1 | 16.72 | H |
| ATOM | 4763 | HA | LYS | C | 150 | -5.338 | 43.279 | -4.796 | 1 | 21.68 | H |
| ATOM | 4764 | HB2 | LYS | C | 150 | -8.019 | 42.826 | -5.528 | 1 | 20.06 | H |
| ATOM | 4765 | HB3 | LYS | C | 150 | -7.04 | 41.612 | -5.241 | 1 | 20.06 | H |
| ATOM | 4766 | HG2 | LYS | C | 150 | -6.802 | 42.373 | -3.03 | 1 | 21.22 | H |
| ATOM | 4767 | HG3 | LYS | C | 150 | -7.877 | 43.506 | -3.335 | 1 | 21.22 | H |
| ATOM | 4768 | HD2 | LYS | C | 150 | -9.084 | 41.898 | -2.339 | 1 | 18.65 | H |
| ATOM | 4769 | HD3 | LYS | C | 150 | -9.386 | 41.675 | -3.884 | 1 | 18.65 | H |
| ATOM | 4770 | HE2 | LYS | C | 150 | -8.986 | 39.612 | -3.029 | 1 | 21.23 | H |
| ATOM | 4771 | HE3 | LYS | C | 150 | -7.686 | 39.987 | -3.864 | 1 | 21.23 | H |
| ATOM | 4772 | HZ1 | LYS | C | 150 | -6.656 | 40.498 | -1.896 | 1 | 18.24 | H |
| ATOM | 4773 | HZ2 | LYS | C | 150 | -7.841 | 40.156 | -1.136 | 1 | 18.24 | H |
| ATOM | 4774 | HZ3 | LYS | C | 150 | -7.11 | 39.123 | 1.841 | 1 | 18.24 | H |
| ATOM | 4775 | N | SER | C | 151 | -4.903 | 41.742 | -6.777 | 1 | 16.11 | N |
| ATOM | 4776 | CA | SER | C | 151 | -4.426 | 41.078 | -7.985 | 1 | 17.4 | C |
| ATOM | 4777 | C | SER | C | 151 | -3.319 | 41.859 | -8.69 | 1 | 14.09 | C |
| ATOM | 4778 | O | SER | C | 151 | -2.799 | 42.846 | -8.168 | 1 | 16.03 | O |
| ATOM | 4779 | CB | SER | C | 151 | -5.585 | 40.834 | -8.952 | 1 | 14.05 | C |
| ATOM | 4780 | OG | SER | C | 151 | -5.188 | 39.954 | -9.988 | 1 | 14.91 | O |
| ATOM | 4781 | H | SER | C | 151 | -4.736 | 41.302 | -6.057 | 1 | 19.33 | H |
| ATOM | 4782 | HA | SER | C | 151 | -4.063 | 40.213 | -7.739 | 1 | 20.89 | H |

TABLE 5-continued

Atomic Coordinates for OMCP-NKG2D (4PDC).

| ATOM | 4783 | HB2 | SER | C | 151 | -6.325 | 40.438 | -8.467 | 1 | 16.86 | H |
|------|------|-----|-----|---|-----|--------|--------|--------|---|-------|---|
| ATOM | 4784 | HB3 | SER | C | 151 | 5.856 | 41.679 | -9.342 | 1 | 16.86 | H |
| ATOM | 4785 | HG | SER | C | 151 | -5.828 | 39.824 | -10.515 | 1 | 17.89 | H |
| ATOM | 4786 | N | TYR | C | 152 | -2.961 | 41.385 | -9.877 | 1 | 12.6 | N |
| ATOM | 4787 | CA | TYR | C | 152 | -1.828 | 41.905 | -10.624 | 1 | 11.73 | C |
| ATOM | 4788 | C | TYR | C | 152 | -2.312 | 42.429 | -11.968 | 1 | 17.09 | C |
| ATOM | 4789 | O | TYR | C | 152 | -3.22 | 41.852 | -12.575 | 1 | 15.23 | O |
| ATOM | 4790 | CB | TYR | C | 152 | -0.77 | 40.814 | -10.824 | 1 | 14.94 | C |
| ATOM | 4791 | CG | TYR | C | 152 | -0.394 | 40.065 | -9.562 | 1 | 13.45 | C |
| ATOM | 4792 | CD1 | TYR | C | 152 | -0.119 | 40.743 | -8.383 | 1 | 17.53 | C |
| ATOM | 4793 | CD2 | TYR | C | 152 | -0.317 | 38.678 | -9.552 | 1 | 13.04 | C |
| ATOM | 4794 | CE1 | TYR | C | 152 | 0.229 | 40.064 | -7.232 | 1 | 15.99 | C |
| ATOM | 4795 | CE2 | TYR | C | 152 | 0.031 | 37.989 | 8.407 | 1 | 17.54 | C |
| ATOM | 4796 | CZ | TYR | C | 152 | 0.303 | 38.688 | -7.246 | 1 | 17.26 | C |
| ATOM | 4797 | OH | TYR | C | 152 | 0.65 | 38.009 | -6.097 | 1 | 14.46 | O |
| ATOM | 4798 | H | TYR | C | 152 | -3.371 | 40.745 | -10.28 | 1 | 15.12 | H |
| ATOM | 4799 | HA | TYR | C | 152 | -1.425 | 42.639 | -10.134 | 1 | 14.07 | H |
| ATOM | 4800 | HB2 | TYR | C | 152 | -1.11 | 40.166 | -11.461 | 1 | 17.93 | H |
| ATOM | 4801 | HB3 | TYR | C | 152 | 0.036 | 41.224 | -11.174 | 1 | 17.93 | H |
| ATOM | 4802 | HD1 | TYR | C | 152 | -0.165 | 41.672 | -8.369 | 1 | 21.04 | H |
| ATOM | 4803 | HD2 | TYR | C | 152 | -0.496 | 38.205 | -10.333 | 1 | 15.65 | H |
| ATOM | 4804 | HE1 | TYR | C | 152 | 0.412 | 40.533 | -6.45 | 1 | 19.18 | H |
| ATOM | 4805 | HE2 | TYR | C | 152 | 0.08 | 37.06 | -8.416 | 1 | 21.05 | H |
| ATOM | 4806 | HH | TYR | C | 152 | 0.657 | 37.182 | -6.243 | 1 | 17.36 | H |
| ATOM | 4807 | N | HIS | C | 153 | -1.711 | 43.521 | -12.428 | 1 | 11.85 | N |
| ATOM | 4808 | CA | HIS | C | 153 | -2.185 | 44.203 | -13.628 | 1 | 13.69 | C |
| ATOM | 4809 | C | HIS | C | 153 | -1.038 | 44.802 | -14.415 | 1 | 13.1 | C |
| ATOM | 4810 | O | HIS | C | 153 | -0.106 | 45.358 | -13.836 | 1 | 13.18 | O |
| ATOM | 4811 | CB | HIS | C | 153 | -3.182 | 45.302 | -13.254 | 1 | 12.79 | C |
| ATOM | 4812 | CG | HIS | C | 153 | -4.22 | 44.86 | -12.274 | 1 | 15.44 | C |
| ATOM | 4813 | ND1 | HIS | C | 153 | -5.444 | 44.357 | -12.661 | 1 | 13.49 | N |
| ATOM | 4814 | CD2 | HIS | C | 153 | -4.21 | 44.83 | -10.92 | 1 | 15.97 | C |
| ATOM | 4815 | CE1 | HIS | C | 153 | -6.146 | 44.043 | -11.587 | 1 | 16.56 | C |
| ATOM | 4816 | NE2 | HIS | C | 153 | -5.419 | 44.317 | -10.518 | 1 | 16.62 | N |
| ATOM | 4817 | H | HIS | C | 153 | -1.025 | 43.888 | -12.063 | 1 | 14.22 | H |
| ATOM | 4818 | HA | HIS | C | 153 | -2.641 | 43.563 | -14.198 | 1 | 16.43 | H |
| ATOM | 4819 | HB2 | HIS | C | 153 | -2.697 | 46.043 | -12.859 | 1 | 15.35 | H |
| ATOM | 4820 | HB3 | HIS | C | 153 | -3.638 | 45.598 | -14.057 | 1 | 15.44 | H |
| ATOM | 4821 | HD1 | HIS | C | 153 | -5.71 | 44.265 | -13.474 | 1 | 16.19 | H |
| ATOM | 4822 | HD2 | HIS | C | 153 | -3.515 | 45.104 | -10.366 | 1 | 19.16 | H |
| ATOM | 4823 | HE1 | HIS | C | 153 | -7.005 | 43.687 | -11.584 | 1 | 19.87 | H |
| ATOM | 4824 | HE2 | HIS | C | 153 | -5.665 | 44.199 | -9.702 | 1 | 19.95 | H |
| ATOM | 4825 | N | TRP | C | 154 | -1.104 | 44.682 | -15.738 | 1 | 15.58 | N |
| ATOM | 4826 | CA | TRP | C | 154 | -0.104 | 45.295 | -16.598 | 1 | 15.13 | C |
| ATOM | 4827 | C | TRP | C | 154 | -0.118 | 46.805 | -16.411 | 1 | 15.13 | C |
| ATOM | 4828 | O | TRP | C | 154 | -1.175 | 47.43 | -16.468 | 1 | 13.3 | O |
| ATOM | 4829 | CB | TRP | C | 154 | -0.353 | 44.977 | -18.078 | 1 | 15.45 | C |
| ATOM | 4830 | CG | TRP | C | 154 | 0.036 | 43.598 | -18.543 | 1 | 17.21 | C |
| ATOM | 4831 | CD1 | TRP | C | 154 | -0.751 | 42.717 | -19.229 | 1 | 18.69 | C |
| ATOM | 4832 | CD2 | TRP | C | 154 | 1.31 | 42.957 | -18.385 | 1 | 17.34 | C |
| ATOM | 4833 | NE1 | TRP | C | 154 | -0.049 | 41.567 | -19.506 | 1 | 16.22 | N |

TABLE 5-continued

Atomic Coordinates for OMCP-NKG2D (4PDC).

| | | | | | | | | | | |
|---|---|---|---|---|---|---|---|---|---|---|
| ATOM | 4834 | CE2 | TRP | C | 154 | 1.217 | 41.687 | -18.995 | 1 | 17.13 | C |
| ATOM | 4835 | CE3 | TRP | C | 154 | 2.518 | 43.329 | -17.783 | 1 | 15.92 | C |
| ATOM | 4836 | CZ2 | TRP | C | 154 | 2.283 | 40.79 | -19.019 | 1 | 16.67 | C |
| ATOM | 4837 | CZ3 | TRP | C | 154 | 3.576 | 42.435 | -17.809 | 1 | 13.5 | C |
| ATOM | 4838 | CH2 | TRP | C | 154 | 3.451 | 41.182 | -18.422 | 1 | 14.99 | C |
| ATOM | 4839 | H | TRP | C | 154 | -1.718 | 44.251 | -16.159 | 1 | 18.7 | H |
| ATOM | 4840 | HA | TRP | C | 154 | 0.775 | 44.964 | -16.357 | 1 | 18.16 | H |
| ATOM | 4841 | HB2 | TRP | C | 154 | -1.301 | 45.083 | -18.256 | 1 | 18.54 | H |
| ATOM | 4842 | HB3 | TRP | C | 154 | 0.147 | 45.612 | -18.613 | 1 | 18.54 | H |
| ATOM | 4843 | HD1 | TRP | C | 154 | -1.633 | 42.875 | -19.48 | 1 | 22.43 | H |
| ATOM | 4844 | HE1 | TRP | C | 154 | -0.357 | 40.881 | -19.924 | 1 | 19.46 | H |
| ATOM | 4845 | HE3 | TRP | C | 154 | 2.608 | 44.16 | -17.375 | 1 | 19.1 | H |
| ATOM | 4846 | HZ2 | TRP | C | 154 | 2.203 | 39.957 | -19.424 | 1 | 20.01 | H |
| ATOM | 4847 | HZ3 | TRP | C | 154 | 4.383 | 42.671 | -17.413 | 1 | 16.2 | H |
| ATOM | 4848 | HH2 | TRP | C | 154 | 4.179 | 40.603 | -18.422 | 1 | 17.99 | H |
| ATOM | 4849 | N | MET | C | 155 | 1.06 | 47.377 | -16.184 | 1 | 13.13 | N |
| ATOM | 4850 | CA | MET | C | 155 | 1.247 | 48.82 | -16.244 | 1 | 15.17 | C |
| ATOM | 4851 | C | MET | C | 155 | 2.264 | 49.134 | -17.341 | 1 | 17.69 | C |
| ATOM | 4852 | O | MET | C | 155 | 2.792 | 48.226 | -17.983 | 1 | 15.06 | O |
| ATOM | 4853 | CB | MET | C | 155 | 1.705 | 49.374 | -14.895 | 1 | 13.1 | C |
| ATOM | 4854 | CG | MET | C | 155 | 2.991 | 48.776 | -14.369 | 1 | 12.38 | C |
| ATOM | 4855 | SD | MET | C | 155 | 3.439 | 49.474 | -12.769 | 1 | 15.66 | S |
| ATOM | 4856 | CE | MET | C | 155 | 4.634 | 48.273 | -12.207 | 1 | 16.77 | C |
| ATOM | 4857 | H | MET | C | 155 | 1.776 | 46.943 | -15.989 | 1 | 15.75 | H |
| ATOM | 4858 | HA | MET | C | 155 | 0.402 | 49.239 | -16.468 | 1 | 18.2 | H |
| ATOM | 4859 | HB2 | MET | C | 155 | 1.841 | 50.33 | -14.983 | 1 | 15.72 | H |
| ATOM | 4860 | HB3 | MET | C | 155 | 1.012 | 49.202 | -14.238 | 1 | 15.72 | H |
| ATOM | 4861 | HG2 | MET | C | 155 | 2.879 | 47.818 | -14.262 | 1 | 14.86 | H |
| ATOM | 4862 | HG3 | MET | C | 155 | 3.71 | 48.962 | -14.994 | 1 | 14.86 | H |
| ATOM | 4863 | HE1 | MET | C | 155 | 4.961 | 48.538 | -11.333 | 1 | 20.13 | H |
| ATOM | 4864 | HE2 | MET | C | 155 | 4.205 | 47.404 | -12.15 | 1 | 20.13 | H |
| ATOM | 4865 | HE3 | MET | C | 155 | 5.369 | 48.239 | -12.839 | 1 | 20.13 | H |
| ATOM | 4866 | N | GLY | C | 156 | 2.542 | 50.415 | -17.549 | 1 | 15.94 | N |
| ATOM | 4867 | CA | GLY | C | 156 | 3.297 | 50.843 | -18.714 | 1 | 17.37 | C |
| ATOM | 4868 | C | GLY | C | 156 | 4.802 | 50.829 | -18.544 | 1 | 19.77 | C |
| ATOM | 4869 | O | GLY | C | 156 | 5.513 | 51.512 | -19.281 | 1 | 21.61 | O |
| ATOM | 4870 | H | GLY | C | 156 | 2.304 | 51.057 | -17.029 | 1 | 19.13 | H |
| ATOM | 4871 | HA2 | GLY | C | 156 | 3.076 | 50.264 | -19.461 | 1 | 20.84 | H |
| ATOM | 4872 | HA3 | GLY | C | 156 | 3.031 | 51.746 | -18.947 | 1 | 20.84 | H |
| ATOM | 4873 | N | LEU | C | 157 | 5.289 | 50.047 | -17.585 | 1 | 18.34 | N |
| ATOM | 4874 | CA | LEU | C | 157 | 6.714 | 50.015 | -17.271 | 1 | 17.73 | C |
| ATOM | 4875 | C | LEU | C | 157 | 7.415 | 48.89 | -18.029 | 1 | 18.37 | C |
| ATOM | 4876 | O | LEU | C | 157 | 7.014 | 47.726 | -17.935 | 1 | 16.44 | O |
| ATOM | 4877 | CB | LEU | C | 157 | 6.922 | 49.845 | -15.762 | 1 | 19.33 | C |
| ATOM | 4878 | CG | LEU | C | 157 | 8.315 | 50.182 | -15.225 | 1 | 17.68 | C |
| ATOM | 4879 | CD1 | LEU | C | 157 | 8.587 | 51.676 | -15.326 | 1 | 18.67 | C |
| ATOM | 4880 | CD2 | LEU | C | 157 | 8.458 | 49.706 | -13.788 | 1 | 20.64 | C |
| ATOM | 4881 | H | LEU | C | 157 | 4.812 | 49.522 | -17.099 | 1 | 22.01 | H |
| ATOM | 4882 | HA | LEU | C | 157 | 7.117 | 50.856 | -17.538 | 1 | 21.28 | H |
| ATOM | 4883 | HB2 | LEU | C | 157 | 6.29 | 50.418 | -15.302 | 1 | 23.19 | H |
| ATOM | 4884 | HB3 | LEU | C | 157 | 6.742 | 48.919 | -15.534 | 1 | 23.19 | H |

TABLE 5-continued

Atomic Coordinates for OMCP-NKG2D (4PDC).

| ATOM | 4885 | HG | LEU | C | 157 | 8.979 | -15.76 | 49.72 | 1 | 21.22 | H |
|---|---|---|---|---|---|---|---|---|---|---|---|
| ATOM | 4886 | HD11 | LEU | C | 157 | 9.474 | -14.979 | 51.859 | 1 | 22.41 | H |
| ATOM | 4887 | HD12 | LEU | C | 157 | 8.533 | -16.257 | 51.944 | 1 | 22.41 | H |
| ATOM | 4888 | HD13 | LEU | C | 157 | 7.922 | -14.805 | 52.153 | 1 | 22.41 | H |
| ATOM | 4889 | HD21 | LEU | C | 157 | 9.346 | -13.469 | 49.93 | 1 | 24.77 | H |
| ATOM | 4890 | HD22 | LEU | C | 157 | 7.788 | -13.242 | 50.147 | 1 | 24.77 | H |
| ATOM | 4891 | HD23 | LEU | C | 157 | 8.327 | -13.759 | 48.745 | 1 | 24.77 | H |
| ATOM | 4892 | N | VAL | C | 158 | 8.462 | -18.774 | 49.247 | 1 | 19.08 | N |
| ATOM | 4893 | CA | VAL | C | 158 | 9.199 | -19.595 | 48.292 | 1 | 18.04 | C |
| ATOM | 4894 | C | VAL | C | 158 | 10.704 | -19.349 | 48.381 | 1 | 20.45 | C |
| ATOM | 4895 | O | VAL | C | 158 | 11.209 | -18.873 | 49.396 | 1 | 18.61 | O |
| ATOM | 4896 | CB | VAL | C | 158 | 8.931 | -21.093 | 48.512 | 1 | 17.89 | C |
| ATOM | 4897 | CG1 | VAL | C | 158 | 7.446 | -21.402 | 48.311 | 1 | 18.67 | C |
| ATOM | 4898 | CG2 | VAL | C | 158 | 9.398 | -21.522 | 49.897 | 1 | 16.63 | C |
| ATOM | 4899 | H | VAL | C | 158 | 8.768 | -18.819 | 50.049 | 1 | 22.89 | H |
| ATOM | 4900 | HA | VAL | C | 158 | 8.911 | -19.369 | 47.394 | 1 | 21.65 | H |
| ATOM | 4901 | HB | VAL | C | 158 | 9.433 | -21.602 | 47.857 | 1 | 21.47 | H |
| ATOM | 4902 | HG11 | VAL | C | 158 | 7.299 | -22.35 | 48.454 | 1 | 22.4 | H |
| ATOM | 4903 | HG12 | VAL | C | 158 | 7.194 | -21.161 | 47.405 | 1 | 22.4 | H |
| ATOM | 4904 | HG13 | VAL | C | 158 | 6.927 | -20.887 | 48.947 | 1 | 22.4 | H |
| ATOM | 4905 | HG21 | VAL | C | 158 | 9.218 | -22.469 | 50.011 | 1 | 19.96 | H |
| ATOM | 4906 | HG22 | VAL | C | 158 | 8.916 | -21.01 | 50.565 | 1 | 19.96 | H |
| ATOM | 4907 | HG23 | VAL | C | 158 | 10.35 | -21.354 | 49.975 | 1 | 19.96 | H |
| ATOM | 4908 | N | HIS | C | 159 | 11.405 | -19.716 | 47.314 | 1 | 16.25 | N |
| ATOM | 4909 | CA | HIS | C | 159 | 12.812 | -19.375 | 47.135 | 1 | 21 | C |
| ATOM | 4910 | C | HIS | C | 159 | 13.698 | -20.616 | 47.078 | 1 | 21.62 | C |
| ATOM | 4911 | O | HIS | C | 159 | 13.47 | -21.516 | 46.273 | 1 | 19.38 | O |
| ATOM | 4912 | CB | HIS | C | 159 | 12.968 | -18.552 | 45.855 | 1 | 25.11 | C |
| ATOM | 4913 | CG | HIS | C | 159 | 14.385 | -18.249 | 45.484 | 1 | 23.93 | C |
| ATOM | 4914 | ND1 | HIS | C | 159 | 15.041 | -18.901 | 44.462 | 1 | 30.14 | N |
| ATOM | 4915 | CD2 | HIS | C | 159 | 15.265 | -17.348 | 45.983 | 1 | 28.59 | C |
| ATOM | 4916 | CE1 | HIS | C | 159 | 16.269 | -18.423 | 44.354 | 1 | 30.59 | C |
| ATOM | 4917 | NE2 | HIS | C | 159 | 16.43 | -17.479 | 45.265 | 1 | 31.14 | N |
| ATOM | 4918 | H | HIS | C | 159 | 11.079 | -20.174 | 46.663 | 1 | 19.5 | H |
| ATOM | 4919 | HA | HIS | C | 159 | 13.104 | -18.83 | 47.882 | 1 | 25.2 | H |
| ATOM | 4920 | HB2 | HIS | C | 159 | 12.507 | -17.706 | 45.971 | 1 | 30.13 | H |
| ATOM | 4921 | HB3 | HIS | C | 159 | 12.57 | -19.043 | 45.119 | 1 | 30.13 | H |
| ATOM | 4922 | HD1 | HIS | C | 159 | 14.706 | -19.525 | 43.974 | 1 | 36.16 | H |
| ATOM | 4923 | HD2 | HIS | C | 159 | 15.112 | -16.756 | 46.683 | 1 | 34.31 | H |
| ATOM | 4924 | HE1 | HIS | C | 159 | 16.91 | -18.703 | 43.742 | 1 | 36.71 | H |
| ATOM | 4925 | HE2 | HIS | C | 159 | 17.147 | -17.022 | 45.39 | 1 | 37.37 | H |
| ATOM | 4926 | N | ILE | C | 160 | 14.703 | -20.656 | 47.947 | 1 | 25.17 | N |
| ATOM | 4927 | CA | ILE | C | 160 | 15.714 | -21.708 | 47.923 | 1 | 25.24 | C |
| ATOM | 4928 | C | ILE | C | 160 | 16.835 | -21.317 | 46.958 | 1 | 32.27 | C |
| ATOM | 4929 | O | ILE | C | 160 | 17.581 | -20.379 | 47.241 | 1 | 31.75 | O |
| ATOM | 4930 | CB | ILE | C | 160 | 16.31 | -21.947 | 49.328 | 1 | 29.66 | C |
| ATOM | 4931 | CG1 | ILE | C | 160 | 15.219 | -22.407 | 50.296 | 1 | 26.24 | C |
| ATOM | 4932 | CG2 | ILE | C | 160 | 17.433 | -22.976 | 49.264 | 1 | 33.94 | C |
| ATOM | 4933 | CD1 | ILE | C | 160 | 15.673 | -22.507 | 51.741 | 1 | 35.2 | C |
| ATOM | 4934 | H | ILE | C | 160 | 14.822 | -20.076 | 48.571 | 1 | 30.21 | H |
| ATOM | 4935 | HA | ILE | C | 160 | 15.314 | -22.535 | 47.613 | 1 | 30.29 | H |

TABLE 5-continued

Atomic Coordinates for OMCP-NKG2D (4PDC).

| | | | | | | | | | | |
|---|---|---|---|---|---|---|---|---|---|---|
| ATOM | 4936 | HB | ILE | C | 160 | 16.677 | 49.653 | -21.11 | 1 | 35.59 | H |
| ATOM | 4937 | HG12 | ILE | C | 160 | 14.91 | 50.022 | -23.284 | 1 | 31.49 | H |
| ATOM | 4938 | HG13 | ILE | C | 160 | 14.485 | 50.26 | -21.774 | 1 | 31.49 | H |
| ATOM | 4939 | HG21 | ILE | C | 160 | 17.79 | 50.156 | -23.108 | 1 | 40.72 | H |
| ATOM | 4940 | HG22 | ILE | C | 160 | 18.129 | 48.674 | -22.646 | 1 | 40.72 | H |
| ATOM | 4941 | HG23 | ILE | C | 160 | 17.077 | 48.923 | -23.811 | 1 | 40.72 | H |
| ATOM | 4942 | HD11 | ILE | C | 160 | 14.926 | 52.285 | -22.803 | 1 | 42.25 | H |
| ATOM | 4943 | HD12 | ILE | C | 160 | 15.974 | 52.038 | -21.635 | 1 | 42.25 | H |
| ATOM | 4944 | HD13 | ILE | C | 160 | 16.4 | 51.799 | -23.147 | 1 | 42.25 | H |
| ATOM | 4945 | N | PRO | C | 161 | 16.965 | 45.817 | -22.025 | 1 | 32.29 | N |
| ATOM | 4946 | CA | PRO | C | 161 | 18.018 | 44.864 | -21.642 | 1 | 33.49 | C |
| ATOM | 4947 | C | PRO | C | 161 | 19.426 | 45.439 | -21.793 | 1 | 38.43 | C |
| ATOM | 4948 | O | PRO | C | 161 | 20.344 | 45.006 | -21.093 | 1 | 39.19 | O |
| ATOM | 4949 | CB | PRO | C | 161 | 17.81 | 43.692 | -22.612 | 1 | 34.26 | C |
| ATOM | 4950 | CG | PRO | C | 161 | 16.429 | 43.848 | -23.134 | 1 | 31.11 | C |
| ATOM | 4951 | CD | PRO | C | 161 | 16.174 | 45.321 | -23.164 | 1 | 27.41 | C |
| ATOM | 4952 | HA | PRO | C | 161 | 17.887 | 44.559 | -20.731 | 1 | 40.18 | H |
| ATOM | 4953 | HB2 | PRO | C | 161 | 18.456 | 43.747 | -23.333 | 1 | 41.12 | H |
| ATOM | 4954 | HB3 | PRO | C | 161 | 17.902 | 42.853 | -22.134 | 1 | 41.12 | H |
| ATOM | 4955 | HG2 | PRO | C | 161 | 16.374 | 43.474 | -24.028 | 1 | 37.33 | H |
| ATOM | 4956 | HG3 | PRO | C | 161 | 15.804 | 43.405 | -22.539 | 1 | 37.33 | H |
| ATOM | 4957 | HD2 | PRO | C | 161 | 16.497 | 45.705 | -23.994 | 1 | 32.89 | H |
| ATOM | 4958 | HD3 | PRO | C | 161 | 15.231 | 45.505 | -23.028 | 1 | 32.89 | H |
| ATOM | 4959 | N | THR | C | 162 | 19.577 | 46.399 | -22.701 | 1 | 41.08 | N |
| ATOM | 4960 | CA | THR | C | 162 | 20.863 | 47.035 | -22.974 | 1 | 43.65 | C |
| ATOM | 4961 | C | THR | C | 162 | 21.495 | 47.605 | -21.709 | 1 | 48.57 | C |
| ATOM | 4962 | O | THR | C | 162 | 22.589 | 47.196 | -21.318 | 1 | 52.38 | O |
| ATOM | 4963 | CB | THR | C | 162 | 20.704 | 48.164 | -24.03 | 1 | 41.19 | C |
| ATOM | 4964 | OG1 | THR | C | 162 | 20.643 | 47.588 | -25.339 | 1 | 51.79 | O |
| ATOM | 4965 | CG2 | THR | C | 162 | 21.861 | 49.168 | -23.983 | 1 | 50.32 | C |
| ATOM | 4966 | H | THR | C | 162 | 18.934 | 46.707 | -23.182 | 1 | 49.29 | H |
| ATOM | 4967 | HA | THR | C | 162 | 21.47 | 46.371 | -23.337 | 1 | 52.38 | H |
| ATOM | 4968 | HB | THR | C | 162 | 19.88 | 48.646 | -23.857 | 1 | 49.42 | H |
| ATOM | 4969 | HG1 | THR | C | 162 | 19.988 | 47.065 | -25.393 | 1 | 62.14 | H |
| ATOM | 4970 | HG21 | THR | C | 162 | 21.73 | 49.857 | -24.653 | 1 | 60.38 | H |
| ATOM | 4971 | HG22 | THR | C | 162 | 21.904 | 49.584 | -23.107 | 1 | 60.38 | H |
| ATOM | 4972 | HG23 | THR | C | 162 | 22.701 | 48.714 | -24.157 | 1 | 60.38 | H |
| ATOM | 4973 | N | ASN | C | 163 | 20.799 | 48.544 | -21.075 | 1 | 46.77 | N |
| ATOM | 4974 | CA | ASN | C | 163 | 21.34 | 49.264 | -19.928 | 1 | 44.73 | C |
| ATOM | 4975 | C | ASN | C | 163 | 20.59 | 48.965 | -18.63 | 1 | 46.38 | C |
| ATOM | 4976 | O | ASN | C | 163 | 20.716 | 49.698 | -17.648 | 1 | 47.39 | O |
| ATOM | 4977 | CB | ASN | C | 163 | 21.324 | 50.768 | -20.213 | 1 | 48.3 | C |
| ATOM | 4978 | CG | ASN | C | 163 | 19.972 | 51.258 | -20.685 | 1 | 47.25 | C |
| ATOM | 4979 | OD1 | ASN | C | 163 | 18.934 | 50.711 | -20.313 | 1 | 46.02 | O |
| ATOM | 4980 | ND2 | ASN | C | 163 | 19.978 | 52.292 | -21.52 | 1 | 46.65 | N |
| ATOM | 4981 | H | ASN | C | 163 | 20.003 | 48.784 | -21.292 | 1 | 56.13 | H |
| ATOM | 4982 | HA | ASN | C | 163 | 22.264 | 48.998 | -19.802 | 1 | 53.68 | H |
| ATOM | 4983 | HB2 | ASN | C | 163 | 21.55 | 51.246 | -19.399 | 1 | 57.96 | H |
| ATOM | 4984 | HB3 | ASN | C | 163 | 21.974 | 50.965 | -20.905 | 1 | 57.96 | H |
| ATOM | 4985 | HD21 | ASN | C | 163 | 19.236 | 52.608 | -21.817 | 1 | 55.98 | H |
| ATOM | 4986 | HD22 | ASN | C | 163 | 20.724 | 52.645 | -21.762 | 1 | 55.98 | H |

TABLE 5-continued

Atomic Coordinates for OMCP-NKG2D (4PDC).

| ATOM | 4987 | N | GLY | C | 164 | 19.813 | -18.633 | 47.885 | 1 | 43.17 | N |
|------|------|------|-----|---|-----|--------|---------|--------|---|-------|---|
| ATOM | 4988 | CA | GLY | C | 164 | 19.118 | -17.441 | 47.429 | 1 | 38.67 | C |
| ATOM | 4989 | C | GLY | C | 164 | 18.202 | -16.815 | 48.466 | 1 | 39.65 | C |
| ATOM | 4990 | O | GLY | C | 164 | 17.958 | -15.609 | 48.435 | 1 | 42.49 | O |
| ATOM | 4991 | H | GLY | C | 164 | 19.673 | -19.326 | 47.394 | 1 | 51.8 | H |
| ATOM | 4992 | HA2 | GLY | C | 164 | 18.584 | -17.664 | 46.651 | 1 | 46.4 | H |
| ATOM | 4993 | HA3 | GLY | C | 164 | 19.772 | -16.775 | 47.165 | 1 | 46.4 | H |
| ATOM | 4994 | N | SER | C | 165 | 17.686 | -17.636 | 49.376 | 1 | 34.82 | N |
| ATOM | 4995 | CA | SER | C | 165 | 16.856 | -17.153 | 50.474 | 1 | 32.2 | C |
| ATOM | 4996 | C | SER | C | 165 | 15.364 | -17.287 | 50.169 | 1 | 27.87 | C |
| ATOM | 4997 | O | SER | C | 165 | 14.943 | -18.223 | 49.486 | 1 | 25.68 | O |
| ATOM | 4998 | CB | SER | C | 165 | 17.193 | -17.917 | 51.756 | 1 | 38.18 | C |
| ATOM | 4999 | OG | SER | C | 165 | 16.391 | -17.475 | 52.837 | 1 | 43.62 | O |
| ATOM | 5000 | H | SER | C | 165 | 17.803 | -18.488 | 49.378 | 1 | 41.79 | H |
| ATOM | 5001 | HA | SER | C | 165 | 17.048 | -16.214 | 50.625 | 1 | 38.64 | H |
| ATOM | 5002 | HB2 | SER | C | 165 | 18.126 | -17.769 | 51.976 | 1 | 45.81 | H |
| ATOM | 5003 | HB3 | SER | C | 165 | 17.032 | -18.863 | 51.611 | 1 | 45.81 | H |
| ATOM | 5004 | HG | SER | C | 165 | 16.586 | -17.903 | 53.533 | 1 | 52.34 | H |
| ATOM | 5005 | N | TRP | C | 166 | 14.579 | -16.34 | 50.679 | 1 | 31.94 | N |
| ATOM | 5006 | CA | TRP | C | 166 | 13.119 | -16.387 | 50.583 | 1 | 23.07 | C |
| ATOM | 5007 | C | TRP | C | 166 | 12.515 | -16.699 | 51.944 | 1 | 27.85 | C |
| ATOM | 5008 | O | TRP | C | 166 | 12.805 | -16.018 | 52.927 | 1 | 29.97 | O |
| ATOM | 5009 | CB | TRP | C | 166 | 12.561 | -15.063 | 50.059 | 1 | 22.45 | C |
| ATOM | 5010 | CG | TRP | C | 166 | 12.817 | -14.846 | 48.608 | 1 | 20.87 | C |
| ATOM | 5011 | CD1 | TRP | C | 166 | 13.887 | -14.214 | 48.054 | 1 | 28.32 | C |
| ATOM | 5012 | CD2 | TRP | C | 166 | 11.989 | -15.267 | 47.519 | 1 | 20.19 | C |
| ATOM | 5013 | NE1 | TRP | C | 166 | 13.779 | -14.212 | 46.685 | 1 | 29.81 | N |
| ATOM | 5014 | CE2 | TRP | C | 166 | 12.622 | -14.853 | 46.331 | 1 | 21.03 | C |
| ATOM | 5015 | CE3 | TRP | C | 166 | 10.773 | -15.951 | 47.434 | 1 | 18.26 | C |
| ATOM | 5016 | CZ2 | TRP | C | 166 | 12.082 | -15.1 | 45.074 | 1 | 20.42 | C |
| ATOM | 5017 | CZ3 | TRP | C | 166 | 10.238 | -16.198 | 46.186 | 1 | 19.14 | C |
| ATOM | 5018 | CH2 | TRP | C | 166 | 10.89 | -15.772 | 45.02 | 1 | 22.75 | C |
| ATOM | 5019 | H | TRP | C | 166 | 14.873 | -15.646 | 51.093 | 1 | 38.33 | H |
| ATOM | 5020 | HA | TRP | C | 166 | 12.861 | -17.091 | 49.968 | 1 | 27.68 | H |
| ATOM | 5021 | HB2 | TRP | C | 166 | 12.974 | -14.334 | 50.547 | 1 | 26.94 | H |
| ATOM | 5022 | HB3 | TRP | C | 166 | 11.601 | -15.051 | 50.197 | 1 | 26.94 | H |
| ATOM | 5023 | HD1 | TRP | C | 166 | 14.591 | -13.838 | 48.532 | 1 | 33.98 | H |
| ATOM | 5024 | HE1 | TRP | C | 166 | 14.345 | -13.865 | 46.139 | 1 | 35.77 | H |
| ATOM | 5025 | HE3 | TRP | C | 166 | 10.335 | -16.237 | 48.203 | 1 | 21.91 | H |
| ATOM | 5026 | HZ2 | TRP | C | 166 | 12.513 | -14.818 | 44.299 | 1 | 24.5 | H |
| ATOM | 5027 | HZ3 | TRP | C | 166 | 9.429 | -16.653 | 46.117 | 1 | 22.96 | H |
| ATOM | 5028 | HH2 | TRP | C | 166 | 10.506 | -15.952 | 44.192 | 1 | 27.3 | H |
| ATOM | 5029 | N | GLN | C | 167 | 11.676 | -17.727 | 52.003 | 1 | 22.33 | N |
| ATOM | 5030 | CA | GLN | C | 167 | 11.066 | -18.126 | 53.265 | 1 | 24.92 | C |
| ATOM | 5031 | C | GLN | C | 167 | 9.614 | -18.554 | 53.084 | 1 | 20.54 | C |
| ATOM | 5032 | O | GLN | C | 167 | 9.185 | -18.912 | 51.984 | 1 | 18.82 | O |
| ATOM | 5033 | CB | GLN | C | 167 | 11.872 | -19.257 | 53.904 | 1 | 26.21 | C |
| ATOM | 5034 | CG | GLN | C | 167 | 11.91 | -20.54 | 53.089 | 1 | 31.52 | C |
| ATOM | 5035 | CD | GLN | C | 167 | 12.781 | -21.61 | 53.73 | 1 | 33.46 | C |
| ATOM | 5036 | OE1 | GLN | C | 167 | 13.768 | -21.306 | 54.399 | 1 | 35.78 | O |
| ATOM | 5037 | NE2 | GLN | C | 167 | 12.412 | -22.87 | 53.532 | 1 | 34.85 | N |

TABLE 5-continued

Atomic Coordinates for OMCP-NKG2D (4PDC).

| | | | | | | | | | | |
|---|---|---|---|---|---|---|---|---|---|---|
| ATOM | 5038 | H | GLN | C | 167 | 11.444 | -18.209 | 51.33 | 1 | 26.8 | H |
| ATOM | 5039 | HA | GLN | C | 167 | 11.08 | -17.37 | 53.873 | 1 | 29.9 | H |
| ATOM | 5040 | HB2 | GLN | C | 167 | 11.482 | -19.467 | 54.767 | 1 | 31.45 | H |
| ATOM | 5041 | HB3 | GLN | C | 167 | 12.787 | -18.958 | 54.024 | 1 | 31.45 | H |
| ATOM | 5042 | HG2 | GLN | C | 167 | 12.269 | -20.347 | 52.209 | 1 | 37.82 | H |
| ATOM | 5043 | HG3 | GLN | C | 167 | 11.009 | -20.892 | 53.011 | 1 | 37.82 | H |
| ATOM | 5044 | HE21 | GLN | C | 167 | 12.872 | -23.511 | 53.873 | 1 | 41.82 | H |
| ATOM | 5045 | HE22 | GLN | C | 167 | 11.713 | -23.044 | 53.062 | 1 | 41.82 | H |
| ATOM | 5046 | N | TRP | C | 168 | 8.865 | -18.504 | 54.18 | 1 | 19.48 | N |
| ATOM | 5047 | CA | TRP | C | 168 | 7.471 | -18.926 | 54.186 | 1 | 24.91 | C |
| ATOM | 5048 | C | TRP | C | 168 | 7.401 | -20.439 | 54.322 | 1 | 28.19 | C |
| ATOM | 5049 | O | TRP | C | 168 | 8.39 | -21.077 | 54.684 | 1 | 29.68 | O |
| ATOM | 5050 | CB | TRP | C | 168 | 6.715 | -18.236 | 55.32 | 1 | 22.9 | C |
| ATOM | 5051 | CG | TRP | C | 168 | 6.806 | -16.746 | 55.241 | 1 | 18.59 | C |
| ATOM | 5052 | CD1 | TRP | C | 168 | 7.589 | -15.932 | 56.003 | 1 | 20.28 | C |
| ATOM | 5053 | CD2 | TRP | C | 168 | 6.101 | -15.89 | 54.331 | 1 | 18.57 | C |
| ATOM | 5054 | NE1 | TRP | C | 168 | 7.41 | -14.62 | 55.631 | 1 | 19.79 | N |
| ATOM | 5055 | CE2 | TRP | C | 168 | 6.501 | -14.568 | 54.607 | 1 | 18.17 | C |
| ATOM | 5056 | CE3 | TRP | C | 168 | 5.168 | -16.114 | 53.313 | 1 | 19.34 | C |
| ATOM | 5057 | CZ2 | TRP | C | 168 | 6 | -13.474 | 53.903 | 1 | 19.51 | C |
| ATOM | 5058 | CZ3 | TRP | C | 168 | 4.672 | -15.028 | 52.614 | 1 | 18.19 | C |
| ATOM | 5059 | CH2 | TRP | C | 168 | 5.09 | -13.724 | 52.912 | 1 | 17.53 | C |
| ATOM | 5060 | H | TRP | C | 168 | 9.146 | -18.225 | 54.943 | 1 | 23.37 | H |
| ATOM | 5061 | HA | TRP | C | 168 | 7.056 | -18.676 | 53.346 | 1 | 29.89 | H |
| ATOM | 5062 | HB2 | TRP | C | 168 | 7.091 | -18.516 | 56.169 | 1 | 27.48 | H |
| ATOM | 5063 | HB3 | TRP | C | 168 | 5.778 | -18.483 | 55.272 | 1 | 27.48 | H |
| ATOM | 5064 | HD1 | TRP | C | 168 | 8.158 | -16.222 | 56.679 | 1 | 24.34 | H |
| ATOM | 5065 | HE1 | TRP | C | 168 | 7.804 | -13.942 | 55.985 | 1 | 23.74 | H |
| ATOM | 5066 | HE3 | TRP | C | 168 | 4.886 | -16.977 | 53.11 | 1 | 23.2 | H |
| ATOM | 5067 | HZ2 | TRP | C | 168 | 6.276 | -12.607 | 54.098 | 1 | 23.42 | H |
| ATOM | 5068 | HZ3 | TRP | C | 168 | 4.051 | -15.166 | 51.936 | 1 | 21.83 | H |
| ATOM | 5069 | HH2 | TRP | C | 168 | 4.739 | -13.013 | 52.427 | 1 | 21.04 | H |
| ATOM | 5070 | N | GLU | C | 169 | 6.242 | -21.02 | 54.03 | 1 | 30.7 | N |
| ATOM | 5071 | CA | GLU | C | 169 | 6.122 | -22.474 | 54.022 | 1 | 35.6 | C |
| ATOM | 5072 | C | GLU | C | 169 | 6.155 | -23.049 | 55.434 | 1 | 36.18 | C |
| ATOM | 5073 | O | GLU | C | 169 | 6.337 | -24.254 | 55.608 | 1 | 37.85 | O |
| ATOM | 5074 | CB | GLU | C | 169 | 4.844 | -22.91 | 53.301 | 1 | 39.61 | C |
| ATOM | 5075 | CG | GLU | C | 169 | 3.559 | -22.49 | 53.974 | 1 | 33.74 | C |
| ATOM | 5076 | CD | GLU | C | 169 | 2.372 | -22.532 | 53.021 | 1 | 38.01 | C |
| ATOM | 5077 | OE1 | GLU | C | 169 | 2.228 | -23.532 | 52.285 | 1 | 37.73 | O |
| ATOM | 5078 | OE2 | GLU | C | 169 | 1.587 | -21.562 | 53.002 | 1 | 35.4 | O1- |
| ATOM | 5079 | H | GLU | C | 169 | 5.517 | -20.6 | 53.835 | 1 | 36.84 | H |
| ATOM | 5080 | HA | GLU | C | 169 | 6.876 | -22.844 | 53.536 | 1 | 42.72 | H |
| ATOM | 5081 | HB2 | GLU | C | 169 | 4.84 | -23.878 | 53.24 | 1 | 47.53 | H |
| ATOM | 5082 | HB3 | GLU | C | 169 | 4.847 | -22.528 | 52.41 | 1 | 47.53 | H |
| ATOM | 5083 | HG2 | GLU | C | 169 | 3.653 | -21.581 | 54.299 | 1 | 40.49 | H |
| ATOM | 5084 | HG3 | GLU | C | 169 | 3.375 | -23.092 | 54.712 | 1 | 40.49 | H |
| ATOM | 5085 | N | ASP | C | 170 | 5.994 | -22.192 | 56.44 | 1 | 34.47 | N |
| ATOM | 5086 | CA | ASP | C | 170 | 6.132 | -22.629 | 57.827 | 1 | 33.57 | C |
| ATOM | 5087 | C | ASP | C | 170 | 7.609 | -22.703 | 58.221 | 1 | 33.88 | C |
| ATOM | 5088 | O | ASP | C | 170 | 7.943 | -23.127 | 59.327 | 1 | 37.21 | O |

TABLE 5-continued

Atomic Coordinates for OMCP-NKG2D (4PDC).

| ATOM | 5089 | CB | ASP | C | 170 | 5.363 | 58.777 | -21.699 | 1 | 36.54 | C |
| --- | --- | --- | --- | --- | --- | --- | --- | --- | --- | --- | --- |
| ATOM | 5090 | CG | ASP | C | 170 | 6.038 | 58.968 | -20.348 | 1 | 37.03 | C |
| ATOM | 5091 | OD1 | ASP | C | 170 | 6.943 | 58.181 | -19.995 | 1 | 34.2 | O |
| ATOM | 5092 | OD2 | ASP | C | 170 | 5.647 | 59.913 | -19.628 | 1 | 37.14 | O1- |
| ATOM | 5093 | H | ASP | C | 170 | 5.805 | 56.348 | -21.358 | 1 | 41.36 | H |
| ATOM | 5094 | HA | ASP | C | 170 | 5.756 | 57.914 | -23.519 | 1 | 40.28 | H |
| ATOM | 5095 | HB2 | ASP | C | 170 | 5.293 | 59.646 | -22.124 | 1 | 43.84 | H |
| ATOM | 5096 | HB3 | ASP | C | 170 | 4.477 | 58.414 | -21.541 | 1 | 43.84 | H |
| ATOM | 5097 | N | GLY | C | 171 | 8.484 | 57.311 | -22.277 | 1 | 32.03 | N |
| ATOM | 5098 | CA | GLY | C | 171 | 9.92 | 57.506 | -22.382 | 1 | 35.58 | C |
| ATOM | 5099 | C | GLY | C | 171 | 10.576 | 57.946 | -21.087 | 1 | 32.1 | C |
| ATOM | 5100 | O | GLY | C | 171 | 11.79 | 57.817 | -20.924 | 1 | 32.64 | O |
| ATOM | 5101 | H | GLY | C | 171 | 8.262 | 56.562 | -21.919 | 1 | 38.44 | H |
| ATOM | 5102 | HA2 | GLY | C | 171 | 10.334 | 56.676 | -22.664 | 1 | 42.69 | H |
| ATOM | 5103 | HA3 | GLY | C | 171 | 10.101 | 58.18 | -23.056 | 1 | 42.69 | H |
| ATOM | 5104 | N | SER | C | 172 | 9.777 | 58.463 | -20.159 | 1 | 32.52 | N |
| ATOM | 5105 | CA | SER | C | 172 | 10.301 | 58.957 | -18.891 | 1 | 30.32 | C |
| ATOM | 5106 | C | SER | C | 172 | 10.86 | 57.828 | -18.032 | 1 | 29.58 | C |
| ATOM | 5107 | O | SER | C | 172 | 10.442 | 56.675 | -18.146 | 1 | 27.69 | O |
| ATOM | 5108 | CB | SER | C | 172 | 9.213 | 59.703 | -18.117 | 1 | 33.73 | C |
| ATOM | 5109 | OG | SER | C | 172 | 8.138 | 58.839 | -17.786 | 1 | 33.64 | O |
| ATOM | 5110 | H | SER | C | 172 | 8.924 | 58.538 | -20.24 | 1 | 39.02 | H |
| ATOM | 5111 | HA | SER | C | 172 | 11.022 | 59.582 | -19.07 | 1 | 36.38 | H |
| ATOM | 5112 | HB2 | SER | C | 172 | 9.595 | 60.058 | -17.299 | 1 | 40.48 | H |
| ATOM | 5113 | HB3 | SER | C | 172 | 8.876 | 60.428 | -18.666 | 1 | 40.48 | H |
| ATOM | 5114 | HG | SER | C | 172 | 7.797 | 58.524 | -18.486 | 1 | 40.37 | H |
| ATOM | 5115 | N | ILE | C | 173 | 11.811 | 58.174 | -17.17 | 1 | 28.71 | N |
| ATOM | 5116 | CA | ILE | C | 173 | 12.416 | 57.214 | -16.256 | 1 | 33.4 | C |
| ATOM | 5117 | C | ILE | C | 173 | 11.462 | 56.904 | -15.106 | 1 | 29.48 | C |
| ATOM | 5118 | O | ILE | C | 173 | 10.612 | 57.725 | -14.757 | 1 | 29.36 | O |
| ATOM | 5119 | CB | ILE | C | 173 | 13.759 | 57.752 | -15.691 | 1 | 31.94 | C |
| ATOM | 5120 | CG1 | ILE | C | 173 | 14.496 | 56.691 | -14.868 | 1 | 40.78 | C |
| ATOM | 5121 | CG2 | ILE | C | 173 | 13.529 | 59 | -14.843 | 1 | 39.11 | C |
| ATOM | 5122 | CD1 | ILE | C | 173 | 14.933 | 55.482 | -15.661 | 1 | 47.43 | C |
| ATOM | 5123 | H | ILE | C | 173 | 12.126 | 58.971 | -17.095 | 1 | 34.45 | H |
| ATOM | 5124 | HA | ILE | C | 173 | 12.596 | 56.388 | -16.732 | 1 | 40.08 | H |
| ATOM | 5125 | HB | ILE | C | 173 | 14.324 | 57.997 | -16.44 | 1 | 38.33 | H |
| ATOM | 5126 | HG12 | ILE | C | 173 | 15.29 | 57.093 | -14.482 | 1 | 48.94 | H |
| ATOM | 5127 | HG13 | ILE | C | 173 | 13.908 | 56.383 | 14.16 | 1 | 48.94 | H |
| ATOM | 5128 | HG21 | ILE | C | 173 | 14.382 | 59.313 | -14.504 | 1 | 46.93 | H |
| ATOM | 5129 | HG22 | ILE | C | 173 | 13.12 | 59.685 | -15.395 | 1 | 46.93 | H |
| ATOM | 5130 | HG23 | ILE | C | 173 | 12.941 | 58.776 | -14.105 | 1 | 46.93 | H |
| ATOM | 5131 | HD11 | ILE | C | 173 | 14.151 | 55.057 | -16.044 | 1 | 56.92 | H |
| ATOM | 5132 | HD12 | ILE | C | 173 | 15.534 | 55.768 | -16.366 | 1 | 56.92 | H |
| ATOM | 5133 | HD13 | ILE | C | 173 | 15.389 | 54.864 | -15.068 | 1 | 56.92 | H |
| ATOM | 5134 | N | LEU | C | 174 | 11.589 | 55.712 | -14.534 | 1 | 25.61 | N |
| ATOM | 5135 | CA | LEU | C | 174 | 10.914 | 55.404 | -13.281 | 1 | 23.61 | C |
| ATOM | 5136 | C | LEU | C | 174 | 11.49 | 56.287 | -12.185 | 1 | 26.93 | C |
| ATOM | 5137 | O | LEU | C | 174 | 12.652 | 56.136 | -11.819 | 1 | 26.37 | O |
| ATOM | 5138 | CB | LEU | C | 174 | 11.087 | 53.932 | -12.917 | 1 | 21.37 | C |
| ATOM | 5139 | CG | LEU | C | 174 | 10.642 | 53.521 | -11.513 | 1 | 18.27 | C |

TABLE 5-continued

Atomic Coordinates for OMCP-NKG2D (4PDC).

| | | | | | | | | | | |
|---|---|---|---|---|---|---|---|---|---|---|
| ATOM | 5140 | CD1 | LEU | C | 174 | 9.132 | -11.367 | 53.664 | 1 | 19.7 | C |
| ATOM | 5141 | CD2 | LEU | C | 174 | 11.086 | -11.213 | 52.1 | 1 | 21.64 | C |
| ATOM | 5142 | H | LEU | C | 174 | 12.059 | -14.851 | 55.066 | 1 | 30.74 | H |
| ATOM | 5143 | HA | LEU | C | 174 | 9.967 | -13.366 | 55.593 | 1 | 28.33 | H |
| ATOM | 5144 | HB2 | LEU | C | 174 | 10.575 | -13.548 | 53.402 | 1 | 25.65 | H |
| ATOM | 5145 | HB3 | LEU | C | 174 | 12.027 | -12.998 | 53.708 | 1 | 25.65 | H |
| ATOM | 5146 | HG | LEU | C | 174 | 11.061 | -10.865 | 54.109 | 1 | 21.92 | H |
| ATOM | 5147 | HD11 | LEU | C | 174 | 8.875 | -10.47 | 53.398 | 1 | 23.64 | H |
| ATOM | 5148 | HD12 | LEU | C | 174 | 8.886 | -11.521 | 54.59 | 1 | 23.64 | H |
| ATOM | 5149 | HD13 | LEU | C | 174 | 8.697 | -12.019 | 53.093 | 1 | 23.64 | H |
| ATOM | 5150 | HD21 | LEU | C | 174 | 10.794 | -10.32 | 51.86 | 1 | 25.97 | H |
| ATOM | 5151 | HD22 | LEU | C | 174 | 10.687 | -11.864 | 51.501 | 1 | 25.97 | H |
| ATOM | 5152 | HD23 | LEU | C | 174 | 12.053 | -11.269 | 52.054 | 1 | 25.97 | H |
| ATOM | 5153 | N | SER | C | 175 | 10.689 | -11.661 | 57.209 | 1 | 26.24 | N |
| ATOM | 5154 | CA | SER | C | 175 | 11.166 | -10.595 | 58.084 | 1 | 23.83 | C |
| ATOM | 5155 | C | SER | C | 175 | 11.378 | -9.308 | 57.288 | 1 | 25.15 | C |
| ATOM | 5156 | O | SER | C | 175 | 10.734 | -9.099 | 56.258 | 1 | 21.9 | O |
| ATOM | 5157 | CB | SER | C | 175 | 10.187 | -10.365 | 59.234 | 1 | 27.9 | C |
| ATOM | 5158 | OG | SER | C | 175 | 10.203 | -11.461 | 60.135 | 1 | 34.12 | O |
| ATOM | 5159 | H | SER | C | 175 | 9.875 | -11.901 | 57.348 | 1 | 31.49 | H |
| ATOM | 5160 | HA | SER | C | 175 | 12.019 | -10.856 | 58.464 | 1 | 28.6 | H |
| ATOM | 5161 | HB2 | SER | C | 175 | 9.293 | -10.266 | 58.873 | 1 | 33.49 | H |
| ATOM | 5162 | HB3 | SER | C | 175 | 10.444 | -9.56 | 59.711 | 1 | 33.49 | H |
| ATOM | 5163 | HG | SER | C | 175 | 9.662 | -11.324 | 60.763 | 1 | 40.94 | H |
| ATOM | 5164 | N | PRO | C | 176 | 12.289 | -8.44 | 57.76 | 1 | 23.75 | N |
| ATOM | 5165 | CA | PRO | C | 176 | 12.646 | -7.232 | 57.005 | 1 | 23.82 | C |
| ATOM | 5166 | C | PRO | C | 176 | 11.56 | -6.157 | 57.003 | 1 | 26.93 | C |
| ATOM | 5167 | O | PRO | C | 176 | 10.702 | -6.138 | 57.885 | 1 | 25 | O |
| ATOM | 5168 | CB | PRO | C | 176 | 13.901 | -6.726 | 57.735 | 1 | 30.63 | C |
| ATOM | 5169 | CG | PRO | C | 176 | 13.79 | -7.259 | 59.11 | 1 | 34.23 | C |
| ATOM | 5170 | CD | PRO | C | 176 | 13.094 | -8.584 | 58.987 | 1 | 32.51 | C |
| ATOM | 5171 | HA | PRO | C | 176 | 12.873 | -7.461 | 56.091 | 1 | 28.59 | H |
| ATOM | 5172 | HB2 | PRO | C | 176 | 13.907 | -5.756 | 57.735 | 1 | 36.75 | H |
| ATOM | 5173 | HB3 | PRO | C | 176 | 14.694 | -7.073 | 57.29 | 1 | 36.75 | H |
| ATOM | 5174 | HG2 | PRO | C | 176 | 13.266 | -6.648 | 59.652 | 1 | 41.08 | H |
| ATOM | 5175 | HG3 | PRO | C | 176 | 14.676 | -7.374 | 59.486 | 1 | 41.08 | H |
| ATOM | 5176 | HD2 | PRO | C | 176 | 12.518 | -8.734 | 59.753 | 1 | 39.01 | H |
| ATOM | 5177 | HD3 | PRO | C | 176 | 13.742 | -9.298 | 58.884 | 1 | 39.01 | H |
| ATOM | 5178 | N | ASN | C | 177 | 11.611 | -5.28 | 56.003 | 1 | 20.91 | N |
| ATOM | 5179 | CA | ASN | C | 177 | 10.723 | -4.124 | 55.914 | 1 | 26.58 | C |
| ATOM | 5180 | C | ASN | C | 177 | 9.249 | -4.507 | 55.841 | 1 | 27.22 | C |
| ATOM | 5181 | O | ASN | C | 177 | 8.392 | 3.795 | 56.36 | 1 | 27.05 | O |
| ATOM | 5182 | CB | ASN | C | 177 | 10.957 | -3.188 | 57.102 | 1 | 28.67 | C |
| ATOM | 5183 | CG | ASN | C | 177 | 12.372 | -2.644 | 57.143 | 1 | 32.73 | C |
| ATOM | 5184 | OD1 | ASN | C | 177 | 12.886 | -2.152 | 56.139 | 1 | 39.2 | O |
| ATOM | 5185 | ND2 | ASN | C | 177 | 13.013 | -2.739 | 58.302 | 1 | 33.01 | N |
| ATOM | 5186 | H | ASN | C | 177 | 12.166 | -5.335 | 55.348 | 1 | 25.1 | H |
| ATOM | 5187 | HA | ASN | C | 177 | 10.937 | -3.632 | 55.106 | 1 | 31.9 | H |
| ATOM | 5188 | HB2 | ASN | C | 177 | 10.799 | -3.676 | 57.926 | 1 | 34.41 | H |
| ATOM | 5189 | HB3 | ASN | C | 177 | 10.348 | -2.436 | 57.039 | 1 | 34.41 | H |
| ATOM | 5190 | HD21 | ASN | C | 177 | 13.818 | -2.444 | 58.374 | 1 | 39.62 | H |

TABLE 5-continued

Atomic Coordinates for OMCP-NKG2D (4PDC).

| | | | | | | | | | | |
|---|---|---|---|---|---|---|---|---|---|---|
| ATOM | 5191 | HD22 | ASN | C | 177 | 12.623 | 58.981 | -3.095 | 1 | 39.62 | H |
| ATOM | 5192 | N | LEU | C | 178 | 8.961 | 55.193 | -5.631 | 1 | 22.55 | N |
| ATOM | 5193 | CA | LEU | C | 178 | 7.586 | 55.018 | -6.087 | 1 | 22.76 | C |
| ATOM | 5194 | C | LEU | C | 178 | 7.205 | 53.547 | -6.144 | 1 | 24.97 | C |
| ATOM | 5195 | O | LEU | C | 178 | 6.143 | 53.162 | -5.657 | 1 | 27.82 | O |
| ATOM | 5196 | CB | LEU | C | 178 | 7.39 | 55.657 | -7.461 | 1 | 21.51 | C |
| ATOM | 5197 | CG | LEU | C | 178 | 7.366 | 57.186 | -7.511 | 1 | 24.49 | C |
| ATOM | 5198 | CD1 | LEU | C | 178 | 7.248 | 57.64 | -8.953 | 1 | 24.38 | C |
| ATOM | 5199 | CD2 | LEU | C | 178 | 6.224 | 57.756 | -6.679 | 1 | 22.93 | C |
| ATOM | 5200 | H | LEU | C | 178 | 9.549 | 54.842 | -6.152 | 1 | 27.06 | H |
| ATOM | 5201 | HA | LEU | C | 178 | 6.989 | 55.459 | -5.463 | 1 | 27.31 | H |
| ATOM | 5202 | HB2 | LEU | C | 178 | 8.113 | 55.363 | -8.037 | 1 | 25.81 | H |
| ATOM | 5203 | HB3 | LEU | C | 178 | 6.546 | 55.345 | -7.822 | 1 | 25.81 | H |
| ATOM | 5204 | HG | LEU | C | 178 | 8.2 | 57.528 | -7.154 | 1 | 29.39 | H |
| ATOM | 5205 | HD11 | LEU | C | 178 | 7.233 | 58.609 | -8.978 | 1 | 29.25 | H |
| ATOM | 5206 | HD12 | LEU | C | 178 | 8.011 | 57.307 | -9.451 | 1 | 29.25 | H |
| ATOM | 5207 | HD13 | LEU | C | 178 | 6.427 | 57.286 | -9.329 | 1 | 29.25 | H |
| ATOM | 5208 | HD21 | LEU | C | 178 | 6.245 | 58.724 | -6.738 | 1 | 27.52 | H |
| ATOM | 5209 | HD22 | LEU | C | 178 | 5.383 | 57.421 | -7.027 | 1 | 27.52 | H |
| ATOM | 5210 | HD23 | LEU | C | 178 | 8.075 | 57.478 | -5.757 | 1 | 27.52 | H |
| ATOM | 5211 | N | LEU | C | 179 | 8.336 | 52.732 | -6.735 | 1 | 19.58 | N |
| ATOM | 5212 | CA | LEU | C | 179 | 7.821 | 51.303 | -6.896 | 1 | 17.86 | C |
| ATOM | 5213 | C | LEU | C | 179 | 8.977 | 50.444 | -6.402 | 1 | 21.63 | C |
| ATOM | 5214 | O | LEU | C | 179 | 10.147 | 50.751 | -6.648 | 1 | 22.35 | O |
| ATOM | 5215 | CB | LEU | C | 179 | 7.558 | 50.971 | 8.367 | 1 | 21.35 | C |
| ATOM | 5216 | CG | LEU | C | 179 | 6.29 | 51.513 | -9.021 | 1 | 19.98 | C |
| ATOM | 5217 | CD1 | LEU | C | 179 | 6.291 | 51.174 | -10.502 | 1 | 19.74 | C |
| ATOM | 5218 | CD2 | LEU | C | 179 | 5.044 | 50.954 | -8.349 | 1 | 21.35 | C |
| ATOM | 5219 | H | LEU | C | 179 | 8.831 | 52.987 | -7.057 | 1 | 23.5 | H |
| ATOM | 5220 | HA | LEU | C | 179 | 7.03 | 51.064 | -6.388 | 1 | 21.44 | H |
| ATOM | 5221 | HB2 | LEU | C | 179 | 8.306 | 51.307 | 8.885 | 1 | 25.62 | H |
| ATOM | 5222 | HB3 | LEU | C | 179 | 7.526 | 50.005 | -8.451 | 1 | 25.62 | H |
| ATOM | 5223 | HG | LEU | C | 179 | 6.274 | 52.479 | -8.932 | 1 | 23.97 | H |
| ATOM | 5224 | HD11 | LEU | C | 179 | 5.482 | 51.524 | -10.906 | 1 | 23.68 | H |
| ATOM | 5225 | HD12 | LEU | C | 179 | 7.07 | 51.578 | -10.917 | 1 | 23.68 | H |
| ATOM | 5226 | HD13 | LEU | C | 179 | 6.324 | 50.21 | -10.605 | 1 | 23.68 | H |
| ATOM | 5227 | HD21 | LEU | C | 179 | 4.259 | 51.318 | -8.788 | 1 | 25.62 | H |
| ATOM | 5228 | HD22 | LEU | C | 179 | 5.05 | 49.987 | -8.429 | 1 | 25.62 | H |
| ATOM | 5229 | HD23 | LEU | C | 179 | 5.049 | 51.209 | -7.414 | 1 | 25.62 | H |
| ATOM | 5230 | N | THR | C | 180 | 8.639 | 49.362 | -5.708 | 1 | 18.15 | N |
| ATOM | 5231 | CA | THR | C | 180 | 9.6 | 48.313 | -5.406 | 1 | 22.56 | C |
| ATOM | 5232 | C | THR | C | 180 | 9.556 | 47.299 | -6.548 | 1 | 20.55 | C |
| ATOM | 5233 | O | THR | C | 180 | 8.552 | 46.607 | -6.729 | 1 | 17.3 | O |
| ATOM | 5234 | CB | THR | C | 180 | 9.293 | 47.614 | -4.066 | 1 | 21.01 | C |
| ATOM | 5235 | OG1 | THR | C | 180 | 9.224 | 48.585 | -3.015 | 1 | 25.27 | O |
| ATOM | 5236 | CG2 | THR | C | 180 | 10.368 | 46.594 | -3.73 | 1 | 28.16 | C |
| ATOM | 5237 | H | THR | C | 180 | 7.851 | 49.213 | -5.399 | 1 | 21.78 | H |
| ATOM | 5238 | HA | THR | C | 180 | 10.492 | 48.691 | -5.362 | 1 | 27.08 | H |
| ATOM | 5239 | HB | THR | C | 180 | 8.443 | 47.151 | -4.132 | 1 | 25.22 | H |
| ATOM | 5240 | HG1 | THR | C | 180 | 8.616 | 49.142 | -3.178 | 1 | 30.32 | H |
| ATOM | 5241 | HG21 | THR | C | 180 | 10.163 | 46.163 | -2.886 | 1 | 33.79 | H |

TABLE 5-continued

Atomic Coordinates for OMCP-NKG2D (4PDC).

| | | | | | | | | | | |
|---|---|---|---|---|---|---|---|---|---|---|
| ATOM | 5242 | HG22 | THR | C | 180 | 10.413 | 45.92 | -4.426 | 1 | 33.79 | H |
| ATOM | 5243 | HG23 | THR | C | 180 | 11.23 | 47.033 | -3.659 | 1 | 33.79 | H |
| ATOM | 5244 | N | ILE | C | 181 | 10.633 | 47.229 | -7.325 | 1 | 19.65 | N |
| ATOM | 5245 | CA | ILE | C | 181 | 10.726 | 46.266 | -8.42 | 1 | 19.28 | C |
| ATOM | 5246 | C | ILE | C | 181 | 11.226 | 44.924 | -7.902 | 1 | 16.96 | C |
| ATOM | 5247 | O | ILE | C | 181 | 12.275 | 44.842 | -7.261 | 1 | 13.49 | O |
| ATOM | 5248 | CB | ILE | C | 181 | 11.659 | 46.76 | -9.54 | 1 | 21.11 | C |
| ATOM | 5249 | CG1 | ILE | C | 181 | 11.236 | 48.15 | -10.022 | 1 | 18.12 | C |
| ATOM | 5250 | CG2 | ILE | C | 181 | 11.664 | 45.776 | -10.704 | 1 | 19.77 | C |
| ATOM | 5251 | CD1 | ILE | C | 181 | 9.805 | 48.234 | -10.525 | 1 | 25.78 | C |
| ATOM | 5252 | H | ILE | C | 181 | 11.327 | 47.73 | -7.24 | 1 | 23.58 | H |
| ATOM | 5253 | HA | ILE | C | 181 | 9.843 | 46.133 | -8.8 | 1 | 23.13 | H |
| ATOM | 5254 | HB | ILE | C | 181 | 12.56 | 46.819 | -9.185 | 1 | 25.33 | H |
| ATOM | 5255 | HG12 | ILE | C | 181 | 11.326 | 48.775 | -9.285 | 1 | 21.74 | H |
| ATOM | 5256 | HG13 | ILE | C | 181 | 11.82 | 48.417 | -10.749 | 1 | 21.74 | H |
| ATOM | 5257 | HG21 | ILE | C | 181 | 12.258 | 46.107 | -11.395 | 1 | 23.73 | H |
| ATOM | 5258 | HG22 | ILE | C | 181 | 11.974 | 44.913 | -10.386 | 1 | 23.73 | H |
| ATOM | 5259 | HG23 | ILE | C | 181 | 10.762 | 45.695 | -11.053 | 1 | 23.73 | H |
| ATOM | 5260 | HD11 | ILE | C | 181 | 9.623 | 49.144 | -10.808 | 1 | 30.93 | H |
| ATOM | 5261 | HD12 | ILE | C | 181 | 9.698 | 47.627 | -11.274 | 1 | 30.93 | H |
| ATOM | 5262 | HD13 | ILE | C | 181 | 9.203 | 47.984 | -9.807 | 1 | 30.93 | H |
| ATOM | 5263 | N | ILE | C | 182 | 10.471 | 43.873 | 8.193 | 1 | 15.47 | N |
| ATOM | 5264 | CA | ILE | C | 182 | 10.754 | 42.552 | -7.654 | 1 | 15.31 | C |
| ATOM | 5265 | C | ILE | C | 182 | 10.921 | 41.53 | -8.77 | 1 | 20.29 | C |
| ATOM | 5266 | O | ILE | C | 182 | 10.081 | 41.426 | -9.662 | 1 | 15.6 | O |
| ATOM | 5267 | CB | ILE | C | 182 | 9.631 | 42.095 | -6.703 | 1 | 19.87 | C |
| ATOM | 5268 | CG1 | ILE | C | 182 | 9.419 | 43.135 | -5.596 | 1 | 18.35 | C |
| ATOM | 5269 | CG2 | ILE | C | 182 | 9.959 | 40.735 | 6.096 | 1 | 17.54 | C |
| ATOM | 5270 | CD1 | ILE | C | 182 | 8.174 | 42.899 | -4.758 | 1 | 19.47 | C |
| ATOM | 5271 | H | ILE | C | 182 | 9.782 | 43.9 | -8.707 | 1 | 18.56 | H |
| ATOM | 5272 | HA | ILE | C | 182 | 11.582 | 42.586 | -7.149 | 1 | 18.37 | H |
| ATOM | 5273 | HB | ILE | C | 182 | 8.81 | 42.015 | -7.212 | 1 | 23.85 | H |
| ATOM | 5274 | HG12 | ILE | C | 182 | 10.185 | 43.117 | -5.001 | 1 | 22.02 | H |
| ATOM | 5275 | HG13 | ILE | C | 182 | 9.34 | 44.012 | -6.003 | 1 | 22.02 | H |
| ATOM | 5276 | HG21 | ILE | C | 182 | 9.237 | 40.472 | -5.504 | 1 | 21.04 | H |
| ATOM | 5277 | HG22 | ILE | C | 182 | 10.054 | 40.085 | -6.811 | 1 | 21.04 | H |
| ATOM | 5278 | HG23 | ILE | C | 182 | 10.788 | 40.803 | -5.598 | 1 | 21.04 | H |
| ATOM | 5279 | HD11 | ILE | C | 182 | 8.111 | 43.594 | -4.084 | 1 | 23.36 | H |
| ATOM | 5280 | HD12 | ILE | C | 182 | 7.395 | 42.926 | -5.335 | 1 | 23.36 | H |
| ATOM | 5281 | HD13 | ILE | C | 182 | 8.241 | 42.03 | -4.331 | 1 | 23.36 | H |
| ATOM | 5282 | N | GLU | C | 183 | 12.013 | 40.776 | -8.717 | 1 | 17.61 | N |
| ATOM | 5283 | CA | GLU | C | 183 | 12.211 | 39.676 | -9.648 | 1 | 20.35 | C |
| ATOM | 5284 | C | GLU | C | 183 | 11.144 | 38.62 | -9.401 | 1 | 20.7 | C |
| ATOM | 5285 | O | GLU | C | 183 | 10.829 | 38.289 | -8.258 | 1 | 21.07 | O |
| ATOM | 5286 | CB | GLU | C | 183 | 13.61 | 39.075 | -9.5 | 1 | 26.3 | C |
| ATOM | 5287 | CG | GLU | C | 183 | 14.73 | 40.031 | -9.891 | 1 | 27.61 | C |
| ATOM | 5288 | CD | GLU | C | 183 | 16.108 | 39.407 | -9.763 | 1 | 38.86 | C |
| ATOM | 5289 | OE1 | GLU | C | 183 | 16.214 | 38.165 | -9.858 | 1 | 36.41 | O |
| ATOM | 5290 | OE2 | GLU | C | 183 | 17.086 | 40.16 | -9.564 | 1 | 42.7 | O1- |
| ATOM | 5291 | H | GLU | C | 183 | 12.653 | 40.881 | -8.152 | 1 | 21.14 | H |
| ATOM | 5292 | HA | GLU | C | 183 | 12.114 | 40.002 | -10.556 | 1 | 24.42 | H |

TABLE 5-continued

Atomic Coordinates for OMCP-NKG2D (4PDC).

| ATOM | 5293 | HB2 | GLU | C | 183 | 13.746 | 38.821 | -8.574 | 1 | 31.56 | H |
|---|---|---|---|---|---|---|---|---|---|---|---|
| ATOM | 5294 | HB3 | GLU | C | 183 | 13.676 | 38.292 | -10.069 | 1 | 31.56 | H |
| ATOM | 5295 | HG2 | GLU | C | 183 | 14.607 | 40.3 | -10.815 | 1 | 33.13 | H |
| ATOM | 5296 | HG3 | GLU | C | 183 | 14.697 | 40.809 | -9.312 | 1 | 33.13 | H |
| ATOM | 5297 | N | MET | C | 184 | 10.573 | 38.109 | -10.482 | 1 | 22.39 | N |
| ATOM | 5298 | CA | MET | C | 184 | 10.573 | 37.098 | -10.391 | 1 | 21.6 | C |
| ATOM | 5299 | C | MET | C | 184 | 9.533 | 36.135 | -11.546 | 1 | 22.55 | C |
| ATOM | 5300 | O | MET | C | 184 | 9.735 | 34.965 | -11.347 | 1 | 23.79 | O |
| ATOM | 5301 | CB | MET | C | 184 | 10.063 | 37.747 | -10.426 | 1 | 20.97 | C |
| ATOM | 5302 | CG | MET | C | 184 | 8.144 | 36.814 | -10.069 | 1 | 19.42 | C |
| ATOM | 5303 | SD | MET | C | 184 | 6.99 | 35.883 | -11.472 | 1 | 22.46 | S |
| ATOM | 5304 | CE | MET | C | 184 | 5.613 | 37.205 | -12.438 | 1 | 23.45 | C |
| ATOM | 5305 | H | MET | C | 184 | 10.773 | 38.334 | -11.287 | 1 | 26.87 | H |
| ATOM | 5306 | HA | MET | C | 184 | 9.624 | 36.618 | -9.553 | 1 | 25.92 | H |
| ATOM | 5307 | HB2 | MET | C | 184 | 8.131 | 38.484 | -9.796 | 1 | 25.17 | H |
| ATOM | 5308 | HB3 | MET | C | 184 | 7.983 | 38.082 | -11.322 | 1 | 25.17 | H |
| ATOM | 5309 | HG2 | MET | C | 184 | 7.298 | 36.177 | -9.405 | 1 | 23.3 | H |
| ATOM | 5310 | HG3 | MET | C | 184 | 6.263 | 37.343 | -9.704 | 1 | 23.3 | H |
| ATOM | 5311 | HE1 | MET | C | 184 | 5.221 | 36.829 | -13.241 | 1 | 28.15 | H |
| ATOM | 5312 | HE2 | MET | C | 184 | 4.927 | 37.64 | -11.907 | 1 | 28.15 | H |
| ATOM | 5313 | HE3 | MET | C | 184 | 6.304 | 37.843 | -12.674 | 1 | 28.15 | H |
| ATOM | 5314 | N | GLN | C | 185 | 9.571 | 36.648 | -12.758 | 1 | 18.88 | N |
| ATOM | 5315 | CA | GLN | C | 185 | 9.795 | 35.862 | -13.96 | 1 | 24.05 | C |
| ATOM | 5316 | C | GLN | C | 185 | 10.736 | 36.628 | -14.88 | 1 | 25.86 | C |
| ATOM | 5317 | O | GLN | C | 185 | 10.834 | 37.853 | -14.793 | 1 | 24.87 | O |
| ATOM | 5318 | CB | GLN | C | 185 | 8.463 | 35.568 | -14.648 | 1 | 25.95 | C |
| ATOM | 5319 | CG | GLN | C | 185 | 8.465 | 34.367 | -15.561 | 1 | 37.07 | C |
| ATOM | 5320 | CD | GLN | C | 185 | 8.668 | 33.057 | -14.826 | 1 | 34.64 | C |
| ATOM | 5321 | OE1 | GLN | C | 185 | 9.787 | 32.701 | -14.462 | 1 | 43.56 | O |
| ATOM | 5322 | NE2 | GLN | C | 185 | 7.578 | 32.33 | -14.609 | 1 | 35.6 | N |
| ATOM | 5323 | H | GLN | C | 185 | 9.327 | 37.459 | -12.911 | 1 | 22.66 | H |
| ATOM | 5324 | HA | GLN | C | 185 | 10.213 | 35.019 | -13.723 | 1 | 28.86 | H |
| ATOM | 5325 | HB2 | GLN | C | 185 | 7.791 | 35.416 | -13.966 | 1 | 31.14 | H |
| ATOM | 5326 | HB3 | GLN | C | 185 | 8.215 | 36.34 | -15.182 | 1 | 31.14 | H |
| ATOM | 5327 | HG2 | GLN | C | 185 | 7.612 | 34.322 | -16.022 | 1 | 44.49 | H |
| ATOM | 5328 | HG3 | GLN | C | 185 | 9.184 | 34.463 | -16.205 | 1 | 44.49 | H |
| ATOM | 5329 | HE21 | GLN | C | 185 | 7.639 | 31.578 | -14.196 | 1 | 42.72 | H |
| ATOM | 5330 | HE22 | GLN | C | 185 | 6.812 | 32.611 | -14.881 | 1 | 42.72 | H |
| ATOM | 5331 | N | LYS | C | 186 | 11.446 | 35.921 | -15.749 | 1 | 25.22 | N |
| ATOM | 5332 | CA | LYS | C | 186 | 12.328 | 36.599 | -16.689 | 1 | 33.47 | C |
| ATOM | 5333 | C | LYS | C | 186 | 11.493 | 37.254 | -17.785 | 1 | 26.33 | C |
| ATOM | 5334 | O | LYS | C | 186 | 10.665 | 36.607 | -18.428 | 1 | 24.54 | O |
| ATOM | 5335 | CB | LYS | C | 186 | 13.351 | 35.63 | -17.283 | 1 | 44.39 | C |
| ATOM | 5336 | CG | LYS | C | 186 | 14.454 | 35.205 | -16.308 | 1 | 62.35 | C |
| ATOM | 5337 | CD | LYS | C | 186 | 15.252 | 36.385 | -15.736 | 1 | 70.73 | C |
| ATOM | 5338 | CE | LYS | C | 186 | 15.913 | 37.222 | -16.825 | 1 | 85.5 | C |
| ATOM | 5339 | NZ | LYS | C | 186 | 16.696 | 38.358 | -16.263 | 1 | 92.86 | N1+ |
| ATOM | 5340 | H | LYS | C | 186 | 11.437 | 35.063 | -15.816 | 1 | 30.26 | H |
| ATOM | 5341 | HA | LYS | C | 186 | 12.812 | 37.298 | -16.222 | 1 | 40.16 | H |
| ATOM | 5342 | HB2 | LYS | C | 186 | 12.889 | 34.829 | -17.573 | 1 | 53.27 | H |
| ATOM | 5343 | HB3 | LYS | C | 186 | 13.778 | 36.056 | -18.044 | 1 | 53.27 | H |

TABLE 5-continued

Atomic Coordinates for OMCP-NKG2D (4PDC).

| ATOM | 5344 | HG2 | LYS | C | 186 | 14.05 | -15.564 | 34.732 | 1 | 74.83 | H |
| --- | --- | --- | --- | --- | --- | --- | --- | --- | --- | --- | --- |
| ATOM | 5345 | HG3 | LYS | C | 186 | 15.075 | -16.771 | 34.622 | 1 | 74.83 | H |
| ATOM | 5346 | HD2 | LYS | C | 186 | 14.653 | -15.237 | 36.961 | 1 | 84.87 | H |
| ATOM | 5347 | HD3 | LYS | C | 186 | 15.949 | -15.154 | 36.044 | 1 | 84.87 | H |
| ATOM | 5348 | HE2 | LYS | C | 186 | 16.519 | -17.334 | 36.66 | 1 | 102.6 | H |
| ATOM | 5349 | HE3 | LYS | C | 186 | 15.228 | -17.407 | 37.586 | 1 | 102.6 | H |
| ATOM | 5350 | HZ1 | LYS | C | 186 | 17.069 | -16.922 | 38.826 | 1 | 111.43 | H |
| ATOM | 5351 | HZ2 | LYS | C | 186 | 16.161 | -15.795 | 38.893 | 1 | 111.43 | H |
| ATOM | 5352 | HZ3 | LYS | C | 186 | 17.337 | -15.729 | 38.05 | 1 | 111.43 | H |
| ATOM | 5353 | N | GLY | C | 187 | 11.707 | -17.977 | 38.55 | 1 | 22.7 | N |
| ATOM | 5354 | CA | GLY | C | 187 | 10.938 | -18.943 | 39.312 | 1 | 24.36 | C |
| ATOM | 5355 | C | GLY | C | 187 | 11.284 | -18.913 | 40.784 | 1 | 21.56 | C |
| ATOM | 5356 | O | GLY | C | 187 | 12.096 | -18.094 | 41.226 | 1 | 17.2 | O |
| ATOM | 5357 | H | GLY | C | 187 | 12.298 | -17.555 | 39.013 | 1 | 27.25 | H |
| ATOM | 5358 | HA2 | GLY | C | 187 | 11.111 | -19.835 | 38.972 | 1 | 29.23 | H |
| ATOM | 5359 | HA3 | GLY | C | 187 | 9.991 | -18.754 | 39.213 | 1 | 29.23 | H |
| ATOM | 5360 | N | ASP | C | 188 | 10.659 | -19.808 | 41.544 | 1 | 18.15 | N |
| ATOM | 5361 | CA | ASP | C | 188 | 10.96 | -19.96 | 42.961 | 1 | 17.36 | C |
| ATOM | 5362 | C | ASP | C | 188 | 9.738 | -19.697 | 43.846 | 1 | 19.06 | C |
| ATOM | 5363 | O | ASP | C | 188 | 9.709 | -20.117 | 45.001 | 1 | 15.87 | O |
| ATOM | 5364 | CB | ASP | C | 188 | 11.509 | -21.365 | 43.226 | 1 | 19.74 | C |
| ATOM | 5365 | CG | ASP | C | 188 | 12.824 | -21.618 | 42.513 | 1 | 23.22 | C |
| ATOM | 5366 | OD1 | ASP | C | 188 | 13.72 | -20.754 | 42.596 | 1 | 19.57 | O |
| ATOM | 5367 | OD2 | ASP | C | 188 | 12.958 | -22.675 | 41.864 | 1 | 26.62 | O1- |
| ATOM | 5368 | H | ASP | C | 188 | 10.05 | -20.344 | 41.258 | 1 | 21.78 | H |
| ATOM | 5369 | HA | ASP | C | 188 | 11.648 | -19.321 | 43.206 | 1 | 20.83 | H |
| ATOM | 5370 | HB2 | ASP | C | 188 | 10.866 | -22.02 | 42.914 | 1 | 23.69 | H |
| ATOM | 5371 | HB3 | ASP | C | 188 | 11.657 | -21.472 | 44.179 | 1 | 23.69 | H |
| ATOM | 5372 | N | CYS | C | 189 | 8.739 | -19.006 | 43.299 | 1 | 16.64 | N |
| ATOM | 5373 | CA | CYS | C | 189 | 7.539 | -18.63 | 44.052 | 1 | 17.86 | C |
| ATOM | 5374 | C | CYS | C | 189 | 7.259 | -17.138 | 43.887 | 1 | 16.95 | C |
| ATOM | 5375 | O | CYS | C | 189 | 7.791 | -16.504 | 42.98 | 1 | 15.25 | O |
| ATOM | 5376 | CB | CYS | C | 189 | 6.326 | -19.447 | 43.596 | 1 | 16.46 | C |
| ATOM | 5377 | SG | CYS | C | 189 | 6.412 | -21.213 | 43.997 | 1 | 19.92 | S |
| ATOM | 5378 | H | CYS | C | 189 | 8.73 | -18.739 | 42.481 | 1 | 19.97 | H |
| ATOM | 5379 | HA | CYS | C | 189 | 7.686 | -18.808 | 44.995 | 1 | 21.43 | H |
| ATOM | 5380 | HB2 | CYS | C | 189 | 6.245 | -19.368 | 42.632 | 1 | 19.75 | H |
| ATOM | 5381 | HB3 | CYS | C | 189 | 5.532 | -19.088 | 44.021 | 1 | 19.75 | H |
| ATOM | 5382 | N | ALA | C | 190 | 6.424 | -16.584 | 44.763 | 1 | 14.88 | N |
| ATOM | 5383 | CA | ALA | C | 190 | 6.146 | -15.149 | 44.757 | 1 | 15.16 | C |
| ATOM | 5384 | C | ALA | C | 190 | 4.655 | -14.854 | 44.804 | 1 | 12.33 | C |
| ATOM | 5385 | O | ALA | C | 190 | 3.901 | -15.487 | 45.546 | 1 | 12.28 | O |
| ATOM | 5386 | CB | ALA | C | 190 | 6.845 | -14.478 | 45.927 | 1 | 18.64 | C |
| ATOM | 5387 | H | ALA | C | 190 | 6.003 | -17.02 | 45.373 | 1 | 17.85 | H |
| ATOM | 5388 | HA | ALA | C | 190 | 6.5 | -14.766 | 43.94 | 1 | 18.19 | H |
| ATOM | 5389 | HB1 | ALA | C | 190 | 6.651 | -13.528 | 45.907 | 1 | 22.37 | H |
| ATOM | 5390 | HB2 | ALA | C | 190 | 7.801 | -14.622 | 45.847 | 1 | 22.37 | H |
| ATOM | 5391 | HB3 | ALA | C | 190 | 6.52 | -14.866 | 46.754 | 1 | 22.37 | H |
| ATOM | 5392 | N | LEU | C | 191 | 4.249 | -13.882 | 43.993 | 1 | 10.76 | N |
| ATOM | 5393 | CA | LEU | C | 191 | 2.888 | -13.375 | 43.985 | 1 | 12.2 | C |
| ATOM | 5394 | C | LEU | C | 191 | 2.805 | -12.132 | 44.849 | 1 | 13.93 | C |

TABLE 5-continued

Atomic Coordinates for OMCP-NKG2D (4PDC).

| ATOM | 5395 | O | LEU | C | 191 | 3.653 | -11.246 | 44.741 | 1 | 12.07 | O |
|------|------|------|-----|---|-----|-------|---------|--------|---|-------|---|
| ATOM | 5396 | CB | LEU | C | 191 | 2.44 | -13.034 | 42.565 | 1 | 11.91 | C |
| ATOM | 5397 | CG | LEU | C | 191 | 2.3 | -14.194 | 41.584 | 1 | 12.77 | C |
| ATOM | 5398 | CD1 | LEU | C | 191 | 2.254 | -13.66 | 40.162 | 1 | 15.07 | C |
| ATOM | 5399 | CD2 | LEU | C | 191 | 1.046 | -14.99 | 41.904 | 1 | 15.63 | C |
| ATOM | 5400 | H | LEU | C | 191 | 4.761 | -13.491 | 43.423 | 1 | 12.91 | H |
| ATOM | 5401 | HA | LEU | C | 191 | 2.288 | -14.046 | 44.347 | 1 | 14.65 | H |
| ATOM | 5402 | HB2 | LEU | C | 191 | 3.085 | -12.416 | 42.186 | 1 | 14.29 | H |
| ATOM | 5403 | HB3 | LEU | C | 191 | 1.575 | -12.599 | 42.619 | 1 | 14.29 | H |
| ATOM | 5404 | HG | LEU | C | 191 | 3.066 | -14.782 | 41.667 | 1 | 15.32 | H |
| ATOM | 5405 | HD11 | LEU | C | 191 | 2.165 | -14.406 | 39.548 | 1 | 18.08 | H |
| ATOM | 5406 | HD12 | LEU | C | 191 | 3.076 | -13.178 | 39.98 | 1 | 18.08 | H |
| ATOM | 5407 | HD13 | LEU | C | 191 | 1.494 | -13.065 | 40.073 | 1 | 18.08 | H |
| ATOM | 5408 | HD21 | LEU | C | 191 | 0.969 | -15.723 | 41.274 | 1 | 18.76 | H |
| ATOM | 5409 | HD22 | LEU | C | 191 | 0.275 | -14.406 | 41.829 | 1 | 18.76 | H |
| ATOM | 5410 | HD23 | LEU | C | 191 | 1.114 | -15.335 | 42.808 | 1 | 18.76 | H |
| ATOM | 5411 | N | TYR | C | 192 | 1.786 | -12.056 | 45.698 | 1 | 12.4 | N |
| ATOM | 5412 | CA | TYR | C | 192 | 1.539 | -10.818 | 46.417 | 1 | 15.75 | C |
| ATOM | 5413 | C | TYR | C | 192 | 0.917 | -9.793 | 45.485 | 1 | 13.37 | C |
| ATOM | 5414 | O | TYR | C | 192 | 0.058 | -10.119 | 44.669 | 1 | 12.8 | O |
| ATOM | 5415 | CB | TYR | C | 192 | 0.619 | -11.01 | 47.621 | 1 | 12.4 | C |
| ATOM | 5416 | CG | TYR | C | 192 | 0.35 | -9.679 | 48.273 | 1 | 17.77 | C |
| ATOM | 5417 | CD1 | TYR | C | 192 | 1.268 | -9.128 | 49.153 | 1 | 19.33 | C |
| ATOM | 5418 | CD2 | TYR | C | 192 | -0.786 | -8.939 | 47.958 | 1 | 18.28 | C |
| ATOM | 5419 | CE1 | TYR | C | 192 | 1.051 | -7.899 | 49.729 | 1 | 17.95 | C |
| ATOM | 5420 | CE2 | TYR | C | 192 | -0.085 | -7.701 | 48.531 | 1 | 20.59 | C |
| ATOM | 5421 | CZ | TYR | C | 192 | -0.287 | -7.187 | 49.416 | 1 | 20.36 | C |
| ATOM | 5422 | OH | TYR | C | 192 | -5.957 | 49.996 | 1 | 19.55 | O | |
| ATOM | 5423 | H | TYR | C | 192 | 1.236 | -12.693 | 45.873 | 1 | 14.88 | H |
| ATOM | 5424 | HA | TYR | C | 192 | 2.383 | -10.463 | 46.736 | 1 | 18.89 | H |
| ATOM | 5425 | HB2 | TYR | C | 192 | 1.047 | -11.591 | 48.268 | 1 | 14.88 | H |
| ATOM | 5426 | HB3 | TYR | C | 192 | -0.226 | -11.388 | 47.329 | 1 | 14.88 | H |
| ATOM | 5427 | HD1 | TYR | C | 192 | 2.038 | -9.603 | 49.366 | 1 | 23.2 | H |
| ATOM | 5428 | HD2 | TYR | C | 192 | -1.407 | -9.286 | 47.36 | 1 | 21.53 | H |
| ATOM | 5429 | HE1 | TYR | C | 192 | 1.673 | -7.548 | 50.325 | 1 | 21.93 | H |
| ATOM | 5430 | HE2 | TYR | C | 192 | -1.777 | -7.219 | 48.322 | 1 | 24.7 | H |
| ATOM | 5431 | HH | TYR | C | 192 | -1.011 | -5.627 | 49.725 | 1 | 23.47 | H |
| ATOM | 5432 | N | ALA | C | 193 | 1.363 | -8.552 | 45.625 | 1 | 14.31 | N |
| ATOM | 5433 | CA | ALA | C | 193 | 0.773 | -7.416 | 44.931 | 1 | 14.94 | C |
| ATOM | 5434 | C | ALA | C | 193 | 0.867 | 6.211 | 45.856 | 1 | 17.89 | C |
| ATOM | 5435 | O | ALA | C | 193 | 1.874 | -6.034 | 46.539 | 1 | 18.07 | O |
| ATOM | 5436 | CB | ALA | C | 193 | 1.488 | -7.146 | 43.614 | 1 | 13.51 | C |
| ATOM | 5437 | H | ALA | C | 193 | 2.025 | -8.337 | 46.13 | 1 | 17.18 | H |
| ATOM | 5438 | HA | ALA | C | 193 | 0.162 | -7.595 | 44.747 | 1 | 17.93 | H |
| ATOM | 5439 | HB1 | ALA | C | 193 | 1.071 | -6.386 | 43.179 | 1 | 16.22 | H |
| ATOM | 5440 | HB2 | ALA | C | 193 | 1.416 | -7.932 | 43.05 | 1 | 14.31 | H |
| ATOM | 5441 | HB3 | ALA | C | 193 | 2.421 | -6.954 | 43.796 | 1 | 16.22 | H |
| ATOM | 5442 | N | SER | C | 194 | -0.171 | -5.385 | 45.893 | 1 | 15.21 | N |
| ATOM | 5443 | CA | SER | C | 194 | -0.15 | -4.22 | 46.773 | 1 | 19.46 | C |
| ATOM | 5444 | C | SER | C | 194 | 0.589 | -3.063 | 46.101 | 1 | 18.48 | C |
| ATOM | 5445 | O | SER | C | 194 | 0.561 | -2.952 | 44.878 | 1 | 20 | O |

TABLE 5-continued

Atomic Coordinates for OMCP-NKG2D (4PDC).

| ATOM | 5446 | CB  | SER | C   | -1.569 | 47.149 | -3.798 | 1 | 18.63 | C   |
|------|------|-----|-----|-----|--------|--------|--------|---|-------|-----|
| ATOM | 5447 | OG  | SER | C   | -2.308 | 45.998 | -3.45  | 1 | 27.89 | O   |
| ATOM | 5448 | H   | SER | C   | -0.889 | 45.428 | -5.472 | 1 | 18.26 | H   |
| ATOM | 5449 | HA  | SER | C   | -0.323 | 47.589 | -4.447 | 1 | 23.36 | H   |
| ATOM | 5450 | HB2 | SER | C   | -1.525 | 47.74  | -3.03  | 1 | 22.35 | H   |
| ATOM | 5451 | HB3 | SER | C   | -2.011 | 47.596 | -4.537 | 1 | 22.35 | H   |
| ATOM | 5452 | HG  | SER | C   | -1.935 | 45.6   | -2.811 | 1 | 33.47 | H   |
| ATOM | 5453 | N   | SER | C   | 1.243  | 46.877 | -2.197 | 1 | 20.9  | N   |
| ATOM | 5454 | CA  | SER | C   | 1.276  | 48.334 | -2.265 | 1 | 24.71 | C   |
| ATOM | 5455 | C   | SER | C   | 2.483  | 48.832 | -3.053 | 1 | 20.24 | C   |
| ATOM | 5456 | O   | SER | C   | 3.625  | 48.682 | -2.618 | 1 | 19.16 | O   |
| ATOM | 5457 | CB  | SER | C   | 1.3    | 48.929 | -0.858 | 1 | 22.44 | C   |
| ATOM | 5458 | OG  | SER | C   | 1.256  | 50.341 | -0.92  | 1 | 28.76 | O   |
| ATOM | 5459 | H   | SER | C   | 1.694  | 46.564 | -1.535 | 1 | 25.08 | H   |
| ATOM | 5460 | HA  | SER | C   | 0.474  | 48.648 | -2.712 | 1 | 29.65 | H   |
| ATOM | 5461 | HB2 | SER | C   | 0.528  | 48.609 | -0.365 | 1 | 26.93 | H   |
| ATOM | 5462 | HB3 | SER | C   | 2.117  | 48.656 | -0.412 | 1 | 26.93 | H   |
| ATOM | 5463 | HG  | SER | C   | 1.27   | 50.663 | -0.144 | 1 | 34.51 | H   |
| ATOM | 5464 | N   | PHE | C   | 2.215  | 49.423 | 4.213  | 1 | 20.32 | N   |
| ATOM | 5465 | CA  | PHE | C   | 3.249  | 50.046 | -5.035 | 1 | 19.27 | C   |
| ATOM | 5466 | C   | PHE | C   | 4.443  | 49.138 | -5.29  | 1 | 23.51 | C   |
| ATOM | 5467 | O   | PHE | C   | 5.581  | 49.456 | -4.933 | 1 | 18.74 | O   |
| ATOM | 5468 | CB  | PHE | C   | 3.708  | 51.345 | -4.384 | 1 | 20.31 | C   |
| ATOM | 5469 | CG  | PHE | C   | 2.685  | 52.432 | -4.451 | 1 | 21.15 | C   |
| ATOM | 5470 | CD1 | PHE | C   | 2.543  | 53.189 | -5.599 | 1 | 21.62 | C   |
| ATOM | 5471 | CD2 | PHE | C   | 1.849  | 52.685 | -3.378 | 1 | 27.55 | C   |
| ATOM | 5472 | CE1 | PHE | C   | 1.592  | 54.182 | -5.673 | 1 | 19.96 | C   |
| ATOM | 5473 | CE2 | PHE | C   | 0.899  | 53.68  | -3.447 | 1 | 23.4  | C   |
| ATOM | 5474 | CZ  | PHE | C   | 0.772  | 54.43  | -4.595 | 1 | 21.78 | C   |
| ATOM | 5475 | H   | PHE | C   | 1.427  | 49.477 | -4.553 | 1 | 24.38 | H   |
| ATOM | 5476 | HA  | PHE | C   | 2.864  | 50.271 | -5.896 | 1 | 23.12 | H   |
| ATOM | 5477 | HB2 | PHE | C   | 3.902  | 51.176 | -3.448 | 1 | 24.38 | H   |
| ATOM | 5478 | HB3 | PHE | C   | 4.507  | 51.658 | -4.836 | 1 | 24.38 | H   |
| ATOM | 5479 | HD1 | PHE | C   | 3.095  | 53.025 | -6.329 | 1 | 25.94 | H   |
| ATOM | 5480 | HD2 | PHE | C   | 1.932  | 52.181 | -2.601 | 1 | 33.05 | H   |
| ATOM | 5481 | HE1 | PHE | C   | 1.508  | 54.688 | -6.448 | 1 | 23.95 | H   |
| ATOM | 5482 | HE2 | PHE | C   | 0.345  | 53.846 | -2.719 | 1 | 28.08 | H   |
| ATOM | 5483 | HZ  | PHE | C   | 0.131  | 55.102 | 4.643  | 1 | 26.14 | H   |
| ATOM | 5484 | N   | LYS | C   | 4.165  | 48.003 | -5.919 | 1 | 18    | N   |
| ATOM | 5485 | CA  | LYS | C   | 5.197  | 47.054 | 6.288  | 1 | 21.33 | C   |
| ATOM | 5486 | C   | LYS | C   | 5.092  | 46.769 | 7.776  | 1 | 18.93 | C   |
| ATOM | 5487 | O   | LYS | C   | 4.018  | 46.905 | -8.367 | 1 | 15.6  | O   |
| ATOM | 5488 | CB  | LYS | C   | 5.064  | 45.765 | -5.474 | 1 | 21.85 | C   |
| ATOM | 5489 | CG  | LYS | C   | 4.958  | 46.002 | -3.977 | 1 | 27.27 | C   |
| ATOM | 5490 | CD  | LYS | C   | 5.109  | 44.719 | -3.183 | 1 | 29.38 | C   |
| ATOM | 5491 | CE  | LYS | C   | 3.988  | 43.739 | -3.459 | 1 | 32.12 | C   |
| ATOM | 5492 | NZ  | LYS | C   | 4.083  | 42.54  | -2.575 | 1 | 44.07 | N1+ |
| ATOM | 5493 | H   | LYS | C   | 3.372  | 47.759 | -6.146 | 1 | 21.6  | H   |
| ATOM | 5494 | HA  | LYS | C   | 6.069  | 47.44  | -6.11  | 1 | 25.6  | H   |
| ATOM | 5495 | HB2 | LYS | C   | 4.264  | 45.296 | -5.759 | 1 | 26.23 | H   |
| ATOM | 5496 | HB3 | LYS | C   | 5.844  | 45.212 | -5.634 | 1 | 26.23 | H   |

TABLE 5-continued

Atomic Coordinates for OMCP-NKG2D (4PDC).

| | | | | | | | | | | |
|---|---|---|---|---|---|---|---|---|---|---|
| ATOM | 5497 | HG2 | LYS | C | 197 | 5.66 | 46.612 | -3.702 | 1 | 32.72 | H |
| ATOM | 5498 | HG3 | LYS | C | 197 | 4.089 | 46.381 | -3.776 | 1 | 32.72 | H |
| ATOM | 5499 | HD2 | LYS | C | 197 | 5.948 | 44.294 | -3.422 | 1 | 35.26 | H |
| ATOM | 5500 | HD3 | LYS | C | 197 | 5.1 | 44.929 | 2.236 | 1 | 35.26 | H |
| ATOM | 5501 | HE2 | LYS | C | 197 | 3.135 | 44.172 | 3.295 | 1 | 38.55 | H |
| ATOM | 5502 | HE3 | LYS | C | 197 | 4.042 | 43.442 | -4.381 | 1 | 38.55 | H |
| ATOM | 5503 | HZ1 | LYS | C | 197 | 3.416 | 41.977 | -2.752 | 1 | 52.89 | H |
| ATOM | 5504 | HZ2 | LYS | C | 197 | 4.857 | 42.123 | -2.71 | 1 | 52.89 | H |
| ATOM | 5505 | HZ3 | LYS | C | 197 | 4.033 | 42.787 | -1.721 | 1 | 52.89 | H |
| ATOM | 5506 | N | GLY | C | 198 | 6.222 | 46.404 | -8.372 | 1 | 13.97 | N |
| ATOM | 5507 | CA | GLY | C | 198 | 6.273 | 45.977 | -9.754 | 1 | 12.15 | C |
| ATOM | 5508 | C | GLY | C | 198 | 6.935 | 44.618 | -9.848 | 1 | 15.82 | C |
| ATOM | 5509 | O | GLY | C | 198 | 8.119 | 44.484 | -9.54 | 1 | 16.91 | O |
| ATOM | 5510 | H | GLY | C | 198 | 6.988 | 46.398 | -7.982 | 1 | 16.76 | H |
| ATOM | 5511 | HA2 | GLY | C | 198 | 5.375 | 45.916 | -10.116 | 1 | 14.58 | H |
| ATOM | 5512 | HA3 | GLY | C | 198 | 6.783 | 46.613 | -10.28 | 1 | 14.58 | H |
| ATOM | 5513 | N | TYR | C | 199 | 6.172 | 43.605 | -10.251 | 1 | 14.27 | N |
| ATOM | 5514 | CA | TYR | C | 199 | 6.716 | 42.267 | -10.466 | 1 | 14.6 | C |
| ATOM | 5515 | C | TYR | C | 199 | 7.146 | 42.099 | -11.92 | 1 | 15.48 | C |
| ATOM | 5516 | O | TYR | C | 199 | 6.36 | 42.327 | -12.829 | 1 | 12.77 | O |
| ATOM | 5517 | CB | TYR | C | 199 | 5.689 | 41.192 | -10.101 | 1 | 14.93 | C |
| ATOM | 5518 | CG | TYR | C | 199 | 5.489 | 41.006 | -8.615 | 1 | 20.52 | C |
| ATOM | 5519 | CD1 | TYR | C | 199 | 6.359 | 40.22 | -7.87 | 1 | 15.96 | C |
| ATOM | 5520 | CD2 | TYR | C | 199 | 4.425 | 41.609 | -7.956 | 1 | 18.27 | C |
| ATOM | 5521 | CE1 | TYR | C | 199 | 6.179 | 40.044 | -6.509 | 1 | 18.35 | C |
| ATOM | 5522 | CE2 | TYR | C | 199 | 4.236 | 41.438 | -6.596 | 1 | 20.42 | C |
| ATOM | 5523 | CZ | TYR | C | 199 | 5.116 | 40.654 | -5.877 | 1 | 22.28 | C |
| ATOM | 5524 | OH | TYR | C | 199 | 4.931 | 40.486 | -4.522 | 1 | 27.53 | O |
| ATOM | 5525 | H | TYR | C | 199 | 5.329 | 43.667 | -10.408 | 1 | 17.12 | H |
| ATOM | 5526 | HA | TYR | C | 199 | 7.496 | 42.145 | -9.903 | 1 | 17.52 | H |
| ATOM | 5527 | HB2 | TYR | C | 199 | 4.833 | 41.436 | -10.486 | 1 | 17.92 | H |
| ATOM | 5528 | HB3 | TYR | C | 199 | 5.983 | 40.344 | -10.468 | 1 | 17.92 | H |
| ATOM | 5529 | HD1 | TYR | C | 199 | 7.077 | 39.807 | -8.293 | 1 | 19.15 | H |
| ATOM | 5530 | HD2 | TYR | C | 199 | 3.83 | 42.137 | -8.438 | 1 | 21.93 | H |
| ATOM | 5531 | HE1 | TYR | C | 199 | 6.771 | 39.517 | -6.024 | 1 | 22.01 | H |
| ATOM | 5532 | HE2 | TYR | C | 199 | 3.52 | 41.849 | -6.168 | 1 | 24.5 | H |
| ATOM | 5533 | HH | TYR | C | 199 | 4.251 | 40.909 | -4.27 | 1 | 33.04 | H |
| ATOM | 5534 | N | ILE | C | 200 | 8.396 | 41.698 | -12.128 | 1 | 16.81 | N |
| ATOM | 5535 | CA | ILE | C | 200 | 8.926 | 41.482 | -13.471 | 1 | 15.74 | C |
| ATOM | 5536 | C | ILE | C | 200 | 8.28 | 40.245 | -14.1 | 1 | 16.52 | C |
| ATOM | 5537 | O | ILE | C | 200 | 8.284 | 39.168 | -13.505 | 1 | 15.2 | O |
| ATOM | 5538 | CB | ILE | C | 200 | 10.46 | 41.318 | -13.442 | 1 | 16.14 | C |
| ATOM | 5539 | CG1 | ILE | C | 200 | 11.1 | 42.522 | -12.738 | 1 | 15.26 | C |
| ATOM | 5540 | CG2 | ILE | C | 200 | 11.01 | 41.152 | -14.861 | 1 | 16.45 | C |
| ATOM | 5541 | CD1 | ILE | C | 200 | 12.613 | 42.437 | -12.586 | 1 | 18.39 | C |
| ATOM | 5542 | H | ILE | C | 200 | 8.964 | 41.543 | -11.501 | 1 | 20.17 | H |
| ATOM | 5543 | HA | ILE | C | 200 | 8.713 | 42.249 | -14.025 | 1 | 18.88 | H |
| ATOM | 5544 | HB | ILE | C | 200 | 10.673 | 40.519 | -12.936 | 1 | 19.37 | H |
| ATOM | 5545 | HG12 | ILE | C | 200 | 10.9 | 43.322 | -13.249 | 1 | 18.31 | H |
| ATOM | 5546 | HG13 | ILE | C | 200 | 10.719 | 42.6 | -11.849 | 1 | 18.31 | H |
| ATOM | 5547 | HG21 | ILE | C | 200 | 11.974 | 41.051 | -14.816 | 1 | 19.74 | H |

TABLE 5-continued

Atomic Coordinates for OMCP-NKG2D (4PDC).

| ATOM | 5548 | HG22 | ILE | C | 200 | 10.613 | 40.363 | -15.263 | 1 | 19.74 | H |
|---|---|---|---|---|---|---|---|---|---|---|---|
| ATOM | 5549 | HG23 | ILE | C | 200 | 10.784 | 41.939 | -15.381 | 1 | 19.74 | H |
| ATOM | 5550 | HD11 | ILE | C | 200 | 12.93 | 43.234 | -12.133 | 1 | 22.06 | H |
| ATOM | 5551 | HD12 | ILE | C | 200 | 12.834 | 41.65 | -12.064 | 1 | 22.06 | H |
| ATOM | 5552 | HD13 | ILE | C | 200 | 13.016 | 42.374 | -13.466 | 1 | 22.06 | H |
| ATOM | 5553 | N | GLU | C | 201 | 7.728 | 40.405 | -15.302 | 1 | 15.15 | N |
| ATOM | 5554 | CA | GLU | C | 201 | 6.998 | 39.327 | -15.966 | 1 | 17.24 | C |
| ATOM | 5555 | C | GLU | C | 201 | 7.281 | 39.288 | -17.467 | 1 | 21.31 | C |
| ATOM | 5556 | O | GLU | C | 201 | 7.635 | 40.302 | -18.076 | 1 | 15.67 | O |
| ATOM | 5557 | CB | GLU | C | 201 | 5.491 | 39.485 | -15.712 | 1 | 17.25 | C |
| ATOM | 5558 | CG | GLU | C | 201 | 4.6 | 38.46 | -16.405 | 1 | 20.61 | C |
| ATOM | 5559 | CD | GLU | C | 201 | 4.918 | 37.025 | -16.012 | 1 | 24.32 | C |
| ATOM | 5560 | OE1 | GLU | C | 201 | 5.957 | 36.492 | -16.457 | 1 | 24.36 | O |
| ATOM | 5561 | OE2 | GLU | C | 201 | 4.12 | 36.426 | -15.262 | 1 | 26.94 | O1- |
| ATOM | 5562 | H | GLU | C | 201 | 7.763 | 41.134 | -15.757 | 1 | 18.18 | H |
| ATOM | 5563 | HA | GLU | C | 201 | 7.277 | 38.479 | -15.587 | 1 | 20.69 | H |
| ATOM | 5564 | HB2 | GLU | C | 201 | 5.33 | 39.412 | -14.758 | 1 | 20.7 | H |
| ATOM | 5565 | HB3 | GLU | C | 201 | 5.218 | 40.364 | -16.02 | 1 | 20.7 | H |
| ATOM | 5566 | HG2 | GLU | C | 201 | 3.676 | 38.637 | -16.17 | 1 | 24.73 | H |
| ATOM | 5567 | HG3 | GLU | C | 201 | 4.718 | 38.54 | -17.365 | 1 | 24.73 | H |
| ATOM | 5568 | N | ASN | C | 202 | 7.143 | 38.099 | -18.05 | 1 | 18.71 | N |
| ATOM | 5569 | CA | ASN | C | 202 | 7.219 | 37.925 | -19.497 | 1 | 20.17 | C |
| ATOM | 5570 | C | ASN | C | 202 | 6.078 | 38.663 | -20.179 | 1 | 18.49 | C |
| ATOM | 5571 | O | ASN | C | 202 | 4.912 | 38.461 | -19.844 | 1 | 16.77 | O |
| ATOM | 5572 | CB | ASN | C | 202 | 7.176 | 36.435 | -19.857 | 1 | 23.56 | C |
| ATOM | 5573 | CG | ASN | C | 202 | 7.406 | 36.177 | -21.341 | 1 | 23.4 | C |
| ATOM | 5574 | OD1 | ASN | C | 202 | 6.838 | 36.85 | -22.202 | 1 | 21.3 | O |
| ATOM | 5575 | ND2 | ASN | C | 202 | 8.248 | 35.191 | -21.643 | 1 | 23.28 | N |
| ATOM | 5576 | H | ASN | C | 202 | 7.002 | 37.368 | -17.621 | 1 | 22.45 | H |
| ATOM | 5577 | HA | ASN | C | 202 | 8.056 | 38.292 | -19.821 | 1 | 24.21 | H |
| ATOM | 5578 | HB2 | ASN | C | 202 | 7.869 | 35.971 | -19.362 | 1 | 28.27 | H |
| ATOM | 5579 | HB3 | ASN | C | 202 | 6.305 | 36.079 | -19.623 | 1 | 28.27 | H |
| ATOM | 5580 | HD21 | ASN | C | 202 | 8.413 | 35.004 | -22.466 | 1 | 27.94 | H |
| ATOM | 5581 | HD22 | ASN | C | 202 | 8.626 | 34.741 | -21.015 | 1 | 27.94 | H |
| ATOM | 5582 | N | CYS | C | 203 | 6.418 | 39.501 | -21.153 | 1 | 15.62 | N |
| ATOM | 5583 | CA | CYS | C | 203 | 5.443 | 40.379 | -21.787 | 1 | 17.19 | C |
| ATOM | 5584 | C | CYS | C | 203 | 4.362 | 39.611 | -22.551 | 1 | 21.25 | C |
| ATOM | 5585 | O | CYS | C | 203 | 3.338 | 40.187 | -22.922 | 1 | 19.77 | O |
| ATOM | 5586 | CB | CYS | C | 203 | 6.159 | 41.353 | -22.727 | 1 | 20.68 | C |
| ATOM | 5587 | SG | CYS | C | 203 | 7.423 | 42.375 | -21.911 | 1 | 23.41 | S |
| ATOM | 5588 | H | CYS | C | 203 | 7.215 | 39.58 | -21.467 | 1 | 18.74 | H |
| ATOM | 5589 | HA | CYS | C | 203 | 5.003 | 40.902 | -21.099 | 1 | 20.63 | H |
| ATOM | 5590 | HB2 | CYS | C | 203 | 6.596 | 40.846 | -23.428 | 1 | 24.82 | H |
| ATOM | 5591 | HB3 | CYS | C | 203 | 5.501 | 41.951 | -23.115 | 1 | 24.82 | H |
| ATOM | 5592 | N | SER | C | 204 | 4.585 | 38.317 | -22.774 | 1 | 16.75 | N |
| ATOM | 5593 | CA | SER | C | 204 | 3.614 | 37.469 | -23.47 | 1 | 19.18 | C |
| ATOM | 5594 | C | SER | C | 204 | 2.544 | 36.908 | -22.539 | 1 | 19.81 | C |
| ATOM | 5595 | O | SER | C | 204 | 1.558 | 36.328 | -22.991 | 1 | 19.37 | O |
| ATOM | 5596 | CB | SER | C | 204 | 4.327 | 36.306 | -24.161 | 1 | 22.12 | C |
| ATOM | 5597 | OG | SER | C | 204 | 5.221 | 36.785 | -25.144 | 1 | 22.09 | O |
| ATOM | 5598 | H | SER | C | 204 | 5.297 | 37.901 | -22.53 | 1 | 20.11 | H |

TABLE 5-continued

Atomic Coordinates for OMCP-NKG2D (4PDC).

| | | | | | | | | | | |
|---|---|---|---|---|---|---|---|---|---|---|
| ATOM | 5599 | HA | SER | C | 204 | 3.169 | -24.152 | 37.996 | 1 | 23.02 | H |
| ATOM | 5600 | HB2 | SER | C | 204 | 4.825 | -23.499 | 35.802 | 1 | 26.54 | H |
| ATOM | 5601 | HB3 | SER | C | 204 | 3.666 | -24.585 | 35.737 | 1 | 26.54 | H |
| ATOM | 5602 | HG | SER | C | 204 | 5.799 | -24.789 | 37.281 | 1 | 26.51 | H |
| ATOM | 5603 | N | THR | C | 205 | 2.747 | -21.237 | 37.067 | 1 | 15.82 | N |
| ATOM | 5604 | CA | THR | C | 205 | 1.848 | -20.254 | 36.478 | 1 | 17.27 | C |
| ATOM | 5605 | C | THR | C | 205 | 0.512 | -20.2 | 37.224 | 1 | 23.16 | C |
| ATOM | 5606 | O | THR | C | 205 | 0.486 | -19.927 | 38.427 | 1 | 18.56 | O |
| ATOM | 5607 | CB | THR | C | 205 | 2.486 | -18.855 | 36.48 | 1 | 20.49 | C |
| ATOM | 5608 | OG1 | THR | C | 205 | 3.798 | -18.927 | 35.907 | 1 | 19.75 | O |
| ATOM | 5609 | CG2 | THR | C | 205 | 1.643 | -17.877 | 35.677 | 1 | 22.93 | C |
| ATOM | 5610 | H | THR | C | 205 | 3.399 | -20.897 | 37.513 | 1 | 18.99 | H |
| ATOM | 5611 | HA | THR | C | 205 | 1.669 | -20.501 | 35.557 | 1 | 20.72 | H |
| ATOM | 5612 | HB | THR | C | 205 | 2.549 | -18.53 | 37.392 | 1 | 24.58 | H |
| ATOM | 5613 | HG1 | THR | C | 205 | 3.751 | -19.208 | 35.117 | 1 | 23.7 | H |
| ATOM | 5614 | HG21 | THR | C | 205 | 2.055 | -16.999 | 35.686 | 1 | 27.51 | H |
| ATOM | 5615 | HG22 | THR | C | 205 | 0.754 | -17.812 | 36.061 | 1 | 27.51 | H |
| ATOM | 5616 | HG23 | THR | C | 205 | 1.568 | -18.181 | 34.759 | 1 | 27.51 | H |
| ATOM | 5617 | N | PRO | C | 206 | -0.604 | -20.459 | 36.517 | 1 | 17.76 | N |
| ATOM | 5618 | CA | PRO | C | 206 | -1.898 | -20.323 | 37.193 | 1 | 19.8 | C |
| ATOM | 5619 | C | PRO | C | 206 | -2.147 | -18.898 | 37.676 | 1 | 20.72 | C |
| ATOM | 5620 | O | PRO | C | 206 | -1.969 | -17.94 | 36.923 | 1 | 18.27 | O |
| ATOM | 5621 | CB | PRO | C | 206 | -2.913 | -20.718 | 36.112 | 1 | 22.87 | C |
| ATOM | 5622 | CG | PRO | C | 206 | -2.139 | -21.513 | 35.122 | 1 | 28.25 | C |
| ATOM | 5623 | CD | PRO | C | 206 | -0.76 | -20.926 | 35.128 | 1 | 20.21 | C |
| ATOM | 5624 | HA | PRO | C | 206 | -1.96 | -20.939 | 37.941 | 1 | 23.76 | H |
| ATOM | 5625 | HB2 | PRO | C | 206 | -3.278 | -19.919 | 35.7 | 1 | 27.44 | H |
| ATOM | 5626 | HB3 | PRO | C | 206 | -3.618 | -21.255 | 36.506 | 1 | 27.44 | H |
| ATOM | 5627 | HG2 | PRO | C | 206 | -2.544 | -21.425 | 34.245 | 1 | 33.91 | H |
| ATOM | 5628 | HG3 | PRO | C | 206 | -2.116 | -22.443 | 35.397 | 1 | 33.91 | H |
| ATOM | 5629 | HD2 | PRO | C | 206 | -0.707 | -20.18 | 34.511 | 1 | 24.25 | H |
| ATOM | 5630 | HD3 | PRO | C | 206 | -0.101 | -21.608 | 34.923 | 1 | 24.25 | H |
| ATOM | 5631 | N | ASN | C | 207 | -2.542 | -18.774 | 38.936 | 1 | 19.76 | N |
| ATOM | 5632 | CA | ASN | C | 207 | -2.912 | -17.49 | 39.512 | 1 | 19.32 | C |
| ATOM | 5633 | C | ASN | C | 207 | -3.985 | -17.689 | 40.567 | 1 | 19.48 | C |
| ATOM | 5634 | O | ASN | C | 207 | -4.119 | -18.782 | 41.121 | 1 | 15.57 | O |
| ATOM | 5635 | CB | ASN | C | 207 | -1.701 | -16.796 | 40.14 | 1 | 18.33 | C |
| ATOM | 5636 | CG | ASN | C | 207 | -0.82 | -16.109 | 39.12 | 1 | 16.71 | C |
| ATOM | 5637 | OD1 | ASN | C | 207 | -1.106 | -14.991 | 38.69 | 1 | 18.99 | O |
| ATOM | 5638 | ND2 | ASN | C | 207 | 0.266 | -16.768 | 38.735 | 1 | 18.7 | N |
| ATOM | 5639 | H | ASN | C | 207 | -2.604 | -19.431 | 39.487 | 1 | 23.72 | H |
| ATOM | 5640 | HA | ASN | C | 207 | -3.268 | -16.915 | 38.816 | 1 | 23.19 | H |
| ATOM | 5641 | HB2 | ASN | C | 207 | -1.163 | -17.457 | 40.603 | 1 | 21.99 | H |
| ATOM | 5642 | HB3 | ASN | C | 207 | -2.013 | -16.124 | 40.767 | 1 | 21.99 | H |
| ATOM | 5643 | HD21 | ASN | C | 207 | 0.799 | -16.42 | 38.157 | 1 | 22.44 | H |
| ATOM | 5644 | HD22 | ASN | C | 207 | 0.437 | -17.544 | 39.064 | 1 | 22.44 | H |
| ATOM | 5645 | N | THR | C | 208 | -4.742 | -16.634 | 40.847 | 1 | 16.68 | N |
| ATOM | 5646 | CA | THR | C | 208 | -5.613 | -16.63 | 42.012 | 1 | 15.95 | C |
| ATOM | 5647 | C | THR | C | 208 | -4.721 | -16.681 | 43.246 | 1 | 17.24 | C |
| ATOM | 5648 | O | THR | C | 208 | -3.514 | -16.471 | 43.148 | 1 | 15.69 | O |
| ATOM | 5649 | CB | THR | C | 208 | -6.522 | -15.393 | 42.041 | 1 | 19.27 | C |

TABLE 5-continued

Atomic Coordinates for OMCP-NKG2D (4PDC).

| ATOM | 5650 | OG1 | THR | C | 208 | -5.725 | -14.204 | 42.005 | 1 | 15.59 | O |
|---|---|---|---|---|---|---|---|---|---|---|---|
| ATOM | 5651 | CG2 | THR | C | 208 | -7.471 | -15.408 | 40.844 | 1 | 21.85 | C |
| ATOM | 5652 | H | THR | C | 208 | -4.77 | -15.912 | 40.38 | 1 | 20.02 | H |
| ATOM | 5653 | HA | THR | C | 208 | -6.172 | -17.423 | 42.003 | 1 | 19.14 | H |
| ATOM | 5654 | HB | THR | C | 208 | -7.053 | -15.402 | 42.853 | 1 | 23.12 | H |
| ATOM | 5655 | HG1 | THR | C | 208 | -6.22 | -13.525 | 42.021 | 1 | 18.71 | H |
| ATOM | 5656 | HG21 | THR | C | 208 | -8.044 | -14.625 | 40.866 | 1 | 26.22 | H |
| ATOM | 5657 | HG22 | THR | C | 208 | -8.025 | -16.204 | 40.869 | 1 | 26.22 | H |
| ATOM | 5658 | HG23 | THR | C | 208 | -6.963 | -15.403 | 40.018 | 1 | 26.22 | H |
| ATOM | 5659 | N | TYR | C | 209 | -5.292 | -16.979 | 44.405 | 1 | 16.72 | N |
| ATOM | 5660 | CA | TYR | C | 209 | -4.47 | -17.141 | 45.597 | 1 | 13.53 | C |
| ATOM | 5661 | C | TYR | C | 209 | -5.203 | -16.759 | 46.876 | 1 | 14.4 | C |
| ATOM | 5662 | O | TYR | C | 209 | -6.437 | -16.687 | 46.914 | 1 | 12.53 | O |
| ATOM | 5663 | CB | TYR | C | 209 | -3.958 | -18.585 | 45.689 | 1 | 14.96 | C |
| ATOM | 5664 | CG | TYR | C | 209 | -5.04 | -19.649 | 45.726 | 1 | 18.5 | C |
| ATOM | 5665 | CD1 | TYR | C | 209 | -5.741 | -19.996 | 44.58 | 1 | 19.53 | C |
| ATOM | 5666 | CD2 | TYR | C | 209 | -5.343 | -20.318 | 46.907 | 1 | 14.68 | C |
| ATOM | 5667 | CE1 | TYR | C | 209 | -6.723 | -20.97 | 44.609 | 1 | 19.93 | C |
| ATOM | 5668 | CE2 | TYR | C | 209 | -6.317 | -21.291 | 46.947 | 1 | 21.82 | C |
| ATOM | 5669 | CZ | TYR | C | 209 | -7.005 | -21.615 | 45.797 | 1 | 26.03 | C |
| ATOM | 5670 | OH | TYR | C | 209 | -7.976 | -22.585 | 45.843 | 1 | 20.92 | O |
| ATOM | 5671 | H | TYR | C | 209 | -6.136 | -17.09 | 44.528 | 1 | 20.07 | H |
| ATOM | 5672 | HA | TYR | C | 209 | -3.696 | -16.561 | 45.52 | 1 | 16.23 | H |
| ATOM | 5673 | HB2 | TYR | C | 209 | -3.432 | -18.675 | 46.5 | 1 | 17.95 | H |
| ATOM | 5674 | HB3 | TYR | C | 209 | -3.399 | -18.764 | 44.917 | 1 | 17.95 | H |
| ATOM | 5675 | HD1 | TYR | C | 209 | -5.551 | -19.562 | 43.78 | 1 | 23.43 | H |
| ATOM | 5676 | HD2 | TYR | C | 209 | -4.881 | -20.102 | 47.685 | 1 | 17.62 | H |
| ATOM | 5677 | HE1 | TYR | C | 209 | -7.187 | -21.191 | 43.834 | 1 | 23.92 | H |
| ATOM | 5678 | HE2 | TYR | C | 209 | -6.511 | -21.727 | 47.745 | 1 | 26.18 | H |
| ATOM | 5679 | HH | TYR | C | 209 | -8.317 | -22.686 | 45.082 | 1 | 25.1 | H |
| ATOM | 5680 | N | ILE | C | 210 | -4.411 | -16.502 | 47.914 | 1 | 12.1 | N |
| ATOM | 5681 | CA | ILE | C | 210 | -4.92 | -16.091 | 49.213 | 1 | 14.56 | C |
| ATOM | 5682 | C | ILE | C | 210 | -4.546 | -17.113 | 50.283 | 1 | 16.31 | C |
| ATOM | 5683 | O | ILE | C | 210 | -3.369 | -17.419 | 50.482 | 1 | 14.03 | O |
| ATOM | 5684 | CB | ILE | C | 210 | -4.37 | -14.707 | 49.618 | 1 | 15.33 | C |
| ATOM | 5685 | CG1 | ILE | C | 210 | -4.746 | -13.661 | 48.564 | 1 | 15.55 | C |
| ATOM | 5686 | CG2 | ILE | C | 210 | -4.904 | -14.3 | 50.989 | 1 | 16.97 | C |
| ATOM | 5687 | CD1 | ILE | C | 210 | -4.066 | -12.314 | 48.749 | 1 | 17.1 | C |
| ATOM | 5688 | H | ILE | C | 210 | -3.554 | -16.562 | 47.886 | 1 | 14.52 | H |
| ATOM | 5689 | HA | ILE | C | 210 | -5.887 | -16.033 | 49.174 | 1 | 17.47 | H |
| ATOM | 5690 | HB | ILE | C | 210 | -3.403 | -14.761 | 49.667 | 1 | 18.39 | H |
| ATOM | 5691 | HG12 | ILE | C | 210 | -5.704 | -13.515 | 48.599 | 1 | 18.66 | H |
| ATOM | 5692 | HG13 | ILE | C | 210 | -4.498 | -13.998 | 47.689 | 1 | 18.66 | H |
| ATOM | 5693 | HG21 | ILE | C | 210 | -4.546 | -13.429 | 51.222 | 1 | 20.36 | H |
| ATOM | 5694 | HG22 | ILE | C | 210 | -4.625 | -14.958 | 51.645 | 1 | 20.36 | H |
| ATOM | 5695 | HG23 | ILE | C | 210 | -5.873 | -14.26 | 50.951 | 1 | 17.1 | H |
| ATOM | 5696 | HD11 | ILE | C | 210 | -4.357 | -11.714 | 48.045 | 1 | 14.52 | H |
| ATOM | 5697 | HD12 | ILE | C | 210 | -3.105 | -12.437 | 48.704 | 1 | 20.51 | H |
| ATOM | 5698 | HD13 | ILE | C | 210 | -4.313 | -11.953 | 49.615 | 1 | 20.51 | H |
| ATOM | 5699 | N | CYS | C | 211 | -5.558 | -17.639 | 50.963 | 1 | 16.07 | N |
| ATOM | 5700 | CA | CYS | C | 211 | -5.348 | -18.544 | 52.082 | 1 | 16.5 | C |

TABLE 5-continued

Atomic Coordinates for OMCP-NKG2D (4PDC).

| | | | | | | | | | |
|---|---|---|---|---|---|---|---|---|---|
| ATOM | 5701 | C | CYS | 211 | -5.448 | -17.768 | 53.379 | 1 | 16.84 | C |
| ATOM | 5702 | O | CYS | 211 | -6.188 | -16.787 | 53.471 | 1 | 17.47 | O |
| ATOM | 5703 | CB | CYS | 211 | -6.366 | -19.685 | 52.068 | 1 | 24.73 | C |
| ATOM | 5704 | SG | CYS | 211 | -6.116 | -20.874 | 50.73 | 1 | 30.48 | S |
| ATOM | 5705 | H | CYS | 211 | 6.386 | -17.484 | 50.791 | 1 | 19.28 | H |
| ATOM | 5706 | HA | CYS | 211 | -4.459 | -18.927 | 52.023 | 1 | 19.81 | H |
| ATOM | 5707 | HB2 | CYS | 211 | -7.255 | -19.31 | 51.969 | 1 | 29.68 | H |
| ATOM | 5708 | HB3 | CYS | 211 | -6.305 | -20.167 | 52.908 | 1 | 29.68 | H |
| ATOM | 5709 | N | MET | 212 | -4.706 | -18.222 | 54.38 | 1 | 19.38 | N |
| ATOM | 5710 | CA | MET | 212 | -4.653 | -17.551 | 55.668 | 1 | 17.22 | C |
| ATOM | 5711 | C | MET | 212 | -4.669 | -18.563 | 56.802 | 1 | 21.46 | C |
| ATOM | 5712 | O | MET | 212 | -4.066 | -19.634 | 56.699 | 1 | 19.72 | O |
| ATOM | 5713 | CB | MET | 212 | -3.402 | -16.681 | 55.756 | 1 | 17.06 | C |
| ATOM | 5714 | CG | MET | 212 | -3.232 | -15.955 | 57.075 | 1 | 20.46 | C |
| ATOM | 5715 | SD | MET | 212 | -1.732 | -14.95 | 57.072 | 1 | 22.92 | S |
| ATOM | 5716 | CE | MET | 212 | -1.636 | -14.465 | 58.792 | 1 | 27.66 | C |
| ATOM | 5717 | H | MET | 212 | -4.217 | -18.928 | 54.337 | 1 | 23.26 | H |
| ATOM | 5718 | HA | MET | 212 | -5.426 | -16.971 | 55.752 | 1 | 20.66 | H |
| ATOM | 5719 | HB2 | MET | 212 | -3.439 | -16.013 | 55.054 | 1 | 20.47 | H |
| ATOM | 5720 | HB3 | MET | 212 | -2.623 | -17.245 | 55.628 | 1 | 20.47 | H |
| ATOM | 5721 | HG2 | MET | 212 | -3.164 | -16.603 | 57.793 | 1 | 24.55 | H |
| ATOM | 5722 | HG3 | MET | 212 | -3.992 | -15.369 | 57.22 | 1 | 24.55 | H |
| ATOM | 5723 | HE1 | MET | 212 | -1.569 | -15.262 | 59.341 | 1 | 33.19 | H |
| ATOM | 5724 | HE2 | MET | 212 | -2.436 | -13.968 | 59.025 | 1 | 33.19 | H |
| ATOM | 5725 | HE3 | MET | 212 | -0.852 | -18.928 | 58.919 | 1 | 33.19 | H |
| ATOM | 5726 | N | GLN | 213 | -5.37 | -18.219 | 57.878 | 1 | 17.77 | N |
| ATOM | 5727 | CA | GLN | 213 | -5.404 | -19.048 | 59.079 | 1 | 25.12 | C |
| ATOM | 5728 | C | GLN | 213 | -5.4 | -18.16 | 60.318 | 1 | 26.47 | C |
| ATOM | 5729 | O | GLN | 213 | -6.282 | -17.319 | 60.489 | 1 | 26.02 | O |
| ATOM | 5730 | CB | GLN | 213 | -6.639 | -19.953 | 59.08 | 1 | 26.62 | C |
| ATOM | 5731 | CG | GLN | 213 | -6.655 | -20.999 | 60.187 | 1 | 29.95 | C |
| ATOM | 5732 | CD | GLN | 213 | -8.002 | -21.689 | 60.315 | 1 | 32.31 | C |
| ATOM | 5733 | OE1 | GLN | 213 | -8.926 | -21.157 | 60.93 | 1 | 30.11 | O |
| ATOM | 5734 | NE2 | GLN | 213 | -8.121 | -22.874 | 59.727 | 1 | 31.23 | N |
| ATOM | 5735 | H | GLN | 213 | -5.84 | -17.502 | 57.938 | 1 | 21.33 | H |
| ATOM | 5736 | HA | GLN | 213 | -4.614 | -19.61 | 59.103 | 1 | 30.14 | H |
| ATOM | 5737 | HB2 | GLN | 213 | -6.682 | -20.421 | 58.232 | 1 | 31.94 | H |
| ATOM | 5738 | HB3 | GLN | 213 | -7.429 | -19.4 | 59.188 | 1 | 31.94 | H |
| ATOM | 5739 | HG2 | GLN | 213 | -6.456 | -20.568 | 61.033 | 1 | 35.94 | H |
| ATOM | 5740 | HG3 | GLN | 213 | -5.987 | -21.676 | 59.993 | 1 | 35.94 | H |
| ATOM | 5741 | HE21 | GLN | 213 | -7.455 | -23.213 | 59.302 | 1 | 37.48 | H |
| ATOM | 5742 | HE22 | GLN | 213 | -8.865 | -23.304 | 59.772 | 1 | 37.48 | H |
| ATOM | 5743 | N | ARG | 214 | -4.398 | -18.344 | 61.171 | 1 | 27.5 | N |
| ATOM | 5744 | CA | ARG | 214 | -4.329 | -17.626 | 62.438 | 1 | 31.88 | C |
| ATOM | 5745 | C | ARG | 214 | -5.318 | -18.229 | 63.436 | 1 | 33.93 | C |
| ATOM | 5746 | O | ARG | 214 | -5.446 | -19.451 | 63.533 | 1 | 35.59 | O |
| ATOM | 5747 | CB | ARG | 214 | -2.905 | -17.664 | 62.994 | 1 | 40.82 | C |
| ATOM | 5748 | CG | ARG | 214 | -1.878 | -17.022 | 62.073 | 1 | 40.28 | C |
| ATOM | 5749 | CD | ARG | 214 | -0.473 | -17.093 | 62.643 | 1 | 53.54 | C |
| ATOM | 5750 | NE | ARG | 214 | -0.373 | -16.438 | 63.945 | 1 | 62.54 | N |
| ATOM | 5751 | CZ | ARG | 214 | -0.186 | -15.133 | 64.121 | 1 | 62.56 | C |

TABLE 5-continued

Atomic Coordinates for OMCP-NKG2D (4PDC).

| | | | | | | | | | | |
|---|---|---|---|---|---|---|---|---|---|---|
| ATOM | 5752 | NH1 | ARG | C | 214 | -0.083 | -14.32 | 63.078 | 1 | 49.8 | N1+ |
| ATOM | 5753 | NH2 | ARG | C | 214 | -0.106 | -14.635 | 65.349 | 1 | 61.54 | N |
| ATOM | 5754 | H | ARG | C | 214 | -3.741 | -18.883 | 61.038 | 1 | 33 | H |
| ATOM | 5755 | HA | ARG | C | 214 | -4.573 | -16.699 | 62.293 | 1 | 38.26 | H |
| ATOM | 5756 | HB2 | ARG | C | 214 | -2.647 | -18.588 | 63.131 | 1 | 48.98 | H |
| ATOM | 5757 | HB3 | ARG | C | 214 | -2.886 | -17.187 | 63.839 | 1 | 48.98 | H |
| ATOM | 5758 | HG2 | ARG | C | 214 | -2.104 | -16.088 | 61.945 | 1 | 48.33 | H |
| ATOM | 5759 | HG3 | ARG | C | 214 | -1.881 | -17.487 | 61.221 | 1 | 48.33 | H |
| ATOM | 5760 | HD2 | ARG | C | 214 | 0.14 | -16.651 | 62.035 | 1 | 64.25 | H |
| ATOM | 5761 | HD3 | ARG | C | 214 | -0.221 | -18.024 | 62.753 | 1 | 64.25 | H |
| ATOM | 5762 | HE | ARG | C | 214 | -0.44 | -16.931 | 64.647 | 1 | 75.04 | H |
| ATOM | 5763 | HH11 | ARG | C | 214 | -0.133 | -14.636 | 62.279 | 1 | 59.76 | H |
| ATOM | 5764 | HH12 | ARG | C | 214 | 0.037 | -13.477 | 63.199 | 1 | 59.76 | H |
| ATOM | 5765 | HH21 | ARG | C | 214 | -0.174 | -15.157 | 66.03 | 1 | 73.85 | H |
| ATOM | 5766 | HH22 | ARG | C | 214 | 0.012 | -13.791 | 65.465 | 1 | 73.85 | H |
| ATOM | 5767 | N | THR | C | 215 | -6.025 | -17.372 | 64.167 | 1 | 36.74 | N |
| ATOM | 5768 | CA | THR | C | 215 | -7.027 | -17.832 | 65.127 | 1 | 41.57 | C |
| ATOM | 5769 | C | THR | C | 215 | -6.376 | -18.393 | 66.389 | 1 | 37.21 | C |
| ATOM | 5770 | O | THR | C | 215 | -5.421 | -17.819 | 66.913 | 1 | 43.79 | O |
| ATOM | 5771 | CB | THR | C | 215 | -7.992 | -16.697 | 65.528 | 1 | 37.58 | C |
| ATOM | 5772 | OG1 | THR | C | 215 | -7.256 | -15.621 | 66.123 | 1 | 31.78 | O |
| ATOM | 5773 | CG2 | THR | C | 215 | -8.75 | -16.184 | 64.313 | 1 | 39.25 | C |
| ATOM | 5774 | H | THR | C | 215 | -5.945 | -16.517 | 64.125 | 1 | 44.09 | H |
| ATOM | 5775 | HA | THR | C | 215 | -7.551 | -18.54 | 64.721 | 1 | 49.88 | H |
| ATOM | 5776 | HB | THR | C | 215 | -8.637 | -17.036 | 66.169 | 1 | 45.09 | H |
| ATOM | 5777 | HG1 | THR | C | 215 | -6.693 | -15.322 | 65.577 | 1 | 38.13 | H |
| ATOM | 5778 | HG21 | THR | C | 215 | -9.354 | -15.471 | 64.576 | 1 | 47.1 | H |
| ATOM | 5779 | HG22 | THR | C | 215 | -9.266 | -16.903 | 63.916 | 1 | 47.1 | H |
| ATOM | 5780 | HG23 | THR | C | 215 | -8.126 | -15.841 | 63.654 | 1 | 47.1 | H |
| TER | 5781 | | THR | C | 215 | | | | | | |
| ATOM | 5782 | N | GLU | D | 93 | -16.518 | -24.144 | 60.935 | 1 | 50.72 | N |
| ATOM | 5783 | CA | GLU | D | 93 | -15.948 | -23.176 | 61.865 | 1 | 55.05 | C |
| ATOM | 5784 | C | GLU | D | 93 | -17.021 | -22.2 | 62.338 | 1 | 56.26 | C |
| ATOM | 5785 | O | GLU | D | 93 | -18.143 | -22.604 | 62.642 | 1 | 53.3 | O |
| ATOM | 5786 | CB | GLU | D | 93 | -15.318 | -23.888 | 63.062 | 1 | 63.84 | C |
| ATOM | 5787 | CG | GLU | D | 93 | -14.372 | -23.016 | 63.872 | 1 | 63.9 | C |
| ATOM | 5788 | CD | GLU | D | 93 | -13.844 | -23.716 | 65.113 | 1 | 77.81 | C |
| ATOM | 5789 | OE1 | GLU | D | 93 | -14.545 | -24.605 | 65.642 | 1 | 77.09 | O |
| ATOM | 5790 | OE2 | GLU | D | 93 | -12.725 | -23.379 | 65.558 | 1 | 78.31 | O1- |
| ATOM | 5791 | HA | GLU | D | 93 | -15.255 | -22.669 | 61.413 | 1 | 66.06 | H |
| ATOM | 5792 | HB2 | GLU | D | 93 | -14.813 | -24.651 | 62.74 | 1 | 76.6 | H |
| ATOM | 5793 | HB3 | GLU | D | 93 | -16.025 | -24.188 | 63.654 | 1 | 76.6 | H |
| ATOM | 5794 | HG2 | GLU | D | 93 | -14.844 | -22.217 | 64.157 | 1 | 76.68 | H |
| ATOM | 5795 | HG3 | GLU | D | 93 | -13.613 | -22.773 | 63.319 | 1 | 76.68 | H |
| ATOM | 5796 | N | SER | D | 94 | -16.675 | -20.918 | 62.405 | 1 | 45.44 | N |
| ATOM | 5797 | CA | SER | D | 94 | -17.646 | -19.894 | 62.768 | 1 | 42.83 | C |
| ATOM | 5798 | C | SER | D | 94 | -16.982 | -18.597 | 63.218 | 1 | 36.2 | C |
| ATOM | 5799 | O | SER | D | 94 | -15.871 | -18.274 | 62.8 | 1 | 34.62 | O |
| ATOM | 5800 | CB | SER | D | 94 | -18.576 | -19.613 | 61.582 | 1 | 47.3 | C |
| ATOM | 5801 | OG | SER | D | 94 | -19.526 | -18.609 | 61.895 | 1 | 57.24 | O |
| ATOM | 5802 | H | SER | D | 94 | -15.886 | -20.616 | 62.245 | 1 | 54.53 | H |

TABLE 5-continued

Atomic Coordinates for OMCP-NKG2D (4PDC).

| ATOM | 5803 | HA | SER | D | 94 | -18.189 | 63.502 | -20.221 | 1 | 51.4 | H |
|------|------|-----|-----|---|----|---------|--------|---------|---|------|---|
| ATOM | 5804 | HB2 | SER | D | 94 | -19.046 | 61.353 | -20.43 | 1 | 56.75 | H |
| ATOM | 5805 | HB3 | SER | D | 94 | -18.042 | 60.828 | -19.317 | 1 | 56.75 | H |
| ATOM | 5806 | HG | SER | D | 94 | -20.025 | 61.234 | -18.47 | 1 | 68.69 | H |
| ATOM | 5807 | N | TYR | D | 94 | -17.673 | 64.086 | -17.866 | 1 | 33.4 | N |
| ATOM | 5808 | CA | TYR | D | 95 | -17.266 | 64.466 | -16.52 | 1 | 33.91 | C |
| ATOM | 5809 | C | TYR | D | 95 | -17.891 | 63.519 | -15.505 | 1 | 30.98 | C |
| ATOM | 5810 | O | TYR | D | 95 | -18.999 | 63.025 | -15.711 | 1 | 31.07 | O |
| ATOM | 5811 | CB | TYR | D | 95 | -17.675 | 65.905 | -16.213 | 1 | 39.04 | C |
| ATOM | 5812 | CG | TYR | D | 95 | -16.785 | 66.949 | -16.84 | 1 | 41.85 | C |
| ATOM | 5813 | CD1 | TYR | D | 95 | -15.603 | 67.336 | -16.227 | 1 | 42.03 | C |
| ATOM | 5814 | CD2 | TYR | D | 95 | -17.13 | 67.557 | -18.04 | 1 | 50.41 | C |
| ATOM | 5815 | CE1 | TYR | D | 95 | -14.785 | 68.293 | -16.79 | 1 | 48.64 | C |
| ATOM | 5816 | CE2 | TYR | D | 95 | -16.319 | 68.517 | -18.613 | 1 | 52.83 | C |
| ATOM | 5817 | CZ | TYR | D | 95 | -15.147 | 68.881 | -17.983 | 1 | 57.25 | C |
| ATOM | 5818 | OH | TYR | D | 95 | -14.331 | 69.837 | -18.545 | 1 | 60.24 | O |
| ATOM | 5819 | H | TYR | D | 95 | -18.394 | 64.473 | -18.132 | 1 | 40.08 | H |
| ATOM | 5820 | HA | TYR | D | 95 | -16.301 | 64.4 | -16.446 | 1 | 40.69 | H |
| ATOM | 5821 | HB2 | TYR | D | 95 | -18.576 | 66.05 | -16.542 | 1 | 46.85 | H |
| ATOM | 5822 | HB3 | TYR | D | 95 | -17.653 | 66.037 | -15.252 | 1 | 46.85 | H |
| ATOM | 5823 | HD1 | TYR | D | 95 | -15.356 | 66.941 | -15.421 | 1 | 50.44 | H |
| ATOM | 5824 | HD2 | TYR | D | 95 | -17.92 | 67.312 | -18.465 | 1 | 60.5 | H |
| ATOM | 5825 | HE1 | TYR | D | 95 | -13.994 | 68.541 | -16.368 | 1 | 58.37 | H |
| ATOM | 5826 | HE2 | TYR | D | 95 | -16.561 | 68.915 | -19.418 | 1 | 63.4 | H |
| ATOM | 5827 | HH | TYR | D | 95 | -14.664 | 70.113 | -19.265 | 1 | 72.28 | H |
| ATOM | 5828 | N | CYS | D | 96 | -17.171 | 63.269 | -14.415 | 1 | 25.95 | N |
| ATOM | 5829 | CA | CYS | D | 96 | -17.651 | 62.404 | -13.343 | 1 | 25 | C |
| ATOM | 5830 | C | CYS | D | 96 | -17.873 | 63.227 | -12.08 | 1 | 26.6 | C |
| ATOM | 5831 | O | CYS | D | 96 | -17.011 | 64.017 | -11.687 | 1 | 24.78 | O |
| ATOM | 5832 | CB | CYS | D | 96 | -16.654 | 61.274 | -13.078 | 1 | 24.34 | C |
| ATOM | 5833 | SG | CYS | D | 96 | -17.22 | 60.018 | -11.906 | 1 | 25.98 | S |
| ATOM | 5834 | H | CYS | D | 96 | -16.388 | 63.595 | -14.272 | 1 | 31.14 | H |
| ATOM | 5835 | HA | CYS | D | 96 | -18.498 | 62.01 | -13.603 | 1 | 30 | H |
| ATOM | 5836 | HB2 | CYS | D | 96 | -16.465 | 60.826 | -13.918 | 1 | 29.21 | H |
| ATOM | 5837 | HB3 | CYS | D | 96 | -15.838 | 61.659 | -12.724 | 1 | 29.21 | H |
| ATOM | 5838 | N | GLY | D | 97 | -19.032 | 63.042 | -11.454 | 1 | 23.68 | N |
| ATOM | 5839 | CA | GLY | D | 97 | -19.358 | 63.738 | -10.223 | 1 | 26.95 | C |
| ATOM | 5840 | C | GLY | D | 97 | -20.783 | 64.263 | -10.206 | 1 | 29.72 | C |
| ATOM | 5841 | O | GLY | D | 97 | -21.654 | 63.711 | -10.88 | 1 | 30.29 | O |
| ATOM | 5842 | H | GLY | D | 97 | -19.651 | 62.512 | -11.73 | 1 | 28.42 | H |
| ATOM | 5843 | HA2 | GLY | D | 97 | -19.245 | 63.135 | -9.472 | 1 | 32.33 | H |
| ATOM | 5844 | HA3 | GLY | D | 97 | -18.755 | 64.489 | -10.108 | 1 | 32.33 | H |
| ATOM | 5845 | N | PRO | D | 98 | -21.033 | 65.333 | -9.432 | 1 | 27.73 | N |
| ATOM | 5846 | CA | PRO | D | 98 | -20.059 | 66.06 | -8.605 | 1 | 26.68 | C |
| ATOM | 5847 | C | PRO | D | 98 | -19.526 | 65.247 | -7.425 | 1 | 25.52 | C |
| ATOM | 5848 | O | PRO | D | 98 | -20.262 | 64.465 | -6.822 | 1 | 24.79 | O |
| ATOM | 5849 | CB | PRO | D | 98 | -20.855 | 67.272 | -8.11 | 1 | 31.02 | C |
| ATOM | 5850 | CG | PRO | D | 98 | -22.272 | 66.852 | -8.178 | 1 | 32.89 | C |
| ATOM | 5851 | CD | PRO | D | 98 | -22.37 | 65.945 | -9.363 | 1 | 31.01 | C |
| ATOM | 5852 | HA | PRO | D | 98 | -19.315 | 66.363 | -9.148 | 1 | 32.02 | H |
| ATOM | 5853 | HB2 | PRO | D | 98 | -20.601 | 67.48 | -7.197 | 1 | 37.23 | H |

TABLE 5-continued

Atomic Coordinates for OMCP-NKG2D (4PDC).

| ATOM | 5854 | HB3 | PRO | D | 98  | -20.692 | 68.03  | -8.693  | 1 | 37.23 | H   |
|------|------|-----|-----|---|-----|---------|--------|---------|---|-------|-----|
| ATOM | 5855 | HG2 | PRO | D | 98  | -22.51  | 66.38  | -7.366  | 1 | 39.46 | H   |
| ATOM | 5856 | HG3 | PRO | D | 98  | -22.837 | 67.632 | -8.298  | 1 | 39.46 | H   |
| ATOM | 5857 | HD2 | PRO | D | 98  | -23.046 | 65.266 | -9.214  | 1 | 37.21 | H   |
| ATOM | 5858 | HD3 | PRO | D | 98  | -22.55  | 66.456 | -10.167 | 1 | 37.21 | H   |
| ATOM | 5859 | N   | CYS | D | 99  | -18.247 | 65.439 | -7.115  | 1 | 22.53 | N   |
| ATOM | 5860 | CA  | CYS | D | 99  | -17.605 | 64.787 | -5.978  | 1 | 24.42 | C   |
| ATOM | 5861 | C   | CYS | D | 99  | -16.595 | 65.739 | -5.345  | 1 | 27.19 | C   |
| ATOM | 5862 | O   | CYS | D | 99  | -16.094 | 66.638 | -6.017  | 1 | 26.74 | O   |
| ATOM | 5863 | CB  | CYS | D | 99  | -16.895 | 63.496 | -6.407  | 1 | 28.73 | C   |
| ATOM | 5864 | SG  | CYS | D | 99  | -17.971 | 62.187 | -7.066  | 1 | 27.37 | S   |
| ATOM | 5865 | H   | CYS | D | 99  | -17.719 | 65.952 | -7.559  | 1 | 27.03 | H   |
| ATOM | 5866 | HA  | CYS | D | 99  | -18.275 | 64.563 | -5.313  | 1 | 29.3  | H   |
| ATOM | 5867 | HB2 | CYS | D | 99  | -16.25  | 63.716 | -7.097  | 1 | 34.48 | H   |
| ATOM | 5868 | HB3 | CYS | D | 99  | -16.432 | 63.131 | -5.637  | 1 | 34.48 | H   |
| ATOM | 5869 | N   | PRO | D | 100 | -16.293 | 65.547 | -4.051  | 1 | 23.29 | N   |
| ATOM | 5870 | CA  | PRO | D | 100 | -15.166 | 66.276 | -3.458  | 1 | 27.44 | C   |
| ATOM | 5871 | C   | PRO | D | 100 | -13.882 | 66.019 | -4.245  | 1 | 28.68 | C   |
| ATOM | 5872 | O   | PRO | D | 100 | -13.681 | 64.904 | -4.73   | 1 | 26.75 | O   |
| ATOM | 5873 | CB  | PRO | D | 100 | -15.073 | 65.703 | -2.043  | 1 | 29.15 | C   |
| ATOM | 5874 | CG  | PRO | D | 100 | -16.42  | 65.125 | -1.767  | 1 | 25.98 | C   |
| ATOM | 5875 | CD  | PRO | D | 100 | -16.95  | 64.656 | -3.079  | 1 | 24.13 | C   |
| ATOM | 5876 | HA  | PRO | D | 100 | -15.349 | 67.228 | -3.42   | 1 | 32.93 | H   |
| ATOM | 5877 | HB2 | PRO | D | 100 | -14.392 | 65.013 | -2.014  | 1 | 34.98 | H   |
| ATOM | 5878 | HB3 | PRO | D | 100 | -14.869 | 66.414 | -1.415  | 1 | 34.98 | H   |
| ATOM | 5879 | HG2 | PRO | D | 100 | -16.333 | 64.382 | -1.15   | 1 | 31.17 | H   |
| ATOM | 5880 | HG3 | PRO | D | 100 | -16.996 | 65.811 | -1.394  | 1 | 31.17 | H   |
| ATOM | 5881 | HD2 | PRO | D | 100 | -16.693 | 63.734 | -3.238  | 1 | 28.95 | H   |
| ATOM | 5882 | HD3 | PRO | D | 100 | -17.913 | 64.769 | -3.115  | 1 | 28.95 | H   |
| ATOM | 5883 | N   | LYS | D | 101 | -13.027 | 67.031 | -4.357  | 1 | 31.41 | N   |
| ATOM | 5884 | CA  | LYS | D | 101 | -11.915 | 66.997 | -5.306  | 1 | 34.02 | C   |
| ATOM | 5885 | C   | LYS | D | 101 | -10.851 | 65.943 | -4.997  | 1 | 34.04 | C   |
| ATOM | 5886 | O   | LYS | D | 101 | -10.078 | 65.57  | -5.884  | 1 | 40.88 | O   |
| ATOM | 5887 | CB  | LYS | D | 101 | -11.254 | 68.377 | -5.379  | 1 | 40.64 | C   |
| ATOM | 5888 | CG  | LYS | D | 101 | -12.15  | 69.458 | -5.975  | 1 | 44.15 | C   |
| ATOM | 5889 | CD  | LYS | D | 101 | -11.383 | 70.749 | -6.223  | 1 | 55.25 | C   |
| ATOM | 5890 | CE  | LYS | D | 101 | -12.306 | 71.866 | -6.691  | 1 | 57.18 | C   |
| ATOM | 5891 | NZ  | LYS | D | 101 | -11.566 | 73.132 | -6.955  | 1 | 56.55 | N1+ |
| ATOM | 5892 | H   | LYS | D | 101 | -13.069 | 67.753 | -3.892  | 1 | 37.69 | H   |
| ATOM | 5893 | HA  | LYS | D | 101 | -12.271 | 66.799 | -6.186  | 1 | 40.82 | H   |
| ATOM | 5894 | HB2 | LYS | D | 101 | -11.011 | 68.655 | -4.482  | 1 | 48.77 | H   |
| ATOM | 5895 | HB3 | LYS | D | 101 | -10.459 | 68.314 | -5.931  | 1 | 48.77 | H   |
| ATOM | 5896 | HG2 | LYS | D | 101 | -12.505 | 69.147 | -6.823  | 1 | 52.98 | H   |
| ATOM | 5897 | HG3 | LYS | D | 101 | -12.874 | 69.649 | -5.358  | 1 | 52.98 | H   |
| ATOM | 5898 | HD2 | LYS | D | 101 | -10.957 | 71.032 | -5.399  | 1 | 66.3  | H   |
| ATOM | 5899 | HD3 | LYS | D | 101 | -10.716 | 70.598 | -6.911  | 1 | 66.3  | H   |
| ATOM | 5900 | HE2 | LYS | D | 101 | -12.743 | 71.594 | -7.513  | 1 | 68.62 | H   |
| ATOM | 5901 | HE3 | LYS | D | 101 | -12.967 | 72.04  | -6.003  | 1 | 68.62 | H   |
| ATOM | 5902 | HZ1 | LYS | D | 101 | -12.132 | 73.763 | -7.226  | 1 | 67.86 | H   |
| ATOM | 5903 | HZ2 | LYS | D | 101 | -11.16  | 73.407 | -6.213  | 1 | 67.86 | H   |
| ATOM | 5904 | HZ3 | LYS | D | 101 | -10.955 | 73     | -7.588  | 1 | 67.86 | H   |

TABLE 5-continued

Atomic Coordinates for OMCP-NKG2D (4PDC).

| | | | | | | | | | | |
|---|---|---|---|---|---|---|---|---|---|---|
| ATOM | 5905 | N | ASN | D | 102 | -10.804 | -3.755 | 65.47 | 1 | 27.12 | N |
| ATOM | 5906 | CA | ASN | D | 102 | -9.836 | -3.366 | 64.445 | 1 | 27.98 | C |
| ATOM | 5907 | C | ASN | D | 102 | -10.503 | -3.072 | 63.098 | 1 | 26.71 | C |
| ATOM | 5908 | O | ASN | D | 102 | -9.946 | -2.36 | 62.263 | 1 | 25.4 | O |
| ATOM | 5909 | CB | ASN | D | 102 | -9.026 | -2.15 | 64.914 | 1 | 30.15 | C |
| ATOM | 5910 | CG | ASN | D | 102 | -9.898 | -1.045 | 65.481 | 1 | 36.72 | C |
| ATOM | 5911 | OD1 | ASN | D | 102 | -11.12 | -1.062 | 65.332 | 1 | 37.16 | O |
| ATOM | 5912 | ND2 | ASN | D | 102 | -9.271 | -0.078 | 66.145 | 1 | 41.06 | N |
| ATOM | 5913 | H | ASN | D | 102 | -11.322 | 3.118 | 65.725 | 1 | 32.55 | H |
| ATOM | 5914 | HA | ASN | D | 102 | -9.215 | -4.099 | 64.311 | 1 | 33.58 | H |
| ATOM | 5915 | HB2 | ASN | D | 102 | -8.535 | -1.787 | 64.16 | 1 | 36.19 | H |
| ATOM | 5916 | HB3 | ASN | D | 102 | -8.409 | -2.43 | 65.608 | 1 | 36.19 | H |
| ATOM | 5917 | HD21 | ASN | D | 102 | -9.72 | 0.571 | 66.485 | 1 | 49.28 | H |
| ATOM | 5918 | HD22 | ASN | D | 102 | -8.416 | -0.102 | 66.233 | 1 | 49.28 | H |
| ATOM | 5919 | N | TRP | D | 103 | -11.696 | -3.63 | 62.897 | 1 | 25.27 | N |
| ATOM | 5920 | CA | TRP | D | 103 | -12.4 | -3.534 | 61.619 | 1 | 19.72 | C |
| ATOM | 5921 | C | TRP | D | 103 | -12.378 | -4.872 | 60.891 | 1 | 20.07 | C |
| ATOM | 5922 | O | TRP | D | 103 | -12.24 | -5.927 | 61.516 | 1 | 20.39 | O |
| ATOM | 5923 | CB | TRP | D | 103 | -13.853 | -3.094 | 61.822 | 1 | 22.5 | C |
| ATOM | 5924 | CG | TRP | D | 103 | -14.018 | -1.636 | 62.103 | 1 | 21.05 | C |
| ATOM | 5925 | CD1 | TRP | D | 103 | -13.247 | -0.865 | 62.919 | 1 | 26.32 | C |
| ATOM | 5926 | CD2 | TRP | D | 103 | -15.014 | -0.768 | 61.552 | 1 | 22.01 | C |
| ATOM | 5927 | NE1 | TRP | D | 103 | -13.708 | 0.43 | 62.92 | 1 | 31.25 | N |
| ATOM | 5928 | CE2 | TRP | D | 103 | -14.792 | 0.516 | 62.088 | 1 | 23.75 | C |
| ATOM | 5929 | CE3 | TRP | D | 103 | -16.075 | -0.952 | 60.66 | 1 | 21.83 | C |
| ATOM | 5930 | CZ2 | TRP | D | 103 | -15.589 | 1.611 | 61.759 | 1 | 26.02 | C |
| ATOM | 5931 | CZ3 | TRP | D | 103 | -16.868 | 0.136 | 60.336 | 1 | 24.01 | C |
| ATOM | 5932 | CH2 | TRP | D | 103 | -16.62 | 1.401 | 60.884 | 1 | 22.41 | C |
| ATOM | 5933 | H | TRP | D | 103 | -12.124 | -4.077 | 63.494 | 1 | 30.33 | H |
| ATOM | 5934 | HA | TRP | D | 103 | -11.959 | -2.876 | 61.06 | 1 | 23.66 | H |
| ATOM | 5935 | HB2 | TRP | D | 103 | -14.225 | -3.583 | 62.572 | 1 | 27 | H |
| ATOM | 5936 | HB3 | TRP | D | 103 | -14.355 | -3.298 | 61.017 | 1 | 27 | H |
| ATOM | 5937 | HD1 | TRP | D | 103 | -12.52 | -1.172 | 63.412 | 1 | 31.59 | H |
| ATOM | 5938 | HE1 | TRP | D | 103 | -13.369 | 1.081 | 63.369 | 1 | 37.5 | H |
| ATOM | 5939 | HE3 | TRP | D | 103 | -16.245 | 1.789 | 60.292 | 1 | 26.2 | H |
| ATOM | 5940 | HZ2 | TRP | D | 103 | -15.427 | 2.452 | 62.122 | 1 | 31.22 | H |
| ATOM | 5941 | HZ3 | TRP | D | 103 | -17.577 | 0.025 | 59.744 | 1 | 28.82 | H |
| ATOM | 5942 | HH2 | TRP | D | 103 | -17.169 | 2.114 | 60.649 | 1 | 26.9 | H |
| ATOM | 5943 | N | ILE | D | 104 | -12.524 | -4.821 | 59.571 | 1 | 16.86 | N |
| ATOM | 5944 | CA | ILE | D | 104 | -12.597 | -6.027 | 58.755 | 1 | 17.78 | C |
| ATOM | 5945 | C | ILE | D | 104 | -13.993 | -6.627 | 58.831 | 1 | 18.2 | C |
| ATOM | 5946 | O | ILE | D | 104 | -14.975 | -5.944 | 58.549 | 1 | 18.57 | O |
| ATOM | 5947 | CB | ILE | D | 104 | -12.255 | -5.735 | 57.281 | 1 | 20.02 | C |
| ATOM | 5948 | CG1 | ILE | D | 104 | -10.857 | -5.119 | 57.168 | 1 | 20.67 | C |
| ATOM | 5949 | CG2 | ILE | D | 104 | -12.338 | -7.015 | 56.446 | 1 | 19.79 | C |
| ATOM | 5950 | CD1 | ILE | D | 104 | -10.571 | -4.483 | 55.825 | 1 | 17.1 | C |
| ATOM | 5951 | H | ILE | D | 104 | -12.585 | -4.092 | 59.12 | 1 | 20.23 | H |
| ATOM | 5952 | HA | ILE | D | 104 | -11.965 | -6.681 | 59.091 | 1 | 21.34 | H |
| ATOM | 5953 | HB | ILE | D | 104 | -12.901 | -5.099 | 56.935 | 1 | 24.02 | H |
| ATOM | 5954 | HG12 | ILE | D | 104 | -10.197 | -5.815 | 57.313 | 1 | 24.8 | H |
| ATOM | 5955 | HG13 | ILE | D | 104 | -10.763 | -4.432 | 57.847 | 1 | 24.8 | H |

TABLE 5-continued

Atomic Coordinates for OMCP-NKG2D (4PDC).

| ATOM | 5956 | HG21 | ILE | D | 104 | -12.12 | 55.525 | -6.805 | 1 | 23.75 | H |
|------|------|------|-----|---|-----|--------|--------|--------|---|-------|---|
| ATOM | 5957 | HG22 | ILE | D | 104 | -13.24 | 56.5 | -7.368 | 1 | 23.75 | H |
| ATOM | 5958 | HG23 | ILE | D | 104 | -11.707 | 56.798 | -7.662 | 1 | 23.75 | H |
| ATOM | 5959 | HD11 | ILE | D | 104 | -9.673 | 55.834 | -4.118 | 1 | 20.52 | H |
| ATOM | 5960 | HD12 | ILE | D | 104 | -11.215 | 55.668 | -3.774 | 1 | 20.52 | H |
| ATOM | 5961 | HD13 | ILE | D | 104 | -10.648 | 55.134 | -5.159 | 1 | 20.52 | H |
| ATOM | 5962 | N | CYS | D | 105 | -14.076 | 59.199 | -7.902 | 1 | 17.45 | N |
| ATOM | 5963 | CA | CYS | D | 105 | -15.354 | 59.239 | -8.602 | 1 | 17.74 | C |
| ATOM | 5964 | C | CYS | D | 105 | -15.465 | 58.067 | -9.573 | 1 | 21.3 | C |
| ATOM | 5965 | O | CYS | D | 105 | -14.56 | 57.821 | -10.371 | 1 | 19.85 | O |
| ATOM | 5966 | CB | CYS | D | 105 | -15.524 | 60.563 | -9.345 | 1 | 20.49 | C |
| ATOM | 5967 | SG | CYS | D | 105 | -17.186 | 60.797 | -10.022 | 1 | 29.47 | S |
| ATOM | 5968 | H | CYS | D | 105 | -13.404 | 59.431 | -8.385 | 1 | 20.94 | H |
| ATOM | 5969 | HA | CYS | D | 105 | -16.073 | 59.163 | -7.955 | 1 | 21.29 | H |
| ATOM | 5970 | HB2 | CYS | D | 105 | -15.347 | 61.293 | -8.731 | 1 | 24.59 | H |
| ATOM | 5971 | HB3 | CYS | D | 105 | -14.895 | 60.592 | -10.083 | 1 | 24.59 | H |
| ATOM | 5972 | N | TYR | D | 106 | -16.577 | 57.343 | -9.481 | 1 | 17.44 | N |
| ATOM | 5973 | CA | TYR | D | 106 | -16.858 | 56.216 | -10.365 | 1 | 18.5 | C |
| ATOM | 5974 | C | TYR | D | 106 | -18.354 | 56.134 | -10.632 | 1 | 19.85 | C |
| ATOM | 5975 | O | TYR | D | 106 | -19.139 | 55.879 | -9.718 | 1 | 18.05 | O |
| ATOM | 5976 | CB | TYR | D | 106 | -16.362 | 54.902 | -9.755 | 1 | 15.27 | C |
| ATOM | 5977 | CG | TYR | D | 106 | -16.488 | 53.707 | -10.675 | 1 | 17.55 | C |
| ATOM | 5978 | CD1 | TYR | D | 106 | -15.878 | 53.702 | -11.922 | 1 | 20.29 | C |
| ATOM | 5979 | CD2 | TYR | D | 106 | -17.202 | 52.577 | -10.293 | 1 | 20.08 | C |
| ATOM | 5980 | CE1 | TYR | D | 106 | -15.981 | 52.613 | -12.768 | 1 | 20.5 | C |
| ATOM | 5981 | CE2 | TYR | D | 106 | -17.309 | 51.476 | -11.136 | 1 | 18.23 | C |
| ATOM | 5982 | CZ | TYR | D | 106 | -16.692 | 51.502 | -12.373 | 1 | 22.08 | C |
| ATOM | 5983 | OH | TYR | D | 106 | -16.785 | 50.418 | -13.224 | 1 | 18.81 | O |
| ATOM | 5984 | H | TYR | D | 106 | -17.196 | 57.488 | -8.902 | 1 | 20.92 | H |
| ATOM | 5985 | HA | TYR | D | 106 | -16.403 | 56.351 | -11.211 | 1 | 22.2 | H |
| ATOM | 5986 | HB2 | TYR | D | 106 | -15.425 | 55 | -9.524 | 1 | 18.33 | H |
| ATOM | 5987 | HB3 | TYR | D | 106 | -16.879 | 54.715 | -8.956 | 1 | 18.33 | H |
| ATOM | 5988 | HD1 | TYR | D | 106 | -15.394 | 54.448 | -12.195 | 1 | 24.35 | H |
| ATOM | 5989 | HD2 | TYR | D | 106 | -17.616 | 52.557 | -9.46 | 1 | 24.1 | H |
| ATOM | 5990 | HE1 | TYR | D | 106 | -15.565 | 52.629 | -13.6 | 1 | 24.6 | H |
| ATOM | 5991 | HE2 | TYR | D | 106 | -17.79 | 50.727 | -10.869 | 1 | 21.87 | H |
| ATOM | 5992 | HH | TYR | D | 106 | -17.243 | 49.811 | -12.867 | 1 | 22.58 | H |
| ATOM | 5993 | N | LYS | D | 107 | -18.732 | 56.351 | -11.888 | 1 | 16.29 | N |
| ATOM | 5994 | CA | LYS | D | 107 | -20.132 | 56.364 | -12.294 | 1 | 20.57 | C |
| ATOM | 5995 | C | LYS | D | 107 | -20.916 | 57.33 | -11.404 | 1 | 24.05 | C |
| ATOM | 5996 | O | LYS | D | 107 | -21.998 | 57.015 | -10.907 | 1 | 17.53 | O |
| ATOM | 5997 | CB | LYS | D | 107 | -20.708 | 54.947 | -12.249 | 1 | 20.83 | C |
| ATOM | 5998 | CG | LYS | D | 107 | -19.963 | 53.987 | -13.184 | 1 | 20.22 | C |
| ATOM | 5999 | CD | LYS | D | 107 | -20.505 | 52.566 | -13.145 | 1 | 20.35 | C |
| ATOM | 6000 | CE | LYS | D | 107 | -19.817 | 51.694 | -14.198 | 1 | 23.07 | C |
| ATOM | 6001 | NZ | LYS | D | 107 | -20.217 | 50.259 | -14.138 | 1 | 21 | N1+ |
| ATOM | 6002 | H | LYS | D | 107 | -18.185 | 56.495 | -12.536 | 1 | 19.55 | H |
| ATOM | 6003 | HA | LYS | D | 107 | -20.193 | 56.682 | -13.208 | 1 | 24.68 | H |
| ATOM | 6004 | HB2 | LYS | D | 107 | -20.637 | 54.604 | -11.344 | 1 | 24.99 | H |
| ATOM | 6005 | HB3 | LYS | D | 107 | -21.638 | 54.974 | -12.523 | 1 | 24.99 | H |
| ATOM | 6006 | HG2 | LYS | D | 107 | -20.041 | 54.311 | -14.094 | 1 | 24.26 | H |

TABLE 5-continued

Atomic Coordinates for OMCP-NKG2D (4PDC).

| | | | | | | | | | | |
|---|---|---|---|---|---|---|---|---|---|---|
| ATOM | 6007 | HG3 | LYS | D | 107 | -19.029 | 53.957 | -12.923 | 1 | 24.26 | H |
| ATOM | 6008 | HD2 | LYS | D | 107 | -20.338 | 52.18 | -12.271 | 1 | 24.42 | H |
| ATOM | 6009 | HD3 | LYS | D | 107 | -21.457 | 52.579 | -13.332 | 1 | 24.42 | H |
| ATOM | 6010 | HE2 | LYS | D | 107 | -20.045 | 52.029 | -15.08 | 1 | 27.69 | H |
| ATOM | 6011 | HE3 | LYS | D | 107 | -18.857 | 51.741 | -14.065 | 1 | 27.69 | H |
| ATOM | 6012 | HZ1 | LYS | D | 107 | -21.095 | 50.182 | -14.267 | 1 | 25.2 | H |
| ATOM | 6013 | HZ2 | LYS | D | 107 | -19.791 | 49.797 | -14.768 | 1 | 25.2 | H |
| ATOM | 6014 | HZ3 | LYS | D | 107 | -20.011 | 49.919 | -13.341 | 1 | 25.2 | H |
| ATOM | 6015 | N | ASN | D | 108 | -20.318 | 58.503 | -11.205 | 1 | 23.09 | N |
| ATOM | 6016 | CA | ASN | D | 108 | -20.912 | 59.622 | -10.473 | 1 | 24.38 | C |
| ATOM | 6017 | C | ASN | D | 108 | -21.096 | 59.378 | -8.976 | 1 | 22.29 | C |
| ATOM | 6018 | O | ASN | D | 108 | -21.565 | 60.261 | -8.262 | 1 | 28.01 | O |
| ATOM | 6019 | CB | ASN | D | 108 | -22.253 | 60.012 | -11.103 | 1 | 25.1 | C |
| ATOM | 6020 | CG | ASN | D | 108 | -22.084 | 60.642 | -12.471 | 1 | 28.43 | C |
| ATOM | 6021 | OD1 | ASN | D | 108 | -21.044 | 61.229 | -12.769 | 1 | 25.66 | O |
| ATOM | 6022 | ND2 | ASN | D | 108 | -23.107 | 60.529 | -13.31 | 1 | 30.87 | N |
| ATOM | 6023 | H | ASN | D | 108 | -19.53 | 58.682 | -11.5 | 1 | 27.71 | H |
| ATOM | 6024 | HA | ASN | D | 108 | -20.321 | 60.386 | -10.565 | 1 | 29.25 | H |
| ATOM | 6025 | HB2 | ASN | D | 108 | -22.8 | 59.217 | -11.203 | 1 | 30.12 | H |
| ATOM | 6026 | HB3 | ASN | D | 108 | -22.698 | 60.654 | -10.529 | 1 | 30.12 | H |
| ATOM | 6027 | HD21 | ASN | D | 108 | -23.057 | 60.871 | -14.098 | 1 | 37.04 | H |
| ATOM | 6028 | HD22 | ASN | D | 108 | -23.82 | 60.115 | -13.066 | 1 | 37.04 | H |
| ATOM | 6029 | N | ASN | D | 109 | -20.704 | 58.205 | -8.494 | 1 | 21.22 | N |
| ATOM | 6030 | CA | ASN | D | 109 | -20.646 | 57.967 | -7.056 | 1 | 19.34 | C |
| ATOM | 6031 | C | ASN | D | 109 | -19.262 | 58.34 | -6.533 | 1 | 19.61 | C |
| ATOM | 6032 | O | ASN | D | 109 | -18.267 | 58.162 | -7.232 | 1 | 16.71 | O |
| ATOM | 6033 | CB | ASN | D | 109 | -20.973 | 56.512 | -6.733 | 1 | 19.32 | C |
| ATOM | 6034 | CG | ASN | D | 109 | -22.421 | 56.167 | -7.013 | 1 | 25.66 | C |
| ATOM | 6035 | OD1 | ASN | D | 109 | -23.322 | 56.973 | -6.77 | 1 | 19.34 | O |
| ATOM | 6036 | ND2 | ASN | D | 109 | -22.652 | 54.969 | -7.533 | 1 | 19.02 | N |
| ATOM | 6037 | H | ASN | D | 109 | -20.467 | 57.532 | -8.974 | 1 | 25.47 | H |
| ATOM | 6038 | HA | ASN | D | 109 | -21.3 | 58.53 | -6.613 | 1 | 23.2 | H |
| ATOM | 6039 | HB2 | ASN | D | 109 | -20.415 | 55.934 | -7.278 | 1 | 23.19 | H |
| ATOM | 6040 | HB3 | ASN | D | 109 | -20.801 | 56.35 | -5.792 | 1 | 23.19 | H |
| ATOM | 6041 | HD21 | ASN | D | 109 | -23.457 | 54.725 | -7.71 | 1 | 22.82 | H |
| ATOM | 6042 | HD22 | ASN | D | 109 | -21.996 | 54.436 | -7.693 | 1 | 22.82 | H |
| ATOM | 6043 | N | CYS | D | 110 | -19.204 | 58.867 | -5.312 | 1 | 17.46 | N |
| ATOM | 6044 | CA | CYS | D | 110 | -17.941 | 59.308 | -4.726 | 1 | 16.88 | C |
| ATOM | 6045 | C | CYS | D | 110 | -17.547 | 58.402 | -3.573 | 1 | 19.16 | C |
| ATOM | 6046 | O | CYS | D | 110 | -18.374 | 58.079 | -2.725 | 1 | 17.29 | O |
| ATOM | 6047 | CB | CYS | D | 110 | -18.047 | 60.751 | -4.237 | 1 | 22.6 | C |
| ATOM | 6048 | SG | CYS | D | 110 | -18.972 | 61.837 | -5.338 | 1 | 23.11 | S |
| ATOM | 6049 | H | CYS | D | 110 | -19.886 | 58.981 | -4.801 | 1 | 20.95 | H |
| ATOM | 6050 | HA | CYS | D | 110 | -17.244 | 59.265 | -5.399 | 1 | 20.25 | H |
| ATOM | 6051 | HB2 | CYS | D | 110 | -18.493 | 60.756 | -3.375 | 1 | 27.12 | H |
| ATOM | 6052 | HB3 | CYS | D | 110 | -17.153 | 61.116 | -4.145 | 1 | 27.12 | H |
| ATOM | 6053 | N | TYR | D | 111 | -16.28 | 58.001 | -3.545 | 1 | 18.03 | N |
| ATOM | 6054 | CA | TYR | D | 111 | -15.768 | 57.132 | -2.489 | 1 | 17.44 | C |
| ATOM | 6055 | C | TYR | D | 111 | -14.471 | 57.677 | -1.92 | 1 | 15.34 | C |
| ATOM | 6056 | O | TYR | D | 111 | -13.731 | 58.388 | -2.6 | 1 | 20.2 | O |
| ATOM | 6057 | CB | TYR | D | 111 | -15.515 | 55.718 | -3.016 | 1 | 18.77 | C |

TABLE 5-continued

Atomic Coordinates for OMCP-NKG2D (4PDC).

| ATOM | 6058 | CG | TYR | D | 111 | -16.678 | 55.089 | -3.737 | 1 | 20.6 | C |
| ATOM | 6059 | CD1 | TYR | D | 111 | -16.879 | 55.308 | -5.09 | 1 | 15.51 | C |
| ATOM | 6060 | CD2 | TYR | D | 111 | -17.561 | 54.251 | -3.07 | 1 | 20.76 | C |
| ATOM | 6061 | CE1 | TYR | D | 111 | -17.936 | 54.723 | -5.757 | 1 | 18.59 | C |
| ATOM | 6062 | CE2 | TYR | D | 111 | -18.625 | 53.664 | -3.728 | 1 | 17.85 | C |
| ATOM | 6063 | CZ | TYR | D | 111 | -17.936 | 53.903 | -5.071 | 1 | 18.9 | C |
| ATOM | 6064 | OH | TYR | D | 111 | -18.806 | 53.323 | -5.732 | 1 | 19.85 | O |
| ATOM | 6065 | H | TYR | D | 111 | -15.691 | 58.22 | 4.132 | 1 | 21.63 | H |
| ATOM | 6066 | HA | TYR | D | 111 | -16.418 | 57.08 | -1.772 | 1 | 20.92 | H |
| ATOM | 6067 | HB2 | TYR | D | 111 | -14.769 | 55.748 | -3.635 | 1 | 22.52 | H |
| ATOM | 6068 | HB3 | TYR | D | 111 | -15.291 | 55.145 | -2.266 | 1 | 22.52 | H |
| ATOM | 6069 | HD1 | TYR | D | 111 | -16.294 | 55.862 | -5.556 | 1 | 18.61 | H |
| ATOM | 6070 | HD2 | TYR | D | 111 | -17.44 | 54.089 | -2.162 | 1 | 24.91 | H |
| ATOM | 6071 | HE1 | TYR | D | 111 | -18.064 | 54.885 | 6.664 | 1 | 22.3 | H |
| ATOM | 6072 | HE2 | TYR | D | 111 | -19.212 | 53.11 | -3.267 | 1 | 21.42 | H |
| ATOM | 6073 | HH | TYR | D | 111 | -19.863 | 53.553 | -6.54 | 1 | 23.82 | H |
| ATOM | 6074 | N | GLN | D | 112 | -14.19 | 57.329 | -0.673 | 1 | 17.91 | N |
| ATOM | 6075 | CA | GLN | D | 112 | -12.866 | 57.552 | -0.119 | 1 | 20.98 | C |
| ATOM | 6076 | C | GLN | D | 112 | -13.417 | 56.483 | 0.914 | 1 | 18.4 | C |
| ATOM | 6077 | O | GLN | D | 112 | -12.75 | 56.045 | 1.668 | 1 | 17.57 | O |
| ATOM | 6078 | CB | GLN | D | 112 | -11.326 | 58.949 | 0.496 | 1 | 23.03 | C |
| ATOM | 6079 | CG | GLN | D | 112 | -10.317 | 59.331 | 0.905 | 1 | 24.86 | C |
| ATOM | 6080 | CD | GLN | D | 112 | -10.317 | 59.175 | -0.225 | 1 | 29.43 | C |
| ATOM | 6081 | OE1 | GLN | D | 112 | -9.797 | 58.083 | -0.469 | 1 | 32.59 | O |
| ATOM | 6082 | NE2 | GLN | D | 112 | -10.033 | 60.27 | -0.92 | 1 | 35.19 | N |
| ATOM | 6083 | H | GLN | D | 112 | -14.747 | 56.965 | -0.128 | 1 | 21.49 | H |
| ATOM | 6084 | HA | GLN | D | 112 | -12.211 | 57.483 | -0.831 | 1 | 25.18 | H |
| ATOM | 6085 | HB2 | GLN | D | 112 | -13.057 | 59.602 | -0.152 | 1 | 27.63 | H |
| ATOM | 6086 | HB3 | GLN | D | 112 | -13.306 | 58.987 | 1.29 | 1 | 27.63 | H |
| ATOM | 6087 | HG2 | GLN | D | 112 | -11.318 | 60.259 | 1.187 | 1 | 29.83 | H |
| ATOM | 6088 | HG3 | GLN | D | 112 | -11.045 | 58.76 | 1.637 | 1 | 29.83 | H |
| ATOM | 6089 | HE21 | GLN | D | 112 | -9.469 | 60.234 | -1.568 | 1 | 42.23 | H |
| ATOM | 6090 | HE22 | GLN | D | 112 | -10.414 | 61.015 | -0.721 | 1 | 42.23 | H |
| ATOM | 6091 | N | PHE | D | 113 | -11.293 | 56.059 | 0.921 | 1 | 15.24 | N |
| ATOM | 6092 | CA | PHE | D | 113 | -10.808 | 55.082 | 1.878 | 1 | 19.47 | C |
| ATOM | 6093 | C | PHE | D | 113 | -10.013 | 55.796 | 2.963 | 1 | 22.57 | C |
| ATOM | 6094 | O | PHE | D | 113 | -9.202 | 56.678 | 2.676 | 1 | 28.44 | O |
| ATOM | 6095 | CB | PHE | D | 113 | -9.955 | 54.026 | 1.172 | 1 | 25.43 | C |
| ATOM | 6096 | CG | PHE | D | 113 | -10.73 | 53.179 | 0.198 | 1 | 22.13 | C |
| ATOM | 6097 | CD1 | PHE | D | 113 | -11.227 | 53.727 | -0.976 | 1 | 29.41 | C |
| ATOM | 6098 | CD2 | PHE | D | 113 | -10.953 | 51.836 | 0.45 | 1 | 23.89 | C |
| ATOM | 6099 | CE1 | PHE | D | 113 | -11.94 | 52.951 | -1.877 | 1 | 30.31 | C |
| ATOM | 6100 | CE2 | PHE | D | 113 | -11.666 | 51.054 | -0.447 | 1 | 21.37 | C |
| ATOM | 6101 | CZ | PHE | D | 113 | -12.16 | 51.613 | -1.61 | 1 | 23.83 | C |
| ATOM | 6102 | H | PHE | D | 113 | -10.692 | 56.33 | 0.369 | 1 | 18.29 | H |
| ATOM | 6103 | HA | PHE | D | 113 | -11.562 | 54.637 | 2.294 | 1 | 23.37 | H |
| ATOM | 6104 | HB2 | PHE | D | 113 | -9.247 | 54.472 | 0.681 | 1 | 30.51 | H |
| ATOM | 6105 | HB3 | PHE | D | 113 | -9.571 | 53.436 | 1.839 | 1 | 30.51 | H |
| ATOM | 6106 | HD1 | PHE | D | 113 | -11.084 | 54.627 | -1.159 | 1 | 35.29 | H |
| ATOM | 6107 | HD2 | PHE | D | 113 | -10.625 | 51.455 | 1.232 | 1 | 28.66 | H |
| ATOM | 6108 | HE1 | PHE | D | 113 | -12.27 | 53.33 | -2.659 | 1 | 36.37 | H |

TABLE 5-continued

Atomic Coordinates for OMCP-NKG2D (4PDC).

| ATOM | 6109 | HE2 | PHE | D | 113 | -11.812 | -0.265 | 50.154 | 1 | 25.65 | H |
|------|------|-----|-----|---|-----|---------|--------|--------|---|-------|---|
| ATOM | 6110 | HZ  | PHE | D | 113 | -12.637 | -2.213 | 51.089 | 1 | 28.6  | H |
| ATOM | 6111 | N   | PHE | D | 114 | -10.275 | 4.209  | 55.42  | 1 | 21.22 | N |
| ATOM | 6112 | CA  | PHE | D | 114 | -9.633  | 5.368  | 56.027 | 1 | 22.84 | C |
| ATOM | 6113 | C   | PHE | D | 114 | -8.84   | 6.111  | 54.967 | 1 | 25.57 | C |
| ATOM | 6114 | O   | PHE | D | 114 | -9.409  | 6.59   | 53.987 | 1 | 20.97 | O |
| ATOM | 6115 | CB  | PHE | D | 114 | -10.682 | 6.28   | 56.665 | 1 | 25.74 | C |
| ATOM | 6116 | CG  | PHE | D | 114 | -11.434 | 5.629  | 57.787 | 1 | 22.57 | C |
| ATOM | 6117 | CD1 | PHE | D | 114 | -12.523 | 4.817  | 57.53  | 1 | 23.79 | C |
| ATOM | 6118 | CD2 | PHE | D | 114 | -11.041 | 5.819  | 59.102 | 1 | 30.88 | C |
| ATOM | 6119 | CE1 | PHE | D | 114 | -13.208 | 4.209  | 58.562 | 1 | 26.61 | C |
| ATOM | 6120 | CE2 | PHE | D | 114 | -11.723 | 5.214  | 60.139 | 1 | 23.44 | C |
| ATOM | 6121 | CZ  | PHE | D | 114 | -12.809 | 4.409  | 59.869 | 1 | 28.06 | C |
| ATOM | 6122 | H   | PHE | D | 114 | -10.835 | 4.413  | 54.801 | 1 | 25.46 | H |
| ATOM | 6123 | HA  | PHE | D | 114 | -9.02   | 5.073  | 56.719 | 1 | 27.4  | H |
| ATOM | 6124 | HB2 | PHE | D | 114 | -11.325 | 6.54   | 55.987 | 1 | 30.89 | H |
| ATOM | 6125 | HB3 | PHE | D | 114 | -10.24  | 7.067  | 57.019 | 1 | 30.89 | H |
| ATOM | 6126 | HD1 | PHE | D | 114 | -12.796 | 4.678  | 56.652 | 1 | 28.55 | H |
| ATOM | 6127 | HD2 | PHE | D | 114 | -10.308 | 6.361  | 59.288 | 1 | 37.05 | H |
| ATOM | 6128 | HE1 | PHE | D | 114 | -13.941 | 3.667  | 58.378 | 1 | 31.94 | H |
| ATOM | 6129 | HE2 | PHE | D | 114 | -11.451 | 5.351  | 61.018 | 1 | 28.13 | H |
| ATOM | 6130 | HZ  | PHE | D | 114 | -13.271 | 4.001  | 60.565 | 1 | 33.67 | H |
| ATOM | 6131 | N   | ASP | D | 115 | -7.526  | 6.199  | 55.161 | 1 | 23.12 | N |
| ATOM | 6132 | CA  | ASP | D | 115 | -6.645  | 6.737  | 54.131 | 1 | 26.22 | C |
| ATOM | 6133 | C   | ASP | D | 115 | -6.365  | 8.228  | 54.317 | 1 | 30.31 | C |
| ATOM | 6134 | O   | ASP | D | 115 | -5.656  | 8.831  | 53.516 | 1 | 25.41 | O |
| ATOM | 6135 | CB  | ASP | D | 115 | -5.328  | 5.957  | 54.096 | 1 | 27.72 | C |
| ATOM | 6136 | CG  | ASP | D | 115 | -4.615  | 5.94   | 55.436 | 1 | 34.76 | C |
| ATOM | 6137 | OD1 | ASP | D | 115 | -5.1    | 6.587  | 56.389 | 1 | 33.82 | O |
| ATOM | 6138 | OD2 | ASP | D | 115 | -3.558  | 5.282  | 55.53  | 1 | 32.71 | O1- |
| ATOM | 6139 | H   | ASP | D | 115 | -7.122  | 5.954  | 55.879 | 1 | 27.74 | H |
| ATOM | 6140 | HA  | ASP | D | 115 | -7.075  | 6.626  | 53.269 | 1 | 31.46 | H |
| ATOM | 6141 | HB2 | ASP | D | 115 | -4.735  | 6.367  | 53.447 | 1 | 33.26 | H |
| ATOM | 6142 | HB3 | ASP | D | 115 | -5.512  | 5.039  | 53.843 | 1 | 33.26 | H |
| ATOM | 6143 | N   | GLU | D | 116 | -6.92   | 8.817  | 55.373 | 1 | 29.51 | N |
| ATOM | 6144 | CA  | GLU | D | 116 | -6.821  | 10.259 | 55.578 | 1 | 35.02 | C |
| ATOM | 6145 | C   | GLU | D | 116 | -7.96   | 10.921 | 54.814 | 1 | 33.34 | C |
| ATOM | 6146 | O   | GLU | D | 116 | -9.096  | 10.94  | 55.282 | 1 | 33.54 | O |
| ATOM | 6147 | CB  | GLU | D | 116 | -6.88   | 10.624 | 57.067 | 1 | 38.38 | C |
| ATOM | 6148 | CG  | GLU | D | 116 | -5.921  | 9.836  | 57.96  | 1 | 42.91 | C |
| ATOM | 6149 | CD  | GLU | D | 116 | -6.444  | 8.458  | 58.351 | 1 | 44.87 | C |
| ATOM | 6150 | OE1 | GLU | D | 116 | -7.627  | 8.155  | 58.078 | 1 | 38.52 | O |
| ATOM | 6151 | OE2 | GLU | D | 116 | -5.664  | 7.673  | 58.934 | 1 | 52.44 | O1- |
| ATOM | 6152 | H   | GLU | D | 116 | -7.36   | 8.404  | 55.986 | 1 | 35.41 | H |
| ATOM | 6153 | HA  | GLU | D | 116 | -5.98   | 10.58  | 55.216 | 1 | 42.03 | H |
| ATOM | 6154 | HB2 | GLU | D | 116 | -7.781  | 10.462 | 57.389 | 1 | 46.06 | H |
| ATOM | 6155 | HB3 | GLU | D | 116 | -6.665  | 11.565 | 57.163 | 1 | 46.06 | H |
| ATOM | 6156 | HG2 | GLU | D | 116 | -5.768  | 10.338 | 58.775 | 1 | 51.49 | H |
| ATOM | 6157 | HG3 | GLU | D | 116 | -5.083  | 9.712  | 57.487 | 1 | 51.49 | H |
| ATOM | 6158 | N   | SER | D | 117 | -7.65   | 11.457 | 53.636 | 1 | 30.25 | N |
| ATOM | 6159 | CA  | SER | D | 117 | -8.674  | 11.907 | 52.697 | 1 | 27.86 | C |

TABLE 5-continued

Atomic Coordinates for OMCP-NKG2D (4PDC).

| | | | | | | | | | | |
|---|---|---|---|---|---|---|---|---|---|---|
| ATOM | 6160 | C | SER | D | 117 | -9.509 | 53.219 | 13.077 | 1 | 33.38 | C |
| ATOM | 6161 | O | SER | D | 117 | -8.988 | 53.81 | 14.022 | 1 | 30.47 | O |
| ATOM | 6162 | CB | SER | D | 117 | -8.028 | 51.365 | 12.297 | 1 | 31.01 | C |
| ATOM | 6163 | OG | SER | D | 117 | -7.15 | 51.529 | 13.392 | 1 | 34.1 | O |
| ATOM | 6164 | H | SER | D | 117 | -6.845 | 53.355 | 11.571 | 1 | 36.3 | H |
| ATOM | 6165 | HA | SER | D | 117 | -9.279 | 52.525 | 11.169 | 1 | 33.44 | H |
| ATOM | 6166 | HB2 | SER | D | 117 | -8.725 | 50.737 | 12.543 | 1 | 37.21 | H |
| ATOM | 6167 | HB3 | SER | D | 117 | -7.527 | 51.024 | 11.539 | 1 | 37.21 | H |
| ATOM | 6168 | HG | SER | D | 117 | -6.803 | 50.792 | 13.595 | 1 | 40.92 | H |
| ATOM | 6169 | N | LYS | D | 118 | -10.814 | 52.976 | 12.992 | 1 | 27.74 | N |
| ATOM | 6170 | CA | LYS | D | 118 | -11.771 | 53.385 | 14.015 | 1 | 27.96 | C |
| ATOM | 6171 | C | LYS | D | 118 | -12.805 | 52.284 | 14.202 | 1 | 31.8 | C |
| ATOM | 6172 | O | LYS | D | 118 | -12.946 | 51.409 | 13.343 | 1 | 27.27 | O |
| ATOM | 6173 | CB | LYS | D | 118 | -11.533 | 54.689 | 13.619 | 1 | 25.67 | C |
| ATOM | 6174 | CG | LYS | D | 118 | -12.464 | 55.875 | 13.44 | 1 | 29.25 | C |
| ATOM | 6175 | CD | LYS | D | 118 | -12.293 | 57.075 | 12.904 | 1 | 36.12 | C |
| ATOM | 6176 | CE | LYS | D | 118 | -11.416 | 58.312 | 12.827 | 1 | 36.2 | C |
| ATOM | 6177 | NZ | LYS | D | 118 | -10.988 | 58.767 | 14.175 | 1 | 46.64 | N1+ |
| ATOM | 6178 | H | LYS | D | 118 | -11.179 | 52.564 | 12.332 | 1 | 33.29 | H |
| ATOM | 6179 | HA | LYS | D | 118 | -11.309 | 53.523 | 14.856 | 1 | 33.55 | H |
| ATOM | 6180 | HB2 | LYS | D | 118 | -12.928 | 54.55 | 12.778 | 1 | 30.81 | H |
| ATOM | 6181 | HB3 | LYS | D | 118 | -13.105 | 54.921 | 14.31 | 1 | 30.81 | H |
| ATOM | 6182 | HG2 | LYS | D | 118 | -11.146 | 56.114 | 14.297 | 1 | 35.1 | H |
| ATOM | 6183 | HG3 | LYS | D | 118 | -10.836 | 55.645 | 12.806 | 1 | 35.1 | H |
| ATOM | 6184 | HD2 | LYS | D | 118 | -12.615 | 56.876 | 12.011 | 1 | 43.34 | H |
| ATOM | 6185 | HD3 | LYS | D | 118 | -13.039 | 57.269 | 13.493 | 1 | 43.34 | H |
| ATOM | 6186 | HE2 | LYS | D | 118 | -10.621 | 58.108 | 12.31 | 1 | 43.44 | H |
| ATOM | 6187 | HE3 | LYS | D | 118 | -11.914 | 59.031 | 12.408 | 1 | 43.44 | H |
| ATOM | 6188 | HZ1 | LYS | D | 118 | -10.477 | 59.492 | 14.103 | 1 | 55.96 | H |
| ATOM | 6189 | HZ2 | LYS | D | 118 | -11.701 | 58.965 | 14.67 | 1 | 55.96 | H |
| ATOM | 6190 | HZ3 | LYS | D | 118 | -10.524 | 58.125 | 14.58 | 1 | 55.96 | H |
| ATOM | 6191 | N | ASN | D | 119 | -13.531 | 52.314 | 15.316 | 1 | 28.46 | N |
| ATOM | 6192 | CA | ASN | D | 119 | -14.632 | 51.378 | 15.495 | 1 | 27.04 | C |
| ATOM | 6193 | C | ASN | D | 119 | -15.773 | 51.811 | 14.585 | 1 | 24.03 | C |
| ATOM | 6194 | O | ASN | D | 119 | -15.713 | 52.884 | 13.985 | 1 | 24.95 | O |
| ATOM | 6195 | CB | ASN | D | 119 | -15.068 | 51.301 | 16.964 | 1 | 27.48 | C |
| ATOM | 6196 | CG | ASN | D | 119 | -15.649 | 52.6 | 17.483 | 1 | 26.83 | C |
| ATOM | 6197 | OD1 | ASN | D | 119 | -16.565 | 53.173 | 16.895 | 1 | 25.34 | O |
| ATOM | 6198 | ND2 | ASN | D | 119 | -15.119 | 53.069 | 18.606 | 1 | 37.21 | N |
| ATOM | 6199 | H | ASN | D | 119 | -13.408 | 52.858 | 15.971 | 1 | 34.15 | H |
| ATOM | 6200 | HA | ASN | D | 119 | -14.345 | 50.494 | 15.22 | 1 | 32.45 | H |
| ATOM | 6201 | HB2 | ASN | D | 119 | -15.747 | 50.613 | 17.054 | 1 | 32.97 | H |
| ATOM | 6202 | HB3 | ASN | D | 119 | -14.298 | 51.079 | 17.51 | 1 | 32.97 | H |
| ATOM | 6203 | HD21 | ASN | D | 119 | -15.411 | 53.803 | 18.945 | 1 | 44.65 | H |
| ATOM | 6204 | HD22 | ASN | D | 119 | -14.484 | 52.638 | 18.994 | 1 | 44.65 | H |
| ATOM | 6205 | N | TRP | D | 120 | -16.807 | 50.986 | 14.472 | 1 | 21.37 | N |
| ATOM | 6206 | CA | TRP | D | 120 | -17.855 | 51.238 | 13.492 | 1 | 24.98 | C |
| ATOM | 6207 | C | TRP | D | 120 | -18.589 | 52.545 | 13.77 | 1 | 24.15 | C |
| ATOM | 6208 | O | TRP | D | 120 | -18.945 | 53.274 | 12.844 | 1 | 19.58 | O |
| ATOM | 6209 | CB | TRP | D | 120 | -18.855 | 50.083 | 13.46 | 1 | 21.6 | C |
| ATOM | 6210 | CG | TRP | D | 120 | -19.879 | 50.242 | 12.386 | 1 | 23.54 | C |

TABLE 5-continued

Atomic Coordinates for OMCP-NKG2D (4PDC).

| ATOM | 6211 | CD1 | TRP | D | 120 | -19.797 | 49.787 | 11.102 | 1 | 24.11 | C |
|------|------|-----|-----|---|-----|---------|--------|--------|---|-------|---|
| ATOM | 6212 | CD2 | TRP | D | 120 | -21.137 | 50.917 | 12.493 | 1 | 26.63 | C |
| ATOM | 6213 | NE1 | TRP | D | 120 | -20.927 | 50.135 | 10.404 | 1 | 25.43 | N |
| ATOM | 6214 | CE2 | TRP | D | 120 | -21.766 | 50.828 | 11.236 | 1 | 27.74 | C |
| ATOM | 6215 | CE3 | TRP | D | 120 | -21.793 | 51.587 | 13.531 | 1 | 30.26 | C |
| ATOM | 6216 | CZ2 | TRP | D | 120 | -23.02 | 51.379 | 10.989 | 1 | 28.23 | C |
| ATOM | 6217 | CZ3 | TRP | D | 120 | -23.036 | 52.136 | 13.283 | 1 | 28.53 | C |
| ATOM | 6218 | CH2 | TRP | D | 120 | -23.637 | 52.03 | 12.022 | 1 | 29.49 | C |
| ATOM | 6219 | H | TRP | D | 120 | -16.924 | 50.278 | 14.947 | 1 | 25.65 | H |
| ATOM | 6220 | HA | TRP | D | 120 | -17.452 | 51.305 | 12.612 | 1 | 29.98 | H |
| ATOM | 6221 | HB2 | TRP | D | 120 | -18.377 | 49.255 | 13.3 | 1 | 25.92 | H |
| ATOM | 6222 | HB3 | TRP | D | 120 | -19.317 | 50.041 | 14.312 | 1 | 25.92 | H |
| ATOM | 6223 | HD1 | TRP | D | 120 | -19.079 | 49.312 | 10.75 | 1 | 28.93 | H |
| ATOM | 6224 | HE1 | TRP | D | 120 | -21.084 | 49.945 | 9.58 | 1 | 30.52 | H |
| ATOM | 6225 | HE3 | TRP | D | 120 | -21.4 | 51.661 | 14.37 | 1 | 36.31 | H |
| ATOM | 6226 | HZ2 | TRP | D | 120 | -23.421 | 51.312 | 10.153 | 1 | 33.87 | H |
| ATOM | 6227 | HZ3 | TRP | D | 120 | -23.482 | 52.583 | 13.965 | 1 | 34.24 | H |
| ATOM | 6228 | HH2 | TRP | D | 120 | -24.475 | 52.408 | 11.885 | 1 | 35.38 | H |
| ATOM | 6229 | N | TYR | D | 121 | -18.808 | 52.839 | 15.047 | 1 | 27.37 | N |
| ATOM | 6230 | CA | TYR | D | 121 | -19.558 | 54.028 | 15.438 | 1 | 29.38 | C |
| ATOM | 6231 | C | TYR | D | 121 | -18.799 | 55.295 | 15.065 | 1 | 22.01 | C |
| ATOM | 6232 | O | TYR | D | 121 | -19.365 | 56.214 | 14.481 | 1 | 23.03 | O |
| ATOM | 6233 | CB | TYR | D | 121 | -19.857 | 54.001 | 16.939 | 1 | 32.74 | C |
| ATOM | 6234 | CG | TYR | D | 121 | -20.587 | 52.751 | 17.378 | 1 | 29.99 | C |
| ATOM | 6235 | CD1 | TYR | D | 121 | -21.946 | 52.598 | 17.144 | 1 | 35.21 | C |
| ATOM | 6236 | CD2 | TYR | D | 121 | -19.911 | 51.718 | 18.016 | 1 | 32.98 | C |
| ATOM | 6237 | CE1 | TYR | D | 121 | -22.616 | 51.452 | 17.538 | 1 | 36.69 | C |
| ATOM | 6238 | CE2 | TYR | D | 121 | -20.571 | 50.569 | 18.414 | 1 | 36.17 | C |
| ATOM | 6239 | CZ | TYR | D | 121 | -21.922 | 50.442 | 18.172 | 1 | 40.29 | C |
| ATOM | 6240 | OH | TYR | D | 121 | -22.582 | 49.3 | 18.566 | 1 | 49.6 | O |
| ATOM | 6241 | H | TYR | D | 121 | -18.531 | 52.365 | 15.709 | 1 | 32.84 | H |
| ATOM | 6242 | HA | TYR | D | 121 | -20.405 | 54.036 | 14.964 | 1 | 35.25 | H |
| ATOM | 6243 | HB2 | TYR | D | 121 | -19.02 | 54.046 | 17.428 | 1 | 39.29 | H |
| ATOM | 6244 | HB3 | TYR | D | 121 | -20.412 | 54.765 | 17.163 | 1 | 39.29 | H |
| ATOM | 6245 | HD1 | TYR | D | 121 | -22.416 | 53.277 | 16.716 | 1 | 42.26 | H |
| ATOM | 6246 | HD2 | TYR | D | 121 | -19 | 51.801 | 18.18 | 1 | 39.57 | H |
| ATOM | 6247 | HE1 | TYR | D | 121 | -23.527 | 51.364 | 17.376 | 1 | 44.02 | H |
| ATOM | 6248 | HE2 | TYR | D | 121 | -20.106 | 49.887 | 18.842 | 1 | 43.4 | H |
| ATOM | 6249 | HH | TYR | D | 121 | -22.045 | 48.771 | 18.937 | 1 | 59.52 | H |
| ATOM | 6250 | N | GLU | D | 122 | -17.513 | 55.332 | 15.395 | 1 | 23.53 | N |
| ATOM | 6251 | CA | GLU | D | 122 | -16.664 | 56.463 | 15.044 | 1 | 26.93 | C |
| ATOM | 6252 | C | GLU | D | 122 | -16.509 | 56.579 | 13.53 | 1 | 25.72 | C |
| ATOM | 6253 | O | GLU | D | 122 | -16.406 | 57.68 | 12.991 | 1 | 23.66 | O |
| ATOM | 6254 | CB | GLU | D | 122 | -15.294 | 56.318 | 15.702 | 1 | 31.25 | C |
| ATOM | 6255 | CG | GLU | D | 122 | -15.338 | 56.331 | 17.223 | 1 | 35.27 | C |
| ATOM | 6256 | CD | GLU | D | 122 | -14.056 | 55.821 | 17.855 | 1 | 43.03 | C |
| ATOM | 6257 | OE1 | GLU | D | 122 | -13.27 | 55.135 | 17.162 | 1 | 42.6 | O |
| ATOM | 6258 | OE2 | GLU | D | 122 | -13.837 | 56.104 | 19.051 | 1 | 53.83 | O1- |
| ATOM | 6259 | H | GLU | D | 122 | -17.105 | 54.71 | 15.826 | 1 | 28.23 | H |
| ATOM | 6260 | HA | GLU | D | 122 | -17.071 | 57.281 | 15.37 | 1 | 32.32 | H |
| ATOM | 6261 | HB2 | GLU | D | 122 | -14.902 | 55.475 | 15.424 | 1 | 37.5 | H |

TABLE 5-continued

Atomic Coordinates for OMCP-NKG2D (4PDC).

| | | | | | | | | | | |
|---|---|---|---|---|---|---|---|---|---|---|
| ATOM | 6262 | HB3 | GLU | D | 122 | -14.73 | 57.053 | 15.415 | 1 | 37.5 | H |
| ATOM | 6263 | HG2 | GLU | D | 122 | -15.48 | 57.241 | 17.526 | 1 | 42.33 | H |
| ATOM | 6264 | HG3 | GLU | D | 122 | -16.066 | 55.764 | 17.522 | 1 | 42.33 | H |
| ATOM | 6265 | N | SER | D | 122 | -16.486 | 55.436 | 12.848 | 1 | 21.52 | N |
| ATOM | 6266 | CA | SER | D | 123 | -16.412 | 55.419 | 11.391 | 1 | 23.2 | C |
| ATOM | 6267 | C | SER | D | 123 | -17.68 | 56.03 | 10.804 | 1 | 23.42 | C |
| ATOM | 6268 | O | SER | D | 123 | -17.62 | 56.862 | 9.898 | 1 | 20.31 | O |
| ATOM | 6269 | CB | SER | D | 123 | -16.216 | 53.993 | 10.871 | 1 | 21.62 | C |
| ATOM | 6270 | OG | SER | D | 123 | -14.982 | 53.454 | 11.306 | 1 | 19.63 | O |
| ATOM | 6271 | H | SER | D | 123 | -16.512 | 54.655 | 13.208 | 1 | 25.82 | H |
| ATOM | 6272 | HA | SER | D | 123 | -15.656 | 55.954 | 11.103 | 1 | 27.84 | H |
| ATOM | 6273 | HB2 | SER | D | 123 | -16.938 | 53.435 | 11.202 | 1 | 25.94 | H |
| ATOM | 6274 | HB3 | SER | D | 123 | -16.229 | 54.007 | 9.901 | 1 | 25.94 | H |
| ATOM | 6275 | HG | SER | D | 123 | -14.957 | 53.434 | 12.146 | 1 | 23.55 | H |
| ATOM | 6276 | N | GLN | D | 124 | -18.827 | 55.611 | 11.331 | 1 | 20.37 | N |
| ATOM | 6277 | CA | GLN | D | 124 | -20.107 | 56.17 | 10.922 | 1 | 24.01 | C |
| ATOM | 6278 | C | GLN | D | 124 | -20.123 | 57.683 | 11.103 | 1 | 25.04 | C |
| ATOM | 6279 | O | GLN | D | 124 | -20.549 | 58.42 | 10.214 | 1 | 21.92 | O |
| ATOM | 6280 | CB | GLN | D | 124 | -21.238 | 55.534 | 11.725 | 1 | 28.29 | C |
| ATOM | 6281 | CG | GLN | D | 124 | -22.605 | 56.135 | 11.471 | 1 | 32.29 | C |
| ATOM | 6282 | CD | GLN | D | 124 | -23.667 | 55.497 | 12.338 | 1 | 34.18 | C |
| ATOM | 6283 | OE1 | GLN | D | 124 | -23.49 | 55.356 | 13.549 | 1 | 37.41 | O |
| ATOM | 6284 | NE2 | GLN | D | 124 | -24.773 | 55.089 | 11.722 | 1 | 37.93 | N |
| ATOM | 6285 | H | GLN | D | 124 | -18.888 | 55.975 | 11.933 | 1 | 24.45 | H |
| ATOM | 6286 | HA | GLN | D | 124 | -20.255 | 55 | 9.983 | 1 | 28.81 | H |
| ATOM | 6287 | HB2 | GLN | D | 124 | -21.284 | 54.591 | 11.501 | 1 | 33.95 | H |
| ATOM | 6288 | HB3 | GLN | D | 124 | -21.042 | 55.636 | 12.669 | 1 | 33.95 | H |
| ATOM | 6289 | HG2 | GLN | D | 124 | -22.579 | 57.083 | 11.672 | 1 | 38.75 | H |
| ATOM | 6290 | HG3 | GLN | D | 124 | -22.848 | 55.995 | 10.543 | 1 | 38.75 | H |
| ATOM | 6291 | HE21 | GLN | D | 124 | -25.405 | 54.72 | 12.174 | 1 | 45.51 | H |
| ATOM | 6292 | HE22 | GLN | D | 124 | -24.855 | 55.194 | 10.873 | 1 | 45.51 | H |
| ATOM | 6293 | N | ALA | D | 125 | -19.652 | 58.135 | 12.26 | 1 | 25.98 | N |
| ATOM | 6294 | CA | ALA | D | 125 | -19.64 | 59.555 | 12.584 | 1 | 27.07 | C |
| ATOM | 6295 | C | ALA | D | 125 | -18.721 | 60.311 | 11.636 | 1 | 24.27 | C |
| ATOM | 6296 | O | ALA | D | 125 | -19.057 | 61.397 | 11.168 | 1 | 27.08 | O |
| ATOM | 6297 | CB | ALA | D | 125 | -19.207 | 59.766 | 14.027 | 1 | 26.32 | C |
| ATOM | 6298 | H | ALA | D | 125 | -19.331 | 57.633 | 12.88 | 1 | 31.18 | H |
| ATOM | 6299 | HA | ALA | D | 125 | -20.537 | 59.912 | 12.483 | 1 | 32.48 | H |
| ATOM | 6300 | HB1 | ALA | D | 125 | -19.206 | 60.716 | 14.221 | 1 | 31.59 | H |
| ATOM | 6301 | HB2 | ALA | D | 125 | -19.830 | 59.309 | 14.613 | 1 | 131.59 | H |
| ATOM | 6302 | HB3 | ALA | D | 125 | -18.315 | 59.403 | 14.144 | 1 | 131.59 | H |
| ATOM | 6303 | N | SER | D | 126 | -17.562 | 59.727 | 11.351 | 1 | 125.39 | N |
| ATOM | 6304 | CA | SER | D | 126 | -16.606 | 60.338 | 10.437 | 1 | 125.90 | C |
| ATOM | 6305 | C | SER | D | 126 | -17.233 | 60.587 | 9.066 | 1 | 121.76 | C |
| ATOM | 6306 | O | SER | D | 126 | -17.156 | 61.693 | 8.535 | 1 | 120.77 | O |
| ATOM | 6307 | CB | SER | D | 126 | -15.363 | 59.460 | 10.298 | 1 | 124.59 | C |
| ATOM | 6308 | OG | SER | D | 126 | -14.403 | 60.072 | 9.456 | 1 | 123.90 | O |
| ATOM | 6309 | H | SER | D | 126 | -17.305 | 58.973 | 11.676 | 1 | 130.47 | H |
| ATOM | 6310 | HA | SER | D | 126 | -16.328 | 61.195 | 10.798 | 1 | 131.08 | H |
| ATOM | 6311 | HB2 | SER | D | 126 | -14.973 | 59.325 | 11.175 | 1 | 129.51 | H |
| ATOM | 6312 | HB3 | SER | D | 126 | -15.621 | 58.607 | 9.915 | 1 | 129.51 | H |

TABLE 5-continued

Atomic Coordinates for OMCP-NKG2D (4PDC).

| ATOM | 6313 | HG | SER | D | 126 | -13.725 | 59.580 | 9.388 | 128.69 | H |
|---|---|---|---|---|---|---|---|---|---|---|
| ATOM | 6314 | N | CYS | D | 127 | -17.866 | 59.564 | 8.501 | 122.12 | N |
| ATOM | 6315 | CA | CYS | D | 127 | -18.500 | 59.692 | 7.192 | 122.37 | C |
| ATOM | 6316 | C | CYS | D | 127 | -19.619 | 60.731 | 7.206 | 123.64 | C |
| ATOM | 6317 | O | CYS | D | 127 | -19.765 | 61.513 | 6.260 | 123.85 | O |
| ATOM | 6318 | CB | CYS | D | 127 | -19.053 | 58.341 | 6.731 | 123.71 | C |
| ATOM | 6319 | SG | CYS | D | 127 | -17.786 | 57.091 | 6.427 | 120.25 | S |
| ATOM | 6320 | H | CYS | D | 127 | -17.943 | 58.784 | 8.855 | 126.54 | H |
| ATOM | 6321 | HA | CYS | D | 127 | -17.834 | 59.978 | 6.548 | 126.84 | H |
| ATOM | 6322 | HB2 | CYS | D | 127 | -19.648 | 57.998 | 7.415 | 128.45 | H |
| ATOM | 6323 | HB3 | CYS | D | 127 | -19.544 | 58.471 | 5.905 | 128.45 | H |
| ATOM | 6324 | N | MET | D | 128 | -20.406 | 60.737 | 8.277 | 124.97 | N |
| ATOM | 6325 | CA | MET | D | 128 | -21.524 | 61.668 | 8.398 | 126.23 | C |
| ATOM | 6326 | C | MET | D | 128 | -21.036 | 63.111 | 8.394 | 126.46 | C |
| ATOM | 6327 | O | MET | D | 128 | -21.642 | 63.975 | 7.764 | 129.60 | O |
| ATOM | 6328 | CB | MET | D | 128 | -22.322 | 61.394 | 9.673 | 127.84 | C |
| ATOM | 6329 | CG | MET | D | 128 | -23.246 | 60.187 | 9.582 | 142.42 | C |
| ATOM | 6330 | SD | MET | D | 128 | -24.266 | 59.966 | 11.056 | 163.01 | S |
| ATOM | 6331 | CE | MET | D | 128 | -25.311 | 61.419 | 10.970 | 161.60 | C |
| ATOM | 6332 | H | MET | D | 128 | -20.314 | 60.209 | 8.950 | 129.96 | H |
| ATOM | 6333 | HA | MET | D | 128 | -22.120 | 61.539 | 7.643 | 131.47 | H |
| ATOM | 6334 | HB2 | MET | D | 128 | -21.701 | 61.237 | 10.401 | 133.41 | H |
| ATOM | 6335 | HB3 | MET | D | 128 | -22.869 | 62.171 | 9.871 | 133.41 | H |
| ATOM | 6336 | HG2 | MET | D | 128 | -23.839 | 60.301 | 8.823 | 150.90 | H |
| ATOM | 6337 | HG3 | MET | D | 128 | -22.710 | 59.388 | 9.467 | 150.90 | H |
| ATOM | 6338 | HE1 | MET | D | 128 | -25.919 | 61.416 | 11.726 | 173.92 | H |
| ATOM | 6339 | HE2 | MET | D | 128 | -24.752 | 62.212 | 10.998 | 173.92 | H |
| ATOM | 6340 | HE3 | MET | D | 128 | -25.814 | 61.398 | 10.141 | 173.92 | H |
| ATOM | 6341 | N | SER | D | 129 | -19.934 | 63.362 | 9.092 | 127.28 | N |
| ATOM | 6342 | CA | SER | D | 129 | -19.385 | 64.711 | 9.196 | 130.17 | C |
| ATOM | 6343 | C | SER | D | 129 | -18.834 | 65.196 | 7.859 | 128.90 | C |
| ATOM | 6344 | O | SER | D | 129 | -18.574 | 66.386 | 7.686 | 128.22 | O |
| ATOM | 6345 | CB | SER | D | 129 | -18.286 | 64.764 | 10.259 | 135.60 | C |
| ATOM | 6346 | OG | SER | D | 129 | -17.121 | 64.078 | 9.831 | 130.81 | O |
| ATOM | 6347 | H | SER | D | 129 | -19.482 | 62.766 | 9.517 | 132.74 | H |
| ATOM | 6348 | HA | SER | D | 129 | -20.092 | 65.318 | 9.466 | 136.20 | H |
| ATOM | 6349 | HB2 | SER | D | 129 | -18.059 | 65.691 | 10.431 | 142.72 | H |
| ATOM | 6350 | HB3 | SER | D | 129 | -18.614 | 64.348 | 11.072 | 142.72 | H |
| ATOM | 6351 | HG | SER | D | 129 | -17.301 | 63.272 | 9.680 | 136.97 | H |
| ATOM | 6352 | N | GLN | D | 130 | -18.659 | 64.270 | 6.920 | 127.90 | N |
| ATOM | 6353 | CA | GLN | D | 130 | -18.164 | 64.603 | 5.589 | 125.08 | C |
| ATOM | 6354 | C | GLN | D | 130 | -19.291 | 64.546 | 4.564 | 125.68 | C |
| ATOM | 6355 | O | GLN | D | 130 | -19.051 | 64.318 | 3.379 | 125.29 | O |
| ATOM | 6356 | CB | GLN | D | 130 | -17.035 | 63.654 | 5.189 | 127.46 | C |
| ATOM | 6357 | CG | GLN | D | 130 | -15.877 | 63.654 | 6.167 | 129.13 | C |
| ATOM | 6358 | CD | GLN | D | 130 | -14.797 | 62.669 | 5.790 | 126.28 | C |
| ATOM | 6359 | OE1 | GLN | D | 130 | -14.110 | 62.843 | 4.786 | 125.42 | O |
| ATOM | 6360 | NE2 | GLN | D | 130 | -14.637 | 61.625 | 6.598 | 126.08 | N |
| ATOM | 6361 | H | GLN | D | 130 | -18.821 | 63.433 | 7.032 | 133.48 | H |
| ATOM | 6362 | HA | GLN | D | 130 | -17.811 | 65.506 | 5.599 | 130.10 | H |
| ATOM | 6363 | HB2 | GLN | D | 130 | -17.385 | 62.751 | 5.141 | 132.95 | H |

TABLE 5-continued

Atomic Coordinates for OMCP-NKG2D (4PDC).

| | | | | | | | | | |
|---|---|---|---|---|---|---|---|---|---|
| ATOM | 6364 | HB3 | GLN | D | 130 | -16.692 | 63.922 | 4.322 | H |
| ATOM | 6365 | HG2 | GLN | D | 130 | -15.482 | 64.539 | 6.190 | H |
| ATOM | 6366 | HG3 | GLN | D | 130 | -16.207 | 63.415 | 7.047 | H |
| ATOM | 6367 | HE21 | GLN | D | 130 | -14.034 | 61.036 | 6.425 | H |
| ATOM | 6368 | HE22 | GLN | D | 130 | -15.136 | 61.539 | 7.293 | H |
| ATOM | 6369 | N | ASN | D | 131 | -20.515 | 64.766 | 5.035 | N |
| ATOM | 6370 | CA | ASN | D | 131 | -21.699 | 64.750 | 4.182 | C |
| ATOM | 6371 | C | ASN | D | 131 | -21.772 | 63.462 | 3.370 | C |
| ATOM | 6372 | O | ASN | D | 131 | -21.989 | 63.485 | 2.157 | O |
| ATOM | 6373 | CB | ASN | D | 131 | -21.704 | 65.965 | 3.251 | C |
| ATOM | 6374 | CG | ASN | D | 131 | -23.039 | 66.164 | 2.559 | C |
| ATOM | 6375 | OD1 | ASN | D | 131 | -24.084 | 65.767 | 3.074 | O |
| ATOM | 6376 | ND2 | ASN | D | 131 | -23.009 | 66.779 | 1.382 | N |
| ATOM | 6377 | H | ASN | D | 131 | -20.689 | 64.929 | 5.861 | H |
| ATOM | 6378 | HA | ASN | D | 131 | -22.490 | 64.797 | 4.740 | H |
| ATOM | 6379 | HB2 | ASN | D | 131 | -21.512 | 66.761 | 3.770 | H |
| ATOM | 6380 | HB3 | ASN | D | 131 | -21.026 | 65.842 | 2.568 | H |
| ATOM | 6381 | HD21 | ASN | D | 131 | -23.740 | 66.916 | 0.950 | H |
| ATOM | 6382 | HD22 | ASN | D | 131 | -22.259 | 67.041 | 1.052 | H |
| ATOM | 6383 | N | ALA | D | 132 | -21.587 | 62.341 | 4.058 | N |
| ATOM | 6384 | CA | ALA | D | 132 | -21.549 | 61.035 | 3.420 | C |
| ATOM | 6385 | C | ALA | D | 132 | -22.010 | 59.962 | 4.394 | C |
| ATOM | 6386 | O | ALA | D | 132 | -22.408 | 60.258 | 5.521 | O |
| ATOM | 6387 | CB | ALA | D | 132 | -20.139 | 60.734 | 2.924 | C |
| ATOM | 6388 | H | ALA | D | 132 | -21.479 | 62.313 | 4.911 | H |
| ATOM | 6389 | HA | ALA | D | 132 | -22.148 | 61.033 | 2.657 | H |
| ATOM | 6390 | HB1 | ALA | D | 132 | -20.133 | 59.860 | 2.502 | H |
| ATOM | 6391 | HB2 | ALA | D | 132 | -19.879 | 61.413 | 2.282 | H |
| ATOM | 6392 | HB3 | ALA | D | 132 | -19.530 | 60.741 | 3.679 | H |
| ATOM | 6393 | N | SER | D | 133 | -21.960 | 58.712 | 3.950 | N |
| ATOM | 6394 | CA | SER | D | 133 | -22.241 | 57.581 | 4.818 | C |
| ATOM | 6395 | C | SER | D | 133 | -21.204 | 56.498 | 4.567 | C |
| ATOM | 6396 | O | SER | D | 133 | -20.410 | 56.591 | 3.631 | O |
| ATOM | 6397 | CB | SER | D | 133 | -23.655 | 57.042 | 4.580 | C |
| ATOM | 6398 | OG | SER | D | 133 | -23.728 | 56.304 | 3.372 | O |
| ATOM | 6399 | H | SER | D | 133 | -21.763 | 58.493 | 3.142 | H |
| ATOM | 6400 | HA | SER | D | 133 | -22.172 | 57.861 | 5.744 | H |
| ATOM | 6401 | HB2 | SER | D | 133 | -23.898 | 56.461 | 5.318 | H |
| ATOM | 6402 | HB3 | SER | D | 133 | -24.272 | 57.788 | 4.530 | H |
| ATOM | 6403 | HG | SER | D | 133 | -23.521 | 56.795 | 2.723 | H |
| ATOM | 6404 | N | LEU | D | 134 | -21.197 | 55.478 | 5.414 | N |
| ATOM | 6405 | CA | LEU | D | 134 | -20.356 | 54.318 | 5.176 | C |
| ATOM | 6406 | C | LEU | D | 134 | -20.763 | 53.669 | 3.859 | C |
| ATOM | 6407 | O | LEU | D | 134 | -21.874 | 53.883 | 3.376 | O |
| ATOM | 6408 | CB | LEU | D | 134 | -20.465 | 53.326 | 6.331 | C |
| ATOM | 6409 | CG | LEU | D | 134 | -19.715 | 53.750 | 7.595 | C |
| ATOM | 6410 | CD1 | LEU | D | 134 | -20.135 | 52.914 | 8.797 | C |
| ATOM | 6411 | CD2 | LEU | D | 134 | -18.214 | 53.647 | 7.381 | C |
| ATOM | 6412 | H | LEU | D | 134 | -21.669 | 55.435 | 6.132 | H |
| ATOM | 6413 | HA | LEU | D | 134 | -19.431 | 54.601 | 5.104 | H |
| ATOM | 6414 | HB2 | LEU | D | 134 | -21.401 | 53.222 | 6.565 | H |

TABLE 5-continued

Atomic Coordinates for OMCP-NKG2D (4PDC).

| | | | | | | | | | |
|---|---|---|---|---|---|---|---|---|---|
| ATOM | 6415 | HB3 | LEU | D | 134 | -20.102 | 52.473 | 6.045 | H |
| ATOM | 6416 | HG | LEU | D | 134 | -19.925 | 54.677 | 7.789 | H |
| ATOM | 6417 | HD11 | LEU | D | 134 | -19.640 | 53.211 | 9.576 | H |
| ATOM | 6418 | HD12 | LEU | D | 134 | -21.087 | 53.030 | 8.944 | H |
| ATOM | 6419 | HD13 | LEU | D | 134 | -19.939 | 51.981 | 8.616 | H |
| ATOM | 6420 | HD21 | LEU | D | 134 | -17.760 | 53.920 | 8.194 | H |
| ATOM | 6421 | HD22 | LEU | D | 134 | -17.988 | 52.728 | 7.169 | H |
| ATOM | 6422 | HD23 | LEU | D | 134 | -17.959 | 54.228 | 6.648 | H |
| ATOM | 6423 | N | LEU | D | 135 | -19.852 | 52.894 | 3.279 | N |
| ATOM | 6424 | CA | LEU | D | 135 | -20.103 | 52.208 | 2.015 | C |
| ATOM | 6425 | C | LEU | D | 135 | -21.457 | 51.505 | 1.999 | C |
| ATOM | 6426 | O | LEU | D | 135 | -21.796 | 50.755 | 2.914 | O |
| ATOM | 6427 | CB | LEU | D | 135 | -18.996 | 51.190 | 1.734 | C |
| ATOM | 6428 | CG | LEU | D | 135 | -19.162 | 50.301 | 0.498 | C |
| ATOM | 6429 | CD1 | LEU | D | 135 | -19.189 | 51.135 | -0.777 | C |
| ATOM | 6430 | CD2 | LEU | D | 135 | -18.048 | 49.257 | 0.440 | C |
| ATOM | 6431 | H | LEU | D | 135 | -19.068 | 52.747 | 3.602 | H |
| ATOM | 6432 | HA | LEU | D | 135 | -20.098 | 52.861 | 1.298 | H |
| ATOM | 6433 | HB2 | LEU | D | 135 | -18.163 | 51.674 | 1.627 | H |
| ATOM | 6434 | HB3 | LEU | D | 135 | -18.927 | 50.601 | 2.501 | H |
| ATOM | 6435 | HG | LEU | D | 135 | -20.007 | 49.829 | 0.562 | H |
| ATOM | 6436 | HD11 | LEU | D | 135 | -19.295 | 50.543 | -1.539 | H |
| ATOM | 6437 | HD12 | LEU | D | 135 | -19.935 | 51.754 | -0.733 | H |
| ATOM | 6438 | HD13 | LEU | D | 135 | -18.356 | 51.625 | -0.852 | H |
| ATOM | 6439 | HD21 | LEU | D | 135 | -18.172 | 48.707 | -0.349 | H |
| ATOM | 6440 | HD22 | LEU | D | 135 | -17.192 | 49.712 | 0.395 | H |
| ATOM | 6441 | HD23 | LEU | D | 135 | -18.089 | 48.707 | 1.238 | H |
| ATOM | 6442 | N | LYS | D | 136 | -22.225 | 51.785 | 0.953 | N |
| ATOM | 6443 | CA | LYS | D | 136 | -23.470 | 51.084 | 0.685 | C |
| ATOM | 6444 | C | LYS | D | 136 | -23.326 | 50.350 | -0.635 | C |
| ATOM | 6445 | O | LYS | D | 136 | -23.061 | 50.967 | -1.664 | O |
| ATOM | 6446 | CB | LYS | D | 136 | -24.652 | 52.054 | 0.638 | C |
| ATOM | 6447 | CG | LYS | D | 136 | -25.972 | 51.387 | 0.267 | C |
| ATOM | 6448 | CD | LYS | D | 136 | -27.137 | 52.358 | 0.370 | C |
| ATOM | 6449 | CE | LYS | D | 136 | -28.427 | 51.738 | -0.151 | C |
| ATOM | 6450 | NZ | LYS | D | 136 | -29.569 | 52.692 | -0.091 | N1+ |
| ATOM | 6451 | H | LYS | D | 136 | -22.040 | 52.391 | 0.372 | H |
| ATOM | 6452 | HA | LYS | D | 136 | -23.633 | 50.432 | 1.512 | H |
| ATOM | 6453 | HB2 | LYS | D | 136 | -24.759 | 52.460 | 1.385 | H |
| ATOM | 6454 | HB3 | LYS | D | 136 | -24.468 | 52.739 | -0.024 | H |
| ATOM | 6455 | HG2 | LYS | D | 136 | -25.923 | 51.067 | -0.648 | H |
| ATOM | 6456 | HG3 | LYS | D | 136 | -26.138 | 50.648 | 0.872 | H |
| ATOM | 6457 | HD2 | LYS | D | 136 | -27.270 | 52.601 | 1.300 | H |
| ATOM | 6458 | HD3 | LYS | D | 136 | -26.944 | 53.148 | -0.159 | H |
| ATOM | 6459 | HE2 | LYS | D | 136 | -28.302 | 51.473 | -1.076 | H |
| ATOM | 6460 | HE3 | LYS | D | 136 | -28.650 | 50.965 | 0.391 | H |
| ATOM | 6461 | HZ1 | LYS | D | 136 | -25.923 | 52.302 | -0.401 | H |
| ATOM | 6462 | HZ2 | LYS | D | 136 | -26.138 | 52.947 | 0.751 | H |
| ATOM | 6463 | HZ3 | LYS | D | 136 | -29.708 | 53.410 | -0.585 | H |
| ATOM | 6464 | N | VAL | D | 137 | -29.391 | 49.032 | -0.592 | N |
| ATOM | 6465 | CA | VAL | D | 137 | -23.377 | 48.194 | -1.777 | C |

TABLE 5-continued

Atomic Coordinates for OMCP-NKG2D (4PDC).

| | | | | | | | | | |
|---|---|---|---|---|---|---|---|---|---|
| ATOM | 6466 | C | VAL | D | 137 | -24.767 | 47.914 | -2.328 | 115.82 | C |
| ATOM | 6467 | O | VAL | D | 137 | -25.542 | 47.181 | -1.714 | 117.01 | O |
| ATOM | 6468 | CB | VAL | D | 137 | -22.661 | 46.870 | -1.462 | 118.73 | C |
| ATOM | 6469 | CG1 | VAL | D | 137 | -22.505 | 46.037 | -2.723 | 121.27 | C |
| ATOM | 6470 | CG2 | VAL | D | 137 | -21.293 | 47.142 | -0.828 | 119.01 | C |
| ATOM | 6471 | H | VAL | D | 137 | -23.670 | 48.594 | 0.126 | 118.00 | H |
| ATOM | 6472 | HA | VAL | D | 137 | -22.867 | 48.663 | -2.456 | 117.76 | H |
| ATOM | 6473 | HB | VAL | D | 137 | -23.193 | 46.363 | -0.829 | 122.47 | H |
| ATOM | 6474 | HG11 | VAL | D | 137 | -22.052 | 45.209 | -2.500 | 125.53 | H |
| ATOM | 6475 | HG12 | VAL | D | 137 | -23.384 | 45.846 | -3.086 | 125.53 | H |
| ATOM | 6476 | HG13 | VAL | D | 137 | -21.981 | 46.537 | -3.368 | 122.82 | H |
| ATOM | 6477 | HG21 | VAL | D | 137 | -20.859 | 46.296 | -0.638 | 122.82 | H |
| ATOM | 6478 | HG22 | VAL | D | 137 | -20.755 | 47.658 | -1.449 | 119.25 | H |
| ATOM | 6479 | HG23 | VAL | D | 137 | -21.420 | 47.641 | -0.006 | 119.44 | H |
| ATOM | 6480 | N | TYR | D | 138 | -25.068 | 48.500 | -3.485 | 115.98 | N |
| ATOM | 6481 | CA | TYR | D | 138 | -26.410 | 48.453 | -4.061 | 120.40 | C |
| ATOM | 6482 | C | TYR | D | 138 | -26.439 | 47.849 | -5.467 | 119.25 | C |
| ATOM | 6483 | O | TYR | D | 138 | -21.420 | 47.551 | -5.991 | 119.44 | O |
| ATOM | 6484 | CB | TYR | D | 138 | -25.068 | 49.865 | -4.106 | 116.40 | C |
| ATOM | 6485 | CG | TYR | D | 138 | -26.405 | 50.758 | -5.170 | 115.53 | C |
| ATOM | 6486 | CD1 | TYR | D | 138 | -26.952 | 50.820 | -6.446 | 118.12 | C |
| ATOM | 6487 | CD2 | TYR | D | 138 | -25.293 | 51.544 | -4.897 | 120.57 | C |
| ATOM | 6488 | CE1 | TYR | D | 138 | -26.406 | 51.635 | -7.419 | 118.07 | C |
| ATOM | 6489 | CE2 | TYR | D | 138 | -24.742 | 52.366 | -5.864 | 114.74 | C |
| ATOM | 6490 | CZ | TYR | D | 138 | -25.298 | 52.407 | -7.121 | 119.68 | C |
| ATOM | 6491 | OH | TYR | D | 138 | -24.748 | 53.225 | -8.080 | 118.98 | O |
| ATOM | 6492 | H | TYR | D | 138 | -24.502 | 48.937 | -3.963 | 119.18 | H |
| ATOM | 6493 | HA | TYR | D | 138 | -26.976 | 47.909 | -3.492 | 124.48 | H |
| ATOM | 6494 | HB2 | TYR | D | 138 | -27.958 | 49.795 | -4.283 | 119.68 | H |
| ATOM | 6495 | HB3 | TYR | D | 138 | -26.863 | 50.291 | -3.247 | 119.68 | H |
| ATOM | 6496 | HD1 | TYR | D | 138 | -27.696 | 50.301 | -6.650 | 121.75 | H |
| ATOM | 6497 | HD2 | TYR | D | 138 | -24.913 | 51.519 | -4.049 | 124.68 | H |
| ATOM | 6498 | HE1 | TYR | D | 138 | -26.782 | 51.666 | -8.269 | 121.68 | H |
| ATOM | 6499 | HE2 | TYR | D | 138 | -23.996 | 52.885 | -5.666 | 117.69 | H |
| ATOM | 6500 | HH | TYR | D | 138 | -25.181 | 53.160 | -8.797 | 122.78 | H |
| ATOM | 6501 | N | SER | D | 139 | -25.271 | 47.667 | -6.080 | 118.67 | N |
| ATOM | 6502 | CA | SER | D | 139 | -25.222 | 47.169 | -7.456 | 120.25 | C |
| ATOM | 6503 | C | SER | D | 139 | -23.873 | 46.574 | -7.844 | 124.81 | C |
| ATOM | 6504 | O | SER | D | 139 | -22.843 | 47.241 | -7.753 | 116.53 | O |
| ATOM | 6505 | CB | SER | D | 139 | -25.563 | 48.296 | -8.428 | 118.66 | C |
| ATOM | 6506 | OG | SER | D | 139 | -25.305 | 47.903 | -9.763 | 122.13 | O |
| ATOM | 6507 | H | SER | D | 139 | -24.502 | 47.821 | -5.728 | 122.40 | H |
| ATOM | 6508 | HA | SER | D | 139 | -25.891 | 46.475 | -7.560 | 124.30 | H |
| ATOM | 6509 | HB2 | SER | D | 139 | -26.504 | 48.515 | -8.339 | 122.39 | H |
| ATOM | 6510 | HB3 | SER | D | 139 | -25.021 | 49.071 | -8.216 | 122.39 | H |
| ATOM | 6511 | HG | SER | D | 139 | -25.496 | 48.530 | -10.289 | 124.30 | H |
| ATOM | 6512 | N | LYS | D | 140 | -23.891 | 45.327 | -8.307 | 126.55 | N |
| ATOM | 6513 | CA | LYS | D | 140 | -22.670 | 44.654 | -8.737 | 122.07 | C |
| ATOM | 6514 | C | LYS | D | 140 | -22.131 | 45.225 | -10.041 | 125.49 | C |
| ATOM | 6515 | O | LYS | D | 140 | -20.981 | 44.981 | -10.396 | 128.27 | O |
| ATOM | 6516 | CB | LYS | D | 140 | -22.907 | 43.153 | -8.904 | 125.37 | C |

TABLE 5-continued

Atomic Coordinates for OMCP-NKG2D (4PDC).

| | | | | | | | | | |
|---|---|---|---|---|---|---|---|---|---|
| ATOM | 6517 | CG  | LYS | D | 140 | -22.861 | 42.373 | -7.607  | 128.96 | C |
| ATOM | 6518 | CD  | LYS | D | 140 | -22.757 | 40.877 | -7.865  | 134.51 | C |
| ATOM | 6519 | CE  | LYS | D | 140 | -22.573 | 40.100 | -6.570  | 136.49 | C |
| ATOM | 6520 | NZ  | LYS | D | 140 | -22.353 | 38.648 | -6.819  | 149.97 | N1+ |
| ATOM | 6521 | H   | LYS | D | 140 | -24.601 | 44.848 | -8.383  | 126.49 | H |
| ATOM | 6522 | HA  | LYS | D | 140 | -21.990 | 44.774 | -8.056  | 127.44 | H |
| ATOM | 6523 | HB2 | LYS | D | 140 | -23.783 | 43.018 | -9.299  | 130.45 | H |
| ATOM | 6524 | HB3 | LYS | D | 140 | -22.224 | 42.792 | -9.491  | 130.45 | H |
| ATOM | 6525 | HG2 | LYS | D | 140 | -22.085 | 42.648 | -7.094  | 134.76 | H |
| ATOM | 6526 | HG3 | LYS | D | 140 | -23.673 | 42.539 | -7.103  | 134.76 | H |
| ATOM | 6527 | HD2 | LYS | D | 140 | -23.571 | 40.568 | -8.292  | 141.41 | H |
| ATOM | 6528 | HD3 | LYS | D | 140 | -21.992 | 40.703 | -8.435  | 141.41 | H |
| ATOM | 6529 | HE2 | LYS | D | 140 | -21.801 | 40.447 | -6.097  | 143.79 | H |
| ATOM | 6530 | HE3 | LYS | D | 140 | -23.370 | 40.196 | -6.025  | 143.79 | H |
| ATOM | 6531 | HZ1 | LYS | D | 140 | -22.249 | 38.220 | -6.046  | 159.97 | H |
| ATOM | 6532 | HZ2 | LYS | D | 140 | -23.051 | 38.304 | -7.249  | 159.97 | H |
| ATOM | 6533 | HZ3 | LYS | D | 140 | -21.622 | 38.532 | -7.314  | 159.97 | H |
| ATOM | 6534 | N   | GLU | D | 141 | -22.959 | 45.974 | -10.758 | 121.06 | N |
| ATOM | 6535 | CA  | GLU | D | 141 | -22.523 | 46.596 | -12.001 | 123.91 | C |
| ATOM | 6536 | C   | GLU | D | 141 | -21.994 | 48.009 | -11.753 | 124.83 | C |
| ATOM | 6537 | O   | GLU | D | 141 | -20.867 | 48.325 | -12.135 | 123.48 | O |
| ATOM | 6538 | CB  | GLU | D | 141 | -23.666 | 46.614 | -13.015 | 131.80 | C |
| ATOM | 6539 | CG  | GLU | D | 141 | -23.913 | 45.254 | -13.656 | 135.80 | C |
| ATOM | 6540 | CD  | GLU | D | 141 | -25.007 | 45.285 | -14.707 | 140.22 | C |
| ATOM | 6541 | OE1 | GLU | D | 141 | -26.098 | 45.818 | -14.415 | 142.25 | O |
| ATOM | 6542 | OE2 | GLU | D | 141 | -24.775 | 44.777 | -15.825 | 136.77 | O1- |
| ATOM | 6543 | H   | GLU | D | 141 | -23.776 | 46.138 | -10.547 | 125.27 | H |
| ATOM | 6544 | HA  | GLU | D | 141 | -21.800 | 46.070 | -12.378 | 128.69 | H |
| ATOM | 6545 | HB2 | GLU | D | 141 | -24.482 | 46.886 | -12.566 | 138.16 | H |
| ATOM | 6546 | HB3 | GLU | D | 141 | -23.451 | 47.243 | -13.722 | 138.16 | H |
| ATOM | 6547 | HG2 | GLU | D | 141 | -23.096 | 44.954 | -14.084 | 142.96 | H |
| ATOM | 6548 | HG3 | GLU | D | 141 | -24.178 | 44.624 | -12.968 | 142.96 | H |
| ATOM | 6549 | N   | ASP | D | 142 | -22.795 | 48.851 | -11.106 | 122.91 | N |
| ATOM | 6550 | CA  | ASP | D | 142 | -22.382 | 50.226 | -10.809 | 121.81 | C |
| ATOM | 6551 | C   | ASP | D | 142 | -21.179 | 50.272 | -9.870  | 117.14 | C |
| ATOM | 6552 | O   | ASP | D | 142 | -20.484 | 51.284 | -9.793  | 118.60 | O |
| ATOM | 6553 | CB  | ASP | D | 142 | -23.534 | 51.015 | -10.182 | 123.08 | C |
| ATOM | 6554 | CG  | ASP | D | 142 | -24.591 | 51.429 | -11.192 | 129.65 | C |
| ATOM | 6555 | OD1 | ASP | D | 142 | -24.549 | 50.952 | -12.347 | 132.81 | O |
| ATOM | 6556 | OD2 | ASP | D | 142 | -25.474 | 52.232 | -10.819 | 129.12 | O1- |
| ATOM | 6557 | H   | ASP | D | 142 | -23.584 | 48.654 | -10.827 | 127.49 | H |
| ATOM | 6558 | HA  | ASP | D | 142 | -22.133 | 50.666 | -11.637 | 126.17 | H |
| ATOM | 6559 | HB2 | ASP | D | 142 | -23.963 | 50.465 | -9.508  | 127.70 | H |
| ATOM | 6560 | HB3 | ASP | D | 142 | -23.179 | 51.821 | -9.774  | 127.70 | H |
| ATOM | 6561 | N   | GLN | D | 143 | -20.951 | 49.180 | -9.149  | 117.82 | N |
| ATOM | 6562 | CA  | GLN | D | 143 | -19.869 | 49.108 | -8.173  | 120.33 | C |
| ATOM | 6563 | C   | GLN | D | 143 | -19.029 | 47.858 | -8.395  | 117.41 | C |
| ATOM | 6564 | O   | GLN | D | 143 | -18.528 | 47.255 | -7.444  | 116.39 | O |
| ATOM | 6565 | CB  | GLN | D | 143 | -20.433 | 49.119 | -6.754  | 116.84 | C |
| ATOM | 6566 | CG  | GLN | D | 143 | -20.301 | 50.301 | -6.464  | 119.15 | C |
| ATOM | 6567 | CD  | GLN | D | 143 | -21.996 | 50.201 | -5.100  | 115.77 | C |

TABLE 5-continued

Atomic Coordinates for OMCP-NKG2D (4PDC).

| ATOM | 6568 | OE1 | GLN | D | 143 | -22.746 | 49.264 | -4.827 | O |
|------|------|-----|-----|---|-----|---------|--------|--------|---|
| ATOM | 6569 | NE2 | GLN | D | 143 | -21.696 | 51.156 | -4.229 | N |
| ATOM | 6570 | H | GLN | D | 143 | -21.414 | 48.458 | -9.208 | H |
| ATOM | 6571 | HA | GLN | D | 143 | -19.294 | 49.882 | -8.276 | H |
| ATOM | 6572 | HB2 | GLN | D | 143 | -20.944 | 48.306 | -6.615 | H |
| ATOM | 6573 | HB3 | GLN | D | 143 | -19.695 | 49.155 | -6.125 | H |
| ATOM | 6574 | HG2 | GLN | D | 143 | -20.832 | 51.120 | -6.493 | H |
| ATOM | 6575 | HG3 | GLN | D | 143 | -22.054 | 50.327 | -7.130 | H |
| ATOM | 6576 | HE21 | GLN | D | 143 | -22.039 | 51.141 | -3.440 | H |
| ATOM | 6577 | HE22 | GLN | D | 143 | -21.159 | 51.789 | -4.453 | H |
| ATOM | 6578 | N | ASP | D | 144 | -18.880 | 47.478 | -9.659 | N |
| ATOM | 6579 | CA | ASP | D | 144 | -18.187 | 46.248 | -10.016 | C |
| ATOM | 6580 | C | ASP | D | 144 | -16.735 | 46.242 | -9.540 | C |
| ATOM | 6581 | O | ASP | D | 144 | -16.177 | 45.186 | -9.256 | O |
| ATOM | 6582 | CB | ASP | D | 144 | -18.247 | 46.025 | -11.534 | C |
| ATOM | 6583 | CG | ASP | D | 144 | -17.787 | 47.234 | -12.330 | C |
| ATOM | 6584 | OD1 | ASP | D | 144 | -17.622 | 48.322 | -11.741 | O |
| ATOM | 6585 | OD2 | ASP | D | 144 | -17.611 | 47.097 | -13.558 | O1- |
| ATOM | 6586 | H | ASP | D | 144 | -19.175 | 47.921 | -10.335 | H |
| ATOM | 6587 | HA | ASP | D | 144 | -18.639 | 45.503 | -9.590 | H |
| ATOM | 6588 | HB2 | ASP | D | 144 | -17.672 | 45.278 | -11.765 | H |
| ATOM | 6589 | HB3 | ASP | D | 144 | -19.162 | 45.830 | -11.788 | H |
| ATOM | 6590 | N | LEU | D | 145 | -16.128 | 47.417 | -9.434 | N |
| ATOM | 6591 | CA | LEU | D | 145 | -14.718 | 47.487 | -9.074 | C |
| ATOM | 6592 | C | LEU | D | 145 | -14.485 | 47.240 | -7.581 | C |
| ATOM | 6593 | O | LEU | D | 145 | -13.340 | 47.622 | -7.132 | O |
| ATOM | 6594 | CB | LEU | D | 145 | -14.139 | 48.835 | -9.498 | C |
| ATOM | 6595 | CG | LEU | D | 145 | -14.106 | 49.032 | -11.021 | C |
| ATOM | 6596 | CD1 | LEU | D | 145 | -13.556 | 50.397 | -11.374 | C |
| ATOM | 6597 | CD2 | LEU | D | 145 | -13.283 | 47.949 | -11.725 | C |
| ATOM | 6598 | H | LEU | D | 145 | -16.504 | 48.179 | -9.563 | H |
| ATOM | 6599 | HA | LEU | D | 145 | -14.240 | 46.798 | -9.562 | H |
| ATOM | 6600 | HB2 | LEU | D | 145 | -14.683 | 49.543 | -9.118 | H |
| ATOM | 6601 | HB3 | LEU | D | 145 | -13.230 | 48.905 | -9.168 | H |
| ATOM | 6602 | HG | LEU | D | 145 | -15.013 | 48.982 | -11.361 | H |
| ATOM | 6603 | HD11 | LEU | D | 145 | -13.546 | 50.493 | -12.339 | H |
| ATOM | 6604 | HD12 | LEU | D | 145 | -14.123 | 51.077 | -10.979 | H |
| ATOM | 6605 | HD13 | LEU | D | 145 | -12.654 | 50.474 | -11.024 | H |
| ATOM | 6606 | HD21 | LEU | D | 145 | -13.293 | 48.117 | -12.680 | H |
| ATOM | 6607 | HD22 | LEU | D | 145 | -12.372 | 47.979 | -11.392 | H |
| ATOM | 6608 | HD23 | LEU | D | 145 | -13.676 | 47.082 | -11.537 | H |
| ATOM | 6609 | N | LEU | D | 146 | -15.561 | 47.059 | -6.818 | N |
| ATOM | 6610 | CA | LEU | D | 146 | -15.431 | 46.629 | -5.427 | C |
| ATOM | 6611 | C | LEU | D | 146 | -14.819 | 45.229 | -5.369 | C |
| ATOM | 6612 | O | LEU | D | 146 | -14.308 | 44.808 | -4.332 | O |
| ATOM | 6613 | CB | LEU | D | 146 | -16.784 | 46.644 | -4.710 | C |
| ATOM | 6614 | CG | LEU | D | 146 | -17.430 | 48.005 | -4.436 | C |
| ATOM | 6615 | CD1 | LEU | D | 146 | -18.798 | 47.820 | -3.797 | C |
| ATOM | 6616 | CD2 | LEU | D | 146 | -16.545 | 48.849 | -3.537 | C |
| ATOM | 6617 | H | LEU | D | 146 | -16.372 | 47.177 | -7.079 | H |
| ATOM | 6618 | HA | LEU | D | 146 | -14.836 | 47.238 | -4.961 | H |

TABLE 5-continued

Atomic Coordinates for OMCP-NKG2D (4PDC).

| ATOM | 6619 | HB2 | LEU | D | 146 | -17.413 | 46.135 | -5.246 | 123.45 | H |
|---|---|---|---|---|---|---|---|---|---|---|
| ATOM | 6620 | HB3 | LEU | D | 146 | -16.673 | 46.206 | -3.851 | 123.45 | H |
| ATOM | 6621 | HG | LEU | D | 146 | -17.548 | 48.477 | -5.275 | 121.51 | H |
| ATOM | 6622 | HD11 | LEU | D | 146 | -19.189 | 48.692 | -3.632 | 120.71 | H |
| ATOM | 6623 | HD12 | LEU | D | 146 | -19.362 | 47.312 | -4.400 | 120.71 | H |
| ATOM | 6624 | HD13 | LEU | D | 146 | -18.692 | 47.340 | -2.960 | 120.71 | H |
| ATOM | 6625 | HD21 | LEU | D | 146 | -16.977 | 49.703 | -3.381 | 121.67 | H |
| ATOM | 6626 | HD22 | LEU | D | 146 | -16.416 | 48.384 | -2.695 | 121.67 | H |
| ATOM | 6627 | HD23 | LEU | D | 146 | -15.689 | 48.986 | -3.974 | 121.67 | H |
| ATOM | 6628 | N | LYS | D | 147 | -14.872 | 44.513 | -6.490 | 114.65 | N |
| ATOM | 6629 | CA | LYS | D | 147 | -14.213 | 43.214 | -6.620 | 117.93 | C |
| ATOM | 6630 | C | LYS | D | 147 | -12.713 | 43.325 | -6.339 | 115.43 | C |
| ATOM | 6631 | O | LYS | D | 147 | -12.098 | 42.393 | -5.821 | 116.29 | O |
| ATOM | 6632 | CB | LYS | D | 147 | -14.423 | 42.649 | -8.031 | 122.58 | C |
| ATOM | 6633 | CG | LYS | D | 147 | -13.517 | 43.312 | -9.070 | 145.24 | C |
| ATOM | 6634 | CD | LYS | D | 147 | -13.950 | 43.075 | -10.516 | 179.42 | C |
| ATOM | 6635 | CE | LYS | D | 147 | -13.696 | 44.304 | -11.398 | 190.15 | C |
| ATOM | 6636 | NZ | LYS | D | 147 | -12.667 | 44.084 | -12.457 | 103.814 | N1+ |
| ATOM | 6637 | H | LYS | D | 147 | -15.290 | 44.761 | -7.199 | 117.58 | H |
| ATOM | 6638 | HA | LYS | D | 147 | -14.598 | 42.593 | -5.982 | 121.51 | H |
| ATOM | 6639 | HB2 | LYS | D | 147 | -14.228 | 41.699 | -8.024 | 127.09 | H |
| ATOM | 6640 | HB3 | LYS | D | 147 | -15.344 | 42.796 | -8.298 | 127.09 | H |
| ATOM | 6641 | HG2 | LYS | D | 147 | -13.514 | 44.269 | -8.915 | 154.29 | H |
| ATOM | 6642 | HG3 | LYS | D | 147 | -12.618 | 42.961 | -8.969 | 154.29 | H |
| ATOM | 6643 | HD2 | LYS | D | 147 | -13.447 | 42.331 | -10.882 | 195.30 | H |
| ATOM | 6644 | HD3 | LYS | D | 147 | -14.900 | 42.879 | -10.536 | 195.30 | H |
| ATOM | 6645 | HE2 | LYS | D | 147 | -14.526 | 44.550 | -11.837 | 108.118 | H |
| ATOM | 6646 | HE3 | LYS | D | 147 | -13.392 | 45.034 | -10.836 | 108.118 | H |
| ATOM | 6647 | HZ1 | LYS | D | 147 | -12.923 | 43.424 | -12.998 | 124.611 | H |
| ATOM | 6648 | HZ2 | LYS | D | 147 | -12.561 | 44.826 | -12.937 | 124.611 | H |
| ATOM | 6649 | HZ3 | LYS | D | 147 | -11.889 | 43.866 | -12.085 | 124.6 | H |
| ATOM | 6650 | N | LEU | D | 148 | -12.136 | 44.472 | -6.685 | 114.11 | N |
| ATOM | 6651 | CA | LEU | D | 148 | -10.686 | 44.663 | -6.635 | 114.27 | C |
| ATOM | 6652 | C | LEU | D | 148 | -10.199 | 45.320 | -5.346 | 114.62 | C |
| ATOM | 6653 | O | LEU | D | 148 | -9.001 | 45.581 | -5.189 | 117.22 | O |
| ATOM | 6654 | CB | LEU | D | 148 | -10.235 | 45.508 | -7.827 | 114.41 | C |
| ATOM | 6655 | CG | LEU | D | 148 | -10.319 | 44.864 | -9.212 | 121.00 | C |
| ATOM | 6656 | CD1 | LEU | D | 148 | -9.959 | 45.879 | -10.272 | 122.02 | C |
| ATOM | 6657 | CD2 | LEU | D | 148 | -9.408 | 43.651 | -9.311 | 124.34 | C |
| ATOM | 6658 | H | LEU | D | 148 | -12.567 | 45.165 | -6.956 | 116.94 | H |
| ATOM | 6659 | HA | LEU | D | 148 | -10.256 | 43.797 | -6.706 | 117.12 | H |
| ATOM | 6660 | HB2 | LEU | D | 148 | -10.780 | 46.309 | -7.852 | 117.29 | H |
| ATOM | 6661 | HB3 | LEU | D | 148 | -9.308 | 45.758 | -7.685 | 117.29 | H |
| ATOM | 6662 | HG | LEU | D | 148 | -11.230 | 44.571 | -9.371 | 125.20 | H |
| ATOM | 6663 | HD11 | LEU | D | 148 | -10.016 | 45.457 | -11.144 | 126.42 | H |
| ATOM | 6664 | HD12 | LEU | D | 148 | -10.580 | 46.622 | -10.222 | 126.42 | H |
| ATOM | 6665 | HD13 | LEU | D | 148 | -9.054 | 46.192 | -10.115 | 126.42 | H |
| ATOM | 6666 | HD21 | LEU | D | 148 | -9.487 | 43.270 | -10.199 | 129.20 | H |
| ATOM | 6667 | HD22 | LEU | D | 148 | -8.493 | 43.930 | -9.151 | 129.20 | H |
| ATOM | 6668 | HD23 | LEU | D | 148 | -9.677 | 42.999 | -8.645 | 129.20 | H |
| ATOM | 6669 | N | VAL | D | 149 | -11.114 | 45.590 | -4.424 | 118.94 | N |

TABLE 5-continued

Atomic Coordinates for OMCP-NKG2D (4PDC).

| ATOM | 6670 | CA | VAL | D | 149 | -10.744 | -3.176 | 46.245 | 118.09 | C |
|---|---|---|---|---|---|---|---|---|---|---|
| ATOM | 6671 | O | VAL | D | 149 | -9.970 | -2.268 | 45.299 | 114.58 | C |
| ATOM | 6672 | O | VAL | D | 149 | -10.466 | -1.876 | 44.240 | 114.09 | O |
| ATOM | 6673 | CB | VAL | D | 149 | -11.983 | -2.430 | 46.778 | 119.00 | C |
| ATOM | 6674 | CG1 | VAL | D | 149 | -11.624 | -1.013 | 47.240 | 115.72 | C |
| ATOM | 6675 | CG2 | VAL | D | 149 | -12.601 | -3.214 | 47.914 | 115.52 | C |
| ATOM | 6676 | H | VAL | D | 149 | -11.951 | -4.495 | 45.406 | 122.73 | H |
| ATOM | 6677 | HA | VAL | D | 149 | -10.170 | -3.377 | 47.001 | 121.71 | H |
| ATOM | 6678 | HB | VAL | D | 149 | -12.640 | -2.359 | 46.068 | 122.80 | H |
| ATOM | 6679 | HG11 | VAL | D | 149 | -12.426 | -0.576 | 47.568 | 118.87 | H |
| ATOM | 6680 | HG12 | VAL | D | 149 | -11.261 | -0.519 | 46.489 | 118.87 | H |
| ATOM | 6681 | HG13 | VAL | D | 149 | -10.964 | -1.070 | 47.949 | 118.87 | H |
| ATOM | 6682 | HG21 | VAL | D | 149 | -13.379 | -2.736 | 48.240 | 118.62 | H |
| ATOM | 6683 | HG22 | VAL | D | 149 | -11.947 | -3.309 | 48.624 | 118.62 | H |
| ATOM | 6684 | HG23 | VAL | D | 149 | -12.863 | -4.089 | 47.587 | 118.62 | H |
| ATOM | 6685 | N | LYS | D | 150 | -8.748 | -1.934 | 45.704 | 111.38 | N |
| ATOM | 6686 | CA | LYS | D | 150 | -7.897 | -1.021 | 44.949 | 113.03 | C |
| ATOM | 6687 | C | LYS | D | 150 | -8.243 | 0.428 | 45.267 | 112.12 | C |
| ATOM | 6688 | O | LYS | D | 150 | -8.703 | 0.733 | 46.366 | 111.51 | O |
| ATOM | 6689 | CB | LYS | D | 150 | -6.421 | -1.290 | 45.270 | 115.75 | C |
| ATOM | 6690 | CG | LYS | D | 150 | -5.427 | -0.510 | 44.415 | 118.85 | C |
| ATOM | 6691 | CD | LYS | D | 150 | -4.028 | -0.525 | 45.031 | 125.97 | C |
| ATOM | 6692 | CE | LYS | D | 150 | -2.999 | -1.170 | 44.123 | 128.15 | C |
| ATOM | 6693 | NZ | LYS | D | 150 | -2.862 | -0.512 | 42.800 | 127.44 | N1+ |
| ATOM | 6694 | H | LYS | D | 150 | -8.384 | -2.228 | 46.425 | 113.65 | H |
| ATOM | 6695 | HA | LYS | D | 150 | -8.034 | -1.166 | 43.999 | 115.63 | H |
| ATOM | 6696 | HB2 | LYS | D | 150 | -6.243 | -2.234 | 45.139 | 118.90 | H |
| ATOM | 6697 | HB3 | LYS | D | 150 | -6.259 | -1.054 | 46.197 | 118.90 | H |
| ATOM | 6698 | HG2 | LYS | D | 150 | -5.719 | 0.412 | 44.345 | 122.62 | H |
| ATOM | 6699 | HG3 | LYS | D | 150 | -5.376 | -0.914 | 43.535 | 122.62 | H |
| ATOM | 6700 | HD2 | LYS | D | 150 | -4.053 | -1.027 | 45.861 | 131.17 | H |
| ATOM | 6701 | HD3 | LYS | D | 150 | -3.748 | 0.388 | 45.203 | 131.17 | H |
| ATOM | 6702 | HE2 | LYS | D | 150 | -3.254 | -2.093 | 43.968 | 133.78 | H |
| ATOM | 6703 | HE3 | LYS | D | 150 | -2.133 | -1.137 | 44.560 | 133.78 | H |
| ATOM | 6704 | HZ1 | LYS | D | 150 | -3.639 | -0.535 | 42.367 | 132.92 | H |
| ATOM | 6705 | HZ2 | LYS | D | 150 | -2.246 | -0.932 | 42.314 | 132.92 | H |
| ATOM | 6706 | HZ3 | LYS | D | 150 | -2.616 | 0.337 | 42.907 | 132.92 | H |
| ATOM | 6707 | N | SER | D | 151 | -8.011 | 1.308 | 44.299 | 19.93 | N |
| ATOM | 6708 | CA | SER | D | 151 | -8.161 | 2.751 | 44.483 | 117.48 | C |
| ATOM | 6709 | C | SER | D | 151 | -9.629 | 3.165 | 44.513 | 115.32 | C |
| ATOM | 6710 | O | SER | D | 151 | -10.520 | 2.361 | 44.226 | 111.83 | O |
| ATOM | 6711 | CB | SER | D | 151 | -7.461 | 3.220 | 45.765 | 114.44 | C |
| ATOM | 6712 | OG | SER | D | 151 | -7.316 | 4.629 | 45.776 | 115.79 | O |
| ATOM | 6713 | H | SER | D | 151 | -7.760 | 1.090 | 43.506 | 111.92 | H |
| ATOM | 6714 | HA | SER | D | 151 | -7.742 | 3.205 | 43.735 | 120.98 | H |
| ATOM | 6715 | HB2 | SER | D | 151 | -6.582 | 2.812 | 45.812 | 117.33 | H |
| ATOM | 6716 | HB3 | SER | D | 151 | -7.993 | 2.952 | 46.531 | 117.33 | H |
| ATOM | 6717 | HG | SER | D | 151 | -6.857 | 4.875 | 45.117 | 118.95 | H |
| ATOM | 6718 | N | TYR | D | 152 | -9.849 | 4.428 | 44.872 | 114.15 | N |
| ATOM | 6719 | CA | TYR | D | 152 | -11.134 | 5.099 | 44.731 | 114.23 | C |
| ATOM | 6720 | O | TYR | D | 152 | -11.546 | 5.719 | 46.065 | 115.88 | C |

TABLE 5-continued

Atomic Coordinates for OMCP-NKG2D (4PDC).

| ATOM | 6721 | O | TYR | D | 152 | -10.765 | 46.681 | 6.436 | 115.07 | O |
| ATOM | 6722 | CB | TYR | D | 152 | -11.037 | 43.620 | 6.152 | 114.66 | C |
| ATOM | 6723 | CG | TYR | D | 152 | -10.793 | 42.275 | 5.507 | 114.16 | C |
| ATOM | 6724 | CD1 | TYR | D | 152 | -9.544 | 41.942 | 4.993 | 116.37 | C |
| ATOM | 6725 | CD2 | TYR | D | 152 | -11.819 | 41.354 | 5.375 | 112.96 | C |
| ATOM | 6726 | CE1 | TYR | D | 152 | -9.327 | 40.728 | 4.372 | 116.79 | C |
| ATOM | 6727 | CE2 | TYR | D | 152 | -11.611 | 40.138 | 4.758 | 117.09 | C |
| ATOM | 6728 | CZ | TYR | D | 152 | -10.365 | 39.830 | 4.257 | 115.39 | C |
| ATOM | 6729 | OH | TYR | D | 152 | -10.164 | 38.616 | 3.641 | 119.34 | O |
| ATOM | 6730 | H | TYR | D | 152 | -9.243 | 45.214 | 4.934 | 116.98 | H |
| ATOM | 6731 | HA | TYR | D | 152 | -11.809 | 44.477 | 4.449 | 117.08 | H |
| ATOM | 6732 | HB2 | TYR | D | 152 | -10.298 | 43.809 | 6.751 | 117.59 | H |
| ATOM | 6733 | HB3 | TYR | D | 152 | -11.870 | 43.574 | 6.647 | 117.59 | H |
| ATOM | 6734 | HD1 | TYR | D | 152 | -8.845 | 42.551 | 5.062 | 119.64 | H |
| ATOM | 6735 | HD2 | TYR | D | 152 | -12.664 | 41.561 | 5.704 | 115.55 | H |
| ATOM | 6736 | HE1 | TYR | D | 152 | -8.486 | 40.518 | 4.035 | 120.15 | H |
| ATOM | 6737 | HE2 | TYR | D | 152 | -12.309 | 39.529 | 4.679 | 114.80 | H |
| ATOM | 6738 | HH | TYR | D | 152 | -10.877 | 38.172 | 3.641 | 120.50 | H |
| ATOM | 6739 | N | HIS | D | 153 | -12.762 | 46.519 | 5.418 | 123.21 | N |
| ATOM | 6740 | CA | HIS | D | 153 | -13.195 | 47.868 | 5.791 | 115.60 | C |
| ATOM | 6741 | C | HIS | D | 153 | -14.638 | 47.906 | 6.274 | 114.87 | C |
| ATOM | 6742 | O | HIS | D | 153 | -15.492 | 47.185 | 5.761 | 115.50 | O |
| ATOM | 6743 | CB | HIS | D | 153 | -13.048 | 48.819 | 4.603 | 115.53 | C |
| ATOM | 6744 | CG | HIS | D | 153 | -11.822 | 48.574 | 3.783 | 114.96 | C |
| ATOM | 6745 | ND1 | HIS | D | 153 | -10.655 | 49.285 | 3.958 | 117.33 | N |
| ATOM | 6746 | CD2 | HIS | D | 153 | -11.579 | 47.690 | 2.786 | 114.80 | C |
| ATOM | 6747 | CE1 | HIS | D | 153 | -9.747 | 48.853 | 3.100 | 115.17 | C |
| ATOM | 6748 | NE2 | HIS | D | 153 | -10.283 | 47.885 | 2.377 | 117.80 | N |
| ATOM | 6749 | H | HIS | D | 153 | -13.358 | 46.064 | 4.996 | 114.81 | H |
| ATOM | 6750 | HA | HIS | D | 153 | -12.630 | 48.194 | 6.509 | 118.72 | H |
| ATOM | 6751 | HB2 | HIS | D | 153 | -13.819 | 48.715 | 4.023 | 117.84 | H |
| ATOM | 6752 | HB3 | HIS | D | 153 | -13.007 | 49.730 | 4.935 | 117.95 | H |
| ATOM | 6753 | HD1 | HIS | D | 153 | -10.537 | 49.914 | 4.533 | 117.76 | H |
| ATOM | 6754 | HD2 | HIS | D | 153 | -12.179 | 47.069 | 2.441 | 118.21 | H |
| ATOM | 6755 | HE1 | HIS | D | 153 | -8.879 | 49.175 | 3.020 | 121.36 | H |
| ATOM | 6756 | HE2 | HIS | D | 153 | -9.884 | 47.448 | 1.753 | 117.77 | H |
| ATOM | 6757 | N | TRP | D | 154 | -14.911 | 48.764 | 7.251 | 114.83 | N |
| ATOM | 6758 | CA | TRP | D | 154 | -16.280 | 48.975 | 7.703 | 118.59 | C |
| ATOM | 6759 | C | TRP | D | 154 | -17.160 | 49.471 | 6.558 | 116.71 | C |
| ATOM | 6760 | O | TRP | D | 154 | -16.792 | 50.405 | 5.843 | 115.23 | O |
| ATOM | 6761 | CB | TRP | D | 154 | -16.340 | 49.994 | 8.849 | 120.54 | C |
| ATOM | 6762 | CG | TRP | D | 154 | -15.871 | 49.510 | 10.190 | 119.81 | C |
| ATOM | 6763 | CD1 | TRP | D | 154 | -14.965 | 50.126 | 11.007 | 123.78 | C |
| ATOM | 6764 | CD2 | TRP | D | 154 | -16.298 | 48.331 | 10.886 | 121.11 | C |
| ATOM | 6765 | NE1 | TRP | D | 154 | -14.798 | 49.402 | 12.160 | 123.26 | N |
| ATOM | 6766 | CE2 | TRP | D | 154 | -15.602 | 48.295 | 12.112 | 123.65 | C |
| ATOM | 6767 | CE3 | TRP | D | 154 | -17.194 | 47.300 | 10.591 | 119.42 | C |
| ATOM | 6768 | CZ2 | TRP | D | 154 | -15.774 | 47.269 | 13.040 | 125.29 | C |
| ATOM | 6769 | CZ3 | TRP | D | 154 | -17.362 | 46.281 | 11.514 | 122.46 | C |
| ATOM | 6770 | CH2 | TRP | D | 154 | -16.657 | 46.275 | 12.723 | 125.53 | C |
| ATOM | 6771 | H | TRP | D | 154 | -14.324 | 49.234 | 7.667 | 117.80 | H |

TABLE 5-continued

Atomic Coordinates for OMCP-NKG2D (4PDC).

| | | | | | | | | | | | |
|---|---|---|---|---|---|---|---|---|---|---|---|
| ATOM | 6772 | HA | TRP | D | 154 | -16.644 | 48.135 | 8.024 | 122.30 | | H |
| ATOM | 6773 | HB2 | TRP | D | 154 | -15.789 | 50.756 | 8.609 | 124.65 | | H |
| ATOM | 6774 | HB3 | TRP | D | 154 | -17.260 | 50.283 | 8.952 | 124.65 | | H |
| ATOM | 6775 | HD1 | TRP | D | 154 | -14.527 | 50.922 | 10.811 | 128.53 | | H |
| ATOM | 6776 | HE1 | TRP | D | 154 | -14.270 | 49.609 | 12.808 | 127.92 | | H |
| ATOM | 6777 | HE3 | TRP | D | 154 | -17.667 | 47.298 | 9.790 | 123.30 | | H |
| ATOM | 6778 | HZ2 | TRP | D | 154 | -15.305 | 47.261 | 13.843 | 130.35 | | H |
| ATOM | 6779 | HZ3 | TRP | D | 154 | -17.957 | 45.591 | 11.329 | 126.95 | | H |
| ATOM | 6780 | HH2 | TRP | D | 154 | -16.791 | 45.577 | 13.323 | 130.63 | | H |
| ATOM | 6781 | N | MET | D | 155 | -18.321 | 48.845 | 6.392 | 116.33 | | N |
| ATOM | 6782 | CA | MET | D | 155 | -19.362 | 49.379 | 5.519 | 114.51 | | C |
| ATOM | 6783 | C | MET | D | 155 | -20.595 | 49.713 | 6.361 | 117.12 | | C |
| ATOM | 6784 | O | MET | D | 155 | -20.603 | 49.497 | 7.573 | 119.71 | | O |
| ATOM | 6785 | CB | MET | D | 155 | -19.704 | 48.392 | 4.397 | 115.94 | | C |
| ATOM | 6786 | CG | MET | D | 155 | -19.896 | 46.957 | 4.840 | 116.64 | | C |
| ATOM | 6787 | SD | MET | D | 155 | -20.468 | 45.915 | 3.480 | 119.78 | | S |
| ATOM | 6788 | CE | MET | D | 155 | -20.186 | 44.291 | 4.179 | 121.22 | | C |
| ATOM | 6789 | H | MET | D | 155 | -18.533 | 48.105 | 6.776 | 119.60 | | H |
| ATOM | 6790 | HA | MET | D | 155 | -19.035 | 50.194 | 5.107 | 117.42 | | H |
| ATOM | 6791 | HB2 | MET | D | 155 | -20.528 | 48.680 | 3.974 | 119.13 | | H |
| ATOM | 6792 | HB3 | MET | D | 155 | -18.984 | 48.403 | 3.747 | 119.13 | | H |
| ATOM | 6793 | HG2 | MET | D | 155 | -19.050 | 46.605 | 5.158 | 119.97 | | H |
| ATOM | 6794 | HG3 | MET | D | 155 | -20.560 | 46.927 | 5.547 | 119.97 | | H |
| ATOM | 6795 | HE1 | MET | D | 155 | -20.458 | 43.619 | 3.535 | 125.46 | | H |
| ATOM | 6796 | HE2 | MET | D | 155 | -19.242 | 44.194 | 4.381 | 125.46 | | H |
| ATOM | 6797 | HE3 | MET | D | 155 | -20.709 | 44.202 | 4.992 | 125.46 | | H |
| ATOM | 6798 | N | GLY | D | 156 | -21.629 | 50.248 | 5.719 | 119.69 | | N |
| ATOM | 6799 | CA | GLY | D | 156 | -22.778 | 50.784 | 6.429 | 120.08 | | C |
| ATOM | 6800 | C | GLY | D | 156 | -23.884 | 49.782 | 6.697 | 127.40 | | C |
| ATOM | 6801 | O | GLY | D | 156 | -25.047 | 50.157 | 6.856 | 125.15 | | O |
| ATOM | 6802 | H | GLY | D | 156 | -21.686 | 50.313 | 4.863 | 123.63 | | H |
| ATOM | 6803 | HA2 | GLY | D | 156 | -22.484 | 51.139 | 7.282 | 124.09 | | H |
| ATOM | 6804 | HA3 | GLY | D | 156 | -23.155 | 51.514 | 5.913 | 124.09 | | H |
| ATOM | 6805 | N | LEU | D | 157 | -23.523 | 48.505 | 6.755 | 122.24 | | N |
| ATOM | 6806 | CA | LEU | D | 157 | -24.486 | 47.457 | 7.038 | 124.99 | | C |
| ATOM | 6807 | O | LEU | D | 157 | -24.748 | 47.391 | 8.542 | 132.61 | | O |
| ATOM | 6808 | O | LEU | D | 157 | -23.816 | 47.402 | 9.348 | 132.90 | | O |
| ATOM | 6809 | CB | LEU | D | 157 | -23.981 | 46.116 | 6.506 | 127.86 | | C |
| ATOM | 6810 | CG | LEU | D | 157 | -25.030 | 45.102 | 6.053 | 131.65 | | C |
| ATOM | 6811 | CD1 | LEU | D | 157 | -25.857 | 45.622 | 4.884 | 133.53 | | C |
| ATOM | 6812 | CD2 | LEU | D | 157 | -24.345 | 43.799 | 5.675 | 134.82 | | C |
| ATOM | 6813 | H | LEU | D | 157 | -22.720 | 48.221 | 6.632 | 126.69 | | H |
| ATOM | 6814 | HA | LEU | D | 157 | -25.323 | 47.663 | 6.594 | 129.98 | | H |
| ATOM | 6815 | HB2 | LEU | D | 157 | -23.408 | 46.293 | 5.743 | 133.43 | | H |
| ATOM | 6816 | HB3 | LEU | D | 157 | -23.459 | 45.693 | 7.205 | 133.43 | | H |
| ATOM | 6817 | HG | LEU | D | 157 | -25.633 | 44.921 | 6.790 | 137.98 | | H |
| ATOM | 6818 | HD11 | LEU | D | 157 | -25.102 | 44.947 | 4.632 | 140.23 | | H |
| ATOM | 6819 | HD12 | LEU | D | 157 | -26.507 | 46.434 | 5.156 | 140.23 | | H |
| ATOM | 6820 | HD13 | LEU | D | 157 | -26.312 | 45.808 | 4.137 | 140.23 | | H |
| ATOM | 6821 | HD21 | LEU | D | 157 | -25.266 | 43.161 | 5.389 | 141.79 | | H |
| ATOM | 6822 | HD22 | LEU | D | 157 | -23.720 | 43.968 | 4.953 | 141.79 | | H |

TABLE 5-continued

Atomic Coordinates for OMCP-NKG2D (4PDC).

| ATOM | 6823 | HD23 | LEU | D | 157 | -23.871 | 43.456 | 6.449 | H |
|------|------|------|-----|---|-----|---------|--------|-------|---|
| ATOM | 6824 | N | VAL | D | 158 | -26.026 | 47.342 | 8.902 | N |
| ATOM | 6825 | CA | VAL | D | 158 | -26.462 | 47.376 | 10.293 | C |
| ATOM | 6826 | C | VAL | D | 158 | -27.282 | 46.133 | 10.623 | C |
| ATOM | 6827 | O | VAL | D | 158 | -28.183 | 45.762 | 9.871 | O |
| ATOM | 6828 | CB | VAL | D | 158 | -27.307 | 48.635 | 10.579 | C |
| ATOM | 6829 | CG1 | VAL | D | 158 | -27.896 | 48.591 | 11.984 | C |
| ATOM | 6830 | CG2 | VAL | D | 158 | -26.472 | 49.890 | 10.392 | C |
| ATOM | 6831 | H | VAL | D | 158 | -26.677 | 47.288 | 8.342 | H |
| ATOM | 6832 | HA | VAL | D | 158 | -25.685 | 47.392 | 10.873 | H |
| ATOM | 6833 | HB | VAL | D | 158 | -28.043 | 48.669 | 9.948 | H |
| ATOM | 6834 | HG11 | VAL | D | 158 | -28.419 | 49.394 | 12.131 | H |
| ATOM | 6835 | HG12 | VAL | D | 158 | -28.461 | 47.807 | 12.064 | H |
| ATOM | 6836 | HG13 | VAL | D | 158 | -28.545 | 48.545 | 12.628 | H |
| ATOM | 6837 | HG21 | VAL | D | 158 | -27.172 | 50.666 | 10.577 | H |
| ATOM | 6838 | HG22 | VAL | D | 158 | -27.024 | 49.863 | 11.006 | H |
| ATOM | 6839 | HG23 | VAL | D | 158 | -25.721 | 49.922 | 9.477 | H |
| ATOM | 6840 | N | HIS | D | 159 | -26.151 | 45.501 | 11.751 | N |
| ATOM | 6841 | CA | HIS | D | 159 | -26.974 | 44.309 | 12.176 | C |
| ATOM | 6842 | C | HIS | D | 159 | -27.698 | 44.685 | 13.029 | C |
| ATOM | 6843 | O | HIS | D | 159 | -28.905 | 45.584 | 13.867 | O |
| ATOM | 6844 | CB | HIS | D | 159 | -28.829 | 43.370 | 12.962 | C |
| ATOM | 6845 | CG | HIS | D | 159 | -26.785 | 41.969 | 13.065 | C |
| ATOM | 6846 | ND1 | HIS | D | 159 | -27.304 | 41.062 | 13.981 | N |
| ATOM | 6847 | CD2 | HIS | D | 159 | -26.815 | 41.318 | 12.369 | C |
| ATOM | 6848 | CE1 | HIS | D | 159 | -28.266 | 39.914 | 13.845 | C |
| ATOM | 6849 | NE2 | HIS | D | 159 | -27.454 | 40.043 | 12.874 | N |
| ATOM | 6850 | H | HIS | D | 159 | -28.340 | 45.743 | 12.289 | H |
| ATOM | 6851 | HA | HIS | D | 159 | -26.348 | 43.835 | 11.392 | H |
| ATOM | 6852 | HB2 | HIS | D | 159 | -28.018 | 43.334 | 12.524 | H |
| ATOM | 6853 | HB3 | HIS | D | 159 | -25.920 | 43.715 | 13.863 | H |
| ATOM | 6854 | HD1 | HIS | D | 159 | -26.683 | 41.219 | 14.552 | H |
| ATOM | 6855 | HD2 | HIS | D | 159 | -26.191 | 41.669 | 11.679 | H |
| ATOM | 6856 | HE1 | HIS | D | 159 | -28.781 | 39.145 | 14.347 | H |
| ATOM | 6857 | HE2 | HIS | D | 159 | -27.305 | 39.427 | 12.601 | H |
| ATOM | 6858 | N | ILE | D | 160 | -28.875 | 43.984 | 12.807 | N |
| ATOM | 6859 | CA | ILE | D | 160 | -30.011 | 44.209 | 13.553 | C |
| ATOM | 6860 | C | ILE | D | 160 | -31.243 | 43.001 | 14.446 | C |
| ATOM | 6861 | O | ILE | D | 160 | -31.530 | 41.970 | 13.955 | O |
| ATOM | 6862 | CB | ILE | D | 160 | -31.991 | 44.447 | 12.609 | C |
| ATOM | 6863 | CG1 | ILE | D | 160 | -32.433 | 45.623 | 11.674 | C |
| ATOM | 6864 | CG2 | ILE | D | 160 | -32.142 | 44.725 | 13.407 | C |
| ATOM | 6865 | CD1 | ILE | D | 160 | -33.694 | 45.674 | 10.476 | C |
| ATOM | 6866 | H | ILE | D | 160 | -33.047 | 43.361 | 12.218 | H |
| ATOM | 6867 | HA | ILE | D | 160 | -31.139 | 44.990 | 14.119 | H |
| ATOM | 6868 | HB | ILE | D | 160 | -32.571 | 43.650 | 12.074 | H |
| ATOM | 6869 | HG12 | ILE | D | 160 | -32.255 | 46.450 | 12.168 | H |
| ATOM | 6870 | HG13 | ILE | D | 160 | -31.229 | 45.551 | 11.355 | H |
| ATOM | 6871 | HG21 | ILE | D | 160 | -33.883 | 43.961 | 13.974 | H |
| ATOM | 6872 | HG22 | ILE | D | 160 | -33.555 | 45.516 | 13.952 | H |
| ATOM | 6873 | HG23 | ILE | D | 160 | -34.430 | 44.872 | 12.793 | H |

TABLE 5-continued

Atomic Coordinates for OMCP-NKG2D (4PDC).

| | | | | | | | | | | |
|---|---|---|---|---|---|---|---|---|---|---|
| ATOM | 6874 | HD11 | ILE | D | 160 | -32.806 | 46.440 | 9.932 | 177.27 | H |
| ATOM | 6875 | HD12 | ILE | D | 160 | -32.939 | 44.857 | 9.964 | 177.27 | H |
| ATOM | 6876 | HD13 | ILE | D | 160 | -33.965 | 45.757 | 10.778 | 177.27 | H |
| ATOM | 6877 | N | PRO | D | 161 | -31.256 | 43.117 | 15.758 | 191.91 | N |
| ATOM | 6878 | CA | PRO | D | 161 | -31.459 | 41.971 | 16.655 | 100.819 | C |
| ATOM | 6879 | C | PRO | D | 161 | -32.918 | 41.531 | 16.773 | 107.618 | C |
| ATOM | 6880 | O | PRO | D | 161 | -33.184 | 40.448 | 17.295 | 110.218 | O |
| ATOM | 6881 | CB | PRO | D | 161 | -30.946 | 42.484 | 18.008 | 104.117 | C |
| ATOM | 6882 | CG | PRO | D | 161 | -30.073 | 43.643 | 17.685 | 192.23 | C |
| ATOM | 6883 | CD | PRO | D | 161 | -30.672 | 44.267 | 16.470 | 190.01 | C |
| ATOM | 6884 | HA | PRO | D | 161 | -30.917 | 41.218 | 16.370 | 121.017 | H |
| ATOM | 6885 | HB2 | PRO | D | 161 | -31.696 | 42.763 | 18.557 | 125.010 | H |
| ATOM | 6886 | HB3 | PRO | D | 161 | -30.439 | 41.786 | 18.451 | 125.010 | H |
| ATOM | 6887 | HG2 | PRO | D | 161 | -30.073 | 44.268 | 18.426 | 110.618 | H |
| ATOM | 6888 | HG3 | PRO | D | 161 | -29.173 | 43.331 | 17.500 | 110.618 | H |
| ATOM | 6889 | HD2 | PRO | D | 161 | -31.365 | 44.898 | 16.720 | 108.011 | H |
| ATOM | 6890 | HD3 | PRO | D | 161 | -29.984 | 44.687 | 15.930 | 108.011 | H |
| ATOM | 6891 | N | THR | D | 162 | -33.845 | 42.358 | 16.298 | 107.812 | N |
| ATOM | 6892 | CA | THR | D | 162 | -35.265 | 42.042 | 16.398 | 113.312 | C |
| ATOM | 6893 | C | THR | D | 162 | -35.606 | 40.838 | 15.526 | 113.812 | C |
| ATOM | 6894 | O | THR | D | 162 | -36.327 | 39.935 | 15.953 | 117.217 | O |
| ATOM | 6895 | CB | THR | D | 162 | -36.158 | 43.231 | 15.977 | 116.015 | C |
| ATOM | 6896 | OG1 | THR | D | 162 | -36.171 | 43.348 | 14.549 | 118.614 | O |
| ATOM | 6897 | CG2 | THR | D | 162 | -35.669 | 44.537 | 16.597 | 119.318 | C |
| ATOM | 6898 | H | THR | D | 162 | -33.677 | 43.109 | 15.914 | 129.319 | H |
| ATOM | 6899 | HA | THR | D | 162 | -35.476 | 41.818 | 17.318 | 135.918 | H |
| ATOM | 6900 | HB | THR | D | 162 | -37.063 | 43.072 | 16.288 | 139.217 | H |
| ATOM | 6901 | HG1 | THR | D | 162 | -36.656 | 43.994 | 14.318 | 142.316 | H |
| ATOM | 6902 | HG21 | THR | D | 162 | -36.242 | 45.270 | 16.321 | 143.216 | H |
| ATOM | 6903 | HG22 | THR | D | 162 | -35.687 | 44.471 | 17.565 | 143.216 | H |
| ATOM | 6904 | HG23 | THR | D | 162 | -34.761 | 44.721 | 16.310 | 143.216 | H |
| ATOM | 6905 | N | ASN | D | 163 | -35.079 | 40.834 | 14.305 | 109.719 | N |
| ATOM | 6906 | CA | ASN | D | 163 | -35.341 | 39.764 | 13.348 | 106.911 | C |
| ATOM | 6907 | C | ASN | D | 163 | -34.070 | 39.304 | 12.634 | 199.24 | C |
| ATOM | 6908 | O | ASN | D | 163 | -34.132 | 38.638 | 11.599 | 196.09 | O |
| ATOM | 6909 | CB | ASN | D | 163 | -36.389 | 40.223 | 12.329 | 110.719 | C |
| ATOM | 6910 | CG | ASN | D | 163 | -36.099 | 41.606 | 11.774 | 109.316 | C |
| ATOM | 6911 | OD1 | ASN | D | 163 | -34.944 | 41.980 | 11.575 | 198.35 | O |
| ATOM | 6912 | ND2 | ASN | D | 163 | -37.154 | 42.377 | 11.533 | 116.018 | N |
| ATOM | 6913 | H | ASN | D | 163 | -34.559 | 41.449 | 14.003 | 131.715 | H |
| ATOM | 6914 | HA | ASN | D | 163 | -35.705 | 39.001 | 13.824 | 128.219 | H |
| ATOM | 6915 | HB2 | ASN | D | 163 | -36.404 | 39.599 | 11.587 | 132.915 | H |
| ATOM | 6916 | HB3 | ASN | D | 163 | -37.258 | 40.249 | 12.759 | 132.915 | H |
| ATOM | 6917 | HD21 | ASN | D | 163 | -37.044 | 43.170 | 11.218 | 139.219 | H |
| ATOM | 6918 | HD22 | ASN | D | 163 | -37.947 | 42.084 | 11.692 | 139.219 | H |
| ATOM | 6919 | N | GLY | D | 164 | -32.918 | 41.449 | 14.003 | 116.018 | N |
| ATOM | 6920 | CA | GLY | D | 164 | -31.634 | 39.661 | 13.195 | 196.98 | C |
| ATOM | 6921 | C | GLY | D | 164 | -31.365 | 39.227 | 12.670 | 187.96 | C |
| ATOM | 6922 | O | GLY | D | 164 | -30.536 | 39.684 | 11.248 | 179.64 | O |
| ATOM | 6923 | H | GLY | D | 164 | -32.856 | 40.162 | 10.548 | 169.70 | H |
| ATOM | 6924 | HA2 | GLY | D | 164 | -30.926 | 39.570 | 13.237 | 116.317 | H |
| | | | | | | | | 13.892 | 105.516 | H |

TABLE 5-continued

Atomic Coordinates for OMCP-NKG2D (4PDC).

| ATOM | 6925 | HA3 | GLY | D | 164 | -31.595 | 38.258 | 12.689 | 105.516 | H |
| --- | --- | --- | --- | --- | --- | --- | --- | --- | --- | --- |
| ATOM | 6926 | N | SER | D | 165 | -32.062 | 40.732 | 10.822 | 181.83 | N |
| ATOM | 6927 | CA | SER | D | 165 | -31.935 | 41.238 | 9.460 | 171.12 | C |
| ATOM | 6928 | C | SER | D | 165 | -30.735 | 42.170 | 9.313 | 157.71 | C |
| ATOM | 6929 | O | SER | D | 165 | -30.340 | 42.844 | 10.265 | 155.24 | O |
| ATOM | 6930 | CB | SER | D | 165 | -33.213 | 41.973 | 9.050 | 173.02 | C |
| ATOM | 6931 | OG | SER | D | 165 | -33.077 | 42.556 | 7.766 | 171.30 | O |
| ATOM | 6932 | H | SER | D | 165 | -32.620 | 41.171 | 11.307 | 198.19 | H |
| ATOM | 6933 | HA | SER | D | 165 | -31.810 | 40.491 | 8.855 | 185.34 | H |
| ATOM | 6934 | HB2 | SER | D | 165 | -33.948 | 41.341 | 9.033 | 187.63 | H |
| ATOM | 6935 | HB3 | SER | D | 165 | -33.394 | 42.674 | 9.696 | 187.63 | H |
| ATOM | 6936 | HG | SER | D | 165 | -33.785 | 42.955 | 7.555 | 185.56 | H |
| ATOM | 6937 | N | TRP | D | 166 | -30.159 | 42.193 | 8.114 | 141.62 | N |
| ATOM | 6938 | CA | TRP | D | 166 | -29.122 | 43.161 | 7.768 | 141.01 | C |
| ATOM | 6939 | C | TRP | D | 166 | -29.709 | 44.238 | 6.867 | 135.15 | C |
| ATOM | 6940 | O | TRP | D | 166 | -30.344 | 43.933 | 5.858 | 133.29 | O |
| ATOM | 6941 | CB | TRP | D | 166 | -27.942 | 42.481 | 7.067 | 131.04 | C |
| ATOM | 6942 | CG | TRP | D | 166 | -27.138 | 41.590 | 7.958 | 132.96 | C |
| ATOM | 6943 | CD1 | TRP | D | 166 | -27.222 | 40.232 | 8.050 | 139.24 | C |
| ATOM | 6944 | CD2 | TRP | D | 166 | -26.124 | 41.993 | 8.889 | 133.27 | C |
| ATOM | 6945 | NE1 | TRP | D | 166 | -26.324 | 39.763 | 8.979 | 136.80 | N |
| ATOM | 6946 | CE2 | TRP | D | 166 | -25.639 | 40.824 | 9.509 | 132.66 | C |
| ATOM | 6947 | CE3 | TRP | D | 166 | -25.582 | 43.227 | 9.257 | 132.29 | C |
| ATOM | 6948 | CZ2 | TRP | D | 166 | -24.637 | 40.854 | 10.475 | 131.08 | C |
| ATOM | 6949 | CZ3 | TRP | D | 166 | -24.586 | 43.254 | 10.217 | 129.48 | C |
| ATOM | 6950 | CH2 | TRP | D | 166 | -24.125 | 42.074 | 10.815 | 129.86 | C |
| ATOM | 6951 | H | TRP | D | 166 | -30.355 | 41.652 | 7.476 | 149.94 | H |
| ATOM | 6952 | HA | TRP | D | 166 | -28.795 | 43.584 | 8.577 | 149.21 | H |
| ATOM | 6953 | HB2 | TRP | D | 166 | -28.282 | 41.940 | 6.337 | 137.24 | H |
| ATOM | 6954 | HB3 | TRP | D | 166 | -27.349 | 43.165 | 6.720 | 137.24 | H |
| ATOM | 6955 | HD1 | TRP | D | 166 | -27.803 | 39.700 | 7.556 | 147.09 | H |
| ATOM | 6956 | HE1 | TRP | D | 166 | -26.212 | 38.938 | 9.194 | 144.16 | H |
| ATOM | 6957 | HE3 | TRP | D | 166 | -25.883 | 44.014 | 8.865 | 138.74 | H |
| ATOM | 6958 | HZ2 | TRP | D | 166 | -24.328 | 40.072 | 10.873 | 137.29 | H |
| ATOM | 6959 | HZ3 | TRP | D | 166 | -24.218 | 44.069 | 10.470 | 135.37 | H |
| ATOM | 6960 | HH2 | TRP | D | 166 | -23.455 | 42.123 | 11.457 | 135.83 | H |
| ATOM | 6961 | N | GLN | D | 167 | -29.503 | 45.497 | 7.238 | 134.74 | N |
| ATOM | 6962 | CA | GLN | D | 167 | -29.909 | 46.611 | 6.392 | 136.36 | C |
| ATOM | 6963 | C | GLN | D | 167 | -28.873 | 47.728 | 6.465 | 132.14 | C |
| ATOM | 6964 | O | GLN | D | 167 | -27.979 | 47.711 | 7.315 | 128.97 | O |
| ATOM | 6965 | CB | GLN | D | 167 | -31.294 | 47.127 | 6.800 | 143.23 | C |
| ATOM | 6966 | CG | GLN | D | 167 | -31.323 | 47.983 | 8.059 | 142.74 | C |
| ATOM | 6967 | CD | GLN | D | 167 | -32.719 | 48.487 | 8.383 | 145.63 | C |
| ATOM | 6968 | OE1 | GLN | D | 167 | -33.717 | 47.883 | 7.991 | 148.25 | O |
| ATOM | 6969 | NE2 | GLN | D | 167 | -32.795 | 49.599 | 9.102 | 146.85 | N |
| ATOM | 6970 | H | GLN | D | 167 | -29.130 | 45.732 | 7.976 | 141.69 | H |
| ATOM | 6971 | HA | GLN | D | 167 | -29.960 | 46.308 | 5.472 | 143.63 | H |
| ATOM | 6972 | HB2 | GLN | D | 167 | -31.649 | 47.663 | 6.074 | 151.88 | H |
| ATOM | 6973 | HB3 | GLN | D | 167 | -31.874 | 46.364 | 6.953 | 151.88 | H |
| ATOM | 6974 | HG2 | GLN | D | 167 | -31.012 | 47.454 | 8.810 | 151.28 | H |
| ATOM | 6975 | HG3 | GLN | D | 167 | -30.747 | 48.753 | 7.932 | 151.28 | H |

TABLE 5-continued

Atomic Coordinates for OMCP-NKG2D (4PDC).

| ATOM | 6976 | HE21 | GLN | D | 167 | -33.563 | 49.925 | 9.312 | H |
| --- | --- | --- | --- | --- | --- | --- | --- | --- | --- |
| ATOM | 6977 | HE22 | GLN | D | 167 | -32.076 | 49.994 | 9.360 | H |
| ATOM | 6978 | N | TRP | D | 168 | -28.992 | 48.694 | 5.561 | N |
| ATOM | 6979 | CA | TRP | D | 168 | -28.064 | 49.813 | 5.524 | C |
| ATOM | 6980 | C | TRP | D | 168 | -28.475 | 50.864 | 6.546 | C |
| ATOM | 6981 | O | TRP | D | 168 | -29.618 | 50.874 | 7.009 | O |
| ATOM | 6982 | CB | TRP | D | 168 | -28.007 | 50.400 | 4.117 | C |
| ATOM | 6983 | CG | TRP | D | 168 | -27.611 | 49.378 | 3.104 | C |
| ATOM | 6984 | CD1 | TRP | D | 168 | -28.412 | 48.801 | 2.163 | C |
| ATOM | 6985 | CD2 | TRP | D | 168 | -26.317 | 48.788 | 2.946 | C |
| ATOM | 6986 | NE1 | TRP | D | 168 | -27.694 | 47.894 | 1.423 | N |
| ATOM | 6987 | CE2 | TRP | D | 168 | -26.404 | 47.868 | 1.882 | C |
| ATOM | 6988 | CE3 | TRP | D | 168 | -25.090 | 48.953 | 3.596 | C |
| ATOM | 6989 | CZ2 | TRP | D | 168 | -25.312 | 47.116 | 1.454 | C |
| ATOM | 6990 | CZ3 | TRP | D | 168 | -24.008 | 48.207 | 3.169 | C |
| ATOM | 6991 | CH2 | TRP | D | 168 | -24.127 | 47.296 | 2.111 | C |
| ATOM | 6992 | H | TRP | D | 168 | -29.604 | 48.723 | 4.958 | H |
| ATOM | 6993 | HA | TRP | D | 168 | -27.176 | 49.498 | 5.755 | H |
| ATOM | 6994 | HB2 | TRP | D | 168 | -28.884 | 50.740 | 3.877 | H |
| ATOM | 6995 | HB3 | TRP | D | 168 | -27.354 | 51.116 | 4.096 | H |
| ATOM | 6996 | HD1 | TRP | D | 168 | -29.313 | 48.995 | 2.041 | H |
| ATOM | 6997 | HE1 | TRP | D | 168 | -28.004 | 47.421 | 0.775 | H |
| ATOM | 6998 | HE3 | TRP | D | 168 | -25.004 | 49.554 | 4.301 | H |
| ATOM | 6999 | HZ2 | TRP | D | 168 | -25.387 | 46.512 | 0.750 | H |
| ATOM | 7000 | HZ3 | TRP | D | 168 | -23.188 | 48.308 | 3.595 | H |
| ATOM | 7001 | HH2 | TRP | D | 168 | -23.381 | 46.810 | 1.845 | H |
| ATOM | 7002 | N | GLU | D | 169 | -27.541 | 51.742 | 6.905 | N |
| ATOM | 7003 | CA | GLU | D | 169 | -27.781 | 52.721 | 7.962 | C |
| ATOM | 7004 | C | GLU | D | 169 | -28.861 | 53.734 | 7.566 | C |
| ATOM | 7005 | O | GLU | D | 169 | -29.420 | 54.412 | 8.425 | O |
| ATOM | 7006 | CB | GLU | D | 169 | -26.473 | 53.442 | 8.329 | C |
| ATOM | 7007 | CG | GLU | D | 169 | -25.907 | 54.339 | 7.239 | C |
| ATOM | 7008 | CD | GLU | D | 169 | -24.412 | 54.619 | 7.405 | C |
| ATOM | 7009 | OE1 | GLU | D | 169 | -23.995 | 55.125 | 8.473 | O |
| ATOM | 7010 | OE2 | GLU | D | 169 | -23.651 | 54.335 | 6.457 | O1- |
| ATOM | 7011 | H | GLU | D | 169 | -26.759 | 51.790 | 6.551 | H |
| ATOM | 7012 | HA | GLU | D | 169 | -28.091 | 52.254 | 8.753 | H |
| ATOM | 7013 | HB2 | GLU | D | 169 | -26.634 | 53.996 | 9.109 | H |
| ATOM | 7014 | HB3 | GLU | D | 169 | -25.800 | 52.775 | 8.537 | H |
| ATOM | 7015 | HG2 | GLU | D | 169 | -26.036 | 53.909 | 6.379 | H |
| ATOM | 7016 | HG3 | GLU | D | 169 | -26.374 | 55.189 | 7.256 | H |
| ATOM | 7017 | N | ASP | D | 170 | -29.163 | 53.822 | 6.273 | N |
| ATOM | 7018 | CA | ASP | D | 170 | -30.212 | 54.719 | 5.789 | C |
| ATOM | 7019 | C | ASP | D | 170 | -31.587 | 54.053 | 5.821 | C |
| ATOM | 7020 | O | ASP | D | 170 | -32.580 | 54.645 | 5.407 | O |
| ATOM | 7021 | CB | ASP | D | 170 | -29.900 | 55.192 | 4.366 | C |
| ATOM | 7022 | CG | ASP | D | 170 | -30.035 | 54.083 | 3.334 | C |
| ATOM | 7023 | OD1 | ASP | D | 170 | -30.204 | 52.907 | 3.720 | O |
| ATOM | 7024 | OD2 | ASP | D | 170 | -29.959 | 54.387 | 2.127 | O1- |
| ATOM | 7025 | H | ASP | D | 170 | -28.774 | 53.372 | 5.652 | H |
| ATOM | 7026 | HA | ASP | D | 170 | -30.246 | 55.501 | 6.362 | H |

TABLE 5-continued

Atomic Coordinates for OMCP-NKG2D (4PDC).

| ATOM | 7027 | HB2 | ASP | D | 170 | -30.517 | 55.901 | 4.127 | 130.92 | H |
|---|---|---|---|---|---|---|---|---|---|---|
| ATOM | 7028 | HB3 | ASP | D | 170 | -28.988 | 55.521 | 4.335 | 130.92 | H |
| ATOM | 7029 | N | GLY | D | 171 | -31.629 | 52.808 | 6.286 | 131.62 | N |
| ATOM | 7030 | CA | GLY | D | 171 | -32.877 | 52.081 | 6.423 | 131.76 | C |
| ATOM | 7031 | C | GLY | D | 171 | -33.213 | 51.178 | 5.248 | 132.34 | C |
| ATOM | 7032 | O | GLY | D | 171 | -34.017 | 50.259 | 5.393 | 136.75 | O |
| ATOM | 7033 | H | GLY | D | 171 | -30.937 | 52.361 | 6.531 | 137.95 | H |
| ATOM | 7034 | HA2 | GLY | D | 171 | -32.836 | 51.532 | 7.221 | 138.11 | H |
| ATOM | 7035 | HA3 | GLY | D | 171 | -33.603 | 52.715 | 6.531 | 138.11 | H |
| ATOM | 7036 | N | SER | D | 172 | -32.609 | 51.426 | 4.088 | 129.62 | N |
| ATOM | 7037 | CA | SER | D | 172 | -32.938 | 50.654 | 2.888 | 131.61 | C |
| ATOM | 7038 | C | SER | D | 172 | -32.552 | 49.188 | 3.061 | 130.37 | C |
| ATOM | 7039 | O | SER | D | 172 | -31.747 | 48.846 | 3.927 | 133.60 | O |
| ATOM | 7040 | CB | SER | D | 172 | -32.246 | 51.240 | 1.650 | 133.37 | C |
| ATOM | 7041 | OG | SER | D | 172 | -30.837 | 51.125 | 1.737 | 130.18 | O |
| ATOM | 7042 | H | SER | D | 172 | -32.009 | 52.031 | 3.968 | 135.54 | H |
| ATOM | 7043 | HA | SER | D | 172 | -33.895 | 50.696 | 2.742 | 137.93 | H |
| ATOM | 7044 | HB2 | SER | D | 172 | -32.552 | 50.761 | 0.864 | 140.04 | H |
| ATOM | 7045 | HB3 | SER | D | 172 | -32.479 | 52.179 | 1.576 | 140.04 | H |
| ATOM | 7046 | HG | SER | D | 172 | -30.619 | 50.316 | 1.800 | 136.22 | H |
| ATOM | 7047 | N | ILE | D | 173 | -33.139 | 48.325 | 2.236 | 134.65 | N |
| ATOM | 7048 | CA | ILE | D | 173 | -32.919 | 46.889 | 2.352 | 135.81 | C |
| ATOM | 7049 | C | ILE | D | 173 | -31.672 | 46.444 | 1.600 | 132.48 | C |
| ATOM | 7050 | O | ILE | D | 173 | -31.201 | 47.117 | 0.676 | 125.43 | O |
| ATOM | 7051 | CB | ILE | D | 173 | -34.131 | 46.073 | 1.827 | 136.56 | C |
| ATOM | 7052 | CG1 | ILE | D | 173 | -34.365 | 46.330 | 0.332 | 138.02 | C |
| ATOM | 7053 | CG2 | ILE | D | 173 | -35.382 | 46.407 | 2.633 | 143.13 | C |
| ATOM | 7054 | CD1 | ILE | D | 173 | -35.348 | 45.372 | -0.303 | 140.93 | C |
| ATOM | 7055 | H | ILE | D | 173 | -33.671 | 48.548 | 1.598 | 141.58 | H |
| ATOM | 7056 | HA | ILE | D | 173 | -32.796 | 46.667 | 3.289 | 142.97 | H |
| ATOM | 7057 | HB | ILE | D | 173 | -33.936 | 45.130 | 1.945 | 143.88 | H |
| ATOM | 7058 | HG12 | ILE | D | 173 | -34.713 | 47.229 | 0.220 | 145.63 | H |
| ATOM | 7059 | HG13 | ILE | D | 173 | -33.521 | 46.243 | -0.137 | 145.63 | H |
| ATOM | 7060 | HG21 | ILE | D | 173 | -36.126 | 45.888 | 2.289 | 151.76 | H |
| ATOM | 7061 | HG22 | ILE | D | 173 | -35.225 | 46.186 | 3.564 | 151.76 | H |
| ATOM | 7062 | HG23 | ILE | D | 173 | -35.570 | 47.355 | 2.544 | 151.76 | H |
| ATOM | 7063 | HD11 | ILE | D | 173 | -35.444 | 45.595 | -1.242 | 149.11 | H |
| ATOM | 7064 | HD12 | ILE | D | 173 | -35.010 | 44.467 | -0.211 | 149.11 | H |
| ATOM | 7065 | HD13 | ILE | D | 173 | -36.203 | 45.453 | 0.147 | 149.11 | H |
| ATOM | 7066 | N | LEU | D | 174 | -31.153 | 45.293 | 2.007 | 131.77 | N |
| ATOM | 7067 | CA | LEU | D | 174 | -30.037 | 44.657 | 1.330 | 127.52 | C |
| ATOM | 7068 | C | LEU | D | 174 | -30.557 | 43.827 | 0.166 | 125.72 | C |
| ATOM | 7069 | O | LEU | D | 174 | -31.252 | 42.838 | 0.374 | 130.63 | O |
| ATOM | 7070 | CB | LEU | D | 174 | -29.257 | 43.784 | 2.312 | 131.85 | C |
| ATOM | 7071 | CG | LEU | D | 174 | -28.071 | 42.986 | 1.764 | 133.37 | C |
| ATOM | 7072 | CD1 | LEU | D | 174 | -27.043 | 43.905 | 1.129 | 126.92 | C |
| ATOM | 7073 | CD2 | LEU | D | 174 | -27.441 | 42.169 | 2.880 | 126.89 | C |
| ATOM | 7074 | H | LEU | D | 174 | -31.438 | 44.853 | 2.688 | 138.12 | H |
| ATOM | 7075 | HA | LEU | D | 174 | -29.440 | 45.337 | 0.980 | 133.02 | H |
| ATOM | 7076 | HB2 | LEU | D | 174 | -28.912 | 44.357 | 3.015 | 138.22 | H |
| ATOM | 7077 | HB3 | LEU | D | 174 | -29.874 | 43.144 | 2.700 | 138.22 | H |

TABLE 5-continued

Atomic Coordinates for OMCP-NKG2D (4PDC).

| ATOM | 7078 | HG | LEU | D | 174 | -28.389 | 42.372 | 1.084 | 140.04 | H |
|---|---|---|---|---|---|---|---|---|---|---|
| ATOM | 7079 | HD11 | LEU | D | 174 | -26.307 | 43.370 | 0.793 | 132.31 | H |
| ATOM | 7080 | HD12 | LEU | D | 174 | -27.461 | 44.389 | 0.400 | 132.31 | H |
| ATOM | 7081 | HD13 | LEU | D | 174 | -26.721 | 44.528 | 1.799 | 132.31 | H |
| ATOM | 7082 | HD21 | LEU | D | 174 | -26.692 | 41.669 | 2.521 | 132.27 | H |
| ATOM | 7083 | HD22 | LEU | D | 174 | -27.134 | 42.771 | 3.577 | 132.27 | H |
| ATOM | 7084 | HD23 | LEU | D | 174 | -28.105 | 41.559 | 3.239 | 132.27 | H |
| ATOM | 7085 | N | SER | D | 175 | -30.242 | 44.239 | -1.058 | 127.73 | N |
| ATOM | 7086 | CA | SER | D | 175 | -30.653 | 43.479 | -2.231 | 123.91 | C |
| ATOM | 7087 | C | SER | D | 175 | -30.187 | 42.029 | -2.083 | 128.76 | C |
| ATOM | 7088 | O | SER | D | 175 | -28.991 | 41.786 | -1.925 | 127.41 | O |
| ATOM | 7089 | CB | SER | D | 175 | -30.077 | 44.098 | -3.505 | 126.73 | C |
| ATOM | 7090 | OG | SER | D | 175 | -30.445 | 43.344 | -4.648 | 122.87 | O |
| ATOM | 7091 | H | SER | D | 175 | -29.793 | 44.951 | -1.234 | 133.27 | H |
| ATOM | 7092 | HA | SER | D | 175 | -31.620 | 43.485 | -2.297 | 128.69 | H |
| ATOM | 7093 | HB2 | SER | D | 175 | -30.419 | 45.000 | -3.600 | 132.07 | H |
| ATOM | 7094 | HB3 | SER | D | 175 | -29.110 | 44.116 | -3.438 | 132.07 | H |
| ATOM | 7095 | HG | SER | D | 175 | -30.123 | 43.694 | -5.340 | 127.44 | H |
| ATOM | 7096 | N | PRO | D | 176 | -31.127 | 41.063 | -2.098 | 125.88 | N |
| ATOM | 7097 | CA | PRO | D | 176 | -30.728 | 39.659 | -1.923 | 127.19 | C |
| ATOM | 7098 | C | PRO | D | 176 | -29.657 | 39.204 | -2.916 | 126.97 | C |
| ATOM | 7099 | O | PRO | D | 176 | -29.693 | 39.601 | -4.079 | 127.85 | O |
| ATOM | 7100 | CB | PRO | D | 176 | -32.035 | 38.891 | -2.155 | 123.99 | C |
| ATOM | 7101 | CG | PRO | D | 176 | -33.107 | 39.860 | -1.828 | 125.30 | C |
| ATOM | 7102 | CD | PRO | D | 176 | -32.588 | 41.204 | -2.234 | 125.95 | C |
| ATOM | 7103 | HA | PRO | D | 176 | -30.418 | 39.504 | -1.017 | 132.63 | H |
| ATOM | 7104 | HB2 | PRO | D | 176 | -32.092 | 38.614 | -3.082 | 128.78 | H |
| ATOM | 7105 | HB3 | PRO | D | 176 | -32.073 | 38.123 | -1.563 | 128.78 | H |
| ATOM | 7106 | HG2 | PRO | D | 176 | -33.907 | 39.638 | -2.330 | 130.36 | H |
| ATOM | 7107 | HG3 | PRO | D | 176 | -33.285 | 39.837 | -0.875 | 130.36 | H |
| ATOM | 7108 | HD2 | PRO | D | 176 | -32.825 | 41.393 | -3.155 | 131.14 | H |
| ATOM | 7109 | HD3 | PRO | D | 176 | -32.919 | 41.889 | -1.633 | 131.14 | H |
| ATOM | 7110 | N | ASN | D | 177 | -28.715 | 38.392 | -2.442 | 124.96 | N |
| ATOM | 7111 | CA | ASN | D | 177 | -27.667 | 37.810 | -3.280 | 124.54 | C |
| ATOM | 7112 | C | ASN | D | 177 | -26.704 | 38.844 | -3.866 | 129.77 | C |
| ATOM | 7113 | O | ASN | D | 177 | -26.083 | 38.603 | -4.900 | 133.58 | O |
| ATOM | 7114 | CB | ASN | D | 177 | -28.291 | 36.990 | -4.415 | 130.08 | C |
| ATOM | 7115 | CG | ASN | D | 177 | -29.188 | 35.884 | -3.905 | 129.31 | C |
| ATOM | 7116 | OD1 | ASN | D | 177 | -30.398 | 35.883 | -4.142 | 127.98 | O |
| ATOM | 7117 | ND2 | ASN | D | 177 | -28.598 | 34.933 | -3.193 | 130.03 | N |
| ATOM | 7118 | H | ASN | D | 177 | -28.660 | 38.158 | -1.616 | 129.95 | H |
| ATOM | 7119 | HA | ASN | D | 177 | -27.144 | 37.202 | -2.735 | 129.44 | H |
| ATOM | 7120 | HB2 | ASN | D | 177 | -28.825 | 37.576 | -4.974 | 136.09 | H |
| ATOM | 7121 | HB3 | ASN | D | 177 | -27.583 | 36.585 | -4.940 | 136.09 | H |
| ATOM | 7122 | HD21 | ASN | D | 177 | -29.062 | 34.281 | -2.879 | 136.03 | H |
| ATOM | 7123 | HD22 | ASN | D | 177 | -27.752 | 34.969 | -3.046 | 136.03 | H |
| ATOM | 7124 | N | LEU | D | 178 | -26.577 | 39.988 | -3.202 | 129.98 | N |
| ATOM | 7125 | CA | LEU | D | 178 | -25.592 | 40.989 | -3.594 | 125.52 | C |
| ATOM | 7126 | C | LEU | D | 178 | -24.290 | 40.721 | -2.851 | 126.67 | C |
| ATOM | 7127 | O | LEU | D | 178 | -23.228 | 40.588 | -3.463 | 128.33 | O |
| ATOM | 7128 | CB | LEU | D | 178 | -26.098 | 42.400 | -3.295 | 126.47 | C |

TABLE 5-continued

Atomic Coordinates for OMCP-NKG2D (4PDC).

| | | | | | | | | | |
|---|---|---|---|---|---|---|---|---|---|
| ATOM | 7129 | CG | LEU | D | 178 | -25.654 | 43.482 | -4.281 | C |
| ATOM | 7130 | CD1 | LEU | D | 178 | -26.117 | 44.846 | -3.805 | C |
| ATOM | 7131 | CD2 | LEU | D | 178 | -24.150 | 43.470 | -4.484 | C |
| ATOM | 7132 | H | LEU | D | 178 | -27.051 | 40.209 | -2.520 | H |
| ATOM | 7133 | HA | LEU | D | 178 | -25.423 | 40.919 | -4.546 | H |
| ATOM | 7134 | HB2 | LEU | D | 178 | -27.068 | 42.385 | -3.298 | H |
| ATOM | 7135 | HB3 | LEU | D | 178 | -25.781 | 42.659 | -2.416 | H |
| ATOM | 7136 | HG | LEU | D | 178 | -26.070 | 43.312 | -5.141 | H |
| ATOM | 7137 | HD11 | LEU | D | 178 | -25.727 | 45.025 | -2.934 | H |
| ATOM | 7138 | HD12 | LEU | D | 178 | -25.826 | 45.518 | -4.442 | H |
| ATOM | 7139 | HD13 | LEU | D | 178 | -27.085 | 44.847 | -3.741 | H |
| ATOM | 7140 | HD21 | LEU | D | 178 | -23.910 | 44.168 | -5.113 | H |
| ATOM | 7141 | HD22 | LEU | D | 178 | -23.716 | 43.630 | -3.631 | H |
| ATOM | 7142 | HD23 | LEU | D | 178 | -23.885 | 42.605 | -4.833 | H |
| ATOM | 7143 | N | LEU | D | 179 | -24.389 | 40.630 | -1.528 | N |
| ATOM | 7144 | CA | LEU | D | 179 | -23.244 | 40.332 | -0.679 | C |
| ATOM | 7145 | C | LEU | D | 179 | -23.321 | 38.920 | -0.113 | C |
| ATOM | 7146 | O | LEU | D | 179 | -24.408 | 38.392 | 0.125 | O |
| ATOM | 7147 | CB | LEU | D | 179 | -23.155 | 41.335 | 0.469 | C |
| ATOM | 7148 | CG | LEU | D | 179 | -22.856 | 42.788 | 0.096 | C |
| ATOM | 7149 | CD1 | LEU | D | 179 | -22.901 | 43.661 | 1.336 | C |
| ATOM | 7150 | CD2 | LEU | D | 179 | -21.504 | 42.910 | -0.586 | C |
| ATOM | 7151 | H | LEU | D | 179 | -25.123 | 40.739 | -1.093 | H |
| ATOM | 7152 | HA | LEU | D | 179 | -22.432 | 40.403 | -1.205 | H |
| ATOM | 7153 | HB2 | LEU | D | 179 | -24.003 | 41.329 | 0.941 | H |
| ATOM | 7154 | HB3 | LEU | D | 179 | -22.453 | 41.043 | 1.071 | H |
| ATOM | 7155 | HG | LEU | D | 179 | -23.535 | 43.104 | -0.521 | H |
| ATOM | 7156 | HD11 | LEU | D | 179 | -22.710 | 44.577 | 1.083 | H |
| ATOM | 7157 | HD12 | LEU | D | 179 | -23.786 | 43.604 | 1.729 | H |
| ATOM | 7158 | HD13 | LEU | D | 179 | -22.237 | 43.346 | 1.968 | H |
| ATOM | 7159 | HD21 | LEU | D | 179 | -21.346 | 43.840 | -0.809 | H |
| ATOM | 7160 | HD22 | LEU | D | 179 | -20.816 | 42.593 | 0.020 | H |
| ATOM | 7161 | HD23 | LEU | D | 179 | -21.508 | 42.372 | -1.393 | H |
| ATOM | 7162 | N | THR | D | 180 | -22.153 | 38.316 | 0.088 | N |
| ATOM | 7163 | CA | THR | D | 180 | -22.040 | 37.069 | 0.827 | C |
| ATOM | 7164 | C | THR | D | 180 | -21.583 | 37.388 | 2.242 | C |
| ATOM | 7165 | O | THR | D | 180 | -20.446 | 37.813 | 2.455 | O |
| ATOM | 7166 | CB | THR | D | 180 | -21.059 | 36.099 | 0.154 | C |
| ATOM | 7167 | OG1 | THR | D | 180 | -21.581 | 35.709 | -1.122 | O |
| ATOM | 7168 | CG2 | THR | D | 180 | -20.847 | 34.854 | 1.006 | C |
| ATOM | 7169 | H | THR | D | 180 | -21.401 | 38.616 | -0.201 | H |
| ATOM | 7170 | HA | THR | D | 180 | -22.910 | 36.642 | 0.875 | H |
| ATOM | 7171 | HB | THR | D | 180 | -20.203 | 36.538 | 0.032 | H |
| ATOM | 7172 | HG1 | THR | D | 180 | -21.682 | 36.386 | -1.610 | H |
| ATOM | 7173 | HG21 | THR | D | 180 | -20.225 | 34.253 | 0.566 | H |
| ATOM | 7174 | HG22 | THR | D | 180 | -20.486 | 35.102 | 1.872 | H |
| ATOM | 7175 | HG23 | THR | D | 180 | -21.691 | 34.394 | 1.137 | H |
| ATOM | 7176 | N | ILE | D | 181 | -22.478 | 37.187 | 3.204 | N |
| ATOM | 7177 | CA | ILE | D | 181 | -22.186 | 37.469 | 4.602 | C |
| ATOM | 7178 | C | ILE | D | 181 | -21.541 | 36.264 | 5.269 | C |
| ATOM | 7179 | O | ILE | D | 181 | -22.102 | 35.168 | 5.252 | O |

TABLE 5-continued

Atomic Coordinates for OMCP-NKG2D (4PDC).

| ATOM | 7180 | CB | ILE | D | 181 | -23.459 | 37.851 | 5.386 | 125.11 | C |
| --- | --- | --- | --- | --- | --- | --- | --- | --- | --- | --- |
| ATOM | 7181 | CG1 | ILE | D | 181 | -24.171 | 39.037 | 4.725 | 125.99 | C |
| ATOM | 7182 | CG2 | ILE | D | 181 | -23.116 | 38.174 | 6.841 | 132.01 | C |
| ATOM | 7183 | CD1 | ILE | D | 181 | -23.360 | 40.323 | 4.695 | 129.24 | C |
| ATOM | 7184 | H | ILE | D | 181 | -23.271 | 36.883 | 3.069 | 126.93 | H |
| ATOM | 7185 | HA | ILE | D | 181 | -21.565 | 38.212 | 4.654 | 127.81 | H |
| ATOM | 7186 | HB | ILE | D | 181 | -24.062 | 37.091 | 5.377 | 130.13 | H |
| ATOM | 7187 | HG12 | ILE | D | 181 | -24.382 | 38.800 | 3.809 | 131.19 | H |
| ATOM | 7188 | HG13 | ILE | D | 181 | -24.990 | 39.218 | 5.213 | 131.19 | H |
| ATOM | 7189 | HG21 | ILE | D | 181 | -23.930 | 38.411 | 7.312 | 138.41 | H |
| ATOM | 7190 | HG22 | ILE | D | 181 | -22.711 | 37.393 | 7.250 | 138.41 | H |
| ATOM | 7191 | HG23 | ILE | D | 181 | -22.494 | 38.918 | 6.861 | 135.08 | H |
| ATOM | 7192 | HD11 | ILE | D | 181 | -23.883 | 41.016 | 4.262 | 135.08 | H |
| ATOM | 7193 | HD12 | ILE | D | 181 | -23.151 | 40.586 | 5.605 | 135.08 | H |
| ATOM | 7194 | HD13 | ILE | D | 181 | -22.541 | 40.168 | 4.198 | 135.08 | H |
| ATOM | 7195 | N | ILE | D | 182 | -20.375 | 36.484 | 5.873 | 123.72 | N |
| ATOM | 7196 | CA | ILE | D | 182 | -19.615 | 35.416 | 6.521 | 122.37 | C |
| ATOM | 7197 | C | ILE | D | 182 | -19.531 | 35.640 | 8.024 | 122.69 | C |
| ATOM | 7198 | O | ILE | D | 182 | -19.146 | 36.717 | 8.478 | 117.58 | O |
| ATOM | 7199 | CB | ILE | D | 182 | -18.184 | 35.315 | 5.950 | 120.91 | C |
| ATOM | 7200 | CG1 | ILE | D | 182 | -18.233 | 35.144 | 4.428 | 119.30 | C |
| ATOM | 7201 | CG2 | ILE | D | 182 | -17.422 | 34.159 | 6.609 | 118.99 | C |
| ATOM | 7202 | CD1 | ILE | D | 182 | -16.890 | 35.250 | 3.753 | 120.70 | C |
| ATOM | 7203 | H | ILE | D | 182 | -19.997 | 37.255 | 5.922 | 128.47 | H |
| ATOM | 7204 | HA | ILE | D | 182 | -20.062 | 34.569 | 6.366 | 126.85 | H |
| ATOM | 7205 | HB | ILE | D | 182 | -17.716 | 36.141 | 6.149 | 125.09 | H |
| ATOM | 7206 | HG12 | ILE | D | 182 | -18.598 | 34.269 | 4.225 | 123.16 | H |
| ATOM | 7207 | HG13 | ILE | D | 182 | -18.805 | 35.833 | 4.056 | 123.16 | H |
| ATOM | 7208 | HG21 | ILE | D | 182 | -16.528 | 34.116 | 6.235 | 122.78 | H |
| ATOM | 7209 | HG22 | ILE | D | 182 | -17.373 | 34.318 | 7.565 | 122.78 | H |
| ATOM | 7210 | HG23 | ILE | D | 182 | -17.894 | 33.330 | 6.435 | 122.78 | H |
| ATOM | 7211 | HD11 | ILE | D | 182 | -17.007 | 35.131 | 2.797 | 124.84 | H |
| ATOM | 7212 | HD12 | ILE | D | 182 | -16.513 | 36.125 | 3.934 | 124.84 | H |
| ATOM | 7213 | HD13 | ILE | D | 182 | -16.305 | 34.559 | 4.103 | 124.84 | H |
| ATOM | 7214 | N | GLU | D | 183 | -19.895 | 34.615 | 8.789 | 124.20 | N |
| ATOM | 7215 | CA | GLU | D | 183 | -19.788 | 34.661 | 10.241 | 126.38 | C |
| ATOM | 7216 | C | GLU | D | 183 | -18.337 | 34.472 | 10.651 | 131.18 | C |
| ATOM | 7217 | O | GLU | D | 183 | -17.673 | 33.538 | 10.205 | 129.96 | O |
| ATOM | 7218 | CB | GLU | D | 183 | -20.662 | 33.587 | 10.888 | 135.36 | C |
| ATOM | 7219 | CG | GLU | D | 183 | -22.150 | 33.765 | 10.648 | 146.80 | C |
| ATOM | 7220 | CD | GLU | D | 183 | -22.982 | 32.679 | 11.304 | 173.69 | C |
| ATOM | 7221 | OE1 | GLU | D | 183 | -22.398 | 31.680 | 11.776 | 179.19 | O |
| ATOM | 7222 | OE2 | GLU | D | 183 | -24.222 | 32.825 | 11.351 | 181.50 | O1- |
| ATOM | 7223 | H | GLU | D | 183 | -20.210 | 33.874 | 8.486 | 129.04 | H |
| ATOM | 7224 | HA | GLU | D | 183 | -20.085 | 35.529 | 10.557 | 131.66 | H |
| ATOM | 7225 | HB2 | GLU | D | 183 | -20.407 | 32.722 | 10.531 | 142.43 | H |
| ATOM | 7226 | HB3 | GLU | D | 183 | -20.514 | 33.602 | 11.847 | 142.43 | H |
| ATOM | 7227 | HG2 | GLU | D | 183 | -22.430 | 34.619 | 11.013 | 156.15 | H |
| ATOM | 7228 | HG3 | GLU | D | 183 | -22.322 | 33.739 | 9.694 | 156.15 | H |
| ATOM | 7229 | N | MET | D | 184 | -17.846 | 35.363 | 11.502 | 130.31 | N |
| ATOM | 7230 | CA | MET | D | 184 | -16.458 | 35.313 | 11.938 | 129.78 | C |

TABLE 5-continued

Atomic Coordinates for OMCP-NKG2D (4PDC).

| ATOM | 7231 | C | MET | D | 184 | -16.376 | 35.603 | 13.430 | 135.79 | C |
| ATOM | 7232 | O | MET | D | 184 | -16.026 | 34.731 | 14.229 | 137.59 | O |
| ATOM | 7233 | CB | MET | D | 184 | -15.621 | 36.315 | 11.147 | 127.05 | C |
| ATOM | 7234 | CG | MET | D | 184 | -14.138 | 36.253 | 11.442 | 126.53 | C |
| ATOM | 7235 | SD | MET | D | 184 | -13.261 | 37.651 | 10.735 | 130.02 | S |
| ATOM | 7236 | CE | MET | D | 184 | -13.846 | 38.985 | 11.783 | 131.51 | C |
| ATOM | 7237 | I | MET | D | 184 | -18.299 | 36.010 | 11.843 | 136.37 | H |
| ATOM | 7238 | HA | MET | D | 184 | -16.104 | 34.426 | 11.768 | 135.73 | H |
| ATOM | 7239 | HB2 | MET | D | 184 | -15.741 | 36.142 | 10.200 | 132.46 | H |
| ATOM | 7240 | HB3 | MET | D | 184 | -15.927 | 37.211 | 11.357 | 132.46 | H |
| ATOM | 7241 | HG2 | MET | D | 184 | -14.002 | 36.265 | 12.403 | 131.83 | H |
| ATOM | 7242 | HG3 | MET | D | 184 | -13.770 | 35.441 | 11.062 | 131.83 | H |
| ATOM | 7243 | HE1 | MET | D | 184 | -13.435 | 39.816 | 11.496 | 137.82 | H |
| ATOM | 7244 | HE2 | MET | D | 184 | -14.811 | 39.049 | 11.703 | 137.82 | H |
| ATOM | 7245 | HE3 | MET | D | 184 | -13.602 | 38.795 | 12.702 | 137.82 | H |
| ATOM | 7246 | N | GLN | D | 185 | -16.705 | 36.837 | 13.791 | 133.99 | N |
| ATOM | 7247 | CA | GLN | D | 185 | -16.777 | 37.246 | 15.185 | 137.58 | C |
| ATOM | 7248 | C | GLN | D | 185 | -18.202 | 37.678 | 15.488 | 140.84 | C |
| ATOM | 7249 | O | GLN | D | 185 | -18.821 | 38.383 | 14.691 | 136.32 | O |
| ATOM | 7250 | CB | GLN | D | 185 | -15.797 | 38.383 | 15.470 | 140.17 | C |
| ATOM | 7251 | CG | GLN | D | 185 | -15.634 | 38.706 | 16.944 | 146.92 | C |
| ATOM | 7252 | CD | GLN | D | 185 | -14.883 | 37.625 | 17.695 | 155.70 | C |
| ATOM | 7253 | OE1 | GLN | D | 185 | -13.773 | 37.249 | 17.317 | 153.14 | O |
| ATOM | 7254 | NE2 | GLN | D | 185 | -15.487 | 37.116 | 18.763 | 159.98 | N |
| ATOM | 7255 | H | GLN | D | 185 | -16.894 | 37.467 | 13.236 | 140.79 | H |
| ATOM | 7256 | HA | GLN | D | 185 | -16.554 | 36.495 | 15.756 | 145.09 | H |
| ATOM | 7257 | HB2 | GLN | D | 185 | -14.925 | 38.137 | 15.124 | 148.21 | H |
| ATOM | 7258 | HB3 | GLN | D | 185 | -16.111 | 39.185 | 15.025 | 148.21 | H |
| ATOM | 7259 | HG2 | GLN | D | 185 | -15.139 | 39.535 | 17.034 | 156.30 | H |
| ATOM | 7260 | HG3 | GLN | D | 185 | -16.512 | 38.797 | 17.347 | 156.30 | H |
| ATOM | 7261 | HE21 | GLN | D | 185 | -15.101 | 36.500 | 19.222 | 171.97 | H |
| ATOM | 7262 | HE22 | GLN | D | 185 | -16.264 | 37.402 | 18.995 | 171.97 | H |
| ATOM | 7263 | N | LYS | D | 186 | -18.723 | 37.242 | 16.631 | 146.47 | N |
| ATOM | 7264 | CA | LYS | D | 186 | -20.057 | 37.639 | 17.061 | 145.40 | C |
| ATOM | 7265 | C | LYS | D | 186 | -20.143 | 39.158 | 17.171 | 139.69 | C |
| ATOM | 7266 | O | LYS | D | 186 | -19.414 | 39.777 | 17.947 | 141.64 | O |
| ATOM | 7267 | CB | LYS | D | 186 | -20.405 | 36.981 | 18.398 | 151.52 | C |
| ATOM | 7268 | CG | LYS | D | 186 | -20.680 | 35.489 | 18.289 | 165.11 | C |
| ATOM | 7269 | CD | LYS | D | 186 | -19.861 | 34.683 | 19.288 | 184.25 | C |
| ATOM | 7270 | CE | LYS | D | 186 | -20.168 | 33.195 | 19.180 | 186.61 | C |
| ATOM | 7271 | NZ | LYS | D | 186 | -18.935 | 32.360 | 19.163 | 176.57 | N1+ |
| ATOM | 7272 | H | LYS | D | 186 | -18.321 | 36.712 | 17.176 | 155.77 | H |
| ATOM | 7273 | HA | LYS | D | 186 | -20.705 | 37.346 | 16.402 | 154.47 | H |
| ATOM | 7274 | HB2 | LYS | D | 186 | -19.662 | 37.103 | 19.010 | 161.82 | H |
| ATOM | 7275 | HB3 | LYS | D | 186 | -21.200 | 37.405 | 18.758 | 161.82 | H |
| ATOM | 7276 | HG2 | LYS | D | 186 | -21.619 | 35.325 | 18.466 | 178.14 | H |
| ATOM | 7277 | HG3 | LYS | D | 186 | -20.450 | 35.188 | 17.397 | 178.14 | H |
| ATOM | 7278 | HD2 | LYS | D | 186 | -18.917 | 34.814 | 19.108 | 101.110 | H |
| ATOM | 7279 | HD3 | LYS | D | 186 | -20.076 | 34.975 | 20.188 | 101.110 | H |
| ATOM | 7280 | HE2 | LYS | D | 186 | -20.703 | 32.926 | 19.943 | 103.914 | H |
| ATOM | 7281 | HE3 | LYS | D | 186 | -20.654 | 33.031 | 18.357 | 103.914 | H |

TABLE 5-continued

Atomic Coordinates for OMCP-NKG2D (4PDC).

| ATOM | 7282 | HZ1 | LYS | D | 186 | -19.151 | 31.500 | 19.100 | 191.88 | H |
|------|------|-----|-----|---|-----|---------|--------|--------|--------|---|
| ATOM | 7283 | HZ2 | LYS | D | 186 | -18.426 | 32.583 | 18.467 | 191.88 | H |
| ATOM | 7284 | HZ3 | LYS | D | 186 | -18.471 | 32.488 | 19.912 | 191.88 | H |
| ATOM | 7285 | N | GLY | D | 187 | -21.027 | 39.755 | 16.379 | 138.31 | N |
| ATOM | 7286 | CA | GLY | D | 187 | -21.164 | 41.200 | 16.353 | 135.66 | C |
| ATOM | 7287 | C | GLY | D | 187 | -22.311 | 41.654 | 15.477 | 129.40 | C |
| ATOM | 7288 | O | GLY | D | 187 | -22.977 | 40.839 | 14.843 | 128.79 | O |
| ATOM | 7289 | H | GLY | D | 187 | -21.560 | 39.342 | 15.845 | 145.97 | H |
| ATOM | 7290 | HA2 | GLY | D | 187 | -21.318 | 41.526 | 17.254 | 142.79 | H |
| ATOM | 7291 | HA3 | GLY | D | 187 | -20.345 | 41.596 | 16.018 | 142.79 | H |
| ATOM | 7292 | N | ASP | D | 188 | -22.528 | 42.966 | 15.435 | 130.44 | N |
| ATOM | 7293 | CA | ASP | D | 188 | -23.660 | 43.549 | 14.722 | 129.39 | C |
| ATOM | 7294 | C | ASP | D | 188 | -23.208 | 44.460 | 13.580 | 129.72 | C |
| ATOM | 7295 | O | ASP | D | 188 | -24.003 | 45.223 | 13.031 | 131.13 | O |
| ATOM | 7296 | CB | ASP | D | 188 | -24.540 | 44.327 | 15.705 | 137.77 | C |
| ATOM | 7297 | CG | ASP | D | 188 | -25.117 | 43.439 | 16.801 | 139.59 | C |
| ATOM | 7298 | OD1 | ASP | D | 188 | -25.551 | 42.311 | 16.485 | 140.77 | O |
| ATOM | 7299 | OD2 | ASP | D | 188 | -25.127 | 43.863 | 17.977 | 138.82 | O1- |
| ATOM | 7300 | H | ASP | D | 188 | -22.025 | 43.548 | 15.819 | 136.53 | H |
| ATOM | 7301 | HA | ASP | D | 188 | -24.195 | 42.835 | 14.341 | 135.27 | H |
| ATOM | 7302 | HB2 | ASP | D | 188 | -24.007 | 45.019 | 16.128 | 145.33 | H |
| ATOM | 7303 | HB3 | ASP | D | 188 | -25.280 | 44.726 | 15.221 | 145.33 | H |
| ATOM | 7304 | N | CYS | D | 189 | -21.928 | 44.372 | 13.230 | 129.33 | N |
| ATOM | 7305 | CA | CYS | D | 189 | -21.362 | 45.161 | 12.140 | 127.86 | C |
| ATOM | 7306 | C | CYS | D | 189 | -20.576 | 44.256 | 11.195 | 125.45 | C |
| ATOM | 7307 | O | CYS | D | 189 | -20.198 | 43.145 | 11.568 | 123.49 | O |
| ATOM | 7308 | CB | CYS | D | 189 | -20.468 | 46.272 | 12.692 | 128.54 | C |
| ATOM | 7309 | SG | CYS | D | 189 | -21.349 | 47.483 | 13.716 | 129.86 | S |
| ATOM | 7310 | H | CYS | D | 189 | -21.358 | 43.854 | 13.613 | 135.19 | H |
| ATOM | 7311 | HA | CYS | D | 189 | -22.082 | 45.573 | 11.637 | 133.43 | H |
| ATOM | 7312 | HB2 | CYS | D | 189 | -19.773 | 45.872 | 13.238 | 134.24 | H |
| ATOM | 7313 | HB3 | CYS | D | 189 | -20.067 | 46.749 | 11.948 | 134.24 | H |
| ATOM | 7314 | N | ALA | D | 190 | -20.337 | 44.731 | 9.975 | 122.91 | N |
| ATOM | 7315 | CA | ALA | D | 190 | -19.680 | 43.915 | 8.960 | 122.33 | C |
| ATOM | 7316 | C | ALA | D | 190 | -18.577 | 44.667 | 8.221 | 120.44 | C |
| ATOM | 7317 | O | ALA | D | 190 | -18.711 | 45.845 | 7.890 | 120.09 | O |
| ATOM | 7318 | CB | ALA | D | 190 | -20.702 | 43.395 | 7.971 | 121.39 | C |
| ATOM | 7319 | H | ALA | D | 190 | -20.546 | 45.522 | 9.710 | 127.50 | H |
| ATOM | 7320 | HA | ALA | D | 190 | -19.273 | 43.149 | 9.394 | 126.80 | H |
| ATOM | 7321 | HB1 | ALA | D | 190 | -20.250 | 42.855 | 7.304 | 125.67 | H |
| ATOM | 7322 | HB2 | ALA | D | 190 | -21.355 | 42.856 | 8.446 | 125.67 | H |
| ATOM | 7323 | HB3 | ALA | D | 190 | -21.141 | 44.148 | 7.545 | 125.67 | H |
| ATOM | 7324 | N | LEU | D | 191 | -17.484 | 43.959 | 7.972 | 117.46 | N |
| ATOM | 7325 | CA | LEU | D | 191 | -16.381 | 44.479 | 7.183 | 117.75 | C |
| ATOM | 7326 | C | LEU | D | 191 | -16.573 | 44.087 | 5.727 | 115.67 | C |
| ATOM | 7327 | O | LEU | D | 191 | -16.806 | 42.915 | 5.429 | 116.92 | O |
| ATOM | 7328 | CB | LEU | D | 191 | -15.052 | 43.935 | 7.699 | 115.85 | C |
| ATOM | 7329 | CG | LEU | D | 191 | -14.674 | 44.331 | 9.125 | 117.91 | C |
| ATOM | 7330 | CD1 | LEU | D | 191 | -13.616 | 43.387 | 9.665 | 117.38 | C |
| ATOM | 7331 | CD2 | LEU | D | 191 | -14.181 | 45.770 | 9.157 | 116.48 | C |
| ATOM | 7332 | H | LEU | D | 191 | -17.356 | 43.157 | 8.256 | 120.95 | H |

TABLE 5-continued

Atomic Coordinates for OMCP-NKG2D (4PDC).

| ATOM | 7333 | HA | LEU | D | 191 | -16.364 | 45.447 | 7.244 | 121.30 | H |
|---|---|---|---|---|---|---|---|---|---|---|
| ATOM | 7334 | HB2 | LEU | D | 191 | -15.087 | 42.966 | 7.668 | 119.03 | H |
| ATOM | 7335 | HB3 | LEU | D | 191 | -14.346 | 44.251 | 7.115 | 119.03 | H |
| ATOM | 7336 | HG | LEU | D | 191 | -15.458 | 44.265 | 9.693 | 121.50 | H |
| ATOM | 7337 | HD11 | LEU | D | 191 | -13.388 | 43.652 | 10.569 | 120.86 | H |
| ATOM | 7338 | HD12 | LEU | D | 191 | -13.969 | 42.483 | 9.664 | 120.86 | H |
| ATOM | 7339 | HD13 | LEU | D | 191 | -12.830 | 43.436 | 9.097 | 120.86 | H |
| ATOM | 7340 | HD21 | LEU | D | 191 | -13.946 | 46.003 | 10.069 | 119.78 | H |
| ATOM | 7341 | HD22 | LEU | D | 191 | -13.402 | 45.850 | 8.584 | 119.78 | H |
| ATOM | 7342 | HD23 | LEU | D | 191 | -14.888 | 46.353 | 8.838 | 119.78 | H |
| ATOM | 7343 | N | TYR | D | 192 | -16.495 | 45.052 | 4.819 | 115.37 | N |
| ATOM | 7344 | CA | TYR | D | 192 | -16.479 | 44.714 | 3.406 | 113.02 | C |
| ATOM | 7345 | C | TYR | D | 192 | -15.140 | 44.117 | 3.025 | 116.84 | C |
| ATOM | 7346 | O | TYR | D | 192 | -14.100 | 44.556 | 3.500 | 113.73 | O |
| ATOM | 7347 | CB | TYR | D | 192 | -16.737 | 45.919 | 2.500 | 114.04 | C |
| ATOM | 7348 | CG | TYR | D | 192 | -16.606 | 45.490 | 1.060 | 115.73 | C |
| ATOM | 7349 | CD1 | TYR | D | 192 | -17.668 | 44.878 | 0.411 | 115.86 | C |
| ATOM | 7350 | CD2 | TYR | D | 192 | -15.399 | 45.615 | 0.376 | 115.68 | C |
| ATOM | 7351 | CE1 | TYR | D | 192 | -17.553 | 44.440 | -0.884 | 116.16 | C |
| ATOM | 7352 | CE2 | TYR | D | 192 | -15.272 | 45.172 | -0.928 | 116.99 | C |
| ATOM | 7353 | CZ | TYR | D | 192 | -16.358 | 44.585 | -1.552 | 118.72 | C |
| ATOM | 7354 | OH | TYR | D | 192 | -16.257 | 44.134 | -2.845 | 120.02 | O |
| ATOM | 7355 | H | TYR | D | 192 | -16.451 | 45.893 | 4.992 | 118.45 | H |
| ATOM | 7356 | HA | TYR | D | 192 | -17.166 | 44.052 | 3.231 | 115.62 | H |
| ATOM | 7357 | HB2 | TYR | D | 192 | -17.637 | 46.252 | 2.645 | 116.85 | H |
| ATOM | 7358 | HB3 | TYR | D | 192 | -16.082 | 46.611 | 2.680 | 116.85 | H |
| ATOM | 7359 | HD1 | TYR | D | 192 | -18.477 | 44.774 | 0.858 | 119.03 | H |
| ATOM | 7360 | HD2 | TYR | D | 192 | -14.670 | 46.006 | 0.800 | 118.82 | H |
| ATOM | 7361 | HE1 | TYR | D | 192 | -18.279 | 44.042 | -1.308 | 119.40 | H |
| ATOM | 7362 | HE2 | TYR | D | 192 | -14.466 | 45.270 | -1.381 | 120.39 | H |
| ATOM | 7363 | HH | TYR | D | 192 | -15.484 | 44.279 | -3.140 | 124.03 | H |
| ATOM | 7364 | N | ALA | D | 193 | -15.174 | 43.130 | 2.136 | 116.16 | N |
| ATOM | 7365 | CA | ALA | D | 193 | -13.962 | 42.620 | 1.512 | 115.91 | C |
| ATOM | 7366 | C | ALA | D | 193 | -13.261 | 41.994 | 0.167 | 117.11 | C |
| ATOM | 7367 | O | ALA | D | 193 | -15.458 | 41.709 | -0.137 | 114.31 | O |
| ATOM | 7368 | CB | ALA | D | 193 | -13.279 | 41.614 | 2.413 | 117.57 | C |
| ATOM | 7369 | H | ALA | D | 193 | -15.894 | 42.736 | 1.876 | 119.39 | H |
| ATOM | 7370 | HA | ALA | D | 193 | -13.349 | 43.356 | 1.360 | 119.09 | H |
| ATOM | 7371 | HB1 | ALA | D | 193 | -12.476 | 41.292 | 1.974 | 121.09 | H |
| ATOM | 7372 | HB2 | ALA | D | 193 | -13.047 | 42.047 | 3.250 | 121.09 | H |
| ATOM | 7373 | HB3 | ALA | D | 193 | -13.885 | 40.876 | 2.578 | 121.09 | H |
| ATOM | 7374 | N | SER | D | 194 | -13.261 | 41.795 | -0.642 | 113.16 | N |
| ATOM | 7375 | CA | SER | D | 194 | -13.424 | 41.159 | -1.940 | 119.38 | C |
| ATOM | 7376 | C | SER | D | 194 | -13.783 | 41.994 | -1.736 | 115.86 | C |
| ATOM | 7377 | O | SER | D | 194 | -13.257 | 39.688 | -0.811 | 117.79 | O |
| ATOM | 7378 | CB | SER | D | 194 | -12.134 | 41.288 | -2.759 | 116.87 | C |
| ATOM | 7379 | OG | SER | D | 194 | -12.254 | 40.631 | -4.006 | 119.40 | O |
| ATOM | 7380 | H | SER | D | 194 | -12.452 | 42.020 | -0.461 | 115.79 | H |
| ATOM | 7381 | HA | SER | D | 194 | -14.144 | 41.590 | -2.427 | 123.26 | H |
| ATOM | 7382 | HB2 | SER | D | 194 | -11.953 | 42.228 | -2.914 | 120.25 | H |
| ATOM | 7383 | HB3 | SER | D | 194 | -11.404 | 40.888 | -2.261 | 120.25 | H |

TABLE 5-continued

Atomic Coordinates for OMCP-NKG2D (4PDC).

| ATOM | 7384 | HG | SER | D | 194 | -11.540 | 40.711 | -4.442 | H |
|---|---|---|---|---|---|---|---|---|---|
| ATOM | 7385 | N | SER | D | 195 | -14.655 | 39.097 | -2.558 | N |
| ATOM | 7386 | CA | SER | D | 195 | -15.382 | 39.753 | -3.644 | C |
| ATOM | 7387 | C | SER | D | 195 | -16.864 | 39.846 | -3.286 | C |
| ATOM | 7388 | O | SER | D | 195 | -17.570 | 38.835 | -3.271 | O |
| ATOM | 7389 | CB | SER | D | 195 | -15.212 | 38.984 | -4.953 | C |
| ATOM | 7390 | OG | SER | D | 195 | -15.833 | 39.680 | -6.022 | O |
| ATOM | 7391 | H | SER | D | 195 | -14.851 | 38.262 | -2.497 | H |
| ATOM | 7392 | HA | SER | D | 195 | -15.037 | 40.652 | -3.768 | H |
| ATOM | 7393 | HB2 | SER | D | 195 | -14.266 | 38.888 | -5.144 | H |
| ATOM | 7394 | HB3 | SER | D | 195 | -15.623 | 38.110 | -4.863 | H |
| ATOM | 7395 | HG | SER | D | 195 | -15.736 | 39.252 | -6.738 | H |
| ATOM | 7396 | N | PHE | D | 196 | -17.323 | 41.062 | -3.010 | N |
| ATOM | 7397 | CA | PHE | D | 196 | -18.681 | 41.297 | -2.521 | C |
| ATOM | 7398 | C | PHE | D | 196 | -18.989 | 40.392 | -1.338 | C |
| ATOM | 7399 | O | PHE | D | 196 | -19.992 | 39.680 | -1.320 | O |
| ATOM | 7400 | CB | PHE | D | 196 | -19.699 | 41.099 | -3.646 | C |
| ATOM | 7401 | CG | PHE | D | 196 | -19.660 | 42.189 | -4.674 | C |
| ATOM | 7402 | CD1 | PHE | D | 196 | -18.851 | 42.083 | -5.789 | C |
| ATOM | 7403 | CD2 | PHE | D | 196 | -20.415 | 43.336 | -4.509 | C |
| ATOM | 7404 | CE1 | PHE | D | 196 | -18.805 | 43.095 | -6.725 | C |
| ATOM | 7405 | CE2 | PHE | D | 196 | -20.372 | 44.349 | -5.443 | C |
| ATOM | 7406 | CZ | PHE | D | 196 | -19.567 | 44.230 | -6.549 | C |
| ATOM | 7407 | H | PHE | D | 196 | -16.860 | 41.782 | -3.098 | H |
| ATOM | 7408 | HA | PHE | D | 196 | -18.750 | 42.215 | -2.218 | H |
| ATOM | 7409 | HB2 | PHE | D | 196 | -19.513 | 40.259 | -4.095 | H |
| ATOM | 7410 | HB3 | PHE | D | 196 | -20.590 | 41.080 | -3.264 | H |
| ATOM | 7411 | HD1 | PHE | D | 196 | -18.334 | 41.320 | -5.911 | H |
| ATOM | 7412 | HD2 | PHE | D | 196 | -20.960 | 43.423 | -3.761 | H |
| ATOM | 7413 | HE1 | PHE | D | 196 | -18.261 | 43.011 | -7.475 | H |
| ATOM | 7414 | HE2 | PHE | D | 196 | -20.888 | 45.114 | -5.323 | H |
| ATOM | 7415 | HZ | PHE | D | 196 | -19.540 | 44.911 | -7.181 | H |
| ATOM | 7416 | N | LYS | D | 197 | -18.103 | 40.436 | -0.351 | N |
| ATOM | 7417 | CA | LYS | D | 197 | -18.266 | 39.684 | 0.880 | C |
| ATOM | 7418 | C | LYS | D | 197 | -18.416 | 40.637 | 2.051 | C |
| ATOM | 7419 | O | LYS | D | 197 | -17.959 | 41.781 | 2.004 | O |
| ATOM | 7420 | CB | LYS | D | 197 | -17.076 | 38.744 | 1.114 | C |
| ATOM | 7421 | CG | LYS | D | 197 | -17.860 | 37.490 | 0.254 | C |
| ATOM | 7422 | CD | LYS | D | 197 | -17.105 | 36.941 | 0.414 | C |
| ATOM | 7423 | CE | LYS | D | 197 | -15.837 | 36.661 | -0.433 | C |
| ATOM | 7424 | NZ | LYS | D | 197 | -15.895 | 35.393 | -0.468 | N1+ |
| ATOM | 7425 | H | LYS | D | 197 | -14.589 | 34.675 | -0.373 | H |
| ATOM | 7426 | HA | LYS | D | 197 | -17.383 | 40.906 | 0.822 | H |
| ATOM | 7427 | HB2 | LYS | D | 197 | -19.071 | 39.146 | 0.913 | H |
| ATOM | 7428 | HB3 | LYS | D | 197 | -16.256 | 39.222 | 2.043 | H |
| ATOM | 7429 | HG2 | LYS | D | 197 | -17.075 | 38.466 | 0.517 | H |
| ATOM | 7430 | HG3 | LYS | D | 197 | -17.860 | 36.941 | -0.678 | H |
| ATOM | 7431 | HD2 | LYS | D | 197 | -17.184 | 37.185 | 0.128 | H |
| ATOM | 7432 | HD3 | LYS | D | 197 | -15.073 | 37.744 | 1.344 | H |
| ATOM | 7433 | HE2 | LUS | D | 197 | -15.738 | 36.402 | -0.061 | H |
| ATOM | 7434 | HE3 | LYS | D | 197 | -16.559 | 34.792 | -1.343 | H |

TABLE 5-continued

Atomic Coordinates for OMCP-NKG2D (4PDC).

| ATOM | 7435 | HZ1  | LYS | D | 197 | -14.658 | 33.943 | -0.969 | 122.47 | H |
| ---- | ---- | ---- | --- | - | --- | ------- | ------ | ------ | ------ | - |
| ATOM | 7436 | HZ2  | LYS | D | 197 | -13.961 | 35.204 | -0.812 | 122.47 | H |
| ATOM | 7437 | HZ3  | LYS | D | 197 | -14.350 | 34.440 | 0.356  | 122.47 | H |
| ATOM | 7438 | N    | GLY | D | 198 | -19.080 | 40.155 | 3.094  | 120.04 | N |
| ATOM | 7439 | CA   | GLY | D | 198 | -19.195 | 40.872 | 4.344  | 119.36 | C |
| ATOM | 7440 | C    | GLY | D | 198 | -18.810 | 39.944 | 5.473  | 116.53 | C |
| ATOM | 7441 | O    | GLY | D | 198 | -19.383 | 38.868 | 5.610  | 123.62 | O |
| ATOM | 7442 | H    | GLY | D | 198 | -19.482 | 39.394 | 3.096  | 124.05 | H |
| ATOM | 7443 | HA2  | GLY | D | 198 | -18.603 | 41.640 | 4.346  | 123.23 | H |
| ATOM | 7444 | HA3  | GLY | D | 198 | -20.108 | 41.172 | 4.476  | 123.23 | H |
| ATOM | 7445 | N    | TYR | D | 199 | -17.821 | 40.349 | 6.262  | 115.37 | N |
| ATOM | 7446 | CA   | TYR | D | 199 | -17.404 | 39.590 | 7.436  | 116.35 | C |
| ATOM | 7447 | C    | TYR | D | 199 | -17.961 | 40.233 | 8.696  | 119.39 | C |
| ATOM | 7448 | O    | TYR | D | 199 | -17.670 | 41.391 | 8.988  | 122.65 | O |
| ATOM | 7449 | CB   | TYR | D | 199 | -15.879 | 39.512 | 7.523  | 121.01 | C |
| ATOM | 7450 | CG   | TYR | D | 199 | -15.236 | 38.665 | 6.450  | 115.07 | C |
| ATOM | 7451 | CD1  | TYR | D | 199 | -15.126 | 39.129 | 5.146  | 119.90 | C |
| ATOM | 7452 | CD2  | TYR | D | 199 | -14.730 | 37.408 | 6.742  | 117.60 | C |
| ATOM | 7453 | CE1  | TYR | D | 199 | -14.536 | 38.361 | 4.162  | 114.62 | C |
| ATOM | 7454 | CE2  | TYR | D | 199 | -14.134 | 36.631 | 5.763  | 118.84 | C |
| ATOM | 7455 | CZ   | TYR | D | 199 | -14.039 | 37.115 | 4.476  | 115.72 | C |
| ATOM | 7456 | OH   | TYR | D | 199 | -13.448 | 36.351 | 3.498  | 118.51 | O |
| ATOM | 7457 | H    | TYR | D | 199 | -17.370 | 41.070 | 6.137  | 118.44 | H |
| ATOM | 7458 | HA   | TYR | D | 199 | -17.753 | 38.687 | 7.375  | 119.62 | H |
| ATOM | 7459 | HB2  | TYR | D | 199 | -15.517 | 40.409 | 7.447  | 125.22 | H |
| ATOM | 7460 | HB3  | TYR | D | 199 | -15.636 | 39.133 | 8.383  | 125.22 | H |
| ATOM | 7461 | HD1  | TYR | D | 199 | -15.459 | 39.970 | 4.930  | 123.88 | H |
| ATOM | 7462 | HD2  | TYR | D | 199 | -14.792 | 37.081 | 7.611  | 121.12 | H |
| ATOM | 7463 | HE1  | TYR | D | 199 | -14.470 | 38.685 | 3.293  | 117.55 | H |
| ATOM | 7464 | HE2  | TYR | D | 199 | -13.799 | 35.789 | 5.973  | 122.61 | H |
| ATOM | 7465 | HH   | TYR | D | 199 | -13.459 | 36.762 | 2.766  | 122.22 | H |
| ATOM | 7466 | N    | ILE | D | 200 | -18.760 | 39.478 | 9.443  | 124.76 | N |
| ATOM | 7467 | CA   | ILE | D | 200 | -19.354 | 39.983 | 10.674 | 123.61 | C |
| ATOM | 7468 | C    | ILE | D | 200 | -18.272 | 40.156 | 11.733 | 126.05 | C |
| ATOM | 7469 | O    | ILE | D | 200 | -17.486 | 39.242 | 11.981 | 124.51 | O |
| ATOM | 7470 | CB   | ILE | D | 200 | -20.449 | 39.045 | 11.204 | 125.21 | C |
| ATOM | 7471 | CG1  | ILE | D | 200 | -21.472 | 38.752 | 10.102 | 125.80 | C |
| ATOM | 7472 | CG2  | ILE | D | 200 | -21.132 | 39.664 | 12.427 | 127.37 | C |
| ATOM | 7473 | CD1  | ILE | D | 200 | -22.495 | 37.695 | 10.470 | 132.98 | C |
| ATOM | 7474 | H    | ILE | D | 200 | -18.974 | 38.667 | 9.257  | 129.71 | H |
| ATOM | 7475 | HA   | ILE | D | 200 | -19.753 | 40.850 | 10.504 | 128.33 | H |
| ATOM | 7476 | HB   | ILE | D | 200 | -20.037 | 38.209 | 11.472 | 130.25 | H |
| ATOM | 7477 | HG12 | ILE | D | 200 | -21.953 | 39.569 | 9.898  | 130.95 | H |
| ATOM | 7478 | HG13 | ILE | D | 200 | -21.000 | 38.443 | 9.313  | 130.95 | H |
| ATOM | 7479 | HG21 | ILE | D | 200 | -21.818 | 39.058 | 12.745 | 132.84 | H |
| ATOM | 7480 | HG22 | ILE | D | 200 | -20.468 | 39.807 | 13.119 | 132.84 | H |
| ATOM | 7481 | HG23 | ILE | D | 200 | -21.530 | 40.511 | 12.170 | 132.84 | H |
| ATOM | 7482 | HD11 | ILE | D | 200 | -18.974 | 37.570 | 9.724  | 139.58 | H |
| ATOM | 7483 | HD12 | ILE | D | 200 | -23.102 | 36.864 | 10.665 | 139.58 | H |
| ATOM | 7484 | HD13 | ILE | D | 200 | -22.034 | 37.992 | 11.251 | 139.58 | H |
| ATOM | 7485 | N    | GLU | D | 201 | -18.251 | 41.329 | 12.359 | 125.97 | N |

TABLE 5-continued

Atomic Coordinates for OMCP-NKG2D (4PDC).

| ATOM | 7486 | CA | GLU | D | 201 | -17.193 | 41.698 | 13.295 | 127.39 | C |
|---|---|---|---|---|---|---|---|---|---|---|
| ATOM | 7487 | C | GLU | D | 201 | -17.754 | 42.496 | 14.470 | 126.93 | C |
| ATOM | 7488 | O | GLU | D | 201 | -18.775 | 43.171 | 14.345 | 125.15 | O |
| ATOM | 7489 | CB | GLU | D | 201 | -16.114 | 42.507 | 12.562 | 122.39 | C |
| ATOM | 7490 | CG | GLU | D | 201 | -15.018 | 43.107 | 13.435 | 130.66 | C |
| ATOM | 7491 | CD | GLU | D | 201 | -14.139 | 42.058 | 14.079 | 134.67 | C |
| ATOM | 7492 | OE1 | GLU | D | 201 | -12.954 | 41.963 | 13.696 | 137.53 | O |
| ATOM | 7493 | OE2 | GLU | D | 201 | -14.628 | 41.333 | 14.970 | 142.28 | O1- |
| ATOM | 7494 | H | GLU | D | 201 | -18.849 | 41.939 | 12.256 | 131.16 | H |
| ATOM | 7495 | HA | GLU | D | 201 | -16.782 | 40.892 | 13.645 | 132.87 | H |
| ATOM | 7496 | HB2 | GLU | D | 201 | -15.683 | 41.926 | 11.916 | 126.87 | H |
| ATOM | 7497 | HB3 | GLU | D | 201 | -16.546 | 43.241 | 12.097 | 126.80 | H |
| ATOM | 7498 | HG2 | GLU | D | 201 | -14.454 | 43.675 | 12.887 | 136.80 | H |
| ATOM | 7499 | HG3 | GLU | D | 201 | -15.428 | 43.629 | 14.142 | 136.80 | H |
| ATOM | 7500 | N | ASN | D | 202 | -17.082 | 42.406 | 15.611 | 131.13 | N |
| ATOM | 7501 | CA | ASN | D | 202 | -17.415 | 43.226 | 16.767 | 131.58 | C |
| ATOM | 7502 | C | ASN | D | 202 | -17.351 | 44.709 | 16.409 | 128.02 | C |
| ATOM | 7503 | O | ASN | D | 202 | -16.326 | 45.199 | 15.934 | 127.55 | O |
| ATOM | 7504 | CB | ASN | D | 202 | -16.463 | 42.920 | 17.926 | 133.82 | C |
| ATOM | 7505 | CG | ASN | D | 202 | -16.877 | 43.595 | 19.223 | 140.88 | C |
| ATOM | 7506 | OD1 | ASN | D | 202 | -17.685 | 44.526 | 19.228 | 137.61 | O |
| ATOM | 7507 | ND2 | ASN | D | 202 | -16.317 | 43.129 | 20.332 | 146.74 | N |
| ATOM | 7508 | H | ASN | D | 202 | -16.421 | 41.870 | 15.742 | 137.35 | H |
| ATOM | 7509 | HA | ASN | D | 202 | -18.318 | 43.022 | 17.055 | 137.89 | H |
| ATOM | 7510 | HB2 | ASN | D | 202 | -16.449 | 41.962 | 18.078 | 140.59 | H |
| ATOM | 7511 | HB3 | ASN | D | 202 | -15.574 | 43.232 | 17.695 | 140.59 | H |
| ATOM | 7512 | HD21 | ASN | D | 202 | -16.516 | 43.476 | 21.094 | 156.09 | H |
| ATOM | 7513 | HD22 | ASN | D | 202 | -15.754 | 42.479 | 20.290 | 156.09 | H |
| ATOM | 7514 | N | CYS | D | 203 | -18.448 | 45.418 | 16.648 | 131.67 | N |
| ATOM | 7515 | CA | CYS | D | 203 | -18.552 | 46.823 | 16.270 | 132.67 | C |
| ATOM | 7516 | C | CYS | D | 203 | -17.468 | 47.680 | 16.919 | 130.69 | C |
| ATOM | 7517 | O | CYS | D | 203 | -17.086 | 48.716 | 16.382 | 128.93 | O |
| ATOM | 7518 | CB | CYS | D | 203 | -19.932 | 47.370 | 16.639 | 128.67 | C |
| ATOM | 7519 | SG | CYS | D | 203 | -21.284 | 46.744 | 15.612 | 135.00 | S |
| ATOM | 7520 | H | CYS | D | 203 | -19.152 | 45.107 | 17.032 | 138.00 | H |
| ATOM | 7521 | HA | CYS | D | 203 | -18.451 | 46.896 | 15.308 | 139.21 | H |
| ATOM | 7522 | HB2 | CYS | D | 203 | -20.125 | 47.130 | 17.559 | 134.41 | H |
| ATOM | 7523 | HB3 | CYS | D | 203 | -19.917 | 48.336 | 16.550 | 134.41 | H |
| ATOM | 7524 | N | SER | D | 204 | -16.966 | 47.234 | 18.066 | 129.38 | N |
| ATOM | 7525 | CA | SER | D | 204 | -16.014 | 48.019 | 18.843 | 130.77 | C |
| ATOM | 7526 | C | SER | D | 204 | -14.590 | 47.917 | 18.316 | 128.07 | C |
| ATOM | 7527 | O | SER | D | 204 | -13.735 | 48.720 | 18.680 | 128.24 | O |
| ATOM | 7528 | CB | SER | D | 204 | -16.041 | 47.577 | 20.308 | 133.15 | C |
| ATOM | 7529 | OG | SER | D | 204 | -17.311 | 47.822 | 20.885 | 137.66 | O |
| ATOM | 7530 | H | SER | D | 204 | -17.163 | 46.474 | 18.418 | 135.26 | H |
| ATOM | 7531 | HA | SER | D | 204 | -16.277 | 48.952 | 18.809 | 136.93 | H |
| ATOM | 7532 | HB2 | SER | D | 204 | -15.851 | 46.627 | 20.355 | 139.78 | H |
| ATOM | 7533 | HB3 | SER | D | 204 | -15.370 | 48.075 | 20.800 | 139.78 | H |
| ATOM | 7534 | HG | SER | D | 204 | -17.314 | 47.576 | 21.688 | 145.19 | H |
| ATOM | 7535 | N | THR | D | 205 | -14.331 | 46.924 | 17.472 | 131.36 | N |
| ATOM | 7536 | CA | THR | D | 205 | -12.979 | 46.684 | 16.975 | 130.91 | C |

TABLE 5-continued

Atomic Coordinates for OMCP-NKG2D (4PDC).

| | | | | | | | | | |
|---|---|---|---|---|---|---|---|---|---|
| ATOM | 7537 | C | THR | D | 205 | -12.561 | 47.749 | 15.956 | C |
| ATOM | 7538 | O | THR | D | 205 | -13.268 | 47.974 | 14.975 | O |
| ATOM | 7539 | CB | THR | D | 205 | -12.869 | 45.296 | 16.324 | C |
| ATOM | 7540 | OG1 | THR | D | 205 | -13.239 | 44.290 | 17.277 | O |
| ATOM | 7541 | CG2 | THR | D | 205 | -11.447 | 45.032 | 15.835 | C |
| ATOM | 7542 | H | THR | D | 205 | -14.920 | 46.375 | 17.171 | H |
| ATOM | 7543 | HA | THR | D | 205 | -12.357 | 46.719 | 17.719 | H |
| ATOM | 7544 | HB | THR | D | 205 | -13.467 | 45.251 | 15.562 | H |
| ATOM | 7545 | HG1 | THR | D | 205 | -13.181 | 43.529 | 16.928 | H |
| ATOM | 7546 | HG21 | THR | D | 205 | -11.394 | 44.154 | 15.428 | H |
| ATOM | 7547 | HG22 | THR | D | 205 | -11.193 | 45.700 | 15.179 | H |
| ATOM | 7548 | HG23 | THR | D | 205 | -10.827 | 45.072 | 16.580 | H |
| ATOM | 7549 | N | PRO | D | 206 | -11.413 | 48.410 | 16.184 | N |
| ATOM | 7550 | CA | PRO | D | 206 | -10.936 | 49.381 | 15.192 | C |
| ATOM | 7551 | C | PRO | D | 206 | -10.597 | 48.762 | 13.834 | C |
| ATOM | 7552 | O | PRO | D | 206 | -9.898 | 47.749 | 13.760 | O |
| ATOM | 7553 | CB | PRO | D | 206 | -9.674 | 49.960 | 15.845 | C |
| ATOM | 7554 | CG | PRO | D | 206 | -9.855 | 49.738 | 17.291 | C |
| ATOM | 7555 | CD | PRO | D | 206 | -10.598 | 48.444 | 17.410 | C |
| ATOM | 7556 | HA | PRO | D | 206 | -11.589 | 50.088 | 15.070 | H |
| ATOM | 7557 | HB2 | PRO | D | 206 | -8.892 | 49.488 | 15.520 | H |
| ATOM | 7558 | HB3 | PRO | D | 206 | -9.610 | 50.908 | 15.648 | H |
| ATOM | 7559 | HG2 | PRO | D | 206 | -8.988 | 49.676 | 17.721 | H |
| ATOM | 7560 | HG3 | PRO | D | 206 | -10.372 | 50.466 | 17.669 | H |
| ATOM | 7561 | HD2 | PRO | D | 206 | -9.978 | 47.698 | 17.426 | H |
| ATOM | 7562 | HD3 | PRO | D | 206 | -11.167 | 48.452 | 18.195 | H |
| ATOM | 7563 | N | ASN | D | 207 | -11.101 | 49.384 | 12.772 | N |
| ATOM | 7564 | CA | ASN | D | 207 | -10.802 | 48.982 | 11.404 | C |
| ATOM | 7565 | C | ASN | D | 207 | -10.805 | 50.193 | 10.486 | C |
| ATOM | 7566 | O | ASN | D | 207 | -11.816 | 51.228 | 10.813 | O |
| ATOM | 7567 | CB | ASN | D | 207 | -11.816 | 47.951 | 10.899 | C |
| ATOM | 7568 | CG | ASN | D | 207 | -11.586 | 46.572 | 11.476 | C |
| ATOM | 7569 | OD1 | ASN | D | 207 | -12.271 | 46.152 | 12.410 | O |
| ATOM | 7570 | ND2 | ASN | D | 207 | -10.620 | 45.858 | 10.922 | N |
| ATOM | 7571 | H | ASN | D | 207 | -11.631 | 50.060 | 12.822 | H |
| ATOM | 7572 | HA | ASN | D | 207 | -9.919 | 48.579 | 11.374 | H |
| ATOM | 7573 | HB2 | ASN | D | 207 | -12.708 | 48.237 | 11.150 | H |
| ATOM | 7574 | HB3 | ASN | D | 207 | -11.748 | 47.888 | 9.933 | H |
| ATOM | 7575 | HD21 | ASN | D | 207 | -10.448 | 45.067 | 11.213 | H |
| ATOM | 7576 | HD22 | ASN | D | 207 | -10.163 | 46.185 | 10.270 | H |
| ATOM | 7577 | Z | ASN | D | 207 | -10.153 | 50.066 | 9.337 | N |
| ATOM | 7578 | CA | THR | D | 208 | -10.243 | 51.086 | 8.302 | C |
| ATOM | 7579 | C | THR | D | 208 | -11.686 | 51.128 | 7.807 | C |
| ATOM | 7580 | O | THR | D | 208 | -12.457 | 50.211 | 8.075 | O |
| ATOM | 7581 | CB | THR | D | 208 | -9.287 | 50.797 | 7.138 | C |
| ATOM | 7582 | OG1 | THR | D | 208 | -9.593 | 49.516 | 6.576 | O |
| ATOM | 7583 | CG2 | THR | D | 208 | -7.842 | 50.802 | 7.622 | C |
| ATOM | 7584 | H | THR | D | 208 | -9.652 | 49.398 | 9.132 | H |
| ATOM | 7585 | HA | THR | D | 208 | -10.019 | 51.952 | 8.678 | H |
| ATOM | 7586 | HB | THR | D | 208 | -9.386 | 51.482 | 6.458 | H |
| ATOM | 7587 | HG1 | THR | D | 208 | -9.072 | 49.351 | 5.937 | H |

TABLE 5-continued

Atomic Coordinates for OMCP-NKG2D (4PDC).

| | | | | | | | | | | |
|---|---|---|---|---|---|---|---|---|---|---|
| ATOM | 7588 | HG21 | THR | D | 208 | -7.244 | 50.618 | 6.881 | 128.17 | H |
| ATOM | 7589 | HG22 | THR | D | 208 | -7.622 | 51.668 | 7.999 | 128.17 | H |
| ATOM | 7590 | HG23 | THR | D | 208 | -7.719 | 50.121 | 8.303 | 128.17 | H |
| ATOM | 7591 | N | TYR | D | 209 | -12.065 | 52.188 | 7.099 | 118.19 | N |
| ATOM | 7592 | CA | TYR | D | 209 | -13.438 | 52.291 | 6.614 | 118.43 | C |
| ATOM | 7593 | C | TYR | D | 209 | -13.528 | 53.013 | 5.280 | 118.76 | C |
| ATOM | 7594 | O | TYR | D | 209 | -12.606 | 53.722 | 4.865 | 118.98 | O |
| ATOM | 7595 | CB | TYR | D | 209 | -14.322 | 52.995 | 7.651 | 118.49 | C |
| ATOM | 7596 | CG | TYR | D | 209 | -13.825 | 54.355 | 8.083 | 119.96 | C |
| ATOM | 7597 | CD1 | TYR | D | 209 | -12.821 | 54.477 | 9.032 | 123.84 | C |
| ATOM | 7598 | CD2 | TYR | D | 209 | -14.367 | 55.516 | 7.550 | 121.18 | C |
| ATOM | 7599 | CE1 | TYR | D | 209 | -12.364 | 55.717 | 9.433 | 123.52 | C |
| ATOM | 7600 | CE2 | TYR | D | 209 | -13.918 | 56.763 | 7.947 | 123.67 | C |
| ATOM | 7601 | CZ | TYR | D | 209 | -12.914 | 56.856 | 8.887 | 125.34 | C |
| ATOM | 7602 | OH | TYR | D | 209 | -12.459 | 58.091 | 9.288 | 125.68 | O |
| ATOM | 7603 | H | TYR | D | 209 | -11.557 | 52.849 | 6.888 | 121.83 | H |
| ATOM | 7604 | HA | TYR | D | 209 | -13.789 | 51.396 | 6.487 | 122.12 | H |
| ATOM | 7605 | HB2 | TYR | D | 209 | -15.209 | 53.112 | 7.275 | 122.19 | H |
| ATOM | 7606 | HB3 | TYR | D | 209 | -14.375 | 52.437 | 8.443 | 122.19 | H |
| ATOM | 7607 | HD1 | TYR | D | 209 | -12.446 | 53.711 | 9.401 | 128.60 | H |
| ATOM | 7608 | HD2 | TYR | D | 209 | -15.043 | 55.455 | 6.914 | 125.42 | H |
| ATOM | 7609 | HE1 | TYR | D | 209 | -11.688 | 55.783 | 10.068 | 128.22 | H |
| ATOM | 7610 | HE2 | TYR | D | 209 | -14.288 | 57.533 | 7.579 | 128.40 | H |
| ATOM | 7611 | HH | TYR | D | 209 | -11.853 | 58.001 | 9.862 | 130.82 | H |
| ATOM | 7612 | N | ILE | D | 210 | -14.657 | 52.805 | 4.615 | 117.13 | N |
| ATOM | 7613 | CA | ILE | D | 210 | -14.930 | 53.405 | 3.322 | 115.89 | C |
| ATOM | 7614 | C | ILE | D | 210 | -16.147 | 54.297 | 3.433 | 116.38 | C |
| ATOM | 7615 | O | ILE | D | 210 | -17.221 | 53.836 | 3.825 | 116.32 | O |
| ATOM | 7616 | CB | ILE | D | 210 | -15.183 | 52.337 | 2.244 | 115.95 | C |
| ATOM | 7617 | CG1 | ILE | D | 210 | -13.990 | 51.379 | 2.155 | 122.22 | C |
| ATOM | 7618 | CG2 | ILE | D | 210 | -15.457 | 52.997 | 0.902 | 116.76 | C |
| ATOM | 7619 | CD1 | ILE | D | 210 | -14.247 | 50.150 | 1.290 | 122.46 | C |
| ATOM | 7620 | H | ILE | D | 210 | -15.296 | 52.307 | 4.902 | 120.56 | H |
| ATOM | 7621 | HA | ILE | D | 210 | -14.173 | 53.947 | 3.049 | 119.06 | H |
| ATOM | 7622 | HB | ILE | D | 210 | -15.967 | 51.826 | 2.498 | 119.13 | H |
| ATOM | 7623 | HG12 | ILE | D | 210 | -13.235 | 51.856 | 1.775 | 126.67 | H |
| ATOM | 7624 | HG13 | ILE | D | 210 | -13.769 | 51.072 | 3.048 | 126.67 | H |
| ATOM | 7625 | HG21 | ILE | D | 210 | -15.614 | 52.308 | 0.238 | 120.12 | H |
| ATOM | 7626 | HG22 | ILE | D | 210 | -16.240 | 53.563 | 0.983 | 120.12 | H |
| ATOM | 7627 | HG23 | ILE | D | 210 | -14.687 | 53.531 | 0.650 | 120.12 | H |
| ATOM | 7628 | HD11 | ILE | D | 210 | -13.451 | 49.596 | 1.284 | 126.95 | H |
| ATOM | 7629 | HD12 | ILE | D | 210 | -14.993 | 49.653 | 1.662 | 126.95 | H |
| ATOM | 7630 | HD13 | ILE | D | 210 | -14.458 | 50.438 | 0.388 | 126.95 | H |
| ATOM | 7631 | N | CYS | D | 211 | -15.976 | 55.568 | 3.085 | 114.23 | N |
| ATOM | 7632 | CA | CYS | D | 211 | -17.094 | 56.494 | 3.006 | 116.85 | C |
| ATOM | 7633 | C | CYS | D | 211 | -17.596 | 56.584 | 1.574 | 118.03 | C |
| ATOM | 7634 | O | CYS | D | 211 | -16.827 | 56.422 | 0.622 | 115.29 | O |
| ATOM | 7635 | CB | CYS | D | 211 | -16.693 | 57.878 | 3.515 | 121.08 | C |
| ATOM | 7636 | SG | CYS | D | 211 | -16.320 | 57.907 | 5.274 | 127.03 | S |
| ATOM | 7637 | H | CYS | D | 211 | -15.216 | 55.919 | 2.888 | 117.07 | H |
| ATOM | 7638 | HA | CYS | D | 211 | -17.819 | 56.166 | 3.561 | 120.22 | H |

TABLE 5-continued

Atomic Coordinates for OMCP-NKG2D (4PDC).

| ATOM | 7639 | HB2 | CYS | D | 211 | -15.901 | 58.171 | 3.037 | 125.30 | H |
| --- | --- | --- | --- | --- | --- | --- | --- | --- | --- | --- |
| ATOM | 7640 | HB3 | CYS | D | 211 | -17.423 | 58.496 | 3.354 | 125.30 | H |
| ATOM | 7641 | N | MET | D | 212 | -18.892 | 56.843 | 1.434 | 117.13 | N |
| ATOM | 7642 | CA | MET | D | 212 | -19.522 | 56.931 | 0.127 | 120.63 | C |
| ATOM | 7643 | C | MET | D | 212 | -20.557 | 58.047 | 0.075 | 121.00 | C |
| ATOM | 7644 | O | MET | D | 212 | -21.345 | 58.230 | 1.007 | 120.37 | O |
| ATOM | 7645 | CB | MET | D | 212 | -20.182 | 55.597 | -0.230 | 118.86 | C |
| ATOM | 7646 | CG | MET | D | 212 | -21.001 | 55.619 | -1.511 | 120.28 | C |
| ATOM | 7647 | SD | MET | D | 212 | -21.817 | 54.042 | -1.811 | 122.14 | S |
| ATOM | 7648 | CE | MET | D | 212 | -22.962 | 54.507 | -3.108 | 127.72 | C |
| ATOM | 7649 | H | MET | D | 212 | -19.432 | 56.974 | 2.090 | 120.55 | H |
| ATOM | 7650 | HA | MET | D | 212 | -18.838 | 57.110 | -0.538 | 124.76 | H |
| ATOM | 7651 | HB2 | MET | D | 212 | -19.488 | 54.927 | -0.336 | 122.63 | H |
| ATOM | 7652 | HB3 | MET | D | 212 | -20.774 | 55.341 | 0.494 | 122.63 | H |
| ATOM | 7653 | HG2 | MET | D | 212 | -21.684 | 56.305 | -1.441 | 124.34 | H |
| ATOM | 7654 | HG3 | MET | D | 212 | -20.415 | 55.805 | -2.262 | 124.34 | H |
| ATOM | 7655 | HE1 | MET | D | 212 | -23.477 | 53.728 | -3.368 | 133.26 | H |
| ATOM | 7656 | HE2 | MET | D | 212 | -23.554 | 55.199 | -2.773 | 133.26 | H |
| ATOM | 7657 | HE3 | MET | D | 212 | -22.459 | 54.841 | -3.867 | 133.26 | H |
| ATOM | 7658 | N | GLN | D | 213 | -20.540 | 58.781 | -1.031 | 116.69 | N |
| ATOM | 7659 | CA | GLN | D | 213 | -21.591 | 59.731 | -1.354 | 122.03 | C |
| ATOM | 7660 | C | GLN | D | 213 | -22.309 | 59.236 | -2.599 | 122.94 | C |
| ATOM | 7661 | O | GLN | D | 213 | -21.704 | 59.102 | -3.664 | 120.77 | O |
| ATOM | 7662 | CB | GLN | D | 213 | -21.026 | 61.135 | -1.587 | 118.19 | C |
| ATOM | 7663 | CG | GLN | D | 213 | -20.428 | 61.794 | -0.357 | 125.42 | C |
| ATOM | 7664 | CD | GLN | D | 213 | -19.984 | 63.221 | -0.629 | 127.60 | C |
| ATOM | 7665 | OE1 | GLN | D | 213 | -19.786 | 63.611 | -1.781 | 128.10 | O |
| ATOM | 7666 | NE2 | GLN | D | 213 | -19.833 | 64.008 | 0.431 | 128.85 | N |
| ATOM | 7667 | H | GLN | D | 213 | -19.916 | 58.744 | -1.622 | 120.02 | H |
| ATOM | 7668 | HA | GLN | D | 213 | -22.229 | 59.771 | -0.624 | 126.43 | H |
| ATOM | 7669 | HB2 | GLN | D | 213 | -20.328 | 61.080 | -2.258 | 121.83 | H |
| ATOM | 7670 | HB3 | GLN | D | 213 | -21.741 | 61.707 | -1.908 | 121.83 | H |
| ATOM | 7671 | HG2 | GLN | D | 213 | -21.095 | 61.815 | 0.348 | 130.50 | H |
| ATOM | 7672 | HG3 | GLN | D | 213 | -19.654 | 61.287 | -0.069 | 130.50 | H |
| ATOM | 7673 | HE21 | GLN | D | 213 | -19.583 | 64.825 | 0.328 | 134.62 | H |
| ATOM | 7674 | HE22 | GLN | D | 213 | -19.985 | 63.701 | 1.220 | 134.62 | H |
| ATOM | 7675 | N | ARG | D | 214 | -23.594 | 58.939 | -2.457 | 125.52 | N |
| ATOM | 7676 | CA | ARG | D | 214 | -24.407 | 58.541 | -3.592 | 132.54 | C |
| ATOM | 7677 | C | ARG | D | 214 | -24.815 | 59.790 | -4.356 | 140.12 | C |
| ATOM | 7678 | O | ARG | D | 214 | -25.017 | 60.850 | -3.763 | 143.97 | O |
| ATOM | 7679 | CB | ARG | D | 214 | -25.639 | 57.758 | -3.136 | 130.59 | C |
| ATOM | 7680 | CG | ARG | D | 214 | -26.467 | 57.167 | -4.271 | 132.12 | C |
| ATOM | 7681 | CD | ARG | D | 214 | -25.894 | 55.846 | -4.775 | 128.20 | C |
| ATOM | 7682 | NE | ARG | D | 214 | -26.798 | 55.208 | -5.732 | 127.38 | N |
| ATOM | 7683 | CZ | ARG | D | 214 | -26.767 | 55.390 | -7.050 | 128.78 | C |
| ATOM | 7684 | NH1 | ARG | D | 214 | -25.862 | 56.189 | -7.606 | 127.43 | N |
| ATOM | 7685 | NH2 | ARG | D | 214 | -27.649 | 54.766 | -7.819 | 126.83 | N1+ |
| ATOM | 7686 | H | ARG | D | 214 | -24.019 | 58.961 | -1.710 | 130.63 | H |
| ATOM | 7687 | HA | ARG | D | 214 | -23.885 | 57.976 | -4.183 | 139.04 | H |
| ATOM | 7688 | HB2 | ARG | D | 214 | -25.349 | 57.025 | -2.571 | 136.70 | H |
| ATOM | 7689 | HB3 | ARG | D | 214 | -26.215 | 58.352 | -2.630 | 136.70 | H |

TABLE 5-continued

Atomic Coordinates for OMCP-NKG2D (4PDC).

| | | | | | | | | | | |
|---|---|---|---|---|---|---|---|---|---|---|
| ATOM | 7690 | HG2 | ARG | D | 214 | -27.369 | 57.004 | -3.954 | 138.54 | H |
| ATOM | 7691 | HG3 | ARG | D | 214 | -26.481 | 57.793 | -5.012 | 138.54 | H |
| ATOM | 7692 | HD2 | ARG | D | 214 | -25.047 | 56.011 | -5.220 | 133.84 | H |
| ATOM | 7693 | HD3 | ARG | D | 214 | -25.768 | 55.243 | -4.026 | 133.84 | H |
| ATOM | 7694 | HE | ARG | D | 214 | -27.395 | 54.674 | -5.418 | 132.85 | H |
| ATOM | 7695 | HH11 | ARG | D | 214 | -25.290 | 56.599 | -7.113 | 132.91 | H |
| ATOM | 7696 | HH12 | ARG | D | 214 | -25.851 | -8.459 | 56.297 | 132.91 | H |
| ATOM | 7697 | HH21 | ARG | D | 214 | -28.235 | -7.466 | 54.245 | 132.19 | H |
| ATOM | 7698 | HH22 | ARG | D | 214 | -27.629 | 54.875 | -8.672 | 132.19 | H |
| ATOM | 7699 | N | THR | D | 215 | -24.923 | 59.656 | -5.672 | 149.40 | N |
| ATOM | 7700 | CA | THR | D | 215 | -25.345 | 60.749 | -6.538 | 147.09 | C |
| ATOM | 7701 | C | THR | D | 215 | -26.665 | 61.379 | -6.091 | 138.12 | C |
| ATOM | 7702 | O | THR | D | 215 | -27.251 | 62.193 | -6.808 | 143.45 | O |
| ATOM | 7703 | CB | THR | D | 215 | -25.504 | 60.261 | -7.984 | 143.89 | C |
| ATOM | 7704 | OG1 | THR | D | 215 | -24.958 | 58.940 | -8.113 | 151.06 | O |
| ATOM | 7705 | CG2 | THR | D | 215 | -24.794 | 61.194 | -8.917 | 144.94 | C |
| ATOM | 7706 | H | THR | D | 215 | -24.753 | 58.927 | -6.095 | 159.28 | H |
| ATOM | 7707 | HA | THR | D | 215 | -24.664 | 61.440 | -6.528 | 156.50 | H |
| ATOM | 7708 | HB | THR | D | 215 | -26.445 | 60.247 | -8.220 | 152.66 | H |
| ATOM | 7709 | HG1 | THR | D | 215 | -25.043 | 58.670 | -8.903 | 161.28 | H |
| ATOM | 7710 | HG21 | THR | D | 215 | -25.168 | 62.086 | -8.841 | 153.93 | H |
| ATOM | 7711 | HG22 | THR | D | 215 | -23.850 | 61.228 | -8.697 | 153.93 | H |
| ATOM | 7712 | HG23 | THR | D | 215 | -24.893 | 60.887 | -9.832 | 153.93 | H |
| TER | 7713 | | THR | D | 215 | | | | 1 | |
| ATOM | 7714 | N | GLY | E | 0 | -1.565 | 40.227 | -65.921 | 124.87 | N |
| ATOM | 7715 | CA | GLY | E | 0 | -1.695 | 39.502 | -64.623 | 125.57 | C |
| ATOM | 7716 | C | GLY | E | 0 | -2.109 | 40.445 | -63.512 | 123.21 | C |
| ATOM | 7717 | O | GLY | E | 0 | -2.318 | 41.635 | -63.745 | 121.52 | O |
| ATOM | 7718 | H1 | GLY | E | 0 | -2.226 | 39.984 | -66.465 | 129.85 | H |
| ATOM | 7719 | H2 | GLY | E | 0 | -1.608 | 41.105 | -65.776 | 129.85 | H |
| ATOM | 7720 | H3 | GLY | E | 0 | -0.783 | 40.027 | -66.296 | 129.85 | H |
| ATOM | 7721 | HA2 | GLY | E | 0 | -2.363 | 38.803 | -64.704 | 130.68 | H |
| ATOM | 7722 | HA3 | GLY | E | 0 | -0.846 | 39.096 | -64.388 | 130.68 | H |
| ATOM | 7723 | N | HIS | E | 1 | -2.229 | 39.916 | -62.300 | 120.53 | N |
| ATOM | 7724 | CA | HIS | E | 1 | -2.640 | 40.720 | -61.155 | 119.68 | C |
| ATOM | 7725 | C | HIS | E | 1 | -1.777 | 40.422 | -59.946 | 118.24 | C |
| ATOM | 7726 | O | HIS | E | 1 | -1.189 | 39.348 | -59.847 | 115.98 | O |
| ATOM | 7727 | CB | HIS | E | 1 | -4.111 | 40.469 | -60.821 | 119.17 | C |
| ATOM | 7728 | CG | HIS | E | 1 | -5.048 | 40.824 | -61.931 | 122.06 | C |
| ATOM | 7729 | ND1 | HIS | E | 1 | -5.356 | 42.128 | -62.255 | 123.79 | N |
| ATOM | 7730 | CD2 | HIS | E | 1 | -5.744 | 40.047 | -62.794 | 122.57 | C |
| ATOM | 7731 | CE1 | HIS | E | 1 | -6.202 | 42.139 | -63.270 | 122.50 | C |
| ATOM | 7732 | NE2 | HIS | E | 1 | -6.454 | 40.889 | -63.614 | 122.56 | N |
| ATOM | 7733 | H | HIS | E | 1 | -2.078 | 39.090 | -62.113 | 124.63 | H |
| ATOM | 7734 | HA | HIS | E | 1 | -2.537 | 41.660 | -61.374 | 123.61 | H |
| ATOM | 7735 | HB2 | HIS | E | 1 | -4.231 | 39.528 | -60.622 | 123.00 | H |
| ATOM | 7736 | HB3 | HIS | E | 1 | -4.352 | 41.003 | -60.047 | 123.00 | H |
| ATOM | 7737 | HD1 | HIS | E | 1 | -5.045 | 42.826 | -61.859 | 128.55 | H |
| ATOM | 7738 | HD2 | HIS | E | 1 | -5.743 | 39.118 | -62.823 | 127.08 | H |
| ATOM | 7739 | HE1 | HIS | E | 1 | -6.559 | 42.897 | -63.672 | 127.00 | H |
| ATOM | 7740 | HE2 | HIS | E | 1 | -6.977 | 40.642 | -64.251 | 127.08 | H |

TABLE 5-continued

Atomic Coordinates for OMCP-NKG2D (4PDC).

| ATOM | 7741 | N | LYS | E | 2 | -1.704 | 41.383 | -59.031 | 118.21 | N |
|------|------|---|-----|---|---|--------|--------|---------|--------|---|
| ATOM | 7742 | CA | LYS | E | 2 | -0.948 | 41.206 | -57.804 | 117.86 | C |
| ATOM | 7743 | C | LYS | E | 2 | 1.636 | 41.890 | -56.629 | 119.00 | C |
| ATOM | 7744 | O | LYS | E | 2 | -2.239 | 42.957 | -56.769 | 119.28 | O |
| ATOM | 7745 | CB | LYS | E | 2 | 0.478 | 41.736 | -57.970 | 123.19 | C |
| ATOM | 7746 | CG | LYS | E | 2 | 0.564 | 43.187 | -58.389 | 127.11 | C |
| ATOM | 7747 | CD | LYS | E | 2 | 1.980 | 43.554 | -58.803 | 134.68 | C |
| ATOM | 7748 | CE | LYS | E | 2 | 2.079 | 45.021 | -59.188 | 138.27 | C |
| ATOM | 7749 | NZ | LYS | E | 2 | 3.461 | 45.403 | -59.589 | 138.97 | N1+ |
| ATOM | 7750 | H | LYS | E | 2 | -2.086 | 42.150 | -59.100 | 121.85 | H |
| ATOM | 7751 | HA | LYS | E | 2 | -0.891 | 40.259 | -57.605 | 121.44 | H |
| ATOM | 7752 | HB2 | LYS | E | 2 | -0.943 | 41.647 | -57.123 | 127.83 | H |
| ATOM | 7753 | HB3 | LYS | E | 2 | 0.929 | 41.208 | -58.647 | 127.83 | H |
| ATOM | 7754 | HG2 | LYS | E | 2 | -0.024 | 43.338 | -59.145 | 132.53 | H |
| ATOM | 7755 | HG3 | LYS | E | 2 | 0.307 | 43.752 | -57.644 | 132.53 | H |
| ATOM | 7756 | HD2 | LYS | E | 2 | 2.584 | 43.392 | -58.061 | 141.61 | H |
| ATOM | 7757 | HD3 | LYS | E | 2 | 2.239 | 43.020 | -59.570 | 141.61 | H |
| ATOM | 7758 | HE2 | LYS | E | 2 | 1.489 | 45.194 | -59.937 | 145.93 | H |
| ATOM | 7759 | HE3 | LYS | E | 2 | 1.824 | 45.567 | -58.428 | 145.93 | H |
| ATOM | 7760 | HZ1 | LYS | E | 2 | 4.024 | 45.259 | -58.915 | 146.77 | H |
| ATOM | 7761 | HZ2 | LYS | E | 2 | 3.719 | 44.919 | -60.290 | 146.77 | H |
| ATOM | 7762 | HZ3 | LYS | E | 2 | 3.487 | 46.265 | -59.808 | 146.77 | H |
| ATOM | 7763 | N | LEU | E | 3 | -1.558 | 41.235 | -55.477 | 115.59 | N |
| ATOM | 7764 | CA | LEU | E | 3 | -2.079 | 41.766 | -54.229 | 113.41 | C |
| ATOM | 7765 | C | LEU | E | 3 | 0.905 | 41.903 | -53.273 | 113.12 | C |
| ATOM | 7766 | O | LEU | E | 3 | -0.228 | 40.922 | -52.981 | 112.97 | O |
| ATOM | 7767 | CB | LEU | E | 3 | -3.160 | 40.847 | -53.661 | 114.06 | C |
| ATOM | 7768 | CG | LEU | E | 3 | -3.893 | 41.275 | -52.390 | 112.36 | C |
| ATOM | 7769 | CD1 | LEU | E | 3 | -4.662 | 42.573 | -52.590 | 115.83 | C |
| ATOM | 7770 | CD2 | LEU | E | 3 | -4.825 | 40.167 | -51.968 | 111.74 | C |
| ATOM | 7771 | H | LEU | E | 3 | -1.197 | 40.458 | -55.394 | 118.71 | H |
| ATOM | 7772 | HA | LEU | E | 3 | -2.463 | 42.644 | -54.380 | 116.10 | H |
| ATOM | 7773 | HB2 | LEU | E | 3 | -3.835 | 40.727 | -54.346 | 116.87 | H |
| ATOM | 7774 | HB3 | LEU | E | 3 | -2.748 | 39.990 | -53.471 | 116.87 | H |
| ATOM | 7775 | HG | LEU | E | 3 | -3.246 | 41.413 | -51.681 | 114.83 | H |
| ATOM | 7776 | HD11 | LEU | E | 3 | -5.110 | 42.805 | -51.761 | 118.99 | H |
| ATOM | 7777 | HD1 | LEU | E | 3 | -4.039 | 43.274 | -52.837 | 118.99 | H |
| ATOM | 7778 | HD12 | LEU | E | 3 | -5.315 | 42.447 | -53.296 | 118.99 | H |
| ATOM | 7779 | HD21 | LEU | E | 3 | -5.291 | 40.437 | -51.162 | 114.08 | H |
| ATOM | 7780 | HD22 | LEU | E | 3 | -5.462 | 40.003 | -52.680 | 114.08 | H |
| ATOM | 7781 | HD23 | LEU | E | 3 | -4.305 | 39.366 | -51.798 | 114.08 | H |
| ATOM | 7782 | N | ALA | E | 4 | -0.654 | 43.124 | -52.813 | 113.44 | N |
| ATOM | 7783 | CA | ALA | E | 4 | 0.497 | 43.406 | -51.961 | 117.16 | C |
| ATOM | 7784 | C | ALA | E | 4 | -0.878 | 43.927 | -50.597 | 116.57 | C |
| ATOM | 7785 | O | ALA | E | 4 | 0.060 | 44.720 | -50.492 | 118.34 | O |
| ATOM | 7786 | CB | ALA | E | 4 | 1.416 | 44.405 | -52.632 | 116.90 | C |
| ATOM | 7787 | H | ALA | E | 4 | -1.140 | 43.813 | -52.981 | 116.13 | H |
| ATOM | 7788 | HA | ALA | E | 4 | 0.995 | 42.586 | -51.822 | 122.01 | H |
| ATOM | 7789 | HB1 | ALA | E | 4 | 2.172 | 44.578 | -52.050 | 122.01 | H |
| ATOM | 7790 | HB2 | ALA | E | 4 | 1.723 | 44.035 | -53.474 | 122.01 | H |
| ATOM | 7791 | HB3 | ALA | E | 4 | 0.925 | 45.227 | -52.791 | 122.01 | H |

TABLE 5-continued

Atomic Coordinates for OMCP-NKG2D (4PDC).

| ATOM | 7792 | N    | PHE | E | 5 | 0.753  | 43.463 | -49.563 | 115.63 | N |
|------|------|------|-----|---|---|--------|--------|---------|--------|---|
| ATOM | 7793 | CA   | PHE | E | 5 | 0.549  | 43.919 | -48.195 | 113.64 | C |
| ATOM | 7794 | C    | PHE | E | 5 | 1.836  | 44.553 | -47.690 | 114.46 | C |
| ATOM | 7795 | O    | PHE | E | 5 | 2.882  | 43.911 | -47.705 | 113.48 | O |
| ATOM | 7796 | CB   | PHE | E | 5 | 0.153  | 42.757 | -47.285 | 112.69 | C |
| ATOM | 7797 | CG   | PHE | E | 5 | -1.145 | 42.107 | -47.655 | 112.18 | C |
| ATOM | 7798 | CD1  | PHE | E | 5 | -1.202 | 41.174 | -48.674 | 113.36 | C |
| ATOM | 7799 | CD2  | PHE | E | 5 | -2.305 | 42.415 | -46.970 | 113.02 | C |
| ATOM | 7800 | CE1  | PHE | E | 5 | -2.394 | 40.571 | -49.012 | 116.36 | C |
| ATOM | 7801 | CE2  | PHE | E | 5 | -3.500 | 41.813 | -47.302 | 113.36 | C |
| ATOM | 7802 | CZ   | PHE | E | 5 | -3.545 | 40.890 | -48.324 | 116.42 | C |
| ATOM | 7803 | H    | PHE | E | 5 | 1.366  | 42.864 | -49.633 | 118.75 | H |
| ATOM | 7804 | HA   | PHE | E | 5 | -0.156 | 44.585 | -48.174 | 116.37 | H |
| ATOM | 7805 | HB2  | PHE | E | 5 | 0.845  | 42.079 | -47.327 | 115.23 | H |
| ATOM | 7806 | HB3  | PHE | E | 5 | 0.070  | 43.087 | -46.377 | 115.23 | H |
| ATOM | 7807 | HD1  | PHE | E | 5 | -0.429 | 40.956 | -49.142 | 116.03 | H |
| ATOM | 7808 | HD2  | PHE | E | 5 | -2.280 | 43.038 | -46.280 | 115.63 | H |
| ATOM | 7809 | HE1  | PHE | E | 5 | -2.422 | 39.947 | -49.701 | 119.63 | H |
| ATOM | 7810 | HE2  | PHE | E | 5 | -4.276 | 42.030 | -46.837 | 116.03 | H |
| ATOM | 7811 | HZ   | PHE | E | 5 | -4.350 | 40.483 | -48.550 | 119.70 | H |
| ATOM | 7812 | N    | ASN | E | 6 | 1.761  | 45.806 | -47.252 | 114.65 | N |
| ATOM | 7813 | CA   | ASN | E | 6 | 2.928  | 46.501 | -46.714 | 115.88 | C |
| ATOM | 7814 | C    | ASN | E | 6 | 2.745  | 46.820 | -45.232 | 116.33 | C |
| ATOM | 7815 | O    | ASN | E | 6 | 2.007  | 47.736 | -44.871 | 115.03 | O |
| ATOM | 7816 | CB   | ASN | E | 6 | 3.201  | 47.786 | -47.499 | 119.07 | C |
| ATOM | 7817 | CG   | ASN | E | 6 | 4.557  | 48.391 | -47.170 | 126.15 | C |
| ATOM | 7818 | OD1  | ASN | E | 6 | 4.646  | 49.449 | -46.550 | 133.75 | O |
| ATOM | 7819 | ND2  | ASN | E | 6 | 5.622  | 47.706 | -47.572 | 123.45 | N |
| ATOM | 7820 | H    | ASN | E | 6 | 1.042  | 46.279 | -47.255 | 117.58 | H |
| ATOM | 7821 | HA   | ASN | E | 6 | 3.704  | 45.926 | -46.802 | 119.05 | H |
| ATOM | 7822 | HB2  | ASN | E | 6 | 3.181  | 47.588 | -48.448 | 122.89 | H |
| ATOM | 7823 | HB3  | ASN | E | 6 | 2.519  | 48.441 | -47.282 | 122.89 | H |
| ATOM | 7824 | HD21 | ASN | E | 6 | 6.412  | 48.005 | -47.411 | 128.14 | H |
| ATOM | 7825 | HD22 | ASN | E | 6 | 5.522  | 46.963 | -47.994 | 128.14 | H |
| ATOM | 7826 | N    | PHE | E | 7 | 3.411  | 46.041 | -44.385 | 113.46 | N |
| ATOM | 7827 | CA   | PHE | E | 7 | 3.355  | 46.228 | -42.942 | 116.36 | C |
| ATOM | 7828 | C    | PHE | E | 7 | 4.478  | 47.139 | -42.488 | 115.66 | C |
| ATOM | 7829 | O    | PHE | E | 7 | 5.634  | 46.909 | -42.829 | 114.02 | O |
| ATOM | 7830 | CB   | PHE | E | 7 | 3.464  | 44.888 | -42.217 | 114.45 | C |
| ATOM | 7831 | CG   | PHE | E | 7 | 2.371  | 43.929 | -42.549 | 113.89 | C |
| ATOM | 7832 | CD1  | PHE | E | 7 | 2.434  | 43.159 | -43.700 | 113.75 | C |
| ATOM | 7833 | CD2  | PHE | E | 7 | 1.285  | 43.779 | -41.705 | 113.24 | C |
| ATOM | 7834 | CE1  | PHE | E | 7 | 1.425  | 42.267 | -44.007 | 113.98 | C |
| ATOM | 7835 | CE2  | PHE | E | 7 | 0.270  | 42.887 | -42.009 | 116.30 | C |
| ATOM | 7836 | CZ   | PHE | E | 7 | 0.342  | 42.131 | -43.161 | 116.68 | C |
| ATOM | 7837 | H    | PHE | E | 7 | 3.912  | 45.386 | -44.628 | 116.16 | H |
| ATOM | 7838 | HA   | PHE | E | 7 | 2.509  | 46.639 | -42.702 | 119.63 | H |
| ATOM | 7839 | HB2  | PHE | E | 7 | 4.307  | 44.472 | -42.456 | 117.33 | H |
| ATOM | 7840 | HB3  | PHE | E | 7 | 3.437  | 45.048 | -41.260 | 117.33 | H |
| ATOM | 7841 | HD1  | PHE | E | 7 | 3.160  | 43.248 | -44.274 | 116.50 | H |
| ATOM | 7842 | HD2  | PHE | E | 7 | 1.232  | 44.289 | -40.928 | 115.89 | H |

TABLE 5-continued

Atomic Coordinates for OMCP-NKG2D (4PDC).

| ATOM | 7843 | HE1 | PHE | E | 7 | 1.474 | 41.757 | -44.784 | 116.77 | H |
|---|---|---|---|---|---|---|---|---|---|---|
| ATOM | 7844 | HE2 | PHE | E | 7 | -0.457 | 42.796 | -41.437 | 119.56 | H |
| ATOM | 7845 | HZ | PHE | E | 7 | -0.337 | 41.530 | -43.367 | 120.02 | H |
| ATOM | 7846 | N | ASN | E | 8 | 4.139 | 48.165 | -41.715 | 118.72 | N |
| ATOM | 7847 | CA | ASN | E | 8 | 5.147 | 49.064 | -41.166 | 117.71 | C |
| ATOM | 7848 | C | ASN | E | 8 | 4.955 | 49.290 | -39.675 | 118.89 | C |
| ATOM | 7849 | O | ASN | E | 8 | 3.850 | 49.591 | -39.218 | 116.16 | O |
| ATOM | 7850 | CB | ASN | E | 8 | 5.124 | 50.406 | -41.893 | 117.97 | C |
| ATOM | 7851 | CG | ASN | E | 8 | 6.231 | 51.331 | -41.433 | 121.21 | C |
| ATOM | 7852 | OD1 | ASN | E | 8 | 7.411 | 51.033 | -41.604 | 124.65 | O |
| ATOM | 7853 | ND2 | ASN | E | 8 | 5.856 | 52.462 | -40.850 | 123.34 | N |
| ATOM | 7854 | H | ASN | E | 8 | 3.332 | 48.362 | -41.493 | 122.47 | H |
| ATOM | 7855 | HA | ASN | E | 8 | 6.023 | 48.669 | -41.297 | 121.25 | H |
| ATOM | 7856 | HB2 | ASN | E | 8 | 5.236 | 50.253 | -42.845 | 121.57 | H |
| ATOM | 7857 | HB3 | ASN | E | 8 | 4.275 | 50.844 | -41.724 | 121.57 | H |
| ATOM | 7858 | HD21 | ASN | E | 8 | 6.449 | 53.019 | -40.572 | 128.01 | H |
| ATOM | 7859 | HD22 | ASN | E | 8 | 5.020 | 52.638 | -40.751 | 128.01 | H |
| ATOM | 7860 | N | LEU | E | 9 | 6.043 | 49.124 | -38.928 | 115.50 | N |
| ATOM | 7861 | CA | LEU | E | 9 | 6.083 | 49.460 | -37.513 | 116.76 | C |
| ATOM | 7862 | C | LEU | E | 9 | 7.182 | 50.492 | -37.294 | 119.62 | C |
| ATOM | 7863 | O | LEU | E | 9 | 8.365 | 50.183 | -37.428 | 118.29 | O |
| ATOM | 7864 | CB | LEU | E | 9 | 6.330 | 48.214 | -36.656 | 117.53 | C |
| ATOM | 7865 | CG | LEU | E | 9 | 6.418 | 48.451 | -35.145 | 116.67 | C |
| ATOM | 7866 | CD1 | LEU | E | 9 | 5.120 | 49.012 | -34.599 | 122.09 | C |
| ATOM | 7867 | CD2 | LEU | E | 9 | 6.781 | 47.164 | -34.417 | 117.22 | C |
| ATOM | 7868 | H | LEU | E | 9 | 6.786 | 48.811 | -39.228 | 118.60 | H |
| ATOM | 7869 | HA | LEU | E | 9 | 5.236 | 49.851 | -37.249 | 120.12 | H |
| ATOM | 7870 | HB2 | LEU | E | 9 | 5.605 | 47.589 | -36.809 | 121.03 | H |
| ATOM | 7871 | HB3 | LEU | E | 9 | 7.167 | 47.812 | -36.935 | 121.03 | H |
| ATOM | 7872 | HG | LEU | E | 9 | 7.119 | 49.099 | -34.970 | 120.00 | H |
| ATOM | 7873 | HD11 | LEU | E | 9 | 5.213 | 49.149 | -33.644 | 126.51 | H |
| ATOM | 7874 | HD12 | LEU | E | 9 | 4.933 | 49.857 | -35.038 | 126.51 | H |
| ATOM | 7875 | HD13 | LEU | E | 9 | 4.405 | 48.381 | -34.776 | 126.51 | H |
| ATOM | 7876 | HD21 | LEU | E | 9 | 6.830 | 47.343 | -33.465 | 120.67 | H |
| ATOM | 7877 | HD22 | LEU | E | 9 | 6.098 | 46.498 | -34.594 | 120.67 | H |
| ATOM | 7878 | HD23 | LEU | E | 9 | 7.641 | 46.851 | -34.740 | 120.67 | H |
| ATOM | 7879 | N | GLU | E | 10 | 6.781 | 51.720 | -36.979 | 118.79 | N |
| ATOM | 7880 | CA | GLU | E | 10 | 7.726 | 52.814 | -36.766 | 125.42 | C |
| ATOM | 7881 | C | GLU | E | 10 | 7.809 | 53.176 | -35.290 | 125.51 | C |
| ATOM | 7882 | O | GLU | E | 10 | 6.822 | 53.608 | -34.700 | 124.74 | O |
| ATOM | 7883 | CB | GLU | E | 10 | 7.326 | 54.046 | -37.582 | 123.36 | C |
| ATOM | 7884 | CG | GLU | E | 10 | 8.326 | 55.197 | -37.512 | 131.78 | C |
| ATOM | 7885 | CD | GLU | E | 10 | 7.883 | 56.420 | -38.300 | 132.30 | C |
| ATOM | 7886 | OE1 | GLU | E | 10 | 6.687 | 56.775 | -38.234 | 136.09 | O |
| ATOM | 7887 | OE2 | GLU | E | 10 | 8.732 | 57.026 | -38.988 | 136.34 | O1- |
| ATOM | 7888 | H | GLU | E | 10 | 5.958 | 51.949 | -36.880 | 122.55 | H |
| ATOM | 7889 | HA | GLU | E | 10 | 8.608 | 52.534 | -37.059 | 130.51 | H |
| ATOM | 7890 | HB2 | GLU | E | 10 | 7.230 | 53.788 | -38.512 | 128.04 | H |
| ATOM | 7891 | HB3 | GLU | E | 10 | 6.471 | 54.375 | -37.248 | 128.04 | H |
| ATOM | 7892 | HG2 | GLU | E | 10 | 8.438 | 55.462 | -36.586 | 138.14 | H |
| ATOM | 7893 | HG3 | GLU | E | 10 | 9.174 | 54.897 | -37.876 | 138.14 | H |

TABLE 5-continued

Atomic Coordinates for OMCP-NKG2D (4PDC).

| | | | | | | | | | | |
|---|---|---|---|---|---|---|---|---|---|---|
| ATOM | 7894 | N | ILE | E | 11 | 8.988 | 52.981 | -34.703 | 128.61 | N |
| ATOM | 7895 | CA | ILE | E | 11 | 9.253 | 53.384 | -33.326 | 125.78 | C |
| ATOM | 7896 | C | ILE | E | 11 | 10.184 | 54.588 | -33.321 | 124.72 | C |
| ATOM | 7897 | O | ILE | E | 11 | 11.389 | 54.450 | -33.528 | 124.06 | O |
| ATOM | 7898 | CB | ILE | E | 11 | 9.891 | 52.248 | -32.498 | 131.17 | C |
| ATOM | 7899 | CG1 | ILE | E | 11 | 9.015 | 50.995 | -32.536 | 130.05 | C |
| ATOM | 7900 | CG2 | ILE | E | 11 | 10.114 | 52.692 | -31.056 | 130.83 | C |
| ATOM | 7901 | CD1 | ILE | E | 11 | 9.421 | 50.004 | -33.599 | 130.44 | C |
| ATOM | 7902 | H | ILE | E | 11 | 9.662 | 52.612 | -35.089 | 134.34 | H |
| ATOM | 7903 | HA | ILE | E | 11 | 8.420 | 53.640 | -32.900 | 130.94 | H |
| ATOM | 7904 | HB | ILE | E | 11 | 10.752 | 52.031 | -32.888 | 137.40 | H |
| ATOM | 7905 | HG12 | ILE | E | 11 | 9.070 | 50.548 | -31.677 | 136.06 | H |
| ATOM | 7906 | HG13 | ILE | E | 11 | 8.098 | 51.259 | -32.712 | 136.06 | H |
| ATOM | 7907 | HG21 | ILE | E | 11 | 10.515 | 51.962 | -30.560 | 137.00 | H |
| ATOM | 7908 | HG22 | ILE | E | 11 | 10.706 | 53.461 | -31.051 | 137.00 | H |
| ATOM | 7909 | HG23 | ILE | E | 11 | 9.259 | 52.930 | -30.664 | 136.53 | H |
| ATOM | 7910 | HD11 | ILE | E | 11 | 8.824 | 49.240 | -33.563 | 136.53 | H |
| ATOM | 7911 | HD12 | ILE | E | 11 | 9.361 | 50.431 | -34.468 | 136.53 | H |
| ATOM | 7912 | HD13 | ILE | E | 11 | 10.334 | 49.719 | -33.432 | 136.53 | H |
| ATOM | 7913 | N | ASN | E | 12 | 9.610 | 55.765 | -33.095 | 126.17 | N |
| ATOM | 7914 | CA | ASN | E | 12 | 10.364 | 57.010 | -33.023 | 130.19 | C |
| ATOM | 7915 | C | ASN | E | 12 | 10.274 | 57.565 | -31.611 | 133.21 | C |
| ATOM | 7916 | O | ASN | E | 12 | 9.309 | 58.238 | -31.259 | 128.03 | O |
| ATOM | 7917 | CB | ASN | E | 12 | 9.830 | 58.023 | -34.042 | 128.09 | C |
| ATOM | 7918 | CG | ASN | E | 12 | 10.710 | 59.256 | -34.166 | 134.34 | C |
| ATOM | 7919 | OD1 | ASN | E | 12 | 11.388 | 59.657 | -33.218 | 128.23 | O |
| ATOM | 7920 | ND2 | ASN | E | 12 | 10.701 | 59.869 | -35.347 | 137.26 | N |
| ATOM | 7921 | H | ASN | E | 12 | 8.765 | 55.869 | -32.977 | 131.41 | H |
| ATOM | 7922 | HA | ASN | E | 12 | 11.297 | 56.834 | -33.225 | 136.22 | H |
| ATOM | 7923 | HB2 | ASN | E | 12 | 9.784 | 57.599 | -34.914 | 133.71 | H |
| ATOM | 7924 | HB3 | ASN | E | 12 | 8.947 | 58.312 | -33.766 | 133.71 | H |
| ATOM | 7925 | HD21 | ASN | E | 12 | 11.181 | 60.571 | -35.471 | 144.71 | H |
| ATOM | 7926 | HD22 | ASN | E | 12 | 10.214 | 59.562 | -35.986 | 144.71 | H |
| ATOM | 7927 | N | GLY | E | 13 | 11.280 | 57.273 | -30.797 | 133.39 | N |
| ATOM | 7928 | CA | GLY | E | 13 | 11.269 | 57.704 | -29.414 | 137.75 | C |
| ATOM | 7929 | C | GLY | E | 13 | 10.163 | 57.015 | -28.639 | 137.43 | C |
| ATOM | 7930 | O | GLY | E | 13 | 10.112 | 55.786 | -28.582 | 137.21 | O |
| ATOM | 7931 | H | GLY | E | 13 | 11.979 | 56.827 | -31.024 | 140.07 | H |
| ATOM | 7932 | HA2 | GLY | E | 13 | 12.120 | 57.492 | -28.998 | 145.30 | H |
| ATOM | 7933 | HA3 | GLY | E | 13 | 11.130 | 58.663 | -29.371 | 145.30 | H |
| ATOM | 7934 | N | SER | E | 14 | 9.260 | 57.809 | -28.068 | 144.23 | N |
| ATOM | 7935 | CA | SER | E | 14 | 8.265 | 57.294 | -27.129 | 148.10 | C |
| ATOM | 7936 | C | SER | E | 14 | 6.947 | 56.870 | -27.780 | 145.20 | C |
| ATOM | 7937 | O | SER | E | 14 | 6.185 | 56.108 | -27.185 | 144.70 | O |
| ATOM | 7938 | CB | SER | E | 14 | 7.978 | 58.343 | -26.052 | 144.32 | C |
| ATOM | 7939 | OG | SER | E | 14 | 7.497 | 59.546 | -26.627 | 149.63 | O |
| ATOM | 7940 | H | SER | E | 14 | 9.201 | 58.655 | -28.209 | 153.08 | H |
| ATOM | 7941 | HA | SER | E | 14 | 8.635 | 56.514 | -26.686 | 157.72 | H |
| ATOM | 7942 | HB2 | SER | E | 14 | 7.309 | 57.995 | -25.444 | 153.18 | H |
| ATOM | 7943 | HB3 | SER | E | 14 | 8.799 | 58.531 | -25.570 | 153.18 | H |
| ATOM | 7944 | HG | SER | E | 14 | 7.345 | 60.111 | -26.024 | 159.56 | H |

TABLE 5-continued

Atomic Coordinates for OMCP-NKG2D (4PDC).

| ATOM | 7945 | N | ASP | E | 15 | 6.670 | 57.358 | −28.986 | 147.04 | N |
|---|---|---|---|---|---|---|---|---|---|---|
| ATOM | 7946 | CA | ASP | E | 15 | 5.445 | 56.970 | −29.683 | 151.32 | C |
| ATOM | 7947 | C | ASP | E | 15 | 5.751 | 55.979 | −30.804 | 146.88 | C |
| ATOM | 7948 | O | ASP | E | 15 | 6.834 | 55.997 | −31.394 | 142.45 | O |
| ATOM | 7949 | CB | ASP | E | 15 | 4.707 | 58.201 | −30.229 | 155.08 | C |
| ATOM | 7950 | CG | ASP | E | 15 | 5.515 | 58.970 | −31.250 | 156.39 | C |
| ATOM | 7951 | OD1 | ASP | E | 15 | 6.755 | 58.979 | −31.140 | 157.41 | O |
| ATOM | 7952 | OD2 | ASP | E | 15 | 4.907 | 59.575 | −32.160 | 164.51 | O1− |
| ATOM | 7953 | H | ASP | E | 15 | 7.168 | 57.909 | −29.420 | 156.44 | H |
| ATOM | 7954 | HA | ASP | E | 15 | 4.855 | 56.529 | −29.052 | 161.58 | H |
| ATOM | 7955 | HB2 | ASP | E | 15 | 3.884 | 57.913 | −30.654 | 166.10 | H |
| ATOM | 7956 | HB3 | ASP | E | 15 | 4.507 | 58.801 | −29.493 | 166.10 | H |
| ATOM | 7957 | N | THR | E | 16 | 4.790 | 55.100 | −31.069 | 140.99 | N |
| ATOM | 7958 | CA | THR | E | 16 | 4.933 | 54.071 | −32.088 | 135.68 | C |
| ATOM | 7959 | C | THR | E | 16 | 3.735 | 54.097 | −33.026 | 138.72 | C |
| ATOM | 7960 | O | THR | E | 16 | 2.618 | 54.422 | −32.613 | 133.45 | O |
| ATOM | 7961 | CB | THR | E | 16 | 5.068 | 52.671 | −31.464 | 138.05 | C |
| ATOM | 7962 | OG1 | THR | E | 16 | 3.910 | 52.381 | −30.674 | 148.80 | O |
| ATOM | 7963 | CG2 | THR | E | 16 | 6.302 | 52.596 | −30.585 | 139.99 | C |
| ATOM | 7964 | H | THR | E | 16 | 4.032 | 55.080 | −30.662 | 149.19 | H |
| ATOM | 7965 | HA | THR | E | 16 | 5.731 | 54.249 | −32.611 | 142.82 | H |
| ATOM | 7966 | HB | THR | E | 16 | 5.153 | 52.009 | −32.168 | 145.66 | H |
| ATOM | 7967 | HG1 | THR | E | 16 | 3.980 | 51.618 | −30.331 | 158.56 | H |
| ATOM | 7968 | HG21 | THR | E | 16 | 6.378 | 51.711 | −30.196 | 147.99 | H |
| ATOM | 7969 | HG22 | THR | E | 16 | 7.095 | 52.779 | −31.112 | 147.99 | H |
| ATOM | 7970 | HG23 | THR | E | 16 | 6.240 | 53.250 | −29.871 | 147.99 | H |
| ATOM | 7971 | N | HIS | E | 17 | 3.974 | 53.758 | −34.290 | 131.94 | N |
| ATOM | 7972 | CA | HIS | E | 17 | 2.917 | 53.737 | −35.295 | 133.04 | C |
| ATOM | 7973 | C | HIS | E | 17 | 2.903 | 52.408 | −36.036 | 125.75 | C |
| ATOM | 7974 | O | HIS | E | 17 | 3.919 | 51.976 | −36.579 | 121.85 | O |
| ATOM | 7975 | CB | HIS | E | 17 | 3.093 | 54.890 | −36.284 | 133.14 | C |
| ATOM | 7976 | CG | HIS | E | 17 | 3.093 | 56.242 | −35.639 | 143.36 | C |
| ATOM | 7977 | ND1 | HIS | E | 17 | 4.224 | 56.801 | −35.083 | 149.33 | N |
| ATOM | 7978 | CD2 | HIS | E | 17 | 2.098 | 57.141 | −35.454 | 148.56 | C |
| ATOM | 7979 | CE1 | HIS | E | 17 | 3.926 | 57.989 | −34.587 | 147.74 | C |
| ATOM | 7980 | NE2 | HIS | E | 17 | 2.643 | 58.219 | −34.799 | 151.13 | N |
| ATOM | 7981 | H | HIS | E | 17 | 4.747 | 53.533 | −34.592 | 138.33 | H |
| ATOM | 7982 | HA | HIS | E | 17 | 2.059 | 53.846 | −34.855 | 139.65 | H |
| ATOM | 7983 | HB2 | HIS | E | 17 | 3.940 | 54.781 | −36.744 | 139.77 | H |
| ATOM | 7984 | HB3 | HIS | E | 17 | 2.365 | 54.867 | −36.924 | 139.77 | H |
| ATOM | 7985 | HD1 | HIS | E | 17 | 5.001 | 56.435 | −35.063 | 159.20 | H |
| ATOM | 7986 | HD2 | HIS | E | 17 | 1.213 | 57.048 | −35.722 | 158.27 | H |
| ATOM | 7987 | HE1 | HIS | E | 17 | 4.519 | 58.565 | −34.161 | 147.28 | H |
| ATOM | 7988 | HE2 | HIS | E | 17 | 2.218 | 58.929 | −34.565 | 161.35 | H |
| ATOM | 7989 | N | SER | E | 18 | 1.744 | 51.762 | −36.039 | 118.75 | N |
| ATOM | 7990 | CA | SER | E | 18 | 1.548 | 50.514 | −36.761 | 118.70 | C |
| ATOM | 7991 | C | SER | E | 18 | 0.600 | 50.766 | −37.917 | 122.66 | C |
| ATOM | 7992 | O | SER | E | 18 | −0.503 | 51.269 | −37.710 | 122.11 | O |
| ATOM | 7993 | CB | SER | E | 18 | 0.987 | 49.434 | −35.839 | 121.15 | C |
| ATOM | 7994 | OG | SER | E | 18 | 1.713 | 49.382 | −34.625 | 125.66 | O |
| ATOM | 7995 | H | SER | E | 18 | 1.042 | 52.032 | −35.621 | 122.50 | H |

TABLE 5-continued

Atomic Coordinates for OMCP-NKG2D (4PDC).

| | | | | | | | | | |
|---|---|---|---|---|---|---|---|---|---|
| ATOM | 7996 | HA | SER | E | 18 | 2.396 | 50.207 | -37.118 | 122.43 H |
| ATOM | 7997 | HB2 | SER | E | 18 | 0.059 | 49.637 | -35.643 | 125.38 H |
| ATOM | 7998 | HB3 | SER | E | 18 | 1.052 | 48.574 | -36.283 | 125.38 H |
| ATOM | 7999 | HG | SER | E | 18 | 1.396 | 48.785 | -34.125 | 130.79 H |
| ATOM | 8000 | N | THR | E | 19 | 1.029 | 50.431 | -39.131 | 116.84 N |
| ATOM | 8001 | CA | THR | E | 19 | 0.194 | 50.639 | -40.306 | 118.45 C |
| ATOM | 8002 | C | THR | E | 19 | 0.315 | 49.485 | -41.295 | 115.64 C |
| ATOM | 8003 | O | THR | E | 19 | 1.355 | 48.834 | -41.386 | 115.74 O |
| ATOM | 8004 | CB | THR | E | 19 | 0.553 | 51.957 | -41.024 | 119.60 C |
| ATOM | 8005 | OG1 | THR | E | 19 | 1.853 | 51.848 | -41.611 | 127.97 O |
| ATOM | 8006 | CG2 | THR | E | 19 | 0.540 | 53.128 | -40.050 | 125.33 C |
| ATOM | 8007 | H | THR | E | 19 | 1.798 | 50.084 | -39.299 | 120.21 H |
| ATOM | 8008 | HA | THR | E | 19 | -0.733 | 50.696 | -40.025 | 122.14 H |
| ATOM | 8009 | HB | THR | E | 19 | -0.100 | 52.132 | -41.720 | 123.52 H |
| ATOM | 8010 | HG1 | THR | E | 19 | 2.425 | 51.696 | -41.015 | 133.57 H |
| ATOM | 8011 | HG21 | THR | E | 19 | 0.766 | 53.948 | -40.514 | 130.39 H |
| ATOM | 8012 | HG22 | THR | E | 19 | -0.342 | 53.221 | -39.657 | 130.39 H |
| ATOM | 8013 | HG23 | THR | E | 19 | 1.186 | 52.977 | -39.342 | 130.39 H |
| ATOM | 8014 | N | VAL | E | 20 | -0.767 | 49.227 | -42.020 | 113.81 N |
| ATOM | 8015 | CA | VAL | E | 20 | -0.733 | 48.293 | -43.138 | 113.33 C |
| ATOM | 8016 | C | VAL | E | 20 | -1.448 | 48.899 | -44.341 | 117.42 C |
| ATOM | 8017 | O | VAL | E | 20 | -2.502 | 49.514 | -44.192 | 115.32 O |
| ATOM | 8018 | CB | VAL | E | 20 | -1.387 | 46.947 | -42.794 | 113.54 C |
| ATOM | 8019 | CG1 | VAL | E | 20 | -1.103 | 45.934 | -43.893 | 112.41 C |
| ATOM | 8020 | CG2 | VAL | E | 20 | -0.887 | 46.429 | -41.450 | 115.63 C |
| ATOM | 8021 | H | VAL | E | 20 | -1.538 | 49.583 | -41.884 | 116.57 H |
| ATOM | 8022 | HA | VAL | E | 20 | 0.190 | 48.127 | -43.386 | 116.00 H |
| ATOM | 8023 | HB | VAL | E | 20 | -2.348 | 47.066 | -42.734 | 116.24 H |
| ATOM | 8024 | HG11 | VAL | E | 20 | -1.522 | 45.091 | -43.660 | 114.89 H |
| ATOM | 8025 | HG12 | VAL | E | 20 | -1.466 | 46.266 | -44.729 | 114.89 H |
| ATOM | 8026 | HG13 | VAL | E | 20 | -0.144 | 45.816 | -43.972 | 114.89 H |
| ATOM | 8027 | HG21 | VAL | E | 20 | -1.316 | 45.580 | -41.260 | 118.75 H |
| ATOM | 8028 | HG22 | VAL | E | 20 | 0.075 | 46.311 | -41.496 | 118.75 H |
| ATOM | 8029 | HG23 | VAL | E | 20 | -1.109 | 47.074 | -40.761 | 118.75 H |
| ATOM | 8030 | N | ASP | E | 21 | -0.848 | 48.729 | -45.518 | 115.97 N |
| ATOM | 8031 | CA | ASP | E | 21 | -1.440 | 49.125 | -46.794 | 121.15 C |
| ATOM | 8032 | C | ASP | E | 21 | -1.657 | 47.896 | -47.664 | 118.26 C |
| ATOM | 8033 | O | ASP | E | 21 | -0.754 | 47.072 | -47.817 | 117.18 O |
| ATOM | 8034 | CB | ASP | E | 21 | -0.544 | 50.116 | -47.543 | 122.93 C |
| ATOM | 8035 | CG | ASP | E | 21 | -0.289 | 51.386 | -46.761 | 124.35 C |
| ATOM | 8036 | OD1 | ASP | E | 21 | -1.220 | 51.871 | -46.088 | 125.88 O1- |
| ATOM | 8037 | OD2 | ASP | E | 21 | 0.849 | 51.897 | -46.822 | 127.99 O |
| ATOM | 8038 | H | ASP | E | 21 | -0.070 | 48.373 | -45.604 | 119.17 H |
| ATOM | 8039 | HA | ASP | E | 21 | -2.300 | 49.546 | -46.635 | 125.38 H |
| ATOM | 8040 | HB2 | ASP | E | 21 | 0.312 | 49.696 | -47.720 | 127.51 H |
| ATOM | 8041 | HB3 | ASP | E | 21 | -0.973 | 50.360 | -48.378 | 127.51 H |
| ATOM | 8042 | N | VAL | E | 22 | -2.853 | 47.775 | -48.230 | 115.73 N |
| ATOM | 8043 | CA | VAL | E | 22 | -3.147 | 46.699 | -49.170 | 116.91 C |
| ATOM | 8044 | C | VAL | E | 22 | -3.314 | 47.289 | -50.559 | 118.18 C |
| ATOM | 8045 | O | VAL | E | 22 | -4.196 | 48.120 | -50.785 | 118.14 O |
| ATOM | 8046 | CB | VAL | E | 22 | -4.411 | 45.929 | -48.787 | 113.15 C |

TABLE 5-continued

Atomic Coordinates for OMCP-NKG2D (4PDC).

| | | | | | | | | | |
|---|---|---|---|---|---|---|---|---|---|
| ATOM | 8047 | CG1 | VAL | E | 22 | -4.570 | 44.701 | -49.670 | 118.48 C |
| ATOM | 8048 | CG2 | VAL | E | 22 | -4.362 | 45.523 | -47.319 | 114.73 C |
| ATOM | 8049 | H | VAL | E | 22 | -3.514 | 48.305 | -48.086 | 118.88 H |
| ATOM | 8050 | HA | VAL | E | 22 | -2.403 | 46.077 | -49.189 | 120.29 H |
| ATOM | 8051 | HB | VAL | E | 22 | -5.184 | 46.499 | -48.919 | 115.79 H |
| ATOM | 8052 | HG11 | VAL | E | 22 | -5.376 | 44.228 | -49.411 | 122.17 H |
| ATOM | 8053 | HG12 | VAL | E | 22 | -4.635 | 44.985 | -50.595 | 122.17 H |
| ATOM | 8054 | HG13 | VAL | E | 22 | -3.797 | 44.127 | -49.554 | 122.17 H |
| ATOM | 8055 | HG21 | VAL | E | 22 | -5.172 | 45.036 | -47.099 | 117.68 H |
| ATOM | 8056 | HG22 | VAL | E | 22 | -3.587 | 44.958 | -47.173 | 117.68 H |
| ATOM | 8057 | HG23 | VAL | E | 22 | -4.298 | 46.322 | -46.773 | 117.68 H |
| ATOM | 8058 | N | ASP | E | 23 | -2.464 | 46.854 | -51.482 | 115.34 N |
| ATOM | 8059 | CA | ASP | E | 23 | -2.482 | 47.357 | -52.849 | 119.21 C |
| ATOM | 8060 | C | ASP | E | 23 | -2.905 | 46.259 | -53.817 | 119.78 C |
| ATOM | 8061 | O | ASP | E | 23 | -2.353 | 45.158 | -53.794 | 118.41 O |
| ATOM | 8062 | CB | ASP | E | 23 | -1.103 | 47.894 | -53.253 | 121.71 C |
| ATOM | 8063 | CG | ASP | E | 23 | -0.614 | 49.015 | -52.347 | 127.17 C |
| ATOM | 8064 | OD1 | ASP | E | 23 | -1.453 | 49.705 | -51.735 | 125.29 O |
| ATOM | 8065 | OD2 | ASP | E | 23 | 0.618 | 49.212 | -52.256 | 137.02 O1- |
| ATOM | 8066 | H | ASP | E | 23 | -1.859 | 46.260 | -51.339 | 118.40 H |
| ATOM | 8067 | HA | ASP | E | 23 | -3.122 | 48.083 | -52.914 | 123.05 H |
| ATOM | 8068 | HB2 | ASP | E | 23 | -0.458 | 47.171 | -53.209 | 126.06 H |
| ATOM | 8069 | HB3 | ASP | E | 23 | -1.152 | 48.240 | -54.157 | 126.06 H |
| ATOM | 8070 | N | LEU | E | 24 | -3.888 | 46.567 | -54.659 | 116.92 N |
| ATOM | 8071 | CA | LEU | E | 24 | -4.251 | 45.703 | -55.777 | 117.78 C |
| ATOM | 8072 | C | LEU | E | 24 | -3.735 | 46.318 | -57.072 | 120.26 C |
| ATOM | 8073 | O | LEU | E | 24 | -4.165 | 47.398 | -57.462 | 121.27 O |
| ATOM | 8074 | CB | LEU | E | 24 | -5.768 | 45.506 | -55.844 | 117.65 C |
| ATOM | 8075 | CG | LEU | E | 24 | -6.282 | 44.629 | -56.988 | 120.38 C |
| ATOM | 8076 | CD1 | LEU | E | 24 | -5.743 | 43.211 | -56.874 | 120.35 C |
| ATOM | 8077 | CD2 | LEU | E | 24 | -7.803 | 44.623 | -57.009 | 121.16 C |
| ATOM | 8078 | H | LEU | E | 24 | -4.365 | 47.280 | -54.603 | 120.30 H |
| ATOM | 8079 | HA | LEU | E | 24 | -3.835 | 44.834 | -55.662 | 121.34 H |
| ATOM | 8080 | HB2 | LEU | E | 24 | -6.060 | 45.098 | -55.014 | 121.18 H |
| ATOM | 8081 | HB3 | LEU | E | 24 | -6.184 | 46.377 | -55.938 | 121.18 H |
| ATOM | 8082 | HG | LEU | E | 24 | -5.973 | 44.999 | -57.831 | 124.45 H |
| ATOM | 8083 | HD11 | LEU | E | 24 | -6.087 | 42.683 | -57.612 | 124.42 H |
| ATOM | 8084 | HD12 | LEU | E | 24 | -4.774 | 43.237 | -56.909 | 124.42 H |
| ATOM | 8085 | HD13 | LEU | E | 24 | -6.034 | 42.830 | -56.031 | 124.42 H |
| ATOM | 8086 | HD21 | LEU | E | 24 | -8.106 | 44.062 | -57.740 | 125.39 H |
| ATOM | 8087 | HD22 | LEU | E | 24 | -8.128 | 44.271 | -56.165 | 125.39 H |
| ATOM | 8088 | HD23 | LEU | E | 24 | -8.120 | 45.531 | -57.134 | 125.39 H |
| ATOM | 8089 | N | ASP | E | 25 | -2.807 | 45.630 | -57.729 | 119.76 N |
| ATOM | 8090 | CA | ASP | E | 25 | -2.193 | 46.137 | -58.953 | 122.73 C |
| ATOM | 8091 | C | ASP | E | 25 | -1.618 | 47.542 | -58.756 | 127.17 C |
| ATOM | 8092 | O | ASP | E | 25 | -1.913 | 48.462 | -59.520 | 123.98 O |
| ATOM | 8093 | CB | ASP | E | 25 | -3.211 | 46.124 | -60.095 | 121.06 C |
| ATOM | 8094 | CG | ASP | E | 25 | -3.666 | 44.718 | -60.449 | 122.08 C |
| ATOM | 8095 | OD1 | ASP | E | 25 | -2.862 | 43.783 | -60.271 | 120.88 O |
| ATOM | 8096 | OD2 | ASP | E | 25 | -4.820 | 44.541 | -60.895 | 123.06 O1- |
| ATOM | 8097 | H | ASP | E | 25 | -2.513 | 44.860 | -57.485 | 123.71 H |

TABLE 5-continued

Atomic Coordinates for OMCP-NKG2D (4PDC).

| ATOM | 8098 | HA | ASP | E | 25 | -1.462 | 45.550 | -59.201 | 127.28 | H |
|---|---|---|---|---|---|---|---|---|---|---|
| ATOM | 8099 | HB2 | ASP | E | 25 | -3.992 | 46.636 | -59.830 | 125.27 | H |
| ATOM | 8100 | HB3 | ASP | E | 25 | -2.807 | 46.518 | -60.884 | 125.27 | H |
| ATOM | 8101 | N | ASP | E | 26 | -0.796 | 47.691 | -57.720 | 125.96 | N |
| ATOM | 8102 | CA | ASP | E | 26 | -0.129 | 48.958 | -57.415 | 132.50 | C |
| ATOM | 8103 | C | ASP | E | 26 | -1.125 | 50.097 | -57.208 | 132.04 | C |
| ATOM | 8104 | O | ASP | E | 26 | -0.835 | 51.257 | -57.508 | 130.72 | O |
| ATOM | 8105 | CB | ASP | E | 26 | 0.862 | 49.324 | -58.527 | 134.94 | C |
| ATOM | 8106 | CG | ASP | E | 26 | 2.007 | 48.334 | -58.635 | 143.04 | C |
| ATOM | 8107 | OD1 | ASP | E | 26 | 2.488 | 47.863 | -57.580 | 138.49 | O |
| ATOM | 8108 | OD2 | ASP | E | 26 | 2.426 | 48.024 | -59.773 | 145.93 | O1- |
| ATOM | 8109 | H | ASP | E | 26 | -0.603 | 47.061 | -57.168 | 131.15 | H |
| ATOM | 8110 | HA | ASP | E | 26 | 0.375 | 48.854 | -56.593 | 139.00 | H |
| ATOM | 8111 | HB2 | ASP | E | 26 | 0.394 | 49.337 | -59.377 | 141.93 | H |
| ATOM | 8112 | HB3 | ASP | E | 26 | 1.237 | 50.199 | -58.341 | 141.93 | H |
| ATOM | 8113 | N | SER | E | 27 | -2.300 | 49.749 | -56.696 | 127.41 | N |
| ATOM | 8114 | CA | SER | E | 27 | -3.304 | 50.730 | -56.305 | 126.12 | C |
| ATOM | 8115 | C | SER | E | 27 | -3.839 | 50.370 | -54.923 | 125.00 | C |
| ATOM | 8116 | O | SER | E | 27 | -4.302 | 49.252 | -54.707 | 122.30 | O |
| ATOM | 8117 | CB | SER | E | 27 | -4.438 | 50.781 | -57.328 | 127.19 | C |
| ATOM | 8118 | OG | SER | E | 27 | -5.564 | 51.464 | -56.803 | 135.60 | O |
| ATOM | 8119 | H | SER | E | 27 | -2.544 | 48.935 | -56.562 | 132.89 | H |
| ATOM | 8120 | HA | SER | E | 27 | -2.895 | 51.608 | -56.257 | 131.34 | H |
| ATOM | 8121 | HB2 | SER | E | 27 | -4.128 | 51.247 | -58.120 | 132.63 | H |
| ATOM | 8122 | HB3 | SER | E | 27 | -4.697 | 49.874 | -57.556 | 132.63 | H |
| ATOM | 8123 | HG | SER | E | 27 | -6.179 | 51.484 | -57.375 | 142.72 | H |
| ATOM | 8124 | N | GLN | E | 28 | -3.763 | 51.311 | -53.985 | 120.78 | N |
| ATOM | 8125 | CA | GLN | E | 28 | -4.183 | 51.043 | -52.614 | 121.26 | C |
| ATOM | 8126 | C | GLN | E | 28 | -5.695 | 50.879 | -52.532 | 120.87 | C |
| ATOM | 8127 | O | GLN | E | 28 | -6.443 | 51.709 | -53.055 | 118.20 | O |
| ATOM | 8128 | CB | GLN | E | 28 | -3.725 | 52.167 | -51.683 | 122.63 | C |
| ATOM | 8129 | CG | GLN | E | 28 | -3.899 | 51.850 | -50.211 | 123.18 | C |
| ATOM | 8130 | CD | GLN | E | 28 | -3.629 | 53.049 | -49.326 | 123.30 | C |
| ATOM | 8131 | OE1 | GLN | E | 28 | -4.462 | 53.945 | -49.208 | 129.76 | O |
| ATOM | 8132 | NE2 | GLN | E | 28 | -2.458 | 53.076 | -48.708 | 125.07 | N |
| ATOM | 8133 | H | GLN | E | 28 | -3.472 | 52.109 | -54.117 | 124.94 | H |
| ATOM | 8134 | HA | GLN | E | 28 | -3.774 | 50.217 | -52.313 | 125.51 | H |
| ATOM | 8135 | HB2 | GLN | E | 28 | -2.784 | 52.339 | -51.840 | 127.15 | H |
| ATOM | 8136 | HB3 | GLN | E | 28 | -4.242 | 52.964 | -51.878 | 127.15 | H |
| ATOM | 8137 | HG2 | GLN | E | 28 | -4.812 | 51.561 | -50.054 | 127.82 | H |
| ATOM | 8138 | HG3 | GLN | E | 28 | -3.279 | 51.147 | -49.962 | 127.82 | H |
| ATOM | 8139 | HE21 | GLN | E | 28 | -2.257 | 53.736 | -48.194 | 130.08 | H |
| ATOM | 8140 | HE22 | GLN | E | 28 | -1.897 | 52.433 | -48.820 | 130.08 | H |
| ATOM | 8141 | N | ILE | E | 29 | -6.137 | 49.807 | -51.873 | 116.99 | N |
| ATOM | 8142 | CA | ILE | E | 29 | -7.560 | 49.506 | -51.751 | 118.10 | C |
| ATOM | 8143 | C | ILE | E | 29 | -8.009 | 49.446 | -50.291 | 117.82 | C |
| ATOM | 8144 | O | ILE | E | 29 | -9.179 | 49.671 | -49.990 | 116.96 | O |
| ATOM | 8145 | CB | ILE | E | 29 | -7.919 | 48.170 | -52.445 | 117.51 | C |
| ATOM | 8146 | CG1 | ILE | E | 29 | -7.158 | 46.996 | -51.819 | 118.43 | C |
| ATOM | 8147 | CG2 | ILE | E | 29 | -7.625 | 48.259 | -53.938 | 121.63 | C |
| ATOM | 8148 | CD1 | ILE | E | 29 | -7.710 | 45.630 | -52.204 | 114.47 | C |

TABLE 5-continued

Atomic Coordinates for OMCP-NKG2D (4PDC).

| ATOM | 8149 | H | ILE | E | 29 | -5.626 | 49.235 | -51.484 | 120.39 | H |
|------|------|------|-----|---|----|--------|--------|---------|--------|---|
| ATOM | 8150 | HA | ILE | E | 29 | -8.065 | 50.211 | -52.186 | 121.72 | H |
| ATOM | 8151 | HB | ILE | E | 29 | -8.869 | 48.012 | -52.331 | 121.02 | H |
| ATOM | 8152 | HG12 | ILE | E | 29 | -6.233 | 47.034 | -52.108 | 122.12 | H |
| ATOM | 8153 | HG13 | ILE | E | 29 | -7.204 | 47.074 | -50.853 | 122.12 | H |
| ATOM | 8154 | HG21 | ILE | E | 29 | -7.855 | 47.415 | -54.356 | 125.95 | H |
| ATOM | 8155 | HG22 | ILE | E | 29 | -8.155 | 48.974 | -54.322 | 125.95 | H |
| ATOM | 8156 | HG23 | ILE | E | 29 | -6.681 | 48.443 | -54.063 | 125.95 | H |
| ATOM | 8157 | HD11 | ILE | E | 29 | -7.179 | 44.943 | -51.771 | 117.36 | H |
| ATOM | 8158 | HD12 | ILE | E | 29 | -8.632 | 45.570 | -51.911 | 117.36 | H |
| ATOM | 8159 | HD13 | ILE | E | 29 | -7.660 | 45.530 | -53.167 | 117.36 | H |
| ATOM | 8160 | N | ILE | E | 30 | 7.077 | 49.137 | -49.395 | 116.02 | N |
| ATOM | 8161 | CA | ILE | E | 30 | -7.363 | 49.058 | -47.965 | 115.82 | C |
| ATOM | 8162 | C | ILE | E | 30 | -6.210 | 49.679 | -47.184 | 116.69 | C |
| ATOM | 8163 | O | ILE | E | 30 | -5.058 | 49.618 | -47.614 | 118.17 | O |
| ATOM | 8164 | CB | ILE | E | 30 | -7.569 | 47.595 | -47.501 | 116.57 | C |
| ATOM | 8165 | CG1 | ILE | E | 30 | -8.733 | 46.939 | -48.247 | 115.95 | C |
| ATOM | 8166 | CG2 | ILE | E | 30 | -7.827 | 47.525 | -46.004 | 117.26 | C |
| ATOM | 8167 | CD1 | ILE | E | 30 | -8.751 | 45.428 | -48.111 | 116.72 | C |
| ATOM | 8168 | H | ILE | E | 30 | -8.258 | 48.966 | -49.593 | 119.23 | H |
| ATOM | 8169 | HA | ILE | E | 30 | -8.170 | 49.558 | -47.769 | 118.99 | H |
| ATOM | 8170 | HB | ILE | E | 30 | -6.761 | 47.096 | -47.696 | 119.88 | H |
| ATOM | 8171 | HG12 | ILE | E | 30 | -9.568 | 47.280 | -47.890 | 119.14 | H |
| ATOM | 8172 | HG13 | ILE | E | 30 | -8.664 | 47.153 | -49.190 | 119.14 | H |
| ATOM | 8173 | HG21 | ILE | E | 30 | -7.952 | 46.598 | -45.749 | 120.72 | H |
| ATOM | 8174 | HG22 | ILE | E | 30 | -7.065 | 47.899 | -45.535 | 120.72 | H |
| ATOM | 8175 | HG23 | ILE | E | 30 | -8.626 | 48.036 | -45.798 | 120.72 | H |
| ATOM | 8176 | HD11 | ILE | E | 30 | -9.509 | 45.076 | -48.603 | 120.06 | H |
| ATOM | 8177 | HD12 | ILE | E | 30 | -7.925 | 45.069 | -48.473 | 120.06 | H |
| ATOM | 8178 | HD13 | ILE | E | 30 | -8.829 | 45.196 | -47.172 | 120.06 | H |
| ATOM | 8179 | N | THR | E | 31 | -6.519 | 50.278 | -46.039 | 116.82 | N |
| ATOM | 8180 | CA | THR | E | 31 | -5.482 | 50.768 | -45.141 | 115.25 | C |
| ATOM | 8181 | C | THR | E | 31 | -5.893 | 50.529 | -43.693 | 115.57 | C |
| ATOM | 8182 | O | THR | E | 31 | -7.079 | 50.454 | -43.371 | 117.03 | O |
| ATOM | 8183 | CB | THR | E | 31 | -5.179 | 52.269 | -45.372 | 120.77 | C |
| ATOM | 8184 | OG1 | THR | E | 31 | -3.995 | 52.640 | -44.653 | 124.59 | O |
| ATOM | 8185 | CG2 | THR | E | 31 | -6.341 | 53.143 | -44.936 | 122.38 | C |
| ATOM | 8186 | H | THR | E | 31 | -7.322 | 50.414 | -45.761 | 120.18 | H |
| ATOM | 8187 | HA | THR | E | 31 | -4.665 | 50.271 | -45.304 | 118.30 | H |
| ATOM | 8188 | HB | THR | E | 31 | -5.032 | 52.418 | -46.320 | 124.93 | H |
| ATOM | 8189 | HG1 | THR | E | 31 | -3.342 | 52.184 | -44.919 | 129.51 | H |
| ATOM | 8190 | HG21 | THR | E | 31 | -6.130 | 54.077 | -45.090 | 126.85 | H |
| ATOM | 8191 | HG22 | THR | E | 31 | -7.137 | 52.913 | -45.441 | 126.85 | H |
| ATOM | 8192 | HG23 | THR | E | 31 | -6.518 | 53.012 | -43.991 | 115.94 | H |
| ATOM | 8193 | N | PHE | E | 32 | -4.890 | 50.416 | -42.831 | 116.83 | N |
| ATOM | 8194 | CA | PHE | E | 32 | -5.070 | 50.053 | -41.431 | 118.16 | C |
| ATOM | 8195 | C | PHE | E | 32 | -4.106 | 50.905 | -40.613 | 114.88 | C |
| ATOM | 8196 | O | PHE | E | 32 | -2.923 | 50.965 | -40.937 | 112.85 | O |
| ATOM | 8197 | CB | PHE | E | 32 | 4.81 | 48.553 | -41.239 | 115.97 | C |
| ATOM | 8198 | CG | PHE | E | 32 | -4.831 | 48.096 | -39.805 | 115.97 | C |
| ATOM | 8199 | CD1 | PHE | E | 32 | -6.027 | 47.872 | -39.151 | 115.86 | C |

TABLE 5-continued

Atomic Coordinates for OMCP-NKG2D (4PDC).

| ATOM | 8200 | CD2 | PHE | E | 32 | -3.646 | -39.121 | 47.864 | 117.02 | C |
|---|---|---|---|---|---|---|---|---|---|---|
| ATOM | 8201 | CE1 | PHE | E | 32 | -6.045 | -37.834 | 47.442 | 120.56 | C |
| ATOM | 8202 | CE2 | PHE | E | 32 | -3.658 | -37.807 | 47.430 | 116.71 | C |
| ATOM | 8203 | CZ | PHE | E | 32 | -4.858 | -37.163 | 47.220 | 121.71 | C |
| ATOM | 8204 | H | PHE | E | 32 | -4.067 | -43.042 | 47.220 | 119.12 | H |
| ATOM | 8205 | HA | PHE | E | 32 | -5.978 | -41.154 | 50.549 | 120.19 | H |
| ATOM | 8206 | HB2 | PHE | E | 32 | -5.494 | -41.716 | 50.252 | 115.42 | H |
| ATOM | 8207 | HB3 | PHE | E | 32 | -3.937 | -41.603 | 48.056 | 115.42 | H |
| ATOM | 8208 | HD1 | PHE | E | 32 | -6.829 | -39.597 | 48.339 | 119.03 | H |
| ATOM | 8209 | HD2 | PHE | E | 32 | -2.834 | -39.551 | 48.021 | 120.42 | H |
| ATOM | 8210 | HE1 | PHE | E | 32 | -6.857 | -37.402 | 48.004 | 124.68 | H |
| ATOM | 8211 | HE2 | PHE | E | 32 | -2.856 | -37.358 | 47.300 | 120.05 | H |
| ATOM | 8212 | HZ | PHE | E | 32 | -4.868 | -36.279 | 47.284 | 126.05 | H |
| ATOM | 8213 | Z | PHE | E | 32 | -4.611 | -39.580 | 46.931 | 121.77 | N |
| ATOM | 8214 | CA | ASP | E | 33 | -3.809 | -38.833 | 51.580 | 124.90 | C |
| ATOM | 8215 | O | ASP | E | 33 | -3.354 | -37.464 | 52.557 | 126.03 | C |
| ATOM | 8216 | O | ASP | E | 33 | 2.901 | -36.628 | 52.053 | 124.42 | C |
| ATOM | 8217 | CB | ASP | E | 33 | -4.596 | -38.656 | 52.838 | 123.77 | C |
| ATOM | 8218 | CG | ASP | E | 33 | -5.878 | -37.849 | 53.866 | 127.99 | C |
| ATOM | 8219 | OD1 | ASP | E | 33 | -6.013 | -37.102 | 53.692 | 126.15 | O |
| ATOM | 8220 | OD2 | ASP | E | 33 | -6.762 | -37.959 | 54.571 | 130.81 | O1- |
| ATOM | 8221 | H | ASP | E | 33 | -5.415 | -39.290 | 51.492 | 126.13 | H |
| ATOM | 8222 | HA | ASP | E | 33 | -3.013 | -39.348 | 52.761 | 129.88 | H |
| ATOM | 8223 | HB2 | ASP | E | 33 | -4.036 | -38.194 | 54.509 | 128.52 | H |
| ATOM | 8224 | HB3 | ASP | E | 33 | -4.838 | -39.531 | 54.207 | 128.52 | H |
| ATOM | 8225 | N | GLY | E | 34 | -3.480 | -37.238 | 50.750 | 121.69 | N |
| ATOM | 8226 | CA | GLY | E | 34 | -3.124 | -35.963 | 50.158 | 125.18 | C |
| ATOM | 8227 | C | GLY | E | 34 | -4.353 | -35.137 | 49.841 | 124.85 | C |
| ATOM | 8228 | O | GLY | E | 34 | -4.330 | -34.301 | 48.938 | 124.27 | O |
| ATOM | 8229 | H | GLY | E | 34 | -3.772 | -37.816 | 50.184 | 126.03 | H |
| ATOM | 8230 | HA2 | GLY | E | 34 | -2.629 | -36.111 | 49.338 | 130.22 | H |
| ATOM | 8231 | HA3 | GLY | E | 34 | -2.564 | -35.463 | 50.773 | 130.22 | H |
| ATOM | 8232 | N | LYS | E | 35 | -5.429 | -35.381 | 50.583 | 124.67 | N |
| ATOM | 8233 | CA | LYS | E | 35 | -6.686 | -34.661 | 50.404 | 127.22 | C |
| ATOM | 8234 | O | LYS | E | 35 | -7.814 | -35.616 | 50.034 | 126.78 | C |
| ATOM | 8235 | O | LYS | E | 35 | -8.439 | -35.477 | 48.984 | 129.19 | O |
| ATOM | 8236 | CB | LYS | E | 35 | -7.049 | -33.898 | 51.681 | 130.19 | C |
| ATOM | 8237 | CG | LYS | E | 35 | -8.397 | -33.184 | 51.631 | 133.78 | C |
| ATOM | 8238 | CD | LYS | E | 35 | -8.744 | -32.557 | 52.972 | 133.80 | C |
| ATOM | 8239 | CE | LYS | E | 35 | -10.123 | -31.915 | 52.940 | 141.60 | C |
| ATOM | 8240 | NZ | LYS | E | 35 | -10.580 | -31.489 | 54.294 | 139.39 | N1+ |
| ATOM | 8241 | H | LYS | E | 35 | -5.456 | -35.970 | 51.209 | 129.61 | H |
| ATOM | 8242 | HA | LYS | E | 35 | -6.585 | -34.018 | 49.685 | 132.67 | H |
| ATOM | 8243 | HB2 | LYS | E | 35 | -6.367 | -33.228 | 51.847 | 136.23 | H |
| ATOM | 8244 | HB3 | LYS | E | 35 | -7.076 | -34.525 | 52.421 | 136.23 | H |
| ATOM | 8245 | HG2 | LYS | E | 35 | -9.090 | -33.824 | 51.406 | 140.53 | H |
| ATOM | 8246 | HG3 | LYS | E | 35 | -8.362 | -32.479 | 50.966 | 140.53 | H |
| ATOM | 8247 | HD2 | LYS | E | 35 | -8.093 | -31.870 | 53.184 | 140.56 | H |
| ATOM | 8248 | HD3 | LYS | E | 35 | -8.744 | -33.244 | 53.657 | 140.56 | H |
| ATOM | 8249 | HE2 | LYS | E | 35 | -10.763 | -32.555 | 52.594 | 149.92 | H |
| ATOM | 8250 | HE3 | LYS | E | 35 | -10.094 | -31.130 | 52.371 | 149.92 | H |

TABLE 5-continued

Atomic Coordinates for OMCP-NKG2D (4PDC).

| | | | | | | | | | |
|---|---|---|---|---|---|---|---|---|---|
| ATOM | 8251 | HZ1 | LYS | E | 35 | -10.621 | 54.837 | -32.193 | 147.26 | H |
| ATOM | 8252 | HZ2 | LYS | E | 35 | -11.387 | 54.240 | -31.118 | 147.26 | H |
| ATOM | 8253 | HZ3 | LYS | E | 35 | -10.011 | 54.634 | -30.895 | 147.26 | H |
| ATOM | 8254 | N | ASP | E | 36 | -8.070 | 50.912 | -36.581 | 126.84 | N |
| ATOM | 8255 | CA | ASP | E | 36 | -9.188 | 50.744 | -37.498 | 125.99 | C |
| ATOM | 8256 | C | ASP | E | 36 | -8.724 | 50.409 | -38.907 | 122.89 | C |
| ATOM | 8257 | O | ASP | E | 36 | -7.639 | 50.805 | -39.332 | 121.76 | O |
| ATOM | 8258 | CB | ASP | E | 36 | -10.043 | 52.011 | -37.524 | 131.28 | C |
| ATOM | 8259 | CG | ASP | E | 36 | -10.676 | 52.313 | -36.178 | 134.69 | C |
| ATOM | 8260 | OD1 | ASP | E | 36 | -11.667 | 51.640 | -35.823 | 135.73 | O |
| ATOM | 8261 | OD2 | ASP | E | 36 | -10.185 | 53.223 | -35.478 | 137.15 | O1- |
| ATOM | 8262 | H | ASP | E | 36 | -7.604 | 51.621 | -36.726 | 132.21 | H |
| ATOM | 8263 | HA | ASP | E | 36 | -9.744 | 50.014 | -37.185 | 131.19 | H |
| ATOM | 8264 | HB2 | ASP | E | 36 | -9.485 | 52.766 | -37.769 | 137.54 | H |
| ATOM | 8265 | HB3 | ASP | E | 36 | -10.756 | 51.900 | -38.173 | 137.54 | H |
| ATOM | 8266 | N | ILE | E | 37 | -9.559 | 49.663 | -39.619 | 120.05 | N |
| ATOM | 8267 | CA | ILE | E | 37 | -9.321 | 49.351 | -41.018 | 119.38 | C |
| ATOM | 8268 | C | ILE | E | 37 | -10.347 | 50.116 | -41.835 | 118.03 | C |
| ATOM | 8269 | O | ILE | E | 37 | -11.438 | 50.406 | -41.347 | 116.80 | O |
| ATOM | 8270 | CB | ILE | E | 37 | -9.424 | 47.836 | -41.289 | 117.86 | C |
| ATOM | 8271 | CG1 | ILE | E | 37 | -8.817 | 47.486 | -42.648 | 117.25 | C |
| ATOM | 8272 | CG2 | ILE | E | 37 | -10.872 | 47.365 | -41.198 | 120.70 | C |
| ATOM | 8273 | CD1 | ILE | E | 37 | -8.468 | 46.019 | -42.783 | 117.20 | C |
| ATOM | 8274 | H | ILE | E | 37 | -10.283 | 49.319 | -39.307 | 124.06 | H |
| ATOM | 8275 | HA | ILE | E | 37 | -8.435 | 49.652 | -41.273 | 123.26 | H |
| ATOM | 8276 | HB | ILE | E | 37 | 8.915 | 47.374 | -40.605 | 121.43 | H |
| ATOM | 8277 | HG12 | ILE | E | 37 | -9.455 | 47.707 | -43.344 | 120.70 | H |
| ATOM | 8278 | HG13 | ILE | E | 37 | -8.002 | 47.999 | -42.770 | 120.70 | H |
| ATOM | 8279 | HG21 | ILE | E | 37 | -10.905 | 46.411 | -41.372 | 124.84 | H |
| ATOM | 8280 | HG22 | ILE | E | 37 | -11.209 | 47.550 | -40.307 | 124.84 | H |
| ATOM | 8281 | HG23 | ILE | E | 37 | -11.401 | 47.841 | -41.858 | 124.84 | H |
| ATOM | 8282 | HD11 | ILE | E | 37 | -8.090 | 45.864 | -43.663 | 120.64 | H |
| ATOM | 8283 | HD12 | ILE | E | 37 | -7.823 | 45.784 | -42.099 | 120.64 | H |
| ATOM | 8284 | HD13 | ILE | E | 37 | -9.275 | 45.492 | -42.673 | 120.64 | H |
| ATOM | 8285 | N | ARG | E | 38 | -10.007 | 50.450 | -43.072 | 117.17 | N |
| ATOM | 8286 | CA | ARG | E | 38 | -10.945 | 51.180 | -43.913 | 118.63 | C |
| ATOM | 8287 | C | ARG | E | 38 | -10.678 | 50.981 | -45.400 | 115.53 | C |
| ATOM | 8288 | O | ARG | E | 38 | -9.529 | 50.822 | -45.817 | 113.55 | O |
| ATOM | 8289 | CB | ARG | E | 38 | -10.905 | 52.672 | -43.576 | 121.12 | C |
| ATOM | 8290 | CG | ARG | E | 38 | -9.612 | 53.367 | -43.935 | 124.59 | C |
| ATOM | 8291 | CD | ARG | E | 38 | -9.632 | 54.826 | -43.497 | 134.01 | C |
| ATOM | 8292 | NE | ARG | E | 38 | -8.473 | 55.561 | -44.000 | 136.68 | N |
| ATOM | 8293 | CZ | ARG | E | 38 | -8.437 | 56.219 | -45.156 | 139.43 | C |
| ATOM | 8294 | NH1 | ARG | E | 38 | -9.501 | 56.252 | -45.953 | 138.87 | N1+ |
| ATOM | 8295 | NH2 | ARG | E | 38 | -7.330 | 56.851 | -45.519 | 139.19 | N |
| ATOM | 8296 | H | ARG | E | 38 | -9.253 | 50.270 | -43.444 | 120.60 | H |
| ATOM | 8297 | HA | ARG | E | 38 | -11.842 | 50.859 | -43.729 | 122.36 | H |
| ATOM | 8298 | HB2 | ARG | E | 38 | -11.621 | 53.117 | -44.056 | 125.34 | H |
| ATOM | 8299 | HB3 | ARG | E | 38 | -11.040 | 52.777 | -42.621 | 125.34 | H |
| ATOM | 8300 | HG2 | ARG | E | 38 | -8.874 | 52.925 | -43.487 | 129.50 | H |
| ATOM | 8301 | HG3 | ARG | E | 38 | -9.488 | 53.339 | -44.896 | 129.50 | H |

TABLE 5-continued

Atomic Coordinates for OMCP-NKG2D (4PDC).

| | | | | | | | | | | |
|---|---|---|---|---|---|---|---|---|---|---|
| ATOM | 8302 | HD2 | ARG | E | 38 | -10.433 | 55.252 | -43.841 | 140.81 | H |
| ATOM | 8303 | HD3 | ARG | E | 38 | -9.621 | 54.869 | -42.528 | 140.81 | H |
| ATOM | 8304 | HE | ARG | E | 38 | -7.764 | 55.568 | -43.514 | 144.02 | H |
| ATOM | 8305 | HH11 | ARG | E | 38 | -10.222 | 55.844 | -45.724 | 146.64 | H |
| ATOM | 8306 | HH12 | ARG | E | 38 | -9.467 | 56.681 | -46.698 | 146.64 | H |
| ATOM | 8307 | HH21 | ARG | E | 38 | -6.639 | 56.834 | -45.008 | 147.03 | H |
| ATOM | 8308 | HH22 | ARG | E | 38 | -7.304 | 57.279 | -46.264 | 147.03 | H |
| ATOM | 8309 | N | PRO | E | 39 | -11.746 | 50.991 | -46.210 | 116.34 | N |
| ATOM | 8310 | CA | PRO | E | 39 | -11.558 | 50.928 | -47.660 | 117.96 | C |
| ATOM | 8311 | C | PRO | E | 39 | -11.021 | 52.249 | -48.203 | 117.79 | C |
| ATOM | 8312 | O | PRO | E | 39 | -11.322 | 53.300 | -47.639 | 117.56 | O |
| ATOM | 8313 | CB | PRO | E | 39 | -12.968 | 50.636 | -48.183 | 116.77 | C |
| ATOM | 8314 | CG | PRO | E | 39 | 13.872 | 51.230 | -47.161 | 125.13 | C |
| ATOM | 8315 | CD | PRO | E | 39 | 13.172 | 51.069 | -45.840 | 116.34 | C |
| ATOM | 8316 | HA | PRO | E | 39 | -10.961 | 50.203 | -47.900 | 121.55 | H |
| ATOM | 8317 | HB2 | PRO | E | 39 | -13.095 | 51.063 | -49.045 | 120.12 | H |
| ATOM | 8318 | HB3 | PRO | E | 39 | -13.103 | 49.678 | -48.249 | 120.12 | H |
| ATOM | 8319 | HG2 | PRO | E | 39 | -14.013 | 52.169 | -47.360 | 130.16 | H |
| ATOM | 8320 | HG3 | PRO | E | 39 | -14.716 | 50.753 | -47.159 | 130.16 | H |
| ATOM | 8321 | HD2 | PRO | E | 39 | -13.332 | 51.842 | -45.276 | 119.60 | H |
| ATOM | 8322 | HD3 | PRO | E | 39 | -13.453 | 50.249 | -45.406 | 119.60 | H |
| ATOM | 8323 | N | THR | E | 40 | -10.224 | 52.189 | -49.267 | 116.36 | N |
| ATOM | 8324 | CA | THR | E | 40 | -9.672 | 53.389 | -49.895 | 118.13 | C |
| ATOM | 8325 | C | THR | E | 40 | -9.954 | 53.377 | -51.393 | 118.97 | C |
| ATOM | 8326 | O | THR | E | 40 | -9.306 | 54.076 | -52.169 | 126.46 | O |
| ATOM | 8327 | CB | THR | E | 40 | -8.149 | 53.511 | -49.662 | 119.81 | C |
| ATOM | 8328 | OG1 | THR | E | 40 | -7.473 | 52.405 | -50.272 | 121.82 | O |
| ATOM | 8329 | CG2 | THR | E | 40 | -7.832 | 53.535 | -48.171 | 120.16 | C |
| ATOM | 8330 | H | THR | E | 40 | -9.985 | 51.456 | -49.649 | 119.64 | H |
| ATOM | 8331 | HA | THR | E | 40 | -10.098 | 54.172 | -49.514 | 121.76 | H |
| ATOM | 8332 | HB | THR | E | 40 | -7.829 | 54.338 | -50.055 | 123.77 | H |
| ATOM | 8333 | HG1 | THR | E | 40 | -7.623 | 52.397 | -51.098 | 126.18 | H |
| ATOM | 8334 | HG21 | THR | E | 40 | -6.874 | 53.611 | -48.037 | 124.19 | H |
| ATOM | 8335 | HG22 | THR | E | 40 | -8.270 | 54.292 | -47.752 | 124.19 | H |
| ATOM | 8336 | HG23 | THR | E | 40 | -8.145 | 52.718 | -47.752 | 124.19 | H |
| ATOM | 8337 | N | ILE | E | 41 | -10.930 | 52.569 | -51.783 | 121.52 | N |
| ATOM | 8338 | CA | ILE | E | 41 | -11.361 | 52.471 | -53.166 | 121.60 | C |
| ATOM | 8339 | C | ILE | E | 41 | -12.865 | 52.188 | -53.133 | 121.26 | C |
| ATOM | 8340 | O | ILE | E | 41 | -13.332 | 51.475 | -52.245 | 120.35 | O |
| ATOM | 8341 | CB | ILE | E | 41 | -10.587 | 51.364 | -53.925 | 122.21 | C |
| ATOM | 8342 | CG1 | ILE | E | 41 | -10.776 | 51.488 | -55.437 | 127.01 | C |
| ATOM | 8343 | CG2 | ILE | E | 41 | -11.002 | 49.983 | -53.443 | 122.35 | C |
| ATOM | 8344 | CD1 | ILE | E | 41 | -10.107 | 52.705 | -56.037 | 123.85 | C |
| ATOM | 8345 | H | ILE | E | 41 | -11.368 | 52.055 | -51.251 | 125.82 | H |
| ATOM | 8346 | HA | ILE | E | 41 | -11.214 | 53.318 | -53.616 | 125.92 | H |
| ATOM | 8347 | HB | ILE | E | 41 | -9.642 | 51.476 | -53.733 | 126.65 | H |
| ATOM | 8348 | HG12 | ILE | E | 41 | -10.401 | 50.702 | -55.865 | 132.41 | H |
| ATOM | 8349 | HG13 | ILE | E | 41 | -11.725 | 51.546 | -55.630 | 132.41 | H |
| ATOM | 8350 | HG21 | ILE | E | 41 | -10.501 | 49.313 | -53.936 | 126.82 | H |
| ATOM | 8351 | HG22 | ILE | E | 41 | -10.811 | 49.908 | -52.495 | 126.82 | H |
| ATOM | 8352 | HG23 | ILE | E | 41 | -11.952 | 49.867 | -53.600 | 126.82 | H |

TABLE 5-continued

Atomic Coordinates for OMCP-NKG2D (4PDC).

| | | | | | | | | | |
|---|---|---|---|---|---|---|---|---|---|
| ATOM | 8353 | HD11 | ILE | E | 41 | -10.271 | 52.716 | -56.993 | 128.62 | H |
| ATOM | 8354 | HD12 | ILE | E | 41 | -10.479 | 53.503 | -55.629 | 128.62 | H |
| ATOM | 8355 | HD13 | ILE | E | 41 | -9.154 | 52.659 | -55.864 | 128.62 | H |
| ATOM | 8356 | N | PRO | E | 42 | -13.636 | 52.768 | -54.072 | 123.49 | N |
| ATOM | 8357 | CA | PRO | E | 42 | -15.093 | 52.589 | -54.005 | 124.92 | C |
| ATOM | 8358 | C | PRO | E | 42 | -15.578 | 51.136 | -53.948 | 123.20 | C |
| ATOM | 8359 | O | PRO | E | 42 | -16.532 | 50.858 | -53.219 | 122.70 | O |
| ATOM | 8360 | CB | PRO | E | 42 | -15.575 | 53.260 | -55.294 | 131.54 | C |
| ATOM | 8361 | CG | PRO | E | 42 | -14.576 | 54.332 | -55.538 | 129.15 | C |
| ATOM | 8362 | CD | PRO | E | 42 | -13.256 | 53.771 | -55.086 | 124.13 | C |
| ATOM | 8363 | HA | PRO | E | 42 | -15.451 | 53.072 | -53.245 | 129.90 | H |
| ATOM | 8364 | HB2 | PRO | E | 42 | -15.577 | 52.617 | -56.020 | 137.85 | H |
| ATOM | 8365 | HB3 | PRO | E | 42 | -16.460 | 53.635 | -55.159 | 137.85 | H |
| ATOM | 8366 | HG2 | PRO | E | 42 | -14.551 | 54.544 | -56.484 | 134.98 | H |
| ATOM | 8367 | HG3 | PRO | E | 42 | -14.809 | 55.118 | -55.019 | 134.98 | H |
| ATOM | 8368 | HD2 | PRO | E | 42 | -12.799 | 53.346 | -55.828 | 128.96 | H |
| ATOM | 8369 | HD3 | PRO | E | 42 | -12.713 | 54.468 | -54.685 | 128.96 | H |
| ATOM | 8370 | N | PHE | E | 43 | -14.949 | 50.224 | -54.683 | 122.14 | N |
| ATOM | 8371 | CA | PHE | E | 43 | -15.479 | 48.865 | -54.768 | 122.57 | C |
| ATOM | 8372 | C | PHE | E | 43 | -15.282 | 48.081 | -53.469 | 119.70 | C |
| ATOM | 8373 | O | PHE | E | 43 | -15.809 | 46.981 | -53.327 | 122.95 | O |
| ATOM | 8374 | CB | PHE | E | 43 | -14.863 | 48.109 | -55.963 | 122.38 | C |
| ATOM | 8375 | CG | PHE | E | 43 | -13.453 | 47.620 | -55.747 | 120.54 | C |
| ATOM | 8376 | CD1 | PHE | E | 43 | -13.203 | 46.454 | -55.040 | 122.45 | C |
| ATOM | 8377 | CD2 | PHE | E | 43 | -12.382 | 48.296 | -56.303 | 121.86 | C |
| ATOM | 8378 | CE1 | PHE | E | 43 | -11.912 | 45.996 | -54.859 | 125.06 | C |
| ATOM | 8379 | CE2 | PHE | E | 43 | -11.085 | 47.839 | -56.127 | 120.17 | C |
| ATOM | 8380 | CZ | PHE | E | 43 | -10.852 | 46.686 | -55.403 | 126.57 | C |
| ATOM | 8381 | H | PHE | E | 43 | -14.228 | 50.361 | -55.133 | 127.09 | H |
| ATOM | 8382 | HA | PHE | E | 43 | -16.434 | 48.922 | -54.926 | 127.54 | H |
| ATOM | 8383 | HB2 | PHE | E | 43 | -15.415 | 47.335 | -56.156 | 127.54 | H |
| ATOM | 8384 | HB3 | PHE | E | 43 | -14.854 | 48.702 | -56.731 | 124.65 | H |
| ATOM | 8385 | HD1 | PHE | E | 43 | -13.913 | 45.984 | -54.667 | 126.94 | H |
| ATOM | 8386 | HD2 | PHE | E | 43 | -12.532 | 49.074 | -56.789 | 126.23 | H |
| ATOM | 8387 | HE1 | PHE | E | 43 | -11.759 | 45.218 | -54.372 | 130.07 | H |
| ATOM | 8388 | HE2 | PHE | E | 43 | -10.372 | 48.309 | -56.496 | 124.21 | H |
| ATOM | 8389 | HZ | PHE | E | 43 | -9.983 | 46.378 | -55.283 | 123.05 | H |
| ATOM | 8390 | N | MET | E | 44 | -14.556 | 48.657 | -52.513 | 121.06 | N |
| ATOM | 8391 | CA | MET | E | 44 | -14.353 | 48.017 | -51.212 | 122.24 | C |
| ATOM | 8392 | C | MET | E | 44 | -15.333 | 48.520 | -50.151 | 119.63 | C |
| ATOM | 8393 | O | MET | E | 44 | -15.417 | 47.962 | -49.059 | 119.76 | O |
| ATOM | 8394 | CB | MET | E | 44 | -12.917 | 48.239 | -50.730 | 121.55 | C |
| ATOM | 8395 | CG | MET | E | 44 | -11.878 | 47.391 | -51.456 | 121.18 | C |
| ATOM | 8396 | SD | MET | E | 44 | -12.224 | 45.620 | -51.414 | 121.18 | S |
| ATOM | 8397 | CE | MET | E | 44 | -12.382 | 48.309 | -49.660 | 117.95 | C |
| ATOM | 8398 | H | MET | E | 44 | -14.167 | 49.420 | -52.592 | 127.65 | H |
| ATOM | 8399 | HA | MET | E | 44 | -14.480 | 47.061 | -51.318 | 125.27 | H |
| ATOM | 8400 | HB2 | MET | E | 44 | -12.685 | 49.171 | -50.866 | 123.72 | H |
| ATOM | 8401 | HB3 | MET | E | 44 | -12.869 | 48.023 | -49.786 | 123.72 | H |
| ATOM | 8402 | HG2 | MET | E | 44 | -11.846 | 47.665 | -52.386 | 125.86 | H |
| ATOM | 8403 | HG3 | MET | E | 44 | -11.013 | 47.534 | -51.041 | 125.86 | H |

TABLE 5-continued

Atomic Coordinates for OMCP-NKG2D (4PDC).

| | | | | | | | | | | |
|---|---|---|---|---|---|---|---|---|---|---|
| ATOM | 8404 | HE1 | MET | E | 44 | -12.572 | 44.383 | -49.515 | 121.55 | H |
| ATOM | 8405 | HE2 | MET | E | 44 | -11.550 | 45.564 | -49.223 | 121.55 | H |
| ATOM | 8406 | HE3 | MET | E | 44 | -13.107 | 45.865 | -49.312 | 121.55 | H |
| ATOM | 8407 | N | ILE | E | 45 | -16.073 | 49.575 | -50.467 | 127.83 | N |
| ATOM | 8408 | CA | ILE | E | 45 | -17.051 | 49.108 | -49.527 | 122.95 | C |
| ATOM | 8409 | C | ILE | E | 45 | -18.164 | 49.096 | -49.288 | 121.71 | C |
| ATOM | 8410 | O | ILE | E | 45 | -18.742 | 48.560 | -50.231 | 121.43 | O |
| ATOM | 8411 | CB | ILE | E | 45 | -17.634 | 51.442 | -50.029 | 124.78 | C |
| ATOM | 8412 | CG1 | ILE | E | 45 | -16.560 | 52.530 | -49.916 | 125.65 | C |
| ATOM | 8413 | CG2 | ILE | E | 45 | -18.877 | 51.838 | -49.221 | 132.38 | C |
| ATOM | 8414 | CD1 | ILE | E | 45 | -16.940 | 53.868 | -50.511 | 138.64 | C |
| ATOM | 8415 | H | ILE | E | 45 | -16.029 | 49.999 | -51.214 | 133.40 | H |
| ATOM | 8416 | HA | ILE | E | 45 | -16.612 | 50.275 | -48.678 | 127.54 | H |
| ATOM | 8417 | HB | ILE | E | 45 | -17.884 | 51.344 | -50.961 | 129.73 | H |
| ATOM | 8418 | HG12 | ILE | E | 45 | -16.363 | 52.672 | -48.977 | 130.78 | H |
| ATOM | 8419 | HG13 | ILE | E | 45 | -15.761 | 52.223 | -50.372 | 130.78 | H |
| ATOM | 8420 | HG21 | ILE | E | 45 | -19.219 | 52.680 | -49.561 | 138.86 | H |
| ATOM | 8421 | HG22 | ILE | E | 45 | -19.549 | 51.145 | -49.316 | 138.86 | H |
| ATOM | 8422 | HG23 | ILE | E | 45 | -18.630 | 51.934 | -48.288 | 138.86 | H |
| ATOM | 8423 | HD11 | ILE | E | 45 | -16.202 | 54.487 | -50.392 | 146.36 | H |
| ATOM | 8424 | HD12 | ILE | E | 45 | -17.125 | 53.752 | -51.456 | 146.36 | H |
| ATOM | 8425 | HD13 | ILE | E | 45 | -17.729 | 54.203 | -50.057 | 146.36 | H |
| ATOM | 8426 | N | GLY | E | 46 | -18.445 | 48.832 | -48.015 | 119.01 | N |
| ATOM | 8427 | CA | GLY | E | 46 | -19.499 | 47.909 | -47.638 | 126.57 | C |
| ATOM | 8428 | C | GLY | E | 46 | -19.056 | 46.457 | -47.589 | 128.55 | C |
| ATOM | 8429 | O | GLY | E | 46 | -19.844 | 45.577 | -47.242 | 127.44 | O |
| ATOM | 8430 | H | GLY | E | 46 | -18.032 | 49.181 | -47.346 | 122.81 | H |
| ATOM | 8431 | HA2 | GLY | E | 46 | -19.837 | 48.152 | -46.762 | 131.88 | H |
| ATOM | 8432 | HA3 | GLY | E | 46 | -20.228 | 47.981 | -48.274 | 131.88 | H |
| ATOM | 8433 | N | ASP | E | 47 | -17.800 | 46.196 | -47.936 | 125.13 | N |
| ATOM | 8434 | CA | ASP | E | 47 | -17.279 | 44.834 | -47.895 | 120.13 | C |
| ATOM | 8435 | C | ASP | E | 47 | -17.364 | 44.271 | -46.477 | 119.36 | C |
| ATOM | 8436 | O | ASP | E | 47 | -16.968 | 44.931 | -45.520 | 123.09 | O |
| ATOM | 8437 | CB | ASP | E | 47 | -15.838 | 44.793 | -48.394 | 123.01 | C |
| ATOM | 8438 | CG | ASP | E | 47 | -15.165 | 43.465 | -48.107 | 125.88 | C |
| ATOM | 8439 | OD1 | ASP | E | 47 | -15.541 | 42.456 | -48.738 | 125.43 | O |
| ATOM | 8440 | OD2 | ASP | E | 47 | -14.260 | 43.431 | -47.248 | 129.08 | O1- |
| ATOM | 8441 | H | ASP | E | 47 | -17.231 | 46.786 | -48.198 | 130.15 | H |
| ATOM | 8442 | HA | ASP | E | 47 | -17.816 | 44.271 | -48.475 | 124.15 | H |
| ATOM | 8443 | HB2 | ASP | E | 47 | -15.831 | 44.933 | -49.354 | 127.62 | H |
| ATOM | 8444 | HB3 | ASP | E | 47 | -15.329 | 45.490 | -47.952 | 127.62 | H |
| ATOM | 8445 | N | GLU | E | 48 | -17.891 | 43.056 | -46.351 | 116.14 | N |
| ATOM | 8446 | CA | GLU | E | 48 | -18.090 | 42.431 | -45.044 | 121.48 | C |
| ATOM | 8447 | C | GLU | E | 48 | -17.292 | 41.133 | -44.913 | 117.74 | C |
| ATOM | 8448 | O | GLU | E | 48 | -17.473 | 40.382 | -43.958 | 120.31 | O |
| ATOM | 8449 | CB | GLU | E | 48 | -19.587 | 42.164 | -44.805 | 122.20 | C |
| ATOM | 8450 | CG | GLU | E | 48 | -20.255 | 41.340 | -45.897 | 125.85 | C |
| ATOM | 8451 | CD | GLU | E | 48 | -21.750 | 41.133 | -45.672 | 129.32 | C |
| ATOM | 8452 | OE1 | GLU | E | 48 | -22.447 | 40.770 | -46.643 | 134.96 | O |
| ATOM | 8453 | OE2 | GLU | E | 48 | -22.226 | 41.325 | -44.535 | 126.64 | O1- |
| ATOM | 8454 | H | GLU | E | 48 | -18.143 | 42.568 | -47.012 | 119.37 | H |

TABLE 5-continued

Atomic Coordinates for OMCP-NKG2D (4PDC).

| ATOM | 8455 | HA   | GLU | E | 48 | -17.783 | 43.040 | -44.354 | 125.77 | H |
|------|------|------|-----|---|----|---------|--------|---------|--------|---|
| ATOM | 8456 | HB2  | GLU | E | 48 | -19.688 | 41.684 | -43.969 | 126.64 | H |
| ATOM | 8457 | HB3  | GLU | E | 48 | -20.050 | 43.015 | -44.753 | 126.64 | H |
| ATOM | 8458 | HG2  | GLU | E | 48 | -20.141 | 41.793 | -46.747 | 131.02 | H |
| ATOM | 8459 | HG3  | GLU | E | 48 | -19.836 | 40.466 | -45.931 | 131.02 | H |
| ATOM | 8460 | N    | ILE | E | 49 | -16.399 | 40.887 | -45.867 | 120.94 | N |
| ATOM | 8461 | CA   | ILE | E | 49 | -15.620 | 39.649 | -45.906 | 118.17 | C |
| ATOM | 8462 | C    | ILE | E | 49 | -14.134 | 39.889 | -45.647 | 117.63 | C |
| ATOM | 8463 | O    | ILE | E | 49 | -13.544 | 39.294 | -44.747 | 120.44 | O |
| ATOM | 8464 | CB   | ILE | E | 49 | -15.778 | 38.951 | -47.266 | 121.61 | C |
| ATOM | 8465 | CG1  | ILE | E | 49 | -17.244 | 38.564 | -47.486 | 123.02 | C |
| ATOM | 8466 | CG2  | ILE | E | 49 | -14.893 | 37.713 | -47.346 | 120.19 | C |
| ATOM | 8467 | CD1  | ILE | E | 49 | -17.580 | 38.261 | -48.922 | 130.12 | C |
| ATOM | 8468 | H    | ILE | E | 49 | -16.222 | 41.428 | -46.512 | 125.13 | H |
| ATOM | 8469 | HA   | ILE | E | 49 | -15.950 | 39.048 | -45.220 | 121.81 | H |
| ATOM | 8470 | HB   | ILE | E | 49 | -15.512 | 39.569 | -47.965 | 125.94 | H |
| ATOM | 8471 | HG12 | ILE | E | 49 | -17.442 | 37.773 | -46.961 | 127.63 | H |
| ATOM | 8472 | HG13 | ILE | E | 49 | -17.808 | 39.299 | -47.198 | 127.63 | H |
| ATOM | 8473 | HG21 | ILE | E | 49 | -16.222 | 37.295 | -48.213 | 124.23 | H |
| ATOM | 8474 | HG22 | ILE | E | 49 | -15.950 | 39.048 | -47.233 | 124.23 | H |
| ATOM | 8475 | HG23 | ILE | E | 49 | -15.149 | 37.096 | -46.643 | 124.23 | H |
| ATOM | 8476 | HD11 | ILE | E | 49 | -18.519 | 38.026 | -48.983 | 136.14 | H |
| ATOM | 8477 | HD12 | ILE | E | 49 | -17.400 | 39.047 | -49.461 | 136.14 | H |
| ATOM | 8478 | HD13 | ILE | E | 49 | -17.033 | 37.519 | -49.224 | 136.14 | H |
| ATOM | 8479 | N    | PHE | E | 50 | -13.528 | 40.757 | -46.443 | 114.54 | N |
| ATOM | 8480 | CA   | PHE | E | 50 | -12.085 | 40.946 | -46.383 | 117.11 | C |
| ATOM | 8481 | C    | PHE | E | 50 | -11.662 | 41.946 | -45.309 | 116.26 | C |
| ATOM | 8482 | O    | PHE | E | 50 | -10.690 | 41.706 | -44.593 | 113.97 | O |
| ATOM | 8483 | CB   | PHE | E | 50 | -11.576 | 41.369 | -47.758 | 115.93 | C |
| ATOM | 8484 | CG   | PHE | E | 50 | -12.024 | 40.337 | -48.816 | 117.08 | C |
| ATOM | 8485 | CD1  | PHE | E | 50 | -10.955 | 39.286 | -49.001 | 117.90 | C |
| ATOM | 8486 | CD2  | PHE | E | 50 | -12.980 | 40.391 | -49.591 | 120.60 | C |
| ATOM | 8487 | CE1  | PHE | E | 50 | -11.200 | 38.319 | -49.958 | 119.37 | C |
| ATOM | 8488 | CE2  | PHE | E | 50 | -13.230 | 39.428 | -50.552 | 120.80 | C |
| ATOM | 8489 | CZ   | PHE | E | 50 | -12.342 | 38.391 | -50.733 | 120.26 | C |
| ATOM | 8490 | H    | PHE | E | 50 | -13.927 | 41.248 | -47.026 | 117.44 | H |
| ATOM | 8491 | HA   | PHE | E | 50 | -11.672 | 40.095 | -46.167 | 120.53 | H |
| ATOM | 8492 | HB2  | PHE | E | 50 | -12.024 | 42.187 | -48.023 | 119.11 | H |
| ATOM | 8493 | HB3  | PHE | E | 50 | -10.618 | 41.515 | -47.709 | 119.11 | H |
| ATOM | 8494 | HD1  | PHE | E | 50 | -10.186 | 39.232 | -48.480 | 121.48 | H |
| ATOM | 8495 | HD2  | PHE | E | 50 | -13.584 | 41.088 | -49.472 | 124.72 | H |
| ATOM | 8496 | HE1  | PHE | E | 50 | -10.598 | 37.621 | -50.081 | 123.24 | H |
| ATOM | 8497 | HE2  | PHE | E | 50 | -13.999 | 39.479 | -51.073 | 124.96 | H |
| ATOM | 8498 | HZ   | PHE | E | 50 | -12.507 | 37.744 | -51.381 | 124.31 | H |
| ATOM | 8499 | N    | LEU | E | 51 | -12.392 | 43.050 | -45.180 | 116.41 | N |
| ATOM | 8500 | CA   | LEU | E | 51 | -12.055 | 44.057 | -44.177 | 116.35 | C |
| ATOM | 8501 | C    | LEU | E | 51 | -12.009 | 43.470 | -42.757 | 115.68 | C |
| ATOM | 8502 | O    | LEU | E | 51 | -11.023 | 43.665 | -42.044 | 114.16 | O |
| ATOM | 8503 | CB   | LEU | E | 51 | -13.045 | 45.228 | -44.226 | 117.16 | C |
| ATOM | 8504 | CG   | LEU | E | 51 | -13.007 | 46.120 | -45.473 | 118.54 | C |
| ATOM | 8505 | CD1  | LEU | E | 51 | -14.064 | 47.212 | -45.365 | 124.77 | C |

TABLE 5-continued

Atomic Coordinates for OMCP-NKG2D (4PDC).

| ATOM | 8506 | CD2 | LEU | E | 51 | -11.630 | 46.737 | -45.699 | 122.00 | C |
|---|---|---|---|---|---|---|---|---|---|---|
| ATOM | 8507 | H | LEU | E | 51 | -13.082 | 43.240 | -45.657 | 119.69 | H |
| ATOM | 8508 | HA | LEU | E | 51 | -11.174 | 44.410 | -44.377 | 119.62 | H |
| ATOM | 8509 | HB2 | LEU | E | 51 | -13.943 | 44.866 | -44.161 | 120.59 | H |
| ATOM | 8510 | HB3 | LEU | E | 51 | -12.875 | 45.799 | -43.461 | 120.59 | H |
| ATOM | 8511 | HG | LEU | E | 51 | -13.219 | 45.579 | -46.250 | 122.25 | H |
| ATOM | 8512 | HD11 | LEU | E | 51 | -14.027 | 47.767 | -46.160 | 129.72 | H |
| ATOM | 8513 | HD12 | LEU | E | 51 | -14.938 | 46.799 | -45.290 | 129.72 | H |
| ATOM | 8514 | HD13 | LEU | E | 51 | -13.883 | 47.749 | -44.578 | 129.72 | H |
| ATOM | 8515 | HD21 | LEU | E | 51 | -11.659 | 47.289 | -46.496 | 126.40 | H |
| ATOM | 8516 | HD22 | LEU | E | 51 | -11.398 | 47.278 | -44.929 | 126.40 | H |
| ATOM | 8517 | HD23 | LEU | E | 51 | -10.981 | 46.025 | -45.812 | 126.40 | H |
| ATOM | 8518 | N | PRO | E | 52 | -13.065 | 42.750 | -42.337 | 115.67 | N |
| ATOM | 8519 | CA | PRO | E | 52 | -13.023 | 42.226 | -40.962 | 115.66 | C |
| ATOM | 8520 | C | PRO | E | 52 | -11.952 | 41.159 | -40.777 | 115.48 | C |
| ATOM | 8521 | O | PRO | E | 52 | -11.369 | 41.065 | -39.700 | 115.44 | O |
| ATOM | 8522 | CB | PRO | E | 52 | -14.425 | 41.638 | -40.758 | 119.47 | C |
| ATOM | 8523 | CG | PRO | E | 52 | -14.947 | 41.399 | -42.123 | 123.22 | C |
| ATOM | 8524 | CD | PRO | E | 52 | -14.344 | 42.450 | -43.001 | 119.17 | C |
| ATOM | 8525 | HA | PRO | E | 52 | -12.878 | 42.946 | -40.328 | 119.99 | H |
| ATOM | 8526 | HB2 | PRO | E | 52 | -14.362 | 40.806 | -40.264 | 123.36 | H |
| ATOM | 8527 | HB3 | PRO | E | 52 | -14.982 | 42.277 | -40.285 | 123.36 | H |
| ATOM | 8528 | HG2 | PRO | E | 52 | -14.680 | 40.515 | -42.421 | 127.86 | H |
| ATOM | 8529 | HG3 | PRO | E | 52 | -15.914 | 41.477 | -42.117 | 127.86 | H |
| ATOM | 8530 | HD2 | PRO | E | 52 | -14.189 | 42.099 | -43.892 | 123.00 | H |
| ATOM | 8531 | HD3 | PRO | E | 52 | -14.908 | 43.239 | -43.021 | 123.00 | H |
| ATOM | 8532 | N | PHE | E | 53 | -11.697 | 40.378 | -41.822 | 113.56 | N |
| ATOM | 8533 | CA | PHE | E | 53 | -10.656 | 39.358 | -41.790 | 117.24 | C |
| ATOM | 8534 | C | PHE | E | 53 | -9.283 | 40.010 | -41.632 | 114.01 | C |
| ATOM | 8535 | O | PHE | E | 53 | -8.506 | 39.630 | -40.757 | 113.44 | O |
| ATOM | 8536 | CB | PHE | E | 53 | -10.709 | 38.506 | -43.064 | 116.33 | C |
| ATOM | 8537 | CG | PHE | E | 53 | -9.659 | 37.431 | -43.128 | 115.12 | C |
| ATOM | 8538 | CD1 | PHE | E | 53 | -9.837 | 36.229 | -42.465 | 117.88 | C |
| ATOM | 8539 | CD2 | PHE | E | 53 | -8.505 | 37.614 | -43.867 | 112.71 | C |
| ATOM | 8540 | CE1 | PHE | E | 53 | -8.878 | 35.234 | -42.530 | 114.56 | C |
| ATOM | 8541 | CE2 | PHE | E | 53 | -7.540 | 36.622 | -43.934 | 114.02 | C |
| ATOM | 8542 | CZ | PHE | E | 53 | -7.729 | 35.432 | -43.263 | 113.27 | C |
| ATOM | 8543 | H | PHE | E | 53 | -12.120 | 40.419 | -42.570 | 116.27 | H |
| ATOM | 8544 | HA | PHE | E | 53 | -10.804 | 38.775 | -41.030 | 120.68 | H |
| ATOM | 8545 | HB2 | PHE | E | 53 | -11.577 | 38.076 | -43.115 | 119.60 | H |
| ATOM | 8546 | HB3 | PHE | E | 53 | -10.585 | 39.086 | -43.832 | 119.60 | H |
| ATOM | 8547 | HD1 | PHE | E | 53 | -10.611 | 36.089 | -41.967 | 121.46 | H |
| ATOM | 8548 | HD2 | PHE | E | 53 | -8.372 | 38.416 | -44.320 | 115.25 | H |
| ATOM | 8549 | HE1 | PHE | E | 53 | -9.008 | 34.433 | -42.076 | 117.48 | H |
| ATOM | 8550 | HE2 | PHE | E | 53 | -6.766 | 36.759 | -44.431 | 116.83 | H |
| ATOM | 8551 | HZ | PHE | E | 53 | -7.083 | 34.764 | -43.307 | 115.93 | H |
| ATOM | 8552 | N | TYR | E | 54 | -8.997 | 41.002 | -42.470 | 112.77 | N |
| ATOM | 8553 | CA | TYR | E | 54 | -7.711 | 41.685 | -42.426 | 113.18 | C |
| ATOM | 8554 | C | TYR | E | 54 | -7.531 | 42.456 | -41.122 | 114.10 | C |
| ATOM | 8555 | O | TYR | E | 54 | -6.416 | 42.550 | -40.606 | 112.95 | O |
| ATOM | 8556 | CB | TYR | E | 54 | -7.557 | 42.641 | -43.614 | 113.17 | C |

TABLE 5-continued

Atomic Coordinates for OMCP-NKG2D (4PDC).

| | | | | | | | | | | | |
|---|---|---|---|---|---|---|---|---|---|---|---|
| ATOM | 8557 | CG | TYR | E | 54 | -7.431 | 41.959 | -44.968 | 115.46 | C | |
| ATOM | 8558 | CD1 | TYR | E | 54 | -6.845 | 40.702 | -45.094 | 112.49 | C | |
| ATOM | 8559 | CD2 | TYR | E | 54 | -7.897 | 42.581 | -46.121 | 114.64 | C | |
| ATOM | 8560 | CE1 | TYR | E | 54 | -6.735 | 40.083 | -46.336 | 115.66 | C | |
| ATOM | 8561 | CE2 | TYR | E | 54 | -7.789 | 41.974 | -47.361 | 114.01 | C | |
| ATOM | 8562 | CZ | TYR | E | 54 | -7.212 | 40.726 | -47.462 | 113.86 | C | |
| ATOM | 8563 | OH | TYR | E | 54 | -7.117 | 40.130 | -48.694 | 115.59 | O | |
| ATOM | 8564 | H | TYR | E | 54 | -9.532 | 41.298 | -43.074 | 115.33 | H | |
| ATOM | 8565 | HA | TYR | E | 54 | -7.003 | 41.024 | -42.481 | 115.81 | H | |
| ATOM | 8566 | HB2 | TYR | E | 54 | -8.335 | 43.219 | -43.649 | 115.80 | H | |
| ATOM | 8567 | HB3 | TYR | E | 54 | -6.759 | 43.176 | -43.480 | 115.80 | H | |
| ATOM | 8568 | HD1 | TYR | E | 54 | -6.526 | 40.267 | -44.336 | 114.99 | H | |
| ATOM | 8569 | HD2 | TYR | E | 54 | -8.290 | 43.421 | -46.058 | 117.56 | H | |
| ATOM | 8570 | HE1 | TYR | E | 54 | -6.345 | 39.241 | -46.407 | 118.79 | H | |
| ATOM | 8571 | HE2 | TYR | E | 54 | -8.111 | 42.403 | -48.120 | 116.81 | H | |
| ATOM | 8572 | HH | TYR | E | 54 | -7.445 | 40.632 | -49.283 | 118.71 | H | |
| ATOM | 8573 | N | LYS | E | 55 | 8.612 | 43.018 | -40.592 | 111.71 | N | |
| ATOM | 8574 | CA | LYS | E | 55 | -8.514 | 43.757 | -39.335 | 115.22 | C | |
| ATOM | 8575 | C | LYS | E | 55 | -7.955 | 42.845 | -38.248 | 113.95 | C | |
| ATOM | 8576 | O | LYS | E | 55 | -7.113 | 43.257 | -37.454 | 116.50 | O | |
| ATOM | 8577 | CB | LYS | E | 55 | -9.871 | 44.321 | -38.913 | 116.70 | C | |
| ATOM | 8578 | CG | LYS | E | 55 | 9.803 | 45.205 | -37.669 | 120.44 | C | |
| ATOM | 8579 | CD | LYS | E | 55 | -11.158 | 45.809 | -37.335 | 127.75 | C | |
| ATOM | 8580 | CE | LYS | E | 55 | -11.074 | 46.749 | -36.141 | 130.79 | C | |
| ATOM | 8581 | NZ | LYS | E | 55 | -12.385 | 47.406 | -35.858 | 131.93 | N1+ | |
| ATOM | 8582 | H | LYS | E | 55 | -9.401 | 42.989 | -40.931 | 114.05 | H | |
| ATOM | 8583 | HA | LYS | E | 55 | -7.902 | 44.500 | -39.451 | 118.27 | H | |
| ATOM | 8584 | HB2 | LYS | E | 55 | -10.227 | 44.857 | -39.639 | 120.04 | H | |
| ATOM | 8585 | HB3 | LYS | E | 55 | -10.471 | 43.584 | -38.722 | 120.04 | H | |
| ATOM | 8586 | HG2 | LYS | E | 55 | -9.515 | 44.671 | -36.912 | 124.53 | H | |
| ATOM | 8587 | HG3 | LYS | E | 55 | -9.178 | 45.930 | -37.825 | 124.53 | H | |
| ATOM | 8588 | HD2 | LYS | E | 55 | -11.479 | 46.315 | -38.098 | 133.29 | H | |
| ATOM | 8589 | HD3 | LYS | E | 55 | -11.780 | 45.098 | -37.118 | 133.29 | H | |
| ATOM | 8590 | HE2 | LYS | E | 55 | -10.812 | 46.244 | -35.355 | 136.95 | H | |
| ATOM | 8591 | HE3 | LYS | E | 55 | -10.421 | 47.443 | -36.326 | 136.95 | H | |
| ATOM | 8592 | HZ1 | LYS | E | 55 | -12.308 | 47.949 | -35.157 | 138.32 | H | |
| ATOM | 8593 | HZ2 | LYS | E | 55 | -12.645 | 47.881 | -36.565 | 138.32 | H | |
| ATOM | 8594 | HZ3 | LYS | E | 55 | -13.001 | 46.790 | -35.681 | 138.32 | H | |
| ATOM | 8595 | N | ASN | E | 56 | -8.406 | 41.596 | -38.236 | 112.27 | N | |
| ATOM | 8596 | CA | ASN | E | 56 | 7.924 | 40.627 | -37.264 | 113.08 | C | |
| ATOM | 8597 | C | ASN | E | 56 | -6.491 | 40.185 | -37.546 | 115.68 | C | |
| ATOM | 8598 | O | ASN | E | 56 | -5.659 | 40.159 | -36.642 | 113.45 | O | |
| ATOM | 8599 | CB | ASN | E | 56 | -8.843 | 39.404 | -37.234 | 120.81 | C | |
| ATOM | 8600 | CG | ASN | E | 56 | -10.166 | 39.686 | -36.549 | 125.65 | C | |
| ATOM | 8601 | OD1 | ASN | E | 56 | -10.228 | 40.453 | -35.587 | 132.51 | O | |
| ATOM | 8602 | ND2 | ASN | E | 56 | -11.234 | 39.066 | -37.040 | 127.48 | N | |
| ATOM | 8603 | H | ASN | E | 56 | -8.993 | 41.285 | -38.782 | 114.72 | H | |
| ATOM | 8604 | HA | ASN | E | 56 | -7.941 | 41.032 | -36.383 | 115.70 | H | |
| ATOM | 8605 | HB2 | ASN | E | 56 | -9.029 | 39.126 | -38.145 | 124.97 | H | |
| ATOM | 8606 | HB3 | ASN | E | 56 | -8.402 | 38.687 | -36.752 | 124.97 | H | |
| ATOM | 8607 | HD21 | ASN | E | 56 | -12.007 | 39.194 | -36.685 | 132.98 | H | |

TABLE 5-continued

Atomic Coordinates for OMCP-NKG2D (4PDC).

| ATOM | 8608 | HD22 | ASN | E | 56 | -11.152 | 38.536 | -37.712 | 132.98 | H |
|------|------|------|-----|---|----|---------|--------|---------|--------|---|
| ATOM | 8609 | N | VAL | E | 57 | -6.209 | 39.830 | -38.795 | 112.98 | N |
| ATOM | 8610 | CA | VAL | E | 57 | -4.869 | 39.403 | -39.172 | 111.78 | C |
| ATOM | 8611 | O | VAL | E | 57 | -3.849 | 40.512 | -38.932 | 110.70 | O |
| ATOM | 8612 | O | VAL | E | 57 | -2.742 | 40.250 | -38.470 | 112.79 | O |
| ATOM | 8613 | CB | VAL | E | 57 | -4.811 | 38.970 | -40.651 | 115.00 | C |
| ATOM | 8614 | CG1 | VAL | E | 57 | -3.373 | 38.701 | -41.085 | 113.02 | C |
| ATOM | 8615 | CG2 | VAL | E | 57 | -5.665 | 37.734 | -40.867 | 111.75 | C |
| ATOM | 8616 | H | VAL | E | 57 | -6.776 | 39.828 | -39.441 | 115.57 | H |
| ATOM | 8617 | HA | VAL | E | 57 | -4.616 | 38.641 | -38.627 | 114.14 | H |
| ATOM | 8618 | HB | VAL | E | 57 | -5.166 | 39.682 | -41.205 | 118.00 | H |
| ATOM | 8619 | HG11 | VAL | E | 57 | -3.369 | 38.432 | -42.016 | 115.62 | H |
| ATOM | 8620 | HG12 | VAL | E | 57 | -2.853 | 39.513 | -40.972 | 115.62 | H |
| ATOM | 8621 | HG13 | VAL | E | 57 | -3.004 | 37.993 | -40.533 | 115.62 | H |
| ATOM | 8622 | HG21 | VAL | E | 57 | -5.617 | 37.476 | -41.801 | 114.10 | H |
| ATOM | 8623 | HG22 | VAL | E | 57 | -5.327 | 37.016 | -40.308 | 115.09 | H |
| ATOM | 8624 | HG23 | VAL | E | 57 | -6.582 | 37.938 | -40.626 | 114.10 | H |
| ATOM | 8625 | N | PHE | E | 58 | -4.216 | 41.746 | -39.259 | 112.71 | N |
| ATOM | 8626 | CA | PHE | E | 58 | -3.288 | 42.862 | -39.119 | 112.91 | C |
| ATOM | 8627 | C | PHE | E | 58 | -1.881 | 43.177 | -37.645 | 115.14 | C |
| ATOM | 8628 | O | PHE | E | 58 | -3.030 | 43.346 | -37.236 | 112.36 | O |
| ATOM | 8629 | CB | PHE | E | 58 | -3.814 | 44.103 | -39.851 | 110.07 | C |
| ATOM | 8630 | CG | PHE | E | 58 | -3.890 | 43.946 | -41.352 | 113.18 | C |
| ATOM | 8631 | CD1 | PHE | E | 58 | -3.394 | 42.810 | -41.982 | 113.27 | C |
| ATOM | 8632 | CD2 | PHE | E | 58 | -4.463 | 44.938 | -42.135 | 115.09 | C |
| ATOM | 8633 | CE1 | PHE | E | 58 | -3.470 | 42.667 | -43.360 | 114.15 | C |
| ATOM | 8634 | CE2 | PHE | E | 58 | -4.542 | 44.799 | -43.518 | 114.94 | C |
| ATOM | 8635 | CZ | PHE | E | 58 | -4.045 | 43.664 | -44.127 | 115.54 | C |
| ATOM | 8636 | H | PHE | E | 58 | -4.991 | 41.964 | -39.561 | 115.25 | H |
| ATOM | 8637 | HA | PHE | E | 58 | -2.441 | 42.616 | -39.523 | 115.49 | H |
| ATOM | 8638 | HB2 | PHE | E | 58 | -4.708 | 44.300 | -39.529 | 112.09 | H |
| ATOM | 8639 | HB3 | PHE | E | 58 | -3.226 | 44.850 | -39.662 | 112.09 | H |
| ATOM | 8640 | HD1 | PHE | E | 58 | -3.008 | 42.135 | -41.471 | 115.93 | H |
| ATOM | 8641 | HD2 | PHE | E | 58 | -4.801 | 45.703 | -41.731 | 118.11 | H |
| ATOM | 8642 | HE1 | PHE | E | 58 | -3.134 | 41.902 | -43.768 | 116.98 | H |
| ATOM | 8643 | HE2 | PHE | E | 58 | -4.928 | 45.471 | -44.032 | 117.92 | H |
| ATOM | 8644 | HZ | PHE | E | 58 | -4.095 | 43.571 | -45.051 | 118.65 | H |
| ATOM | 8645 | N | SER | E | 59 | -4.088 | 43.250 | -36.844 | 112.44 | N |
| ATOM | 8646 | CA | SER | E | 59 | -3.935 | 43.540 | -35.418 | 115.47 | C |
| ATOM | 8647 | C | SER | E | 59 | -3.058 | 42.488 | -34.743 | 115.91 | C |
| ATOM | 8648 | O | SER | E | 59 | -2.148 | 42.820 | -33.978 | 114.84 | O |
| ATOM | 8649 | CB | SER | E | 59 | -5.299 | 43.608 | -34.727 | 119.05 | C |
| ATOM | 8650 | OG | SER | E | 59 | -6.086 | 44.656 | -35.260 | 126.66 | O |
| ATOM | 8651 | H | SER | E | 59 | -4.902 | 43.137 | -37.098 | 114.93 | H |
| ATOM | 8652 | HA | SER | E | 59 | -3.503 | 44.402 | -35.315 | 118.56 | H |
| ATOM | 8653 | HB2 | SER | E | 59 | -5.763 | 42.766 | -34.860 | 117.92 | H |
| ATOM | 8654 | HB3 | SER | E | 59 | -5.165 | 43.766 | -33.779 | 118.65 | H |
| ATOM | 8655 | HG | SER | E | 59 | -6.211 | 44.532 | -36.082 | 122.86 | H |
| ATOM | 8656 | N | GLU | E | 60 | -3.325 | 41.221 | -35.046 | 112.44 | N |
| ATOM | 8657 | CA | GLU | E | 60 | -2.553 | 40.120 | -34.483 | 131.99 | C |
| ATOM | 8658 | C | GLU | E | 60 | -1.097 | 40.145 | -34.956 | 114.24 | C |

TABLE 5-continued

Atomic Coordinates for OMCP-NKG2D (4PDC).

| | | | | | | | | | |
|---|---|---|---|---|---|---|---|---|---|
| ATOM | 8659 | O | GLU | E | 60 | -0.192 | 39.806 | -34.197 | 118.48 | O |
| ATOM | 8660 | CB | GLU | E | 60 | -3.198 | 38.780 | -34.844 | 119.87 | C |
| ATOM | 8661 | CG | GLU | E | 60 | -4.571 | 38.559 | -34.219 | 127.96 | C |
| ATOM | 8662 | CD | GLU | E | 60 | -4.514 | 38.305 | -32.722 | 141.64 | C |
| ATOM | 8663 | OE1 | GLU | E | 60 | -3.399 | 38.165 | -32.175 | 141.26 | O |
| ATOM | 8664 | OE2 | GLU | E | 60 | -5.592 | 38.243 | -32.090 | 150.70 | O1- |
| ATOM | 8665 | H | GLU | E | 60 | -3.952 | 40.972 | -35.579 | 117.09 | H |
| ATOM | 8666 | HA | GLU | E | 60 | -2.553 | 40.199 | -33.517 | 119.30 | H |
| ATOM | 8667 | HB2 | GLU | E | 60 | -3.302 | 38.734 | -35.808 | 123.84 | H |
| ATOM | 8668 | HB3 | GLU | E | 60 | -2.618 | 38.064 | -34.543 | 123.84 | H |
| ATOM | 8669 | HG2 | GLU | E | 60 | -5.114 | 39.348 | -34.367 | 133.56 | H |
| ATOM | 8670 | HG3 | GLU | E | 60 | -4.986 | 37.788 | -34.637 | 133.56 | H |
| ATOM | 8671 | N | PHE | E | 61 | -0.873 | 40.545 | -36.206 | 115.60 | N |
| ATOM | 8672 | CA | PHE | E | 61 | 0.484 | 40.651 | -36.745 | 114.83 | C |
| ATOM | 8673 | C | PHE | E | 61 | 1.364 | 41.506 | -35.841 | 113.77 | C |
| ATOM | 8674 | O | PHE | E | 61 | 2.510 | 41.154 | -35.556 | 115.86 | O |
| ATOM | 8675 | CB | PHE | E | 61 | 0.466 | 41.242 | -38.161 | 113.27 | C |
| ATOM | 8676 | CG | PHE | E | 61 | 1.838 | 41.467 | -38.745 | 110.38 | C |
| ATOM | 8677 | CD1 | PHE | E | 61 | 2.456 | 40.482 | -39.495 | 110.57 | C |
| ATOM | 8678 | CD2 | PHE | E | 61 | 2.506 | 42.668 | -38.548 | 112.22 | C |
| ATOM | 8679 | CE1 | PHE | E | 61 | 3.722 | 40.689 | -40.033 | 113.44 | C |
| ATOM | 8680 | CE2 | PHE | E | 61 | 3.764 | 42.881 | -39.087 | 112.04 | C |
| ATOM | 8681 | CZ | PHE | E | 61 | 4.372 | 41.889 | -39.825 | 112.36 | C |
| ATOM | 8682 | H | PHE | E | 61 | -1.491 | 40.762 | -36.764 | 118.72 | H |
| ATOM | 8683 | HA | PHE | E | 61 | 0.875 | 39.764 | -36.795 | 117.79 | H |
| ATOM | 8684 | HB2 | PHE | E | 61 | 0.010 | 40.634 | -38.748 | 115.92 | H |
| ATOM | 8685 | HB3 | PHE | E | 61 | 0.011 | 42.099 | -38.136 | 115.92 | H |
| ATOM | 8686 | HD1 | PHE | E | 61 | 2.022 | 39.671 | -39.635 | 112.69 | H |
| ATOM | 8687 | HD2 | PHE | E | 61 | 2.102 | 43.341 | -38.049 | 114.66 | H |
| ATOM | 8688 | HE1 | PHE | E | 61 | 4.129 | 40.019 | -40.534 | 116.13 | H |
| ATOM | 8689 | HE2 | PHE | E | 61 | 4.201 | 43.689 | -38.944 | 114.45 | H |
| ATOM | 8690 | HZ | PHE | E | 61 | 5.217 | 42.029 | -40.187 | 114.83 | H |
| ATOM | 8691 | N | PHE | E | 62 | 0.821 | 42.630 | -35.385 | 113.88 | N |
| ATOM | 8692 | CA | PHE | E | 62 | 1.579 | 43.544 | -34.541 | 115.96 | C |
| ATOM | 8693 | C | PHE | E | 62 | 1.603 | 43.105 | -33.079 | 114.71 | C |
| ATOM | 8694 | O | PHE | E | 62 | 2.630 | 43.211 | -32.414 | 111.05 | O |
| ATOM | 8695 | CB | PHE | E | 62 | 1.008 | 44.956 | -34.649 | 116.31 | C |
| ATOM | 8696 | CG | PHE | E | 62 | 1.245 | 45.598 | -35.986 | 116.94 | C |
| ATOM | 8697 | CD1 | PHE | E | 62 | 2.509 | 46.039 | -36.340 | 116.08 | C |
| ATOM | 8698 | CD2 | PHE | E | 62 | 0.207 | 45.758 | -36.888 | 113.45 | C |
| ATOM | 8699 | CE1 | PHE | E | 62 | 2.734 | 46.631 | -37.569 | 116.16 | C |
| ATOM | 8700 | CE2 | PHE | E | 62 | 0.424 | 46.349 | -38.117 | 115.64 | C |
| ATOM | 8701 | CZ | PHE | E | 62 | 1.691 | 46.784 | -38.459 | 117.68 | C |
| ATOM | 8702 | H | PHE | E | 62 | 0.017 | 42.886 | -35.551 | 116.66 | H |
| ATOM | 8703 | HA | PHE | E | 62 | 2.496 | 43.571 | -34.856 | 119.16 | H |
| ATOM | 8704 | HB2 | PHE | E | 62 | 0.049 | 44.918 | -34.503 | 115.58 | H |
| ATOM | 8705 | HB3 | PHE | E | 62 | 1.422 | 45.515 | -33.973 | 119.30 | H |
| ATOM | 8706 | HD1 | PHE | E | 62 | 3.214 | 45.937 | -35.743 | 116.15 | H |
| ATOM | 8707 | HD2 | PHE | E | 62 | -0.647 | 45.467 | -36.663 | 119.39 | H |
| ATOM | 8708 | HE1 | PHE | E | 62 | 3.587 | 46.923 | -37.795 | 119.39 | H |
| ATOM | 8709 | HE2 | PHE | E | 62 | -0.281 | 46.451 | -38.715 | 118.77 | H |

TABLE 5-continued

Atomic Coordinates for OMCP-NKG2D (4PDC).

| | | | | | | | | | | |
|---|---|---|---|---|---|---|---|---|---|---|
| ATOM | 8710 | HZ | PHE | E | 62 | 1.839 | 47.182 | -39.287 | 121.21 | H |
| ATOM | 8711 | N | SER | E | 63 | 0.479 | 42.603 | -32.580 | 114.62 | N |
| ATOM | 8712 | CA | SER | E | 63 | 0.375 | 42.269 | -31.163 | 117.58 | C |
| ATOM | 8713 | C | SER | E | 63 | 1.149 | 40.993 | -30.833 | 118.25 | C |
| ATOM | 8714 | O | SER | E | 63 | 1.469 | 40.744 | -29.675 | 115.30 | O |
| ATOM | 8715 | CB | SER | E | 63 | 1.092 | 42.124 | -30.749 | 121.93 | C |
| ATOM | 8716 | OG | SER | E | 63 | -1.698 | 41.011 | -31.375 | 126.07 | O |
| ATOM | 8717 | H | SER | E | 63 | -0.233 | 42.446 | -33.036 | 117.54 | H |
| ATOM | 8718 | HA | SER | E | 63 | 0.760 | 42.992 | -30.643 | 121.09 | H |
| ATOM | 8719 | HB2 | SER | E | 63 | -1.136 | 42.007 | -29.787 | 126.31 | H |
| ATOM | 8720 | HB3 | SER | E | 63 | -1.571 | 42.928 | -31.006 | 126.31 | H |
| ATOM | 8721 | HG | SER | E | 63 | -2.501 | 40.948 | -31.136 | 131.29 | H |
| ATOM | 8722 | N | LEU | E | 63 | 1.453 | 40.196 | -31.854 | 115.25 | N |
| ATOM | 8723 | CA | LEU | E | 64 | 2.259 | 38.989 | -31.684 | 116.15 | C |
| ATOM | 8724 | C | LEU | E | 64 | 3.760 | 39.284 | -31.762 | 118.76 | C |
| ATOM | 8725 | O | LEU | E | 64 | 4.583 | 38.437 | -31.411 | 113.28 | O |
| ATOM | 8726 | CB | LEU | E | 64 | 1.895 | 37.948 | -32.745 | 118.37 | C |
| ATOM | 8727 | CG | LEU | E | 64 | 0.535 | 37.263 | -32.613 | 126.98 | C |
| ATOM | 8728 | CD1 | LEU | E | 64 | 0.210 | 36.496 | -33.888 | 124.22 | C |
| ATOM | 8729 | CD2 | LEU | E | 64 | 0.517 | 36.335 | -31.413 | 122.89 | C |
| ATOM | 8730 | H | LEU | E | 64 | 1.201 | 40.334 | -32.665 | 118.30 | H |
| ATOM | 8731 | HA | LEU | E | 64 | 2.074 | 38.606 | -30.813 | 119.38 | H |
| ATOM | 8732 | HB2 | LEU | E | 64 | 1.912 | 38.384 | -33.612 | 122.05 | H |
| ATOM | 8733 | HB3 | LEU | E | 64 | 2.569 | 37.251 | -32.725 | 122.05 | H |
| ATOM | 8734 | HG | LEU | E | 64 | -0.150 | 37.938 | -32.483 | 132.37 | H |
| ATOM | 8735 | HD11 | LEU | E | 64 | -0.655 | 36.069 | -33.787 | 129.07 | H |
| ATOM | 8736 | HD12 | LEU | E | 64 | 0.187 | 37.118 | -34.633 | 129.07 | H |
| ATOM | 8737 | HD13 | LEU | E | 64 | 0.895 | 35.827 | -34.037 | 129.07 | H |
| ATOM | 8738 | HD21 | LEU | E | 64 | -0.355 | 35.915 | -31.353 | 127.46 | H |
| ATOM | 8739 | HD22 | LEU | E | 64 | 1.203 | 35.660 | -31.526 | 127.46 | H |
| ATOM | 8740 | HD23 | LEU | E | 64 | 0.691 | 36.853 | -30.611 | 127.46 | H |
| ATOM | 8741 | N | PHE | E | 65 | 4.118 | 40.475 | -32.233 | 116.54 | N |
| ATOM | 8742 | CA | PHE | E | 65 | 5.526 | 40.845 | -32.337 | 116.39 | C |
| ATOM | 8743 | C | PHE | E | 65 | 6.045 | 41.265 | -30.970 | 118.01 | C |
| ATOM | 8744 | O | PHE | E | 65 | 5.574 | 42.242 | -30.391 | 117.22 | O |
| ATOM | 8745 | CB | PHE | E | 65 | 5.726 | 41.971 | -33.354 | 114.80 | C |
| ATOM | 8746 | CG | PHE | E | 65 | 7.166 | 42.375 | -33.535 | 114.42 | C |
| ATOM | 8747 | CD1 | PHE | E | 65 | 8.128 | 41.434 | -33.870 | 116.17 | C |
| ATOM | 8748 | CD2 | PHE | E | 65 | 7.554 | 43.693 | -33.380 | 115.24 | C |
| ATOM | 8749 | CE1 | PHE | E | 65 | 9.454 | 41.805 | -34.040 | 114.97 | C |
| ATOM | 8750 | CE2 | PHE | E | 65 | 8.876 | 44.070 | -33.549 | 114.62 | C |
| ATOM | 8751 | CZ | PHE | E | 65 | 9.824 | 43.127 | -33.876 | 116.09 | C |
| ATOM | 8752 | H | PHE | E | 65 | 3.569 | 41.082 | -32.497 | 119.85 | H |
| ATOM | 8753 | HA | PHE | E | 65 | 6.038 | 40.075 | -32.632 | 119.67 | H |
| ATOM | 8754 | HB2 | PHE | E | 65 | 5.390 | 41.678 | -34.216 | 117.76 | H |
| ATOM | 8755 | HB3 | PHE | E | 65 | 5.234 | 42.752 | -33.057 | 117.76 | H |
| ATOM | 8756 | HD1 | PHE | E | 65 | 7.883 | 40.544 | -33.979 | 119.41 | H |
| ATOM | 8757 | HD2 | PHE | E | 65 | 6.919 | 44.335 | -33.157 | 118.29 | H |
| ATOM | 8758 | HE1 | PHE | E | 65 | 10.092 | 41.166 | -34.262 | 117.96 | H |
| ATOM | 8759 | HE2 | PHE | E | 65 | 9.124 | 44.959 | -33.439 | 117.55 | H |
| ATOM | 8760 | HZ | PHE | E | 65 | 10.712 | 43.379 | -33.991 | 119.31 | H |

TABLE 5-continued

Atomic Coordinates for OMCP-NKG2D (4PDC).

| ATOM | 8761 | N | ARG | E | 66 | 7.018 | 40.520 | -30.459 | 118.88 | N |
|---|---|---|---|---|---|---|---|---|---|---|
| ATOM | 8762 | CA | ARG | E | 66 | 7.536 | 40.756 | -29.118 | 120.69 | C |
| ATOM | 8763 | C | ARG | E | 66 | 8.694 | 41.748 | -29.143 | 118.93 | C |
| ATOM | 8764 | O | ARG | E | 66 | 9.834 | 41.401 | -28.836 | 116.41 | O |
| ATOM | 8765 | CB | ARG | E | 66 | 7.968 | 39.434 | -28.484 | 125.21 | C |
| ATOM | 8766 | CG | ARG | E | 66 | 6.879 | 38.373 | -28.539 | 129.70 | C |
| ATOM | 8767 | CD | ARG | E | 66 | 7.008 | 37.358 | -27.421 | 135.51 | C |
| ATOM | 8768 | NE | ARG | E | 66 | 8.129 | 36.441 | -27.606 | 145.62 | N |
| ATOM | 8769 | CZ | ARG | E | 66 | 8.038 | 35.247 | -28.185 | 149.30 | C |
| ATOM | 8770 | NH1 | ARG | E | 66 | 6.876 | 34.804 | -28.652 | 148.42 | N1+ |
| ATOM | 8771 | NH2 | ARG | E | 66 | 9.117 | 34.488 | -28.298 | 150.83 | N |
| ATOM | 8772 | H | ARG | E | 66 | 7.397 | 39.868 | -30.872 | 122.66 | H |
| ATOM | 8773 | HA | ARG | E | 66 | 6.831 | 41.134 | -28.570 | 124.83 | H |
| ATOM | 8774 | HB2 | ARG | E | 66 | 8.743 | 39.094 | -28.958 | 130.25 | H |
| ATOM | 8775 | HB3 | ARG | E | 66 | 8.190 | 39.588 | -27.552 | 130.25 | H |
| ATOM | 8776 | HG2 | ARG | E | 66 | 6.013 | 38.803 | -28.458 | 135.64 | H |
| ATOM | 8777 | HG3 | ARG | E | 66 | 6.939 | 37.901 | -29.384 | 135.64 | H |
| ATOM | 8778 | HD2 | ARG | E | 66 | 7.142 | 37.828 | -26.583 | 142.61 | H |
| ATOM | 8779 | HD3 | ARG | E | 66 | 6.195 | 36.831 | -27.378 | 142.61 | H |
| ATOM | 8780 | HE | ARG | E | 66 | 8.901 | 36.691 | -27.322 | 154.74 | H |
| ATOM | 8781 | HH11 | ARG | E | 66 | 6.170 | 35.290 | -28.581 | 158.11 | H |
| ATOM | 8782 | HH12 | ARG | E | 66 | 6.829 | 34.030 | -29.025 | 158.11 | H |
| ATOM | 8783 | HH21 | ARG | E | 66 | 9.873 | 34.768 | -27.999 | 160.99 | H |
| ATOM | 8784 | HH22 | ARG | E | 66 | 9.062 | 33.716 | -28.674 | 160.99 | H |
| ATOM | 8785 | N | ARG | E | 67 | 8.380 | 42.984 | -29.513 | 118.67 | N |
| ATOM | 8786 | CA | ARG | E | 67 | 9.361 | 44.059 | -29.578 | 120.20 | C |
| ATOM | 8787 | C | ARG | E | 67 | 10.020 | 44.281 | -28.218 | 121.69 | C |
| ATOM | 8788 | O | ARG | E | 67 | 9.332 | 44.366 | -27.204 | 117.08 | O |
| ATOM | 8789 | CB | ARG | E | 67 | 8.685 | 45.349 | -30.057 | 121.97 | C |
| ATOM | 8790 | CG | ARG | E | 67 | 9.601 | 46.559 | -30.135 | 127.90 | C |
| ATOM | 8791 | CD | ARG | E | 67 | 8.884 | 47.772 | -30.720 | 140.95 | C |
| ATOM | 8792 | NE | ARG | E | 67 | 8.218 | 48.579 | -29.698 | 159.70 | N |
| ATOM | 8793 | CZ | ARG | E | 67 | 6.960 | 48.412 | -29.296 | 172.67 | C |
| ATOM | 8794 | NH1 | ARG | E | 67 | 6.199 | 47.460 | -29.821 | 175.12 | N1+ |
| ATOM | 8795 | NH2 | ARG | E | 67 | 6.457 | 49.206 | -28.360 | 172.00 | N |
| ATOM | 8796 | H | ARG | E | 67 | 7.587 | 43.230 | -29.736 | 122.41 | H |
| ATOM | 8797 | HA | ARG | E | 67 | 10.053 | 43.823 | -30.216 | 124.24 | H |
| ATOM | 8798 | HB2 | ARG | E | 67 | 8.323 | 45.197 | -30.944 | 126.37 | H |
| ATOM | 8799 | HB3 | ARG | E | 67 | 7.964 | 45.566 | -29.444 | 126.37 | H |
| ATOM | 8800 | HG2 | ARG | E | 67 | 9.906 | 46.787 | -29.243 | 133.48 | H |
| ATOM | 8801 | HG3 | ARG | E | 67 | 10.358 | 46.350 | -30.705 | 133.48 | H |
| ATOM | 8802 | HD2 | ARG | E | 67 | 9.532 | 48.335 | -31.172 | 149.14 | H |
| ATOM | 8803 | HD3 | ARG | E | 67 | 8.211 | 47.468 | -31.349 | 149.14 | H |
| ATOM | 8804 | HE | ARG | E | 67 | 8.673 | 49.208 | -29.328 | 171.64 | H |
| ATOM | 8805 | HH11 | ARG | E | 67 | 6.518 | 46.941 | -30.429 | 190.15 | H |
| ATOM | 8806 | HH12 | ARG | E | 67 | 5.388 | 47.361 | -29.554 | 190.15 | H |
| ATOM | 8807 | HH21 | ARG | E | 67 | 6.944 | 49.825 | -28.014 | 186.40 | H |
| ATOM | 8808 | HH22 | ARG | E | 67 | 5.645 | 49.101 | -28.097 | 186.40 | H |
| ATOM | 8809 | N | VAL | E | 68 | 11.348 | 44.362 | -28.193 | 122.03 | N |
| ATOM | 8810 | CA | VAL | E | 68 | 12.059 | 44.659 | -26.953 | 120.34 | C |
| ATOM | 8811 | C | VAL | E | 68 | 12.343 | 46.156 | -26.894 | 122.74 | C |

TABLE 5-continued

Atomic Coordinates for OMCP-NKG2D (4PDC).

| | | | | | | | | | |
|---|---|---|---|---|---|---|---|---|---|
| ATOM | 8812 | Q | VAL | E | 68 | 12.682 | 46.762 | -27.912 | 125.42 | Q |
| ATOM | 8813 | CB | VAL | E | 68 | 13.384 | 43.867 | -26.823 | 127.96 | C |
| ATOM | 8814 | CG1 | VAL | E | 68 | 13.108 | 42.374 | -26.817 | 130.54 | C |
| ATOM | 8815 | CG2 | VAL | E | 68 | 14.361 | 44.220 | -27.936 | 128.18 | C |
| ATOM | 8816 | H | VAL | E | 68 | 11.858 | 44.250 | -28.877 | 126.44 | H |
| ATOM | 8817 | HA | VAL | E | 68 | 11.494 | 44.428 | -26.199 | 124.41 | H |
| ATOM | 8818 | HB | VAL | E | 68 | 13.803 | 44.095 | -25.978 | 133.55 | H |
| ATOM | 8819 | HG11 | VAL | E | 68 | 13.950 | 41.899 | -26.735 | 136.65 | H |
| ATOM | 8820 | HG12 | VAL | E | 68 | 12.534 | 42.163 | -26.064 | 136.65 | H |
| ATOM | 8821 | HG13 | VAL | E | 68 | 12.670 | 42.131 | -27.647 | 136.65 | H |
| ATOM | 8822 | HG21 | VAL | E | 68 | 15.174 | 43.705 | -27.818 | 133.82 | H |
| ATOM | 8823 | HG22 | VAL | E | 68 | 13.954 | 44.008 | -28.791 | 133.82 | H |
| ATOM | 8824 | HG23 | VAL | E | 68 | 14.560 | 45.169 | -27.891 | 133.82 | H |
| ATOM | 8825 | N | PRO | E | 69 | 12.187 | 46.769 | -25.710 | 121.06 | N |
| ATOM | 8826 | CA | PRO | E | 69 | 12.539 | 48.190 | -25.618 | 124.69 | C |
| ATOM | 8827 | C | PRO | E | 69 | 14.021 | 48.401 | -25.907 | 122.26 | C |
| ATOM | 8828 | O | PRO | E | 69 | 14.823 | 47.522 | -25.593 | 119.66 | O |
| ATOM | 8829 | CB | PRO | E | 69 | 12.198 | 48.553 | -24.168 | 120.34 | C |
| ATOM | 8830 | CG | PRO | E | 69 | 11.276 | 47.473 | -23.698 | 122.90 | C |
| ATOM | 8831 | CD | PRO | E | 69 | 12.539 | 46.241 | -24.428 | 124.19 | C |
| ATOM | 8832 | HA | PRO | E | 69 | 12.002 | 48.721 | -26.227 | 129.63 | H |
| ATOM | 8833 | HB2 | PRO | E | 69 | 13.009 | 48.566 | -23.636 | 124.40 | H |
| ATOM | 8834 | HB3 | PRO | E | 69 | 11.756 | 49.416 | -24.142 | 124.40 | H |
| ATOM | 8835 | HG2 | PRO | E | 69 | 11.377 | 47.353 | -22.741 | 127.48 | H |
| ATOM | 8836 | HG3 | PRO | E | 69 | 10.361 | 47.709 | -23.918 | 127.48 | H |
| ATOM | 8837 | HD2 | PRO | E | 69 | 12.400 | 45.786 | -23.949 | 129.03 | H |
| ATOM | 8838 | HD3 | PRO | E | 69 | 10.926 | 45.661 | -24.573 | 129.03 | H |
| ATOM | 8839 | N | THR | E | 70 | 14.370 | 49.538 | -26.499 | 124.37 | N |
| ATOM | 8840 | CA | THR | E | 70 | 15.756 | 49.821 | -26.866 | 129.94 | C |
| ATOM | 8841 | C | THR | E | 70 | 16.152 | 51.237 | -26.484 | 129.58 | C |
| ATOM | 8842 | O | THR | E | 70 | 15.305 | 52.123 | -26.385 | 129.43 | O |
| ATOM | 8843 | CB | THR | E | 70 | 15.997 | 49.653 | -28.383 | 131.13 | C |
| ATOM | 8844 | OG1 | THR | E | 70 | 15.358 | 50.722 | -29.092 | 133.21 | O |
| ATOM | 8845 | CG2 | THR | E | 70 | 15.456 | 48.325 | -28.879 | 133.64 | C |
| ATOM | 8846 | H | THR | E | 70 | 13.820 | 50.168 | -26.701 | 129.24 | H |
| ATOM | 8847 | HA | THR | E | 70 | 16.341 | 49.205 | -26.396 | 135.92 | H |
| ATOM | 8848 | HB | THR | E | 70 | 16.951 | 49.677 | -28.560 | 137.36 | H |
| ATOM | 8849 | HG1 | THR | E | 70 | 15.486 | 50.636 | -29.918 | 139.85 | H |
| ATOM | 8850 | HG21 | THR | E | 70 | 15.615 | 48.237 | -29.832 | 140.36 | H |
| ATOM | 8851 | HG22 | THR | E | 70 | 15.895 | 47.594 | -28.417 | 140.36 | H |
| ATOM | 8852 | HG23 | THR | E | 70 | 14.501 | 48.274 | -28.713 | 140.36 | H |
| ATOM | 8853 | N | SER | E | 71 | 17.447 | 51.439 | -26.274 | 128.05 | N |
| ATOM | 8854 | CA | SER | E | 71 | 17.991 | 52.775 | -26.086 | 133.59 | C |
| ATOM | 8855 | C | SER | E | 71 | 18.133 | 53.456 | -27.445 | 132.14 | C |
| ATOM | 8856 | O | SER | E | 71 | 18.290 | 54.673 | -27.528 | 134.41 | O |
| ATOM | 8857 | CB | SER | E | 71 | 19.339 | 52.713 | -25.369 | 130.01 | C |
| ATOM | 8858 | OG | SER | E | 71 | 20.249 | 51.897 | -26.084 | 138.73 | O |
| ATOM | 8859 | H | SER | E | 71 | 18.036 | 50.813 | -26.236 | 133.66 | H |
| ATOM | 8860 | HA | SER | E | 71 | 17.379 | 53.298 | -25.543 | 140.31 | H |
| ATOM | 8861 | HB2 | SER | E | 71 | 19.703 | 53.610 | -25.303 | 136.01 | H |
| ATOM | 8862 | HB3 | SER | E | 71 | 19.209 | 52.342 | -24.483 | 136.01 | H |

TABLE 5-continued

Atomic Coordinates for OMCP-NKG2D (4PDC).

| ATOM | 8863 | HG | SER E | 71 | 20.986 | 51.869 | -25.682 | 146.48 | H |
| --- | --- | --- | --- | --- | --- | --- | --- | --- | --- |
| ATOM | 8864 | N | THR E | 72 | 18.084 | 52.655 | -28.507 | 129.50 | N |
| ATOM | 8865 | CA | THR E | 72 | 18.097 | 53.166 | -29.873 | 129.84 | C |
| ATOM | 8866 | C | THR E | 72 | 16.844 | 54.008 | -30.118 | 128.11 | C |
| ATOM | 8867 | O | THR E | 72 | 15.733 | 53.480 | -30.080 | 128.11 | O |
| ATOM | 8868 | CB | THR E | 72 | 18.157 | 52.014 | -30.900 | 132.89 | C |
| ATOM | 8869 | OG1 | THR E | 72 | 19.282 | 51.168 | -30.614 | 137.51 | O |
| ATOM | 8870 | CG2 | THR E | 72 | 18.275 | 52.554 | -32.320 | 135.87 | C |
| ATOM | 8871 | H | THR E | 72 | 18.043 | 51.797 | -28.459 | 135.40 | H |
| ATOM | 8872 | HA | THR E | 72 | 18.875 | 53.730 | -30.000 | 135.81 | H |
| ATOM | 8873 | HB | THR E | 72 | 17.342 | 51.491 | -30.841 | 139.47 | H |
| ATOM | 8874 | HG1 | THR E | 72 | 19.318 | 50.540 | -31.171 | 145.01 | H |
| ATOM | 8875 | HG21 | THR E | 72 | 18.312 | 51.820 | -32.952 | 143.05 | H |
| ATOM | 8876 | HG22 | THR E | 72 | 17.507 | 53.110 | -32.527 | 143.05 | H |
| ATOM | 8877 | HG23 | THR E | 72 | 19.082 | 53.086 | -32.406 | 143.05 | H |
| ATOM | 8878 | N | PRO E | 73 | 17.014 | 55.318 | -30.378 | 133.46 | N |
| ATOM | 8879 | CA | PRO E | 73 | 15.854 | 56.220 | -30.408 | 132.41 | C |
| ATOM | 8880 | C | PRO E | 73 | 14.911 | 56.022 | -31.595 | 126.60 | C |
| ATOM | 8881 | O | PRO E | 73 | 13.739 | 56.379 | -31.482 | 130.39 | O |
| ATOM | 8882 | CB | PRO E | 73 | 16.497 | 57.609 | -30.470 | 129.80 | C |
| ATOM | 8883 | CG | PRO E | 73 | 17.797 | 57.390 | -31.135 | 129.20 | C |
| ATOM | 8884 | CD | PRO E | 73 | 18.267 | 56.028 | -30.697 | 134.72 | C |
| ATOM | 8885 | HA | PRO E | 73 | 15.349 | 56.141 | -29.584 | 138.89 | H |
| ATOM | 8886 | HB2 | PRO E | 73 | 15.939 | 58.206 | -30.993 | 135.76 | H |
| ATOM | 8887 | HB3 | PRO E | 73 | 16.623 | 57.953 | -29.572 | 135.76 | H |
| ATOM | 8888 | HG2 | PRO E | 73 | 17.677 | 57.415 | -32.097 | 135.04 | H |
| ATOM | 8889 | HG3 | PRO E | 73 | 18.425 | 58.073 | -30.852 | 135.04 | H |
| ATOM | 8890 | HD2 | PRO E | 73 | 18.732 | 55.582 | -31.422 | 141.67 | H |
| ATOM | 8891 | HD3 | PRO E | 73 | 18.824 | 56.101 | -29.907 | 141.67 | H |
| ATOM | 8892 | N | TYR E | 74 | 15.402 | 55.472 | -32.703 | 127.41 | N |
| ATOM | 8893 | CA | TYR E | 74 | 14.567 | 55.297 | -33.890 | 122.57 | C |
| ATOM | 8894 | C | TYR E | 74 | 14.741 | 53.922 | -34.522 | 123.86 | C |
| ATOM | 8895 | O | TYR E | 74 | 15.859 | 53.493 | -34.810 | 123.15 | O |
| ATOM | 8896 | CB | TYR E | 74 | 14.878 | 56.382 | -34.925 | 123.62 | C |
| ATOM | 8897 | CG | TYR E | 74 | 13.905 | 56.415 | -36.084 | 123.55 | C |
| ATOM | 8898 | CD1 | TYR E | 74 | 14.120 | 55.645 | -37.221 | 121.50 | C |
| ATOM | 8899 | CD2 | TYR E | 74 | 12.770 | 57.211 | -36.038 | 123.88 | C |
| ATOM | 8900 | CE1 | TYR E | 74 | 13.232 | 55.673 | -38.283 | 125.17 | C |
| ATOM | 8901 | CE2 | TYR E | 74 | 11.875 | 57.244 | -37.094 | 127.31 | C |
| ATOM | 8902 | CZ | TYR E | 74 | 12.112 | 56.473 | -38.214 | 125.37 | C |
| ATOM | 8903 | OH | TYR E | 74 | 11.224 | 56.503 | -39.265 | 128.87 | O |
| ATOM | 8904 | H | TYR E | 74 | 16.211 | 55.193 | -32.794 | 132.90 | H |
| ATOM | 8905 | HA | TYR E | 74 | 13.636 | 55.390 | -33.633 | 127.09 | H |
| ATOM | 8906 | HB2 | TYR E | 74 | 14.849 | 57.247 | -34.489 | 128.34 | H |
| ATOM | 8907 | HB3 | TYR E | 74 | 15.765 | 56.225 | -35.286 | 128.34 | H |
| ATOM | 8908 | HD1 | TYR E | 74 | 14.875 | 55.105 | -37.271 | 125.80 | H |
| ATOM | 8909 | HD2 | TYR E | 74 | 12.608 | 57.732 | -35.286 | 128.65 | H |
| ATOM | 8910 | HE1 | TYR E | 74 | 13.390 | 55.153 | -39.038 | 130.20 | H |
| ATOM | 8911 | HE2 | TYR E | 74 | 11.119 | 57.784 | -37.050 | 132.77 | H |
| ATOM | 8912 | HH | TYR E | 74 | 10.592 | 57.028 | -39.092 | 134.65 | H |
| ATOM | 8913 | N | GLU E | 75 | 13.616 | 53.243 | -34.736 | 123.34 | N |

TABLE 5-continued

Atomic Coordinates for OMCP-NKG2D (4PDC).

| ATOM | 8914 | CA | GLU | E | 75 | 13.590 | 51.973 | −35.452 | 122.00 | C |
| ATOM | 8915 | C | GLU | E | 75 | 12.361 | 51.911 | −36.345 | 122.18 | C |
| ATOM | 8916 | O | GLU | E | 75 | 11.232 | 52.031 | −35.868 | 122.80 | O |
| ATOM | 8917 | CB | GLU | E | 75 | 13.585 | 50.783 | −34.486 | 125.87 | C |
| ATOM | 8918 | CG | GLU | E | 75 | 14.930 | 50.477 | −33.863 | 125.87 | C |
| ATOM | 8919 | CD | GLU | E | 75 | 15.016 | 49.060 | −33.322 | 131.04 | C |
| ATOM | 8920 | OE1 | GLU | E | 75 | 14.083 | 48.630 | −32.606 | 123.10 | O |
| ATOM | 8921 | OE2 | GLU | E | 75 | 16.021 | 48.375 | −33.619 | 130.63 | O1− |
| ATOM | 8922 | H | GLU | E | 75 | 12.841 | 53.503 | −34.469 | 128.00 | H |
| ATOM | 8923 | HA | GLU | E | 75 | 14.378 | 51.906 | −36.013 | 126.40 | H |
| ATOM | 8924 | HB2 | GLU | E | 75 | 12.962 | 50.971 | −33.766 | 126.99 | H |
| ATOM | 8925 | HB3 | GLU | E | 75 | 13.297 | 49.993 | −34.970 | 126.99 | H |
| ATOM | 8926 | HG2 | GLU | E | 75 | 15.621 | 50.584 | −34.535 | 131.05 | H |
| ATOM | 8927 | HG3 | GLU | E | 75 | 15.084 | 51.090 | −33.127 | 131.05 | H |
| ATOM | 8928 | N | ASP | E | 76 | 12.598 | 51.733 | −37.641 | 118.47 | N |
| ATOM | 8929 | CA | ASP | E | 76 | 11.532 | 51.564 | −38.616 | 121.95 | C |
| ATOM | 8930 | C | ASP | E | 76 | 11.628 | 50.178 | −39.234 | 116.59 | C |
| ATOM | 8931 | O | ASP | E | 76 | 12.632 | 49.831 | −39.851 | 116.66 | O |
| ATOM | 8932 | CB | ASP | E | 76 | 11.610 | 52.637 | −39.701 | 119.62 | C |
| ATOM | 8933 | CG | ASP | E | 76 | 10.424 | 52.599 | −40.638 | 125.99 | C |
| ATOM | 8934 | OD1 | ASP | E | 76 | 9.322 | 53.005 | −40.215 | 130.46 | O |
| ATOM | 8935 | OD2 | ASP | E | 76 | 10.590 | 52.164 | −41.797 | 134.44 | O1− |
| ATOM | 8936 | H | ASP | E | 76 | 13.386 | 51.706 | −37.984 | 122.16 | H |
| ATOM | 8937 | HA | ASP | E | 76 | 10.674 | 51.641 | −38.171 | 126.34 | H |
| ATOM | 8938 | HB2 | ASP | E | 76 | 11.634 | 53.511 | −39.282 | 123.54 | H |
| ATOM | 8939 | HB3 | ASP | E | 76 | 12.413 | 52.498 | −40.227 | 123.54 | H |
| ATOM | 8940 | N | LEU | E | 77 | 10.574 | 49.392 | −39.056 | 115.41 | N |
| ATOM | 8941 | CA | LEU | E | 77 | 10.537 | 48.025 | −39.553 | 116.17 | C |
| ATOM | 8942 | C | LEU | E | 77 | 9.455 | 47.893 | −40.609 | 115.56 | C |
| ATOM | 8943 | O | LEU | E | 77 | 8.319 | 48.306 | −40.388 | 117.25 | O |
| ATOM | 8944 | CB | LEU | E | 77 | 10.286 | 47.048 | −38.405 | 115.28 | C |
| ATOM | 8945 | CG | LEU | E | 77 | 11.389 | 46.987 | −37.350 | 116.96 | C |
| ATOM | 8946 | CD1 | LEU | E | 77 | 10.879 | 46.320 | −36.093 | 121.16 | C |
| ATOM | 8947 | CD2 | LEU | E | 77 | 12.592 | 46.234 | −37.902 | 119.76 | C |
| ATOM | 8948 | H | LEU | E | 77 | 9.858 | 49.631 | −38.643 | 118.50 | H |
| ATOM | 8949 | HA | LEU | E | 77 | 11.390 | 47.807 | −39.960 | 119.40 | H |
| ATOM | 8950 | HB2 | LEU | E | 77 | 9.466 | 47.305 | −37.955 | 118.34 | H |
| ATOM | 8951 | HB3 | LEU | E | 77 | 10.188 | 46.157 | −38.775 | 118.34 | H |
| ATOM | 8952 | HG | LEU | E | 77 | 11.669 | 47.888 | −37.126 | 120.35 | H |
| ATOM | 8953 | HD11 | LEU | E | 77 | 11.594 | 46.292 | −35.438 | 125.39 | H |
| ATOM | 8954 | HD12 | LEU | E | 77 | 10.131 | 46.831 | −35.746 | 125.39 | H |
| ATOM | 8955 | HD13 | LEU | E | 77 | 10.593 | 45.418 | −36.309 | 125.39 | H |
| ATOM | 8956 | HD21 | LEU | E | 77 | 13.284 | 46.203 | −37.223 | 123.72 | H |
| ATOM | 8957 | HD22 | LEU | E | 77 | 12.319 | 45.333 | −38.138 | 123.72 | H |
| ATOM | 8958 | HD23 | LEU | E | 77 | 12.921 | 46.697 | −38.689 | 123.72 | H |
| ATOM | 8959 | N | THR | E | 78 | 9.813 | 47.329 | −41.759 | 114.27 | N |
| ATOM | 8960 | CA | THR | E | 78 | 8.840 | 47.089 | −42.818 | 114.26 | C |
| ATOM | 8961 | C | THR | E | 78 | 8.861 | 45.634 | −43.248 | 114.87 | C |
| ATOM | 8962 | O | THR | E | 78 | 9.922 | 45.020 | −43.355 | 112.85 | O |
| ATOM | 8963 | CB | THR | E | 78 | 9.100 | 47.973 | −44.050 | 115.27 | C |
| ATOM | 8964 | OG1 | THR | E | 78 | 9.102 | 49.353 | −43.665 | 119.62 | O |

TABLE 5-continued

Atomic Coordinates for OMCP-NKG2D (4PDC).

| | | | | | | | | | | |
|---|---|---|---|---|---|---|---|---|---|---|
| ATOM | 8965 | CG2 | THR | E | 78 | 8.035 | 47.754 | -45.113 | 115.91 | C |
| ATOM | 8966 | H | THR | E | 78 | 10.612 | 47.075 | -41.950 | 117.12 | H |
| ATOM | 8967 | HA | THR | E | 78 | 7.952 | 47.292 | -42.484 | 117.11 | H |
| ATOM | 8968 | HB | THR | E | 78 | 9.962 | 47.746 | -44.431 | 118.32 | H |
| ATOM | 8969 | HG1 | THR | E | 78 | 9.704 | 49.491 | -43.096 | 123.54 | H |
| ATOM | 8970 | HG21 | THR | E | 78 | 8.213 | 48.317 | -45.882 | 119.09 | H |
| ATOM | 8971 | HG22 | THR | E | 78 | 8.035 | 46.826 | -45.396 | 119.09 | H |
| ATOM | 8972 | HG23 | THR | E | 78 | 7.160 | 47.974 | -44.757 | 119.09 | H |
| ATOM | 8973 | N | TYR | E | 78 | 7.670 | 45.095 | -43.484 | 113.27 | N |
| ATOM | 8974 | CA | TYR | E | 79 | 7.514 | 43.775 | -44.072 | 114.20 | C |
| ATOM | 8975 | C | TYR | E | 79 | 6.573 | 43.872 | -45.256 | 114.36 | C |
| ATOM | 8976 | O | TYR | E | 79 | 5.421 | 44.279 | -45.111 | 113.68 | O |
| ATOM | 8977 | CB | TYR | E | 79 | 6.982 | 42.777 | -43.049 | 113.72 | C |
| ATOM | 8978 | CG | TYR | E | 79 | 6.699 | 41.404 | -43.618 | 114.03 | C |
| ATOM | 8979 | CD1 | TYR | E | 79 | 7.700 | 40.665 | -44.239 | 115.69 | C |
| ATOM | 8980 | CD2 | TYR | E | 79 | 5.438 | 40.835 | -43.512 | 113.78 | C |
| ATOM | 8981 | CE1 | TYR | E | 79 | 7.447 | 39.401 | -44.750 | 115.27 | C |
| ATOM | 8982 | CE2 | TYR | E | 79 | 5.177 | 39.579 | -44.016 | 112.76 | C |
| ATOM | 8983 | CZ | TYR | E | 79 | 6.182 | 38.865 | -44.635 | 115.58 | C |
| ATOM | 8984 | OH | TYR | E | 79 | 5.914 | 37.609 | -45.136 | 114.38 | O |
| ATOM | 8985 | H | TYR | E | 79 | 6.924 | 45.484 | -43.308 | 115.93 | H |
| ATOM | 8986 | HA | TYR | E | 79 | 8.375 | 43.460 | -44.390 | 117.04 | H |
| ATOM | 8987 | HB2 | TYR | E | 79 | 7.638 | 42.675 | -42.342 | 116.47 | H |
| ATOM | 8988 | HB3 | TYR | E | 79 | 6.153 | 43.120 | -42.681 | 116.47 | H |
| ATOM | 8989 | HD1 | TYR | E | 79 | 8.553 | 41.027 | -44.317 | 118.83 | H |
| ATOM | 8990 | HD2 | TYR | E | 79 | 4.756 | 41.311 | -43.096 | 116.54 | H |
| ATOM | 8991 | HE1 | TYR | E | 79 | 8.124 | 38.920 | -45.167 | 118.32 | H |
| ATOM | 8992 | HE2 | TYR | E | 79 | 4.325 | 39.215 | -43.940 | 115.31 | H |
| ATOM | 8993 | HH | TYR | E | 79 | 6.606 | 37.285 | -45.484 | 117.25 | H |
| ATOM | 8994 | N | PHE | E | 80 | 7.078 | 43.501 | -46.426 | 113.15 | N |
| ATOM | 8995 | CA | PHE | E | 80 | 6.317 | 43.575 | -47.664 | 114.24 | C |
| ATOM | 8996 | C | PHE | E | 80 | 6.024 | 42.162 | -48.125 | 116.30 | C |
| ATOM | 8997 | O | PHE | E | 80 | 6.934 | 41.349 | -48.213 | 115.43 | O |
| ATOM | 8998 | CB | PHE | E | 80 | 7.102 | 44.352 | -48.722 | 117.01 | C |
| ATOM | 8999 | CG | PHE | E | 80 | 6.447 | 44.383 | -50.071 | 119.40 | C |
| ATOM | 9000 | CD1 | PHE | E | 80 | 5.421 | 45.272 | -50.337 | 118.32 | C |
| ATOM | 9001 | CD2 | PHE | E | 80 | 6.877 | 43.541 | -51.084 | 119.37 | C |
| ATOM | 9002 | CE1 | PHE | E | 80 | 4.824 | 45.310 | -51.585 | 123.34 | C |
| ATOM | 9003 | CE2 | PHE | E | 80 | 6.285 | 43.574 | -52.334 | 118.06 | C |
| ATOM | 9004 | CZ | PHE | E | 80 | 5.259 | 44.459 | -52.585 | 118.37 | C |
| ATOM | 9005 | H | PHE | E | 80 | 7.876 | 43.197 | -46.529 | 115.78 | H |
| ATOM | 9006 | HA | PHE | E | 80 | 5.476 | 44.031 | -47.504 | 117.09 | H |
| ATOM | 9007 | HB2 | PHE | E | 80 | 7.206 | 45.269 | -48.422 | 120.41 | H |
| ATOM | 9008 | HB3 | PHE | E | 80 | 7.975 | 43.941 | -48.827 | 120.41 | H |
| ATOM | 9009 | HD1 | PHE | E | 80 | 5.125 | 45.846 | -49.668 | 121.98 | H |
| ATOM | 9010 | HD2 | PHE | E | 80 | 7.569 | 42.942 | -50.920 | 123.25 | H |
| ATOM | 9011 | HE1 | PHE | E | 80 | 4.13 | 45.908 | -51.751 | 128.00 | H |
| ATOM | 9012 | HE2 | PHE | E | 80 | 6.579 | 43.000 | -53.004 | 121.67 | H |
| ATOM | 9013 | HZ | PHE | E | 80 | 4.858 | 44.482 | -53.424 | 122.04 | H |
| ATOM | 9014 | N | TYR | E | 81 | 4.751 | 41.864 | -48.376 | 113.87 | N |
| ATOM | 9015 | CA | TYR | E | 81 | 4.354 | 40.551 | -48.870 | 115.55 | C |

TABLE 5-continued

Atomic Coordinates for OMCP-NKG2D (4PDC).

| ATOM | 9016 | C | TYR | E | 81 | 3.404 | 40.698 | -50.049 | 117.93 | C |
| ATOM | 9017 | O | TYR | E | 81 | 2.378 | 41.378 | -49.952 | 114.45 | O |
| ATOM | 9018 | CB | TYR | E | 81 | 3.696 | 39.715 | -47.768 | 113.17 | C |
| ATOM | 9019 | CG | TYR | E | 81 | 3.300 | 38.345 | -48.261 | 115.78 | C |
| ATOM | 9020 | CD1 | TYR | E | 81 | 4.237 | 37.324 | -48.352 | 119.61 | C |
| ATOM | 9021 | CD2 | TYR | E | 81 | 1.998 | 38.077 | -48.663 | 118.88 | C |
| ATOM | 9022 | CE1 | TYR | E | 81 | 3.887 | 36.072 | -48.816 | 119.41 | C |
| ATOM | 9023 | CE2 | TYR | E | 81 | 1.640 | 36.827 | -49.130 | 117.69 | C |
| ATOM | 9024 | CZ | TYR | E | 81 | 2.586 | 35.829 | -49.203 | 117.85 | C |
| ATOM | 9025 | OH | TYR | E | 81 | 2.237 | 34.580 | -49.670 | 117.84 | O |
| ATOM | 9026 | H | TYR | E | 81 | 4.095 | 42.409 | -48.267 | 116.64 | H |
| ATOM | 9027 | HA | TYR | E | 81 | 5.143 | 40.076 | -49.177 | 118.66 | H |
| ATOM | 9028 | HB2 | TYR | E | 81 | 4.322 | 39.604 | -47.036 | 115.81 | H |
| ATOM | 9029 | HB3 | TYR | E | 81 | 2.897 | 40.169 | -47.459 | 115.81 | H |
| ATOM | 9030 | HD1 | TYR | E | 81 | 5.115 | 37.485 | -48.092 | 123.54 | H |
| ATOM | 9031 | HD2 | TYR | E | 81 | 1.357 | 38.749 | -48.615 | 122.66 | H |
| ATOM | 9032 | HE1 | TYR | E | 81 | 4.525 | 35.397 | -48.868 | 123.29 | H |
| ATOM | 9033 | HE2 | TYR | E | 81 | 0.763 | 36.660 | -49.392 | 121.22 | H |
| ATOM | 9034 | HH | TYR | E | 81 | 1.421 | 34.566 | -49.870 | 121.41 | H |
| ATOM | 9035 | N | GLU | E | 82 | 3.755 | 40.055 | -51.159 | 115.98 | N |
| ATOM | 9036 | CA | GLU | E | 82 | 3.003 | 40.184 | -52.399 | 114.65 | C |
| ATOM | 9037 | C | GLU | E | 82 | 2.789 | 38.829 | -53.047 | 114.84 | C |
| ATOM | 9038 | O | GLU | E | 82 | 3.732 | 38.055 | -53.188 | 117.94 | O |
| ATOM | 9039 | CB | GLU | E | 82 | 3.737 | 41.109 | -53.373 | 118.04 | C |
| ATOM | 9040 | CG | GLU | E | 82 | 3.018 | 41.338 | -54.689 | 116.30 | C |
| ATOM | 9041 | CD | GLU | E | 82 | 3.879 | 42.074 | -55.695 | 122.72 | C |
| ATOM | 9042 | OE1 | GLU | E | 82 | 4.616 | 41.397 | -56.440 | 120.02 | O |
| ATOM | 9043 | OE2 | GLU | E | 82 | 3.824 | 43.322 | -55.736 | 120.27 | O1- |
| ATOM | 9044 | H | GLU | E | 82 | 4.434 | 39.531 | -51.219 | 119.17 | H |
| ATOM | 9045 | HA | GLU | E | 82 | 2.134 | 40.571 | -52.208 | 117.57 | H |
| ATOM | 9046 | HB2 | GLU | E | 82 | 3.857 | 41.974 | -52.949 | 121.64 | H |
| ATOM | 9047 | HB3 | GLU | E | 82 | 4.604 | 40.722 | -53.575 | 121.64 | H |
| ATOM | 9048 | HG2 | GLU | E | 82 | 2.774 | 40.481 | -55.071 | 119.56 | H |
| ATOM | 9049 | HG3 | GLU | E | 82 | 2.223 | 41.870 | -54.527 | 119.56 | H |
| ATOM | 9050 | N | CYS | E | 83 | 1.547 | 38.545 | -53.433 | 115.34 | N |
| ATOM | 9051 | CA | CYS | E | 83 | 1.264 | 37.378 | -54.257 | 112.96 | C |
| ATOM | 9052 | C | CYS | E | 83 | 0.843 | 37.867 | -55.639 | 119.15 | C |
| ATOM | 9053 | O | CYS | E | 83 | 0.264 | 38.947 | -55.785 | 115.77 | O |
| ATOM | 9054 | CB | CYS | E | 83 | 0.197 | 36.477 | -53.621 | 116.84 | C |
| ATOM | 9055 | SG | CYS | E | 83 | -1.483 | 37.137 | -53.496 | 123.13 | S |
| ATOM | 9056 | H | CYS | E | 83 | 0.854 | 39.012 | -53.230 | 118.41 | H |
| ATOM | 9057 | HA | CYS | E | 83 | 2.076 | 36.857 | -54.357 | 115.56 | H |
| ATOM | 9058 | HB2 | CYS | E | 83 | 0.144 | 35.661 | -54.142 | 120.21 | H |
| ATOM | 9059 | HB3 | CYS | E | 83 | 0.486 | 36.260 | -52.720 | 120.21 | H |
| ATOM | 9060 | N | ASP | E | 84 | 1.163 | 37.066 | -56.648 | 117.04 | N |
| ATOM | 9061 | CA | ASP | E | 84 | 0.974 | 37.441 | -58.041 | 117.78 | C |
| ATOM | 9062 | C | ASP | E | 84 | 0.295 | 36.299 | -58.783 | 119.08 | C |
| ATOM | 9063 | O | ASP | E | 84 | 0.770 | 35.164 | -58.744 | 116.97 | O |
| ATOM | 9064 | CB | ASP | E | 84 | 2.325 | 37.778 | -58.678 | 120.88 | C |
| ATOM | 9065 | CG | ASP | E | 84 | 2.208 | 38.205 | -60.131 | 125.61 | C |
| ATOM | 9066 | OD1 | ASP | E | 84 | 1.845 | 37.363 | -60.982 | 120.93 | O |

TABLE 5-continued

Atomic Coordinates for OMCP-NKG2D (4PDC).

| ATOM | 9067 | OD2 | ASP | E | 84 | 2.505 | 39.382 | -60.423 | 120.27 | O1- |
|---|---|---|---|---|---|---|---|---|---|---|
| ATOM | 9068 | H | ASP | E | 84 | 1.500 | 36.281 | -56.547 | 120.45 | H |
| ATOM | 9069 | HA | ASP | E | 84 | 0.405 | 38.224 | -58.092 | 121.34 | H |
| ATOM | 9070 | HB2 | ASP | E | 84 | 2.734 | 38.506 | -58.184 | 125.05 | H |
| ATOM | 9071 | HB3 | ASP | E | 84 | 2.895 | 36.993 | -58.642 | 125.05 | H |
| ATOM | 9072 | N | TYR | E | 85 | -0.824 | 36.598 | -59.437 | 118.50 | N |
| ATOM | 9073 | CA | TYR | E | 85 | -1.525 | 35.609 | -60.252 | 119.06 | C |
| ATOM | 9074 | C | TYR | E | 85 | -1.499 | 36.041 | -61.713 | 120.41 | C |
| ATOM | 9075 | O | TYR | E | 85 | 2.219 | 36.955 | -62.124 | 120.32 | O |
| ATOM | 9076 | CB | TYR | E | 85 | -2.960 | 35.422 | -59.768 | 118.28 | C |
| ATOM | 9077 | CG | TYR | E | 85 | 3.596 | 34.138 | -60.246 | 118.94 | C |
| ATOM | 9078 | CD1 | TYR | E | 85 | -3.038 | 32.910 | -59.929 | 119.95 | C |
| ATOM | 9079 | CD2 | TYR | E | 85 | -4.760 | 34.154 | -61.002 | 123.18 | C |
| ATOM | 9080 | CE1 | TYR | E | 85 | -3.613 | 31.733 | -60.354 | 120.65 | C |
| ATOM | 9081 | CE2 | TYR | E | 85 | 5.345 | 32.979 | -61.430 | 125.96 | C |
| ATOM | 9082 | CZ | TYR | E | 85 | -4.767 | 31.772 | -61.099 | 123.05 | C |
| ATOM | 9083 | OH | TYR | E | 85 | -5.337 | 30.594 | -61.524 | 126.20 | O |
| ATOM | 9084 | H | TYR | E | 85 | -1.201 | 37.371 | -59.426 | 122.20 | H |
| ATOM | 9085 | HA | TYR | E | 85 | -1.068 | 34.757 | -60.180 | 122.87 | H |
| ATOM | 9086 | HB2 | TYR | E | 85 | 2.965 | 35.412 | -58.798 | 121.94 | H |
| ATOM | 9087 | HB3 | TYR | E | 85 | -3.499 | 36.160 | -60.093 | 121.94 | H |
| ATOM | 9088 | HD1 | TYR | E | 85 | -2.259 | 32.880 | -59.422 | 123.94 | H |
| ATOM | 9089 | HD2 | TYR | E | 85 | -5.152 | 34.968 | -61.222 | 127.82 | H |
| ATOM | 9090 | HE1 | TYR | E | 85 | -3.226 | 30.917 | -60.134 | 124.78 | H |
| ATOM | 9091 | HE2 | TYR | E | 85 | -6.124 | 33.002 | -61.937 | 131.15 | H |
| ATOM | 9092 | HH | TYR | E | 85 | -6.033 | 30.755 | -61.966 | 131.44 | H |
| ATOM | 9093 | N | THR | E | 86 | -0.648 | 35.368 | -62.481 | 121.39 | N |
| ATOM | 9094 | CA | THR | E | 86 | -0.390 | 35.705 | -63.874 | 120.93 | C |
| ATOM | 9095 | C | THR | E | 86 | -0.293 | 34.414 | -64.674 | 121.34 | C |
| ATOM | 9096 | O | THR | E | 86 | 0.496 | 33.532 | -64.334 | 119.84 | O |
| ATOM | 9097 | CB | THR | E | 86 | 0.921 | 36.515 | -64.029 | 122.67 | C |
| ATOM | 9098 | OG1 | THR | E | 86 | 0.862 | 37.696 | -63.217 | 124.63 | O |
| ATOM | 9099 | CG2 | THR | E | 86 | 1.149 | 36.917 | -65.478 | 123.65 | C |
| ATOM | 9100 | H | THR | E | 86 | -0.196 | 34.690 | -62.206 | 125.66 | H |
| ATOM | 9101 | HA | THR | E | 86 | -1.125 | 36.233 | -64.223 | 125.12 | H |
| ATOM | 9102 | HB | THR | E | 86 | 1.670 | 35.969 | -63.744 | 127.20 | H |
| ATOM | 9103 | HG1 | THR | E | 86 | 0.765 | 37.485 | -62.410 | 129.56 | H |
| ATOM | 9104 | HG21 | THR | E | 86 | 1.973 | 37.423 | -65.555 | 128.38 | H |
| ATOM | 9105 | HG22 | THR | E | 86 | 1.212 | 36.126 | -66.035 | 128.38 | H |
| ATOM | 9106 | HG23 | THR | E | 86 | 0.412 | 37.466 | -65.790 | 128.38 | H |
| ATOM | 9107 | N | ASP | E | 87 | -1.096 | 34.300 | -65.727 | 122.89 | N |
| ATOM | 9108 | CA | ASP | E | 87 | -1.097 | 33.101 | -66.563 | 123.19 | C |
| ATOM | 9109 | C | ASP | E | 87 | -1.404 | 31.876 | -65.703 | 126.71 | C |
| ATOM | 9110 | O | ASP | E | 87 | -0.771 | 30.830 | -65.835 | 123.26 | O |
| ATOM | 9111 | CB | ASP | E | 87 | 0.252 | 32.946 | -67.275 | 125.03 | C |
| ATOM | 9112 | CG | ASP | E | 87 | 0.247 | 31.838 | -68.316 | 128.16 | C |
| ATOM | 9113 | OD1 | ASP | E | 87 | -0.798 | 31.626 | -68.965 | 124.41 | O |
| ATOM | 9114 | OD2 | ASP | E | 87 | 1.295 | 31.180 | -68.478 | 126.54 | O1- |
| ATOM | 9115 | H | ASP | E | 87 | -1.653 | 34.904 | -65.981 | 127.47 | H |
| ATOM | 9116 | HA | ASP | E | 87 | -1.789 | 33.181 | -67.237 | 127.83 | H |
| ATOM | 9117 | HB2 | ASP | E | 87 | 0.469 | 33.778 | -67.725 | 130.03 | H |

TABLE 5-continued

Atomic Coordinates for OMCP-NKG2D (4PDC).

| | | | | | | | | | | |
|---|---|---|---|---|---|---|---|---|---|---|
| ATOM | 9118 | HB3 | ASP | E | 87 | 0.934 | 32.737 | -66.618 | 130.03 | H |
| ATOM | 9119 | N | ASN | E | 88 | -2.372 | 32.032 | -64.803 | 129.28 | N |
| ATOM | 9120 | CA | ASN | E | 88 | -2.802 | 30.961 | -63.906 | 125.51 | C |
| ATOM | 9121 | C | ASN | E | 88 | -1.681 | 30.405 | -63.031 | 123.64 | C |
| ATOM | 9122 | O | ASN | E | 88 | -1.812 | 29.322 | -62.465 | 124.76 | O |
| ATOM | 9123 | CB | ASN | E | 88 | -3.430 | 29.821 | -64.709 | 129.13 | C |
| ATOM | 9124 | CG | ASN | E | 88 | -4.619 | 30.277 | -65.532 | 135.20 | C |
| ATOM | 9125 | OD1 | ASN | E | 88 | -4.620 | 30.161 | -66.757 | 140.38 | O |
| ATOM | 9126 | ND2 | ASN | E | 88 | 5.637 | 30.804 | -64.860 | 137.30 | N |
| ATOM | 9127 | H | ASN | E | 88 | -2.804 | 32.767 | -64.690 | 135.13 | H |
| ATOM | 9128 | HA | ASN | E | 88 | -3.486 | 31.313 | -63.314 | 130.61 | H |
| ATOM | 9129 | HB2 | ASN | E | 88 | -2.766 | 29.457 | -65.316 | 134.96 | H |
| ATOM | 9130 | HB3 | ASN | E | 88 | -3.735 | 29.133 | -64.097 | 134.96 | H |
| ATOM | 9131 | HD21 | ASN | E | 88 | -6.335 | 31.078 | -65.282 | 144.76 | H |
| ATOM | 9132 | HD22 | ASN | E | 88 | -5.599 | 30.871 | -64.004 | 144.76 | H |
| ATOM | 9133 | N | LYS | E | 89 | -0.585 | 31.150 | -62.920 | 120.99 | N |
| ATOM | 9134 | CA | LYS | E | 89 | 0.543 | 30.745 | -62.087 | 122.61 | C |
| ATOM | 9135 | C | LYS | E | 89 | 0.681 | 31.653 | -60.868 | 118.77 | C |
| ATOM | 9136 | O | LYS | E | 89 | 0.632 | 32.882 | -60.978 | 117.15 | O |
| ATOM | 9137 | CB | LYS | E | 89 | 1.835 | 30.748 | -62.902 | 124.56 | C |
| ATOM | 9138 | CG | LYS | E | 89 | 1.924 | 29.593 | -63.887 | 135.41 | C |
| ATOM | 9139 | CD | LYS | E | 89 | 3.119 | 29.732 | -64.818 | 145.55 | C |
| ATOM | 9140 | CE | LYS | E | 89 | 3.242 | 28.527 | -65.737 | 146.80 | C |
| ATOM | 9141 | NZ | LYS | E | 89 | 1.975 | 28.255 | -66.473 | 149.89 | N1+ |
| ATOM | 9142 | H | LYS | E | 89 | -0.469 | 31.902 | -63.320 | 125.19 | H |
| ATOM | 9143 | HA | LYS | E | 89 | 0.391 | 29.841 | -61.770 | 127.14 | H |
| ATOM | 9144 | HB2 | LYS | E | 89 | 1.888 | 31.575 | -63.406 | 129.48 | H |
| ATOM | 9145 | HB3 | LYS | E | 89 | 2.590 | 30.682 | -62.296 | 129.48 | H |
| ATOM | 9146 | HG2 | LYS | E | 89 | 2.018 | 28.762 | -63.396 | 142.50 | H |
| ATOM | 9147 | HG3 | LYS | E | 89 | 1.120 | 29.573 | -64.428 | 142.50 | H |
| ATOM | 9148 | HD2 | LYS | E | 89 | 3.008 | 30.524 | -65.367 | 154.66 | H |
| ATOM | 9149 | HD3 | LYS | E | 89 | 3.930 | 29.799 | -64.291 | 154.66 | H |
| ATOM | 9150 | HE2 | LYS | E | 89 | 3.941 | 28.695 | -66.389 | 156.16 | H |
| ATOM | 9151 | HE3 | LYS | E | 89 | 3.459 | 27.744 | -65.207 | 156.16 | H |
| ATOM | 9152 | HZ1 | LYS | E | 89 | 1.755 | 28.959 | -66.971 | 159.87 | H |
| ATOM | 9153 | HZ2 | LYS | E | 89 | 2.077 | 27.546 | -67.001 | 159.87 | H |
| ATOM | 9154 | HZ3 | LYS | E | 89 | 1.317 | 28.093 | -65.895 | 159.87 | H |
| ATOM | 9155 | N | SER | E | 90 | 0.843 | 31.024 | -59.709 | 116.33 | N |
| ATOM | 9156 | CA | SER | E | 90 | 0.971 | 31.729 | -58.442 | 117.73 | C |
| ATOM | 9157 | C | SER | E | 90 | 2.439 | 31.908 | -58.084 | 118.63 | C |
| ATOM | 9158 | O | SER | E | 90 | 3.171 | 30.928 | -57.975 | 117.42 | O |
| ATOM | 9159 | CB | SER | E | 90 | 0.257 | 30.961 | -57.328 | 117.54 | C |
| ATOM | 9160 | OG | SER | E | 90 | -1.103 | 30.730 | -57.645 | 120.05 | O |
| ATOM | 9161 | H | SER | E | 90 | 0.883 | 30.169 | -59.631 | 119.60 | H |
| ATOM | 9162 | HA | SER | E | 90 | 0.565 | 32.607 | -58.518 | 121.27 | H |
| ATOM | 9163 | HB2 | SER | E | 90 | 0.699 | 30.107 | -57.203 | 121.05 | H |
| ATOM | 9164 | HB3 | SER | E | 90 | 0.305 | 31.479 | -56.509 | 121.05 | H |
| ATOM | 9165 | HG | SER | E | 90 | -1.501 | 31.461 | -57.755 | 124.06 | H |
| ATOM | 9166 | N | THR | E | 91 | 2.864 | 33.157 | -57.912 | 117.55 | N |
| ATOM | 9167 | CA | THR | E | 91 | 4.222 | 33.455 | -57.473 | 114.99 | C |
| ATOM | 9168 | C | THR | E | 91 | 4.178 | 34.462 | -56.329 | 120.38 | C |

TABLE 5-continued

Atomic Coordinates for OMCP-NKG2D (4PDC).

| | | | | | | | | | |
|---|---|---|---|---|---|---|---|---|---|
| ATOM | 9169 | O | THR | E | 91 | 3.207 | 35.208 | −56.177 | 119.44 O |
| ATOM | 9170 | CB | THR | E | 91 | 5.096 | 34.001 | −58.621 | 118.36 C |
| ATOM | 9171 | OG1 | THR | E | 91 | 4.482 | 35.159 | −59.191 | 117.75 O |
| ATOM | 9172 | CG2 | THR | E | 91 | 5.280 | 32.946 | −59.702 | 121.31 C |
| ATOM | 9173 | H | THR | E | 91 | 2.379 | 33.855 | −58.045 | 121.06 H |
| ATOM | 9174 | HA | THR | E | 91 | 4.634 | 32.641 | −57.142 | 117.98 H |
| ATOM | 9175 | HB | THR | E | 91 | 5.971 | 34.239 | −58.274 | 122.03 H |
| ATOM | 9176 | HG1 | THR | E | 91 | 4.394 | 35.756 | −58.607 | 121.30 H |
| ATOM | 9177 | HG21 | THR | E | 91 | 5.830 | 33.299 | −60.419 | 125.58 H |
| ATOM | 9178 | HG22 | THR | E | 91 | 5.712 | 32.161 | −59.329 | 125.58 H |
| ATOM | 9179 | HG23 | THR | E | 91 | 4.417 | 32.689 | −60.064 | 117.07 H |
| ATOM | 9180 | N | PHE | E | 92 | 5.232 | 34.465 | −55.523 | 119.25 N |
| ATOM | 9181 | CA | PHE | E | 92 | 5.250 | 35.231 | −54.287 | 124.03 C |
| ATOM | 9182 | C | PHE | E | 92 | 6.563 | 35.971 | −54.119 | 120.37 C |
| ATOM | 9183 | O | PHE | E | 92 | 7.601 | 35.561 | −54.641 | 118.30 O |
| ATOM | 9184 | CB | PHE | E | 92 | 5.015 | 34.308 | −53.091 | 120.97 C |
| ATOM | 9185 | CG | PHE | E | 92 | 3.758 | 33.502 | −53.192 | 119.39 C |
| ATOM | 9186 | CD1 | PHE | E | 92 | 2.557 | 34.006 | −52.722 | 124.13 C |
| ATOM | 9187 | CD2 | PHE | E | 92 | 3.773 | 32.244 | −53.771 | 118.89 C |
| ATOM | 9188 | CE1 | PHE | E | 92 | 1.397 | 33.266 | −52.819 | 117.65 C |
| ATOM | 9189 | CE2 | PHE | E | 92 | 2.616 | 31.498 | −53.871 | 124.23 C |
| ATOM | 9190 | CZ | PHE | E | 92 | 1.426 | 32.010 | −53.395 | 120.48 C |
| ATOM | 9191 | H | PHE | E | 92 | 5.957 | 34.027 | −55.672 | 123.10 H |
| ATOM | 9192 | HA | PHE | E | 92 | 4.535 | 35.885 | −54.308 | 121.96 H |
| ATOM | 9193 | HB2 | PHE | E | 92 | 5.760 | 33.690 | −53.022 | 121.96 H |
| ATOM | 9194 | HB3 | PHE | E | 92 | 4.959 | 34.846 | −52.287 | 123.27 H |
| ATOM | 9195 | HD1 | PHE | E | 92 | 2.533 | 34.850 | −52.333 | 128.95 H |
| ATOM | 9196 | HD2 | PHE | E | 92 | 4.573 | 31.895 | −54.092 | 122.66 H |
| ATOM | 9197 | HE1 | PHE | E | 92 | 0.596 | 33.612 | −52.498 | 121.19 H |
| ATOM | 9198 | HE2 | PHE | E | 92 | 2.638 | 30.653 | −54.259 | 129.08 H |
| ATOM | 9199 | HZ | PHE | E | 92 | 0.644 | 31.510 | −53.461 | 120.31 H |
| ATOM | 9200 | N | ASP | E | 93 | 6.497 | 37.065 | −53.374 | 122.87 N |
| ATOM | 9201 | CA | ASP | E | 93 | 7.647 | 37.915 | −53.135 | 121.59 C |
| ATOM | 9202 | C | ASP | E | 93 | 7.507 | 38.528 | −51.752 | 120.77 C |
| ATOM | 9203 | O | ASP | E | 93 | 6.409 | 38.918 | −51.354 | 124.57 O |
| ATOM | 9204 | CB | ASP | E | 93 | 7.743 | 39.002 | −54.211 | 132.86 C |
| ATOM | 9205 | CG | ASP | E | 93 | 8.998 | 39.840 | −54.085 | 121.96 C |
| ATOM | 9206 | OD1 | ASP | E | 93 | 9.991 | 39.332 | −53.526 | 132.28 O |
| ATOM | 9207 | OD2 | ASP | E | 93 | 8.994 | 41.002 | −54.550 | 130.92 O1− |
| ATOM | 9208 | H | ASP | E | 93 | 5.779 | 37.340 | −52.989 | 124.37 H |
| ATOM | 9209 | HA | ASP | E | 93 | 8.458 | 37.382 | −53.158 | 127.44 H |
| ATOM | 9210 | HB2 | ASP | E | 93 | 7.748 | 38.582 | −55.085 | 129.48 H |
| ATOM | 9211 | HB3 | ASP | E | 93 | 6.978 | 39.594 | −54.131 | 129.48 H |
| ATOM | 9212 | N | GLN | E | 94 | 8.60 | 38.592 | −51.005 | 121.93 N |
| ATOM | 9213 | CA | GLN | E | 94 | 8.567 | 39.269 | −49.718 | 121.60 C |
| ATOM | 9215 | C | GLN | E | 94 | 9.897 | 39.936 | −49.420 | 125.96 C |
| ATOM | 9215 | O | GLN | E | 94 | 10.960 | 39.425 | −49.778 | 122.95 O |
| ATOM | 9216 | CB | GLN | E | 94 | 8.184 | 38.298 | −48.590 | 118.61 C |
| ATOM | 9217 | CG | GLN | E | 94 | 9.153 | 37.149 | −48.353 | 122.48 C |
| ATOM | 9218 | CD | GLN | E | 94 | 8.735 | 36.253 | −47.190 | 131.39 C |
| ATOM | 9219 | OE1 | GLN | E | 94 | 7.596 | 36.309 | −46.716 | 122.85 O |

TABLE 5-continued

Atomic Coordinates for OMCP-NKG2D (4PDC).

| ATOM | 9220 | NE2 | GLN | E | 94 | 9.662 | 35.422 | -46.724 | 133.95 | N |
| --- | --- | --- | --- | --- | --- | --- | --- | --- | --- | --- |
| ATOM | 9221 | H | GLN | E | 94 | 9.365 | 38.258 | -51.217 | 126.32 | H |
| ATOM | 9222 | HA | GLN | E | 94 | 7.890 | 39.963 | -49.750 | 125.92 | H |
| ATOM | 9223 | HB2 | GLN | E | 94 | 8.120 | 38.800 | -47.762 | 122.33 | H |
| ATOM | 9224 | HB3 | GLN | E | 94 | 7.320 | 37.910 | -48.799 | 122.33 | H |
| ATOM | 9225 | HG2 | GLN | E | 94 | 9.197 | 36.603 | -49.153 | 126.97 | H |
| ATOM | 9226 | HG3 | GLN | E | 94 | 10.030 | 37.513 | -48.151 | 126.97 | H |
| ATOM | 9227 | HE21 | GLN | E | 94 | 9.478 | 34.895 | -46.070 | 140.74 | H |
| ATOM | 9228 | HE22 | GLN | E | 94 | 10.446 | 35.411 | -47.078 | 140.74 | H |
| ATOM | 9229 | N | ASP | E | 95 | 9.812 | 41.095 | -48.774 | 119.56 | N |
| ATOM | 9230 | CA | ASP | E | 95 | 10.979 | 41.896 | -48.435 | 123.21 | C |
| ATOM | 9231 | C | ASP | E | 95 | 10.903 | 42.330 | -46.983 | 120.85 | C |
| ATOM | 9232 | O | ASP | E | 95 | 9.814 | 42.501 | -46.431 | 116.26 | O |
| ATOM | 9233 | CB | ASP | E | 95 | 11.077 | 43.129 | -49.338 | 122.27 | C |
| ATOM | 9234 | CG | ASP | E | 95 | 11.333 | 42.774 | -50.787 | 129.57 | C |
| ATOM | 9235 | OD1 | ASP | E | 95 | 12.132 | 41.848 | -51.043 | 135.45 | O |
| ATOM | 9236 | OD2 | ASP | E | 95 | 10.733 | 43.425 | -51.668 | 131.38 | O1- |
| ATOM | 9237 | H | ASP | E | 95 | 9.070 | 41.446 | -48.517 | 123.47 | H |
| ATOM | 9238 | HA | ASP | E | 95 | 11.781 | 41.364 | -48.554 | 127.85 | H |
| ATOM | 9239 | HB2 | ASP | E | 95 | 10.242 | 43.621 | -49.293 | 126.72 | H |
| ATOM | 9240 | HB3 | ASP | E | 95 | 11.808 | 43.687 | -49.032 | 126.72 | H |
| ATOM | 9241 | N | TYR | E | 96 | 12.072 | 42.504 | -46.380 | 115.26 | N |
| ATOM | 9242 | CA | TYR | E | 96 | 12.200 | 43.027 | -45.028 | 116.09 | C |
| ATOM | 9243 | C | TYR | E | 96 | 13.083 | 44.268 | -45.060 | 118.85 | C |
| ATOM | 9244 | O | TYR | E | 96 | 14.186 | 44.218 | -45.609 | 118.14 | O |
| ATOM | 9245 | CB | TYR | E | 96 | 12.814 | 41.990 | -44.091 | 117.29 | C |
| ATOM | 9246 | CG | TYR | E | 96 | 12.171 | 40.625 | -44.131 | 119.72 | C |
| ATOM | 9247 | CD1 | TYR | E | 96 | 12.520 | 39.700 | -45.108 | 119.79 | C |
| ATOM | 9248 | CD2 | TYR | E | 96 | 11.234 | 40.250 | -43.177 | 118.62 | C |
| ATOM | 9249 | CE1 | TYR | E | 96 | 11.944 | 38.446 | -45.140 | 122.85 | C |
| ATOM | 9250 | CE2 | TYR | E | 96 | 10.652 | 38.999 | -43.201 | 120.70 | C |
| ATOM | 9251 | CZ | TYR | E | 96 | 11.012 | 38.099 | -44.185 | 120.85 | C |
| ATOM | 9252 | OH | TYR | E | 96 | 10.437 | 36.849 | -44.213 | 124.95 | O |
| ATOM | 9253 | H | TYR | E | 96 | 12.828 | 42.319 | -46.746 | 118.31 | H |
| ATOM | 9254 | HA | TYR | E | 96 | 11.326 | 43.275 | -44.688 | 119.31 | H |
| ATOM | 9255 | HB2 | TYR | E | 96 | 13.749 | 41.879 | -44.325 | 120.75 | H |
| ATOM | 9256 | HB3 | TYR | E | 96 | 12.745 | 42.318 | -43.181 | 120.75 | H |
| ATOM | 9257 | HD1 | TYR | E | 96 | 13.149 | 39.930 | -45.753 | 123.75 | H |
| ATOM | 9258 | HD2 | TYR | E | 96 | 10.992 | 40.855 | -42.513 | 122.34 | H |
| ATOM | 9259 | HE1 | TYR | E | 96 | 12.184 | 37.838 | -45.801 | 127.42 | H |
| ATOM | 9260 | HE2 | TYR | E | 96 | 10.024 | 38.762 | -42.558 | 124.84 | H |
| ATOM | 9261 | HH | TYR | E | 96 | 9.891 | 36.770 | -43.580 | 129.94 | H |
| ATOM | 9262 | N | LEU | E | 97 | 12.606 | 45.365 | -44.474 | 114.66 | N |
| ATOM | 9263 | CA | LEU | E | 97 | 13.385 | 46.602 | -44.404 | 120.71 | C |
| ATOM | 9264 | C | LEU | E | 97 | 13.605 | 47.025 | -42.961 | 117.15 | C |
| ATOM | 9265 | O | LEU | E | 97 | 12.681 | 46.998 | -42.143 | 115.93 | O |
| ATOM | 9266 | CB | LEU | E | 97 | 12.698 | 47.752 | -45.151 | 118.74 | C |
| ATOM | 9267 | CG | LEU | E | 97 | 12.170 | 47.515 | -46.563 | 124.83 | C |
| ATOM | 9268 | CD1 | LEU | E | 97 | 11.391 | 48.729 | -47.041 | 131.08 | C |
| ATOM | 9269 | CD2 | LEU | E | 97 | 13.316 | 47.219 | -47.496 | 124.75 | C |
| ATOM | 9270 | H | LEU | E | 97 | 11.831 | 45.420 | -44.106 | 117.60 | H |

TABLE 5-continued

Atomic Coordinates for OMCP-NKG2D (4PDC).

| ATOM | 9271 | HA | LEU | E | 97 | 14.253 | 46.453 | -44.811 | 124.85 | H |
|------|------|-----|-----|---|----|--------|--------|---------|--------|---|
| ATOM | 9272 | HB2 | LEU | E | 97 | 11.942 | 48.039 | -44.617 | 122.48 | H |
| ATOM | 9273 | HB3 | LEU | E | 97 | 13.334 | 48.482 | -45.212 | 122.48 | H |
| ATOM | 9274 | HG | LEU | E | 97 | 11.574 | 46.750 | -46.559 | 129.80 | H |
| ATOM | 9275 | HD11 | LEU | E | 97 | 11.064 | 48.560 | -46.559 | 137.30 | H |
| ATOM | 9276 | HD12 | LEU | E | 97 | 10.645 | 48.881 | -47.938 | 137.30 | H |
| ATOM | 9277 | HD13 | LEU | E | 97 | 11.979 | 49.500 | -46.440 | 137.30 | H |
| ATOM | 9278 | HD21 | LEU | E | 97 | 12.965 | 47.071 | -47.043 | 129.70 | H |
| ATOM | 9279 | HD22 | LEU | E | 97 | 13.923 | 47.976 | -48.388 | 129.70 | H |
| ATOM | 9280 | HD23 | LEU | E | 97 | 13.778 | 46.425 | -47.500 | 129.70 | H |
| ATOM | 9281 | N | TYR | E | 98 | 14.840 | 47.417 | -47.186 | 115.72 | N |
| ATOM | 9282 | CA | TYR | E | 98 | 15.182 | 48.046 | -42.665 | 118.67 | C |
| ATOM | 9283 | C | TYR | E | 98 | 15.675 | 49.456 | -41.401 | 122.10 | C |
| ATOM | 9284 | O | TYR | E | 98 | 16.701 | 49.630 | -41.704 | 118.15 | O |
| ATOM | 9285 | CB | TYR | E | 98 | 16.247 | 47.242 | -42.363 | 119.19 | C |
| ATOM | 9286 | CG | TYR | E | 98 | 16.571 | 47.797 | -40.655 | 123.54 | C |
| ATOM | 9287 | CD1 | TYR | E | 98 | 17.573 | 48.742 | -39.287 | 125.80 | C |
| ATOM | 9288 | CD2 | TYR | E | 98 | 15.864 | 47.387 | -39.119 | 122.25 | C |
| ATOM | 9289 | CE1 | TYR | E | 98 | 17.866 | 49.257 | -38.165 | 124.47 | C |
| ATOM | 9290 | CE2 | TYR | E | 98 | 16.153 | 47.895 | -37.872 | 122.72 | C |
| ATOM | 9291 | CZ | TYR | E | 98 | 17.154 | 48.829 | -36.913 | 126.85 | C |
| ATOM | 9292 | OH | TYR | E | 98 | 17.446 | 49.337 | -36.774 | 129.33 | O |
| ATOM | 9293 | H | TYR | E | 98 | 15.511 | 47.325 | -35.533 | 118.86 | H |
| ATOM | 9294 | HA | TYR | E | 98 | 14.392 | 48.107 | -43.196 | 122.40 | H |
| ATOM | 9295 | HB2 | TYR | E | 98 | 15.930 | 46.333 | -40.843 | 123.03 | H |
| ATOM | 9296 | HB3 | TYR | E | 98 | 17.064 | 47.243 | -40.540 | 123.03 | H |
| ATOM | 9297 | HD1 | TYR | E | 98 | 18.056 | 49.032 | -41.177 | 130.96 | H |
| ATOM | 9298 | HD2 | TYR | E | 98 | 15.187 | 46.755 | -39.859 | 126.70 | H |
| ATOM | 9299 | HE1 | TYR | E | 98 | 18.543 | 49.887 | -38.256 | 129.36 | H |
| ATOM | 9300 | HE2 | TYR | E | 98 | 15.674 | 47.609 | -37.774 | 127.26 | H |
| ATOM | 9301 | HH | TYR | E | 98 | 16.941 | 48.995 | -36.169 | 135.20 | H |
| ATOM | 9302 | N | ASN | E | 99 | 14.934 | 50.454 | -34.956 | 119.00 | N |
| ATOM | 9303 | CA | ASN | E | 99 | 15.201 | 51.846 | -41.232 | 117.34 | C |
| ATOM | 9304 | C | ASN | E | 99 | 15.317 | 52.027 | -41.579 | 124.69 | C |
| ATOM | 9305 | O | ASN | E | 99 | 16.193 | 52.735 | -43.095 | 120.15 | O |
| ATOM | 9306 | CB | ASN | E | 99 | 16.465 | 52.334 | -43.589 | 118.40 | C |
| ATOM | 9307 | CG | ASN | E | 99 | 16.290 | 52.391 | -40.868 | 118.42 | C |
| ATOM | 9308 | OD1 | ASN | E | 99 | 15.170 | 52.483 | -39.355 | 119.63 | O |
| ATOM | 9309 | ND2 | ASN | E | 99 | 17.393 | 52.334 | -38.856 | 123.08 | N |
| ATOM | 9310 | H | ASN | E | 99 | 14.263 | 50.350 | -38.623 | 122.81 | H |
| ATOM | 9311 | HA | ASN | E | 99 | 14.460 | 52.391 | -40.704 | 120.80 | H |
| ATOM | 9312 | HB2 | ASN | E | 99 | 17.195 | 51.726 | -41.272 | 122.08 | H |
| ATOM | 9313 | HB3 | ASN | E | 99 | 16.681 | 53.226 | -41.064 | 122.08 | H |
| ATOM | 9314 | HD21 | ASN | E | 99 | 17.342 | 52.363 | -41.180 | 127.69 | H |
| ATOM | 9315 | HD22 | ASN | E | 99 | 18.161 | 52.269 | -37.765 | 119.11 | H |
| ATOM | 9316 | N | GLY | E | 100 | 14.419 | 51.373 | -39.006 | 123.08 | N |
| ATOM | 9317 | CA | GLY | E | 100 | 14.309 | 51.561 | -43.825 | 122.08 | C |
| ATOM | 9318 | C | GLY | E | 100 | 15.283 | 50.739 | -45.260 | 125.95 | C |
| ATOM | 9319 | O | GLY | E | 100 | 15.210 | 50.742 | -46.080 | 124.82 | O |
| ATOM | 9320 | H | GLY | E | 100 | 13.856 | 50.807 | -47.308 | 122.93 | H |
| ATOM | 9321 | HA2 | GLY | E | 100 | 13.410 | 51.329 | -45.541 | 126.49 | H |

TABLE 5-continued

Atomic Coordinates for OMCP-NKG2D (4PDC).

| ATOM | 9322 | HA3 | GLY | E | 100 | 14.457 | 52.497 | -45.467 | H |
|---|---|---|---|---|---|---|---|---|---|
| ATOM | 9323 | N | GLU | E | 101 | 16.189 | 50.032 | -45.410 | N |
| ATOM | 9324 | CA | GLU | E | 101 | 17.208 | 49.242 | -46.095 | C |
| ATOM | 9325 | C | GLU | E | 101 | 16.874 | 47.756 | -46.068 | C |
| ATOM | 9326 | O | GLU | E | 101 | 16.667 | 47.178 | -44.996 | O |
| ATOM | 9327 | CB | GLU | E | 101 | 18.576 | 49.483 | -45.457 | C |
| ATOM | 9328 | CG | GLU | E | 101 | 19.701 | 48.678 | -46.079 | C |
| ATOM | 9329 | CD | GLU | E | 101 | 21.060 | 49.064 | -45.529 | C |
| ATOM | 9330 | OE1 | GLU | E | 101 | 21.512 | 50.198 | -45.804 | O |
| ATOM | 9331 | OE2 | GLU | E | 101 | 21.673 | 48.237 | -44.819 | O1- |
| ATOM | 9332 | H | GLU | E | 101 | 16.236 | 49.993 | -44.552 | H |
| ATOM | 9333 | HA | GLU | E | 101 | 17.255 | 49.522 | -47.022 | H |
| ATOM | 9334 | HB2 | GLU | E | 101 | 18.800 | 50.422 | -45.548 | H |
| ATOM | 9335 | HB3 | GLU | E | 101 | 18.528 | 49.247 | -44.518 | H |
| ATOM | 9336 | HG2 | GLU | E | 101 | 19.558 | 47.737 | -45.893 | H |
| ATOM | 9337 | HG3 | GLU | E | 101 | 19.709 | 48.831 | -47.037 | H |
| ATOM | 9338 | N | GLU | E | 102 | 16.828 | 47.141 | -47.248 | N |
| ATOM | 9339 | CA | GLU | E | 102 | 16.530 | 45.717 | -47.360 | C |
| ATOM | 9340 | C | GLU | E | 102 | 17.575 | 44.873 | -46.653 | C |
| ATOM | 9341 | O | GLU | E | 102 | 18.764 | 45.180 | -46.681 | O |
| ATOM | 9342 | CB | GLU | E | 102 | 16.447 | 45.279 | -48.826 | C |
| ATOM | 9343 | CG | GLU | E | 102 | 15.053 | 45.320 | -49.420 | C |
| ATOM | 9344 | CD | GLU | E | 102 | 14.891 | 44.382 | -50.604 | C |
| ATOM | 9345 | OE1 | GLU | E | 102 | 14.841 | 43.150 | -50.386 | O |
| ATOM | 9346 | OE2 | GLU | E | 102 | 14.807 | 44.875 | -51.749 | O1- |
| ATOM | 9347 | H | GLU | E | 102 | 16.968 | 47.529 | -48.003 | H |
| ATOM | 9348 | HA | GLU | E | 102 | 15.671 | 45.541 | -46.945 | H |
| ATOM | 9349 | HB2 | GLU | E | 102 | 17.009 | 45.865 | -49.357 | H |
| ATOM | 9350 | HB3 | GLU | E | 102 | 16.769 | 44.367 | -48.896 | H |
| ATOM | 9351 | HG2 | GLU | E | 102 | 14.413 | 45.059 | -48.740 | H |
| ATOM | 9352 | HG3 | GLU | E | 102 | 14.866 | 46.222 | -49.724 | H |
| ATOM | 9353 | N | TYR | E | 103 | 17.121 | 43.797 | -46.025 | N |
| ATOM | 9354 | CA | TYR | E | 103 | 18.031 | 42.827 | -45.444 | C |
| ATOM | 9355 | C | TYR | E | 103 | 17.377 | 41.454 | -45.470 | C |
| ATOM | 9356 | O | TYR | E | 103 | 16.155 | 41.338 | -45.607 | O |
| ATOM | 9357 | CB | TYR | E | 103 | 18.430 | 43.236 | -44.021 | C |
| ATOM | 9358 | CG | TYR | E | 103 | 17.330 | 43.173 | -42.978 | C |
| ATOM | 9359 | CD1 | TYR | E | 103 | 16.273 | 44.078 | -42.985 | C |
| ATOM | 9360 | CD2 | TYR | E | 103 | 17.374 | 42.232 | -41.961 | C |
| ATOM | 9361 | CE1 | TYR | E | 103 | 15.279 | 44.024 | -42.020 | C |
| ATOM | 9362 | CE2 | TYR | E | 103 | 16.388 | 42.171 | -40.994 | C |
| ATOM | 9363 | CZ | TYR | E | 103 | 15.344 | 43.065 | -41.029 | C |
| ATOM | 9364 | OH | TYR | E | 103 | 14.370 | 43.002 | -40.059 | O |
| ATOM | 9365 | H | TYR | E | 103 | 16.289 | 43.607 | -45.923 | H |
| ATOM | 9366 | HA | TYR | E | 103 | 18.837 | 42.786 | -45.982 | H |
| ATOM | 9367 | HB2 | TYR | E | 103 | 19.144 | 42.651 | -43.724 | H |
| ATOM | 9368 | HB3 | TYR | E | 103 | 18.752 | 44.151 | -44.046 | H |
| ATOM | 9369 | HD1 | TYR | E | 103 | 16.226 | 44.722 | -43.654 | H |
| ATOM | 9370 | HD2 | TYR | E | 103 | 18.076 | 41.623 | -41.935 | H |
| ATOM | 9371 | HE1 | TYR | E | 103 | 14.573 | 44.630 | -42.040 | H |
| ATOM | 9372 | HE2 | TYR | E | 103 | 16.430 | 41.528 | -40.324 | H |

TABLE 5-continued

Atomic Coordinates for OMCP-NKG2D (4PDC).

| | | | | | | | | | |
|---|---|---|---|---|---|---|---|---|---|
| ATOM | 9373 | HH | TYR | E | 103 | 14.536 | 42.375 | -39.526 | H |
| ATOM | 9374 | N | THR | E | 104 | 18.199 | 40.415 | -45.378 | N |
| ATOM | 9375 | CA | THR | E | 104 | 17.706 | 39.043 | -45.423 | C |
| ATOM | 9376 | C | THR | E | 104 | 18.453 | 38.129 | -44.461 | C |
| ATOM | 9377 | O | THR | E | 104 | 18.024 | 37.003 | -44.211 | O |
| ATOM | 9378 | CB | THR | E | 104 | 17.830 | 38.452 | -46.844 | C |
| ATOM | 9379 | OG1 | THR | E | 104 | 19.214 | 38.270 | -47.169 | O |
| ATOM | 9380 | CG2 | THR | E | 104 | 17.185 | 39.369 | -47.872 | C |
| ATOM | 9381 | H | THR | E | 104 | 19.052 | 40.478 | -45.288 | H |
| ATOM | 9382 | HA | THR | E | 104 | 16.768 | 39.037 | -45.176 | H |
| ATOM | 9383 | HB | THR | E | 104 | 17.377 | 37.595 | -46.875 | H |
| ATOM | 9384 | HG1 | THR | E | 104 | 19.287 | 37.948 | -47.941 | H |
| ATOM | 9385 | HG21 | THR | E | 104 | 17.271 | 38.985 | -48.758 | H |
| ATOM | 9386 | HG22 | THR | E | 104 | 16.244 | 39.485 | -47.668 | H |
| ATOM | 9387 | HG23 | THR | E | 104 | 17.620 | 40.236 | -47.860 | H |
| ATOM | 9388 | N | VAL | E | 105 | 19.570 | 38.612 | -43.925 | N |
| ATOM | 9389 | CA | VAL | E | 105 | 20.446 | 37.784 | -43.105 | C |
| ATOM | 9390 | C | VAL | E | 105 | 20.199 | 37.994 | -41.613 | C |
| ATOM | 9391 | O | VAL | E | 105 | 20.247 | 39.116 | -41.110 | O |
| ATOM | 9392 | CB | VAL | E | 105 | 21.928 | 38.072 | -43.414 | C |
| ATOM | 9393 | CG1 | VAL | E | 105 | 22.838 | 37.197 | -42.560 | C |
| ATOM | 9394 | CG2 | VAL | E | 105 | 22.214 | 37.842 | -44.892 | C |
| ATOM | 9395 | H | VAL | E | 105 | 19.844 | 39.421 | -44.023 | H |
| ATOM | 9396 | HA | VAL | E | 105 | 20.275 | 36.850 | -43.307 | H |
| ATOM | 9397 | HB | VAL | E | 105 | 22.121 | 39.000 | -43.210 | H |
| ATOM | 9398 | HG11 | VAL | E | 105 | 23.762 | 37.400 | -42.775 | H |
| ATOM | 9399 | HG12 | VAL | E | 105 | 22.667 | 37.385 | -41.624 | H |
| ATOM | 9400 | HG13 | VAL | E | 105 | 22.649 | 36.265 | -42.751 | H |
| ATOM | 9401 | HG21 | VAL | E | 105 | 23.150 | 38.028 | -45.064 | H |
| ATOM | 9402 | HG22 | VAL | E | 105 | 22.014 | 36.918 | -45.111 | H |
| ATOM | 9403 | HG23 | VAL | E | 105 | 21.655 | 38.435 | -45.417 | H |
| ATOM | 9404 | N | LYS | E | 106 | 19.944 | 36.892 | -40.916 | N |
| ATOM | 9405 | CA | LYS | E | 106 | 19.775 | 36.896 | -39.469 | C |
| ATOM | 9406 | C | LYS | E | 106 | 21.133 | 36.835 | -38.787 | C |
| ATOM | 9407 | O | LYS | E | 106 | 21.998 | 36.062 | -39.198 | O |
| ATOM | 9408 | CB | LYS | E | 106 | 18.914 | 35.706 | -39.033 | C |
| ATOM | 9409 | CG | LYS | E | 106 | 18.726 | 35.569 | -37.528 | C |
| ATOM | 9410 | CD | LYS | E | 106 | 18.189 | 34.196 | -37.165 | C |
| ATOM | 9411 | CE | LYS | E | 106 | 17.955 | 34.067 | -35.665 | C |
| ATOM | 9412 | NZ | LYS | E | 106 | 19.210 | 34.241 | -34.879 | N1+ |
| ATOM | 9413 | H | LYS | E | 106 | 19.862 | 36.112 | -41.269 | H |
| ATOM | 9414 | HA | LYS | E | 106 | 19.330 | 37.714 | -39.198 | H |
| ATOM | 9415 | HB2 | LYS | E | 106 | 18.035 | 35.799 | -39.431 | H |
| ATOM | 9416 | HB3 | LYS | E | 106 | 19.331 | 34.890 | -39.351 | H |
| ATOM | 9417 | HG2 | LYS | E | 106 | 19.581 | 35.689 | -37.086 | H |
| ATOM | 9418 | HG3 | LYS | E | 106 | 18.092 | 36.236 | -37.222 | H |
| ATOM | 9419 | HD2 | LYS | E | 106 | 17.343 | 34.054 | -37.618 | H |
| ATOM | 9420 | HD3 | LYS | E | 106 | 18.831 | 33.520 | -37.432 | H |
| ATOM | 9421 | HE2 | LYS | E | 106 | 17.325 | 34.748 | -35.382 | H |
| ATOM | 9422 | HE3 | LYS | E | 106 | 17.600 | 33.184 | -35.475 | H |
| ATOM | 9423 | HZ1 | LYS | E | 106 | 19.805 | 33.622 | -35.116 | H |

TABLE 5-continued

Atomic Coordinates for OMCP-NKG2D (4PDC).

| | | | | | | | | | |
|---|---|---|---|---|---|---|---|---|---|
| ATOM | 9424 | HZ2 | LYS | E | 106 | 19.554 | -35.031 | 165.26 | H |
| ATOM | 9425 | HZ3 | LYS | E | 106 | 19.038 | -34.010 | 165.26 | H |
| ATOM | 9426 | N | THR | E | 107 | 21.315 | -37.752 | 130.36 | N |
| ATOM | 9427 | CA | THR | E | 107 | 22.519 | -36.926 | 139.31 | C |
| ATOM | 9428 | C | THR | E | 107 | 22.178 | -37.598 | 141.69 | C |
| ATOM | 9429 | O | THR | E | 107 | 21.024 | -35.588 | 135.99 | O |
| ATOM | 9430 | CB | THR | E | 107 | 23.125 | -36.604 | 136.74 | C |
| ATOM | 9431 | OG1 | THR | E | 107 | 22.180 | -36.691 | 134.87 | O |
| ATOM | 9432 | CG2 | THR | E | 107 | 23.513 | -36.013 | 137.13 | C |
| ATOM | 9433 | H | THR | E | 107 | 20.751 | -39.643 | 136.43 | H |
| ATOM | 9434 | HA | THR | E | 107 | 23.185 | -38.253 | 147.17 | H |
| ATOM | 9435 | HB | THR | E | 107 | 23.925 | -37.505 | 144.09 | H |
| ATOM | 9436 | HG1 | THR | E | 107 | 22.509 | -37.369 | 141.85 | H |
| ATOM | 9437 | HG21 | THR | E | 107 | 23.893 | -36.149 | 144.55 | H |
| ATOM | 9438 | HG22 | THR | E | 107 | 24.169 | -35.885 | 144.55 | H |
| ATOM | 9439 | HG23 | THR | E | 107 | 22.730 | -37.860 | 144.55 | H |
| ATOM | 9440 | N | GLN | E | 108 | 23.180 | -38.474 | 141.22 | N |
| ATOM | 9441 | CA | GLN | E | 108 | 23.017 | -38.582 | 151.91 | C |
| ATOM | 9442 | C | GLN | E | 108 | 22.373 | -39.735 | 144.49 | C |
| ATOM | 9443 | O | GLN | E | 108 | 21.587 | -36.784 | 143.27 | O |
| ATOM | 9444 | CB | GLN | E | 108 | 24.372 | -34.731 | 168.26 | C |
| ATOM | 9445 | CG | GLN | E | 108 | 24.287 | -32.379 | 183.56 | C |
| ATOM | 9446 | CD | GLN | E | 108 | 23.781 | -31.602 | 191.50 | C |
| ATOM | 9447 | OE1 | GLN | E | 108 | 23.967 | -33.049 | 189.80 | O |
| ATOM | 9448 | NE2 | GLN | E | 108 | 23.130 | -32.303 | 195.77 | N |
| ATOM | 9449 | H | GLN | E | 108 | 23.966 | -33.179 | 149.46 | H |
| ATOM | 9450 | HA | GLN | E | 108 | 22.444 | -34.397 | 162.30 | H |
| ATOM | 9451 | HB2 | GLN | E | 108 | 24.936 | -32.563 | 181.91 | H |
| ATOM | 9452 | HB3 | GLN | E | 108 | 24.781 | -34.833 | 181.91 | H |
| ATOM | 9453 | HG2 | GLN | E | 108 | 25.171 | -33.701 | 100.217 | H |
| ATOM | 9454 | HG3 | GLN | E | 108 | 23.677 | -33.827 | 100.217 | H |
| ATOM | 9455 | HE21 | GLN | E | 108 | 22.823 | -32.456 | 114.912 | H |
| ATOM | 9456 | HE22 | GLN | E | 108 | 23.014 | -31.982 | 114.912 | H |
| ATOM | 9457 | N | GLN | E | 108 | 22.717 | -31.555 | 145.66 | N |
| ATOM | 9458 | CA | GLU | E | 109 | 22.231 | -33.016 | 142.78 | C |
| ATOM | 9459 | C | GLU | E | 109 | 20.706 | -31.711 | 140.26 | C |
| ATOM | 9460 | O | GLU | E | 109 | 20.050 | -32.288 | 131.16 | O |
| ATOM | 9461 | CB | GLU | E | 109 | 22.860 | -31.207 | 142.62 | C |
| ATOM | 9462 | CG | GLU | E | 109 | 22.975 | -31.196 | 152.37 | C |
| ATOM | 9463 | CD | GLU | E | 109 | 23.398 | -32.238 | 159.49 | C |
| ATOM | 9464 | OE1 | GLU | E | 109 | 23.528 | -31.304 | 162.06 | O |
| ATOM | 9465 | OE2 | GLU | E | 109 | 23.602 | -32.724 | 151.48 | O1- |
| ATOM | 9466 | H | GLU | E | 109 | 23.234 | -32.764 | 154.80 | H |
| ATOM | 9467 | HA | GLU | E | 109 | 22.502 | -31.686 | 151.33 | H |
| ATOM | 9468 | HB2 | GLU | E | 109 | 22.317 | -33.881 | 151.15 | H |
| ATOM | 9469 | HB3 | GLU | E | 109 | 23.754 | -32.845 | 151.15 | H |
| ATOM | 9470 | HG2 | GLU | E | 109 | 23.638 | -30.359 | 162.84 | H |
| ATOM | 9471 | HG3 | GLU | E | 109 | 22.113 | -30.791 | 162.84 | H |
| ATOM | 9472 | N | ALA | E | 110 | 20.150 | -33.209 | 141.90 | N |
| ATOM | 9473 | CA | ALA | E | 110 | 18.712 | -30.001 | 133.67 | C |
| ATOM | 9474 | C | ALA | E | 110 | 18.339 | -29.837 | 135.94 | C |

TABLE 5-continued

Atomic Coordinates for OMCP-NKG2D (4PDC).

| ATOM | 9475 | O | ALA | E | 110 | 18.587 | 41.730 | -29.225 | 134.30 | O |
|------|------|------|------|---|-----|--------|--------|---------|--------|---|
| ATOM | 9476 | CB | ALA | E | 110 | 18.270 | 38.958 | -28.455 | 141.21 | C |
| ATOM | 9477 | H | ALA | E | 110 | 20.590 | 39.258 | -29.263 | 150.29 | H |
| ATOM | 9478 | HA | ALA | E | 110 | 18.247 | 38.869 | -30.495 | 140.41 | H |
| ATOM | 9479 | HB1 | ALA | E | 110 | 17.312 | 39.086 | -28.372 | 149.45 | H |
| ATOM | 9480 | HB2 | ALA | E | 110 | 18.490 | 38.020 | -28.344 | 149.45 | H |
| ATOM | 9481 | HB3 | ALA | E | 110 | 18.734 | 39.488 | -27.787 | 149.45 | H |
| ATOM | 9482 | N | THR | E | 111 | 17.745 | 41.129 | -31.226 | 123.46 | N |
| ATOM | 9483 | CA | THR | E | 111 | 17.372 | 42.476 | -31.620 | 123.33 | C |
| ATOM | 9484 | C | THR | E | 111 | 15.999 | 42.480 | -32.272 | 119.12 | C |
| ATOM | 9485 | O | THR | E | 111 | 15.517 | 41.447 | -32.737 | 117.50 | O |
| ATOM | 9486 | CB | THR | E | 111 | 18.375 | 43.062 | -32.609 | 121.03 | C |
| ATOM | 9487 | OG1 | THR | E | 111 | 18.395 | 42.245 | -33.786 | 119.06 | O |
| ATOM | 9488 | CG2 | THR | E | 111 | 19.769 | 43.117 | -31.995 | 130.25 | C |
| ATOM | 9489 | H | THR | E | 111 | 17.546 | 40.530 | -31.811 | 128.16 | H |
| ATOM | 9490 | HA | THR | E | 111 | 17.342 | 43.047 | -30.837 | 128.00 | H |
| ATOM | 9491 | HB | THR | E | 111 | 18.107 | 43.963 | -32.846 | 125.24 | H |
| ATOM | 9492 | HG1 | THR | E | 111 | 18.944 | 42.555 | -34.341 | 122.88 | H |
| ATOM | 9493 | HG21 | THR | E | 111 | 20.397 | 43.491 | -32.633 | 136.30 | H |
| ATOM | 9494 | HG22 | THR | E | 111 | 19.759 | 43.673 | -31.200 | 136.30 | H |
| ATOM | 9495 | HG23 | THR | E | 111 | 20.060 | 42.225 | -31.753 | 136.30 | H |
| ATOM | 9496 | N | ASN | E | 112 | 15.383 | 43.653 | -32.322 | 118.03 | N |
| ATOM | 9497 | CA | ASN | E | 112 | 14.118 | 43.813 | -33.014 | 118.86 | C |
| ATOM | 9498 | C | ASN | E | 112 | 14.283 | 43.492 | -34.496 | 118.90 | C |
| ATOM | 9499 | O | ASN | E | 112 | 13.396 | 42.909 | -35.116 | 115.74 | O |
| ATOM | 9500 | CB | ASN | E | 112 | 13.581 | 45.231 | -32.820 | 119.71 | C |
| ATOM | 9501 | CG | ASN | E | 112 | 13.143 | 45.494 | -31.389 | 124.98 | C |
| ATOM | 9502 | OD1 | ASN | E | 112 | 12.646 | 44.597 | -30.710 | 122.68 | O |
| ATOM | 9503 | ND2 | ASN | E | 112 | 13.331 | 46.723 | -30.923 | 122.07 | N |
| ATOM | 9504 | H | ASN | E | 112 | 15.680 | 44.375 | -31.960 | 121.63 | H |
| ATOM | 9505 | HA | ASN | E | 112 | 13.472 | 43.192 | -32.642 | 122.63 | H |
| ATOM | 9506 | HB2 | ASN | E | 112 | 14.278 | 45.867 | -33.044 | 123.65 | H |
| ATOM | 9507 | HB3 | ASN | E | 112 | 12.813 | 45.361 | -33.399 | 123.65 | H |
| ATOM | 9508 | HD21 | ASN | E | 112 | 13.098 | 46.918 | -30.118 | 126.49 | H |
| ATOM | 9509 | HD22 | ASN | E | 112 | 13.684 | 47.325 | -31.426 | 126.49 | H |
| ATOM | 9510 | N | LYS | E | 113 | 15.439 | 43.854 | -35.047 | 116.41 | N |
| ATOM | 9511 | CA | LYS | E | 113 | 15.739 | 43.600 | -36.451 | 115.65 | C |
| ATOM | 9512 | C | LYS | E | 113 | 15.712 | 42.103 | -36.766 | 116.82 | C |
| ATOM | 9513 | O | LYS | E | 113 | 15.106 | 41.673 | -37.751 | 116.67 | O |
| ATOM | 9514 | CB | LYS | E | 113 | 17.102 | 44.193 | -36.806 | 120.54 | C |
| ATOM | 9515 | CG | LYS | E | 113 | 17.454 | 44.125 | -38.276 | 120.47 | C |
| ATOM | 9516 | CD | LYS | E | 113 | 18.816 | 44.753 | -38.539 | 122.73 | C |
| ATOM | 9517 | CE | LYS | E | 113 | 19.154 | 44.754 | -40.019 | 124.48 | C |
| ATOM | 9518 | NZ | LYS | E | 113 | 20.513 | 45.300 | -40.281 | 126.06 | N1+ |
| ATOM | 9519 | H | LYS | E | 113 | 16.072 | 44.253 | -34.623 | 119.69 | H |
| ATOM | 9520 | HA | LYS | E | 113 | 15.069 | 44.035 | -37.002 | 118.78 | H |
| ATOM | 9521 | HB2 | LYS | E | 113 | 17.112 | 45.127 | -36.544 | 124.65 | H |
| ATOM | 9522 | HB3 | LYS | E | 113 | 17.787 | 43.710 | -36.317 | 124.65 | H |
| ATOM | 9523 | HG2 | LYS | E | 113 | 17.486 | 43.197 | -38.557 | 124.56 | H |
| ATOM | 9524 | HG3 | LYS | E | 113 | 16.789 | 44.611 | -38.789 | 124.56 | H |
| ATOM | 9525 | HD2 | LYS | E | 113 | 18.809 | 45.672 | -38.228 | 127.28 | H |

TABLE 5-continued

Atomic Coordinates for OMCP-NKG2D (4PDC).

| | | | | | | | | | |
|---|---|---|---|---|---|---|---|---|---|
| ATOM | 9526 | HD3 | LYS | E | 113 | 19.497 | 44.246 | −38.071 | H |
| ATOM | 9527 | HE2 | LYS | E | 113 | 19.125 | 43.844 | −40.352 | H |
| ATOM | 9528 | HE3 | LYS | E | 113 | 18.511 | 45.305 | −40.492 | H |
| ATOM | 9529 | HZ1 | LYS | E | 113 | 20.565 | 46.139 | −39.988 | H |
| ATOM | 9530 | HZ2 | LYS | E | 113 | 21.124 | 44.808 | −39.861 | H |
| ATOM | 9531 | HZ3 | LYS | E | 113 | 20.682 | 45.288 | −41.155 | H |
| ATOM | 9532 | N | ASN | E | 114 | 16.360 | 41.307 | −35.924 | N |
| ATOM | 9533 | CA | ASN | E | 114 | 16.389 | 39.862 | −36.127 | C |
| ATOM | 9534 | C | ASN | E | 114 | 15.036 | 39.200 | −35.892 | C |
| ATOM | 9535 | O | ASN | E | 114 | 14.623 | 38.335 | −36.663 | O |
| ATOM | 9536 | CB | ASN | E | 114 | 17.440 | 39.224 | −35.217 | C |
| ATOM | 9537 | CG | ASN | E | 114 | 18.851 | 39.385 | −35.758 | C |
| ATOM | 9538 | OD1 | ASN | E | 114 | 19.069 | 39.370 | −36.971 | O |
| ATOM | 9539 | ND2 | ASN | E | 114 | 19.815 | 39.537 | −34.858 | N |
| ATOM | 9540 | H | ASN | E | 114 | 16.790 | 41.576 | −35.230 | H |
| ATOM | 9541 | HA | ASN | E | 114 | 16.648 | 39.684 | −37.045 | H |
| ATOM | 9542 | HB2 | ASN | E | 114 | 17.402 | 39.647 | −34.345 | H |
| ATOM | 9543 | HB3 | ASN | E | 114 | 17.255 | 38.276 | −35.136 | H |
| ATOM | 9544 | HD21 | ASN | E | 114 | 20.631 | 39.631 | −35.114 | H |
| ATOM | 9545 | HD22 | ASN | E | 114 | 19.624 | 39.540 | −34.019 | H |
| ATOM | 9546 | N | MET | E | 115 | 14.350 | 39.596 | −34.827 | N |
| ATOM | 9547 | CA | MET | E | 115 | 13.049 | 39.018 | −34.518 | C |
| ATOM | 9548 | C | MET | E | 115 | 12.046 | 39.333 | −35.625 | C |
| ATOM | 9549 | O | MET | E | 115 | 11.231 | 38.490 | −36.006 | O |
| ATOM | 9550 | CB | MET | E | 115 | 12.536 | 39.543 | −33.179 | C |
| ATOM | 9551 | CG | MET | E | 115 | 11.267 | 38.858 | −32.708 | C |
| ATOM | 9552 | SD | MET | E | 115 | 10.596 | 39.578 | −31.197 | S |
| ATOM | 9553 | CE | MET | E | 115 | 11.976 | 39.355 | −30.071 | C |
| ATOM | 9554 | H | MET | E | 115 | 14.614 | 40.195 | −34.270 | H |
| ATOM | 9555 | HA | MET | E | 115 | 13.142 | 38.056 | −34.444 | H |
| ATOM | 9556 | HB2 | MET | E | 115 | 13.218 | 39.402 | −32.505 | H |
| ATOM | 9557 | HB3 | MET | E | 115 | 12.348 | 40.491 | −33.265 | H |
| ATOM | 9558 | HG2 | MET | E | 115 | 10.592 | 38.933 | −33.400 | H |
| ATOM | 9559 | HG3 | MET | E | 115 | 11.460 | 37.923 | −32.533 | H |
| ATOM | 9560 | HE1 | MET | E | 115 | 11.735 | 39.711 | −29.202 | H |
| ATOM | 9561 | HE2 | MET | E | 115 | 12.173 | 38.408 | −29.998 | H |
| ATOM | 9562 | HE3 | MET | E | 115 | 12.748 | 39.828 | −30.420 | H |
| ATOM | 9563 | N | TRP | E | 116 | 12.109 | 40.558 | −36.130 | N |
| ATOM | 9564 | CA | TRP | E | 116 | 11.240 | 40.990 | −37.216 | C |
| ATOM | 9565 | C | TRP | E | 116 | 11.452 | 40.113 | −38.447 | C |
| ATOM | 9566 | O | TRP | E | 116 | 10.498 | 39.712 | −39.112 | O |
| ATOM | 9567 | CB | TRP | E | 116 | 11.515 | 42.458 | −37.544 | C |
| ATOM | 9568 | CG | TRP | E | 116 | 10.633 | 43.043 | −38.607 | C |
| ATOM | 9569 | CD1 | TRP | E | 116 | 10.933 | 43.189 | −39.929 | C |
| ATOM | 9570 | CD2 | TRP | E | 116 | 9.312 | 43.572 | −38.435 | C |
| ATOM | 9571 | NE1 | TRP | E | 116 | 9.883 | 43.779 | −40.593 | N |
| ATOM | 9572 | CE2 | TRP | E | 116 | 8.874 | 44.021 | −39.699 | C |
| ATOM | 9573 | CE3 | TRP | E | 116 | 8.459 | 43.711 | −37.336 | C |
| ATOM | 9574 | CZ2 | TRP | E | 116 | 7.624 | 44.603 | −39.892 | C |
| ATOM | 9575 | CZ3 | TRP | E | 116 | 7.216 | 44.288 | −37.531 | C |
| ATOM | 9576 | CH2 | TRP | E | 116 | 6.811 | 44.726 | −38.799 | C |

TABLE 5-continued

Atomic Coordinates for OMCP-NKG2D (4PDC).

| | | | | | | | | | | |
|---|---|---|---|---|---|---|---|---|---|---|
| ATOM | 9577 | H | TRP | E | 116 | 12.653 | 41.165 | -35.857 | 114.98 | H |
| ATOM | 9578 | HA | TRP | E | 116 | 10.314 | 40.907 | -36.938 | 118.56 | H |
| ATOM | 9579 | HB2 | TRP | E | 116 | 11.390 | 42.983 | -36.738 | 115.17 | H |
| ATOM | 9580 | HB3 | TRP | E | 116 | 12.432 | 42.540 | -37.847 | 115.17 | H |
| ATOM | 9581 | HD1 | TRP | E | 116 | 11.734 | 42.930 | -40.324 | 114.44 | H |
| ATOM | 9582 | HE1 | TRP | E | 116 | 9.862 | 43.961 | -41.433 | 117.57 | H |
| ATOM | 9583 | HE3 | TRP | E | 116 | 8.723 | 43.427 | -36.491 | 113.69 | H |
| ATOM | 9584 | HZ2 | TRP | E | 116 | 7.351 | 44.891 | -40.733 | 117.11 | H |
| ATOM | 9585 | HZ3 | TRP | E | 116 | 6.639 | 44.385 | -36.808 | 119.05 | H |
| ATOM | 9586 | HH2 | TRP | E | 116 | 5.967 | 45.105 | -38.901 | 116.94 | H |
| ATOM | 9587 | N | LEU | E | 117 | 12.714 | 39.810 | -38.725 | 113.03 | N |
| ATOM | 9588 | CA | LEU | E | 117 | 13.093 | 39.003 | -39.878 | 113.36 | C |
| ATOM | 9589 | C | LEU | E | 117 | 12.619 | 37.564 | -39.748 | 115.88 | C |
| ATOM | 9590 | O | LEU | E | 117 | 12.149 | 36.968 | -40.719 | 115.15 | O |
| ATOM | 9591 | CB | LEU | E | 117 | 14.618 | 39.027 | -40.063 | 113.94 | C |
| ATOM | 9592 | CG | LEU | E | 117 | 15.204 | 38.145 | -41.175 | 115.98 | C |
| ATOM | 9593 | CD1 | LEU | E | 117 | 14.745 | 38.606 | -42.552 | 116.70 | C |
| ATOM | 9594 | CD2 | LEU | E | 117 | 16.725 | 38.130 | -41.103 | 124.05 | C |
| ATOM | 9595 | H | LEU | E | 117 | 13.384 | 40.067 | -38.251 | 115.63 | H |
| ATOM | 9596 | HA | LEU | E | 117 | 12.688 | 39.381 | -40.674 | 116.03 | H |
| ATOM | 9597 | HB2 | LEU | E | 117 | 14.884 | 39.940 | -40.254 | 116.73 | H |
| ATOM | 9598 | HB3 | LEU | E | 117 | 15.027 | 38.744 | -39.230 | 116.73 | H |
| ATOM | 9599 | HG | LEU | E | 117 | 14.892 | 37.235 | -41.048 | 119.17 | H |
| ATOM | 9600 | HD11 | LEU | E | 117 | 15.135 | 38.026 | -43.225 | 120.03 | H |
| ATOM | 9601 | HD12 | LEU | E | 117 | 13.777 | 38.559 | -42.594 | 120.03 | H |
| ATOM | 9602 | HD13 | LEU | E | 117 | 15.039 | 39.520 | -42.693 | 120.03 | H |
| ATOM | 9603 | HD21 | LEU | E | 117 | 17.069 | 37.567 | -41.814 | 128.86 | H |
| ATOM | 9604 | HD22 | LEU | E | 117 | 17.055 | 39.036 | -41.209 | 128.86 | H |
| ATOM | 9605 | HD23 | LEU | E | 117 | 16.997 | 37.777 | -40.241 | 128.86 | H |
| ATOM | 9606 | N | THR | E | 118 | 12.748 | 37.002 | -38.552 | 111.16 | N |
| ATOM | 9607 | CA | THR | E | 118 | 12.450 | 35.592 | -38.362 | 115.63 | C |
| ATOM | 9608 | C | THR | E | 118 | 10.994 | 35.308 | -37.997 | 115.23 | C |
| ATOM | 9609 | O | THR | E | 118 | 10.612 | 34.141 | -37.919 | 116.44 | O |
| ATOM | 9610 | CB | THR | E | 118 | 13.340 | 34.974 | -37.268 | 117.43 | C |
| ATOM | 9611 | OG1 | THR | E | 118 | 13.079 | 35.606 | -36.008 | 119.94 | O |
| ATOM | 9612 | CG2 | THR | E | 118 | 14.807 | 35.139 | -37.623 | 121.12 | C |
| ATOM | 9613 | H | THR | E | 118 | 13.004 | 37.412 | -37.840 | 113.39 | H |
| ATOM | 9614 | HA | THR | E | 118 | 12.639 | 35.124 | -39.190 | 118.76 | H |
| ATOM | 9615 | HB | THR | E | 118 | 13.149 | 34.026 | -37.197 | 120.92 | H |
| ATOM | 9616 | HG1 | THR | E | 118 | 12.273 | 35.500 | -35.795 | 123.93 | H |
| ATOM | 9617 | HG21 | THR | E | 118 | 15.362 | 34.748 | -36.930 | 125.34 | H |
| ATOM | 9618 | HG22 | THR | E | 118 | 14.996 | 34.697 | -38.465 | 125.34 | H |
| ATOM | 9619 | HG23 | THR | E | 118 | 15.024 | 36.081 | -37.707 | 125.34 | H |
| ATOM | 9620 | N | THR | E | 119 | 10.183 | 36.346 | -37.781 | 113.58 | N |
| ATOM | 9621 | CA | THR | E | 119 | 8.800 | 36.131 | -37.326 | 112.81 | C |
| ATOM | 9622 | C | THR | E | 119 | 7.709 | 36.798 | -38.158 | 115.49 | C |
| ATOM | 9623 | O | THR | E | 119 | 6.530 | 36.502 | -37.968 | 114.16 | O |
| ATOM | 9624 | CB | THR | E | 119 | 8.595 | 36.627 | -35.875 | 112.82 | C |
| ATOM | 9625 | OG1 | THR | E | 119 | 8.665 | 38.059 | -35.835 | 112.89 | O |
| ATOM | 9626 | CG2 | THR | E | 119 | 9.626 | 36.020 | -34.943 | 117.46 | C |
| ATOM | 9627 | H | THR | E | 119 | 10.401 | 37.171 | -37.886 | 116.30 | H |

TABLE 5-continued

Atomic Coordinates for OMCP-NKG2D (4PDC).

| | | | | | | | | | |
|---|---|---|---|---|---|---|---|---|---|
| ATOM | 9628 | HA | THR | E | 119 | 8.624 | 35.177 | −37.333 | 115.37 | H |
| ATOM | 9629 | HB | THR | E | 119 | 7.717 | 36.348 | −35.570 | 115.38 | H |
| ATOM | 9630 | HG1 | THR | E | 119 | 9.416 | 38.318 | −36.110 | 115.47 | H |
| ATOM | 9631 | HG21 | THR | E | 119 | 9.484 | 36.341 | −34.038 | 120.95 | H |
| ATOM | 9632 | HG22 | THR | E | 119 | 9.551 | 35.053 | −34.950 | 120.95 | H |
| ATOM | 9633 | HG23 | THR | E | 119 | 10.518 | 36.270 | −35.229 | 120.95 | H |
| ATOM | 9634 | N | SER | E | 120 | 8.075 | 37.705 | −39.056 | 111.68 | N |
| ATOM | 9635 | CA | SER | E | 120 | 7.067 | 38.444 | −39.814 | 115.43 | C |
| ATOM | 9636 | C | SER | E | 120 | 6.196 | 37.531 | −40.684 | 112.04 | C |
| ATOM | 9637 | O | SER | E | 120 | 4.966 | 37.593 | −40.619 | 110.68 | O |
| ATOM | 9638 | CB | SER | E | 120 | 7.737 | 39.510 | −40.682 | 114.31 | C |
| ATOM | 9639 | OG | SER | E | 120 | 8.074 | 40.644 | −39.901 | 113.97 | O |
| ATOM | 9640 | H | SER | E | 120 | 8.888 | 37.911 | −39.244 | 114.01 | H |
| ATOM | 9641 | HA | SER | E | 120 | 6.482 | 38.899 | −39.189 | 118.51 | H |
| ATOM | 9642 | HB2 | SER | E | 120 | 8.546 | 39.140 | −41.070 | 117.18 | H |
| ATOM | 9643 | HB3 | SER | E | 120 | 7.124 | 39.778 | −41.384 | 117.18 | H |
| ATOM | 9644 | HG | SER | E | 120 | 8.604 | 40.424 | −39.288 | 116.76 | H |
| ATOM | 9645 | N | GLU | E | 121 | 6.827 | 36.691 | −41.502 | 113.53 | N |
| ATOM | 9646 | CA | GLU | E | 121 | 6.080 | 35.770 | −42.357 | 116.10 | C |
| ATOM | 9647 | C | GLU | E | 121 | 5.202 | 34.861 | −41.501 | 114.09 | C |
| ATOM | 9648 | O | GLU | E | 121 | 4.025 | 34.658 | −41.788 | 114.66 | O |
| ATOM | 9649 | CB | GLU | E | 121 | 7.030 | 34.933 | −43.222 | 118.39 | C |
| ATOM | 9650 | CG | GLU | E | 121 | 6.315 | 34.029 | −44.220 | 117.83 | C |
| ATOM | 9651 | CD | GLU | E | 121 | 7.270 | 33.236 | −45.097 | 126.57 | C |
| ATOM | 9652 | OE1 | GLU | E | 121 | 8.499 | 33.395 | −45.946 | 129.79 | O |
| ATOM | 9653 | OE2 | GLU | E | 121 | 6.786 | 32.450 | −45.940 | 128.08 | O1- |
| ATOM | 9654 | H | GLU | E | 121 | 7.681 | 36.635 | −41.580 | 116.24 | H |
| ATOM | 9655 | HA | GLU | E | 121 | 5.503 | 36.279 | −42.947 | 119.32 | H |
| ATOM | 9656 | HB2 | GLU | E | 121 | 7.606 | 35.532 | −43.723 | 122.07 | H |
| ATOM | 9657 | HB3 | GLU | E | 121 | 7.566 | 34.370 | −42.642 | 122.07 | H |
| ATOM | 9658 | HG2 | GLU | E | 121 | 5.761 | 33.399 | −43.734 | 121.40 | H |
| ATOM | 9659 | HG3 | GLU | E | 121 | 5.762 | 34.576 | −44.800 | 121.40 | H |
| ATOM | 9660 | N | PHE | E | 122 | 5.798 | 34.331 | −40.439 | 113.77 | N |
| ATOM | 9661 | CA | PHE | E | 122 | 5.101 | 33.510 | −39.458 | 114.62 | C |
| ATOM | 9662 | C | PHE | E | 122 | 3.851 | 34.212 | −38.924 | 114.41 | C |
| ATOM | 9663 | O | PHE | E | 122 | 2.760 | 33.641 | −38.928 | 113.91 | O |
| ATOM | 9664 | CB | PHE | E | 122 | 6.072 | 33.171 | −38.319 | 116.68 | C |
| ATOM | 9665 | CG | PHE | E | 122 | 5.445 | 32.476 | −37.144 | 116.24 | C |
| ATOM | 9666 | CD1 | PHE | E | 122 | 5.386 | 31.093 | −37.091 | 119.07 | C |
| ATOM | 9667 | CD2 | PHE | E | 122 | 4.959 | 33.204 | −36.070 | 117.52 | C |
| ATOM | 9668 | CE1 | PHE | E | 122 | 4.830 | 30.451 | −36.003 | 120.81 | C |
| ATOM | 9669 | CE2 | PHE | E | 122 | 4.398 | 32.568 | −34.980 | 121.23 | C |
| ATOM | 9670 | CZ | PHE | E | 122 | 4.337 | 31.189 | −34.944 | 122.10 | C |
| ATOM | 9671 | H | PHE | E | 122 | 6.633 | 34.438 | −40.261 | 116.53 | H |
| ATOM | 9672 | HA | PHE | E | 122 | 4.825 | 32.680 | −39.877 | 117.54 | H |
| ATOM | 9673 | HB2 | PHE | E | 122 | 6.766 | 32.589 | −38.667 | 120.02 | H |
| ATOM | 9674 | HB3 | PHE | E | 122 | 6.469 | 33.994 | −37.995 | 120.02 | H |
| ATOM | 9675 | HD1 | PHE | E | 122 | 5.717 | 30.591 | −37.801 | 122.89 | H |
| ATOM | 9676 | HD2 | PHE | E | 122 | 4.998 | 34.133 | −36.089 | 121.02 | H |
| ATOM | 9677 | HE1 | PHE | E | 122 | 4.787 | 29.522 | −35.983 | 124.98 | H |
| ATOM | 9678 | HE2 | PHE | E | 122 | 4.067 | 33.068 | −34.268 | 125.48 | H |

TABLE 5-continued

Atomic Coordinates for OMCP-NKG2D (4PDC).

| ATOM | 9679 | HZ | PHE | E | 122 | 3.959 | 30.758 | -34.211 | 126.52 | H |
| --- | --- | --- | --- | --- | --- | --- | --- | --- | --- | --- |
| ATOM | 9680 | N | ARG | E | 123 | 4.008 | 35.459 | -38.491 | 19.96 | N |
| ATOM | 9681 | CA | ARG | E | 123 | 2.915 | 36.190 | -37.862 | 112.21 | C |
| ATOM | 9682 | C | ARG | E | 123 | 1.821 | 36.555 | -38.871 | 113.20 | C |
| ATOM | 9683 | O | ARG | E | 123 | 0.660 | 36.720 | -38.501 | 116.26 | O |
| ATOM | 9684 | CB | ARG | E | 123 | 3.461 | 37.442 | -37.164 | 113.63 | C |
| ATOM | 9685 | CG | ARG | E | 123 | 4.080 | 37.153 | -35.797 | 114.82 | C |
| ATOM | 9686 | CD | ARG | E | 123 | 5.182 | 38.138 | -35.440 | 119.31 | C |
| ATOM | 9687 | NE | ARG | E | 123 | 4.809 | 39.485 | -35.833 | 125.00 | N |
| ATOM | 9688 | CZ | ARG | E | 123 | 5.551 | 40.304 | -36.569 | 113.96 | C |
| ATOM | 9689 | NH1 | ARG | E | 123 | 6.763 | 39.963 | -36.994 | 117.77 | N1+ |
| ATOM | 9690 | NH2 | ARG | E | 123 | 5.076 | 41.500 | -36.857 | 120.81 | N |
| ATOM | 9691 | H | ARG | E | 123 | 4.741 | 35.905 | -38.551 | 111.95 | H |
| ATOM | 9692 | HA | ARG | E | 123 | 2.513 | 35.625 | -37.183 | 114.65 | H |
| ATOM | 9693 | HB2 | ARG | E | 123 | 4.147 | 37.839 | -37.724 | 116.36 | H |
| ATOM | 9694 | HB3 | ARG | E | 123 | 2.735 | 38.072 | -37.035 | 116.36 | H |
| ATOM | 9695 | HG2 | ARG | E | 123 | 3.391 | 37.212 | -35.117 | 117.78 | H |
| ATOM | 9696 | HG3 | ARG | E | 123 | 4.464 | 36.262 | -35.805 | 117.78 | H |
| ATOM | 9697 | HD2 | ARG | E | 123 | 5.326 | 38.127 | -34.481 | 123.17 | H |
| ATOM | 9698 | HD3 | ARG | E | 123 | 5.996 | 37.896 | -35.908 | 123.17 | H |
| ATOM | 9699 | HE | ARG | E | 123 | 4.045 | 39.776 | -35.567 | 130.00 | H |
| ATOM | 9700 | HH11 | ARG | E | 123 | 7.080 | 39.185 | -36.811 | 121.33 | H |
| ATOM | 9701 | HH12 | ARG | E | 123 | 7.225 | 40.516 | -37.464 | 121.33 | H |
| ATOM | 9702 | HH21 | ARG | E | 123 | 4.296 | 41.732 | -36.579 | 124.98 | H |
| ATOM | 9703 | HH22 | ARG | E | 123 | 5.547 | 42.049 | -37.323 | 124.98 | H |
| ATOM | 9704 | N | LEU | E | 124 | 2.184 | 36.657 | -40.146 | 111.77 | N |
| ATOM | 9705 | CA | LEU | E | 124 | 1.207 | 36.917 | -41.200 | 112.92 | C |
| ATOM | 9706 | C | LEU | E | 124 | 0.445 | 35.654 | -41.598 | 114.87 | C |
| ATOM | 9707 | O | LEU | E | 124 | -0.771 | 35.691 | -41.805 | 114.46 | O |
| ATOM | 9708 | CB | LEU | E | 124 | 1.890 | 37.508 | -42.437 | 114.80 | C |
| ATOM | 9709 | CG | LEU | E | 124 | 1.021 | 37.592 | -43.700 | 111.83 | C |
| ATOM | 9710 | CD1 | LEU | E | 124 | -0.216 | 38.439 | -43.460 | 115.58 | C |
| ATOM | 9711 | CD2 | LEU | E | 124 | 1.822 | 38.135 | -44.871 | 114.19 | C |
| ATOM | 9712 | H | LEU | E | 124 | 2.993 | 36.579 | -40.429 | 114.12 | H |
| ATOM | 9713 | HA | LEU | E | 124 | 0.561 | 37.565 | -40.877 | 115.50 | H |
| ATOM | 9714 | HB2 | LEU | E | 124 | 2.182 | 38.408 | -42.225 | 117.76 | H |
| ATOM | 9715 | HB3 | LEU | E | 124 | 2.661 | 36.961 | -42.652 | 117.76 | H |
| ATOM | 9716 | HG | LEU | E | 124 | 0.725 | 36.698 | -43.934 | 114.19 | H |
| ATOM | 9717 | HD11 | LEU | E | 124 | -0.740 | 38.470 | -44.276 | 118.69 | H |
| ATOM | 9718 | HD12 | LEU | E | 124 | -0.738 | 38.040 | -42.746 | 118.69 | H |
| ATOM | 9719 | HD13 | LEU | E | 124 | 0.059 | 39.335 | -43.209 | 118.69 | H |
| ATOM | 9720 | HD21 | LEU | E | 124 | 1.250 | 38.177 | -45.652 | 117.03 | H |
| ATOM | 9721 | HD22 | LEU | E | 124 | 2.144 | 39.022 | -44.648 | 117.03 | H |
| ATOM | 9722 | HD23 | LEU | E | 124 | 2.572 | 37.544 | -45.041 | 117.03 | H |
| ATOM | 9723 | N | LYS | E | 125 | 1.158 | 34.538 | -41.705 | 113.01 | N |
| ATOM | 9724 | CA | LYS | E | 125 | 0.593 | 33.347 | -42.336 | 115.82 | C |
| ATOM | 9725 | C | LYS | E | 125 | -0.148 | 32.421 | -41.379 | 117.64 | C |
| ATOM | 9726 | O | LYS | E | 125 | -0.543 | 31.320 | -41.758 | 113.71 | O |
| ATOM | 9727 | CB | LYS | E | 125 | 1.698 | 32.572 | -43.050 | 113.96 | C |
| ATOM | 9728 | CG | LYS | E | 125 | 2.202 | 33.285 | -44.298 | 120.01 | C |
| ATOM | 9729 | CD | LYS | E | 125 | 3.130 | 32.408 | -45.114 | 123.78 | C |

TABLE 5-continued

Atomic Coordinates for OMCP-NKG2D (4PDC).

| ATOM | 9730 | CE  | LYS | E | 125 | 3.436  | 33.035 | -46.467 | 122.29 | C   |
|------|------|-----|-----|---|-----|--------|--------|---------|--------|-----|
| ATOM | 9731 | NZ  | LYS | E | 125 | 4.222  | 32.110 | -47.321 | 126.85 | N1+ |
| ATOM | 9732 | H   | LYS | E | 125 | 1.965  | 34.443 | -41.424 | 115.61 | H   |
| ATOM | 9733 | HA  | LYS | E | 125 | -0.043 | 33.633 | -43.010 | 118.98 | H   |
| ATOM | 9734 | HB2 | LYS | E | 125 | 2.448  | 32.461 | -42.444 | 116.76 | H   |
| ATOM | 9735 | HB3 | LYS | E | 125 | 1.355  | 31.705 | -43.317 | 116.76 | H   |
| ATOM | 9736 | HG2 | LYS | E | 125 | 1.446  | 33.526 | -44.855 | 124.01 | H   |
| ATOM | 9737 | HG3 | LYS | E | 125 | 2.691  | 34.080 | -44.035 | 124.01 | H   |
| ATOM | 9738 | HD2 | LYS | E | 125 | 3.965  | 32.292 | -44.635 | 128.53 | H   |
| ATOM | 9739 | HD3 | LYS | E | 125 | 2.707  | 31.548 | -45.265 | 128.53 | H   |
| ATOM | 9740 | HE2 | LYS | E | 125 | 2.604  | 33.238 | -46.922 | 126.74 | H   |
| ATOM | 9741 | HE3 | LYS | E | 125 | 3.955  | 33.844 | -46.335 | 126.74 | H   |
| ATOM | 9742 | HZ1 | LYS | E | 125 | 4.392  | 32.492 | -48.106 | 132.22 | H   |
| ATOM | 9743 | HZ2 | LYS | E | 125 | 4.993  | 31.910 | -46.923 | 132.22 | H   |
| ATOM | 9744 | HZ3 | LYS | E | 125 | 3.764  | 31.359 | -47.457 | 132.22 | H   |
| ATOM | 9745 | N   | LYS | E | 126 | -0.352 | 32.867 | -40.145 | 115.49 | N   |
| ATOM | 9746 | CA  | LYS | E | 126 | -1.062 | 32.056 | -39.168 | 114.17 | C   |
| ATOM | 9747 | C   | LYS | E | 126 | -2.423 | 31.628 | -39.718 | 114.30 | C   |
| ATOM | 9748 | O   | LYS | E | 126 | -2.765 | 30.447 | -39.682 | 114.19 | O   |
| ATOM | 9749 | CB  | LYS | E | 126 | -1.230 | 32.826 | -37.862 | 113.34 | C   |
| ATOM | 9750 | CG  | LYS | E | 126 | -1.750 | 31.990 | -36.705 | 116.84 | C   |
| ATOM | 9751 | CD  | LYS | E | 126 | -1.636 | 32.761 | -35.400 | 120.30 | C   |
| ATOM | 9752 | CE  | LYS | E | 126 | -2.149 | 31.960 | -34.218 | 123.97 | C   |
| ATOM | 9753 | NZ  | LYS | E | 126 | -1.883 | 32.674 | -32.933 | 126.21 | N1+ |
| ATOM | 9754 | H   | LYS | E | 126 | -0.091 | 33.632 | -39.851 | 118.59 | H   |
| ATOM | 9755 | HA  | LYS | E | 126 | -0.546 | 31.257 | -38.983 | 117.00 | H   |
| ATOM | 9756 | HB2 | LYS | E | 126 | -0.368 | 33.187 | -37.601 | 116.00 | H   |
| ATOM | 9757 | HB3 | LYS | E | 126 | -1.858 | 33.551 | -38.007 | 116.00 | H   |
| ATOM | 9758 | HG2 | LYS | E | 126 | -2.684 | 31.775 | -36.855 | 120.21 | H   |
| ATOM | 9759 | HG3 | LYS | E | 126 | -1.223 | 31.179 | -36.630 | 120.21 | H   |
| ATOM | 9760 | HD2 | LYS | E | 126 | -0.704 | 32.977 | -35.238 | 124.36 | H   |
| ATOM | 9761 | HD3 | LYS | E | 126 | -2.161 | 33.575 | -35.464 | 124.36 | H   |
| ATOM | 9762 | HE2 | LYS | E | 126 | -3.106 | 31.835 | -34.305 | 128.76 | H   |
| ATOM | 9763 | HE3 | LYS | E | 126 | -1.697 | 31.103 | -34.190 | 128.76 | H   |
| ATOM | 9764 | HZ1 | LYS | E | 126 | -1.008 | 32.800 | -32.830 | 131.45 | H   |
| ATOM | 9765 | HZ2 | LYS | E | 126 | -2.290 | 33.466 | -32.935 | 131.45 | H   |
| ATOM | 9766 | HZ3 | LYS | E | 126 | -2.188 | 32.193 | -32.249 | 131.45 | H   |
| ATOM | 9767 | N   | TRP | E | 127 | -3.177 | 32.587 | -40.254 | 113.47 | N   |
| ATOM | 9768 | CA  | TRP | E | 127 | -4.497 | 32.314 | -40.828 | 124.36 | C   |
| ATOM | 9769 | C   | TRP | E | 127 | -4.575 | 32.682 | -42.311 | 114.64 | C   |
| ATOM | 9770 | O   | TRP | E | 127 | -5.632 | 32.557 | -42.929 | 113.48 | O   |
| ATOM | 9771 | CB  | TRP | E | 127 | -5.573 | 33.078 | -40.053 | 113.26 | C   |
| ATOM | 9772 | CG  | TRP | E | 127 | -5.758 | 32.580 | -38.653 | 116.00 | C   |
| ATOM | 9773 | CD1 | TRP | E | 127 | -5.306 | 33.163 | -37.508 | 116.46 | C   |
| ATOM | 9774 | CD2 | TRP | E | 127 | -6.437 | 31.386 | -38.256 | 114.01 | C   |
| ATOM | 9775 | NE1 | TRP | E | 127 | -5.666 | 32.408 | -36.419 | 120.27 | N   |
| ATOM | 9776 | CE2 | TRP | E | 127 | -6.365 | 31.312 | -36.851 | 119.93 | C   |
| ATOM | 9777 | CE3 | TRP | E | 127 | -7.108 | 30.374 | -38.951 | 120.52 | C   |
| ATOM | 9778 | CZ2 | TRP | E | 127 | -6.931 | 30.266 | -36.129 | 117.91 | C   |
| ATOM | 9779 | CZ3 | TRP | E | 127 | -7.672 | 29.339 | -38.232 | 122.57 | C   |
| ATOM | 9780 | CH2 | TRP | E | 127 | -7.579 | 29.291 | -36.835 | 125.03 | C   |

TABLE 5-continued

Atomic Coordinates for OMCP-NKG2D (4PDC).

| | | | | | | | | | | |
|---|---|---|---|---|---|---|---|---|---|---|
| ATOM | 9781 | H | TRP | E | 127 | -2.944 | 33.413 | -40.298 | 116.16 | H |
| ATOM | 9782 | HA | TRP | E | 127 | -4.686 | 31.367 | -40.745 | 116.03 | H |
| ATOM | 9783 | HB2 | TRP | E | 127 | -5.322 | 34.014 | -40.006 | 115.92 | H |
| ATOM | 9784 | HB3 | TRP | E | 127 | -6.420 | 32.986 | -40.517 | 115.92 | H |
| ATOM | 9785 | HD1 | TRP | E | 127 | -4.823 | 33.957 | -37.470 | 119.75 | H |
| ATOM | 9786 | HE1 | TRP | E | 127 | -5.484 | 32.594 | -35.599 | 124.32 | H |
| ATOM | 9787 | HE3 | TRP | E | 127 | -7.174 | 30.400 | -39.878 | 124.62 | H |
| ATOM | 9788 | HZ2 | TRP | E | 127 | -6.873 | 30.232 | -35.201 | 121.50 | H |
| ATOM | 9789 | HZ3 | TRP | E | 127 | -8.119 | 28.660 | -38.684 | 127.09 | H |
| ATOM | 9790 | HH2 | TRP | E | 127 | -7.969 | 28.581 | -36.378 | 130.03 | H |
| ATOM | 9791 | N | PHE | E | 128 | -3.452 | 33.118 | -42.876 | 113.43 | N |
| ATOM | 9792 | CA | PHE | E | 128 | -3.425 | 33.694 | -44.221 | 112.84 | C |
| ATOM | 9793 | C | PHE | E | 128 | -2.168 | 33.275 | -44.986 | 114.69 | C |
| ATOM | 9794 | O | PHE | E | 128 | -1.174 | 33.999 | -44.999 | 114.50 | O |
| ATOM | 9795 | CB | PHE | E | 128 | -3.509 | 35.223 | -44.122 | 115.03 | C |
| ATOM | 9796 | CG | PHE | E | 128 | -3.640 | 35.922 | -45.446 | 115.62 | C |
| ATOM | 9797 | CD1 | PHE | E | 128 | -4.757 | 35.729 | -46.242 | 114.48 | C |
| ATOM | 9798 | CD2 | PHE | E | 128 | -2.660 | 36.800 | -45.879 | 117.09 | C |
| ATOM | 9799 | CE1 | PHE | E | 128 | -4.884 | 36.381 | -47.456 | 114.50 | C |
| ATOM | 9800 | CE2 | PHE | E | 128 | -2.780 | 37.454 | -47.092 | 118.86 | C |
| ATOM | 9801 | CZ | PHE | E | 128 | -3.895 | 37.245 | -47.881 | 119.29 | C |
| ATOM | 9802 | H | PHE | E | 128 | -2.680 | 33.091 | -42.497 | 116.11 | H |
| ATOM | 9803 | HA | PHE | E | 128 | -4.198 | 33.381 | -44.717 | 115.40 | H |
| ATOM | 9804 | HB2 | PHE | E | 128 | -4.283 | 35.457 | -43.587 | 118.04 | H |
| ATOM | 9805 | HB3 | PHE | E | 128 | -2.703 | 35.551 | -43.694 | 118.04 | H |
| ATOM | 9806 | HD1 | PHE | E | 128 | -5.426 | 35.147 | -45.961 | 117.38 | H |
| ATOM | 9807 | HD2 | PHE | E | 128 | -1.906 | 36.942 | -45.353 | 120.50 | H |
| ATOM | 9808 | HE1 | PHE | E | 128 | -5.636 | 36.239 | -47.985 | 117.40 | H |
| ATOM | 9809 | HE2 | PHE | E | 128 | -2.112 | 38.036 | -47.376 | 122.63 | H |
| ATOM | 9810 | HZ | PHE | E | 128 | -3.979 | 37.684 | -48.696 | 123.15 | H |
| ATOM | 9811 | N | ASP | E | 129 | -2.214 | 32.108 | -45.627 | 114.98 | N |
| ATOM | 9812 | CA | ASP | E | 129 | -1.055 | 31.599 | -46.357 | 114.76 | C |
| ATOM | 9813 | C | ASP | E | 129 | -1.064 | 32.076 | -47.809 | 117.71 | C |
| ATOM | 9814 | O | ASP | E | 129 | -1.931 | 32.851 | -48.215 | 115.50 | O |
| ATOM | 9815 | CB | ASP | E | 129 | -0.998 | 30.064 | -46.290 | 114.79 | C |
| ATOM | 9816 | CG | ASP | E | 129 | -2.224 | 29.383 | -46.902 | 119.45 | C |
| ATOM | 9817 | OD1 | ASP | E | 129 | -2.824 | 29.921 | -47.858 | 114.89 | O |
| ATOM | 9818 | OD2 | ASP | E | 129 | -2.571 | 28.277 | -46.430 | 117.87 | O1- |
| ATOM | 9819 | H | ASP | E | 129 | -2.903 | 31.593 | -45.653 | 117.98 | H |
| ATOM | 9820 | HA | ASP | E | 129 | -0.250 | 31.942 | -45.939 | 117.72 | H |
| ATOM | 9821 | HB2 | ASP | E | 129 | -0.215 | 29.757 | -46.773 | 117.74 | H |
| ATOM | 9822 | HB3 | ASP | E | 129 | -0.940 | 29.792 | -45.361 | 117.74 | H |
| ATOM | 9823 | N | GLY | E | 130 | -0.093 | 31.611 | -48.587 | 115.51 | N |
| ATOM | 9824 | CA | GLY | E | 130 | -0.049 | 32.047 | -49.964 | 115.30 | C |
| ATOM | 9825 | C | GLY | E | 130 | -1.162 | 31.724 | -50.821 | 117.27 | C |
| ATOM | 9826 | O | GLY | E | 130 | -1.603 | 32.546 | -51.628 | 113.78 | O |
| ATOM | 9827 | H | GLY | E | 130 | 0.499 | 31.040 | -48.337 | 118.61 | H |
| ATOM | 9828 | HA2 | GLY | E | 130 | 0.188 | 33.007 | -49.984 | 118.37 | H |
| ATOM | 9829 | HA3 | GLY | E | 130 | 0.824 | 31.618 | -50.358 | 118.37 | H |
| ATOM | 9830 | N | GLU | E | 131 | -1.702 | 30.522 | -50.651 | 111.94 | N |
| ATOM | 9831 | CA | GLU | E | 131 | -2.873 | 30.109 | -51.409 | 116.34 | C |

TABLE 5-continued

Atomic Coordinates for OMCP-NKG2D (4PDC).

| ATOM | 9832 | C | GLU | E | 131 | -4.066 | 31.011 | -51.092 | 117.14 | C |
|---|---|---|---|---|---|---|---|---|---|---|
| ATOM | 9833 | O | GLU | E | 131 | -4.838 | 31.359 | -51.984 | 115.64 | O |
| ATOM | 9834 | CB | GLU | E | 131 | -3.210 | 28.648 | -51.121 | 118.79 | C |
| ATOM | 9835 | CG | GLU | E | 131 | -4.237 | 28.065 | -52.074 | 125.42 | C |
| ATOM | 9836 | CD | GLU | E | 131 | -4.437 | 26.574 | -51.886 | 125.71 | C |
| ATOM | 9837 | OE1 | GLU | E | 131 | -3.919 | 26.017 | -50.892 | 123.82 | O |
| ATOM | 9838 | OE2 | GLU | E | 131 | -5.110 | 25.960 | -52.743 | 128.51 | O1- |
| ATOM | 9839 | H | GLU | E | 131 | -1.409 | 29.929 | -50.101 | 114.32 | H |
| ATOM | 9840 | HA | GLU | E | 131 | -2.680 | 30.190 | -52.357 | 119.61 | H |
| ATOM | 9841 | HB2 | GLU | E | 131 | -2.401 | 28.118 | -51.195 | 122.54 | H |
| ATOM | 9842 | HB3 | GLU | E | 131 | -3.567 | 28.580 | -50.221 | 122.54 | H |
| ATOM | 9843 | HG2 | GLU | E | 131 | -5.090 | 28.503 | -51.925 | 130.51 | H |
| ATOM | 9844 | HG3 | GLU | E | 131 | -3.942 | 28.215 | -52.986 | 130.51 | H |
| ATOM | 9845 | N | ASP | E | 132 | -4.207 | 31.390 | -49.824 | 114.43 | N |
| ATOM | 9846 | CA | ASP | E | 132 | -5.244 | 32.334 | -49.421 | 116.97 | C |
| ATOM | 9847 | C | ASP | E | 132 | -5.081 | 33.673 | -50.140 | 115.70 | C |
| ATOM | 9848 | O | ASP | E | 132 | -6.053 | 34.244 | -50.630 | 113.91 | O |
| ATOM | 9849 | CB | ASP | E | 132 | -5.220 | 32.562 | -47.904 | 115.21 | C |
| ATOM | 9850 | CG | ASP | E | 132 | -5.483 | 31.294 | -47.113 | 117.73 | C |
| ATOM | 9851 | OD1 | ASP | E | 132 | -6.201 | 30.405 | -47.621 | 116.20 | O |
| ATOM | 9852 | OD2 | ASP | E | 132 | -4.974 | 31.192 | -45.972 | 115.44 | O1- |
| ATOM | 9853 | H | ASP | E | 132 | -3.713 | 31.114 | -49.176 | 117.31 | H |
| ATOM | 9854 | HA | ASP | E | 132 | -6.112 | 31.971 | -49.656 | 120.37 | H |
| ATOM | 9855 | HB2 | ASP | E | 132 | -4.346 | 32.898 | -47.649 | 118.25 | H |
| ATOM | 9856 | HB3 | ASP | E | 132 | -5.905 | 33.208 | -47.671 | 118.25 | H |
| ATOM | 9857 | N | CYS | E | 133 | -3.849 | 34.168 | -50.198 | 112.86 | N |
| ATOM | 9858 | CA | CYS | E | 133 | -3.571 | 35.454 | -50.826 | 112.73 | C |
| ATOM | 9859 | C | CYS | E | 133 | -3.981 | 35.443 | -52.295 | 114.86 | C |
| ATOM | 9860 | O | CYS | E | 133 | -4.539 | 36.417 | -52.798 | 115.23 | O |
| ATOM | 9861 | CB | CYS | E | 133 | -2.086 | 35.805 | -50.691 | 121.39 | C |
| ATOM | 9862 | SG | CYS | E | 133 | -1.610 | 37.374 | -51.458 | 123.37 | S |
| ATOM | 9863 | H | CYS | E | 133 | -3.153 | 33.776 | -49.880 | 115.43 | H |
| ATOM | 9864 | HA | CYS | E | 133 | -4.084 | 36.143 | -50.376 | 115.28 | H |
| ATOM | 9865 | HB2 | CYS | E | 133 | -1.864 | 35.860 | -49.749 | 125.67 | H |
| ATOM | 9866 | HB3 | CYS | E | 133 | -1.562 | 35.103 | -51.109 | 125.67 | H |
| ATOM | 9867 | N | ILE | E | 134 | -3.718 | 34.331 | -52.974 | 113.95 | N |
| ATOM | 9868 | CA | ILE | E | 134 | -4.075 | 34.191 | -54.382 | 113.37 | C |
| ATOM | 9869 | C | ILE | E | 134 | -5.593 | 34.152 | -54.551 | 114.47 | C |
| ATOM | 9870 | O | ILE | E | 134 | -6.141 | 34.750 | -55.476 | 112.81 | O |
| ATOM | 9871 | CB | ILE | E | 134 | -3.457 | 32.910 | -54.996 | 118.31 | C |
| ATOM | 9872 | CG1 | ILE | E | 134 | -1.924 | 32.990 | -54.988 | 113.13 | C |
| ATOM | 9873 | CG2 | ILE | E | 134 | -3.982 | 32.670 | -56.416 | 119.91 | C |
| ATOM | 9874 | CD1 | ILE | E | 134 | -1.336 | 34.002 | -55.955 | 113.23 | C |
| ATOM | 9875 | H | ILE | E | 134 | -3.332 | 33.639 | -52.641 | 116.74 | H |
| ATOM | 9876 | HA | ILE | E | 134 | -3.735 | 34.955 | -54.873 | 116.04 | H |
| ATOM | 9877 | HB | ILE | E | 134 | -3.721 | 32.156 | -54.447 | 121.97 | H |
| ATOM | 9878 | HG12 | ILE | E | 134 | -1.632 | 33.232 | -54.096 | 115.76 | H |
| ATOM | 9879 | HG13 | ILE | E | 134 | -1.568 | 32.118 | -55.222 | 115.76 | H |
| ATOM | 9880 | HG21 | ILE | E | 134 | -3.576 | 31.863 | -56.770 | 123.89 | H |
| ATOM | 9881 | HG22 | ILE | E | 134 | -4.946 | 32.569 | -56.382 | 123.89 | H |
| ATOM | 9882 | HG23 | ILE | E | 134 | -3.748 | 33.430 | -56.971 | 123.89 | H |

TABLE 5-continued

Atomic Coordinates for OMCP-NKG2D (4PDC).

| ATOM | 9883 | HD11 | ILE | E | 134 | -0.369 | 33.983 | -55.881 | 115.87 | H |
|---|---|---|---|---|---|---|---|---|---|---|
| ATOM | 9884 | HD12 | ILE | E | 134 | -1.604 | 33.769 | -56.858 | 115.87 | H |
| ATOM | 9885 | HD13 | ILE | E | 134 | -1.668 | 34.885 | -55.728 | 115.87 | H |
| ATOM | 9886 | N | MET | E | 135 | -6.274 | 33.436 | -53.663 | 114.36 | N |
| ATOM | 9887 | CA | MET | E | 135 | -7.724 | 33.324 | -53.753 | 116.92 | C |
| ATOM | 9888 | C | MET | E | 135 | -8.391 | 34.654 | -53.402 | 116.18 | C |
| ATOM | 9889 | O | MET | E | 135 | -9.399 | 35.025 | -54.011 | 114.50 | O |
| ATOM | 9890 | CB | MET | E | 135 | -8.230 | 32.199 | -52.849 | 117.85 | C |
| ATOM | 9891 | CG | MET | E | 135 | -7.779 | 30.819 | -53.309 | 116.72 | C |
| ATOM | 9892 | SD | MET | E | 135 | -8.442 | 30.370 | -54.924 | 124.82 | S |
| ATOM | 9893 | CE | MET | E | 135 | -10.125 | 29.954 | -54.479 | 172.84 | C |
| ATOM | 9894 | H | MET | E | 135 | -5.923 | 33.010 | -53.003 | 117.23 | H |
| ATOM | 9895 | HA | MET | E | 135 | -7.959 | 33.093 | -54.666 | 120.30 | H |
| ATOM | 9896 | HB2 | MET | E | 135 | -7.892 | 32.341 | -51.951 | 121.42 | H |
| ATOM | 9897 | HB3 | MET | E | 135 | -9.200 | 32.211 | -52.844 | 121.42 | H |
| ATOM | 9898 | HG2 | MET | E | 135 | -6.811 | 30.806 | -53.368 | 120.06 | H |
| ATOM | 9899 | HG3 | MET | E | 135 | -8.080 | 30.158 | -52.666 | 120.06 | H |
| ATOM | 9900 | HE1 | MET | E | 135 | -10.606 | 29.688 | -55.278 | 187.41 | H |
| ATOM | 9901 | HE2 | MET | E | 135 | -10.111 | 29.222 | -53.842 | 187.41 | H |
| ATOM | 9902 | HE3 | MET | E | 135 | -7.832 | 30.731 | -54.081 | 111.58 | H |
| ATOM | 9903 | N | HIS | E | 136 | -8.310 | 35.373 | -52.432 | 114.06 | N |
| ATOM | 9904 | CA | HIS | E | 136 | -8.086 | 36.721 | -52.129 | 114.28 | C |
| ATOM | 9905 | C | HIS | E | 136 | -8.963 | 37.640 | -53.325 | 117.87 | C |
| ATOM | 9906 | O | HIS | E | 136 | -7.610 | 38.424 | -53.693 | 112.00 | O |
| ATOM | 9907 | CB | HIS | E | 136 | -8.065 | 37.302 | -50.899 | 116.23 | C |
| ATOM | 9908 | CG | HIS | E | 136 | -8.066 | 36.709 | -49.603 | 114.57 | C |
| ATOM | 9909 | ND1 | HIS | E | 136 | -8.528 | 37.421 | -48.422 | 114.11 | N |
| ATOM | 9910 | CD2 | HIS | E | 136 | -8.511 | 35.474 | -49.298 | 119.48 | C |
| ATOM | 9911 | CE1 | HIS | E | 136 | -8.798 | 36.650 | -47.447 | 116.55 | C |
| ATOM | 9912 | NE2 | HIS | E | 136 | -7.180 | 35.463 | -47.952 | 113.89 | N |
| ATOM | 9913 | H | HIS | E | 136 | -9.262 | 35.107 | -51.939 | 116.87 | H |
| ATOM | 9914 | HA | HIS | E | 136 | -6.656 | 36.688 | -51.948 | 114.40 | H |
| ATOM | 9915 | HB2 | HIS | E | 136 | -7.780 | 37.142 | -50.979 | 114.40 | H |
| ATOM | 9916 | HB3 | HIS | E | 136 | -7.815 | 38.256 | -50.865 | 117.48 | H |
| ATOM | 9917 | HD1 | HIS | E | 136 | -8.642 | 38.239 | -48.334 | 116.93 | H |
| ATOM | 9918 | HD2 | HIS | E | 136 | -8.606 | 34.765 | -49.890 | 114.40 | H |
| ATOM | 9919 | HE1 | HIS | E | 136 | -9.106 | 36.900 | -46.556 | 116.15 | H |
| ATOM | 9920 | HE2 | HIS | E | 136 | -6.903 | 34.793 | -47.509 | 119.86 | H |
| ATOM | 9921 | N | LEU | E | 137 | -6.548 | 37.539 | -53.922 | 113.80 | N |
| ATOM | 9922 | CA | LEU | E | 137 | -6.548 | 38.344 | -55.086 | 114.11 | C |
| ATOM | 9923 | C | LEU | E | 137 | -7.567 | 38.163 | -56.209 | 114.94 | C |
| ATOM | 9924 | O | LEU | E | 137 | -8.077 | 39.134 | -56.758 | 116.40 | O |
| ATOM | 9925 | CB | LEU | E | 137 | -5.142 | 37.980 | -55.573 | 113.09 | C |
| ATOM | 9926 | CG | LEU | E | 137 | -4.711 | 38.506 | -56.945 | 115.68 | C |
| ATOM | 9927 | CD1 | LEU | E | 137 | -4.834 | 40.023 | -57.025 | 119.57 | C |
| ATOM | 9928 | CD2 | LEU | E | 137 | -3.285 | 38.070 | -57.252 | 116.15 | C |
| ATOM | 9929 | H | LEU | E | 137 | -6.280 | 37.003 | -53.668 | 116.56 | H |
| ATOM | 9930 | HA | LEU | E | 137 | -6.545 | 39.281 | -54.833 | 116.93 | H |
| ATOM | 9931 | HB2 | LEU | E | 137 | -4.504 | 38.317 | -54.925 | 115.71 | H |
| ATOM | 9932 | HB3 | LEU | E | 137 | -5.079 | 37.012 | -55.607 | 115.71 | H |
| ATOM | 9933 | HG | LEU | E | 137 | -5.290 | 38.125 | -57.623 | 118.82 | H |

TABLE 5-continued

Atomic Coordinates for OMCP-NKG2D (4PDC).

| ATOM | 9934 | HD11 | LEU | E | 137 | -4.553 | 40.316 | -57.906 | 123.48 | H |
|---|---|---|---|---|---|---|---|---|---|---|
| ATOM | 9935 | HD12 | LEU | E | 137 | -5.759 | 40.272 | -56.873 | 123.48 | H |
| ATOM | 9936 | HD13 | LEU | E | 137 | -4.267 | 40.422 | -56.346 | 123.48 | H |
| ATOM | 9937 | HD21 | LEU | E | 137 | -3.031 | 38.412 | -58.123 | 119.37 | H |
| ATOM | 9938 | HD22 | LEU | E | 137 | -2.693 | 38.425 | -56.570 | 119.37 | H |
| ATOM | 9939 | HD23 | LEU | E | 137 | -3.245 | 37.100 | -57.252 | 119.37 | H |
| ATOM | 9940 | N | ARG | E | 138 | -7.872 | 36.915 | -56.536 | 115.03 | N |
| ATOM | 9941 | CA | ARG | E | 138 | -8.821 | 36.624 | -57.599 | 117.21 | C |
| ATOM | 9942 | C | ARG | E | 138 | -10.223 | 37.129 | -57.242 | 118.67 | C |
| ATOM | 9943 | O | ARG | E | 138 | -10.941 | 37.654 | -58.093 | 117.07 | O |
| ATOM | 9944 | CB | ARG | E | 138 | -8.835 | 35.121 | -57.883 | 117.26 | C |
| ATOM | 9945 | CG | ARG | E | 138 | -7.536 | 34.621 | -58.502 | 118.09 | C |
| ATOM | 9946 | CD | ARG | E | 138 | -7.529 | 33.110 | -58.664 | 122.76 | C |
| ATOM | 9947 | NE | ARG | E | 138 | -8.525 | 32.659 | -59.628 | 125.06 | N |
| ATOM | 9948 | CZ | ARG | E | 138 | -8.955 | 31.407 | -59.728 | 130.07 | C |
| ATOM | 9949 | NH1 | ARG | E | 138 | -8.479 | 30.470 | -58.918 | 128.66 | N1+ |
| ATOM | 9950 | NH2 | ARG | E | 138 | -9.870 | 31.092 | -60.635 | 131.23 | N |
| ATOM | 9951 | H | ARG | E | 138 | -7.542 | 36.217 | -56.156 | 118.04 | H |
| ATOM | 9952 | HA | ARG | E | 138 | -8.537 | 37.078 | -58.408 | 120.66 | H |
| ATOM | 9953 | HB2 | ARG | E | 138 | -8.973 | 34.644 | -57.050 | 120.72 | H |
| ATOM | 9954 | HB3 | ARG | E | 138 | -9.556 | 34.924 | -58.501 | 120.72 | H |
| ATOM | 9955 | HG2 | ARG | E | 138 | -7.426 | 35.020 | -59.380 | 121.70 | H |
| ATOM | 9956 | HG3 | ARG | E | 138 | -6.794 | 34.867 | -57.928 | 121.70 | H |
| ATOM | 9957 | HD2 | ARG | E | 138 | -6.655 | 32.828 | -58.978 | 127.31 | H |
| ATOM | 9958 | HD3 | ARG | E | 138 | -7.727 | 32.698 | -57.809 | 127.31 | H |
| ATOM | 9959 | HE | ARG | E | 138 | -8.856 | 33.242 | -60.167 | 130.07 | H |
| ATOM | 9960 | HH11 | ARG | E | 138 | -7.888 | 30.673 | -58.328 | 134.40 | H |
| ATOM | 9961 | HH12 | ARG | E | 138 | -8.761 | 29.661 | -58.985 | 134.40 | H |
| ATOM | 9962 | HH21 | ARG | E | 138 | -10.180 | 31.697 | -61.161 | 137.48 | H |
| ATOM | 9963 | HH22 | ARG | E | 138 | -10.149 | 30.281 | -60.700 | 137.48 | H |
| ATOM | 9964 | N | SER | E | 139 | -10.603 | 36.994 | -55.978 | 116.32 | N |
| ATOM | 9965 | CA | SER | E | 139 | -11.907 | 37.474 | -55.534 | 116.34 | C |
| ATOM | 9966 | C | SER | E | 139 | -11.968 | 39.002 | -55.579 | 117.91 | C |
| ATOM | 9967 | O | SER | E | 139 | -13.011 | 39.582 | -55.889 | 116.73 | O |
| ATOM | 9968 | CB | SER | E | 139 | -12.210 | 36.973 | -54.121 | 115.40 | C |
| ATOM | 9969 | OG | SER | E | 139 | -12.117 | 35.559 | -54.052 | 115.94 | O |
| ATOM | 9970 | H | SER | E | 139 | -10.129 | 36.630 | -55.359 | 119.59 | H |
| ATOM | 9971 | HA | SER | E | 139 | -12.590 | 37.128 | -56.129 | 119.61 | H |
| ATOM | 9972 | HB2 | SER | E | 139 | -11.569 | 37.361 | -53.504 | 118.47 | H |
| ATOM | 9973 | HB3 | SER | E | 139 | -13.109 | 37.242 | -53.877 | 118.47 | H |
| ATOM | 9974 | HG | SER | E | 139 | -12.668 | 35.209 | -54.582 | 119.13 | H |
| ATOM | 9975 | N | LEU | E | 140 | -10.851 | 39.657 | -55.274 | 116.92 | N |
| ATOM | 9976 | CA | LEU | E | 140 | -10.813 | 41.119 | -55.262 | 116.54 | C |
| ATOM | 9977 | C | LEU | E | 140 | -10.772 | 41.679 | -56.680 | 116.09 | C |
| ATOM | 9978 | O | LEU | E | 140 | -11.345 | 42.734 | -56.953 | 120.02 | O |
| ATOM | 9979 | CB | LEU | E | 140 | -9.612 | 41.620 | -54.459 | 114.74 | C |
| ATOM | 9980 | CG | LEU | E | 140 | -9.696 | 41.416 | -52.944 | 113.44 | C |
| ATOM | 9981 | CD1 | LEU | E | 140 | -8.341 | 41.666 | -52.303 | 116.07 | C |
| ATOM | 9982 | CD2 | LEU | E | 140 | -10.762 | 42.310 | -52.316 | 117.46 | C |
| ATOM | 9983 | H | LEU | E | 140 | -10.105 | 39.281 | -55.070 | 120.30 | H |
| ATOM | 9984 | HA | LEU | E | 140 | -11.617 | 41.450 | -54.834 | 119.85 | H |

TABLE 5-continued

Atomic Coordinates for OMCP-NKG2D (4PDC).

| ATOM | 9985 | HB2 | LEU | E | 140 | -8.820 | -54.771 | 41.157 | 117.68 | H |
|---|---|---|---|---|---|---|---|---|---|---|
| ATOM | 9986 | HB3 | LEU | E | 140 | -9.514 | -54.618 | 42.572 | 117.68 | H |
| ATOM | 9987 | HG | LEU | E | 140 | -9.941 | -52.766 | 40.494 | 116.13 | H |
| ATOM | 9988 | HD11 | LEU | E | 140 | -8.415 | -51.346 | 41.532 | 119.28 | H |
| ATOM | 9989 | HD12 | LEU | E | 140 | -7.696 | -51.045 | 41.045 | 119.28 | H |
| ATOM | 9990 | HD13 | LEU | E | 140 | -8.068 | -52.676 | 42.578 | 119.28 | H |
| ATOM | 9991 | HD21 | LEU | E | 140 | -10.784 | -51.359 | 42.151 | 120.95 | H |
| ATOM | 9992 | HD22 | LEU | E | 140 | -10.540 | -52.493 | 43.238 | 120.95 | H |
| ATOM | 9993 | HD23 | LEU | E | 140 | -11.624 | -52.707 | 42.096 | 120.95 | H |
| ATOM | 9994 | N | VAL | E | 141 | -10.099 | -57.583 | 40.975 | 119.49 | N |
| ATOM | 9995 | CA | VAL | E | 141 | -10.106 | -58.987 | 41.360 | 119.08 | C |
| ATOM | 9996 | C | VAL | E | 141 | -11.545 | -59.499 | 41.319 | 121.59 | C |
| ATOM | 9997 | O | VAL | E | 141 | -11.956 | -60.284 | 42.169 | 125.99 | O |
| ATOM | 9998 | CB | VAL | E | 141 | -9.200 | -59.836 | 40.441 | 119.66 | C |
| ATOM | 9999 | CG1 | VAL | E | 141 | -9.450 | -61.326 | 40.649 | 122.61 | C |
| ATOM | 10000 | CG2 | VAL | E | 141 | -7.733 | -59.517 | 40.702 | 118.87 | C |
| ATOM | 10001 | H | VAL | E | 141 | -9.633 | -57.409 | 40.274 | 123.39 | H |
| ATOM | 10002 | HA | VAL | E | 141 | -9.779 | -59.071 | 42.270 | 122.90 | H |
| ATOM | 10003 | HB | VAL | E | 141 | -9.396 | -59.623 | 39.515 | 123.59 | H |
| ATOM | 10004 | HG11 | VAL | E | 141 | -8.868 | -61.829 | 40.059 | 127.13 | H |
| ATOM | 10005 | HG12 | VAL | E | 141 | -10.378 | -61.522 | 40.445 | 127.13 | H |
| ATOM | 10006 | HG13 | VAL | E | 141 | -9.260 | -61.551 | 41.573 | 127.13 | H |
| ATOM | 10007 | HG21 | VAL | E | 141 | -7.183 | -60.059 | 40.116 | 122.64 | H |
| ATOM | 10008 | HG22 | VAL | E | 141 | -7.528 | -59.717 | 41.629 | 122.64 | H |
| ATOM | 10009 | HG23 | VAL | E | 141 | -7.579 | -58.576 | 40.525 | 122.64 | H |
| ATOM | 10010 | N | ARG | E | 142 | -12.307 | -59.033 | 40.335 | 119.07 | N |
| ATOM | 10011 | CA | ARG | E | 142 | -13.704 | -59.429 | 40.192 | 124.24 | C |
| ATOM | 10012 | C | ARG | E | 142 | -14.533 | -59.009 | 41.405 | 126.35 | C |
| ATOM | 10013 | O | ARG | E | 142 | -15.269 | -59.821 | 41.966 | 128.20 | O |
| ATOM | 10014 | CB | ARG | E | 142 | -14.294 | -58.832 | 38.913 | 125.76 | C |
| ATOM | 10015 | CG | ARG | E | 142 | -15.783 | -59.070 | 38.721 | 136.68 | C |
| ATOM | 10016 | CD | ARG | E | 142 | -16.117 | -60.548 | 38.625 | 144.40 | C |
| ATOM | 10017 | NE | ARG | E | 142 | -17.545 | -60.761 | 38.399 | 154.59 | N |
| ATOM | 10018 | CZ | ARG | E | 142 | -18.135 | -60.717 | 37.208 | 159.95 | C |
| ATOM | 10019 | NH1 | ARG | E | 142 | -17.425 | -60.469 | 36.115 | 156.87 | N1+ |
| ATOM | 10020 | NH2 | ARG | E | 142 | -19.440 | -60.921 | 37.109 | 168.51 | N |
| ATOM | 10021 | H | ARG | E | 142 | -12.037 | -58.483 | 39.733 | 122.89 | H |
| ATOM | 10022 | HA | ARG | E | 142 | -13.751 | -60.395 | 40.119 | 129.09 | H |
| ATOM | 10023 | HB2 | ARG | E | 142 | -13.835 | -59.219 | 38.151 | 130.91 | H |
| ATOM | 10024 | HB3 | ARG | E | 142 | -14.150 | -57.872 | 38.925 | 130.91 | H |
| ATOM | 10025 | HG2 | ARG | E | 142 | -16.071 | -58.641 | 37.900 | 144.02 | H |
| ATOM | 10026 | HG3 | ARG | E | 142 | -16.265 | -58.700 | 39.478 | 144.02 | H |
| ATOM | 10027 | HD2 | ARG | E | 142 | -15.872 | -60.986 | 39.455 | 153.28 | H |
| ATOM | 10028 | HD3 | ARG | E | 142 | -15.631 | -60.939 | 37.882 | 153.28 | H |
| ATOM | 10029 | HE | ARG | E | 142 | -18.038 | -60.927 | 39.084 | 165.51 | H |
| ATOM | 10030 | HH11 | ARG | E | 142 | -16.578 | -60.334 | 36.173 | 168.25 | H |
| ATOM | 10031 | HH12 | ARG | E | 142 | -17.813 | -60.442 | 35.347 | 168.25 | H |
| ATOM | 10032 | HH21 | ARG | E | 142 | -19.905 | -61.084 | 37.814 | 182.22 | H |
| ATOM | 10033 | HH22 | ARG | E | 142 | -19.822 | -60.894 | 36.339 | 182.22 | H |
| ATOM | 10034 | N | LYS | E | 143 | -14.416 | -57.745 | 41.805 | 123.88 | N |
| ATOM | 10035 | CA | LYS | E | 143 | -15.118 | -57.251 | 42.986 | 128.82 | C |

TABLE 5-continued

Atomic Coordinates for OMCP-NKG2D (4PDC).

| | | | | | | | | | |
|---|---|---|---|---|---|---|---|---|---|
| ATOM | 10036 | C | LYS | E | 143 | -14.736 | 44.212 | -58.065 | 128.57 | C |
| ATOM | 10037 | O | LYS | E | 143 | -15.592 | 44.986 | -58.488 | 131.07 | O |
| ATOM | 10038 | CB | LYS | E | 143 | -14.800 | 43.246 | -55.778 | 123.54 | C |
| ATOM | 10039 | CG | LYS | E | 143 | -15.219 | 42.147 | -54.829 | 128.69 | C |
| ATOM | 10040 | CD | LYS | E | 143 | -15.096 | 42.597 | -53.378 | 128.36 | C |
| ATOM | 10041 | CE | LYS | E | 143 | -16.233 | 43.528 | -52.982 | 135.13 | C |
| ATOM | 10042 | NZ | LYS | E | 143 | -16.120 | 43.988 | -51.571 | 139.13 | N1+ |
| ATOM | 10043 | H | LYS | E | 143 | -13.935 | 41.408 | -57.152 | 128.66 | H |
| ATOM | 10044 | HA | LYS | E | 143 | -16.074 | 42.849 | -57.337 | 134.59 | H |
| ATOM | 10045 | HB2 | LYS | E | 143 | -13.842 | 43.363 | -55.685 | 128.25 | H |
| ATOM | 10046 | HB3 | LYS | E | 143 | -15.255 | 44.057 | -55.503 | 128.25 | H |
| ATOM | 10047 | HG2 | LYS | E | 143 | -16.144 | 41.911 | -54.998 | 134.42 | H |
| ATOM | 10048 | HG3 | LYS | E | 143 | -14.645 | 41.375 | -54.959 | 134.42 | H |
| ATOM | 10049 | HD2 | LYS | E | 143 | -15.124 | 41.819 | -52.799 | 134.03 | H |
| ATOM | 10050 | HD3 | LYS | E | 143 | -14.259 | 43.072 | -53.261 | 134.03 | H |
| ATOM | 10051 | HE2 | LYS | E | 143 | -16.218 | 44.309 | -53.557 | 142.15 | H |
| ATOM | 10052 | HE3 | LYS | E | 143 | -17.076 | 43.059 | -53.080 | 142.15 | H |
| ATOM | 10053 | HZ1 | LYS | E | 143 | -16.137 | 43.289 | -51.021 | 146.95 | H |
| ATOM | 10054 | HZ2 | LYS | E | 143 | -15.355 | 44.429 | -51.455 | 146.95 | H |
| ATOM | 10055 | HZ3 | LYS | E | 143 | -16.798 | 44.529 | -51.372 | 146.95 | H |
| ATOM | 10056 | N | MET | E | 144 | -13.436 | 44.376 | -58.272 | 125.28 | N |
| ATOM | 10057 | CA | MET | E | 144 | -12.900 | 45.547 | -58.948 | 127.97 | C |
| ATOM | 10058 | C | MET | E | 144 | -13.406 | 45.645 | -60.384 | 135.15 | C |
| ATOM | 10059 | O | MET | E | 144 | -13.712 | 46.735 | -60.871 | 134.51 | O |
| ATOM | 10060 | CB | MET | E | 144 | -11.370 | 45.506 | -58.919 | 125.24 | C |
| ATOM | 10061 | CG | MET | E | 144 | -10.688 | 46.653 | -59.650 | 129.40 | C |
| ATOM | 10062 | SD | MET | E | 144 | -10.298 | 46.242 | -61.360 | 142.62 | S |
| ATOM | 10063 | CE | MET | E | 144 | -9.018 | 45.007 | -61.143 | 135.57 | C |
| ATOM | 10064 | H | MET | E | 144 | -12.835 | 43.813 | -58.026 | 130.34 | H |
| ATOM | 10065 | HA | MET | E | 144 | -13.182 | 46.340 | -58.465 | 133.56 | H |
| ATOM | 10066 | HB2 | MET | E | 144 | -11.078 | 45.533 | -57.994 | 130.28 | H |
| ATOM | 10067 | HB3 | MET | E | 144 | -11.076 | 44.679 | -59.330 | 130.28 | H |
| ATOM | 10068 | HG2 | MET | E | 144 | -11.278 | 47.423 | -59.653 | 135.29 | H |
| ATOM | 10069 | HG3 | MET | E | 144 | -9.859 | 46.870 | -59.196 | 135.29 | H |
| ATOM | 10070 | HE1 | MET | E | 144 | -8.721 | 44.703 | -62.015 | 142.68 | H |
| ATOM | 10071 | HE2 | MET | E | 144 | -8.276 | 45.403 | -60.660 | 142.68 | H |
| ATOM | 10072 | HE3 | MET | E | 144 | -9.381 | 44.262 | -60.639 | 142.68 | H |
| ATOM | 10073 | N | GLU | E | 145 | -13.501 | 44.505 | -61.059 | 131.93 | N |
| ATOM | 10074 | CA | GLU | E | 145 | -13.949 | 44.488 | -62.446 | 131.71 | C |
| ATOM | 10075 | C | GLU | E | 145 | -15.462 | 44.676 | -62.551 | 130.25 | C |
| ATOM | 10076 | O | GLU | E | 145 | -15.959 | 45.154 | -63.568 | 133.30 | O |
| ATOM | 10077 | CB | GLU | E | 145 | -13.522 | 43.186 | -63.125 | 133.36 | C |
| ATOM | 10078 | CG | GLU | E | 145 | -12.021 | 43.118 | -63.401 | 135.77 | C |
| ATOM | 10079 | CD | GLU | E | 145 | -11.606 | 41.844 | -64.115 | 137.01 | C |
| ATOM | 10080 | OE1 | GLU | E | 145 | -12.430 | 40.908 | -64.196 | 136.72 | O |
| ATOM | 10081 | OE2 | GLU | E | 145 | -10.454 | 41.782 | -64.598 | 137.94 | O1- |
| ATOM | 10082 | H | GLU | E | 145 | -13.313 | 43.729 | -60.738 | 138.32 | H |
| ATOM | 10083 | HA | GLU | E | 145 | -13.526 | 45.222 | -62.919 | 138.05 | H |
| ATOM | 10084 | HB2 | GLU | E | 145 | -13.754 | 42.440 | -62.550 | 140.04 | H |
| ATOM | 10085 | HB3 | GLU | E | 145 | -13.986 | 43.107 | -63.973 | 140.04 | H |
| ATOM | 10086 | HG2 | GLU | E | 145 | -11.769 | 43.869 | -63.960 | 142.93 | H |

TABLE 5-continued

Atomic Coordinates for OMCP-NKG2D (4PDC).

| | | | | | | | | | |
|---|---|---|---|---|---|---|---|---|---|
| ATOM | 10087 | HG3 | GLU | E | 145 | -11.544 | 43.157 | -62.558 | 142.93 H |
| ATOM | 10088 | N | ASP | E | 146 | -16.188 | 44.314 | -61.498 | 133.13 N |
| ATOM | 10089 | CA | ASP | E | 146 | -17.638 | 44.488 | -61.473 | 133.34 C |
| ATOM | 10090 | C | ASP | E | 146 | -18.047 | 45.808 | -60.815 | 139.24 C |
| ATOM | 10091 | O | ASP | E | 146 | -19.225 | 46.021 | -60.525 | 145.17 O |
| ATOM | 10092 | CB | ASP | E | 146 | -18.306 | 43.323 | -60.738 | 133.65 C |
| ATOM | 10093 | CG | ASP | E | 146 | -18.110 | 41.998 | -61.444 | 138.71 C |
| ATOM | 10094 | OD1 | ASP | E | 146 | -17.633 | 42.000 | -62.600 | 144.37 O |
| ATOM | 10095 | OD2 | ASP | E | 146 | -18.444 | 40.953 | -60.846 | 137.49 O1- |
| ATOM | 10096 | H | ASP | E | 146 | -15.864 | 43.964 | -60.782 | 139.75 H |
| ATOM | 10097 | HA | ASP | E | 146 | -17.969 | 44.495 | -62.385 | 140.00 H |
| ATOM | 10098 | HB2 | ASP | E | 146 | -17.924 | 43.249 | -59.850 | 140.39 H |
| ATOM | 10099 | HB3 | ASP | E | 146 | -19.259 | 43.492 | -60.677 | 140.39 H |
| ATOM | 10100 | N | SER | E | 147 | -17.081 | 46.693 | -60.585 | 136.27 N |
| ATOM | 10101 | CA | SER | E | 147 | -17.357 | 47.964 | -59.919 | 139.56 C |
| ATOM | 10102 | C | SER | E | 147 | -18.193 | 48.896 | -60.799 | 140.84 C |
| ATOM | 10103 | O | SER | E | 147 | -17.812 | 49.204 | -61.926 | 141.91 O |
| ATOM | 10104 | CB | SER | E | 147 | -16.049 | 48.657 | -59.528 | 140.67 C |
| ATOM | 10105 | OG | SER | E | 147 | -16.299 | 49.901 | -58.895 | 139.95 O |
| ATOM | 10106 | H | SER | E | 147 | -16.257 | 46.582 | -60.805 | 143.52 H |
| ATOM | 10107 | HA | SER | E | 147 | -17.859 | 47.792 | -59.107 | 147.47 H |
| ATOM | 10108 | HB2 | SER | E | 147 | -15.561 | 48.084 | -58.916 | 148.80 H |
| ATOM | 10109 | HB3 | SER | E | 147 | -15.523 | 48.811 | -60.329 | 148.80 H |
| ATOM | 10110 | HG | SER | E | 147 | -15.573 | 50.269 | -58.687 | 147.94 H |
| ATOM | 10111 | N | LYS | E | 148 | -19.326 | 49.349 | -60.270 | 144.08 N |
| ATOM | 10112 | CA | LYS | E | 148 | -20.219 | 50.241 | -61.006 | 149.92 C |
| ATOM | 10113 | C | LYS | E | 148 | -19.658 | 51.658 | -61.121 | 148.76 C |
| ATOM | 10114 | O | LYS | E | 148 | -20.209 | 52.494 | -61.838 | 151.47 O |
| ATOM | 10115 | CB | LYS | E | 148 | -21.595 | 50.281 | -60.339 | 147.47 C |
| ATOM | 10116 | CG | LYS | E | 148 | -22.494 | 49.113 | -60.710 | 150.15 C |
| ATOM | 10117 | CD | LYS | E | 148 | -23.784 | 49.125 | -59.908 | 147.36 C |
| ATOM | 10118 | CE | LYS | E | 148 | -24.808 | 48.165 | -60.488 | 150.24 C |
| ATOM | 10119 | NZ | LYS | E | 148 | -24.266 | 46.787 | -60.642 | 151.53 N1+ |
| ATOM | 10120 | H | LYS | E | 148 | -19.603 | 49.153 | -59.479 | 152.90 H |
| ATOM | 10121 | HA | LYS | E | 148 | -20.335 | 49.894 | -61.905 | 159.91 H |
| ATOM | 10122 | HB2 | LYS | E | 148 | -21.476 | 50.269 | -59.376 | 156.96 H |
| ATOM | 10123 | HB3 | LYS | E | 148 | -22.047 | 51.098 | -60.604 | 156.96 H |
| ATOM | 10124 | HG2 | LYS | E | 148 | -22.721 | 49.170 | -61.651 | 160.18 H |
| ATOM | 10125 | HG3 | LYS | E | 148 | -22.029 | 48.282 | -60.526 | 160.18 H |
| ATOM | 10126 | HD2 | LYS | E | 148 | -23.596 | 48.855 | -58.995 | 156.83 H |
| ATOM | 10127 | HD3 | LYS | E | 148 | -24.162 | 50.018 | -59.922 | 156.83 H |
| ATOM | 10128 | HE2 | LYS | E | 148 | -25.575 | 48.123 | -59.896 | 160.29 H |
| ATOM | 10129 | HE3 | LYS | E | 148 | -25.079 | 48.481 | -61.364 | 160.29 H |
| ATOM | 10130 | HZ1 | LYS | E | 148 | -24.890 | 46.252 | -60.983 | 161.84 H |
| ATOM | 10131 | HZ2 | LYS | E | 148 | -23.562 | 46.796 | -59.850 | 161.84 H |
| ATOM | 10132 | HZ3 | LYS | E | 148 | -24.014 | 46.470 | -61.187 | 153.83 H |
| ATOM | 10133 | N | ARG | E | 149 | -18.566 | 51.925 | -60.411 | 158.71 N |
| ATOM | 10134 | CA | ARG | E | 149 | -17.911 | 53.229 | -60.464 | 157.83 C |
| ATOM | 10135 | C | ARG | E | 149 | -17.092 | 53.366 | -61.747 | 157.91 C |
| ATOM | 10136 | O | ARG | E | 149 | -17.518 | 54.015 | -62.704 | 155.33 O |
| ATOM | 10137 | CB | ARG | E | 149 | -17.015 | 53.422 | -59.237 | | C |

TABLE 5-continued

Atomic Coordinates for OMCP-NKG2D (4PDC).

| | | | | | | | | | |
|---|---|---|---|---|---|---|---|---|---|
| ATOM | 10138 | CG | ARG | E | 149 | -16.391 | 54.807 | -59.099 | 152.08 | C |
| ATOM | 10139 | CD | ARG | E | 149 | -17.379 | 55.834 | -58.558 | 150.40 | C |
| ATOM | 10140 | NE | ARG | E | 149 | -16.679 | 56.984 | -57.985 | 149.43 | N |
| ATOM | 10141 | CZ | ARG | E | 149 | -16.619 | 57.279 | -56.687 | 145.97 | C |
| ATOM | 10142 | NH1 | ARG | E | 149 | -17.237 | 56.531 | -55.780 | 136.16 | N1+ |
| ATOM | 10143 | NH2 | ARG | E | 149 | -15.943 | 58.348 | -56.292 | 150.80 | N |
| ATOM | 10144 | H | ARG | E | 149 | -18.180 | 51.363 | -59.887 | 164.60 | H |
| ATOM | 10145 | HA | ARG | E | 149 | -18.586 | 53.925 | -60.460 | 170.45 | H |
| ATOM | 10146 | HB2 | ARG | E | 149 | -17.545 | 53.260 | -58.441 | 166.39 | H |
| ATOM | 10147 | HB3 | ARG | E | 149 | -16.291 | 52.779 | -59.281 | 166.39 | H |
| ATOM | 10148 | HG2 | ARG | E | 149 | -15.641 | 54.757 | -58.486 | 162.50 | H |
| ATOM | 10149 | HG3 | ARG | E | 149 | -16.091 | 55.108 | -59.971 | 162.50 | H |
| ATOM | 10150 | HD2 | ARG | E | 149 | -17.944 | 56.150 | -59.280 | 160.48 | H |
| ATOM | 10151 | HD3 | ARG | E | 149 | -17.917 | 55.427 | -57.861 | 160.48 | H |
| ATOM | 10152 | HE | ARG | E | 149 | -16.273 | 57.511 | -58.530 | 159.32 | H |
| ATOM | 10153 | HH11 | ARG | E | 149 | -17.678 | 55.834 | -56.025 | 143.39 | H |
| ATOM | 10154 | HH12 | ARG | E | 149 | -17.191 | 56.739 | -54.947 | 143.39 | H |
| ATOM | 10155 | HH21 | ARG | E | 149 | -15.543 | 58.842 | -56.871 | 160.96 | H |
| ATOM | 10156 | HH22 | ARG | E | 149 | -15.906 | 58.549 | -55.457 | 160.96 | H |
| TER | 10157 | | ARG | E | 149 | | | | | |
| ATOM | 10158 | N | GLY | F | 0 | -3.228 | 29.760 | 20.619 | 129.41 | N |
| ATOM | 10159 | CA | GLY | F | 0 | -3.768 | 30.515 | 19.453 | 126.44 | C |
| ATOM | 10160 | C | GLY | F | 0 | -4.157 | 29.577 | 18.329 | 126.73 | C |
| ATOM | 10161 | O | GLY | F | 0 | -4.379 | 28.388 | 18.561 | 125.80 | O |
| ATOM | 10162 | H1 | GLY | F | 0 | -3.701 | 29.959 | 21.346 | 135.29 | H |
| ATOM | 10163 | H2 | GLY | F | 0 | -3.283 | 28.886 | 20.459 | 135.29 | H |
| ATOM | 10164 | H3 | GLY | F | 0 | -2.376 | 29.984 | 20.750 | 135.29 | H |
| ATOM | 10165 | HA2 | GLY | F | 0 | -4.551 | 31.019 | 19.723 | 131.73 | H |
| ATOM | 10166 | HA3 | GLY | F | 0 | -3.097 | 31.133 | 19.124 | 131.73 | H |
| ATOM | 10167 | N | HIS | F | 1 | -4.237 | 30.106 | 17.110 | 121.94 | N |
| ATOM | 10168 | CA | HIS | F | 1 | -4.640 | 29.302 | 15.960 | 120.81 | C |
| ATOM | 10169 | C | HIS | F | 1 | -3.752 | 29.565 | 14.754 | 120.41 | C |
| ATOM | 10170 | O | HIS | F | 1 | -3.175 | 30.643 | 14.618 | 118.02 | O |
| ATOM | 10171 | CB | HIS | F | 1 | -6.099 | 29.577 | 15.600 | 119.93 | C |
| ATOM | 10172 | CG | HIS | F | 1 | -7.065 | 29.227 | 16.687 | 124.76 | C |
| ATOM | 10173 | ND1 | HIS | F | 1 | -7.406 | 27.926 | 16.989 | 125.09 | N |
| ATOM | 10174 | CD2 | HIS | F | 1 | -7.762 | 30.008 | 17.546 | 126.11 | C |
| ATOM | 10175 | CE1 | HIS | F | 1 | -8.273 | 27.921 | 17.986 | 127.35 | C |
| ATOM | 10176 | NE2 | HIS | F | 1 | -8.505 | 29.171 | 18.343 | 127.19 | N |
| ATOM | 10177 | H | HIS | F | 1 | -4.063 | 30.927 | 16.923 | 126.33 | H |
| ATOM | 10178 | HA | HIS | F | 1 | -4.561 | 28.363 | 16.190 | 124.97 | H |
| ATOM | 10179 | HB2 | HIS | F | 1 | -6.200 | 30.522 | 15.405 | 123.91 | H |
| ATOM | 10180 | HB3 | HIS | F | 1 | -6.331 | 29.053 | 14.817 | 123.91 | H |
| ATOM | 10181 | HD1 | HIS | F | 1 | -7.103 | 27.227 | 16.590 | 130.10 | H |
| ATOM | 10182 | HD2 | HIS | F | 1 | -7.742 | 30.937 | 17.589 | 131.34 | H |
| ATOM | 10183 | HE1 | HIS | F | 1 | -8.654 | 27.166 | 18.372 | 132.82 | H |
| ATOM | 10184 | HE2 | HIS | F | 1 | -9.036 | 29.421 | 18.972 | 132.63 | H |
| ATOM | 10185 | N | LYS | F | 2 | -3.635 | 28.568 | 13.884 | 117.59 | N |
| ATOM | 10186 | CA | LYS | F | 2 | -2.874 | 28.734 | 12.658 | 118.28 | C |
| ATOM | 10187 | C | LYS | F | 2 | -3.516 | 27.985 | 11.498 | 119.46 | C |
| ATOM | 10188 | O | LYS | F | 2 | -4.114 | 26.920 | 11.668 | 115.97 | O |

TABLE 5-continued

Atomic Coordinates for OMCP-NKG2D (4PDC).

| ATOM | 10189 | CB | LYS | F | 2 | -1.424 | 28.284 | 12.858 | 121.88 | C |
|---|---|---|---|---|---|---|---|---|---|---|
| ATOM | 10190 | CG | LYS | F | 2 | -1.243 | 26.852 | 13.311 | 129.22 | C |
| ATOM | 10191 | CD | LYS | F | 2 | 0.205 | 26.606 | 13.713 | 130.79 | C |
| ATOM | 10192 | CE | LYS | F | 2 | 0.429 | 25.175 | 14.167 | 140.64 | C |
| ATOM | 10193 | NZ | LYS | F | 2 | 1.839 | 24.947 | 14.592 | 146.99 | N1+ |
| ATOM | 10194 | H | LYS | F | 2 | -3.985 | 27.788 | 13.982 | 121.11 | H |
| ATOM | 10195 | HA | LYS | F | 2 | -2.861 | 29.676 | 12.428 | 121.93 | H |
| ATOM | 10196 | HB2 | LYS | F | 2 | -0.953 | 28.385 | 12.017 | 126.26 | H |
| ATOM | 10197 | HB3 | LYS | F | 2 | -1.015 | 28.855 | 13.528 | 126.26 | H |
| ATOM | 10198 | HG2 | LYS | F | 2 | -1.810 | 26.681 | 14.079 | 135.07 | H |
| ATOM | 10199 | HG3 | LYS | F | 2 | -1.467 | 26.252 | 12.583 | 135.07 | H |
| ATOM | 10200 | HD2 | LYS | F | 2 | 0.781 | 26.775 | 12.951 | 136.94 | H |
| ATOM | 10201 | HD3 | LYS | F | 2 | 0.438 | 27.196 | 14.446 | 136.94 | H |
| ATOM | 10202 | HE2 | LYS | F | 2 | -0.150 | 24.985 | 14.921 | 148.77 | H |
| ATOM | 10203 | HE3 | LYS | F | 2 | 0.233 | 24.573 | 13.433 | 148.77 | H |
| ATOM | 10204 | HZ1 | LYS | F | 2 | 2.043 | 25.487 | 15.270 | 156.39 | H |
| ATOM | 10205 | HZ2 | LYS | F | 2 | 1.944 | 24.103 | 14.854 | 156.39 | H |
| ATOM | 10206 | HZ3 | LYS | F | 2 | 2.391 | 25.111 | 13.914 | 156.39 | H |
| ATOM | 10207 | N | LEU | F | 3 | -3.404 | 28.589 | 10.321 | 118.68 | N |
| ATOM | 10208 | CA | LEU | F | 3 | -3.925 | 28.030 | 9.086 | 117.42 | C |
| ATOM | 10209 | C | LEU | F | 3 | -2.752 | 27.857 | 8.134 | 116.58 | C |
| ATOM | 10210 | O | LEU | F | 3 | -2.066 | 28.828 | 7.807 | 115.05 | O |
| ATOM | 10211 | CB | LEU | F | 3 | -4.995 | 28.945 | 8.485 | 115.28 | C |
| ATOM | 10212 | CG | LEU | F | 3 | -5.747 | 28.440 | 7.256 | 118.11 | C |
| ATOM | 10213 | CD1 | LEU | F | 3 | -6.670 | 27.286 | 7.622 | 117.93 | C |
| ATOM | 10214 | CD2 | LEU | F | 3 | -6.527 | 29.581 | 6.615 | 115.66 | C |
| ATOM | 10215 | H | LEU | F | 3 | -3.016 | 29.349 | 10.212 | 122.41 | H |
| ATOM | 10216 | HA | LEU | F | 3 | -4.319 | 27.160 | 9.258 | 120.90 | H |
| ATOM | 10217 | HB2 | LEU | F | 3 | -5.657 | 29.121 | 9.171 | 118.34 | H |
| ATOM | 10218 | HB3 | LEU | F | 3 | -4.568 | 29.779 | 8.234 | 118.34 | H |
| ATOM | 10219 | HG | LEU | F | 3 | -5.105 | 28.115 | 6.606 | 121.73 | H |
| ATOM | 10220 | HD11 | LEU | F | 3 | -7.134 | 26.987 | 6.824 | 121.52 | H |
| ATOM | 10221 | HD12 | LEU | F | 3 | -6.139 | 26.561 | 7.987 | 121.52 | H |
| ATOM | 10222 | HD13 | LEU | F | 3 | -7.312 | 27.592 | 8.282 | 121.52 | H |
| ATOM | 10223 | HD21 | LEU | F | 3 | -6.998 | 29.243 | 5.837 | 118.80 | H |
| ATOM | 10224 | HD22 | LEU | F | 3 | -7.162 | 29.931 | 7.260 | 118.80 | H |
| ATOM | 10225 | HD23 | LEU | F | 3 | -5.906 | 30.278 | 6.349 | 118.80 | H |
| ATOM | 10226 | N | ALA | F | 4 | -2.520 | 26.620 | 7.706 | 117.17 | N |
| ATOM | 10227 | CA | ALA | F | 4 | -1.347 | 26.278 | 6.911 | 113.80 | C |
| ATOM | 10228 | C | ALA | F | 4 | -1.737 | 25.668 | 5.570 | 118.72 | C |
| ATOM | 10229 | O | ALA | F | 4 | -2.616 | 24.807 | 5.492 | 115.41 | O |
| ATOM | 10230 | CB | ALA | F | 4 | -0.455 | 25.321 | 7.681 | 116.99 | C |
| ATOM | 10231 | H | ALA | F | 4 | -3.037 | 25.951 | 7.865 | 120.60 | H |
| ATOM | 10232 | HA | ALA | F | 4 | -0.839 | 27.085 | 6.736 | 116.56 | H |
| ATOM | 10233 | HB1 | ALA | F | 4 | 0.319 | 25.105 | 7.138 | 120.38 | H |
| ATOM | 10234 | HB2 | ALA | F | 4 | -0.172 | 25.747 | 8.506 | 120.38 | H |
| ATOM | 10235 | HB3 | ALA | F | 4 | -0.955 | 24.514 | 7.880 | 120.38 | H |
| ATOM | 10236 | N | PHE | F | 5 | -1.065 | 26.132 | 4.522 | 114.07 | N |
| ATOM | 10237 | CA | PHE | F | 5 | -1.247 | 25.619 | 3.171 | 115.88 | C |
| ATOM | 10238 | C | PHE | F | 5 | 0.038 | 24.967 | 2.696 | 117.08 | C |
| ATOM | 10239 | O | PHE | F | 5 | 1.085 | 25.610 | 2.658 | 119.17 | O |

TABLE 5-continued

Atomic Coordinates for OMCP-NKG2D (4PDC).

| ATOM | 10240 | CB | PHE | F | 5 | -1.642 | 26.742 | 2.213 | 111.34 | C |
|---|---|---|---|---|---|---|---|---|---|---|
| ATOM | 10241 | CG | PHE | F | 5 | -2.919 | 27.422 | 2.580 | 110.85 | C |
| ATOM | 10242 | CD1 | PHE | F | 5 | -2.940 | 28.405 | 3.554 | 113.28 | C |
| ATOM | 10243 | CD2 | PHE | F | 5 | -4.100 | 27.084 | 1.953 | 112.14 | C |
| ATOM | 10244 | CE1 | PHE | F | 5 | -4.120 | 29.036 | 3.893 | 113.84 | C |
| ATOM | 10245 | CE2 | PHE | F | 5 | 5.280 | 27.712 | 2.288 | 111.37 | C |
| ATOM | 10246 | CZ | PHE | F | 5 | -5.291 | 28.686 | 3.258 | 114.78 | C |
| ATOM | 10247 | H | PHE | F | 5 | -0.481 | 26.761 | 4.571 | 116.89 | H |
| ATOM | 10248 | HA | PHE | F | 5 | -1.951 | 24.952 | 3.169 | 119.06 | H |
| ATOM | 10249 | HB2 | PHE | F | 5 | -0.940 | 27.411 | 2.209 | 113.61 | H |
| ATOM | 10250 | HB3 | PHE | F | 5 | -1.749 | 26.371 | 1.323 | 113.61 | H |
| ATOM | 10251 | HD1 | PHE | F | 5 | -2.151 | 28.643 | 3.984 | 115.93 | H |
| ATOM | 10252 | HD2 | PHE | F | 5 | -4.100 | 26.425 | 1.296 | 114.56 | H |
| ATOM | 10253 | HE1 | PHE | F | 5 | -4.124 | 29.695 | 4.549 | 116.61 | H |
| ATOM | 10254 | HE2 | PHE | F | 5 | -6.070 | 27.475 | 1.859 | 113.65 | H |
| ATOM | 10255 | HZ | PHE | F | 5 | -6.087 | 29.109 | 3.484 | 117.73 | H |
| ATOM | 10256 | N | ASN | F | 5 | -0.047 | 23.691 | 2.336 | 116.88 | N |
| ATOM | 10257 | CA | ASN | F | 6 | 1.106 | 22.963 | 1.838 | 114.07 | C |
| ATOM | 10258 | C | ASN | F | 6 | 0.919 | 22.591 | 0.376 | 116.67 | C |
| ATOM | 10259 | O | ASN | F | 6 | 0.153 | 21.682 | 0.056 | 116.36 | O |
| ATOM | 10260 | CB | ASN | F | 6 | 1.348 | 21.713 | 2.679 | 120.64 | C |
| ATOM | 10261 | CG | ASN | F | 6 | 2.626 | 21.000 | 2.300 | 126.49 | C |
| ATOM | 10262 | OD1 | ASN | F | 6 | 2.607 | 20.029 | 1.548 | 133.61 | O |
| ATOM | 10263 | ND2 | ASN | F | 6 | 3.748 | 21.486 | 2.814 | 126.66 | N |
| ATOM | 10264 | H | ASN | F | 6 | -0.768 | 23.223 | 2.373 | 120.26 | H |
| ATOM | 10265 | HA | ASN | F | 6 | 1.892 | 23.528 | 1.906 | 116.89 | H |
| ATOM | 10266 | HB2 | ASN | F | 6 | 1.411 | 21.966 | 3.613 | 124.77 | H |
| ATOM | 10267 | HB3 | ASN | F | 6 | 0.611 | 21.096 | 2.550 | 124.77 | H |
| ATOM | 10268 | HD21 | ASN | F | 6 | 4.502 | 21.116 | 2.629 | 132.00 | H |
| ATOM | 10269 | HD22 | ASN | F | 6 | 3.722 | 22.171 | 3.333 | 132.00 | H |
| ATOM | 10270 | N | PHE | F | 7 | 1.618 | 23.318 | -0.497 | 114.97 | N |
| ATOM | 10271 | CA | PHE | F | 7 | 1.580 | 23.101 | -1.939 | 112.47 | C |
| ATOM | 10272 | C | PHE | F | 7 | 2.716 | 22.190 | -2.376 | 115.61 | C |
| ATOM | 10273 | O | PHE | F | 7 | 3.871 | 22.427 | -2.029 | 116.76 | O |
| ATOM | 10274 | CB | PHE | F | 7 | 1.695 | 24.426 | -2.696 | 112.90 | C |
| ATOM | 10275 | CG | PHE | F | 7 | 0.586 | 25.391 | -2.415 | 112.41 | C |
| ATOM | 10276 | CD1 | PHE | F | 7 | 0.627 | 26.208 | -1.299 | 115.02 | C |
| ATOM | 10277 | CD2 | PHE | F | 7 | -0.491 | 25.494 | -3.277 | 113.17 | C |
| ATOM | 10278 | CE1 | PHE | F | 7 | -0.392 | 27.108 | -1.041 | 114.33 | C |
| ATOM | 10279 | CE2 | PHE | F | 7 | -1.516 | 26.392 | -3.023 | 115.79 | C |
| ATOM | 10280 | CZ | PHE | F | 7 | -1.463 | 27.200 | -1.902 | 114.48 | C |
| ATOM | 10281 | H | PHE | F | 7 | 2.138 | 23.963 | -0.267 | 117.96 | H |
| ATOM | 10282 | HA | PHE | F | 7 | 0.739 | 22.681 | -2.180 | 114.96 | H |
| ATOM | 10283 | HB2 | PHE | F | 7 | 2.529 | 24.855 | -2.448 | 115.48 | H |
| ATOM | 10284 | HB3 | PHE | F | 7 | 1.692 | 24.242 | -3.649 | 115.48 | H |
| ATOM | 10285 | HD1 | PHE | F | 7 | 1.348 | 26.150 | -0.714 | 118.02 | H |
| ATOM | 10286 | HD2 | PHE | F | 7 | -0.530 | 24.953 | -4.032 | 115.81 | H |
| ATOM | 10287 | HE1 | PHE | F | 7 | -0.355 | 27.649 | -0.285 | 117.19 | H |
| ATOM | 10288 | HE2 | PHE | F | 7 | -2.238 | 26.452 | -3.607 | 118.95 | H |
| ATOM | 10289 | HZ | PHE | F | 7 | -2.150 | 27.803 | -1.729 | 117.38 | H |
| ATOM | 10290 | N | ASN | F | 8 | 2.390 | 21.165 | -3.153 | 117.16 | N |

TABLE 5-continued

Atomic Coordinates for OMCP-NKG2D (4PDC).

| ATOM | 10291 | CA | ASN | F | 8 | 3.399 | 20.249 | -3.662 | 118.00 | C |
|------|-------|-----|-----|---|---|-------|--------|--------|--------|---|
| ATOM | 10292 | C | ASN | F | 8 | 3.214 | 19.985 | -5.147 | 119.06 | C |
| ATOM | 10293 | O | ASN | F | 8 | 2.111 | 19.667 | -5.601 | 119.50 | O |
| ATOM | 10294 | CB | ASN | F | 8 | 3.363 | 18.931 | -2.891 | 121.59 | C |
| ATOM | 10295 | CG | ASN | F | 8 | 4.399 | 17.940 | -3.386 | 125.54 | C |
| ATOM | 10296 | OD1 | ASN | F | 8 | 4.066 | 16.957 | -4.047 | 128.38 | O |
| ATOM | 10297 | ND2 | ASN | F | 8 | 5.664 | 18.203 | -3.080 | 127.01 | N |
| ATOM | 10298 | H | ASN | F | 8 | 1.588 | 20.978 | -3.400 | 120.60 | H |
| ATOM | 10299 | HA | ASN | F | 8 | 4.275 | 20.645 | -3.536 | 121.60 | H |
| ATOM | 10300 | HB2 | ASN | F | 8 | 3.540 | 19.108 | -1.953 | 125.91 | H |
| ATOM | 10301 | HB3 | ASN | F | 8 | 2.487 | 18.527 | -2.993 | 125.91 | H |
| ATOM | 10302 | HD21 | ASN | F | 8 | 6.288 | 17.671 | -3.338 | 132.41 | H |
| ATOM | 10303 | HD22 | ASN | F | 8 | 5.859 | 18.906 | -2.624 | 132.41 | H |
| ATOM | 10304 | N | LEU | F | 9 | 4.302 | 20.141 | -5.894 | 117.68 | N |
| ATOM | 10305 | CA | LEU | F | 9 | 4.342 | 19.779 | -7.306 | 118.16 | C |
| ATOM | 10306 | C | LEU | F | 9 | 5.423 | 18.732 | -7.510 | 119.22 | C |
| ATOM | 10307 | O | LEU | F | 9 | 6.607 | 19.007 | -7.327 | 116.70 | O |
| ATOM | 10308 | CB | LEU | F | 9 | 4.610 | 21.001 | -8.190 | 112.54 | C |
| ATOM | 10309 | CG | LEU | F | 9 | 4.756 | 20.712 | -9.690 | 115.42 | C |
| ATOM | 10310 | CD1 | LEU | F | 9 | 3.456 | 20.192 | -10.273 | 121.54 | C |
| ATOM | 10311 | CD2 | LEU | F | 9 | 5.212 | 21.955 | -10.437 | 117.32 | C |
| ATOM | 10312 | H | LEU | F | 9 | 5.044 | 20.461 | -5.600 | 121.21 | H |
| ATOM | 10313 | HA | LEU | F | 9 | 3.490 | 19.395 | -7.564 | 121.79 | H |
| ATOM | 10314 | HB2 | LEU | F | 9 | 3.874 | 21.624 | -8.084 | 115.05 | H |
| ATOM | 10315 | HB3 | LEU | F | 9 | 5.434 | 21.419 | -7.893 | 115.05 | H |
| ATOM | 10316 | HG | LEU | F | 9 | 5.431 | 20.027 | -9.813 | 118.50 | H |
| ATOM | 10317 | HD11 | LEU | F | 9 | 3.581 | 20.020 | -11.219 | 125.85 | H |
| ATOM | 10318 | HD12 | LEU | F | 9 | 3.211 | 19.372 | -9.816 | 125.85 | H |
| ATOM | 10319 | HD13 | LEU | F | 9 | 2.764 | 20.860 | -10.146 | 125.85 | H |
| ATOM | 10320 | HD21 | LEU | F | 9 | 5.295 | 21.744 | -11.380 | 120.79 | H |
| ATOM | 10321 | HD22 | LEU | F | 9 | 4.554 | 22.657 | -10.312 | 120.79 | H |
| ATOM | 10322 | HD23 | LEU | F | 9 | 6.070 | 22.238 | -10.084 | 120.79 | H |
| ATOM | 10323 | N | GLU | F | 10 | 4.995 | 17.529 | -7.874 | 121.49 | N |
| ATOM | 10324 | CA | GLU | F | 10 | 5.898 | 16.421 | -8.146 | 123.67 | C |
| ATOM | 10325 | C | GLU | F | 10 | 6.031 | 16.251 | -9.654 | 124.38 | C |
| ATOM | 10326 | O | GLU | F | 10 | 5.045 | 15.994 | -10.343 | 121.67 | O |
| ATOM | 10327 | CB | GLU | F | 10 | 5.380 | 15.135 | -7.494 | 128.50 | C |
| ATOM | 10328 | CG | GLU | F | 10 | 6.252 | 13.911 | -7.718 | 139.90 | C |
| ATOM | 10329 | CD | GLU | F | 10 | 5.703 | 12.675 | -7.023 | 146.88 | C |
| ATOM | 10330 | OE1 | GLU | F | 10 | 5.964 | 11.553 | -7.505 | 153.49 | O |
| ATOM | 10331 | OE2 | GLU | F | 10 | 5.010 | 12.825 | -5.994 | 153.38 | O1- |
| ATOM | 10332 | H | GLU | F | 10 | 4.165 | 17.326 | -7.973 | 125.79 | H |
| ATOM | 10333 | HA | GLU | F | 10 | 6.775 | 16.620 | -7.780 | 128.41 | H |
| ATOM | 10334 | HB2 | GLU | F | 10 | 5.316 | 15.279 | -6.537 | 134.20 | H |
| ATOM | 10335 | HB3 | GLU | F | 10 | 4.501 | 14.939 | -7.854 | 134.20 | H |
| ATOM | 10336 | HG2 | GLU | F | 10 | 6.301 | 13.726 | -8.668 | 147.88 | H |
| ATOM | 10337 | HG3 | GLU | F | 10 | 7.139 | 14.085 | -7.366 | 147.88 | H |
| ATOM | 10338 | N | ILE | F | 11 | 7.251 | 16.419 | -10.156 | 123.21 | N |
| ATOM | 10339 | CA | ILE | F | 11 | 7.533 | 16.310 | -11.584 | 125.02 | C |
| ATOM | 10340 | C | ILE | F | 11 | 8.327 | 15.040 | -11.859 | 129.40 | C |
| ATOM | 10341 | O | ILE | F | 11 | 9.479 | 14.924 | -11.444 | 128.51 | O |

TABLE 5-continued

Atomic Coordinates for OMCP-NKG2D (4PDC).

| ATOM | 10342 | CB   | ILE | F | 11 | 8.328  | 17.527 | -12.103 | 122.20 | C |
|------|-------|------|-----|---|----|--------|--------|---------|--------|---|
| ATOM | 10343 | CG1  | ILE | F | 11 | 7.615  | 18.831 | -11.736 | 124.16 | C |
| ATOM | 10344 | CG2  | ILE | F | 11 | 8.526  | 17.429 | -13.613 | 124.02 | C |
| ATOM | 10345 | CD1  | ILE | F | 11 | 8.442  | 20.071 | -11.975 | 125.01 | C |
| ATOM | 10346 | H    | ILE | F | 11 | 7.945  | 16.260 | -9.681  | 127.85 | H |
| ATOM | 10347 | HA   | ILE | F | 11 | 6.697  | 16.600 | -12.073 | 130.03 | H |
| ATOM | 10348 | HB   | ILE | F | 11 | 9.200  | 17.526 | -11.679 | 126.63 | H |
| ATOM | 10349 | HG12 | ILE | F | 11 | 6.808  | 18.906 | -12.270 | 128.88 | H |
| ATOM | 10350 | HG13 | ILE | F | 11 | 7.384  | 18.806 | -10.794 | 128.99 | H |
| ATOM | 10351 | HG21 | ILE | F | 11 | 9.027  | 18.203 | -13.916 | 128.83 | H |
| ATOM | 10352 | HG22 | ILE | F | 11 | 9.016  | 16.617 | -13.815 | 128.83 | H |
| ATOM | 10353 | HG23 | ILE | F | 11 | 7.657  | 17.408 | -14.044 | 130.01 | H |
| ATOM | 10354 | HD11 | ILE | F | 11 | 7.923  | 20.850 | -11.720 | 130.01 | H |
| ATOM | 10355 | HD12 | ILE | F | 11 | 9.248  | 20.020 | -11.438 | 130.01 | H |
| ATOM | 10356 | HD13 | ILE | F | 11 | 8.672  | 20.120 | -12.916 | 132.32 | H |
| ATOM | 10357 | N    | ASN | F | 12 | 7.703  | 14.090 | -12.549 | 139.08 | N |
| ATOM | 10358 | CA   | ASN | F | 12 | 8.372  | 12.856 | -12.939 | 141.01 | C |
| ATOM | 10359 | C    | ASN | F | 12 | 8.394  | 12.742 | -14.461 | 132.24 | C |
| ATOM | 10360 | O    | ASN | F | 12 | 7.444  | 12.261 | -15.081 | 142.36 | O |
| ATOM | 10361 | CB   | ASN | F | 12 | 7.683  | 11.646 | -12.306 | 149.52 | C |
| ATOM | 10362 | CG   | ASN | F | 12 | 8.618  | 10.462 | -12.149 | 151.85 | C |
| ATOM | 10363 | OD1  | ASN | F | 12 | 9.445  | 10.190 | -13.019 | 149.58 | O |
| ATOM | 10364 | ND2  | ASN | F | 12 | 8.501  | 9.760  | -11.027 | 138.78 | N |
| ATOM | 10365 | H    | ASN | F | 12 | 6.884  | 14.138 | -12.805 | 146.89 | H |
| ATOM | 10366 | HA   | ASN | F | 12 | 9.289  | 12.879 | -12.625 | 150.83 | H |
| ATOM | 10367 | HB2  | ASN | F | 12 | 7.358  | 11.891 | -11.426 | 150.83 | H |
| ATOM | 10368 | HB3  | ASN | F | 12 | 6.943  | 11.372 | -12.870 | 159.50 | H |
| ATOM | 10369 | HD21 | ASN | F | 12 | 9.008  | 9.079  | -10.891 | 159.50 | H |
| ATOM | 10370 | HD22 | ASN | F | 12 | 7.918  | 9.986  | -10.437 | 143.87 | H |
| ATOM | 10371 | N    | GLY | F | 13 | 9.490  | 13.206 | -15.057 | 137.61 | N |
| ATOM | 10372 | CA   | GLY | F | 13 | 9.594  | 13.288 | -16.500 | 134.27 | C |
| ATOM | 10373 | C    | GLY | F | 13 | 8.548  | 14.247 | -17.031 | 138.41 | C |
| ATOM | 10374 | O    | GLY | F | 13 | 8.500  | 15.409 | -16.628 | 152.65 | O |
| ATOM | 10375 | H    | GLY | F | 13 | 10.190 | 13.479 | -14.639 | 145.13 | H |
| ATOM | 10376 | HA2  | GLY | F | 13 | 10.474 | 13.609 | -16.752 | 145.13 | H |
| ATOM | 10377 | HA3  | GLY | F | 13 | 9.451  | 12.414 | -16.895 | 132.43 | H |
| ATOM | 10378 | N    | SER | F | 14 | 7.700  | 13.754 | -17.927 | 138.16 | N |
| ATOM | 10379 | CA   | SER | F | 14 | 6.603  | 14.550 | -18.467 | 138.46 | C |
| ATOM | 10380 | C    | SER | F | 14 | 5.368  | 14.442 | -17.574 | 134.82 | C |
| ATOM | 10381 | O    | SER | F | 14 | 4.368  | 15.130 | -17.790 | 140.70 | O |
| ATOM | 10382 | CB   | SER | F | 14 | 6.270  | 14.101 | -19.894 | 140.46 | C |
| ATOM | 10383 | OG   | SER | F | 14 | 5.954  | 12.720 | -19.938 | 138.92 | O |
| ATOM | 10384 | H    | SER | F | 14 | 7.739  | 12.955 | -18.242 | 145.79 | H |
| ATOM | 10385 | HA   | SER | F | 14 | 6.872  | 15.481 | -18.499 | 148.84 | H |
| ATOM | 10386 | HB2  | SER | F | 14 | 5.508  | 14.609 | -20.213 | 148.84 | H |
| ATOM | 10387 | HB3  | SER | F | 14 | 7.038  | 14.266 | -20.462 | 132.43 | H |
| ATOM | 10388 | HG   | SER | F | 14 | 5.288  | 12.562 | -19.450 | 148.55 | H |
| ATOM | 10389 | N    | ASP | F | 15 | 5.451  | 13.578 | -16.567 | 136.67 | N |
| ATOM | 10390 | CA   | ASP | F | 15 | 4.350  | 13.349 | -15.640 | 137.21 | C |
| ATOM | 10391 | C    | ASP | F | 15 | 4.410  | 14.336 | -14.473 | 136.51 | C |
| ATOM | 10392 | O    | ASP | F | 15 | 5.475  | 14.545 | -13.888 | 127.52 | O |

TABLE 5-continued

Atomic Coordinates for OMCP-NKG2D (4PDC).

| ATOM | 10393 | CB | ASP | F | 15 | 4.402 | -15.119 | 11.911 | 143.65 | C |
|---|---|---|---|---|---|---|---|---|---|---|
| ATOM | 10394 | CG | ASP | F | 15 | 3.030 | -14.934 | 11.302 | 150.64 | C |
| ATOM | 10395 | OD1 | ASP | F | 15 | 2.191 | -15.853 | 11.418 | 156.62 | O |
| ATOM | 10396 | OD2 | ASP | F | 15 | 2.794 | -13.868 | 10.697 | 155.33 | O1- |
| ATOM | 10397 | H | ASP | F | 15 | 6.148 | -16.398 | 13.103 | 144.00 | H |
| ATOM | 10398 | HA | ASP | F | 15 | 3.508 | -16.105 | 13.476 | 144.65 | H |
| ATOM | 10399 | HB2 | ASP | F | 15 | 4.890 | -15.754 | 11.363 | 152.39 | H |
| ATOM | 10400 | HB3 | ASP | F | 15 | 4.852 | -14.260 | 11.903 | 152.39 | H |
| ATOM | 10401 | N | THR | F | 16 | 3.269 | -14.138 | 14.937 | 129.26 | N |
| ATOM | 10402 | CA | THR | F | 16 | 3.188 | -13.000 | 15.852 | 130.25 | C |
| ATOM | 10403 | C | THR | F | 16 | 1.993 | -12.102 | 15.543 | 131.07 | C |
| ATOM | 10404 | O | THR | F | 16 | 0.939 | -12.576 | 15.126 | 134.24 | O |
| ATOM | 10405 | CB | THR | F | 16 | 3.080 | -13.451 | 17.323 | 127.23 | C |
| ATOM | 10406 | OG1 | THR | F | 16 | 1.821 | -14.099 | 17.538 | 133.36 | O |
| ATOM | 10407 | CG2 | THR | F | 16 | 4.217 | -14.394 | 17.692 | 129.69 | C |
| ATOM | 10408 | H | THR | F | 16 | 2.525 | -14.556 | 14.831 | 135.11 | H |
| ATOM | 10409 | HA | THR | F | 16 | 3.993 | -12.467 | 15.762 | 136.30 | H |
| ATOM | 10410 | HB | THR | F | 16 | 3.137 | -12.672 | 17.898 | 132.67 | H |
| ATOM | 10411 | HG1 | THR | F | 16 | 1.758 | -14.346 | 18.338 | 140.03 | H |
| ATOM | 10412 | HG21 | THR | F | 16 | 4.134 | -14.667 | 18.619 | 135.62 | H |
| ATOM | 10413 | HG22 | THR | F | 16 | 5.070 | -13.948 | 17.570 | 135.62 | H |
| ATOM | 10414 | HG23 | THR | F | 16 | 4.190 | -15.183 | 17.128 | 135.62 | H |
| ATOM | 10415 | N | HIS | F | 17 | 2.176 | -10.799 | 15.746 | 127.94 | N |
| ATOM | 10416 | CA | HIS | F | 17 | 1.086 | -9.832 | 15.654 | 128.47 | C |
| ATOM | 10417 | C | HIS | F | 17 | 1.094 | -8.941 | 16.890 | 123.00 | C |
| ATOM | 10418 | O | HIS | F | 17 | 2.112 | -8.337 | 17.220 | 121.84 | O |
| ATOM | 10419 | CB | HIS | F | 17 | 1.207 | -8.985 | 14.388 | 130.82 | C |
| ATOM | 10420 | CG | HIS | F | 17 | 1.084 | -9.773 | 13.122 | 144.45 | C |
| ATOM | 10421 | ND1 | HIS | F | 17 | 2.129 | -10.499 | 12.592 | 146.02 | N |
| ATOM | 10422 | CD2 | HIS | F | 17 | 0.037 | -9.954 | 12.283 | 147.05 | C |
| ATOM | 10423 | CE1 | HIS | F | 17 | 1.733 | -11.089 | 11.479 | 148.47 | C |
| ATOM | 10424 | NE2 | HIS | F | 17 | 0.467 | -10.775 | 11.269 | 152.45 | N |
| ATOM | 10425 | H | HIS | F | 17 | 2.935 | -10.446 | 15.943 | 133.53 | H |
| ATOM | 10426 | HA | HIS | F | 17 | 0.239 | -10.304 | 15.625 | 134.16 | H |
| ATOM | 10427 | HB2 | HIS | F | 17 | 2.075 | -8.551 | 14.385 | 136.99 | H |
| ATOM | 10428 | HB3 | HIS | F | 17 | 0.505 | -8.316 | 14.391 | 136.99 | H |
| ATOM | 10429 | HD1 | HIS | F | 17 | 2.917 | -10.557 | 12.931 | 155.22 | H |
| ATOM | 10430 | HD2 | HIS | F | 17 | -0.813 | -9.589 | 12.374 | 156.46 | H |
| ATOM | 10431 | HE1 | HIS | F | 17 | 2.255 | -11.635 | 10.936 | 158.17 | H |
| ATOM | 10432 | HE2 | HIS | F | 17 | -0.011 | -11.042 | 10.605 | 162.94 | H |
| ATOM | 10433 | N | SER | F | 18 | -0.044 | -8.879 | 17.573 | 117.98 | N |
| ATOM | 10434 | CA | SER | F | 18 | -0.177 | -8.094 | 18.794 | 120.45 | C |
| ATOM | 10435 | C | SER | F | 18 | -1.131 | -6.932 | 18.561 | 121.00 | C |
| ATOM | 10436 | O | SER | F | 18 | -2.266 | -7.135 | 18.124 | 123.24 | O |
| ATOM | 10437 | CB | SER | F | 18 | 0.180 | -8.971 | 19.942 | 122.54 | C |
| ATOM | 10438 | OG | SER | F | 18 | -0.679 | -10.082 | 20.143 | 130.00 | O |
| ATOM | 10439 | H | SER | F | 18 | -0.765 | -9.289 | 17.345 | 121.57 | H |
| ATOM | 10440 | HA | SER | F | 18 | 2.255 | -7.734 | 19.041 | 124.54 | H |
| ATOM | 10441 | HB2 | SER | F | 18 | -1.568 | -9.294 | 19.727 | 127.05 | H |
| ATOM | 10442 | HB3 | SER | F | 18 | -0.706 | -8.442 | 20.754 | 127.05 | H |
| ATOM | 10443 | HG | SER | F | 18 | -0.107 | -10.555 | 20.775 | 136.00 | H |

TABLE 5-continued

Atomic Coordinates for OMCP-NKG2D (4PDC).

| ATOM | 10444 | N    | THR | F | 19 | -0.665 | 18.867 | -5.722 | 117.83 | N  |
|------|-------|------|-----|---|----|--------|--------|--------|--------|----|
| ATOM | 10445 | CA   | THR | F | 19 | -1.425 | 18.615 | -4.501 | 118.00 | C  |
| ATOM | 10446 | C    | THR | F | 19 | -1.416 | 19.828 | -3.570 | 116.45 | C  |
| ATOM | 10447 | O    | THR | F | 19 | -0.451 | 20.592 | -3.537 | 114.39 | O  |
| ATOM | 10448 | CB   | THR | F | 19 | -0.853 | 17.389 | -3.744 | 122.55 | C  |
| ATOM | 10449 | OG1  | THR | F | 19 | -0.964 | 16.223 | -4.568 | 132.42 | O  |
| ATOM | 10450 | CG2  | THR | F | 19 | -1.601 | 17.142 | -2.441 | 134.29 | C  |
| ATOM | 10451 | H    | THR | F | 19 | 0.103  | 19.228 | -5.581 | 121.39 | H  |
| ATOM | 10452 | HA   | THR | F | 19 | -2.346 | 18.421 | -4.735 | 121.60 | H  |
| ATOM | 10453 | HB   | THR | F | 19 | 0.081  | 17.548 | -3.535 | 127.06 | H  |
| ATOM | 10454 | HG1  | THR | F | 19 | -0.656 | 15.555 | -4.164 | 138.90 | H  |
| ATOM | 10455 | HG21 | THR | F | 19 | -1.226 | 16.372 | -1.985 | 141.15 | H  |
| ATOM | 10456 | HG22 | THR | F | 19 | -1.526 | 17.917 | -1.863 | 141.15 | H  |
| ATOM | 10457 | HG23 | THR | F | 19 | -2.539 | 16.975 | -2.624 | 141.15 | H  |
| ATOM | 10458 | N    | VAL | F | 20 | -2.497 | 20.001 | -2.817 | 115.56 | N  |
| ATOM | 10459 | CA   | VAL | F | 20 | -2.525 | 20.990 | -1.749 | 113.89 | C  |
| ATOM | 10460 | C    | VAL | F | 20 | -3.255 | 20.430 | -0.534 | 118.50 | C  |
| ATOM | 10461 | O    | VAL | F | 20 | -4.337 | 19.854 | -0.660 | 118.47 | O  |
| ATOM | 10462 | CB   | VAL | F | 20 | -3.205 | 22.307 | -2.177 | 112.52 | C  |
| ATOM | 10463 | CG1  | VAL | F | 20 | -2.985 | 23.371 | -1.111 | 115.06 | C  |
| ATOM | 10464 | CG2  | VAL | F | 20 | -2.673 | 22.791 | -3.519 | 117.29 | C  |
| ATOM | 10465 | H    | VAL | F | 20 | -3.228 | 19.557 | -2.906 | 118.67 | H  |
| ATOM | 10466 | HA   | VAL | F | 20 | -1.615 | 21.194 | -1.484 | 116.67 | H  |
| ATOM | 10467 | HB   | VAL | F | 20 | -4.160 | 22.159 | -2.265 | 115.03 | H  |
| ATOM | 10468 | HG11 | VAL | F | 20 | -3.417 | 24.193 | -1.393 | 118.07 | H  |
| ATOM | 10469 | HG12 | VAL | F | 20 | -3.369 | 23.065 | -0.275 | 118.07 | H  |
| ATOM | 10470 | HG13 | VAL | F | 20 | -2.032 | 23.518 | -1.005 | 118.07 | H  |
| ATOM | 10471 | HG21 | VAL | F | 20 | -3.121 | 23.618 | -3.757 | 120.75 | H  |
| ATOM | 10472 | HG22 | VAL | F | 20 | -1.718 | 22.941 | -3.444 | 120.75 | H  |
| ATOM | 10473 | HG23 | VAL | F | 20 | -2.850 | 22.114 | -4.191 | 120.75 | H  |
| ATOM | 10474 | N    | ASP | F | 21 | -2.642 | 20.603 | 0.634  | 116.80 | N  |
| ATOM | 10475 | CA   | ASP | F | 21 | -3.255 | 20.265 | 1.914  | 117.58 | C  |
| ATOM | 10476 | C    | ASP | F | 21 | -3.462 | 21.536 | 2.730  | 117.01 | C  |
| ATOM | 10477 | O    | ASP | F | 21 | -2.575 | 22.388 | 2.787  | 115.14 | O  |
| ATOM | 10478 | CB   | ASP | F | 21 | -2.381 | 19.285 | 2.699  | 120.49 | C  |
| ATOM | 10479 | CG   | ASP | F | 21 | -2.160 | 17.976 | 1.967  | 126.72 | C  |
| ATOM | 10480 | OD1  | ASP | F | 21 | -3.111 | 17.480 | 1.325  | 129.73 | O  |
| ATOM | 10481 | OD2  | ASP | F | 21 | -1.031 | 17.446 | 2.035  | 137.52 | O1-|
| ATOM | 10482 | H    | ASP | F | 21 | -1.848 | 20.923 | 0.712  | 120.16 | H  |
| ATOM | 10483 | HA   | ASP | F | 21 | -4.120 | 19.853 | 1.760  | 121.09 | H  |
| ATOM | 10484 | HB2  | ASP | F | 21 | -1.514 | 19.690 | 2.856  | 124.59 | H  |
| ATOM | 10485 | HB3  | ASP | F | 21 | -2.812 | 19.086 | 3.545  | 124.59 | H  |
| ATOM | 10486 | N    | VAL | F | 22 | -4.628 | 21.667 | 3.355  | 114.74 | N  |
| ATOM | 10487 | CA   | VAL | F | 22 | -4.883 | 22.786 | 4.259  | 114.88 | C  |
| ATOM | 10488 | C    | VAL | F | 22 | -5.074 | 22.258 | 5.674  | 115.42 | C  |
| ATOM | 10489 | O    | VAL | F | 22 | -5.919 | 21.397 | 5.914  | 116.90 | O  |
| ATOM | 10490 | CB   | VAL | F | 22 | -6.116 | 23.601 | 3.839  | 116.70 | C  |
| ATOM | 10491 | CG1  | VAL | F | 22 | -6.207 | 24.883 | 4.654  | 116.95 | C  |
| ATOM | 10492 | CG2  | VAL | F | 22 | -6.058 | 23.927 | 2.351  | 115.61 | C  |
| ATOM | 10493 | H    | VAL | F | 22 | -5.288 | 21.121 | 3.274  | 117.68 | H  |
| ATOM | 10494 | HA   | VAL | F | 22 | -4.114 | 23.378 | 4.257  | 117.85 | H  |

TABLE 5-continued

Atomic Coordinates for OMCP-NKG2D (4PDC).

| | | | | | | | | | |
|---|---|---|---|---|---|---|---|---|---|
| ATOM | 10495 | HB | VAL | F | 22 | -6.916 | 23.078 | 4.004 | H |
| ATOM | 10496 | HG11 | VAL | F | 22 | -6.991 | 25.380 | 4.373 | H |
| ATOM | 10497 | HG12 | VAL | F | 22 | -6.280 | 24.654 | 5.594 | H |
| ATOM | 10498 | HG13 | VAL | F | 22 | -5.408 | 25.411 | 4.503 | H |
| ATOM | 10499 | HG21 | VAL | F | 22 | -6.845 | 24.441 | 2.110 | H |
| ATOM | 10500 | HG22 | VAL | F | 22 | -5.257 | 24.445 | 2.172 | H |
| ATOM | 10501 | HG23 | VAL | F | 2 | -6.036 | 23.099 | 1.847 | H |
| ATOM | 10502 | N | ASP | F | 23 | -4.271 | 22.776 | 6.598 | N |
| ATOM | 10503 | CA | ASP | F | 23 | -4.308 | 22.361 | 7.994 | C |
| ATOM | 10504 | C | ASP | F | 23 | -4.743 | 23.509 | 8.899 | C |
| ATOM | 10505 | O | ASP | F | 23 | -4.200 | 24.612 | 8.815 | O |
| ATOM | 10506 | CB | ASP | F | 23 | -2.935 | 21.862 | 8.448 | C |
| ATOM | 10507 | CG | ASP | F | 23 | -2.429 | 20.687 | 7.628 | C |
| ATOM | 10508 | OD1 | ASP | F | 23 | -3.251 | 19.964 | 7.023 | O |
| ATOM | 10509 | OD2 | ASP | F | 23 | -1.196 | 20.485 | 7.601 | O1- |
| ATOM | 10510 | H | ASP | F | 23 | -3.684 | 23.383 | 6.436 | H |
| ATOM | 10511 | HA | ASP | F | 23 | -4.945 | 21.636 | 8.096 | H |
| ATOM | 10512 | HB2 | ASP | F | 23 | -2.293 | 22.584 | 8.363 | H |
| ATOM | 10513 | HB3 | ASP | F | 23 | -2.993 | 21.577 | 9.373 | H |
| ATOM | 10514 | N | LEU | F | 24 | -5.720 | 23.238 | 9.758 | N |
| ATOM | 10515 | CA | LEU | F | 24 | -6.114 | 24.167 | 10.813 | C |
| ATOM | 10516 | C | LEU | F | 24 | -5.627 | 23.618 | 12.149 | C |
| ATOM | 10517 | O | LEU | F | 24 | -6.105 | 22.581 | 12.603 | O |
| ATOM | 10518 | CB | LEU | F | 24 | -7.631 | 24.360 | 10.835 | C |
| ATOM | 10519 | CG | LEU | F | 24 | -8.183 | 25.284 | 11.926 | C |
| ATOM | 10520 | CD1 | LEU | F | 24 | -7.713 | 26.717 | 11.715 | C |
| ATOM | 10521 | CD2 | LEU | F | 24 | -9.702 | 25.220 | 11.967 | C |
| ATOM | 10522 | H | LEU | F | 24 | -6.177 | 22.510 | 9.751 | H |
| ATOM | 10523 | HA | LEU | F | 24 | -5.695 | 25.028 | 10.662 | H |
| ATOM | 10524 | HB2 | LEU | F | 24 | -7.903 | 24.729 | 9.980 | H |
| ATOM | 10525 | HB3 | LEU | F | 24 | -8.046 | 23.492 | 10.956 | H |
| ATOM | 10526 | HG | LEU | F | 24 | -7.850 | 24.986 | 12.787 | H |
| ATOM | 10527 | HD11 | LEU | F | 24 | -8.078 | 27.275 | 12.419 | H |
| ATOM | 10528 | HD12 | LEU | F | 24 | -6.743 | 26.738 | 11.745 | H |
| ATOM | 10529 | HD13 | LEU | F | 24 | -8.025 | 27.027 | 10.851 | H |
| ATOM | 10530 | HD21 | LEU | F | 24 | -10.024 | 25.813 | 12.664 | H |
| ATOM | 10531 | HD22 | LEU | F | 24 | -10.052 | 25.499 | 11.107 | H |
| ATOM | 10532 | HD23 | LEU | F | 24 | -9.974 | 24.308 | 12.156 | H |
| ATOM | 10533 | N | ASP | F | 25 | -4.675 | 24.310 | 12.767 | N |
| ATOM | 10534 | CA | ASP | F | 25 | -4.059 | 23.837 | 14.002 | C |
| ATOM | 10535 | C | ASP | F | 25 | -3.507 | 22.423 | 13.815 | C |
| ATOM | 10536 | O | ASP | F | 25 | -3.845 | 21.506 | 14.564 | O |
| ATOM | 10537 | CB | ASP | F | 25 | -5.064 | 23.874 | 15.157 | C |
| ATOM | 10538 | CG | ASP | F | 25 | -5.581 | 25.275 | 15.433 | C |
| ATOM | 10539 | OD1 | ASP | F | 25 | -4.835 | 26.240 | 15.169 | O |
| ATOM | 10540 | OD2 | ASP | F | 25 | -6.731 | 25.415 | 15.905 | O1- |
| ATOM | 10541 | H | ASP | F | 25 | -4.366 | 25.063 | 12.489 | H |
| ATOM | 10542 | HA | ASP | F | 25 | -3.318 | 24.420 | 14.230 | H |
| ATOM | 10543 | HB2 | ASP | F | 25 | -5.823 | 23.312 | 14.935 | H |
| ATOM | 10544 | HB3 | ASP | F | 25 | -4.634 | 23.548 | 15.963 | H |
| ATOM | 10545 | N | ASP | F | 26 | -2.662 | 22.266 | 12.799 | N |

TABLE 5-continued

Atomic Coordinates for OMCP-NKG2D (4PDC).

| | | | | | | | | | |
|---|---|---|---|---|---|---|---|---|---|
| ATOM | 10546 | CA | ASP | F | 26 | -2.002 | 20.994 | 12.492 | 136.24 C |
| ATOM | 10547 | C | ASP | F | 26 | -2.989 | 19.837 | 12.303 | 134.78 C |
| ATOM | 10548 | O | ASP | F | 26 | -2.632 | 18.668 | 12.463 | 143.46 O |
| ATOM | 10549 | CB | ASP | F | 26 | -0.987 | 20.646 | 13.588 | 140.63 C |
| ATOM | 10550 | CG | ASP | F | 26 | 0.210 | 21.582 | 13.591 | 147.72 C |
| ATOM | 10551 | OD1 | ASP | F | 26 | 1.038 | 21.493 | 12.657 | 156.36 O |
| ATOM | 10552 | OD2 | ASP | F | 26 | 0.328 | 22.403 | 14.526 | 147.17 O1- |
| ATOM | 10553 | H | ASP | F | 26 | -2.448 | 22.899 | 12.256 | 132.93 H |
| ATOM | 10554 | HA | ASP | F | 26 | -1.511 | 21.095 | 11.662 | 143.49 H |
| ATOM | 10555 | HB2 | ASP | F | 26 | -1.421 | 20.710 | 14.453 | 148.76 H |
| ATOM | 10556 | HB3 | ASP | F | 26 | -0.663 | 19.743 | 13.445 | 148.76 H |
| ATOM | 10557 | N | SER | F | 27 | -4.227 | 20.173 | 11.955 | 132.09 N |
| ATOM | 10558 | CA | SER | F | 27 | -5.231 | 19.180 | 11.597 | 134.04 C |
| ATOM | 10559 | C | SER | F | 27 | -5.743 | 19.470 | 10.195 | 127.53 C |
| ATOM | 10560 | O | SER | F | 27 | -6.229 | 20.565 | 9.922 | 125.46 O |
| ATOM | 10561 | CB | SER | F | 27 | -6.386 | 19.183 | 12.596 | 135.84 C |
| ATOM | 10562 | OG | SER | F | 27 | -7.408 | 18.294 | 12.181 | 139.50 O |
| ATOM | 10563 | H | SER | F | 27 | -4.513 | 20.984 | 11.919 | 138.51 H |
| ATOM | 10564 | HA | SER | F | 27 | -4.827 | 18.298 | 11.600 | 140.85 H |
| ATOM | 10565 | HB2 | SER | F | 27 | -6.055 | 18.903 | 13.463 | 143.01 H |
| ATOM | 10566 | HB3 | SER | F | 27 | -6.752 | 20.080 | 12.654 | 143.01 H |
| ATOM | 10567 | HG | SER | F | 27 | -8.039 | 18.302 | 12.736 | 147.40 H |
| ATOM | 10568 | N | GLN | F | 28 | -5.626 | 18.486 | 9.309 | 127.54 N |
| ATOM | 10569 | CA | GLN | F | 28 | -6.030 | 18.651 | 7.918 | 123.96 C |
| ATOM | 10570 | C | GLN | F | 28 | -7.541 | 18.819 | 7.811 | 123.35 C |
| ATOM | 10571 | O | GLN | F | 28 | -8.295 | 18.020 | 8.367 | 123.17 O |
| ATOM | 10572 | CB | GLN | F | 28 | -5.567 | 17.450 | 7.091 | 127.17 C |
| ATOM | 10573 | CG | GLN | F | 28 | -5.639 | 17.658 | 5.595 | 125.49 C |
| ATOM | 10574 | CD | GLN | F | 28 | -5.293 | 16.399 | 4.820 | 129.69 C |
| ATOM | 10575 | OE1 | GLN | F | 28 | -4.307 | 16.362 | 4.086 | 131.67 O |
| ATOM | 10576 | NE2 | GLN | F | 28 | -6.104 | 15.361 | 4.984 | 133.72 N |
| ATOM | 10577 | H | GLN | F | 28 | -5.312 | 17.706 | 9.491 | 133.05 H |
| ATOM | 10578 | HA | GLN | F | 28 | -5.610 | 19.447 | 7.556 | 128.76 H |
| ATOM | 10579 | HB2 | GLN | F | 28 | -4.644 | 17.254 | 7.317 | 132.60 H |
| ATOM | 10580 | HB3 | GLN | F | 28 | -6.126 | 16.688 | 7.310 | 132.60 H |
| ATOM | 10581 | HG2 | GLN | F | 28 | -6.540 | 17.922 | 5.355 | 130.58 H |
| ATOM | 10582 | HG3 | GLN | F | 28 | -5.009 | 18.351 | 5.341 | 130.58 H |
| ATOM | 10583 | HE21 | GLN | F | 28 | -5.950 | 14.625 | 4.566 | 140.46 H |
| ATOM | 10584 | HE22 | GLN | F | 28 | -6.783 | 15.424 | 5.508 | 140.46 H |
| ATOM | 10585 | N | ILE | F | 29 | -7.974 | 19.862 | 7.102 | 118.13 N |
| ATOM | 10586 | CA | ILE | F | 29 | -9.397 | 20.159 | 6.940 | 118.44 C |
| ATOM | 10587 | C | ILE | F | 29 | -9.830 | 20.136 | 5.472 | 117.32 C |
| ATOM | 10588 | O | ILE | F | 29 | -11.008 | 19.952 | 5.170 | 115.77 O |
| ATOM | 10589 | CB | ILE | F | 29 | -9.757 | 21.539 | 7.544 | 116.85 C |
| ATOM | 10590 | CG1 | ILE | F | 29 | -8.943 | 22.655 | 6.879 | 118.54 C |
| ATOM | 10591 | CG2 | ILE | F | 29 | -9.505 | 21.533 | 9.044 | 121.09 C |
| ATOM | 10592 | CD1 | ILE | F | 29 | -9.442 | 24.060 | 7.198 | 116.42 C |
| ATOM | 10593 | H | ILE | F | 29 | -7.456 | 20.418 | 6.700 | 121.76 H |
| ATOM | 10594 | HA | ILE | F | 29 | -9.912 | 19.486 | 7.411 | 122.13 H |
| ATOM | 10595 | HB | ILE | F | 29 | -10.699 | 21.708 | 7.389 | 120.22 H |
| ATOM | 10596 | HG12 | ILE | F | 29 | -8.024 | 22.592 | 7.181 | 122.25 H |

TABLE 5-continued

Atomic Coordinates for OMCP-NKG2D (4PDC).

| ATOM | 10597 | HG13 | ILE | F | 29 | -8.982  | 22.538 | 5.917  | 122.25 | H |
|------|-------|------|-----|---|----|---------|--------|--------|--------|---|
| ATOM | 10598 | HG21 | ILE | F | 29 | -9.735  | 22.404 | 9.405  | 125.31 | H |
| ATOM | 10599 | HG22 | ILE | F | 29 | -10.056 | 20.848 | 9.454  | 125.31 | H |
| ATOM | 10600 | HG23 | ILE | F | 29 | -8.568  | 21.345 | 9.206  | 125.31 | H |
| ATOM | 10601 | HD11 | ILE | F | 29 | -8.879  | 24.705 | 6.742  | 119.71 | H |
| ATOM | 10602 | HD12 | ILE | F | 29 | -10.358 | 24.147 | 6.891  | 119.71 | H |
| ATOM | 10603 | HD13 | ILE | F | 29 | -9.399  | 24.201 | 8.156  | 119.71 | H |
| ATOM | 10604 | N    | ILE | F | 30 | -8.874  | 20.338 | 4.571  | 118.05 | N |
| ATOM | 10605 | CA   | ILE | F | 30 | -9.146  | 20.395 | 3.137  | 116.43 | C |
| ATOM | 10606 | C    | ILE | F | 30 | -7.997  | 19.753 | 2.372  | 117.64 | C |
| ATOM | 10607 | O    | ILE | F | 30 | -6.847  | 19.815 | 2.805  | 116.22 | O |
| ATOM | 10608 | CB   | ILE | F | 30 | -9.324  | 21.855 | 2.635  | 116.66 | C |
| ATOM | 10609 | CG1  | ILE | F | 30 | -10.499 | 22.548 | 3.327  | 119.53 | C |
| ATOM | 10610 | CG2  | ILE | F | 30 | -9.533  | 21.893 | 1.120  | 117.34 | C |
| ATOM | 10611 | CD1  | ILE | F | 30 | -10.513 | 24.061 | 3.112  | 122.20 | C |
| ATOM | 10612 | H    | ILE | F | 30 | -8.044  | 20.446 | 4.768  | 121.66 | H |
| ATOM | 10613 | HA   | ILE | F | 30 | -9.959  | 19.902 | 2.943  | 119.72 | H |
| ATOM | 10614 | HB   | ILE | F | 30 | -8.515  | 22.348 | 2.842  | 120.00 | H |
| ATOM | 10615 | HG12 | ILE | F | 30 | -11.329 | 22.189 | 2.974  | 123.44 | H |
| ATOM | 10616 | HG13 | ILE | F | 30 | -10.445 | 22.382 | 4.281  | 123.44 | H |
| ATOM | 10617 | HG21 | ILE | F | 30 | -9.641  | 22.816 | 0.840  | 120.81 | H |
| ATOM | 10618 | HG22 | ILE | F | 30 | -8.759  | 21.503 | 0.685  | 120.81 | H |
| ATOM | 10619 | HG23 | ILE | F | 30 | -10.329 | 21.385 | 0.899  | 120.81 | H |
| ATOM | 10620 | HD11 | ILE | F | 30 | -11.278 | 24.438 | 3.574  | 126.64 | H |
| ATOM | 10621 | HD12 | ILE | F | 30 | -9.692  | 24.437 | 3.468  | 126.64 | H |
| ATOM | 10622 | HD13 | ILE | F | 30 | -10.576 | 24.244 | 2.161  | 126.64 | H |
| ATOM | 10623 | N    | THR | F | 31 | -8.312  | 19.148 | 1.231  | 118.54 | N |
| ATOM | 10624 | CA   | THR | F | 31 | -7.291  | 18.625 | 0.330  | 118.58 | C |
| ATOM | 10625 | C    | THR | F | 31 | -7.672  | 18.886 | -1.126 | 120.44 | C |
| ATOM | 10626 | O    | THR | F | 31 | -8.849  | 19.000 | -1.466 | 119.16 | O |
| ATOM | 10627 | CB   | THR | F | 31 | -7.064  | 17.111 | 0.539  | 120.21 | C |
| ATOM | 10628 | OG1  | THR | F | 31 | -5.973  | 16.673 | -0.278 | 130.33 | O |
| ATOM | 10629 | CG2  | THR | F | 31 | -8.309  | 16.315 | 0.191  | 126.70 | C |
| ATOM | 10630 | H    | THR | F | 31 | -9.117  | 19.028 | 0.954  | 122.25 | H |
| ATOM | 10631 | HA   | THR | F | 31 | -6.453  | 19.080 | 0.507  | 122.30 | H |
| ATOM | 10632 | HB   | THR | F | 31 | -6.850  | 16.947 | 1.471  | 124.26 | H |
| ATOM | 10633 | HG1  | THR | F | 31 | -5.273  | 17.088 | -0.070 | 136.39 | H |
| ATOM | 10634 | HG21 | THR | F | 31 | -8.147  | 15.369 | 0.328  | 132.04 | H |
| ATOM | 10635 | HG22 | THR | F | 31 | -9.048  | 16.594 | 0.753  | 132.04 | H |
| ATOM | 10636 | HG23 | THR | F | 31 | -8.547  | 16.463 | -0.738 | 132.04 | H |
| ATOM | 10637 | N    | PHE | F | 32 | -6.655  | 18.973 | -1.976 | 119.67 | N |
| ATOM | 10638 | CA   | PHE | F | 32 | -6.820  | 19.291 | -3.391 | 118.78 | C |
| ATOM | 10639 | C    | PHE | F | 32 | -5.886  | 18.375 | -4.181 | 119.20 | C |
| ATOM | 10640 | O    | PHE | F | 32 | -4.713  | 18.254 | -3.833 | 116.31 | O |
| ATOM | 10641 | CB   | PHE | F | 32 | -6.511  | 20.772 | -3.633 | 115.72 | C |
| ATOM | 10642 | CG   | PHE | F | 32 | -6.536  | 21.186 | -5.076 | 118.98 | C |
| ATOM | 10643 | CD1  | PHE | F | 32 | -7.727  | 21.534 | -5.696 | 119.61 | C |
| ATOM | 10644 | CD2  | PHE | F | 32 | -5.362  | 21.262 | -5.804 | 116.15 | C |
| ATOM | 10645 | CE1  | PHE | F | 32 | -7.745  | 21.928 | -7.026 | 120.12 | C |
| ATOM | 10646 | CE2  | PHE | F | 32 | -5.374  | 21.660 | -7.130 | 117.52 | C |
| ATOM | 10647 | CZ   | PHE | F | 32 | -6.568  | 21.992 | -7.741 | 120.04 | C |

TABLE 5-continued

Atomic Coordinates for OMCP-NKG2D (4PDC).

| ATOM | 10648 | H | PHE F | 32 | -5.835 | 18.848 | -1.750 | 123.60 | H |
|---|---|---|---|---|---|---|---|---|---|
| ATOM | 10649 | HA | PHE F | 32 | -7.734 | 19.114 | -3.663 | 122.53 | H |
| ATOM | 10650 | HB2 | PHE F | 32 | -7.168 | 21.307 | -3.162 | 118.87 | H |
| ATOM | 10651 | HB3 | PHE F | 32 | -5.625 | 20.964 | -3.288 | 123.54 | H |
| ATOM | 10652 | HD1 | PHE F | 32 | -8.523 | 21.492 | -5.217 | 119.38 | H |
| ATOM | 10653 | HD2 | PHE F | 32 | -4.555 | 21.039 | -5.399 | 124.14 | H |
| ATOM | 10654 | HE1 | PHE F | 32 | -8.550 | 22.153 | -7.433 | 121.02 | H |
| ATOM | 10655 | HE2 | PHE F | 32 | -4.579 | 21.699 | -7.611 | 124.04 | H |
| ATOM | 10656 | HZ | PHE F | 32 | -6.578 | 22.257 | -8.632 | 119.97 | H |
| ATOM | 10657 | N | ASP F | 32 | -6.405 | 17.714 | -5.216 | 121.68 | N |
| ATOM | 10658 | CA | ASP F | 33 | -5.646 | 16.676 | -5.927 | 127.22 | C |
| ATOM | 10659 | C | ASP F | 33 | -5.216 | 17.090 | -7.332 | 129.98 | C |
| ATOM | 10660 | O | ASP F | 33 | -4.852 | 16.243 | -8.152 | 124.51 | O |
| ATOM | 10661 | CB | ASP F | 33 | -6.465 | 15.379 | -6.003 | 128.43 | C |
| ATOM | 10662 | CG | ASP F | 33 | -7.686 | 15.488 | -6.923 | 123.84 | C |
| ATOM | 10663 | OD1 | ASP F | 33 | -7.945 | 16.569 | -7.497 | 125.95 | O |
| ATOM | 10664 | OD2 | ASP F | 33 | -8.402 | 14.475 | -7.060 | 123.96 | O1- |
| ATOM | 10665 | H | ASP F | 33 | -7.196 | 17.846 | -5.528 | 126.01 | H |
| ATOM | 10666 | HA | ASP F | 33 | -4.841 | 16.483 | -5.421 | 129.41 | H |
| ATOM | 10667 | HB2 | ASP F | 33 | -5.899 | 14.669 | -6.343 | 129.41 | H |
| ATOM | 10668 | HB3 | ASP F | 33 | -6.781 | 15.154 | -5.114 | 124.60 | H |
| ATOM | 10669 | N | GLY F | 34 | -5.262 | 18.390 | -7.604 | 123.43 | N |
| ATOM | 10670 | CA | GLY F | 34 | -4.859 | 18.922 | -8.894 | 123.46 | C |
| ATOM | 10671 | C | GLY F | 34 | -6.046 | 19.347 | -9.735 | 127.08 | C |
| ATOM | 10672 | O | GLY F | 34 | -5.911 | 20.193 | -10.618 | 129.52 | O |
| ATOM | 10673 | H | GLY F | 34 | -5.527 | 18.991 | -7.048 | 128.12 | H |
| ATOM | 10674 | HA2 | GLY F | 34 | -4.284 | 19.692 | -8.762 | 128.12 | H |
| ATOM | 10675 | HA3 | GLY F | 34 | -4.362 | 18.246 | -9.382 | 124.09 | H |
| ATOM | 10676 | N | LYS F | 35 | -7.206 | 18.754 | -9.457 | 131.50 | N |
| ATOM | 10677 | CA | LYS F | 35 | -8.438 | 19.056 | -10.187 | 123.95 | C |
| ATOM | 10678 | C | LYS F | 35 | -9.588 | 19.327 | -9.223 | 124.63 | C |
| ATOM | 10679 | O | LYS F | 35 | -10.257 | 20.354 | -9.316 | 136.85 | O |
| ATOM | 10680 | CB | LYS F | 35 | -8.813 | 17.902 | -11.122 | 153.02 | C |
| ATOM | 10681 | CG | LYS F | 35 | -9.995 | 18.210 | -12.039 | 167.53 | C |
| ATOM | 10682 | CD | LYS F | 35 | -10.999 | 17.062 | -12.114 | 193.83 | C |
| ATOM | 10683 | CE | LYS F | 35 | -10.483 | 15.894 | -12.943 | 102.515 | C |
| ATOM | 10684 | NZ | LYS F | 35 | -9.481 | 15.062 | -12.222 | 102.515 | N1+ |
| ATOM | 10685 | H | LYS F | 35 | -7.308 | 18.164 | -8.840 | 128.91 | H |
| ATOM | 10686 | HA | LYS F | 35 | -8.302 | 19.851 | -10.726 | 137.80 | H |
| ATOM | 10687 | HB2 | LYS F | 35 | -8.049 | 17.693 | -11.683 | 144.22 | H |
| ATOM | 10688 | HB3 | LYS F | 35 | -9.048 | 17.128 | -10.586 | 144.22 | H |
| ATOM | 10689 | HG2 | LYS F | 35 | -10.459 | 18.993 | -11.704 | 163.63 | H |
| ATOM | 10690 | HG3 | LYS F | 35 | -9.664 | 18.378 | -12.935 | 163.63 | H |
| ATOM | 10691 | HD2 | LYS F | 35 | -11.179 | 16.739 | -11.218 | 181.03 | H |
| ATOM | 10692 | HD3 | LYS F | 35 | -11.818 | 17.383 | -12.523 | 181.03 | H |
| ATOM | 10693 | HE2 | LYS F | 35 | -11.230 | 15.323 | -13.181 | 112.519 | H |
| ATOM | 10694 | HE3 | LYS F | 35 | -10.062 | 16.239 | -13.746 | 112.519 | H |
| ATOM | 10695 | HZ1 | LYS F | 35 | -9.843 | 14.724 | -11.482 | 123.016 | H |
| ATOM | 10696 | HZ2 | LYS F | 35 | -9.209 | 14.394 | -12.743 | 123.016 | H |
| ATOM | 10697 | HZ3 | LYS F | 35 | -8.778 | 15.559 | -11.998 | 123.016 | H |
| ATOM | 10698 | N | ASP F | 36 | -9.807 | 18.396 | -8.299 | 124.43 | N |

TABLE 5-continued

Atomic Coordinates for OMCP-NKG2D (4PDC).

| | | | | | | | | | |
|---|---|---|---|---|---|---|---|---|---|
| ATOM | 10699 | CA | ASP | F | 36 | -10.926 | 18.476 | -7.367 | 125.36 C |
| ATOM | 10700 | C | ASP | F | 36 | -10.472 | 18.842 | -5.959 | 123.53 C |
| ATOM | 10701 | O | ASP | F | 36 | -9.384 | 18.462 | -5.523 | 120.70 O |
| ATOM | 10702 | CB | ASP | F | 36 | -11.679 | 17.146 | -7.340 | 130.39 C |
| ATOM | 10703 | CG | ASP | F | 36 | -12.330 | 16.821 | -8.671 | 138.61 C |
| ATOM | 10704 | OD1 | ASP | F | 36 | -12.966 | 17.723 | -9.258 | 137.40 O |
| ATOM | 10705 | OD2 | ASP | F | 36 | -12.199 | 15.669 | -9.134 | 142.12 O1- |
| ATOM | 10706 | H | ASP | F | 36 | -9.314 | 17.699 | -8.191 | 129.32 H |
| ATOM | 10707 | HA | ASP | F | 36 | -11.541 | 19.162 | -7.671 | 130.43 H |
| ATOM | 10708 | HB2 | ASP | F | 36 | -11.056 | 16.433 | -7.128 | 136.46 H |
| ATOM | 10709 | HB3 | ASP | F | 36 | -12.376 | 17.189 | -6.667 | 136.46 H |
| ATOM | 10710 | N | ILE | F | 37 | -11.317 | 19.592 | -5.262 | 122.26 N |
| ATOM | 10711 | CA | ILE | F | 37 | -11.081 | 19.940 | -3.868 | 119.23 C |
| ATOM | 10712 | C | ILE | F | 37 | -12.106 | 19.217 | -3.019 | 120.45 C |
| ATOM | 10713 | O | ILE | F | 37 | -13.226 | 18.982 | -3.467 | 115.18 O |
| ATOM | 10714 | CB | ILE | F | 37 | -11.176 | 21.460 | -3.636 | 119.93 C |
| ATOM | 10715 | CG1 | ILE | F | 37 | -10.676 | 21.821 | -2.235 | 123.69 C |
| ATOM | 10716 | CG2 | ILE | F | 37 | -12.600 | 21.958 | -3.851 | 119.45 C |
| ATOM | 10717 | CD1 | ILE | F | 37 | -10.392 | 23.301 | -2.070 | 121.55 C |
| ATOM | 10718 | H | ILE | F | 37 | -12.046 | 19.918 | -5.581 | 126.71 H |
| ATOM | 10719 | HA | ILE | F | 37 | -10.197 | 19.642 | -3.604 | 123.08 H |
| ATOM | 10720 | HB | ILE | F | 37 | -10.602 | 21.899 | -4.283 | 123.92 H |
| ATOM | 10721 | HG12 | ILE | F | 37 | -11.351 | 21.572 | -1.585 | 128.43 H |
| ATOM | 10722 | HG13 | ILE | F | 37 | -9.854 | 21.337 | -2.060 | 128.43 H |
| ATOM | 10723 | HG21 | ILE | F | 37 | -12.625 | 22.916 | -3.698 | 123.34 H |
| ATOM | 10724 | HG22 | ILE | F | 37 | -12.868 | 21.762 | -4.762 | 123.34 H |
| ATOM | 10725 | HG23 | ILE | F | 37 | -13.190 | 21.507 | -3.227 | 123.34 H |
| ATOM | 10726 | HD11 | ILE | F | 37 | -10.080 | 23.463 | -1.166 | 125.86 H |
| ATOM | 10727 | HD12 | ILE | F | 37 | -9.710 | 23.564 | -2.708 | 125.86 H |
| ATOM | 10728 | HD13 | ILE | F | 37 | -11.208 | 23.799 | -2.233 | 125.86 H |
| ATOM | 10729 | N | ARG | F | 38 | -11.738 | 18.858 | -1.797 | 117.84 N |
| ATOM | 10730 | CA | ARG | F | 38 | -12.697 | 18.217 | -0.916 | 120.68 C |
| ATOM | 10731 | C | ARG | F | 38 | -12.396 | 18.455 | 0.558 | 119.35 C |
| ATOM | 10732 | O | ARG | F | 38 | -11.235 | 18.589 | 0.953 | 118.38 O |
| ATOM | 10733 | CB | ARG | F | 38 | -12.754 | 16.714 | -1.198 | 122.95 C |
| ATOM | 10734 | CG | ARG | F | 38 | -11.423 | 16.000 | -1.117 | 128.32 C |
| ATOM | 10735 | CD | ARG | F | 38 | -11.562 | 14.534 | -1.510 | 133.42 C |
| ATOM | 10736 | NE | ARG | F | 38 | -10.260 | 13.892 | -1.685 | 143.09 N |
| ATOM | 10737 | CZ | ARG | F | 38 | -9.592 | 13.252 | -0.728 | 144.56 C |
| ATOM | 10738 | NH1 | ARG | F | 38 | -10.092 | 13.147 | 0.498 | 141.53 N1+ |
| ATOM | 10739 | NH2 | ARG | F | 38 | -8.414 | 12.710 | -1.002 | 157.47 N |
| ATOM | 10740 | H | ARG | F | 38 | -10.954 | 18.971 | -1.461 | 121.40 H |
| ATOM | 10741 | HA | ARG | F | 38 | -13.576 | 18.584 | -1.098 | 124.81 H |
| ATOM | 10742 | HB2 | ARG | F | 38 | -13.348 | 16.301 | -0.551 | 127.54 H |
| ATOM | 10743 | HB3 | ARG | F | 38 | -13.104 | 16.580 | -2.092 | 128.32 H |
| ATOM | 10744 | HG2 | ARG | F | 38 | -10.795 | 16.421 | -1.725 | 133.98 H |
| ATOM | 10745 | HG3 | ARG | F | 38 | -11.091 | 16.041 | -0.207 | 133.98 H |
| ATOM | 10746 | HD2 | ARG | F | 38 | -12.041 | 14.060 | -0.812 | 140.11 H |
| ATOM | 10747 | HD3 | ARG | F | 38 | -12.045 | 14.473 | -2.349 | 140.11 H |
| ATOM | 10748 | HE | ARG | F | 38 | -9.899 | 13.931 | -2.465 | 151.71 H |
| ATOM | 10749 | HH11 | ARG | F | 38 | -10.856 | 13.497 | 0.682 | 149.84 H |

TABLE 5-continued

Atomic Coordinates for OMCP-NKG2D (4PDC).

| | | | | | | | | | | |
|---|---|---|---|---|---|---|---|---|---|---|
| ATOM | 10750 | HH12 | ARG | F | 38 | -9.651 | 12.730 | 1.107 | 149.84 | H |
| ATOM | 10751 | HH21 | ARG | F | 38 | -8.085 | 12.773 | -1.794 | 168.96 | H |
| ATOM | 10752 | HH22 | ARG | F | 38 | -7.979 | 12.293 | -0.388 | 168.96 | H |
| ATOM | 10753 | N | PRO | F | 39 | -13.454 | 18.510 | 1.378 | 118.43 | N |
| ATOM | 10754 | CA | PRO | F | 39 | -13.287 | 18.624 | 2.828 | 118.67 | C |
| ATOM | 10755 | CF | PRO | F | 39 | -12.741 | 17.328 | 3.420 | 121.97 | C |
| ATOM | 10756 | O | PRO | F | 39 | 13.015 | 16.261 | 2.874 | 121.02 | O |
| ATOM | 10757 | CB | PRO | F | 39 | -14.706 | 18.905 | 3.320 | 122.75 | C |
| ATOM | 10758 | CG | PRO | F | 39 | -15.585 | 18.250 | 2.306 | 122.23 | C |
| ATOM | 10759 | CD | PRO | F | 39 | -14.875 | 18.401 | 0.993 | 122.99 | C |
| ATOM | 10760 | HA | PRO | F | 39 | -12.704 | 19.365 | 3.054 | 122.40 | H |
| ATOM | 10761 | HB2 | PRO | F | 39 | -14.835 | 18.509 | 4.196 | 127.30 | H |
| ATOM | 10762 | HB3 | PRO | F | 39 | -14.861 | 19.862 | 3.346 | 127.30 | H |
| ATOM | 10763 | HG2 | PRO | F | 39 | -15.696 | 17.312 | 2.528 | 126.68 | H |
| ATOM | 10764 | HG3 | PRO | F | 39 | -16.445 | 18.699 | 2.282 | 126.68 | H |
| ATOM | 10765 | HD2 | PRO | F | 39 | -15.016 | 17.616 | 0.441 | 127.59 | H |
| ATOM | 10766 | HD3 | PRO | F | 39 | -15.166 | 19.209 | 0.543 | 127.59 | H |
| ATOM | 10767 | N | THR | F | 40 | -11.976 | 17.424 | 4.505 | 117.56 | N |
| ATOM | 10768 | CA | THR | F | 40 | -11.433 | 16.245 | 5.182 | 119.85 | C |
| ATOM | 10769 | C | THR | F | 40 | -11.726 | 16.306 | 6.680 | 121.64 | C |
| ATOM | 10770 | O | THR | F | 40 | -11.068 | 15.646 | 7.482 | 125.05 | O |
| ATOM | 10771 | CB | THR | F | 40 | -9.914 | 16.121 | 4.970 | 122.38 | C |
| ATOM | 10772 | OG1 | THR | F | 40 | -9.253 | 17.246 | 5.562 | 122.26 | O |
| ATOM | 10773 | CG2 | THR | F | 40 | -9.581 | 16.061 | 3.486 | 126.29 | C |
| ATOM | 10774 | H | THR | F | 40 | -11.755 | 18.169 | 4.874 | 121.07 | H |
| ATOM | 10775 | HA | THR | F | 40 | -11.855 | 15.449 | 4.823 | 123.82 | H |
| ATOM | 10776 | HB | THR | F | 40 | -9.596 | 15.305 | 5.387 | 126.85 | H |
| ATOM | 10777 | HG1 | THR | F | 40 | -8.423 | 17.183 | 5.449 | 126.71 | H |
| ATOM | 10778 | HG21 | THR | F | 40 | -8.622 | 15.983 | 3.364 | 131.55 | H |
| ATOM | 10779 | HG22 | THR | F | 40 | -10.014 | 15.294 | 3.080 | 131.55 | H |
| ATOM | 10780 | HG23 | THR | F | 40 | -9.890 | 16.868 | 3.044 | 131.55 | H |
| ATOM | 10781 | N | ILE | F | 41 | -12.714 | 17.115 | 7.042 | 120.01 | N |
| ATOM | 10782 | CA | ILE | F | 41 | -13.138 | 17.273 | 8.426 | 120.07 | C |
| ATOM | 10783 | C | ILE | F | 41 | -14.638 | 17.573 | 8.393 | 121.37 | C |
| ATOM | 10784 | O | ILE | F | 41 | -15.103 | 18.248 | 7.473 | 119.23 | O |
| ATOM | 10785 | CB | ILE | F | 41 | -12.348 | 18.400 | 9.131 | 120.97 | C |
| ATOM | 10786 | CG1 | ILE | F | 41 | -12.551 | 18.369 | 10.647 | 125.82 | C |
| ATOM | 10787 | CG2 | ILE | F | 41 | -12.723 | 19.766 | 8.564 | 119.25 | C |
| ATOM | 10788 | CD1 | ILE | F | 41 | -11.871 | 17.205 | 11.329 | 128.28 | C |
| ATOM | 10789 | H | ILE | F | 41 | -13.164 | 17.595 | 6.490 | 124.01 | H |
| ATOM | 10790 | HA | ILE | F | 41 | -12.997 | 16.444 | 8.909 | 124.09 | H |
| ATOM | 10791 | HB | ILE | F | 41 | -11.405 | 18.256 | 8.956 | 125.16 | H |
| ATOM | 10792 | HG12 | ILE | F | 41 | -12.191 | 19.186 | 11.027 | 130.99 | H |
| ATOM | 10793 | HG13 | ILE | F | 41 | -13.500 | 18.310 | 10.834 | 130.99 | H |
| ATOM | 10794 | HG21 | ILE | F | 41 | -12.213 | 20.450 | 9.024 | 123.10 | H |
| ATOM | 10795 | HG22 | ILE | F | 41 | -12.517 | 19.780 | 7.616 | 123.10 | H |
| ATOM | 10796 | HG23 | ILE | F | 41 | -13.673 | 19.913 | 8.698 | 123.10 | H |
| ATOM | 10797 | HD11 | ILE | F | 41 | -12.044 | 17.254 | 12.282 | 133.93 | H |
| ATOM | 10798 | HD12 | ILE | F | 41 | -12.227 | 16.378 | 10.969 | 133.93 | H |
| ATOM | 10799 | HD13 | ILE | F | 41 | -10.917 | 17.255 | 11.162 | 133.93 | H |
| ATOM | 10800 | N | PRO | F | 42 | -15.407 | 17.061 | 9.370 | 122.08 | N |

TABLE 5-continued

Atomic Coordinates for OMCP-NKG2D (4PDC).

| ATOM | 10801 | CA | PRO | F | 42 | -16.864 | 17.242 | 9.291 | 125.38 | C |
|---|---|---|---|---|---|---|---|---|---|---|
| ATOM | 10802 | C | PRO | F | 42 | -17.359 | 18.688 | 9.171 | 123.43 | C |
| ATOM | 10803 | O | PRO | F | 42 | -18.349 | 18.910 | 8.474 | 122.02 | O |
| ATOM | 10804 | CB | PRO | F | 42 | -17.353 | 16.627 | 10.603 | 129.94 | C |
| ATOM | 10805 | CG | PRO | F | 42 | -16.363 | 15.564 | 10.893 | 128.27 | C |
| ATOM | 10806 | CD | PRO | F | 42 | -15.038 | 16.104 | 10.431 | 125.21 | C |
| ATOM | 10807 | HA | PRO | F | 42 | -17.220 | 16.726 | 8.551 | 130.46 | H |
| ATOM | 10808 | HB2 | PRO | F | 42 | -17.354 | 17.299 | 11.302 | 135.92 | H |
| ATOM | 10809 | HB3 | PRO | F | 42 | -18.239 | 16.251 | 10.481 | 135.92 | H |
| ATOM | 10810 | HG2 | PRO | F | 42 | -16.346 | 15.387 | 11.846 | 133.93 | H |
| ATOM | 10811 | HG3 | PRO | F | 42 | -16.594 | 14.761 | 10.400 | 133.93 | H |
| ATOM | 10812 | HD2 | PRO | F | 42 | -14.588 | 16.563 | 11.158 | 130.25 | H |
| ATOM | 10813 | HD3 | PRO | F | 42 | -14.490 | 15.391 | 10.067 | 130.25 | H |
| ATOM | 10814 | N | PHE | F | 43 | -16.709 | 19.651 | 9.818 | 123.12 | N |
| ATOM | 10815 | CA | PHE | F | 43 | -17.256 | 21.005 | 9.831 | 124.79 | C |
| ATOM | 10816 | C | PHE | F | 43 | -17.066 | 21.713 | 8.486 | 123.64 | C |
| ATOM | 10817 | O | PHE | F | 43 | -17.626 | 22.787 | 8.262 | 121.80 | O |
| ATOM | 10818 | CB | PHE | F | 43 | -16.650 | 21.828 | 10.981 | 127.53 | C |
| ATOM | 10819 | CG | PHE | F | 43 | -15.249 | 22.323 | 10.736 | 122.90 | C |
| ATOM | 10820 | CD1 | PHE | F | 43 | -15.021 | 23.465 | 9.986 | 124.94 | C |
| ATOM | 10821 | CD2 | PHE | F | 43 | -14.165 | 21.676 | 11.301 | 125.76 | C |
| ATOM | 10822 | CE1 | PHE | F | 43 | -13.736 | 23.932 | 9.777 | 125.31 | C |
| ATOM | 10823 | CE2 | PHE | F | 43 | -12.876 | 22.141 | 11.097 | 125.44 | C |
| ATOM | 10824 | CZ | PHE | F | 43 | -12.663 | 23.270 | 10.336 | 123.75 | C |
| ATOM | 10825 | H | PHE | F | 43 | -15.970 | 19.552 | 10.246 | 127.75 | H |
| ATOM | 10826 | HA | PHE | F | 43 | -18.211 | 20.945 | 9.992 | 129.75 | H |
| ATOM | 10827 | HB2 | PHE | F | 43 | -17.212 | 22.604 | 11.136 | 133.04 | H |
| ATOM | 10828 | HB3 | PHE | F | 43 | -16.630 | 21.277 | 11.779 | 133.04 | H |
| ATOM | 10829 | HD1 | PHE | F | 43 | -15.740 | 23.916 | 9.606 | 129.93 | H |
| ATOM | 10830 | HD2 | PHE | F | 43 | -14.302 | 20.913 | 11.816 | 130.91 | H |
| ATOM | 10831 | HE1 | PHE | F | 43 | -13.595 | 24.694 | 9.263 | 130.37 | H |
| ATOM | 10832 | HE2 | PHE | F | 43 | -12.154 | 21.691 | 11.473 | 130.53 | H |
| ATOM | 10833 | HZ | PHE | F | 43 | -11.798 | 23.582 | 10.195 | 128.50 | H |
| ATOM | 10834 | N | MET | F | 44 | -16.306 | 21.100 | 7.584 | 122.56 | N |
| ATOM | 10835 | CA | MET | F | 44 | -16.106 | 21.657 | 6.248 | 122.07 | C |
| ATOM | 10836 | C | MET | F | 44 | -17.100 | 21.090 | 5.233 | 125.90 | C |
| ATOM | 10837 | O | MET | F | 44 | -17.186 | 21.573 | 4.099 | 124.02 | O |
| ATOM | 10838 | CB | MET | F | 44 | -14.672 | 21.401 | 5.776 | 123.53 | C |
| ATOM | 10839 | CG | MET | F | 44 | -13.629 | 22.258 | 6.480 | 117.23 | C |
| ATOM | 10840 | SD | MET | F | 44 | -13.962 | 24.032 | 6.367 | 124.19 | S |
| ATOM | 10841 | CE | MET | F | 44 | -14.044 | 24.258 | 4.597 | 116.78 | C |
| ATOM | 10842 | H | MET | F | 44 | -15.893 | 20.357 | 7.720 | 127.07 | H |
| ATOM | 10843 | HA | MET | F | 44 | -16.230 | 22.618 | 6.295 | 126.49 | H |
| ATOM | 10844 | HB2 | MET | F | 44 | -14.451 | 20.471 | 5.940 | 128.24 | H |
| ATOM | 10845 | HB3 | MET | F | 44 | -14.618 | 21.589 | 4.826 | 128.24 | H |
| ATOM | 10846 | HG2 | MET | F | 44 | -13.609 | 22.019 | 7.420 | 120.67 | H |
| ATOM | 10847 | HG3 | MET | F | 44 | -12.763 | 22.092 | 6.078 | 120.67 | H |
| ATOM | 10848 | HE1 | MET | F | 44 | -14.222 | 25.193 | 4.407 | 120.13 | H |
| ATOM | 10849 | HE2 | MET | F | 44 | -13.196 | 23.996 | 4.206 | 120.13 | H |
| ATOM | 10850 | HE3 | MET | F | 44 | -14.758 | 23.706 | 4.242 | 120.13 | H |
| ATOM | 10851 | N | ILE | F | 45 | -17.856 | 20.074 | 5.637 | 123.53 | N |

TABLE 5-continued

Atomic Coordinates for OMCP-NKG2D (4PDC).

| | | | | | | | | | |
|---|---|---|---|---|---|---|---|---|---|
| ATOM | 10852 | CA | ILE | F | 45 | -18.861 | 19.487 | 4.759 | C |
| ATOM | 10853 | C | ILE | F | 45 | -19.891 | 20.542 | 4.379 | C |
| ATOM | 10854 | O | ILE | F | 45 | -20.445 | 21.213 | 5.246 | O |
| ATOM | 10855 | CB | ILE | F | 45 | -19.570 | 18.284 | 5.427 | C |
| ATOM | 10856 | CG1 | ILE | F | 45 | -18.585 | 17.130 | 5.642 | C |
| ATOM | 10857 | CG2 | ILE | F | 45 | -20.768 | 17.817 | 4.596 | C |
| ATOM | 10858 | CD1 | ILE | F | 45 | -18.072 | 16.491 | 4.363 | C |
| ATOM | 10859 | H | ILE | F | 45 | -17.806 | 19.707 | 6.413 | H |
| ATOM | 10860 | HA | ILE | F | 45 | -18.433 | 19.174 | 3.947 | H |
| ATOM | 10861 | HB | ILE | F | 45 | -19.896 | 18.569 | 6.295 | H |
| ATOM | 10862 | HG12 | ILE | F | 45 | -17.818 | 17.464 | 6.132 | H |
| ATOM | 10863 | HG13 | ILE | F | 45 | -19.027 | 16.438 | 6.159 | H |
| ATOM | 10864 | HG21 | ILE | F | 45 | -21.188 | 17.065 | 5.043 | H |
| ATOM | 10865 | HG22 | ILE | F | 45 | -21.400 | 18.549 | 4.516 | H |
| ATOM | 10866 | HG23 | ILE | F | 45 | -20.458 | 17.550 | 3.717 | H |
| ATOM | 10867 | HD11 | ILE | F | 45 | -17.459 | 15.775 | 4.593 | H |
| ATOM | 10868 | HD12 | ILE | F | 45 | -18.824 | 16.136 | 3.864 | H |
| ATOM | 10869 | HD13 | ILE | F | 45 | -17.613 | 17.164 | 3.837 | H |
| ATOM | 10870 | N | GLY | F | 46 | -20.129 | 20.692 | 3.080 | N |
| ATOM | 10871 | CA | GLY | F | 46 | -21.162 | 21.585 | 2.590 | C |
| ATOM | 10872 | C | GLY | F | 46 | -20.766 | 23.050 | 2.590 | C |
| ATOM | 10873 | O | GLY | F | 46 | -21.596 | 23.918 | 2.325 | O |
| ATOM | 10874 | H | GLY | F | 46 | -19.699 | 20.281 | 2.459 | H |
| ATOM | 10875 | HA2 | GLY | F | 46 | -21.392 | 21.336 | 1.681 | H |
| ATOM | 10876 | HA3 | GLY | F | 46 | -21.954 | 21.487 | 3.141 | H |
| ATOM | 10877 | N | ASP | F | 47 | -19.503 | 23.332 | 2.889 | N |
| ATOM | 10878 | CA | ASP | F | 47 | -19.003 | 24.700 | 2.842 | C |
| ATOM | 10879 | C | ASP | F | 47 | -19.092 | 25.225 | 1.417 | C |
| ATOM | 10880 | O | ASP | F | 47 | -18.683 | 24.548 | 0.479 | O |
| ATOM | 10881 | CB | ASP | F | 47 | -17.561 | 24.767 | 3.347 | C |
| ATOM | 10882 | CG | ASP | F | 47 | -16.915 | 26.115 | 3.090 | C |
| ATOM | 10883 | OD1 | ASP | F | 47 | -17.287 | 27.091 | 3.769 | O |
| ATOM | 10884 | OD2 | ASP | F | 47 | -16.032 | 26.196 | 2.212 | O1- |
| ATOM | 10885 | H | ASP | F | 47 | -18.915 | 22.749 | 3.122 | H |
| ATOM | 10886 | HA | ASP | F | 47 | -19.552 | 25.262 | 3.410 | H |
| ATOM | 10887 | HB2 | ASP | F | 47 | -17.553 | 24.607 | 4.304 | H |
| ATOM | 10888 | HB3 | ASP | F | 47 | -17.034 | 24.090 | 2.893 | H |
| ATOM | 10889 | N | GLU | F | 48 | -19.637 | 26.426 | 1.256 | N |
| ATOM | 10890 | CA | GLU | F | 48 | -19.825 | 27.004 | -0.074 | C |
| ATOM | 10891 | C | GLU | F | 48 | -19.089 | 28.332 | -0.224 | C |
| ATOM | 10892 | O | GLU | F | 48 | -19.333 | 29.078 | -1.173 | O |
| ATOM | 10893 | CB | GLU | F | 48 | -21.321 | 27.185 | -0.365 | C |
| ATOM | 10894 | CG | GLU | F | 48 | -22.059 | 28.030 | 0.656 | C |
| ATOM | 10895 | CD | GLU | F | 48 | -23.557 | 28.110 | 0.393 | C |
| ATOM | 10896 | OE1 | GLU | F | 48 | -23.975 | 28.028 | -0.781 | O |
| ATOM | 10897 | OE2 | GLU | F | 48 | -24.316 | 28.257 | 1.368 | O1- |
| ATOM | 10898 | H | GLU | F | 48 | -19.907 | 26.928 | 1.900 | H |
| ATOM | 10899 | HA | GLU | F | 48 | -19.467 | 26.390 | -0.734 | H |
| ATOM | 10900 | HB2 | GLU | F | 48 | -21.420 | 27.614 | -1.229 | H |
| ATOM | 10901 | HB3 | GLU | F | 48 | -21.742 | 26.311 | -0.384 | H |
| ATOM | 10902 | HG2 | GLU | F | 48 | -21.930 | 27.643 | 1.536 | H |

TABLE 5-continued

Atomic Coordinates for OMCP-NKG2D (4PDC).

| ATOM | 10903 | HG3 | GLU | F | 48 | -21.702 | 28.932 | 0.635 | 131.18 | H |
|---|---|---|---|---|---|---|---|---|---|---|
| ATOM | 10904 | N | ILE | F | 49 | -18.176 | 28.615 | 0.701 | 121.84 | N |
| ATOM | 10905 | CA | ILE | F | 49 | -17.393 | 29.848 | 0.657 | 119.58 | C |
| ATOM | 10906 | C | ILE | F | 49 | -15.911 | 29.570 | 0.422 | 121.99 | C |
| ATOM | 10907 | O | ILE | F | 49 | -15.314 | 30.091 | -0.521 | 118.32 | O |
| ATOM | 10908 | CB | ILE | F | 49 | -17.560 | 30.650 | 1.958 | 122.04 | C |
| ATOM | 10909 | CG1 | ILE | F | 49 | -19.021 | 31.077 | 2.119 | 119.68 | C |
| ATOM | 10910 | CG2 | ILE | F | 49 | -16.648 | 31.883 | 1.960 | 122.59 | C |
| ATOM | 10911 | CD1 | ILE | F | 49 | -19.377 | 31.490 | 3.521 | 129.80 | C |
| ATOM | 10912 | H | ILE | F | 49 | -17.990 | 28.106 | 1.369 | 126.21 | H |
| ATOM | 10913 | HA | ILE | F | 49 | -17.714 | 30.397 | -0.075 | 123.50 | H |
| ATOM | 10914 | HB | ILE | F | 49 | -17.317 | 30.082 | 2.707 | 126.45 | H |
| ATOM | 10915 | HG12 | ILE | F | 49 | -19.192 | 31.832 | 1.534 | 123.61 | H |
| ATOM | 10916 | HG13 | ILE | F | 49 | -19.594 | 30.334 | 1.874 | 123.61 | H |
| ATOM | 10917 | HG21 | ILE | F | 49 | -16.775 | 32.368 | 2.791 | 127.11 | H |
| ATOM | 10918 | HG22 | ILE | F | 49 | -15.726 | 31.594 | 1.883 | 127.11 | H |
| ATOM | 10919 | HG23 | ILE | F | 49 | -16.882 | 32.449 | 1.208 | 127.11 | H |
| ATOM | 10920 | HD11 | ILE | F | 49 | -20.312 | 31.747 | 3.546 | 135.76 | H |
| ATOM | 10921 | HD12 | ILE | F | 49 | -19.222 | 30.743 | 4.119 | 135.76 | H |
| ATOM | 10922 | HD13 | ILE | F | 49 | -18.820 | 32.242 | 3.779 | 135.76 | H |
| ATOM | 10923 | N | PHE | F | 50 | -15.317 | 28.749 | 1.279 | 114.92 | N |
| ATOM | 10924 | CA | PHE | F | 50 | -13.876 | 28.544 | 1.238 | 118.72 | C |
| ATOM | 10925 | C | PHE | F | 50 | -13.449 | 27.474 | 0.235 | 115.47 | C |
| ATOM | 10926 | O | PHE | F | 50 | -12.438 | 27.643 | -0.442 | 115.17 | O |
| ATOM | 10927 | CB | PHE | F | 50 | -13.374 | 28.203 | 2.637 | 114.79 | C |
| ATOM | 10928 | CG | PHE | F | 50 | -13.688 | 29.267 | 3.644 | 120.85 | C |
| ATOM | 10929 | CD1 | PHE | F | 50 | -12.912 | 30.413 | 3.720 | 123.04 | C |
| ATOM | 10930 | CD2 | PHE | F | 50 | -14.778 | 29.144 | 4.488 | 121.71 | C |
| ATOM | 10931 | CE1 | PHE | F | 50 | -13.206 | 31.407 | 4.633 | 121.89 | C |
| ATOM | 10932 | CE2 | PHEF | | 50 | -15.074 | 30.134 | 5.408 | 121.18 | C |
| ATOM | 10933 | CZ | PHE | F | 50 | -14.288 | 31.268 | 5.475 | 119.57 | C |
| ATOM | 10934 | H | PHE | F | 50 | -15.724 | 28.301 | 1.890 | 117.90 | H |
| ATOM | 10935 | HA | PHE | F | 50 | -13.454 | 29.376 | 0.972 | 122.46 | H |
| ATOM | 10936 | HB2 | PHE | F | 50 | -13.794 | 27.379 | 2.930 | 117.74 | H |
| ATOM | 10937 | HB3 | PHE | F | 50 | -12.411 | 28.092 | 2.608 | 117.74 | H |
| ATOM | 10938 | HD1 | PHE | F | 50 | -12.181 | 30.512 | 3.153 | 127.65 | H |
| ATOM | 10939 | HD2 | PHE | F | 50 | -15.310 | 28.383 | 4.445 | 126.06 | H |
| ATOM | 10940 | HE1 | PHE | F | 50 | -12.674 | 32.169 | 4.681 | 126.27 | H |
| ATOM | 10941 | HE2 | PHE | F | 50 | -15.805 | 30.039 | 5.975 | 125.42 | H |
| ATOM | 10942 | HZ | PHE | F | 50 | -14.486 | 31.934 | 6.094 | 123.49 | H |
| ATOM | 10943 | N | LEU | F | 51 | -14.215 | 26.389 | 0.130 | 115.59 | N |
| ATOM | 10944 | CA | LEU | F | 51 | -13.877 | 25.314 | -0.803 | 116.84 | C |
| ATOM | 10945 | C | LEU | F | 51 | -13.816 | 25.809 | -2.251 | 117.50 | C |
| ATOM | 10946 | O | LEU | F | 51 | -12.842 | 25.549 | -2.949 | 114.18 | O |
| ATOM | 10947 | CB | LEU | F | 51 | -14.878 | 24.157 | -0.695 | 127.65 | C |
| ATOM | 10948 | CG | LEU | F | 51 | -14.747 | 23.235 | 0.521 | 116.15 | C |
| ATOM | 10949 | CD1 | LEU | F | 51 | -15.930 | 22.279 | 0.591 | 123.56 | C |
| ATOM | 10950 | CD2 | LEU | F | 51 | -13.442 | 22.452 | 0.490 | 125.39 | C |
| ATOM | 10951 | H | LEU | F | 51 | -14.931 | 26.251 | 0.585 | 118.07 | H |
| ATOM | 10952 | HA | LEU | F | 51 | -13.000 | 24.967 | -0.573 | 120.21 | H |
| ATOM | 10953 | HB2 | LEU | F | 51 | -15.772 | 24.533 | -0.673 | 119.38 | H |

TABLE 5-continued

Atomic Coordinates for OMCP-NKG2D (4PDC).

| | | | | | | | | | |
|---|---|---|---|---|---|---|---|---|---|
| ATOM | 10954 | HB3 | LEU | F | 51 | -14.785 | 23.603 | -1.485 | H |
| ATOM | 10955 | HG | LEU | F | 51 | -14.751 | 23.775 | 1.327 | H |
| ATOM | 10956 | HD11 | LEU | F | 51 | -15.826 | 21.705 | 1.367 | H |
| ATOM | 10957 | HD12 | LEU | F | 51 | -16.748 | 22.794 | 0.667 | H |
| ATOM | 10958 | HD13 | LEU | F | 51 | -15.950 | 21.742 | -0.217 | H |
| ATOM | 10959 | HD21 | LEU | F | 51 | -13.398 | 21.882 | 1.274 | H |
| ATOM | 10960 | HD22 | LEU | F | 51 | -13.418 | 21.911 | -0.314 | H |
| ATOM | 10961 | HD23 | LEU | F | 51 | -12.700 | 23.076 | 0.492 | H |
| ATOM | 10962 | N | PRO | F | 52 | -14.858 | 26.512 | -2.718 | N |
| ATOM | 10963 | CA | PRO | F | 52 | -14.770 | 27.012 | -4.094 | C |
| ATOM | 10964 | C | PRO | F | 52 | -13.685 | 28.072 | -4.276 | C |
| ATOM | 10965 | O | PRO | F | 52 | -13.036 | 28.106 | -5.322 | O |
| ATOM | 10966 | CB | PRO | F | 52 | -16.167 | 27.601 | -4.350 | C |
| ATOM | 10967 | CG | PRO | F | 52 | -16.760 | 27.811 | -3.003 | C |
| ATOM | 10968 | CD | PRO | F | 52 | -16.194 | 26.736 | -2.139 | C |
| ATOM | 10969 | HA | PRO | F | 52 | -14.611 | 26.279 | -4.710 | H |
| ATOM | 10970 | HB2 | PRO | F | 52 | -16.084 | 28.443 | -4.822 | H |
| ATOM | 10971 | HB3 | PRO | F | 52 | -16.697 | 26.971 | -4.862 | H |
| ATOM | 10972 | HG2 | PRO | F | 52 | -16.507 | 28.686 | -2.669 | H |
| ATOM | 10973 | HG3 | PRO | F | 52 | -17.725 | 27.732 | -3.057 | H |
| ATOM | 10974 | HD2 | PRO | F | 52 | -16.119 | 27.042 | -1.222 | H |
| ATOM | 10975 | HD3 | PRO | F | 52 | -16.731 | 25.930 | -2.204 | H |
| ATOM | 10976 | N | PHE | F | 53 | -13.485 | 28.921 | -3.273 | N |
| ATOM | 10977 | CA | PHE | F | 53 | -12.478 | 29.970 | -3.374 | C |
| ATOM | 10978 | C | PHE | F | 53 | -11.083 | 29.361 | -3.477 | C |
| ATOM | 10979 | O | PHE | F | 53 | -10.293 | 29.756 | -4.334 | O |
| ATOM | 10980 | CB | PHE | F | 53 | -12.555 | 30.922 | -2.180 | C |
| ATOM | 10981 | CG | PHE | F | 53 | -11.510 | 32.002 | -2.204 | C |
| ATOM | 10982 | CD1 | PHE | F | 53 | -11.679 | 33.131 | -2.989 | C |
| ATOM | 10983 | CD2 | PHE | F | 53 | -10.356 | 31.885 | -1.448 | C |
| ATOM | 10984 | CE1 | PHE | F | 53 | -10.719 | 34.123 | -3.016 | C |
| ATOM | 10985 | CE2 | PHE | F | 53 | -9.392 | 32.879 | -1.470 | C |
| ATOM | 10986 | CZ | PHE | F | 53 | -9.574 | 33.995 | -2.256 | C |
| ATOM | 10987 | H | PHE | F | 53 | -13.916 | 28.910 | -2.528 | H |
| ATOM | 10988 | HA | PHE | F | 53 | -12.640 | 30.486 | -4.179 | H |
| ATOM | 10989 | HB2 | PHE | F | 53 | -13.425 | 31.350 | -2.176 | H |
| ATOM | 10990 | HB3 | PHE | F | 53 | -12.436 | 30.411 | -1.364 | H |
| ATOM | 10991 | HD1 | PHE | F | 53 | -12.448 | 33.222 | -3.504 | H |
| ATOM | 10992 | HD2 | PHE | F | 53 | -10.229 | 31.133 | -0.916 | H |
| ATOM | 10993 | HE1 | PHE | F | 53 | -10.844 | 34.877 | -3.546 | H |
| ATOM | 10994 | HE2 | PHE | F | 53 | -8.620 | 32.791 | -0.958 | H |
| ATOM | 10995 | HZ | PHE | F | 53 | -8.927 | 34.664 | -2.272 | H |
| ATOM | 10996 | N | TYR | F | 54 | -13.916 | 28.389 | -2.616 | N |
| ATOM | 10997 | CA | TYR | F | 54 | -9.500 | 27.707 | -2.649 | C |
| ATOM | 10998 | C | TYR | F | 54 | -9.324 | 26.904 | -3.935 | C |
| ATOM | 10999 | O | TYR | F | 54 | -8.222 | 26.831 | -4.473 | O |
| ATOM | 11000 | CB | TYR | F | 54 | -9.338 | 26.783 | -1.436 | C |
| ATOM | 11001 | CG | TYR | F | 54 | -9.215 | 27.502 | -0.107 | C |
| ATOM | 11002 | CD1 | TYR | F | 54 | -8.682 | 28.785 | -0.029 | C |
| ATOM | 11003 | CD2 | TYR | F | 54 | -9.637 | 26.899 | 1.070 | C |
| ATOM | 11004 | CE1 | TYR | F | 54 | -8.575 | 29.442 | 1.182 | C |

TABLE 5-continued

Atomic Coordinates for OMCP-NKG2D (4PDC).

| ATOM | 11005 | CE2 | TYR | F | 54 | -9.531 | 27.545 | 2.282 | 113.82 | C |
|---|---|---|---|---|---|---|---|---|---|---|
| ATOM | 11006 | CZ | TYR | F | 54 | -9.002 | 28.814 | 2.333 | 114.13 | C |
| ATOM | 11007 | OH | TYR | F | 54 | -8.901 | 29.461 | 3.537 | 113.26 | O |
| ATOM | 11008 | H | TYR | F | 54 | -11.322 | 28.106 | -2.003 | 116.22 | H |
| ATOM | 11009 | HA | TYR | F | 54 | -8.793 | 28.371 | -2.614 | 116.57 | H |
| ATOM | 11010 | HB2 | TYR | F | 54 | -10.112 | 26.201 | -1.384 | 114.92 | H |
| ATOM | 11011 | HB3 | TYR | F | 54 | -8.536 | 26.250 | -1.557 | 114.92 | H |
| ATOM | 11012 | HD1 | TYR | F | 54 | -8.395 | 29.208 | -0.805 | 118.05 | H |
| ATOM | 11013 | HD2 | TYR | F | 54 | -9.996 | 26.041 | 1.039 | 117.67 | H |
| ATOM | 11014 | HE1 | TYR | F | 54 | -8.217 | 30.299 | 1.221 | 115.61 | H |
| ATOM | 11015 | HE2 | TYR | F | 54 | -9.820 | 27.127 | 3.061 | 116.58 | H |
| ATOM | 11016 | HH | TYR | F | 54 | -9.194 | 28.970 | 4.152 | 115.91 | H |
| ATOM | 11017 | N | LYS | F | 54 | -10.403 | 26.303 | -4.429 | 113.00 | N |
| ATOM | 11018 | CA | LYS | F | 55 | -10.321 | 25.526 | -5.661 | 115.12 | C |
| ATOM | 11019 | C | LYS | F | 55 | -9.743 | 26.382 | -6.786 | 114.25 | C |
| ATOM | 11020 | O | LYS | F | 55 | -8.873 | 25.934 | -7.535 | 115.64 | O |
| ATOM | 11021 | CB | LYS | F | 55 | -11.695 | 24.982 | -6.060 | 117.19 | C |
| ATOM | 11022 | CG | LYS | F | 55 | -11.638 | 23.938 | -7.159 | 118.78 | C |
| ATOM | 11023 | CD | LYS | F | 55 | -13.025 | 23.546 | -7.643 | 122.88 | C |
| ATOM | 11024 | CE | LYS | F | 55 | -12.935 | 22.564 | -8.795 | 127.95 | C |
| ATOM | 11025 | NZ | LYS | F | 55 | -14.263 | 22.302 | -9.406 | 135.34 | N1+ |
| ATOM | 11026 | H | LYS | F | 55 | -11.186 | 26.330 | -4.075 | 115.60 | H |
| ATOM | 11027 | HA | LYS | F | 55 | -9.727 | 24.772 | -5.522 | 118.15 | H |
| ATOM | 11028 | HB2 | LYS | F | 55 | -12.108 | 24.574 | -5.283 | 120.62 | H |
| ATOM | 11029 | HB3 | LYS | F | 55 | -12.243 | 25.717 | -6.376 | 120.62 | H |
| ATOM | 11030 | HG2 | LYS | F | 55 | -11.145 | 24.296 | -7.913 | 122.53 | H |
| ATOM | 11031 | HG3 | LYS | F | 55 | -11.200 | 23.142 | -6.820 | 122.53 | H |
| ATOM | 11032 | HD2 | LYS | F | 55 | -13.512 | 23.124 | -6.918 | 127.45 | H |
| ATOM | 11033 | HD3 | LYS | F | 55 | -13.495 | 24.337 | -7.950 | 127.45 | H |
| ATOM | 11034 | HE2 | LYS | F | 55 | -12.354 | 22.929 | -9.480 | 133.53 | H |
| ATOM | 11035 | HE3 | LYS | F | 55 | -12.581 | 21.722 | -8.469 | 133.53 | H |
| ATOM | 11036 | HZ1 | LYS | F | 55 | -14.180 | 21.724 | -10.078 | 142.41 | H |
| ATOM | 11037 | HZ2 | LYS | F | 55 | -14.816 | 21.961 | -8.798 | 142.41 | H |
| ATOM | 11038 | HZ3 | LYS | F | 55 | -14.609 | 23.060 | -9.719 | 142.41 | H |
| ATOM | 11039 | N | ASN | F | 56 | -10.210 | 27.622 | -6.886 | 112.64 | N |
| ATOM | 11040 | CA | ASN | F | 56 | -9.713 | 28.541 | -7.906 | 115.26 | C |
| ATOM | 11041 | C | ASN | F | 56 | -8.293 | 29.017 | -7.618 | 116.59 | C |
| ATOM | 11042 | O | ASN | F | 56 | -7.447 | 29.059 | -8.511 | 115.03 | O |
| ATOM | 11043 | CB | ASN | F | 56 | -10.640 | 29.751 | -8.028 | 118.33 | C |
| ATOM | 11044 | CG | ASN | F | 56 | -11.983 | 29.397 | -8.634 | 128.04 | C |
| ATOM | 11045 | OD1 | ASN | F | 56 | -12.091 | 28.463 | -9.428 | 130.73 | O |
| ATOM | 11046 | ND2 | ASN | F | 56 | -13.016 | 30.147 | -8.264 | 132.03 | N |
| ATOM | 11047 | H | ASN | F | 56 | -10.815 | 27.957 | -6.376 | 115.17 | H |
| ATOM | 11048 | HA | ASN | F | 56 | -9.706 | 28.085 | -8.762 | 118.31 | H |
| ATOM | 11049 | HB2 | ASN | F | 56 | -10.797 | 30.119 | -7.144 | 122.00 | H |
| ATOM | 11050 | HB3 | ASN | F | 56 | -10.220 | 30.416 | -8.595 | 122.00 | H |
| ATOM | 11051 | HD21 | ASN | F | 56 | -13.799 | 29.986 | -8.264 | 138.43 | H |
| ATOM | 11052 | HD22 | ASN | F | 56 | -12.901 | 30.792 | -7.708 | 138.43 | H |
| ATOM | 11053 | N | VAL | F | 57 | -8.039 | 29.391 | -6.370 | 112.10 | N |
| ATOM | 11054 | CA | VAL | F | 57 | -6.714 | 29.855 | -5.972 | 112.15 | C |
| ATOM | 11055 | C | VAL | F | 57 | -5.674 | 28.762 | -6.181 | 112.63 | C |

TABLE 5-continued

Atomic Coordinates for OMCP-NKG2D (4PDC).

| ATOM | 11056 | O | VAL | F | 57 | -4.603 | -6.738 | 29.015 | 116.24 | O |
|---|---|---|---|---|---|---|---|---|---|---|
| ATOM | 11057 | CB | VAL | F | 57 | -6.708 | -4.500 | 30.312 | 112.42 | C |
| ATOM | 11058 | CG1 | VAL | F | 57 | -5.284 | -4.000 | 30.566 | 113.82 | C |
| ATOM | 11059 | CG2 | VAL | F | 57 | -7.555 | -4.342 | 31.571 | 113.89 | C |
| ATOM | 11060 | H | VAL | F | 57 | -8.617 | -5.733 | 29.386 | 114.52 | H |
| ATOM | 11061 | HA | VAL | F | 57 | -6.467 | -6.522 | 30.615 | 114.57 | H |
| ATOM | 11062 | HB | VAL | F | 57 | -7.100 | -3.951 | 29.615 | 114.90 | H |
| ATOM | 11063 | HG11 | VAL | F | 57 | -5.321 | -3.074 | 30.851 | 116.59 | H |
| ATOM | 11064 | HG12 | VAL | F | 57 | -4.772 | -4.074 | 29.745 | 116.59 | H |
| ATOM | 11065 | HG13 | VAL | F | 57 | -4.878 | -4.544 | 31.260 | 116.59 | H |
| ATOM | 11066 | HG21 | VAL | F | 57 | -7.541 | -3.412 | 31.845 | 116.67 | H |
| ATOM | 11067 | HG22 | VAL | F | 57 | -7.184 | -4.900 | 32.272 | 116.67 | H |
| ATOM | 11068 | HG23 | VAL | F | 57 | -8.464 | -4.617 | 31.375 | 116.67 | H |
| ATOM | 11069 | N | PHE | F | 57 | -5.994 | -5.740 | 27.548 | 112.82 | N |
| ATOM | 11070 | CA | PHE | F | 58 | -5.062 | -5.830 | 26.430 | 113.09 | C |
| ATOM | 11071 | C | PHE | F | 58 | -4.801 | -7.285 | 26.058 | 114.82 | C |
| ATOM | 11072 | O | PHE | F | 58 | -3.660 | -7.676 | 25.848 | 112.06 | O |
| ATOM | 11073 | CB | PHE | F | 58 | -5.588 | -5.070 | 25.207 | 112.73 | C |
| ATOM | 11074 | CG | PHE | F | 58 | -5.695 | -3.578 | 25.402 | 112.49 | C |
| ATOM | 11075 | CD1 | PHE | F | 58 | -5.281 | -2.974 | 26.581 | 112.83 | C |
| ATOM | 11076 | CD2 | PHE | F | 58 | -6.213 | -2.777 | 24.396 | 113.83 | C |
| ATOM | 11077 | CE1 | PHE | F | 58 | -5.388 | -1.603 | 26.751 | 113.49 | C |
| ATOM | 11078 | CE2 | PHE | F | 58 | -6.322 | -1.405 | 24.566 | 116.44 | C |
| ATOM | 11079 | CZ | PHE | F | 58 | -5.906 | -0.821 | 25.747 | 111.02 | C |
| ATOM | 11080 | H | PHE | F | 58 | -6.749 | -5.381 | 27.346 | 115.38 | H |
| ATOM | 11081 | HA | PHE | F | 58 | -4.217 | -5.431 | 26.690 | 115.71 | H |
| ATOM | 11082 | HB2 | PHE | F | 58 | -6.473 | -5.403 | 24.991 | 115.28 | H |
| ATOM | 11083 | HB3 | PHE | F | 58 | -4.988 | -5.227 | 24.461 | 115.28 | H |
| ATOM | 11084 | HD1 | PHE | F | 58 | -4.931 | -3.496 | 27.267 | 115.39 | H |
| ATOM | 11085 | HD2 | PHE | F | 58 | -6.497 | -3.166 | 23.600 | 116.60 | H |
| ATOM | 11086 | HE1 | PHE | F | 58 | -5.107 | -1.211 | 27.546 | 116.19 | H |
| ATOM | 11087 | HE2 | PHE | F | 58 | -6.672 | -0.878 | 23.884 | 119.73 | H |
| ATOM | 11088 | HZ | PHE | F | 58 | -5.975 | 0.099 | 25.862 | 113.22 | H |
| ATOM | 11089 | N | SER | F | 59 | -5.853 | -8.089 | 25.970 | 112.82 | N |
| ATOM | 11090 | CA | SER | F | 59 | -5.685 | -9.486 | 25.598 | 116.28 | C |
| ATOM | 11091 | C | SER | F | 59 | -4.855 | -10.229 | 26.649 | 118.53 | C |
| ATOM | 11092 | O | SER | F | 59 | -4.011 | -11.056 | 26.307 | 115.62 | O |
| ATOM | 11093 | CB | SER | F | 59 | -7.046 | -10.159 | 25.406 | 119.61 | C |
| ATOM | 11094 | OG | SER | F | 59 | -7.896 | -9.896 | 26.504 | 129.67 | O |
| ATOM | 11095 | H | SER | F | 59 | -6.667 | -7.853 | 26.119 | 115.39 | H |
| ATOM | 11096 | HA | SER | F | 59 | -5.208 | -9.532 | 24.754 | 119.54 | H |
| ATOM | 11097 | HB2 | SER | F | 59 | -6.917 | -11.118 | 25.329 | 123.54 | H |
| ATOM | 11098 | HB3 | SER | F | 59 | -7.458 | -9.815 | 24.598 | 123.54 | H |
| ATOM | 11099 | HG | SER | F | 59 | -7.551 | -10.189 | 27.212 | 135.60 | H |
| ATOM | 11100 | N | GLU | F | 60 | -5.070 | -9.914 | 27.925 | 117.84 | N |
| ATOM | 11101 | CA | GLU | F | 60 | -4.311 | -10.554 | 29.000 | 115.88 | C |
| ATOM | 11102 | C | GLU | F | 60 | -2.856 | -10.090 | 29.027 | 114.19 | C |
| ATOM | 11103 | O | GLU | F | 60 | -1.958 | -10.859 | 29.374 | 116.59 | O |
| ATOM | 11104 | CB | GLU | F | 60 | -4.966 | -10.286 | 30.356 | 119.52 | C |
| ATOM | 11105 | CG | GLU | F | 60 | -6.207 | -11.124 | 30.607 | 126.68 | C |
| ATOM | 11106 | CD | GLU | F | 60 | -5.906 | -12.609 | 30.696 | 134.90 | C |

TABLE 5-continued

Atomic Coordinates for OMCP-NKG2D (4PDC).

| ATOM | 11107 | OE1 | GLU | F | 60 | -5.129 | 31.593 | -13.010 | 137.82 | O |
|---|---|---|---|---|---|---|---|---|---|---|
| ATOM | 11108 | OE2 | GLU | F | 60 | -6.442 | 29.866 | -13.377 | 135.67 | O1- |
| ATOM | 11109 | H | GLU | F | 60 | -5.646 | 28.194 | -9.335 | 121.40 | H |
| ATOM | 11110 | HA | GLU | F | 60 | -4.313 | 28.855 | -11.513 | 119.05 | H |
| ATOM | 11111 | HB2 | GLU | F | 60 | -5.223 | 30.400 | -9.352 | 123.42 | H |
| ATOM | 11112 | HB3 | GLU | F | 60 | -4.326 | 31.058 | -10.485 | 123.42 | H |
| ATOM | 11113 | HG2 | GLU | F | 60 | -6.833 | 29.877 | -10.988 | 132.02 | H |
| ATOM | 11114 | HG3 | GLU | F | 60 | -6.610 | 31.445 | -10.849 | 132.02 | H |
| ATOM | 11115 | N | PHE | F | 61 | -2.630 | 28.671 | -8.829 | 116.80 | N |
| ATOM | 11116 | CA | PHE | F | 61 | -1.278 | 28.576 | -8.290 | 113.01 | C |
| ATOM | 11117 | C | PHE | F | 61 | -0.415 | 27.700 | -9.188 | 115.28 | C |
| ATOM | 11118 | O | PHE | F | 61 | 0.721 | 28.048 | -9.504 | 114.04 | O |
| ATOM | 11119 | CB | PHE | F | 61 | -1.302 | 28.013 | -6.866 | 112.89 | C |
| ATOM | 11120 | CG | PHE | F | 61 | 0.067 | 27.780 | -6.272 | 111.72 | C |
| ATOM | 11121 | CD1 | PHE | F | 61 | 0.710 | 26.560 | -6.430 | 112.06 | C |
| ATOM | 11122 | CD2 | PHE | F | 61 | 0.698 | 28.775 | -5.538 | 112.10 | C |
| ATOM | 11123 | CE1 | PHE | F | 61 | 1.968 | 26.342 | -5.878 | 114.29 | C |
| ATOM | 11124 | CE2 | PHE | F | 61 | 1.954 | 28.563 | -4.982 | 112.57 | C |
| ATOM | 11125 | CZ | PHE | F | 61 | 2.589 | 27.347 | -5.152 | 111.10 | C |
| ATOM | 11126 | H | PHE | F | 61 | -3.247 | 28.479 | -8.262 | 120.16 | H |
| ATOM | 11127 | HA | PHE | F | 61 | -0.883 | 29.462 | -8.260 | 115.61 | H |
| ATOM | 11128 | HB2 | PHE | F | 61 | -1.771 | 28.638 | -6.292 | 115.46 | H |
| ATOM | 11129 | HB3 | PHE | F | 61 | -1.768 | 27.162 | -6.876 | 115.46 | H |
| ATOM | 11130 | HD1 | PHE | F | 61 | 0.299 | 25.884 | -6.917 | 114.47 | H |
| ATOM | 11131 | HD2 | PHE | F | 61 | 0.277 | 29.596 | -5.421 | 114.52 | H |
| ATOM | 11132 | HE1 | PHE | F | 61 | 2.391 | 25.522 | -5.994 | 117.15 | H |
| ATOM | 11133 | HE2 | PHE | F | 61 | 2.368 | 29.240 | -4.496 | 115.08 | H |
| ATOM | 11134 | HZ | PHE | F | 61 | 3.429 | 27.203 | -4.781 | 113.32 | H |
| ATOM | 11135 | N | PHE | F | 62 | -0.962 | 26.564 | -9.605 | 115.38 | N |
| ATOM | 11136 | CA | PHE | F | 62 | -0.203 | 25.622 | -10.419 | 114.52 | C |
| ATOM | 11137 | C | PHE | F | 62 | -0.191 | 26.018 | -11.891 | 114.12 | C |
| ATOM | 11138 | O | PHE | F | 62 | 0.847 | 25.938 | -12.546 | 117.38 | O |
| ATOM | 11139 | CB | PHE | F | 62 | -0.762 | 24.209 | -10.254 | 117.80 | C |
| ATOM | 11140 | CG | PHE | F | 62 | -0.503 | 23.620 | -8.899 | 118.12 | C |
| ATOM | 11141 | CD1 | PHE | F | 62 | 0.767 | 23.192 | -8.550 | 117.73 | C |
| ATOM | 11142 | CD2 | PHE | F | 62 | -1.521 | 23.503 | -7.972 | 113.87 | C |
| ATOM | 11143 | CE1 | PHE | F | 62 | 1.015 | 22.657 | -7.305 | 114.74 | C |
| ATOM | 11144 | CE2 | PHE | F | 62 | -1.279 | 22.972 | -6.723 | 116.22 | C |
| ATOM | 11145 | CZ | PHE | F | 62 | -0.008 | 22.548 | -6.389 | 116.45 | C |
| ATOM | 11146 | H | PHE | F | 62 | -1.767 | 26.316 | -9.432 | 118.46 | H |
| ATOM | 11147 | HA | PHE | F | 62 | 0.715 | 25.614 | -10.108 | 117.42 | H |
| ATOM | 11148 | HB2 | PHE | F | 62 | -1.722 | 24.233 | -10.389 | 121.36 | H |
| ATOM | 11149 | HB3 | PHE | F | 62 | -0.350 | 23.630 | -10.914 | 121.28 | H |
| ATOM | 11150 | HD1 | PHE | F | 62 | 1.461 | 23.267 | -9.165 | 116.64 | H |
| ATOM | 11151 | HD2 | PHE | F | 62 | -2.378 | 23.790 | -8.191 | 117.69 | H |
| ATOM | 11152 | HE1 | PHE | F | 62 | 1.872 | 22.372 | -7.082 | 113.87 | H |
| ATOM | 11153 | HE2 | PHE | F | 62 | -1.972 | 22.897 | -6.108 | 119.47 | H |
| ATOM | 11154 | HZ | PHE | F | 62 | 0.155 | 22.185 | -5.548 | 119.74 | H |
| ATOM | 11155 | N | SER | F | 63 | -1.332 | 26.448 | -12.416 | 115.98 | N |
| ATOM | 11156 | CA | SER | F | 63 | -1.421 | 26.766 | -13.841 | 118.60 | C |
| ATOM | 11157 | C | SER | F | 63 | -0.623 | 28.019 | -14.201 | 116.33 | C |

TABLE 5-continued

Atomic Coordinates for OMCP-NKG2D (4PDC).

| | | | | | | | | | |
|---|---|---|---|---|---|---|---|---|---|
| ATOM | 11158 | O | SER | F | 63 | -0.291 | 28.231 | -15.362 | O |
| ATOM | 11159 | CB | SER | F | 63 | -2.885 | 26.932 | -14.267 | C |
| ATOM | 11160 | OG | SER | F | 63 | -3.490 | 28.031 | -13.617 | O |
| ATOM | 11161 | H | SER | F | 63 | -2.062 | 26.565 | -11.977 | H |
| ATOM | 11162 | HA | SER | F | 63 | -1.050 | 26.026 | -14.347 | H |
| ATOM | 11163 | HB2 | SER | F | 63 | -2.918 | 27.076 | -15.225 | H |
| ATOM | 11164 | HB3 | SER | F | 63 | -3.372 | 26.125 | -14.037 | H |
| ATOM | 11165 | HG | SER | F | 63 | -4.290 | 28.105 | -13.863 | H |
| ATOM | 11166 | N | LEU | F | 64 | -0.302 | 28.840 | -13.206 | N |
| ATOM | 11167 | CA | LEU | F | 64 | 0.496 | 30.041 | -13.437 | C |
| ATOM | 11168 | C | LEU | F | 64 | 1.991 | 29.730 | -13.469 | C |
| ATOM | 11169 | O | LEU | F | 64 | 2.785 | 30.540 | -13.943 | O |
| ATOM | 11170 | CB | LEU | F | 64 | 0.224 | 31.088 | -12.353 | C |
| ATOM | 11171 | CG | LEU | F | 64 | -1.059 | 31.911 | -12.474 | C |
| ATOM | 11172 | CD1 | LEU | F | 64 | -1.282 | 32.718 | -11.207 | C |
| ATOM | 11173 | CD2 | LEU | F | 64 | -0.993 | 32.831 | -13.679 | C |
| ATOM | 11174 | H | LEU | F | 64 | -0.534 | 28.724 | -12.386 | H |
| ATOM | 11175 | HA | LEU | F | 64 | 0.250 | 30.424 | -14.293 | H |
| ATOM | 11176 | HB2 | LEU | F | 64 | 0.190 | 30.632 | -11.498 | H |
| ATOM | 11177 | HB3 | LEU | F | 64 | 0.964 | 31.715 | -12.350 | H |
| ATOM | 11178 | HG | LEU | F | 64 | -1.813 | 31.312 | -12.590 | H |
| ATOM | 11179 | HD11 | LEU | F | 64 | -2.099 | 33.233 | -11.301 | H |
| ATOM | 11180 | HD12 | LEU | F | 64 | -1.359 | 32.110 | -10.456 | H |
| ATOM | 11181 | HD13 | LEU | F | 64 | -0.528 | 33.314 | -11.076 | H |
| ATOM | 11182 | HD21 | LEU | F | 64 | -1.817 | 33.340 | -13.732 | H |
| ATOM | 11183 | HD22 | LEU | F | 64 | -0.238 | 33.432 | -13.576 | H |
| ATOM | 11184 | HD23 | LEU | F | 64 | -0.882 | 32.295 | -14.479 | H |
| ATOM | 11185 | N | PHE | F | 65 | 2.371 | 28.568 | -12.946 | N |
| ATOM | 11186 | CA | PHE | F | 65 | 3.784 | 28.206 | -12.848 | C |
| ATOM | 11187 | C | PHE | F | 65 | 4.326 | 27.740 | -14.195 | C |
| ATOM | 11188 | O | PHE | F | 65 | 3.872 | 26.736 | -14.741 | O |
| ATOM | 11189 | CB | PHE | F | 65 | 3.987 | 27.113 | -11.797 | C |
| ATOM | 11190 | CG | PHE | F | 65 | 5.433 | 26.750 | -11.565 | C |
| ATOM | 11191 | CD1 | PHE | F | 65 | 6.370 | 27.728 | -11.278 | C |
| ATOM | 11192 | CD2 | PHE | F | 65 | 5.845 | 25.432 | -11.616 | C |
| ATOM | 11193 | CE1 | PHE | F | 65 | 7.694 | 27.395 | -11.059 | C |
| ATOM | 11194 | CE2 | PHE | F | 65 | 7.169 | 25.093 | -11.392 | C |
| ATOM | 11195 | CZ | PHE | F | 65 | 8.092 | 26.076 | -11.117 | C |
| ATOM | 11196 | H | PHE | F | 65 | 1.833 | 27.972 | -12.641 | H |
| ATOM | 11197 | HA | PHE | F | 65 | 4.292 | 28.985 | -12.573 | H |
| ATOM | 11198 | HB2 | PHE | F | 65 | 3.619 | 27.419 | -10.954 | H |
| ATOM | 11199 | HB3 | PHE | F | 65 | 3.523 | 26.312 | -12.087 | H |
| ATOM | 11200 | HD1 | PHE | F | 65 | 6.108 | 28.619 | -11.239 | H |
| ATOM | 11201 | HD2 | PHE | F | 65 | 5.225 | 24.764 | -11.803 | H |
| ATOM | 11202 | HE1 | PHE | F | 65 | 8.316 | 28.061 | -10.870 | H |
| ATOM | 11203 | HE2 | PHE | F | 65 | 7.436 | 24.202 | -11.434 | H |
| ATOM | 11204 | HZ | PHE | F | 65 | 8.982 | 25.851 | -10.969 | H |
| ATOM | 11205 | N | ARG | F | 66 | 5.282 | 28.493 | -14.731 | N |
| ATOM | 11206 | CA | ARG | F | 66 | 5.986 | 28.096 | -15.943 | C |
| ATOM | 11207 | C | ARG | F | 66 | 7.345 | 27.528 | -15.594 | C |
| ATOM | 11208 | O | ARG | F | 66 | 8.085 | 28.103 | -14.797 | O |

| | |
|---|---|
| 119.99 | O |
| 122.18 | C |
| 124.58 | O |
| 119.18 | H |
| 122.32 | H |
| 126.61 | H |
| 126.61 | H |
| 129.50 | H |
| 115.47 | N |
| 115.54 | C |
| 118.63 | C |
| 113.90 | O |
| 115.69 | C |
| 116.40 | C |
| 117.92 | C |
| 121.55 | C |
| 118.57 | H |
| 118.64 | H |
| 118.83 | H |
| 118.83 | H |
| 119.68 | H |
| 121.51 | H |
| 121.51 | H |
| 121.51 | H |
| 125.87 | H |
| 125.87 | H |
| 125.87 | H |
| 114.47 | N |
| 114.00 | C |
| 119.33 | C |
| 118.05 | O |
| 112.53 | C |
| 113.60 | C |
| 113.02 | C |
| 113.09 | C |
| 115.49 | C |
| 115.62 | C |
| 116.41 | C |
| 117.36 | H |
| 116.80 | H |
| 115.03 | H |
| 115.03 | H |
| 115.62 | H |
| 115.71 | H |
| 118.58 | H |
| 118.74 | H |
| 119.69 | H |
| 115.25 | N |
| 117.61 | C |
| 125.02 | C |
| 125.04 | O |

TABLE 5-continued

Atomic Coordinates for OMCP-NKG2D (4PDC).

| ATOM | 11209 | CB | ARG | F | 66 | 6.142 | 29.273 | -16.894 | 118.04 | C |
|---|---|---|---|---|---|---|---|---|---|---|
| ATOM | 11210 | CG | ARG | F | 66 | 4.896 | 29.554 | -17.694 | 122.17 | C |
| ATOM | 11211 | CD | ARG | F | 66 | 4.516 | 30.995 | -17.574 | 124.66 | C |
| ATOM | 11212 | NE | ARG | F | 66 | 5.588 | 31.875 | -18.023 | 126.85 | N |
| ATOM | 11213 | CZ | ARG | F | 66 | 5.720 | 33.140 | -17.643 | 126.45 | C |
| ATOM | 11214 | NH1 | ARG | F | 66 | 4.850 | 33.681 | -16.797 | 125.82 | N1+ |
| ATOM | 11215 | NH2 | ARG | F | 66 | 6.724 | 33.865 | -18.107 | 129.31 | N |
| ATOM | 11216 | H | ARG | F | 66 | 5.544 | 29.245 | -14.407 | 118.30 | H |
| ATOM | 11217 | HA | ARG | F | 66 | 5.476 | 27.406 | -16.396 | 121.13 | H |
| ATOM | 11218 | HB2 | ARG | F | 66 | 6.352 | 30.068 | -16.379 | 121.65 | H |
| ATOM | 11219 | HB3 | ARG | F | 66 | 6.860 | 29.082 | -17.517 | 121.65 | H |
| ATOM | 11220 | HG2 | ARG | F | 66 | 5.060 | 29.356 | -18.629 | 126.60 | H |
| ATOM | 11221 | HG3 | ARG | F | 66 | 4.165 | 29.014 | -17.356 | 126.60 | H |
| ATOM | 11222 | HD2 | ARG | F | 66 | 3.734 | 31.165 | -18.123 | 129.59 | H |
| ATOM | 11223 | HD3 | ARG | F | 66 | 4.325 | 31.199 | -16.646 | 129.59 | H |
| ATOM | 11224 | HE | ARG | F | 66 | 6.139 | 31.571 | -18.609 | 132.21 | H |
| ATOM | 11225 | HH11 | ARG | F | 66 | 4.195 | 33.211 | -16.495 | 130.99 | H |
| ATOM | 11226 | HH12 | ARG | F | 66 | 4.940 | 34.500 | -16.552 | 130.99 | H |
| ATOM | 11227 | HH21 | ARG | F | 66 | 7.289 | 33.516 | -18.654 | 135.18 | H |
| ATOM | 11228 | HH22 | ARG | F | 66 | 6.814 | 34.684 | -17.861 | 135.18 | H |
| ATOM | 11229 | N | ARG | F | 67 | 7.660 | 26.395 | -16.206 | 121.33 | N |
| ATOM | 11230 | CA | ARG | F | 67 | 8.865 | 25.653 | -15.896 | 125.35 | C |
| ATOM | 11231 | C | ARG | F | 67 | 9.889 | 25.840 | -17.006 | 130.18 | C |
| ATOM | 11232 | O | ARG | F | 67 | 9.701 | 26.664 | -17.904 | 129.69 | O |
| ATOM | 11233 | CB | ARG | F | 67 | 8.526 | 24.172 | -15.705 | 122.56 | C |
| ATOM | 11234 | CG | ARG | F | 67 | 7.327 | 23.950 | -14.797 | 121.84 | C |
| ATOM | 11235 | CD | ARG | F | 67 | 7.287 | 22.543 | -14.225 | 123.91 | C |
| ATOM | 11236 | NE | ARG | F | 67 | 7.381 | 21.509 | -15.253 | 127.20 | N |
| ATOM | 11237 | CZ | ARG | F | 67 | 6.343 | 20.966 | -15.883 | 131.04 | C |
| ATOM | 11238 | NH1 | ARG | F | 67 | 5.103 | 21.355 | -15.613 | 127.45 | N1+ |
| ATOM | 11239 | NH2 | ARG | F | 67 | 6.548 | 20.027 | -16.798 | 129.30 | N |
| ATOM | 11240 | H | ARG | F | 67 | 7.178 | 26.030 | -16.818 | 125.59 | H |
| ATOM | 11241 | HA | ARG | F | 67 | 9.246 | 25.989 | -15.069 | 130.42 | H |
| ATOM | 11242 | HB2 | ARG | F | 67 | 8.324 | 23.781 | -16.570 | 127.07 | H |
| ATOM | 11243 | HB3 | ARG | F | 67 | 9.289 | 23.723 | -15.309 | 127.07 | H |
| ATOM | 11244 | HG2 | ARG | F | 67 | 7.370 | 24.575 | -14.056 | 126.21 | H |
| ATOM | 11245 | HG3 | ARG | F | 67 | 6.513 | 24.092 | -15.306 | 126.21 | H |
| ATOM | 11246 | HD2 | ARG | F | 67 | 8.034 | 22.429 | -13.617 | 128.69 | H |
| ATOM | 11247 | HD3 | ARG | F | 67 | 6.451 | 22.419 | -13.751 | 128.69 | H |
| ATOM | 11248 | HE | ARG | F | 67 | 8.166 | 21.230 | -15.466 | 132.65 | H |
| ATOM | 11249 | HH11 | ARG | F | 67 | 4.962 | 21.962 | -15.021 | 132.94 | H |
| ATOM | 11250 | HH12 | ARG | F | 67 | 4.440 | 20.998 | -16.028 | 132.94 | H |
| ATOM | 11251 | HH21 | ARG | F | 67 | 7.349 | 19.771 | -16.980 | 135.16 | H |
| ATOM | 11252 | HH22 | ARG | F | 67 | 5.880 | 19.676 | -17.211 | 135.16 | H |
| ATOM | 11253 | N | VAL | F | 68 | 10.975 | 25.085 | -16.925 | 132.53 | N |
| ATOM | 11254 | CA | VAL | F | 68 | 11.988 | 25.069 | -17.970 | 134.51 | C |
| ATOM | 11255 | C | VAL | F | 68 | 12.281 | 23.609 | -18.307 | 138.41 | C |
| ATOM | 11256 | O | VAL | F | 68 | 12.207 | 22.750 | -17.429 | 136.57 | O |
| ATOM | 11257 | CB | VAL | F | 68 | 13.276 | 25.800 | -17.529 | 141.03 | C |
| ATOM | 11258 | CG1 | VAL | F | 68 | 13.813 | 25.221 | -16.223 | 139.01 | C |
| ATOM | 11259 | CG2 | VAL | F | 68 | 14.334 | 25.746 | -18.624 | 143.43 | C |

TABLE 5-continued

Atomic Coordinates for OMCP-NKG2D (4PDC).

| | | | | | | | | | |
|---|---|---|---|---|---|---|---|---|---|
| ATOM | 11260 | H | VAL | F | 68 | 11.152 | 24.564 | -16.264 | 139.04 | H |
| ATOM | 11261 | HA | VAL | F | 68 | 11.642 | 25.505 | -18.763 | 141.42 | H |
| ATOM | 11262 | HB | VAL | F | 68 | 13.063 | 26.733 | -17.371 | 149.24 | H |
| ATOM | 11263 | HG11 | VAL | F | 68 | 14.619 | 25.699 | -15.974 | 146.81 | H |
| ATOM | 11264 | HG12 | VAL | F | 68 | 13.140 | 25.323 | -15.532 | 146.81 | H |
| ATOM | 11265 | HG13 | VAL | F | 68 | 14.014 | 24.280 | -16.354 | 146.81 | H |
| ATOM | 11266 | HG21 | VAL | F | 68 | 15.128 | 26.213 | -18.318 | 152.11 | H |
| ATOM | 11267 | HG22 | VAL | F | 68 | 14.547 | 24.819 | -18.811 | 152.11 | H |
| ATOM | 11268 | HG23 | VAL | F | 68 | 13.985 | 26.174 | -19.421 | 152.11 | H |
| ATOM | 11269 | N | PRO | F | 69 | 12.585 | 23.312 | -19.583 | 140.10 | N |
| ATOM | 11270 | CA | PRO | F | 69 | 12.933 | 21.923 | -19.904 | 143.70 | C |
| ATOM | 11271 | C | PRO | F | 69 | 14.276 | 21.526 | -19.307 | 146.21 | C |
| ATOM | 11272 | O | PRO | F | 69 | 15.248 | 22.268 | -19.453 | 149.34 | O |
| ATOM | 11273 | CB | PRO | F | 69 | 12.994 | 21.915 | -21.437 | 142.03 | C |
| ATOM | 11274 | CG | PRO | F | 69 | 12.269 | 23.147 | -21.865 | 144.28 | C |
| ATOM | 11275 | CD | PRO | F | 69 | 12.538 | 24.147 | -20.794 | 137.27 | C |
| ATOM | 11276 | HA | PRO | F | 69 | 12.243 | 21.314 | -19.599 | 152.45 | H |
| ATOM | 11277 | HB2 | PRO | F | 69 | 13.919 | 21.944 | -21.728 | 150.44 | H |
| ATOM | 11278 | HB3 | PRO | F | 69 | 12.552 | 21.122 | -21.777 | 150.44 | H |
| ATOM | 11279 | HG2 | PRO | F | 69 | 12.619 | 23.453 | -22.716 | 153.14 | H |
| ATOM | 11280 | HG3 | PRO | F | 69 | 11.319 | 22.961 | -21.930 | 153.14 | H |
| ATOM | 11281 | HD2 | PRO | F | 69 | 13.392 | 24.582 | -20.941 | 144.72 | H |
| ATOM | 11282 | HD3 | PRO | F | 69 | 11.813 | 24.789 | -20.737 | 144.72 | H |
| ATOM | 11283 | N | THR | F | 70 | 14.325 | 20.373 | -18.647 | 148.67 | N |
| ATOM | 11284 | CA | THR | F | 70 | 15.550 | 19.908 | -18.009 | 160.44 | C |
| ATOM | 11285 | C | THR | F | 70 | 15.727 | 18.407 | -18.178 | 159.62 | C |
| ATOM | 11286 | O | THR | F | 70 | 14.758 | 17.671 | -18.367 | 155.15 | O |
| ATOM | 11287 | CB | THR | F | 70 | 15.565 | 20.240 | -16.507 | 159.77 | C |
| ATOM | 11288 | OG1 | THR | F | 70 | 14.479 | 19.568 | -15.855 | 158.31 | O |
| ATOM | 11289 | CG2 | THR | F | 70 | 15.441 | 21.742 | -16.286 | 162.29 | C |
| ATOM | 11290 | H | THR | F | 70 | 13.657 | 19.840 | -18.554 | 158.41 | H |
| ATOM | 11291 | HA | THR | F | 70 | 16.309 | 20.349 | -18.422 | 172.53 | H |
| ATOM | 11292 | HB | THR | F | 70 | 16.404 | 19.943 | -16.121 | 171.73 | H |
| ATOM | 11293 | HG1 | THR | F | 70 | 14.482 | 19.746 | -15.034 | 169.97 | H |
| ATOM | 11294 | HG21 | THR | F | 70 | 15.451 | 21.939 | -15.336 | 174.75 | H |
| ATOM | 11295 | HG22 | THR | F | 70 | 16.182 | 22.201 | -16.711 | 174.75 | H |
| ATOM | 11296 | HG23 | THR | F | 70 | 14.609 | 22.065 | -16.666 | 174.75 | H |
| ATOM | 11297 | N | SER | F | 71 | 16.978 | 17.966 | -18.107 | 161.53 | N |
| ATOM | 11298 | CA | SER | F | 71 | 17.303 | 16.549 | -18.178 | 166.52 | C |
| ATOM | 11299 | C | SER | F | 71 | 16.917 | 15.841 | -16.883 | 161.49 | C |
| ATOM | 11300 | O | SER | F | 71 | 16.835 | 14.613 | -16.840 | 159.94 | O |
| ATOM | 11301 | CB | SER | F | 71 | 18.795 | 16.361 | -18.457 | 170.57 | C |
| ATOM | 11302 | OG | SER | F | 71 | 19.580 | 17.021 | -17.479 | 174.17 | O |
| ATOM | 11303 | H | SER | F | 71 | 17.665 | 18.476 | -18.016 | 173.84 | H |
| ATOM | 11304 | HA | SER | F | 71 | 16.805 | 16.144 | -18.905 | 179.82 | H |
| ATOM | 11305 | HB2 | SER | F | 71 | 19.002 | 15.414 | -18.441 | 184.68 | H |
| ATOM | 11306 | HB3 | SER | F | 71 | 19.002 | 16.731 | -19.330 | 184.68 | H |
| ATOM | 11307 | HG | SER | F | 71 | 20.396 | 16.911 | -17.642 | 189.01 | H |
| ATOM | 11308 | N | THR | F | 72 | 16.682 | 16.626 | -15.833 | 162.01 | N |
| ATOM | 11309 | CA | THR | F | 72 | 16.339 | 16.091 | -14.517 | 154.74 | C |
| ATOM | 11310 | C | THR | F | 72 | 15.134 | 15.150 | -14.598 | 149.84 | C |

TABLE 5-continued

Atomic Coordinates for OMCP-NKG2D (4PDC).

| | | | | | | | | | |
|---|---|---|---|---|---|---|---|---|---|
| ATOM | 11311 | O | THR | F | 72 | 14.027 | -14.906 | 153.35 | O |
| ATOM | 11312 | CB | THR | F | 72 | 16.026 | -13.522 | 157.21 | C |
| ATOM | 11313 | OG1 | THR | F | 72 | 17.057 | -13.583 | 159.71 | O |
| ATOM | 11314 | CG2 | THR | F | 72 | 15.929 | -12.103 | 149.20 | C |
| ATOM | 11315 | H | THR | F | 72 | 16.715 | -15.859 | 174.41 | H |
| ATOM | 11316 | HA | THR | F | 72 | 17.093 | -14.173 | 165.69 | H |
| ATOM | 11317 | HB | THR | F | 72 | 15.176 | -13.753 | 168.66 | H |
| ATOM | 11318 | HG1 | THR | F | 72 | 18.840 | -13.042 | 171.65 | H |
| ATOM | 11319 | HG21 | THR | F | 72 | 15.732 | -11.485 | 159.04 | H |
| ATOM | 11320 | HG22 | THR | F | 72 | 15.223 | -12.049 | 159.04 | H |
| ATOM | 11321 | HG23 | THR | F | 72 | 16.769 | -11.848 | 159.04 | H |
| ATOM | 11322 | N | PRO | F | 73 | 15.345 | -14.327 | 147.67 | N |
| ATOM | 11323 | CA | PRO | F | 73 | 14.252 | -14.470 | 142.23 | C |
| ATOM | 11324 | C | PRO | F | 73 | 13.246 | -13.323 | 144.81 | C |
| ATOM | 11325 | O | PRO | F | 73 | 12.230 | -13.393 | 143.07 | O |
| ATOM | 11326 | CB | PRO | F | 73 | 14.984 | -14.503 | 143.10 | C |
| ATOM | 11327 | CG | PRO | F | 73 | 16.189 | -13.668 | 142.60 | C |
| ATOM | 11328 | CD | PRO | F | 73 | 16.597 | -13.901 | 144.19 | C |
| ATOM | 11329 | HA | PRO | F | 73 | 13.788 | -15.311 | 150.67 | H |
| ATOM | 11330 | HB2 | PRO | F | 73 | 14.422 | -14.121 | 151.72 | H |
| ATOM | 11331 | HB3 | PRO | F | 73 | 15.231 | -15.416 | 151.72 | H |
| ATOM | 11332 | HG2 | PRO | F | 73 | 15.967 | -12.734 | 151.12 | H |
| ATOM | 11333 | HG3 | PRO | F | 73 | 16.894 | -13.946 | 151.12 | H |
| ATOM | 11334 | HD2 | PRO | F | 73 | 16.923 | -13.078 | 153.02 | H |
| ATOM | 11335 | HD3 | PRO | F | 73 | 17.261 | -14.607 | 153.02 | H |
| ATOM | 11336 | N | TYR | F | 74 | 13.524 | -12.280 | 143.68 | N |
| ATOM | 11337 | CA | TYR | F | 74 | 12.612 | -11.146 | 136.00 | C |
| ATOM | 11338 | C | TYR | F | 74 | 12.852 | -10.302 | 134.98 | C |
| ATOM | 11339 | O | TYR | F | 74 | 13.985 | -9.931 | 137.75 | O |
| ATOM | 11340 | CB | TYR | F | 74 | 12.740 | -10.271 | 134.00 | C |
| ATOM | 11341 | CG | TYR | F | 74 | 11.779 | -9.107 | 133.28 | C |
| ATOM | 11342 | CD1 | TYR | F | 74 | 10.522 | -9.231 | 137.86 | C |
| ATOM | 11343 | CD2 | TYR | F | 74 | 12.124 | -7.884 | 131.82 | C |
| ATOM | 11344 | CE1 | TYR | F | 74 | 9.637 | -8.173 | 140.32 | C |
| ATOM | 11345 | CE2 | TYR | F | 74 | 11.245 | -6.819 | 128.53 | C |
| ATOM | 11346 | CZ | TYR | F | 74 | 10.003 | -6.969 | 135.36 | C |
| ATOM | 11347 | OH | TYR | F | 74 | 9.120 | -5.915 | 137.99 | O |
| ATOM | 11348 | H | TYR | F | 74 | 14.230 | -12.204 | 152.42 | H |
| ATOM | 11349 | HA | TYR | F | 74 | 11.702 | -11.479 | 143.20 | H |
| ATOM | 11350 | HB2 | TYR | F | 74 | 12.565 | -10.814 | 140.80 | H |
| ATOM | 11351 | HB3 | TYR | F | 74 | 13.641 | -9.913 | 140.80 | H |
| ATOM | 11352 | HD1 | TYR | F | 74 | 12.477 | -10.042 | 145.43 | H |
| ATOM | 11353 | HD2 | TYR | F | 74 | 10.273 | -7.781 | 138.18 | H |
| ATOM | 11354 | HE1 | TYR | F | 74 | 12.961 | -8.272 | 148.39 | H |
| ATOM | 11355 | HE2 | TYR | F | 74 | 8.799 | -6.006 | 134.24 | H |
| ATOM | 11356 | HH | TYR | F | 74 | 9.464 | -5.246 | 145.59 | H |
| ATOM | 11357 | N | GLU | F | 75 | 11.767 | -9.998 | 132.78 | N |
| ATOM | 11358 | CA | GLU | F | 75 | 11.816 | -9.141 | 125.81 | C |
| ATOM | 11359 | C | GLU | F | 75 | 10.590 | -8.235 | 129.12 | C |
| ATOM | 11360 | O | GLU | F | 75 | 9.484 | -8.649 | 130.51 | O |
| ATOM | 11361 | CB | GLU | F | 75 | 11.892 | -9.974 | 135.92 | C |

TABLE 5-continued

Atomic Coordinates for OMCP-NKG2D (4PDC).

| ATOM | 11362 | CG | GLU | F | 75 | 13.193 | 18.358 | -10.729 | 138.70 | C |
|------|-------|------|-----|---|----|--------|--------|---------|--------|----|
| ATOM | 11363 | CD | GLU | F | 75 | 13.265 | 19.711 | -11.411 | 141.84 | C |
| ATOM | 11364 | OE1 | GLU | F | 75 | 12.460 | 19.955 | -12.333 | 139.49 | O |
| ATOM | 11365 | OE2 | GLU | F | 75 | 14.120 | 20.535 | -11.018 | 143.44 | O1- |
| ATOM | 11366 | H | GLU | F | 75 | 10.977 | 15.524 | -10.282 | 139.33 | H |
| ATOM | 11367 | HA | GLU | F | 75 | 12.607 | 16.843 | -8.581 | 130.97 | H |
| ATOM | 11368 | HB2 | GLU | F | 75 | 11.174 | 18.154 | -10.626 | 143.10 | H |
| ATOM | 11369 | HB3 | GLU | F | 75 | 11.781 | 18.928 | -9.383 | 143.10 | H |
| ATOM | 11370 | HG2 | GLU | F | 75 | 13.934 | 18.294 | -10.107 | 146.44 | H |
| ATOM | 11371 | HG3 | GLU | F | 75 | 13.269 | 17.672 | -11.411 | 146.44 | H |
| ATOM | 11372 | N | ASP | F | 76 | 10.798 | 17.370 | -6.998 | 127.11 | N |
| ATOM | 11373 | CA | ASP | F | 76 | 9.716 | 17.527 | -6.037 | 125.30 | C |
| ATOM | 11374 | C | ASP | F | 76 | 9.802 | 18.922 | -5.426 | 118.73 | C |
| ATOM | 11375 | O | ASP | F | 76 | 10.778 | 19.253 | -4.754 | 119.05 | O |
| ATOM | 11376 | CB | ASP | F | 76 | 9.793 | 16.447 | -4.956 | 125.98 | C |
| ATOM | 11377 | CG | ASP | F | 76 | 8.511 | 16.323 | -4.158 | 133.41 | C |
| ATOM | 11378 | OD1 | ASP | F | 76 | 7.419 | 16.365 | -4.766 | 128.50 | O |
| ATOM | 11379 | OD2 | ASP | F | 76 | 8.596 | 16.176 | -2.919 | 144.45 | O1- |
| ATOM | 11380 | H | ASP | F | 76 | 11.571 | 17.585 | -6.687 | 132.53 | H |
| ATOM | 11381 | HA | ASP | F | 76 | 8.864 | 17.444 | -6.493 | 130.36 | H |
| ATOM | 11382 | HB2 | ASP | F | 76 | 9.969 | 15.591 | -5.377 | 131.18 | H |
| ATOM | 11383 | HB3 | ASP | F | 76 | 10.509 | 16.667 | -4.340 | 131.18 | H |
| ATOM | 11384 | N | LEU | F | 77 | 8.786 | 19.738 | -5.689 | 115.80 | N |
| ATOM | 11385 | CA | LEU | F | 77 | 8.767 | 21.135 | -5.256 | 115.34 | C |
| ATOM | 11386 | C | LEU | F | 77 | 7.693 | 21.357 | -4.206 | 119.57 | C |
| ATOM | 11387 | O | LEU | F | 77 | 6.536 | 20.990 | -4.414 | 116.25 | O |
| ATOM | 11388 | CB | LEU | F | 77 | 8.520 | 22.055 | -6.447 | 113.25 | C |
| ATOM | 11389 | CG | LEU | F | 77 | 9.510 | 21.914 | -7.604 | 118.29 | C |
| ATOM | 11390 | CD1 | LEU | F | 77 | 8.906 | 22.436 | -8.889 | 124.51 | C |
| ATOM | 11391 | CD2 | LEU | F | 77 | 10.790 | 22.653 | -7.281 | 121.55 | C |
| ATOM | 11392 | H | LEU | F | 77 | 8.083 | 19.504 | -6.125 | 118.96 | H |
| ATOM | 11393 | HA | LEU | F | 77 | 9.626 | 21.362 | -4.868 | 118.41 | H |
| ATOM | 11394 | HB2 | LEU | F | 77 | 7.635 | 21.872 | -6.798 | 115.90 | H |
| ATOM | 11395 | HB3 | LEU | F | 77 | 8.562 | 22.974 | -6.138 | 115.90 | H |
| ATOM | 11396 | HG | LEU | F | 77 | 9.724 | 20.976 | -7.728 | 121.95 | H |
| ATOM | 11397 | HD11 | LEU | F | 77 | 9.553 | 22.336 | -9.605 | 129.41 | H |
| ATOM | 11398 | HD12 | LEU | F | 77 | 8.106 | 21.927 | -9.092 | 129.41 | H |
| ATOM | 11399 | HD13 | LEU | F | 77 | 8.682 | 23.373 | -8.775 | 129.41 | H |
| ATOM | 11400 | HD21 | LEU | F | 77 | 11.407 | 22.554 | -8.024 | 125.86 | H |
| ATOM | 11401 | HD22 | LEU | F | 77 | 10.587 | 23.591 | -7.143 | 125.86 | H |
| ATOM | 11402 | HD23 | LEU | F | 77 | 11.178 | 22.276 | -6.476 | 125.86 | H |
| ATOM | 11403 | N | THR | F | 78 | 8.072 | 21.965 | -3.086 | 113.26 | N |
| ATOM | 11404 | CA | THR | F | 78 | 7.124 | 22.221 | -2.009 | 115.50 | C |
| ATOM | 11405 | C | THR | F | 78 | 7.129 | 23.689 | -1.608 | 115.27 | C |
| ATOM | 11406 | O | THR | F | 78 | 8.182 | 24.310 | -1.481 | 115.80 | O |
| ATOM | 11407 | CB | THR | F | 78 | 7.432 | 21.361 | -0.771 | 115.66 | C |
| ATOM | 11408 | OG1 | THR | F | 78 | 7.512 | 19.982 | -1.150 | 121.65 | O |
| ATOM | 11409 | CG2 | THR | F | 78 | 6.354 | 21.526 | 0.287 | 119.77 | C |
| ATOM | 11410 | H | THR | F | 78 | 8.872 | 22.239 | -2.925 | 115.91 | H |
| ATOM | 11411 | HA | THR | F | 78 | 6.231 | 21.997 | -2.315 | 118.60 | H |
| ATOM | 11412 | HB | THR | F | 78 | 8.280 | 21.639 | -0.389 | 118.96 | H |

TABLE 5-continued

Atomic Coordinates for OMCP-NKG2D (4PDC).

| ATOM | 11413 | HG1  | THR | F | 78 | 8.122 | 19.875 | -1.718 | 125.98 | H |
| ---- | ----- | ---- | --- | - | -- | ----- | ------ | ------ | ------ | - |
| ATOM | 11414 | HG21 | THR | F | 78 | 6.562 | 20.978 | 1.060  | 123.73 | H |
| ATOM | 11415 | HG22 | THR | F | 78 | 6.299 | 22.454 | 0.563  | 123.73 | H |
| ATOM | 11416 | HG23 | THR | F | 78 | 5.494 | 21.252 | -0.071 | 123.73 | H |
| ATOM | 11417 | N    | TYR | F | 78 | 5.934 | 24.232 | -1.417 | 114.59 | N |
| ATOM | 11418 | CA   | TYR | F | 79 | 5.771 | 25.580 | -1.417 | 114.36 | C |
| ATOM | 11419 | C    | TYR | F | 79 | 4.795 | 25.527 | -0.895 | 113.77 | C |
| ATOM | 11420 | O    | TYR | F | 79 | 3.654 | 25.085 | 0.268  | 111.30 | O |
| ATOM | 11421 | CB   | TYR | F | 79 | 5.286 | 26.537 | 0.126  | 115.36 | C |
| ATOM | 11422 | CG   | TYR | F | 79 | 4.973 | 27.937 | -1.984 | 112.43 | C |
| ATOM | 11423 | CD1  | TYR | F | 79 | 5.935 | 28.706 | -1.494 | 114.93 | C |
| ATOM | 11424 | CD2  | TYR | F | 79 | 3.715 | 28.493 | -0.856 | 115.01 | C |
| ATOM | 11425 | CE1  | TYR | F | 79 | 5.651 | 29.988 | -1.685 | 116.52 | C |
| ATOM | 11426 | CE2  | TYR | F | 79 | 3.424 | 29.768 | -0.417 | 112.69 | C |
| ATOM | 11427 | CZ   | TYR | F | 79 | 4.392 | 30.510 | -1.249 | 114.82 | C |
| ATOM | 11428 | OH   | TYR | F | 79 | 4.099 | 31.784 | -0.614 | 118.09 | O |
| ATOM | 11429 | H    | TYR | F | 79 | 5.191 | 23.833 | -0.184 | 117.51 | H |
| ATOM | 11430 | HA   | TYR | F | 79 | 6.624 | 25.901 | -1.585 | 117.24 | H |
| ATOM | 11431 | HB2  | TYR | F | 79 | 5.975 | 26.611 | -0.564 | 118.43 | H |
| ATOM | 11432 | HB3  | TYR | F | 79 | 4.477 | 26.175 | -2.663 | 118.43 | H |
| ATOM | 11433 | HD1  | TYR | F | 79 | 6.785 | 28.354 | -2.378 | 117.91 | H |
| ATOM | 11434 | HD2  | TYR | F | 79 | 3.056 | 27.995 | -0.721 | 118.01 | H |
| ATOM | 11435 | HE1  | TYR | F | 79 | 6.305 | 30.491 | -2.112 | 119.83 | H |
| ATOM | 11436 | HE2  | TYR | F | 79 | 2.575 | 31.784 | 0.012  | 115.23 | H |
| ATOM | 11437 | HH   | TYR | F | 79 | 4.774 | 32.127 | -1.383 | 121.71 | H |
| ATOM | 11438 | N    | PHE | F | 80 | 5.280 | 25.957 | 0.179  | 114.96 | N |
| ATOM | 11439 | CA   | PHE | F | 80 | 4.514 | 25.945 | 1.426  | 115.84 | C |
| ATOM | 11440 | C    | PHE | F | 80 | 4.224 | 27.377 | 2.660  | 115.28 | C |
| ATOM | 11441 | O    | PHE | F | 80 | 5.138 | 28.191 | 3.071  | 115.47 | O |
| ATOM | 11442 | CB   | PHE | F | 80 | 5.287 | 25.213 | 3.150  | 120.98 | C |
| ATOM | 11443 | CG   | PHE | F | 80 | 4.626 | 25.256 | 3.754  | 122.06 | C |
| ATOM | 11444 | CD1  | PHE | F | 80 | 3.607 | 24.372 | 5.097  | 122.52 | C |
| ATOM | 11445 | CD2  | PHE | F | 80 | 5.030 | 26.173 | 5.411  | 119.44 | C |
| ATOM | 11446 | CE1  | PHE | F | 80 | 3.000 | 24.406 | 6.052  | 124.51 | C |
| ATOM | 11447 | CE2  | PHE | F | 80 | 4.426 | 26.211 | 6.653  | 120.54 | C |
| ATOM | 11448 | CZ   | PHE | F | 80 | 3.412 | 25.328 | 7.295  | 120.28 | C |
| ATOM | 11449 | H    | PHE | F | 80 | 6.075 | 26.269 | 1.522  | 117.96 | H |
| ATOM | 11450 | HA   | PHE | F | 80 | 3.671 | 23.809 | 5.855  | 119.00 | H |
| ATOM | 11451 | HB2  | PHE | F | 80 | 5.381 | 26.833 | 6.854  | 125.17 | H |
| ATOM | 11452 | HB3  | PHE | F | 80 | 6.163 | 25.353 | 7.929  | 125.17 | H |
| ATOM | 11453 | HD1  | PHE | F | 80 | 3.327 | 23.749 | 8.432  | 127.02 | H |
| ATOM | 11454 | HD2  | PHE | F | 80 | 5.714 | 26.771 | 3.295  | 123.33 | H |
| ATOM | 11455 | HE1  | PHE | F | 80 | 2.316 | 23.809 | 3.746  | 129.42 | H |
| ATOM | 11456 | HE2  | PHE | F | 80 | 4.704 | 26.833 | 7.929  | 124.65 | H |
| ATOM | 11457 | HZ   | PHE | F | 80 | 3.005 | 25.353 | 3.500  | 124.33 | H |
| ATOM | 11458 | N    | TYR | F | 81 | 2.952 | 27.686 | 3.842  | 113.47 | N |
| ATOM | 11459 | CA   | TYR | F | 81 | 2.553 | 29.014 | 4.780  | 115.11 | C |
| ATOM | 11460 | C    | TYR | F | 81 | 1.595 | 28.918 | 5.855  | 117.28 | C |
| ATOM | 11461 | O    | TYR | F | 81 | 0.586 | 28.208 | 4.869  | 114.65 | O |
| ATOM | 11462 | CB   | TYR | F | 81 | 1.905 | 29.803 | 2.614  | 112.73 | C |
| ATOM | 11463 | CG   | TYR | F | 81 | 1.506 | 31.189 | 3.044  | 117.49 | C |

TABLE 5-continued

Atomic Coordinates for OMCP-NKG2D (4PDC).

| | | | | | | | | | |
|---|---|---|---|---|---|---|---|---|---|
| ATOM | 11464 | CD1 | TYR | F | 81 | 2.430 | 32.225 | 3.046 | 116.62 | C |
| ATOM | 11465 | CD2 | TYR | F | 81 | 0.213 | 31.459 | 3.469 | 114.65 | C |
| ATOM | 11466 | CE1 | TYR | F | 81 | 2.073 | 33.496 | 3.451 | 119.10 | C |
| ATOM | 11467 | CE2 | TYR | F | 81 | -0.152 | 32.725 | 3.879 | 118.37 | C |
| ATOM | 11468 | CZ | TYR | F | 81 | 0.781 | 33.739 | 3.866 | 119.41 | C |
| ATOM | 11469 | OH | TYR | F | 81 | 0.420 | 35.004 | 4.267 | 120.36 | O |
| ATOM | 11470 | H | TYR | F | 81 | 2.295 | 27.140 | 3.193 | 116.17 | H |
| ATOM | 11471 | HA | TYR | F | 81 | 3.341 | 29.499 | 4.038 | 118.13 | H |
| ATOM | 11472 | HB2 | TYR | F | 81 | 2.535 | 29.884 | 1.881 | 115.28 | H |
| ATOM | 11473 | HB3 | TYR | F | 81 | 1.107 | 29.337 | 2.318 | 115.28 | H |
| ATOM | 11474 | HD1 | TYR | F | 81 | 3.302 | 32.061 | 2.768 | 119.95 | H |
| ATOM | 11475 | HD2 | TYR | F | 81 | -0.418 | 30.776 | 3.480 | 117.58 | H |
| ATOM | 11476 | HE1 | TYR | F | 81 | 2.700 | 34.182 | 3.444 | 122.92 | H |
| ATOM | 11477 | HE2 | TYR | F | 81 | -1.023 | 32.894 | 4.157 | 122.05 | H |
| ATOM | 11478 | HH | TYR | F | 81 | -0.389 | 35.014 | 4.493 | 124.43 | H |
| ATOM | 11479 | N | GLU | F | 82 | 1.910 | 29.648 | 5.991 | 115.52 | N |
| ATOM | 11480 | CA | GLU | F | 82 | 1.145 | 29.563 | 7.224 | 115.50 | C |
| ATOM | 11481 | C | GLU | F | 82 | 0.925 | 30.935 | 7.832 | 119.21 | C |
| ATOM | 11482 | O | GLU | F | 82 | 1.858 | 31.731 | 7.929 | 116.31 | O |
| ATOM | 11483 | CB | GLU | F | 82 | 1.865 | 28.661 | 8.228 | 118.78 | C |
| ATOM | 11484 | CG | GLU | F | 82 | 1.115 | 28.456 | 9.537 | 121.18 | C |
| ATOM | 11485 | CD | GLU | F | 82 | 1.954 | 27.739 | 10.577 | 128.40 | C |
| ATOM | 11486 | OE1 | GLU | F | 82 | 2.678 | 28.425 | 11.330 | 128.83 | O |
| ATOM | 11487 | OE2 | GLU | F | 82 | 1.893 | 26.492 | 10.637 | 129.39 | O1- |
| ATOM | 11488 | H | GLU | F | 82 | 2.567 | 30.202 | 6.022 | 118.63 | H |
| ATOM | 11489 | HA | GLU | F | 82 | 0.278 | 29.173 | 7.034 | 118.59 | H |
| ATOM | 11490 | HB2 | GLU | F | 82 | 1.996 | 27.789 | 7.824 | 122.54 | H |
| ATOM | 11491 | HB3 | GLU | F | 82 | 2.725 | 29.056 | 8.440 | 122.54 | H |
| ATOM | 11492 | HG2 | GLU | F | 82 | 0.864 | 29.321 | 9.897 | 125.42 | H |
| ATOM | 11493 | HG3 | GLU | F | 82 | 0.323 | 27.922 | 9.369 | 125.42 | H |
| ATOM | 11494 | N | CYS | F | 83 | -0.314 | 31.205 | 8.236 | 116.05 | N |
| ATOM | 11495 | CA | CYS | F | 83 | -0.618 | 32.408 | 8.996 | 114.60 | C |
| ATOM | 11496 | C | CYS | F | 83 | -1.077 | 31.989 | 10.386 | 117.53 | C |
| ATOM | 11497 | O | CYS | F | 83 | -1.688 | 30.932 | 10.562 | 119.01 | O |
| ATOM | 11498 | CB | CYS | F | 83 | -1.672 | 33.270 | 8.287 | 121.05 | C |
| ATOM | 11499 | SG | CYS | F | 83 | -3.338 | 32.591 | 8.159 | 120.77 | S |
| ATOM | 11500 | H | CYS | F | 83 | -0.996 | 30.705 | 8.082 | 119.26 | H |
| ATOM | 11501 | HA | CYS | F | 83 | 0.189 | 32.937 | 9.092 | 117.52 | H |
| ATOM | 11502 | HB2 | CYS | F | 83 | -1.742 | 34.112 | 8.763 | 125.26 | H |
| ATOM | 11503 | HB3 | CYS | F | 83 | -1.363 | 33.440 | 7.383 | 125.26 | H |
| ATOM | 11504 | N | ASP | F | 84 | -0.746 | 32.815 | 11.370 | 113.89 | N |
| ATOM | 11505 | CA | ASP | F | 84 | -1.007 | 32.510 | 12.768 | 117.39 | C |
| ATOM | 11506 | C | ASP | F | 84 | -1.702 | 33.696 | 13.425 | 121.87 | C |
| ATOM | 11507 | O | ASP | F | 84 | -1.286 | 34.844 | 13.257 | 119.44 | O |
| ATOM | 11508 | CB | ASP | F | 84 | 0.302 | 32.175 | 13.492 | 119.88 | C |
| ATOM | 11509 | CG | ASP | F | 84 | 0.095 | 31.813 | 14.952 | 129.70 | C |
| ATOM | 11510 | OD1 | ASP | F | 84 | -0.328 | 32.693 | 15.737 | 123.11 | O |
| ATOM | 11511 | OD2 | ASP | F | 84 | -0.378 | 30.651 | 15.318 | 131.40 | O1- |
| ATOM | 11512 | H | ASP | F | 84 | -0.361 | 33.574 | 11.250 | 116.67 | H |
| ATOM | 11513 | HA | ASP | F | 84 | -1.595 | 31.740 | 12.826 | 120.87 | H |
| ATOM | 11514 | HB2 | ASP | F | 84 | 0.721 | 31.418 | 13.053 | 123.86 | H |

TABLE 5-continued

Atomic Coordinates for OMCP-NKG2D (4PDC).

| ATOM | 11515 | HB3 | ASP | F | 84 | 0.889 | 32.946 | 13.456 | 123.86 | H |
|---|---|---|---|---|---|---|---|---|---|---|
| ATOM | 11516 | N | TYR | F | 85 | -2.766 | 33.406 | 14.165 | 117.83 | N |
| ATOM | 11517 | CA | TYR | F | 85 | -3.500 | 34.426 | 14.897 | 120.90 | C |
| ATOM | 11518 | C | TYR | F | 85 | -3.523 | 34.050 | 16.370 | 121.48 | C |
| ATOM | 11519 | O | TYR | F | 85 | -4.217 | 33.118 | 16.776 | 122.77 | O |
| ATOM | 11520 | CB | TYR | F | 85 | -4.918 | 34.575 | 14.344 | 120.94 | C |
| ATOM | 11521 | CG | TYR | F | 85 | -5.590 | 35.873 | 14.726 | 119.46 | C |
| ATOM | 11522 | CD1 | TYR | F | 85 | -5.044 | 37.093 | 14.351 | 123.95 | C |
| ATOM | 11523 | CD2 | TYR | F | 85 | -6.781 | 35.880 | 15.443 | 124.58 | C |
| ATOM | 11524 | CE1 | TYR | F | 85 | -5.652 | 38.284 | 14.690 | 121.09 | C |
| ATOM | 11525 | CE2 | TYR | F | 85 | -7.401 | 37.068 | 15.784 | 125.21 | C |
| ATOM | 11526 | CZ | TYR | F | 85 | -6.831 | 38.266 | 15.402 | 124.37 | C |
| ATOM | 11527 | OH | TYR | F | 85 | -7.436 | 39.454 | 15.734 | 124.90 | O |
| ATOM | 11528 | H | TYR | F | 85 | -3.086 | 32.614 | 14.260 | 121.40 | H |
| ATOM | 11529 | HA | TYR | F | 85 | -3.045 | 35.278 | 14.806 | 125.08 | H |
| ATOM | 11530 | HB2 | TYR | F | 85 | -4.881 | 34.535 | 13.375 | 125.13 | H |
| ATOM | 11531 | HB3 | TYR | F | 85 | -5.463 | 33.848 | 14.683 | 125.13 | H |
| ATOM | 11532 | HD1 | TYR | F | 85 | -4.248 | 37.108 | 13.870 | 128.73 | H |
| ATOM | 11533 | HD2 | TYR | F | 85 | -7.165 | 35.073 | 15.699 | 129.50 | H |
| ATOM | 11534 | HE1 | TYR | F | 85 | -5.272 | 39.093 | 14.434 | 125.31 | H |
| ATOM | 11535 | HE2 | TYR | F | 85 | -8.196 | 37.059 | 16.266 | 130.25 | H |
| ATOM | 11536 | HH | TYR | F | 85 | -8.142 | 39.306 | 16.164 | 129.88 | H |
| ATOM | 11537 | N | THR | F | 86 | -2.739 | 34.777 | 17.158 | 120.16 | N |
| ATOM | 11538 | CA | THR | F | 86 | -2.580 | 34.497 | 18.577 | 123.51 | C |
| ATOM | 11539 | C | THR | F | 86 | -2.558 | 35.808 | 19.355 | 122.77 | C |
| ATOM | 11540 | O | THR | F | 86 | -1.775 | 36.704 | 19.040 | 122.32 | O |
| ATOM | 11541 | CB | THR | F | 86 | -1.280 | 33.708 | 18.847 | 127.41 | C |
| ATOM | 11542 | OG1 | THR | F | 86 | -1.277 | 32.503 | 18.069 | 122.82 | O |
| ATOM | 11543 | CG2 | THR | F | 86 | -1.153 | 33.353 | 20.320 | 124.65 | C |
| ATOM | 11544 | H | THR | F | 86 | -2.280 | 35.452 | 16.887 | 124.20 | H |
| ATOM | 11545 | HA | THR | F | 86 | -3.331 | 33.967 | 18.889 | 128.22 | H |
| ATOM | 11546 | HB | THR | F | 86 | -0.517 | 34.252 | 18.598 | 132.89 | H |
| ATOM | 11547 | HG1 | THR | F | 86 | -1.322 | 32.690 | 17.251 | 127.38 | H |
| ATOM | 11548 | HG21 | THR | F | 86 | -0.333 | 32.858 | 20.472 | 129.58 | H |
| ATOM | 11549 | HG22 | THR | F | 86 | -1.138 | 34.161 | 20.856 | 129.58 | H |
| ATOM | 11550 | HG23 | THR | F | 86 | -1.906 | 32.806 | 20.596 | 129.58 | H |
| ATOM | 11551 | N | ASP | F | 87 | -3.415 | 35.920 | 20.367 | 121.80 | N |
| ATOM | 11552 | CA | ASP | F | 87 | -3.493 | 37.140 | 21.166 | 121.76 | C |
| ATOM | 11553 | C | ASP | F | 87 | -3.709 | 38.351 | 20.255 | 125.94 | C |
| ATOM | 11554 | O | ASP | F | 87 | -3.058 | 39.382 | 20.404 | 124.45 | O |
| ATOM | 11555 | CB | ASP | F | 87 | -2.221 | 37.313 | 22.002 | 124.06 | C |
| ATOM | 11556 | CG | ASP | F | 87 | -2.336 | 38.433 | 23.021 | 125.87 | C |
| ATOM | 11557 | OD1 | ASP | F | 87 | -3.451 | 38.663 | 23.533 | 126.46 | O |
| ATOM | 11558 | OD2 | ASP | F | 87 | -1.309 | 39.082 | 23.305 | 127.96 | O1- |
| ATOM | 11559 | H | ASP | F | 87 | -3.962 | 35.304 | 20.612 | 126.15 | H |
| ATOM | 11560 | HA | ASP | F | 87 | -4.248 | 37.077 | 21.772 | 126.11 | H |
| ATOM | 11561 | HB2 | ASP | F | 87 | -2.043 | 36.489 | 22.480 | 128.88 | H |
| ATOM | 11562 | HB3 | ASP | F | 87 | -1.480 | 37.521 | 21.411 | 128.88 | H |
| ATOM | 11563 | N | ASN | F | 88 | -4.611 | 38.192 | 19.291 | 122.91 | N |
| ATOM | 11564 | CA | ASN | F | 88 | -4.971 | 39.255 | 18.351 | 124.97 | C |
| ATOM | 11565 | C | ASN | F | 88 | -3.803 | 39.741 | 17.489 | 123.23 | C |

TABLE 5-continued

Atomic Coordinates for OMCP-NKG2D (4PDC).

| ATOM | 11566 | O | ASN | F | 88 | -3.880 | 40.805 | 16.877 | 124.47 | O |
|---|---|---|---|---|---|---|---|---|---|---|
| ATOM | 11567 | CB | ASN | F | 88 | -5.580 | 40.433 | 19.112 | 125.84 | C |
| ATOM | 11568 | CG | ASN | F | 88 | -6.788 | 40.027 | 19.930 | 136.58 | C |
| ATOM | 11569 | OD1 | ASN | F | 88 | -6.720 | 39.928 | 21.155 | 144.27 | O |
| ATOM | 11570 | ND2 | ASN | F | 88 | -7.905 | 39.783 | 19.253 | 140.67 | N |
| ATOM | 11571 | H | ASN | F | 88 | -5.040 | 37.459 | 19.157 | 127.49 | H |
| ATOM | 11572 | HA | ASN | F | 88 | -5.651 | 38.913 | 17.750 | 129.96 | H |
| ATOM | 11573 | HB2 | ASN | F | 88 | -4.916 | 40.798 | 19.717 | 131.01 | H |
| ATOM | 11574 | HB3 | ASN | F | 88 | -5.861 | 41.110 | 18.477 | 131.01 | H |
| ATOM | 11575 | HD2 | ASN | F | 88 | -8.619 | 39.549 | 19.671 | 148.81 | H |
| ATOM | 11576 | HD22 | ASN | F | 88 | -7.914 | 39.859 | 18.396 | 148.81 | H |
| ATOM | 11577 | N | LYS | F | 89 | -2.736 | 38.952 | 17.429 | 119.11 | N |
| ATOM | 11578 | CA | LYS | F | 89 | -1.563 | 39.305 | 16.639 | 123.78 | C |
| ATOM | 11579 | C | LYS | F | 89 | -1.421 | 38.394 | 15.422 | 122.87 | C |
| ATOM | 11580 | O | LYS | F | 89 | -1.475 | 37.167 | 15.537 | 122.29 | O |
| ATOM | 11581 | CB | LYS | F | 89 | -0.303 | 39.240 | 17.503 | 126.55 | C |
| ATOM | 11582 | CG | LYS | F | 89 | -0.226 | 40.350 | 18.549 | 132.53 | C |
| ATOM | 11583 | CD | LYS | F | 89 | 0.900 | 40.113 | 19.546 | 146.00 | C |
| ATOM | 11584 | CE | LYS | F | 89 | 1.075 | 41.298 | 20.484 | 156.99 | C |
| ATOM | 11585 | NZ | LYS | F | 89 | -0.193 | 41.656 | 21.180 | 156.00 | N1+ |
| ATOM | 11586 | H | LYS | F | 89 | -2.667 | 38.200 | 17.840 | 122.93 | H |
| ATOM | 11587 | HA | LYS | F | 89 | -1.661 | 40.216 | 16.321 | 128.53 | H |
| ATOM | 11588 | HB2 | LYS | F | 89 | -0.286 | 38.390 | 17.970 | 131.86 | H |
| ATOM | 11589 | HB3 | LYS | F | 89 | -0.475 | 39.318 | 16.930 | 131.86 | H |
| ATOM | 11590 | HG2 | LYS | F | 89 | -0.226 | 40.350 | 18.104 | 139.04 | H |
| ATOM | 11591 | HG3 | LYS | F | 89 | -1.062 | 41.197 | 19.040 | 139.04 | H |
| ATOM | 11592 | HD2 | LYS | F | 89 | 0.695 | 39.330 | 20.080 | 155.20 | H |
| ATOM | 11593 | HD3 | LYS | F | 89 | 1.732 | 39.982 | 19.064 | 155.20 | H |
| ATOM | 11594 | HE2 | LYS | F | 89 | 1.737 | 41.076 | 21.158 | 168.38 | H |
| ATOM | 11595 | HE3 | LYS | F | 89 | 1.366 | 42.069 | 19.972 | 168.38 | H |
| ATOM | 11596 | HZ1 | LYS | F | 89 | -0.817 | 41.870 | 20.583 | 167.20 | H |
| ATOM | 11597 | HZ2 | LYS | F | 89 | -0.479 | 40.965 | 21.663 | 167.20 | H |
| ATOM | 11598 | HZ3 | LYS | F | 89 | -0.058 | 42.350 | 21.720 | 167.20 | H |
| ATOM | 11599 | N | SER | F | 90 | -1.243 | 39.015 | 14.259 | 120.20 | N |
| ATOM | 11600 | CA | SER | F | 90 | -1.063 | 38.297 | 13.002 | 120.82 | C |
| ATOM | 11601 | C | SER | F | 90 | 0.418 | 38.076 | 12.691 | 121.90 | C |
| ATOM | 11602 | O | SER | F | 90 | 1.195 | 39.028 | 12.641 | 119.40 | O |
| ATOM | 11603 | CB | SER | F | 90 | -1.719 | 39.065 | 11.852 | 122.35 | C |
| ATOM | 11604 | OG | SER | F | 90 | -3.108 | 39.241 | 12.070 | 120.82 | O |
| ATOM | 11605 | H | SER | F | 90 | -1.223 | 39.870 | 14.171 | 124.24 | H |
| ATOM | 11606 | HA | SER | F | 90 | -1.490 | 37.428 | 13.068 | 124.98 | H |
| ATOM | 11607 | HB2 | SER | F | 90 | -1.300 | 39.937 | 11.779 | 126.83 | H |
| ATOM | 11608 | HB3 | SER | F | 90 | -1.591 | 38.568 | 11.029 | 126.83 | H |
| ATOM | 11609 | HG | SER | F | 90 | -3.486 | 38.493 | 12.133 | 124.99 | H |
| ATOM | 11610 | N | THR | F | 91 | 0.805 | 36.820 | 12.486 | 114.45 | N |
| ATOM | 11611 | CA | THR | F | 91 | 2.164 | 36.504 | 12.056 | 122.20 | C |
| ATOM | 11612 | C | THR | F | 91 | 2.125 | 35.449 | 10.960 | 121.21 | C |
| ATOM | 11613 | O | THR | F | 91 | 1.136 | 34.728 | 10.808 | 120.13 | O |
| ATOM | 11614 | CB | THR | F | 91 | 3.048 | 36.012 | 13.223 | 122.36 | C |
| ATOM | 11615 | OG1 | THR | F | 91 | 2.488 | 34.825 | 13.793 | 121.83 | O |
| ATOM | 11616 | CG2 | THR | F | 91 | 3.171 | 37.091 | 14.297 | 125.53 | C |

TABLE 5-continued

Atomic Coordinates for OMCP-NKG2D (4PDC).

| ATOM | 11617 | H    | THR | F | 91 | 0.299  | 36.132 | 12.589 | 117.34 | H   |
|------|-------|------|-----|---|----|--------|--------|--------|--------|-----|
| ATOM | 11618 | HA   | THR | F | 91 | 2.571  | 37.304 | 11.688 | 126.63 | H   |
| ATOM | 11619 | HB   | THR | F | 91 | 3.937  | 35.816 | 12.888 | 126.83 | H   |
| ATOM | 11620 | HG1  | THR | F | 91 | 2.443  | 34.221 | 13.212 | 126.19 | H   |
| ATOM | 11621 | HG21 | THR | F | 91 | 3.727  | 36.772 | 15.025 | 130.64 | H   |
| ATOM | 11622 | HG22 | THR | F | 91 | 3.571  | 37.890 | 13.920 | 130.64 | H   |
| ATOM | 11623 | HG23 | THR | F | 91 | 2.293  | 37.312 | 14.646 | 130.64 | H   |
| ATOM | 11624 | N    | PHE | F | 91 | 3.210  | 35.371 | 10.198 | 118.86 | N   |
| ATOM | 11625 | CA   | PHE | F | 92 | 3.250  | 34.542 | 9.005  | 117.69 | C   |
| ATOM | 11626 | C    | PHE | F | 92 | 4.564  | 33.793 | 8.890  | 121.66 | C   |
| ATOM | 11627 | O    | PHE | F | 92 | 5.582  | 34.199 | 9.449  | 117.52 | O   |
| ATOM | 11628 | CB   | PHE | F | 92 | 3.034  | 35.404 | 7.762  | 116.77 | C   |
| ATOM | 11629 | CG   | PHE | F | 92 | 1.834  | 36.297 | 7.852  | 117.86 | C   |
| ATOM | 11630 | CD1  | PHE | F | 92 | 0.583  | 35.834 | 7.480  | 120.94 | C   |
| ATOM | 11631 | CD2  | PHE | F | 92 | 1.955  | 37.598 | 8.316  | 119.25 | C   |
| ATOM | 11632 | CE1  | PHE | F | 92 | -0.527 | 36.654 | 7.567  | 120.21 | C   |
| ATOM | 11633 | CE2  | PHE | F | 92 | 0.852  | 38.419 | 8.407  | 121.07 | C   |
| ATOM | 11634 | CZ   | PHE | F | 92 | -0.390 | 37.951 | 8.033  | 118.70 | C   |
| ATOM | 11635 | H    | PHE | F | 92 | 3.942  | 35.793 | 10.354 | 122.63 | H   |
| ATOM | 11636 | HA   | PHE | F | 92 | 2.533  | 33.890 | 9.047  | 121.23 | H   |
| ATOM | 11637 | HB2  | PHE | F | 92 | 3.814  | 35.967 | 7.632  | 120.13 | H   |
| ATOM | 11638 | HB3  | PHE | F | 92 | 2.915  | 34.823 | 6.994  | 120.13 | H   |
| ATOM | 11639 | HD1  | PHE | F | 92 | 0.489  | 34.963 | 7.168  | 125.13 | H   |
| ATOM | 11640 | HD2  | PHE | F | 92 | 2.790  | 37.919 | 8.571  | 123.10 | H   |
| ATOM | 11641 | HE1  | PHE | F | 92 | -1.363 | 36.335 | 7.314  | 124.25 | H   |
| ATOM | 11642 | HE2  | PHE | F | 92 | 0.946  | 39.290 | 8.719  | 125.28 | H   |
| ATOM | 11643 | HZ   | PHE | F | 92 | -1.134 | 38.506 | 8.092  | 122.43 | H   |
| ATOM | 11644 | N    | ASP | F | 93 | 4.528  | 32.693 | 8.151  | 118.85 | N   |
| ATOM | 11645 | CA   | ASP | F | 93 | 5.714  | 31.893 | 7.904  | 119.59 | C   |
| ATOM | 11646 | C    | ASP | F | 93 | 5.583  | 31.237 | 6.539  | 121.25 | C   |
| ATOM | 11647 | O    | ASP | F | 93 | 4.484  | 30.852 | 6.130  | 115.85 | O   |
| ATOM | 11648 | CB   | ASP | F | 93 | 5.887  | 30.841 | 9.000  | 123.31 | C   |
| ATOM | 11649 | CG   | ASP | F | 93 | 7.131  | 29.997 | 8.810  | 131.07 | C   |
| ATOM | 11650 | OD1  | ASP | F | 93 | 8.143  | 30.533 | 8.309  | 132.52 | O1- |
| ATOM | 11651 | OD2  | ASP | F | 93 | 7.093  | 28.797 | 9.164  | 133.33 | O   |
| ATOM | 11652 | H    | ASP | F | 93 | 3.817  | 32.386 | 7.778  | 122.62 | H   |
| ATOM | 11653 | HA   | ASP | F | 93 | 6.497  | 32.466 | 7.898  | 123.51 | H   |
| ATOM | 11654 | HB2  | ASP | F | 93 | 5.955  | 31.288 | 9.859  | 127.98 | H   |
| ATOM | 11655 | HB3  | ASP | F | 93 | 5.119  | 30.249 | 8.994  | 127.98 | H   |
| ATOM | 11656 | N    | GLN | F | 94 | 6.695  | 31.128 | 5.825  | 116.48 | N   |
| ATOM | 11657 | CA   | GLN | F | 94 | 6.698  | 30.390 | 4.575  | 121.95 | C   |
| ATOM | 11658 | C    | GLN | F | 94 | 8.029  | 29.686 | 4.368  | 120.37 | C   |
| ATOM | 11659 | O    | GLN | F | 94 | 9.078  | 30.195 | 4.754  | 117.80 | O   |
| ATOM | 11660 | CB   | GLN | F | 94 | 6.378  | 31.314 | 3.394  | 116.26 | C   |
| ATOM | 11661 | CG   | GLN | F | 94 | 7.372  | 32.427 | 3.149  | 121.74 | C   |
| ATOM | 11662 | CD   | GLN | F | 94 | 7.010  | 33.272 | 1.933  | 128.61 | C   |
| ATOM | 11663 | OE1  | GLN | F | 94 | 5.878  | 33.231 | 1.442  | 123.71 | O   |
| ATOM | 11664 | NE2  | GLN | F | 94 | 7.976  | 34.041 | 1.440  | 134.71 | N   |
| ATOM | 11665 | H    | GLN | F | 94 | 7.454  | 31.469 | 6.042  | 119.77 | H   |
| ATOM | 11666 | HA   | GLN | F | 94 | 6.007  | 29.709 | 4.613  | 126.34 | H   |
| ATOM | 11667 | HB2  | GLN | F | 94 | 6.337  | 30.777 | 2.587  | 119.52 | H   |

TABLE 5-continued

Atomic Coordinates for OMCP-NKG2D (4PDC).

| ATOM | 11668 | HB3 | GLN | F | 94 | 5.513 | 31.725 | 3.553 | 119.52 | H |
|---|---|---|---|---|---|---|---|---|---|---|
| ATOM | 11669 | HG2 | GLN | F | 94 | 7.393 | 33.009 | 3.925 | 126.09 | H |
| ATOM | 11670 | HG3 | GLN | F | 94 | 8.249 | 32.042 | 2.998 | 126.09 | H |
| ATOM | 11671 | HE21 | GLN | F | 94 | 7.823 | 34.537 | 0.754 | 141.66 | H |
| ATOM | 11672 | HE22 | GLN | F | 94 | 8.754 | 34.042 | 1.806 | 141.66 | H |
| ATOM | 11673 | N | ASP | F | 95 | 7.961 | 28.494 | 3.780 | 119.52 | N |
| ATOM | 11674 | CA | ASP | F | 95 | 9.139 | 27.680 | 3.502 | 119.57 | C |
| ATOM | 11675 | C | ASP | F | 95 | 9.090 | 27.193 | 2.064 | 121.52 | C |
| ATOM | 11676 | O | ASP | F | 95 | 8.010 | 27.017 | 1.496 | 117.71 | O |
| ATOM | 11677 | CB | ASP | F | 95 | 9.219 | 26.471 | 4.443 | 124.75 | C |
| ATOM | 11678 | CG | ASP | F | 95 | 9.408 | 26.861 | 5.898 | 136.23 | C |
| ATOM | 11679 | OD1 | ASP | F | 95 | 10.173 | 27.809 | 6.181 | 135.86 | O |
| ATOM | 11680 | OD2 | ASP | F | 95 | 8.792 | 26.202 | 6.762 | 136.50 | O1- |
| ATOM | 11681 | H | ASP | F | 95 | 7.225 | 28.128 | 3.527 | 123.42 | H |
| ATOM | 11682 | HA | ASP | F | 95 | 9.939 | 28.216 | 3.619 | 123.48 | H |
| ATOM | 11683 | HB2 | ASP | F | 95 | 8.395 | 25.964 | 4.375 | 129.70 | H |
| ATOM | 11684 | HB3 | ASP | F | 95 | 9.971 | 25.918 | 4.182 | 129.70 | H |
| ATOM | 11685 | N | TYR | F | 96 | 10.266 | 26.978 | 1.488 | 117.67 | N |
| ATOM | 11686 | CA | TYR | F | 96 | 10.397 | 26.363 | 0.173 | 117.08 | C |
| ATOM | 11687 | C | TYR | F | 96 | 11.265 | 25.123 | 0.294 | 120.00 | C |
| ATOM | 11688 | O | TYR | F | 96 | 12.344 | 25.188 | 0.880 | 120.02 | O |
| ATOM | 11689 | CB | TYR | F | 96 | 11.028 | 27.329 | -0.828 | 118.79 | C |
| ATOM | 11690 | CG | TYR | F | 96 | 10.392 | 28.694 | -0.885 | 116.85 | C |
| ATOM | 11691 | CD1 | TYR | F | 96 | 10.737 | 29.681 | 0.029 | 118.78 | C |
| ATOM | 11692 | CD2 | TYR | F | 96 | 9.463 | 29.005 | -1.866 | 117.98 | C |
| ATOM | 11693 | CE1 | TYR | F | 96 | 10.164 | 30.932 | -0.025 | 120.39 | C |
| ATOM | 11694 | CE2 | TYR | F | 96 | 8.886 | 30.254 | -1.929 | 116.11 | C |
| ATOM | 11695 | CZ | TYR | F | 96 | 9.239 | 31.214 | -1.006 | 120.26 | C |
| ATOM | 11696 | OH | TYR | F | 96 | 8.666 | 32.462 | -1.069 | 122.81 | O |
| ATOM | 11697 | H | TYR | F | 96 | 11.020 | 27.185 | 1.848 | 121.20 | H |
| ATOM | 11698 | HA | TYR | F | 96 | 9.523 | 26.101 | -0.155 | 120.50 | H |
| ATOM | 11699 | HB2 | TYR | F | 96 | 11.962 | 27.451 | -0.593 | 122.55 | H |
| ATOM | 11700 | HB3 | TYR | F | 96 | 10.965 | 26.940 | -1.715 | 122.55 | H |
| ATOM | 11701 | HD1 | TYR | F | 96 | 11.361 | 29.492 | 0.692 | 122.54 | H |
| ATOM | 11702 | HD2 | TYR | F | 96 | 9.223 | 28.358 | -2.489 | 121.57 | H |
| ATOM | 11703 | HE1 | TYR | F | 96 | 10.401 | 31.583 | 0.595 | 124.47 | H |
| ATOM | 11704 | HE2 | TYR | F | 96 | 8.261 | 30.447 | -2.590 | 119.33 | H |
| ATOM | 11705 | HH | TYR | F | 96 | 8.124 | 32.497 | -1.710 | 127.37 | H |
| ATOM | 11706 | N | LEU | F | 97 | 10.806 | 24.001 | -0.258 | 119.54 | N |
| ATOM | 11707 | CA | LEU | F | 97 | 11.617 | 22.782 | -0.290 | 121.34 | C |
| ATOM | 11708 | C | LEU | F | 97 | 11.827 | 22.285 | -1.721 | 121.46 | C |
| ATOM | 11709 | O | LEU | F | 97 | 10.891 | 22.245 | -2.520 | 115.94 | O |
| ATOM | 11710 | CB | LEU | F | 97 | 10.973 | 21.670 | 0.540 | 121.85 | C |
| ATOM | 11711 | CG | LEU | F | 97 | 10.355 | 22.043 | 1.891 | 124.09 | C |
| ATOM | 11712 | CD1 | LEU | F | 97 | 9.634 | 20.841 | 2.480 | 134.93 | C |
| ATOM | 11713 | CD2 | LEU | F | 97 | 11.413 | 22.551 | 2.856 | 131.03 | C |
| ATOM | 11714 | H | LEU | F | 97 | 10.031 | 23.918 | -0.621 | 123.45 | H |
| ATOM | 11715 | HA | LEU | F | 97 | 12.488 | 22.973 | 0.091 | 125.61 | H |
| ATOM | 11716 | HB2 | LEU | F | 97 | 10.267 | 21.272 | 0.008 | 126.22 | H |
| ATOM | 11717 | HB3 | LEU | F | 97 | 11.652 | 21.000 | 0.717 | 126.22 | H |
| ATOM | 11718 | HG | LEU | F | 97 | 9.704 | 22.749 | 1.758 | 128.91 | H |

TABLE 5-continued

Atomic Coordinates for OMCP-NKG2D (4PDC).

| ATOM | 11719 | HD11 | LEU | F | 97 | 9.248 | 21.092 | 3.334 | 141.92 | H |
|---|---|---|---|---|---|---|---|---|---|---|
| ATOM | 11720 | HD12 | LEU | F | 97 | 8.934 | 20.563 | 1.869 | 141.92 | H |
| ATOM | 11721 | HD13 | LEU | F | 97 | 10.271 | 20.120 | 2.603 | 141.92 | H |
| ATOM | 11722 | HD21 | LEU | F | 97 | 10.989 | 22.777 | 3.699 | 137.24 | H |
| ATOM | 11723 | HD22 | LEU | F | 97 | 12.074 | 21.855 | 2.995 | 137.24 | H |
| ATOM | 11724 | HD23 | LEU | F | 97 | 11.835 | 23.338 | 2.476 | 137.24 | H |
| ATOM | 11725 | N | TYR | F | 98 | 13.066 | 21.914 | -2.030 | 121.23 | N |
| ATOM | 11726 | CA | TYR | F | 98 | 13.397 | 21.259 | -3.293 | 118.28 | C |
| ATOM | 11727 | C | TYR | F | 98 | 13.879 | 19.850 | -2.981 | 122.72 | C |
| ATOM | 11728 | O | TYR | F | 98 | 14.924 | 19.675 | -2.353 | 120.74 | O |
| ATOM | 11729 | CB | TYR | F | 98 | 14.465 | 22.044 | -4.058 | 118.19 | C |
| ATOM | 11730 | CG | TYR | F | 98 | 14.779 | 21.475 | -5.426 | 121.19 | C |
| ATOM | 11731 | CD1 | TYR | F | 98 | 13.950 | 21.729 | -6.511 | 123.23 | C |
| ATOM | 11732 | CD2 | TYR | F | 98 | 15.905 | 20.689 | -5.632 | 123.20 | C |
| ATOM | 11733 | CE1 | TYR | F | 98 | 14.233 | 21.213 | -7.764 | 129.19 | C |
| ATOM | 11734 | CE2 | TYR | F | 98 | 16.196 | 20.170 | -6.879 | 124.25 | C |
| ATOM | 11735 | CZ | TYR | F | 98 | 15.357 | 20.434 | -7.941 | 127.82 | C |
| ATOM | 11736 | OH | TYR | F | 98 | 15.644 | 19.918 | -9.183 | 133.31 | O |
| ATOM | 11737 | H | TYR | F | 98 | 13.744 | 22.032 | -1.515 | 125.47 | H |
| ATOM | 11738 | HA | TYR | F | 98 | 12.603 | 21.199 | -3.846 | 121.94 | H |
| ATOM | 11739 | HB2 | TYR | F | 98 | 14.157 | 22.955 | -4.179 | 121.83 | H |
| ATOM | 11740 | HB3 | TYR | F | 98 | 15.286 | 22.041 | -3.541 | 121.83 | H |
| ATOM | 11741 | HD1 | TYR | F | 98 | 13.192 | 22.254 | -6.393 | 127.87 | H |
| ATOM | 11742 | HD2 | TYR | F | 98 | 16.473 | 20.508 | -4.918 | 127.84 | H |
| ATOM | 11743 | HE1 | TYR | F | 98 | 13.668 | 21.391 | -8.482 | 135.03 | H |
| ATOM | 11744 | HE2 | TYR | F | 98 | 16.953 | 19.644 | -7.001 | 129.10 | H |
| ATOM | 11745 | HH | TYR | F | 98 | 15.057 | 20.155 | -9.736 | 139.98 | H |
| ATOM | 11746 | N | ASN | F | 99 | 13.103 | 18.855 | -3.405 | 120.11 | N |
| ATOM | 11747 | CA | ASN | F | 99 | 13.368 | 17.458 | -3.066 | 123.25 | C |
| ATOM | 11748 | C | ASN | F | 99 | 13.517 | 17.267 | -1.558 | 125.58 | C |
| ATOM | 11749 | O | ASN | F | 99 | 14.394 | 16.536 | -1.090 | 121.44 | O |
| ATOM | 11750 | CB | ASN | F | 99 | 14.621 | 16.955 | -3.789 | 122.66 | C |
| ATOM | 11751 | CG | ASN | F | 99 | 14.430 | 16.862 | -5.291 | 124.21 | C |
| ATOM | 11752 | OD1 | ASN | F | 99 | 13.320 | 16.636 | -5.779 | 125.43 | O |
| ATOM | 11753 | ND2 | ASN | F | 99 | 15.517 | 17.028 | -6.034 | 121.89 | N |
| ATOM | 11754 | H | ASN | F | 99 | 12.407 | 18.965 | -3.899 | 124.13 | H |
| ATOM | 11755 | HA | ASN | F | 99 | 12.619 | 16.918 | -3.360 | 127.90 | H |
| ATOM | 11756 | HB2 | ASN | F | 99 | 15.353 | 17.567 | -3.617 | 127.19 | H |
| ATOM | 11757 | HB3 | ASN | F | 99 | 14.842 | 16.070 | -3.459 | 127.19 | H |
| ATOM | 11758 | HD21 | ASN | F | 99 | 15.462 | 16.985 | -6.891 | 126.27 | H |
| ATOM | 11759 | HD22 | ASN | F | 99 | 16.275 | 17.180 | -5.658 | 126.27 | H |
| ATOM | 11760 | N | GLY | F | 100 | 12.658 | 17.940 | -0.799 | 120.75 | N |
| ATOM | 11761 | CA | GLY | F | 100 | 12.618 | 17.775 | 0.642 | 127.43 | C |
| ATOM | 11762 | C | GLY | F | 100 | 13.626 | 18.633 | 1.379 | 125.00 | C |
| ATOM | 11763 | O | GLY | F | 100 | 13.587 | 18.729 | 2.607 | 123.15 | O |
| ATOM | 11764 | H | GLY | F | 100 | 12.084 | 18.504 | -1.103 | 124.90 | H |
| ATOM | 11765 | HA2 | GLY | F | 100 | 11.732 | 18.004 | 0.965 | 127.90 | H |
| ATOM | 11766 | HA3 | GLY | F | 100 | 12.792 | 16.847 | 0.862 | 127.90 | H |
| ATOM | 11767 | N | GLU | F | 101 | 14.529 | 19.255 | 0.628 | 132.92 | N |
| ATOM | 11768 | CA | GLU | F | 101 | 15.572 | 20.100 | 1.201 | 128.99 | C |
| ATOM | 11769 | C | GLU | F | 101 | 15.137 | 21.559 | 1.206 | 126.31 | C |

TABLE 5-continued

Atomic Coordinates for OMCP-NKG2D (4PDC).

| ATOM | 11770 | O   | GLU | F | 101 | 14.827 | 22.123 | 0.158  | 122.95 | O  |
|------|-------|-----|-----|---|-----|--------|--------|--------|--------|----|
| ATOM | 11771 | CB  | GLU | F | 101 | 16.874 | 19.947 | 0.413  | 128.96 | C  |
| ATOM | 11772 | CG  | GLU | F | 101 | 18.114 | 20.440 | 1.148  | 143.62 | C  |
| ATOM | 11773 | CD  | GLU | F | 101 | 18.632 | 19.442 | 2.169  | 155.65 | C  |
| ATOM | 11774 | OE1 | GLU | F | 101 | 18.669 | 18.230 | 1.862  | 148.87 | O  |
| ATOM | 11775 | OE2 | GLU | F | 101 | 19.007 | 19.872 | 3.280  | 157.62 | O1-|
| ATOM | 11776 | H   | GLU | F | 101 | 14.560 | 19.203 | -0.230 | 132.65 | H  |
| ATOM | 11777 | HA  | GLU | F | 101 | 15.737 | 19.828 | 2.117  | 134.79 | H  |
| ATOM | 11778 | HB2 | GLU | F | 101 | 17.006 | 19.008 | 0.209  | 134.75 | H  |
| ATOM | 11779 | HB3 | GLU | F | 101 | 16.799 | 20.453 | -0.411 | 134.75 | H  |
| ATOM | 11780 | HG2 | GLU | F | 101 | 18.819 | 20.603 | 0.503  | 152.34 | H  |
| ATOM | 11781 | HG3 | GLU | F | 101 | 17.897 | 21.262 | 1.616  | 152.34 | H  |
| ATOM | 11782 | N   | GLU | F | 102 | 15.126 | 22.176 | 2.383  | 128.54 | N  |
| ATOM | 11783 | CA  | GLU | F | 102 | 14.689 | 23.561 | 2.500  | 125.54 | C  |
| ATOM | 11784 | C   | GLU | F | 102 | 15.733 | 24.512 | 1.927  | 124.67 | C  |
| ATOM | 11785 | O   | GLU | F | 102 | 15.936 | 24.287 | 2.062  | 121.93 | O  |
| ATOM | 11786 | CB  | GLU | F | 102 | 14.396 | 23.912 | 3.962  | 133.49 | C  |
| ATOM | 11787 | CG  | GLU | F | 102 | 13.833 | 25.312 | 4.156  | 137.89 | C  |
| ATOM | 11788 | CD  | GLU | F | 102 | 13.340 | 25.561 | 5.574  | 147.13 | C  |
| ATOM | 11789 | OE1 | GLU | F | 102 | 13.153 | 26.742 | 5.939  | 146.84 | O  |
| ATOM | 11790 | OE2 | GLU | F | 102 | 13.134 | 24.578 | 6.319  | 151.60 | O1-|
| ATOM | 11791 | H   | GLU | F | 102 | 15.366 | 21.816 | 3.126  | 134.25 | H  |
| ATOM | 11792 | HA  | GLU | F | 102 | 13.869 | 23.677 | 1.995  | 130.65 | H  |
| ATOM | 11793 | HB2 | GLU | F | 102 | 13.749 | 23.281 | 4.312  | 140.19 | H  |
| ATOM | 11794 | HB3 | GLU | F | 102 | 15.221 | 23.852 | 4.469  | 140.19 | H  |
| ATOM | 11795 | HG2 | GLU | F | 102 | 14.527 | 25.961 | 3.962  | 145.47 | H  |
| ATOM | 11796 | HG3 | GLU | F | 102 | 13.084 | 25.437 | 3.553  | 145.47 | H  |
| ATOM | 11797 | N   | TYR | F | 103 | 15.269 | 25.577 | 1.284  | 119.00 | N  |
| ATOM | 11798 | CA  | TYR | F | 103 | 16.175 | 26.558 | 0.700  | 123.12 | C  |
| ATOM | 11799 | C   | TYR | F | 103 | 15.507 | 27.925 | 0.622  | 124.60 | C  |
| ATOM | 11800 | O   | TYR | F | 103 | 14.283 | 28.026 | 0.729  | 118.78 | O  |
| ATOM | 11801 | CB  | TYR | F | 103 | 16.632 | 26.099 | -0.686 | 118.11 | C  |
| ATOM | 11802 | CG  | TYR | F | 103 | 15.564 | 26.151 | -1.759 | 120.57 | C  |
| ATOM | 11803 | CD1 | TYR | F | 103 | 14.489 | 25.272 | -1.743 | 119.73 | C  |
| ATOM | 11804 | CD2 | TYR | F | 103 | 15.647 | 27.066 | -2.802 | 119.76 | C  |
| ATOM | 11805 | CE1 | TYR | F | 103 | 13.516 | 25.314 | -2.731 | 117.89 | C  |
| ATOM | 11806 | CE2 | TYR | F | 103 | 14.681 | 27.117 | -3.790 | 115.45 | C  |
| ATOM | 11807 | CZ  | TYR | F | 103 | 13.618 | 26.236 | -3.751 | 118.31 | C  |
| ATOM | 11808 | OH  | TYR | F | 103 | 12.652 | 26.280 | -4.734 | 117.87 | O  |
| ATOM | 11809 | H   | TYR | F | 103 | 14.435 | 25.755 | 1.172  | 122.80 | H  |
| ATOM | 11810 | HA  | TYR | F | 103 | 16.960 | 26.639 | 1.265  | 127.75 | H  |
| ATOM | 11811 | HB2 | TYR | F | 103 | 17.364 | 26.667 | -0.974 | 121.74 | H  |
| ATOM | 11812 | HB3 | TYR | F | 103 | 16.939 | 25.181 | -0.622 | 121.74 | H  |
| ATOM | 11813 | HD1 | TYR | F | 103 | 14.417 | 24.650 | -1.056 | 123.67 | H  |
| ATOM | 11814 | HD2 | TYR | F | 103 | 16.362 | 27.660 | -2.831 | 123.72 | H  |
| ATOM | 11815 | HE1 | TYR | F | 103 | 12.798 | 24.722 | -2.705 | 121.47 | H  |
| ATOM | 11816 | HE2 | TYR | F | 103 | 14.749 | 27.738 | -3.751 | 118.54 | H  |
| ATOM | 11817 | HH  | TYR | F | 103 | 12.834 | 26.883 | -4.479 | 121.44 | H  |
| ATOM | 11818 | N   | THR | F | 104 | 16.319 | 28.969 | -5.290 | 120.25 | N  |
| ATOM | 11819 | CA  | THR | F | 104 | 15.819 | 30.341 | 0.452  | 119.66 | C  |
| ATOM | 11820 | C   | THR | F | 104 | 16.621 | 31.227 | -0.581 | 124.00 | C  |

TABLE 5-continued

Atomic Coordinates for OMCP-NKG2D (4PDC).

| | | | | | | | | | |
|---|---|---|---|---|---|---|---|---|---|
| ATOM | 11821 | O | THR | F | 104 | 16.243 | 32.373 | -0.830 | 125.47 O |
| ATOM | 11822 | CB | THR | F | 104 | 15.834 | 31.022 | 1.762 | 123.07 C |
| ATOM | 11823 | OG1 | THR | F | 104 | 17.182 | 31.117 | 2.235 | 127.80 O |
| ATOM | 11824 | CG2 | THR | F | 104 | 14.996 | 30.247 | 2.763 | 127.54 C |
| ATOM | 11825 | H | THR | F | 104 | 17.174 | 28.907 | 0.378 | 124.30 H |
| ATOM | 11826 | HA | THR | F | 104 | 14.901 | 30.322 | 0.064 | 123.59 H |
| ATOM | 11827 | HB | THR | F | 104 | 15.461 | 31.914 | 1.682 | 127.69 H |
| ATOM | 11828 | HG1 | THR | F | 104 | 15.017 | 31.487 | 2.989 | 133.36 H |
| ATOM | 11829 | HG21 | THR | F | 104 | 15.017 | 30.689 | 3.626 | 133.05 H |
| ATOM | 11830 | HG22 | THR | F | 104 | 14.077 | 30.196 | 2.457 | 133.05 H |
| ATOM | 11831 | HG23 | THR | F | 104 | 15.345 | 29.347 | 2.861 | 133.05 H |
| ATOM | 11832 | N | VAL | F | 105 | 17.720 | 30.704 | -1.118 | 121.71 N |
| ATOM | 11833 | CA | VAL | F | 105 | 18.623 | 31.506 | -1.936 | 119.03 C |
| ATOM | 11834 | C | VAL | F | 105 | 18.462 | 31.235 | -3.432 | 121.46 C |
| ATOM | 11835 | O | VAL | F | 105 | 18.561 | 30.094 | -3.889 | 120.83 O |
| ATOM | 11836 | CB | VAL | F | 105 | 20.087 | 31.255 | -1.536 | 126.65 C |
| ATOM | 11837 | CG1 | VAL | F | 105 | 21.028 | 32.107 | -2.377 | 128.48 C |
| ATOM | 11838 | CG2 | VAL | F | 105 | 20.282 | 31.546 | -0.051 | 123.67 C |
| ATOM | 11839 | H | VAL | F | 105 | 17.965 | 29.885 | -1.023 | 126.06 H |
| ATOM | 11840 | HA | VAL | F | 105 | 18.430 | 32.445 | -1.784 | 122.83 H |
| ATOM | 11841 | HB | VAL | F | 105 | 20.304 | 30.322 | -1.692 | 131.98 H |
| ATOM | 11842 | HG11 | VAL | F | 105 | 21.942 | 31.930 | -2.105 | 134.18 H |
| ATOM | 11843 | HG12 | VAL | F | 105 | 20.910 | 31.879 | -3.312 | 134.18 H |
| ATOM | 11844 | HG13 | VAL | F | 105 | 20.816 | 33.043 | -2.236 | 134.18 H |
| ATOM | 11845 | HG21 | VAL | F | 105 | 21.028 | 31.382 | 0.183 | 128.41 H |
| ATOM | 11846 | HG22 | VAL | F | 105 | 20.056 | 32.474 | 0.121 | 128.41 H |
| ATOM | 11847 | HG23 | VAL | F | 105 | 19.703 | 30.963 | 0.464 | 128.41 H |
| ATOM | 11848 | N | LYS | F | 106 | 18.229 | 32.302 | -4.187 | 119.36 N |
| ATOM | 11849 | CA | LYS | F | 106 | 18.092 | 32.220 | -5.634 | 129.10 C |
| ATOM | 11850 | C | LYS | F | 106 | 19.465 | 32.283 | -6.295 | 129.24 C |
| ATOM | 11851 | O | LYS | F | 106 | 20.302 | 33.093 | -5.904 | 132.55 O |
| ATOM | 11852 | CB | LYS | F | 106 | 17.203 | 33.358 | -6.144 | 129.53 C |
| ATOM | 11853 | CG | LYS | F | 106 | 17.008 | 33.392 | -7.652 | 135.32 C |
| ATOM | 11854 | CD | LYS | F | 106 | 16.478 | 34.740 | -8.106 | 137.47 C |
| ATOM | 11855 | CE | LYS | F | 106 | 16.168 | 34.747 | -9.600 | 150.78 C |
| ATOM | 11856 | NZ | LYS | F | 106 | 17.386 | 34.542 | -10.437 | 152.11 N1+ |
| ATOM | 11857 | H | LYS | F | 106 | 18.145 | 33.100 | -3.877 | 123.23 H |
| ATOM | 11858 | HA | LYS | F | 106 | 17.676 | 31.377 | -5.871 | 134.92 H |
| ATOM | 11859 | HB2 | LYS | F | 106 | 16.327 | 33.272 | -5.738 | 135.44 H |
| ATOM | 11860 | HB3 | LYS | F | 106 | 17.602 | 34.203 | -5.882 | 135.44 H |
| ATOM | 11861 | HG2 | LYS | F | 106 | 17.859 | 33.236 | -8.090 | 142.38 H |
| ATOM | 11862 | HG3 | LYS | F | 106 | 16.367 | 32.710 | -7.909 | 142.38 H |
| ATOM | 11863 | HD2 | LYS | F | 106 | 15.660 | 34.941 | -7.626 | 144.96 H |
| ATOM | 11864 | HD3 | LYS | F | 106 | 17.145 | 35.422 | -7.932 | 144.96 H |
| ATOM | 11865 | HE2 | LYS | F | 106 | 15.544 | 34.031 | -9.797 | 160.93 H |
| ATOM | 11866 | HE3 | LYS | F | 106 | 15.779 | 35.603 | -9.839 | 160.93 H |
| ATOM | 11867 | HZ1 | LYS | F | 106 | 17.166 | 34.552 | -11.300 | 162.53 H |
| ATOM | 11868 | HZ2 | LYS | F | 106 | 17.975 | 35.191 | -10.281 | 162.53 H |
| ATOM | 11869 | HZ3 | LYS | F | 106 | 17.760 | 33.758 | -10.243 | 162.53 H |
| ATOM | 11870 | N | THR | F | 107 | 19.691 | 31.424 | -7.287 | 131.35 N |
| ATOM | 11871 | CA | THR | F | 107 | 20.912 | 31.469 | -8.090 | 136.12 C |

TABLE 5-continued

Atomic Coordinates for OMCP-NKG2D (4PDC).

| | | | | | | | | |
|---|---|---|---|---|---|---|---|---|
| ATOM | 11872 | C | THR | F | 107 | 20.608 | 32.090 | -9.449 | 143.02 | C |
| ATOM | 11873 | O | THR | F | 107 | 19.463 | 32.429 | -9.740 | 133.93 | O |
| ATOM | 11874 | CB | THR | F | 107 | 21.524 | 30.071 | -8.287 | 139.11 | C |
| ATOM | 11875 | OG1 | THR | F | 107 | 20.604 | 29.231 | -8.994 | 141.98 | O |
| ATOM | 11876 | CG2 | THR | F | 107 | 21.855 | 29.442 | -6.942 | 137.13 | C |
| ATOM | 11877 | H | THR | F | 107 | 19.147 | 30.798 | -7.517 | 137.62 | H |
| ATOM | 11878 | HA | THR | F | 107 | 21.567 | 32.026 | -7.642 | 143.34 | H |
| ATOM | 11879 | HB | THR | F | 107 | 22.345 | 30.149 | -8.797 | 146.93 | H |
| ATOM | 11880 | HG1 | THR | F | 107 | 20.936 | 28.468 | -9.103 | 150.37 | H |
| ATOM | 11881 | HG21 | THR | F | 107 | 22.240 | 28.562 | -7.073 | 144.55 | H |
| ATOM | 11882 | HG22 | THR | F | 107 | 22.491 | 29.997 | -6.464 | 144.55 | H |
| ATOM | 11883 | HG23 | THR | F | 107 | 21.048 | 29.357 | -6.409 | 144.55 | H |
| ATOM | 11884 | N | GLN | F | 108 | 21.632 | 32.231 | -10.284 | 147.01 | N |
| ATOM | 11885 | CA | GLN | F | 108 | 21.497 | 32.983 | -11.527 | 154.07 | C |
| ATOM | 11886 | C | GLN | F | 108 | 20.864 | 32.173 | -12.657 | 153.72 | C |
| ATOM | 11887 | O | GLN | F | 108 | 20.083 | 32.708 | -13.446 | 154.72 | O |
| ATOM | 11888 | CB | GLN | F | 108 | 22.867 | 33.498 | -11.976 | 167.40 | C |
| ATOM | 11889 | CG | GLN | F | 108 | 23.526 | 34.461 | -10.992 | 174.36 | C |
| ATOM | 11890 | CD | GLN | F | 108 | 22.732 | 35.740 | -10.791 | 178.47 | C |
| ATOM | 11891 | OE1 | GLN | F | 108 | 21.891 | 36.101 | -11.615 | 179.85 | O |
| ATOM | 11892 | NE2 | GLN | F | 108 | 22.997 | 36.433 | -9.688 | 178.07 | N |
| ATOM | 11893 | H | GLN | F | 108 | 22.415 | 31.902 | -10.154 | 156.42 | H |
| ATOM | 11894 | HA | GLN | F | 108 | 20.930 | 33.753 | -11.364 | 164.88 | H |
| ATOM | 11895 | HB2 | GLN | F | 108 | 23.462 | 32.741 | -12.091 | 180.88 | H |
| ATOM | 11896 | HB3 | GLN | F | 108 | 22.763 | 33.965 | -12.820 | 180.88 | H |
| ATOM | 11897 | HG2 | GLN | F | 108 | 23.610 | 34.022 | -10.130 | 189.23 | H |
| ATOM | 11898 | HG3 | GLN | F | 108 | 24.403 | 34.703 | -11.327 | 189.23 | H |
| ATOM | 11899 | HE21 | GLN | F | 108 | 22.575 | 37.165 | -9.529 | 193.69 | H |
| ATOM | 11900 | HE22 | GLN | F | 108 | 23.591 | 36.149 | -9.135 | 193.69 | H |
| ATOM | 11901 | N | GLU | F | 109 | 21.200 | 30.890 | -12.737 | 154.38 | N |
| ATOM | 11902 | CA | GLU | F | 109 | 20.771 | 30.063 | -13.861 | 155.52 | C |
| ATOM | 11903 | C | GLU | F | 109 | 19.268 | 29.776 | -13.827 | 149.42 | C |
| ATOM | 11904 | O | GLU | F | 109 | 18.635 | 29.804 | -12.770 | 141.41 | O |
| ATOM | 11905 | CB | GLU | F | 109 | 21.559 | 28.746 | -13.896 | 159.16 | C |
| ATOM | 11906 | CG | GLU | F | 109 | 21.309 | 27.793 | -12.727 | 162.14 | C |
| ATOM | 11907 | CD | GLU | F | 109 | 22.090 | 28.152 | -11.473 | 166.16 | C |
| ATOM | 11908 | OE1 | GLU | F | 109 | 22.681 | 29.252 | -11.421 | 164.71 | O |
| ATOM | 11909 | OE2 | GLU | F | 109 | 22.112 | 27.325 | -10.536 | 167.28 | O1- |
| ATOM | 11910 | H | GLU | F | 109 | 21.676 | 30.474 | -12.154 | 165.26 | H |
| ATOM | 11911 | HA | GLU | F | 109 | 20.960 | 30.540 | -14.685 | 166.62 | H |
| ATOM | 11912 | HB2 | GLU | F | 109 | 21.328 | 28.272 | -14.711 | 170.99 | H |
| ATOM | 11913 | HB3 | GLU | F | 109 | 22.506 | 28.955 | -13.902 | 170.99 | H |
| ATOM | 11914 | HG2 | GLU | F | 109 | 20.365 | 27.812 | -12.505 | 174.57 | H |
| ATOM | 11915 | HG3 | GLU | F | 109 | 21.567 | 26.897 | -12.992 | 174.57 | H |
| ATOM | 11916 | N | ALA | F | 110 | 18.709 | 29.500 | -15.002 | 143.62 | N |
| ATOM | 11917 | CA | ALA | F | 110 | 17.279 | 29.251 | -15.145 | 141.53 | C |
| ATOM | 11918 | C | ALA | F | 110 | 16.936 | 27.807 | -14.800 | 141.29 | C |
| ATOM | 11919 | O | ALA | F | 110 | 17.257 | 26.886 | -15.551 | 139.37 | O |
| ATOM | 11920 | CB | ALA | F | 110 | 16.829 | 29.575 | -16.559 | 142.06 | C |
| ATOM | 11921 | H | ALA | F | 110 | 19.144 | 29.450 | -15.742 | 152.34 | H |
| ATOM | 11922 | HA | ALA | F | 110 | 16.795 | 29.829 | -14.535 | 149.84 | H |

TABLE 5-continued

Atomic Coordinates for OMCP-NKG2D (4PDC).

| | | | | | | | | | |
|---|---|---|---|---|---|---|---|---|---|
| ATOM | 11923 | HB1 | ALA | F | 110 | 15.877 | -16.634 | 29.403 | 150.48 | H |
| ATOM | 11924 | HB2 | ALA | F | 110 | 17.012 | -16.742 | 30.510 | 150.48 | H |
| ATOM | 11925 | HB3 | ALA | F | 110 | 17.317 | -17.182 | 29.014 | 150.48 | H |
| ATOM | 11926 | N | THR | F | 111 | 16.278 | -13.659 | 27.623 | 131.19 | N |
| ATOM | 11927 | CA | THR | F | 111 | 15.901 | -13.185 | 26.300 | 128.12 | C |
| ATOM | 11928 | C | THR | F | 111 | 14.513 | -12.563 | 26.335 | 126.09 | C |
| ATOM | 11929 | O | THR | F | 111 | 14.038 | -12.146 | 27.391 | 123.00 | O |
| ATOM | 11930 | CB | THR | F | 111 | 16.895 | -12.140 | 25.766 | 131.61 | C |
| ATOM | 11931 | OG1 | THR | F | 111 | 16.881 | -10.986 | 26.618 | 123.43 | O |
| ATOM | 11932 | CG2 | THR | F | 111 | 18.309 | -12.718 | 25.704 | 134.93 | C |
| ATOM | 11933 | H | THR | F | 111 | 16.036 | -13.136 | 28.261 | 137.43 | H |
| ATOM | 11934 | HA | THR | F | 111 | 15.885 | -13.933 | 25.683 | 133.75 | H |
| ATOM | 11935 | HB | THR | F | 111 | 16.634 | -11.879 | 24.869 | 137.94 | H |
| ATOM | 11936 | HG1 | THR | F | 111 | 17.422 | -10.411 | 26.332 | 128.12 | H |
| ATOM | 11937 | HG21 | THR | F | 111 | 18.925 | -12.050 | 25.366 | 141.92 | H |
| ATOM | 11938 | HG22 | THR | F | 111 | 18.326 | -13.489 | 25.115 | 141.92 | H |
| ATOM | 11939 | HG23 | THR | F | 111 | 18.594 | -12.992 | 26.590 | 141.92 | H |
| ATOM | 11940 | N | ASN | F | 112 | 13.867 | -12.499 | 25.178 | 121.68 | N |
| ATOM | 11941 | CA | ASN | F | 112 | 12.586 | -11.820 | 25.072 | 122.81 | C |
| ATOM | 11942 | C | ASN | F | 112 | 12.736 | -10.350 | 25.457 | 122.60 | C |
| ATOM | 11943 | O | ASN | F | 112 | 11.832 | -9.758 | 26.046 | 118.34 | O |
| ATOM | 11944 | CB | ASN | F | 112 | 12.023 | -11.945 | 23.655 | 125.23 | C |
| ATOM | 11945 | CG | ASN | F | 112 | 11.577 | -13.359 | 23.326 | 130.83 | C |
| ATOM | 11946 | OD1 | ASN | F | 112 | 11.337 | -14.171 | 24.221 | 129.96 | O |
| ATOM | 11947 | ND2 | ASN | F | 112 | 11.458 | -13.658 | 22.038 | 131.13 | N |
| ATOM | 11948 | H | ASN | F | 112 | 14.149 | -12.841 | 24.441 | 126.01 | H |
| ATOM | 11949 | HA | ASN | F | 112 | 11.956 | -12.230 | 25.685 | 127.37 | H |
| ATOM | 11950 | HB2 | ASN | F | 112 | 12.709 | -11.691 | 23.019 | 130.28 | H |
| ATOM | 11951 | HB3 | ASN | F | 112 | 11.255 | -11.360 | 23.567 | 130.28 | H |
| ATOM | 11952 | HD21 | ASN | F | 112 | 11.209 | -14.446 | 21.801 | 137.36 | H |
| ATOM | 11953 | HD22 | ASN | F | 112 | 11.631 | -13.063 | 21.441 | 137.36 | H |
| ATOM | 11954 | N | LYS | F | 113 | 13.890 | -9.774 | 25.129 | 118.06 | N |
| ATOM | 11955 | CA | LYS | F | 113 | 14.159 | -8.374 | 25.425 | 117.23 | C |
| ATOM | 11956 | C | LYS | F | 113 | 14.117 | -8.124 | 26.924 | 115.57 | C |
| ATOM | 11957 | O | LYS | F | 113 | 13.505 | -7.160 | 27.381 | 120.36 | O |
| ATOM | 11958 | CB | LYS | F | 113 | 15.518 | -7.957 | 24.858 | 122.25 | C |
| ATOM | 11959 | CG | LYS | F | 113 | 15.804 | -6.465 | 24.952 | 119.36 | C |
| ATOM | 11960 | CD | LYS | F | 113 | 17.161 | -6.130 | 24.356 | 125.27 | C |
| ATOM | 11961 | CE | LYS | F | 113 | 17.450 | -4.645 | 24.430 | 123.84 | C |
| ATOM | 11962 | NZ | LYS | F | 113 | 18.808 | -4.317 | 23.913 | 130.60 | N1+ |
| ATOM | 11963 | H | LYS | F | 113 | 14.537 | -10.178 | 24.732 | 121.67 | H |
| ATOM | 11964 | HA | LYS | F | 113 | 13.477 | -7.824 | 25.009 | 120.67 | H |
| ATOM | 11965 | HB2 | LYS | F | 113 | 15.553 | -8.206 | 23.921 | 126.70 | H |
| ATOM | 11966 | HB3 | LYS | F | 113 | 16.215 | -8.422 | 25.346 | 126.70 | H |
| ATOM | 11967 | HG2 | LYS | F | 113 | 15.804 | -6.196 | 25.883 | 123.23 | H |
| ATOM | 11968 | HG3 | LYS | F | 113 | 15.125 | -5.977 | 24.459 | 123.23 | H |
| ATOM | 11969 | HD2 | LYS | F | 113 | 17.177 | -6.397 | 23.424 | 130.32 | H |
| ATOM | 11970 | HD3 | LYS | F | 113 | 17.852 | -6.599 | 24.851 | 130.32 | H |
| ATOM | 11971 | HE2 | LYS | F | 113 | 17.401 | -4.356 | 25.355 | 128.61 | H |
| ATOM | 11972 | HE3 | LYS | F | 113 | 16.798 | -4.166 | 23.895 | 128.61 | H |
| ATOM | 11973 | HZ1 | LYS | F | 113 | 18.878 | -4.568 | 23.062 | 136.72 | H |

TABLE 5-continued

Atomic Coordinates for OMCP-NKG2D (4PDC).

| ATOM | 11974 | HZ2  | LYS | F | 113 | 19.427 | 24.392 | -4.741  | 136.72 | H |
|------|-------|------|-----|---|-----|--------|--------|---------|--------|---|
| ATOM | 11975 | HZ3  | LYS | F | 113 | 18.951 | 23.968 | -3.440  | 136.72 | H |
| ATOM | 11976 | N    | ASN | F | 114 | 14.770 | 27.687 | -8.994  | 115.69 | N |
| ATOM | 11977 | CA   | ASN | F | 114 | 14.793 | 29.140 | -8.867  | 119.32 | C |
| ATOM | 11978 | C    | ASN | F | 114 | 13.446 | 29.792 | -9.159  | 120.12 | C |
| ATOM | 11979 | O    | ASN | F | 114 | 13.054 | 30.750 | -8.496  | 117.64 | O |
| ATOM | 11980 | CB   | ASN | F | 114 | 15.845 | 29.734 | -9.800  | 123.98 | C |
| ATOM | 11981 | CG   | ASN | F | 114 | 17.251 | 29.576 | -9.266  | 126.05 | C |
| ATOM | 11982 | OD1  | ASN | F | 114 | 17.485 | 29.674 | -8.060  | 123.54 | O |
| ATOM | 11983 | ND2  | ASN | F | 114 | 18.198 | 29.334 | -10.163 | 128.63 | N |
| ATOM | 11984 | H    | ASN | F | 114 | 15.208 | 27.387 | -9.670  | 118.83 | H |
| ATOM | 11985 | HA   | ASN | F | 114 | 15.041 | 29.369 | -7.958  | 123.19 | H |
| ATOM | 11986 | HB2  | ASN | F | 114 | 15.798 | 29.283 | -10.658 | 128.78 | H |
| ATOM | 11987 | HB3  | ASN | F | 114 | 15.671 | 30.681 | -9.912  | 128.78 | H |
| ATOM | 11988 | HD21 | ASN | F | 114 | 19.015 | 29.237 | -9.910  | 134.35 | H |
| ATOM | 11989 | HD22 | ASN | F | 114 | 17.996 | 29.275 | -10.997 | 134.35 | H |
| ATOM | 11990 | N    | MET | F | 115 | 12.749 | 29.282 | -10.164 | 118.73 | N |
| ATOM | 11991 | CA   | MET | F | 115 | 11.481 | 29.867 | -10.572 | 122.34 | C |
| ATOM | 11992 | C    | MET | F | 115 | 10.409 | 29.580 | -9.524  | 117.47 | C |
| ATOM | 11993 | O    | MET | F | 115 | 9.539  | 30.411 | -9.270  | 119.13 | O |
| ATOM | 11994 | CB   | MET | F | 115 | 11.063 | 29.327 | -11.943 | 124.76 | C |
| ATOM | 11995 | CG   | MET | F | 115 | 12.071 | 29.623 | -13.060 | 134.49 | C |
| ATOM | 11996 | SD   | MET | F | 115 | 11.705 | 28.781 | -14.614 | 153.25 | S |
| ATOM | 11997 | CE   | MET | F | 115 | 10.474 | 29.881 | -15.303 | 135.96 | C |
| ATOM | 11998 | H    | MET | F | 115 | 12.988 | 28.598 | -10.627 | 122.48 | H |
| ATOM | 11999 | HA   | MET | F | 115 | 11.591 | 30.827 | -10.652 | 126.81 | H |
| ATOM | 12000 | HB2  | MET | F | 115 | 10.962 | 28.365 | -11.883 | 129.71 | H |
| ATOM | 12001 | HB3  | MET | F | 115 | 10.217 | 29.732 | -12.193 | 129.71 | H |
| ATOM | 12002 | HG2  | MET | F | 115 | 12.074 | 30.578 | -13.234 | 141.38 | H |
| ATOM | 12003 | HG3  | MET | F | 115 | 12.952 | 29.340 | -12.769 | 141.38 | H |
| ATOM | 12004 | HE1  | MET | F | 115 | 10.187 | 29.534 | -16.162 | 143.15 | H |
| ATOM | 12005 | HE2  | MET | F | 115 | 9.719  | 29.930 | -14.696 | 143.15 | H |
| ATOM | 12006 | HE3  | MET | F | 115 | 10.866 | 30.762 | -15.416 | 143.15 | H |
| ATOM | 12007 | N    | TRP | F | 116 | 10.477 | 28.397 | -8.921  | 115.95 | N |
| ATOM | 12008 | CA   | TRP | F | 116 | 9.571  | 28.024 | -7.839  | 116.43 | C |
| ATOM | 12009 | C    | TRP | F | 116 | 9.757  | 28.966 | -6.659  | 117.46 | C |
| ATOM | 12010 | O    | TRP | F | 116 | 8.794  | 29.369 | -6.003  | 113.97 | O |
| ATOM | 12011 | CB   | TRP | F | 116 | 9.830  | 26.579 | -7.413  | 117.21 | C |
| ATOM | 12012 | CG   | TRP | F | 116 | 8.910  | 26.053 | -6.352  | 114.30 | C |
| ATOM | 12013 | CD1  | TRP | F | 116 | 9.177  | 25.930 | -5.020  | 116.57 | C |
| ATOM | 12014 | CD2  | TRP | F | 116 | 7.579  | 25.557 | -6.541  | 114.31 | C |
| ATOM | 12015 | NE1  | TRP | F | 116 | 8.094  | 25.392 | -4.366  | 115.96 | N |
| ATOM | 12016 | CE2  | TRP | F | 116 | 7.098  | 25.158 | -5.277  | 114.58 | C |
| ATOM | 12017 | CE3  | TRP | F | 116 | 6.746  | 25.414 | -7.655  | 114.42 | C |
| ATOM | 12018 | CZ2  | TRP | F | 116 | 5.824  | 24.620 | -5.099  | 117.85 | C |
| ATOM | 12019 | CZ3  | TRP | F | 116 | 5.477  | 24.887 | -7.475  | 112.40 | C |
| ATOM | 12020 | CH2  | TRP | F | 116 | 5.031  | 24.492 | -6.209  | 114.26 | C |
| ATOM | 12021 | H    | TRP | F | 116 | 11.046 | 27.785 | -9.124  | 119.15 | H |
| ATOM | 12022 | HA   | TRP | F | 116 | 8.654  | 28.094 | -8.146  | 119.71 | H |
| ATOM | 12023 | HB2  | TRP | F | 116 | 9.735  | 26.007 | -8.191  | 120.66 | H |
| ATOM | 12024 | HB3  | TRP | F | 116 | 10.736 | 26.515 | -7.071  | 120.66 | H |

TABLE 5-continued

Atomic Coordinates for OMCP-NKG2D (4PDC).

| | | | | | | | | | |
|---|---|---|---|---|---|---|---|---|---|
| ATOM | 12025 | HD1 | TRP | F | 116 | 9.977 | 26.174 | -4.613 | H |
| ATOM | 12026 | HE1 | TRP | F | 116 | 8.047 | 25.233 | -3.522 | H |
| ATOM | 12027 | HE3 | TRP | F | 116 | 7.037 | 25.670 | -8.501 | H |
| ATOM | 12028 | HZ2 | TRP | F | 116 | 5.522 | 24.363 | -4.257 | H |
| ATOM | 12029 | HZ3 | TRP | F | 116 | 4.915 | 24.787 | -8.210 | H |
| ATOM | 12030 | HH2 | TRP | F | 116 | 4.174 | 24.144 | -6.117 | H |
| ATOM | 12031 | N | LEU | F | 117 | 11.014 | 29.315 | -6.407 | N |
| ATOM | 12032 | CA | LEU | F | 117 | 11.380 | 30.189 | -5.300 | C |
| ATOM | 12033 | C | LEU | F | 117 | 10.905 | 31.619 | -5.506 | C |
| ATOM | 12034 | O | LEU | F | 117 | 10.428 | 32.268 | -4.571 | O |
| ATOM | 12035 | CB | LEU | F | 117 | 12.897 | 30.180 | -5.108 | C |
| ATOM | 12036 | CG | LEU | F | 117 | 13.448 | 31.119 | -4.034 | C |
| ATOM | 12037 | CD1 | LEU | F | 117 | 12.913 | 30.744 | -2.657 | C |
| ATOM | 12038 | CD2 | LEU | F | 117 | 14.966 | 31.092 | -4.048 | C |
| ATOM | 12039 | H | LEU | F | 117 | 11.687 | 29.052 | -6.874 | H |
| ATOM | 12040 | HA | LEU | F | 117 | 10.973 | 29.853 | -4.486 | H |
| ATOM | 12041 | HB2 | LEU | F | 117 | 13.169 | 29.280 | -4.870 | H |
| ATOM | 12042 | HB3 | LEU | F | 117 | 13.311 | 30.430 | -5.948 | H |
| ATOM | 12043 | HG | LEU | F | 117 | 13.163 | 32.025 | -4.230 | H |
| ATOM | 12044 | HD11 | LEU | F | 117 | 13.279 | 31.355 | -1.999 | H |
| ATOM | 12045 | HD12 | LEU | F | 117 | 11.945 | 30.809 | -2.666 | H |
| ATOM | 12046 | HD13 | LEU | F | 117 | 13.182 | 29.835 | -2.450 | H |
| ATOM | 12047 | HD21 | LEU | F | 117 | 15.298 | 31.692 | -3.362 | H |
| ATOM | 12048 | HD22 | LEU | F | 117 | 15.266 | 30.187 | -3.871 | H |
| ATOM | 12049 | HD23 | LEU | F | 117 | 15.278 | 31.380 | -4.920 | H |
| ATOM | 12050 | N | THR | F | 118 | 11.042 | 32.121 | -6.726 | N |
| ATOM | 12051 | CA | THR | F | 118 | 10.730 | 33.519 | -6.985 | C |
| ATOM | 12052 | C | THR | F | 118 | 9.255 | 33.762 | -7.325 | C |
| ATOM | 12053 | O | THR | F | 118 | 8.828 | 34.914 | -7.373 | O |
| ATOM | 12054 | CB | THR | F | 118 | 11.598 | 34.082 | -8.133 | C |
| ATOM | 12055 | OG1 | THR | F | 118 | 11.412 | 33.302 | -9.320 | O |
| ATOM | 12056 | CG2 | THR | F | 118 | 13.070 | 34.063 | -7.747 | C |
| ATOM | 12057 | H | THR | F | 118 | 11.311 | 31.679 | -7.414 | H |
| ATOM | 12058 | HA | THR | F | 118 | 10.933 | 34.031 | -6.187 | H |
| ATOM | 12059 | HB | THR | F | 118 | 11.341 | 35.000 | -8.309 | H |
| ATOM | 12060 | HG1 | THR | F | 118 | 10.606 | 33.323 | -9.554 | H |
| ATOM | 12061 | HG21 | THR | F | 118 | 13.607 | 34.417 | -8.472 | H |
| ATOM | 12062 | HG22 | THR | F | 118 | 13.211 | 34.605 | -6.955 | H |
| ATOM | 12063 | HG23 | THR | F | 118 | 13.352 | 33.153 | -7.561 | H |
| ATOM | 12064 | N | THR | F | 119 | 8.475 | 32.701 | -7.541 | N |
| ATOM | 12065 | CA | THR | F | 119 | 7.098 | 32.874 | -8.023 | C |
| ATOM | 12066 | C | THR | F | 119 | 6.010 | 32.287 | -7.133 | C |
| ATOM | 12067 | O | THR | F | 119 | 4.835 | 32.608 | -7.309 | O |
| ATOM | 12068 | CB | THR | F | 119 | 6.908 | 32.252 | -9.429 | C |
| ATOM | 12069 | OG1 | THR | F | 119 | 6.994 | 30.823 | -9.354 | O |
| ATOM | 12070 | CG2 | THR | F | 119 | 7.938 | 32.794 | -10.407 | C |
| ATOM | 12071 | H | THR | F | 119 | 8.712 | 31.883 | -7.419 | H |
| ATOM | 12072 | HA | THR | F | 119 | 6.924 | 33.825 | -8.102 | H |
| ATOM | 12073 | HB | THR | F | 119 | 6.029 | 32.495 | -9.760 | H |
| ATOM | 12074 | HG1 | THR | F | 119 | 7.746 | 30.596 | -9.056 | H |
| ATOM | 12075 | HG21 | THR | F | 119 | 7.806 | 32.396 | -11.281 | H |

TABLE 5-continued

Atomic Coordinates for OMCP-NKG2D (4PDC).

| ATOM | 12076 | HG22 | THR | F | 119 | 7.850 | 33.757 | -10.482 | 127.6 | H |
|------|-------|------|-----|---|-----|-------|--------|---------|-------|---|
| ATOM | 12077 | HG23 | THR | F | 119 | 8.833 | 32.582 | -10.096 | 127.16 | H |
| ATOM | 12078 | N | SER | F | 120 | 6.372 | 31.435 | -6.184 | 114.66 | N |
| ATOM | 12079 | CA | SER | F | 120 | 5.353 | 30.736 | -5.405 | 113.72 | C |
| ATOM | 12080 | C | SER | F | 120 | 4.494 | 31.689 | -4.583 | 115.42 | C |
| ATOM | 12081 | O | SER | F | 120 | 3.267 | 31.564 | -4.561 | 114.45 | O |
| ATOM | 12082 | CB | SER | F | 120 | 6.000 | 29.701 | -4.490 | 113.00 | C |
| ATOM | 12083 | OG | SER | F | 120 | 6.308 | 28.529 | -5.215 | 113.36 | O |
| ATOM | 12084 | H | SER | F | 120 | 7.183 | 31.245 | -5.972 | 117.59 | H |
| ATOM | 12085 | HA | SER | F | 120 | 4.766 | 30.264 | -6.016 | 116.46 | H |
| ATOM | 12086 | HB2 | SER | F | 120 | 6.817 | 30.070 | -4.121 | 115.60 | H |
| ATOM | 12087 | HB3 | SER | F | 120 | 5.382 | 29.479 | -3.776 | 115.60 | H |
| ATOM | 12088 | HG | SER | F | 120 | 6.841 | 28.709 | -5.839 | 116.03 | H |
| ATOM | 12089 | N | GLU | F | 121 | 5.127 | 32.640 | -3.906 | 112.33 | N |
| ATOM | 12090 | CA | GLU | F | 121 | 4.374 | 33.607 | -3.114 | 115.40 | C |
| ATOM | 12091 | C | GLU | F | 121 | 3.490 | 34.461 | -4.020 | 115.41 | C |
| ATOM | 12092 | O | GLU | F | 121 | 2.297 | 34.645 | -3.758 | 113.55 | O |
| ATOM | 12093 | CB | GLU | F | 121 | 5.317 | 34.491 | -2.307 | 117.29 | C |
| ATOM | 12094 | CG | GLU | F | 121 | 4.607 | 35.381 | -1.317 | 119.47 | C |
| ATOM | 12095 | CD | GLU | F | 121 | 5.568 | 36.252 | -0.541 | 126.69 | C |
| ATOM | 12096 | OE1 | GLU | F | 121 | 6.760 | 35.884 | -0.447 | 127.63 | O |
| ATOM | 12097 | OE2 | GLU | F | 121 | 5.132 | 37.303 | -0.028 | 131.22 | O1- |
| ATOM | 12098 | H | GLU | F | 121 | 5.980 | 32.748 | -3.888 | 114.80 | H |
| ATOM | 12099 | HA | GLU | F | 121 | 3.801 | 33.131 | -2.493 | 118.48 | H |
| ATOM | 12100 | HB2 | GLU | F | 121 | 5.931 | 33.926 | -1.813 | 120.74 | H |
| ATOM | 12101 | HB3 | GLU | F | 121 | 5.811 | 35.061 | -2.918 | 120.74 | H |
| ATOM | 12102 | HG2 | GLU | F | 121 | 3.992 | 35.960 | -1.794 | 123.37 | H |
| ATOM | 12103 | HG3 | GLU | F | 121 | 4.122 | 34.828 | -0.684 | 123.37 | H |
| ATOM | 12104 | N | PHE | F | 122 | 4.095 | 34.977 | -5.083 | 113.83 | N |
| ATOM | 12105 | CA | PHE | F | 122 | 3.375 | 35.708 | -6.123 | 114.10 | C |
| ATOM | 12106 | C | PHE | F | 122 | 2.122 | 34.964 | -6.586 | 115.86 | C |
| ATOM | 12107 | O | PHE | F | 122 | 1.038 | 35.545 | -6.674 | 114.66 | O |
| ATOM | 12108 | CB | PHE | F | 122 | 4.314 | 35.954 | -7.308 | 115.83 | C |
| ATOM | 12109 | CG | PHE | F | 122 | 3.651 | 36.569 | -8.505 | 117.67 | C |
| ATOM | 12110 | CD1 | PHE | F | 122 | 3.586 | 37.944 | -8.644 | 116.84 | C |
| ATOM | 12111 | CD2 | PHE | F | 122 | 3.124 | 35.770 | -9.510 | 115.73 | C |
| ATOM | 12112 | CE1 | PHE | F | 122 | 2.991 | 38.512 | -9.751 | 119.00 | C |
| ATOM | 12113 | CE2 | PHE | F | 122 | 2.525 | 36.331 | -10.617 | 121.26 | C |
| ATOM | 12114 | CZ | PHE | F | 122 | 2.461 | 37.707 | -10.740 | 121.83 | C |
| ATOM | 12115 | H | PHE | F | 122 | 4.940 | 34.915 | -5.230 | 116.59 | H |
| ATOM | 12116 | HA | PHE | F | 122 | 3.101 | 36.570 | -5.772 | 116.92 | H |
| ATOM | 12117 | HB2 | PHE | F | 122 | 5.023 | 36.552 | -7.024 | 119.00 | H |
| ATOM | 12118 | HB3 | PHE | F | 122 | 4.694 | 35.105 | -7.585 | 119.00 | H |
| ATOM | 12119 | HD1 | PHE | F | 122 | 3.942 | 38.490 | -7.982 | 120.21 | H |
| ATOM | 12120 | HD2 | PHE | F | 122 | 3.166 | 34.845 | -9.430 | 118.87 | H |
| ATOM | 12121 | HE1 | PHE | F | 122 | 2.946 | 39.438 | -9.831 | 122.80 | H |
| ATOM | 12122 | HE2 | PHE | F | 122 | 2.170 | 35.786 | -11.281 | 125.51 | H |
| ATOM | 12123 | HZ | PHE | F | 122 | 2.057 | 38.089 | -11.485 | 126.20 | H |
| ATOM | 12124 | N | ARG | F | 123 | 2.271 | 33.671 | -6.857 | 114.87 | N |
| ATOM | 12125 | CA | ARG | F | 123 | 1.185 | 32.875 | -7.423 | 115.14 | C |
| ATOM | 12126 | C | ARG | F | 123 | 0.102 | 32.529 | -6.394 | 116.12 | C |

TABLE 5-continued

Atomic Coordinates for OMCP-NKG2D (4PDC).

| ATOM | 12127 | O | ARG | F | 123 | -1.047 | 32.276 | -6.759 | 115.25 | O |
|------|-------|-----|-----|---|-----|--------|--------|--------|--------|---|
| ATOM | 12128 | CB | ARG | F | 123 | 1.752 | 31.598 | -8.055 | 117.25 | C |
| ATOM | 12129 | CG | ARG | F | 123 | 2.417 | 31.851 | -9.407 | 115.66 | C |
| ATOM | 12130 | CD | ARG | F | 123 | 2.949 | 30.582 | -10.069 | 116.20 | C |
| ATOM | 12131 | NE | ARG | F | 123 | 4.170 | 30.101 | -9.428 | 117.22 | N |
| ATOM | 12132 | CZ | ARG | F | 123 | 4.237 | 29.081 | -8.574 | 113.04 | C |
| ATOM | 12133 | NH1 | ARG | F | 123 | 3.150 | 28.391 | -8.242 | 111.59 | N1+ |
| ATOM | 12134 | NH2 | ARG | F | 123 | 5.408 | 28.743 | -8.054 | 113.48 | N |
| ATOM | 12135 | H | ARG | F | 123 | 2.996 | 33.228 | -6.721 | 117.85 | H |
| ATOM | 12136 | HA | ARG | F | 123 | 0.763 | 33.388 | -8.129 | 118.17 | H |
| ATOM | 12137 | HB2 | ARG | F | 123 | 2.418 | 31.220 | -7.460 | 120.70 | H |
| ATOM | 12138 | HB3 | ARG | F | 123 | 1.030 | 30.965 | -8.191 | 120.70 | H |
| ATOM | 12139 | HG2 | ARG | F | 123 | 1.767 | 32.250 | -10.006 | 118.79 | H |
| ATOM | 12140 | HG3 | ARG | F | 123 | 3.164 | 32.456 | -9.280 | 118.79 | H |
| ATOM | 12141 | HD2 | ARG | F | 123 | 2.278 | 29.884 | -10.005 | 119.44 | H |
| ATOM | 12142 | HD3 | ARG | F | 123 | 3.149 | 30.769 | -11.000 | 119.44 | H |
| ATOM | 12143 | HE | ARG | F | 123 | 4.904 | 30.508 | -9.617 | 120.67 | H |
| ATOM | 12144 | HH11 | ARG | F | 123 | 2.387 | 28.605 | -8.575 | 113.91 | H |
| ATOM | 12145 | HH12 | ARG | F | 123 | 3.210 | 27.734 | -7.691 | 113.91 | H |
| ATOM | 12146 | HH21 | ARG | F | 123 | 6.116 | 29.182 | -8.266 | 116.17 | H |
| ATOM | 12147 | HH22 | ARG | F | 123 | 5.460 | 28.083 | -7.505 | 116.17 | H |
| ATOM | 12148 | N | LEU | F | 124 | 0.455 | 32.535 | -5.113 | 115.08 | N |
| ATOM | 12149 | CA | LEU | F | 124 | -0.532 | 32.315 | -4.062 | 116.64 | C |
| ATOM | 12150 | C | LEU | F | 124 | -1.329 | 33.584 | -3.789 | 117.66 | C |
| ATOM | 12151 | O | LEU | F | 124 | -2.555 | 33.542 | -3.651 | 114.64 | O |
| ATOM | 12152 | CB | LEU | F | 124 | 0.137 | 31.848 | -2.766 | 112.40 | C |
| ATOM | 12153 | CG | LEU | F | 124 | -0.767 | 31.818 | -1.525 | 115.66 | C |
| ATOM | 12154 | CD1 | LEU | F | 124 | -1.960 | 30.901 | -1.736 | 118.94 | C |
| ATOM | 12155 | CD2 | LEU | F | 124 | 0.001 | 31.410 | -0.273 | 112.65 | C |
| ATOM | 12156 | H | LEU | F | 124 | 1.256 | 32.662 | -4.827 | 118.10 | H |
| ATOM | 12157 | HA | LEU | F | 124 | -1.151 | 31.626 | -4.347 | 119.97 | H |
| ATOM | 12158 | HB2 | LEU | F | 124 | 0.473 | 30.948 | -2.903 | 114.88 | H |
| ATOM | 12159 | HB3 | LEU | F | 124 | 0.877 | 32.443 | -2.572 | 114.88 | H |
| ATOM | 12160 | HG | LEU | F | 124 | -1.112 | 32.712 | -1.376 | 118.80 | H |
| ATOM | 12161 | HD11 | LEU | F | 124 | -2.507 | 30.907 | -0.935 | 122.72 | H |
| ATOM | 12162 | HD12 | LEU | F | 124 | -2.475 | 31.223 | -2.492 | 122.72 | H |
| ATOM | 12163 | HD13 | LEU | F | 124 | -1.639 | 30.003 | -1.912 | 122.72 | H |
| ATOM | 12164 | HD21 | LEU | F | 124 | -0.607 | 31.405 | 0.482 | 115.18 | H |
| ATOM | 12165 | HD22 | LEU | F | 124 | 0.373 | 30.524 | -0.406 | 115.18 | H |
| ATOM | 12166 | HD23 | LEU | F | 124 | -0.628 | 32.049 | -0.120 | 115.18 | H |
| ATOM | 12167 | N | LYS | F | 125 | -1.208 | 34.711 | -3.714 | 116.52 | N |
| ATOM | 12168 | CA | LYS | F | 125 | -1.934 | 35.923 | -3.146 | 113.85 | C |
| ATOM | 12169 | C | LYS | F | 125 | -2.316 | 36.817 | -4.144 | 118.09 | C |
| ATOM | 12170 | O | LYS | F | 125 | -0.117 | 37.935 | -3.802 | 117.06 | O |
| ATOM | 12171 | CB | LYS | F | 125 | 0.491 | 36.732 | -2.443 | 116.06 | C |
| ATOM | 12172 | CG | LYS | F | 125 | 1.351 | 36.018 | -1.252 | 120.08 | C |
| ATOM | 12173 | CD | LYS | F | 125 | 1.664 | 36.960 | -0.420 | 122.60 | C |
| ATOM | 12174 | CE | LYS | F | 125 | 2.510 | 36.362 | 0.940 | 123.37 | C |
| ATOM | 12175 | NZ | LYS | F | 125 | 0.183 | 37.267 | 1.764 | 123.92 | N1+ |
| ATOM | 12176 | H | LYS | F | 125 | -1.854 | 34.801 | -3.985 | 119.83 | H |
| ATOM | 12177 | HA | LYS | F | 125 | -1.854 | 35.662 | -2.471 | 116.62 | H |

TABLE 5-continued

Atomic Coordinates for OMCP-NKG2D (4PDC).

| | | | | | | | | | |
|---|---|---|---|---|---|---|---|---|---|
| ATOM | 12178 | HB2 | LYS | F | 125 | 0.595 | 36.915 | -3.076 | H |
| ATOM | 12179 | HB3 | LYS | F | 125 | -0.499 | 37.566 | -2.127 | H |
| ATOM | 12180 | HG2 | LYS | F | 125 | -0.219 | 35.674 | -0.688 | H |
| ATOM | 12181 | HG3 | LYS | F | 125 | 1.052 | 35.291 | -1.567 | H |
| ATOM | 12182 | HD2 | LYS | F | 125 | 2.188 | 37.123 | -0.881 | H |
| ATOM | 12183 | HD3 | LYS | F | 125 | 0.874 | 37.794 | -0.283 | H |
| ATOM | 12184 | HE2 | LYS | F | 125 | 0.834 | 36.205 | 1.417 | H |
| ATOM | 12185 | HE3 | LYS | F | 125 | 2.142 | 35.527 | 0.818 | H |
| ATOM | 12186 | HZ1 | LYS | F | 125 | 3.282 | 37.423 | 1.348 | H |
| ATOM | 12187 | HZ2 | LYS | F | 125 | 2.090 | 38.041 | 1.894 | H |
| ATOM | 12188 | HZ3 | LYS | F | 125 | 2.678 | 36.891 | 2.553 | H |
| ATOM | 12189 | N | LYS | F | 126 | -2.143 | 36.328 | -5.363 | N |
| ATOM | 12190 | CA | LYS | F | 126 | -2.855 | 37.102 | -6.371 | C |
| ATOM | 12191 | C | LYS | F | 126 | -4.200 | 37.597 | -5.829 | C |
| ATOM | 12192 | O | LYS | F | 126 | -4.500 | 38.788 | -5.906 | O |
| ATOM | 12193 | CB | LYS | F | 126 | -3.057 | 36.270 | -7.637 | C |
| ATOM | 12194 | CG | LYS | F | 126 | -3.569 | 37.060 | -8.822 | C |
| ATOM | 12195 | CD | LYS | F | 126 | -3.293 | 36.319 | -10.120 | C |
| ATOM | 12196 | CE | LYS | F | 126 | -3.981 | 36.970 | -11.302 | C |
| ATOM | 12197 | NZ | LYS | F | 126 | -3.627 | 36.281 | -12.575 | N1+ |
| ATOM | 12198 | H | LYS | F | 126 | -1.883 | 35.553 | -5.630 | H |
| ATOM | 12199 | HA | LYS | F | 126 | -2.323 | 37.879 | -6.605 | H |
| ATOM | 12200 | HB2 | LYS | F | 126 | -2.207 | 35.876 | -7.889 | H |
| ATOM | 12201 | HB3 | LYS | F | 126 | -3.700 | 35.569 | -7.449 | H |
| ATOM | 12202 | HG2 | LYS | F | 126 | -4.528 | 36.270 | -8.738 | H |
| ATOM | 12203 | HG3 | LYS | F | 126 | -3.119 | 37.918 | -8.857 | H |
| ATOM | 12204 | HD2 | LYS | F | 126 | -2.338 | 36.318 | -10.289 | H |
| ATOM | 12205 | HD3 | LYS | F | 126 | -3.620 | 35.409 | -10.043 | H |
| ATOM | 12206 | HE2 | LYS | F | 126 | -4.943 | 36.917 | -11.183 | H |
| ATOM | 12207 | HE3 | LYS | F | 126 | -3.700 | 37.896 | -11.367 | H |
| ATOM | 12208 | HZ1 | LYS | F | 126 | -4.039 | 36.675 | -13.258 | H |
| ATOM | 12209 | HZ2 | LYS | F | 126 | -2.748 | 36.318 | -12.706 | H |
| ATOM | 12210 | HZ3 | LYS | F | 126 | -3.878 | 35.427 | -12.538 | H |
| ATOM | 12211 | N | TRP | F | 127 | -4.983 | 36.690 | -5.245 | N |
| ATOM | 12212 | CA | TRP | F | 127 | -6.284 | 37.040 | -4.663 | C |
| ATOM | 12213 | C | TRP | F | 127 | -6.357 | 36.731 | -3.163 | C |
| ATOM | 12214 | O | TRP | F | 127 | -7.408 | 36.886 | -2.532 | O |
| ATOM | 12215 | CB | TRP | F | 127 | -7.397 | 36.293 | -5.400 | C |
| ATOM | 12216 | CG | TRP | F | 127 | -7.543 | 36.706 | -6.833 | C |
| ATOM | 12217 | CD1 | TRP | F | 127 | -7.053 | 36.059 | -7.931 | C |
| ATOM | 12218 | CD2 | TRP | F | 127 | -8.229 | 37.863 | -7.323 | C |
| ATOM | 12219 | NE1 | TRP | F | 127 | -7.390 | 36.744 | -9.075 | N |
| ATOM | 12220 | CE2 | TRP | F | 127 | -8.114 | 37.854 | -8.729 | C |
| ATOM | 12221 | CE3 | TRP | F | 127 | -8.930 | 38.906 | -6.710 | C |
| ATOM | 12222 | CZ2 | TRP | F | 127 | -8.675 | 38.847 | -9.531 | C |
| ATOM | 12223 | CZ3 | TRP | F | 127 | -9.486 | 39.891 | -7.507 | C |
| ATOM | 12224 | CH2 | TRP | F | 127 | -9.353 | 39.854 | -8.904 | C |
| ATOM | 12225 | H | TRP | F | 127 | -4.783 | 35.856 | -5.172 | H |
| ATOM | 12226 | HA | TRP | F | 127 | -6.434 | 37.991 | -4.779 | H |
| ATOM | 12227 | HB2 | TRP | F | 127 | -7.202 | 35.343 | -5.382 | H |
| ATOM | 12228 | HB3 | TRP | F | 127 | -8.240 | 36.466 | -4.953 | H |

TABLE 5-continued

Atomic Coordinates for OMCP-NKG2D (4PDC).

| ATOM | 12229 | HD1 | TRP | F | 127 | -6.560 | -7.908 | 35.270 | 120.46 | H |
| ATOM | 12230 | HE1 | TRP | F | 127 | -7.183 | -9.877 | 36.511 | 121.10 | H |
| ATOM | 12231 | HE3 | TRP | F | 127 | -9.022 | -5.785 | 38.937 | 123.59 | H |
| ATOM | 12232 | HZ2 | TRP | F | 127 | -8.589 | -10.457 | 38.826 | 123.59 | H |
| ATOM | 12233 | HZ3 | TRP | F | 127 | -9.954 | -7.111 | 40.589 | 120.69 | H |
| ATOM | 12234 | HH2 | TRP | F | 127 | -9.737 | -9.415 | 40.530 | 127.70 | H |
| ATOM | 12235 | N | PHE | F | 128 | -5.230 | -2.599 | 36.311 | 113.38 | N |
| ATOM | 12236 | CA | PHE | F | 128 | -5.188 | -1.243 | 35.772 | 117.23 | C |
| ATOM | 12237 | C | PHE | F | 128 | -3.938 | -0.498 | 36.245 | 116.62 | C |
| ATOM | 12238 | O | PHE | F | 128 | -2.925 | -0.476 | 35.552 | 114.93 | O |
| ATOM | 12239 | CB | PHE | F | 128 | -5.234 | -1.310 | 34.241 | 112.61 | C |
| ATOM | 12240 | CG | PHE | F | 128 | -5.412 | 0.020 | 33.567 | 115.61 | C |
| ATOM | 12241 | CD1 | PHE | F | 128 | -6.504 | 0.818 | 33.855 | 117.23 | C |
| ATOM | 12242 | CD2 | PHE | F | 128 | -4.503 | 0.454 | 32.619 | 113.57 | C |
| ATOM | 12243 | CE1 | PHE | F | 128 | -6.674 | 2.031 | 33.226 | 114.89 | C |
| ATOM | 12244 | CE2 | PHE | F | 128 | -4.668 | 1.669 | 31.985 | 116.18 | C |
| ATOM | 12245 | CZ | PHE | F | 128 | -5.756 | 2.459 | 32.288 | 114.81 | C |
| ATOM | 12246 | H | PHE | F | 128 | -4.463 | -2.987 | 36.329 | 116.05 | H |
| ATOM | 12247 | HA | PHE | F | 128 | -5.967 | -0.753 | 36.079 | 120.67 | H |
| ATOM | 12248 | HB2 | PHE | F | 128 | -5.976 | -1.876 | 33.977 | 115.13 | H |
| ATOM | 12249 | HB3 | PHE | F | 128 | -4.402 | -1.693 | 33.922 | 115.13 | H |
| ATOM | 12250 | HD1 | PHE | F | 128 | -7.126 | 0.536 | 34.486 | 120.67 | H |
| ATOM | 12251 | HD2 | PHE | F | 128 | -3.767 | -0.075 | 32.412 | 116.29 | H |
| ATOM | 12252 | HE1 | PHE | F | 128 | -7.409 | 2.563 | 33.432 | 117.87 | H |
| ATOM | 12253 | HE2 | PHE | F | 128 | -4.047 | 1.954 | 31.355 | 119.41 | H |
| ATOM | 12254 | HZ | PHE | F | 128 | -5.870 | 3.278 | 31.864 | 117.78 | H |
| ATOM | 12255 | N | ASP | F | 129 | -4.011 | 0.108 | 37.426 | 116.80 | N |
| ATOM | 12256 | CA | ASP | F | 129 | -2.863 | 0.828 | 37.972 | 117.78 | C |
| ATOM | 12257 | C | ASP | F | 129 | -2.895 | 2.290 | 37.537 | 119.18 | C |
| ATOM | 12258 | O | ASP | F | 129 | -3.800 | 2.714 | 36.814 | 116.91 | O |
| ATOM | 12259 | CB | ASP | F | 129 | -2.819 | 0.714 | 39.504 | 118.37 | C |
| ATOM | 12260 | CG | ASP | F | 129 | -4.066 | 1.263 | 40.185 | 116.63 | C |
| ATOM | 12261 | OD1 | ASP | F | 129 | -4.707 | 2.181 | 39.642 | 116.14 | O |
| ATOM | 12262 | OD2 | ASP | F | 129 | -4.394 | 0.779 | 41.289 | 116.62 | O1- |
| ATOM | 12263 | H | ASP | F | 129 | -4.708 | 0.119 | 37.928 | 120.16 | H |
| ATOM | 12264 | HA | ASP | F | 129 | -2.050 | 0.432 | 37.621 | 121.34 | H |
| ATOM | 12265 | HB2 | ASP | F | 129 | -2.055 | 1.212 | 39.834 | 122.04 | H |
| ATOM | 12266 | HB3 | ASP | F | 129 | -2.734 | -0.221 | 39.747 | 122.04 | H |
| ATOM | 12267 | N | GLY | F | 130 | -1.900 | 3.052 | 37.976 | 115.15 | N |
| ATOM | 12268 | CA | GLY | F | 130 | -1.783 | 4.450 | 37.608 | 117.82 | C |
| ATOM | 12269 | C | GLY | F | 130 | -2.997 | 5.277 | 37.984 | 116.60 | C |
| ATOM | 12270 | O | GLY | F | 130 | -3.425 | 6.147 | 37.224 | 114.67 | O |
| ATOM | 12271 | H | GLY | F | 130 | -1.273 | 2.775 | 38.496 | 118.18 | H |
| ATOM | 12272 | HA2 | GLY | F | 130 | -1.654 | 4.518 | 36.649 | 121.38 | H |
| ATOM | 12273 | HA3 | GLY | F | 130 | -1.007 | 4.832 | 38.048 | 121.38 | H |
| ATOM | 12274 | N | GLU | F | 131 | -3.560 | 5.010 | 39.156 | 113.72 | N |
| ATOM | 12275 | CA | GLU | F | 131 | -4.732 | 5.751 | 39.598 | 118.76 | C |
| ATOM | 12276 | C | GLU | F | 131 | -5.928 | 5.433 | 38.710 | 116.47 | C |
| ATOM | 12277 | O | GLU | F | 131 | -6.715 | 6.322 | 38.380 | 113.63 | O |
| ATOM | 12278 | CB | GLU | F | 131 | -5.052 | 5.440 | 41.056 | 119.73 | C |
| ATOM | 12279 | CG | GLU | F | 131 | -6.078 | 6.382 | 41.653 | 126.43 | C |

TABLE 5-continued

Atomic Coordinates for OMCP-NKG2D (4PDC).

| ATOM | 12280 | CD | GLU | F | 131 | -6.202 | 43.154 | 6.229 | 127.13 | C |
| --- | --- | --- | --- | --- | --- | --- | --- | --- | --- | --- |
| ATOM | 12281 | OE1 | GLU | F | 131 | -5.568 | 43.715 | 5.309 | 119.31 | O |
| ATOM | 12282 | OE2 | GLU | F | 131 | -6.931 | 43.773 | 7.034 | 131.50 | O1- |
| ATOM | 12283 | H | GLU | F | 131 | -3.285 | 39.709 | 4.412 | 116.47 | H |
| ATOM | 12284 | HA | GLU | F | 131 | -4.550 | 39.527 | 6.702 | 122.52 | H |
| ATOM | 12285 | HB2 | GLU | F | 131 | -4.239 | 41.579 | 5.514 | 123.68 | H |
| ATOM | 12286 | HB3 | GLU | F | 131 | -5.404 | 41.115 | 4.538 | 123.68 | H |
| ATOM | 12287 | HG2 | GLU | F | 131 | -5.816 | 41.260 | 6.196 | 131.71 | H |
| ATOM | 12288 | HG3 | GLU | F | 131 | -6.067 | 41.465 | 7.296 | 131.71 | H |
| ATOM | 12289 | N | ASP | F | 132 | -6.067 | 38.318 | 4.169 | 115.33 | N |
| ATOM | 12290 | CA | ASP | F | 132 | -7.115 | 37.374 | 3.801 | 113.35 | C |
| ATOM | 12291 | C | ASP | F | 132 | -6.949 | 36.086 | 4.596 | 114.58 | C |
| ATOM | 12292 | O | ASP | F | 132 | -7.918 | 35.557 | 5.137 | 115.18 | O |
| ATOM | 12293 | CB | ASP | F | 132 | -7.094 | 37.063 | 2.305 | 115.90 | C |
| ATOM | 12294 | CG | ASP | F | 132 | -7.322 | 38.286 | 1.444 | 117.33 | C |
| ATOM | 12295 | OD1 | ASP | F | 132 | -8.013 | 39.232 | 1.887 | 116.63 | O |
| ATOM | 12296 | OD2 | ASP | F | 132 | -6.809 | 38.292 | 0.308 | 118.06 | O1- |
| ATOM | 12297 | H | ASP | F | 132 | -5.575 | 38.581 | 3.515 | 118.40 | H |
| ATOM | 12298 | HA | ASP | F | 132 | -7.980 | 37.756 | 4.018 | 116.02 | H |
| ATOM | 12299 | HB2 | ASP | F | 132 | -6.229 | 36.690 | 2.073 | 119.08 | H |
| ATOM | 12300 | HB3 | ASP | F | 132 | -7.794 | 36.422 | 2.107 | 119.08 | H |
| ATOM | 12301 | N | CYS | F | 133 | -5.716 | 35.591 | 4.680 | 114.32 | N |
| ATOM | 12302 | CA | CYS | F | 133 | -5.449 | 34.328 | 5.364 | 114.59 | C |
| ATOM | 12303 | C | CYS | F | 133 | -5.892 | 34.382 | 6.825 | 115.41 | C |
| ATOM | 12304 | O | CYS | F | 133 | -6.499 | 33.441 | 7.328 | 114.68 | O |
| ATOM | 12305 | CB | CYS | F | 133 | -3.964 | 33.968 | 5.286 | 118.53 | C |
| ATOM | 12306 | SG | CYS | F | 133 | -3.547 | 32.418 | 6.119 | 124.44 | S |
| ATOM | 12307 | H | CYS | F | 133 | -5.017 | 35.968 | 4.350 | 117.18 | H |
| ATOM | 12308 | HA | CYS | F | 133 | -5.951 | 33.622 | 4.927 | 117.51 | H |
| ATOM | 12309 | HB2 | CYS | F | 133 | -3.712 | 33.881 | 4.353 | 122.24 | H |
| ATOM | 12310 | HB3 | CYS | F | 133 | -3.448 | 34.677 | 5.702 | 122.24 | H |
| ATOM | 12311 | N | ILE | F | 134 | -5.593 | 35.489 | 7.496 | 114.80 | N |
| ATOM | 12312 | CA | ILE | F | 134 | -5.980 | 35.661 | 8.890 | 112.54 | C |
| ATOM | 12313 | C | ILE | F | 134 | -7.507 | 35.701 | 9.031 | 114.20 | C |
| ATOM | 12314 | O | ILE | F | 134 | -8.068 | 35.120 | 9.957 | 114.69 | O |
| ATOM | 12315 | CB | ILE | F | 134 | -5.370 | 36.952 | 9.483 | 114.54 | C |
| ATOM | 12316 | CG1 | ILE | F | 134 | -5.842 | 36.854 | 9.542 | 115.52 | C |
| ATOM | 12317 | CG2 | ILE | F | 134 | -5.935 | 37.240 | 10.873 | 118.23 | C |
| ATOM | 12318 | CD1 | ILE | F | 134 | -3.302 | 35.789 | 10.488 | 120.56 | C |
| ATOM | 12319 | H | ILE | F | 134 | -5.165 | 36.157 | 7.165 | 117.76 | H |
| ATOM | 12320 | HA | ILE | F | 134 | -5.650 | 34.908 | 9.406 | 115.05 | H |
| ATOM | 12321 | HB | ILE | F | 134 | -5.604 | 37.692 | 8.902 | 117.45 | H |
| ATOM | 12322 | HG12 | ILE | F | 134 | -3.512 | 36.651 | 8.653 | 118.62 | H |
| ATOM | 12323 | HG13 | ILE | F | 134 | -3.489 | 37.710 | 9.832 | 118.62 | H |
| ATOM | 12324 | HG21 | ILE | F | 134 | -5.533 | 38.054 | 11.214 | 121.87 | H |
| ATOM | 12325 | HG22 | ILE | F | 134 | -6.896 | 37.348 | 10.806 | 121.87 | H |
| ATOM | 12326 | HG23 | ILE | F | 134 | -5.725 | 36.496 | 11.459 | 121.87 | H |
| ATOM | 12327 | HD11 | ILE | F | 134 | -2.333 | 35.802 | 10.457 | 124.67 | H |
| ATOM | 12328 | HD12 | ILE | F | 134 | -3.608 | 35.983 | 11.388 | 124.67 | H |
| ATOM | 12329 | HD13 | ILE | F | 134 | -3.631 | 34.921 | 10.206 | 124.67 | H |
| ATOM | 12330 | N | MET | F | 135 | -8.184 | 36.386 | 8.117 | 112.68 | N |

TABLE 5-continued

Atomic Coordinates for OMCP-NKG2D (4PDC).

| ATOM | 12331 | CA | MET | F | 135 | -9.635 | 36.491 | 8.203 | 114.96 | C |
| ATOM | 12332 | C | MET | F | 135 | -10.291 | 35.143 | 7.899 | 117.64 | C |
| ATOM | 12333 | O | MET | F | 135 | -11.291 | 34.786 | 8.528 | 118.23 | O |
| ATOM | 12334 | CB | MET | F | 135 | -10.156 | 37.577 | 7.261 | 115.55 | C |
| ATOM | 12335 | CG | MET | F | 135 | -9.677 | 38.983 | 7.625 | 118.93 | C |
| ATOM | 12336 | SD | MET | F | 135 | -10.279 | 39.567 | 9.225 | 125.83 | S |
| ATOM | 12337 | CE | MET | F | 135 | -11.971 | 39.939 | 8.804 | 123.03 | C |
| ATOM | 12338 | H | MET | F | 135 | -7.833 | 36.795 | 7.446 | 115.22 | H |
| ATOM | 12339 | HA | MET | F | 135 | -9.872 | 36.751 | 9.107 | 117.96 | H |
| ATOM | 12340 | HB2 | MET | F | 135 | -9.852 | 37.384 | 6.360 | 118.66 | H |
| ATOM | 12341 | HB3 | MET | F | 135 | -11.126 | 37.577 | 7.288 | 118.66 | H |
| ATOM | 12342 | HG2 | MET | F | 135 | -8.707 | 38.985 | 7.655 | 122.72 | H |
| ATOM | 12343 | HG3 | MET | F | 135 | -9.986 | 39.605 | 6.947 | 122.72 | H |
| ATOM | 12344 | HE1 | MET | F | 135 | -12.427 | 40.272 | 9.593 | 127.63 | H |
| ATOM | 12345 | HE2 | MET | F | 135 | -11.982 | 40.613 | 8.107 | 127.63 | H |
| ATOM | 12346 | HE3 | MET | F | 135 | -12.403 | 39.129 | 8.490 | 127.63 | H |
| ATOM | 12347 | N | HIS | F | 136 | -9.727 | 34.394 | 6.950 | 117.74 | N |
| ATOM | 12348 | CA | HIS | F | 136 | -10.191 | 33.034 | 6.677 | 114.38 | C |
| ATOM | 12349 | C | HIS | F | 136 | -10.007 | 32.155 | 7.908 | 115.88 | C |
| ATOM | 12350 | O | HIS | F | 136 | -10.899 | 31.400 | 8.284 | 115.42 | O |
| ATOM | 12351 | CB | HIS | F | 136 | -9.443 | 32.412 | 5.489 | 116.15 | C |
| ATOM | 12352 | CG | HIS | F | 136 | -9.875 | 32.932 | 4.152 | 115.03 | C |
| ATOM | 12353 | ND1 | HIS | F | 136 | -9.959 | 32.127 | 3.035 | 115.21 | N |
| ATOM | 12354 | CD2 | HIS | F | 136 | -10.236 | 34.172 | 3.748 | 113.64 | C |
| ATOM | 12355 | CE1 | HIS | F | 136 | -10.355 | 32.850 | 2.003 | 115.34 | C |
| ATOM | 12356 | NE2 | HIS | F | 136 | -10.530 | 34.094 | 2.408 | 115.92 | N |
| ATOM | 12357 | H | HIS | F | 136 | -9.074 | 34.650 | 6.451 | 121.29 | H |
| ATOM | 12358 | HA | HIS | F | 136 | -11.136 | 33.058 | 6.461 | 117.26 | H |
| ATOM | 12359 | HB2 | HIS | F | 136 | -8.495 | 32.598 | 5.586 | 119.38 | H |
| ATOM | 12360 | HB3 | HIS | F | 136 | -9.591 | 31.453 | 5.495 | 119.38 | H |
| ATOM | 12361 | HD2 | HIS | F | 136 | -10.277 | 31.286 | 3.013 | 118.25 | H |
| ATOM | 12362 | HE1 | HIS | F | 136 | -10.489 | 34.935 | 4.279 | 116.36 | H |
| ATOM | 12363 | HE2 | HIS | F | 136 | -10.788 | 32.535 | 1.138 | 118.41 | H |
| ATOM | 12364 | N | LEU | F | 137 | -8.833 | 34.749 | 1.914 | 119.10 | N |
| ATOM | 12365 | CA | LEU | F | 137 | -8.515 | 32.255 | 8.523 | 114.21 | C |
| ATOM | 12366 | C | LEU | F | 137 | -9.530 | 31.483 | 9.717 | 116.46 | C |
| ATOM | 12367 | O | LEU | F | 137 | -5.239 | 31.739 | 10.832 | 116.07 | O |
| ATOM | 12368 | CB | LEU | F | 137 | -10.045 | 30.804 | 11.433 | 116.54 | C |
| ATOM | 12369 | CG | LEU | F | 137 | -7.101 | 31.819 | 10.196 | 116.82 | C |
| ATOM | 12370 | CD1 | LEU | F | 137 | -6.696 | 31.348 | 11.597 | 117.25 | C |
| ATOM | 12371 | CD2 | LEU | F | 137 | -6.909 | 29.855 | 11.775 | 121.45 | C |
| ATOM | 12372 | H | LEU | F | 137 | -8.195 | 31.707 | 11.858 | 116.99 | H |
| ATOM | 12373 | HA | LEU | F | 137 | -8.542 | 32.769 | 8.263 | 117.06 | H |
| ATOM | 12374 | HB2 | LEU | F | 137 | -6.472 | 30.538 | 9.499 | 119.75 | H |
| ATOM | 12375 | HB3 | LEU | F | 137 | -7.000 | 31.425 | 9.572 | 120.18 | H |
| ATOM | 12376 | HG | LEU | F | 137 | -7.240 | 32.784 | 10.182 | 120.18 | H |
| ATOM | 12377 | HD11 | LEU | F | 137 | -6.640 | 31.808 | 12.254 | 120.69 | H |
| ATOM | 12378 | HD12 | LEU | F | 137 | -7.848 | 29.603 | 12.672 | 125.74 | H |
| ATOM | 12379 | HD13 | LEU | F | 137 | -6.372 | 29.653 | 11.641 | 125.74 | H |
| ATOM | 12380 | HD21 | LEU | F | 137 | -4.994 | 31.404 | 12.747 | 120.39 | H |

TABLE 5-continued

Atomic Coordinates for OMCP-NKG2D (4PDC).

| | | | | | | | | | |
|---|---|---|---|---|---|---|---|---|---|
| ATOM | 12382 | HD22 | LEU | F | 137 | -4.682 | 31.271 | 11.195 | H |
| ATOM | 12383 | HD23 | LEU | F | 137 | -5.136 | 32.670 | 11.797 | H |
| ATOM | 12384 | N | ARG | F | 138 | -9.817 | 33.006 | 11.100 | N |
| ATOM | 12385 | CA | ARG | F | 138 | -10.767 | 33.360 | 12.147 | C |
| ATOM | 12386 | C | ARG | F | 138 | -12.162 | 32.844 | 11.802 | C |
| ATOM | 12387 | O | ARG | F | 138 | -12.903 | 32.389 | 12.676 | O |
| ATOM | 12388 | CB | ARG | F | 138 | -10.791 | 34.875 | 12.353 | C |
| ATOM | 12389 | CG | ARG | F | 138 | -9.496 | 35.437 | 12.926 | C |
| ATOM | 12390 | CD | ARG | F | 138 | -9.536 | 36.954 | 13.003 | C |
| ATOM | 12391 | NE | ARG | F | 138 | -10.564 | 37.424 | 13.925 | N |
| ATOM | 12392 | CZ | ARG | F | 138 | -10.969 | 38.686 | 14.016 | C |
| ATOM | 12393 | NH1 | ARG | F | 138 | -10.435 | 39.618 | 13.241 | N1+ |
| ATOM | 12394 | NH2 | ARG | F | 138 | -11.917 | 39.018 | 14.882 | N |
| ATOM | 12395 | H | ARG | F | 138 | -9.477 | 33.681 | 10.690 | H |
| ATOM | 12396 | HA | ARG | F | 138 | -10.490 | 32.946 | 12.979 | H |
| ATOM | 12397 | HB2 | ARG | F | 138 | -10.948 | 35.305 | 11.498 | H |
| ATOM | 12398 | HB3 | ARG | F | 138 | -11.507 | 35.096 | 12.969 | H |
| ATOM | 12399 | HG2 | ARG | F | 138 | -9.364 | 35.090 | 13.822 | H |
| ATOM | 12400 | HG3 | ARG | F | 138 | -8.755 | 35.181 | 12.354 | H |
| ATOM | 12401 | HD2 | ARG | F | 138 | -8.678 | 37.281 | 13.315 | H |
| ATOM | 12402 | HD3 | ARG | F | 138 | -9.731 | 37.313 | 12.123 | H |
| ATOM | 12403 | HE | ARG | F | 138 | -10.932 | 36.845 | 14.443 | H |
| ATOM | 12404 | HH11 | ARG | F | 138 | -9.821 | 39.407 | 12.676 | H |
| ATOM | 12405 | HH12 | ARG | F | 138 | -10.700 | 40.433 | 13.303 | H |
| ATOM | 12406 | HH21 | ARG | F | 138 | -12.267 | 38.417 | 15.388 | H |
| ATOM | 12407 | HH22 | ARG | F | 138 | -12.178 | 39.836 | 14.942 | H |
| ATOM | 12408 | N | SER | F | 139 | -12.505 | 32.898 | 10.520 | N |
| ATOM | 12409 | CA | SER | F | 139 | -13.798 | 32.413 | 10.056 | C |
| ATOM | 12410 | C | SER | F | 139 | -13.890 | 30.893 | 10.165 | C |
| ATOM | 12411 | O | SER | F | 139 | -14.945 | 30.348 | 10.492 | O |
| ATOM | 12412 | CB | SER | F | 139 | -14.042 | 32.855 | 8.613 | C |
| ATOM | 12413 | OG | SER | F | 139 | -14.120 | 34.266 | 8.526 | O |
| ATOM | 12414 | H | SER | F | 139 | -12.003 | 33.212 | 9.896 | H |
| ATOM | 12415 | HA | SER | F | 139 | -14.496 | 32.797 | 10.609 | H |
| ATOM | 12416 | HB2 | SER | F | 139 | -13.308 | 32.545 | 8.059 | H |
| ATOM | 12417 | HB3 | SER | F | 139 | -14.877 | 32.473 | 8.302 | H |
| ATOM | 12418 | HG | SER | F | 139 | -13.402 | 34.611 | 8.793 | H |
| ATOM | 12419 | N | LEU | F | 140 | -12.783 | 30.210 | 9.897 | N |
| ATOM | 12420 | CA | LEU | F | 140 | -12.766 | 28.753 | 9.949 | C |
| ATOM | 12421 | C | LEU | F | 140 | -12.769 | 28.260 | 11.394 | C |
| ATOM | 12422 | O | LEU | F | 140 | -13.346 | 27.216 | 11.695 | O |
| ATOM | 12423 | CB | LEU | F | 140 | -11.554 | 28.201 | 9.195 | C |
| ATOM | 12424 | CG | LEU | F | 140 | -11.611 | 28.339 | 7.669 | C |
| ATOM | 12425 | CD1 | LEU | F | 140 | -10.258 | 28.037 | 7.052 | C |
| ATOM | 12426 | CD2 | LEU | F | 140 | -12.680 | 27.431 | 7.075 | C |
| ATOM | 12427 | H | LEU | F | 140 | -12.030 | 30.565 | 9.682 | H |
| ATOM | 12428 | HA | LEU | F | 140 | -13.566 | 28.415 | 9.517 | H |
| ATOM | 12429 | HB2 | LEU | F | 140 | -10.762 | 28.671 | 9.500 | H |
| ATOM | 12430 | HB3 | LEU | F | 140 | -11.469 | 27.257 | 9.399 | H |
| ATOM | 12431 | HG | LEU | F | 140 | -11.841 | 29.254 | 7.446 | H |
| ATOM | 12432 | HD11 | LEU | F | 140 | -10.323 | 28.132 | 6.088 | H |

TABLE 5-continued

Atomic Coordinates for OMCP-NKG2D (4PDC).

| ATOM | 12433 | HD12 | LEU | F | 140 | -9.605 | 28.662 | 7.402 | 123.96 | H |
|------|-------|------|-----|---|-----|--------|--------|-------|--------|---|
| ATOM | 12434 | HD13 | LEU | F | 140 | -10.003 | 27.129 | 7.279 | 123.96 | H |
| ATOM | 12435 | HD21 | LEU | F | 140 | -12.689 | 27.542 | 6.112 | 125.46 | H |
| ATOM | 12436 | HD22 | LEU | F | 140 | -12.473 | 26.510 | 7.300 | 125.46 | H |
| ATOM | 12437 | HD23 | LEU | F | 140 | -13.543 | 27.676 | 7.445 | 125.46 | H |
| ATOM | 12438 | N | VAL | F | 141 | -12.132 | 29.008 | 12.288 | 119.00 | N |
| ATOM | 12439 | CA | VAL | F | 141 | -12.164 | 28.668 | 13.704 | 123.28 | C |
| ATOM | 12440 | C | VAL | F | 141 | -13.590 | 28.802 | 14.237 | 125.21 | C |
| ATOM | 12441 | O | VAL | F | 141 | -14.020 | 28.017 | 15.081 | 124.34 | O |
| ATOM | 12442 | CB | VAL | F | 141 | -11.210 | 29.556 | 14.528 | 119.95 | C |
| ATOM | 12443 | CG1 | VAL | F | 141 | -11.452 | 29.377 | 16.024 | 126.02 | C |
| ATOM | 12444 | CG2 | VAL | F | 141 | -9.758 | 29.225 | 14.198 | 124.20 | C |
| ATOM | 12445 | H | VAL | F | 141 | -11.678 | 29.714 | 12.101 | 122.80 | H |
| ATOM | 12446 | HA | VAL | F | 141 | -11.886 | 27.745 | 13.814 | 127.94 | H |
| ATOM | 12447 | HB | VAL | F | 141 | -11.367 | 30.487 | 14.305 | 123.94 | H |
| ATOM | 12448 | HG11 | VAL | F | 141 | -10.838 | 29.947 | 16.514 | 131.23 | H |
| ATOM | 12449 | HG12 | VAL | F | 141 | -12.368 | 29.624 | 16.227 | 131.23 | H |
| ATOM | 12450 | HG13 | VAL | F | 141 | -11.300 | 28.448 | 16.259 | 131.23 | H |
| ATOM | 12451 | HG21 | VAL | F | 141 | -9.177 | 29.794 | 14.727 | 129.04 | H |
| ATOM | 12452 | HG22 | VAL | F | 141 | -9.591 | 28.293 | 14.410 | 129.04 | H |
| ATOM | 12453 | HG23 | VAL | F | 141 | -9.605 | 29.382 | 13.253 | 129.04 | H |
| ATOM | 12454 | N | ARG | F | 142 | -14.315 | 29.802 | 13.745 | 121.37 | N |
| ATOM | 12455 | CA | ARG | F | 142 | -15.718 | 29.978 | 14.107 | 123.25 | C |
| ATOM | 12456 | C | ARG | F | 142 | -16.534 | 28.742 | 13.722 | 130.62 | C |
| ATOM | 12457 | O | ARG | F | 142 | -17.319 | 28.235 | 14.525 | 127.61 | O |
| ATOM | 12458 | CB | ARG | F | 142 | -16.286 | 31.230 | 13.436 | 128.79 | C |
| ATOM | 12459 | CG | ARG | F | 142 | -17.776 | 31.456 | 13.656 | 134.59 | C |
| ATOM | 12460 | CD | ARG | F | 142 | -18.109 | 31.669 | 15.122 | 136.74 | C |
| ATOM | 12461 | NE | ARG | F | 142 | -19.526 | 31.963 | 15.311 | 143.29 | N |
| ATOM | 12462 | CZ | ARG | F | 142 | -20.073 | 33.164 | 15.149 | 147.11 | C |
| ATOM | 12463 | NH1 | ARG | F | 142 | -19.325 | 34.201 | 14.794 | 140.67 | N1+ |
| ATOM | 12464 | NH2 | ARG | F | 142 | -21.373 | 33.330 | 15.342 | 153.09 | N |
| ATOM | 12465 | H | ARG | F | 142 | -14.017 | 30.395 | 13.197 | 125.65 | H |
| ATOM | 12466 | HA | ARG | F | 142 | -15.785 | 30.095 | 15.068 | 127.90 | H |
| ATOM | 12467 | HB2 | ARG | F | 142 | -15.818 | 32.006 | 13.782 | 134.55 | H |
| ATOM | 12468 | HB3 | ARG | F | 142 | -16.138 | 31.161 | 12.479 | 134.55 | H |
| ATOM | 12469 | HG2 | ARG | F | 142 | -18.054 | 32.244 | 13.164 | 141.50 | H |
| ATOM | 12470 | HG3 | ARG | F | 142 | -18.265 | 30.678 | 13.345 | 141.50 | H |
| ATOM | 12471 | HD2 | ARG | F | 142 | -17.896 | 30.864 | 15.619 | 144.08 | H |
| ATOM | 12472 | HD3 | ARG | F | 142 | -17.595 | 32.419 | 15.461 | 144.08 | H |
| ATOM | 12473 | HE | ARG | F | 142 | -20.043 | 31.315 | 15.542 | 151.95 | H |
| ATOM | 12474 | HH11 | ARG | F | 142 | -18.480 | 34.099 | 14.666 | 148.80 | H |
| ATOM | 12475 | HH12 | ARG | F | 142 | -19.684 | 34.975 | 14.691 | 148.80 | H |
| ATOM | 12476 | HH21 | ARG | F | 142 | -21.862 | 32.662 | 15.573 | 163.71 | H |
| ATOM | 12477 | HH22 | ARG | F | 142 | -21.727 | 34.107 | 15.239 | 163.71 | H |
| ATOM | 12478 | N | LYS | F | 143 | -16.343 | 28.261 | 12.495 | 124.90 | N |
| ATOM | 12479 | CA | LYS | F | 143 | -17.016 | 27.049 | 12.034 | 128.02 | C |
| ATOM | 12480 | C | LYS | F | 143 | -16.646 | 25.854 | 12.897 | 128.44 | C |
| ATOM | 12481 | O | LYS | F | 143 | -17.509 | 25.084 | 13.314 | 128.33 | O |
| ATOM | 12482 | CB | LYS | F | 143 | -16.656 | 26.740 | 10.581 | 127.89 | C |
| ATOM | 12483 | CG | LYS | F | 143 | -17.165 | 27.743 | 9.576 | 121.75 | C |

TABLE 5-continued

Atomic Coordinates for OMCP-NKG2D (4PDC).

| ATOM | 12484 | CD  | LYS F | 143 | -16.613 | 27.446 | 8.190  | 124.93 | C   |
|------|-------|-----|-------|-----|---------|--------|--------|--------|-----|
| ATOM | 12485 | CE  | LYS F | 143 | -17.698 | 26.971 | 7.242  | 133.41 | C   |
| ATOM | 12486 | NZ  | LYS F | 143 | -18.262 | 25.655 | 7.631  | 138.22 | N1+ |
| ATOM | 12487 | H   | LYS F | 143 | -15.826 | 28.619 | 11.908 | 129.88 | H   |
| ATOM | 12488 | HA  | LYS F | 143 | -17.976 | 27.177 | 12.089 | 133.63 | H   |
| ATOM | 12489 | HB2 | LYS F | 143 | -15.689 | 26.711 | 10.502 | 133.47 | H   |
| ATOM | 12490 | HB3 | LYS F | 143 | -17.028 | 25.876 | 10.347 | 133.47 | H   |
| ATOM | 12491 | HG2 | LYS F | 143 | -18.133 | 27.697 | 9.536  | 126.10 | H   |
| ATOM | 12492 | HG3 | LYS F | 143 | -16.879 | 27.697 | 9.835  | 126.10 | H   |
| ATOM | 12493 | HD2 | LYS F | 143 | -16.221 | 28.633 | 7.822  | 129.91 | H   |
| ATOM | 12494 | HD3 | LYS F | 143 | -15.942 | 28.253 | 8.256  | 129.91 | H   |
| ATOM | 12495 | HE2 | LYS F | 143 | -18.420 | 26.748 | 7.239  | 140.09 | H   |
| ATOM | 12496 | HE3 | LYS F | 143 | -17.324 | 27.618 | 6.351  | 140.09 | H   |
| ATOM | 12497 | HZ1 | LYS F | 143 | -17.620 | 26.886 | 7.635  | 145.86 | H   |
| ATOM | 12498 | HZ2 | LYS F | 143 | -18.619 | 25.038 | 8.445  | 145.86 | H   |
| ATOM | 12499 | HZ3 | LYS F | 143 | -18.893 | 25.706 | 7.052  | 145.86 | H   |
| ATOM | 12500 | N   | MET F | 144 | -15.350 | 25.412 | 13.146 | 124.38 | N   |
| ATOM | 12501 | CA  | MET F | 144 | -14.836 | 25.703 | 13.866 | 127.30 | C   |
| ATOM | 12502 | C   | MET F | 144 | -15.415 | 24.550 | 15.276 | 134.88 | C   |
| ATOM | 12503 | O   | MET F | 144 | -15.839 | 24.490 | 15.735 | 135.17 | O   |
| ATOM | 12504 | CB  | MET F | 144 | -13.307 | 23.429 | 13.910 | 131.14 | C   |
| ATOM | 12505 | CG  | MET F | 144 | -12.660 | 24.597 | 14.523 | 131.20 | C   |
| ATOM | 12506 | SD  | MET F | 144 | -11.998 | 23.367 | 16.160 | 144.38 | S   |
| ATOM | 12507 | CE  | MET F | 144 | -10.619 | 23.709 | 15.748 | 136.74 | C   |
| ATOM | 12508 | H   | MET F | 144 | -14.743 | 24.779 | 12.906 | 129.26 | H   |
| ATOM | 12509 | HA  | MET F | 144 | -15.793 | 26.263 | 13.389 | 132.76 | H   |
| ATOM | 12510 | HB2 | MET F | 144 | -12.973 | 23.745 | 13.004 | 137.36 | H   |
| ATOM | 12511 | HB3 | MET F | 144 | -13.035 | 24.685 | 14.435 | 137.36 | H   |
| ATOM | 12512 | HG2 | MET F | 144 | -13.323 | 25.365 | 14.605 | 137.44 | H   |
| ATOM | 12513 | HG3 | MET F | 144 | -11.930 | 22.664 | 13.955 | 137.44 | H   |
| ATOM | 12514 | HE1 | MET F | 144 | -10.168 | 25.040 | 16.566 | 144.09 | H   |
| ATOM | 12515 | HE2 | MET F | 144 | -10.007 | 24.296 | 15.172 | 144.09 | H   |
| ATOM | 12516 | HE3 | MET F | 144 | -10.956 | 25.565 | 15.290 | 144.09 | H   |
| ATOM | 12517 | N   | GLU F | 145 | -15.455 | 25.636 | 15.948 | 129.62 | N   |
| ATOM | 12518 | CA  | GLU F | 145 | -15.954 | 25.704 | 17.316 | 135.30 | C   |
| ATOM | 12519 | C   | GLU F | 145 | -17.462 | 25.475 | 17.409 | 133.13 | C   |
| ATOM | 12520 | O   | GLU F | 145 | -17.954 | 24.977 | 18.420 | 134.65 | O   |
| ATOM | 12521 | CB  | GLU F | 145 | -15.597 | 27.055 | 17.934 | 131.57 | C   |
| ATOM | 12522 | CG  | GLU F | 145 | -14.112 | 27.209 | 18.208 | 133.34 | C   |
| ATOM | 12523 | CD  | GLU F | 145 | -13.765 | 28.538 | 18.842 | 132.82 | C   |
| ATOM | 12524 | OE1 | GLU F | 145 | -14.628 | 29.444 | 18.853 | 141.83 | O   |
| ATOM | 12525 | OE2 | GLU F | 145 | -12.625 | 28.672 | 19.332 | 137.68 | O1- |
| ATOM | 12526 | H   | GLU F | 145 | -15.197 | 26.392 | 15.631 | 135.54 | H   |
| ATOM | 12527 | HA  | GLU F | 145 | -15.518 | 25.015 | 17.841 | 142.36 | H   |
| ATOM | 12528 | HB2 | GLU F | 145 | -15.864 | 27.150 | 17.324 | 137.89 | H   |
| ATOM | 12529 | HB3 | GLU F | 145 | -16.069 | 27.760 | 18.776 | 137.89 | H   |
| ATOM | 12530 | HG2 | GLU F | 145 | -13.828 | 26.506 | 18.813 | 140.00 | H   |
| ATOM | 12531 | HG3 | GLU F | 145 | -13.628 | 27.142 | 17.370 | 140.00 | H   |
| ATOM | 12532 | N   | ASP F | 146 | -18.190 | 25.837 | 16.359 | 133.24 | N   |
| ATOM | 12533 | CA  | ASP F | 146 | -19.641 | 25.667 | 16.339 | 137.33 | C   |
| ATOM | 12534 | C   | ASP F | 146 | -20.054 | 24.299 | 15.791 | 142.30 | C   |

TABLE 5-continued

Atomic Coordinates for OMCP-NKG2D (4PDC).

| ATOM | 12535 | O | ASP | F | 146 | -21.244 | 24.010 | 15.660 | 150.59 | O |
|---|---|---|---|---|---|---|---|---|---|---|
| ATOM | 12536 | CB | ASP | F | 146 | -20.292 | 26.776 | 15.510 | 134.15 | C |
| ATOM | 12537 | CG | ASP | F | 146 | -20.188 | 28.139 | 16.169 | 138.34 | C |
| ATOM | 12538 | OD1 | ASP | F | 146 | -19.944 | 28.201 | 17.393 | 139.97 | O |
| ATOM | 12539 | OD2 | ASP | F | 146 | -20.362 | 29.152 | 15.460 | 137.23 | O1- |
| ATOM | 12540 | H | ASP | F | 146 | -17.868 | 26.186 | 15.641 | 139.88 | H |
| ATOM | 12541 | HA | ASP | F | 146 | -19.976 | 25.737 | 17.247 | 144.79 | H |
| ATOM | 12542 | HB2 | ASP | F | 146 | -19.853 | 26.825 | 14.647 | 140.97 | H |
| ATOM | 12543 | HB3 | ASP | F | 146 | -21.233 | 26.570 | 15.393 | 140.97 | H |
| ATOM | 12544 | N | SER | F | 147 | -19.073 | 23.459 | 15.476 | 144.15 | N |
| ATOM | 12545 | CA | SER | F | 147 | -19.348 | 22.137 | 14.921 | 150.25 | C |
| ATOM | 12546 | C | SER | F | 147 | -20.056 | 21.244 | 15.935 | 151.65 | C |
| ATOM | 12547 | O | SER | F | 147 | -19.657 | 21.172 | 17.098 | 147.99 | O |
| ATOM | 12548 | CB | SER | F | 147 | -18.052 | 21.468 | 14.460 | 145.00 | C |
| ATOM | 12549 | OG | SER | F | 147 | -18.303 | 20.164 | 13.961 | 148.06 | O |
| ATOM | 12550 | H | SER | F | 147 | -18.236 | 23.631 | 15.575 | 152.98 | H |
| ATOM | 12551 | HA | SER | F | 147 | -19.928 | 22.233 | 14.149 | 160.30 | H |
| ATOM | 12552 | HB2 | SER | F | 147 | -17.654 | 22.003 | 13.756 | 154.00 | H |
| ATOM | 12553 | HB3 | SER | F | 147 | -17.444 | 21.406 | 15.213 | 154.00 | H |
| ATOM | 12554 | HG | SER | F | 147 | -17.584 | 19.809 | 13.712 | 157.67 | H |
| ATOM | 12555 | N | LYS | F | 148 | -21.095 | 20.552 | 15.474 | 156.81 | N |
| ATOM | 12556 | CA | LYS | F | 148 | -21.896 | 19.678 | 16.328 | 160.25 | C |
| ATOM | 12557 | C | LYS | F | 148 | -21.256 | 18.299 | 16.469 | 162.99 | C |
| ATOM | 12558 | O | LYS | F | 148 | -21.945 | 17.311 | 16.731 | 162.68 | O |
| ATOM | 12559 | CB | LYS | F | 148 | -23.312 | 19.528 | 15.761 | 156.25 | C |
| ATOM | 12560 | CG | LYS | F | 148 | -23.992 | 20.839 | 15.384 | 164.67 | C |
| ATOM | 12561 | CD | LYS | F | 148 | -25.039 | 21.247 | 16.406 | 171.20 | C |
| ATOM | 12562 | CE | LYS | F | 148 | -25.557 | 22.651 | 16.134 | 176.82 | C |
| ATOM | 12563 | NZ | LYS | F | 148 | -24.495 | 23.682 | 16.310 | 175.60 | N1+ |
| ATOM | 12564 | H | LYS | F | 148 | -21.360 | 20.572 | 14.656 | 168.17 | H |
| ATOM | 12565 | HA | LYS | F | 148 | -21.964 | 20.071 | 17.211 | 172.30 | H |
| ATOM | 12566 | HB2 | LYS | F | 148 | -23.268 | 18.980 | 14.962 | 167.50 | H |
| ATOM | 12567 | HB3 | LYS | F | 148 | -23.866 | 19.091 | 16.426 | 167.50 | H |
| ATOM | 12568 | HG2 | LYS | F | 148 | -23.325 | 21.542 | 15.336 | 177.61 | H |
| ATOM | 12569 | HG3 | LYS | F | 148 | -24.431 | 20.736 | 14.525 | 177.61 | H |
| ATOM | 12570 | HD2 | LYS | F | 148 | -25.788 | 20.632 | 16.361 | 185.44 | H |
| ATOM | 12571 | HD3 | LYS | F | 148 | -24.645 | 21.234 | 17.292 | 185.44 | H |
| ATOM | 12572 | HE2 | LYS | F | 148 | -25.877 | 22.701 | 15.219 | 192.19 | H |
| ATOM | 12573 | HE3 | LYS | F | 148 | -26.277 | 22.850 | 16.752 | 192.19 | H |
| ATOM | 12574 | HZ1 | LYS | F | 148 | -23.822 | 23.524 | 15.749 | 190.72 | H |
| ATOM | 12575 | HZ2 | LYS | F | 148 | -24.826 | 24.491 | 16.145 | 190.72 | H |
| ATOM | 12576 | HZ3 | LYS | F | 148 | -24.187 | 23.660 | 17.145 | 190.72 | H |
| ATOM | 12577 | N | ARG | F | 149 | -19.938 | 18.236 | 16.295 | 162.51 | N |
| ATOM | 12578 | CA | ARG | F | 149 | -19.219 | 16.968 | 16.305 | 165.70 | C |
| ATOM | 12579 | C | ARG | F | 149 | -17.746 | 17.180 | 16.640 | 170.51 | C |
| ATOM | 12580 | O | ARG | F | 149 | -17.410 | 17.718 | 17.718 | 179.82 | O |
| ATOM | 12581 | CB | ARG | F | 149 | -19.361 | 16.277 | 14.948 | 159.09 | C |
| ATOM | 12582 | CG | ARG | F | 149 | -18.637 | 14.951 | 14.834 | 153.79 | C |
| ATOM | 12583 | CD | ARG | F | 149 | -18.960 | 14.289 | 13.514 | 143.18 | C |
| ATOM | 12584 | NE | ARG | F | 149 | -18.021 | 13.226 | 13.181 | 143.60 | N |
| ATOM | 12585 | CZ | ARG | F | 149 | -18.019 | 12.580 | 12.021 | 140.65 | C |

TABLE 5-continued

Atomic Coordinates for OMCP-NKG2D (4PDC).

| ATOM | 12586 | NH1  | ARG | F | 149 | -18.915 | 12.894 | 11.095 | N1+ |
| ---- | ----- | ---- | --- | - | --- | ------- | ------ | ------ | --- |
| ATOM | 12587 | NH2  | ARG | F | 149 | -17.125 | 11.627 | 11.791 | N   |
| ATOM | 12588 | H    | ARG | F | 149 | -19.434 | 18.921 | 16.169 | H   |
| ATOM | 12589 | HA   | ARG | F | 149 | -19.603 | 16.389 | 16.982 | H   |
| ATOM | 12590 | HB2  | ARG | F | 149 | -20.303 | 16.112 | 14.782 | H   |
| ATOM | 12591 | HB3  | ARG | F | 149 | -19.007 | 16.865 | 14.263 | H   |
| ATOM | 12592 | HG2  | ARG | F | 149 | -17.679 | 15.101 | 14.877 | H   |
| ATOM | 12593 | HG3  | ARG | F | 149 | -18.921 | 14.363 | 15.551 | H   |
| ATOM | 12594 | HD2  | ARG | F | 149 | -19.848 | 13.902 | 13.562 | H   |
| ATOM | 12595 | HD3  | ARG | F | 149 | -18.925 | 14.954 | 12.808 | H   |
| ATOM | 12596 | HE   | ARG | F | 149 | -17.372 | 13.078 | 13.725 | H   |
| ATOM | 12597 | HH11 | ARG | F | 149 | -19.492 | 13.514 | 11.246 | H   |
| ATOM | 12598 | HH12 | ARG | F | 149 | -18.919 | 12.478 | 10.342 | H   |
| ATOM | 12599 | HH21 | ARG | F | 149 | -16.546 | 11.425 | 12.394 | H   |
| ATOM | 12600 | HH22 | ARG | F | 149 | -17.127 | 11.207 | 11.040 | H   |

SEQUENCE LISTING

<160> NUMBER OF SEQ ID NOS: 69

<210> SEQ ID NO 1
<211> LENGTH: 944
<212> TYPE: DNA
<213> ORGANISM: Artificial Sequence
<220> FEATURE:
<223> OTHER INFORMATION: SYNTHESIZED

<400> SEQUENCE: 1

```
cacaaactcg cattcaactt caatctagaa ataaatggca gtgatacaca ttctacagta       60
gatgtatatc ttgatgattc tcaaattata acgtttgatg gaaaagatat ccgtccaacc      120
atcccgttca tgataggtga tgaaattttc ttaccgtttt ataaaaatgt gtttagtgag      180
tttttctctc tgtttagaag agttcctaca agtactccat atgaagactt gacatatttt     240
tatgaatgcg actatacaga caataaatct acatttgatc agttttatct ttataatggc      300
gaagaatata ctgtcaaaac acaggaggcc actaataaaa atatgtggct aactacttcc      360
gagtttagac taaaaaaatg gttcgatggc gaagattgta taatgcatct tagatcgtta      420
gttagaaaaa tggaggacag taaacgaaac actggtggta ccggaagtag cggtagtagt      480
gattacaagg acgatgacga caagcaccac catcatcatc atcaccacgg tagcagcggc      540
agcagtgccc ccacctctag cagcacaaag aagacccagc tgcaactgga acacctcctg      600
ctggacctgc agatgatcct gaacggcatc aacaactaca gaaccccaa gctgaccgcc       660
atgctgacca aaagttttta catgcccaag aaggccaccg agcttaaaca cctgcaatgc      720
cttgaggagg agctgaagcc ctggaggagg tactgaacct ggcccagagc aagaactttc      780
atctgaggcc cagggacctg attagcaaca tcaacgtgat cgtgttggag ttgaagggca      840
gcgagaccac gttcatgtgc gagtacgccg acgagacggc caccatagtg gagtttctta      900
acaggtggat caccttctca cagtctatca tcagcaccct gacc                      944
```

<210> SEQ ID NO 2
<211> LENGTH: 315
<212> TYPE: PRT
<213> ORGANISM: Artificial Sequence
<220> FEATURE:
<223> OTHER INFORMATION: SYNTHESIZED

<400> SEQUENCE: 2

```
His Lys Leu Ala Phe Asn Phe Asn Leu Glu Ile Asn Gly Ser Asp Thr
1               5                   10                  15

His Ser Thr Val Asp Val Tyr Leu Asp Asp Ser Gln Ile Ile Thr Phe
            20                  25                  30

Asp Gly Lys Asp Ile Arg Pro Thr Ile Pro Phe Met Ile Gly Asp Glu
        35                  40                  45

Ile Phe Leu Pro Phe Tyr Lys Asn Val Phe Ser Glu Phe Phe Ser Leu
    50                  55                  60

Phe Arg Arg Val Pro Thr Ser Thr Pro Tyr Glu Asp Leu Thr Tyr Phe
65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
            100                 105                 110

Lys Asn Met Trp Leu Thr Thr Ser Glu Phe Arg Leu Lys Lys Trp Phe
        115                 120                 125

Asp Gly Glu Asp Cys Ile Met His Leu Arg Ser Leu Val Arg Lys Met
```

```
                130             135             140
Glu Asp Ser Lys Arg Asn Thr Gly Gly Thr Gly Ser Ser Gly Ser Ser
145                 150                 155                 160

Asp Tyr Lys Asp Asp Asp Lys His His His His His His His
                165                 170                 175

Gly Ser Ser Gly Ser Ser Ala Pro Thr Ser Ser Ser Thr Lys Lys Thr
            180                 185                 190

Gln Leu Gln Leu Glu His Leu Leu Leu Asp Leu Gln Met Ile Leu Asn
        195                 200                 205

Gly Ile Asn Asn Tyr Lys Asn Pro Lys Leu Thr Ala Met Leu Thr Lys
    210                 215                 220

Lys Phe Tyr Met Pro Lys Lys Ala Thr Glu Leu Lys His Leu Gln Cys
225                 230                 235                 240

Leu Glu Glu Glu Leu Lys Pro Leu Glu Glu Val Leu Asn Leu Ala Gln
                245                 250                 255

Ser Lys Asn Phe His Leu Arg Pro Arg Asp Leu Ile Ser Asn Ile Asn
                260                 265                 270

Val Ile Val Leu Glu Leu Lys Gly Ser Glu Thr Thr Phe Met Cys Glu
            275                 280                 285

Tyr Ala Asp Glu Thr Ala Thr Ile Val Glu Phe Leu Asn Arg Trp Ile
    290                 295                 300

Thr Phe Ser Gln Ser Ile Ile Ser Thr Leu Thr
305                 310                 315

<210> SEQ ID NO 3
<211> LENGTH: 9
<212> TYPE: PRT
<213> ORGANISM: Homo sapiens

<400> SEQUENCE: 3

Ser Val Tyr Asp Phe Phe Val Trp Leu
1               5

<210> SEQ ID NO 4
<211> LENGTH: 8
<212> TYPE: PRT
<213> ORGANISM: Homo sapiens

<400> SEQUENCE: 4

Ser Ile Ile Asn Phe Glu Lys Leu
1               5

<210> SEQ ID NO 5
<211> LENGTH: 133
<212> TYPE: PRT
<213> ORGANISM: Homo sapiens

<400> SEQUENCE: 5

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 6
<211> LENGTH: 133
<212> TYPE: PRT
<213> ORGANISM: Artificial Sequence
<220> FEATURE:
<223> OTHER INFORMATION: SYNTHESIZED

<400> SEQUENCE: 6

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Ala Met Leu Thr Lys Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
        130

<210> SEQ ID NO 7
<211> LENGTH: 152
<212> TYPE: PRT
<213> ORGANISM: Artificial Sequence
<220> FEATURE:
<223> OTHER INFORMATION: SYNTHESIZED

<400> SEQUENCE: 7

His Lys Leu Ala Phe Asn Phe Asn Leu Glu Ile Asn Gly Ser Asp Thr
1               5                   10                  15

His Ser Thr Val Asp Val Tyr Leu Asp Asp Ser Gln Ile Ile Thr Phe
            20                  25                  30

Asp Gly Lys Asp Ile Arg Pro Thr Ile Pro Phe Met Ile Gly Asp Glu
        35                  40                  45

Ile Phe Leu Pro Phe Tyr Lys Asn Val Phe Ser Glu Phe Phe Ser Leu
    50                  55                  60

Phe Arg Arg Val Pro Thr Ser Thr Pro Tyr Glu Asp Leu Thr Tyr Phe
65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
```

```
                100             105              110
Lys Asn Met Trp Leu Thr Thr Ser Glu Phe Arg Leu Lys Lys Trp Phe
        115                 120                 125
Asp Gly Glu Asp Cys Ile Met His Leu Arg Ser Leu Val Arg Lys Met
    130                 135                 140
Glu Asp Ser Lys Arg Asn Thr Gly
145                 150
```

```
<210> SEQ ID NO 8
<211> LENGTH: 28
<212> TYPE: PRT
<213> ORGANISM: Artificial Sequence
<220> FEATURE:
<223> OTHER INFORMATION: SYNTHESIZED

<400> SEQUENCE: 8

Gly Ser Ser Gly Ser Ser Asp Tyr Lys Asp Asp Asp Lys His His
1               5                   10                  15

His His His His His Gly Ser Ser Gly Ser Ser
            20                  25
```

```
<210> SEQ ID NO 9
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 9

Asp Tyr Lys Asp Asp Asp Lys
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 10

Tyr Pro Tyr Asp Val Pro Asp Tyr Ala
1               5
```

```
<210> SEQ ID NO 11
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 11

Glu Gln Lys Leu Ile Ser Glu Glu Asp Leu
1               5                   10
```

```
<210> SEQ ID NO 12
<211> LENGTH: 14
<212> TYPE: PRT
<213> ORGANISM: Artificial Sequence
<220> FEATURE:
<223> OTHER INFORMATION: SYNTHESIZED

<400> SEQUENCE: 12

Gly Lys Pro Ile Pro Asn Pro Leu Leu Gly Leu Asp Ser Thr
1               5                   10
```

```
<210> SEQ ID NO 13
<211> LENGTH: 150
<212> TYPE: PRT
<213> ORGANISM: Cowpox virus

<400> SEQUENCE: 13
```

Gly His Lys Leu Ala Phe Asn Phe Asn Leu Glu Ile Asn Gly Ser Asp
1               5                   10                  15

Thr His Ser Thr Val Asp Val Tyr Leu Asp Asp Ser Gln Ile Ile Thr
            20                  25                  30

Phe Asp Gly Lys Asp Ile Arg Pro Thr Ile Pro Phe Met Ile Gly Asp
        35                  40                  45

Glu Ile Phe Leu Pro Phe Tyr Lys Asn Val Phe Ser Glu Phe Phe Ser
    50                  55                  60

Leu Phe Arg Arg Val Pro Thr Ser Thr Pro Tyr Glu Asp Leu Thr Tyr
65                  70                  75                  80

Phe Tyr Glu Cys Asp Tyr Thr Asp Asn Lys Ser Thr Phe Asp Gln Phe
                85                  90                  95

Tyr Leu Tyr Asn Gly Glu Glu Tyr Thr Val Lys Thr Gln Glu Ala Thr
            100                 105                 110

Asn Lys Asn Met Trp Leu Thr Thr Ser Glu Phe Arg Leu Lys Lys Trp
        115                 120                 125

Phe Asp Gly Glu Asp Cys Ile Met His Leu Arg Ser Leu Val Arg Lys
    130                 135                 140

Met Glu Asp Ser Lys Arg
145                 150

```
<210> SEQ ID NO 14
<211> LENGTH: 150
<212> TYPE: PRT
<213> ORGANISM: Monkeypox virus

<400> SEQUENCE: 14
```

His Lys Leu Val His Tyr Phe Asn Leu Lys Ile Asn Gly Ser Asp Ile
1               5                   10                  15

Thr Asn Thr Ala Asp Ile Leu Leu Asp Asn Tyr Pro Ile Met Thr Phe
            20                  25                  30

Asp Gly Lys Asp Ile Tyr Pro Ser Ile Ala Phe Met Val Gly Asn Lys
        35                  40                  45

Leu Phe Leu Asp Leu Tyr Lys Asn Ile Phe Val Glu Phe Phe Arg Leu
    50                  55                  60

Phe Arg Val Ser Val Ser Ser Gln Tyr Glu Glu Leu Glu Tyr Tyr Tyr
65                  70                  75                  80

Ser Cys Asp Tyr Thr Asn Asn Arg Pro Thr Ile Lys Gln His Tyr Phe
                85                  90                  95

Tyr Asn Gly Glu Glu Tyr Thr Glu Ile Asp Arg Ser Lys Lys Ala Thr
            100                 105                 110

Asn Lys Asn Ser Trp Leu Ile Thr Ser Gly Phe Arg Leu Gln Lys Trp
        115                 120                 125

Phe Asp Ser Glu Asp Cys Ile Ile Tyr Leu Arg Ser Leu Val Arg Arg
    130                 135                 140

Met Glu Asp Ser Asn Lys
145                 150

```
<210> SEQ ID NO 15
<211> LENGTH: 181
```

```
<212> TYPE: PRT
<213> ORGANISM: Homo sapiens

<400> SEQUENCE: 15

Met Glu Pro His Ser Leu Arg Tyr Asn Leu Thr Val Leu Ser Trp Asp
1               5                   10                  15

Gly Ser Val Gln Ser Gly Phe Leu Thr Glu Val His Leu Asp Gly Gln
            20                  25                  30

Pro Phe Leu Arg Cys Arg Asp Arg Gln Lys Cys Arg Ala Lys Pro Gln
        35                  40                  45

Gly Gln Trp Ala Glu Asp Val Leu Gly Asn Lys Thr Trp Asp Arg Glu
    50                  55                  60

Thr Arg Asp Leu Thr Gly Asn Gly Lys Asp Leu Arg Met Thr Leu Ala
65                  70                  75                  80

His Ile Lys Asp Gln Lys Glu Gly Leu His Ser Leu Gln Glu Ile Arg
                85                  90                  95

Val Cys Glu Ile His Glu Asp Asn Ser Thr Arg Ser Ser Gln His Phe
            100                 105                 110

Tyr Tyr Asp Gly Glu Leu Phe Leu Ser Gln Asn Leu Glu Thr Lys Glu
        115                 120                 125

Trp Thr Met Pro Gln Ser Ser Arg Ala Gln Thr Leu Ala Met Asn Val
    130                 135                 140

Arg Asn Phe Leu Lys Glu Asp Ala Met Lys Thr Lys Thr His Tyr His
145                 150                 155                 160

Ala Met His Ala Asp Cys Leu Gln Glu Leu Arg Arg Tyr Leu Lys Ser
                165                 170                 175

Gly Val Val Leu Arg
            180

<210> SEQ ID NO 16
<211> LENGTH: 180
<212> TYPE: PRT
<213> ORGANISM: Homo sapiens

<400> SEQUENCE: 16

Met Glu Pro His Ser Leu Arg Tyr Asn Leu Met Val Leu Ser Gln Asp
1               5                   10                  15

Gly Ser Val Gln Ser Gly Phe Leu Ala Glu Gly His Leu Asp Gly Gln
            20                  25                  30

Pro Phe Leu Arg Tyr Asp Arg Gln Lys Arg Arg Ala Lys Pro Gln Gly
        35                  40                  45

Gln Trp Ala Glu Asp Val Leu Gly Ala Glu Thr Trp Asp Thr Glu Thr
    50                  55                  60

Glu Asp Leu Thr Glu Asn Gly Gln Asp Leu Arg Arg Thr Leu Thr His
65                  70                  75                  80

Ile Lys Asp Gln Lys Gly Gly Leu His Ser Leu Gln Glu Ile Arg Val
                85                  90                  95

Cys Glu Ile His Glu Asp Ser Ser Thr Arg Gly Ser Arg His Phe Tyr
            100                 105                 110

Tyr Asn Gly Glu Leu Phe Leu Ser Gln Asn Leu Glu Thr Gln Glu Ser
        115                 120                 125

Thr Val Pro Gln Ser Ser Arg Ala Gln Thr Leu Ala Met Asn Val Thr
    130                 135                 140

Asn Phe Trp Lys Glu Asp Ala Met Lys Thr Lys Thr His Tyr Arg Ala
145                 150                 155                 160
```

```
Met Gln Ala Asp Cys Leu Gln Lys Leu Gln Arg Tyr Leu Lys Ser Gly
                165                 170                 175

Val Ala Ile Arg
            180

<210> SEQ ID NO 17
<211> LENGTH: 178
<212> TYPE: PRT
<213> ORGANISM: Homo sapiens

<400> SEQUENCE: 17

Asp Ala His Ser Leu Trp Tyr Asn Phe Thr Ile Ile His Leu Pro Arg
1               5                   10                  15

His Gly Gln Gln Trp Cys Glu Val Gln Ser Gln Val Asp Gln Lys Asn
            20                  25                  30

Phe Leu Ser Tyr Asp Cys Gly Ser Asp Lys Val Leu Ser Met Gly His
        35                  40                  45

Leu Glu Glu Gln Leu Tyr Ala Thr Asp Ala Trp Gly Lys Gln Leu Glu
    50                  55                  60

Met Leu Arg Glu Val Gly Gln Arg Leu Arg Leu Glu Leu Ala Asp Thr
65                  70                  75                  80

Glu Leu Glu Asp Phe Thr Pro Ser Gly Pro Leu Thr Leu Gln Val Arg
                85                  90                  95

Met Ser Cys Glu Cys Glu Ala Asp Gly Tyr Ile Arg Gly Ser Trp Gln
            100                 105                 110

Phe Ser Phe Asp Gly Arg Lys Phe Leu Leu Phe Asp Ser Asn Asn Arg
        115                 120                 125

Lys Trp Thr Val Val His Ala Gly Ala Arg Arg Met Lys Glu Lys Trp
    130                 135                 140

Glu Lys Asp Ser Gly Leu Thr Thr Phe Phe Lys Met Val Ser Met Arg
145                 150                 155                 160

Asp Cys Lys Ser Trp Leu Arg Asp Phe Leu Met His Arg Lys Lys Arg
                165                 170                 175

Leu Glu

<210> SEQ ID NO 18
<211> LENGTH: 174
<212> TYPE: PRT
<213> ORGANISM: Homo sapiens

<400> SEQUENCE: 18

Asp Ala His Ser Leu Arg Cys Asn Leu Thr Ile Lys Asp Pro Thr Pro
1               5                   10                  15

Ala Asp Pro Leu Trp Tyr Glu Ala Lys Cys Phe Val Gly Glu Ile Leu
            20                  25                  30

Ile Leu His Leu Ser Asn Ile Asn Lys Thr Met Thr Ser Gly Asp Pro
        35                  40                  45

Gly Glu Thr Ala Asn Ala Thr Glu Val Lys Lys Cys Leu Thr Gln Pro
    50                  55                  60

Leu Lys Asn Leu Cys Gln Lys Leu Arg Asn Lys Val Ser Asn Thr Lys
65                  70                  75                  80

Val Asp Thr His Lys Thr Asn Gly Tyr Pro His Leu Gln Val Thr Met
                85                  90                  95

Ile Tyr Pro Gln Ser Gln Gly Arg Thr Pro Ser Ala Thr Trp Glu Phe
            100                 105                 110

Asn Ile Ser Asp Ser Tyr Phe Phe Thr Phe Tyr Thr Glu Asn Met Ser
```

```
              115                 120                 125
Trp Arg Ser Ala Asn Asp Glu Ser Gly Val Ile Met Asn Lys Trp Lys
        130                 135                 140

Asp Asp Gly Glu Phe Val Lys Gln Leu Lys Phe Leu Ile His Glu Cys
145                 150                 155                 160

Ser Gln Lys Met Asp Glu Phe Leu Lys Gln Ser Lys Glu Lys
                165                 170
```

```
<210> SEQ ID NO 19
<211> LENGTH: 16
<212> TYPE: PRT
<213> ORGANISM: Homo sapiens

<400> SEQUENCE: 19

Leu Thr Ile Ile Glu Met Gln Lys Gly Asp Cys Ala Leu Tyr Ala Ser
1               5                   10                  15

<210> SEQ ID NO 20
<211> LENGTH: 16
<212> TYPE: PRT
<213> ORGANISM: Chlorocebus sabaeus

<400> SEQUENCE: 20

Leu Thr Ile Ile Glu Met Gln Lys Gly Glu Cys Ala Leu Tyr Ala Ser
1               5                   10                  15

<210> SEQ ID NO 21
<211> LENGTH: 16
<212> TYPE: PRT
<213> ORGANISM: Callithrix jacchus

<400> SEQUENCE: 21

Leu Thr Ile Ile Glu Met Gln Lys Gly Asp Cys Ala Val Tyr Ala Ser
1               5                   10                  15

<210> SEQ ID NO 22
<211> LENGTH: 16
<212> TYPE: PRT
<213> ORGANISM: Mus musculus

<400> SEQUENCE: 22

Leu Thr Leu Val Glu Ile Pro Lys Gly Ser Cys Ala Val Tyr Gly Ser
1               5                   10                  15

<210> SEQ ID NO 23
<211> LENGTH: 16
<212> TYPE: PRT
<213> ORGANISM: Rattus rattus

<400> SEQUENCE: 23

Leu Thr Leu Val Lys Thr Pro Ser Gly Thr Cys Ala Val Tyr Gly Ser
1               5                   10                  15

<210> SEQ ID NO 24
<211> LENGTH: 16
<212> TYPE: PRT
<213> ORGANISM: Cavia porcellus

<400> SEQUENCE: 24

Leu Thr Leu Met Asp Thr Gln Asn Gly Lys Cys Ala Leu Tyr Gly Ser
1               5                   10                  15

<210> SEQ ID NO 25
```

-continued

```
<211> LENGTH: 16
<212> TYPE: PRT
<213> ORGANISM: Marmotini

<400> SEQUENCE: 25

Leu Thr Leu Val Glu Met Gln Asn Gly Thr Cys Ile Val Tyr Gly Ser
1               5                   10                  15

<210> SEQ ID NO 26
<211> LENGTH: 16
<212> TYPE: PRT
<213> ORGANISM: Peromyscus keeni

<400> SEQUENCE: 26

Leu Thr Val Val Glu Met Gln Ser Gly Ser Cys Ala Val Tyr Gly Ser
1               5                   10                  15

<210> SEQ ID NO 27
<211> LENGTH: 16
<212> TYPE: PRT
<213> ORGANISM: Heterocephalus glaber

<400> SEQUENCE: 27

Leu Ser Met Val Glu Met Gln Asn Gly Thr Cys Ala Val Tyr Ala Ser
1               5                   10                  15

<210> SEQ ID NO 28
<211> LENGTH: 16
<212> TYPE: PRT
<213> ORGANISM: Microtus ochrogaster

<400> SEQUENCE: 28

Leu Thr Leu Val Glu Met Gln Arg Gly Ser Cys Ala Val Tyr Gly Ser
1               5                   10                  15

<210> SEQ ID NO 29
<211> LENGTH: 16
<212> TYPE: PRT
<213> ORGANISM: Sorex araneus

<400> SEQUENCE: 29

Val Ser Ile Val Glu Met Gln Gly Gly Asn Cys Ala Val Tyr Gly Ser
1               5                   10                  15

<210> SEQ ID NO 30
<211> LENGTH: 16
<212> TYPE: PRT
<213> ORGANISM: Condylura cristata

<400> SEQUENCE: 30

Val Thr Val Tyr Glu Met Gln Asn Gly Ser Cys Ala Val Tyr Gly Ser
1               5                   10                  15

<210> SEQ ID NO 31
<211> LENGTH: 16
<212> TYPE: PRT
<213> ORGANISM: Cricetulus griseus

<400> SEQUENCE: 31

Leu Thr Leu Val Glu Met Gln Asn Gly Ser Cys Ala Val Tyr Gly Ser
1               5                   10                  15

<210> SEQ ID NO 32
<211> LENGTH: 16
<212> TYPE: PRT
```

<213> ORGANISM: Felis catus

<400> SEQUENCE: 32

Leu Thr Met Val Asp Met Gln Asn Gly Thr Cys Ala Val Tyr Gly Ser
1               5                   10                  15

<210> SEQ ID NO 33
<211> LENGTH: 5
<212> TYPE: PRT
<213> ORGANISM: Cowpox virus

<400> SEQUENCE: 33

Ala Ser Ser Phe Lys
1               5

<210> SEQ ID NO 34
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 34

Tyr Ile Asn Met
1

<210> SEQ ID NO 35
<211> LENGTH: 108
<212> TYPE: PRT
<213> ORGANISM: Artificial Sequence
<220> FEATURE:
<223> OTHER INFORMATION: SYNTHESIZED

<400> SEQUENCE: 35

Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
                20                  25                  30

His Trp Tyr Gln Gln Lys Pro Gly Gln Ala Pro Val Leu Val Ile Tyr
            35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
                85                  90                  95

Trp Val Phe Gly Gly Gly Thr Gln Leu Thr Val Leu
            100                 105

<210> SEQ ID NO 36
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 36

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val

```
                35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Phe Gly Tyr Tyr Leu Asp Tyr Trp Gly Gln Gly Thr
            100                 105                 110

Leu Val Thr Val Ser Ser
            115

<210> SEQ ID NO 37
<211> LENGTH: 110
<212> TYPE: PRT
<213> ORGANISM: Artificial Sequence
<220> FEATURE:
<223> OTHER INFORMATION: SYNTHESIZED

<400> SEQUENCE: 37

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
     50                 55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu
            100                 105                 110

<210> SEQ ID NO 38
<211> LENGTH: 121
<212> TYPE: PRT
<213> ORGANISM: Artificial Sequence
<220> FEATURE:
<223> OTHER INFORMATION: SYNTHESIZED

<400> SEQUENCE: 38

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110
```

```
Gln Gly Thr Thr Val Thr Val Ser Ser
        115                 120
```

```
<210> SEQ ID NO 39
<211> LENGTH: 246
<212> TYPE: PRT
<213> ORGANISM: Artificial Sequence
<220> FEATURE:
<223> OTHER INFORMATION: SYNTHESIZED

<400> SEQUENCE: 39

Gln Pro Val Leu Thr Gln Pro Ser Ser Val Ser Val Ala Pro Gly Glu
1               5                   10                  15

Thr Ala Arg Ile Pro Cys Gly Gly Asp Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
                85                  90                  95

Trp Val Phe Gly Gly Gly Thr Gln Leu Thr Val Leu Gly Gly Gly Gly
            100                 105                 110

Ser Gly Gly Gly Gly Ser Gly Gly Gly Ser Gly Gly Gly Gly Ser
        115                 120                 125

Glu Val Gln Leu Val Glu Ser Gly Gly Val Val Gln Pro Gly Gly
    130                 135                 140

Ser Leu Arg Leu Ser Cys Ala Ala Ser Gly Phe Thr Phe Ser Ser Tyr
145                 150                 155                 160

Gly Met His Trp Val Arg Gln Ala Pro Gly Lys Gly Leu Glu Trp Val
                165                 170                 175

Ala Phe Ile Arg Tyr Asp Gly Ser Asn Lys Tyr Tyr Ala Asp Ser Val
            180                 185                 190

Lys Gly Arg Phe Thr Ile Ser Arg Asp Asn Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Lys Asp Arg Phe Gly Tyr Tyr Leu Asp Tyr Trp Gly Gln Gly Thr
225                 230                 235                 240

Leu Val Thr Val Ser Ser
                245
```

```
<210> SEQ ID NO 40
<211> LENGTH: 246
<212> TYPE: PRT
<213> ORGANISM: Artificial Sequence
<220> FEATURE:
<223> OTHER INFORMATION: SYNTHESIZED

<400> SEQUENCE: 40

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45
```

Ala Phe Ile Arg Tyr Asp Gly Ser Asn Lys Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Phe Gly Tyr Tyr Leu Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Gly Gly Gly Ser Gln Pro Val Leu Thr Gln
            130                 135                 140

Pro Ser Ser Val Ser Val Ala Pro Gly Glu Thr Ala Arg Ile Pro Cys
145                 150                 155                 160

Gly Gly Asp Asp Ile Glu Thr Lys Ser Val His Trp Tyr Gln Gln Lys
                165                 170                 175

Pro Gly Gln Ala Pro Val Leu Val Ile Tyr Asp Asp Asp Arg Pro
                180                 185                 190

Ser Gly Ile Pro Glu Arg Phe Phe Gly Ser Asn Ser Gly Asn Thr Ala
            195                 200                 205

Thr Leu Ser Ile Ser Arg Val Glu Ala Gly Asp Glu Ala Asp Tyr Tyr
210                 215                 220

Cys Gln Val Trp Asp Asp Asn Asn Asp Glu Trp Val Phe Gly Gly Gly
225                 230                 235                 240

Thr Gln Leu Thr Val Leu
                245

<210> SEQ ID NO 41
<211> LENGTH: 251
<212> TYPE: PRT
<213> ORGANISM: Artificial Sequence
<220> FEATURE:
<223> OTHER INFORMATION: SYNTHESIZED
<400> SEQUENCE: 41

Gln Ser Ala Leu Thr Gln Pro Ala Ser Val Ser Gly Ser Pro Gly Gln
  1               5                  10                  15

Ser Ile Thr Ile Ser Cys Ser Gly Ser Ser Ser Asn Ile Gly Asn Asn
                 20                  25                  30

Ala Val Asn Trp Tyr Gln Gln Leu Pro Gly Lys Ala Pro Lys Leu Leu
             35                  40                  45

Ile Tyr Tyr Asp Asp Leu Leu Pro Ser Gly Val Ser Asp Arg Phe Ser
 50                  55                  60

Gly Ser Lys Ser Gly Thr Ser Ala Phe Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Gly Pro Val Phe Gly Gly Gly Thr Lys Leu Thr Val Leu Gly Gly
                100                 105                 110

Gly Gly Ser Gly Gly Gly Gly Ser Gly Gly Gly Gly Ser Gly Gly Gly
            115                 120                 125

Gly Ser Gln Val Gln Leu Val Glu Ser Gly Gly Gly Leu Val Lys Pro
            130                 135                 140

Gly Gly Ser Leu Arg Leu Ser Cys Ala Ala Ser Gly Phe Thr Phe Ser
145                 150                 155                 160

```
Ser Tyr Gly Met His Trp Val Arg Gln Ala Pro Gly Lys Gly Leu Glu
                165                 170                 175

Trp Val Ala Phe Ile Arg Tyr Asp Gly Ser Asn Lys Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Lys Asp Arg Gly Leu Gly Asp Gly Thr Tyr Phe Asp Tyr
225                 230                 235                 240

Trp Gly Gln Gly Thr Thr Val Thr Val Ser Ser
                245                 250
```

<210> SEQ ID NO 42
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 42

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val
        115
```

<210> SEQ ID NO 43
<211> LENGTH: 407
<212> TYPE: PRT
<213> ORGANISM: Artificial Sequence
<220> FEATURE:
<223> OTHER INFORMATION: SYNTHESIZED

<400> SEQUENCE: 43

```
Gln Pro Val Leu Thr Gln Pro Ser Ser Val Ser Val Ala Pro Gly Glu
1               5                   10                  15

Thr Ala Arg Ile Pro Cys Gly Gly Asp Ile Glu Thr Lys Ser Val
            20                  25                  30

His Trp Tyr Gln Gln Lys Pro Gly Gln Ala Pro Val Leu Val Ile Tyr
        35                  40                  45

Asp Asp Asp Asp Arg Pro Ser Gly Ile Pro Glu Arg Phe Phe Gly Ser
    50                  55                  60

Asn Ser Gly Asn Thr Ala Thr Leu Ser Ile Ser Arg Val Glu Ala Gly
65                  70                  75                  80

Asp Glu Ala Asp Tyr Tyr Cys Gln Val Trp Asp Asp Asn Asn Asp Glu
```

```
                    85                  90                  95
Trp Val Phe Gly Gly Gly Thr Gln Leu Thr Val Leu Gly Gly Gly
                100                 105                 110
Ser Gly Gly Gly Gly Ser Gly Gly Gly Ser Gly Gly Gly Gly Ser
                115                 120                 125
Glu Val Gln Leu Val Glu Ser Gly Gly Val Val Gln Pro Gly Gly
                130                 135                 140
Ser Leu Arg Leu Ser Cys Ala Ala Ser Gly Phe Thr Phe Ser Ser Tyr
145                 150                 155                 160
Gly Met His Trp Val Arg Gln Ala Pro Gly Lys Gly Leu Glu Trp Val
                165                 170                 175
Ala Phe Ile Arg Tyr Asp Gly Ser Asn Lys Tyr Tyr Ala Asp Ser Val
                180                 185                 190
Lys Gly Arg Phe Thr Ile Ser Arg Asp Asn Ser Lys Asn Thr Leu Tyr
                195                 200                 205
Leu Gln Met Asn Ser Leu Arg Ala Glu Asp Thr Ala Val Tyr Tyr Cys
                210                 215                 220
Ala Lys Asp Arg Phe Gly Tyr Tyr Leu Asp Tyr Trp Gly Gln Gly Thr
225                 230                 235                 240
Leu Val Thr Val Ser Ser Gly Gly Ser Ser Gly Ser Ser Gly Ser Ser
                245                 250                 255
His His His His His His His Gly Gly Ser Ser Gly Ser Ser Gly
                260                 265                 270
Ser Ser Ala Pro Thr Ser Ser Ser Thr Lys Lys Thr Gln Leu Gln Leu
                275                 280                 285
Glu His Leu Leu Leu Asp Leu Gln Met Ile Leu Asn Gly Ile Asn Asn
                290                 295                 300
Tyr Lys Asn Pro Lys Leu Thr Ala Met Leu Thr Lys Lys Phe Tyr Met
305                 310                 315                 320
Pro Lys Lys Ala Thr Glu Leu Lys His Leu Gln Cys Leu Glu Glu Glu
                325                 330                 335
Leu Lys Pro Leu Glu Glu Val Leu Asn Leu Ala Gln Ser Lys Asn Phe
                340                 345                 350
His Leu Arg Pro Arg Asp Leu Ile Ser Asn Ile Asn Val Ile Val Leu
                355                 360                 365
Glu Leu Lys Gly Ser Glu Thr Thr Phe Met Cys Glu Tyr Ala Asp Glu
                370                 375                 380
Thr Ala Thr Ile Val Glu Phe Leu Asn Arg Trp Ile Thr Phe Ser Gln
385                 390                 395                 400
Ser Ile Ile Ser Thr Leu Thr
                405

<210> SEQ ID NO 44
<211> LENGTH: 407
<212> TYPE: PRT
<213> ORGANISM: Artificial Sequence
<220> FEATURE:
<223> OTHER INFORMATION: SYNTHESIZED

<400> SEQUENCE: 44

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Tyr
                20                  25                  30
Gly Met His Trp Val Arg Gln Ala Pro Gly Lys Gly Leu Glu Trp Val
```

```
                35                  40                  45
Ala Phe Ile Arg Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Phe Gly Tyr Tyr Leu Asp Tyr Trp Gly Gln Gly Thr
                100                 105                 110

Leu Val Thr Val Ser Ser Gly Gly Gly Gly Ser Gly Gly Gly Gly Ser
                115                 120                 125

Gly Gly Gly Gly Ser Gly Gly Gly Ser Gln Pro Val Leu Thr Gln
130                 135                 140

Pro Ser Ser Val Ser Val Ala Pro Gly Glu Thr Ala Arg Ile Pro Cys
145                 150                 155                 160

Gly Gly Asp Asp Ile Glu Thr Lys Ser Val His Trp Tyr Gln Gln Lys
                165                 170                 175

Pro Gly Gln Ala Pro Val Leu Val Ile Tyr Asp Asp Asp Arg Pro
                180                 185                 190

Ser Gly Ile Pro Glu Arg Phe Phe Gly Ser Asn Ser Gly Asn Thr Ala
                195                 200                 205

Thr Leu Ser Ile Ser Arg Val Glu Ala Gly Asp Glu Ala Asp Tyr Tyr
210                 215                 220

Cys Gln Val Trp Asp Asp Asn Asn Asp Glu Trp Val Phe Gly Gly
225                 230                 235                 240

Thr Gln Leu Thr Val Leu Gly Gly Ser Ser Gly Ser Ser Gly Ser Ser
                245                 250                 255

His His His His His His His Gly Gly Ser Ser Gly Ser Ser Gly
                260                 265                 270

Ser Ser Ala Pro Thr Ser Ser Ser Thr Lys Lys Thr Gln Leu Gln Leu
                275                 280                 285

Glu His Leu Leu Leu Asp Leu Gln Met Ile Leu Asn Gly Ile Asn Asn
290                 295                 300

Tyr Lys Asn Pro Lys Leu Thr Ala Met Leu Thr Lys Lys Phe Tyr Met
305                 310                 315                 320

Pro Lys Lys Ala Thr Glu Leu Lys His Leu Gln Cys Leu Glu Glu Glu
                325                 330                 335

Leu Lys Pro Leu Glu Glu Val Leu Asn Leu Ala Gln Ser Lys Asn Phe
                340                 345                 350

His Leu Arg Pro Arg Asp Leu Ile Ser Asn Ile Asn Val Ile Val Leu
                355                 360                 365

Glu Leu Lys Gly Ser Glu Thr Thr Phe Met Cys Glu Tyr Ala Asp Glu
                370                 375                 380

Thr Ala Thr Ile Val Glu Phe Leu Asn Arg Trp Ile Thr Phe Ser Gln
385                 390                 395                 400

Ser Ile Ile Ser Thr Leu Thr
                405

<210> SEQ ID NO 45
<211> LENGTH: 412
<212> TYPE: PRT
<213> ORGANISM: Artificial Sequence
<220> FEATURE:
<223> OTHER INFORMATION: SYNTHESIZED
```

```
<400> SEQUENCE: 45

Gln Ser Ala Leu Thr Gln Pro Ala Ser Val Ser Gly Ser Pro Gly Gln
1               5                   10                  15

Ser Ile Thr Ile Ser Cys Ser Gly Ser Ser Ser Asn Ile Gly Asn Asn
            20                  25                  30

Ala Val Asn Trp Tyr Gln Gln Leu Pro Gly Lys Ala Pro Lys Leu Leu
        35                  40                  45

Ile Tyr Tyr Asp Asp Leu Leu Pro Ser Gly Val Ser Asp Arg Phe Ser
    50                  55                  60

Gly Ser Lys Ser Gly Thr Ser Ala Phe Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gly
            100                 105                 110

Gly Gly Ser Gly Gly Gly Gly Ser Gly Gly Gly Gly Ser Gly Gly Gly
            115                 120                 125

Gly Ser Gln Val Gln Leu Val Glu Ser Gly Gly Gly Leu Val Lys Pro
        130                 135                 140

Gly Gly Ser Leu Arg Leu Ser Cys Ala Ala Ser Gly Phe Thr Phe Ser
145                 150                 155                 160

Ser Tyr Gly Met His Trp Val Arg Gln Ala Pro Gly Lys Gly Leu Glu
                165                 170                 175

Trp Val Ala Phe Ile Arg Tyr Asp Gly Ser Asn Lys Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Lys Asp Arg Gly Leu Gly Asp Gly Thr Tyr Phe Asp Tyr
225                 230                 235                 240

Trp Gly Gln Gly Thr Thr Val Thr Val Ser Ser Gly Gly Ser Ser Gly
                245                 250                 255

Ser Ser Gly Ser Ser His His His His His His Gly Gly Ser
            260                 265                 270

Ser Gly Ser Ser Gly Ser Ser Ala Pro Thr Ser Ser Ser Thr Lys Lys
        275                 280                 285

Thr Gln Leu Gln Leu Glu His Leu Leu Leu Asp Leu Gln Met Ile Leu
    290                 295                 300

Asn Gly Ile Asn Asn Tyr Lys Asn Pro Lys Leu Thr Ala Met Leu Thr
305                 310                 315                 320

Lys Lys Phe Tyr Met Pro Lys Lys Ala Thr Glu Leu Lys His Leu Gln
                325                 330                 335

Cys Leu Glu Glu Glu Leu Lys Pro Leu Glu Glu Val Leu Asn Leu Ala
            340                 345                 350

Gln Ser Lys Asn Phe His Leu Arg Pro Arg Asp Leu Ile Ser Asn Ile
        355                 360                 365

Asn Val Ile Val Leu Glu Leu Lys Gly Ser Glu Thr Thr Phe Met Cys
    370                 375                 380

Glu Tyr Ala Asp Glu Thr Ala Thr Ile Val Glu Phe Leu Asn Arg Trp
385                 390                 395                 400

Ile Thr Phe Ser Gln Ser Ile Ile Ser Thr Leu Thr
                405                 410
```

<210> SEQ ID NO 46
<211> LENGTH: 412
<212> TYPE: PRT
<213> ORGANISM: Artificial Sequence
<220> FEATURE:
<223> OTHER INFORMATION: SYNTHESIZED

<400> SEQUENCE: 46

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Gly Asp Gly Thr Tyr Phe Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Gly Ser Gly Gly Gly Gly Ser Gln Ser Ala
    130                 135                 140

Leu Thr Gln Pro Ala Ser Val Ser Gly Ser Pro Gly Gln Ser Ile Thr
145                 150                 155                 160

Ile Ser Cys Ser Gly Ser Ser Asn Ile Gly Asn Asn Ala Val Asn
                165                 170                 175

Trp Tyr Gln Gln Leu Pro Gly Lys Ala Pro Lys Leu Leu Ile Tyr Tyr
            180                 185                 190

Asp Asp Leu Leu Pro Ser Gly Val Ser Asp Arg Phe Ser Gly Ser Lys
        195                 200                 205

Ser Gly Thr Ser Ala Phe Leu Ala Ile Ser Gly Leu Gln Ser Glu Asp
    210                 215                 220

Glu Ala Asp Tyr Tyr Cys Ala Ala Trp Asp Asp Ser Leu Asn Gly Pro
225                 230                 235                 240

Val Phe Gly Gly Gly Thr Lys Leu Thr Val Leu Gly Gly Ser Ser Gly
                245                 250                 255

Ser Ser Gly Ser Ser His His His His His His His Gly Gly Ser
            260                 265                 270

Ser Gly Ser Gly Ser Ser Ala Pro Thr Ser Ser Ser Thr Lys Lys
        275                 280                 285

Thr Gln Leu Gln Leu Glu His Leu Leu Leu Asp Leu Gln Met Ile Leu
    290                 295                 300

Asn Gly Ile Asn Asn Tyr Lys Asn Pro Lys Leu Thr Ala Met Leu Thr
305                 310                 315                 320

Lys Lys Phe Tyr Met Pro Lys Lys Ala Thr Glu Leu Lys His Leu Gln
                325                 330                 335

Cys Leu Glu Glu Glu Leu Lys Pro Leu Glu Glu Val Leu Asn Leu Ala
            340                 345                 350

Gln Ser Lys Asn Phe His Leu Arg Pro Arg Asp Leu Ile Ser Asn Ile
        355                 360                 365

```
Asn Val Ile Val Leu Glu Leu Lys Gly Ser Glu Thr Thr Phe Met Cys
        370                 375                 380

Glu Tyr Ala Asp Glu Thr Ala Thr Ile Val Glu Phe Leu Asn Arg Trp
385                 390                 395                 400

Ile Thr Phe Ser Gln Ser Ile Ile Ser Thr Leu Thr
            405                 410
```

<210> SEQ ID NO 47
<211> LENGTH: 840
<212> TYPE: DNA
<213> ORGANISM: Artificial Sequence
<220> FEATURE:
<223> OTHER INFORMATION: SYNTHESIZED

<400> SEQUENCE: 47

```
gccttcaccg tgactgtgcc caaggatctg tacgtcgtgg agtacggctc caacatgaca      60
atcgagtgca agttccccgt ggagaagcag ctggacctgg cggcactgat cgtgtactgg     120
gagatggagg acaagaacat catccagttc gttcatggcg aagaggatct caaggtgcag     180
cacagcagct acaggcagag ggcccgactg ctgaaggacc agctgagcct gggcaacgcc     240
gcactgcaaa tcaccgacgt gaagctgcag gacgctggcg tgtacaggtg tatgataagc     300
tacggcggag ctgactacaa gagaatcacg gttaaggtaa acgcccccta cggggggcagt    360
agcggaagct ccggctcaag ccaccaccat catcatcatc accacggcgg cagcagcggg     420
agctcaggta gcagtggtgg ggcacctacc tcttccagca ccaagaagac gcagctccag     480
ttggaacacc ttctccttga cctccagatg atcctgaacg gcatcaacaa ctacaaaaat     540
cccaagctga ccgcgatgct gacgaagaaa ttctacatgc aaagaaggc caccgagctg     600
aaacacctgc agtgtcttga ggaggaactt aagccgctcg aggaggtact gaacctggcc     660
cagagtaaga acttccacct gaggcccagg gacctcatca gcaacatcaa tgtgatcgtc     720
cttgagctta agggcagcga gaccaccttc atgtgcgagt atgcggacga aacggccaca     780
atcgtcgagt ttctgaatag gtggatcact ttcagccaga gcatcatctc tacccctgacc    840
```

<210> SEQ ID NO 48
<211> LENGTH: 280
<212> TYPE: PRT
<213> ORGANISM: Artificial Sequence
<220> FEATURE:
<223> OTHER INFORMATION: SYNTHESIZED

<400> SEQUENCE: 48

```
Ala Phe Thr Val Thr Val Pro Lys Asp Leu Tyr Val Val Glu Tyr Gly
1               5                   10                  15

Ser Asn Met Thr Ile Glu Cys Lys Phe Pro Val Glu Lys Gln Leu Asp
            20                  25                  30

Leu Ala Ala Leu Ile Val Tyr Trp Glu Met Glu Asp Lys Asn Ile Ile
        35                  40                  45

Gln Phe Val His Gly Glu Glu Asp Leu Lys Val Gln His Ser Ser Tyr
    50                  55                  60

Arg Gln Arg Ala Arg Leu Leu Lys Asp Gln Leu Ser Leu Gly Asn Ala
65                  70                  75                  80

Ala Leu Gln Ile Thr Asp Val Lys Leu Gln Asp Ala Gly Val Tyr Arg
                85                  90                  95

Cys Met Ile Ser Tyr Gly Gly Ala Asp Tyr Lys Arg Ile Thr Val Lys
            100                 105                 110
```

```
Val Asn Ala Pro Tyr Gly Gly Ser Gly Ser Ser Gly Ser Ser His
            115                 120                 125

His His His His His His Gly Gly Ser Ser Gly Ser Ser Gly Ser
    130                 135                 140

Ser Gly Gly Ala Pro Thr Ser Ser Thr Lys Lys Thr Gln Leu Gln
145                 150                 155                 160

Leu Glu His Leu Leu Leu Asp Leu Gln Met Ile Leu Asn Gly Ile Asn
                165                 170                 175

Asn Tyr Lys Asn Pro Lys Leu Thr Ala Met Leu Thr Lys Lys Phe Tyr
                180                 185                 190

Met Pro Lys Lys Ala Thr Glu Leu Lys His Leu Gln Cys Leu Glu Glu
            195                 200                 205

Glu Leu Lys Pro Leu Glu Glu Val Leu Asn Leu Ala Gln Ser Lys Asn
    210                 215                 220

Phe His Leu Arg Pro Arg Asp Leu Ile Ser Asn Ile Asn Val Ile Val
225                 230                 235                 240

Leu Glu Leu Lys Gly Ser Glu Thr Thr Phe Met Cys Glu Tyr Ala Asp
                245                 250                 255

Glu Thr Ala Thr Ile Val Glu Phe Leu Asn Arg Trp Ile Thr Phe Ser
            260                 265                 270

Gln Ser Ile Ile Ser Thr Leu Thr
            275                 280

<210> SEQ ID NO 49
<211> LENGTH: 771
<212> TYPE: DNA
<213> ORGANISM: Artificial Sequence
<220> FEATURE:
<223> OTHER INFORMATION: SYNTHESIZED

<400> SEQUENCE: 49
ctgtacatca tcgagcacgg cagtaacgtg accctggagt gcaacttcga caccggcagc    60
cacgtgaatc tgggcgccat cacagcttca ctgcagaagg tggagaatga cacctctccc   120
cacagggagc gagccaccct gcttgaggaa caactgcctc tcggcaaggc cagcttccac   180
atccccagg tgcaggtgag ggacgagggc cagtaccagt gcataatcat ctacggcgtg    240
gcctgggact acaagtacct gacacttaag gtgaaagcct ccggcggttc ttccggctct   300
tcaggcagct cacaccatca tcatcatcac caccatggcg gcagcagcgg gagctctggt   360
agcagtggcg gtgcccccac cagcagtagc actaagaaga cccagctgca actggagcac   420
ttgctcctgg acctgcaaat gatcctcaac ggcatcaaca actataagaa ccccaagctg   480
acggccatgc tgaccaaaaa gttctacatg cccaagaagg ccaccgagtt gaaacacttg   540
cagtgcctgg aggaggagct gaagcccctg aagaggtgc tgaacctggc ccagagcaag   600
aatttcatc tgaggcctag ggacctgatt agcaacatca cgtgatcgt gttggagctt    660
aaaggctccg agaccacctt tatgtgcgag tacgccgacg agaccgcgac tatcgtggag   720
ttcctgaaca ggtggatcac cttttcacag agcatcataa gcacactgac c            771

<210> SEQ ID NO 50
<211> LENGTH: 257
<212> TYPE: PRT
<213> ORGANISM: Artificial Sequence
<220> FEATURE:
<223> OTHER INFORMATION: SYNTHESIZED

<400> SEQUENCE: 50
```

```
Leu Tyr Ile Ile Glu His Gly Ser Asn Val Thr Leu Glu Cys Asn Phe
1               5                   10                  15

Asp Thr Gly Ser His Val Asn Leu Gly Ala Ile Thr Ala Ser Leu Gln
            20                  25                  30

Lys Val Glu Asn Asp Thr Ser Pro His Arg Glu Arg Ala Thr Leu Leu
        35                  40                  45

Glu Glu Gln Leu Pro Leu Gly Lys Ala Ser Phe His Ile Pro Gln Val
50                  55                  60

Gln Val Arg Asp Glu Gly Gln Tyr Gln Cys Ile Ile Tyr Gly Val
65                  70                  75                  80

Ala Trp Asp Tyr Lys Tyr Leu Thr Leu Lys Val Lys Ala Ser Gly Gly
                85                  90                  95

Ser Ser Gly Ser Ser Gly Ser Ser His His His His His His
            100                 105                 110

Gly Gly Ser Ser Gly Ser Ser Gly Ser Gly Ala Pro Thr Ser
            115                 120                 125

Ser Ser Thr Lys Lys Thr Gln Leu Gln Leu Glu His Leu Leu Leu Asp
        130                 135                 140

Leu Gln Met Ile Leu Asn Gly Ile Asn Asn Tyr Lys Asn Pro Lys Leu
145                 150                 155                 160

Thr Ala Met Leu Thr Lys Lys Phe Tyr Met Pro Lys Lys Ala Thr Glu
                165                 170                 175

Leu Lys His Leu Gln Cys Leu Glu Glu Leu Lys Pro Leu Glu Glu
            180                 185                 190

Val Leu Asn Leu Ala Gln Ser Lys Asn Phe His Leu Arg Pro Arg Asp
        195                 200                 205

Leu Ile Ser Asn Ile Asn Val Ile Val Leu Glu Leu Lys Gly Ser Glu
210                 215                 220

Thr Thr Phe Met Cys Glu Tyr Ala Asp Glu Thr Ala Thr Ile Val Glu
225                 230                 235                 240

Phe Leu Asn Arg Trp Ile Thr Phe Ser Gln Ser Ile Ile Ser Thr Leu
                245                 250                 255

Thr

<210> SEQ ID NO 51
<211> LENGTH: 245
<212> TYPE: PRT
<213> ORGANISM: Homo sapiens

<400> SEQUENCE: 51

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110
```

```
Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
                245
```

<210> SEQ ID NO 52
<211> LENGTH: 176
<212> TYPE: PRT
<213> ORGANISM: Homo sapiens

<400> SEQUENCE: 52

```
Met Arg Ile Phe Ala Val Phe Ile Phe Met Thr Tyr Trp His Leu Leu
1               5                   10                  15

Asn Ala Pro Tyr Asn Lys Ile Asn Gln Arg Ile Leu Val Val Asp Pro
                20                  25                  30

Val Thr Ser Glu His Glu Leu Thr Cys Gln Ala Glu Gly Tyr Pro Lys
            35                  40                  45

Ala Glu Val Ile Trp Thr Ser Ser Asp His Gln Val Leu Ser Gly Lys
        50                  55                  60

Thr Thr Thr Thr Asn Ser Lys Arg Glu Glu Lys Leu Phe Asn Val Thr
65                  70                  75                  80

Ser Thr Leu Arg Ile Asn Thr Thr Thr Asn Glu Ile Phe Tyr Cys Thr
                85                  90                  95

Phe Arg Arg Leu Asp Pro Glu Glu Asn His Thr Ala Glu Leu Val Ile
                100                 105                 110

Pro Glu Leu Pro Leu Ala His Pro Pro Asn Glu Arg Thr His Leu Val
            115                 120                 125

Ile Leu Gly Ala Ile Leu Leu Cys Leu Gly Val Ala Leu Thr Phe Ile
        130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175
```

<210> SEQ ID NO 53
<211> LENGTH: 290
<212> TYPE: PRT
<213> ORGANISM: Homo sapiens

<400> SEQUENCE: 53

```
Met Arg Ile Phe Ala Val Phe Ile Phe Met Thr Tyr Trp His Leu Leu
1               5                   10                  15
```

```
Asn Ala Phe Thr Val Thr Val Pro Lys Asp Leu Tyr Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 54
<211> LENGTH: 272
<212> TYPE: PRT
<213> ORGANISM: Homo sapiens

<400> SEQUENCE: 54

Ile Phe Leu Leu Leu Met Leu Ser Leu Glu Leu Gln Leu His Gln Ile
1               5                   10                  15

Ala Ala Leu Phe Thr Val Thr Val Pro Lys Glu Leu Tyr Ile Ile Glu
                20                  25                  30

His Gly Ser Asn Val Thr Leu Glu Cys Asn Phe Asp Thr Gly Ser His
            35                  40                  45

Val Asn Leu Gly Ala Ile Thr Ala Ser Leu Gln Lys Val Glu Asn Asp
50                  55                  60

Thr Ser Pro His Arg Glu Arg Ala Thr Leu Leu Glu Glu Gln Leu Pro
65                  70                  75                  80

Leu Gly Lys Ala Ser Phe His Ile Pro Gln Val Gln Val Arg Asp Glu
                85                  90                  95
```

Gly Gln Tyr Gln Cys Ile Ile Ile Tyr Gly Val Ala Trp Asp Tyr Lys
                100                 105                 110

Tyr Leu Thr Leu Lys Val Lys Ala Ser Tyr Arg Lys Ile Asn Thr His
            115                 120                 125

Ile Leu Lys Val Pro Glu Thr Asp Glu Val Glu Leu Thr Cys Gln Ala
130                 135                 140

Thr Gly Tyr Pro Leu Ala Glu Val Ser Trp Pro Asn Val Ser Val Pro
145                 150                 155                 160

Ala Asn Thr Ser His Ser Arg Thr Pro Glu Gly Leu Tyr Gln Val Thr
                165                 170                 175

Ser Val Leu Arg Leu Lys Pro Pro Gly Arg Asn Phe Ser Cys Val
            180                 185                 190

Phe Trp Asn Thr His Val Arg Glu Leu Thr Leu Ala Ser Ile Asp Leu
        195                 200                 205

Gln Ser Gln Met Glu Pro Arg Thr His Pro Thr Trp Leu Leu His Ile
    210                 215                 220

Phe Ile Pro Phe Cys Ile Ile Ala Phe Ile Phe Ile Ala Thr Val Ile
225                 230                 235                 240

Ala Leu Arg Lys Gln Leu Cys Gln Lys Leu Tyr Ser Ser Lys Asp Thr
                245                 250                 255

Thr Lys Arg Pro Val Thr Thr Thr Lys Arg Glu Val Asn Ser Ala Ile
            260                 265                 270

<210> SEQ ID NO 55
<211> LENGTH: 283
<212> TYPE: PRT
<213> ORGANISM: Homo sapiens

<400> SEQUENCE: 55

Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp

```
                195                 200                 205
Leu Gln Ser Gln Met Glu Pro Arg Thr His Pro Thr Trp Leu Leu His
    210                 215                 220

Ile Phe Ile Pro Phe Cys Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Lys Arg Glu Val Asn Ser Ala
            260                 265                 270

Val Asn Leu Asn Leu Trp Ser Trp Glu Pro Gly
                275                 280

<210> SEQ ID NO 56
<211> LENGTH: 183
<212> TYPE: PRT
<213> ORGANISM: Homo sapiens

<400> SEQUENCE: 56

Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Thr Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95

Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
        115                 120                 125

Leu Lys Lys Val Arg Ser Val Asn Ser Leu Met Val Ala Ser Leu Thr
    130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys Val Leu
            180

<210> SEQ ID NO 57
<211> LENGTH: 133
<212> TYPE: PRT
<213> ORGANISM: Homo sapiens

<400> SEQUENCE: 57

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Ile Asn Cys Asp
        35                  40                  45

Gly Phe Tyr Leu Ile Ser Leu Lys Gly Tyr Phe Ser Gln Glu Val Asn
```

-continued

```
            50                  55                  60
Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                     85                  90                  95

Asp Lys Val Tyr Leu Asn Val Thr Thr Asp Asn Thr Ser Leu Asp Asp
                100                 105                 110

Phe His Val Asn Gly Gly Glu Leu Ile Leu Ile His Gln Asn Pro Gly
            115                 120                 125

Glu Phe Cys Val Leu
        130

<210> SEQ ID NO 58
<211> LENGTH: 423
<212> TYPE: PRT
<213> ORGANISM: Homo sapiens

<400> SEQUENCE: 58

Gln Val Ser His Arg Tyr Pro Arg Ile Gln Ser Ile Lys Val Gln Phe
  1               5                  10                  15

Thr Glu Tyr Lys Lys Glu Lys Gly Phe Ile Leu Thr Ser Gln Lys Glu
                 20                  25                  30

Asp Glu Ile Met Lys Val Gln Asn Asn Ser Val Ile Ile Asn Cys Asp
             35                  40                  45

Gly Phe Tyr Leu Ile Ser Leu Lys Gly Tyr Phe Ser Gln Glu Val Asn
 50                  55                  60

Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                     85                  90                  95

Asp Lys Val Tyr Leu Asn Val Thr Thr Asp Asn Thr Ser Leu Asp Asp
                100                 105                 110

Phe His Val Asn Gly Gly Glu Leu Ile Leu Ile His Gln Asn Pro Gly
            115                 120                 125

Glu Phe Cys Val Leu Gly Gly Ser Gly Gly Ser Gly Gly Gly Ser
        130                 135                 140

Gly Gln Val Ser His Arg Tyr Pro Arg Ile Gln Ser Ile Lys Val Gln
145                 150                 155                 160

Phe Thr Glu Tyr Lys Lys Glu Lys Gly Phe Ile Leu Thr Ser Gln Lys
                165                 170                 175

Glu Asp Glu Ile Met Lys Val Gln Asn Asn Ser Val Ile Ile Asn Cys
            180                 185                 190

Asp Gly Phe Tyr Leu Ile Ser Leu Lys Gly Tyr Phe Ser Gln Glu Val
        195                 200                 205

Asn Ile Ser Leu His Tyr Gln Lys Asp Glu Glu Pro Leu Phe Gln Leu
    210                 215                 220

Lys Lys Val Arg Ser Val Asn Ser Leu Met Val Ala Ser Leu Thr Tyr
225                 230                 235                 240

Lys Asp Lys Val Tyr Leu Asn Val Thr Thr Asp Asn Thr Ser Leu Asp
                245                 250                 255

Asp Phe His Val Asn Gly Gly Glu Leu Ile Leu Ile His Gln Asn Pro
            260                 265                 270

Gly Glu Phe Cys Val Leu Gly Gly Ser Gly Gly Ser Gly Gly Gly
        275                 280                 285
```

```
Ser Gly Gln Val Ser His Arg Tyr Pro Arg Ile Gln Ser Ile Lys Val
    290                 295                 300
Gln Phe Thr Glu Tyr Lys Lys Glu Lys Gly Phe Ile Leu Thr Ser Gln
305                 310                 315                 320
Lys Glu Asp Glu Ile Met Lys Val Gln Asn Asn Ser Val Ile Ile Asn
                325                 330                 335
Cys Asp Gly Phe Tyr Leu Ile Ser Leu Lys Gly Tyr Phe Ser Gln Glu
                340                 345                 350
Val Asn Ile Ser Leu His Tyr Gln Lys Asp Glu Glu Pro Leu Phe Gln
                355                 360                 365
Leu Lys Lys Val Arg Ser Val Asn Ser Leu Met Val Ala Ser Leu Thr
    370                 375                 380
Tyr Lys Asp Lys Val Tyr Leu Asn Val Thr Thr Asp Asn Thr Ser Leu
385                 390                 395                 400
Asp Asp Phe His Val Asn Gly Gly Glu Leu Ile Leu Ile His Gln Asn
                405                 410                 415
Pro Gly Glu Phe Cys Val Leu
                420

<210> SEQ ID NO 59
<211> LENGTH: 133
<212> TYPE: PRT
<213> ORGANISM: Artificial Sequence
<220> FEATURE:
<223> OTHER INFORMATION: SYNTHESIZED

<400> SEQUENCE: 59

Gln Val Ser His Arg Tyr Pro Arg Ile Gln Ser Ile Lys Val Gln Phe
1               5                   10                  15
Thr Glu Tyr Lys Lys Glu Lys Gly Phe Ile Leu Thr Ser Gln Lys Glu
                20                  25                  30
Asp Glu Ile Met Lys Val Gln Asn Asn Ser Val Ile Ile Asn Cys Asp
            35                  40                  45
Gly Phe Tyr Leu Ile Ser Leu Lys Gly Tyr Phe Ser Gln Glu Val Asn
    50                  55                  60
Ile Ser Leu His Tyr Gln Lys Asp Glu Glu Pro Leu Phe Gln Leu Lys
65                  70                  75                  80
Lys Val Arg Ser Val Asn Ser Leu Met Val Ala Ser Leu Thr Tyr Lys
                85                  90                  95
Asp Lys Val Tyr Leu Asn Val Thr Thr Asp Asn Thr Ser Leu Asp Asp
                100                 105                 110
Phe His Val Ala Gly Gly Glu Leu Ile Leu Ile His Gln Asn Pro Gly
            115                 120                 125
Glu Ala Cys Val Leu
    130

<210> SEQ ID NO 60
<211> LENGTH: 423
<212> TYPE: PRT
<213> ORGANISM: Artificial Sequence
<220> FEATURE:
<223> OTHER INFORMATION: SYNTHESIZED

<400> SEQUENCE: 60

Gln Val Ser His Arg Tyr Pro Arg Ile Gln Ser Ile Lys Val Gln Phe
1               5                   10                  15
Thr Glu Tyr Lys Lys Glu Lys Gly Phe Ile Leu Thr Ser Gln Lys Glu
                20                  25                  30
```

```
Asp Glu Ile Met Lys Val Gln Asn Asn Ser Val Ile Ile Asn Cys Asp
            35                  40                  45

Gly Phe Tyr Leu Ile Ser Leu Lys Gly Tyr Phe Ser Gln Glu Val Asn
        50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Ala Gly Glu Leu Ile Leu Ile His Gln Asn Pro Gly
        115                 120                 125

Glu Ala Cys Val Leu Gly Gly Ser Gly Gly Ser Gly Gly Gly Ser
    130                 135                 140

Gly Gln Val Ser His Arg Tyr Pro Arg Ile Gln Ser Ile Lys Val Gln
145                 150                 155                 160

Phe Thr Glu Tyr Lys Lys Glu Lys Gly Phe Ile Leu Thr Ser Gln Lys
                165                 170                 175

Glu Asp Glu Ile Met Lys Val Gln Asn Asn Ser Val Ile Ile Asn Cys
            180                 185                 190

Asp Gly Phe Tyr Leu Ile Ser Leu Lys Gly Tyr Phe Ser Gln Glu Val
        195                 200                 205

Asn Ile Ser Leu His Tyr Gln Lys Asp Glu Glu Pro Leu Phe Gln Leu
    210                 215                 220

Lys Lys Val Arg Ser Val Asn Ser Leu Met Val Ala Ser Leu Thr Tyr
225                 230                 235                 240

Lys Asp Lys Val Tyr Leu Asn Val Thr Thr Asp Asn Thr Ser Leu Asp
                245                 250                 255

Asp Phe His Val Ala Gly Gly Glu Leu Ile Leu Ile His Gln Asn Pro
            260                 265                 270

Gly Glu Ala Cys Val Leu Gly Gly Ser Gly Gly Ser Gly Gly Gly
        275                 280                 285

Ser Gly Gln Val Ser His Arg Tyr Pro Arg Ile Gln Ser Ile Lys Val
    290                 295                 300

Gln Phe Thr Glu Tyr Lys Lys Glu Lys Gly Phe Ile Leu Thr Ser Gln
305                 310                 315                 320

Lys Glu Asp Glu Ile Met Lys Val Gln Asn Asn Ser Val Ile Ile Asn
                325                 330                 335

Cys Asp Gly Phe Tyr Leu Ile Ser Leu Lys Gly Tyr Phe Ser Gln Glu
            340                 345                 350

Val Asn Ile Ser Leu His Tyr Gln Lys Asp Glu Glu Pro Leu Phe Gln
        355                 360                 365

Leu Lys Lys Val Arg Ser Val Asn Ser Leu Met Val Ala Ser Leu Thr
370                 375                 380

Tyr Lys Asp Lys Val Tyr Leu Asn Val Thr Thr Asp Asn Thr Ser Leu
385                 390                 395                 400

Asp Asp Phe His Val Ala Gly Gly Glu Leu Ile Leu Ile His Gln Asn
                405                 410                 415

Pro Gly Glu Phe Cys Val Leu
            420

<210> SEQ ID NO 61
<211> LENGTH: 423
```

```
<212> TYPE: PRT
<213> ORGANISM: Artificial Sequence
<220> FEATURE:
<223> OTHER INFORMATION: SYNTHESIZED

<400> SEQUENCE: 61

Gln Val Ser His Arg Tyr Pro Arg Ile Gln Ser Ile Lys Val Gln Phe
1               5                   10                  15

Thr Glu Tyr Lys Lys Glu Lys Gly Phe Ile Leu Thr Ser Gln Lys Glu
            20                  25                  30

Asp Glu Ile Met Lys Val Gln Asn Asn Ser Val Ile Asn Cys Asp
        35                  40                  45

Gly Phe Tyr Leu Ile Ser Leu Lys Gly Tyr Phe Ser Gln Glu Val Asn
    50                  55                  60

Ile Ser Leu His Tyr Gln Lys Asp Glu Glu Pro Leu Phe Gln Leu Lys
65                  70                  75                  80

Lys Val Arg Ser Val Asn Ser Leu Met Val Ala Ser Leu Thr Tyr Lys
                85                  90                  95

Asp Lys Val Tyr Leu Asn Val Thr Thr Asp Asn Thr Ser Leu Asp Asp
            100                 105                 110

Phe His Val Ala Gly Gly Glu Leu Ile Leu Ile His Gln Asn Pro Gly
        115                 120                 125

Glu Ala Cys Val Leu Gly Gly Ser Gly Gly Gly Ser Gly Gly Gly Ser
130                 135                 140

Gly Gln Val Ser His Arg Tyr Pro Arg Ile Gln Ser Ile Lys Val Gln
145                 150                 155                 160

Phe Thr Glu Tyr Lys Lys Glu Lys Gly Phe Ile Leu Thr Ser Gln Lys
                165                 170                 175

Glu Asp Glu Ile Met Lys Val Gln Asn Asn Ser Val Ile Ile Asn Cys
            180                 185                 190

Asp Gly Phe Tyr Leu Ile Ser Leu Lys Gly Tyr Phe Ser Gln Glu Val
        195                 200                 205

Asn Ile Ser Leu His Tyr Gln Lys Asp Glu Glu Pro Leu Phe Gln Leu
    210                 215                 220

Lys Lys Val Arg Ser Val Asn Ser Leu Met Val Ala Ser Leu Thr Tyr
225                 230                 235                 240

Lys Asp Lys Val Tyr Leu Asn Val Thr Thr Asp Asn Thr Ser Leu Asp
                245                 250                 255

Asp Phe His Val Asn Gly Gly Glu Leu Ile Leu Ile His Gln Asn Pro
            260                 265                 270

Gly Glu Phe Cys Val Leu Gly Gly Ser Gly Gly Gly Ser Gly Gly Gly
        275                 280                 285

Ser Gly Gln Val Ser His Arg Tyr Pro Arg Ile Gln Ser Ile Lys Val
    290                 295                 300

Gln Phe Thr Glu Tyr Lys Lys Glu Lys Gly Phe Ile Leu Thr Ser Gln
305                 310                 315                 320

Lys Glu Asp Glu Ile Met Lys Val Gln Asn Asn Ser Val Ile Ile Asn
                325                 330                 335

Cys Asp Gly Phe Tyr Leu Ile Ser Leu Lys Gly Tyr Phe Ser Gln Glu
            340                 345                 350

Val Asn Ile Ser Leu His Tyr Gln Lys Asp Glu Glu Pro Leu Phe Gln
        355                 360                 365

Leu Lys Lys Val Arg Ser Val Asn Ser Leu Met Val Ala Ser Leu Thr
    370                 375                 380
```

```
Tyr Lys Asp Lys Val Tyr Leu Asn Val Thr Thr Asp Asn Thr Ser Leu
385                 390                 395                 400

Asp Asp Phe His Val Asn Gly Gly Glu Leu Ile Leu Ile His Gln Asn
            405                 410                 415

Pro Gly Glu Phe Cys Val Leu
            420
```

<210> SEQ ID NO 62
<211> LENGTH: 605
<212> TYPE: PRT
<213> ORGANISM: Artificial Sequence
<220> FEATURE:
<223> OTHER INFORMATION: SYNTHESIZED

<400> SEQUENCE: 62

```
His Lys Leu Ala Phe Asn Phe Asn Leu Glu Ile Asn Gly Ser Asp Thr
1               5                   10                  15

His Ser Thr Val Asp Val Tyr Leu Asp Asp Ser Gln Ile Ile Thr Phe
                20                  25                  30

Asp Gly Lys Asp Ile Arg Pro Thr Ile Pro Phe Met Ile Gly Asp Glu
            35                  40                  45

Ile Phe Leu Pro Phe Tyr Lys Asn Val Phe Ser Glu Phe Phe Ser Leu
50                  55                  60

Phe Arg Arg Val Pro Thr Ser Thr Pro Tyr Glu Asp Leu Thr Tyr Phe
65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
            100                 105                 110

Lys Asn Met Trp Leu Thr Thr Ser Glu Phe Arg Leu Lys Lys Trp Phe
            115                 120                 125

Asp Gly Glu Asp Cys Ile Met His Leu Arg Ser Leu Val Arg Lys Met
130                 135                 140

Glu Asp Ser Lys Arg Asn Thr Gly Gly Gly Ser Ser Gly Ser Ser Gly
145                 150                 155                 160

Ser Ser His His His His His His Gly Gly Ser Gly Ser
                165                 170                 175

Ser Gly Ser Ser Gly Gly Gln Val Ser His Arg Tyr Pro Arg Ile Gln
            180                 185                 190

Ser Ile Lys Val Gln Phe Thr Glu Tyr Lys Lys Glu Lys Gly Phe Ile
            195                 200                 205

Leu Thr Ser Gln Lys Glu Asp Glu Ile Met Lys Val Gln Asn Asn Ser
            210                 215                 220

Val Ile Ile Asn Cys Asp Gly Phe Tyr Leu Ile Ser Leu Lys Gly Tyr
225                 230                 235                 240

Phe Ser Gln Glu Val Asn Ile Ser Leu His Tyr Gln Lys Asp Glu Glu
                245                 250                 255

Pro Leu Phe Gln Leu Lys Lys Val Arg Ser Val Asn Ser Leu Met Val
            260                 265                 270

Ala Ser Leu Thr Tyr Lys Asp Lys Val Tyr Leu Asn Val Thr Thr Asp
            275                 280                 285

Asn Thr Ser Leu Asp Asp Phe His Val Asn Gly Gly Glu Leu Ile Leu
            290                 295                 300

Ile His Gln Asn Pro Gly Glu Phe Cys Val Leu Gly Gly Ser Gly Gly
305                 310                 315                 320
```

```
Gly Ser Gly Gly Gly Ser Gly Gln Val Ser His Arg Tyr Pro Arg Ile
            325                 330                 335
Gln Ser Ile Lys Val Gln Phe Thr Glu Tyr Lys Lys Glu Lys Gly Phe
        340                 345                 350
Ile Leu Thr Ser Gln Lys Glu Asp Glu Ile Met Lys Val Gln Asn Asn
        355                 360                 365
Ser Val Ile Ile Asn Cys Asp Gly Phe Tyr Leu Ile Ser Leu Lys Gly
370                 375                 380
Tyr Phe Ser Gln Glu Val Asn Ile Ser Leu His Tyr Gln Lys Asp Glu
385                 390                 395                 400
Glu Pro Leu Phe Gln Leu Lys Lys Val Arg Ser Val Asn Ser Leu Met
                405                 410                 415
Val Ala Ser Leu Thr Tyr Lys Asp Lys Val Tyr Leu Asn Val Thr Thr
                420                 425                 430
Asp Asn Thr Ser Leu Asp Asp Phe His Val Asn Gly Gly Glu Leu Ile
                435                 440                 445
Leu Ile His Gln Asn Pro Gly Glu Phe Cys Val Leu Gly Gly Ser Gly
        450                 455                 460
Gly Gly Ser Gly Gly Gly Ser Gly Gln Val Ser His Arg Tyr Pro Arg
465                 470                 475                 480
Ile Gln Ser Ile Lys Val Gln Phe Thr Glu Tyr Lys Lys Glu Lys Gly
                485                 490                 495
Phe Ile Leu Thr Ser Gln Lys Glu Asp Glu Ile Met Lys Val Gln Asn
                500                 505                 510
Asn Ser Val Ile Ile Asn Cys Asp Gly Phe Tyr Leu Ile Ser Leu Lys
                515                 520                 525
Gly Tyr Phe Ser Gln Glu Val Asn Ile Ser Leu His Tyr Gln Lys Asp
        530                 535                 540
Glu Glu Pro Leu Phe Gln Leu Lys Lys Val Arg Ser Val Asn Ser Leu
545                 550                 555                 560
Met Val Ala Ser Leu Thr Tyr Lys Asp Lys Val Tyr Leu Asn Val Thr
                565                 570                 575
Thr Asp Asn Thr Ser Leu Asp Asp Phe His Val Asn Gly Gly Glu Leu
                580                 585                 590
Ile Leu Ile His Gln Asn Pro Gly Glu Phe Cys Val Leu
        595                 600                 605

<210> SEQ ID NO 63
<211> LENGTH: 605
<212> TYPE: PRT
<213> ORGANISM: Artificial Sequence
<220> FEATURE:
<223> OTHER INFORMATION: SYNTHESIZED

<400> SEQUENCE: 63

His Lys Leu Ala Phe Asn Phe Asn Leu Glu Ile Asn Gly Ser Asp Thr
1               5                   10                  15
His Ser Thr Val Asp Val Tyr Leu Asp Asp Ser Gln Ile Ile Thr Phe
                20                  25                  30
Asp Gly Lys Asp Ile Arg Pro Thr Ile Pro Phe Met Ile Gly Asp Glu
        35                  40                  45
Ile Phe Leu Pro Phe Tyr Lys Asn Val Phe Ser Glu Phe Phe Ser Leu
    50                  55                  60
Phe Arg Arg Val Pro Thr Ser Thr Pro Tyr Glu Asp Leu Thr Tyr Phe
65                  70                  75                  80
```

```
Tyr Glu Cys Asp Tyr Thr Asp Asn Lys Ser Thr Phe Asp Gln Phe Tyr
             85                  90                  95

Leu Tyr Asn Gly Glu Glu Tyr Thr Val Lys Thr Gln Glu Ala Thr Asn
        100                 105                 110

Lys Asn Met Trp Leu Thr Thr Ser Glu Phe Arg Leu Lys Lys Trp Phe
        115                 120                 125

Asp Gly Glu Asp Cys Ile Met His Leu Arg Ser Leu Val Arg Lys Met
        130                 135                 140

Glu Asp Ser Lys Arg Asn Thr Gly Gly Ser Gly Ser Ser Gly
145                 150                 155                 160

Ser Ser His His His His His His Gly Gly Ser Ser Gly Ser
                165                 170                 175

Ser Gly Ser Ser Gly Gly Gln Val Ser His Arg Tyr Pro Arg Ile Gln
        180                 185                 190

Ser Ile Lys Val Gln Phe Thr Glu Tyr Lys Lys Glu Lys Gly Phe Ile
        195                 200                 205

Leu Thr Ser Gln Lys Glu Asp Glu Ile Met Lys Val Gln Asn Asn Ser
        210                 215                 220

Val Ile Ile Asn Cys Asp Gly Phe Tyr Leu Ile Ser Leu Lys Gly Tyr
225                 230                 235                 240

Phe Ser Gln Glu Val Asn Ile Ser Leu His Tyr Gln Lys Asp Glu Glu
                245                 250                 255

Pro Leu Phe Gln Leu Lys Lys Val Arg Ser Val Asn Ser Leu Met Val
        260                 265                 270

Ala Ser Leu Thr Tyr Lys Asp Lys Val Tyr Leu Asn Val Thr Thr Asp
        275                 280                 285

Asn Thr Ser Leu Asp Asp Phe His Val Ala Gly Gly Glu Leu Ile Leu
        290                 295                 300

Ile His Gln Asn Pro Gly Glu Ala Cys Val Leu Gly Gly Ser Gly Gly
305                 310                 315                 320

Gly Ser Gly Gly Gly Ser Gly Gln Val Ser His Arg Tyr Pro Arg Ile
                325                 330                 335

Gln Ser Ile Lys Val Gln Phe Thr Glu Tyr Lys Lys Glu Lys Gly Phe
        340                 345                 350

Ile Leu Thr Ser Gln Lys Glu Asp Glu Ile Met Lys Val Gln Asn Asn
        355                 360                 365

Ser Val Ile Ile Asn Cys Asp Gly Phe Tyr Leu Ile Ser Leu Lys Gly
        370                 375                 380

Tyr Phe Ser Gln Glu Val Asn Ile Ser Leu His Tyr Gln Lys Asp Glu
385                 390                 395                 400

Glu Pro Leu Phe Gln Leu Lys Lys Val Arg Ser Val Asn Ser Leu Met
        405                 410                 415

Val Ala Ser Leu Thr Tyr Lys Asp Lys Val Tyr Leu Asn Val Thr Thr
        420                 425                 430

Asp Asn Thr Ser Leu Asp Asp Phe His Val Ala Gly Gly Glu Leu Ile
        435                 440                 445

Leu Ile His Gln Asn Pro Gly Glu Ala Cys Val Leu Gly Gly Ser Gly
        450                 455                 460

Gly Gly Ser Gly Gly Gly Ser Gly Gln Val Ser His Arg Tyr Pro Arg
465                 470                 475                 480

Ile Gln Ser Ile Lys Val Gln Phe Thr Glu Tyr Lys Lys Glu Lys Gly
                485                 490                 495

Phe Ile Leu Thr Ser Gln Lys Glu Asp Glu Ile Met Lys Val Gln Asn
```

```
                    500                 505                 510
Asn Ser Val Ile Ile Asn Cys Asp Gly Phe Tyr Leu Ile Ser Leu Lys
            515                 520                 525

Gly Tyr Phe Ser Gln Glu Val Asn Ile Ser Leu His Tyr Gln Lys Asp
            530                 535                 540

Glu Glu Pro Leu Phe Gln Leu Lys Lys Val Arg Ser Val Asn Ser Leu
545                 550                 555                 560

Met Val Ala Ser Leu Thr Tyr Lys Asp Lys Val Tyr Leu Asn Val Thr
                565                 570                 575

Thr Asp Asn Thr Ser Leu Asp Asp Phe His Val Asn Gly Gly Glu Leu
            580                 585                 590

Ile Leu Ile His Gln Asn Pro Gly Glu Phe Cys Val Leu
            595                 600                 605

<210> SEQ ID NO 64
<211> LENGTH: 605
<212> TYPE: PRT
<213> ORGANISM: Artificial Sequence
<220> FEATURE:
<223> OTHER INFORMATION: SYNTHESIZED

<400> SEQUENCE: 64

His Lys Leu Ala Phe Asn Phe Asn Leu Glu Ile Asn Gly Ser Asp Thr
1               5                   10                  15

His Ser Thr Val Asp Val Tyr Leu Asp Asp Ser Gln Ile Ile Thr Phe
            20                  25                  30

Asp Gly Lys Asp Ile Arg Pro Thr Ile Pro Phe Met Ile Gly Asp Glu
        35                  40                  45

Ile Phe Leu Pro Phe Tyr Lys Asn Val Phe Ser Glu Phe Phe Ser Leu
    50                  55                  60

Phe Arg Arg Val Pro Thr Ser Thr Pro Tyr Glu Asp Leu Thr Tyr Phe
65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
            100                 105                 110

Lys Asn Met Trp Leu Thr Thr Ser Glu Phe Arg Leu Lys Lys Trp Phe
        115                 120                 125

Asp Gly Glu Asp Cys Ile Met His Leu Arg Ser Leu Val Arg Lys Met
    130                 135                 140

Glu Asp Ser Lys Arg Asn Thr Gly Gly Gly Ser Ser Gly Ser Ser Gly
145                 150                 155                 160

Ser Ser His His His His His His Gly Gly Ser Ser Gly Ser
                165                 170                 175

Ser Gly Ser Ser Gly Gly Gln Val Ser His Arg Tyr Pro Arg Ile Gln
            180                 185                 190

Ser Ile Lys Val Gln Phe Thr Glu Tyr Lys Lys Glu Lys Gly Phe Ile
        195                 200                 205

Leu Thr Ser Gln Lys Glu Asp Glu Ile Met Lys Val Gln Asn Asn Ser
    210                 215                 220

Val Ile Ile Asn Cys Asp Gly Phe Tyr Leu Ile Ser Leu Lys Gly Tyr
225                 230                 235                 240

Phe Ser Gln Glu Val Asn Ile Ser Leu His Tyr Gln Lys Asp Glu Glu
                245                 250                 255

Pro Leu Phe Gln Leu Lys Lys Val Arg Ser Val Asn Ser Leu Met Val
```

```
                260                 265                 270
Ala Ser Leu Thr Tyr Lys Asp Lys Val Tyr Leu Asn Val Thr Thr Asp
            275                 280                 285

Asn Thr Ser Leu Asp Asp Phe His Val Ala Gly Gly Glu Leu Ile Leu
        290                 295                 300

Ile His Gln Asn Pro Gly Glu Ala Cys Val Leu Gly Gly Ser Gly Gly
305                 310                 315                 320

Gly Ser Gly Gly Gly Ser Gly Gln Val Ser His Arg Tyr Pro Arg Ile
                325                 330                 335

Gln Ser Ile Lys Val Gln Phe Thr Glu Tyr Lys Lys Glu Lys Gly Phe
            340                 345                 350

Ile Leu Thr Ser Gln Lys Glu Asp Glu Ile Met Lys Val Gln Asn Asn
        355                 360                 365

Ser Val Ile Ile Asn Cys Asp Gly Phe Tyr Leu Ile Ser Leu Lys Gly
    370                 375                 380

Tyr Phe Ser Gln Glu Val Asn Ile Ser Leu His Tyr Gln Lys Asp Glu
385                 390                 395                 400

Glu Pro Leu Phe Gln Leu Lys Lys Val Arg Ser Val Asn Ser Leu Met
                405                 410                 415

Val Ala Ser Leu Thr Tyr Lys Asp Lys Val Tyr Leu Asn Val Thr Thr
            420                 425                 430

Asp Asn Thr Ser Leu Asp Asp Phe His Val Asn Gly Gly Glu Leu Ile
        435                 440                 445

Leu Ile His Gln Asn Pro Gly Glu Phe Cys Val Leu Gly Gly Ser Gly
    450                 455                 460

Gly Gly Ser Gly Gly Gly Ser Gly Gln Val Ser His Arg Tyr Pro Arg
465                 470                 475                 480

Ile Gln Ser Ile Lys Val Gln Phe Thr Glu Tyr Lys Lys Glu Lys Gly
                485                 490                 495

Phe Ile Leu Thr Ser Gln Lys Glu Asp Glu Ile Met Lys Val Gln Asn
            500                 505                 510

Asn Ser Val Ile Ile Asn Cys Asp Gly Phe Tyr Leu Ile Ser Leu Lys
        515                 520                 525

Gly Tyr Phe Ser Gln Glu Val Asn Ile Ser Leu His Tyr Gln Lys Asp
    530                 535                 540

Glu Glu Pro Leu Phe Gln Leu Lys Lys Val Arg Ser Val Asn Ser Leu
545                 550                 555                 560

Met Val Ala Ser Leu Thr Tyr Lys Asp Lys Val Tyr Leu Asn Val Thr
                565                 570                 575

Thr Asp Asn Thr Ser Leu Asp Asp Phe His Val Asn Gly Gly Glu Leu
            580                 585                 590

Ile Leu Ile His Gln Asn Pro Gly Glu Phe Cys Val Leu
        595                 600                 605

<210> SEQ ID NO 65
<211> LENGTH: 205
<212> TYPE: PRT
<213> ORGANISM: Homo sapiens

<400> SEQUENCE: 65

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30
```

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
 50                  55                  60

Gly Leu Ala Gly Val Ser Leu Thr Gly Gly Leu Ser Tyr Lys Glu Asp
65                   70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
                115                 120                 125

Ala Leu Ala Leu Thr Val Asp Leu Pro Pro Ala Ser Ser Glu Ala Arg
            130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 66
<211> LENGTH: 639
<212> TYPE: PRT
<213> ORGANISM: Artificial Sequence
<220> FEATURE:
<223> OTHER INFORMATION: SYNTHESIZED

<400> SEQUENCE: 66

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
                20                  25                  30

Ala Gly Leu Leu Asp Leu Arg Gln Gly Met Phe Ala Gln Leu Val Ala
            35                  40                  45

Gln Asn Val Leu Leu Ile Asp Gly Pro Leu Ser Trp Tyr Ser Asp Pro
 50                  55                  60

Gly Leu Ala Gly Val Ser Leu Thr Gly Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
                100                 105                 110

Ser Leu Ala Leu His Leu Gln Pro Leu Arg Ser Ala Ala Gly Ala Ala
                115                 120                 125

Ala Leu Ala Leu Thr Val Asp Leu Pro Pro Ala Ser Ser Glu Ala Arg
            130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

```
Pro Glu Ile Pro Ala Gly Leu Pro Ser Pro Arg Ser Glu Gly Gly Ser
        195                 200                 205

Gly Gly Gly Ser Gly Gly Ser Gly Ala Cys Pro Trp Ala Val Ser
210                 215                 220

Gly Ala Arg Ala Ser Pro Gly Ser Ala Ala Ser Pro Arg Leu Arg Glu
225                 230                 235                 240

Gly Pro Glu Leu Ser Pro Asp Asp Pro Ala Gly Leu Leu Asp Leu Arg
                245                 250                 255

Gln Gly Met Phe Ala Gln Leu Val Ala Gln Asn Val Leu Leu Ile Asp
            260                 265                 270

Gly Pro Leu Ser Trp Tyr Ser Asp Pro Gly Leu Ala Gly Val Ser Leu
        275                 280                 285

Thr Gly Gly Leu Ser Tyr Lys Glu Asp Thr Lys Glu Leu Val Val Ala
290                 295                 300

Lys Ala Gly Val Tyr Tyr Val Phe Phe Gln Leu Glu Leu Arg Arg Val
305                 310                 315                 320

Val Ala Gly Glu Gly Ser Gly Ser Val Ser Leu Ala Leu His Leu Gln
                325                 330                 335

Pro Leu Arg Ser Ala Gly Ala Ala Ala Leu Ala Leu Thr Val Asp
            340                 345                 350

Leu Pro Pro Ala Ser Ser Glu Ala Arg Asn Ser Ala Phe Gly Phe Gln
        355                 360                 365

Gly Arg Leu Leu His Leu Ser Ala Gly Gln Arg Leu Gly Val His Leu
370                 375                 380

His Thr Glu Ala Arg Ala Arg His Ala Trp Gln Leu Thr Gln Gly Ala
385                 390                 395                 400

Thr Val Leu Gly Leu Phe Arg Val Thr Pro Glu Ile Pro Ala Gly Leu
                405                 410                 415

Pro Ser Pro Arg Ser Glu Gly Ser Gly Gly Ser Gly Gly
            420                 425                 430

Ser Gly Ala Cys Pro Trp Ala Val Ser Gly Ala Arg Ala Ser Pro Gly
        435                 440                 445

Ser Ala Ala Ser Pro Arg Leu Arg Glu Gly Pro Glu Leu Ser Pro Asp
450                 455                 460

Asp Pro Ala Gly Leu Leu Asp Leu Arg Gln Gly Met Phe Ala Gln Leu
465                 470                 475                 480

Val Ala Gln Asn Val Leu Leu Ile Asp Gly Pro Leu Ser Trp Tyr Ser
                485                 490                 495

Asp Pro Gly Leu Ala Gly Val Ser Leu Thr Gly Gly Leu Ser Tyr Lys
            500                 505                 510

Glu Asp Thr Lys Glu Leu Val Val Ala Lys Ala Gly Val Tyr Tyr Val
        515                 520                 525

Phe Phe Gln Leu Glu Leu Arg Arg Val Val Ala Gly Glu Gly Ser Gly
530                 535                 540

Ser Val Ser Leu Ala Leu His Leu Gln Pro Leu Arg Ser Ala Gly
545                 550                 555                 560

Ala Ala Ala Leu Ala Leu Thr Val Asp Leu Pro Pro Ala Ser Ser Glu
                565                 570                 575

Ala Arg Asn Ser Ala Phe Gly Phe Gln Gly Arg Leu Leu His Leu Ser
            580                 585                 590

Ala Gly Gln Arg Leu Gly Val His Leu His Thr Glu Ala Arg Ala Arg
        595                 600                 605

His Ala Trp Gln Leu Thr Gln Gly Ala Thr Val Leu Gly Leu Phe Arg
```

```
                610                 615                 620
Val Thr Pro Glu Ile Pro Ala Gly Leu Pro Ser Pro Arg Ser Glu
625                 630                 635
```

<210> SEQ ID NO 67
<211> LENGTH: 821
<212> TYPE: PRT
<213> ORGANISM: Artificial Sequence
<220> FEATURE:
<223> OTHER INFORMATION: SYNTHESIZED

<400> SEQUENCE: 67

```
His Lys Leu Ala Phe Asn Phe Asn Leu Glu Ile Asn Gly Ser Asp Thr
1               5                   10                  15

His Ser Thr Val Asp Val Tyr Leu Asp Asp Ser Gln Ile Ile Thr Phe
            20                  25                  30

Asp Gly Lys Asp Ile Arg Pro Thr Ile Pro Phe Met Ile Gly Asp Glu
        35                  40                  45

Ile Phe Leu Pro Phe Tyr Lys Asn Val Phe Ser Glu Phe Phe Ser Leu
    50                  55                  60

Phe Arg Arg Val Pro Thr Ser Thr Pro Tyr Glu Asp Leu Thr Tyr Phe
65                  70                  75                  80

Tyr Glu Cys Asp Tyr Thr Asp Asn Lys Ser Thr Phe Asp Gln Phe Tyr
                85                  90                  95

Leu Tyr Asn Gly Glu Glu Tyr Thr Val Lys Thr Gln Glu Ala Thr Asn
            100                 105                 110

Lys Asn Met Trp Leu Thr Thr Ser Glu Phe Arg Leu Lys Lys Trp Phe
        115                 120                 125

Asp Gly Glu Asp Cys Ile Met His Leu Arg Ser Leu Val Arg Lys Met
130                 135                 140

Glu Asp Ser Lys Arg Asn Thr Gly Gly Gly Ser Ser Gly Ser Ser Gly
145                 150                 155                 160

Ser Ser His His His His His His Gly Gly Ser Ser Gly Ser
                165                 170                 175

Ser Gly Ser Ser Gly Gly Ala Cys Pro Trp Ala Val Ser Gly Ala Arg
            180                 185                 190

Ala Ser Pro Gly Ser Ala Ala Ser Pro Arg Leu Arg Glu Gly Pro Glu
        195                 200                 205

Leu Ser Pro Asp Asp Pro Ala Gly Leu Leu Asp Leu Arg Gln Gly Met
    210                 215                 220

Phe Ala Gln Leu Val Ala Gln Asn Val Leu Leu Ile Asp Gly Pro Leu
225                 230                 235                 240

Ser Trp Tyr Ser Asp Pro Gly Leu Ala Gly Val Ser Leu Thr Gly Gly
                245                 250                 255

Leu Ser Tyr Lys Glu Asp Thr Lys Glu Leu Val Val Ala Lys Ala Gly
            260                 265                 270

Val Tyr Tyr Val Phe Phe Gln Leu Glu Leu Arg Arg Val Val Ala Gly
        275                 280                 285

Glu Gly Ser Gly Ser Val Ser Leu Ala Leu His Leu Gln Pro Leu Arg
    290                 295                 300

Ser Ala Ala Gly Ala Ala Ala Leu Ala Leu Thr Val Asp Leu Pro Pro
305                 310                 315                 320

Ala Ser Ser Glu Ala Arg Asn Ser Ala Phe Gly Phe Gln Gly Arg Leu
                325                 330                 335

Leu His Leu Ser Ala Gly Gln Arg Leu Gly Val His Leu His Thr Glu
```

```
            340                 345                 350
Ala Arg Ala Arg His Ala Trp Gln Leu Thr Gln Gly Ala Thr Val Leu
            355                 360                 365
Gly Leu Phe Arg Val Thr Pro Glu Ile Pro Ala Gly Leu Pro Ser Pro
            370                 375                 380
Arg Ser Glu Gly Gly Ser Gly Gly Gly Ser Gly Gly Ser Gly Ala
385                 390                 395                 400
Cys Pro Trp Ala Val Ser Gly Ala Arg Ala Ser Pro Gly Ser Ala Ala
                    405                 410                 415
Ser Pro Arg Leu Arg Glu Gly Pro Glu Leu Ser Pro Asp Asp Pro Ala
                    420                 425                 430
Gly Leu Leu Asp Leu Arg Gln Gly Met Phe Ala Gln Leu Val Ala Gln
                    435                 440                 445
Asn Val Leu Leu Ile Asp Gly Pro Leu Ser Trp Tyr Ser Asp Pro Gly
                    450                 455                 460
Leu Ala Gly Val Ser Leu Thr Gly Gly Leu Ser Tyr Lys Glu Asp Thr
465                 470                 475                 480
Lys Glu Leu Val Val Ala Lys Ala Gly Val Tyr Tyr Val Phe Phe Gln
                    485                 490                 495
Leu Glu Leu Arg Arg Val Val Ala Gly Glu Gly Ser Gly Ser Val Ser
                    500                 505                 510
Leu Ala Leu His Leu Gln Pro Leu Arg Ser Ala Ala Gly Ala Ala Ala
                    515                 520                 525
Leu Ala Leu Thr Val Asp Leu Pro Pro Ala Ser Ser Glu Ala Arg Asn
                    530                 535                 540
Ser Ala Phe Gly Phe Gln Gly Arg Leu Leu His Leu Ser Ala Gly Gln
545                 550                 555                 560
Arg Leu Gly Val His Leu His Thr Glu Ala Arg Ala Arg His Ala Trp
                    565                 570                 575
Gln Leu Thr Gln Gly Ala Thr Val Leu Gly Leu Phe Arg Val Thr Pro
                    580                 585                 590
Glu Ile Pro Ala Gly Leu Pro Ser Pro Arg Ser Glu Gly Gly Ser Gly
                    595                 600                 605
Gly Gly Ser Gly Gly Gly Ser Gly Ala Cys Pro Trp Ala Val Ser Gly
                    610                 615                 620
Ala Arg Ala Ser Pro Gly Ser Ala Ala Ser Pro Arg Leu Arg Glu Gly
625                 630                 635                 640
Pro Glu Leu Ser Pro Asp Asp Pro Ala Gly Leu Leu Asp Leu Arg Gln
                    645                 650                 655
Gly Met Phe Ala Gln Leu Val Ala Gln Asn Val Leu Leu Ile Asp Gly
                    660                 665                 670
Pro Leu Ser Trp Tyr Ser Asp Pro Gly Leu Ala Gly Val Ser Leu Thr
                    675                 680                 685
Gly Gly Leu Ser Tyr Lys Glu Asp Thr Lys Glu Leu Val Val Ala Lys
                    690                 695                 700
Ala Gly Val Tyr Tyr Val Phe Phe Gln Leu Glu Leu Arg Arg Val Val
705                 710                 715                 720
Ala Gly Glu Gly Ser Gly Ser Val Ser Leu Ala Leu His Leu Gln Pro
                    725                 730                 735
Leu Arg Ser Ala Ala Gly Ala Ala Ala Leu Ala Leu Thr Val Asp Leu
                    740                 745                 750
Pro Pro Ala Ser Ser Glu Ala Arg Asn Ser Ala Phe Gly Phe Gln Gly
                    755                 760                 765
```

-continued

```
Arg Leu Leu His Leu Ser Ala Gly Gln Arg Leu Gly Val His Leu His
    770                 775                 780

Thr Glu Ala Arg Ala Arg His Ala Trp Gln Leu Thr Gln Gly Ala Thr
785                 790                 795                 800

Val Leu Gly Leu Phe Arg Val Thr Pro Glu Ile Pro Ala Gly Leu Pro
                805                 810                 815

Ser Pro Arg Ser Glu
            820

<210> SEQ ID NO 68
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 68

Ala Ala Ala Leu
1

<210> SEQ ID NO 69
<211> LENGTH: 31
<212> TYPE: PRT
<213> ORGANISM: Artificial Sequence
<220> FEATURE:
<223> OTHER INFORMATION: SYNTHESIZED

<400> SEQUENCE: 69

Met Gly Ile Leu Pro Ser Pro Gly Met Pro Ala Leu Leu Ser Leu Val
1               5                   10                  15

Ser Leu Leu Ser Val Leu Leu Met Gly Cys Val Ala Glu Thr Gly
            20                  25                  30
```

What is claimed is:

1. A method of expanding cytotoxic lymphocytes ex vivo, comprising culturing a population of lymphocytes in the presence of a chimeric peptide, wherein the chimeric peptide comprises an orthopoxvirus major histocompatibility complex class 1-like protein (OMCP) peptide linked to an interleukin-2 (IL-2) mutant peptide comprising the amino acid sequence of SEQ ID NO: 5 comprising at least one mutation, wherein the at least one mutation is R38A, F42K, or C125S relative to SEQ ID NO: 5 wherein the OMCP peptide comprises an amino acid sequence selected from the group consisting of SEQ ID NO: 7, SEQ ID NO: 13, and SEQ ID NO: 14, and wherein the population of lymphocytes comprises cytotoxic lymphocytes.

2. The method of claim 1, wherein the OMCP peptide comprises the amino acid sequence of SEQ ID NO: 7.

3. The method of claim 1, wherein the OMCP peptide comprises the amino acid sequence of SEQ ID NO: 13.

4. The method of claim 3, wherein the OMCP peptide comprises the amino acid sequence of SEQ ID NO: 14.

5. The method of claim 1, wherein the cytotoxic lymphocytes comprise CD8+ T cells and/or NK cells.

* * * * *